US006495354B2

(12) United States Patent
Chappell et al.

(10) Patent No.: US 6,495,354 B2
(45) Date of Patent: Dec. 17, 2002

(54) SYNTHASES

(75) Inventors: Joseph Chappell, Lexington, KY (US);
Kathleen R. Manna, Georgetown, IN (US); Joseph P. Noel, San Diego, CA (US); Courtney M. Starks, La Jolla, CA (US)

(73) Assignees: University of Kentucky Research Foundation, Lexington, KY (US); The Salk Institute for Biological Studies, San Diego, CA (US)

( * ) Notice: Subject to any disclaimer, the term of this patent is extended or adjusted under 35 U.S.C. 154(b) by 0 days.

(21) Appl. No.: 09/887,586

(22) Filed: Jun. 22, 2001

(65) Prior Publication Data

US 2002/0094556 A1 Jul. 18, 2002

Related U.S. Application Data

(62) Division of application No. 09/398,395, filed on Sep. 17, 1999.
(60) Provisional application No. 60/150,262, filed on Aug. 23, 1999, provisional application No. 60/130,628, filed on Apr. 22, 1999, and provisional application No. 60/100,993, filed on Sep. 18, 1998.

(51) Int. Cl.[7] .......................... C12N 9/00; C12N 9/88; C07H 21/04
(52) U.S. Cl. ..................... 435/183; 435/4; 435/232; 435/468; 800/283; 800/284; 800/285; 800/289; 536/23.2
(58) Field of Search .................. 435/183, 4, 232, 435/468; 800/283, 284, 285, 289; 536/23.2

(56) References Cited

U.S. PATENT DOCUMENTS

| 5,589,619 A | 12/1996 | Chappell et al. |
| 5,824,774 A | 10/1998 | Chappell et al. |
| 5,849,526 A | 12/1998 | Pichersky |
| 5,871,988 A | 2/1999 | Croteau et al. |
| 5,876,964 A | 3/1999 | Croteau et al. |
| 5,891,697 A | 4/1999 | Croteau et al. |
| 5,981,843 A | 11/1999 | Chappell et al. |
| 5,994,114 A | 11/1999 | Croteau et al. |
| 6,008,043 A | 12/1999 | Croteau et al. |

FOREIGN PATENT DOCUMENTS

| EP | 0 768 381 | 4/1997 |
| WO | WO 95/11913 | 5/1995 |
| WO | WO 96/36697 | 11/1996 |
| WO | WO 97/15584 | 5/1997 |
| WO | WO 97/38571 | 10/1997 |
| WO | WO 97/38703 | 10/1997 |
| WO | WO 99/02030 | 1/1999 |
| WO | WO 99/15624 | 4/1999 |
| WO | WO 99/18118 | 4/1999 |
| WO | WO 99/19460 | 4/1999 |
| WO | WO 99/37139 | 7/1999 |
| WO | WO 99/38957 | 8/1999 |

OTHER PUBLICATIONS

Starks et al., "Structural Basis for Cyclic Terpene Biosynthesis by Tobacco 5–Epi–Aristolochene Synthase," *Science*, 1997, 227:1815–1820.

Chappell, "The Biochemistry and Molecular Biology of Isoprenoid Metabolism," *Plant Physiol.*, 1995, 107:1–6.

Facchini et al., "Gene family for an elicitor–induced sesquiterpene cyclase in tobacco," *Proc. Natl. Acad. Sci. USA*, 1992, 89:11088–11092.

Corey et al., "Isolation of an *Arabidopsis thaliana* gene encoding cycloartenol synthase by functional expression in a yeast mutant lacking lanosterol synthase by the use of a chromatographic screen," *Proc. Natl. Acad. Sci. USA*, 1993, 90:11628–11632.

Bohlmann et al., "Terpenoid–based defenses in conifers: cDNA cloning, characterization, and functional expression of wound–inducible (E)–α–bisabolene synthase from grand fir (*Abies grandis*)," *Proc. Natl. Acad. Sci. USA*, 1998, 95:6756–6761.

Colby et al., "Germacrene C synthase from *Lycopersicon esculentum* cv. VFNT Cherry tomato: cDNA isolation, characterization, and bacterial expression of the multiple product sesquiterpene cyclase," *Proc. Natl. Acad. Sci. USA*, 1998, 95:2216–2221.

Devarenne et al., "Molecular Characterization of Tobacco Squalene Synthase and Regulation in Response to Fungal Elicitor," *Arch. Biochem. Biophys.*, 1998, 349(2):205–215.

Back et al., "Cloning and Bacterial Expression of a Sesquiterpene Cyclase from *Hyoscyamus muticus* and Its Molecular Comparison to Related Terpene Cyclases," *J. Biol. Chem.*, 1995, 270(13):7375–7381.

Yin et al., "Regulation of Sesquiterpene Cyclase Gene Expression—Charaacterization of an Elicitor–and Pathogen–Inducible Promoter," *Plant Physiol.*, 1997, 115:437–451.

Mathis et al., "Pre–Steady–State Study of Recombinant Sesquiterpene Cyclases," *Biochemistry*, 36(27)8340–8348.

Back et al., "Identifying functional domains within terpene cyclases using a domain–swapping strategy," *Proc. Natl. Acad. Sci. USA*, 1996, 93:6841–6845.

(List continued on next page.)

Primary Examiner—Mary K. Zeman
Assistant Examiner—Lori A. Clow
(74) Attorney, Agent, or Firm—Fish & Richardson P.C., P.A.

(57) ABSTRACT

Novel synthases and the corresponding nucleic acids encoding such synthases are disclosed herein. Such synthases possess an active site pocket that includes key amino acid residues that are modified to generate desired terpenoid reaction intermediates and products. Synthase modifications are designed based on, e.g., the three-dimensional coordinates of tobacco 5-epi-aristolochene synthase with or without a substrate bound in the active site.

86 Claims, 4 Drawing Sheets

OTHER PUBLICATIONS

Newman et al., "Characterization of the TAC box, a cis–element within an elicitor–inducible sesquiterpene cyclase promoter," *Plant J.*, 1998, 16(1):1–12.

Crock et al., "Isolation of bacterial expression of a sesquiterpene synthase cDNA clone from peppermint (Mentha χ piperita, L.) that produces the aphid alarm pheromone (E)–β–farnesene," *Proc. Natl. Acad. Sci. USA*, 1997, 94:12833–12838.

Wildung et al., "A cDNA Clone for Taxadiene Synthase, the Diterpene Cyclase That Catalyzes the Committed Step of Taxol Biosynthesis," *J. Biol. Chem.*, 1996, 271(16):9201–9204.

Chen et al., "Cloning, Expression, and Characterization of (+)–δ–Cadinene Synthase: A Catalyst for Cotton Phytoalexin Biosynthesis," *Arch. Biochem. Biophys.*, 1995, 324(2):255–266.

Bohlmann et al., "Plant terpenoid synthases: Molecular biology and phylogeneic analysis," *Proc. Natl. Acad. Sci. USA*, 1998, 95:4126–4133.

Cane et al., "Trichodiene Synthase. Substrate Specificity and Inhibition," *Biochemistry*, 1995, 34:2471–2479.

Pyun et al., "Regiospecificiy and Isotope Effects Associated with the Methyl–Methylene Eliminations in the Enzyme–Catalyzed Biosynthesis of (R)–and (S)–Limonene," *J. Org. Chem.*, 1993, 58(15):3998–4009.

Anderson et al., "Farnesyl Diphosphate Synthethase—Molecular Cloning, Sequence, and Expression of an Essential Gene From *Saccharomyces cerevisiae*," *J. Biol. Chem.*, 1989, 264(32):19176–19184.

Song et al., "Yeast farnesyl–diphosphate synthase: Site–directed mutagenesis of residues in highly conserved prenyltransferase domains I and II," *Proc. Natl. Acad. Sci. USA*, 1994, 91:3044–3048.

Ohnuma et al., "A Role of the Amino Acid Residue Located on the Fifth Position before the First Aspartate–rich Motif of Farnesyl Diphosphate Synthase on Determination of the Final Product," *J. Biol. Chem.*, 1996, 271(48):30748–30754.

Tarshis et al., "Regulation of product chain length by isoprenyl disphosphate synthases," *Proc. Natl. Acad. Sci. USA*, 1996, 93:15018–15023.

Tarshis et al., "Crystal Structure of Recombinant Farnesyl Diphosphate Synthase at 2,6–Å Resolution," *Biochemistry*, 1994, 33:10871–10877.

Mau et al., "Cloning of casbene synthase cDNA: Evidence for conserved structural features among terpenoid cyclases in plants," *Proc. Natl. Acad. Sci. USA*, 1994, 91:8497–8501.

Wendt et al., "Structure and Function of a Squalene Cyclase," *Science*, 1997, 277:1811–1815.

Cane et al., "Trichodienc Synthase. Identification of Active Site Residues by Site–Directed Mutagenesis," *Biochemistry*, 1995, 34:2480–2488.

Cane et al., "Trichodiene Biosynthesis and the Stereochemistry of the Enzymatic Cyclization of Farnesyl Pyrophosphate," *Bioorg. Chem.*, 1985, 13(3):246–265.

Wheeler et al., "Direct demonstration of the isomerization component of the monoterpene cyclase reaction using a cyclopropylcarbinyl pyrophosphate substrate analog," *Proc. Natl. Acad. Sci. USA*, 1987, 84(14):4856–4859.

Pyun et al., "Stereochemistry of the Proton Elimination in the Formation of (+)–and (–)–α–Pinene by Monterpene Cyclases from Sage (*Salvia Officinalis*)," *Arch. Biochem. Biophys.*, 1994, 308(2):488–496.

Croteau, "Evidence for the Ionization Stepsin Monoterpene Cyclization Reactions Using 2–Fluorogeranyl and 2–Fluorolinalyl Pyrophosphates as Substrates," *Arch. Biochem. Biophys.*, 1986, 251(2):777–782.

Croteau et al., "Irreversible Inactivation of Monoterpene Cyclases by a Mechanism–Based Inhibitor," *Arch. Biochem. Biophys.*, 1993, 307(2):397–404.

Rajaonarivony et al., "Characterization and Mechanism of (4S)–Limonene Synthase, A Monoterpene Cyclase from the Glandular Trichomes of Peppermint (Mentha X piperita)," *Arch. Biochem. Biophys.*, 1992, 296(1):49–57.

Rajaonarivony et al., "Evidence for an Essential Histidine Residue in 4S–Limonene Synthase and Other Terpene Cyclases," *Arch. Biochem. Biophys.*, 1992, 299(1):77–82.

Aleshin et al., "Refined Crystal Structures of Glucoamylase from *Aspergillus awamori* var. X100," *J. Mol. Biol.*, 1994, 238:575–591.

Juy et al., "Three–dimensional structure of a thermostable bacterial cellulase," *Nature*, 1992, 357(6373):89–91.

Altschul et al., "Gapped Blast and PSI–Blast: a new generation of protein database search programs," *Nucleic Acids Res.*, 1997, 25(17):3389–3402.

Back, et al., "Expression of a Plant Sesquiterpene Cyclase Gene in *Escherichia coli*," *Arch. Biochem. Biophys.*, 1994, 315(2):527–532.

Cane, "Enzymatic Formation of Sesquiterpenes," *Chem. Rev.*, 1990, 90:1089–1103.

Cane et al., "Aristolochene Biosynthesis and Enzymatic Cyclization of Farnesyl Pyrophosphate," *J. Am. Chem. Soc.*, 1989, 111:8914–8916.

Cane et al., "Overexpression in *Escherichia coli* of Soluble Aristolochene Synthase from *Penicillium roqueforti*," *Arch. Biochem. Biophys.*, 1993, 304(2):415–419.

Hohn et al., "Purification and Characterization of the Sesquiterpene Cyclase Aristolochene Synthase from *Penicillium roqueforti*," *Arch Biochem. Biophys.*, 1989, 272(1):137–143.

Laskovics et al., "Prenyltransferase: Determination of the Binding Mechanism and Individual Kinetic Constants for Farnesylpyrophosphate Synthetase by Rapid Quench and Isotope Partitioning Experiments," *Biochemistry*, 1981, 20(7):1893–1901.

Lesburg et al., "Crystal Structure of Pentalenene Synthase: Mechanistic Insights on Terpenoid Cyclization Reactions in Biology," *Science*, 1997, 277(5333):1820–1824.

Munck et al., "Purification and Characterization of the Sesquiterpene Cyclase Pathchoulol Synthase from *Pogostemon cablin*," *Arch. Biochem. Biophys.*, 1990, 282(1):58–64.

Proctor et al., "Aristolochene Synthase. Isolation, characterization, and bacterial expression of a sesquiterpenoid biosynthetic gene (Ari1) from *Penicillium roqueforti*," *J. Biol. Chem.*, 1993, 268(6):4543–4548.

Vogel et al., "Abietadiene Synthase from Grand Fir (*Abies grandis*)", *J. Biol. Chem.*, 1996, 271(38):23262–23268.

Bohlmann et al., "Monoterpene Synthases from Grand Fir (*Abies grandis*)", *J. Biol. Chem.*, 1997, 272(35):21784–21792.

Starks et al., "Structural Basisfor Cyclic Terpene Biosynthesis by Tobacco 5–Epi–Aristolochene Synthase", *Science*, 1997, 277:1815–1819.

Genbank Accession No: Q40577.
Genbank Accession No: AB022598.
Genbank Accession No: Y18484.
Genbank Accession No: U48796.

Genbank Accession No: AF035631.
Genbank Accession No: L13459.
Genbank Accession No: AF051901.
Genbank Accession No: AF051900.
Genbank Accession No: AF051899.
Genbank Accession No: AF006194.
Genbank Accession No: U92267.
Genbank Accession No: U92266.
Genbank Accession No: AF024615.
Genbank Accession No: U87909.
Gembank Accession No: U87908.
Genbank Accession No: AF006193.
Genbank Accession No: U50768.
Genbank Accession No: L32134.
Genbank Accession No: AF006195.
Genbank Accession No: AJ005588.
Genbank Accession No: Q43714.
Genbank Accession No: AF061285.
Genbank Accession No: AF043299.
Genbank Accession No: AB022719.
Genbank Accession No: AB023816.
Genbank Accession No: AF043298.
Genbank Accession No: AF043300.
Genbank Accession No: AF042382.
Genbank Accession No: B56118.
Genbank Accession No: C56118.
Genbank Accession No: U20187.
Genbank Accession No: U20189.
Genbank Accession No: U20190.
Lesburg et al., *Current Opinion in Structural Biology*, 1998, 8:695–703.

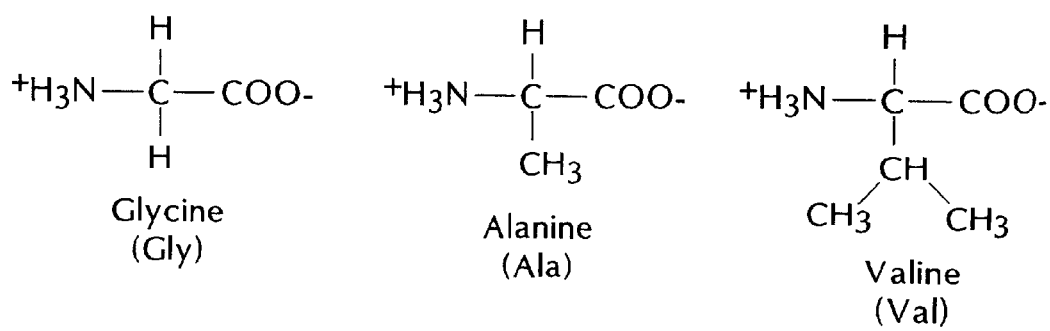
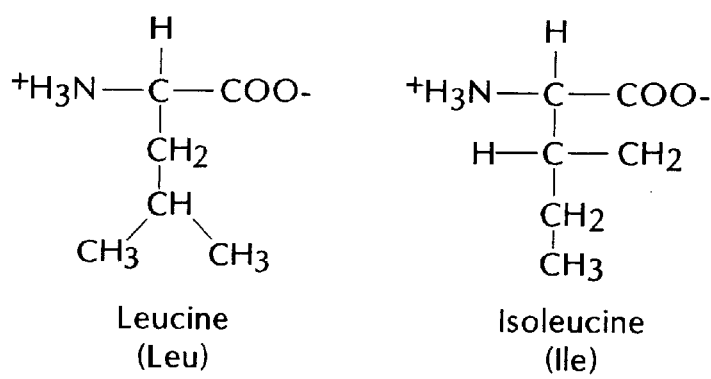
FIG. 2-1
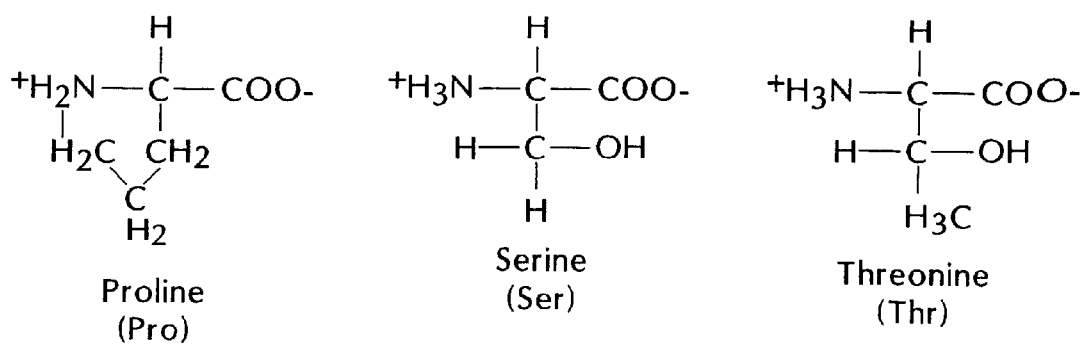
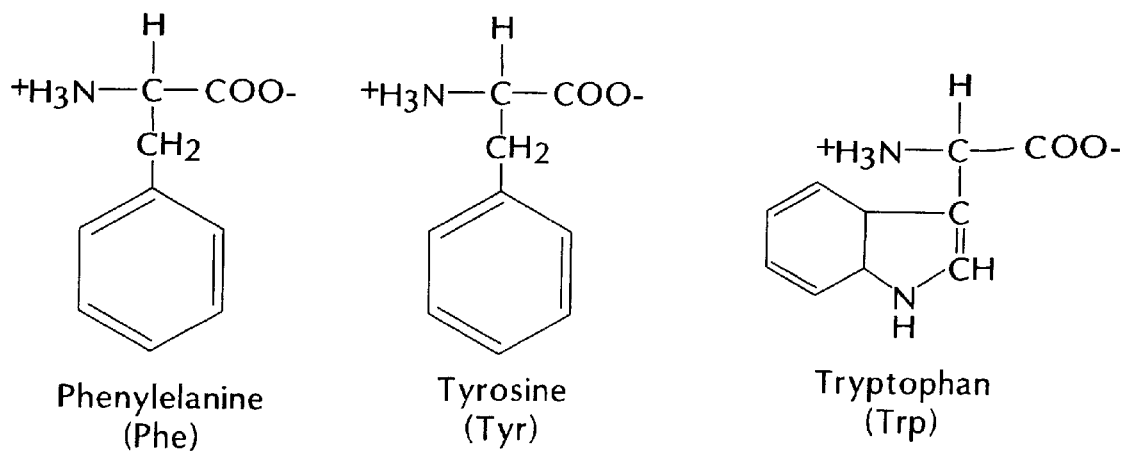

SYNTHASES

CROSS REFERENCE TO RELATED APPLICATION

This application is a divisional of and claims priority under 35 U.S.C. §120 to U.S. application No. 09/398,395, filed Sep. 17, 1999, which claims the benefit of U.S. Provisional Application No. 60/150,262, filed Aug. 23, 1999, U.S. Provisional Application No. 60/130,628, filed Apr. 22, 1999, and U.S. Provisional Application No. 60/100,993 filed Sep. 18, 1998.

This work was supported, in part, with funding from NIH (GM54029 and GM07240) and NSF (IBW-94808152). Therefore, the Unites States Federal Government may have certain rights in the invention.

BACKGROUND OF THE INVENTION

Isoprenoid compounds are organic molecules produced by a wide range of organisms (e.g., plants, bacteria, fungi, etc). To date, over 23,000 individual isoprenoid molecules have been characterized with tens to hundreds of new structures identified each year. These molecules can fulfill a variety of roles. For example, monoterpenes can be used as fragrances and flavors. Sesquiterpenes and diterpenes can serve as pheromones, defensive agents, visual pigments, antitumor drugs, and components of signal transduction pathways. Triterpenes can serve important functions as membrane constituents and precursors of steroid hormones and bile acids. Polyprenols function as photoreceptive agents and cofactor side chains, and can also exist as natural polymers.

The diverse molecular compounds produced by the isoprenoid pathway are created from diphosphate esters of monounsaturated isoprene units. Isoprenes are added together in multiples of 2, 3, or 4 by prenyl transferases to make $C_{10}$, $C_{15}$, and $C_{20}$ units, respectively. The $C_{10}$, $C_{15}$, and $C_{20}$ molecules, named geranyl diphosphate (GPP), farnesyl diphosphate (FPP), and geranylgeranyl diphosphate (GGPP), respectively, serve as substrates for terpene synthases.

Terpene synthases catalyze the production of isoprenoid compounds via one of the most complex reactions known in chemistry or biology. In general, terpene synthases are moderately sized enzymes having molecular weights of about 40 to 100 kD. As an enzyme, terpene synthases can be classified as having low to moderate turnover rates coupled with exquisite reaction specificity and preservation of chirality. Turnover comprises binding of substrate to the enzyme, establishment of substrate conformation, conversion of substrate to product and product release. Reactions can be performed in vitro in aqueous solvents, typically require magnesium ions as cofactors, and the resulting products, which are often highly hydrophobic, can be recovered by partitioning into an organic solvent.

Terpene synthase genes are found in a variety of organisms including bacteria, fungi and plants. Swapping regions approximating exons between different terpene synthases has identified functional domains responsible for terminal enzymatic steps. For example, work performed on 4-epi-aristolochene synthase (TEAS) from *Nicotiana tabacum* (tobacco) and *Hyoscyamus muticus vetispiradiene* synthase (HVS) from henbane revealed that exon 4 and exon 6, respectively, were responsible for reaction product specificity. Combining functional domains resulted in novel enzymes capable of synthesizing new reaction products (U.S. Pat. No. 5,824,774).

Studies have led to proposed reaction mechanisms for isoprenoid production; see, e.g., Cane et al., 1985, Bioorg. Chem., 13:246–265; Wheeler and Croteau, 1987, Proc. Natl. Acad. Sci. USA, 84:4856–4859; and Pyun et al., 1994, Arch. Biochem. Biophys., 308:488–496. The studies used substrate analogs and suicide inhibitors (Croteau, 1994, Arch. Biochem. Biophys., 251:777–782; Cane et al., 1995, Biochemistry, 34:2471–2479; and Croteau et al., 1993, Arch. Biochem. Biophys., 307:397–404), as well as chemical-modifying reagents and site-directed mutagenesis in efforts to identify amino acids essential for catalysis (Cane et al., 1995, Biochemistry, 34:2480–2488; Rajaonarivony et al., 1992, Arch. Biochem. Biophys.+296:49–57; and Rajaonarivony et al., 1992, Arch. Biochem. Biophys., 299:77–82). However, these studies have resulted in limited success in defining the active site due to inherent limitations with these techniques.

SUMMARY OF THE INVENTION

The invention describes a method of identifying alpha-carbon atoms found in the active site of a terpene synthase and describes these atoms in three-dimensional space as well as the spatial relationships among them. The present invention also describes R-groups associated with such alpha-carbons and methods of altering these R-groups in order to create novel terpene synthases capable of generating novel reaction products.

Until the invention taught in this present application, the active site of synthase proteins, the amino acid residues located therein, the amino acid residues involved in catalysis, and the configuration of α-carbons and R-groups within the active site have not been known. The current invention now teaches the structure of synthases, as well as provides the means of making and using the information obtained therefrom to develop and produce new and novel synthases having new and novel synthetic capabilities. The data generated using the methods described herein are useful for creation and production of synthase mutants that can use a variety of isoprenoid substrates and produce a variety of isoprenoid products.

In one embodiment, the invention features an isolated terpene synthase having about 20% or greater sequence identity to residues 265 to 535 of SEQ ID NO: 2. Such a synthase comprises nine α-carbons having interatomic distances in Angstroms between the α-carbons that are ±2.3 Angstroms of the interatomic distances shown in Table 6. The center point of each α-carbon is positioned within a sphere having a radius of 2.3 Angstroms. The center point of each such sphere has the structural coordinates given in Table 5. Each α-carbon has an associated R-group, and the synthase has an ordered arrangement of R-groups associated with each alpha-carbon other than the ordered arrangements of R-groups shown in Table 9. The synthase can have about 25% or greater sequence identity to residues 265 to 535 of SEQ ID 2, or about 35% or greater sequence identity to residues 265 to 535 of SEQ ID 2. Such a synthase can catalyse the formation of a terpenoid product from a monoterpene substrate, a sesquiterpene substrate, or a diterpene substrate. The product can be a cyclic terpenoid hydrocarbon or an acyclic terpenoid hydrocarbon. Either type of product can be hydroxylated or non-hydroxylated. The R-group associated with α-carbon 1 can be selected from one of the following groups: the group consisting of Cys, Ser, and Thr, the group consisting of Phe, Tyr and Trp, the group consisting of Pro, Gly, and Ala, the group consisting of Glu and Asp, the group consisting of Met, Ile, Val and Leu, the group consisting of Arg and Lys, and the group consisting of Gln, Asn and His. R-groups associated with α-carbons 2 to 9 can be any amino acid except those having the ordered arrangements of Table 9. Similarly, the R-group associated with each of α-carbons 2–9 can be selected independently from the group consisting of Cys, Ser and Thr, the group consisting of Phe, Tyr and Trp, the group consisting of Pro, Gly, and Ala, the group consisting of Glu and Asp, the group consisting of Met, Ile, Val and Leu, the group consisting of Arg and Lys, and the group consisting of Gln, Asn and His. In these embodiments, R-groups associated with the remaining eight α-carbons except those having the ordered arrangements of Table 9.

In some embodiments, the ordered arrangement of R-groups associated with α-carbons 1 to 9 is Trp, Ile, Thr, Thr, Tyr, Leu, Cys, Thr and Phe, respectively, Ser, Ile, Thr, Thr, Tyr, Leu, Cys, Thr and Tyr, respectively, Trp, Ile, Thr, Thr, Tyr, Leu, Trp, Thr and Tyr, respectively, Ser, Ile, Thr, Thr, Tyr, Leu, Trp, Thr and Tyr, respectively, or Glu, Ile, Thr, Thr, Tyr, Leu, Cys, Thr and Tyr, respectively.

The invention also features a terpene synthase made by aligning the primary amino acid sequence of a preselected terpene synthase polypeptide to the amino acid sequence of residues 265 to 535 of SEQ ID NO: 2, mutating a nucleic acid encoding the preselected polypeptide at one or more codons for nine amino acid residues in a region of the polypeptide primary amino acid sequence having about 20% or greater sequence identity to residues 265 to 535 of SEQ ID NO: 2, the nine residues in the polypeptide aligning with residues 273, 294, 402, 403, 404, 407, 440, 519 and 520 of SEQ ID NO: 2; and expressing the mutated nucleic acid so that a mutated terpene synthase is made.

The invention also features an isolated terpene synthase having about 20% or greater sequence identity to residues 265 to 535 of SEQ ID NO: 2, the synthase comprising sixteen α-carbons having interatomic distances in Angstroms between the α-carbons that are ±2.3 Angstroms of the interatomic distances given in Table 4. The center point of each α-carbon is positioned within a sphere having a radius of 2.3 Angstroms. The center point of each of the spheres has the structural coordinates given in Table 3. Each α-carbon has an associated R-group, and the synthase has an ordered arrangement of R-groups other than the ordered arrangements of R-groups given in Table 8. The synthase can have about 25% or greater sequence identity to residues 265 to 535 of SEQ ID NO: 2, or about 35% or greater sequence identity to residues 265 to 535 of SEQ ID NO: 2. The synthase can catalyse the formation of a terpenoid product from a monoterpene substrate, a sesquiterpene substrate, or a diterpene substrate. The product can be, for example, a cyclic terpenoid hydrocarbon. The ordered arrangement of R-groups in the synthase associated with α-carbons 1 to 16 can be Cys, Trp, Ile, Ile, Ser, Thr, Thr, Tyr, Leu, Cys, Val, Thr, Tyr, Asp, Phe and Thr, respectively.

The invention also features an isolated terpene synthase having about 20% or greater sequence identity to residues 265 to 535 of SEQ ID NO: 2, the synthase comprising nineteen α-carbons having interatomic distances in Angstroms between the α-carbons that are ±2.3 Angstroms of the interatomic distances given in Table 2. The center point of each α-carbon is positioned within a sphere having a radius of 2.3 Angstroms. The center points of each sphere have the structural coordinates given in Table 1. Each α-carbon has an associated R-group, and the synthase has an ordered arrangement of the R-groups other than the ordered arrangements of R-groups given in Table 7. The synthase can have about 25% or greater sequence identity to residues 265 to 535 of SEQ ID NO: 2, or about 35% or greater sequence identity to residues 265 to 535 of SEQ ID NO: 2. The synthase can catalyse the formation of a terpenoid product from a monoterpene substrate, a sesquiterpene substrate, or a diterpene substrate. The product can be, for example, a cyclic terpenoid hydrocarbon.

The invention also features an isolated protein comprising a first domain having an amino terminal end and a carboxyl terminal end. The first domain comprises amino acids that align structurally in three-dimensional space with a glycosyl hydrolase catalytic core, the glycosyl hydrolase catalytic core selected from the group consisting of amino acids 36 to 230 of glucoamylase protein databank (PDB) code 3GLY of *Aspergillus awamori* and amino acids 36 to 230 of endoglucanase CelD PDB code 1CLC. The isolated protein also comprises a second domain having an amino terminal end and carboxyl terminal end. The second domain comprises amino acids that align structurally in three-dimensional space with avian FPP synthase. The carboxyl terminal end of the first domain is linked to the amino terminal end of the second domain. The second domain has about 20% or greater sequence identity to residues 265 to 535 of SEQ ID NO: 2, and comprises nine α-carbons having interatomic distances in Angstroms between the α-carbons that are ±2.3 Angstroms of the interatomic distances given in Table 6. The center point of each α-carbon is positioned within a sphere having a radius of 2.3 Angstroms, the center point of each sphere having the structural coordinates given in Table 5. Each α-carbon has an associated R-group, and the synthase has an ordered arrangement of R-groups other than the ordered arrangements of R-groups given in Table 9. The protein can have about 25% or greater sequence identity to SEQ ID NO: 2, or about 35% or greater sequence identity to SEQ ID NO: 2. The synthase can catalyse the formation of a terpenoid product from a monoterpene substrate, a sesquiterpene substrate, or a diterpene substrate. The product can be, for example, a cyclic terpenoid hydrocarbon.

The invention also features an isolated synthase having a region with about 40% or greater sequence identity to residues 343 to 606 of SEQ ID NO: 20, wherein one or more amino acid residues of the synthase that align with amino acid residues at positions 348, 351, 372, 375, 376, 454, 479, 480, 481, 482, 485, 519, 523, 597, 600, 601, 605, 607 and 608 of SEQ ID NO: 20 are residues other than amino acids Y, L, C, I, T, Y, S, C, G, H, S, L, G, F, G, Y, D, Y and S, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to residues 316 to 586 of SEQ ID NO: 22, wherein one or more amino acid residues of the synthase that align with amino acid residues at positions 321, 324, 345, 348, 349, 427, 452, 453, 454, 455, 458, 492, 496, 569, 572, 573, 577, 579 and 580 of SEQ ID NO: 22 are residues other than amino acids C, W, N, I, T, Y, S, I, S, G, M, L, D, A, M, L, D, H and G, respectively. In some embodiments, the sequence identity can be about 20% or greater, 25% or greater, or 35% or greater. In some embodiments, one or more ordered arrangements of residues as given in Table 7 are not found in such a synthase.

The invention also features an isolated synthase having a region with about 40% or greater sequence identity to residues 352 to 622 of SEQ ID NO: 58, wherein one or more amino acid residues of the synthase that align with amino acid residues at positions 357, 360, 381, 384, 385, 463, 487, 488, 489, 490, 493, 528, 532, 606, 609, 610, 614, 616 and 617 of SEQ ID NO: 58 are residues other than amino adds Y, M, C, V, T, F, V, S, S, G, I, L, G, F, V, Y, D, Y and T, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to amino acid residues 272 to 540 encoded by SEQ ID NO: 33, wherein one or more amino acid residues of the synthase that align with amino acid residues at positions 277, 280, 301, 304, 305, 383, 408, 409, 410, 411, 414, 448, 452, 524, 527, 528, 532, 534 and 535 encoded by SEQ ID NOS: 33 are residues other than amino adds G, W, I, A, S, Y, T, S, G, Y, L, C, D, M, L, Y. D, Y and T, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to residues 319 to 571 of SEQ ID NO: 42, wherein one or more amino acid residues of the synthase that align with amino acid residues at positions 324, 327, 348, 351, 352, 430, 455, 456, 457, 458, 461, 495, 499, 571, 574, 575, 579, 581 and 582 of SEQ ID NO: 42 are residues other than amino acids I, W, V, I, S, Y, T, T, G, L, V, I, N, T, S, Y, D, Y, and T, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to residues 579 to 847 of SEQ ID NO: 44, wherein one or more amino acid residues of the synthase that align with amino acid residues at positions 584, 587, 606, 609, 610, 688, 713, 714, 715, 716, 719, 753, 757, 831, 834, 835, 839, 841 and 842 of SEQ ID NO: 44 are residues other than amino acids V, S, G, Q, V, Y, S, V, G, L, C, W, N, V, F, Y, D, Y and G, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to residues 495 to 767 of SEQ ID NO: 46, wherein one or more amino acid residues of the synthase that align with amino acid residues at positions 500, 503, 524, 527, 528, 606, 631, 632, 633, 634, 637, 674, 678, 751, 754, 755, 759, 761 and 762 of SEQ ID NO: 46 are residues other than amino acids F, L, A, Q, T, Y, S, I, G, Q, L, S, D, T, I, F, D, F and G, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to residues 295 to 564 of SEQ ID NO: 48, wherein one or more amino add residues of the synthase that align with amino acid residues at positions 300, 303, 324, 327, 328, 406, 431, 432, 433, 434, 437, 471, 475, 548, 551, 552, 556, 558 and 559 of SEQ ID NO: 48 are residues other than amino acids Y, W, A, C, T, Y, S, S, G, M, L, G, D, L, I, Y, D, L and Y, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to residues 307 to 578 of SEQ ID NO: 50, wherein one or more amino acid residues of the synthase that align with amino acid residues at positions 312, 315, 336, 339, 340, 419, 444, 445, 446, 447, 450, 484, 488, 562, 565, 566, 570, 572 and 573 of SEQ ID NO: 50 are residues other than amino acids F, W, A, M, T, Y, N, T, G, M, L, S, D, I, M, Y, D, F and S, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to residues 264 to 533 of SEQ ID NO: 52, wherein one or more amino acid residues of the synthase that align with amino acid residues at positions 269, 272, 293, 296, 297, 375, 401, 402, 403, 404, 407, 441, 445, 517, 520, 521, 525, 527 and 528 of SEQ ID NO: 52 are residues other than amino acids C, W, L, T, S, Y, S, A, G, Y, I, A, N, A, L, Y, D, Y and S, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to residues 585 to 853 of SEQ ID NO: 56, wherein one or more amino acid residues of the synthase that align with amino acid residues at positions 590, 593, 614, 617, 618, 696, 721, 722, 723, 724, 727, 761, 765, 837, 840, 841, 845, 847 and 848 of SEQ ID NO: 56 are residues other than amino acids I, S, S, T, V, Y, S, I, A, L, V, G, N, M, F, Y, D, L and T, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to residues 307 to 574 of SEQ ID NO: 54, wherein one or more amino acid residues of the synthase that align with amino acid residues at positions 312, 315, 336, 339, 340, 418, 443, 444, 445, 446, 449, 483, 487, 560, 563, 564, 566, 568 and 569 of SEQ ID NO: 54 are residues other than amino adds C, W, I, I, T, Y, S, I, S, A, I, L, D, A, I, Y, D, D and G, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to residues 309 to 577 of SEQ ID NO: 24, wherein one or more amino add residues of the synthase that align with amino acid residues at positions 314, 317, 338, 341, 342, 420, 446, 447, 448, 449, 452, 485, 489, 560, 563, 564, 569, 571 and 572 of SEQ ID NO: 24 are residues other than amino acids C, W, N, V, T, Y, I, G, G, I, L, L, D, A, I, Y, D, F and G, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to residues 315 to 584 of SEQ ID NO: 26, wherein one or more amino acid residues of the synthase that align with amino acid residues at positions 320, 323, 344, 347, 348, 426, 451, 452, 453, 454, 457, 492, 496, 568, 571, 572, 576, 578 and 579 of SEQ ID NO: 26 are residues other than amino acids S, W, I, A, T, Y, S, V, A, S, I, L, D, A, I, Y, D, F, and G, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to residues 265 to 536 of SEQ ID NO: 28, wherein one or more amino acid residues of the synthase that align with amino acid residues at positions 270, 273, 294, 297, 298, 376, 401, 402, 403, 404, 407, 440, 444, 518, 521, 522, 528, 530 and 531 of SEQ ID NO: 28 are residues other than amino adds A, W, V, C, G, F, T, S, C, I, M, G, N, C, S, Y, D, Y and S, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to residues 342 to 612 of SEQ ID NO: 30, wherein one or more amino acid residues of the synthase that align with amino acid residues at positions 347, 350, 371, 374, 375, 453, 478, 479, 480, 481, 483, 518, 522, 596, 599, 600, 604, 606 and 607 of SEQ ID NO: 30 are residues other than amino acids F, L, C, V, T, Y, S, S, A, Y, V, L, G, L, L, Y, D, F and S, respectively. In some embodiments, the sequence identity can be about 20% or greater, 25% or greater, or 35% or greater. In some embodiments, one or more of the ordered arrangements of residues as given in Table 7 are not found in such a synthase.

The invention also features an isolated synthase having a region with about 40% or greater sequence identity to residues 273 to 541 of SEQ ID NO: 32, wherein one or more amino acid residues of the synthase that align with amino acid residues at positions 278, 281, 302, 305, 306, 384, 409, 410, 411, 412, 415, 448, 452, 524, 527, 528, 533, 535 and 536 of SEQ ID NO: 32 are residues other than amino acids C, W, I, I, S, Y, T, S, T, Y, L, C, D, I, T, Y, D, Y and T, respectively. In some embodiments, the sequence identity can be about 20% or greater, 25% or greater, or 35% or greater. In some embodiments, one or more ordered arrangements of residues as given in Table 7 are not found in such a synthase.

The invention also features a method for making a terpene synthase, comprising identifying, in a preselected polypeptide having a region with 20% or greater sequence identity to residues 265 to 535 of SEQ ID NO: 2, nine amino acid residues whose α-carbons have interatomic distances in Angstroms between the α-carbons that are ±2.3 Angstroms of the interatomic distances given in Table 6. The center point of each α-carbon is positioned within a sphere having a radius of 2.3 Angstroms. The center point of each sphere has the structural coordinates given in Table 5. The method then comprises synthesizing a polypeptide that is modified from the preselected polypeptide. The modified polypeptide has one or more R-groups associated with the nine α-carbons other than the R-groups associated with the α-carbons in the preselected polypeptide. The synthesizing step can comprise the formation of a nucleic acid encoding the preselected polypeptide in which the coding sequence for one or more amino acids corresponding to the nine α-carbons is replaced by a coding sequence that codes for an amino acid different from the amino acid present in the preselected polypeptide. The preselected polypeptide can be, for example, any one of the polypeptides given in SEQ ID NOS: 2, 4, 6, 8, 10, 12, 20, 22, 24, 26, 28, 30, 32, 34–40, 42, 44, 46, 48, 50, 52, 54, 56, or 58.

The invention also features a method of using a terpene synthase, comprising identifying, in a preselected polypeptide having a region with 20% or greater sequence identity to residues 265 to 535 of SEQ ID NO: 2, amino acid residues at nine positions that align with amino acid residues 273, 294, 402, 403, 404, 407, 440, 519 and 520 of SEQ ID NO: 2; and synthesizing a polypeptide that is modified from the preselected polypeptide. The novel polypeptide is modified by having amino add residues at one or more of the nine positions other than the amino acid residues present in the preselected polypeptide. In some embodiments, the identifying step can comprise identifying sixteen amino acid residues in the preselected polypeptide that align with amino acid residues 270, 273, 294, 297, 298, 402, 403, 404, 407, 440, 516, 519, 520, 525, 527 and 528 of SEQ ID NO: 2, and the synthesizing step can comprise synthesizing a polypeptide that is modified from the preselected polypeptide, the modified polypeptide having amino acid residues at one or more of the sixteen positions other than the amino acid residues present in the preselected polypeptide. In some embodiments, the identifying step can comprise identifying nineteen amino acid residues in the preselected polypeptide that align with amino acid residues 270, 273, 294, 297, 298, 376, 401, 402, 403, 404, 407, 440, 444, 516, 519, 520, 525, 527 and 528 of SEQ ID NO: 2, and the synthesizing step can comprise synthesizing a polypeptide that is modified from the preselected polypeptide, the modified polypeptide having amino acid residues at one or more of the nineteen positions other than the amino acid residues present in the preselected polypeptide. The synthesizing step can comprise the formation of a nucleic acid encoding the preselected polypeptide in which the coding sequence in the nucleic acid coding for one or more of the identified amino acid residues is replaced by a coding sequence that encodes an amino acid different from the amino acid present in the preselected polypeptide. The preselected polypeptide can be, for example, any one of the polypeptides given in SEQ ID NOS: 2, 4, 6, 8, 10, 12, 20, 22, 24, 26 28, 30, 32, 34–40, 42, 44, 46, 48, 50, 52, 54, 56, or 58. The method can further comprise: contacting the modified polypeptide with an isoprenoid substrate under conditions effective for the compound to bind the polypeptide; and measuring the ability of the modified polypeptide to catalyze the formation of a reaction product from the isoprenoid substrate. The isoprenoid substrate can be a monoterpene, a sesquiterpene, or a diterpene.

The invention also features a method of making a terpene synthase, comprising creating a population of nucleic acid molecules that encode polypeptides, the population having members that differ from one another at one or more of nine codons specifying amino acids of a preselected terpene synthase having a region with about 20% or greater sequence identity to residues 265 to 535 of SEQ ID NO: 2, α-carbons of the nine amino acids having interatomic distances in Angstroms between the α-carbons that are ±2.3 Angstroms of the interatomic distances given in Table 6. The center point of each α-carbon is positioned within a sphere having a radius of 2.3 Angstroms, and the center point of each sphere has the structural coordinates given in Table 5. In some embodiments, the codons specify amino acids as described in Tables 1–2 or 3–4 of a preselected terpene synthase. A portion, or all, of the nucleic acid population is expressed so that a population of polypeptides is made. At least one member of the population of polypeptides is a mutant terpene synthase. The expressing step can comprise in vitro transcription and in vitro translation of the nucleic acid population. In some embodiments, the expressing step comprises cloning members of the nucleic acid population into an expression vector, introducing the expression vector into host cells and expressing the cloned nucleic acid population members in the host cells so that the population of polypeptides is made. The preselected terpene synthase polypeptide can be a monoterpene synthase, a sesquiterpene synthase, or a diterpene synthase. The host cells can be prokaryotic cells or eukaryotic cells, including, without limitation, bacterial cells, fungal cells, and animal cells, e.g., mammalian cells or insect cells. The host cells can also be plant cells, e.g., a cell from a Graminaceae plant, a cell from a Legumineae plant, a cell from a Solanaceae plant, a cell from a Brassicaeae plant or a cell from a Conifereae plant.

The invention also features a nucleic acid encoding a synthase as described herein, and a host cell containing such a nucleic acid. The invention also features a transgenic plant containing such a nucleic acid, or a transgenic animal cell culture containing such a nucleic acid.

In some embodiments, a synthase polypeptide of the invention comprises a domain that contains an active site comprised of nine α-carbon atoms having the coordinates of Table 5, and interatomic distances between the α-carbons ±2.3 angstroms of the distances given in Table 5. The α-carbon atoms align structurally in three dimensional space in the presence or absence of bound substrate or substrate analogue, with avian FPP synthase. In another embodiment, a synthase of this invention comprises the following: (i) a first domain containing amino acid residues that align in three-dimensional space (in solution or crystal form, and either having a bound or unbound substrate) with a glycosyl hydrolase catalytic core selected from the group consisting of (a) amino acids 36–230 of glycosyl hydrolase (PDB code 3GLY) of *Aspergillus awarmori*, and (b) amino acids 36–230 of endogluconase CellB (PDB code 1CLC), and (ii) a second domain that aligns structurally in three dimensional space with or without substrate or substrate analogues bound in the active site with avian FPP synthase. The second domain contains an active site comprised of nine, sixteen or nineteen α-carbon atoms having the structural coordinates and interatomic distances of Tables 1–2, 3–4 or 5–6. These α-carbon atoms have R-groups attached thereto that can interact, either directly or indirectly, with an isoprenoid substrate.

The invention also features a method for generating mutant terpene synthases possessing catalytic activity. The method comprises the steps of (a) providing a crystallographic model of a preselected catalytically active terpene synthase having an active site, and (b) using the model to design a terpene synthase having at least one altered R-group in the active site relative to the preselected synthase. The invention also features terpene synthases having altered substrate specificity, methods of making the same, and procedures for generating three-dimensional structures thereof.

Although methods and materials similar or equivalent to those described herein can be used to practice the invention, suitable methods and materials are described below. All publications, patent applications, patents and other references mentioned herein are incorporated by reference in their entirety.

Other aspects, embodiments, advantages, and features of the present invention will become apparent from the specification.

BRIEF DESCRIPTION OF TABLES

Figure 1:
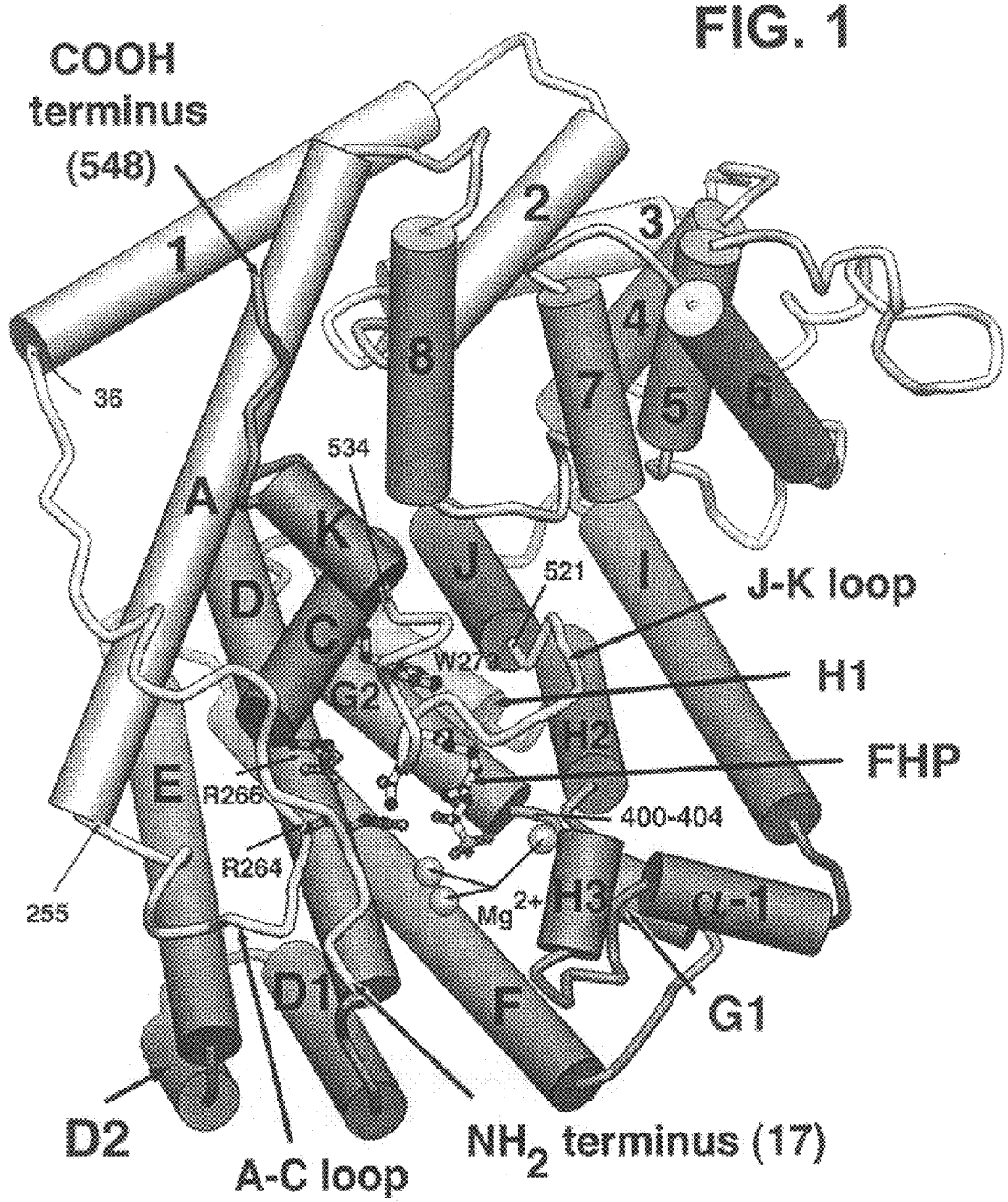
FIG. 1. Schematic representation of tobacco 5-epi-aristolochene synthase (TEAS) with bound farnesyl hydroxyphosphonate (FHP), prepared using the RIBBONS software program of Carson, M. and Bugg, C., J. Mol. Graphics 4:121 (1986). Cylinders 1–8 and A represent α-helices in the $NH_2$-terminal domain; cylinders C, D, D1, D2, E, F, G1, G2, H1, H2, H3, I and α-1 represent α-helices in the COOH-terminal domain.

Table 1. X-ray crystallographic structural coordinates for 19 α-carbons found in the active site of a terpene synthase.

Table 2. Interatomic distances in Angstroms between each α-carbon of Table 1. Each α-carbon occupies a sphere having a radius of 2.3 Angstroms. Interatomic distances are calculated from the center point of each sphere.

Table 3. X-ray crystallographic structural coordinates for 16 α-carbons found in the active site of a terpene synthase.

Table 4. Interatomic distances in Angstroms between each α-carbon of Table 3. Each α-carbon occupies a sphere having a radius of 2.3 Angstroms. Interatomic distances are calculated from the center point of each sphere.

Table 5. X-ray crystallographic structural coordinates for nine α-carbons found in the active site of a terpene synthase.

Table 6. Interatomic distances in Angstroms between each α-carbon of Table 5. Each at α-carbon occupies a sphere having a radius of 2.3 Angstroms. Interatomic distances are calculated from the center point of each sphere.

Table 7. Ordered arrangement of R-groups not found associated with the α-carbons of Table 1.

Table 8. Ordered arrangement of R-groups not found associated with the α-carbons of Table 3.

Table 9. Ordered arrangement of R-groups not found associated with the α-carbons of Table 5.

Table 10. X-ray structural coordinates for TEAS having the substrate analog FHP bound in the active site.

Table 11. X-ray structural coordinates for TEAS in the absence of substrate.

Table 12. Alignment of residues 265–535 of TEAS with a limonene synthase, SEQ ID NO: 22, using the BLASTp alignment program.

Table 13. Alignment of residues 579 to 847 of SEQ ID NO:44 with SEQ ID NO:26, using the BLASTp program.

Table 14. Alignment of residues 265 to 535 of TEAS with SEQ ID NO:48, using the BLASTp program.

Table 15. Alignment of residues 307 to 593 of SEQ ID NO:50 with SEQ ID NO:56 using the BLASTp program.

BRIEF DESCRIPTION OF THE SEQUENCE LISTING

SEQ ID NO:1 is the DNA coding sequence for a tobacco 5-epi-aristolochene synthase (TEAS) protein. Genbank No: Q40577.

SEQ ID NO:2 is the amino acid sequence for the protein encoded by the DNA of SEQ ID NO:1.

SEQ ID NO:3 is the DNA coding sequence for a TEAS protein in which the codon for Trp273 has been changed to a codon for Glu.

SEQ ID NO:4 is the amino acid sequence for the W273E protein encoded by the TEAS DNA of SEQ ID NO:3.

SEQ ID NO:5 is the DNA coding sequence for a TEAS protein in which the codon for Tyr520 has been changed to a codon for Phe.

SEQ ID NO:6 is the amino acid sequence for the Y520F protein encoded by the TEAS DNA of SEQ ID NO:5.

SEQ ID NO:7 is the DNA coding sequence for a TEAS protein in which the codon for Tyr527 has been changed to a codon for Phe.

SEQ ID NO:8 is the amino acid sequence for the Y527F protein encoded by the TEAS DNA of SEQ ID NO:7.

SEQ ID NO:9 is the DNA coding sequence for a TEAS protein in which the codon for Trp273 has been changed to a codon for Ser and the codon for Cys440 has been changed to a codon for Trp.

SEQ ID NO:10 is the amino acid sequence for the W273S/C440W protein encoded by the TEAS DNA of SEQ ID NO:9.

SEQ ID NO:11 is the DNA coding sequence for TEAS proteins in which the codons for Tyr406 and Leu407 have each been changed to the nucleotides NNS.

SEQ ID NO:12 is the amino acid sequence for the population of Y406X/L407X proteins encoded by the TEAS DNA of SEQ ID NO:11, where X is any naturally occurring amino acid.

SEQ ID NO:13 is a DNA primer sequence.
SEQ ID NO:14 is a DNA primer sequence.
SEQ ID NO:15 is a DNA primer sequence.
SEQ ID NO:16 is a DNA primer sequence.
SEQ ID NO:17 is a DNA primer sequence.
SEQ ID NO:18 is a DNA primer sequence.

SEQ ID NO:19 is the DNA coding sequence for a grand fir pinene synthase. Genbank Accession No: U87909.

SEQ ID NO:20 is the amino acid sequence for the protein encoded by the DNA of SEQ ID NO:19.

SEQ ID NO:21 is the DNA coding sequence for a spearmint limonene synthase. Genbank Accession No: L13459.

SEQ ID NO:22 is the amino acid sequence for the protein encoded by the DNA of SEQ ID NO:21.

SEQ ID NO:23 is the DNA coding sequence for a sage 1, 8 cineole synthase. Genbank Accession No: AF051899.

SEQ ID NO:24 is the amino acid sequence for the protein encoded by the DNA of SEQ ID NO:23.

SEQ ID NO:25 is the DNA coding sequence for a sage bornyl diphosphate synthase. Genbank Accession No: AF051900.

SEQ ID NO:26 is the amino acid sequence for the protein encoded by the DNA of SEQ ID NO:25.

SEQ ID NO:27 is the DNA coding sequence for a mint E-b-farnesene synthase. Genbank Accession No: AF024615.

SEQ ID NO:28 is the amino acid sequence for the protein encoded by the DNA of SEQ ID NO:27.

SEQ ID NO:29 is the DNA coding sequence for a grand fir myrcene synthase. Genbank Accession No: U87908.

SEQ ID NO:30 is the amino acid sequence for the protein encoded by the DNA of SEQ ID NO:29.

SEQ ID NO:31 is the DNA coding sequence for a potato vetaspiradiene synthase. Genbank Accession No: AB022598.

SEQ ID NO:32 is the amino acid sequence for the protein encoded by the DNA of SEQ ID NO:31.

SEQ ID NO:33 is the genomic DNA coding sequence for a cotton delta-cadinene synthase. Genbank Accession No: Y18484.

SEQ ID NOS:34–40 are the amino acid sequences for the exons encoded by the DNA of SEQ ID NO:33.

SEQ ID NO:41 is the DNA coding sequence for a castor bean casbene synthase. Genbank Accession No: L32134.

SEQ ID NO:42 is the amino acid sequence for the protein encoded by the DNA of SEQ ID NO:41.

SEQ ID NO:43 is the DNA coding sequence for a yew taxadiene synthase. Genbank Accession No: U48796.

SEQ ID NO:44 is the amino acid sequence for the protein encoded by the DNA of SEQ ID NO:43.

SEQ ID NO:45 is the DNA coding sequence for a grand fir E-alpha-bisabolene synthase. Genbank Accession No: AF006194.

SEQ ID NO:46 is the amino acid sequence for the protein encoded by the DNA of SEQ ID NO:45.

SEQ ID NO:47 is the DNA coding sequence for a grand fir delta-selinene synthase. Genbank Accession No: U92266.

SEQ ID NO:48 is the amino acid sequence for the protein encoded by the DNA of SEQ ID NO:47.

SEQ ID NO:49 is the DNA coding sequence for a grand fir gamma-humulene synthase. Genbank Accession No: U92267.

SEQ ID NO:50 is the amino acid sequence for the protein encoded by the DNA of SEQ ID NO:49.

SEQ ID NO:51 is the DNA coding sequence for a tomato germacrene C synthase. Genbank Accession No: AF035631.

SEQ ID NO:52 is the amino acid sequence for the protein encoded by the DNA of SEQ ID NO:51.

SEQ ID NO:53 is the DNA coding sequence for a sage+sabinene synthase. Genbank Accession No: AF051901.

SEQ ID NO:54 is the amino acid sequence for the protein encoded by the DNA of SEQ ID NO:53.

SEQ ID NO:55 is the DNA coding sequence for a grand fir abietadiene synthase. Genbank Accession No: U50768.

SEQ ID NO:56 is the amino acid sequence for the protein encoded by the DNA of SEQ ID NO:55.

SEQ ID NO:57 is the DNA coding sequence for a grand fir limonene synthase. Genbank Accession No: AF006193.

SEQ ID NO:58 is the amino acid sequence for the protein encoded by the DNA of SEQ ID NO:57.

DETAILED DESCRIPTION

The following terms are used herein:

"α-carbon" refers to the chiral carbon atom found in an amino acid residue. Four substituents are covalently bound to the α-carbon, including an amino group, a carboxyl group, a hydrogen atom, and an R-group.

Figure 2:
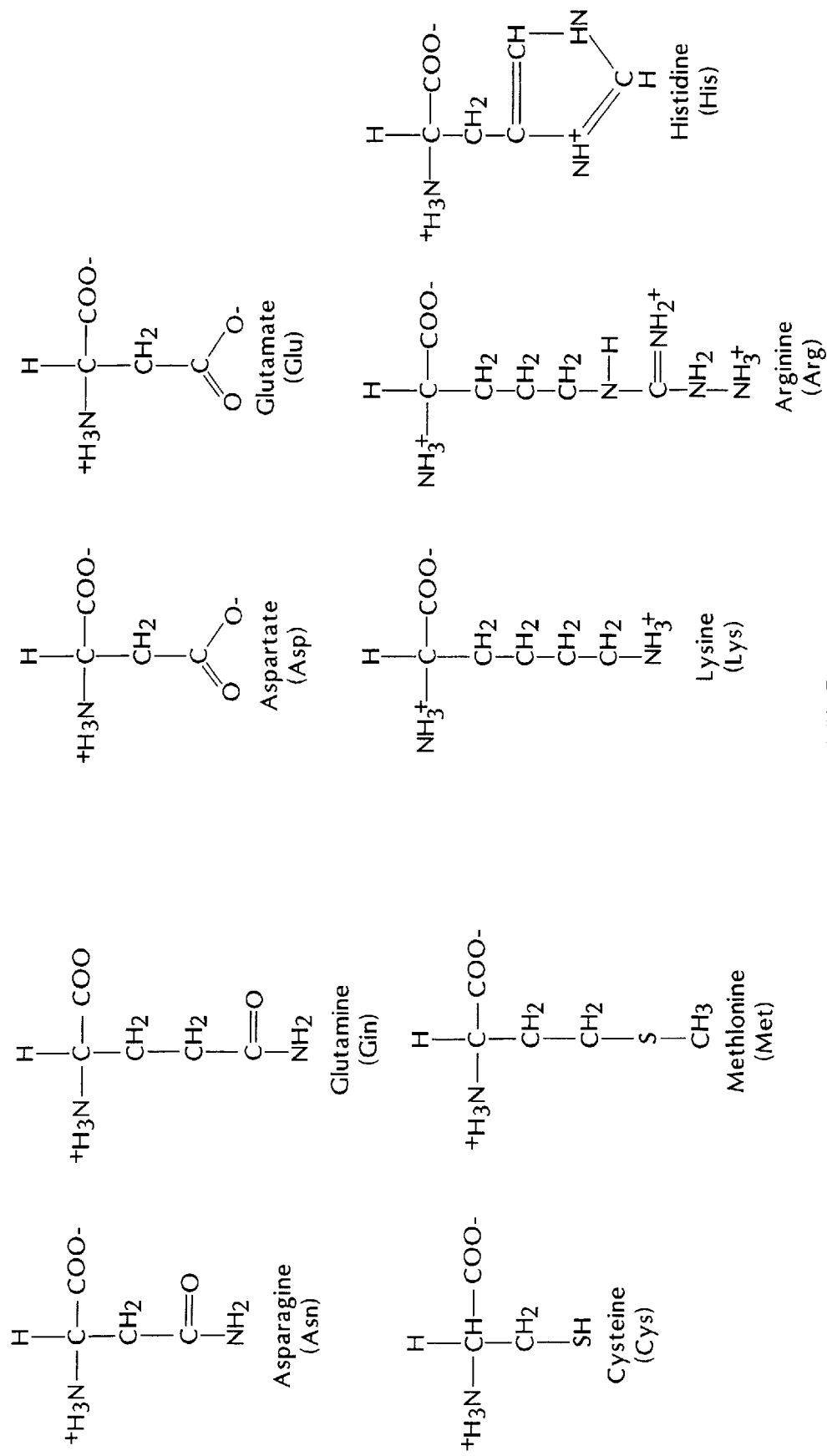
FIG. 2. Structure of twenty natural amino acids showing α-carbons and associated R-groups.

"R-group" refers to a substituent attached to the α-carbon of an amino acid residue that is not involved in peptide bond formation in a protein. An R-group is an important determinant of the overall chemical character of an amino acid. The twenty naturally occurring amino acids found in proteins and the R-groups associated with the α-carbon of each amino acid are listed in FIG. 2. The three-letter and one-letter abbreviations for naturally occurring amino acids are sometimes used herein to refer to the R-group associated with a particular amino add.

"Naturally occurring amino acid" includes L-isomers of the twenty amino acids naturally occurring in proteins. Naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, and lysine. Unless specially indicated, all amino acids referred to in this application are in the L-form. Three-letter and one-letter abbreviations are sometimes used herein to refer to naturally occurring amino acids. These abbreviations are known in the art.

"Unnatural amino acid" includes amino acids that are not naturally found in proteins. Examples of unnatural amino acids included herein are racemic mixtures of selenocysteine and selenomethionine. In addition, unnatural amino acids include the D or L forms of norleucine, para-nitrophenylalanine, homophenylalanine, para-fluorophenylalanine, 3-amino-2-benzylpropionic acid, homoarginine, D-phenylalanine, and the like.

"Positively charged amino acid" includes any naturally occurring or unnatural amino acid having an R-group that carries a positive charge under normal physiological conditions. Examples of positively charged, naturally occurring amino acids include arginine and lysine.

"Negatively charged amino acid" includes any naturally occurring or unnatural amino acid having an R-group that carries a negative charge under normal physiological conditions. Examples of negatively charged, naturally occurring amino acids include aspartic acid and glutamic acid.

"Hydrophobic amino acid" includes any naturally occurring or unnatural amino acid having an uncharged, nonpolar side chain under normal physiological conditions. Examples of naturally occurring hydrophobic amino acids are leucine, isoleucine, valine and methionine.

"Hydrophilic amino acid" includes any naturally occurring or unnatural amino acid having a charged polar side chain. Examples of naturally occurring hydrophilic amino acids include serine, threonine and cysteine.

"Mutant terpene synthase" or "mutated terpene synthase" refers to a synthase polypeptide having a primary amino acid sequence. The center point of the α-carbon of nine residues of the polypeptide is positioned within a sphere having a radius of 2.3 Angstroms; the center points of the nine spheres have the structural coordinates of Table 5 or coordinates which can be rotated and/or translated to coincide with the coordinates of Table 5. The relative interatomic distances between the nine α-carbons is ±2.3 angstroms of the interatomic distances given in Table 6. Each α-carbon has an associated R-group. A mutant synthase differs from a non-mutant synthase in the ordered arrangement of R-groups associated with the nine α-carbons. A mutant synthase has an ordered arrangement of R-groups on the nine α-carbons other than the ordered arrangements of R-groups listed in Table 9. R-groups associated with other α-carbons of the synthase primary amino acid sequence may or may not be the same as in a non-mutated synthase.

In some embodiments, a mutant synthase refers to a synthase in which the center point of the α-carbon of sixteen residues of the polypeptide is positioned within a sphere having a radius of 2.3 Angstroms; the center points of the sixteen spheres have the structural coordinates of Table 3 or coordinates which can be rotated and/or translated to coincide with the coordinates of Table 3. The relative interatomic distances between the nine α-carbons is ±2.3 angstroms of the interatomic distances given in Table 4. Each α-carbon has an associated R-group. A mutant synthase differs from a non-mutant synthase in the ordered arrangement of R-groups associated with the sixteen α-carbons. A mutant synthase has an ordered arrangement of R-groups on the sixteen α-carbons other than the ordered arrangements of R-groups listed in Table 8. R-groups associated with other α-carbons of the synthase primary amino acid sequence may or may not be the same as in a non-mutated synthase.

In some embodiments, a mutant synthase refers to a synthase in which the center point of the α-carbon of nineteen residues of the polypeptide is positioned within a sphere having a radius of 2.3 Angstroms; the center points of the nineteen spheres have the three dimensional coordinates of Table 1 or coordinates which can be rotated and/or translated to coincide with the coordinates of Table 1. The relative interatomic distances between the nineteen α-carbons is ±2.3 angstroms of the interatomic distances given in Table 2. Each α-carbon has an associated R-group. A mutant synthase differs from a non-mutant synthase in the ordered arrangement of R-groups associated with the nineteen α-carbons. A mutant synthase has an ordered arrangement of R-groups on the nineteen α-carbons other than the ordered arrangements of R-groups listed in Table 7. R-groups associated with other α-carbons of the synthase primary amino acid sequence may or may not be the same as in a non-mutated synthase.

"Nonmutated synthase" or "non-mutant synthase" includes a synthase having a primary amino acid sequence comprising nine, sixteen, or nineteen amino acid residues. The center point of each α-carbon of these residues is positioned within a sphere having a radius of 2.3 Angstroms; the center points of the spheres have the three dimensional coordinates of Tables 5, 3, or 1, respectively, or coordinates which can be rotated and/or translated to coincide with the coordinates of Tables 5, 3, or 1. The relative interatomic distances between the nine, sixteen, or nineteen α-carbons is ±2.3 angstroms of the interatomic distances given in Tables 6, 4, or 2, respectively. Each α-carbon has an associated R-group. A non-mutant synthase has an ordered arrangement of R-groups on the nine, sixteen, or nineteen α-carbons as listed in Tables 9, 8, or 7, respectively.

"Degenerate variations thereof" refers to variants of a gene coding sequence by which the same polypeptide is encoded by different nucleotide sequences, due to the degeneracy of the genetic code. For example, synthases of the present invention have a primary amino acid sequence. Degenerate synthase variations are different nucleic acid coding sequences that nevertheless encode the same primary amino acid sequence due to the degeneracy of the genetic code.

"Expression" refers to transcription of a gene or nucleic acid molecule and the translation of that nucleic acid into a polypeptide. Expression of genes also involves processing of RNA into mRNA in eukaryotic systems. It is not necessary for the genes to integrate into the genome of a cell in order to achieve expression. This definition is not limited to expression in a particular system or a particular cell type and includes, without limitation, stable, transient, in vitro, and in vivo expression.

"Promoter" and "promoter regulatory element", refers to a nucleic acid that is involved in controlling expression of a gene. Promoter regulatory elements, and the like, from a variety of sources can be used efficiently to promote gene expression. Promoter regulatory elements include constitutive, tissue-specific, developmental-specific, inducible, subgenomic promoters, and the like. Promoter regulatory elements may also include certain enhancer elements or silencing elements that improve or regulate transcriptional efficiency.

"Active Site" refers to a site in a terpene synthase that binds the hydrophobic portion of a terpene substrate, GPP, FPP, and/or GGPP. The active site can, under certain conditions, catalyze a biosynthetic reaction that allows one or more reaction products to be produced.

"Altered enzymatic specificity" includes an alteration in the ability of a mutant synthase to use a particular terpene substrate or a change in the profile of reaction product(s) from a mutant synthase, compared to the substrate specificity of and the reaction products made by a corresponding non-mutated synthase. Altered specificity may include the ability of a synthase to exhibit different enzymatic parameters relative to a non-mutated synthase (Km, Vmax, etc), and/or to produce products that are different from those that are produced by a corresponding non-mutant synthase.

"Structure coordinates" or "structural coordinates" refers to Cartesian coordinates (x, y, and z positions) derived from mathematical equations involving Fourier synthesis as determined from patterns obtained via diffraction of a monochromatic beam of X-rays by the atoms (scattering centers) of a synthase molecule in crystal form. Diffraction data are used to calculate electron density maps of repeating protein units in the crystal (unit cell). Electron density maps are used to establish the positions of individual atoms within a crystal's unit cell. The absolute values for structural coordinates listed herein convey relative spatial relationships between atoms because the absolute values ascribed to structural coordinates can be changed by rotational and/or translational movement along the x, y and/or z axes, together or separately, while maintaining the same relative spatial relationships among atoms. Thus, a terpene synthase whose absolute values for a set of structural coordinates can be rotationally or translationally adjusted to coincide with the particular values listed in Tables 1, 3, or 5 is considered to have the same structural coordinates as those of Tables 1, 3 or 5. An example of structural coordinates that coincide with the absolute values listed herein after rotation and/or translation are the coordinates of Table 11.

"Heavy atom derivatization" refers to a method of producing a chemically modified form of a synthase crystal. in practice, a crystal is soaked in a solution containing heavy atom salts or organometallic compounds, e.g., lead chloride, gold thiomalate, thimerosal, uranyl acetate and the like, which can diffuse through the crystal and bind to the protein's surface. Locations of the bound heavy atoms can be determined by X-ray diffraction analysis of the soaked crystal. The information is then used to construct phase information which can then be used to construct three-dimensional structures of the enzyme as described in Blundel, T. L., and Johnson, N. L., Protein Crystallography, Academic Press (1976).

"Unit cell" refers to a basic parallelepiped shaped block. Regular assembly of such blocks may construct the entire volume of a crystal. Each unit cell comprises a complete representation of the unit pattern, the repetition of which builds up the crystal.

"Mutagenesis" refers to the substitution of a different amino acid residue at a particular position in the primary amino acid sequence of a protein, thereby changing the R-group present at that position. Mutagenesis can be most easily performed by changing the coding sequence of a nucleic acid encoding the protein so that the coding sequence in the nucleic acid specifies an amino acid residue different from the residue initially present at that position.

"Space Group" refers to the arrangement of symmetry elements within a crystal.

"Molecular replacement" refers to the generation of a preliminary model of a synthase whose structural coordinates are unknown, by orienting and positioning a molecule whose structural coordinates are known within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This in turn can be subject to any of the several forms of refinement to provide a final, accurate structure of the unknown crystal (Lattman, E., 1985, in Methods in Enzymology, 115:55–77; Rossmann, MG., ed., "The Molecular Replacement Method" 1972, Int. Sci. Rev. Ser., No. 13, Gordon & Breach, New York). Using structure coordinates and interatomic distance matrices, molecular replacement may be used to determine the structural coordinates of a crystalline mutant, homologue, or a different crystal form of terpene synthase.

"Recombinant protein" includes a protein that is chemically synthesized or derived biosynthetically from an isolated gene.

"Gene" includes naturally derived or genetically manipulated nucleic acids that contain the information needed to produce a polypeptide.

"Nucleic acid" includes any genetic material comprised of the nucleotides guanine, adenine, thymine, cytosine, uracil, inosine and the like. Nucleic acids may be single-, double-, or triple stranded. Nucleic acids may be deoxyribonucleic acid or ribonucleic acid.

"Genetically manipulated" includes genes that have been modified to contain a different nucleotide sequence from that present in a preselected nulceic acid. Genes can be manipulated by synthetically or via traditional cloning, PCR, chemical gene synthesis, direct or random mutagenesis, and gene shuffling. Genetically manipulated also includes the process of making genes that are degenerate variations of nucleic acids encoding preselected proteins.

"First domain" includes polypeptides having a first and second end wherein the first end can have an amino terminal amino acid with a free amino group and can be linked by a peptide bond to a second amino add. The first end may also be modified through acetylation and the like. The second end of the first domain may or may not have a free carboxyl terminal group.

"Second domain" includes polypeptides having a first and second end wherein the first end can have an amino terminal amino acid and can be linked by a peptide bond to a second amino acid. The second end of the second domain may or may not have a carboxyl terminal group. Typically, the first end of the second domain is linked to the second end of the first domain via a peptide bond.

"Isoprenoid substrate" refers to the $C_{10}$, $C_{15}$, and $C_{20}$ molecules, named geranyl diphosphate (GPP), farnesyl diphosphate (FPP), and geranylgeranyl diphosphate (GGPP), respectively.

"Sequence identity" or "percent sequence identity" refers to the percentage of amino acids or nucleotides that occupy the same relative position when two protein sequences or nucleic acid sequences, a query sequence and a subject sequence, are aligned. The number of amino acid or nucleotide residues that are identical between both the subject and query sequences are counted, divided by the number of residues in the query sequence, and multiplied by 100. The process is repeated until the alignment resulting in the highest percent sequence identity is found. Percent sequence identity can be determined by visual inspection and/or by using various computer programs, e.g., MegAlign (DNASTAR, Inc., Madison, Wis.) or BLAST programs available on the world wide web from the National Center for Biotechnology Information (NCBI). Gaps of one or more residues may sometimes be inserted to maximize sequence alignments to structurally conserved domains of the query sequence, i.e., α-helices, β-sheets and loops.

"Monoterpene product" refers to linear, cyclized, and/or hydroxylated reaction products made from the substrate GPP. "Sesquiterpene produce refers to linear, cyclized, and/or hydroxylated reaction products made from the substrate FPP.

"Diterpene product" refers to linear, cyclized, avid/or hydroxylated reaction products made from the substrate GGPP.

The present invention relates to terpene synthases and mutants thereof from which the position of specific α-carbon atoms and R-groups associated therewith comprising the active site can be determined in three-dimensional space. The invention also relates to structural coordinates of the synthases, use of the structural coordinates to develop structural information related to synthase homologues, mutants, and the like, and to crystal forms of such synthases. Furthermore, the invention provides a method whereby α-carbon structural coordinates for atoms comprising the active site of a preselected terpene synthase can be used to develop synthases in which R-groups associated with active site α-carbon atoms are different from the R-groups found in the preselected terpene synthase. In addition, the present invention provides for the production of novel terpene synthases based on the structural information provided herein and for the use of such synthases to make a variety of isoprenoid compounds.

The present invention further provides, for the first time, crystals of a synthase, as exemplified by tobacco 5epi-aristolochene synthase (TEAS), which are grown in the presence or absence of substrate and substrate analogues, thus allowing definition of the structural coordinates associated therewith. The structural coordinates allow determination of the carbon atoms comprising the active site and R-groups associated therewith. The crystals of the present invention belong to the tetragonal space group $P4_12_12$; the unit cell dimensions vary by a few angstroms between crystals but on average a=126 angstroms, c=122 angstroms, a=b, α=90°, β=90°, and γ=90°.

Structural coordinates are preferably obtained at a resolution of about 2.2 to about 2.8 angstroms for a synthase in the presence and in the absence of bound substrate or substrate analog. Coordinates for a synthase with a substrate analog bound in the active site are given in Table 10. Coordinates for a synthase in the absence of a substrate analog bound in the active site are given in Table 11. Those skilled in the art understand that a set of structure coordinates determined by X-ray crystallography is not without standard error. Therefore, for the purpose of this invention, any set of structure coordinates wherein the active site α-carbons of a synthase, synthase homologue, or mutants thereof, have a root mean square deviation less than ±2.3 angstroms when superimposed using the structural coordinates listed in Table 1, 3, or 5, are considered identical.

A schematic representation of the three-dimensional shape of a synthase is shown in FIG. 1 which was prepared by RIBBONS (Carson and Bugg, 1986, J. Mol. Graphics, 4:121). The synthase shown in FIG. 1 consists entirely of α-helices and short connecting loops and turns, organized into first and second structural domains.

In one embodiment, an isolated synthase of the invention comprises sixteen active site α-carbons having the structural coordinates of Table 3 and the relative distances ±2.3 angstroms of the distances given in Table 4. The active site α-carbons of Table 3 generally are not all contiguous, i.e., are not adjacent to one another in the primary amino acid sequence of a synthase, due to intervening amino acid residues between various active site α-carbons. On the other hand, it should be appreciated that some of the active site α-carbons can be adjacent to one another in some instances. In the embodiment depicted in the TEAS Y527F protein (SEQ ID NO:8), for example, active site α-carbons are adjacent to one another in the primary amino acid sequence at positions 402, 403 and 404, respectively, whereas active site α-carbons at residues 273 and 294 are separated and thus are not adjacent. Thus, the numbering of active site α-carbons given in Tables 1, 2, 3, 4, 5, or 6 is merely for convenience and such α-carbons may reside at any position in the primary amino acid sequence that achieves the structural coordinates given in Tables 1, 3, or 5 and the relative interatomic distances ±2.3 angstroms given in Tables 2, 4, or 6.

An appropriate combination of R-groups, linked to active site α-carbons, can facilitate the formation of one or more desired reaction products. The combination of R-groups selected for use in a terpene synthase of the invention can be any combination other than the ordered arrangements of R-groups and corresponding active site α-carbons shown in Tables 7, 8, or 9. An illustrative example of a suitable arrangement of R-groups and α-carbons is Cys, Trp, Ile, Ile, Ser, Thr, Thr, Tyr, Leu, Cys, Val, Thr, Phe, Asp, Tyr and Thr, associated with active site α-carbons 1 to 16, respectively, of Table 3. Another example of a suitable arrangement of R-groups and α-carbons is Cys, Trp, Ile, Ile, Ser, Thr, Thr, Tyr, Leu, Cys, Val, Thr, Tyr, Asp, Phe, and Thr at active site alpha-carbons 1 to 16, respectively, of Table 3. In some embodiments, a synthase of the invention may have primary amino acid sequences as listed in SEQ ID NO:4, SEQ ID NO:6, SEQ ID NO:8, and SEQ ID NO:10, DNA molecules encoding the same, which are listed in SEQ ID NO:3, SEQ ID NO:5, SEQ ID NO:7, and SEQ ID NO:9, respectively, and degenerate variations thereof. Typically, R-groups found on active site α-carbons are those found in naturally occurring amino acids. See, e.g., FIG. 2. In some embodiments, however, R-groups other than naturally occurring amino acids can be used.

Some arrangements of R-groups and active site α-carbons result in mutant terpene synthases that form reaction products. Such enzymatically active synthases and their corresponding genes are useful to make known terpenoid hydrocarbons, e.g., monoterpenes such as pinene, sesquiterpenes such as delta-cadinene and diterpenes such as abietadiene. Other enzymatically active synthases can be used to make novel terpenoid products.

Some arrangements of R-groups and active site α-carbons may result in mutant terpene synthases that do not form reaction product(s) at a desired rate. Such synthases and their genes are useful as controls in analyses of product formation by enzymatically active mutant synthases. Such synthases and their genes can also be useful in analyses of translation of enzymatically active mutant synthase genes, or as nutritional supplements. Such synthases can be attached to Sepharose beads and used for affinity purification of isoprenoid compounds from crude preparations. In addition, such synthases and their genes can also be useful to develop reagents for various purposes, e.g., immunological reagents to monitor expression of a terpene synthase protein or nucleic add probes or primers to monitor inheritance of a terpene synthase gene in a plant breeding program.

In some embodiments, the α-carbon backbone of a synthase first domain aligns structurally with the catalytic core of glycosyl hydrolases, as exemplified by glucoamylase (Brookhaven Protein Database (PDB) code 3GLY) from *Aspergillus awamori* (Aleshin et al., 1994, J. Mol. Biol., 238:575) and endoglucanase CelD (PDB code ICLC) from *Clostridium thermocelum* (Juy et al., 1992, Nature, 357:89), and the α-carbon backbone of a synthase second domain, which contains the active site, aligns structurally with avian farnesyl diphosphate synthase (FPS), wherein the active site is comprised of 9, 16, or 19 amino acid residues with α-carbon structural coordinates as listed in Tables 1, 3, or 5 and interatomic distances as described in Tables 2, 4, or 6. Such α-carbons have an ordered arrangement of R-groups different from that observed in a non-mutated synthase.

In the present invention, the first domain forms a twisted α-barrel made up of eight short (10 to 15 amino acid residues) helices surrounding a surface cavity filled by ordered water molecules when hydrated. The second domain comprises a two-layered barrel of α-helices surrounding a hydrophobic and aromatic-rich active site pocket. Typically, the second domain contains a substrate binding site. As exemplified in FIG. 1, helix H is disrupted between segments H1 and H2 by an amino acid such as proline, but its interhelical packing with helix G is accommodated by a corresponding kink in helix G between G1 and G2. Within this kink, hydrogen bonds between a hydroxyl group, such as that found on a threonine, and the carbonyl oxygen of other amino acids disrupt the main chain intrahelical hydrogen bonding of helix G thus assisting in producing the structure as determined.

As exemplified by TEAS, terpene synthases of the present invention can have a first domain segment comprising helices A and C (an A-C loop), and a second domain comprising helices J and K (a J-K loop) (FIG. 1). The ordering of these loops upon substrate binding results in a closed, solvent-inaccessible active site pocket. As the J-K loop becomes ordered, a lid-type structure is formed that clamps down over the active site entrance in the presence of substrate and an extended aromatic patch deep within the active site pocket is formed. As the A-C loop becomes ordered, it translates inward toward the active site, positioning certain R groups in this loop at or near the active site. Thus, substrate binding to the active site results in a change in protein conformation.

To identify or create mutant terpene synthases, sequence alignments can be performed to locate specific residues and α-carbons in a preselected polypeptide that have the structural coordinates and interatomic distances of Tables 1–2, 3–4 or 5–6. The preselected polypeptide is used as the subject sequence in the alignment, e.g., the full-length primary amino acid sequence, a region 190 residues in length, a region 220 residues in length, or a region 300 residues in length. The alignment can use residues 265 to 535 of TEAS (SEQ ID NO: 2), which includes the α-carbons of Tables 1, 3 or 5, as the query sequence to align with the preselected polypeptide. The preselected polypeptide and the query sequence can be aligned using the BLASTp 2.0.9 computer program with a BLOSUM 62 scoring matrix, an expect value of 10, a gap open value of 11, an x_dropoff value of 50, a gap extension value of 1, a wordsize of 3 and no filtering of low complexity sequences. As an alternative, the BLASTp 2.0.9 program can be used with a BLOSUM 50 scoring matrix, an expect value of 10, a gap open value 13, an x_dropoff value of 50, a gap extension value of 2, a wordsize of 3 and no filtering of low complexity sequences. Other parameter values can also be used, e.g., a gap extension value from 0 to 4. See Altschul, et al., Nucl. Acids Res. 25:3389–3402.

Regions of the preselected polypeptide with significant sequence identity to residues 265–535 of TEAS, e.g., 20% or greater sequence identity, 25% or greater sequence identity, 35% or greater sequence identity, 40% or greater sequence identity, 50% or greater sequence identity, 60% or greater sequence identity, 70% or greater sequence identity, or 80% or greater sequence identity are examined for specific residues that align with the TEAS residues corresponding to those listed in Tables 1, 3, or 5. In some cases, the output of the computer program alignment identifies a specific residue in the preselected polypeptide for each of the nine, sixteen, or nineteen residues in the query sequence having the structural coordinates and interatomic distances of Tables 1–2, 3–4 or 5–6, with or without gaps introduced by the alignment program. In other cases, a gap is introduced by the alignment program in either the query sequence or the subject sequence such that no direct alignment or a misalignment occurs between one or more of the nine, sixteen, or nineteen residues in the query sequence that are of interest. In either case, the output can be visually inspected, and specific residues can be chosen in the subject sequence after adjusting the alignment so that alpha-helices and beta-sheet regions in the query sequence are maintained and that gaps or insertions in the subject sequence align with loop regions of the query sentence.

Sequence alignments suggest that other terpene synthases have regions with 20% or greater sequence identity to residues 265–535 of TEAS. Therefore, a region of a terpene synthase other than TEAS can be used as the query sequence, e.g., regions of terpene synthases given in SEQ ID NOS: 4, 6, 8, 10, 12, 20, 22, 24, 26, 28, 30, 32, 34–40, 42, 44, 46, 48, 50, 52, 54, 56, or 58, that have significant sequence identity to residues 265–535 of SEQ ID NO: 2. For example, large sequence insertions are present at the amino terminus in taxadiene synthase (SEQ ID NO: 44) with respect to TEAS, or are within solvent-exposed loops in the amino-terminal domain. Thus, regions of taxadiene synthase with greater than 20% sequence identity to SEQ ID NO: 2 are closer to the carboxy-terminal end, e.g., from residue 579 to residue 847 of SEQ ID NO: 44.

Useful regions of other terpene synthases that can be used as the query sequence include, without limitation, residues 343 to 606 of SEQ ID NO: 20, 316 to 586 of SEQ ID NO:

22, residues 352 to 622 of SEQ ID NO: 58, residues 272 to 540 encoded by SEQ ID NO: 33, residues 319 to 571 of SEQ ID NO: 42, residues 579 to 847 of SEQ ID NO: 44, residues 495 to 767 of SEQ ID NO: 46, residues 295 to 564 of SEQ ID NO: 48, residues 307 to 578 of SEQ 10 NO: 50, residues 264 to 533 of SEQ ID NO: 52, residues 585 to 853 of SEQ ID NO: 56, residues 307 to 574 of SEQ ID NO: 54, residues 309 to 577 of SEQ ID NO: 24, residues 315 to 554 of SEQ ID NO: 26, residues 265 to 536 of SEQ ID NO: 28, residues 342 to 612 of SEQ ID NO: 30 and residues 273 to 541 of SEQ ID NO: 32.

One or more of the specific residues in the subject sequence that align with residues in the query sequence are mutated in the preselected polypeptide, e.g, by making mutations in a nucleic acid encoding the polypeptide. The mutant terpene synthase thus created can then be expressed in a host cell and the protein evaluated for enzymatic activity, if desired.

Mutant proteins of the present invention may be prepared in a number of ways including but not limited to oligonucleotide-directed mutagenesis, deletion, chemical mutagenesis, and the like. One or more R-groups associated with the active site α-carbon atoms in a terpene synthase are changed by altering the nucleotide sequence of the corresponding gene. For example, a mutation can be introduced into SEQ ID NO:1, the nucleotide sequence for TEAS, at codons encoding one or more of the following sixteen α-carbons: α-carbon 1=Cys 270; α-carbon 2=Trp 273; α-carbon 3=Ile 294; α-carbon 4=Ile 297; α-carbon 5=Ser298; α-carbon 6=Thr 402; α-carbon 7=Thr 403; α-carbon 8=Tyr 404; α-carbon 9=Leu 407; α-carbon 10=Cys 440; α-carbon 11=Val 516; α-carbon 12=Thr 519; α-carbon 13=Tyr 520; α-carbon 14=Asp 525; α-carbon 15=Tyr 527; or α-carbon 16=Thr 528. The protein encoded by the mutant gene is then produced by expressing the gene in, for example, a bacterial or plant expression system. Alternatively, synthase mutants may be generated by site specific replacement of a particular amino acid with an unnaturally occurring amino acid. As such, synthase mutants may be generated through replacement of an amino acid residue or a particular cysteine or methionine residue with selenocysteine or selenomethionine. This may be achieved by growing a host organism capable of expressing either the wild-type or mutant polypeptide on a growth medium depleted of natural cysteine or methionine or both and growing on medium enriched with either selenocysteine, selenomethionine, or both. These and similar techniques are described in Sambrook et al., (Molecular Cloning, A Laboratory Manual, $2^{nd}$ Ed. (1989) Cold Spring Harbor Laboratory Press).

Another suitable method of creating mutant synthases of the present invention is based on a procedure described in Noel and Tsal (1989) J. Cell. Biochem., 40:309–320. In so doing, the nucleic acid encoding the synthase can be synthetically produced using oligonucleotides having overlapping regions, the oligonucleotides being degenerate at specific bases so that mutations are induced.

According to the present invention, nucleic acid sequences encoding a mutated synthase can be produced by the methods described herein, or any alternative methods available to the skilled artisan. In designing the nucleic acid sequence (gene) of interest, it may be desirable to reengineer the gene for improved expression in a particular expression system. For example. it has been shown that many bacterially derived genes do not express well in plant systems. In some cases, plant-derived genes do not express well in bacteria. This phenomenon may be due to the non-optimal G+C content or A+T content of the gene relative to the expression system being used. For example, the very low G+C content of many bacterial genes results in the generation of sequences mimicking or duplicating plant gene control sequences that are highly A+T rich. The presence of A+T rich sequences within the genes introduced into plants (e.g., TATA box regions normally found in gene promoters) may result in aberrant transcription of the gene(s). In addition, the presence of other regulatory sequences residing in the transcribed mRNA (e.g. polyadenylation signal sequences (AAUAAA) or sequences complementary to small nuclear RNAs involved in pre-mRNA splicing) may lead to RNA instability. Therefore, one goal in the design of genes is to generate nucleic acid sequences that have a G+C content that affords mRNA stability and translation accuracy for a particular expression system.

Due to the plasticity afforded by the redundancy of the genetic code (i.e., some amino acids are specified by more than one codon), evolution of the genomes of different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. Therefore, in reengineering genes for expression, one may wish to determine the codon bias of the organism in which the gene is to be expressed. Looking at the usage of the codons as determined for genes of a particular organism deposited in GenBank can provide this information. After determining the bias thereof, the new gene sequence can be analyzed for restriction enzyme sites as well as other sites that could affect transcription such as exon:intron junctions, polyA addition signals, or RNA polymerase termination signals.

Genes encoding synthases can be placed in an appropriate vector, depending on the artisan's interest, and can be expressed using a suitable expression system. An expression vector, as is well known in the art, typically includes elements that permit replication of said vector within the host cell and may contain one or more phenotypic markers for selection of cells containing said gene. The expression vector will typically contain sequences that control expression such as promoter sequences, ribosome binding sites, and translational initiation and termination sequences. Expression vectors may also contain elements such as subgenomic promoters, a repressor gene or various activator genes. The artisan may also choose to include nucleic acid sequences that result in secretion of the gene product, movement of said product to a particular organelle such as a plant plastid (see U.S. Pat. Nos. 4,762,785; 5,451,513 and 5,545,817), or other sequences that increase the ease of peptide purification, such as an affinity tag.

A wide variety of expression control sequences are useful in expressing mutated synthases when operably linked thereto. Such expression control sequences include, for example, the early and late promoters of SV40 for animal cells, the lac system, the trp system, major operator and promoter systems of phage λ, and the control regions of coat proteins, particularly those from RNA viruses in plants. In *E. coli,* a useful transcriptional control sequence is the T7 RNA polymerase binding promoter, which can be incorporated into a pET vector as described by Studier et al., (1990) Methods Enzymology, 185:60–89.

For expression, a desired gene should be operably linked to the expression control sequence and maintain the appropriate reading frame to permit production of the desired synthase. Any of a wide variety of well-known expression vectors are of use in the present invention. These include, for example, vectors consisting of segments of chromosomal, non-chromosomal and synthetic DNA sequences such as those derived from SV40, bacterial plasmids (including those from *E. coli* such as col E1, pCR1, pBR322 and derivatives thereof, pMB9), wider host range plasmids such as RP4, phage DNA such as phage λ, NM989, M13, and other such systems as described by Sambrook et al., (Molecular Cloning, A Laboratory Manual, $2^{nd}$ Ed. (1989) Cold Spring Harbor Laboratory Press).

A wide variety of host cells are available for expressing synthase mutants of the present invention. Such host cells include, without limitation, bacteria such as *E. coli,* Bacillus and Streptomyces, fungi, yeast, animal cells, plant cells, insect cells, and the like. Preferred embodiments of the present invention include terpene synthase mutants that are expressed in *E. coli* or in plant cells. Said plant cells can either be in suspension culture or a culture on a solid support such as an agar-based medium.

Genes encoding synthases of the present invention can also be expressed in transgenic plant cells. In order to produce transgenic plants, vectors containing a nucleic acid construct encoding a mutant terpene synthase are inserted into the plant genome. Preferably, these recombinant vectors are capable of stable integration into the plant genome. One variable in making a transgenic plant is the choice of a selectable marker gene. A selectable marker gene is used to identify transformed cells against a high background of untransformed cells. Such selectable marker genes include but are not limited to aminoglycoside phosphotransferase gene of transposon Tn5 (Aph II) which encodes resistance to the antibiotics kanamycin, neomycin, and G418, as well as those genes which encode for resistance or tolerance to glyphosate, hygromycin, methotrexate, phosphinothricin, imidazolinones, sulfonylureas, and triazolophyrimidine herbicides, such as chlorosulfuron, bromoxynil, dalapon and the like. In addition to a selectable marker gene, it may be desirable to use a reporter gene. In some instances a reporter gene may be used with a selectable marker. Reporter genes allow the detection of transformed cell and may be used at the discretion of the artisan. A list of these reporter genes is provided in K. Weising et al., 1988, Ann. Rev. Genetics, 22:421.

The genes are expressed either by promoters expressing in all tissues at all times (constitutive promoters), by promoters expressing in specific tissues (tissue-specific promoters), promoters expressing at specific stages of development (developmental promoters), and/or promoter expression in response to a stimulus or stimuli (inducible promoters). The choice of these is at the discretion of the artisan.

Several techniques exist for introducing foreign genes into plant cells, and for obtaining plants that stably maintain and express the introduced gene. Such techniques include acceleration of genetic material coated directly into cells (U.S. Pat. No. 4,945,050). Plant may also be transformed using Agrobacterum technology (U.S. Pat. Nos. 5,177,010, 5,104,310, 5,149,645, 5,469,976, 5,464,763, 4,940,838, 4,693,976, 5,591,616, 5,231,019, 5,463,174, 4,762,785, 5,004,863, and 5,159,135; European Patent Applications 116718, 290799, 320500, 604662, 627752, 0267159, and 0292435. Other transformation technologies include whiskers technology, see U.S. Pat. Nos. 5,302,523 and 5,464,765. Electroporation technology has also been used to transform plants, see WO 87/06614, WO 92109696 and WO 93/21335 and U.S. Pat. Nos. 5,472,869 and 5,384,253. Viral vector expression systems can also be used such as those described in U.S. Pat. Nos. 5,316,931, 5,589,367, 5,811,653, and 5,866,785.

In addition to numerous technologies for transforming plants, the type of tissue that is contacted with the genes of interest may vary as well. Suitable tissue includes, but is not limited to, embryogenic tissue, callus tissue, hypocotyl, meristem and the like. Almost all plant tissues may be transformed during dedifferentiation using the appropriate techniques described herein.

Regardless of the transformation system used, a gene encoding a mutant synthase is preferably incorporated into a gene transfer vector adapted to express said gene in a plant cell by including in the vector an expression control sequence (plant promoter regulatory element). In addition to plant promoter regulatory elements, promoter regulatory elements from a variety of sources can be used efficiently in plant cells to express foreign genes. For example, promoter regulatory elements of bacterial origin. such as the octopine synthase promoter, the nopaline synthase promoter, the mannopine synthase promoter may be used. Promoters of viral origin, such as the cauliflower mosaic virus (35S and 19S) are also desirable. Plant promoter regulatory elements also include, but are not limited to, ribulose-1,6-bisphosphate carboxylase small subunit promoter, beta-conglycinin promoter, phaseolin promoter, ADH promoter, heat-shock promoters, and tissue specific promoters and the like. Numerous promoters are available to skilled artisans for use at their discretion.

It should be understood that not all expression vectors and expression systems function in the same way to express the mutated gene sequences of the present invention. Neither do all host cells function equally well with the same expression system. However, one skilled in the art may make a selection among these vectors, expression control sequences, and host without undue experimentation and without departing from the scope of this invention.

Once a synthase of the present invention is expressed, the protein obtained therefrom can be purified so that structural analysis, modeling, and/or biochemical analysis can be performed, as exemplified herein. The nature of the protein obtained can be dependent on the expression system used. For example, genes, when expressed in mammalian or other eukaryotic cells, may contain latent signal sequences that may result in glycosylation, phosphorylation, or other post-translatonal modifications, which may or may not alter function. Once the proteins are expressed, they can be easily isolated and purified using techniques common to the person having ordinary skill in the art of protein biochemistry and as described in Colligan et al., (1997) Current Protocols in Protein Science, Chanda, V. B., Ed., John Wiley & Sons, Inc. Such techniques often include the use of cation-exchange or anion-exchange chromatography, gel filtration-size exclusion chromatography, and the like. Another technique that may be commonly used is affinity chromatography. Affinity chromatography can include the use of antibodies, substrate analogs, or histidine residues (His-tag technology).

Once purified, mutants of the present invention may be characterized by any of several different properties. For example, such mutants may have altered active site surface charges of one or more charge units. In addition, the mutants may have an altered substrate specificity or spectrum of reaction product relative to a non-mutated synthase.

The present invention allows for the characterization of mutant terpene synthase by crystallization followed by X-ray diffraction. Polypeptide crystallization occurs in solutions where the polypeptide concentration exceeds it solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Compounds known as "precipitants" are often used to decrease the solubility of the polypeptide in a concentrated solution by forming an energetically unfavorable precipitating depleted layer around the polypeptide molecules (Weber, 1991, Advances in Protein Chemistry, 41:1–36). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-20-4 pentanediol, and many of the polyglycols, such as polyethylene glycol.

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, the vessel is sealed and set aside until crystals appear. In the dialysis method, polypeptide is retained in a sealed dialysis membrane that is placed into a solution containing precipitant. Equilibration across the membrane increases the polypeptide and precipitant concentrations thereby causing the polypeptide to reach supersaturation levels.

In the preferred hanging drop technique (McPherson, 1976, J. Biol. Chem., 6300–6306), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant. a crystal of the polypeptide may form.

Another method of crystallization introduces a nucleation site into a concentrated polypeptide solution. Generally, a concentrated polypeptide solution is prepared and a seed crystal of the polypeptide s introduced into this solution. If the concentration of the polypeptide and any precipitants are correct, the seed crystal will provide a nucleation site around which larger crystal forms. In preferred embodiments, the crystals of the present invention are formed in hanging drops with 15% PEG 8000; 200 mM magnesium acetate or magnesium chloride, 100 mM 3-(N-morpholino)-2-hydroxypropanesulfonic acid (pH 7.0), 1 mM dithiothreitol as precipitant.

Some proteins may be recalcitrant to crystallization. However, several techniques are available to the skilled artisan to induce crystallization. The removal of polypeptide segments at the amino or carboxyl terminal end of the protein may facilitate production of crystalline protein samples. Removal of such segments can be done using molecular biology techniques or treatment of the protein with proteases such as trypsin, chymotrypsin, subtilisin. Such procedures can result in the removal of flexible polypeptide segments that may negatively affect crystallization.

The crystals so produced have a wide range of uses. For example, high quality crystals are suitable for X-ray or neutron diffraction analysis to determine the three-dimensional structure of a mutant synthase and to design additional mutants thereof. In addition, crystallization can serve as a further purification method. In some instances, a polypeptide or protein will crystallize from a heterogeneous mixture into crystals. Isolation of such crystals by filtration, centrifugation, etc., followed by redissolving the polypeptide affords a purified solution suitable for use in growing the high-quality crystals needed for diffraction studies. The high-quality crystals may also be dissolved in water and then formulated to provide an aqueous solution having other uses as desired.

Because synthases may crystallize in more than one crystal form, the structural coordinates of (carbons of an active site determined from a synthase or portions thereof, as provided by this invention, are particularly useful to solve the structure of other crystal forms of synthases. The structural coordinates, as provided herein, may also be used to solve the structure of synthases having α-carbons position within the active sites in a manner similar to the wild-type yet having R-groups that may or may not be identical. Furthermore, the structural coordinates disclosed herein may be used to determine the structure of the crystalline form of other proteins with significant amino acid or structural homology to any functional domain of a synthase. One method that may be employed for such purpose is molecular replacement. In this method, the unknown crystal structure, whether it is another crystal form of a synthase, a synthase having a mutated active site, or the crystal of some other protein with significant sequence identity and/or structural homology of a synthase may be determined using the coordinates given in Tables 10 and/or 11. This method provides sufficient structural form for the unknown crystal more efficiently than attempting to determine such information ab initio. In addition, this method can be used to determine whether or not a given synthase in question falls within the scope of this invention.

As further disclosed herein, synthases and mutants thereof may be crystallized in the presence or absence of substrates and substrate analogs. The crystal structures of a series of complexes may then be solved by molecular replacement and compared to that of the wild-type to assist in determination of suitable replacements for R-groups within the active site, thus making synthase mutants according to the present invention.

All mutants of the present inventions may be modeled using the information disclosed herein without necessarily having to crystallize and solve the structure for each and every mutant. For example, one skilled in the art may use one of several specialized computer programs to assist in the process of designing synthases having mutated active sites. Examples of such programs can be as follows: GRID (Goodford, 1985, J. Med. Chem., 28:849–857); MCSS (Miranker and Karplus, 1991, Proteins: Structure, Function and Genetics, 11:29–34); AUTODOCK (Goodsell and Olsen, 1990, Proteins: Structure, Function, and Genetics, 8:195–202); and DOCK (Kuntz et al., 1982, J. Mol. Biol., 161:269–288). In addition, specific computer programs are also available to evaluate specific substrate-active site interactions and the deformation energies and electrostatic interactions resulting therefrom. MODELLER is a computer program often used for homology or comparative modeling of the three-dimensional structure of a protein. A. Sali & T. L. Blundell. J. Mol. Biol. 234, 779–815,1993. A preselected polypeptide sequence to be modeled is aligned with one or more terpene synthases whose crystal structures are known and the MODELLER program is used to calculate a full-atom model, based on optimum satisfaction of spatial restraints. Such restraints can include, inter alia, homologous structures, fluorescence spectroscopy, NMR experiments, or atom-atom potentials of mean force.

The present invention enables synthase mutants to be made and crystal structures thereof to be solved. Moreover, by virtue of the present invention, the location of the active site and the interface of substrate therewith permit the identification of desirable R-groups for mutagenesis. The particular embodiments of this invention are further exemplified in the Examples. However, those skilled in the art will readily appreciate that the specific experiments detailed are only illustrative of the invention as described more fully in the claims, which follow thereafter.

EXAMPLE 1

Generation of Mutant Teas Genes

Construct Generation and Expression.

All mutant enzymes were constructed by the Quick-Change method (Stratagene). Manufacturers instructions were followed, except as noted. Mutations were confirmed by DNA sequencing, and plasmids containing the desired mutation were used to transform BL-21 (DE3) expression cells. Protein was expressed, purified, and stored at –80° C.

TEAS W273S.

The TEAS W273S mutant was generated from a TEAS-pET28b(+) template using the following primers: GTTGAATGCTACTTTTCGGCATTAGGAGTTTAT (sense) (SEQ ID NO:13) and ATAAACTCCTMTGC-CGAAAAGTAGCATTCAAC (antisense) (SEQ ID NO:14). Mutagenesis was carried out according to the manufacturer's instructions, except that sense and antisense strands were generated in separate reactions. For each, 30 plasmid-copying cycles of one minute, annealing at 55" C. and 16 minutes extension at 68° C. were carried out The two reaction mixtures were then combined, heated to 95° C. for 2.5 minutes, and cooled to room temperature before Dpnl treatment.

TEAS C440W

The TEAS C440W mutant was generated from the TEAS-pET28b(+) template using the following primers: GCTAGTGTAATTATATGGCGAGTTATCGATGAC (sense) (SEQ ID NO:15) and GTCATCGATMCTCGC-CATATMTTACACTAGC (antisense) (SEQ ID NO:16).

TEAS W273SIC440W

The TEAS C440WMW273S mutant was constructed from a TEAS W273S-pET28b(+) template using the primers described for generation of TEAS C440W.

TEAS 406/407 Random Library.

For generation of a library of TEAS mutants with random amino acids at positions 406 and 407, two 50 microliter QuickChange reactions were carried out with the TEAS-pET28b(+) template and the primers GCACTAGCAACTACCACATAT-TACNNSNNSGCGACAACATCGTATTTGGGCATG (sense) (SEQ ID NO:17) and CATGCCCAAATACGAT-GTTGTCGCSNNSNNGTAATATGTGG-TAGTTGCTAGTGC (antisense) (SEQ ID NO:18), in which N denotes A, C, G, or T and S denotes C or G.

By this choice of nucleotides, the reaction included primers which coded for all possible amino acid combinations at positions 406 and 407. No adjustment was made for differing numbers of codons among amino acids. In order to ensure efficient reactions, and to minimize the preference for hybridization of wild-type primers to the template, the primers were designed to be longer than those used to generate the mutations described above. In addition, they were HPLC purified prior to use. After 18 cycles of plasmid copying, the reaction was incubated for two hours with Dpnl, ethanol precipitated, and redissolved in 5 microliters water. Each of four 40 microliter aliquots of *E. coli* NovaBlue (Novagen) cells were electroporated with 1.5 microliters of the redissolved DNA. After a recovery period, the cells were plated on kanamycin-LB-agar plates. In order to transfer the newly constructed plasmids to expression cells, the colonies were scraped from all four plates, and used to start an 8 mL culture grown in liquid LB medium at 37° C. for 8 hours. Plasmid purified from this culture was used to transform 20 microliters of competent BL-21 (DE3) cells.

For storage of the constructs, each individual colony was used to inoculate 100 microliters of LB medium containing kanamycin (50 micrograms/mL) in 96-well culture plates. The cells were grown at 37° C. until the $A_{600}$ reached approximately one; 100 microliters of 30% glycerol in LB were then added, and the plates were frozen at –80° C. A set of randomly selected colonies were grown from individual glycerol stocks of some colonies, and plasmids were extracted for sequencing. Approximately 30 percent of the colonies were found to be wild-type. Nucleotide and amino acid sequences for TEAS 406/407 mutant genes and proteins are shown in SEQ ID NOS:11 and 12.

TEAS Y520F

The tyrosine residue at position 520 of SEQ ID NO:2 was changed to a phenylalanine residue by site-directed mutagenesis with primers, in a manner similar to that described above. For Y520F the TAT codon was changed to TTC. The nucleotide sequence of the mutant gene is shown in SEQ ID NO:5.

TEAS Y527F

The tyrosine residue at position 527 of SEQ ID NO:2 was changed to a phenylalanine residue by site-directed mutagenesis with primers, in a manner similar to that described above. For Y527F, the TAC codon at position 527 of the TEAS amino acid sequence was changed to TTC. The nucleotide sequence of the mutant TEAS Y527F gene is shown in SEQ ID No: 7.

TEAS W273E

The tryptophan residue at position 273 of SEQ ID NO:2 was changed to a phenylalanine residue by site-directed mutagenesis with primers, in a manner similar to that described above. For W273E, the TGG codon at position 273 of the TEAS amino acid sequence was changed to GAG. The nucleotide sequence of the mutant gene is shown in SEQ ID NO.:3.

EXAMPLE 2

Expression and Isolation of Synthase Polypeptides

Unless otherwise noted, mutated and non-mutated TEAS proteins were expressed in *Escherichia coli,* purified by metal chelation, anion exchange, and gel filtration chromatography.

Constructs of TEAS and mutant TEAS proteins in the vector pET-28b(+) (Novagen) were expressed in *E. coli* cells. For a typical protein preparation of any of these enzymes, *E. coli* strain BL21 (DE3) cells containing the plasmid construct were grown at 37° C. in 4×1 L terrific broth to an $A_{600}$=1.0. The temperature was dropped to 22° C., and protein expression was induced by adding IPTG to a final concentration of 0.1 mM. After 15–20 h, the cells were harvested by centrifugation, resuspended in 5 mL buffer A (20 mM Tris, 500 mM NaCl, 20 mM imidazole, pH 7.9) per 1 g cells (wet weight), and stirred for 0.5 h at 4° C. The cells were then lysed by sonication, and the resulting lysate was centrifuged for 0.7 h at 82,000× g. The supernatant, containing the protein, was loaded over a 2–3 mL $Ni^{2+}$ chelating histidine affinity column (Qiagen) equilibrated in buffer A, and the column was washed with additional buffer A until the $A_{280}$ of the eluent returned to baseline. The protein was then eluted with a 20–200 mM imidazole gradient in buffer A. Protein-containing fractions were pooled and dialyzed against buffer B (50 mM HEPES, 5 mM MgCl2, 1 mM DTT), then loaded onto an 8 mL MonoQ cation-exchange column (Pharmacia). The column was washed with 20 column volumes buffer B, and the protein was eluted with a 0–500 mM NaCl gradient in buffer B. The resulting protein was further purified by gel filtration on a Superdex-200 column (Pharmacia) in 50 mM Tris, 100 mM NaCl, 5 mM MgCl2, 1 mM DTT, pH 8.0. Purified protein was then dialyzed against 5 mM Tris, 5 mM NaCl, 1 mM DTT, pH 8.0, concentrated to 18–22 mg/mL, and stored at –80° C. in 100° L aliquots until needed.

EXAMPLE 3

Crystallization and Structural Analysis of Synthase Polypeptides

Crystal Growth and Microseeding: All crystallization attempts were carried out by the hanging-drop vapor diffusion method. Concentrated protein was mixed with an equal volume (2–5 uL each) of reservoir solution on a plastic cover slip. The cover slip was then inverted over a well of a plastic 24-well tissue culture plate, containing 0.5–1.0 mL of reservoir solution, ani sealed by a layer of vacuum grease between the well and cover slip. The plates were incubated at 4° C. while the protein concentration in the hanging drop slowly increased by vapor diffusion. Approximately 300 different reservoir solutions, ranging pH 4.5–9 with a variety of precipitants and added salts, were assayed for crystallization of TEAS (SEQ ID NO:2). TEAS crystallized with a reservoir solution of 15% PEG 8000, 100 mM MOPSO (3-[N-morpholino]-2-hydroxypropanesulfonic acid), 200 mM magnesium acetate, 1 mM DTT, pH 6.9–7.3. For microseeding, an existing crystal was crushed in a few uL of precipitant solution, then diluted to 50 microliters. After initial centrifugation to remove large particles, the suspension was serially diluted with additional precipitant solution, and a small volume of a diluted seed stock was added to each new crystallization drop. For macroseeding, crystals which were no longer rapidly growing (usually 2 weeks after drops were set up), were "rinsed" by serially transferring them through two to three drops of reservoir solution. The crystal was then transferred to a fresh drop containing protein and reservoir solution, and equilibrated against a reservoir solution as in the initial growth. Individual crystals varied in their degree of internal order. In some cases, several crystals were screened to identify a well-diffracting crystal with low mosaicity.

Data collection:

Prior to data collection, crystals were transferred to a drop of reservoir solution, or reservoir solution containing a compound to be soaked into the crystal. A small volume of cryoprotectant solution (15% PEG8000, 100 mM MOPSO, 200 mM Mg acetate, 20% ethylene glycol, 1 mM DTT, pH 7) was then added to the drop. After a short equilibration time (1–5 minutes), the crystal was transferred to a drop of cryoprotectant, or cryoprotectant with soaking compound added. After another short equilibration time, the crystal was picked up on a nylon loop, and quickly mounted for data collection in a stream of cold nitrogen gas (90–110K).

The TEAS crystals belonged to the tetragonal space group $P4_12_12$; the unit cell dimensions varied by a few angstroms between crystals, but on average a=126 Å, c=122 Å. The uncomplexed TEAS structure was initially refined to 2.8 Å (Table 11) against data collected from a crystal grown in the presence of 2 mM FHP (Table 10). Electron density at the active site allowed unambiguous modeling of FHP, the A-C and J-K loops, and nine additional residues at the NH, terminus. The refined TEAS-FHP model consisted of residues 17 to 548, three $Mg^2$+ions. 150 water molecules, and one FHP molecule. The three-dimensional coordinates for TEAS in the presence of bound substrate is shown in Table 10. The three-dimensional coordinates for TEAS in the absence of FHP Is shown in Table 11.

Crystals of TEAS complexed with trifluoro-farnesyl diphosphate (F3-FPP) were also prepared. In these crystals, a well-ordered diphosphate binding pocket was also observed. The A-C loop and the NH2-terminal segment exhibited well-defined electron density, the A-C loop was translated toward the active site, and there was strong electron density for the diphosphate moiety of F3-FPP. The hydrophobic pocket, however, remained flexible; the J-K loop and the farnesyl moiety of F3-FPP were disordered.

Homology models were created and energy-minimized using the Swiss PDB viewer interface of the SwissModel program (Peitsch MC (1996), Biochem. Soc. Trans., 24:274279 and Guex N. and Peitsch MC, 1997, Electrophoresis., 18:2714–2723). Active site volumes were calculated with VOIDOO (Kleywegt, G. J., and Jones, T. A., CCP4/ESF-EACBM Newsletter on Protein Crystallography., 29, 26–28, 1993). To make closed active site cavities, the energy-minimized diphosphate moiety from the modeled TEAS cyclase reaction was appended to the residue equivalent to TEAS D301.

TEAS W273S Crystal Structures.

Two TEAS W273S structures, in the presence of FHP, were determined from different crystals; both crystals appeared to be well ordered, as clear main-chain and side-chain density were apparent for residues throughout the protein, including the frequently mobile helices D1, D2, and E. Initial difference electron density maps from both crystals immediately revealed the W273S mutations. The two crystals were designated W273S-1 and W273S-2.

In each structure, the loops surrounding the active site were ordered, resulting in a closed active site pocket. The A/C loop in each structure was translated toward the active site, forming part of its outer rim, as observed in the wild-type TEAS/FHP complex. However, while the J/K loop of W273S-1 adopted the same conformation observed in the wild-type TEAS/FHP complex, the same loop in W273S-2 adopted a different conformation. In this conformation of the J/K loop, Tyr527 moved away from the side chain of residue 273. In addition, Tyr520 and Asp525 were placed distal to the side chain of Asp444. Hydrogen bonds previously observed between the J/K loop, Arg266, and the N-terminal loop were also missing in the W273S-2 structure.

The W273S-2 conformation does not appear to be an effect of the W273S mutation, as it was also observed in a wild-type TEAS crystal soaked with the epi-aristolochene mimic deoxycapsidiol, despite the fact that no electron density was readily apparent for the deoxycapsidiol molecule in that structure. Further, the TEAS active site loops were distant from crystal contacts, and their conformations were not likely to be artifacts of crystal packing. It is possible that at different stages of the TEAS reaction, the enzyme's J/K loop exists in different, defined conformations, and that each of these crystal structures has captured an image of a different conformation. In both W273S structures, residues other than Arg266 and those on the J/K loop did not undergo significant rearrangement from the conformations observed in wild-type TEAS.

In each W273S crystal structure, electron density in the active site suggested that the substrate mimic FHP binds in multiple conformations. Some regions of this density possibly represented bound water molecules in the mutant active site. The presence of water molecules in the mutant active site is consistent with the observation that TEAS W273S gives rise to multiple hydroxylated terpenoid reaction products.

The FHP electron density in each W273S crystal structure was sufficient to suggest that FHP existed in a more extended conformation in the W273S structure, compared to the more tightly folded conformation of FHP in the wild-type TEAS/FHP complex. The observation that the active site of W273S binds multiple conformations of FHP is consistent with the fact that W273S converts FPP to multiple terpenoid hydrocarbon products.

TEAS C440W/W273S: TEAS C440W/W273S crystallized under conditions identical to wild-type TEAS. A 0.3 mm crystal was soaked for 20 minutes in reservoir solution saturated in farnesyl hydroxy phosphate (FHP). After cryoprotection and flash freezing as described for wild-type TEAS, data were collected on a laboratory source with Cu-Kα radiation (MacScience Corp., Japan). A starting model of uncomplexed TEAS (Table 11) (Brookhaven Protein Database Code 5EAT (PDB 5EAT), with waters and magnesiums removed, was positioned against the mutant data with the rigid body module of the software program X-PLOR (A. T. Brunge, X-PLOR Version 3.1—A System for X-Ray Crystallography and NMR Yale University Press, New Haven, 1992, pp. 187–207). Rounds of positional and restrained b-factor refinement with bulk solvent modeling were also carried out in X-PLOR, with manual model building and adjustment carried out in the software program O (Jones, T A, Zou, J Y, Cowan, S W, and Kjeldgaard, M., Acta Cryst. D., 49:148–157, 1993). Additional rounds of refinement and map calculation using the CNS program suite resulted in significantly improved maps; this improvement was likely due to improved bulk solvent modeling.

TEAS C440W:

TEAS C440W crystallized under conditions identical to wild-type TEAS, except that crystals nucleated less readily and were generally smaller. A mutant crystal was soaked for 6 hours in reservoir solution saturated in FHP before flash-freezing and data collection at SSRL beamline 7-1 (Stanford Synchrotoon Radiation Laboratory, Menlo Park, Calif.). A starting model of TEAS-FHP (Table 10), with water molecules, ligands, and residues 523–532 of SEQ ID NO:2 removed, was positioned against the data with the rigid body module of X-PLOR. Rounds of positional and restrained b-factor refinement with bulk solvent and overall anisotropic temperature factor modeling were also carried out in X-PLOR, and manual model building and adjustment were carried out in the software program O. As with the double mutant, electron density maps were noticeably improved after refinement and map calculation in CNS.

EXAMPLE 4

Terpene Synthase Enzyme Assays

Synthase activity assays were carried out based on the assay described in Vogeli and Chappell, Plant Physiol. 94:1860 (1990) and Vogeli, et al., Plant Physiol. 93:182 (1990). In general, radio-labeled ($^3$H or $^{14}$C) substrate was incubated with enzyme at room temperature in a buffered magnesium salt solution (200 mM Tris, pH 8, 50 mM Mg chloride, 1 mM DTT, unless otherwise noted); hydrocarbon products were then selectively extracted into an organic solvent such as hexane. The hexane extract generally was treated with silica gel to remove prenyl alcohols and other oxygenated compounds generated by non-enzymatic hydrolysis of substrate, which partition inefficiently into hexane. Hydrocarbon products present in the hexane phase were quantitated by scintillation counting.

A subsequent extraction with a more polar organic solvent such as ethyl acetate was sometimes carried out. Oxygenated compounds more efficiently partition into ethyl acetate-type solvents. Compounds present in the ethyl acetate phase were also quantitated by scintillation counting.

Substrate concentrations typically ranged from 0.1 nanomolar to 100 micromolar. In some assays, the substrate was not radiolabeled. Reactions generally were carried out in triplicate for each substrate concentration. Protein concentration was determined by the Bradford method. For determination of steady-state kinetic parameters, enzyme concentrations were chosen such that generation of products over time was linear throughout the course of the reaction.

Diterpene synthase assays typically were carried out using $^3$H geranylgeranyl diphosphate (GGPP) and enzyme in 250 mM Tris, 10 mM Mg chloride, 1 mM DTT, pH 8.0. Sesquiterpene synthase assays typically were carried out using $^{14}$C or $^3$H FPP and enzyme in 100 mM Tris, 30 mM Mg chloride, 1 mM DTT, pH 8.0. Monoterpene synthase assays typically were carried out using $^3$H GPP and enzyme. As a control for nonspecific binding of GPP by protein, identical reactions were set up which contained BSA, rather than enzyme.

Product analysis of wild type and mutant TEAS enzymes by Ag-TLC.

Terpenoid hydrocarbon products are not readily separated by thin layer chromatography on normal or reverse-phase plates; however, some can be separated by argentation TLC (Ag-TLC), in which silica plates are first treated with silver nitrate. Ag-TLC described here generally followed the procedure described by Back et al., Arch. Biochem. Biophys. 315:527 (1994). A silica TLC plate was dipped in 15% silver nitrate (aqueous), then dried for 3–5 hours at 110° C. After spotting of tritiated enzymatic products (solvent extract), the plate was developed in benzene:hexane, ethyl acetate (50:50:1, by volume), sprayed with En$^3$Hance (NEN) fluorography spray, placed on film, and exposed for several days to several weeks. Long exposure times were generally necessary, as silver-nitrate treatment of the TLC plate appeared to cause quenching of the fluorography reagent's fluorescence. Alternatively, $^{14}$C labelled products were detected after one to two days without the use of fluorography spray.

EXAMPLE 5

Activity of TEAS W273S

Diterpene Synthase Activity of TEAS W273S.

The TEAS W273S enzyme and radiolabelled GGPP were incubated as described above and hydrocarbon products were extracted with hexane. Oxygenated products were then extracted with ethyl acetate. Reactions using wild-type TEAS gave counts lower than buffer alone. TEAS W273S, on the other hand, gave counts that were significantly higher for both the hexane and ethyl acetate extracts. Hydrocarbon products formed from GGPP by W273S were distinct from the products made by acid-catalyzed loss of diphosphates from GGPP. See FIG. 3.

Sesquiterpene Synthase Activity of TEAS W273S.

Products of FPP turnover by the purified TEAS W273S mutant were analyzed by argentation thin-layer chromatography (Ag-TLC). One major reaction product had an $R_f$ of 0.7 by Ag-TLC, which was distinct from both 5-epi-aristolochene ($R_f$=0.78) and vetispiradiene ($R_f$=0.63) See FIG. 4. Preliminary GC/MS data showed that hexane extracts from FPP turnover by TEAS W273S contained at least four terpene hydrocarbons, with mass spectra distinct from either 5-epi-aristolochene or vetispiradiene. One of these products had a mass spectrum similar to germacrene A.

EXAMPLE 6

Activity of TEAS C440W/W273S

Diterpene Synthase Activity of TEAS C440W/W273S.

The mutant TEAS C440WM273S protein contains a tryptophan residue at position 440 and a serine residue at position 273. Assays with GGPP were carried out using 0.5 micromolar $^3$H GGPP, various concentrations of unlabelled GGPP (Echelon), and enzyme. Reactions were incubated for 60 minutes at room temperature. The TEAS C440W/W273S mutant protein converted GGPP to hexane-extractable products, whereas the wild-type enzyme did not. The results indicated that the product profile was altered compared to wild-type TEAS. Hexane-extractable products of GGPP turnover by the double mutant were analyzed by Ag-TLC. The products included two species ($R_f$=0.11 and 0.28) that were distinct from the hydrolysis product geranyl geraniol ($R_f$=0.0). To verify that products generated by TEAS C440W/W273S from GGPP were not the hydrolysis product, geranylgeraniol, a sample was analyzed by Ag-TLC. A reaction containing $^3$H GGPP (5 μm) and enzyme (40 μm) in 100 microliters buffer was incubated overnight at room temperature. As controls, $^3$H GGPP was incubated in reaction buffer alone and in reaction buffer adjusted to pH 1.5. Both the enzymatic and control reactions were extracted with hexane, which was spotted on an argentation TLC plate, and developed and exposed as described above. The results, shown in FIG. 3, demonstrated that the products formed by TEAS C440WW273S were different from those generated by non-enzymatic degradation of geranylgeranyl diphosphate.

Sesquiterpene Synthase Activity of TEAS C440W/W273S.

Reactions with FPP as substrate were carried out with $^{14}$C FPP (9 μm) and enzyme (160 μm) in reaction buffer (20 μl). After incubating for 30 minutes at room temperature, products made by TEAS C440W/W273S were analyzed by Ag-TLC. The product profile of the double mutant was similar to that of 1 EAS W273S, with the addition of a major product having an $R_f$ of 0.57. The new product was distinct from both 5-epi-aristolochene and vetispiradiene. Several other products were also formed, many of which migrated slowly upon argentation TLC. See FIG. 4.

EXAMPLE 7

Activity of TEAS C440W

Diterpene Synthase Activity of TEAS C440W

Figure 3:
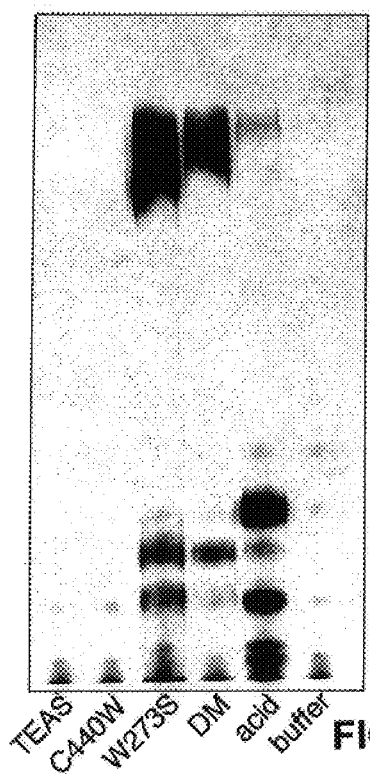
FIG. 3. Autoradiogram of an argentation thin-layer chromatogram of terpenoid hydrocarbon products made by TEAS and mutant TEAS enzymes using GGPP as a substrate. DM: W273S/C440W mutant TEAS enzyme.

Enzyme assays with TEAS C440W were carried out as described in Example 6. As shown in FIG. 3, no hexane-extractable products were detectable by Ag-TLC after an overnight incubation at room temperature with 160 μm of enzyme and 9 μm radiolabeled GGPP in 20 μl volume.

Sesquiterpene Synthase Activity of TEAS C440W

Figure 4:
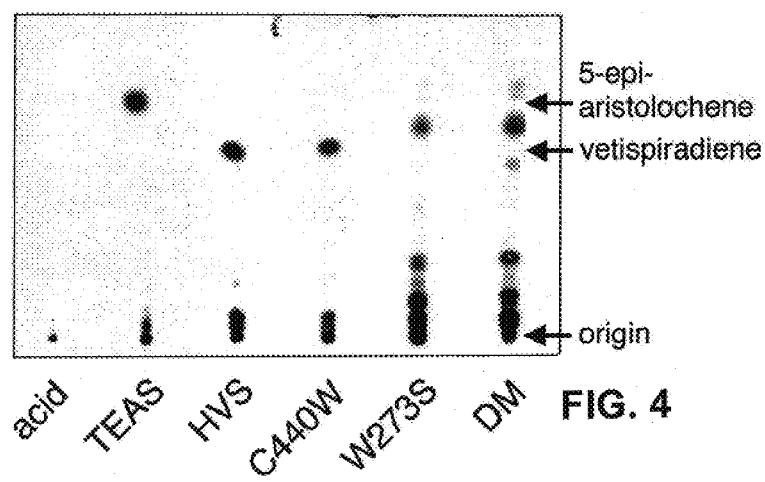
FIG. 4. Autoradiogram of an argentation thin-layer chromatogram of terpenoid hydrocarbon products made by TEAS and mutant TEAS enzymes using FPP as a substrate.

Ag-TLC analysis of the products made from radiolabelled by purified TEAS C440W detected the formation at least one major terpenoid hydrocarbon product ($R_f$ 0.63) that was distinct from 6-epi-aristolochene ($R_f$ 0.78) and vetispiradiene. The reactions product profile on Ag-TLC is shown in FIG. 4. Small amounts of slowly-migrating products ($R_f$ 0–0.09) were also formed.

GC/MS analysis of the hexane extract of TEAS C440W terpenoid hydrocarbon reaction products confirmed that this mutant formed a single major sesquiterpene hydrocarbon product as well as a small number of minor hydroxylated products. The mass spectrum of the major product closely matched the published mass spectrum of the spirocyclic compound hinesene. Hinesene differs from vetispiradiene in the stereochemistry at the C3 methyl group.

EXAMPLE 8

Activity of TEAS W273E

Sesquiterpene Synthase Activity of TEAS W273E. Reactions to determine the products made by TEAS W273E using FPP as substrate were carried out essentially as described above, using radiolabeled FPP. The results indicated that at least one product other than 5epi-aristolochene was formed. The results also indicated that alkylation of TEAS by FPP had occurred. The alkylation was dependent upon the presence of $MgCl_2$ in the reaction mixture. In control experiments, boiled W273E-TEAS, as well as wild-type TEAS and BSA, were not alkylated. These results indicate that alkylation had occurred at position 273 and that the amino acid residue at position 273 is part of the active site.

EXAMPLE 9

Activity of TEAS Y520F

Sesquiterpone Synthase Activity of TEAS Y520F.

Reactions with radiolabeled FPP and TEAS Y520F enzyme were carried out essentially as described above. Reaction products were analysed by Ag-TLC and by GC/MS. A major product of the TEAS Y520F reaction had the same GC retention time as authentic germacrene A and the same mass spectrum as authentic gernacrene A. The retention time and mass spectrum of this product were different from 5-epi-aristolochene.

EXAMPLE 10

Activity of TEAS Y527F

Enzymatic Activity of TEAS Y527F.

A crude extract of TEAS Y527F enzyme was made by inducing expression in E. coli cells, and sonicating the cells. The sonicate was clarified and the supernatant used for enzyme assays. No products were observed in assays using GPP as a substrate, indicating that TEAS Y527F does not have monoterpene synthase activity. Reaction products were obtained using FPP as a substrate. Analysis of these products by Ag-TLC indicated that products other than 5-epi-aristolochene were generated by the TEAS Y527F enzyme.

EXAMPLE 11

Alignment of Terpene Synthase Sequences

Residues 265 to 535 of the TEAS primary amino acid sequence (SEQ ID NO: 2) were aligned with the full-length amino acid sequence of a limonene synthase (SEQ ID NO: 22), using the BLASTp program (NCBI) with a BLOSUM 62 scoring matrix, a gap open value of 11, a gap extension value of 1, an x_dropoff value of 50, an expect value of 10, a wordsize of 3 and no filtering of low complexity sequences. The output of the alignment program, shown in Table 12, included a gap between residues 527 and 528 of the TEAS sequence (numbered as 263 and 264 in the alignment output). Residues 321, 324, 345, 348, 349, 427, 452, 453, 454, 455, 458, 492, 496, 569, 572, 573, 577, 579 and 580 were selected as having the most suitable alignment with the 19 TEAS residues. Residue 580 of limonene cyclase instead of residue 583 was selected as aligning with residue 528 of TEAS, in order to maintain the spatial orientation of structural aspects found in TEAS, i.e., α-helices, β-, sheets and loops shown in FIG. 1 and Table 10.

A region including residues 579 to 847 of the taxadiene primary amino acid sequence of SEQ ID NO: 44 was aligned with the full-length amino acid sequence of a bornyl diphosphate synthase (SEQ ID NO: 26), using the BLASTp program (NCBI) with a BLOSUM 62 scoring matrix, a gap open value of 11, a gap extension value of 1, an x_dropoff value of 50, an expect value of 10, a wordsize of 3 and no filtering of low complexity sequences. The output of the alignment program, shown in Table 13, included a gap between residues 453 and 454 of the bornyl diphosphate synthase sequence. Residues 321, 324, 344, 347, 348, 426, 451, 452, 453, 454, 457, 492, 496, 568, 571, 572, 576, 578 and 579 of the bornyl diphosphate synthase were selected as having the most suitable alignment with residues 584, 587, 606, 609, 610, 688, 713, 714, 715, 716, 719, 753, 757, 831, 834, 835, 839, 841 and 842 of the query region sequence of SEQ ID NO: 44. Residues 453 and 454 of bornyl diphosphate synthase were selected to align with residues 715 and 716 of taxadiene synthase, in order to maintain the spatial orientation of structural aspects expected to be present in taxadiene synthase, i.e., α-helices, β-sheets and loops shown in FIG. 1 and Table 10.

Residues 265 to 535 of the TEAS primary amino acid sequence (SEQ ID NO: 2) were aligned with the full-length amino acid sequence of a δ-selinene synthase (SEQ ID NO: 48), using the BLASTp program (NCBI) with a BLOSUM 50 scoring matrix, a gap open value of 13, a gap extension value of 2, an x_dropoff value of 50, an expect value of 10, a wordsize of 3 and no filtering of low complexity sequences. The output of the alignment program is shown in Table 14. Residues 300, 303, 324, 327, 328, 406, 431, 432, 433, 434, 437, 471, 475, 548, 551, 552, 556, 558 and 559 of SEQ ID NO:48 were selected as having the most suitable alignment with residues 270, 273, 294, 297, 298, 376, 401, 402, 403, 404, 407, 440, 444, 516, 519, 520, 525, 527 and 528 of SEQ ID NO, 2 Residues 307 to 593 of the primary amino acid sequence of γ-humulene synthase (SEQ ID NO: 50) were aligned with the full-length amino acid sequence of abietadiene synthase (SEQ ID NO: 56), using the BLASTp program (NCBI) with a BLOSUM 62 scoring matrix, a gap open value of 11, a gap extension value of 1, an x_dropoff value of 50, an expect value of 10, a wordsize of 3 and no filtering of low complexity sequences. The output of the alignment program is shown in Table 15. Residues 590, 593, 614, 617, 618, 696, 721, 722, 723, 724, 727, 761, 765, 837, 840, 841, 845, 847 and 848 of the diterpene synthase (SEQ ID NO: 56) were selected as having the most suitable alignment with residues 312, 315, 336, 339, 340, 419, 444, 445, 446, 447, 450, 484, 488, 562, 565, 566, 570, 572 and 573 of the sesquiterpene synthase query sequence (SEQ ID NO: 50).

EXAMPLE 12

Generation of Novel Monoterpene Synthase Genes

A DNA sequence encoding a pinene synthase (SEQ ID NO:20) is used to construct a library of mutant pinene synthase genes. Random mutations are introduced at nucleotides encoding one or more of the following nine amino acid residues: L, C, C, G, H, S, L, G and Y, which correspond to positions 351, 372, 480, 481, 482, 485, 519, 600 and 601 of SEQ ID NO:20.

In some cases, the pinene synthase coding sequence is randomly mutated at nucleotides encoding one or more of amino acid residues 348, 375, 376, 597, 605, 607 and 608, which correspond to positions Y, I, T, F, D, Y and S of SEQ ID NO:20. The pinene synthase coding sequence is sometimes mutated at nucleotides encoding one or more of the following amino acid residues: Y, S and G, which correspond to positions 454, 479 and 523 of SEQ ID NO:20. In some cases, mutations at these ten positions are made in addition to mutations at nucleotides encoding the nine residues mentioned above. In other cases, mutations at these ten positions are made without introducing mutations at the nine residues mentioned above.

The pinene synthase coding sequence DNA is inserted in the pET28b(+) vector and mutagenized using the Quick-Change® method, following a protocol similar to that described in Example 1 for the TEAS 406/407 random library. The primers used to generate mutations are synthesized as indicated in Example 1, using N or S as nucleotides in the desired codons in order to generate random mutants.

Specific mutations at one or more of the above 19 pinene synthase amino acid residues are made by site-directed mutagenesis using a protocol similar to that described in Example 1 for TEAS. Primers are made that have specific A, T, C or G substitutions in the codons to be mutated, in order to generate the desired mutant(s).

Random and/or specific mutations are prepared in a manner similar to that described above to alter amino acid residues of other monoterpene synthases, e.g., limonene synthase, (SEQ ID NOS:22 or 58), myrcene synthase (SEQ ID NO:30), +sabinene synthase (SEQ ID NO:54), 1, 8 cineole synthase (SEQ ID NO:24) and +bornyl diphosphate synthase (SEQ ID NO:26), at residues whose α-carbons have the interatomic distances and structural coordinates described in Tables 1–6.

EXAMPLE 13

Generation of Novel Sesquiterpene Synthase Genes

A DNA sequence encoding a cadinene synthase (SEQ ID NO:33) is used construct a library of mutant cadinene synthases. Random mutations are introduced at nucleotides encoding one or more of the following nine amino acid residues: W, I, S, G, Y, L, C, L and Y, which correspond to amino acid residues 280, 301, 409, 410, 411, 414, 448, 527 and 528 encoded by SEQ ID NO:33.

In some cases, the cadinene synthase coding sequence is mutated at nucleotides encoding one or more of amino acid residues G, A, S, M, D, Y and T, which correspond to amino acid residues 277, 304, 305, 524, 532, 534 and 535 encoded by SEQ ID NO:33. In addition, the cadinene synthase coding sequence is sometimes mutated at nucleotides encoding one or more of the following amino acid residues: 383, 408 and 452, which correspond to amino acids Y, T and D encoded by SEQ ID NO:33. In some cases, these mutations are made in addition to mutations at the nine residues mentioned above. In other cases, mutations at these ten residues are made without introducing mutations at the nine residues mentioned above.

The cadinene synthase coding sequence is mutated using the QuickChange® method in the pET28b(+) vector, following a protocol similar to that described in Example 1 for the TEAS 406/407 random library. The primers used to generate mutations are synthesized as indicated in Example 11.

Specific mutations at one or more of the above cadinene synthase amino acid residues are made by site-directed mutagenesis using a protocol similar to that described in Example 1 for TEAS.

Random and/or specific mutations are prepared in a manner similar to that described above to alter amino acid residues of other sesquiterpene synthases, e.g., vetispiradiene synthase (SEQ ID NO:32), germacrene C synthase (SEQ ID NO:52), E-alpha-bisabolene synthase (SEQ ID NO:46), gamma-humulene synthase (SEQ ID NO:50), δ-selinene synthase (SEQ ID NO:48), e-b-farnesene synthase (SEQ ID NO:28), at residues whose α-carbons have the interatomic distances and structural coordinates described in Tables 1–6.

EXAMPLE 14

Generation of Novel Diterpene Synthase Genes

A DNA sequence encoding an abietadiene synthase (SEQ ID NO:56) is used construct a library of mutant abietadiene synthases. Random mutations are introduced at nucleotides encoding one or more of the following nine amino acid residues: S, S, I, A, L, V, G. F and Y, which correspond to positions 593, 614, 722, 723, 724, 727, 761, 840 and 841 of SEQ ID NO:56.

In some cases, the abietadiene synthase coding sequence is mutated at nucleotides encoding one or more of amino acid residues I, S, T, M, D, L and T, which correspond to positions 590, 617, 618, 837, 845, 847 and 848 of SEQ ID NO:56. The abietadiene synthase coding sequence is sometimes mutated at nucleotides encoding one or more of the following amino add residues: Y, S and N, which correspond to positions 696, 721 and 765 of SEQ ID NO:56. In some caes, these mutations are made in addition to mutations at the nine residues mentioned above. In other cases, mutations are made at these ten residues without introducing mutations at the nine residues mentioned above.

The abietadiene synthase coding sequence is mutated using the QuickChange® method in the pET28b(+) vector, following a protocol similar to that described in Example 1 for the TEAS 406/407 random library. The primers used to generate mutations are synthesized as indicated in Example 11.

Specific mutations at one or more of the above abietadiene synthase amino acid residues are made by site-directed mutagenesis using a protocol similar to that described in Example 1 for TEAS.

Random and/or specific mutations are prepared in a manner similar to that described above to alter amino acid residues of other diterpene synthases at amino acid residues whose α-carbons have the interatomic distances and structural coordinates described in Tables 1–6, e.g., casbene synthase (SEQ ID NO:42) and taxadiene synthase (SEQ ID NO:44).

EXAMPLE 15

Expression of Mutant Synthases in Insect, Mammalian and Bacterial Cells

Constructs containing nucleic acids encoding mutant synthases of Examples 12, 13 and/or 14 are introduced into cultured cells of the insect Spodoptera frugiperda using a baculovirus expression vector. After expression of the gene, the mutant enzyme is isolated and purified from each done.

Constructs containing nucleic acids encoding mutant synthases of Examples 12, 13 and/or 14 are introduced into cultured HeLa cells using an expression vector having an SV40 promoter. After expression of the gene, the mutant enzyme is isolated and purified from each clone.

Constructs containing nucleic acids encoding mutant synthases of Examples 12, 13 and/or 14 are introduced into E. coli BL-21 on a plasmid vector as described in Example 1. The mutant synthase gene is expressed and the mutant enzyme is isolated and purified as described in Example 2.

Other Embodiments

To the extent not already indicated, it will be understood by those of ordinary skill in the art that any one of the various specific embodiments herein described and illustrated may be further modified to incorporate features shown in other of the specific embodiments.

It is to be understood that while the invention has been described in conjunction with the Detailed Description thereof, that the foregoing description is intended to illustrate, and not limit the scope of the invention, which is defined by the scope of the appended claims. Other aspects, advantages, and modifications are within the scope of the following claims.

TABLE 1

| α-Carbon | X Position | Y Position | Z Position |
| --- | --- | --- | --- |
| 1 | 119.144 | 43.487 | 44.133 |
| 2 | 120.203 | 38.695 | 43.506 |
| 3 | 114.058 | 43.884 | 41.015 |
| 4 | 109.327 | 46.145 | 41.743 |
| 5 | 110.682 | 46.410 | 45.284 |
| 6 | 99.381 | 42.920 | 45.148 |
| 7 | 103.445 | 38.054 | 44.605 |
| 8 | 106.807 | 36.336 | 45.151 |
| 9 | 107.629 | 38.010 | 41.804 |
| 10 | 109.375 | 34.842 | 40.617 |
| 11 | 111.944 | 37.854 | 37.602 |
| 12 | 110.233 | 31.098 | 47.361 |
| 13 | 109.178 | 33.314 | 52.875 |
| 14 | 115.915 | 32.218 | 48.369 |
| 15 | 118.846 | 34.443 | 51.796 |
| 16 | 116.461 | 32.848 | 54.290 |
| 17 | 114.100 | 38.006 | 55.620 |
| 18 | 116.617 | 41.285 | 51.702 |
| 19 | 114.855 | 43.486 | 54.238 |

TABLE 2

| α-carbon | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| 1 | 0.0 | 5.0 | 6.0 | 10.5 | 9.0 | 19.8 | 16.6 | 14.3 | 13.0 | 13.5 | 11.2 | 15.6 | 16.7 | 12.5 | 11.8 | 15.0 | 13.7 | 8.3 | 11.0 |
| 2 | 5.0 | 0.0 | 8.4 | 13.3 | 12.4 | 21.3 | 16.8 | 13.7 | 12.7 | 11.9 | 10.2 | 13.1 | 15.4 | 9.2 | 9.4 | 12.8 | 13.6 | 9.3 | 12.9 |
| 3 | 6.0 | 8.4 | 0.0 | 5.3 | 6.0 | 15.3 | 12.6 | 11.3 | 8.7 | 10.2 | 7.2 | 14.8 | 16.6 | 13.9 | 15.1 | 17.4 | 15.7 | 11.3 | 13.3 |
| 4 | 10.5 | 13.3 | 5.3 | 0.0 | 3.8 | 11.0 | 10.4 | 10.7 | 8.3 | 11.4 | 9.6 | 16.1 | 17.0 | 16.8 | 18.1 | 19.6 | 16.8 | 13.3 | 13.9 |
| 5 | 9.0 | 12.4 | 6.0 | 3.8 | 0.0 | 11.8 | 11.1 | 10.8 | 9.6 | 12.5 | 11.6 | 15.5 | 15.2 | 15.4 | 15.9 | 17.3 | 13.8 | 10.1 | 10.3 |
| 6 | 19.8 | 21.3 | 15.3 | 11.0 | 11.8 | 0.0 | 6.4 | 9.9 | 10.2 | 13.6 | 15.5 | 16.2 | 15.8 | 20.0 | 22.2 | 21.8 | 18.7 | 18.5 | 18.0 |
| 7 | 16.6 | 16.8 | 12.6 | 10.4 | 11.1 | 6.4 | 0.0 | 3.8 | 5.0 | 7.8 | 11.0 | 10.1 | 11.1 | 14.3 | 17.4 | 17.0 | 15.3 | 15.3 | 15.9 |
| 8 | 14.3 | 13.7 | 11.3 | 10.7 | 10.8 | 9.9 | 3.8 | 0.0 | 3.8 | 5.4 | 9.3 | 6.6 | 8.6 | 10.5 | 13.9 | 13.7 | 12.9 | 12.8 | 14.1 |
| 9 | 13.0 | 12.7 | 8.7 | 8.3 | 9.6 | 10.2 | 5.0 | 3.8 | 0.0 | 3.8 | 6.0 | 9.2 | 12.1 | 12.1 | 15.4 | 16.1 | 15.3 | 13.8 | 15.4 |
| 10 | 13.5 | 11.9 | 10.2 | 11.4 | 12.5 | 13.6 | 7.8 | 5.4 | 3.8 | 0.0 | 5.0 | 7.8 | 12.4 | 10.5 | 14.6 | 15.5 | 16.0 | 14.7 | 17.0 |
| 11 | 11.2 | 10.2 | 7.2 | 9.6 | 11.6 | 15.5 | 11.0 | 9.3 | 6.0 | 5.0 | 0.0 | 12.0 | 16.2 | 12.8 | 16.1 | 18.0 | 18.2 | 15.3 | 17.8 |
| 12 | 15.6 | 13.1 | 14.8 | 16.1 | 15.5 | 16.2 | 10.1 | 6.6 | 9.2 | 7.8 | 12.0 | 0.0 | 6.0 | 5.9 | 10.2 | 9.5 | 11.4 | 12.8 | 14.9 |
| 13 | 16.7 | 15.4 | 16.6 | 17.0 | 15.2 | 15.8 | 11.1 | 8.6 | 12.1 | 12.4 | 16.2 | 6.0 | 0.0 | 8.2 | 9.8 | 7.4 | 7.3 | 11.0 | 11.7 |
| 14 | 12.5 | 9.2 | 13.9 | 16.8 | 15.4 | 20.0 | 14.3 | 10.5 | 12.1 | 10.5 | 12.8 | 5.9 | 8.2 | 0.0 | 5.0 | 6.0 | 9.5 | 9.7 | 12.8 |
| 15 | 11.8 | 9.4 | 15.1 | 18.1 | 15.9 | 22.2 | 17.4 | 13.9 | 15.4 | 14.6 | 16.1 | 10.2 | 9.8 | 5.0 | 0.0 | 3.8 | 7.1 | 7.2 | 10.2 |
| 16 | 15.0 | 12.8 | 17.4 | 19.6 | 17.3 | 21.8 | 17.0 | 13.7 | 16.1 | 15.5 | 18.0 | 9.5 | 7.4 | 6.0 | 3.8 | 0.0 | 5.8 | 8.8 | 10.8 |
| 17 | 13.7 | 13.6 | 15.7 | 16.8 | 13.8 | 18.7 | 15.3 | 12.9 | 15.3 | 16.0 | 18.2 | 11.4 | 7.3 | 9.5 | 7.1 | 5.8 | 0.0 | 5.7 | 5.7 |
| 18 | 8.3 | 9.3 | 11.3 | 13.3 | 10.1 | 18.5 | 15.3 | 12.8 | 13.8 | 14.7 | 15.3 | 12.8 | 11.0 | 9.7 | 7.2 | 8.8 | 5.7 | 0.0 | 3.8 |
| 19 | 11.0 | 12.9 | 13.3 | 13.9 | 10.3 | 18.0 | 15.9 | 14.1 | 15.4 | 17.0 | 17.8 | 14.9 | 11.7 | 12.8 | 10.2 | 10.8 | 5.7 | 3.8 | 0.0 |

TABLE 3

| α-Carbon | X Position | Y Position | Z Position |
|---|---|---|---|
| 1 | 119.144 | 43.487 | 44.133 |
| 2 | 120.203 | 38.695 | 43.506 |
| 3 | 114.058 | 43.884 | 41.015 |
| 4 | 109.327 | 46.145 | 41.743 |
| 5 | 110.682 | 46.410 | 45.284 |
| 6 | 106.807 | 36.336 | 45.151 |
| 7 | 107.629 | 38.010 | 41.804 |
| 8 | 109.375 | 34.842 | 40.617 |
| 9 | 111.944 | 37.854 | 37.602 |
| 10 | 110.233 | 31.098 | 47.361 |
| 11 | 115.915 | 32.218 | 48.369 |
| 12 | 118.846 | 34.443 | 51.796 |
| 13 | 116.461 | 32.848 | 54.290 |
| 14 | 114.100 | 38.006 | 55.620 |
| 15 | 116.617 | 41.285 | 51.702 |
| 16 | 114.855 | 43.486 | 54.238 |

TABLE 4

| α-Carbon | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | 0.0 | 5.0 | 6.0 | 10.5 | 9.0 | 14.3 | 13.0 | 13.5 | 11.2 | 15.6 | 12.5 | 11.8 | 15.0 | 13.7 | 8.3 | 11.0 |
| 2 | 5.0 | 0.0 | 8.4 | 13.3 | 12.4 | 13.7 | 12.7 | 11.9 | 10.2 | 13.1 | 9.2 | 9.4 | 12.8 | 13.6 | 9.3 | 12.9 |
| 3 | 6.0 | 8.4 | 0.0 | 5.3 | 6.0 | 11.3 | 8.7 | 10.2 | 7.2 | 14.8 | 13.9 | 15.1 | 17.4 | 15.7 | 11.3 | 13.3 |
| 4 | 10.5 | 13.3 | 5.3 | 0.0 | 3.8 | 10.7 | 8.3 | 11.4 | 9.6 | 16.1 | 16.8 | 18.1 | 19.6 | 16.8 | 13.3 | 13.9 |
| 5 | 9.0 | 12.4 | 6.0 | 3.8 | 0.0 | 10.8 | 9.6 | 12.5 | 11.6 | 15.5 | 15.4 | 15.9 | 17.3 | 13.8 | 10.1 | 10.3 |
| 6 | 14.3 | 13.7 | 11.3 | 10.7 | 10.8 | 0.0 | 3.8 | 5.4 | 9.3 | 6.6 | 10.5 | 13.9 | 13.7 | 12.9 | 12.8 | 14.1 |
| 7 | 13.0 | 12.7 | 8.7 | 8.3 | 9.6 | 3.8 | 0.0 | 3.8 | 6.0 | 9.2 | 12.1 | 15.4 | 16.1 | 15.3 | 13.8 | 15.4 |
| 8 | 13.5 | 11.9 | 10.2 | 11.4 | 12.5 | 5.4 | 3.8 | 0.0 | 5.0 | 7.8 | 10.5 | 14.6 | 15.5 | 16.0 | 14.7 | 17.0 |
| 9 | 11.2 | 10.2 | 7.2 | 9.6 | 11.6 | 9.3 | 6.0 | 5.0 | 0.0 | 12.0 | 12.8 | 16.1 | 18.0 | 18.2 | 15.3 | 17.8 |
| 10 | 15.6 | 13.1 | 14.8 | 16.1 | 15.5 | 6.6 | 9.2 | 7.8 | 12.0 | 0.0 | 5.9 | 10.2 | 9.5 | 11.4 | 12.8 | 14.9 |
| 11 | 12.5 | 9.2 | 13.9 | 16.8 | 15.4 | 10.5 | 12.1 | 10.5 | 12.8 | 5.9 | 0.0 | 5.0 | 6.0 | 9.5 | 9.7 | 12.8 |
| 12 | 11.8 | 9.4 | 15.1 | 18.1 | 15.9 | 13.9 | 15.4 | 14.6 | 16.1 | 12.2 | 5.0 | 0.0 | 3.8 | 7.1 | 7.2 | 10.2 |
| 13 | 15.0 | 12.8 | 17.4 | 19.6 | 17.3 | 13.7 | 16.1 | 15.5 | 18.0 | 9.5 | 6.0 | 3.8 | 0.0 | 5.8 | 8.8 | 10.8 |
| 14 | 13.7 | 13.6 | 15.7 | 16.8 | 13.8 | 12.9 | 15.3 | 16.0 | 18.2 | 11.4 | 9.5 | 7.1 | 5.8 | 0.0 | 5.7 | 5.7 |
| 15 | 8.3 | 9.3 | 11.3 | 13.3 | 10.1 | 12.8 | 13.8 | 14.7 | 15.3 | 12.8 | 9.7 | 7.2 | 8.8 | 5.7 | 0.0 | 3.8 |
| 16 | 11.0 | 12.9 | 13.3 | 13.9 | 10.3 | 14.1 | 15.4 | 17.0 | 17.8 | 14.9 | 12.8 | 10.2 | 10.8 | 5.7 | 3.8 | 0.0 |

TABLE 5

| α-Carbon | X Position | Y Position | Z Position |
|---|---|---|---|
| 1 | 120.203 | 38.695 | 43.506 |
| 2 | 114.058 | 43.884 | 41.015 |
| 3 | 106.807 | 36.336 | 45.151 |
| 4 | 107.629 | 38.010 | 41.804 |
| 5 | 109.375 | 34.842 | 40.617 |
| 6 | 111.944 | 37.854 | 37.602 |
| 7 | 110.233 | 31.098 | 47.361 |
| 8 | 118.846 | 34.443 | 51.796 |
| 9 | 116.461 | 32.848 | 54.290 |

TABLE 6

| α-Carbon | 1 | 2 | 3 | 4 | 5 | 6 | 7 | 8 | 9 |
|---|---|---|---|---|---|---|---|---|---|
| 1 | 0 | 8.4 | 13.7 | 12.7 | 11.9 | 10.2 | 13.1 | 9.4 | 12.8 |
| 2 | 8.4 | 0 | 11.3 | 8.7 | 10.2 | 7.2 | 14.8 | 15.1 | 17.4 |
| 3 | 13.7 | 11.3 | 0 | 3.8 | 5.4 | 9.3 | 6.6 | 13.9 | 13.7 |
| 4 | 12.7 | 8.7 | 3.8 | 0 | 3.8 | 6 | 9.2 | 15.4 | 16.1 |
| 5 | 11.9 | 10.2 | 5.4 | 3.8 | 0 | 5 | 7.8 | 14.6 | 15.5 |
| 6 | 10.2 | 7.2 | 9.3 | 6 | 5 | 0 | 12 | 16.1 | 18 |
| 7 | 13.1 | 14.8 | 6.6 | 9.2 | 7.8 | 12 | 0 | 10.2 | 9.5 |
| 8 | 9.4 | 15.1 | 13.9 | 15.4 | 14.6 | 16.1 | 10.2 | 0 | 3.8 |
| 9 | 12.8 | 17.4 | 13.7 | 16.1 | 15.5 | 18 | 9.5 | 3.8 | 0 |

TABLE 7

Ordered Arrangement of R-Groups at α-carbons 1–19

| | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| A | C | W | I | I | S | Y | T | T | T | Y | L | C | D | V | T | Y | D | Y | T |
| B | C | W | I | I | S | Y | T | S | T | Y | L | C | D | I | T | Y | D | Y | T |
| C | G | W | I | A | S | Y | T | C | G | Y | L | C | D | M | L | Y | D | Y | T |
| D | G | W | I | A | S | Y | T | S | G | Y | L | C | D | M | L | Y | D | Y | T |
| E | C | W | L | T | S | Y | S | A | G | Y | I | A | N | A | L | Y | D | Y | T |
| F | G | W | L | L | S | Y | S | T | V | H | L | G | D | A | V | Y | D | Y | T |
| G | C | W | L | T | S | Y | S | A | G | Y | I | A | N | A | L | Y | D | Y | S |
| H | L | W | I | T | T | Y | S | V | G | N | L | F | D | V | L | Y | D | F | T |
| I | P | W | I | V | D | Y | S | T | A | G | L | S | D | A | C | Y | D | Y | T |
| J | A | W | V | C | G | F | T | S | C | I | M | G | N | C | S | Y | D | Y | S |
| K | N | F | F | L | G | A | E | I | T | A | T | G | N | I | T | Y | E | F | T |
| L | C | W | N | I | T | Y | S | I | S | G | M | L | D | A | M | Y | D | H | Q |
| M | S | W | V | L | T | Y | S | S | S | Y | L | G | G | V | L | Y | D | F | T |
| N | N | F | F | L | V | N | A | T | L | A | L | G | N | L | S | Y | E | F | T |
| O | C | W | N | I | T | Y | I | S | G | P | L | L | D | A | M | Y | D | H | G |
| P | C | W | N | V | T | Y | I | G | G | I | L | L | D | A | I | Y | D | F | G |
| Q | C | Y | L | L | T | F | A | V | T | M | T | G | N | I | T | Y | D | Y | T |
| R | C | W | I | I | T | Y | S | I | S | A | I | L | D | A | I | Y | D | D | G |
| S | S | W | F | I | V | F | S | S | S | V | I | L | N | V | I | Y | D | H | G |
| T | S | W | I | A | T | Y | S | V | A | S | I | L | D | A | I | Y | D | F | G |
| U | N | W | N | L | T | Y | S | I | S | S | I | F | N | S | M | Y | D | H | G |
| V | F | L | A | Q | T | Y | S | I | G | Q | L | S | D | T | I | F | D | F | G |
| W | I | S | S | T | V | Y | S | I | A | L | V | G | N | M | F | Y | D | L | T |
| X | Y | L | C | I | T | Y | S | C | G | H | S | L | G | F | G | Y | D | Y | S |
| Y | G | S | F | I | T | F | S | S | S | V | I | L | N | A | V | Y | D | H | G |
| Z | Y | W | A | C | T | Y | S | S | G | M | L | G | D | L | I | Y | D | L | Y |
| AA | A | A | N | L | T | N | A | L | T | S | T | C | M | L | L | Y | D | Y | N |
| BB | F | L | C | V | T | Y | S | S | A | Y | V | L | G | L | L | Y | D | F | S |
| CC | F | W | A | M | T | Y | N | T | G | M | L | S | D | I | M | Y | D | F | S |
| DD | Y | M | C | V | T | F | V | S | S | G | I | L | G | F | V | Y | D | Y | T |
| EE | V | S | G | Q | V | Y | S | V | G | L | C | W | N | V | F | Y | D | Y | G |
| FF | C | S | G | T | T | M | F | A | L | G | V | G | N | L | F | Y | D | F | T |
| GG | C | S | G | T | T | M | S | F | A | L | I | G | N | L | F | Y | D | F | T |
| HH | C | A | G | T | T | M | S | F | A | L | I | G | N | V | F | Y | D | Y | T |
| II | I | W | V | I | S | Y | T | T | G | L | V | I | N | T | S | Y | D | Y | T |
| JJ | Y | W | A | C | T | Y | S | S | G | M | L | G | D | L | I | Y | D | L | Y |
| KK | C | W | I | I | S | Y | T | S | T | Y | L | C | D | V | T | Y | D | Y | T |
| LL | C | W | I | I | S | Y | T | T | T | Y | L | C | D | I | T | Y | D | Y | T |
| MM | C | W | N | I | T | Y | S | I | S | G | M | L | D | A | M | Y | D | H | G |
| NN | F | A | A | Q | T | Y | S | I | G | Q | L | S | D | T | I | F | D | F | G |
| OO | F | A | I | A | T | Y | S | V | A | S | I | L | D | A | I | Y | D | F | G |

TABLE 8

Ordered Arrangement of R-Groups at α-carbons 1–16

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| A | C | W | I | I | S | T | T | Y | L | C | V | T | Y | D | Y | T |
| B | C | W | I | I | S | S | T | Y | L | C | I | T | Y | D | Y | T |
| C | G | W | I | A | S | C | G | Y | L | C | M | L | Y | D | Y | T |
| D | G | W | I | A | S | S | G | Y | L | C | M | L | Y | D | Y | T |
| E | C | W | L | T | S | A | G | Y | I | A | A | L | Y | D | Y | T |
| F | G | W | L | L | S | T | V | H | L | G | A | V | Y | D | Y | T |
| G | C | W | L | T | S | A | G | Y | I | A | A | L | Y | D | Y | S |
| H | L | W | I | T | T | V | G | N | L | F | V | L | Y | D | F | T |
| I | P | W | I | V | D | T | A | G | L | S | A | C | Y | D | Y | T |
| J | A | W | V | C | G | S | C | I | M | G | C | S | Y | D | Y | S |
| K | N | F | F | L | G | I | T | A | T | G | I | T | Y | E | F | T |
| L | C | W | N | I | T | I | S | G | M | L | A | M | Y | D | H | Q |
| M | S | W | V | L | T | S | S | Y | L | G | V | L | Y | D | F | T |
| N | N | F | F | L | V | T | L | A | L | G | L | S | Y | E | F | T |
| O | C | W | N | I | T | S | G | P | L | L | A | M | Y | D | H | G |
| P | C | W | N | V | T | G | G | I | L | L | A | I | Y | D | F | G |
| Q | C | Y | L | L | T | V | T | M | T | G | I | T | Y | D | Y | T |
| R | C | W | I | I | T | I | S | A | I | L | A | I | Y | D | D | G |
| S | S | W | F | I | V | S | S | V | I | L | V | I | Y | D | H | G |
| T | S | W | I | A | T | V | A | S | I | L | A | I | Y | D | F | G |
| U | N | W | N | L | T | I | S | S | I | F | S | M | Y | D | H | G |
| V | F | L | A | Q | T | I | G | Q | L | S | T | I | F | D | F | G |
| W | I | S | S | T | V | I | A | L | V | G | M | F | Y | D | L | T |
| X | Y | L | C | I | T | C | G | H | S | L | F | G | Y | D | Y | S |
| Y | G | S | F | I | T | S | S | V | I | L | A | V | Y | D | H | G |
| Z | Y | W | A | C | T | S | G | M | L | G | L | I | Y | D | L | Y |
| AA | A | A | N | L | T | L | T | S | T | C | L | L | Y | D | Y | N |
| BB | F | L | C | V | T | S | A | Y | V | L | L | L | Y | D | F | S |
| CC | F | W | A | M | T | T | G | M | L | S | I | M | Y | D | F | S |
| DD | Y | M | C | V | T | S | S | G | I | L | F | V | Y | D | Y | T |
| EE | V | S | G | Q | V | V | G | L | C | W | V | F | Y | D | Y | G |
| FF | C | S | G | T | T | A | L | G | V | G | L | F | Y | D | F | T |
| GG | C | S | G | T | T | F | A | L | I | G | L | F | Y | D | F | T |
| HH | C | A | G | T | T | F | A | L | I | G | V | F | Y | D | Y | T |
| II | I | W | V | I | S | T | G | L | V | I | T | S | Y | D | Y | T |
| JJ | Y | W | A | C | T | S | G | M | L | G | L | I | Y | D | L | Y |
| KK | C | W | I | I | S | S | T | Y | L | C | V | T | Y | D | Y | T |
| LL | C | W | I | I | S | T | T | Y | L | C | I | T | Y | D | Y | T |
| MM | C | W | N | I | T | I | S | G | M | L | A | M | Y | D | H | G |
| NN | F | A | A | Q | T | I | G | Q | L | S | T | I | F | D | F | G |
| OO | F | A | I | A | T | V | A | S | I | L | A | I | Y | D | F | G |

TABLE 9

Ordered Arrangements of α-Carbons 1–9

| | 1 | 2 | 3 | 4 | 5 | 6 | 7 | 8 | 9 |
|---|---|---|---|---|---|---|---|---|---|
| A | W | I | T | T | Y | L | C | T | Y |
| B | W | I | S | T | Y | L | C | T | Y |
| C | W | I | C | G | Y | L | C | L | Y |
| D | W | I | S | G | Y | L | C | L | Y |
| E | W | L | A | G | Y | I | A | L | Y |
| F | W | L | T | V | H | L | G | V | Y |
| G | W | L | A | G | Y | I | A | L | Y |
| H | W | I | V | G | N | L | F | L | Y |
| I | W | I | T | A | G | L | S | C | Y |
| J | W | V | S | C | I | M | G | S | Y |
| K | F | F | I | T | A | T | G | T | Y |
| L | W | N | I | S | G | M | L | M | Y |
| M | W | V | S | S | Y | L | G | L | Y |
| N | F | F | T | L | A | L | G | S | Y |
| O | W | N | S | G | P | L | L | M | Y |
| P | W | N | G | G | I | L | L | I | Y |
| Q | Y | L | V | T | M | T | G | T | Y |
| R | W | I | I | S | A | I | L | I | Y |
| S | W | F | S | S | V | I | L | I | Y |
| T | W | I | V | A | S | I | L | I | Y |
| U | W | N | I | S | S | I | F | M | Y |
| V | L | A | I | G | Q | L | S | I | F |
| W | S | S | I | A | L | V | G | F | Y |
| X | L | C | C | G | H | S | L | G | Y |
| Y | S | F | S | S | V | I | L | V | Y |
| Z | W | A | S | G | M | L | G | I | Y |
| AA | A | N | L | T | S | T | C | L | Y |
| BB | L | C | S | A | Y | V | L | L | Y |
| CC | W | A | T | G | M | L | S | M | Y |
| DD | M | C | S | S | G | I | L | V | Y |
| EE | S | G | V | G | L | C | W | F | Y |
| FF | S | G | A | L | G | V | G | F | Y |
| GG | S | G | F | A | L | I | G | F | Y |
| HH | A | G | F | A | L | I | G | F | Y |
| II | W | V | T | G | L | V | I | S | Y |
| JJ | W | A | S | G | M | L | G | I | Y |
| KK | W | I | S | T | Y | L | C | T | Y |
| LL | W | I | T | T | Y | L | C | T | Y |
| MM | W | N | I | S | G | M | L | M | Y |
| NN | A | A | I | G | Q | L | S | I | F |
| OO | A | I | V | A | S | I | L | I | Y |

TABLE 10

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 1 | CB | VAL | 17 | 105.641 | 55.031 | 61.062 | 1.00 | 98.26 |
| 2 | CG1 | VAL | 17 | 104.598 | 56.123 | 61.269 | 1.00 | 97.24 |
| 3 | CG2 | VAL | 17 | 105.492 | 53.957 | 62.133 | 1.00 | 94.24 |
| 4 | C | VAL | 17 | 106.842 | 53.842 | 59.190 | 1.00 | 98.89 |
| 5 | O | VAL | 17 | 107.108 | 52.650 | 59.359 | 1.00 | 96.64 |
| 6 | N | VAL | 17 | 104.381 | 53.419 | 59.594 | 1.00 | 99.88 |
| 7 | CA | VAL | 17 | 105.495 | 54.412 | 59.646 | 1.00 | 99.06 |
| 8 | N | ALA | 18 | 107.671 | 54.719 | 58.615 | 1.00 | 98.95 |
| 9 | CA | ALA | 18 | 109.015 | 54.419 | 58.088 | 1.00 | 98.55 |
| 10 | CB | ALA | 18 | 110.007 | 55.478 | 58.572 | 1.00 | 97.57 |
| 11 | C | ALA | 18 | 109.570 | 53.012 | 58.346 | 1.00 | 99.86 |
| 12 | O | ALA | 18 | 109.580 | 52.170 | 57.447 | 1.00 | 100.00 |
| 13 | N | ASP | 19 | 110.068 | 52.793 | 59.562 | 1.00 | 99.07 |
| 14 | CA | ASP | 19 | 110.616 | 51.508 | 60.010 | 1.00 | 97.13 |
| 15 | CB | ASP | 19 | 109.507 | 50.447 | 60.064 | 1.00 | 96.62 |
| 16 | CG | ASP | 19 | 109.503 | 49.666 | 61.370 | 1.00 | 97.86 |
| 17 | OD1 | ASP | 19 | 110.119 | 50.130 | 62.355 | 1.00 | 100.00 |
| 18 | OD2 | ASP | 19 | 108.873 | 48.588 | 61.415 | 1.00 | 97.98 |
| 19 | C | ASP | 19 | 111.849 | 50.931 | 59.301 | 1.00 | 95.44 |
| 20 | O | ASP | 19 | 112.812 | 50.539 | 59.964 | 1.00 | 95.55 |
| 21 | N | PHE | 20 | 111.814 | 50.854 | 57.971 | 1.00 | 91.33 |
| 22 | CA | PHE | 20 | 112.925 | 50.297 | 57.190 | 1.00 | 84.17 |
| 23 | CB | PHE | 20 | 112.630 | 50.377 | 55.686 | 1.00 | 81.03 |
| 24 | CG | PHE | 20 | 111.437 | 49.572 | 55.251 | 1.00 | 77.17 |
| 25 | CD1 | PHE | 20 | 110.691 | 49.971 | 54.147 | 1.00 | 74.72 |
| 26 | CD2 | PHE | 20 | 111.056 | 48.422 | 55.939 | 1.00 | 77.18 |
| 27 | CE1 | PHE | 20 | 109.581 | 49.239 | 53.733 | 1.00 | 72.36 |
| 28 | CE2 | PHE | 20 | 109.947 | 47.681 | 55.535 | 1.00 | 78.10 |
| 29 | CZ | PHE | 20 | 109.207 | 48.092 | 54.428 | 1.00 | 75.86 |
| 30 | C | PHE | 20 | 114.280 | 50.942 | 57.465 | 1.00 | 82.49 |
| 31 | O | PHE | 20 | 114.400 | 52.167 | 57.517 | 1.00 | 84.00 |
| 32 | N | SER | 21 | 115.294 | 50.098 | 57.639 | 1.00 | 78.89 |
| 33 | CA | SER | 21 | 116.656 | 50.560 | 57.895 | 1.00 | 75.96 |
| 34 | CB | SER | 21 | 117.495 | 49.433 | 58.515 | 1.00 | 75.81 |
| 35 | OG | SER | 21 | 117.449 | 48.250 | 57.731 | 1.00 | 80.91 |
| 36 | C | SER | 21 | 117.305 | 51.063 | 56.602 | 1.00 | 69.67 |
| 37 | O | SER | 21 | 117.070 | 50.513 | 55.525 | 1.00 | 70.74 |
| 38 | N | PRO | 22 | 118.111 | 52.134 | 56.691 | 1.00 | 63.25 |
| 39 | CD | PRO | 22 | 118.421 | 52.939 | 57.887 | 1.00 | 60.39 |
| 40 | CA | PRO | 22 | 118.773 | 52.680 | 55.501 | 1.00 | 56.42 |
| 41 | CB | PRO | 22 | 119.362 | 53.994 | 56.018 | 1.00 | 53.56 |
| 42 | CG | PRO | 22 | 119.657 | 53.688 | 57.458 | 1.00 | 61.97 |
| 43 | C | PRO | 22 | 119.847 | 51.746 | 54.939 | 1.00 | 55.70 |
| 44 | O | PRO | 22 | 120.236 | 50.771 | 55.589 | 1.00 | 52.85 |
| 45 | N | SER | 23 | 120.301 | 52.038 | 53.724 | 1.00 | 56.69 |
| 46 | CA | SER | 23 | 121.327 | 51.233 | 53.065 | 1.00 | 53.59 |
| 47 | CB | SER | 23 | 121.600 | 51.775 | 51.660 | 1.00 | 51.37 |
| 48 | OG | SER | 23 | 122.574 | 50.995 | 50.991 | 1.00 | 45.40 |
| 49 | C | SER | 23 | 122.620 | 51.210 | 53.878 | 1.00 | 57.52 |
| 50 | O | SER | 23 | 123.161 | 52.258 | 54.236 | 1.00 | 61.76 |
| 51 | N | LEU | 24 | 123.101 | 50.004 | 54.168 | 1.00 | 58.09 |
| 52 | CA | LEU | 24 | 124.326 | 49.799 | 54.944 | 1.00 | 55.68 |
| 53 | CB | LEU | 24 | 124.545 | 48.301 | 55.191 | 1.00 | 60.54 |
| 54 | CG | LEU | 24 | 123.413 | 47.379 | 55.651 | 1.00 | 67.70 |
| 55 | CD1 | LEU | 24 | 123.810 | 45.934 | 55.385 | 1.00 | 70.01 |
| 56 | CD2 | LEU | 24 | 123.098 | 47.596 | 57.124 | 1.00 | 70.77 |
| 57 | C | LEU | 24 | 125.554 | 50.313 | 54.198 | 1.00 | 51.07 |
| 58 | O | LEU | 24 | 126.529 | 50.754 | 54.808 | 1.00 | 50.23 |
| 59 | N | TRP | 25 | 125.472 | 50.267 | 52.873 | 1.00 | 45.50 |
| 60 | CA | TRP | 25 | 126.563 | 50.636 | 51.977 | 1.00 | 44.42 |
| 61 | CB | TRP | 25 | 126.356 | 49.908 | 50.645 | 1.00 | 46.22 |
| 62 | CG | TRP | 25 | 125.853 | 48.510 | 50.867 | 1.00 | 47.97 |
| 63 | CD2 | TRP | 25 | 126.604 | 47.407 | 51.384 | 1.00 | 50.67 |
| 64 | CE2 | TRP | 25 | 125.700 | 46.331 | 51.553 | 1.00 | 50.91 |
| 65 | CE3 | TRP | 25 | 127.948 | 47.219 | 51.729 | 1.00 | 45.66 |
| 66 | CD1 | TRP | 25 | 124.567 | 48.070 | 50.732 | 1.00 | 49.99 |
| 67 | NE1 | TRP | 25 | 124.466 | 46.765 | 51.147 | 1.00 | 47.16 |
| 68 | CZ2 | TRP | 25 | 126.101 | 45.088 | 52.053 | 1.00 | 52.99 |
| 69 | CZ3 | TRP | 25 | 128.347 | 45.983 | 52.227 | 1.00 | 47.77 |
| 70 | CH2 | TRP | 25 | 127.423 | 44.934 | 52.384 | 1.00 | 51.93 |
| 71 | C | TRP | 25 | 126.893 | 52.110 | 51.744 | 1.00 | 44.49 |
| 72 | O | TRP | 25 | 127.997 | 52.550 | 52.063 | 1.00 | 43.75 |
| 73 | N | GLY | 26 | 125.958 | 52.862 | 51.172 | 1.00 | 47.80 |
| 74 | CA | GLY | 26 | 126.210 | 54.267 | 50.894 | 1.00 | 39.84 |
| 75 | C | GLY | 26 | 126.744 | 54.449 | 49.483 | 1.00 | 44.69 |
| 76 | O | GLY | 26 | 126.375 | 53.696 | 48.580 | 1.00 | 46.55 |
| 77 | N | ASP | 27 | 127.620 | 55.434 | 49.287 | 1.00 | 46.92 |
| 78 | CA | ASP | 27 | 128.200 | 55.708 | 47.966 | 1.00 | 50.38 |
| 79 | CB | ASP | 27 | 128.544 | 57.196 | 47.827 | 1.00 | 57.61 |
| 80 | CG | ASP | 27 | 127.307 | 58.091 | 47.770 | 1.00 | 66.06 |
| 81 | OD1 | ASP | 27 | 126.168 | 57.582 | 47.895 | 1.00 | 64.78 |
| 82 | OD2 | ASP | 27 | 127.482 | 59.318 | 47.597 | 1.00 | 67.46 |
| 83 | C | ASP | 27 | 129.441 | 54.857 | 47.686 | 1.00 | 46.14 |
| 84 | O | ASP | 27 | 130.165 | 55.082 | 46.711 | 1.00 | 47.50 |
| 85 | N | GLN | 28 | 129.642 | 53.855 | 48.536 | 1.00 | 40.05 |
| 86 | CA | GLN | 28 | 130.759 | 52.921 | 48.461 | 1.00 | 28.69 |
| 87 | CB | GLN | 28 | 130.591 | 51.884 | 49.575 | 1.00 | 25.72 |
| 88 | CG | GLN | 28 | 131.624 | 50.781 | 49.615 | 1.00 | 32.15 |
| 89 | CD | GLN | 28 | 131.331 | 49.745 | 50.688 | 1.00 | 33.15 |
| 90 | OE1 | GLN | 28 | 131.873 | 48.643 | 50.665 | 1.00 | 41.21 |
| 91 | NE2 | GLN | 28 | 130.467 | 50.097 | 51.638 | 1.00 | 18.55 |
| 92 | C | GLN | 28 | 130.904 | 52.221 | 47.108 | 1.00 | 27.55 |
| 93 | O | GLN | 28 | 131.974 | 51.709 | 46.787 | 1.00 | 21.99 |
| 94 | N | PHE | 29 | 129.840 | 52.223 | 46.307 | 1.00 | 27.43 |
| 95 | CA | PHE | 29 | 129.874 | 51.561 | 45.004 | 1.00 | 26.63 |
| 96 | CB | PHE | 29 | 128.840 | 50.432 | 44.956 | 1.00 | 33.69 |
| 97 | CG | PHE | 29 | 129.070 | 49.349 | 45.976 | 1.00 | 28.13 |
| 98 | CD1 | PHE | 29 | 128.241 | 49.241 | 47.089 | 1.00 | 26.35 |
| 99 | CD2 | PHE | 29 | 130.103 | 48.428 | 45.817 | 1.00 | 27.32 |
| 100 | CE1 | PHE | 29 | 128.432 | 48.231 | 48.028 | 1.00 | 24.27 |
| 101 | CE2 | PHE | 29 | 130.304 | 47.410 | 46.751 | 1.00 | 28.00 |
| 102 | CZ | PHE | 29 | 129.466 | 47.311 | 47.860 | 1.00 | 16.26 |
| 103 | C | PHE | 29 | 129.712 | 52.451 | 43.771 | 1.00 | 31.14 |
| 104 | O | PHE | 29 | 129.920 | 51.976 | 42.648 | 1.00 | 31.41 |
| 105 | N | LEU | 30 | 129.336 | 53.718 | 43.962 | 1.00 | 33.49 |
| 106 | CA | LEU | 30 | 129.164 | 54.658 | 42.844 | 1.00 | 39.53 |
| 107 | CB | LEU | 30 | 128.857 | 56.065 | 43.366 | 1.00 | 47.74 |
| 108 | CG | LEU | 30 | 127.443 | 56.556 | 43.658 | 1.00 | 54.63 |
| 109 | CD1 | LEU | 30 | 127.508 | 58.033 | 44.036 | 1.00 | 54.01 |
| 110 | CD2 | LEU | 30 | 126.568 | 56.378 | 42.429 | 1.00 | 53.57 |
| 111 | C | LEU | 30 | 130.433 | 54.764 | 42.009 | 1.00 | 40.75 |
| 112 | O | LEU | 30 | 130.384 | 54.947 | 40.787 | 1.00 | 34.99 |
| 113 | N | SER | 31 | 131.565 | 54.671 | 42.696 | 1.00 | 44.10 |
| 114 | CA | SER | 31 | 132.873 | 54.789 | 42.077 | 1.00 | 47.85 |
| 115 | CB | SER | 31 | 133.730 | 55.737 | 42.917 | 1.00 | 53.74 |
| 116 | OG | SER | 31 | 133.671 | 55.353 | 44.281 | 1.00 | 52.06 |
| 117 | C | SER | 31 | 133.669 | 53.515 | 41.851 | 1.00 | 45.38 |
| 118 | O | SER | 31 | 133.909 | 52.743 | 42.782 | 1.00 | 45.28 |
| 119 | N | PHE | 32 | 134.064 | 53.302 | 40.602 | 1.00 | 43.37 |
| 120 | CA | PHE | 32 | 134.905 | 52.172 | 40.232 | 1.00 | 45.26 |
| 121 | CB | PHE | 32 | 134.213 | 50.812 | 40.251 | 1.00 | 42.83 |
| 122 | CG | PHE | 32 | 135.181 | 49.670 | 40.073 | 1.00 | 33.22 |
| 123 | CD1 | PHE | 32 | 136.098 | 49.365 | 41.075 | 1.00 | 29.45 |
| 124 | CD2 | PHE | 32 | 135.266 | 48.984 | 38.858 | 1.00 | 32.90 |
| 125 | CE1 | PHE | 32 | 137.096 | 48.407 | 40.875 | 1.00 | 28.42 |
| 126 | CE2 | PHE | 32 | 136.261 | 48.023 | 38.647 | 1.00 | 27.39 |
| 127 | CZ | PHE | 32 | 137.179 | 47.737 | 39.655 | 1.00 | 28.24 |
| 128 | C | PHE | 32 | 135.601 | 52.358 | 38.896 | 1.00 | 50.87 |
| 129 | O | PHE | 32 | 134.988 | 52.256 | 37.829 | 1.00 | 43.81 |
| 130 | N | SER | 33 | 136.899 | 52.626 | 38.989 | 1.00 | 55.26 |
| 131 | CA | SER | 33 | 137.755 | 52.816 | 37.841 | 1.00 | 61.21 |
| 132 | CB | SER | 33 | 138.587 | 54.094 | 38.017 | 1.00 | 61.87 |
| 133 | OG | SER | 33 | 139.024 | 54.250 | 39.360 | 1.00 | 67.09 |
| 134 | C | SER | 33 | 138.641 | 51.583 | 37.731 | 1.00 | 59.75 |
| 135 | O | SER | 33 | 139.488 | 51.329 | 38.589 | 1.00 | 59.49 |
| 136 | N | ILE | 34 | 138.368 | 50.771 | 36.718 | 1.00 | 60.14 |
| 137 | CA | ILE | 34 | 139.128 | 49.552 | 36.486 | 1.00 | 66.15 |
| 138 | CB | ILE | 34 | 138.426 | 48.639 | 35.442 | 1.00 | 65.50 |
| 139 | CG2 | ILE | 34 | 138.099 | 49.423 | 34.163 | 1.00 | 69.37 |
| 140 | CG1 | ILE | 34 | 139.291 | 47.406 | 35.157 | 1.00 | 65.37 |
| 141 | CD1 | ILE | 34 | 138.715 | 46.458 | 34.122 | 1.00 | 63.17 |
| 142 | C | ILE | 34 | 140.544 | 49.875 | 36.013 | 1.00 | 70.13 |
| 143 | O | ILE | 34 | 140.725 | 50.551 | 35.001 | 1.00 | 76.00 |
| 144 | N | ASP | 35 | 141.545 | 49.454 | 36.782 | 1.00 | 73.05 |
| 145 | CA | ASP | 35 | 142.935 | 49.673 | 36.388 | 1.00 | 70.88 |
| 146 | CB | ASP | 35 | 143.895 | 49.419 | 37.558 | 1.00 | 76.13 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 147 | CG | ASP | 35 | 143.288 | 48.547 | 38.638 | 1.00 | 84.32 |
| 148 | OD1 | ASP | 35 | 142.931 | 47.387 | 38.344 | 1.00 | 92.06 |
| 149 | OD2 | ASP | 35 | 143.155 | 49.030 | 39.784 | 1.00 | 86.08 |
| 150 | C | ASP | 35 | 143.198 | 48.714 | 35.227 | 1.00 | 68.52 |
| 151 | O | ASP | 35 | 143.555 | 47.552 | 35.425 | 1.00 | 65.76 |
| 152 | N | ASN | 36 | 142.940 | 49.214 | 34.019 | 1.00 | 66.53 |
| 153 | CA | ASN | 36 | 143.083 | 48.471 | 32.765 | 1.00 | 67.50 |
| 154 | CB | ASN | 36 | 142.949 | 49.430 | 31.577 | 1.00 | 72.78 |
| 155 | CG | ASN | 36 | 141.889 | 50.497 | 31.804 | 1.00 | 79.82 |
| 156 | OD1 | ASN | 36 | 140.708 | 50.194 | 31.962 | 1.00 | 78.35 |
| 157 | ND2 | ASN | 36 | 142.319 | 51.756 | 31.853 | 1.00 | 84.96 |
| 158 | C | ASN | 36 | 144.383 | 47.686 | 32.646 | 1.00 | 68.26 |
| 159 | O | ASN | 36 | 144.461 | 46.704 | 31.906 | 1.00 | 65.02 |
| 160 | N | GLN | 37 | 145.403 | 48.143 | 33.364 | 1.00 | 71.27 |
| 161 | CA | GLN | 37 | 146.709 | 47.500 | 33.370 | 1.00 | 71.18 |
| 162 | CB | GLN | 37 | 147.721 | 48.431 | 34.048 | 1.00 | 78.38 |
| 163 | CG | GLN | 37 | 149.005 | 47.761 | 34.524 | 1.00 | 90.52 |
| 164 | CD | GLN | 37 | 149.198 | 47.904 | 36.027 | 1.00 | 100.00 |
| 165 | OE1 | GLN | 37 | 148.538 | 48.718 | 36.673 | 1.00 | 100.00 |
| 166 | NE2 | GLN | 37 | 150.106 | 47.105 | 36.592 | 1.00 | 100.00 |
| 167 | C | GLN | 37 | 146.651 | 46.131 | 34.069 | 1.00 | 65.44 |
| 168 | O | GLN | 37 | 147.138 | 45.138 | 33.533 | 1.00 | 63.18 |
| 169 | N | VAL | 38 | 146.023 | 46.086 | 35.244 | 1.00 | 57.92 |
| 170 | CA | VAL | 38 | 145.883 | 44.849 | 36.021 | 1.00 | 51.76 |
| 171 | CB | VAL | 38 | 145.388 | 45.152 | 37.461 | 1.00 | 50.39 |
| 172 | CG1 | VAL | 38 | 145.198 | 43.862 | 38.251 | 1.00 | 44.02 |
| 173 | CG2 | VAL | 38 | 146.371 | 46.071 | 38.166 | 1.00 | 43.36 |
| 174 | C | VAL | 38 | 144.916 | 43.870 | 35.349 | 1.00 | 52.33 |
| 175 | O | VAL | 38 | 145.142 | 42.656 | 35.348 | 1.00 | 48.70 |
| 176 | N | ALA | 39 | 143.858 | 44.412 | 34.752 | 1.00 | 49.41 |
| 177 | CA | ALA | 39 | 142.848 | 43.610 | 34.068 | 1.00 | 48.03 |
| 178 | CB | ALA | 39 | 141.722 | 44.502 | 33.584 | 1.00 | 56.98 |
| 179 | C | ALA | 39 | 143.434 | 42.823 | 32.900 | 1.00 | 47.68 |
| 180 | O | ALA | 39 | 143.178 | 41.627 | 32.759 | 1.00 | 52.03 |
| 181 | N | GLU | 40 | 144.219 | 43.501 | 32.068 | 1.00 | 46.51 |
| 182 | CA | GLU | 40 | 144.855 | 42.881 | 30.908 | 1.00 | 40.96 |
| 183 | CB | GLU | 40 | 145.507 | 43.952 | 30.036 | 1.00 | 49.36 |
| 184 | CG | GLU | 40 | 144.507 | 44.896 | 29.383 | 1.00 | 62.86 |
| 185 | CD | GLU | 40 | 145.161 | 46.109 | 28.745 | 1.00 | 67.78 |
| 186 | OE1 | GLU | 40 | 146.229 | 45.957 | 28.112 | 1.00 | 67.66 |
| 187 | OE2 | GLU | 40 | 144.601 | 47.218 | 28.880 | 1.00 | 70.01 |
| 188 | C | GLU | 40 | 145.893 | 41.852 | 31.337 | 1.00 | 38.90 |
| 189 | O | GLU | 40 | 146.076 | 40.832 | 30.678 | 1.00 | 39.36 |
| 190 | N | LYS | 41 | 146.569 | 42.135 | 32.447 | 1.00 | 41.55 |
| 191 | CA | LYS | 41 | 147.584 | 41.243 | 32.998 | 1.00 | 38.43 |
| 192 | CB | LYS | 41 | 148.219 | 41.884 | 34.236 | 1.00 | 43.42 |
| 193 | CG | LYS | 41 | 149.304 | 41.056 | 34.903 | 1.00 | 55.00 |
| 194 | CD | LYS | 41 | 149.864 | 41.780 | 36.119 | 1.00 | 61.88 |
| 195 | CE | LYS | 41 | 151.040 | 41.028 | 36.721 | 1.00 | 62.99 |
| 196 | NZ | LYS | 41 | 151.665 | 41.794 | 37.835 | 1.00 | 69.92 |
| 197 | C | LYS | 41 | 146.914 | 39.926 | 33.373 | 1.00 | 36.30 |
| 198 | O | LYS | 41 | 147.362 | 38.855 | 32.966 | 1.00 | 34.80 |
| 199 | N | TYR | 42 | 145.823 | 40.027 | 34.132 | 1.00 | 35.61 |
| 200 | CA | TYR | 42 | 145.051 | 38.868 | 34.572 | 1.00 | 29.43 |
| 201 | CB | TYR | 42 | 143.880 | 39.307 | 35.457 | 1.00 | 29.64 |
| 202 | CG | TYR | 42 | 144.229 | 39.658 | 36.890 | 1.00 | 30.55 |
| 203 | CD1 | TYR | 42 | 145.556 | 39.697 | 37.330 | 1.00 | 37.21 |
| 204 | CE1 | TYR | 42 | 145.866 | 40.002 | 38.660 | 1.00 | 37.30 |
| 205 | CD2 | TYR | 42 | 143.222 | 39.937 | 37.814 | 1.00 | 28.62 |
| 206 | CE2 | TYR | 42 | 143.519 | 40.241 | 39.139 | 1.00 | 37.07 |
| 207 | CZ | TYR | 42 | 144.839 | 40.272 | 39.556 | 1.00 | 40.82 |
| 208 | OH | TYR | 42 | 145.121 | 40.567 | 40.869 | 1.00 | 43.81 |
| 209 | C | TYR | 42 | 144.499 | 38.097 | 33.377 | 1.00 | 30.40 |
| 210 | O | TYR | 42 | 144.603 | 36.872 | 33.318 | 1.00 | 29.10 |
| 211 | N | ALA | 43 | 143.920 | 38.827 | 32.426 | 1.00 | 24.33 |
| 212 | CA | ALA | 43 | 143.340 | 38.227 | 31.227 | 1.00 | 29.09 |
| 213 | CB | ALA | 43 | 142.713 | 39.308 | 30.356 | 1.00 | 19.04 |
| 214 | C | ALA | 43 | 144.358 | 37.423 | 30.421 | 1.00 | 29.23 |
| 215 | O | ALA | 43 | 144.074 | 36.308 | 29.984 | 1.00 | 29.14 |
| 216 | N | LYS | 44 | 145.559 | 37.972 | 30.260 | 1.00 | 37.81 |
| 217 | CA | LYS | 44 | 146.637 | 37.371 | 29.491 | 1.00 | 40.64 |
| 218 | C | LYS | 44 | 147.069 | 36.041 | 30.095 | 1.00 | 34.80 |
| 219 | O | LYS | 44 | 147.221 | 35.048 | 29.357 | 1.00 | 35.25 |
| 220 | CB | LYS | 44 | 147.824 | 38.329 | 29.396 | 1.00 | 54.18 |
| 221 | CG | LYS | 44 | 149.001 | 37.784 | 28.605 | 1.00 | 67.03 |
| 222 | CD | LYS | 44 | 150.141 | 38.787 | 28.552 | 1.00 | 79.04 |
| 223 | CE | LYS | 44 | 151.313 | 38.247 | 27.750 | 1.00 | 20.00 |
| 224 | NZ | LYS | 44 | 152.431 | 39.227 | 27.673 | 1.00 | 20.00 |
| 225 | N | GLU | 45 | 147.332 | 36.000 | 31.397 | 1.00 | 31.47 |
| 226 | CA | GLU | 45 | 147.771 | 34.779 | 32.070 | 1.00 | 30.36 |
| 227 | CB | GLU | 45 | 148.288 | 35.080 | 33.480 | 1.00 | 26.58 |
| 228 | CG | GLU | 45 | 149.071 | 33.920 | 34.105 | 1.00 | 19.97 |
| 229 | CD | GLU | 45 | 149.394 | 34.128 | 35.580 | 1.00 | 33.35 |
| 230 | OE1 | GLU | 45 | 149.791 | 33.146 | 36.246 | 1.00 | 31.26 |
| 231 | OE2 | GLU | 45 | 149.249 | 35.264 | 36.080 | 1.00 | 37.21 |
| 232 | C | GLU | 45 | 146.649 | 33.767 | 32.142 | 1.00 | 31.64 |
| 233 | O | GLU | 45 | 146.902 | 32.545 | 32.058 | 1.00 | 38.67 |
| 234 | N | ILE | 46 | 145.415 | 34.225 | 32.299 | 1.00 | 34.27 |
| 235 | CA | ILE | 46 | 144.239 | 33.358 | 32.373 | 1.00 | 30.12 |
| 236 | CG1 | ILE | 46 | 142.942 | 34.181 | 32.608 | 1.00 | 33.74 |
| 237 | CG2 | ILE | 46 | 141.706 | 33.420 | 32.123 | 1.00 | 32.63 |
| 238 | CG1 | ILE | 46 | 142.812 | 34.534 | 34.093 | 1.00 | 34.26 |
| 239 | CD1 | ILE | 46 | 141.644 | 35.444 | 34.407 | 1.00 | 30.01 |
| 240 | C | ILE | 46 | 144.099 | 32.518 | 31.110 | 1.00 | 29.77 |
| 241 | O | ILE | 46 | 143.850 | 31.315 | 31.186 | 1.00 | 30.24 |
| 242 | N | GLU | 47 | 144.283 | 33.156 | 29.956 | 1.00 | 31.42 |
| 243 | CA | GLU | 47 | 144.185 | 32.482 | 28.666 | 1.00 | 37.34 |
| 244 | GB | GLU | 47 | 144.460 | 33.476 | 27.537 | 1.00 | 45.72 |
| 245 | CG | GLU | 47 | 144.290 | 32.896 | 26.137 | 1.00 | 68.61 |
| 246 | CD | GLU | 47 | 144.808 | 33.813 | 25.035 | 1.00 | 79.62 |
| 247 | OE1 | GLU | 47 | 145.302 | 34.922 | 25.339 | 1.00 | 89.55 |
| 248 | OE2 | GLU | 47 | 144.728 | 33.417 | 23.852 | 1.00 | 86.41 |
| 249 | C | GLU | 47 | 145.169 | 31.314 | 28.580 | 1.00 | 37.12 |
| 250 | O | GLU | 47 | 144.860 | 30.275 | 27.997 | 1.00 | 45.60 |
| 251 | N | ALA | 48 | 146.348 | 31.492 | 29.171 | 1.00 | 33.83 |
| 252 | CA | ALA | 48 | 147.378 | 30.459 | 29.170 | 1.00 | 30.76 |
| 253 | CB | ALA | 48 | 148.720 | 31.054 | 29.575 | 1.00 | 33.78 |
| 254 | C | ALA | 48 | 146.986 | 29.323 | 30.110 | 1.00 | 30.08 |
| 255 | O | ALA | 48 | 147.071 | 28.150 | 29.743 | 1.00 | 30.80 |
| 256 | N | LEU | 49 | 146.542 | 29.685 | 31.312 | 1.00 | 27.01 |
| 257 | CA | LEU | 49 | 146.110 | 28.720 | 32.321 | 1.00 | 23.68 |
| 258 | CB | LEU | 49 | 145.793 | 29.445 | 33.628 | 1.00 | 19.74 |
| 259 | CG | LEU | 49 | 146.936 | 30.167 | 34.337 | 1.00 | 15.12 |
| 260 | CD1 | LEU | 49 | 146.368 | 31.161 | 35.328 | 1.00 | 8.67 |
| 261 | CD2 | LEU | 49 | 147.844 | 29.164 | 35.033 | 1.00 | 12.64 |
| 262 | C | LEU | 49 | 144.862 | 27.985 | 31.836 | 1.00 | 24.27 |
| 263 | O | LEU | 49 | 144.610 | 26.842 | 32.214 | 1.00 | 31.26 |
| 264 | N | LYS | 50 | 144.101 | 28.663 | 30.983 | 1.00 | 27.77 |
| 265 | CA | LYS | 50 | 142.863 | 28.154 | 30.394 | 1.00 | 30.88 |
| 266 | CB | LYS | 50 | 142.247 | 29.263 | 29.548 | 1.00 | 31.45 |
| 267 | CG | LYS | 50 | 140.775 | 29.153 | 29.242 | 1.00 | 31.65 |
| 268 | CD | LYS | 50 | 140.333 | 30.468 | 28.621 | 1.00 | 33.98 |
| 269 | CE | LYS | 50 | 138.871 | 30.468 | 28.250 | 1.00 | 42.53 |
| 270 | NZ | LYS | 50 | 138.455 | 31.817 | 27.773 | 1.00 | 47.24 |
| 271 | C | LYS | 50 | 143.120 | 26.925 | 29.527 | 1.00 | 32.84 |
| 272 | O | LYS | 50 | 142.449 | 25.901 | 29.675 | 1.00 | 31.46 |
| 273 | N | GLU | 51 | 144.092 | 27.033 | 28.625 | 1.00 | 33.57 |
| 274 | CA | GLU | 51 | 144.439 | 25.927 | 27.741 | 1.00 | 38.44 |
| 275 | CB | GLU | 51 | 145.286 | 26.416 | 26.566 | 1.00 | 45.31 |
| 276 | CG | GLU | 51 | 145.241 | 25.501 | 25.339 | 1.00 | 54.99 |
| 277 | CD | GLU | 51 | 143.953 | 25.633 | 24.532 | 1.00 | 61.58 |
| 278 | OE1 | GLU | 51 | 143.086 | 26.463 | 24.893 | 1.00 | 63.41 |
| 279 | OE2 | GLU | 51 | 143.815 | 24.912 | 23.519 | 1.00 | 63.99 |
| 280 | C | GLU | 51 | 145.179 | 24.824 | 28.501 | 1.00 | 37.86 |
| 281 | O | GLU | 51 | 145.145 | 23.662 | 28.097 | 1.00 | 43.06 |
| 282 | N | GLN | 52 | 145.867 | 25.192 | 29.582 | 1.00 | 36.20 |
| 283 | CA | GLN | 52 | 146.592 | 24.212 | 30.397 | 1.00 | 38.10 |
| 284 | GB | GLN | 52 | 147.453 | 24.897 | 31.465 | 1.00 | 41.72 |
| 285 | CG | GLN | 52 | 148.691 | 25.615 | 30.943 | 1.00 | 47.34 |
| 286 | CD | GLN | 52 | 149.505 | 26.249 | 32.061 | 1.00 | 49.46 |
| 287 | OE1 | GLN | 52 | 149.640 | 25.683 | 33.145 | 1.00 | 43.98 |
| 288 | NE2 | GLN | 52 | 150.049 | 27.438 | 31.799 | 1.00 | 53.90 |
| 289 | C | GLN | 52 | 145.563 | 23.339 | 31.093 | 1.00 | 38.87 |
| 290 | O | GLN | 52 | 145.732 | 22.122 | 31.219 | 1.00 | 40.47 |
| 291 | N | THR | 53 | 144.501 | 23.991 | 31.554 | 1.00 | 37.87 |
| 292 | CA | THR | 53 | 143.407 | 23.323 | 32.236 | 1.00 | 32.77 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 293 | CB | THR | 53 | 142.541 | 24.347 | 32.992 | 1.00 | 31.08 |
| 294 | OG1 | THR | 53 | 143.315 | 24.933 | 34.050 | 1.00 | 28.04 |
| 295 | CG2 | THR | 53 | 141.296 | 23.685 | 33.569 | 1.00 | 32.90 |
| 296 | C | THR | 53 | 142.570 | 22.522 | 31.233 | 1.00 | 32.05 |
| 297 | O | THR | 53 | 142.013 | 21.476 | 31.573 | 1.00 | 29.73 |
| 298 | N | ARG | 54 | 142.529 | 22.992 | 29.988 | 1.00 | 28.01 |
| 299 | CA | ARG | 54 | 141.785 | 22.312 | 28.933 | 1.00 | 23.69 |
| 300 | CB | ARG | 54 | 141.723 | 23.176 | 27.673 | 1.00 | 23.31 |
| 301 | CG | ARG | 54 | 140.724 | 22.682 | 26.633 | 1.00 | 24.23 |
| 302 | CD | ARG | 54 | 140.755 | 23.527 | 25.360 | 1.00 | 30.78 |
| 303 | NE | ARG | 54 | 140.674 | 24.969 | 25.619 | 1.00 | 45.26 |
| 304 | CZ | ARG | 54 | 139.564 | 25.633 | 25.942 | 1.00 | 46.57 |
| 305 | NH1 | ARG | 54 | 138.405 | 24.999 | 26.058 | 1.00 | 51.75 |
| 306 | NH2 | ARG | 54 | 139.608 | 26.946 | 26.140 | 1.00 | 43.00 |
| 307 | C | ARG | 54 | 142.487 | 20.998 | 28.617 | 1.00 | 30.27 |
| 308 | O | ARG | 54 | 141.842 | 19.955 | 28.479 | 1.00 | 33.41 |
| 309 | N | ASN | 55 | 143.821 | 21.050 | 28.526 | 1.00 | 33.72 |
| 310 | CA | ASN | 55 | 144.648 | 19.899 | 28.240 | 1.00 | 33.22 |
| 311 | C | ASN | 55 | 144.538 | 18.872 | 29.348 | 1.00 | 35.28 |
| 312 | O | ASN | 55 | 144.679 | 17.660 | 29.105 | 1.00 | 35.19 |
| 313 | CB | ASN | 55 | 146.080 | 20.341 | 27.963 | 1.00 | 36.29 |
| 314 | CG | ASN | 55 | 146.150 | 21.264 | 26.761 | 1.00 | 20.00 |
| 315 | OD1 | ASN | 55 | 145.473 | 21.038 | 25.754 | 1.00 | 20.00 |
| 316 | ND2 | ASN | 55 | 146.963 | 22.307 | 26.857 | 1.00 | 20.00 |
| 317 | N | MET | 56 | 144.309 | 19.330 | 30.581 | 1.00 | 34.89 |
| 318 | CA | MET | 56 | 144.150 | 18.442 | 31.734 | 1.00 | 34.60 |
| 319 | CB | MET | 56 | 144.058 | 19.241 | 33.039 | 1.00 | 27.26 |
| 320 | CG | MET | 56 | 145.378 | 19.792 | 33.544 | 1.00 | 38.81 |
| 321 | SD | MET | 56 | 145.237 | 20.594 | 35.159 | 1.00 | 40.35 |
| 322 | CE | MET | 56 | 145.790 | 22.242 | 34.734 | 1.00 | 41.02 |
| 323 | C | MET | 56 | 142.880 | 17.606 | 31.560 | 1.00 | 38.38 |
| 324 | O | MET | 56 | 142.871 | 16.406 | 31.847 | 1.00 | 36.10 |
| 325 | N | LEU | 57 | 141.816 | 18.253 | 31.084 | 1.00 | 33.14 |
| 326 | CA | LEU | 57 | 140.535 | 17.593 | 30.852 | 1.00 | 33.61 |
| 327 | CB | LEU | 57 | 139.444 | 18.633 | 30.566 | 1.00 | 24.13 |
| 328 | CG | LEU | 57 | 138.939 | 19.472 | 31.742 | 1.00 | 25.14 |
| 329 | CD1 | LEU | 57 | 138.092 | 20.624 | 31.235 | 1.00 | 18.69 |
| 330 | CD2 | LEU | 57 | 138.143 | 18.604 | 32.703 | 1.00 | 10.16 |
| 331 | C | LEU | 57 | 140.610 | 16.611 | 29.686 | 1.00 | 37.09 |
| 332 | O | LEU | 57 | 139.922 | 15.588 | 29.679 | 1.00 | 34.95 |
| 333 | N | LEU | 58 | 141.453 | 16.924 | 28.703 | 1.00 | 35.34 |
| 334 | CA | LEU | 58 | 141.605 | 16.071 | 27.533 | 1.00 | 35.75 |
| 335 | CB | LEU | 58 | 141.930 | 16.926 | 26.304 | 1.00 | 33.37 |
| 336 | CG | LEU | 58 | 140.886 | 17.987 | 25.951 | 1.00 | 36.57 |
| 337 | CD1 | LEU | 58 | 141.334 | 18.779 | 24.736 | 1.00 | 34.54 |
| 338 | CD2 | LEU | 58 | 139.540 | 17.333 | 25.691 | 1.00 | 38.57 |
| 339 | C | LEU | 58 | 142.628 | 14.946 | 27.688 | 1.00 | 40.17 |
| 340 | O | LEU | 58 | 143.001 | 14.298 | 26.710 | 1.00 | 38.69 |
| 341 | N | ALA | 59 | 143.066 | 14.697 | 28.922 | 1.00 | 45.53 |
| 342 | CA | ALA | 59 | 144.038 | 13.637 | 29.198 | 1.00 | 52.73 |
| 343 | CB | ALA | 59 | 144.562 | 13.754 | 30.626 | 1.00 | 52.29 |
| 344 | C | ALA | 59 | 143.402 | 12.263 | 28.950 | 1.00 | 60.58 |
| 345 | O | ALA | 59 | 142.320 | 11.962 | 29.450 | 1.00 | 62.17 |
| 346 | N | THR | 60 | 144.084 | 11.432 | 28.168 | 1.00 | 63.55 |
| 347 | CA | THR | 60 | 143.575 | 10.109 | 27.794 | 1.00 | 63.50 |
| 348 | CB | THR | 60 | 144.405 | 9.528 | 26.641 | 1.00 | 63.61 |
| 349 | OG1 | THR | 60 | 145.776 | 9.434 | 27.039 | 1.00 | 67.85 |
| 350 | CG2 | THR | 60 | 144.302 | 10.426 | 25.420 | 1.00 | 59.57 |
| 351 | C | THR | 60 | 143.372 | 9.004 | 28.844 | 1.00 | 64.51 |
| 352 | O | THR | 60 | 142.237 | 8.681 | 29.198 | 1.00 | 69.94 |
| 353 | N | GLY | 61 | 144.470 | 8.435 | 29.337 | 1.00 | 59.72 |
| 354 | CA | GLY | 61 | 144.394 | 7.339 | 30.294 | 1.00 | 59.70 |
| 355 | C | GLY | 61 | 144.087 | 7.572 | 31.767 | 1.00 | 60.15 |
| 356 | O | GLY | 61 | 144.627 | 6.862 | 32.620 | 1.00 | 62.75 |
| 357 | N | MET | 62 | 143.233 | 8.546 | 32.098 | 1.00 | 62.09 |
| 358 | CA | MET | 62 | 142.904 | 8.860 | 33.482 | 1.00 | 62.20 |
| 359 | C | MET | 62 | 141.787 | 7.962 | 34.001 | 1.00 | 57.87 |
| 360 | O | MET | 62 | 140.858 | 7.592 | 33.304 | 1.00 | 60.93 |
| 361 | CB | MET | 62 | 142.512 | 10.333 | 33.619 | 1.00 | 65.78 |
| 362 | CG | MET | 62 | 142.374 | 10.806 | 35.057 | 1.00 | 71.62 |
| 363 | SD | MET | 62 | 141.924 | 12.547 | 35.177 | 1.00 | 20.00 |
| 364 | CE | MET | 62 | 141.630 | 12.940 | 33.455 | 1.00 | 20.00 |
| 365 | N | LYS | 63 | 141.877 | 7.621 | 35.308 | 1.00 | 53.67 |
| 366 | CA | LYS | 63 | 140.886 | 6.787 | 35.975 | 1.00 | 51.44 |
| 367 | CB | LYS | 63 | 141.401 | 6.323 | 37.342 | 1.00 | 55.26 |
| 368 | CG | LYS | 63 | 142.607 | 5.402 | 37.287 | 1.00 | 65.11 |
| 369 | CD | LYS | 63 | 142.968 | 4.915 | 38.682 | 1.00 | 69.24 |
| 370 | CE | LYS | 63 | 144.127 | 3.936 | 38.635 | 1.00 | 76.58 |
| 371 | NZ | LYS | 63 | 144.434 | 3.376 | 39.980 | 1.00 | 78.96 |
| 372 | C | LYS | 63 | 139.576 | 7.543 | 36.173 | 1.00 | 48.71 |
| 373 | O | LYS | 63 | 139.559 | 8.778 | 36.167 | 1.00 | 48.30 |
| 374 | N | LEU | 64 | 138.490 | 6.802 | 36.386 | 1.00 | 44.07 |
| 375 | CA | LEU | 64 | 137.182 | 7.413 | 36.586 | 1.00 | 38.53 |
| 376 | CB | LEU | 64 | 136.100 | 6.343 | 36.778 | 1.00 | 40.14 |
| 377 | CG | LEU | 64 | 134.671 | 6.886 | 36.899 | 1.00 | 35.60 |
| 378 | CD1 | LEU | 64 | 134.283 | 7.589 | 35.606 | 1.00 | 32.53 |
| 379 | CD2 | LEU | 64 | 133.689 | 5.773 | 37.203 | 1.00 | 30.12 |
| 380 | C | LEU | 64 | 137.184 | 8.363 | 37.778 | 1.00 | 32.66 |
| 381 | O | LEU | 64 | 136.773 | 9.515 | 37.650 | 1.00 | 32.91 |
| 382 | N | ALA | 65 | 137.664 | 7.881 | 38.923 | 1.00 | 26.30 |
| 383 | CA | ALA | 65 | 137.721 | 8.683 | 40.141 | 1.00 | 27.29 |
| 384 | CB | ALA | 65 | 138.362 | 7.885 | 41.265 | 1.00 | 26.12 |
| 385 | C | ALA | 65 | 138.482 | 9.988 | 39.919 | 1.00 | 33.96 |
| 386 | O | ALA | 65 | 138.019 | 11.057 | 40.318 | 1.00 | 35.01 |
| 387 | N | ASP | 66 | 139.630 | 9.897 | 39.250 | 1.00 | 35.46 |
| 388 | CA | ASP | 66 | 140.459 | 11.064 | 38.961 | 1.00 | 35.10 |
| 389 | CB | ASP | 66 | 141.776 | 10.646 | 38.298 | 1.00 | 36.60 |
| 390 | CG | ASP | 66 | 142.685 | 9.867 | 39.229 | 1.00 | 34.65 |
| 391 | OD1 | ASP | 66 | 142.611 | 10.067 | 40.461 | 1.00 | 25.86 |
| 392 | OD2 | ASP | 66 | 143.488 | 9.057 | 38.717 | 1.00 | 44.77 |
| 393 | C | ASP | 66 | 139.746 | 12.065 | 38.059 | 1.00 | 31.14 |
| 394 | O | ASP | 66 | 139.846 | 13.276 | 38.266 | 1.00 | 31.51 |
| 395 | N | THR | 67 | 139.045 | 11.552 | 37.051 | 1.00 | 26.69 |
| 396 | CA | THR | 67 | 138.316 | 12.392 | 36.105 | 1.00 | 26.40 |
| 397 | CB | THR | 67 | 137.793 | 11.571 | 34.918 | 1.00 | 25.70 |
| 398 | OG1 | THR | 67 | 138.891 | 10.917 | 34.270 | 1.00 | 27.33 |
| 399 | CG2 | THR | 67 | 137.095 | 12.474 | 33.918 | 1.00 | 28.90 |
| 400 | C | THR | 67 | 137.146 | 13.113 | 36.769 | 1.00 | 24.73 |
| 401 | O | THR | 67 | 136.899 | 14.290 | 36.502 | 1.00 | 27.41 |
| 402 | N | LEU | 68 | 136.425 | 12.401 | 37.629 | 1.00 | 23.13 |
| 403 | CA | LEU | 68 | 135.295 | 12.985 | 38.333 | 1.00 | 18.00 |
| 404 | CB | LEU | 68 | 134.504 | 11.909 | 39.078 | 1.00 | 13.23 |
| 405 | CG | LEU | 68 | 133.804 | 10.871 | 38.201 | 1.00 | 16.24 |
| 406 | CD1 | LEU | 68 | 133.109 | 9.843 | 39.078 | 1.00 | 17.55 |
| 407 | CD2 | LEU | 68 | 132.811 | 11.552 | 37.272 | 1.00 | 7.96 |
| 408 | C | LEU | 68 | 135.787 | 14.047 | 39.305 | 1.00 | 19.40 |
| 409 | O | LEU | 68 | 135.181 | 15.113 | 39.420 | 1.00 | 21.96 |
| 410 | N | ASN | 69 | 136.899 | 13.766 | 39.980 | 1.00 | 17.72 |
| 411 | CA | ASN | 69 | 137.471 | 14.714 | 40.931 | 1.00 | 23.29 |
| 412 | CB | ASN | 69 | 138.608 | 14.071 | 41.728 | 1.00 | 27.45 |
| 413 | CG | ASN | 69 | 138.102 | 13.102 | 42.783 | 1.00 | 44.15 |
| 414 | OD1 | ASN | 69 | 137.171 | 13.413 | 43.530 | 1.00 | 45.05 |
| 415 | ND2 | ASN | 69 | 138.709 | 11.921 | 42.846 | 1.00 | 48.60 |
| 416 | C | ASN | 69 | 137.954 | 15.985 | 40.240 | 1.00 | 21.73 |
| 417 | O | ASN | 69 | 137.784 | 17.083 | 40.764 | 1.00 | 19.56 |
| 418 | N | LEU | 70 | 138.526 | 15.834 | 39.050 | 1.00 | 19.22 |
| 419 | CA | LEU | 70 | 139.012 | 16.979 | 38.293 | 1.00 | 18.06 |
| 420 | CB | LEU | 70 | 139.736 | 16.522 | 37.025 | 1.00 | 14.83 |
| 421 | CG | LEU | 70 | 140.274 | 17.650 | 36.141 | 1.00 | 18.22 |
| 422 | CD1 | LEU | 70 | 141.330 | 18.440 | 36.889 | 1.00 | 15.05 |
| 423 | CD2 | LEU | 70 | 140.845 | 17.078 | 34.862 | 1.00 | 20.94 |
| 424 | C | LEU | 70 | 137.835 | 17.871 | 37.925 | 1.00 | 20.53 |
| 425 | O | LEU | 70 | 137.844 | 19.069 | 38.212 | 1.00 | 23.73 |
| 426 | N | ILE | 71 | 136.817 | 17.269 | 37.312 | 1.00 | 19.75 |
| 427 | CA | ILE | 71 | 135.613 | 17.986 | 36.901 | 1.00 | 16.33 |
| 428 | CB | ILE | 71 | 134.617 | 17.043 | 36.184 | 1.00 | 19.20 |
| 429 | CG2 | ILE | 71 | 133.278 | 17.744 | 35.950 | 1.00 | 17.41 |
| 430 | CG1 | ILE | 71 | 135.216 | 16.574 | 34.856 | 1.00 | 25.29 |
| 431 | CD1 | ILE | 71 | 134.273 | 15.748 | 34.009 | 1.00 | 21.71 |
| 432 | C | ILE | 71 | 134.927 | 18.661 | 38.088 | 1.00 | 15.45 |
| 433 | O | ILE | 71 | 134.507 | 19.813 | 37.991 | 1.00 | 10.60 |
| 434 | N | ASP | 72 | 134.846 | 17.952 | 39.212 | 1.00 | 14.16 |
| 435 | CA | ASP | 72 | 134.222 | 18.477 | 40.425 | 1.00 | 13.13 |
| 436 | CB | ASP | 72 | 134.206 | 17.400 | 41.516 | 1.00 | 9.28 |
| 437 | OG | ASP | 72 | 133.456 | 17.828 | 42.766 | 1.00 | 8.19 |
| 438 | OD1 | ASP | 72 | 132.472 | 18.591 | 42.660 | 1.00 | 19.56 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 439 | OD2 | ASP | 72 | 133.842 | 17.381 | 43.865 | 1.00 | 24.87 |
| 440 | C | ASP | 72 | 134.969 | 19.709 | 40.926 | 1.00 | 20.93 |
| 441 | O | ASP | 72 | 134.357 | 20.734 | 41.230 | 1.00 | 31.87 |
| 442 | N | THR | 73 | 136.298 | 19.618 | 40.980 | 1.00 | 26.21 |
| 443 | CA | THR | 73 | 137.162 | 20.689 | 41.452 | 1.00 | 17.72 |
| 444 | C | THR | 73 | 137.051 | 21.912 | 40.558 | 1.00 | 16.99 |
| 445 | O | THR | 73 | 136.913 | 23.046 | 41.054 | 1.00 | 15.04 |
| 446 | O8 | THR | 73 | 138.627 | 20.258 | 41.508 | 1.00 | 18.68 |
| 447 | OG1 | THR | 73 | 138.771 | 19.152 | 42.406 | 1.00 | 20.00 |
| 448 | CG2 | THR | 73 | 139.503 | 21.413 | 41.971 | 1.00 | 23.27 |
| 449 | N | ILE | 74 | 137.124 | 21.732 | 39.245 | 1.00 | 13.35 |
| 450 | CA | ILE | 74 | 137.024 | 22.837 | 38.298 | 1.00 | 15.24 |
| 451 | CB | ILE | 74 | 137.214 | 22.342 | 36.844 | 1.00 | 17.48 |
| 452 | CG2 | ILE | 74 | 136.841 | 23.434 | 35.843 | 1.00 | 10.21 |
| 453 | CG1 | ILE | 74 | 138.658 | 21.881 | 36.637 | 1.00 | 16.00 |
| 454 | CD1 | ILE | 74 | 138.936 | 21.335 | 35.253 | 1.00 | 19.68 |
| 455 | C | ILE | 74 | 135.677 | 23.554 | 38.431 | 1.00 | 21.97 |
| 456 | O | ILE | 74 | 135.603 | 24.774 | 38.285 | 1.00 | 37.27 |
| 457 | N | GLU | 75 | 134.620 | 22.793 | 38.712 | 1.00 | 24.94 |
| 458 | CA | GLU | 75 | 133.283 | 23.362 | 38.869 | 1.00 | 17.86 |
| 459 | CB | GLU | 75 | 132.216 | 22.266 | 38.893 | 1.00 | 22.45 |
| 460 | CG | GLU | 75 | 131.998 | 21.565 | 37.557 | 1.00 | 23.19 |
| 461 | CD | GLU | 75 | 130.753 | 20.685 | 37.539 | 1.00 | 24.24 |
| 462 | OE1 | GLU | 75 | 130.485 | 19.984 | 38.540 | 1.00 | 11.68 |
| 463 | OE2 | GLU | 75 | 130.041 | 20.699 | 36.513 | 1.00 | 19.29 |
| 464 | C | GLU | 75 | 133.194 | 24.181 | 40.142 | 1.00 | 16.49 |
| 465 | O | GLU | 75 | 132.739 | 25.323 | 40.119 | 1.00 | 18.93 |
| 466 | N | ARG | 76 | 133.640 | 23.590 | 41.248 | 1.00 | 11.73 |
| 467 | CA | ARG | 76 | 133.626 | 24.248 | 42.552 | 1.00 | 15.45 |
| 468 | CB | ARG | 76 | 134.114 | 23.282 | 43.636 | 1.00 | 7.10 |
| 469 | CG | ARG | 76 | 133.198 | 22.097 | 43.899 | 1.00 | 15.61 |
| 470 | CD | ARG | 76 | 133.785 | 21.197 | 44.975 | 1.00 | 12.16 |
| 471 | NE | ARG | 76 | 132.824 | 20.231 | 45.508 | 1.00 | 16.00 |
| 472 | CZ | ARG | 76 | 132.467 | 20.165 | 46.789 | 1.00 | 19.23 |
| 473 | NH1 | ARG | 76 | 132.982 | 21.010 | 47.670 | 1.00 | 26.80 |
| 474 | NH2 | ARG | 76 | 131.618 | 19.234 | 47.202 | 1.00 | 29.06 |
| 475 | C | ARG | 76 | 134.486 | 25.519 | 42.564 | 1.00 | 20.45 |
| 476 | O | ARG | 76 | 134.214 | 26.454 | 43.319 | 1.00 | 19.47 |
| 477 | N | LEU | 77 | 135.525 | 25.539 | 41.732 | 1.00 | 20.12 |
| 478 | CA | LEU | 77 | 136.419 | 26.692 | 41.634 | 1.00 | 19.40 |
| 479 | CB | LEU | 77 | 137.756 | 26.281 | 41.014 | 1.00 | 12.91 |
| 480 | CG | LEU | 77 | 138.678 | 25.382 | 41.843 | 1.00 | 12.12 |
| 481 | CD1 | LEU | 77 | 139.825 | 24.903 | 40.973 | 1.00 | 2.00 |
| 482 | CD2 | LEU | 77 | 139.201 | 26.125 | 43.070 | 1.00 | 4.07 |
| 483 | C | LEU | 77 | 135.796 | 27.823 | 40.818 | 1.00 | 22.31 |
| 484 | O | LEU | 77 | 136.374 | 28.906 | 40.702 | 1.00 | 30.09 |
| 485 | N | GLY | 78 | 134.628 | 27.551 | 40.238 | 1.00 | 26.16 |
| 486 | CA | GLY | 78 | 133.915 | 28.542 | 39.447 | 1.00 | 20.26 |
| 487 | C | GLY | 78 | 134.496 | 28.855 | 38.082 | 1.00 | 16.66 |
| 488 | O | GLY | 78 | 134.185 | 29.898 | 37.504 | 1.00 | 19.22 |
| 489 | N | ILE | 79 | 135.323 | 27.959 | 37.553 | 1.00 | 13.23 |
| 490 | CA | ILE | 79 | 135.938 | 28.179 | 36.247 | 1.00 | 16.00 |
| 491 | CB | ILE | 79 | 137.488 | 28.083 | 36.321 | 1.00 | 14.32 |
| 492 | CG2 | ILE | 79 | 138.055 | 29.257 | 37.111 | 1.00 | 9.65 |
| 493 | CG1 | ILE | 79 | 137.909 | 26.751 | 36.944 | 1.00 | 15.84 |
| 494 | CD1 | ILE | 79 | 139.413 | 26.574 | 37.082 | 1.00 | 20.69 |
| 495 | C | ILE | 79 | 135.420 | 27.216 | 35.185 | 1.00 | 17.13 |
| 496 | O | ILE | 79 | 135.860 | 27.256 | 34.033 | 1.00 | 20.55 |
| 497 | N | SER | 80 | 134.459 | 26.377 | 35.567 | 1.00 | 21.41 |
| 498 | CA | SER | 80 | 133.878 | 25.392 | 34.654 | 1.00 | 23.76 |
| 499 | CB | SER | 80 | 133.004 | 24.393 | 35.419 | 1.00 | 20.88 |
| 500 | OG | SER | 80 | 131.996 | 25.047 | 36.170 | 1.00 | 23.54 |
| 501 | C | SER | 30 | 133.093 | 25.997 | 33.485 | 1.00 | 20.44 |
| 502 | O | SER | 80 | 132.839 | 25.280 | 32.505 | 1.00 | 28.56 |
| 503 | N | TYR | 81 | 132.723 | 27.252 | 33.577 | 1.00 | 18.39 |
| 504 | CA | TYR | 81 | 131.972 | 27.907 | 32.507 | 1.00 | 19.66 |
| 505 | CB | TYR | 81 | 131.389 | 29.244 | 32.986 | 1.00 | 10.58 |
| 506 | CG | TYR | 81 | 132.396 | 30.362 | 33.170 | 1.00 | 19.55 |
| 507 | CD1 | TYR | 81 | 132.635 | 31.285 | 32.151 | 1.00 | 26.56 |
| 508 | CE1 | TYR | 81 | 133.540 | 32.331 | 32.320 | 1.00 | 23.18 |
| 509 | CD2 | TYR | 81 | 133.092 | 30.513 | 34.367 | 1.00 | 12.72 |
| 510 | CE2 | TYR | 81 | 133.998 | 31.555 | 34.546 | 1.00 | 18.75 |
| 511 | CZ | TYR | 81 | 134.218 | 32.460 | 33.519 | 1.00 | 21.59 |
| 512 | OH | TYR | 81 | 135.122 | 33.487 | 33.688 | 1.00 | 23.90 |
| 513 | C | TYR | 81 | 132.814 | 28.103 | 31.240 | 1.00 | 23.33 |
| 514 | O | TYR | 81 | 132.294 | 28.498 | 30.195 | 1.00 | 26.36 |
| 515 | N | HIS | 82 | 134.114 | 27.835 | 31.352 | 1.00 | 27.33 |
| 516 | CA | HIS | 82 | 135.044 | 27.955 | 30.229 | 1.00 | 28.77 |
| 517 | CB | HIS | 82 | 136.471 | 28.227 | 30.724 | 1.00 | 20.70 |
| 518 | CG | HIS | 82 | 136.676 | 29.592 | 31.301 | 1.00 | 18.33 |
| 519 | CD2 | HIS | 82 | 137.002 | 29.989 | 32.553 | 1.00 | 7.90 |
| 520 | ND1 | HIS | 82 | 136.574 | 30.742 | 30.548 | 1.00 | 14.62 |
| 521 | CE1 | HIS | 82 | 136.829 | 31.788 | 31.312 | 1.00 | 11.77 |
| 522 | NE2 | HIS | 82 | 137.091 | 31.359 | 32.533 | 1.00 | 13.85 |
| 523 | C | HIS | 82 | 135.085 | 26.654 | 29.440 | 1.00 | 28.78 |
| 524 | O | HIS | 82 | 135.456 | 26.643 | 28.265 | 1.00 | 31.36 |
| 525 | N | PHE | 83 | 134.719 | 25.557 | 30.098 | 1.00 | 30.57 |
| 526 | CA | PHE | 83 | 134.774 | 24.241 | 29.475 | 1.00 | 32.99 |
| 527 | CB | PHE | 83 | 135.829 | 23.389 | 30.191 | 1.00 | 38.74 |
| 528 | CG | PHE | 83 | 137.052 | 24.157 | 30.603 | 1.00 | 40.58 |
| 529 | CD1 | PHE | 83 | 137.204 | 24.583 | 31.921 | 1.00 | 40.06 |
| 530 | CD2 | PHE | 83 | 138.041 | 24.476 | 29.675 | 1.00 | 41.50 |
| 531 | CE1 | PHE | 83 | 138.320 | 25.318 | 32.309 | 1.00 | 43.27 |
| 532 | CE2 | PHE | 83 | 139.163 | 25.211 | 30.050 | 1.00 | 38.18 |
| 533 | CZ | PHE | 83 | 139.303 | 25.634 | 31.371 | 1.00 | 46.92 |
| 534 | C | PHE | 83 | 133.444 | 23.496 | 29.471 | 1.00 | 32.87 |
| 535 | O | PHE | 83 | 133.378 | 22.340 | 29.886 | 1.00 | 31.33 |
| 536 | N | GLU | 84 | 132.397 | 24.133 | 28.960 | 1.00 | 33.76 |
| 537 | CA | GLU | 84 | 131.086 | 23.496 | 28.929 | 1.00 | 38.03 |
| 538 | CB | GLU | 84 | 129.991 | 24.514 | 28.601 | 1.00 | 47.83 |
| 539 | CG | GLU | 84 | 129.901 | 25.690 | 29.578 | 1.00 | 58.57 |
| 540 | CD | GLU | 84 | 129.403 | 25.312 | 30.975 | 1.00 | 69.66 |
| 541 | OE1 | GLU | 84 | 129.719 | 24.208 | 31.479 | 1.00 | 74.44 |
| 542 | OE2 | GLU | 84 | 128.695 | 26.146 | 31.586 | 1.00 | 66.21 |
| 543 | C | GLU | 84 | 131.030 | 22.314 | 27.966 | 1.00 | 39.30 |
| 544 | O | GLU | 84 | 130.339 | 21.328 | 28.228 | 1.00 | 37.93 |
| 545 | N | LYS | 85 | 131.780 | 22.401 | 26.872 | 1.00 | 37.65 |
| 546 | CA | LYS | 85 | 131.815 | 21.329 | 25.886 | 1.00 | 40.19 |
| 547 | CB | LYS | 85 | 132.367 | 21.839 | 24.551 | 1.00 | 49.51 |
| 548 | CG | LYS | 85 | 132.443 | 20.770 | 23.469 | 1.00 | 57.11 |
| 549 | CD | LYS | 85 | 133.176 | 21.261 | 22.237 | 1.00 | 73.34 |
| 550 | CE | LYS | 85 | 133.280 | 20.160 | 21.180 | 1.00 | 81.58 |
| 551 | NZ | LYS | 85 | 134.029 | 20.532 | 19.952 | 1.00 | 94.03 |
| 552 | C | LYS | 85 | 132.661 | 20.161 | 26.381 | 1.00 | 37.98 |
| 553 | O | LYS | 85 | 132.200 | 19.018 | 28.404 | 1.00 | 43.86 |
| 554 | N | GLU | 86 | 133.894 | 20.461 | 26.784 | 1.00 | 36.06 |
| 555 | CA | GLU | 86 | 134.825 | 19.448 | 27.277 | 1.00 | 32.72 |
| 556 | CB | GLU | 86 | 136.122 | 20.102 | 27.774 | 1.00 | 36.71 |
| 557 | CG | GLU | 86 | 136.998 | 20.743 | 26.698 | 1.00 | 42.45 |
| 558 | CD | GLU | 86 | 136.500 | 22.103 | 26.219 | 1.00 | 44.54 |
| 559 | OE1 | GLU | 86 | 135.646 | 22.720 | 26.891 | 1.00 | 49.68 |
| 560 | OE2 | GLU | 86 | 136.977 | 22.566 | 25.162 | 1.00 | 47.77 |
| 561 | C | GLU | 86 | 134.213 | 18.618 | 28.402 | 1.00 | 29.96 |
| 562 | O | GLU | 86 | 134.254 | 17.389 | 28.370 | 1.00 | 32.06 |
| 563 | N | ILE | 87 | 133.638 | 19.303 | 29.388 | 1.00 | 28.21 |
| 564 | CA | ILE | 87 | 133.013 | 18.648 | 30.534 | 1.00 | 27.11 |
| 565 | CB | ILE | 87 | 132.618 | 19.672 | 31.617 | 1.00 | 28.37 |
| 566 | CG2 | ILE | 87 | 131.813 | 18.996 | 32.729 | 1.00 | 28.34 |
| 567 | CG1 | ILE | 87 | 133.880 | 20.338 | 32.179 | 1.00 | 22.12 |
| 568 | CD1 | ILE | 87 | 133.613 | 21.386 | 33.241 | 1.00 | 21.16 |
| 569 | C | ILE | 87 | 131.795 | 17.815 | 30.150 | 1.00 | 27.00 |
| 570 | O | ILE | 87 | 131.581 | 16.735 | 30.700 | 1.00 | 29.31 |
| 571 | N | ASP | 88 | 131.007 | 18.309 | 29.200 | 1.00 | 31.52 |
| 572 | CA | ASP | 88 | 129.815 | 17.593 | 28.751 | 1.00 | 39.20 |
| 573 | CB | ASP | 88 | 129.009 | 18.445 | 27.764 | 1.00 | 40.43 |
| 574 | CG | ASP | 88 | 127.717 | 17.774 | 27.330 | 1.00 | 36.63 |
| 575 | OD1 | ASP | 88 | 126.845 | 17.539 | 28.194 | 1.00 | 36.19 |
| 576 | OD2 | ASP | 88 | 127.577 | 17.470 | 26.125 | 1.00 | 42.80 |
| 577 | C | ASP | 88 | 130.173 | 16.253 | 28.107 | 1.00 | 40.12 |
| 578 | O | ASP | 88 | 129.660 | 15.210 | 28.513 | 1.00 | 41.11 |
| 579 | N | ASP | 89 | 131.088 | 16.251 | 27.130 | 1.00 | 37.03 |
| 580 | CA | ASP | 89 | 131.496 | 15.096 | 26.397 | 1.00 | 33.87 |
| 581 | C | ASP | 89 | 132.107 | 14.047 | 27.304 | 1.00 | 33.85 |
| 582 | O | ASP | 89 | 132.047 | 12.832 | 26.978 | 1.00 | 33.37 |
| 583 | CB | ASP | 89 | 132.464 | 15.574 | 25.325 | 1.00 | 27.32 |
| 584 | CG | ASP | 89 | 131.779 | 16.561 | 24.391 | 1.00 | 34.13 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 585 | OD1 | ASP | 89 | 130.528 | 16.553 | 24.341 | 1.00 | 20.00 |
| 586 | OD2 | ASP | 89 | 132.481 | 17.345 | 23.721 | 1.00 | 20.00 |
| 587 | N | ILE | 90 | 132.765 | 14.453 | 28.372 | 1.00 | 31.52 |
| 588 | CA | ILE | 90 | 133.385 | 13.527 | 29.308 | 1.00 | 25.50 |
| 589 | CB | ILE | 90 | 134.370 | 14.245 | 30.258 | 1.00 | 22.28 |
| 590 | CG2 | ILE | 90 | 134.861 | 13.285 | 31.328 | 1.00 | 22.91 |
| 591 | CG1 | ILE | 90 | 135.549 | 14.818 | 29.465 | 1.00 | 31.26 |
| 592 | CD1 | ILE | 90 | 136.543 | 15.620 | 30.301 | 1.00 | 31.23 |
| 593 | C | ILE | 90 | 132.297 | 12.836 | 30.124 | 1.00 | 23.61 |
| 594 | O | ILE | 90 | 132.331 | 11.620 | 30.316 | 1.00 | 27.20 |
| 595 | N | LEU | 91 | 131.331 | 13.622 | 30.593 | 1.00 | 23.72 |
| 596 | CA | LEU | 91 | 130.218 | 13.099 | 31.379 | 1.00 | 20.80 |
| 597 | CB | LEU | 91 | 129.469 | 14.238 | 32.071 | 1.00 | 20.19 |
| 598 | CG | LEU | 91 | 130.232 | 14.888 | 33.225 | 1.00 | 17.15 |
| 599 | CD1 | LEU | 91 | 129.464 | 16.078 | 33.772 | 1.00 | 13.18 |
| 600 | CD2 | LEU | 91 | 130.479 | 13.852 | 34.318 | 1.00 | 9.86 |
| 601 | C | LEU | 91 | 129.270 | 12.281 | 30.510 | 1.00 | 22.03 |
| 602 | O | LEU | 91 | 128.649 | 11.334 | 30.988 | 1.00 | 22.93 |
| 603 | N | ASP | 92 | 129.183 | 12.640 | 29.231 | 1.00 | 21.86 |
| 604 | CA | ASP | 92 | 128.337 | 11.930 | 28.276 | 1.00 | 23.86 |
| 605 | CB | ASP | 92 | 128.314 | 12.668 | 26.933 | 1.00 | 30.84 |
| 606 | CG | ASP | 92 | 127.282 | 12.105 | 25.973 | 1.00 | 37.16 |
| 607 | OD1 | ASP | 92 | 126.182 | 12.690 | 25.879 | 1.00 | 34.52 |
| 608 | OD2 | ASP | 92 | 127.568 | 11.083 | 25.309 | 1.00 | 45.02 |
| 609 | C | ASP | 92 | 128.928 | 10.539 | 28.090 | 1.00 | 30.87 |
| 610 | O | ASP | 92 | 128.208 | 9.542 | 28.106 | 1.00 | 38.64 |
| 611 | N | GLN | 93 | 130.247 | 10.490 | 27.914 | 1.00 | 33.31 |
| 612 | CA | GLN | 93 | 130.974 | 9.239 | 27.738 | 1.00 | 34.79 |
| 613 | CB | GLN | 93 | 132.454 | 9.531 | 27.466 | 1.00 | 46.61 |
| 614 | CG | GLN | 93 | 133.345 | 8.300 | 27.331 | 1.00 | 60.12 |
| 615 | CD | GLN | 93 | 134.831 | 8.640 | 27.354 | 1.00 | 75.57 |
| 616 | OE1 | GLN | 93 | 135.217 | 9.801 | 27.510 | 1.00 | 79.60 |
| 617 | NE2 | GLN | 93 | 135.672 | 7.621 | 27.208 | 1.00 | 81.92 |
| 618 | C | GLN | 93 | 130.833 | 8.380 | 28.994 | 1.00 | 35.74 |
| 619 | O | GLN | 93 | 130.620 | 7.171 | 28.906 | 1.00 | 39.97 |
| 620 | N | ILE | 94 | 130.933 | 9.019 | 30.159 | 1.00 | 32.85 |
| 621 | CA | ILE | 94 | 130.817 | 8.326 | 31.441 | 1.00 | 35.57 |
| 622 | CB | ILE | 94 | 131.191 | 9.266 | 32.625 | 1.00 | 33.17 |
| 623 | CG2 | ILE | 94 | 130.909 | 8.588 | 33.969 | 1.00 | 25.21 |
| 624 | CG1 | ILE | 94 | 132.671 | 9.652 | 32.538 | 1.00 | 32.16 |
| 625 | CD1 | ILE | 94 | 133.120 | 10.631 | 33.603 | 1.00 | 32.74 |
| 626 | C | ILE | 94 | 129.407 | 7.770 | 31.645 | 1.00 | 38.37 |
| 627 | O | ILE | 94 | 129.224 | 6.716 | 32.260 | 1.00 | 45.31 |
| 628 | N | TYR | 95 | 128.421 | 8.477 | 31.102 | 1.00 | 38.86 |
| 629 | CA | TYR | 95 | 127.021 | 8.082 | 31.212 | 1.00 | 39.68 |
| 630 | CB | TYR | 95 | 126.122 | 9.249 | 30.784 | 1.00 | 34.17 |
| 631 | CG | TYR | 95 | 124.637 | 8.974 | 30.877 | 1.00 | 27.88 |
| 632 | CD1 | TYR | 95 | 124.060 | 8.539 | 32.070 | 1.00 | 26.18 |
| 633 | CE1 | TYR | 95 | 122.697 | 8.279 | 32.155 | 1.00 | 24.69 |
| 634 | CD2 | TYR | 95 | 123.810 | 9.144 | 29.770 | 1.00 | 21.67 |
| 635 | CE2 | TYR | 95 | 122.447 | 8.888 | 29.845 | 1.00 | 22.88 |
| 636 | CZ | TYR | 95 | 121.896 | 8.454 | 31.039 | 1.00 | 23.25 |
| 637 | OH | TYR | 95 | 120.546 | 8.185 | 31.112 | 1.00 | 32.19 |
| 638 | C | TYR | 95 | 126.715 | 6.846 | 30.369 | 1.00 | 40.10 |
| 639 | O | TYR | 95 | 125.987 | 5.953 | 30.803 | 1.00 | 41.67 |
| 640 | N | ASN | 96 | 127.291 | 6.796 | 29.173 | 1.00 | 40.40 |
| 641 | CA | ASN | 96 | 127.073 | 5.682 | 28.261 | 1.00 | 50.10 |
| 642 | CB | ASN | 96 | 127.273 | 6.146 | 26.815 | 1.00 | 50.46 |
| 643 | CG | ASN | 96 | 126.252 | 7.189 | 26.392 | 1.00 | 53.74 |
| 644 | OD1 | ASN | 96 | 125.093 | 7.141 | 26.806 | 1.00 | 52.90 |
| 645 | ND2 | ASN | 96 | 126.679 | 8.138 | 25.567 | 1.00 | 56.55 |
| 646 | C | ASN | 96 | 127.911 | 4.434 | 28.545 | 1.00 | 54.46 |
| 647 | O | ASN | 96 | 127.502 | 3.324 | 28.202 | 1.00 | 58.60 |
| 648 | N | GLN | 97 | 129.067 | 4.606 | 29.183 | 1.00 | 57.00 |
| 649 | CA | GLN | 97 | 129.933 | 3.469 | 29.494 | 1.00 | 62.35 |
| 650 | CB | GLN | 97 | 131.385 | 3.924 | 29.690 | 1.00 | 63.17 |
| 651 | CG | GLN | 97 | 131.622 | 4.834 | 30.885 | 1.00 | 68.59 |
| 652 | CD | GLN | 97 | 133.052 | 5.351 | 30.970 | 1.00 | 68.54 |
| 653 | OE1 | GLN | 97 | 133.659 | 5.357 | 32.040 | 1.00 | 66.32 |
| 654 | NE2 | GLN | 97 | 133.594 | 5.798 | 29.836 | 1.00 | 59.07 |
| 655 | C | GLN | 97 | 129.458 | 2.654 | 30.698 | 1.00 | 66.41 |
| 656 | O | GLN | 97 | 129.682 | 1.442 | 30.754 | 1.00 | 66.29 |
| 657 | N | ASN | 98 | 128.790 | 3.317 | 31.642 | 1.00 | 75.07 |
| 658 | CA | ASN | 98 | 128.274 | 2.676 | 32.854 | 1.00 | 85.32 |
| 659 | CB | ASN | 98 | 127.000 | 1.878 | 32.554 | 1.00 | 92.56 |
| 660 | CG | ASN | 98 | 125.798 | 2.771 | 32.325 | 1.00 | 97.44 |
| 661 | OD1 | ASN | 98 | 125.273 | 3.375 | 33.262 | 1.00 | 97.63 |
| 662 | ND2 | ASN | 98 | 125.357 | 2.865 | 31.074 | 1.00 | 98.68 |
| 663 | C | ASN | 98 | 129.314 | 1.791 | 33.535 | 1.00 | 89.40 |
| 664 | O | ASN | 98 | 129.073 | 0.612 | 33.812 | 1.00 | 88.19 |
| 665 | N | SER | 99 | 130.486 | 2.369 | 33.779 | 1.00 | 94.53 |
| 666 | CA | SER | 99 | 131.560 | 1.640 | 34.435 | 1.00 | 98.60 |
| 667 | CB | SER | 99 | 132.918 | 2.248 | 34.106 | 1.00 | 99.63 |
| 668 | OG | SER | 99 | 132.996 | 3.591 | 34.559 | 1.00 | 100.00 |
| 669 | C | SER | 99 | 131.332 | 1.673 | 35.926 | 1.00 | 99.96 |
| 670 | O | SER | 99 | 131.030 | 2.717 | 36.500 | 1.00 | 98.72 |
| 671 | N | ASN | 100 | 131.508 | 0.532 | 36.566 | 1.00 | 100.00 |
| 672 | CA | ASN | 100 | 131.294 | 0.473 | 37.995 | 1.00 | 100.00 |
| 673 | CB | ASN | 100 | 130.733 | -0.892 | 38.382 | 1.00 | 97.11 |
| 674 | CG | ASN | 100 | 129.297 | -1.056 | 37.956 | 1.00 | 95.75 |
| 675 | OD1 | ASN | 100 | 128.429 | -0.279 | 38.360 | 1.00 | 86.86 |
| 676 | ND2 | ASN | 100 | 129.028 | -2.069 | 37.139 | 1.00 | 94.51 |
| 677 | C | ASN | 100 | 132.513 | 0.784 | 38.857 | 1.00 | 100.00 |
| 678 | O | ASN | 100 | 133.196 | -0.133 | 39.303 | 1.00 | 100.00 |
| 679 | N | CYS | 101 | 132.829 | 2.068 | 39.047 | 1.00 | 98.98 |
| 680 | CA | CYS | 101 | 133.942 | 2.429 | 39.953 | 1.00 | 94.29 |
| 681 | CB | CYS | 101 | 134.350 | 3.905 | 39.872 | 1.00 | 96.36 |
| 682 | SG | CYS | 101 | 135.708 | 4.382 | 41.017 | 1.00 | 100.00 |
| 683 | C | CYS | 101 | 133.151 | 2.160 | 41.226 | 1.00 | 90.03 |
| 684 | O | CYS | 101 | 132.261 | 2.914 | 41.595 | 1.00 | 89.78 |
| 685 | N | ASN | 102 | 133.483 | 1.057 | 41.870 | 1.00 | 85.97 |
| 686 | CA | ASN | 102 | 132.753 | 0.573 | 43.043 | 1.00 | 81.73 |
| 687 | CB | ASN | 102 | 133.072 | -0.902 | 43.238 | 1.00 | 86.41 |
| 688 | CG | ASN | 102 | 132.971 | -1.688 | 41.962 | 1.00 | 88.71 |
| 689 | OD1 | ASN | 102 | 133.978 | -2.107 | 41.412 | 1.00 | 90.82 |
| 690 | ND2 | ASN | 102 | 131.750 | -1.869 | 41.462 | 1.00 | 81.79 |
| 691 | C | ASN | 102 | 132.652 | 1.257 | 44.413 | 1.00 | 74.07 |
| 692 | O | ASN | 102 | 131.770 | 0.881 | 45.187 | 1.00 | 77.40 |
| 693 | N | ASP | 103 | 133.474 | 2.260 | 44.713 | 1.00 | 58.82 |
| 694 | CA | ASP | 103 | 133.377 | 2.904 | 46.037 | 1.00 | 48.91 |
| 695 | CB | ASP | 103 | 134.746 | 3.418 | 46.524 | 1.00 | 50.06 |
| 696 | CG | ASP | 103 | 135.346 | 4.487 | 45.622 | 1.00 | 54.31 |
| 697 | OD1 | ASP | 103 | 135.589 | 4.210 | 44.429 | 1.00 | 68.60 |
| 698 | OD2 | ASP | 103 | 135.616 | 5.599 | 46.128 | 1.00 | 47.23 |
| 699 | C | ASP | 103 | 132.290 | 3.974 | 46.178 | 1.00 | 38.98 |
| 700 | O | ASP | 103 | 131.875 | 4.585 | 45.198 | 1.00 | 30.42 |
| 701 | N | LEU | 104 | 131.820 | 4.168 | 47.408 | 1.00 | 25.79 |
| 702 | CA | LEU | 104 | 130.764 | 5.139 | 47.702 | 1.00 | 26.09 |
| 703 | CB | LEU | 104 | 130.414 | 5.114 | 49.195 | 1.00 | 14.86 |
| 704 | CG | LEU | 104 | 129.294 | 6.042 | 49.674 | 1.00 | 13.82 |
| 705 | CD1 | LEU | 104 | 127.971 | 5.654 | 49.031 | 1.00 | 10.36 |
| 706 | CD2 | LEU | 104 | 129.171 | 5.996 | 51.191 | 1.00 | 7.52 |
| 707 | C | LEU | 104 | 131.082 | 6.567 | 47.274 | 1.00 | 26.59 |
| 708 | O | LEU | 104 | 130.232 | 7.240 | 46.696 | 1.00 | 27.23 |
| 709 | N | CYS | 105 | 132.297 | 7.021 | 47.574 | 1.00 | 28.20 |
| 710 | CA | CYS | 105 | 132.735 | 8.370 | 47.225 | 1.00 | 24.21 |
| 711 | CB | CYS | 105 | 134.164 | 8.606 | 47.721 | 1.00 | 29.54 |
| 712 | SG | CYS | 105 | 134.889 | 10.178 | 47.188 | 1.00 | 32.14 |
| 713 | C | CYS | 105 | 132.659 | 8.634 | 45.724 | 1.00 | 20.98 |
| 714 | O | CYS | 105 | 132.062 | 9.618 | 45.285 | 1.00 | 24.94 |
| 715 | N | THR | 106 | 133.258 | 7.744 | 44.941 | 1.00 | 22.03 |
| 716 | CA | THR | 106 | 133.261 | 7.890 | 43.489 | 1.00 | 23.52 |
| 717 | CB | THR | 106 | 134.197 | 6.858 | 42.823 | 1.00 | 18.21 |
| 718 | OG1 | THR | 106 | 135.481 | 6.893 | 43.461 | 1.00 | 20.18 |
| 719 | CG2 | THR | 106 | 134.372 | 7.183 | 41.349 | 1.00 | 18.22 |
| 720 | C | THR | 106 | 131.858 | 7.739 | 42.906 | 1.00 | 22.72 |
| 721 | O | THR | 106 | 131.481 | 8.465 | 41.984 | 1.00 | 21.14 |
| 722 | N | SER | 107 | 131.092 | 6.802 | 43.461 | 1.00 | 26.53 |
| 723 | CA | SER | 107 | 129.730 | 6.532 | 43.009 | 1.00 | 24.15 |
| 724 | CB | SER | 107 | 129.158 | 5.312 | 43.735 | 1.00 | 24.72 |
| 725 | OG | SER | 107 | 129.913 | 4.147 | 43.453 | 1.00 | 34.14 |
| 726 | C | SER | 107 | 128.818 | 7.731 | 43.228 | 1.00 | 20.49 |
| 727 | O | SER | 107 | 128.128 | 8.170 | 42.306 | 1.00 | 15.26 |
| 728 | N | ALA | 108 | 128.822 | 8.254 | 44.453 | 1.00 | 18.95 |
| 729 | CA | ALA | 108 | 128.002 | 9.408 | 44.810 | 1.00 | 16.79 |
| 730 | CB | ALA | 108 | 128.168 | 9.732 | 46.282 | 1.00 | 13.84 |

TABLE 10-continued

Structural Coordinates of Tobacco 5-Epi-Aristolochene Synthase
With Farnesyl Hydroxyphosphonate Bound

| Atom | Atom Type | Residue | Residue # | X | Y | Z | OCC | B-factor |
|---|---|---|---|---|---|---|---|---|
| 731 | C | ALA | 108 | 128.349 | 10.623 | 43.953 | 1.00 | 15.33 |
| 732 | O | ALA | 108 | 127.455 | 11.340 | 43.499 | 1.00 | 19.47 |
| 733 | N | LEU | 109 | 129.644 | 10.836 | 43.722 | 1.00 | 10.72 |
| 734 | CA | LEU | 109 | 130.106 | 11.954 | 42.907 | 1.00 | 11.35 |
| 735 | CB | LEU | 109 | 131.627 | 12.093 | 42.993 | 1.00 | 15.00 |
| 736 | CG | LEU | 109 | 132.277 | 13.237 | 42.203 | 1.00 | 19.48 |
| 737 | CD1 | LEU | 109 | 131.670 | 14.577 | 42.596 | 1.00 | 15.00 |
| 738 | CD2 | LEU | 109 | 133.778 | 13.239 | 42.442 | 1.00 | 17.22 |
| 739 | C | LEU | 109 | 129.673 | 11.754 | 41.459 | 1.00 | 15.76 |
| 740 | O | LEU | 109 | 129.216 | 12.692 | 40.807 | 1.00 | 28.55 |
| 741 | N | GLN | 110 | 129.813 | 10.526 | 40.966 | 1.00 | 19.50 |
| 742 | CA | GLN | 110 | 129.417 | 10.184 | 39.600 | 1.00 | 20.50 |
| 743 | CB | GLN | 110 | 129.679 | 8.699 | 39.339 | 1.00 | 24.06 |
| 744 | CG | GLN | 110 | 129.287 | 8.221 | 37.949 | 1.00 | 31.51 |
| 745 | CD | GLN | 110 | 129.373 | 6.711 | 37.797 | 1.00 | 31.57 |
| 746 | OE1 | GLN | 110 | 129.661 | 5.990 | 38.756 | 1.00 | 35.16 |
| 747 | NE2 | GLN | 110 | 129.117 | 6.225 | 36.586 | 1.00 | 34.19 |
| 748 | C | GLN | 110 | 127.926 | 10.478 | 39.414 | 1.00 | 21.12 |
| 749 | O | GLN | 110 | 127.508 | 11.009 | 38.389 | 1.00 | 20.13 |
| 750 | N | PHE | 111 | 127.139 | 10.140 | 40.431 | 1.00 | 23.63 |
| 751 | CA | PHE | 111 | 125.699 | 10.356 | 40.409 | 1.00 | 21.06 |
| 752 | CB | PHE | 111 | 125.065 | 9.729 | 41.655 | 1.00 | 21.44 |
| 753 | CG | PHE | 111 | 123.565 | 9.806 | 41.685 | 1.00 | 18.29 |
| 754 | CD1 | PHE | 111 | 122.795 | 8.933 | 40.924 | 1.00 | 18.70 |
| 755 | CD2 | PHE | 111 | 122.921 | 10.744 | 42.483 | 1.00 | 14.43 |
| 756 | CE1 | PHE | 111 | 121.404 | 8.990 | 40.959 | 1.00 | 18.31 |
| 757 | CE2 | PHE | 111 | 121.533 | 10.810 | 42.523 | 1.00 | 21.91 |
| 758 | CZ | PHE | 111 | 120.773 | 9.929 | 41.758 | 1.00 | 17.47 |
| 759 | C | PHE | 111 | 125.373 | 11.846 | 40.345 | 1.00 | 19.49 |
| 760 | O | PHE | 111 | 124.731 | 12.305 | 39.399 | 1.00 | 17.88 |
| 761 | N | ARG | 112 | 125.857 | 12.598 | 41.332 | 1.00 | 16.34 |
| 762 | CA | ARG | 112 | 125.606 | 14.033 | 41.407 | 1.00 | 8.21 |
| 763 | CB | ARG | 112 | 126.326 | 14.651 | 42.608 | 1.00 | 7.94 |
| 764 | CG | ARG | 112 | 126.081 | 16.153 | 42.745 | 1.00 | 14.61 |
| 765 | CD | ARG | 112 | 126.507 | 16.703 | 44.100 | 1.00 | 22.36 |
| 766 | NE | ARG | 112 | 127.955 | 16.745 | 44.291 | 1.00 | 19.69 |
| 767 | CZ | ARG | 112 | 128.777 | 17.561 | 43.639 | 1.00 | 22.41 |
| 768 | NH1 | ARG | 112 | 128.300 | 18.407 | 42.737 | 1.00 | 29.76 |
| 769 | NH2 | ARG | 112 | 130.073 | 17.555 | 43.915 | 1.00 | 26.92 |
| 770 | C | ARG | 112 | 125.961 | 14.808 | 40.145 | 1.00 | 13.57 |
| 771 | O | ARG | 112 | 125.113 | 15.505 | 39.588 | 1.00 | 17.92 |
| 772 | N | LEU | 113 | 127.205 | 14.676 | 39.693 | 1.00 | 11.94 |
| 773 | CA | LEU | 113 | 127.671 | 15.385 | 38.504 | 1.00 | 14.83 |
| 774 | CB | LEU | 113 | 129.151 | 15.088 | 38.239 | 1.00 | 20.65 |
| 775 | CG | LEU | 113 | 130.149 | 15.516 | 39.322 | 1.00 | 16.72 |
| 776 | CD1 | LEU | 113 | 131.568 | 15.259 | 38.847 | 1.00 | 15.77 |
| 777 | CD2 | LEU | 113 | 129.970 | 16.985 | 39.651 | 1.00 | 21.06 |
| 778 | C | LEU | 113 | 126.840 | 15.108 | 37.256 | 1.00 | 19.17 |
| 779 | O | LEU | 113 | 126.484 | 16.034 | 36.532 | 1.00 | 26.79 |
| 780 | N | LEU | 114 | 126.516 | 13.841 | 37.014 | 1.00 | 23.83 |
| 781 | CA | LEU | 114 | 125.717 | 13.464 | 35.849 | 1.00 | 14.66 |
| 782 | CB | LEU | 114 | 125.668 | 11.943 | 35.703 | 1.00 | 18.52 |
| 783 | CG | LEU | 114 | 126.969 | 11.251 | 35.287 | 1.00 | 19.65 |
| 784 | CD1 | LEU | 114 | 126.800 | 9.746 | 35.362 | 1.00 | 22.06 |
| 785 | CD2 | LEU | 114 | 127.352 | 11.666 | 33.882 | 1.00 | 21.06 |
| 786 | C | LEU | 114 | 124.300 | 14.030 | 35.939 | 1.00 | 15.67 |
| 787 | O | LEU | 114 | 123.787 | 14.596 | 34.972 | 1.00 | 18.67 |
| 788 | N | ARG | 115 | 123.678 | 13.883 | 37.104 | 1.00 | 9.26 |
| 789 | CA | ARG | 115 | 122.328 | 14.387 | 37.328 | 1.00 | 7.86 |
| 790 | CB | ARG | 115 | 121.849 | 14.021 | 38.736 | 1.00 | 10.49 |
| 791 | CG | ARG | 115 | 121.450 | 12.562 | 38.901 | 1.00 | 12.35 |
| 792 | CD | ARG | 115 | 120.323 | 12.202 | 37.949 | 1.00 | 17.12 |
| 793 | NE | ARG | 115 | 119.807 | 10.857 | 38.179 | 1.00 | 21.26 |
| 794 | CZ | ARG | 115 | 118.803 | 10.570 | 39.000 | 1.00 | 15.94 |
| 795 | NH1 | ARG | 115 | 118.199 | 11.537 | 39.676 | 1.00 | 8.20 |
| 796 | NH2 | ARG | 115 | 118.406 | 9.314 | 39.152 | 1.00 | 17.38 |
| 797 | C | ARG | 115 | 122.250 | 15.899 | 37.126 | 1.00 | 13.44 |
| 798 | O | ARG | 115 | 121.379 | 16.390 | 36.402 | 1.00 | 8.27 |
| 799 | N | GLN | 116 | 123.180 | 16.629 | 37.743 | 1.00 | 14.35 |
| 800 | CA | GLN | 116 | 123.225 | 18.086 | 37.629 | 1.00 | 11.93 |
| 801 | CB | GLN | 116 | 124.364 | 18.664 | 38.471 | 1.00 | 4.12 |
| 802 | CG | GLN | 116 | 124.165 | 18.534 | 39.968 | 1.00 | 5.13 |
| 803 | CD | GLN | 116 | 125.303 | 19.142 | 40.768 | 1.00 | 11.78 |
| 804 | OE1 | GLN | 116 | 125.080 | 19.950 | 41.669 | 1.00 | 21.37 |
| 805 | NE2 | GLN | 116 | 126.530 | 18.747 | 40.451 | 1.00 | 11.47 |
| 806 | C | GLN | 116 | 123.392 | 18.530 | 36.183 | 1.00 | 15.48 |
| 807 | O | GLN | 116 | 123.126 | 19.682 | 35.851 | 1.00 | 19.88 |
| 808 | N | HIS | 117 | 123.827 | 17.607 | 35.328 | 1.00 | 19.55 |
| 809 | CA | HIS | 117 | 124.031 | 17.893 | 33.912 | 1.00 | 15.02 |
| 810 | CB | HIS | 117 | 125.405 | 17.392 | 33.460 | 1.00 | 13.78 |
| 811 | CG | HIS | 117 | 126.538 | 18.253 | 33.925 | 1.00 | 17.44 |
| 812 | CD2 | HIS | 117 | 126.999 | 18.525 | 35.169 | 1.00 | 18.38 |
| 813 | ND1 | HIS | 117 | 127.322 | 18.983 | 33.059 | 1.00 | 19.26 |
| 814 | CE1 | HIS | 117 | 128.216 | 19.668 | 33.748 | 1.00 | 20.36 |
| 815 | NE2 | HIS | 117 | 128.042 | 19.408 | 35.031 | 1.00 | 17.37 |
| 816 | C | HIS | 117 | 122.930 | 17.349 | 33.006 | 1.00 | 16.42 |
| 817 | O | HIS | 117 | 123.036 | 17.419 | 31.780 | 1.00 | 15.29 |
| 818 | N | GLY | 118 | 121.872 | 16.813 | 33.613 | 1.00 | 17.98 |
| 819 | CA | GLY | 118 | 120.756 | 16.292 | 32.839 | 1.00 | 21.36 |
| 820 | C | GLY | 118 | 120.761 | 14.800 | 32.521 | 1.00 | 21.11 |
| 821 | O | GLY | 118 | 119.760 | 14.284 | 32.032 | 1.00 | 23.89 |
| 822 | N | PHE | 119 | 121.880 | 14.134 | 32.773 | 1.00 | 20.97 |
| 823 | CA | PHE | 119 | 121.994 | 12.702 | 32.510 | 1.00 | 15.97 |
| 824 | CB | PHE | 119 | 123.465 | 12.282 | 32.477 | 1.00 | 13.26 |
| 825 | CG | PHE | 119 | 124.281 | 13.007 | 31.439 | 1.00 | 19.34 |
| 826 | CD1 | PHE | 119 | 125.155 | 14.025 | 31.808 | 1.00 | 18.10 |
| 827 | CD2 | PHE | 119 | 124.160 | 12.686 | 30.090 | 1.00 | 17.78 |
| 828 | CE1 | PHE | 119 | 125.896 | 14.714 | 30.850 | 1.00 | 14.61 |
| 829 | CE2 | PHE | 119 | 124.896 | 13.370 | 29.122 | 1.00 | 16.11 |
| 830 | CZ | PHE | 119 | 125.765 | 14.386 | 29.503 | 1.00 | 22.05 |
| 831 | C | PHE | 119 | 121.238 | 11.917 | 33.576 | 1.00 | 20.90 |
| 832 | O | PHE | 119 | 121.620 | 11.910 | 34.749 | 1.00 | 17.99 |
| 833 | N | ASN | 120 | 120.157 | 11.263 | 33.161 | 1.00 | 20.78 |
| 834 | CA | ASN | 120 | 119.326 | 10.494 | 34.078 | 1.00 | 23.46 |
| 835 | CB | ASN | 120 | 117.928 | 10.307 | 33.477 | 1.00 | 23.75 |
| 836 | CG | ASN | 120 | 116.919 | 9.766 | 34.481 | 1.00 | 23.50 |
| 837 | OD1 | ASN | 120 | 117.147 | 9.782 | 35.695 | 1.00 | 18.94 |
| 838 | ND2 | ASN | 120 | 115.786 | 9.295 | 33.973 | 1.00 | 24.72 |
| 839 | C | ASN | 120 | 119.940 | 9.145 | 34.447 | 1.00 | 29.37 |
| 840 | O | ASN | 120 | 119.467 | 8.092 | 34.011 | 1.00 | 37.56 |
| 841 | N | ILE | 121 | 120.999 | 9.183 | 35.251 | 1.00 | 30.57 |
| 842 | CA | ILE | 121 | 121.674 | 7.965 | 35.691 | 1.00 | 28.30 |
| 843 | CB | ILE | 121 | 123.118 | 8.250 | 36.202 | 1.00 | 31.51 |
| 844 | CG2 | ILE | 121 | 123.116 | 9.395 | 37.212 | 1.00 | 18.33 |
| 845 | CG1 | ILE | 121 | 123.734 | 6.970 | 36.784 | 1.00 | 34.25 |
| 846 | CD1 | ILE | 121 | 125.160 | 7.119 | 37.270 | 1.00 | 35.18 |
| 847 | C | ILE | 121 | 120.862 | 7.263 | 36.774 | 1.00 | 24.20 |
| 848 | O | ILE | 121 | 120.435 | 7.888 | 37.746 | 1.00 | 29.58 |
| 849 | N | SER | 122 | 120.654 | 5.963 | 36.594 | 1.00 | 28.31 |
| 850 | CA | SER | 122 | 119.886 | 5.158 | 37.538 | 1.00 | 31.22 |
| 851 | CB | SER | 122 | 119.782 | 3.711 | 37.040 | 1.00 | 37.94 |
| 852 | OG | SER | 122 | 119.046 | 2.907 | 37.948 | 1.00 | 37.31 |
| 853 | C | SER | 122 | 120.471 | 5.193 | 38.942 | 1.00 | 26.25 |
| 854 | O | SER | 122 | 121.690 | 5.086 | 39.121 | 1.00 | 36.49 |
| 855 | N | PRO | 123 | 119.606 | 5.367 | 39.956 | 1.00 | 25.72 |
| 856 | CD | PRO | 123 | 118.162 | 5.626 | 39.787 | 1.00 | 24.10 |
| 857 | CA | PRO | 123 | 119.995 | 5.427 | 41.367 | 1.00 | 24.12 |
| 858 | CB | PRO | 123 | 118.807 | 6.139 | 42.015 | 1.00 | 14.52 |
| 859 | CG | PRO | 123 | 117.635 | 5.620 | 41.222 | 1.00 | 18.26 |
| 860 | C | PRO | 123 | 120.266 | 4.057 | 41.978 | 1.00 | 26.29 |
| 861 | O | PRO | 123 | 120.649 | 3.957 | 43.143 | 1.00 | 26.93 |
| 862 | N | GLU | 124 | 120.106 | 3.007 | 41.176 | 1.00 | 31.58 |
| 863 | CA | GLU | 124 | 120.362 | 1.656 | 41.665 | 1.00 | 42.38 |
| 864 | CB | GLU | 124 | 119.734 | 0.614 | 40.749 | 1.00 | 52.63 |
| 865 | CG | GLU | 124 | 118.661 | −0.182 | 41.472 | 1.00 | 66.87 |
| 866 | CD | GLU | 124 | 117.857 | −1.078 | 40.558 | 1.00 | 84.70 |
| 867 | OE1 | GLU | 124 | 118.072 | −1.045 | 39.323 | 1.00 | 92.92 |
| 868 | OE2 | GLU | 124 | 116.995 | −1.820 | 41.075 | 1.00 | 95.72 |
| 869 | C | GLU | 124 | 121.850 | 1.396 | 41.860 | 1.00 | 40.43 |
| 870 | O | GLU | 124 | 122.243 | 0.345 | 42.359 | 1.00 | 40.69 |
| 871 | N | ILE | 125 | 122.665 | 2.383 | 41.493 | 1.00 | 40.56 |
| 872 | CA | ILE | 125 | 124.113 | 2.311 | 41.658 | 1.00 | 33.74 |
| 873 | CB | ILE | 125 | 124.796 | 3.532 | 40.995 | 1.00 | 34.47 |
| 874 | CG2 | ILE | 125 | 124.231 | 4.828 | 41.567 | 1.00 | 35.94 |
| 875 | CG1 | ILE | 125 | 126.317 | 3.471 | 41.176 | 1.00 | 33.47 |
| 876 | CD1 | ILE | 125 | 127.051 | 4.648 | 40.560 | 1.00 | 33.54 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 877 | C | ILE | 125 | 124.397 | 2.311 | 43.166 | 1.00 | 27.96 |
| 878 | O | ILE | 125 | 125.450 | 1.867 | 43.612 | 1.00 | 32.46 |
| 879 | N | PHE | 126 | 123.422 | 2.783 | 43.938 | 1.00 | 24.55 |
| 880 | CA | PHE | 126 | 123.518 | 2.850 | 45.393 | 1.00 | 31.56 |
| 881 | CB | PHE | 126 | 122.701 | 4.034 | 45.925 | 1.00 | 31.55 |
| 882 | CG | PHE | 126 | 123.245 | 5.377 | 45.536 | 1.00 | 36.38 |
| 883 | CD1 | PHE | 126 | 122.701 | 6.079 | 44.465 | 1.00 | 32.78 |
| 884 | CD2 | PHE | 126 | 124.300 | 5.946 | 46.245 | 1.00 | 35.39 |
| 885 | CE1 | PHE | 126 | 123.197 | 7.328 | 44.105 | 1.00 | 32.25 |
| 886 | CE2 | PHE | 126 | 124.805 | 7.194 | 45.894 | 1.00 | 31.56 |
| 887 | CZ | PHE | 126 | 124.252 | 7.889 | 44.820 | 1.00 | 28.07 |
| 888 | C | PHE | 126 | 123.042 | 1.568 | 46.079 | 1.00 | 37.75 |
| 889 | O | PHE | 126 | 122.939 | 1.520 | 47.308 | 1.00 | 36.32 |
| 890 | N | SER | 127 | 122.730 | 0.542 | 45.289 | 1.00 | 42.49 |
| 891 | CA | SER | 127 | 122.268 | -0.732 | 45.836 | 1.00 | 43.38 |
| 892 | CB | SER | 127 | 121.659 | -1.601 | 44.733 | 1.00 | 48.30 |
| 893 | OG | SER | 127 | 120.465 | -1.025 | 44.233 | 1.00 | 59.77 |
| 894 | C | SER | 127 | 123.401 | -1.482 | 46.527 | 1.00 | 39.67 |
| 895 | O | SER | 127 | 123.228 | -2.001 | 47.632 | 1.00 | 35.01 |
| 896 | N | LYS | 128 | 124.567 | -1.503 | 45.886 | 1.00 | 35.16 |
| 897 | CA | LYS | 128 | 125.743 | -2.179 | 46.426 | 1.00 | 36.47 |
| 898 | CB | LYS | 128 | 126.877 | -2.180 | 45.389 | 1.00 | 33.52 |
| 899 | CG | LYS | 128 | 127.146 | -0.834 | 44.732 | 1.00 | 37.85 |
| 900 | CD | LYS | 128 | 128.170 | -0.947 | 43.606 | 1.00 | 37.35 |
| 901 | CE | LYS | 128 | 128.353 | 0.388 | 42.892 | 1.00 | 50.12 |
| 902 | NZ | LYS | 128 | 129.338 | 0.328 | 41.776 | 1.00 | 54.36 |
| 903 | C | LYS | 128 | 126.233 | -1.623 | 47.769 | 1.00 | 38.71 |
| 904 | O | LYS | 128 | 127.102 | -2.217 | 48.412 | 1.00 | 46.49 |
| 905 | N | PHE | 129 | 125.656 | -0.501 | 48.199 | 1.00 | 38.63 |
| 906 | CA | PHE | 129 | 126.028 | 0.135 | 49.466 | 1.00 | 31.98 |
| 907 | CB | PHE | 129 | 126.309 | 1.626 | 49.256 | 1.00 | 24.98 |
| 908 | CG | PHE | 129 | 127.324 | 1.904 | 48.191 | 1.00 | 20.86 |
| 909 | CD1 | PHE | 129 | 126.946 | 2.506 | 46.997 | 1.00 | 19.33 |
| 910 | CD2 | PHE | 129 | 128.653 | 1.537 | 48.368 | 1.00 | 17.79 |
| 911 | CE1 | PHE | 129 | 127.877 | 2.735 | 45.988 | 1.00 | 22.73 |
| 912 | CE2 | PHE | 129 | 129.590 | 1.760 | 47.368 | 1.00 | 19.77 |
| 913 | CZ | PHE | 129 | 129.201 | 2.361 | 46.174 | 1.00 | 17.69 |
| 914 | C | PHE | 129 | 124.929 | -0.024 | 50.509 | 1.00 | 31.84 |
| 915 | O | PHE | 129 | 125.051 | 0.462 | 51.635 | 1.00 | 32.60 |
| 916 | N | GLN | 130 | 123.854 | -0.700 | 50.123 | 1.00 | 40.45 |
| 917 | CA | GLN | 130 | 122.720 | -0.922 | 51.010 | 1.00 | 47.58 |
| 918 | CB | GLN | 130 | 121.456 | -0.310 | 50.403 | 1.00 | 51.16 |
| 919 | CG | GLN | 130 | 121.515 | 1.197 | 50.231 | 1.00 | 50.70 |
| 920 | CD | GLN | 130 | 120.308 | 1.755 | 49.505 | 1.00 | 54.25 |
| 921 | OE1 | GLN | 130 | 119.310 | 1.063 | 49.303 | 1.00 | 62.26 |
| 922 | NE2 | GLN | 130 | 120.394 | 3.017 | 49.105 | 1.00 | 58.79 |
| 923 | C | GLN | 130 | 122.496 | -2.405 | 51.263 | 1.00 | 51.99 |
| 924 | O | GLN | 130 | 122.818 | -3.245 | 50.419 | 1.00 | 55.44 |
| 925 | N | ASP | 131 | 121.945 | -2.723 | 52.431 | 1.00 | 53.38 |
| 926 | CA | ASP | 131 | 121.665 | -4.108 | 52.789 | 1.00 | 60.28 |
| 927 | CB | ASP | 131 | 121.556 | -4.258 | 54.314 | 1.00 | 58.61 |
| 928 | CG | ASP | 131 | 120.311 | -3.596 | 54.892 | 1.00 | 62.05 |
| 929 | OD1 | ASP | 131 | 119.749 | -4.145 | 55.860 | 1.00 | 69.31 |
| 930 | OD2 | ASP | 131 | 119.893 | -2.532 | 54.391 | 1.00 | 65.85 |
| 931 | C | ASP | 131 | 120.382 | -4.583 | 52.103 | 1.00 | 64.98 |
| 932 | O | ASP | 131 | 119.762 | -3.837 | 51.341 | 1.00 | 64.40 |
| 933 | N | GLU | 132 | 119.989 | -5.823 | 52.383 | 1.00 | 70.50 |
| 934 | CA | GLU | 132 | 118.786 | -6.415 | 51.803 | 1.00 | 72.09 |
| 935 | CB | GLU | 132 | 118.735 | -7.913 | 52.120 | 1.00 | 78.41 |
| 936 | CG | GLU | 132 | 119.098 | -8.253 | 53.562 | 1.00 | 92.85 |
| 937 | CD | GLU | 132 | 117.997 | -8.995 | 54.303 | 1.00 | 100.00 |
| 938 | OE1 | GLU | 132 | 116.803 | -8.735 | 54.037 | 1.00 | 100.00 |
| 939 | OE2 | GLU | 132 | 118.331 | -9.837 | 55.165 | 1.00 | 100.00 |
| 940 | C | GLU | 132 | 117.486 | -5.729 | 52.236 | 1.00 | 69.60 |
| 941 | O | GLU | 132 | 116.424 | -5.985 | 51.666 | 1.00 | 67.84 |
| 942 | N | ASN | 133 | 117.575 | 4.849 | 53.230 | 1.00 | 69.95 |
| 943 | CA | ASN | 133 | 116.408 | -4.124 | 53.726 | 1.00 | 71.81 |
| 944 | CB | ASN | 133 | 116.540 | -3.882 | 55.235 | 1.00 | 76.32 |
| 945 | CG | ASN | 133 | 115.238 | -3.425 | 55.873 | 1.00 | 85.38 |
| 946 | OD1 | ASN | 133 | 114.202 | -4.076 | 55.731 | 1.00 | 89.18 |
| 947 | ND2 | ASN | 133 | 115.288 | -2.303 | 56.583 | 1.00 | 85.57 |
| 948 | C | ASN | 133 | 116.214 | -2.794 | 52.982 | 1.00 | 70.23 |
| 949 | O | ASN | 133 | 115.184 | -2.132 | 53.136 | 1.00 | 67.90 |
| 950 | N | GLY | 134 | 117.204 | -2.414 | 52.176 | 1.00 | 67.24 |
| 951 | CA | GLY | 134 | 117.120 | -1.177 | 51.416 | 1.00 | 63.86 |
| 952 | C | GLY | 134 | 117.758 | 0.036 | 52.072 | 1.00 | 61.93 |
| 953 | O | GLY | 134 | 117.712 | 1.138 | 51.520 | 1.00 | 64.71 |
| 954 | N | LYS | 135 | 118.332 | -0.158 | 53.257 | 1.00 | 57.80 |
| 955 | CA | LYS | 135 | 118.989 | 0.921 | 53.993 | 1.00 | 52.54 |
| 956 | CB | LYS | 135 | 118.628 | 0.865 | 55.482 | 1.00 | 54.50 |
| 957 | CG | LYS | 135 | 117.298 | 1.519 | 55.845 | 1.00 | 58.81 |
| 958 | CD | LYS | 135 | 116.106 | 0.776 | 55.259 | 1.00 | 65.64 |
| 959 | CE | LYS | 135 | 114.795 | 1.428 | 55.666 | 1.00 | 66.94 |
| 960 | NZ | LYS | 135 | 114.629 | 1.450 | 57.145 | 1.00 | 67.92 |
| 961 | C | LYS | 135 | 120.505 | 0.859 | 53.827 | 1.00 | 46.30 |
| 962 | O | LYS | 135 | 121.062 | -0.191 | 53.506 | 1.00 | 39.34 |
| 963 | N | PHE | 136 | 121.168 | 1.988 | 54.058 | 1.00 | 40.70 |
| 964 | CA | PHE | 136 | 122.619 | 2.066 | 53.929 | 1.00 | 37.70 |
| 965 | CB | PHE | 136 | 123.082 | 3.525 | 53.941 | 1.00 | 30.32 |
| 966 | CG | PHE | 136 | 122.848 | 4.238 | 52.644 | 1.00 | 18.97 |
| 967 | CD1 | PHE | 136 | 121.752 | 5.079 | 52.485 | 1.00 | 16.88 |
| 968 | CD2 | PHE | 136 | 123.708 | 4.044 | 51.569 | 1.00 | 2.95 |
| 969 | CE1 | PHE | 136 | 121.512 | 5.714 | 51.269 | 1.00 | 9.36 |
| 970 | CE2 | PHE | 136 | 123.478 | 4.674 | 50.350 | 1.00 | 8.37 |
| 971 | CZ | PHE | 136 | 122.376 | 5.510 | 50.200 | 1.00 | 11.64 |
| 972 | C | PHE | 136 | 123.368 | 1.280 | 54.992 | 1.00 | 40.03 |
| 973 | O | PHE | 136 | 123.007 | 1.310 | 56.173 | 1.00 | 36.07 |
| 974 | N | LYS | 137 | 124.404 | 0.564 | 54.554 | 1.00 | 35.20 |
| 975 | CA | LYS | 137 | 125.232 | -0.232 | 55.451 | 1.00 | 37.62 |
| 976 | CB | LYS | 137 | 126.333 | -0.957 | 54.670 | 1.00 | 36.07 |
| 977 | CG | LYS | 137 | 125.845 | -2.039 | 53.721 | 1.00 | 43.95 |
| 978 | CD | LYS | 137 | 127.016 | -2.672 | 52.985 | 1.00 | 45.68 |
| 979 | CE | LYS | 137 | 126.558 | -3.745 | 52.011 | 1.00 | 46.97 |
| 980 | NZ | LYS | 137 | 127.709 | -4.340 | 51.276 | 1.00 | 45.41 |
| 981 | C | LYS | 137 | 125.872 | 0.698 | 56.472 | 1.00 | 42.74 |
| 982 | O | LYS | 137 | 126.612 | 1.614 | 56.108 | 1.00 | 49.71 |
| 983 | N | GLU | 138 | 125.569 | 0.472 | 57.747 | 1.00 | 44.30 |
| 984 | CA | GLU | 138 | 126.116 | 1.290 | 58.824 | 1.00 | 43.35 |
| 985 | CB | GLU | 138 | 125.482 | 0.895 | 60.157 | 1.00 | 48.22 |
| 986 | CG | GLU | 138 | 123.997 | 1.184 | 60.285 | 1.00 | 55.55 |
| 987 | CD | GLU | 138 | 123.703 | 2.650 | 60.528 | 1.00 | 59.82 |
| 988 | OE1 | GLU | 138 | 124.127 | 3.180 | 61.577 | 1.00 | 58.06 |
| 989 | OE2 | GLU | 138 | 123.040 | 3.272 | 59.674 | 1.00 | 70.04 |
| 990 | C | GLU | 138 | 127.641 | 1.172 | 58.913 | 1.00 | 46.10 |
| 991 | O | GLU | 138 | 128.283 | 1.909 | 59.662 | 1.00 | 51.05 |
| 992 | N | SER | 139 | 128.210 | 0.242 | 58.149 | 1.00 | 40.33 |
| 993 | CA | SER | 139 | 129.653 | 0.027 | 58.122 | 1.00 | 37.26 |
| 994 | CB | SER | 139 | 129.975 | -1.354 | 57.541 | 1.00 | 42.99 |
| 995 | OG | SER | 139 | 129.518 | -1.477 | 56.204 | 1.00 | 42.44 |
| 996 | C | SER | 139 | 130.384 | 1.114 | 57.326 | 1.00 | 38.83 |
| 997 | O | SER | 139 | 131.606 | 1.247 | 57.423 | 1.00 | 44.35 |
| 998 | N | LEU | 140 | 129.633 | 1.875 | 56.531 | 1.00 | 35.64 |
| 999 | CA | LEU | 140 | 130.191 | 2.960 | 55.721 | 1.00 | 26.87 |
| 1000 | CB | LEU | 140 | 129.289 | 3.244 | 54.514 | 1.00 | 27.15 |
| 1001 | CG | LEU | 140 | 129.037 | 2.148 | 53.476 | 1.00 | 27.17 |
| 1002 | CD1 | LEU | 140 | 127.955 | 2.607 | 52.511 | 1.00 | 23.24 |
| 1003 | CD2 | LEU | 140 | 130.317 | 1.814 | 52.726 | 1.00 | 21.35 |
| 1004 | C | LEU | 140 | 130.325 | 4.241 | 56.547 | 1.00 | 23.48 |
| 1005 | O | LEU | 140 | 130.817 | 5.254 | 56.054 | 1.00 | 18.12 |
| 1006 | N | ALA | 141 | 129.883 | 4.178 | 57.803 | 1.00 | 21.14 |
| 1007 | CA | ALA | 141 | 129.916 | 5.311 | 58.725 | 1.00 | 23.07 |
| 1008 | CB | ALA | 141 | 129.182 | 4.951 | 60.007 | 1.00 | 13.93 |
| 1009 | C | ALA | 141 | 131.316 | 5.829 | 59.053 | 1.00 | 29.68 |
| 1010 | O | ALA | 141 | 131.465 | 6.917 | 59.614 | 1.00 | 34.02 |
| 1011 | N | SER | 142 | 132.334 | 5.045 | 58.710 | 1.00 | 31.98 |
| 1012 | CA | SER | 142 | 133.723 | 5.413 | 58.963 | 1.00 | 25.78 |
| 1013 | CB | SER | 142 | 134.482 | 4.211 | 59.534 | 1.00 | 27.76 |
| 1014 | OG | SER | 142 | 134.293 | 3.059 | 58.731 | 1.00 | 23.34 |
| 1015 | C | SER | 142 | 134.436 | 5.957 | 57.719 | 1.00 | 26.37 |
| 1016 | O | SER | 142 | 135.629 | 6.255 | 57.761 | 1.00 | 36.05 |
| 1017 | N | ASP | 143 | 133.699 | 6.078 | 56.617 | 1.00 | 19.43 |
| 1018 | CA | ASP | 143 | 134.237 | 6.596 | 55.361 | 1.00 | 13.45 |
| 1019 | CB | ASP | 143 | 133.794 | 5.701 | 54.194 | 1.00 | 12.41 |
| 1020 | CG | ASP | 143 | 134.284 | 6.196 | 52.835 | 1.00 | 22.67 |
| 1021 | OD1 | ASP | 143 | 133.710 | 5.759 | 51.811 | 1.00 | 21.93 |
| 1022 | OD2 | ASP | 143 | 135.239 | 7.004 | 52.778 | 1.00 | 35.17 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 1023 | C | ASP | 143 | 133.727 | 8.025 | 55.162 | 1.00 | 19.69 |
| 1024 | O | ASP | 143 | 132.675 | 8.238 | 54.559 | 1.00 | 21.70 |
| 1025 | N | VAL | 144 | 134.485 | 8.997 | 55.664 | 1.00 | 21.88 |
| 1026 | CA | VAL | 144 | 134.120 | 10.411 | 55.566 | 1.00 | 19.30 |
| 1027 | CB | VAL | 144 | 135.093 | 11.295 | 56.376 | 1.00 | 16.67 |
| 1028 | CG1 | VAL | 144 | 134.789 | 12.769 | 56.155 | 1.00 | 22.12 |
| 1029 | CG2 | VAL | 144 | 134.978 | 10.961 | 57.857 | 1.00 | 20.43 |
| 1030 | C | VAL | 144 | 133.997 | 10.942 | 54.136 | 1.00 | 18.93 |
| 1031 | O | VAL | 144 | 133.012 | 11.603 | 53.801 | 1.00 | 23.53 |
| 1032 | N | LEU | 145 | 134.984 | 10.657 | 53.293 | 1.00 | 15.19 |
| 1033 | CA | LEU | 145 | 134.940 | 11.122 | 51.912 | 1.00 | 18.54 |
| 1034 | CB | LEU | 145 | 136.238 | 10.780 | 51.181 | 1.00 | 22.93 |
| 1035 | CG | LEU | 145 | 137.524 | 11.410 | 51.722 | 1.00 | 23.25 |
| 1036 | CD1 | LEU | 145 | 138.647 | 11.189 | 50.715 | 1.00 | 24.40 |
| 1037 | CD2 | LEU | 145 | 137.327 | 12.898 | 51.968 | 1.00 | 18.75 |
| 1038 | C | LEU | 145 | 133.744 | 10.535 | 51.168 | 1.00 | 23.90 |
| 1039 | O | LEU | 145 | 133.236 | 11.135 | 50.219 | 1.00 | 26.81 |
| 1040 | N | GLY | 146 | 133.303 | 9.358 | 51.610 | 1.00 | 24.92 |
| 1041 | CA | GLY | 146 | 132.159 | 8.705 | 50.999 | 1.00 | 21.44 |
| 1042 | C | GLY | 146 | 130.868 | 9.313 | 51.512 | 1.00 | 19.58 |
| 1043 | O | GLY | 146 | 129.953 | 9.591 | 50.740 | 1.00 | 22.50 |
| 1044 | N | LEU | 147 | 130.805 | 9.524 | 52.823 | 1.00 | 9.20 |
| 1045 | CA | LEU | 147 | 129.643 | 10.116 | 53.467 | 1.00 | 7.33 |
| 1046 | CB | LEU | 147 | 129.849 | 10.163 | 54.980 | 1.00 | 7.87 |
| 1047 | CG | LEU | 147 | 129.927 | 8.831 | 55.721 | 1.00 | 2.02 |
| 1048 | CD1 | LEU | 147 | 130.341 | 9.066 | 57.157 | 1.00 | 8.20 |
| 1049 | CD2 | LEU | 147 | 128.583 | 8.122 | 55.656 | 1.00 | 15.08 |
| 1050 | C | LEU | 147 | 129.388 | 11.527 | 52.945 | 1.00 | 20.24 |
| 1051 | O | LEU | 147 | 128.244 | 11.900 | 52.680 | 1.00 | 27.36 |
| 1052 | N | LEU | 148 | 130.462 | 12.303 | 52.795 | 1.00 | 20.47 |
| 1053 | CA | LEU | 148 | 130.371 | 13.676 | 52.304 | 1.00 | 20.11 |
| 1054 | CB | LEU | 148 | 131.751 | 14.347 | 52.330 | 1.00 | 16.79 |
| 1055 | CG | LEU | 148 | 131.829 | 15.805 | 51.857 | 1.00 | 13.41 |
| 1056 | CD1 | LEU | 148 | 130.897 | 16.683 | 52.683 | 1.00 | 6.32 |
| 1057 | CD2 | LEU | 148 | 133.256 | 16.306 | 51.961 | 1.00 | 9.98 |
| 1058 | C | LEU | 148 | 129.777 | 13.758 | 50.895 | 1.00 | 16.22 |
| 1059 | O | LEU | 148 | 128.838 | 14.520 | 50.657 | 1.00 | 19.05 |
| 1060 | N | ASN | 149 | 130.332 | 12.985 | 49.965 | 1.00 | 14.19 |
| 1061 | CA | ASN | 149 | 129.840 | 12.986 | 48.592 | 1.00 | 19.68 |
| 1062 | CB | ASN | 149 | 130.776 | 12.199 | 47.678 | 1.00 | 17.57 |
| 1063 | CG | ASN | 149 | 132.009 | 12.987 | 47.306 | 1.00 | 21.68 |
| 1064 | OD1 | ASN | 149 | 132.904 | 13.181 | 48.129 | 1.00 | 27.23 |
| 1065 | ND2 | ASN | 149 | 132.055 | 13.469 | 46.067 | 1.00 | 17.93 |
| 1066 | C | ASN | 149 | 128.414 | 12.461 | 48.486 | 1.00 | 24.02 |
| 1067 | O | ASN | 149 | 127.676 | 12.829 | 47.571 | 1.00 | 25.30 |
| 1068 | N | LEU | 150 | 128.033 | 11.596 | 49.424 | 1.00 | 23.15 |
| 1069 | CA | LEU | 150 | 126.685 | 11.049 | 49.449 | 1.00 | 19.85 |
| 1070 | CB | LEU | 150 | 126.606 | 9.844 | 50.391 | 1.00 | 15.00 |
| 1071 | CG | LEU | 150 | 125.224 | 9.198 | 50.548 | 1.00 | 14.74 |
| 1072 | CD1 | LEU | 150 | 124.735 | 8.634 | 49.215 | 1.00 | 8.02 |
| 1073 | CD2 | LEU | 150 | 125.287 | 8.115 | 51.600 | 1.00 | 2.00 |
| 1074 | C | LEU | 150 | 125.745 | 12.153 | 49.925 | 1.00 | 20.18 |
| 1075 | O | LEU | 150 | 124.640 | 12.304 | 49.404 | 1.00 | 22.47 |
| 1076 | N | TYR | 151 | 126.209 | 12.930 | 50.904 | 1.00 | 18.20 |
| 1077 | CA | TYR | 151 | 125.440 | 14.041 | 51.455 | 1.00 | 18.43 |
| 1078 | CB | TYR | 151 | 126.226 | 14.739 | 52.569 | 1.00 | 10.57 |
| 1079 | CG | TYR | 151 | 125.598 | 16.032 | 53.044 | 1.00 | 11.49 |
| 1080 | CD1 | TYR | 151 | 124.759 | 16.056 | 54.156 | 1.00 | 5.47 |
| 1081 | CE1 | TYR | 151 | 124.171 | 17.242 | 54.586 | 1.00 | 8.73 |
| 1082 | CD2 | TYR | 151 | 125.835 | 17.234 | 52.372 | 1.00 | 10.72 |
| 1083 | CE2 | TYR | 151 | 125.250 | 18.421 | 52.791 | 1.00 | 9.08 |
| 1084 | CZ | TYR | 151 | 124.421 | 18.420 | 53.898 | 1.00 | 11.39 |
| 1085 | OH | TYR | 151 | 123.845 | 19.598 | 54.316 | 1.00 | 11.19 |
| 1086 | C | TYR | 151 | 125.117 | 15.041 | 50.355 | 1.00 | 17.39 |
| 1087 | O | TYR | 151 | 123.990 | 15.521 | 50.256 | 1.00 | 26.93 |
| 1088 | N | GLU | 152 | 126.121 | 15.374 | 49.552 | 1.00 | 15.23 |
| 1089 | CA | GLU | 152 | 125.937 | 16.316 | 48.455 | 1.00 | 18.45 |
| 1090 | CB | GLU | 152 | 127.282 | 16.649 | 47.798 | 1.00 | 14.61 |
| 1091 | CG | GLU | 152 | 128.316 | 17.293 | 48.727 | 1.00 | 17.73 |
| 1092 | CD | GLU | 152 | 127.962 | 18.712 | 49.169 | 1.00 | 16.74 |
| 1093 | OE1 | GLU | 152 | 126.980 | 19.292 | 48.662 | 1.00 | 16.63 |
| 1094 | OE2 | GLU | 152 | 128.681 | 19.252 | 50.034 | 1.00 | 22.78 |
| 1095 | C | GLU | 152 | 124.977 | 15.750 | 47.413 | 1.00 | 13.63 |
| 1096 | O | GLU | 152 | 124.114 | 16.463 | 46.904 | 1.00 | 20.19 |
| 1097 | N | ALA | 153 | 125.115 | 14.458 | 47.125 | 1.00 | 18.04 |
| 1098 | CA | ALA | 153 | 124.271 | 13.778 | 46.143 | 1.00 | 14.37 |
| 1099 | CB | ALA | 153 | 124.859 | 12.417 | 45.794 | 1.00 | 13.44 |
| 1100 | C | ALA | 153 | 122.815 | 13.624 | 46.580 | 1.00 | 13.36 |
| 1101 | O | ALA | 153 | 121.921 | 13.577 | 45.738 | 1.00 | 11.20 |
| 1102 | N | SER | 154 | 122.574 | 13.568 | 47.889 | 1.00 | 16.02 |
| 1103 | CA | SER | 154 | 121.218 | 13.413 | 48.416 | 1.00 | 13.22 |
| 1104 | CB | SER | 154 | 121.250 | 13.157 | 49.928 | 1.00 | 8.73 |
| 1105 | OG | SER | 154 | 121.581 | 14.330 | 50.651 | 1.00 | 16.49 |
| 1106 | C | SER | 154 | 120.312 | 14.607 | 48.118 | 1.00 | 14.26 |
| 1107 | O | SER | 154 | 119.087 | 14.504 | 48.207 | 1.00 | 26.54 |
| 1108 | N | HIS | 155 | 120.915 | 15.735 | 47.757 | 1.00 | 14.00 |
| 1109 | CA | HIS | 155 | 120.154 | 16.942 | 47.457 | 1.00 | 8.22 |
| 1110 | CB | HIS | 155 | 120.920 | 18.177 | 47.928 | 1.00 | 2.00 |
| 1111 | CG | HIS | 155 | 120.932 | 18.340 | 49.415 | 1.00 | 2.00 |
| 1112 | CD2 | HIS | 155 | 120.036 | 18.914 | 50.255 | 1.00 | 3.97 |
| 1113 | ND1 | HIS | 155 | 121.946 | 17.856 | 50.211 | 1.00 | 3.74 |
| 1114 | CE1 | HIS | 155 | 121.676 | 18.123 | 51.476 | 1.00 | 12.80 |
| 1115 | NE2 | HIS | 155 | 120.522 | 18.764 | 51.529 | 1.00 | 11.17 |
| 1116 | C | HIS | 155 | 119.742 | 17.092 | 45.997 | 1.00 | 10.18 |
| 1117 | O | HIS | 155 | 119.025 | 18.030 | 45.645 | 1.00 | 16.07 |
| 1118 | N | VAL | 156 | 120.182 | 16.163 | 45.152 | 1.00 | 6.86 |
| 1119 | CA | VAL | 156 | 119.843 | 16.202 | 43.733 | 1.00 | 7.09 |
| 1120 | CB | VAL | 156 | 121.109 | 16.099 | 42.823 | 1.00 | 5.97 |
| 1121 | CG1 | VAL | 156 | 122.161 | 17.113 | 43.248 | 1.00 | 2.00 |
| 1122 | CG2 | VAL | 156 | 121.678 | 14.682 | 42.841 | 1.00 | 4.04 |
| 1123 | C | VAL | 156 | 118.866 | 15.087 | 43.354 | 1.00 | 11.84 |
| 1124 | O | VAL | 156 | 118.644 | 14.827 | 42.170 | 1.00 | 13.76 |
| 1125 | N | ARG | 157 | 118.264 | 14.443 | 44.351 | 1.00 | 12.59 |
| 1126 | CA | ARG | 157 | 117.329 | 13.357 | 44.074 | 1.00 | 21.43 |
| 1127 | CB | ARG | 157 | 117.224 | 12.398 | 45.271 | 1.00 | 17.56 |
| 1128 | CG | ARG | 157 | 116.482 | 12.908 | 46.491 | 1.00 | 22.45 |
| 1129 | CD | ARG | 157 | 116.525 | 11.846 | 47.583 | 1.00 | 26.00 |
| 1130 | NE | ARG | 157 | 115.512 | 12.037 | 48.620 | 1.00 | 35.19 |
| 1131 | CZ | ARG | 157 | 114.360 | 11.370 | 48.676 | 1.00 | 40.41 |
| 1132 | NH1 | ARG | 157 | 114.064 | 10.465 | 47.753 | 1.00 | 42.25 |
| 1133 | NH2 | ARG | 157 | 113.505 | 11.598 | 49.664 | 1.00 | 42.66 |
| 1134 | C | ARG | 157 | 115.945 | 13.815 | 43.609 | 1.00 | 22.46 |
| 1135 | O | ARG | 157 | 115.473 | 14.885 | 43.985 | 1.00 | 28.62 |
| 1136 | N | THR | 158 | 115.334 | 13.012 | 42.740 | 1.00 | 30.57 |
| 1137 | CA | THR | 158 | 114.003 | 13.287 | 42.200 | 1.00 | 23.48 |
| 1138 | CB | THR | 158 | 113.951 | 13.012 | 40.675 | 1.00 | 18.85 |
| 1139 | OG1 | THR | 158 | 114.132 | 11.613 | 40.424 | 1.00 | 23.14 |
| 1140 | CG2 | THR | 158 | 115.044 | 13.781 | 39.959 | 1.00 | 5.29 |
| 1141 | C | THR | 158 | 112.962 | 12.409 | 42.911 | 1.00 | 26.07 |
| 1142 | O | THR | 158 | 113.258 | 11.786 | 43.936 | 1.00 | 29.73 |
| 1143 | N | HIS | 159 | 111.745 | 12.362 | 42.373 | 1.00 | 25.85 |
| 1144 | CA | HIS | 159 | 110.681 | 11.551 | 42.967 | 1.00 | 24.71 |
| 1145 | CB | HIS | 159 | 109.312 | 11.987 | 42.435 | 1.00 | 24.02 |
| 1146 | CG | HIS | 159 | 108.903 | 13.358 | 42.872 | 1.00 | 20.05 |
| 1147 | CD2 | HIS | 159 | 108.888 | 14.538 | 42.209 | 1.00 | 14.66 |
| 1148 | ND1 | HIS | 159 | 108.453 | 13.629 | 44.147 | 1.00 | 22.06 |
| 1149 | CE1 | HIS | 159 | 108.179 | 14.917 | 44.250 | 1.00 | 20.70 |
| 1150 | NE2 | HIS | 159 | 108.434 | 15.492 | 43.088 | 1.00 | 18.69 |
| 1151 | C | HIS | 159 | 110.893 | 10.054 | 42.723 | 1.00 | 28.82 |
| 1152 | O | HIS | 159 | 110.377 | 9.211 | 43.464 | 1.00 | 29.90 |
| 1153 | N | ALA | 160 | 111.674 | 9.733 | 41.695 | 1.00 | 22.36 |
| 1154 | CA | ALA | 160 | 111.966 | 8.351 | 41.341 | 1.00 | 16.69 |
| 1155 | CB | ALA | 160 | 112.118 | 8.233 | 39.835 | 1.00 | 12.78 |
| 1156 | C | ALA | 160 | 113.218 | 7.821 | 42.038 | 1.00 | 24.25 |
| 1157 | O | ALA | 160 | 113.748 | 6.775 | 41.655 | 1.00 | 30.58 |
| 1158 | N | ASP | 161 | 113.679 | 8.531 | 43.066 | 1.00 | 27.69 |
| 1159 | CA | ASP | 161 | 114.880 | 8.134 | 43.800 | 1.00 | 24.25 |
| 1160 | CB | ASP | 161 | 115.968 | 9.212 | 43.669 | 1.00 | 22.91 |
| 1161 | CG | ASP | 161 | 116.356 | 9.495 | 42.222 | 1.00 | 29.35 |
| 1162 | OD1 | ASP | 161 | 116.405 | 8.550 | 41.404 | 1.00 | 29.54 |
| 1163 | OD2 | ASP | 161 | 116.623 | 10.672 | 41.906 | 1.00 | 19.16 |
| 1164 | C | ASP | 161 | 114.626 | 7.840 | 45.281 | 1.00 | 26.01 |
| 1165 | O | ASP | 161 | 115.308 | 8.380 | 46.154 | 1.00 | 34.22 |
| 1166 | N | ASP | 162 | 113.670 | 6.957 | 45.561 | 1.00 | 28.71 |
| 1167 | CA | ASP | 162 | 113.339 | 6.590 | 46.939 | 1.00 | 28.70 |
| 1168 | CB | ASP | 162 | 111.999 | 5.859 | 46.993 | 1.00 | 34.90 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 1169 | CG | ASP | 162 | 110.851 | 6.726 | 46.536 | 1.00 | 42.80 |
| 1170 | OD1 | ASP | 162 | 110.426 | 7.600 | 47.322 | 1.00 | 36.44 |
| 1171 | OD2 | ASP | 162 | 110.386 | 6.543 | 45.389 | 1.00 | 43.54 |
| 1172 | C | ASP | 162 | 114.423 | 5.728 | 47.573 | 1.00 | 27.14 |
| 1173 | O | ASP | 162 | 114.386 | 5.441 | 48.769 | 1.00 | 28.39 |
| 1174 | N | ILE | 163 | 115.378 | 5.302 | 46.756 | 1.00 | 26.67 |
| 1175 | CA | ILE | 163 | 116.485 | 4.486 | 47.229 | 1.00 | 27.39 |
| 1176 | CB | ILE | 163 | 117.250 | 3.866 | 46.030 | 1.00 | 24.84 |
| 1177 | CG2 | ILE | 163 | 118.201 | 4.881 | 45.412 | 1.00 | 29.37 |
| 1178 | CG1 | ILE | 163 | 118.015 | 2.623 | 46.471 | 1.00 | 30.57 |
| 1179 | CD1 | ILE | 163 | 118.639 | 1.863 | 45.323 | 1.00 | 43.90 |
| 1180 | C | ILE | 163 | 117.407 | 5.372 | 48.078 | 1.00 | 28.12 |
| 1181 | O | ILE | 163 | 118.169 | 4.881 | 48.912 | 1.00 | 29.38 |
| 1182 | N | LEU | 164 | 117.277 | 6.686 | 47.890 | 1.00 | 30.46 |
| 1183 | CA | LEU | 164 | 118.070 | 7.684 | 48.607 | 1.00 | 24.33 |
| 1184 | CB | LEU | 164 | 118.646 | 8.695 | 47.612 | 1.00 | 16.04 |
| 1185 | CG | LEU | 164 | 119.602 | 8.181 | 46.538 | 1.00 | 20.33 |
| 1186 | CD1 | LEU | 164 | 119.864 | 9.271 | 45.514 | 1.00 | 22.74 |
| 1187 | CD2 | LEU | 164 | 120.894 | 7.720 | 47.184 | 1.00 | 17.92 |
| 1188 | C | LEU | 164 | 117.259 | 8.441 | 49.658 | 1.00 | 23.88 |
| 1189 | O | LEU | 164 | 117.667 | 9.518 | 50.101 | 1.00 | 32.16 |
| 1190 | N | GLU | 165 | 116.120 | 7.882 | 50.061 | 1.00 | 21.56 |
| 1191 | CA | GLU | 165 | 115.256 | 8.529 | 51.043 | 1.00 | 18.89 |
| 1192 | CB | GLU | 165 | 113.947 | 7.755 | 51.202 | 1.00 | 24.79 |
| 1193 | CG | GLU | 165 | 114.127 | 6.324 | 51.689 | 1.00 | 48.18 |
| 1194 | CD | GLU | 165 | 112.819 | 5.561 | 51.814 | 1.00 | 57.24 |
| 1195 | OE1 | GLU | 165 | 111.765 | 6.076 | 51.375 | 1.00 | 63.77 |
| 1196 | OE2 | GLU | 165 | 112.850 | 4.434 | 52.353 | 1.00 | 62.32 |
| 1197 | C | GLU | 165 | 115.907 | 8.727 | 52.405 | 1.00 | 16.81 |
| 1198 | O | GLU | 165 | 115.598 | 9.687 | 53.106 | 1.00 | 18.04 |
| 1199 | N | ASP | 166 | 116.817 | 7.828 | 52.771 | 1.00 | 23.03 |
| 1200 | CA | ASP | 166 | 117.497 | 7.914 | 54.061 | 1.00 | 27.94 |
| 1201 | CB | ASP | 166 | 117.383 | 6.579 | 54.811 | 1.00 | 35.23 |
| 1202 | CG | ASP | 166 | 115.936 | 6.177 | 55.082 | 1.00 | 50.03 |
| 1203 | OD1 | ASP | 166 | 115.565 | 5.024 | 54.771 | 1.00 | 57.17 |
| 1204 | OD2 | ASP | 166 | 115.169 | 7.013 | 55.606 | 1.00 | 53.93 |
| 1205 | C | ASP | 166 | 118.966 | 8.330 | 53.943 | 1.00 | 24.13 |
| 1206 | O | ASP | 166 | 119.674 | 8.409 | 54.950 | 1.00 | 23.24 |
| 1207 | N | ALA | 167 | 119.401 | 8.638 | 52.721 | 1.00 | 14.78 |
| 1208 | CA | ALA | 167 | 120.780 | 9.044 | 52.443 | 1.00 | 16.72 |
| 1209 | CB | ALA | 167 | 120.993 | 9.169 | 50.948 | 1.00 | 12.70 |
| 1210 | C | ALA | 167 | 121.215 | 10.333 | 53.136 | 1.00 | 24.13 |
| 1211 | O | ALA | 167 | 122.355 | 10.443 | 53.590 | 1.00 | 29.67 |
| 1212 | N | LEU | 168 | 120.317 | 11.313 | 53.193 | 1.00 | 27.80 |
| 1213 | CA | LEU | 168 | 120.614 | 12.590 | 53.831 | 1.00 | 19.27 |
| 1214 | CB | LEU | 168 | 119.540 | 13.623 | 53.487 | 1.00 | 23.80 |
| 1215 | CG | LEU | 168 | 119.706 | 15.016 | 54.099 | 1.00 | 18.12 |
| 1216 | CD1 | LEU | 168 | 121.006 | 15.642 | 53.626 | 1.00 | 19.21 |
| 1217 | CD2 | LEU | 168 | 118.524 | 15.890 | 53.719 | 1.00 | 17.36 |
| 1218 | C | LEU | 168 | 120.730 | 12.450 | 55.343 | 1.00 | 20.39 |
| 1219 | O | LEU | 168 | 121.663 | 12.973 | 55.943 | 1.00 | 26.94 |
| 1220 | N | ALA | 169 | 119.776 | 11.755 | 55.954 | 1.00 | 22.95 |
| 1221 | CA | ALA | 169 | 119.784 | 11.555 | 57.400 | 1.00 | 28.99 |
| 1222 | CB | ALA | 169 | 118.472 | 10.934 | 57.856 | 1.00 | 26.34 |
| 1223 | C | ALA | 169 | 120.959 | 10.676 | 57.816 | 1.00 | 31.11 |
| 1224 | O | ALA | 169 | 121.529 | 10.855 | 58.895 | 1.00 | 32.24 |
| 1225 | N | PHE | 170 | 121.319 | 9.736 | 56.944 | 1.00 | 26.27 |
| 1226 | CA | PHE | 170 | 122.423 | 8.819 | 57.197 | 1.00 | 22.01 |
| 1227 | CB | PHE | 170 | 122.448 | 7.714 | 56.135 | 1.00 | 20.64 |
| 1228 | CG | PHE | 170 | 123.592 | 6.747 | 56.284 | 1.00 | 28.63 |
| 1229 | CD1 | PHE | 170 | 123.622 | 5.837 | 57.338 | 1.00 | 28.29 |
| 1230 | CD2 | PHE | 170 | 124.642 | 6.745 | 55.368 | 1.00 | 25.46 |
| 1231 | CE1 | PHE | 170 | 124.683 | 4.938 | 57.479 | 1.00 | 27.46 |
| 1232 | CE2 | PHE | 170 | 125.706 | 5.850 | 55.500 | 1.00 | 24.24 |
| 1233 | CZ | PHE | 170 | 125.726 | 4.945 | 56.558 | 1.00 | 22.35 |
| 1234 | C | PHE | 170 | 123.752 | 9.564 | 57.205 | 1.00 | 20.63 |
| 1235 | O | PHE | 170 | 124.440 | 9.610 | 58.224 | 1.00 | 23.76 |
| 1236 | N | SER | 171 | 124.095 | 10.156 | 56.066 | 1.00 | 16.15 |
| 1237 | CA | SER | 171 | 125.340 | 10.899 | 55.918 | 1.00 | 12.93 |
| 1238 | CB | SER | 171 | 125.476 | 11.429 | 54.488 | 1.00 | 12.97 |
| 1239 | OG | SER | 171 | 124.397 | 12.281 | 54.152 | 1.00 | 12.50 |
| 1240 | C | SER | 171 | 125.479 | 12.047 | 56.912 | 1.00 | 13.92 |
| 1241 | O | SER | 171 | 126.567 | 12.297 | 57.420 | 1.00 | 15.50 |
| 1242 | N | THR | 172 | 124.372 | 12.726 | 57.205 | 1.00 | 16.38 |
| 1243 | CA | THR | 172 | 124.383 | 13.854 | 58.137 | 1.00 | 16.69 |
| 1244 | CB | THR | 172 | 123.000 | 14.564 | 58.196 | 1.00 | 14.70 |
| 1245 | OG1 | THR | 172 | 122.758 | 15.259 | 56.966 | 1.00 | 12.00 |
| 1246 | CG2 | THR | 172 | 122.946 | 15.559 | 59.348 | 1.00 | 6.76 |
| 1247 | C | THR | 172 | 124.813 | 13.486 | 59.556 | 1.00 | 19.18 |
| 1248 | O | THR | 172 | 125.759 | 14.067 | 60.086 | 1.00 | 22.93 |
| 1249 | N | ILE | 173 | 124.129 | 12.516 | 60.160 | 1.00 | 22.35 |
| 1250 | CA | ILE | 173 | 124.439 | 12.112 | 61.529 | 1.00 | 26.29 |
| 1251 | CB | ILE | 173 | 123.428 | 11.061 | 62.070 | 1.00 | 29.19 |
| 1252 | CG2 | ILE | 173 | 123.553 | 9.747 | 61.305 | 1.00 | 26.89 |
| 1253 | CG1 | ILE | 173 | 123.657 | 10.844 | 63.572 | 1.00 | 34.59 |
| 1254 | CD1 | ILE | 173 | 122.655 | 9.928 | 64.240 | 1.00 | 35.92 |
| 1255 | C | ILE | 173 | 125.868 | 11.602 | 61.702 | 1.00 | 27.07 |
| 1256 | O | ILE | 173 | 126.481 | 11.801 | 62.754 | 1.00 | 30.04 |
| 1257 | N | HIS | 174 | 126.404 | 10.972 | 60.662 | 1.00 | 18.99 |
| 1258 | CA | HIS | 174 | 127.757 | 10.441 | 60.721 | 1.00 | 26.30 |
| 1259 | CB | HIS | 174 | 127.895 | 9.228 | 59.799 | 1.00 | 36.54 |
| 1260 | CG | HIS | 174 | 127.114 | 8.034 | 60.257 | 1.00 | 41.37 |
| 1261 | CD2 | HIS | 174 | 126.355 | 7.147 | 59.571 | 1.00 | 35.65 |
| 1262 | ND1 | HIS | 174 | 127.057 | 7.644 | 61.579 | 1.00 | 39.38 |
| 1263 | CE1 | HIS | 174 | 126.295 | 6.569 | 61.687 | 1.00 | 33.20 |
| 1264 | NE2 | HIS | 174 | 125.857 | 6.248 | 60.483 | 1.00 | 35.00 |
| 1265 | C | HIS | 174 | 128.804 | 11.504 | 60.407 | 1.00 | 27.93 |
| 1266 | O | HIS | 174 | 129.945 | 11.419 | 60.872 | 1.00 | 25.80 |
| 1267 | N | LEU | 175 | 128.410 | 12.508 | 59.626 | 1.00 | 25.88 |
| 1268 | CA | LEU | 175 | 129.312 | 13.600 | 59.280 | 1.00 | 17.20 |
| 1269 | CB | LEU | 175 | 128.804 | 14.376 | 58.066 | 1.00 | 12.92 |
| 1270 | CG | LEU | 175 | 129.069 | 13.747 | 56.696 | 1.00 | 4.37 |
| 1271 | CD1 | LEU | 175 | 128.472 | 14.624 | 55.606 | 1.00 | 2.00 |
| 1272 | CD2 | LEU | 175 | 130.566 | 13.572 | 56.482 | 1.00 | 6.69 |
| 1273 | C | LEU | 175 | 129.459 | 14.530 | 60.470 | 1.00 | 17.96 |
| 1274 | O | LEU | 175 | 130.534 | 15.074 | 60.705 | 1.00 | 30.10 |
| 1275 | N | GLU | 176 | 128.375 | 14.699 | 61.225 | 1.00 | 17.67 |
| 1276 | CA | GLU | 176 | 128.386 | 15.550 | 62.412 | 1.00 | 27.17 |
| 1277 | CB | GLU | 176 | 126.969 | 15.740 | 62.959 | 1.00 | 26.19 |
| 1278 | CG | GLU | 176 | 125.997 | 16.452 | 62.037 | 1.00 | 39.91 |
| 1279 | CD | GLU | 176 | 124.606 | 16.584 | 62.645 | 1.00 | 51.08 |
| 1280 | OE1 | GLU | 176 | 124.184 | 15.676 | 63.398 | 1.00 | 49.19 |
| 1281 | OE2 | GLU | 176 | 123.932 | 17.600 | 62.368 | 1.00 | 52.29 |
| 1282 | C | GLU | 176 | 129.241 | 14.913 | 63.505 | 1.00 | 29.58 |
| 1283 | O | GLU | 176 | 129.953 | 15.604 | 64.237 | 1.00 | 37.29 |
| 1284 | N | SER | 177 | 129.156 | 13.589 | 63.604 | 1.00 | 31.69 |
| 1285 | CA | SER | 177 | 129.883 | 12.816 | 64.607 | 1.00 | 28.71 |
| 1286 | CB | SER | 177 | 129.310 | 11.395 | 64.678 | 1.00 | 24.94 |
| 1287 | OG | SER | 177 | 129.868 | 10.660 | 65.755 | 1.00 | 27.40 |
| 1288 | C | SER | 177 | 131.392 | 12.758 | 64.370 | 1.00 | 25.55 |
| 1289 | O | SER | 177 | 132.177 | 12.795 | 65.324 | 1.00 | 17.66 |
| 1290 | N | ALA | 178 | 131.787 | 12.682 | 63.102 | 1.00 | 17.70 |
| 1291 | CA | ALA | 178 | 133.195 | 12.600 | 62.723 | 1.00 | 19.27 |
| 1292 | CB | ALA | 178 | 133.330 | 11.789 | 61.441 | 1.00 | 22.41 |
| 1293 | C | ALA | 178 | 133.897 | 13.948 | 62.558 | 1.00 | 24.31 |
| 1294 | O | ALA | 178 | 135.107 | 14.054 | 62.769 | 1.00 | 24.74 |
| 1295 | N | ALA | 179 | 133.124 | 14.975 | 62.214 | 1.00 | 25.32 |
| 1296 | CA | ALA | 179 | 133.630 | 16.326 | 61.971 | 1.00 | 25.36 |
| 1297 | CB | ALA | 179 | 132.460 | 17.289 | 61.779 | 1.00 | 32.63 |
| 1298 | C | ALA | 179 | 134.658 | 16.943 | 62.928 | 1.00 | 23.67 |
| 1299 | O | ALA | 179 | 135.706 | 17.420 | 62.487 | 1.00 | 23.47 |
| 1300 | N | PRO | 180 | 134.384 | 16.929 | 64.244 | 1.00 | 21.48 |
| 1301 | CD | PRO | 180 | 133.196 | 16.355 | 64.900 | 1.00 | 20.79 |
| 1302 | CA | PRO | 180 | 135.291 | 17.505 | 65.247 | 1.00 | 20.21 |
| 1303 | CB | PRO | 180 | 134.601 | 17.155 | 66.568 | 1.00 | 10.68 |
| 1304 | CG | PRO | 180 | 133.162 | 17.108 | 66.203 | 1.00 | 16.34 |
| 1305 | C | PRO | 180 | 136.747 | 17.040 | 65.264 | 1.00 | 21.05 |
| 1306 | O | PRO | 180 | 137.623 | 17.772 | 65.722 | 1.00 | 30.38 |
| 1307 | N | HIS | 181 | 137.015 | 15.846 | 64.750 | 1.00 | 24.41 |
| 1308 | CA | HIS | 181 | 138.372 | 15.310 | 64.785 | 1.00 | 20.38 |
| 1309 | CB | HIS | 181 | 138.359 | 13.955 | 65.498 | 1.00 | 22.19 |
| 1310 | CG | HIS | 181 | 137.686 | 13.989 | 66.837 | 1.00 | 20.19 |
| 1311 | CD2 | HIS | 181 | 138.077 | 14.524 | 68.018 | 1.00 | 22.10 |
| 1312 | ND1 | HIS | 181 | 136.437 | 13.448 | 67.055 | 1.00 | 24.79 |
| 1313 | CE1 | HIS | 181 | 136.086 | 13.649 | 68.313 | 1.00 | 28.39 |
| 1314 | NE2 | HIS | 181 | 137.064 | 14.300 | 68.919 | 1.00 | 34.90 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 1315 | C | HIS | 181 | 139.073 | 15.184 | 63.443 | 1.00 | 16.56 |
| 1316 | O | HIS | 181 | 140.138 | 14.575 | 63.351 | 1.00 | 20.78 |
| 1317 | N | LEU | 182 | 138.496 | 15.775 | 62.407 | 1.00 | 19.38 |
| 1318 | CA | LEU | 182 | 139.095 | 15.698 | 61.082 | 1.00 | 19.81 |
| 1319 | CB | LEU | 182 | 138.023 | 15.838 | 59.999 | 1.00 | 12.64 |
| 1320 | CG | LEU | 182 | 136.883 | 14.822 | 60.017 | 1.00 | 9.36 |
| 1321 | CD1 | LEU | 182 | 135.883 | 15.191 | 58.946 | 1.00 | 6.26 |
| 1322 | CD2 | LEU | 182 | 137.414 | 13.405 | 59.808 | 1.00 | 5.44 |
| 1323 | C | LEU | 182 | 140.164 | 16.760 | 60.884 | 1.00 | 23.01 |
| 1324 | O | LEU | 182 | 140.177 | 17.787 | 61.567 | 1.00 | 24.75 |
| 1325 | N | LYS | 183 | 141.071 | 16.492 | 59.953 | 1.00 | 23.75 |
| 1326 | CA | LYS | 183 | 142.139 | 17.426 | 59.646 | 1.00 | 25.95 |
| 1327 | CB | LYS | 183 | 143.300 | 16.712 | 58.948 | 1.00 | 25.08 |
| 1328 | CG | LYS | 183 | 142.946 | 16.106 | 57.600 | 1.00 | 32.88 |
| 1329 | CD | LYS | 183 | 144.157 | 15.465 | 56.949 | 1.00 | 39.75 |
| 1330 | CE | LYS | 183 | 143.804 | 14.905 | 55.581 | 1.00 | 45.64 |
| 1331 | NZ | LYS | 183 | 144.980 | 14.277 | 54.913 | 1.00 | 50.66 |
| 1332 | C | LYS | 183 | 141.590 | 18.522 | 58.747 | 1.00 | 26.52 |
| 1333 | O | LYS | 183 | 140.579 | 18.333 | 58.068 | 1.00 | 31.05 |
| 1334 | N | SER | 184 | 142.247 | 19.675 | 58.769 | 1.00 | 25.24 |
| 1335 | CA | SER | 184 | 141.842 | 20.806 | 57.949 | 1.00 | 18.75 |
| 1336 | CB | SER | 184 | 142.202 | 22.111 | 58.656 | 1.00 | 15.62 |
| 1337 | OG | SER | 184 | 141.536 | 22.192 | 59.906 | 1.00 | 17.72 |
| 1338 | C | SER | 184 | 142.553 | 20.707 | 58.605 | 1.00 | 13.85 |
| 1339 | O | SER | 184 | 143.666 | 20.186 | 56.528 | 1.00 | 23.56 |
| 1340 | N | PRO | 185 | 141.930 | 21.221 | 55.526 | 1.00 | 14.69 |
| 1341 | CD | PRO | 185 | 142.636 | 21.342 | 54.235 | 1.00 | 6.08 |
| 1342 | CA | PRO | 185 | 140.622 | 21.886 | 56.462 | 1.00 | 13.32 |
| 1343 | CB | PRO | 185 | 140.758 | 22.747 | 54.213 | 1.00 | 7.14 |
| 1344 | CG | PRO | 185 | 141.553 | 21.860 | 53.309 | 1.00 | 4.25 |
| 1345 | C | PRO | 185 | 139.378 | 20.990 | 55.368 | 1.00 | 19.26 |
| 1346 | O | PRO | 185 | 138.268 | 21.502 | 55.198 | 1.00 | 22.11 |
| 1347 | N | LEU | 186 | 139.547 | 19.671 | 55.478 | 1.00 | 15.43 |
| 1348 | CA | LEU | 186 | 138.410 | 18.757 | 55.385 | 1.00 | 7.82 |
| 1349 | CB | LEU | 186 | 138.859 | 17.304 | 55.533 | 1.00 | 10.45 |
| 1350 | CG | LEU | 186 | 137.743 | 16.259 | 55.379 | 1.00 | 14.68 |
| 1351 | CD1 | LEU | 186 | 137.199 | 16.257 | 53.953 | 1.00 | 2.00 |
| 1352 | CD2 | LEU | 186 | 138.269 | 14.885 | 55.744 | 1.00 | 10.39 |
| 1353 | C | LEU | 186 | 137.339 | 19.061 | 56.424 | 1.00 | 14.43 |
| 1354 | O | LEU | 186 | 136.147 | 19.062 | 56.114 | 1.00 | 15.11 |
| 1355 | N | ARG | 187 | 137.774 | 19.318 | 57.653 | 1.00 | 11.19 |
| 1356 | CA | ARG | 187 | 136.868 | 19.626 | 58.755 | 1.00 | 10.77 |
| 1357 | CB | ARG | 187 | 137.675 | 19.929 | 60.019 | 1.00 | 9.64 |
| 1358 | CG | ARG | 187 | 136.839 | 20.202 | 61.251 | 1.00 | 12.29 |
| 1359 | CD | ARG | 187 | 137.724 | 20.530 | 62.429 | 1.00 | 17.99 |
| 1360 | NE | ARG | 187 | 136.944 | 20.796 | 63.633 | 1.00 | 40.99 |
| 1361 | CZ | ARG | 187 | 137.468 | 20.982 | 64.841 | 1.00 | 53.63 |
| 1362 | NH1 | ARG | 187 | 138.785 | 20.931 | 65.014 | 1.00 | 54.42 |
| 1363 | NH2 | ARG | 187 | 136.674 | 21.217 | 65.879 | 1.00 | 49.07 |
| 1364 | C | ARG | 187 | 135.949 | 20.804 | 58.424 | 1.00 | 19.68 |
| 1365 | O | ARG | 187 | 134.754 | 20.771 | 58.731 | 1.00 | 20.19 |
| 1366 | N | GLU | 188 | 136.512 | 21.831 | 57.789 | 1.00 | 19.04 |
| 1367 | CA | GLU | 188 | 135.758 | 23.026 | 57.405 | 1.00 | 14.75 |
| 1368 | CB | GLU | 188 | 136.708 | 24.179 | 57.052 | 1.00 | 18.38 |
| 1369 | CG | GLU | 188 | 137.416 | 24.825 | 58.248 | 1.00 | 25.44 |
| 1370 | CD | GLU | 188 | 138.326 | 23.865 | 59.000 | 1.00 | 37.02 |
| 1371 | OE1 | GLU | 188 | 138.143 | 23.708 | 60.228 | 1.00 | 36.96 |
| 1372 | OE2 | GLU | 188 | 139.224 | 23.271 | 58.362 | 1.00 | 33.70 |
| 1373 | C | GLU | 188 | 134.819 | 22.758 | 56.236 | 1.00 | 15.06 |
| 1374 | O | GLU | 188 | 133.720 | 23.317 | 56.176 | 1.00 | 16.38 |
| 1375 | N | GLN | 189 | 135.263 | 21.920 | 55.301 | 1.00 | 12.50 |
| 1376 | CA | GLN | 189 | 134.458 | 21.567 | 54.134 | 1.00 | 10.80 |
| 1377 | CB | GLN | 189 | 135.269 | 20.711 | 53.153 | 1.00 | 10.38 |
| 1378 | CG | GLN | 189 | 134.529 | 20.384 | 51.856 | 1.00 | 9.35 |
| 1379 | CD | GLN | 189 | 135.415 | 19.722 | 50.811 | 1.00 | 16.04 |
| 1380 | OE1 | GLN | 189 | 135.319 | 20.022 | 49.617 | 1.00 | 8.08 |
| 1381 | NE2 | GLN | 189 | 136.277 | 18.812 | 51.254 | 1.00 | 11.78 |
| 1382 | C | GLN | 189 | 133.204 | 20.814 | 54.574 | 1.00 | 12.51 |
| 1383 | O | GLN | 189 | 132.117 | 21.057 | 54.059 | 1.00 | 19.40 |
| 1384 | N | VAL | 190 | 133.363 | 19.920 | 55.546 | 1.00 | 11.87 |
| 1385 | CA | VAL | 190 | 132.250 | 19.139 | 56.070 | 1.00 | 14.05 |
| 1386 | CB | VAL | 190 | 132.750 | 17.975 | 56.967 | 1.00 | 18.34 |
| 1387 | CG1 | VAL | 190 | 131.574 | 17.265 | 57.637 | 1.00 | 19.94 |
| 1388 | CG2 | VAL | 190 | 133.556 | 16.986 | 56.135 | 1.00 | 2.59 |
| 1389 | C | VAL | 190 | 131.300 | 20.031 | 56.865 | 1.00 | 12.69 |
| 1390 | O | VAL | 190 | 130.091 | 20.012 | 56.642 | 1.00 | 16.38 |
| 1391 | N | THR | 191 | 131.858 | 20.822 | 57.777 | 1.00 | 19.11 |
| 1392 | CA | THR | 191 | 131.065 | 21.727 | 58.606 | 1.00 | 20.76 |
| 1393 | CB | THR | 191 | 131.964 | 22.557 | 59.551 | 1.00 | 23.59 |
| 1394 | OG1 | THR | 191 | 132.681 | 21.675 | 60.424 | 1.00 | 29.20 |
| 1395 | CG2 | THR | 191 | 131.130 | 23.511 | 60.391 | 1.00 | 29.68 |
| 1396 | C | THR | 191 | 130.241 | 22.664 | 57.731 | 1.00 | 19.82 |
| 1397 | O | THR | 191 | 129.073 | 22.927 | 58.023 | 1.00 | 24.05 |
| 1398 | N | HIS | 192 | 130.843 | 23.136 | 56.641 | 1.00 | 11.94 |
| 1399 | CA | HIS | 192 | 130.160 | 24.032 | 55.719 | 1.00 | 13.13 |
| 1400 | CB | HIS | 192 | 131.148 | 24.658 | 54.741 | 1.00 | 14.49 |
| 1401 | CG | HIS | 192 | 130.512 | 25.600 | 53.764 | 1.00 | 13.85 |
| 1402 | CD2 | HIS | 192 | 130.320 | 25.503 | 52.428 | 1.00 | 14.30 |
| 1403 | ND1 | HIS | 192 | 129.981 | 26.814 | 54.141 | 1.00 | 17.04 |
| 1404 | CE1 | HIS | 192 | 129.488 | 27.425 | 53.078 | 1.00 | 22.40 |
| 1405 | NE2 | HIS | 192 | 129.681 | 26.651 | 52.025 | 1.00 | 9.94 |
| 1406 | C | HIS | 192 | 129.061 | 23.321 | 54.939 | 1.00 | 15.72 |
| 1407 | O | HIS | 192 | 128.002 | 23.896 | 54.696 | 1.00 | 19.37 |
| 1408 | N | ALA | 193 | 129.331 | 22.085 | 54.524 | 1.00 | 22.40 |
| 1409 | CA | ALA | 193 | 128.367 | 21.288 | 53.766 | 1.00 | 17.47 |
| 1410 | CB | ALA | 193 | 128.993 | 19.976 | 53.333 | 1.00 | 13.16 |
| 1411 | C | ALA | 193 | 127.104 | 21.027 | 54.584 | 1.00 | 18.46 |
| 1412 | O | ALA | 193 | 125.991 | 21.093 | 54.063 | 1.00 | 20.11 |
| 1413 | N | LEU | 194 | 127.285 | 20.747 | 55.870 | 1.00 | 13.26 |
| 1414 | CA | LEU | 194 | 126.165 | 20.488 | 56.763 | 1.00 | 18.67 |
| 1415 | CB | LEU | 194 | 126.669 | 19.948 | 58.103 | 1.00 | 22.98 |
| 1416 | CG | LEU | 194 | 127.424 | 18.615 | 58.050 | 1.00 | 17.83 |
| 1417 | CD1 | LEU | 194 | 127.913 | 18.249 | 59.439 | 1.00 | 22.28 |
| 1418 | CD2 | LEU | 194 | 126.526 | 17.524 | 57.494 | 1.00 | 9.41 |
| 1419 | C | LEU | 194 | 125.325 | 21.745 | 56.977 | 1.00 | 20.18 |
| 1420 | O | LEU | 194 | 124.169 | 21.662 | 57.390 | 1.00 | 28.31 |
| 1421 | N | GLU | 195 | 125.913 | 22.906 | 56.701 | 1.00 | 23.69 |
| 1422 | CA | GLU | 195 | 125.217 | 24.182 | 56.845 | 1.00 | 23.91 |
| 1423 | CB | GLU | 195 | 126.145 | 25.235 | 57.459 | 1.00 | 28.38 |
| 1424 | CG | GLU | 195 | 126.558 | 24.930 | 58.897 | 1.00 | 48.57 |
| 1425 | CD | GLU | 195 | 127.591 | 25.905 | 59.449 | 1.00 | 61.92 |
| 1426 | OE1 | GLU | 195 | 128.341 | 26.515 | 58.652 | 1.00 | 66.87 |
| 1427 | OE2 | GLU | 195 | 127.658 | 26.052 | 60.690 | 1.00 | 55.96 |
| 1428 | C | GLU | 195 | 124.693 | 24.670 | 55.497 | 1.00 | 14.54 |
| 1429 | O | GLU | 195 | 123.721 | 25.422 | 55.436 | 1.00 | 17.77 |
| 1430 | N | GLN | 196 | 125.327 | 24.207 | 54.422 | 1.00 | 10.51 |
| 1431 | CA | GLN | 196 | 124.951 | 24.584 | 53.064 | 1.00 | 9.57 |
| 1432 | CB | GLN | 196 | 125.488 | 25.984 | 52.740 | 1.00 | 9.74 |
| 1433 | CG | GLN | 196 | 125.212 | 26.461 | 51.321 | 1.00 | 13.51 |
| 1434 | CD | GLN | 196 | 123.737 | 26.672 | 51.051 | 1.00 | 18.27 |
| 1435 | OE1 | GLN | 196 | 123.111 | 27.556 | 51.633 | 1.00 | 31.94 |
| 1436 | NE2 | GLN | 196 | 123.174 | 25.862 | 50.162 | 1.00 | 21.35 |
| 1437 | C | GLN | 196 | 125.484 | 23.583 | 52.039 | 1.00 | 8.87 |
| 1438 | O | GLN | 196 | 126.695 | 23.481 | 51.830 | 1.00 | 16.57 |
| 1439 | N | CYS | 197 | 124.577 | 22.837 | 51.415 | 1.00 | 11.72 |
| 1440 | CA | CYS | 197 | 124.963 | 21.865 | 50.398 | 1.00 | 13.36 |
| 1441 | CB | CYS | 197 | 123.821 | 20.882 | 50.114 | 1.00 | 20.25 |
| 1442 | SG | CYS | 197 | 122.310 | 21.605 | 49.432 | 1.00 | 16.36 |
| 1443 | C | CYS | 197 | 125.351 | 22.614 | 49.126 | 1.00 | 11.32 |
| 1444 | O | CYS | 197 | 124.948 | 23.758 | 48.924 | 1.00 | 16.69 |
| 1445 | N | LEU | 198 | 126.134 | 21.965 | 48.274 | 1.00 | 14.40 |
| 1446 | CA | LEU | 198 | 126.594 | 22.580 | 47.038 | 1.00 | 14.31 |
| 1447 | CB | LEU | 198 | 127.688 | 21.717 | 46.394 | 1.00 | 14.46 |
| 1448 | CG | LEU | 198 | 128.283 | 22.186 | 45.060 | 1.00 | 13.58 |
| 1449 | CD1 | LEU | 198 | 128.949 | 23.541 | 45.225 | 1.00 | 9.55 |
| 1450 | CD2 | LEU | 198 | 129.279 | 21.162 | 44.547 | 1.00 | 12.33 |
| 1451 | C | LEU | 198 | 125.478 | 22.848 | 46.034 | 1.00 | 18.46 |
| 1452 | O | LEU | 198 | 125.389 | 23.945 | 45.481 | 1.00 | 26.64 |
| 1453 | N | HIS | 199 | 124.614 | 21.857 | 45.829 | 1.00 | 20.84 |
| 1454 | CA | HIS | 199 | 123.519 | 21.965 | 44.869 | 1.00 | 13.67 |
| 1455 | CB | HIS | 199 | 122.756 | 20.640 | 44.781 | 1.00 | 11.33 |
| 1456 | CG | HIS | 199 | 121.733 | 20.603 | 43.688 | 1.00 | 6.17 |
| 1457 | CD2 | HIS | 199 | 120.389 | 20.445 | 43.729 | 1.00 | 12.38 |
| 1458 | ND1 | HIS | 199 | 122.061 | 20.738 | 42.356 | 1.00 | 10.08 |
| 1459 | CE1 | HIS | 199 | 120.964 | 20.663 | 41.624 | 1.00 | 10.18 |
| 1460 | NE2 | HIS | 199 | 119.935 | 20.486 | 42.432 | 1.00 | 2.01 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 1461 | C | HIS | 199 | 122.540 | 23.111 | 45.108 | 1.00 | 14.52 |
| 1462 | O | HIS | 199 | 122.174 | 23.813 | 44.166 | 1.00 | 13.39 |
| 1463 | N | LYS | 200 | 122.120 | 23.300 | 46.357 | 1.00 | 15.92 |
| 1464 | CA | LYS | 200 | 121.161 | 24.353 | 46.698 | 1.00 | 14.65 |
| 1465 | CB | LYS | 200 | 120.205 | 23.859 | 47.789 | 1.00 | 15.18 |
| 1466 | CG | LYS | 200 | 119.425 | 22.609 | 47.416 | 1.00 | 12.45 |
| 1467 | CD | LYS | 200 | 118.523 | 22.158 | 48.554 | 1.00 | 3.23 |
| 1468 | CE | LYS | 200 | 117.827 | 20.849 | 48.213 | 1.00 | 14.66 |
| 1469 | NZ | LYS | 200 | 116.966 | 20.369 | 49.332 | 1.00 | 22.03 |
| 1470 | C | LYS | 200 | 121.786 | 25.688 | 47.120 | 1.00 | 22.11 |
| 1471 | O | LYS | 200 | 121.101 | 26.541 | 47.693 | 1.00 | 20.41 |
| 1472 | N | GLY | 201 | 123.078 | 25.860 | 46.844 | 1.00 | 21.90 |
| 1473 | CA | GLY | 201 | 123.764 | 27.097 | 47.191 | 1.00 | 14.85 |
| 1474 | C | GLY | 201 | 124.048 | 27.969 | 45.978 | 1.00 | 16.72 |
| 1475 | O | GLY | 201 | 123.992 | 27.489 | 44.842 | 1.00 | 12.09 |
| 1476 | N | VAL | 202 | 124.329 | 29.253 | 46.209 | 1.00 | 11.53 |
| 1477 | CA | VAL | 202 | 124.627 | 30.183 | 45.114 | 1.00 | 11.31 |
| 1478 | CB | VAL | 202 | 124.437 | 31.661 | 45.555 | 1.00 | 9.93 |
| 1479 | CG1 | VAL | 202 | 124.960 | 32.617 | 44.491 | 1.00 | 2.00 |
| 1480 | CG2 | VAL | 202 | 122.964 | 31.937 | 45.803 | 1.00 | 6.34 |
| 1481 | C | VAL | 202 | 126.054 | 29.940 | 44.612 | 1.00 | 10.17 |
| 1482 | O | VAL | 202 | 126.997 | 29.883 | 45.405 | 1.00 | 8.95 |
| 1483 | N | PRO | 203 | 126.222 | 29.774 | 43.286 | 1.00 | 2.10 |
| 1484 | CD | PRO | 203 | 125.136 | 29.796 | 42.290 | 1.00 | 5.19 |
| 1485 | CA | PRO | 203 | 127.509 | 29.524 | 42.628 | 1.00 | 8.34 |
| 1486 | CB | PRO | 203 | 127.168 | 29.704 | 41.154 | 1.00 | 5.82 |
| 1487 | CG | PRO | 203 | 125.785 | 29.152 | 41.087 | 1.00 | 2.00 |
| 1488 | C | PRO | 203 | 128.699 | 30.381 | 43.069 | 1.00 | 18.54 |
| 1489 | O | PRO | 203 | 129.709 | 29.836 | 43.516 | 1.00 | 26.42 |
| 1490 | N | ARG | 204 | 128.591 | 31.704 | 42.951 | 1.00 | 11.17 |
| 1491 | CA | ARG | 204 | 129.687 | 32.582 | 43.357 | 1.00 | 5.94 |
| 1492 | CB | ARG | 204 | 129.366 | 34.047 | 43.061 | 1.00 | 4.29 |
| 1493 | CG | ARG | 204 | 129.405 | 34.440 | 41.587 | 1.00 | 10.69 |
| 1494 | CD | ARG | 204 | 130.821 | 34.543 | 41.033 | 1.00 | 8.35 |
| 1495 | NE | ARG | 204 | 131.410 | 33.242 | 40.725 | 1.00 | 21.05 |
| 1496 | CZ | ARG | 204 | 132.555 | 33.071 | 40.068 | 1.00 | 20.78 |
| 1497 | NH1 | ARG | 204 | 133.250 | 34.121 | 39.644 | 1.00 | 14.75 |
| 1498 | NH2 | ARG | 204 | 132.996 | 31.844 | 39.818 | 1.00 | 16.69 |
| 1499 | C | ARG | 204 | 130.016 | 32.420 | 44.836 | 1.00 | 6.43 |
| 1500 | O | ARG | 204 | 131.185 | 32.304 | 45.207 | 1.00 | 15.01 |
| 1501 | N | VAL | 205 | 128.983 | 32.380 | 45.672 | 1.00 | 2.00 |
| 1502 | CA | VAL | 205 | 129.159 | 32.238 | 47.116 | 1.00 | 3.42 |
| 1503 | CB | VAL | 205 | 127.809 | 32.238 | 47.855 | 1.00 | 2.00 |
| 1504 | CG1 | VAL | 205 | 128.027 | 32.047 | 49.342 | 1.00 | 13.49 |
| 1505 | CG2 | VAL | 205 | 127.064 | 33.530 | 47.594 | 1.00 | 2.00 |
| 1506 | C | VAL | 205 | 129.904 | 30.963 | 47.488 | 1.00 | 7.19 |
| 1507 | O | VAL | 205 | 130.785 | 30.982 | 48.342 | 1.00 | 17.39 |
| 1508 | N | GLU | 206 | 129.543 | 29.854 | 46.851 | 1.00 | 11.33 |
| 1509 | CA | GLU | 206 | 130.188 | 28.579 | 47.136 | 1.00 | 11.44 |
| 1510 | CB | GLU | 206 | 129.348 | 27.417 | 46.606 | 1.00 | 10.75 |
| 1511 | CG | GLU | 206 | 128.033 | 27.237 | 47.340 | 1.00 | 4.42 |
| 1512 | CD | GLU | 206 | 128.208 | 27.226 | 48.845 | 1.00 | 7.68 |
| 1513 | OE1 | GLU | 206 | 128.858 | 26.298 | 49.366 | 1.00 | 15.79 |
| 1514 | OE2 | GLU | 206 | 127.700 | 28.153 | 49.509 | 1.00 | 12.42 |
| 1515 | C | GLU | 206 | 131.598 | 28.528 | 46.568 | 1.00 | 13.88 |
| 1516 | O | GLU | 206 | 132.484 | 27.897 | 47.144 | 1.00 | 16.22 |
| 1517 | N | THR | 207 | 131.792 | 29.199 | 45.438 | 1.00 | 9.73 |
| 1518 | CA | THR | 207 | 133.090 | 29.268 | 44.785 | 1.00 | 13.84 |
| 1519 | CB | THR | 207 | 132.970 | 29.928 | 43.400 | 1.00 | 15.72 |
| 1520 | OG1 | THR | 207 | 132.272 | 29.045 | 42.513 | 1.00 | 13.12 |
| 1521 | CG2 | THR | 207 | 134.338 | 30.250 | 42.827 | 1.00 | 11.92 |
| 1522 | C | THR | 207 | 134.059 | 30.066 | 45.658 | 1.00 | 19.41 |
| 1523 | O | THR | 207 | 135.177 | 29.623 | 45.917 | 1.00 | 27.17 |
| 1524 | N | ARG | 208 | 133.608 | 31.226 | 46.133 | 1.00 | 22.15 |
| 1525 | CA | ARG | 208 | 134.417 | 32.091 | 46.988 | 1.00 | 17.49 |
| 1526 | CB | ARG | 208 | 133.595 | 33.309 | 47.429 | 1.00 | 23.71 |
| 1527 | CG | ARG | 208 | 134.349 | 34.352 | 48.264 | 1.00 | 24.20 |
| 1528 | CD | ARG | 208 | 135.532 | 34.935 | 47.501 | 1.00 | 35.41 |
| 1529 | NE | ARG | 208 | 136.060 | 36.169 | 48.090 | 1.00 | 40.81 |
| 1530 | CZ | ARG | 208 | 136.736 | 36.242 | 49.235 | 1.00 | 40.71 |
| 1531 | NH1 | ARG | 208 | 136.978 | 35.150 | 49.947 | 1.00 | 42.82 |
| 1532 | NH2 | ARG | 208 | 137.194 | 37.412 | 49.658 | 1.00 | 37.98 |
| 1533 | C | ARG | 208 | 134.906 | 31.313 | 48.208 | 1.00 | 19.76 |
| 1534 | O | ARG | 208 | 136.075 | 31.395 | 48.576 | 1.00 | 27.03 |
| 1535 | N | PHE | 209 | 134.010 | 30.534 | 48.809 | 1.00 | 16.90 |
| 1536 | CA | PHE | 209 | 134.350 | 29.734 | 49.979 | 1.00 | 12.93 |
| 1537 | CB | PHE | 209 | 133.090 | 29.165 | 50.632 | 1.00 | 3.91 |
| 1538 | CG | PHE | 209 | 133.377 | 28.292 | 51.818 | 1.00 | 8.27 |
| 1539 | CD1 | PHE | 209 | 133.605 | 28.852 | 53.070 | 1.00 | 5.35 |
| 1540 | CD2 | PHE | 209 | 133.472 | 26.912 | 51.676 | 1.00 | 11.24 |
| 1541 | CE1 | PHE | 209 | 133.928 | 28.052 | 54.162 | 1.00 | 10.99 |
| 1542 | CE2 | PHE | 209 | 133.794 | 26.105 | 52.760 | 1.00 | 7.23 |
| 1543 | CZ | PHE | 209 | 134.023 | 26.677 | 54.007 | 1.00 | 2.00 |
| 1544 | C | PHE | 209 | 135.305 | 28.581 | 49.664 | 1.00 | 16.94 |
| 1545 | O | PHE | 209 | 136.176 | 28.248 | 50.473 | 1.00 | 13.43 |
| 1546 | N | PHE | 210 | 135.112 | 27.942 | 48.514 | 1.00 | 11.91 |
| 1547 | CA | PHE | 210 | 135.960 | 26.823 | 48.126 | 1.00 | 12.01 |
| 1548 | CB | PHE | 210 | 135.384 | 26.105 | 46.901 | 1.00 | 5.35 |
| 1549 | CG | PHE | 210 | 136.131 | 24.854 | 46.525 | 1.00 | 2.00 |
| 1550 | CD1 | PHE | 210 | 136.182 | 23.773 | 47.392 | 1.00 | 7.13 |
| 1551 | CD2 | PHE | 210 | 136.794 | 24.763 | 45.307 | 1.00 | 13.50 |
| 1552 | CE1 | PHE | 210 | 136.883 | 22.617 | 47.052 | 1.00 | 13.12 |
| 1553 | CE2 | PHE | 210 | 137.498 | 23.613 | 44.956 | 1.00 | 10.64 |
| 1554 | CZ | PHE | 210 | 137.542 | 22.539 | 45.830 | 1.00 | 12.55 |
| 1555 | C | PHE | 210 | 137.380 | 27.297 | 47.844 | 1.00 | 15.50 |
| 1556 | O | PHE | 210 | 138.339 | 26.801 | 48.436 | 1.00 | 21.01 |
| 1557 | N | ILE | 211 | 137.500 | 28.290 | 46.970 | 1.00 | 11.89 |
| 1558 | CA | ILE | 211 | 138.798 | 28.834 | 46.601 | 1.00 | 14.18 |
| 1559 | CB | ILE | 211 | 138.663 | 30.000 | 45.604 | 1.00 | 13.95 |
| 1560 | CG2 | ILE | 211 | 140.040 | 30.517 | 45.218 | 1.00 | 23.94 |
| 1561 | CG1 | ILE | 211 | 137.925 | 29.547 | 44.346 | 1.00 | 14.06 |
| 1562 | CD1 | ILE | 211 | 137.734 | 30.656 | 43.335 | 1.00 | 19.84 |
| 1563 | C | ILE | 211 | 139.622 | 29.318 | 47.790 | 1.00 | 11.48 |
| 1564 | O | ILE | 211 | 140.730 | 28.838 | 48.010 | 1.00 | 22.99 |
| 1565 | N | SER | 212 | 139.069 | 30.238 | 48.574 | 1.00 | 11.99 |
| 1566 | CA | SER | 212 | 139.799 | 30.797 | 49.708 | 1.00 | 19.48 |
| 1567 | CB | SER | 212 | 139.279 | 32.205 | 50.044 | 1.00 | 10.83 |
| 1568 | OG | SER | 212 | 137.939 | 32.174 | 50.500 | 1.00 | 32.56 |
| 1569 | C | SER | 212 | 139.902 | 29.954 | 50.979 | 1.00 | 15.60 |
| 1570 | O | SER | 212 | 140.992 | 29.800 | 51.530 | 1.00 | 26.35 |
| 1571 | N | SER | 213 | 138.785 | 29.398 | 51.437 | 1.00 | 18.79 |
| 1572 | CA | SER | 213 | 138.780 | 28.607 | 52.665 | 1.00 | 15.21 |
| 1573 | CB | SER | 213 | 137.426 | 28.737 | 53.372 | 1.00 | 13.39 |
| 1574 | OG | SER | 213 | 137.168 | 30.074 | 53.766 | 1.00 | 19.66 |
| 1575 | C | SER | 213 | 139.141 | 27.126 | 52.543 | 1.00 | 21.19 |
| 1576 | O | SER | 213 | 139.540 | 26.503 | 53.534 | 1.00 | 22.69 |
| 1577 | N | ILE | 214 | 139.021 | 26.558 | 51.345 | 1.00 | 16.22 |
| 1578 | CA | ILE | 214 | 139.308 | 25.138 | 51.177 | 1.00 | 12.65 |
| 1579 | CB | ILE | 214 | 138.047 | 24.354 | 50.712 | 1.00 | 17.01 |
| 1580 | CG2 | ILE | 214 | 138.343 | 22.853 | 50.628 | 1.00 | 14.54 |
| 1581 | CG1 | ILE | 214 | 136.879 | 24.602 | 51.673 | 1.00 | 7.09 |
| 1582 | CD1 | ILE | 214 | 137.175 | 24.247 | 53.124 | 1.00 | 2.16 |
| 1583 | C | ILE | 214 | 140.477 | 24.759 | 50.276 | 1.00 | 14.51 |
| 1584 | O | ILE | 214 | 141.486 | 24.247 | 50.759 | 1.00 | 20.94 |
| 1585 | N | TYR | 215 | 140.342 | 25.006 | 48.975 | 1.00 | 10.71 |
| 1586 | CA | TYR | 215 | 141.378 | 24.634 | 48.016 | 1.00 | 16.76 |
| 1587 | CB | TYR | 215 | 140.914 | 24.914 | 46.587 | 1.00 | 10.15 |
| 1588 | CG | TYR | 215 | 141.523 | 23.975 | 45.569 | 1.00 | 16.49 |
| 1589 | CD1 | TYR | 215 | 141.526 | 22.595 | 45.777 | 1.00 | 14.36 |
| 1590 | CE1 | TYR | 215 | 142.079 | 21.722 | 44.837 | 1.00 | 16.84 |
| 1591 | CD2 | TYR | 215 | 142.090 | 24.463 | 44.393 | 1.00 | 18.93 |
| 1592 | CE2 | TYR | 215 | 142.645 | 23.601 | 43.447 | 1.00 | 14.61 |
| 1593 | CZ | TYR | 215 | 142.636 | 22.232 | 43.676 | 1.00 | 18.72 |
| 1594 | OH | TYR | 215 | 143.191 | 21.375 | 42.749 | 1.00 | 21.97 |
| 1595 | C | TYR | 215 | 142.753 | 25.251 | 48.256 | 1.00 | 22.56 |
| 1596 | O | TYR | 215 | 143.772 | 24.567 | 48.154 | 1.00 | 21.88 |
| 1597 | N | ASP | 216 | 142.780 | 26.538 | 48.582 | 1.00 | 25.86 |
| 1598 | CA | ASP | 216 | 144.032 | 27.239 | 48.841 | 1.00 | 28.90 |
| 1599 | CB | ASP | 216 | 143.745 | 28.708 | 49.155 | 1.00 | 35.55 |
| 1600 | CG | ASP | 216 | 145.000 | 29.514 | 49.373 | 1.00 | 32.91 |
| 1601 | OD1 | ASP | 216 | 145.170 | 30.035 | 50.494 | 1.00 | 33.80 |
| 1602 | OD2 | ASP | 216 | 145.811 | 29.630 | 48.427 | 1.00 | 38.29 |
| 1603 | C | ASP | 216 | 144.782 | 26.590 | 50.002 | 1.00 | 28.68 |
| 1604 | O | ASP | 216 | 146.013 | 26.552 | 50.017 | 1.00 | 35.11 |
| 1605 | N | LYS | 217 | 144.026 | 26.052 | 50.954 | 1.00 | 24.04 |
| 1606 | CA | LYS | 217 | 144.604 | 25.406 | 52.129 | 1.00 | 25.31 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 1607 | CB | LYS | 217 | 143.768 | 25.741 | 53.368 | 1.00 | 17.45 |
| 1608 | CG | LYS | 217 | 143.687 | 27.234 | 53.646 | 1.00 | 28.42 |
| 1609 | CD | LYS | 217 | 142.811 | 27.551 | 54.844 | 1.00 | 36.77 |
| 1610 | CE | LYS | 217 | 142.729 | 29.057 | 55.071 | 1.00 | 36.92 |
| 1611 | NZ | LYS | 217 | 141.758 | 29.426 | 56.143 | 1.00 | 37.10 |
| 1612 | C | LYS | 217 | 144.754 | 23.892 | 51.973 | 1.00 | 25.97 |
| 1613 | O | LYS | 217 | 145.170 | 23.201 | 52.905 | 1.00 | 23.71 |
| 1614 | N | GLU | 218 | 144.429 | 23.385 | 50.788 | 1.00 | 30.40 |
| 1615 | CA | GLU | 218 | 144.528 | 21.958 | 50.504 | 1.00 | 34.37 |
| 1616 | CB | GLU | 218 | 143.655 | 21.603 | 49.297 | 1.00 | 41.93 |
| 1617 | CG | GLU | 218 | 143.462 | 20.114 | 49.073 | 1.00 | 45.33 |
| 1618 | CD | GLU | 218 | 142.740 | 19.451 | 50.226 | 1.00 | 52.39 |
| 1619 | OE1 | GLU | 218 | 141.553 | 19.780 | 50.449 | 1.00 | 49.41 |
| 1620 | OE2 | GLU | 218 | 143.364 | 18.612 | 50.916 | 1.00 | 46.07 |
| 1621 | C | GLU | 218 | 145.982 | 21.585 | 50.228 | 1.00 | 34.68 |
| 1622 | O | GLU | 218 | 146.624 | 22.166 | 49.356 | 1.00 | 31.92 |
| 1623 | N | GLN | 219 | 146.493 | 20.611 | 50.974 | 1.00 | 37.87 |
| 1624 | CA | GLN | 219 | 147.872 | 20.156 | 50.827 | 1.00 | 41.61 |
| 1625 | CB | GLN | 219 | 148.180 | 19.105 | 51.896 | 1.00 | 52.08 |
| 1626 | CG | GLN | 219 | 149.617 | 18.615 | 51.900 | 1.00 | 67.09 |
| 1627 | CD | GLN | 219 | 149.709 | 17.102 | 51.943 | 1.00 | 78.27 |
| 1628 | OE1 | GLN | 219 | 149.305 | 16.470 | 52.917 | 1.00 | 81.71 |
| 1629 | NE2 | GLN | 219 | 150.233 | 16.510 | 50.870 | 1.00 | 80.10 |
| 1630 | C | GLN | 219 | 148.173 | 19.583 | 49.438 | 1.00 | 38.79 |
| 1631 | O | GLN | 219 | 149.260 | 19.789 | 48.893 | 1.00 | 34.89 |
| 1632 | N | SER | 220 | 147.205 | 18.867 | 48.874 | 1.00 | 39.35 |
| 1633 | CA | SER | 220 | 147.359 | 18.252 | 47.556 | 1.00 | 36.65 |
| 1634 | CB | SER | 220 | 146.658 | 16.891 | 47.537 | 1.00 | 48.69 |
| 1635 | OG | SER | 220 | 145.291 | 17.018 | 47.899 | 1.00 | 58.57 |
| 1636 | C | SER | 220 | 146.824 | 19.117 | 46.418 | 1.00 | 30.45 |
| 1637 | O | SER | 220 | 146.651 | 18.639 | 45.297 | 1.00 | 31.98 |
| 1638 | N | LYS | 221 | 146.581 | 20.392 | 46.704 | 1.00 | 25.39 |
| 1639 | CA | LYS | 221 | 146.052 | 21.327 | 45.716 | 1.00 | 18.20 |
| 1640 | CB | LYS | 221 | 145.949 | 22.731 | 46.316 | 1.00 | 17.94 |
| 1641 | CG | LYS | 221 | 147.292 | 23.352 | 46.659 | 1.00 | 24.63 |
| 1642 | CD | LYS | 221 | 147.138 | 24.772 | 47.155 | 1.00 | 32.69 |
| 1643 | CE | LYS | 221 | 148.444 | 25.312 | 47.716 | 1.00 | 42.07 |
| 1644 | NZ | LYS | 221 | 149.547 | 25.257 | 46.720 | 1.00 | 42.25 |
| 1645 | C | LYS | 221 | 146.879 | 21.412 | 44.444 | 1.00 | 15.22 |
| 1646 | O | LYS | 221 | 148.097 | 21.243 | 44.467 | 1.00 | 21.32 |
| 1647 | N | ASN | 222 | 146.196 | 21.660 | 43.333 | 1.00 | 11.20 |
| 1648 | CA | ASN | 222 | 146.853 | 21.818 | 42.048 | 1.00 | 9.54 |
| 1649 | CB | ASN | 222 | 145.993 | 21.250 | 40.919 | 1.00 | 2.46 |
| 1650 | CG | ASN | 222 | 146.599 | 21.488 | 39.550 | 1.00 | 12.07 |
| 1651 | OD1 | ASN | 222 | 146.698 | 22.626 | 39.097 | 1.00 | 10.03 |
| 1652 | ND2 | ASN | 222 | 147.003 | 20.414 | 38.881 | 1.00 | 11.12 |
| 1653 | C | ASN | 222 | 147.032 | 23.322 | 41.885 | 1.00 | 17.59 |
| 1654 | O | ASN | 222 | 146.060 | 24.061 | 41.717 | 1.00 | 21.24 |
| 1655 | N | ASN | 223 | 148.281 | 23.765 | 41.958 | 1.00 | 18.52 |
| 1656 | CA | ASN | 223 | 148.619 | 25.175 | 41.850 | 1.00 | 9.91 |
| 1657 | CB | ASN | 223 | 150.127 | 25.349 | 41.972 | 1.00 | 11.52 |
| 1658 | CG | ASN | 223 | 150.664 | 24.821 | 43.282 | 1.00 | 23.77 |
| 1659 | OD1 | ASN | 223 | 150.579 | 25.491 | 44.311 | 1.00 | 21.40 |
| 1660 | ND2 | ASN | 223 | 151.208 | 23.605 | 43.258 | 1.00 | 21.52 |
| 1661 | C | ASN | 223 | 148.104 | 25.870 | 40.594 | 1.00 | 15.35 |
| 1662 | O | ASN | 223 | 147.668 | 27.019 | 40.662 | 1.00 | 21.88 |
| 1663 | N | VAL | 224 | 148.157 | 25.184 | 39.455 | 1.00 | 10.58 |
| 1664 | CA | VAL | 224 | 147.677 | 25.755 | 38.195 | 1.00 | 18.60 |
| 1665 | CB | VAL | 224 | 147.957 | 24.811 | 37.001 | 1.00 | 24.63 |
| 1666 | CG1 | VAL | 224 | 147.405 | 25.406 | 35.709 | 1.00 | 25.94 |
| 1667 | CG2 | VAL | 224 | 149.449 | 24.558 | 36.873 | 1.00 | 17.27 |
| 1668 | C | VAL | 224 | 146.177 | 26.049 | 38.259 | 1.00 | 23.24 |
| 1669 | O | VAL | 224 | 145.716 | 27.071 | 37.746 | 1.00 | 25.12 |
| 1670 | N | LEU | 225 | 145.423 | 25.146 | 38.886 | 1.00 | 23.80 |
| 1671 | CA | LEU | 225 | 143.980 | 25.313 | 39.032 | 1.00 | 18.51 |
| 1672 | CB | LEU | 225 | 143.314 | 23.994 | 39.434 | 1.00 | 18.23 |
| 1673 | CG | LEU | 225 | 143.337 | 22.844 | 38.424 | 1.00 | 20.30 |
| 1674 | CD1 | LEU | 225 | 142.613 | 21.645 | 39.010 | 1.00 | 18.77 |
| 1675 | CD2 | LEU | 225 | 142.691 | 23.270 | 37.115 | 1.00 | 10.44 |
| 1676 | C | LEU | 225 | 143.652 | 26.392 | 40.061 | 1.00 | 18.24 |
| 1677 | O | LEU | 225 | 142.710 | 27.162 | 39.872 | 1.00 | 22.06 |
| 1678 | N | LEU | 226 | 144.431 | 26.448 | 41.141 | 1.00 | 18.51 |
| 1679 | CA | LEU | 226 | 144.230 | 27.445 | 42.197 | 1.00 | 17.64 |
| 1680 | CB | LEU | 226 | 145.128 | 27.149 | 43.401 | 1.00 | 15.88 |
| 1681 | CG | LEU | 226 | 145.013 | 28.096 | 44.605 | 1.00 | 19.63 |
| 1682 | CD1 | LEU | 226 | 143.633 | 27.996 | 45.235 | 1.00 | 8.24 |
| 1683 | CD2 | LEU | 226 | 146.086 | 27.764 | 45.627 | 1.00 | 2.89 |
| 1684 | C | LEU | 226 | 144.507 | 28.855 | 41.681 | 1.00 | 15.54 |
| 1685 | O | LEU | 226 | 143.753 | 29.785 | 41.966 | 1.00 | 28.19 |
| 1686 | N | ARG | 227 | 145.595 | 29.002 | 40.927 | 1.00 | 22.25 |
| 1687 | CA | ARG | 227 | 145.995 | 30.282 | 40.338 | 1.00 | 21.24 |
| 1688 | CB | ARG | 227 | 147.320 | 30.108 | 39.587 | 1.00 | 25.23 |
| 1689 | CG | ARG | 227 | 147.831 | 31.335 | 38.844 | 1.00 | 26.56 |
| 1690 | CD | ARG | 227 | 148.575 | 32.292 | 39.760 | 1.00 | 33.23 |
| 1691 | NE | ARG | 227 | 149.114 | 33.433 | 39.021 | 1.00 | 27.48 |
| 1692 | CZ | ARG | 227 | 149.516 | 34.568 | 39.585 | 1.00 | 29.44 |
| 1693 | NH1 | ARG | 227 | 149.447 | 34.722 | 40.902 | 1.00 | 31.95 |
| 1694 | NH2 | ARG | 227 | 149.963 | 35.561 | 38.831 | 1.00 | 19.58 |
| 1695 | C | ARG | 227 | 144.911 | 30.745 | 39.367 | 1.00 | 17.48 |
| 1696 | O | ARG | 227 | 144.475 | 31.894 | 39.402 | 1.00 | 22.08 |
| 1697 | N | PHE | 228 | 144.474 | 29.822 | 38.516 | 1.00 | 17.49 |
| 1698 | CA | PHE | 228 | 143.439 | 30.073 | 37.516 | 1.00 | 20.78 |
| 1699 | CB | PHE | 228 | 143.184 | 28.770 | 36.741 | 1.00 | 17.58 |
| 1700 | CG | PHE | 228 | 142.261 | 28.908 | 35.556 | 1.00 | 10.74 |
| 1701 | CD1 | PHE | 228 | 141.685 | 30.128 | 35.214 | 1.00 | 18.32 |
| 1702 | CD2 | PHE | 228 | 141.958 | 27.791 | 34.785 | 1.00 | 13.57 |
| 1703 | CE1 | PHE | 228 | 140.819 | 30.230 | 34.122 | 1.00 | 18.76 |
| 1704 | CE2 | PHE | 228 | 141.095 | 27.883 | 33.692 | 1.00 | 18.93 |
| 1705 | CZ | PHE | 228 | 140.525 | 29.106 | 33.361 | 1.00 | 12.22 |
| 1706 | C | PHE | 228 | 142.158 | 30.552 | 38.205 | 1.00 | 20.33 |
| 1707 | O | PHE | 228 | 141.585 | 31.580 | 37.834 | 1.00 | 17.12 |
| 1708 | N | ALA | 229 | 141.746 | 29.817 | 39.233 | 1.00 | 15.85 |
| 1709 | CA | ALA | 229 | 140.541 | 30.125 | 39.989 | 1.00 | 14.57 |
| 1710 | CB | ALA | 229 | 140.320 | 29.069 | 41.059 | 1.00 | 11.49 |
| 1711 | C | ALA | 229 | 140.572 | 31.513 | 40.619 | 1.00 | 22.21 |
| 1712 | O | ALA | 229 | 139.606 | 32.272 | 40.505 | 1.00 | 26.82 |
| 1713 | N | LYS | 230 | 141.683 | 31.841 | 41.278 | 1.00 | 17.14 |
| 1714 | CA | LYS | 230 | 141.836 | 33.136 | 41.933 | 1.00 | 13.72 |
| 1715 | CB | LYS | 230 | 143.118 | 33.168 | 42.766 | 1.00 | 17.71 |
| 1716 | CG | LYS | 230 | 143.067 | 32.332 | 44.030 | 1.00 | 14.07 |
| 1717 | CD | LYS | 230 | 144.343 | 32.505 | 44.835 | 1.00 | 23.37 |
| 1718 | CE | LYS | 230 | 144.253 | 31.802 | 46.177 | 1.00 | 31.01 |
| 1719 | NZ | LYS | 230 | 145.477 | 32.021 | 46.994 | 1.00 | 32.57 |
| 1720 | C | LYS | 230 | 141.816 | 34.310 | 40.956 | 1.00 | 16.07 |
| 1721 | O | LYS | 230 | 141.111 | 35.292 | 41.176 | 1.00 | 15.73 |
| 1722 | N | LEU | 231 | 142.585 | 34.202 | 39.876 | 1.00 | 17.93 |
| 1723 | CA | LEU | 231 | 142.646 | 35.260 | 38.872 | 1.00 | 20.80 |
| 1724 | CB | LEU | 231 | 143.653 | 34.911 | 37.775 | 1.00 | 18.38 |
| 1725 | CG | LEU | 231 | 145.141 | 34.870 | 38.116 | 1.00 | 16.32 |
| 1726 | CD1 | LEU | 231 | 145.920 | 34.518 | 36.863 | 1.00 | 14.82 |
| 1727 | CD2 | LEU | 231 | 145.593 | 36.212 | 38.658 | 1.00 | 15.83 |
| 1728 | C | LEU | 231 | 141.287 | 35.506 | 38.233 | 1.00 | 24.81 |
| 1729 | O | LEU | 231 | 140.828 | 36.647 | 38.151 | 1.00 | 28.14 |
| 1730 | N | ASP | 232 | 140.648 | 34.427 | 37.790 | 1.00 | 28.52 |
| 1731 | CA | ASP | 232 | 139.344 | 34.503 | 37.139 | 1.00 | 23.60 |
| 1732 | CB | ASP | 232 | 138.878 | 33.104 | 36.736 | 1.00 | 20.22 |
| 1733 | CG | ASP | 232 | 137.737 | 33.137 | 35.742 | 1.00 | 29.93 |
| 1734 | OD1 | ASP | 232 | 138.019 | 33.223 | 34.527 | 1.00 | 24.38 |
| 1735 | OD2 | ASP | 232 | 136.564 | 33.079 | 36.174 | 1.00 | 26.36 |
| 1736 | C | ASP | 232 | 138.300 | 35.170 | 38.032 | 1.00 | 20.67 |
| 1737 | O | ASP | 232 | 137.622 | 36.111 | 37.612 | 1.00 | 15.86 |
| 1738 | N | PHE | 233 | 138.203 | 34.707 | 39.274 | 1.00 | 12.27 |
| 1739 | CA | PHE | 233 | 137.244 | 35.260 | 40.219 | 1.00 | 12.59 |
| 1740 | CB | PHE | 233 | 137.355 | 34.549 | 41.569 | 1.00 | 14.20 |
| 1741 | CG | PHE | 233 | 136.243 | 34.887 | 42.524 | 1.00 | 30.75 |
| 1742 | CD1 | PHE | 233 | 135.130 | 34.058 | 42.634 | 1.00 | 33.32 |
| 1743 | CD2 | PHE | 233 | 136.298 | 36.042 | 43.302 | 1.00 | 29.41 |
| 1744 | CE1 | PHE | 233 | 134.088 | 34.372 | 43.502 | 1.00 | 34.63 |
| 1745 | CE2 | PHE | 233 | 135.263 | 36.365 | 44.172 | 1.00 | 31.81 |
| 1746 | CZ | PHE | 233 | 134.155 | 35.528 | 44.272 | 1.00 | 32.38 |
| 1747 | C | PHE | 233 | 137.452 | 36.760 | 40.407 | 1.00 | 18.84 |
| 1748 | O | PHE | 233 | 136.495 | 37.534 | 40.394 | 1.00 | 24.79 |
| 1749 | N | ASN | 234 | 138.710 | 37.160 | 40.572 | 1.00 | 25.72 |
| 1750 | CA | ASN | 234 | 139.057 | 38.563 | 40.770 | 1.00 | 20.56 |
| 1751 | CB | ASN | 234 | 140.509 | 38.694 | 41.239 | 1.00 | 25.13 |
| 1752 | CG | ASN | 234 | 140.702 | 38.249 | 42.683 | 1.00 | 30.65 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 1753 | OD1 | ASN | 234 | 139.738 | 37.996 | 43.406 | 1.00 | 21.26 |
| 1754 | ND2 | ASN | 234 | 141.957 | 38.162 | 43.109 | 1.00 | 35.99 |
| 1755 | C | ASN | 234 | 138.818 | 39.427 | 39.536 | 1.00 | 18.33 |
| 1756 | O | ASN | 234 | 138.457 | 40.599 | 39.662 | 1.00 | 15.79 |
| 1757 | N | LEU | 235 | 139.019 | 38.848 | 38.353 | 1.00 | 17.45 |
| 1758 | CA | LEU | 235 | 138.814 | 39.567 | 37.097 | 1.00 | 16.13 |
| 1759 | CB | LEU | 235 | 139.402 | 38.789 | 35.920 | 1.00 | 14.09 |
| 1760 | CG | LEU | 235 | 139.233 | 39.426 | 34.534 | 1.00 | 25.16 |
| 1761 | CD1 | LEU | 235 | 139.947 | 40.774 | 34.472 | 1.00 | 16.26 |
| 1762 | CD2 | LEU | 235 | 139.762 | 38.487 | 33.458 | 1.00 | 11.51 |
| 1763 | C | LEU | 235 | 137.329 | 39.812 | 36.866 | 1.00 | 23.53 |
| 1764 | O | LEU | 235 | 136.929 | 40.918 | 36.502 | 1.00 | 30.18 |
| 1765 | N | LEU | 236 | 136.517 | 38.773 | 37.065 | 1.00 | 26.97 |
| 1766 | CA | LEU | 236 | 135.071 | 38.894 | 36.900 | 1.00 | 21.97 |
| 1767 | CB | LEU | 236 | 134.375 | 37.538 | 37.041 | 1.00 | 22.99 |
| 1768 | CG | LEU | 236 | 134.550 | 36.506 | 35.931 | 1.00 | 24.74 |
| 1769 | CD1 | LEU | 236 | 133.601 | 35.347 | 36.187 | 1.00 | 22.83 |
| 1770 | CD2 | LEU | 236 | 134.259 | 37.133 | 34.579 | 1.00 | 26.05 |
| 1771 | C | LEU | 236 | 134.511 | 39.858 | 37.935 | 1.00 | 15.40 |
| 1772 | O | LEU | 236 | 133.581 | 40.602 | 37.646 | 1.00 | 21.06 |
| 1773 | N | GLN | 237 | 135.080 | 39.837 | 39.139 | 1.00 | 13.42 |
| 1774 | CA | GLN | 237 | 134.645 | 40.721 | 40.217 | 1.00 | 14.55 |
| 1775 | CB | GLN | 237 | 135.477 | 40.481 | 41.475 | 1.00 | 14.51 |
| 1776 | CG | GLN | 237 | 135.051 | 41.318 | 42.671 | 1.00 | 12.72 |
| 1777 | CD | GLN | 237 | 135.967 | 41.131 | 43.862 | 1.00 | 12.21 |
| 1778 | OE1 | GLN | 237 | 137.121 | 41.566 | 43.847 | 1.00 | 18.76 |
| 1779 | NE2 | GLN | 237 | 135.460 | 40.483 | 44.900 | 1.00 | 4.88 |
| 1780 | C | GLN | 237 | 134.760 | 42.180 | 39.788 | 1.00 | 22.23 |
| 1781 | O | GLN | 237 | 133.950 | 43.011 | 40.192 | 1.00 | 28.74 |
| 1782 | N | MET | 238 | 135.770 | 42.481 | 38.970 | 1.00 | 29.92 |
| 1783 | CA | MET | 238 | 135.985 | 43.833 | 38.458 | 1.00 | 23.66 |
| 1784 | CB | MET | 238 | 137.275 | 43.906 | 37.638 | 1.00 | 25.72 |
| 1785 | CG | MET | 238 | 138.552 | 43.791 | 38.454 | 1.00 | 26.38 |
| 1786 | SD | MET | 238 | 140.030 | 43.684 | 37.408 | 1.00 | 30.42 |
| 1787 | CE | MET | 238 | 141.233 | 43.058 | 38.580 | 1.00 | 23.83 |
| 1788 | C | MET | 238 | 134.801 | 44.227 | 37.584 | 1.00 | 20.92 |
| 1789 | O | MET | 238 | 134.344 | 45.367 | 37.628 | 1.00 | 20.70 |
| 1790 | N | LEU | 239 | 134.310 | 43.274 | 36.792 | 1.00 | 23.17 |
| 1791 | CA | LEU | 239 | 133.159 | 43.509 | 35.920 | 1.00 | 21.15 |
| 1792 | CB | LEU | 239 | 132.938 | 42.323 | 34.978 | 1.00 | 10.92 |
| 1793 | CG | LEU | 239 | 131.684 | 42.381 | 34.100 | 1.00 | 20.20 |
| 1794 | CD1 | LEU | 239 | 131.748 | 43.579 | 33.166 | 1.00 | 9.66 |
| 1795 | CD2 | LEU | 239 | 131.541 | 41.089 | 33.309 | 1.00 | 10.55 |
| 1796 | C | LEU | 239 | 131.908 | 43.732 | 36.764 | 1.00 | 14.68 |
| 1797 | O | LEU | 239 | 131.129 | 44.645 | 36.501 | 1.00 | 23.63 |
| 1798 | N | HIS | 240 | 131.735 | 42.904 | 37.788 | 1.00 | 15.07 |
| 1799 | CA | HIS | 240 | 130.587 | 43.015 | 38.680 | 1.00 | 19.33 |
| 1800 | CB | HIS | 240 | 130.619 | 41.913 | 39.746 | 1.00 | 16.76 |
| 1801 | CG | HIS | 240 | 130.661 | 40.525 | 39.185 | 1.00 | 12.10 |
| 1802 | CD2 | HIS | 240 | 130.296 | 40.039 | 37.973 | 1.00 | 12.51 |
| 1803 | ND1 | HIS | 240 | 131.144 | 39.449 | 39.897 | 1.00 | 8.57 |
| 1804 | CE1 | HIS | 240 | 131.077 | 38.362 | 39.150 | 1.00 | 16.05 |
| 1805 | NE2 | HIS | 240 | 130.567 | 38.692 | 37.979 | 1.00 | 13.30 |
| 1806 | C | HIS | 240 | 130.610 | 44.383 | 39.344 | 1.00 | 21.46 |
| 1807 | O | HIS | 240 | 129.572 | 45.034 | 39.481 | 1.00 | 28.61 |
| 1808 | N | LYS | 241 | 131.809 | 44.819 | 39.728 | 1.00 | 24.98 |
| 1809 | CA | LYS | 241 | 132.008 | 46.118 | 40.364 | 1.00 | 19.85 |
| 1810 | CB | LYS | 241 | 133.469 | 46.281 | 40.782 | 1.00 | 18.41 |
| 1811 | CG | LYS | 241 | 133.855 | 45.556 | 42.057 | 1.00 | 18.41 |
| 1812 | CD | LYS | 241 | 135.348 | 45.688 | 42.297 | 1.00 | 29.39 |
| 1813 | CE | LYS | 241 | 135.667 | 45.861 | 43.769 | 1.00 | 43.69 |
| 1814 | NZ | LYS | 241 | 137.131 | 45.987 | 43.991 | 1.00 | 46.04 |
| 1815 | C | LYS | 241 | 131.604 | 47.252 | 39.419 | 1.00 | 23.69 |
| 1816 | O | LYS | 241 | 130.983 | 48.229 | 39.845 | 1.00 | 14.81 |
| 1817 | N | GLN | 242 | 131.954 | 47.107 | 38.140 | 1.00 | 20.70 |
| 1818 | CA | GLN | 242 | 131.615 | 48.099 | 37.120 | 1.00 | 28.94 |
| 1819 | CB | GLN | 242 | 132.262 | 47.748 | 35.775 | 1.00 | 29.06 |
| 1820 | CG | GLN | 242 | 133.775 | 47.862 | 35.748 | 1.00 | 39.14 |
| 1821 | CD | GLN | 242 | 134.359 | 47.517 | 34.392 | 1.00 | 42.97 |
| 1822 | OE1 | GLN | 242 | 134.324 | 46.363 | 33.962 | 1.00 | 48.36 |
| 1823 | NE2 | GLN | 242 | 134.904 | 48.519 | 33.710 | 1.00 | 39.66 |
| 1824 | C | GLN | 242 | 130.103 | 48.163 | 36.943 | 1.00 | 33.40 |
| 1825 | O | GLN | 242 | 129.514 | 49.246 | 36.938 | 1.00 | 40.80 |
| 1826 | N | GLU | 243 | 129.487 | 46.992 | 36.807 | 1.00 | 33.80 |
| 1827 | CA | GLU | 243 | 128.044 | 46.884 | 36.631 | 1.00 | 22.54 |
| 1828 | CB | GLU | 243 | 127.647 | 45.420 | 36.466 | 1.00 | 15.53 |
| 1829 | CG | GLU | 243 | 128.204 | 44.778 | 35.210 | 1.00 | 15.70 |
| 1830 | CD | GLU | 243 | 127.938 | 43.290 | 35.137 | 1.00 | 18.78 |
| 1831 | OE1 | GLU | 243 | 127.639 | 42.675 | 36.178 | 1.00 | 18.01 |
| 1832 | OE2 | GLU | 243 | 128.040 | 42.727 | 34.032 | 1.00 | 15.89 |
| 1833 | C | GLU | 243 | 127.290 | 47.495 | 37.806 | 1.00 | 20.49 |
| 1834 | O | GLU | 243 | 126.351 | 48.266 | 37.611 | 1.00 | 18.81 |
| 1835 | N | LEU | 244 | 127.715 | 47.159 | 39.022 | 1.00 | 12.97 |
| 1836 | CA | LEU | 244 | 127.079 | 47.675 | 40.231 | 1.00 | 15.01 |
| 1837 | CB | LEU | 244 | 127.676 | 46.999 | 41.467 | 1.00 | 12.34 |
| 1838 | CG | LEU | 244 | 127.144 | 47.436 | 42.832 | 1.00 | 12.62 |
| 1839 | CD1 | LEU | 244 | 125.628 | 47.332 | 42.881 | 1.00 | 24.09 |
| 1840 | CD2 | LEU | 244 | 127.780 | 46.582 | 43.908 | 1.00 | 9.05 |
| 1841 | C | LEU | 244 | 127.213 | 49.191 | 40.335 | 1.00 | 22.78 |
| 1842 | O | LEU | 244 | 126.328 | 49.868 | 40.863 | 1.00 | 27.46 |
| 1843 | N | ALA | 245 | 128.325 | 49.725 | 39.838 | 1.00 | 31.72 |
| 1844 | CA | ALA | 245 | 128.560 | 51.167 | 39.856 | 1.00 | 30.71 |
| 1845 | CB | ALA | 245 | 129.998 | 51.476 | 39.466 | 1.00 | 26.12 |
| 1846 | C | ALA | 245 | 127.589 | 51.860 | 38.893 | 1.00 | 29.98 |
| 1847 | O | ALA | 245 | 127.005 | 52.887 | 39.226 | 1.00 | 32.44 |
| 1848 | N | GLN | 246 | 127.410 | 51.256 | 37.718 | 1.00 | 29.03 |
| 1849 | CA | GLN | 246 | 126.528 | 51.754 | 36.668 | 1.00 | 31.14 |
| 1850 | CB | GLN | 246 | 126.689 | 50.868 | 35.430 | 1.00 | 31.92 |
| 1851 | CG | GLN | 246 | 125.845 | 51.244 | 34.232 | 1.00 | 41.36 |
| 1852 | CD | GLN | 246 | 125.970 | 50.235 | 33.109 | 1.00 | 48.09 |
| 1853 | OE1 | GLN | 246 | 127.023 | 49.627 | 32.919 | 1.00 | 49.29 |
| 1854 | NE2 | GLN | 246 | 124.887 | 50.043 | 32.361 | 1.00 | 55.11 |
| 1855 | C | GLN | 246 | 125.074 | 51.762 | 37.119 | 1.00 | 34.84 |
| 1856 | O | GLN | 246 | 124.297 | 52.637 | 36.732 | 1.00 | 42.31 |
| 1857 | N | VAL | 247 | 124.719 | 50.762 | 37.921 | 1.00 | 39.27 |
| 1858 | CA | VAL | 247 | 123.360 | 50.631 | 38.441 | 1.00 | 38.03 |
| 1859 | CB | VAL | 247 | 123.069 | 49.138 | 38.742 | 1.00 | 38.04 |
| 1860 | CG1 | VAL | 247 | 122.330 | 48.954 | 40.059 | 1.00 | 39.31 |
| 1861 | CG2 | VAL | 247 | 122.270 | 48.526 | 37.603 | 1.00 | 37.60 |
| 1862 | C | VAL | 247 | 123.144 | 51.507 | 39.667 | 1.00 | 37.49 |
| 1863 | O | VAL | 247 | 122.012 | 51.862 | 39.998 | 1.00 | 33.11 |
| 1864 | N | SER | 248 | 124.231 | 51.871 | 40.340 | 1.00 | 39.80 |
| 1865 | CA | SER | 248 | 124.173 | 52.736 | 41.515 | 1.00 | 43.54 |
| 1866 | CB | SER | 248 | 125.456 | 52.604 | 42.352 | 1.00 | 41.35 |
| 1867 | OG | SER | 248 | 125.482 | 51.368 | 43.057 | 1.00 | 23.81 |
| 1868 | C | SER | 248 | 123.963 | 54.195 | 41.093 | 1.00 | 41.56 |
| 1869 | O | SER | 248 | 123.288 | 54.976 | 41.783 | 1.00 | 39.28 |
| 1870 | N | ARG | 249 | 124.591 | 54.559 | 39.974 | 1.00 | 40.01 |
| 1871 | CA | ARG | 249 | 124.467 | 55.901 | 39.421 | 1.00 | 47.97 |
| 1872 | CB | ARG | 249 | 125.475 | 56.127 | 38.290 | 1.00 | 51.84 |
| 1873 | CG | ARG | 249 | 126.912 | 56.292 | 38.747 | 1.00 | 62.62 |
| 1874 | CD | ARG | 249 | 127.836 | 56.501 | 37.563 | 1.00 | 69.45 |
| 1875 | NE | ARG | 249 | 129.065 | 55.731 | 37.713 | 1.00 | 78.07 |
| 1876 | CZ | ARG | 249 | 129.491 | 54.824 | 36.840 | 1.00 | 81.11 |
| 1877 | NH1 | ARG | 249 | 128.795 | 54.570 | 35.737 | 1.00 | 75.69 |
| 1878 | NH2 | ARG | 249 | 130.602 | 54.145 | 37.087 | 1.00 | 86.20 |
| 1879 | C | ARG | 249 | 123.051 | 56.058 | 38.890 | 1.00 | 43.68 |
| 1880 | O | ARG | 249 | 122.402 | 57.072 | 39.127 | 1.00 | 45.81 |
| 1881 | N | TRP | 250 | 122.588 | 55.030 | 38.183 | 1.00 | 38.57 |
| 1882 | CA | TRP | 250 | 121.247 | 55.000 | 37.613 | 1.00 | 34.46 |
| 1883 | CB | TRP | 250 | 121.060 | 53.682 | 36.851 | 1.00 | 37.42 |
| 1884 | CG | TRP | 250 | 119.635 | 53.325 | 36.551 | 1.00 | 37.50 |
| 1885 | CD2 | TRP | 250 | 118.745 | 52.545 | 37.341 | 1.00 | 32.98 |
| 1886 | CE2 | TRP | 250 | 117.516 | 52.464 | 36.652 | 1.00 | 39.28 |
| 1887 | CE3 | TRP | 250 | 118.867 | 51.909 | 38.585 | 1.00 | 32.90 |
| 1888 | CD1 | TRP | 250 | 118.931 | 53.672 | 35.413 | 1.00 | 28.29 |
| 1889 | NE1 | TRP | 250 | 117.658 | 53.159 | 35.479 | 1.00 | 36.07 |
| 1890 | CZ2 | TRP | 250 | 116.411 | 51.771 | 37.167 | 1.00 | 40.28 |
| 1891 | CZ3 | TRP | 250 | 117.770 | 51.221 | 39.098 | 1.00 | 33.00 |
| 1892 | CH2 | TRP | 250 | 116.557 | 51.159 | 38.388 | 1.00 | 34.10 |
| 1893 | C | TRP | 250 | 120.215 | 55.131 | 38.731 | 1.00 | 31.76 |
| 1894 | O | TRP | 250 | 119.207 | 55.820 | 38.583 | 1.00 | 38.62 |
| 1895 | N | TRP | 251 | 120.499 | 54.493 | 39.861 | 1.00 | 29.34 |
| 1896 | CA | TRP | 251 | 119.611 | 54.513 | 41.017 | 1.00 | 28.23 |
| 1897 | CB | TRP | 251 | 120.041 | 53.431 | 42.003 | 1.00 | 24.43 |
| 1898 | CG | TRP | 251 | 119.164 | 53.309 | 43.196 | 1.00 | 27.54 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 1899 | CD2 | TRP | 251 | 117.813 | 52.824 | 43.224 | 1.00 | 28.47 |
| 1900 | CE2 | TRP | 251 | 117.394 | 52.848 | 44.576 | 1.00 | 30.61 |
| 1901 | CE3 | TRP | 251 | 116.921 | 52.373 | 42.246 | 1.00 | 22.56 |
| 1902 | CD1 | TRP | 251 | 119.493 | 53.603 | 44.486 | 1.00 | 29.85 |
| 1903 | NE1 | TRP | 251 | 118.439 | 53.327 | 45.321 | 1.00 | 28.21 |
| 1904 | CZ2 | TRP | 251 | 116.117 | 52.434 | 44.974 | 1.00 | 27.80 |
| 1905 | CZ3 | TRP | 251 | 115.646 | 51.959 | 42.641 | 1.00 | 16.40 |
| 1906 | CH2 | TRP | 251 | 115.261 | 51.995 | 43.993 | 1.00 | 23.32 |
| 1907 | C | TRP | 251 | 119.575 | 55.877 | 41.703 | 1.00 | 37.98 |
| 1908 | O | TRP | 251 | 118.564 | 56.243 | 42.309 | 1.00 | 45.16 |
| 1909 | N | LYS | 252 | 120.685 | 56.610 | 41.636 | 1.00 | 42.00 |
| 1910 | CA | LYS | 252 | 120.758 | 57.938 | 42.238 | 1.00 | 42.12 |
| 1911 | CB | LYS | 252 | 122.198 | 58.328 | 42.551 | 1.00 | 47.95 |
| 1912 | CG | LYS | 252 | 122.598 | 58.028 | 43.975 | 1.00 | 54.42 |
| 1913 | CD | LYS | 252 | 123.720 | 58.943 | 44.418 | 1.00 | 63.61 |
| 1914 | CE | LYS | 252 | 123.889 | 58.896 | 45.923 | 1.00 | 76.47 |
| 1915 | NZ | LYS | 252 | 124.827 | 59.944 | 46.407 | 1.00 | 82.00 |
| 1916 | C | LYS | 252 | 120.113 | 58.992 | 41.348 | 1.00 | 43.32 |
| 1917 | O | LYS | 252 | 119.528 | 59.955 | 41.845 | 1.00 | 40.24 |
| 1918 | N | ASP | 253 | 120.220 | 58.802 | 40.033 | 1.00 | 41.81 |
| 1919 | CA | ASP | 253 | 119.621 | 59.715 | 39.061 | 1.00 | 42.20 |
| 1920 | CB | ASP | 253 | 119.991 | 59.305 | 37.632 | 1.00 | 46.23 |
| 1921 | CG | ASP | 253 | 121.475 | 59.448 | 37.340 | 1.00 | 56.62 |
| 1922 | OD1 | ASP | 253 | 122.222 | 59.973 | 38.197 | 1.00 | 59.66 |
| 1923 | OD2 | ASP | 253 | 121.896 | 59.029 | 36.240 | 1.00 | 59.43 |
| 1924 | C | ASP | 253 | 118.100 | 59.701 | 39.208 | 1.00 | 46.95 |
| 1925 | O | ASP | 253 | 117.404 | 60.508 | 38.597 | 1.00 | 47.82 |
| 1926 | N | LEU | 254 | 117.600 | 58.743 | 39.987 | 1.00 | 50.43 |
| 1927 | CA | LEU | 254 | 116.172 | 58.596 | 40.253 | 1.00 | 52.57 |
| 1928 | CB | LEU | 254 | 115.777 | 57.116 | 40.236 | 1.00 | 51.09 |
| 1929 | CG | LEU | 254 | 116.036 | 56.357 | 38.930 | 1.00 | 52.73 |
| 1930 | CD1 | LEU | 254 | 115.673 | 54.894 | 39.102 | 1.00 | 50.16 |
| 1931 | CD2 | LEU | 254 | 115.244 | 56.974 | 37.788 | 1.00 | 48.48 |
| 1932 | C | LEU | 254 | 115.867 | 59.205 | 41.619 | 1.00 | 50.66 |
| 1933 | O | LEU | 254 | 114.780 | 59.735 | 41.848 | 1.00 | 48.89 |
| 1934 | N | ASP | 255 | 116.838 | 59.099 | 42.522 | 1.00 | 54.73 |
| 1935 | CA | ASP | 255 | 116.750 | 59.641 | 43.875 | 1.00 | 59.42 |
| 1936 | CB | ASP | 255 | 116.930 | 61.167 | 43.829 | 1.00 | 63.16 |
| 1937 | CG | ASP | 255 | 117.232 | 61.774 | 45.193 | 1.00 | 70.47 |
| 1938 | OD1 | ASP | 255 | 117.674 | 61.045 | 46.110 | 1.00 | 70.14 |
| 1939 | OD2 | ASP | 255 | 117.030 | 62.997 | 45.344 | 1.00 | 79.11 |
| 1940 | C | ASP | 255 | 115.476 | 59.260 | 44.640 | 1.00 | 56.10 |
| 1941 | O | ASP | 255 | 114.834 | 60.106 | 45.263 | 1.00 | 54.97 |
| 1942 | N | PHE | 256 | 115.127 | 57.977 | 44.602 | 1.00 | 55.78 |
| 1943 | CA | PHE | 256 | 113.946 | 57.486 | 45.308 | 1.00 | 55.28 |
| 1944 | CB | PHE | 256 | 113.556 | 56.093 | 44.808 | 1.00 | 51.79 |
| 1945 | CG | PHE | 256 | 113.024 | 56.079 | 43.407 | 1.00 | 52.55 |
| 1946 | CD1 | PHE | 256 | 113.356 | 55.051 | 42.537 | 1.00 | 55.14 |
| 1947 | CD2 | PHE | 256 | 112.186 | 57.091 | 42.955 | 1.00 | 58.21 |
| 1948 | CE1 | PHE | 256 | 112.862 | 55.028 | 41.236 | 1.00 | 57.90 |
| 1949 | CE2 | PHE | 256 | 111.687 | 57.077 | 41.656 | 1.00 | 60.53 |
| 1950 | CZ | PHE | 256 | 112.026 | 56.042 | 40.796 | 1.00 | 57.76 |
| 1951 | C | PHE | 256 | 114.199 | 57.438 | 46.812 | 1.00 | 60.70 |
| 1952 | O | PHE | 256 | 113.292 | 57.162 | 47.596 | 1.00 | 62.84 |
| 1953 | N | VAL | 257 | 115.442 | 57.704 | 47.203 | 1.00 | 64.41 |
| 1954 | CA | VAL | 257 | 115.834 | 57.697 | 48.606 | 1.00 | 64.01 |
| 1955 | CB | VAL | 257 | 117.373 | 57.799 | 48.757 | 1.00 | 62.36 |
| 1956 | CG1 | VAL | 257 | 117.789 | 57.482 | 50.187 | 1.00 | 60.29 |
| 1957 | CG2 | VAL | 257 | 118.068 | 56.864 | 47.774 | 1.00 | 58.27 |
| 1958 | C | VAL | 257 | 115.179 | 58.870 | 49.333 | 1.00 | 65.72 |
| 1959 | O | VAL | 257 | 114.849 | 58.771 | 50.517 | 1.00 | 64.55 |
| 1960 | N | THR | 258 | 114.977 | 59.971 | 48.609 | 1.00 | 66.40 |
| 1961 | CA | THR | 258 | 114.364 | 61.171 | 49.175 | 1.00 | 65.40 |
| 1962 | CB | THR | 258 | 115.200 | 62.437 | 48.870 | 1.00 | 65.98 |
| 1963 | OG1 | THR | 258 | 115.282 | 62.633 | 47.453 | 1.00 | 65.25 |
| 1964 | CG2 | THR | 258 | 116.608 | 62.302 | 49.442 | 1.00 | 64.28 |
| 1965 | C | THR | 258 | 112.919 | 61.399 | 48.716 | 1.00 | 62.28 |
| 1966 | O | THR | 258 | 112.066 | 61.769 | 49.524 | 1.00 | 62.30 |
| 1967 | N | THR | 259 | 112.649 | 61.182 | 47.428 | 1.00 | 58.00 |
| 1968 | CA | THR | 259 | 111.303 | 61.372 | 46.879 | 1.00 | 53.45 |
| 1969 | CB | THR | 259 | 111.300 | 61.402 | 45.332 | 1.00 | 48.24 |
| 1970 | OG1 | THR | 259 | 111.730 | 60.136 | 44.818 | 1.00 | 47.10 |
| 1971 | CG2 | THR | 259 | 112.221 | 62.496 | 44.817 | 1.00 | 44.78 |
| 1972 | C | THR | 259 | 110.320 | 60.303 | 47.358 | 1.00 | 54.85 |
| 1973 | O | THR | 259 | 109.147 | 60.593 | 47.593 | 1.00 | 58.40 |
| 1974 | N | LEU | 260 | 110.802 | 59.069 | 47.492 | 1.00 | 54.85 |
| 1975 | CA | LEU | 260 | 109.977 | 57.952 | 47.958 | 1.00 | 57.07 |
| 1976 | CB | LEU | 260 | 109.811 | 56.907 | 46.845 | 1.00 | 54.53 |
| 1977 | CG | LEU | 260 | 109.191 | 57.346 | 45.511 | 1.00 | 54.02 |
| 1978 | CD1 | LEU | 260 | 109.216 | 56.192 | 44.523 | 1.00 | 47.30 |
| 1979 | CD2 | LEU | 260 | 107.765 | 57.838 | 45.715 | 1.00 | 53.62 |
| 1980 | C | LEU | 260 | 110.655 | 57.326 | 49.183 | 1.00 | 59.06 |
| 1981 | O | LEU | 260 | 111.135 | 56.190 | 49.132 | 1.00 | 61.18 |
| 1982 | N | PRO | 261 | 110.672 | 58.057 | 50.314 | 1.00 | 59.80 |
| 1983 | CD | PRO | 261 | 110.004 | 59.362 | 50.474 | 1.00 | 57.03 |
| 1984 | CA | PRO | 261 | 111.281 | 57.634 | 51.582 | 1.00 | 60.02 |
| 1985 | CB | PRO | 261 | 111.144 | 58.883 | 52.452 | 1.00 | 59.64 |
| 1986 | CG | PRO | 261 | 109.865 | 59.476 | 51.972 | 1.00 | 61.83 |
| 1987 | C | PRO | 261 | 110.685 | 56.401 | 52.265 | 1.00 | 56.67 |
| 1988 | O | PRO | 261 | 111.317 | 55.811 | 53.143 | 1.00 | 54.94 |
| 1989 | N | TYR | 262 | 109.475 | 56.019 | 51.869 | 1.00 | 55.28 |
| 1990 | CA | TYR | 262 | 108.813 | 54.855 | 52.455 | 1.00 | 52.74 |
| 1991 | CB | TYR | 262 | 107.309 | 54.898 | 52.167 | 1.00 | 46.52 |
| 1992 | CG | TYR | 262 | 106.954 | 54.869 | 50.695 | 1.00 | 38.58 |
| 1993 | CD1 | TYR | 262 | 106.624 | 53.671 | 50.062 | 1.00 | 30.09 |
| 1994 | CE1 | TYR | 262 | 106.295 | 53.636 | 48.711 | 1.00 | 29.27 |
| 1995 | CD2 | TYR | 262 | 106.944 | 56.039 | 49.936 | 1.00 | 34.60 |
| 1996 | CE2 | TYR | 262 | 106.614 | 56.015 | 48.581 | 1.00 | 37.08 |
| 1997 | CZ | TYR | 262 | 106.290 | 54.809 | 47.974 | 1.00 | 32.64 |
| 1998 | OH | TYR | 262 | 105.961 | 54.776 | 46.635 | 1.00 | 7.43 |
| 1999 | C | TYR | 262 | 109.398 | 53.534 | 51.956 | 1.00 | 52.07 |
| 2000 | O | TYR | 262 | 109.356 | 52.522 | 52.656 | 1.00 | 51.95 |
| 2001 | N | ALA | 263 | 109.957 | 53.565 | 50.748 | 1.00 | 48.22 |
| 2002 | CA | ALA | 263 | 110.545 | 52.386 | 50.120 | 1.00 | 49.01 |
| 2003 | CB | ALA | 263 | 110.701 | 52.627 | 48.623 | 1.00 | 44.24 |
| 2004 | C | ALA | 263 | 111.879 | 51.943 | 50.723 | 1.00 | 52.04 |
| 2005 | O | ALA | 263 | 112.458 | 52.631 | 51.567 | 1.00 | 52.30 |
| 2006 | N | ARG | 264 | 112.333 | 50.766 | 50.297 | 1.00 | 53.43 |
| 2007 | CA | ARG | 264 | 113.592 | 50.196 | 50.752 | 1.00 | 48.17 |
| 2008 | CB | ARG | 264 | 113.499 | 48.670 | 50.889 | 1.00 | 40.34 |
| 2009 | CG | ARG | 264 | 112.624 | 48.166 | 52.030 | 1.00 | 43.53 |
| 2010 | CD | ARG | 264 | 112.450 | 46.639 | 51.996 | 1.00 | 35.92 |
| 2011 | NE | ARG | 264 | 111.772 | 46.200 | 50.774 | 1.00 | 44.75 |
| 2012 | CZ | ARG | 264 | 110.964 | 45.144 | 50.679 | 1.00 | 49.82 |
| 2013 | NH1 | ARG | 264 | 110.714 | 44.385 | 51.738 | 1.00 | 51.07 |
| 2014 | NH2 | ARG | 264 | 110.385 | 44.857 | 49.518 | 1.00 | 37.04 |
| 2015 | C | ARG | 264 | 114.676 | 50.512 | 49.742 | 1.00 | 49.03 |
| 2016 | O | ARG | 264 | 114.453 | 50.444 | 48.527 | 1.00 | 47.55 |
| 2017 | N | ASP | 265 | 115.848 | 50.870 | 50.252 | 1.00 | 50.80 |
| 2018 | CA | ASP | 265 | 116.987 | 51.164 | 49.392 | 1.00 | 51.29 |
| 2019 | CB | ASP | 265 | 117.728 | 52.418 | 49.877 | 1.00 | 52.76 |
| 2020 | CG | ASP | 265 | 118.690 | 52.955 | 48.843 | 1.00 | 54.37 |
| 2021 | OD1 | ASP | 265 | 118.782 | 52.363 | 47.747 | 1.00 | 50.00 |
| 2022 | OD2 | ASP | 265 | 119.358 | 53.972 | 49.120 | 1.00 | 60.30 |
| 2023 | C | ASP | 265 | 117.903 | 49.933 | 49.419 | 1.00 | 45.08 |
| 2024 | O | ASP | 265 | 118.824 | 49.846 | 50.238 | 1.00 | 39.53 |
| 2025 | N | ARG | 266 | 117.614 | 48.973 | 48.541 | 1.00 | 41.67 |
| 2026 | CA | ARG | 266 | 118.377 | 47.732 | 48.462 | 1.00 | 37.99 |
| 2027 | CB | ARG | 266 | 117.528 | 46.574 | 48.983 | 1.00 | 38.78 |
| 2028 | CG | ARG | 266 | 116.957 | 46.771 | 50.372 | 1.00 | 29.99 |
| 2029 | CD | ARG | 266 | 118.028 | 46.593 | 51.418 | 1.00 | 37.48 |
| 2030 | NE | ARG | 266 | 117.503 | 46.781 | 52.764 | 1.00 | 38.27 |
| 2031 | CZ | ARG | 266 | 117.416 | 47.958 | 53.376 | 1.00 | 45.66 |
| 2032 | NH1 | ARG | 266 | 117.822 | 49.066 | 52.763 | 1.00 | 38.28 |
| 2033 | NH2 | ARG | 266 | 116.920 | 48.027 | 54.603 | 1.00 | 42.90 |
| 2034 | C | ARG | 266 | 118.826 | 47.429 | 47.034 | 1.00 | 33.86 |
| 2035 | O | ARG | 266 | 118.671 | 46.306 | 46.542 | 1.00 | 40.81 |
| 2036 | N | VAL | 267 | 119.392 | 48.431 | 46.371 | 1.00 | 25.69 |
| 2037 | CA | VAL | 267 | 119.845 | 48.257 | 45.000 | 1.00 | 20.97 |
| 2038 | CB | VAL | 267 | 120.143 | 49.611 | 44.326 | 1.00 | 21.69 |
| 2039 | CG1 | VAL | 267 | 121.384 | 50.264 | 44.933 | 1.00 | 20.36 |
| 2040 | CG2 | VAL | 267 | 120.292 | 49.420 | 42.828 | 1.00 | 8.30 |
| 2041 | C | VAL | 267 | 121.058 | 47.333 | 44.913 | 1.00 | 27.40 |
| 2042 | O | VAL | 267 | 121.231 | 46.616 | 43.926 | 1.00 | 36.12 |
| 2043 | N | VAL | 268 | 121.889 | 47.347 | 45.952 | 1.00 | 30.76 |
| 2044 | CA | VAL | 268 | 123.080 | 46.503 | 46.008 | 1.00 | 32.68 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 2045 | CB | VAL | 268 | 123.998 | 46.904 | 47.190 | 1.00 | 35.53 |
| 2046 | CG1 | VAL | 268 | 125.220 | 46.001 | 47.245 | 1.00 | 32.24 |
| 2047 | CG2 | VAL | 268 | 124.420 | 48.355 | 47.058 | 1.00 | 33.69 |
| 2048 | C | VAL | 268 | 122.623 | 45.058 | 46.196 | 1.00 | 29.06 |
| 2049 | O | VAL | 268 | 123.119 | 44.144 | 45.533 | 1.00 | 25.58 |
| 2050 | N | GLU | 269 | 121.662 | 44.878 | 47.100 | 1.00 | 24.94 |
| 2051 | CA | GLU | 269 | 121.087 | 43.573 | 47.406 | 1.00 | 22.59 |
| 2052 | CB | GLU | 269 | 120.083 | 43.692 | 48.558 | 1.00 | 16.86 |
| 2053 | CG | GLU | 269 | 120.705 | 43.939 | 49.942 | 1.00 | 22.84 |
| 2054 | CD | GLU | 269 | 121.136 | 45.385 | 50.200 | 1.00 | 25.18 |
| 2055 | OE1 | GLU | 269 | 121.417 | 45.713 | 51.374 | 1.00 | 24.26 |
| 2056 | OE2 | GLU | 269 | 121.194 | 46.198 | 49.255 | 1.00 | 23.69 |
| 2057 | C | GLU | 269 | 120.404 | 43.001 | 46.167 | 1.00 | 21.52 |
| 2058 | O | GLU | 269 | 120.423 | 41.789 | 45.941 | 1.00 | 22.99 |
| 2059 | N | CYS | 270 | 119.814 | 43.885 | 45.365 | 1.00 | 16.93 |
| 2060 | CA | CYS | 270 | 119.144 | 43.487 | 44.133 | 1.00 | 15.61 |
| 2061 | CB | CYS | 270 | 118.305 | 44.637 | 43.577 | 1.00 | 14.26 |
| 2062 | SG | CYS | 270 | 116.923 | 45.097 | 44.637 | 1.00 | 24.62 |
| 2063 | C | CYS | 270 | 120.191 | 43.065 | 43.117 | 1.00 | 19.83 |
| 2064 | O | CYS | 270 | 119.922 | 42.239 | 42.245 | 1.00 | 25.94 |
| 2065 | N | TYR | 271 | 121.382 | 43.648 | 43.220 | 1.00 | 25.82 |
| 2066 | CA | TYR | 271 | 122.464 | 43.290 | 42.315 | 1.00 | 22.31 |
| 2067 | CB | TYR | 271 | 123.616 | 44.296 | 42.366 | 1.00 | 15.29 |
| 2068 | CG | TYR | 271 | 124.715 | 43.914 | 41.408 | 1.00 | 11.26 |
| 2069 | CD1 | TYR | 271 | 124.592 | 44.174 | 40.043 | 1.00 | 9.23 |
| 2070 | CE1 | TYR | 271 | 125.534 | 43.705 | 39.135 | 1.00 | 12.75 |
| 2071 | CD2 | TYR | 271 | 125.821 | 43.184 | 41.844 | 1.00 | 6.39 |
| 2072 | CE2 | TYR | 271 | 126.767 | 42.709 | 40.946 | 1.00 | 6.94 |
| 2073 | CZ | TYR | 271 | 126.615 | 42.970 | 39.594 | 1.00 | 11.07 |
| 2074 | OH | TYR | 271 | 127.525 | 42.467 | 38.702 | 1.00 | 9.47 |
| 2075 | C | TYR | 271 | 122.973 | 41.904 | 42.692 | 1.00 | 23.07 |
| 2076 | O | TYR | 271 | 123.318 | 41.104 | 41.820 | 1.00 | 22.92 |
| 2077 | N | PHE | 272 | 123.037 | 41.639 | 43.997 | 1.00 | 17.89 |
| 2078 | CA | PHE | 272 | 123.484 | 40.344 | 44.500 | 1.00 | 17.87 |
| 2079 | CB | PHE | 272 | 123.481 | 40.329 | 46.033 | 1.00 | 20.14 |
| 2080 | CG | PHE | 272 | 123.722 | 38.967 | 46.625 | 1.00 | 18.24 |
| 2081 | CD1 | PHE | 272 | 124.998 | 38.409 | 46.631 | 1.00 | 20.70 |
| 2082 | CD2 | PHE | 272 | 122.669 | 38.232 | 47.160 | 1.00 | 19.50 |
| 2083 | CE1 | PHE | 272 | 125.219 | 37.139 | 47.159 | 1.00 | 15.25 |
| 2084 | CE2 | PHE | 272 | 122.881 | 36.961 | 47.690 | 1.00 | 17.71 |
| 2085 | CZ | PHE | 272 | 124.159 | 36.414 | 47.689 | 1.00 | 12.72 |
| 2086 | C | PHE | 272 | 122.540 | 39.273 | 43.972 | 1.00 | 20.61 |
| 2087 | O | PHE | 272 | 122.974 | 38.200 | 43.550 | 1.00 | 26.50 |
| 2088 | N | TRP | 273 | 121.248 | 39.594 | 43.982 | 1.00 | 24.31 |
| 2089 | CA | TRP | 273 | 120.203 | 38.695 | 43.506 | 1.00 | 20.50 |
| 2090 | CB | TRP | 273 | 118.831 | 39.335 | 43.724 | 1.00 | 22.07 |
| 2091 | CG | TRP | 273 | 117.820 | 38.395 | 44.280 | 1.00 | 22.11 |
| 2092 | CD2 | TRP | 273 | 117.499 | 38.205 | 45.661 | 1.00 | 17.16 |
| 2093 | CE2 | TRP | 273 | 116.513 | 37.193 | 45.726 | 1.00 | 18.77 |
| 2094 | CE3 | TRP | 273 | 117.949 | 38.789 | 46.851 | 1.00 | 16.10 |
| 2095 | CD1 | TRP | 273 | 117.036 | 37.522 | 43.580 | 1.00 | 22.90 |
| 2096 | NE1 | TRP | 273 | 116.250 | 36.794 | 44.442 | 1.00 | 15.33 |
| 2097 | CZ2 | TRP | 273 | 115.969 | 36.750 | 46.938 | 1.00 | 8.52 |
| 2098 | CZ3 | TRP | 273 | 117.408 | 38.351 | 48.057 | 1.00 | 19.38 |
| 2099 | CH2 | TRP | 273 | 116.428 | 37.339 | 48.088 | 1.00 | 25.09 |
| 2100 | C | TRP | 273 | 120.401 | 38.389 | 42.024 | 1.00 | 19.25 |
| 2101 | O | TRP | 273 | 120.291 | 37.239 | 41.596 | 1.00 | 26.32 |
| 2102 | N | ALA | 274 | 120.705 | 39.424 | 41.247 | 1.00 | 15.42 |
| 2103 | CA | ALA | 274 | 120.925 | 39.267 | 39.815 | 1.00 | 17.00 |
| 2104 | CB | ALA | 274 | 120.927 | 40.622 | 39.138 | 1.00 | 8.15 |
| 2105 | C | ALA | 274 | 122.240 | 38.538 | 39.553 | 1.00 | 21.87 |
| 2106 | O | ALA | 274 | 122.394 | 37.858 | 38.535 | 1.00 | 24.79 |
| 2107 | N | LEU | 275 | 123.188 | 38.694 | 40.474 | 1.00 | 18.76 |
| 2108 | CA | LEU | 275 | 124.487 | 38.045 | 40.354 | 1.00 | 20.76 |
| 2109 | CB | LEU | 275 | 125.505 | 38.712 | 41.281 | 1.00 | 15.67 |
| 2110 | CG | LEU | 275 | 126.937 | 38.176 | 41.221 | 1.00 | 6.06 |
| 2111 | CD1 | LEU | 275 | 127.475 | 38.257 | 39.798 | 1.00 | 5.14 |
| 2112 | CD2 | LEU | 275 | 127.812 | 38.960 | 42.179 | 1.00 | 9.22 |
| 2113 | C | LEU | 275 | 124.351 | 36.560 | 40.684 | 1.00 | 19.71 |
| 2114 | O | LEU | 275 | 125.130 | 35.731 | 40.206 | 1.00 | 17.59 |
| 2115 | N | GLY | 276 | 123.356 | 36.239 | 41.507 | 1.00 | 22.38 |
| 2116 | CA | GLY | 276 | 123.098 | 34.860 | 41.880 | 1.00 | 15.02 |
| 2117 | C | GLY | 276 | 122.429 | 34.101 | 40.747 | 1.00 | 8.27 |
| 2118 | O | GLY | 276 | 122.574 | 32.885 | 40.641 | 1.00 | 21.39 |
| 2119 | N | VAL | 277 | 121.693 | 34.825 | 39.904 | 1.00 | 9.55 |
| 2120 | CA | VAL | 277 | 120.992 | 34.245 | 38.758 | 1.00 | 6.19 |
| 2121 | CB | VAL | 277 | 119.950 | 35.238 | 38.201 | 1.00 | 4.45 |
| 2122 | CG1 | VAL | 277 | 119.236 | 34.660 | 36.994 | 1.00 | 2.00 |
| 2123 | CG2 | VAL | 277 | 118.946 | 35.576 | 39.284 | 1.00 | 2.00 |
| 2124 | C | VAL | 277 | 122.003 | 33.848 | 37.686 | 1.00 | 9.32 |
| 2125 | O | VAL | 277 | 121.872 | 32.807 | 37.042 | 1.00 | 17.27 |
| 2126 | N | TYR | 278 | 122.992 | 34.711 | 37.481 | 1.00 | 13.83 |
| 2127 | CA | TYR | 278 | 124.082 | 34.466 | 36.543 | 1.00 | 17.57 |
| 2128 | CB | TYR | 278 | 123.644 | 34.476 | 35.067 | 1.00 | 14.31 |
| 2129 | CG | TYR | 278 | 122.485 | 35.368 | 34.675 | 1.00 | 21.92 |
| 2130 | CD1 | TYR | 278 | 122.304 | 36.630 | 35.242 | 1.00 | 28.06 |
| 2131 | CE1 | TYR | 278 | 121.249 | 37.454 | 34.839 | 1.00 | 17.69 |
| 2132 | CD2 | TYR | 278 | 121.581 | 34.952 | 33.698 | 1.00 | 10.48 |
| 2133 | CE2 | TYR | 278 | 120.532 | 35.762 | 33.290 | 1.00 | 15.32 |
| 2134 | CZ | TYR | 278 | 120.371 | 37.012 | 33.860 | 1.00 | 20.32 |
| 2135 | OH | TYR | 278 | 119.341 | 37.820 | 33.432 | 1.00 | 16.49 |
| 2136 | C | TYR | 278 | 125.236 | 35.423 | 36.790 | 1.00 | 22.42 |
| 2137 | O | TYR | 278 | 125.024 | 36.609 | 37.052 | 1.00 | 24.68 |
| 2138 | N | PHE | 279 | 126.454 | 34.883 | 36.756 | 1.00 | 20.65 |
| 2139 | CA | PHE | 279 | 127.665 | 35.662 | 36.998 | 1.00 | 24.23 |
| 2140 | CB | PHE | 279 | 128.474 | 35.036 | 38.140 | 1.00 | 19.97 |
| 2141 | CG | PHE | 279 | 129.063 | 33.694 | 37.800 | 1.00 | 27.50 |
| 2142 | CD1 | PHE | 279 | 130.278 | 33.600 | 37.124 | 1.00 | 27.56 |
| 2143 | CD2 | PHE | 279 | 128.387 | 32.523 | 38.120 | 1.00 | 26.31 |
| 2144 | CE1 | PHE | 279 | 130.804 | 32.363 | 36.770 | 1.00 | 27.48 |
| 2145 | CE2 | PHE | 279 | 128.906 | 31.283 | 37.770 | 1.00 | 27.51 |
| 2146 | CZ | PHE | 279 | 130.116 | 31.202 | 37.093 | 1.00 | 26.58 |
| 2147 | C | PHE | 279 | 128.564 | 35.797 | 35.773 | 1.00 | 22.60 |
| 2148 | O | PHE | 279 | 129.420 | 36.681 | 35.727 | 1.00 | 29.14 |
| 2149 | N | GLU | 280 | 128.404 | 34.893 | 34.811 | 1.00 | 26.53 |
| 2150 | CA | GLU | 280 | 129.217 | 34.909 | 33.599 | 1.00 | 25.23 |
| 2151 | CB | GLU | 280 | 128.759 | 33.832 | 32.608 | 1.00 | 31.74 |
| 2152 | CG | GLU | 280 | 129.004 | 32.392 | 33.056 | 1.00 | 26.55 |
| 2153 | CD | GLU | 280 | 127.873 | 31.806 | 33.899 | 1.00 | 40.41 |
| 2154 | OE1 | GLU | 280 | 127.909 | 30.581 | 34.149 | 1.00 | 41.01 |
| 2155 | OE2 | GLU | 280 | 126.949 | 32.549 | 34.307 | 1.00 | 31.27 |
| 2156 | C | GLU | 280 | 129.195 | 36.276 | 32.928 | 1.00 | 28.72 |
| 2157 | O | GLU | 280 | 128.169 | 36.958 | 32.918 | 1.00 | 21.31 |
| 2158 | N | PRO | 281 | 130.346 | 36.702 | 32.382 | 1.00 | 31.20 |
| 2159 | CD | PRO | 281 | 131.607 | 35.942 | 32.368 | 1.00 | 29.80 |
| 2160 | CA | PRO | 281 | 130.511 | 37.988 | 31.697 | 1.00 | 31.18 |
| 2161 | CB | PRO | 281 | 131.976 | 37.949 | 31.246 | 1.00 | 36.16 |
| 2162 | CG | PRO | 281 | 132.274 | 36.479 | 31.137 | 1.00 | 35.87 |
| 2163 | C | PRO | 281 | 129.561 | 38.213 | 30.522 | 1.00 | 29.70 |
| 2164 | O | PRO | 281 | 129.196 | 39.352 | 30.226 | 1.00 | 29.95 |
| 2165 | N | GLN | 282 | 129.161 | 37.126 | 29.866 | 1.00 | 27.63 |
| 2166 | CA | GLN | 282 | 128.252 | 37.194 | 28.722 | 1.00 | 28.39 |
| 2167 | CB | GLN | 282 | 128.174 | 35.832 | 28.028 | 1.00 | 34.10 |
| 2168 | CG | GLN | 282 | 127.630 | 34.717 | 28.912 | 1.00 | 45.80 |
| 2169 | CD | GLN | 282 | 127.714 | 33.351 | 28.264 | 1.00 | 47.83 |
| 2170 | OE1 | GLN | 282 | 128.543 | 32.523 | 28.647 | 1.00 | 54.06 |
| 2171 | NE2 | GLN | 282 | 126.848 | 33.101 | 27.285 | 1.00 | 41.38 |
| 2172 | C | GLN | 282 | 126.851 | 37.640 | 29.133 | 1.00 | 25.75 |
| 2173 | O | GLN | 282 | 126.061 | 38.071 | 28.294 | 1.00 | 34.41 |
| 2174 | N | TYR | 283 | 126.553 | 37.521 | 30.425 | 1.00 | 26.54 |
| 2175 | CA | TYR | 283 | 125.254 | 37.910 | 30.972 | 1.00 | 26.30 |
| 2176 | CB | TYR | 283 | 124.765 | 36.853 | 31.966 | 1.00 | 19.61 |
| 2177 | CG | TYR | 283 | 124.537 | 35.506 | 31.323 | 1.00 | 13.47 |
| 2178 | CD1 | TYR | 283 | 125.030 | 34.339 | 31.901 | 1.00 | 13.33 |
| 2179 | CE1 | TYR | 283 | 124.852 | 33.099 | 31.286 | 1.00 | 15.49 |
| 2180 | CD2 | TYR | 283 | 123.853 | 35.402 | 30.112 | 1.00 | 18.67 |
| 2181 | CE2 | TYR | 283 | 123.669 | 34.173 | 29.490 | 1.00 | 23.42 |
| 2182 | CZ | TYR | 283 | 124.172 | 33.026 | 30.079 | 1.00 | 14.24 |
| 2183 | OH | TYR | 283 | 124.002 | 31.817 | 29.448 | 1.00 | 22.41 |
| 2184 | C | TYR | 283 | 125.304 | 39.287 | 31.632 | 1.00 | 29.24 |
| 2185 | O | TYR | 283 | 124.504 | 39.599 | 32.517 | 1.00 | 27.80 |
| 2186 | N | SER | 284 | 126.244 | 40.108 | 31.170 | 1.00 | 29.09 |
| 2187 | CA | SER | 284 | 126.438 | 41.461 | 31.673 | 1.00 | 24.35 |
| 2188 | CB | SER | 284 | 127.644 | 42.103 | 30.981 | 1.00 | 29.60 |
| 2189 | OG | SER | 284 | 127.873 | 43.418 | 31.456 | 1.00 | 29.67 |
| 2190 | C | SER | 284 | 125.192 | 42.315 | 31.451 | 1.00 | 23.95 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 2191 | O | SER | 284 | 124.647 | 42.882 | 32.396 | 1.00 | 16.24 |
| 2192 | N | GLN | 285 | 124.743 | 42.393 | 30.199 | 1.00 | 29.77 |
| 2193 | CA | GLN | 285 | 123.556 | 43.173 | 29.852 | 1.00 | 36.37 |
| 2194 | CB | GLN | 285 | 123.313 | 43.138 | 28.339 | 1.00 | 36.36 |
| 2195 | CG | GLN | 285 | 122.119 | 43.974 | 27.883 | 1.00 | 42.33 |
| 2196 | CD | GLN | 285 | 121.887 | 43.913 | 26.382 | 1.00 | 47.38 |
| 2197 | OE1 | GLN | 285 | 122.208 | 42.919 | 25.727 | 1.00 | 45.82 |
| 2198 | NE2 | GLN | 285 | 121.321 | 44.981 | 25.832 | 1.00 | 47.01 |
| 2199 | C | GLN | 285 | 122.328 | 42.638 | 30.588 | 1.00 | 40.35 |
| 2200 | O | GLN | 285 | 121.503 | 43.413 | 31.076 | 1.00 | 46.67 |
| 2201 | N | ALA | 286 | 122.242 | 41.312 | 30.686 | 1.00 | 38.34 |
| 2202 | CA | ALA | 286 | 121.136 | 40.637 | 31.356 | 1.00 | 27.14 |
| 2203 | CB | ALA | 286 | 121.252 | 39.136 | 31.170 | 1.00 | 34.43 |
| 2204 | C | ALA | 286 | 121.067 | 40.983 | 32.837 | 1.00 | 24.71 |
| 2205 | O | ALA | 286 | 119.996 | 41.319 | 33.346 | 1.00 | 32.18 |
| 2206 | N | ARG | 287 | 122.203 | 40.891 | 33.526 | 1.00 | 17.67 |
| 2207 | CA | ARG | 287 | 122.261 | 41.212 | 34.951 | 1.00 | 17.77 |
| 2208 | CB | ARG | 287 | 123.680 | 41.046 | 35.504 | 1.00 | 14.04 |
| 2209 | CG | ARG | 287 | 124.013 | 39.659 | 36.008 | 1.00 | 21.57 |
| 2210 | CD | ARG | 287 | 125.294 | 39.673 | 36.828 | 1.00 | 20.38 |
| 2211 | NE | ARG | 287 | 126.451 | 40.078 | 36.033 | 1.00 | 14.48 |
| 2212 | CZ | ARG | 287 | 127.080 | 39.293 | 35.162 | 1.00 | 22.09 |
| 2213 | NH1 | ARG | 287 | 126.670 | 38.049 | 34.959 | 1.00 | 17.96 |
| 2214 | NH2 | ARG | 287 | 128.132 | 39.749 | 34.497 | 1.00 | 25.61 |
| 2215 | C | ARG | 287 | 121.802 | 42.642 | 35.207 | 1.00 | 24.30 |
| 2216 | O | ARG | 287 | 120.942 | 42.877 | 36.046 | 1.00 | 22.53 |
| 2217 | N | VAL | 288 | 122.358 | 43.583 | 34.449 | 1.00 | 32.79 |
| 2218 | CA | VAL | 288 | 122.031 | 45.001 | 34.586 | 1.00 | 35.93 |
| 2219 | CB | VAL | 288 | 122.800 | 45.853 | 33.543 | 1.00 | 42.80 |
| 2220 | CG1 | VAL | 288 | 122.484 | 47.329 | 33.718 | 1.00 | 45.42 |
| 2221 | CG2 | VAL | 288 | 124.294 | 45.622 | 33.682 | 1.00 | 39.26 |
| 2222 | C | VAL | 288 | 120.525 | 45.246 | 34.470 | 1.00 | 30.79 |
| 2223 | O | VAL | 288 | 119.927 | 45.888 | 35.339 | 1.00 | 27.62 |
| 2224 | N | MET | 289 | 119.914 | 44.698 | 33.422 | 1.00 | 25.59 |
| 2225 | CA | MET | 289 | 118.473 | 44.837 | 33.202 | 1.00 | 20.40 |
| 2226 | CB | MET | 289 | 118.055 | 44.123 | 31.908 | 1.00 | 11.02 |
| 2227 | CG | MET | 289 | 118.675 | 44.684 | 30.646 | 1.00 | 17.69 |
| 2228 | SD | MET | 289 | 118.236 | 43.769 | 29.151 | 1.00 | 29.61 |
| 2229 | CE | MET | 289 | 117.076 | 44.873 | 28.424 | 1.00 | 23.00 |
| 2230 | C | MET | 289 | 117.692 | 44.246 | 34.383 | 1.00 | 20.89 |
| 2231 | O | MET | 289 | 116.762 | 44.861 | 34.901 | 1.00 | 25.06 |
| 2232 | N | LEU | 290 | 118.104 | 43.063 | 34.825 | 1.00 | 20.72 |
| 2233 | CA | LEU | 290 | 117.448 | 42.379 | 35.935 | 1.00 | 15.74 |
| 2234 | CB | LEU | 290 | 118.020 | 40.969 | 36.078 | 1.00 | 14.98 |
| 2235 | CG | LEU | 290 | 117.497 | 40.044 | 37.174 | 1.00 | 16.12 |
| 2236 | CD1 | LEU | 290 | 115.981 | 39.981 | 37.142 | 1.00 | 16.37 |
| 2237 | CD2 | LEU | 290 | 118.098 | 38.659 | 36.964 | 1.00 | 19.76 |
| 2238 | C | LEU | 290 | 117.530 | 43.139 | 37.261 | 1.00 | 21.50 |
| 2239 | O | LEU | 290 | 116.561 | 43.172 | 38.019 | 1.00 | 23.53 |
| 2240 | N | VAL | 291 | 118.675 | 43.761 | 37.534 | 1.00 | 24.67 |
| 2241 | CA | VAL | 291 | 118.858 | 44.518 | 38.773 | 1.00 | 28.92 |
| 2242 | CB | VAL | 291 | 120.280 | 45.113 | 38.893 | 1.00 | 30.77 |
| 2243 | CG1 | VAL | 291 | 120.439 | 45.822 | 40.234 | 1.00 | 27.10 |
| 2244 | CG2 | VAL | 291 | 121.324 | 44.033 | 38.742 | 1.00 | 35.91 |
| 2245 | C | VAL | 291 | 117.872 | 45.679 | 38.826 | 1.00 | 33.69 |
| 2246 | O | VAL | 291 | 117.266 | 45.950 | 39.867 | 1.00 | 38.64 |
| 2247 | N | LYS | 292 | 117.722 | 46.360 | 37.693 | 1.00 | 32.65 |
| 2248 | CA | LYS | 292 | 116.819 | 47.500 | 37.589 | 1.00 | 29.16 |
| 2249 | CB | LYS | 292 | 116.961 | 48.155 | 36.213 | 1.00 | 28.67 |
| 2250 | CG | LYS | 292 | 118.314 | 40.814 | 35.986 | 1.00 | 28.14 |
| 2251 | CD | LYS | 292 | 118.440 | 49.353 | 34.575 | 1.00 | 36.09 |
| 2252 | CE | LYS | 292 | 119.765 | 50.059 | 34.370 | 1.00 | 37.49 |
| 2253 | NZ | LYS | 292 | 119.962 | 50.417 | 32.940 | 1.00 | 42.24 |
| 2254 | C | LYS | 292 | 115.369 | 47.102 | 37.849 | 1.00 | 25.46 |
| 2255 | O | LYS | 292 | 114.633 | 47.829 | 38.514 | 1.00 | 23.99 |
| 2256 | N | THR | 293 | 114.984 | 45.922 | 37.365 | 1.00 | 28.08 |
| 2257 | CA | THR | 293 | 113.627 | 45.401 | 37.536 | 1.00 | 20.11 |
| 2258 | CB | THR | 293 | 113.385 | 44.183 | 36.617 | 1.00 | 19.93 |
| 2259 | OG1 | THR | 293 | 113.325 | 44.619 | 35.252 | 1.00 | 19.22 |
| 2260 | CG2 | THR | 293 | 112.095 | 43.472 | 36.972 | 1.00 | 14.44 |
| 2261 | C | THR | 293 | 113.326 | 45.026 | 38.987 | 1.00 | 22.63 |
| 2262 | O | THR | 293 | 112.286 | 45.405 | 39.524 | 1.00 | 30.10 |
| 2263 | N | ILE | 294 | 114.239 | 44.295 | 39.621 | 1.00 | 23.15 |
| 2264 | CA | ILE | 294 | 114.058 | 43.884 | 41.015 | 1.00 | 22.01 |
| 2265 | CB | ILE | 294 | 115.232 | 43.007 | 41.522 | 1.00 | 19.34 |
| 2266 | CG2 | ILE | 294 | 114.962 | 42.546 | 42.958 | 1.00 | 19.45 |
| 2267 | CG1 | ILE | 294 | 115.430 | 41.799 | 40.604 | 1.00 | 12.44 |
| 2268 | CD1 | ILE | 294 | 116.564 | 40.876 | 41.017 | 1.00 | 23.70 |
| 2269 | C | ILE | 294 | 113.959 | 45.113 | 41.910 | 1.00 | 21.14 |
| 2270 | O | ILE | 294 | 113.097 | 45.193 | 42.789 | 1.00 | 23.19 |
| 2271 | N | SER | 295 | 114.841 | 46.075 | 41.664 | 1.00 | 27.23 |
| 2272 | CA | SER | 295 | 114.879 | 47.310 | 42.435 | 1.00 | 36.44 |
| 2273 | CB | SER | 295 | 116.063 | 48.167 | 41.979 | 1.00 | 38.02 |
| 2274 | OG | SER | 295 | 116.508 | 49.015 | 43.021 | 1.00 | 50.33 |
| 2275 | C | SER | 295 | 113.566 | 48.077 | 42.265 | 1.00 | 33.20 |
| 2276 | O | SER | 295 | 112.984 | 48.562 | 43.239 | 1.00 | 27.63 |
| 2277 | N | MET | 296 | 113.083 | 48.124 | 41.026 | 1.00 | 32.18 |
| 2278 | CA | MET | 296 | 111.843 | 48.816 | 40.685 | 1.00 | 33.20 |
| 2279 | CB | MET | 296 | 111.659 | 48.829 | 39.165 | 1.00 | 33.02 |
| 2280 | CG | MET | 296 | 110.820 | 49.978 | 38.637 | 1.00 | 34.84 |
| 2281 | SD | MET | 296 | 111.653 | 51.571 | 38.807 | 1.00 | 40.22 |
| 2282 | CE | MET | 296 | 110.937 | 52.162 | 40.336 | 1.00 | 31.58 |
| 2283 | C | MET | 296 | 110.617 | 48.181 | 41.343 | 1.00 | 36.25 |
| 2284 | O | MET | 296 | 109.831 | 48.871 | 41.997 | 1.00 | 35.27 |
| 2285 | N | ILE | 297 | 110.462 | 46.867 | 41.172 | 1.00 | 36.41 |
| 2286 | CA | ILE | 297 | 109.327 | 46.145 | 41.743 | 1.00 | 31.22 |
| 2287 | CB | ILE | 297 | 109.240 | 44.681 | 41.222 | 1.00 | 30.61 |
| 2288 | CG2 | ILE | 297 | 110.401 | 43.850 | 41.748 | 1.00 | 32.13 |
| 2289 | CG1 | ILE | 297 | 107.915 | 44.039 | 41.647 | 1.00 | 25.21 |
| 2290 | CD1 | ILE | 297 | 106.681 | 44.725 | 41.088 | 1.00 | 9.77 |
| 2291 | C | ILE | 297 | 109.362 | 46.151 | 43.266 | 1.00 | 28.01 |
| 2292 | O | ILE | 297 | 108.333 | 45.964 | 43.914 | 1.00 | 33.37 |
| 2293 | N | SER | 298 | 110.544 | 46.369 | 43.834 | 1.00 | 26.49 |
| 2294 | CA | SER | 298 | 110.682 | 46.410 | 45.284 | 1.00 | 31.31 |
| 2295 | CB | SER | 298 | 112.152 | 46.511 | 45.692 | 1.00 | 36.65 |
| 2296 | OG | SER | 298 | 112.281 | 46.533 | 47.106 | 1.00 | 34.52 |
| 2297 | C | SER | 298 | 109.921 | 47.616 | 45.810 | 1.00 | 31.13 |
| 2298 | O | SER | 298 | 109.331 | 47.567 | 46.888 | 1.00 | 32.44 |
| 2299 | N | ILE | 299 | 109.932 | 48.693 | 45.029 | 1.00 | 31.80 |
| 2300 | CA | ILE | 299 | 109.239 | 49.923 | 45.390 | 1.00 | 37.55 |
| 2301 | CB | ILE | 299 | 109.648 | 51.086 | 44.462 | 1.00 | 44.76 |
| 2302 | CG2 | ILE | 299 | 108.809 | 52.326 | 44.753 | 1.00 | 45.64 |
| 2303 | CG1 | ILE | 299 | 111.135 | 51.390 | 44.645 | 1.00 | 46.63 |
| 2304 | CD1 | ILE | 299 | 111.656 | 52.438 | 43.707 | 1.00 | 51.58 |
| 2305 | C | ILE | 299 | 107.735 | 49.710 | 45.315 | 1.00 | 31.48 |
| 2306 | O | ILE | 299 | 107.008 | 50.072 | 46.238 | 1.00 | 32.42 |
| 2307 | N | VAL | 300 | 107.277 | 49.101 | 44.224 | 1.00 | 27.09 |
| 2308 | CA | VAL | 300 | 105.855 | 48.824 | 44.037 | 1.00 | 23.95 |
| 2309 | CB | VAL | 300 | 105.598 | 48.080 | 42.709 | 1.00 | 22.51 |
| 2310 | CG1 | VAL | 300 | 104.108 | 47.876 | 42.494 | 1.00 | 20.37 |
| 2311 | CG2 | VAL | 300 | 106.190 | 48.867 | 41.552 | 1.00 | 20.21 |
| 2312 | C | VAL | 300 | 105.349 | 47.990 | 45.211 | 1.00 | 23.59 |
| 2313 | O | VAL | 300 | 104.247 | 48.204 | 45.714 | 1.00 | 30.31 |
| 2314 | N | ASP | 301 | 106.186 | 47.072 | 45.674 | 1.00 | 24.66 |
| 2315 | CA | ASP | 301 | 105.837 | 46.226 | 46.802 | 1.00 | 31.65 |
| 2316 | CB | ASP | 301 | 106.879 | 45.121 | 46.975 | 1.00 | 25.48 |
| 2317 | CG | ASP | 301 | 106.523 | 44.163 | 48.087 | 1.00 | 24.95 |
| 2318 | OD1 | ASP | 301 | 105.672 | 43.277 | 47.869 | 1.00 | 37.24 |
| 2319 | OD2 | ASP | 301 | 107.075 | 44.309 | 49.193 | 1.00 | 32.62 |
| 2320 | C | ASP | 301 | 105.762 | 47.078 | 48.065 | 1.00 | 33.30 |
| 2321 | O | ASP | 301 | 104.847 | 46.930 | 48.874 | 1.00 | 36.41 |
| 2322 | N | ASP | 302 | 106.737 | 47.971 | 48.218 | 1.00 | 41.65 |
| 2323 | CA | ASP | 302 | 106.805 | 48.866 | 49.369 | 1.00 | 43.94 |
| 2324 | CB | ASP | 302 | 108.124 | 49.650 | 49.353 | 1.00 | 49.38 |
| 2325 | CG | ASP | 302 | 109.322 | 48.798 | 49.744 | 1.00 | 55.74 |
| 2326 | OD1 | ASP | 302 | 109.246 | 48.101 | 50.780 | 1.00 | 59.49 |
| 2327 | OD2 | ASP | 302 | 110.344 | 48.833 | 49.024 | 1.00 | 52.10 |
| 2328 | C | ASP | 302 | 105.619 | 49.831 | 49.416 | 1.00 | 43.11 |
| 2329 | O | ASP | 302 | 105.198 | 50.257 | 50.493 | 1.00 | 44.18 |
| 2330 | N | THR | 303 | 105.081 | 50.159 | 48.243 | 1.00 | 38.88 |
| 2331 | CA | THR | 303 | 103.945 | 51.069 | 48.123 | 1.00 | 33.20 |
| 2332 | CB | THR | 303 | 103.745 | 51.514 | 46.660 | 1.00 | 41.14 |
| 2333 | OG1 | THR | 303 | 104.965 | 52.075 | 46.158 | 1.00 | 39.42 |
| 2334 | CG2 | THR | 303 | 102.643 | 52.555 | 46.564 | 1.00 | 44.39 |
| 2335 | C | THR | 303 | 102.652 | 50.426 | 48.624 | 1.00 | 36.28 |
| 2336 | O | THR | 303 | 101.930 | 51.016 | 49.425 | 1.00 | 44.91 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 2337 | N | PHE | 304 | 102.367 | 49.218 | 48.143 | 1.00 | 33.21 |
| 2338 | CA | PHE | 304 | 101.167 | 48.478 | 48.532 | 1.00 | 26.28 |
| 2339 | CB | PHE | 304 | 101.005 | 47.234 | 47.653 | 1.00 | 23.04 |
| 2340 | CG | PHE | 304 | 100.431 | 47.509 | 46.293 | 1.00 | 14.95 |
| 2341 | CD1 | PHE | 304 | 101.250 | 47.901 | 45.239 | 1.00 | 16.64 |
| 2342 | CD2 | PHE | 304 | 99.068 | 47.352 | 46.059 | 1.00 | 16.64 |
| 2343 | CE1 | PHE | 304 | 100.720 | 48.132 | 43.968 | 1.00 | 20.58 |
| 2344 | CE2 | PHE | 304 | 98.527 | 47.580 | 44.793 | 1.00 | 13.24 |
| 2345 | CZ | PHE | 304 | 99.355 | 47.971 | 43.746 | 1.00 | 15.28 |
| 2346 | C | PHE | 304 | 101.183 | 48.032 | 49.993 | 1.00 | 34.53 |
| 2347 | O | PHE | 304 | 100.135 | 47.926 | 50.632 | 1.00 | 38.46 |
| 2348 | N | ASP | 305 | 102.379 | 47.778 | 50.515 | 1.00 | 40.19 |
| 2349 | CA | ASP | 305 | 102.544 | 47.300 | 51.881 | 1.00 | 46.42 |
| 2350 | CB | ASP | 305 | 103.774 | 46.399 | 51.968 | 1.00 | 58.96 |
| 2351 | CG | ASP | 305 | 103.431 | 44.933 | 51.845 | 1.00 | 70.39 |
| 2352 | OD1 | ASP | 305 | 102.647 | 44.572 | 50.940 | 1.00 | 75.74 |
| 2353 | OD2 | ASP | 305 | 103.957 | 44.140 | 52.656 | 1.00 | 75.60 |
| 2354 | C | ASP | 305 | 102.605 | 48.324 | 53.001 | 1.00 | 47.79 |
| 2355 | O | ASP | 305 | 101.936 | 48.161 | 54.022 | 1.00 | 46.25 |
| 2356 | N | ALA | 306 | 103.425 | 49.357 | 52.831 | 1.00 | 52.07 |
| 2357 | CA | ALA | 306 | 103.574 | 50.362 | 53.875 | 1.00 | 54.53 |
| 2358 | CB | ALA | 306 | 104.958 | 50.240 | 54.518 | 1.00 | 57.28 |
| 2359 | C | ALA | 306 | 103.312 | 51.807 | 53.462 | 1.00 | 53.39 |
| 2360 | O | ALA | 306 | 103.971 | 52.718 | 53.965 | 1.00 | 58.62 |
| 2361 | N | TYR | 307 | 102.345 | 52.030 | 52.576 | 1.00 | 51.30 |
| 2362 | CA | TYR | 307 | 102.045 | 53.395 | 52.165 | 1.00 | 53.81 |
| 2363 | CB | TYR | 307 | 103.107 | 53.918 | 51.195 | 1.00 | 48.52 |
| 2364 | CG | TYR | 307 | 103.396 | 55.388 | 51.392 | 1.00 | 55.69 |
| 2365 | CD1 | TYR | 307 | 103.963 | 55.847 | 52.581 | 1.00 | 59.86 |
| 2366 | CE1 | TYR | 307 | 104.206 | 57.200 | 52.789 | 1.00 | 62.54 |
| 2367 | CD2 | TYR | 307 | 103.077 | 56.324 | 50.411 | 1.00 | 56.20 |
| 2368 | CE2 | TYR | 307 | 103.315 | 57.683 | 50.608 | 1.00 | 59.89 |
| 2369 | CZ | TYR | 307 | 103.878 | 58.112 | 51.801 | 1.00 | 62.92 |
| 2370 | OH | TYR | 307 | 104.112 | 59.451 | 52.009 | 1.00 | 66.19 |
| 2371 | C | TYR | 307 | 100.647 | 53.640 | 51.597 | 1.00 | 59.33 |
| 2372 | O | TYR | 307 | 99.752 | 54.078 | 52.320 | 1.00 | 66.09 |
| 2373 | N | GLY | 308 | 100.473 | 53.364 | 50.307 | 1.00 | 59.69 |
| 2374 | CA | GLY | 308 | 99.199 | 53.580 | 49.636 | 1.00 | 58.39 |
| 2375 | C | GLY | 308 | 97.924 | 53.122 | 50.326 | 1.00 | 60.86 |
| 2376 | O | GLY | 308 | 97.925 | 52.163 | 51.101 | 1.00 | 61.04 |
| 2377 | N | THR | 309 | 96.833 | 53.833 | 50.044 | 1.00 | 60.72 |
| 2378 | CA | THR | 309 | 95.522 | 53.524 | 50.609 | 1.00 | 57.07 |
| 2379 | CB | THR | 309 | 94.751 | 54.807 | 50.989 | 1.00 | 55.19 |
| 2380 | OG1 | THR | 309 | 94.651 | 55.667 | 49.847 | 1.00 | 47.62 |
| 2381 | CG2 | THR | 309 | 95.461 | 55.538 | 52.117 | 1.00 | 46.57 |
| 2382 | C | THR | 309 | 94.693 | 52.722 | 49.609 | 1.00 | 59.08 |
| 2383 | O | THR | 309 | 94.996 | 52.709 | 48.415 | 1.00 | 56.21 |
| 2384 | N | VAL | 310 | 93.631 | 52.089 | 50.107 | 1.00 | 60.80 |
| 2385 | CA | VAL | 310 | 92.737 | 51.264 | 49.295 | 1.00 | 62.84 |
| 2386 | CB | VAL | 310 | 91.430 | 50.932 | 50.059 | 1.00 | 64.23 |
| 2387 | CG1 | VAL | 310 | 90.667 | 49.821 | 49.351 | 1.00 | 66.80 |
| 2388 | CG2 | VAL | 310 | 91.737 | 50.534 | 51.498 | 1.00 | 61.87 |
| 2389 | C | VAL | 310 | 92.390 | 51.903 | 47.947 | 1.00 | 63.74 |
| 2390 | O | VAL | 310 | 92.469 | 51.244 | 46.904 | 1.00 | 60.65 |
| 2391 | N | LYS | 311 | 92.038 | 53.189 | 47.972 | 1.00 | 65.40 |
| 2392 | CA | LYS | 311 | 91.687 | 53.926 | 46.755 | 1.00 | 65.81 |
| 2393 | CB | LYS | 311 | 91.121 | 55.301 | 47.105 | 1.00 | 70.45 |
| 2394 | CG | LYS | 311 | 89.696 | 55.305 | 47.621 | 1.00 | 74.65 |
| 2395 | CD | LYS | 311 | 89.175 | 56.734 | 47.692 | 1.00 | 77.16 |
| 2396 | CE | LYS | 311 | 87.719 | 56.787 | 48.120 | 1.00 | 75.45 |
| 2397 | NZ | LYS | 311 | 87.239 | 58.194 | 48.137 | 1.00 | 78.70 |
| 2398 | C | LYS | 311 | 92.889 | 54.116 | 45.842 | 1.00 | 63.97 |
| 2399 | O | LYS | 311 | 92.840 | 53.788 | 44.658 | 1.00 | 64.41 |
| 2400 | N | GLU | 312 | 93.961 | 54.670 | 46.403 | 1.00 | 60.54 |
| 2401 | CA | GLU | 312 | 95.195 | 54.931 | 45.665 | 1.00 | 57.43 |
| 2402 | CB | GLU | 312 | 96.263 | 55.516 | 46.596 | 1.00 | 59.85 |
| 2403 | CG | GLU | 312 | 95.900 | 56.859 | 47.194 | 1.00 | 66.27 |
| 2404 | CD | GLU | 312 | 97.024 | 57.438 | 48.033 | 1.00 | 69.45 |
| 2405 | OE1 | GLU | 312 | 37.396 | 56.817 | 49.051 | 1.00 | 71.29 |
| 2406 | OE2 | GLU | 312 | 97.544 | 58.514 | 47.666 | 1.00 | 70.23 |
| 2407 | C | GLU | 312 | 95.750 | 53.679 | 44.989 | 1.00 | 53.28 |
| 2408 | O | GLU | 312 | 96.133 | 53.715 | 43.815 | 1.00 | 44.50 |
| 2409 | N | LEU | 313 | 95.787 | 52.577 | 45.736 | 1.00 | 45.10 |
| 2410 | CA | LEU | 313 | 96.290 | 51.310 | 45.222 | 1.00 | 40.42 |
| 2411 | CB | LEU | 313 | 96.361 | 50.267 | 46.343 | 1.00 | 35.64 |
| 2412 | CG | LEU | 313 | 97.263 | 50.614 | 47.534 | 1.00 | 32.14 |
| 2413 | CD1 | LEU | 313 | 97.226 | 49.501 | 48.569 | 1.00 | 28.15 |
| 2414 | CD2 | LEU | 313 | 98.687 | 50.861 | 47.061 | 1.00 | 26.11 |
| 2415 | C | LEU | 313 | 95.430 | 50.800 | 44.071 | 1.00 | 41.37 |
| 2416 | O | LEU | 313 | 95.950 | 50.275 | 43.085 | 1.00 | 39.82 |
| 2417 | N | GLU | 314 | 94.116 | 50.981 | 44.193 | 1.00 | 41.16 |
| 2418 | CA | GLU | 314 | 93.180 | 50.553 | 43.156 | 1.00 | 41.35 |
| 2419 | CB | GLU | 314 | 91.737 | 50.728 | 43.636 | 1.00 | 45.36 |
| 2420 | CG | GLU | 314 | 90.674 | 50.326 | 42.612 | 1.00 | 51.16 |
| 2421 | CD | GLU | 314 | 90.717 | 48.848 | 42.251 | 1.00 | 56.61 |
| 2422 | OE1 | GLU | 314 | 90.469 | 48.007 | 43.144 | 1.00 | 55.46 |
| 2423 | OE2 | GLU | 314 | 90.988 | 48.530 | 41.071 | 1.00 | 49.16 |
| 2424 | C | GLU | 314 | 93.417 | 51.357 | 41.880 | 1.00 | 38.64 |
| 2425 | O | GLU | 314 | 93.315 | 50.828 | 40.772 | 1.00 | 41.77 |
| 2426 | N | ALA | 315 | 93.742 | 52.634 | 42.047 | 1.00 | 37.56 |
| 2427 | CA | ALA | 315 | 94.012 | 53.513 | 40.917 | 1.00 | 37.09 |
| 2428 | CB | ALA | 315 | 94.024 | 54.961 | 41.375 | 1.00 | 41.02 |
| 2429 | C | ALA | 315 | 95.354 | 53.146 | 40.292 | 1.00 | 37.51 |
| 2430 | O | ALA | 315 | 95.522 | 53.222 | 39.074 | 1.00 | 40.72 |
| 2431 | N | TYR | 316 | 96.301 | 52.741 | 41.138 | 1.00 | 37.47 |
| 2432 | CA | TYR | 316 | 97.641 | 52.351 | 40.698 | 1.00 | 36.60 |
| 2433 | CB | TYR | 316 | 98.567 | 52.189 | 41.908 | 1.00 | 42.76 |
| 2434 | CG | TYR | 316 | 100.045 | 52.214 | 41.576 | 1.00 | 47.70 |
| 2435 | CD1 | TYR | 316 | 100.701 | 53.421 | 41.323 | 1.00 | 50.35 |
| 2436 | CE1 | TYR | 316 | 102.064 | 53.456 | 41.029 | 1.00 | 47.09 |
| 2437 | CD2 | TYR | 316 | 100.792 | 51.038 | 41.526 | 1.00 | 50.58 |
| 2438 | CE2 | TYR | 316 | 102.158 | 51.063 | 41.232 | 1.00 | 51.96 |
| 2439 | CZ | TYR | 316 | 102.785 | 52.276 | 40.986 | 1.00 | 46.31 |
| 2440 | OH | TYR | 316 | 104.130 | 52.308 | 40.697 | 1.00 | 45.69 |
| 2441 | C | TYR | 316 | 97.582 | 51.047 | 39.909 | 1.00 | 38.30 |
| 2442 | O | TYR | 316 | 98.142 | 50.949 | 38.812 | 1.00 | 29.96 |
| 2443 | N | THR | 317 | 96.890 | 50.058 | 40.473 | 1.00 | 34.49 |
| 2444 | CA | THR | 317 | 96.731 | 48.752 | 39.839 | 1.00 | 33.58 |
| 2445 | CB | THR | 317 | 95.811 | 47.831 | 40.671 | 1.00 | 29.35 |
| 2446 | OG1 | THR | 317 | 96.347 | 47.676 | 41.990 | 1.00 | 30.19 |
| 2447 | CG2 | THR | 317 | 95.691 | 46.460 | 40.020 | 1.00 | 28.64 |
| 2448 | C | THR | 317 | 96.125 | 48.922 | 38.448 | 1.00 | 38.84 |
| 2449 | O | THR | 317 | 98.624 | 48.363 | 37.470 | 1.00 | 37.70 |
| 2450 | N | ASP | 318 | 95.070 | 49.731 | 38.369 | 1.00 | 39.63 |
| 2451 | CA | ASP | 318 | 94.385 | 49.987 | 37.110 | 1.00 | 43.25 |
| 2452 | CB | ASP | 318 | 93.115 | 50.806 | 37.351 | 1.00 | 53.81 |
| 2453 | CG | ASP | 318 | 92.282 | 50.972 | 36.094 | 1.00 | 64.26 |
| 2454 | OD1 | ASP | 318 | 91.830 | 49.947 | 35.538 | 1.00 | 68.93 |
| 2455 | OD2 | ASP | 318 | 92.088 | 52.126 | 35.656 | 1.00 | 69.91 |
| 2456 | C | ASP | 318 | 95.292 | 50.706 | 36.118 | 1.00 | 38.89 |
| 2457 | O | ASP | 318 | 95.280 | 50.406 | 34.922 | 1.00 | 35.65 |
| 2458 | N | ALA | 319 | 96.081 | 51.651 | 36.622 | 1.00 | 39.85 |
| 2459 | CA | ALA | 319 | 97.001 | 52.409 | 35.783 | 1.00 | 39.48 |
| 2460 | CB | ALA | 319 | 97.716 | 53.462 | 36.610 | 1.00 | 45.21 |
| 2461 | C | ALA | 319 | 98.007 | 51.469 | 35.123 | 1.00 | 36.47 |
| 2462 | O | ALA | 319 | 98.261 | 51.564 | 33.920 | 1.00 | 28.06 |
| 2463 | N | ILE | 320 | 98.547 | 50.541 | 35.912 | 1.00 | 36.88 |
| 2464 | CA | ILE | 320 | 99.514 | 49.560 | 35.422 | 1.00 | 35.98 |
| 2465 | CB | ILE | 320 | 99.994 | 48.620 | 36.561 | 1.00 | 43.40 |
| 2466 | CG2 | ILE | 320 | 100.784 | 47.443 | 35.991 | 1.00 | 44.99 |
| 2467 | CG1 | ILE | 320 | 100.834 | 49.397 | 37.582 | 1.00 | 45.58 |
| 2468 | CD1 | ILE | 320 | 102.173 | 49.891 | 37.054 | 1.00 | 39.26 |
| 2469 | C | ILE | 320 | 98.911 | 48.712 | 34.307 | 1.00 | 31.85 |
| 2470 | O | ILE | 320 | 99.544 | 48.506 | 33.271 | 1.00 | 32.45 |
| 2471 | N | GLN | 321 | 97.680 | 48.245 | 34.518 | 1.00 | 27.13 |
| 2472 | CA | GLN | 321 | 96.980 | 47.414 | 33.538 | 1.00 | 29.80 |
| 2473 | CB | GLN | 321 | 95.592 | 48.053 | 34.053 | 1.00 | 37.41 |
| 2474 | CG | GLN | 321 | 95.581 | 46.336 | 35.422 | 1.00 | 37.33 |
| 2475 | CD | GLN | 321 | 96.510 | 45.136 | 35.508 | 1.00 | 42.33 |
| 2476 | OE1 | GLN | 321 | 96.690 | 44.398 | 34.536 | 1.00 | 43.16 |
| 2477 | NE2 | GLN | 321 | 97.108 | 44.938 | 36.679 | 1.00 | 35.06 |
| 2478 | C | GLN | 321 | 96.856 | 48.101 | 32.180 | 1.00 | 30.46 |
| 2479 | O | GLN | 321 | 97.066 | 47.474 | 31.139 | 1.00 | 25.13 |
| 2480 | N | ARG | 322 | 96.519 | 49.390 | 32.199 | 1.00 | 36.61 |
| 2481 | CA | ARG | 322 | 96.384 | 50.171 | 30.971 | 1.00 | 40.97 |
| 2482 | CB | ARG | 322 | 95.779 | 51.549 | 31.264 | 1.00 | 48.13 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 2483 | CG | ARG | 322 | 94.261 | 51.612 | 31.176 | 1.00 | 58.29 |
| 2484 | CD | ARG | 322 | 93.581 | 50.836 | 32.290 | 1.00 | 66.64 |
| 2485 | NE | ARG | 322 | 92.125 | 50.822 | 32.134 | 1.00 | 76.38 |
| 2486 | CZ | ARG | 322 | 91.326 | 51.868 | 32.344 | 1.00 | 74.78 |
| 2487 | NH1 | ARG | 322 | 91.827 | 53.035 | 32.727 | 1.00 | 73.98 |
| 2488 | NH2 | ARG | 322 | 90.019 | 51.751 | 32.157 | 1.00 | 73.84 |
| 2489 | C | ARG | 322 | 97.737 | 50.347 | 30.290 | 1.00 | 39.65 |
| 2490 | O | ARG | 322 | 97.848 | 50.233 | 29.067 | 1.00 | 46.16 |
| 2491 | N | TRP | 323 | 98.757 | 50.635 | 31.094 | 1.00 | 37.39 |
| 2492 | CA | TRP | 323 | 100.118 | 50.828 | 30.607 | 1.00 | 35.58 |
| 2493 | CB | TRP | 323 | 100.663 | 49.535 | 29.990 | 1.00 | 36.83 |
| 2494 | CG | TRP | 323 | 102.169 | 49.447 | 29.979 | 1.00 | 41.47 |
| 2495 | CD2 | TRP | 323 | 103.017 | 49.048 | 31.063 | 1.00 | 38.37 |
| 2496 | CE2 | TRP | 323 | 104.351 | 49.089 | 30.594 | 1.00 | 38.29 |
| 2497 | CE3 | TRP | 323 | 102.779 | 48.656 | 32.390 | 1.00 | 36.27 |
| 2498 | CD1 | TRP | 323 | 103.003 | 49.714 | 28.922 | 1.00 | 40.25 |
| 2499 | NE1 | TRP | 323 | 104.312 | 49.500 | 29.286 | 1.00 | 39.37 |
| 2500 | CZ2 | TRP | 323 | 105.439 | 48.753 | 31.402 | 1.00 | 30.80 |
| 2501 | CZ3 | TRP | 323 | 103.863 | 48.322 | 33.192 | 1.00 | 34.06 |
| 2502 | CH2 | TRP | 323 | 105.178 | 48.374 | 32.691 | 1.00 | 37.92 |
| 2503 | C | TRP | 323 | 100.182 | 51.976 | 29.606 | 1.00 | 36.88 |
| 2504 | O | TRP | 323 | 100.522 | 51.788 | 28.437 | 1.00 | 30.80 |
| 2505 | N | ASP | 324 | 99.781 | 53.157 | 30.066 | 1.00 | 48.71 |
| 2506 | CA | ASP | 324 | 99.797 | 54.366 | 29.249 | 1.00 | 54.17 |
| 2507 | CB | ASP | 324 | 98.462 | 54.586 | 28.537 | 1.00 | 56.16 |
| 2508 | CG | ASP | 324 | 98.585 | 55.547 | 27.366 | 1.00 | 58.43 |
| 2509 | OD1 | ASP | 324 | 98.956 | 56.724 | 27.575 | 1.00 | 59.06 |
| 2510 | OD2 | ASP | 324 | 98.328 | 55.120 | 26.222 | 1.00 | 57.24 |
| 2511 | C | ASP | 324 | 100.076 | 55.543 | 30.165 | 1.00 | 57.09 |
| 2512 | O | ASP | 324 | 99.468 | 55.671 | 31.230 | 1.00 | 54.89 |
| 2513 | N | ILE | 325 | 100.977 | 56.414 | 29.729 | 1.00 | 60.16 |
| 2514 | CA | ILE | 325 | 101.377 | 57.584 | 30.495 | 1.00 | 64.12 |
| 2515 | CB | ILE | 325 | 102.559 | 58.286 | 29.788 | 1.00 | 67.78 |
| 2516 | CG2 | ILE | 325 | 102.072 | 59.013 | 28.542 | 1.00 | 68.84 |
| 2517 | CG1 | ILE | 325 | 103.325 | 59.185 | 30.768 | 1.00 | 71.40 |
| 2518 | CD1 | ILE | 325 | 104.716 | 59.579 | 30.273 | 1.00 | 78.93 |
| 2519 | C | ILE | 325 | 100.219 | 58.560 | 30.760 | 1.00 | 62.87 |
| 2520 | O | ILE | 325 | 100.248 | 59.325 | 31.723 | 1.00 | 55.53 |
| 2521 | N | ASN | 326 | 99.181 | 58.489 | 29.931 | 1.00 | 63.16 |
| 2522 | CA | ASN | 326 | 98.008 | 59.347 | 30.075 | 1.00 | 60.43 |
| 2523 | CB | ASN | 326 | 97.060 | 59.157 | 28.891 | 1.00 | 58.85 |
| 2524 | CG | ASN | 326 | 97.208 | 60.240 | 27.858 | 1.00 | 58.26 |
| 2525 | OD1 | ASN | 326 | 97.005 | 61.420 | 28.150 | 1.00 | 61.96 |
| 2526 | ND2 | ASN | 326 | 97.564 | 59.854 | 26.640 | 1.00 | 59.50 |
| 2527 | C | ASN | 326 | 97.247 | 59.093 | 31.370 | 1.00 | 61.39 |
| 2528 | O | ASN | 326 | 96.561 | 59.982 | 31.875 | 1.00 | 62.82 |
| 2529 | N | GLU | 327 | 97.378 | 57.881 | 31.904 | 1.00 | 59.66 |
| 2530 | CA | GLU | 327 | 96.691 | 57.498 | 33.136 | 1.00 | 62.98 |
| 2531 | CB | GLU | 327 | 96.563 | 55.973 | 33.216 | 1.00 | 64.39 |
| 2532 | CG | GLU | 327 | 96.087 | 55.299 | 31.933 | 1.00 | 69.30 |
| 2533 | CD | GLU | 327 | 94.708 | 55.750 | 31.491 | 1.00 | 70.48 |
| 2534 | OE1 | GLU | 327 | 93.784 | 55.783 | 32.335 | 1.00 | 72.78 |
| 2535 | OE2 | GLU | 327 | 94.548 | 56.067 | 30.291 | 1.00 | 63.31 |
| 2536 | C | GLU | 327 | 97.414 | 58.011 | 34.380 | 1.00 | 62.97 |
| 2537 | O | GLU | 327 | 96.972 | 57.771 | 35.505 | 1.00 | 62.71 |
| 2538 | N | ILE | 328 | 98.510 | 58.734 | 34.169 | 1.00 | 64.24 |
| 2539 | CA | ILE | 328 | 99.316 | 59.270 | 35.264 | 1.00 | 67.30 |
| 2540 | CB | ILE | 328 | 100.636 | 59.886 | 34.729 | 1.00 | 69.70 |
| 2541 | CG2 | ILE | 328 | 100.372 | 61.245 | 34.069 | 1.00 | 69.85 |
| 2542 | CG1 | ILE | 328 | 101.657 | 60.013 | 35.863 | 1.00 | 72.49 |
| 2543 | CD1 | ILE | 328 | 103.047 | 60.424 | 35.409 | 1.00 | 71.67 |
| 2544 | C | ILE | 328 | 98.577 | 60.298 | 36.122 | 1.00 | 66.37 |
| 2545 | O | ILE | 328 | 98.763 | 60.349 | 37.340 | 1.00 | 61.63 |
| 2546 | N | ASP | 329 | 97.711 | 61.082 | 35.485 | 1.00 | 70.35 |
| 2547 | CA | ASP | 329 | 96.950 | 62.128 | 36.163 | 1.00 | 73.14 |
| 2548 | CB | ASP | 329 | 96.212 | 62.987 | 35.134 | 1.00 | 73.34 |
| 2549 | CG | ASP | 329 | 97.154 | 63.620 | 34.123 | 1.00 | 75.99 |
| 2550 | OD1 | ASP | 329 | 97.861 | 64.584 | 34.486 | 1.00 | 75.75 |
| 2551 | OD2 | ASP | 329 | 97.193 | 63.140 | 32.970 | 1.00 | 74.82 |
| 2552 | C | ASP | 329 | 95.978 | 61.611 | 37.219 | 1.00 | 73.26 |
| 2553 | O | ASP | 329 | 95.637 | 62.332 | 38.159 | 1.00 | 73.84 |
| 2554 | N | ARG | 330 | 95.539 | 60.366 | 37.065 | 1.00 | 70.87 |
| 2555 | CA | ARG | 330 | 94.616 | 59.756 | 38.019 | 1.00 | 70.53 |
| 2556 | CB | ARG | 330 | 93.932 | 58.535 | 37.393 | 1.00 | 71.49 |
| 2557 | CG | ARG | 330 | 93.145 | 58.845 | 36.129 | 1.00 | 78.19 |
| 2558 | CD | ARG | 330 | 92.435 | 57.612 | 35.591 | 1.00 | 85.11 |
| 2559 | NE | ARG | 330 | 91.756 | 57.889 | 34.326 | 1.00 | 94.74 |
| 2560 | CZ | ARG | 330 | 90.865 | 57.082 | 33.754 | 1.00 | 98.54 |
| 2561 | NH1 | ARG | 330 | 90.532 | 55.934 | 34.331 | 1.00 | 100.00 |
| 2562 | NH2 | ARG | 330 | 90.309 | 57.424 | 32.599 | 1.00 | 94.40 |
| 2563 | C | ARG | 330 | 95.358 | 59.345 | 39.291 | 1.00 | 67.20 |
| 2564 | O | ARG | 330 | 94.749 | 59.145 | 40.345 | 1.00 | 61.95 |
| 2565 | N | LEU | 331 | 96.681 | 59.252 | 39.183 | 1.00 | 66.11 |
| 2566 | CA | LEU | 331 | 97.539 | 58.857 | 40.295 | 1.00 | 65.38 |
| 2567 | CB | LEU | 331 | 98.727 | 58.047 | 39.768 | 1.00 | 70.15 |
| 2568 | CG | LEU | 331 | 98.430 | 56.802 | 38.933 | 1.00 | 71.98 |
| 2569 | CD1 | LEU | 331 | 99.710 | 56.289 | 38.300 | 1.00 | 67.56 |
| 2570 | CD2 | LEU | 331 | 97.789 | 55.739 | 39.806 | 1.00 | 72.35 |
| 2571 | C | LEU | 331 | 98.081 | 60.056 | 41.057 | 1.00 | 59.96 |
| 2572 | O | LEU | 331 | 98.432 | 61.069 | 40.456 | 1.00 | 60.57 |
| 2573 | N | PRO | 332 | 98.145 | 59.962 | 42.397 | 1.00 | 56.66 |
| 2574 | CD | PRO | 332 | 97.661 | 58.870 | 43.257 | 1.00 | 52.18 |
| 2575 | CA | PRO | 332 | 98.666 | 61.070 | 43.204 | 1.00 | 60.33 |
| 2576 | CB | PRO | 332 | 98.458 | 60.578 | 44.640 | 1.00 | 54.14 |
| 2577 | CG | PRO | 332 | 98.462 | 59.090 | 44.507 | 1.00 | 53.96 |
| 2578 | C | PRO | 332 | 100.144 | 61.294 | 42.871 | 1.00 | 65.03 |
| 2579 | O | PRO | 332 | 100.817 | 60.386 | 42.381 | 1.00 | 68.68 |
| 2580 | N | ASP | 333 | 100.637 | 62.500 | 43.136 | 1.00 | 70.86 |
| 2581 | CA | ASP | 333 | 102.021 | 62.876 | 42.839 | 1.00 | 72.50 |
| 2582 | CB | ASP | 333 | 102.362 | 64.220 | 43.489 | 1.00 | 76.30 |
| 2583 | CG | ASP | 333 | 101.737 | 65.396 | 42.760 | 1.00 | 73.02 |
| 2584 | OD1 | ASP | 333 | 101.290 | 66.343 | 43.438 | 1.00 | 75.36 |
| 2585 | OD2 | ASP | 333 | 101.700 | 65.378 | 41.510 | 1.00 | 70.83 |
| 2586 | C | ASP | 333 | 103.146 | 61.873 | 43.105 | 1.00 | 69.45 |
| 2587 | O | ASP | 333 | 104.019 | 61.694 | 42.254 | 1.00 | 64.53 |
| 2588 | N | TYR | 334 | 103.139 | 61.226 | 44.269 | 1.00 | 65.65 |
| 2589 | CA | TYR | 334 | 104.195 | 60.267 | 44.590 | 1.00 | 64.14 |
| 2590 | CB | TYR | 334 | 104.180 | 59.900 | 46.080 | 1.00 | 67.04 |
| 2591 | CG | TYR | 334 | 103.162 | 58.858 | 46.484 | 1.00 | 71.84 |
| 2592 | CD1 | TYR | 334 | 101.827 | 59.199 | 46.688 | 1.00 | 74.21 |
| 2593 | CE1 | TYR | 334 | 100.895 | 58.243 | 47.086 | 1.00 | 74.47 |
| 2594 | CD2 | TYR | 334 | 103.542 | 57.531 | 46.685 | 1.00 | 72.86 |
| 2595 | CE2 | TYR | 334 | 102.620 | 56.570 | 47.081 | 1.00 | 72.07 |
| 2596 | CZ | TYR | 334 | 101.299 | 56.932 | 47.281 | 1.00 | 72.74 |
| 2597 | OH | TYR | 334 | 100.386 | 55.982 | 47.675 | 1.00 | 69.90 |
| 2598 | C | TYR | 334 | 104.143 | 59.015 | 43.714 | 1.00 | 59.49 |
| 2599 | O | TYR | 334 | 105.181 | 58.466 | 43.341 | 1.00 | 58.89 |
| 2600 | N | MET | 335 | 102.933 | 58.575 | 43.379 | 1.00 | 51.53 |
| 2601 | CA | MET | 335 | 102.762 | 57.401 | 42.533 | 1.00 | 48.12 |
| 2602 | CB | MET | 335 | 101.340 | 56.854 | 42.637 | 1.00 | 45.40 |
| 2603 | CG | MET | 335 | 100.979 | 56.325 | 44.006 | 1.00 | 34.82 |
| 2604 | SD | MET | 335 | 99.387 | 55.502 | 44.005 | 1.00 | 37.30 |
| 2605 | CE | MET | 335 | 99.776 | 53.994 | 44.867 | 1.00 | 41.41 |
| 2606 | C | MET | 335 | 103.082 | 57.727 | 41.081 | 1.00 | 48.13 |
| 2607 | O | MET | 335 | 103.354 | 56.826 | 40.287 | 1.00 | 55.57 |
| 2608 | N | LYS | 336 | 103.032 | 59.013 | 40.738 | 1.00 | 48.65 |
| 2609 | CA | LYS | 336 | 103.332 | 59.465 | 39.380 | 1.00 | 50.84 |
| 2610 | CB | LYS | 336 | 103.004 | 60.953 | 39.213 | 1.00 | 55.94 |
| 2611 | CG | LYS | 336 | 101.524 | 61.301 | 39.255 | 1.00 | 63.40 |
| 2612 | CD | LYS | 336 | 101.298 | 62.758 | 38.857 | 1.00 | 63.31 |
| 2613 | CE | LYS | 336 | 99.820 | 63.092 | 38.764 | 1.00 | 60.22 |
| 2614 | NZ | LYS | 336 | 99.580 | 64.473 | 38.271 | 1.00 | 62.57 |
| 2615 | C | LYS | 336 | 104.810 | 59.237 | 39.080 | 1.00 | 51.33 |
| 2616 | O | LYS | 336 | 105.187 | 58.938 | 37.943 | 1.00 | 47.74 |
| 2617 | N | ILE | 337 | 105.638 | 59.382 | 40.114 | 1.00 | 45.10 |
| 2618 | CA | ILE | 337 | 107.079 | 59.195 | 39.996 | 1.00 | 46.36 |
| 2619 | CB | ILE | 337 | 107.805 | 59.607 | 41.297 | 1.00 | 48.91 |
| 2620 | CG2 | ILE | 337 | 109.309 | 59.641 | 41.067 | 1.00 | 50.47 |
| 2621 | CG1 | ILE | 337 | 107.330 | 60.986 | 41.759 | 1.00 | 50.88 |
| 2622 | CD1 | ILE | 337 | 107.888 | 61.407 | 43.105 | 1.00 | 47.89 |
| 2623 | C | ILE | 337 | 107.380 | 57.725 | 39.712 | 1.00 | 47.32 |
| 2624 | O | ILE | 337 | 108.140 | 57.402 | 38.795 | 1.00 | 52.27 |
| 2625 | N | SER | 338 | 106.755 | 56.844 | 40.491 | 1.00 | 42.57 |
| 2626 | CA | SER | 338 | 106.928 | 55.401 | 40.351 | 1.00 | 32.89 |
| 2627 | CB | SER | 338 | 106.120 | 54.663 | 41.424 | 1.00 | 29.02 |
| 2628 | OG | SER | 338 | 106.339 | 55.198 | 42.718 | 1.00 | 33.47 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 2629 | C | SER | 338 | 106.465 | 54.933 | 38.975 | 1.00 | 31.60 |
| 2630 | O | SER | 338 | 107.214 | 54.287 | 38.243 | 1.00 | 27.59 |
| 2631 | N | TYR | 339 | 105.239 | 55.311 | 38.621 | 1.00 | 33.89 |
| 2632 | CA | TYR | 339 | 104.622 | 54.932 | 37.353 | 1.00 | 39.75 |
| 2633 | CB | TYR | 339 | 103.204 | 55.508 | 37.265 | 1.00 | 42.11 |
| 2634 | CG | TYR | 339 | 102.367 | 54.908 | 36.157 | 1.00 | 46.50 |
| 2635 | CD1 | TYR | 339 | 101.682 | 53.709 | 36.348 | 1.00 | 48.25 |
| 2636 | CE1 | TYR | 339 | 100.924 | 53.144 | 35.327 | 1.00 | 52.79 |
| 2637 | CD2 | TYR | 339 | 102.270 | 55.530 | 34.915 | 1.00 | 42.98 |
| 2638 | CE2 | TYR | 339 | 101.515 | 54.976 | 33.890 | 1.00 | 51.56 |
| 2639 | CZ | TYR | 339 | 100.845 | 53.784 | 34.100 | 1.00 | 54.29 |
| 2640 | OH | TYR | 339 | 100.100 | 53.236 | 33.080 | 1.00 | 56.73 |
| 2641 | C | TYR | 339 | 105.414 | 55.309 | 36.101 | 1.00 | 43.13 |
| 2642 | O | TYR | 339 | 105.531 | 54.502 | 35.174 | 1.00 | 41.07 |
| 2643 | N | LYS | 340 | 105.941 | 56.531 | 36.064 | 1.00 | 49.11 |
| 2644 | CA | LYS | 340 | 106.706 | 56.989 | 34.903 | 1.00 | 49.74 |
| 2645 | CB | LYS | 340 | 106.894 | 58.508 | 34.934 | 1.00 | 58.08 |
| 2646 | CG | LYS | 340 | 107.553 | 59.059 | 33.674 | 1.00 | 64.41 |
| 2647 | CD | LYS | 340 | 107.642 | 60.573 | 33.694 | 1.00 | 69.77 |
| 2648 | CE | LYS | 340 | 108.246 | 61.097 | 32.403 | 1.00 | 73.44 |
| 2649 | NZ | LYS | 340 | 108.256 | 62.584 | 32.365 | 1.00 | 82.14 |
| 2650 | C | LYS | 340 | 108.062 | 56.297 | 34.800 | 1.00 | 44.71 |
| 2651 | O | LYS | 340 | 108.506 | 55.938 | 33.703 | 1.00 | 34.93 |
| 2652 | N | ALA | 341 | 108.712 | 56.114 | 35.948 | 1.00 | 36.45 |
| 2653 | CA | ALA | 341 | 110.013 | 55.456 | 36.003 | 1.00 | 36.97 |
| 2654 | CB | ALA | 341 | 110.517 | 55.415 | 37.439 | 1.00 | 35.42 |
| 2655 | C | ALA | 341 | 109.897 | 54.041 | 35.444 | 1.00 | 35.71 |
| 2656 | O | ALA | 341 | 110.791 | 53.561 | 34.746 | 1.00 | 34.74 |
| 2657 | N | ILE | 342 | 108.766 | 53.399 | 35.734 | 1.00 | 29.99 |
| 2658 | CA | ILE | 342 | 108.487 | 52.041 | 35.283 | 1.00 | 21.08 |
| 2659 | CB | ILE | 342 | 107.231 | 51.472 | 35.982 | 1.00 | 16.81 |
| 2660 | CG2 | ILE | 342 | 106.786 | 50.171 | 35.309 | 1.00 | 10.96 |
| 2661 | CG1 | ILE | 342 | 107.523 | 51.275 | 37.476 | 1.00 | 10.78 |
| 2662 | CD1 | ILE | 342 | 106.333 | 50.884 | 38.324 | 1.00 | 2.00 |
| 2663 | C | ILE | 342 | 108.336 | 51.939 | 33.771 | 1.00 | 28.67 |
| 2664 | O | ILE | 342 | 108.949 | 51.071 | 33.150 | 1.00 | 32.50 |
| 2665 | N | LEU | 343 | 107.530 | 52.821 | 33.180 | 1.00 | 33.81 |
| 2666 | CA | LEU | 343 | 107.320 | 52.809 | 31.732 | 1.00 | 37.97 |
| 2667 | CB | LEU | 343 | 106.208 | 53.774 | 31.317 | 1.00 | 41.50 |
| 2668 | CG | LEU | 343 | 104.822 | 53.594 | 31.932 | 1.00 | 46.77 |
| 2669 | CD1 | LEU | 343 | 103.831 | 54.537 | 31.267 | 1.00 | 48.11 |
| 2670 | CD2 | LEU | 343 | 104.375 | 52.165 | 31.759 | 1.00 | 43.32 |
| 2671 | C | LEU | 343 | 108.596 | 53.177 | 30.995 | 1.00 | 41.41 |
| 2672 | O | LEU | 343 | 108.880 | 52.626 | 29.932 | 1.00 | 43.16 |
| 2673 | N | ASP | 344 | 109.348 | 54.126 | 31.552 | 1.00 | 45.08 |
| 2674 | CA | ASP | 344 | 110.601 | 54.563 | 30.942 | 1.00 | 51.08 |
| 2675 | CB | ASP | 344 | 111.144 | 55.820 | 31.628 | 1.00 | 57.96 |
| 2676 | CG | ASP | 344 | 110.754 | 57.098 | 30.903 | 1.00 | 64.16 |
| 2677 | OD1 | ASP | 344 | 110.680 | 57.090 | 29.654 | 1.00 | 69.36 |
| 2678 | OD2 | ASP | 344 | 110.526 | 58.117 | 31.588 | 1.00 | 65.04 |
| 2679 | C | ASP | 344 | 111.643 | 53.461 | 30.980 | 1.00 | 50.69 |
| 2680 | O | ASP | 344 | 112.415 | 53.301 | 30.034 | 1.00 | 53.80 |
| 2681 | N | LEU | 345 | 111.661 | 52.709 | 32.078 | 1.00 | 47.98 |
| 2682 | CA | LEU | 345 | 112.594 | 51.599 | 32.242 | 1.00 | 43.23 |
| 2683 | CB | LEU | 345 | 112.384 | 50.925 | 33.599 | 1.00 | 45.16 |
| 2684 | CG | LEU | 345 | 113.317 | 49.773 | 33.977 | 1.00 | 44.62 |
| 2685 | CD1 | LEU | 345 | 114.752 | 50.267 | 34.070 | 1.00 | 45.63 |
| 2686 | CD2 | LEU | 345 | 112.875 | 49.186 | 35.307 | 1.00 | 42.33 |
| 2687 | C | LEU | 345 | 112.364 | 50.585 | 31.129 | 1.00 | 42.19 |
| 2688 | O | LEU | 345 | 113.315 | 50.068 | 30.541 | 1.00 | 47.47 |
| 2689 | N | TYR | 346 | 111.094 | 50.311 | 30.844 | 1.00 | 38.09 |
| 2690 | CA | TYR | 346 | 110.731 | 49.372 | 29.793 | 1.00 | 36.61 |
| 2691 | CB | TYR | 346 | 109.298 | 48.878 | 29.983 | 1.00 | 32.28 |
| 2692 | CG | TYR | 346 | 109.211 | 47.802 | 31.038 | 1.00 | 30.73 |
| 2693 | CD1 | TYR | 346 | 108.903 | 48.110 | 32.361 | 1.00 | 22.11 |
| 2694 | CE1 | TYR | 346 | 108.895 | 47.122 | 33.346 | 1.00 | 24.69 |
| 2695 | CD2 | TYR | 346 | 109.503 | 46.477 | 30.722 | 1.00 | 35.15 |
| 2696 | CE2 | TYR | 346 | 109.499 | 45.484 | 31.694 | 1.00 | 26.34 |
| 2697 | CZ | TYR | 346 | 109.198 | 45.809 | 33.000 | 1.00 | 27.54 |
| 2698 | OH | TYR | 346 | 109.224 | 44.812 | 33.948 | 1.00 | 22.51 |
| 2699 | C | TYR | 346 | 110.954 | 49.953 | 28.403 | 1.00 | 39.45 |
| 2700 | O | TYR | 346 | 111.086 | 49.213 | 27.429 | 1.00 | 37.79 |
| 2701 | N | LYS | 347 | 110.995 | 51.281 | 28.320 | 1.00 | 44.42 |
| 2702 | CA | LYS | 347 | 111.256 | 51.958 | 27.056 | 1.00 | 45.72 |
| 2703 | CB | LYS | 347 | 110.797 | 53.418 | 27.105 | 1.00 | 49.09 |
| 2704 | CG | LYS | 347 | 109.313 | 53.604 | 26.824 | 1.00 | 54.73 |
| 2705 | CD | LYS | 347 | 108.959 | 53.084 | 25.433 | 1.00 | 58.88 |
| 2706 | CE | LYS | 347 | 107.471 | 53.195 | 25.149 | 1.00 | 58.70 |
| 2707 | NZ | LYS | 347 | 107.129 | 52.632 | 23.816 | 1.00 | 45.34 |
| 2708 | C | LYS | 347 | 112.756 | 51.874 | 26.810 | 1.00 | 44.56 |
| 2709 | O | LYS | 347 | 113.201 | 51.803 | 25.666 | 1.00 | 44.20 |
| 2710 | N | ASP | 348 | 113.524 | 51.865 | 27.901 | 1.00 | 45.25 |
| 2711 | CA | ASP | 348 | 114.977 | 51.748 | 27.829 | 1.00 | 43.43 |
| 2712 | CB | ASP | 348 | 115.630 | 52.041 | 29.188 | 1.00 | 41.08 |
| 2713 | CG | ASP | 348 | 115.545 | 53.509 | 29.584 | 1.00 | 45.56 |
| 2714 | OD1 | ASP | 348 | 115.741 | 54.388 | 28.716 | 1.00 | 50.29 |
| 2715 | OD2 | ASP | 348 | 115.293 | 53.787 | 30.775 | 1.00 | 46.84 |
| 2716 | C | ASP | 348 | 115.308 | 50.325 | 27.394 | 1.00 | 44.57 |
| 2717 | O | ASP | 348 | 116.186 | 50.116 | 26.555 | 1.00 | 45.03 |
| 2718 | N | TYR | 349 | 114.585 | 49.355 | 27.959 | 1.00 | 43.55 |
| 2719 | CA | TYR | 349 | 114.773 | 47.943 | 27.627 | 1.00 | 42.30 |
| 2720 | CB | TYR | 349 | 113.813 | 47.054 | 28.429 | 1.00 | 41.29 |
| 2721 | CG | TYR | 349 | 114.128 | 46.916 | 29.906 | 1.00 | 37.24 |
| 2722 | CD1 | TYR | 349 | 113.181 | 46.393 | 30.785 | 1.00 | 30.06 |
| 2723 | CE1 | TYR | 349 | 113.458 | 46.247 | 32.142 | 1.00 | 36.46 |
| 2724 | CD2 | TYR | 349 | 115.368 | 47.293 | 30.424 | 1.00 | 41.76 |
| 2725 | CE2 | TYR | 349 | 115.656 | 47.151 | 31.783 | 1.00 | 40.50 |
| 2726 | CZ | TYR | 349 | 114.694 | 46.627 | 32.633 | 1.00 | 36.99 |
| 2727 | OH | TYR | 349 | 114.960 | 46.491 | 33.975 | 1.00 | 36.59 |
| 2728 | C | TYR | 349 | 114.520 | 47.741 | 26.139 | 1.00 | 42.51 |
| 2729 | O | TYR | 349 | 115.308 | 47.094 | 25.446 | 1.00 | 42.03 |
| 2730 | N | GLU | 350 | 113.411 | 48.296 | 25.656 | 1.00 | 44.24 |
| 2731 | CA | GLU | 350 | 113.053 | 48.199 | 24.244 | 1.00 | 46.89 |
| 2732 | CB | GLU | 350 | 111.734 | 48.929 | 23.969 | 1.00 | 49.81 |
| 2733 | CG | GLU | 350 | 110.509 | 48.270 | 24.589 | 1.00 | 54.69 |
| 2734 | CD | GLU | 350 | 109.214 | 49.033 | 24.347 | 1.00 | 58.54 |
| 2735 | OE1 | GLU | 350 | 108.144 | 48.491 | 24.695 | 1.00 | 62.24 |
| 2736 | OE2 | GLU | 350 | 109.253 | 50.168 | 23.822 | 1.00 | 64.71 |
| 2737 | C | GLU | 350 | 114.162 | 48.811 | 23.397 | 1.00 | 48.29 |
| 2738 | O | GLU | 350 | 114.491 | 48.294 | 22.334 | 1.00 | 45.94 |
| 2739 | N | LYS | 351 | 114.763 | 49.884 | 23.909 | 1.00 | 53.89 |
| 2740 | CA | LYS | 351 | 115.841 | 50.591 | 23.222 | 1.00 | 58.14 |
| 2741 | CB | LYS | 351 | 116.053 | 51.971 | 23.855 | 1.00 | 63.43 |
| 2742 | CG | LYS | 351 | 116.916 | 52.921 | 23.031 | 1.00 | 71.72 |
| 2743 | CD | LYS | 351 | 116.247 | 53.286 | 21.711 | 1.00 | 77.97 |
| 2744 | CE | LYS | 351 | 117.122 | 54.218 | 20.885 | 1.00 | 83.68 |
| 2745 | NZ | LYS | 351 | 116.483 | 54.588 | 19.591 | 1.00 | 83.73 |
| 2746 | C | LYS | 351 | 117.155 | 49.795 | 23.215 | 1.00 | 57.54 |
| 2747 | O | LYS | 351 | 117.873 | 49.784 | 22.209 | 1.00 | 56.27 |
| 2748 | N | GLU | 352 | 117.465 | 49.142 | 24.336 | 1.00 | 56.46 |
| 2749 | CA | GLU | 352 | 118.684 | 48.334 | 24.458 | 1.00 | 52.60 |
| 2750 | CB | GLU | 352 | 118.847 | 47.801 | 25.890 | 1.00 | 50.25 |
| 2751 | CG | GLU | 352 | 119.239 | 48.828 | 26.943 | 1.00 | 58.10 |
| 2752 | CD | GLU | 352 | 119.464 | 48.194 | 28.311 | 1.00 | 59.00 |
| 2753 | OE1 | GLU | 352 | 118.655 | 48.447 | 29.232 | 1.00 | 57.55 |
| 2754 | OE2 | GLU | 352 | 120.447 | 47.435 | 28.468 | 1.00 | 53.94 |
| 2755 | C | GLU | 352 | 118.645 | 47.140 | 23.508 | 1.00 | 49.57 |
| 2756 | O | GLU | 352 | 119.671 | 46.735 | 22.957 | 1.00 | 45.55 |
| 2757 | N | LEU | 353 | 117.448 | 46.587 | 23.327 | 1.00 | 44.88 |
| 2758 | CA | LEU | 353 | 117.239 | 45.432 | 22.463 | 1.00 | 44.80 |
| 2759 | CB | LEU | 353 | 116.116 | 44.561 | 23.034 | 1.00 | 35.61 |
| 2760 | CG | LEU | 353 | 116.304 | 44.125 | 24.489 | 1.00 | 30.68 |
| 2761 | CD1 | LEU | 353 | 115.030 | 43.507 | 25.030 | 1.00 | 31.93 |
| 2762 | CD2 | LEU | 353 | 117.468 | 43.156 | 24.597 | 1.00 | 32.93 |
| 2763 | C | LEU | 353 | 116.937 | 45.806 | 21.011 | 1.00 | 48.25 |
| 2764 | O | LEU | 353 | 116.878 | 44.933 | 20.140 | 1.00 | 48.95 |
| 2765 | N | SER | 354 | 116.756 | 47.101 | 20.751 | 1.00 | 54.12 |
| 2766 | CA | SER | 354 | 116.468 | 47.595 | 19.403 | 1.00 | 58.83 |
| 2767 | CB | SER | 354 | 116.356 | 49.122 | 19.395 | 1.00 | 64.47 |
| 2768 | OG | SER | 354 | 115.196 | 49.571 | 20.072 | 1.00 | 73.04 |
| 2769 | C | SER | 354 | 117.534 | 47.171 | 18.400 | 1.00 | 58.85 |
| 2770 | O | SER | 354 | 117.226 | 46.900 | 17.237 | 1.00 | 60.25 |
| 2771 | N | SER | 355 | 118.784 | 47.119 | 18.857 | 1.00 | 59.55 |
| 2772 | CA | SER | 355 | 119.918 | 46.731 | 18.022 | 1.00 | 60.93 |
| 2773 | CB | SER | 355 | 121.219 | 46.840 | 18.823 | 1.00 | 58.82 |
| 2774 | OG | SER | 355 | 122.333 | 46.392 | 18.071 | 1.00 | 61.05 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 2775 | C | SER | 355 | 119.772 | 45.316 | 17.455 | 1.00 | 67.50 |
| 2776 | O | SER | 355 | 119.753 | 45.125 | 16.239 | 1.00 | 72.60 |
| 2777 | N | ALA | 356 | 119.640 | 44.338 | 18.345 | 1.00 | 68.57 |
| 2778 | CA | ALA | 358 | 119.501 | 42.943 | 17.946 | 1.00 | 67.55 |
| 2779 | CB | ALA | 356 | 119.690 | 42.040 | 19.152 | 1.00 | 63.74 |
| 2780 | C | ALA | 356 | 118.163 | 42.642 | 17.278 | 1.00 | 69.18 |
| 2781 | O | ALA | 356 | 118.071 | 41.754 | 16.434 | 1.00 | 70.23 |
| 2782 | N | GLY | 357 | 117.131 | 43.385 | 17.661 | 1.00 | 69.13 |
| 2783 | CA | GLY | 357 | 115.811 | 43.152 | 17.102 | 1.00 | 62.21 |
| 2784 | C | GLY | 357 | 115.027 | 42.258 | 18.039 | 1.00 | 59.93 |
| 2785 | O | GLY | 357 | 114.203 | 41.443 | 17.604 | 1.00 | 60.71 |
| 2786 | N | ARG | 358 | 115.322 | 42.391 | 19.332 | 1.00 | 54.34 |
| 2787 | CA | ARG | 358 | 114.669 | 41.616 | 20.385 | 1.00 | 52.71 |
| 2788 | CB | ARG | 358 | 115.713 | 40.882 | 21.231 | 1.00 | 45.26 |
| 2789 | CG | ARG | 358 | 116.561 | 39.896 | 20.442 | 1.00 | 47.78 |
| 2790 | CD | ARG | 358 | 117.644 | 39.275 | 21.309 | 1.00 | 47.12 |
| 2791 | NE | ARG | 358 | 117.083 | 38.456 | 22.383 | 1.00 | 44.42 |
| 2792 | CZ | ARG | 358 | 117.206 | 38.724 | 23.681 | 1.00 | 39.46 |
| 2793 | NH1 | ARG | 358 | 117.871 | 39.797 | 24.083 | 1.00 | 37.90 |
| 2794 | NH2 | ARG | 358 | 116.684 | 37.905 | 24.583 | 1.00 | 43.78 |
| 2795 | C | ARG | 358 | 113.817 | 42.522 | 21.282 | 1.00 | 55.62 |
| 2796 | O | ARG | 358 | 113.676 | 42.268 | 22.479 | 1.00 | 60.74 |
| 2797 | N | SER | 359 | 113.286 | 43.596 | 20.699 | 1.00 | 54.17 |
| 2798 | CA | SER | 359 | 112.440 | 44.548 | 21.419 | 1.00 | 49.75 |
| 2799 | CB | SER | 359 | 112.373 | 45.887 | 20.671 | 1.00 | 46.10 |
| 2800 | OG | SER | 359 | 113.659 | 46.424 | 20.441 | 1.00 | 39.24 |
| 2801 | C | SER | 359 | 111.030 | 43.979 | 21.584 | 1.00 | 51.35 |
| 2802 | O | SER | 359 | 110.321 | 44.294 | 22.549 | 1.00 | 51.03 |
| 2803 | N | HIS | 360 | 110.642 | 43.145 | 20.619 | 1.00 | 48.18 |
| 2804 | CA | HIS | 360 | 109.339 | 42.484 | 20.566 | 1.00 | 49.55 |
| 2805 | CB | HIS | 360 | 109.165 | 41.769 | 19.214 | 1.00 | 55.45 |
| 2806 | CG | HIS | 360 | 110.191 | 40.706 | 18.955 | 1.00 | 57.94 |
| 2807 | CD2 | HIS | 360 | 111.485 | 40.791 | 18.565 | 1.00 | 58.70 |
| 2808 | ND1 | HIS | 360 | 109.933 | 39.363 | 19.134 | 1.00 | 62.62 |
| 2809 | CE1 | HIS | 360 | 111.028 | 38.668 | 18.875 | 1.00 | 63.83 |
| 2810 | NE2 | HIS | 360 | 111.985 | 39.511 | 18.527 | 1.00 | 63.77 |
| 2811 | C | HIS | 360 | 109.105 | 41.483 | 21.705 | 1.00 | 51.67 |
| 2812 | O | HIS | 360 | 108.023 | 40.886 | 21.795 | 1.00 | 56.00 |
| 2813 | N | ILE | 361 | 110.115 | 41.294 | 22.552 | 1.00 | 44.35 |
| 2814 | CA | ILE | 361 | 110.005 | 40.352 | 23.659 | 1.00 | 40.02 |
| 2815 | CB | ILE | 361 | 111.217 | 39.396 | 23.719 | 1.00 | 40.34 |
| 2816 | CG2 | ILE | 361 | 111.350 | 38.631 | 22.412 | 1.00 | 38.81 |
| 2817 | CG1 | ILE | 361 | 112.490 | 40.174 | 24.052 | 1.00 | 45.99 |
| 2818 | CD1 | ILE | 361 | 113.742 | 39.324 | 24.096 | 1.00 | 38.31 |
| 2819 | C | ILE | 361 | 109.837 | 41.012 | 25.022 | 1.00 | 38.58 |
| 2820 | O | ILE | 361 | 109.629 | 40.323 | 26.018 | 1.00 | 46.53 |
| 2821 | N | VAL | 362 | 109.920 | 42.339 | 25.068 | 1.00 | 34.37 |
| 2822 | CA | VAL | 362 | 109.784 | 43.073 | 26.323 | 1.00 | 36.05 |
| 2823 | CB | VAL | 362 | 110.133 | 44.567 | 26.131 | 1.00 | 44.38 |
| 2824 | CG1 | VAL | 362 | 110.157 | 45.290 | 27.474 | 1.00 | 28.09 |
| 2825 | CG2 | VAL | 362 | 111.470 | 44.705 | 25.420 | 1.00 | 50.90 |
| 2826 | C | VAL | 362 | 108.372 | 42.959 | 26.899 | 1.00 | 35.07 |
| 2827 | O | VAL | 362 | 108.187 | 43.012 | 28.113 | 1.00 | 27.77 |
| 2828 | N | CYS | 363 | 107.383 | 42.770 | 26.025 | 1.00 | 37.13 |
| 2829 | CA | CYS | 363 | 105.980 | 42.653 | 26.437 | 1.00 | 34.16 |
| 2830 | CB | CYS | 363 | 105.066 | 42.483 | 25.215 | 1.00 | 29.73 |
| 2831 | SG | CYS | 363 | 105.447 | 41.051 | 24.179 | 1.00 | 41.96 |
| 2832 | C | CYS | 363 | 105.730 | 41.520 | 27.434 | 1.00 | 32.61 |
| 2833 | O | CYS | 363 | 104.887 | 41.646 | 28.325 | 1.00 | 25.38 |
| 2834 | N | HIS | 364 | 106.481 | 40.429 | 27.292 | 1.00 | 28.31 |
| 2835 | CA | HIS | 364 | 106.356 | 39.267 | 28.168 | 1.00 | 20.38 |
| 2836 | CB | HIS | 364 | 107.304 | 38.159 | 27.713 | 1.00 | 19.91 |
| 2837 | CG | HIS | 364 | 107.064 | 37.696 | 26.309 | 1.00 | 25.64 |
| 2838 | CD2 | HIS | 364 | 107.777 | 37.887 | 25.173 | 1.00 | 29.90 |
| 2839 | ND1 | HIS | 364 | 105.976 | 36.929 | 25.954 | 1.00 | 34.65 |
| 2840 | CE1 | HIS | 364 | 106.028 | 36.667 | 24.659 | 1.00 | 33.79 |
| 2841 | NE2 | HIS | 364 | 107.111 | 37.237 | 24.162 | 1.00 | 27.05 |
| 2842 | C | HIS | 364 | 106.646 | 39.635 | 29.622 | 1.00 | 28.17 |
| 2843 | O | HIS | 364 | 105.942 | 39.200 | 30.537 | 1.00 | 27.54 |
| 2844 | N | ALA | 365 | 107.685 | 40.440 | 29.826 | 1.00 | 30.22 |
| 2845 | CA | ALA | 365 | 108.067 | 40.880 | 31.163 | 1.00 | 30.86 |
| 2846 | CB | ALA | 365 | 109.427 | 41.574 | 31.120 | 1.00 | 34.60 |
| 2847 | C | ALA | 365 | 107.007 | 41.822 | 31.725 | 1.00 | 31.03 |
| 2848 | O | ALA | 365 | 106.752 | 41.838 | 32.931 | 1.00 | 31.19 |
| 2849 | N | ILE | 366 | 106.389 | 42.596 | 30.835 | 1.00 | 36.30 |
| 2850 | CA | ILE | 366 | 105.347 | 43.550 | 31.208 | 1.00 | 36.55 |
| 2851 | CB | ILE | 366 | 105.016 | 44.504 | 30.034 | 1.00 | 41.23 |
| 2852 | CG2 | ILE | 366 | 103.857 | 45.419 | 30.403 | 1.00 | 40.62 |
| 2853 | CG1 | ILE | 366 | 106.253 | 45.331 | 29.668 | 1.00 | 35.62 |
| 2854 | CD1 | ILE | 366 | 106.065 | 46.231 | 28.468 | 1.00 | 29.32 |
| 2855 | C | ILE | 366 | 104.070 | 42.845 | 31.667 | 1.00 | 30.85 |
| 2856 | O | ILE | 366 | 103.524 | 43.173 | 32.722 | 1.00 | 28.50 |
| 2857 | N | GLU | 367 | 103.613 | 41.867 | 30.886 | 1.00 | 25.21 |
| 2858 | CA | GLU | 367 | 102.404 | 41.117 | 31.223 | 1.00 | 22.77 |
| 2859 | CB | GLU | 367 | 102.095 | 40.069 | 30.153 | 1.00 | 32.06 |
| 2860 | CG | GLU | 367 | 101.926 | 40.626 | 28.736 | 1.00 | 41.69 |
| 2861 | CD | GLU | 367 | 100.870 | 41.721 | 28.629 | 1.00 | 48.62 |
| 2862 | OE1 | GLU | 367 | 99.829 | 41.633 | 29.321 | 1.00 | 48.68 |
| 2863 | OE2 | GLU | 367 | 101.083 | 42.670 | 27.841 | 1.00 | 43.16 |
| 2864 | C | GLU | 367 | 102.539 | 40.448 | 32.585 | 1.00 | 20.02 |
| 2865 | O | GLU | 367 | 101.555 | 40.297 | 33.314 | 1.00 | 20.91 |
| 2866 | N | ARG | 368 | 103.766 | 40.057 | 32.923 | 1.00 | 21.53 |
| 2867 | CA | ARG | 368 | 104.055 | 39.422 | 34.205 | 1.00 | 14.50 |
| 2868 | CB | ARG | 368 | 105.406 | 38.709 | 34.159 | 1.00 | 17.59 |
| 2869 | CG | ARG | 368 | 105.427 | 37.442 | 33.319 | 1.00 | 13.40 |
| 2870 | CD | ARG | 368 | 104.602 | 36.338 | 33.960 | 1.00 | 17.58 |
| 2871 | NE | ARG | 368 | 104.843 | 35.044 | 33.325 | 1.00 | 25.37 |
| 2872 | CZ | ARG | 368 | 104.380 | 33.884 | 33.784 | 1.00 | 29.88 |
| 2873 | NH1 | ARG | 368 | 103.641 | 33.847 | 34.887 | 1.00 | 15.72 |
| 2874 | NH2 | ARG | 368 | 104.669 | 32.757 | 33.146 | 1.00 | 25.60 |
| 2875 | C | ARG | 368 | 104.058 | 40.473 | 35.306 | 1.00 | 22.28 |
| 2876 | O | ARG | 368 | 103.674 | 40.193 | 36.444 | 1.00 | 25.28 |
| 2877 | N | MET | 369 | 104.489 | 41.686 | 34.965 | 1.00 | 23.23 |
| 2878 | CA | MET | 369 | 104.513 | 42.774 | 35.933 | 1.00 | 22.69 |
| 2879 | CB | MET | 369 | 105.234 | 44.001 | 35.371 | 1.00 | 21.94 |
| 2880 | CG | MET | 369 | 105.216 | 45.178 | 36.332 | 1.00 | 33.04 |
| 2881 | SD | MET | 369 | 106.226 | 46.580 | 35.855 | 1.00 | 30.05 |
| 2882 | CE | MET | 369 | 106.788 | 47.105 | 37.492 | 1.00 | 22.46 |
| 2883 | C | MET | 369 | 103.088 | 43.138 | 36.329 | 1.00 | 21.30 |
| 2884 | O | MET | 369 | 102.794 | 43.316 | 37.513 | 1.00 | 25.30 |
| 2885 | N | LYS | 370 | 102.207 | 43.230 | 35.332 | 1.00 | 22.42 |
| 2886 | CA | LYS | 370 | 100.798 | 43.555 | 35.562 | 1.00 | 21.17 |
| 2887 | CB | LYS | 370 | 100.033 | 43.596 | 34.237 | 1.00 | 18.37 |
| 2888 | CG | LYS | 370 | 100.498 | 44.679 | 33.272 | 1.00 | 19.38 |
| 2889 | CD | LYS | 370 | 99.724 | 44.628 | 31.959 | 1.00 | 22.90 |
| 2890 | CE | LYS | 370 | 100.144 | 45.754 | 31.026 | 1.00 | 25.30 |
| 2891 | NZ | LYS | 370 | 99.370 | 45.760 | 29.753 | 1.00 | 26.14 |
| 2892 | C | LYS | 370 | 100.184 | 42.503 | 36.480 | 1.00 | 22.60 |
| 2893 | O | LYS | 370 | 99.433 | 42.830 | 37.404 | 1.00 | 22.82 |
| 2894 | N | GLU | 371 | 100.540 | 41.243 | 36.233 | 1.00 | 20.87 |
| 2895 | CA | GLU | 371 | 100.060 | 40.117 | 37.027 | 1.00 | 17.91 |
| 2896 | CB | GLU | 371 | 100.633 | 38.805 | 36.473 | 1.00 | 17.04 |
| 2897 | CG | GLU | 371 | 100.291 | 37.558 | 37.281 | 1.00 | 14.89 |
| 2898 | CD | GLU | 371 | 100.951 | 36.307 | 36.737 | 1.00 | 33.96 |
| 2899 | OE1 | GLU | 371 | 100.246 | 35.281 | 36.624 | 1.00 | 49.48 |
| 2900 | OE2 | GLU | 371 | 102.162 | 36.342 | 36.433 | 1.00 | 39.35 |
| 2901 | C | GLU | 371 | 100.459 | 40.291 | 38.491 | 1.00 | 14.70 |
| 2902 | O | GLU | 371 | 99.629 | 40.116 | 39.389 | 1.00 | 15.00 |
| 2903 | N | VAL | 372 | 101.727 | 40.624 | 38.718 | 1.00 | 16.52 |
| 2904 | CA | VAL | 372 | 102.246 | 40.830 | 40.066 | 1.00 | 17.45 |
| 2905 | CB | VAL | 372 | 103.747 | 41.232 | 40.043 | 1.00 | 17.58 |
| 2906 | CG1 | VAL | 372 | 104.258 | 41.453 | 41.450 | 1.00 | 3.56 |
| 2907 | CG2 | VAL | 372 | 104.575 | 40.156 | 39.365 | 1.00 | 18.80 |
| 2908 | C | VAL | 372 | 101.455 | 41.919 | 40.782 | 1.00 | 21.27 |
| 2909 | O | VAL | 372 | 101.101 | 41.767 | 41.952 | 1.00 | 23.46 |
| 2910 | N | VAL | 373 | 101.155 | 43.000 | 40.063 | 1.00 | 26.12 |
| 2911 | CA | VAL | 373 | 100.407 | 44.123 | 40.629 | 1.00 | 29.37 |
| 2912 | CB | VAL | 373 | 100.425 | 45.356 | 39.694 | 1.00 | 33.84 |
| 2913 | CG1 | VAL | 373 | 99.736 | 46.537 | 40.366 | 1.00 | 27.54 |
| 2914 | CG2 | VAL | 373 | 101.861 | 45.724 | 39.335 | 1.00 | 29.76 |
| 2915 | C | VAL | 373 | 98.962 | 43.754 | 40.969 | 1.00 | 29.64 |
| 2916 | O | VAL | 373 | 98.462 | 44.135 | 42.030 | 1.00 | 27.43 |
| 2917 | N | ARG | 374 | 98.298 | 43.015 | 40.078 | 1.00 | 27.06 |
| 2918 | CA | ARG | 374 | 96.916 | 42.587 | 40.315 | 1.00 | 22.92 |
| 2919 | CB | ARG | 374 | 96.438 | 41.626 | 39.225 | 1.00 | 20.10 |
| 2920 | CG | ARG | 374 | 96.101 | 42.257 | 37.897 | 1.00 | 18.80 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 2921 | CD | ARG | 374 | 95.627 | 41.191 | 36.924 | 1.00 | 11.40 |
| 2922 | NE | ARG | 374 | 96.410 | 41.194 | 35.692 | 1.00 | 20.17 |
| 2923 | CZ | ARG | 374 | 96.956 | 40.112 | 35.146 | 1.00 | 19.94 |
| 2924 | NH1 | ARG | 374 | 96.810 | 38.924 | 35.720 | 1.00 | 26.31 |
| 2925 | NH2 | ARG | 374 | 97.655 | 40.218 | 34.025 | 1.00 | 24.45 |
| 2926 | C | ARG | 374 | 96.835 | 41.858 | 41.646 | 1.00 | 26.89 |
| 2927 | O | ARG | 374 | 95.964 | 42.134 | 42.472 | 1.00 | 32.47 |
| 2928 | N | ASN | 375 | 97.766 | 40.931 | 41.842 | 1.00 | 27.68 |
| 2929 | CA | ASN | 375 | 97.827 | 40.133 | 43.055 | 1.00 | 25.57 |
| 2930 | CB | ASN | 375 | 98.776 | 38.955 | 42.850 | 1.00 | 30.36 |
| 2931 | CG | ASN | 375 | 98.299 | 38.009 | 41.756 | 1.00 | 32.94 |
| 2932 | OD1 | ASN | 375 | 97.594 | 38.415 | 40.827 | 1.00 | 25.76 |
| 2933 | ND2 | ASN | 375 | 98.677 | 36.741 | 41.865 | 1.00 | 30.37 |
| 2934 | C | ASN | 375 | 98.213 | 40.958 | 44.279 | 1.00 | 26.96 |
| 2935 | O | ASN | 375 | 97.819 | 40.632 | 45.399 | 1.00 | 21.31 |
| 2936 | N | TYR | 376 | 98.980 | 42.026 | 44.062 | 1.00 | 33.99 |
| 2937 | CA | TYR | 376 | 99.381 | 42.920 | 45.148 | 1.00 | 33.87 |
| 2938 | CB | TYR | 376 | 100.362 | 43.986 | 44.645 | 1.00 | 39.17 |
| 2939 | CG | TYR | 376 | 101.823 | 43.579 | 44.628 | 1.00 | 42.30 |
| 2940 | CD1 | TYR | 376 | 102.765 | 44.344 | 43.940 | 1.00 | 40.53 |
| 2941 | CE1 | TYR | 376 | 104.111 | 43.997 | 43.934 | 1.00 | 45.46 |
| 2942 | CD2 | TYR | 376 | 102.268 | 42.440 | 45.312 | 1.00 | 43.05 |
| 2943 | CE2 | TYR | 376 | 103.614 | 42.088 | 45.313 | 1.00 | 42.63 |
| 2944 | CZ | TYR | 376 | 104.531 | 42.868 | 44.623 | 1.00 | 48.37 |
| 2945 | OH | TYR | 376 | 105.865 | 42.523 | 44.621 | 1.00 | 39.23 |
| 2946 | C | TYR | 376 | 98.122 | 43.605 | 45.668 | 1.00 | 29.88 |
| 2947 | O | TYR | 376 | 97.942 | 43.773 | 46.874 | 1.00 | 27.89 |
| 2948 | N | ASN | 377 | 97.252 | 43.984 | 44.733 | 1.00 | 29.64 |
| 2949 | CA | ASN | 377 | 95.987 | 44.642 | 45.043 | 1.00 | 31.75 |
| 2950 | CB | ASN | 377 | 95.304 | 45.094 | 43.748 | 1.00 | 34.90 |
| 2951 | CG | ASN | 377 | 94.116 | 45.999 | 43.999 | 1.00 | 40.49 |
| 2952 | OD1 | ASN | 377 | 92.992 | 45.532 | 44.178 | 1.00 | 42.59 |
| 2953 | ND2 | ASN | 377 | 94.360 | 47.303 | 44.011 | 1.00 | 34.81 |
| 2954 | C | ASN | 377 | 95.084 | 43.674 | 45.804 | 1.00 | 28.41 |
| 2955 | O | ASN | 377 | 94.538 | 44.015 | 46.857 | 1.00 | 30.58 |
| 2956 | N | VAL | 378 | 94.952 | 42.460 | 45.274 | 1.00 | 17.90 |
| 2957 | CA | VAL | 378 | 94.131 | 41.426 | 45.900 | 1.00 | 17.33 |
| 2958 | CB | VAL | 378 | 94.186 | 40.112 | 45.086 | 1.00 | 10.51 |
| 2959 | CG1 | VAL | 378 | 93.423 | 39.012 | 45.789 | 1.00 | 11.35 |
| 2960 | CG2 | VAL | 378 | 93.612 | 40.332 | 43.698 | 1.00 | 13.48 |
| 2961 | C | VAL | 378 | 94.616 | 41.163 | 47.327 | 1.00 | 25.35 |
| 2962 | O | VAL | 378 | 93.813 | 40.997 | 48.248 | 1.00 | 27.43 |
| 2963 | N | GLU | 379 | 95.936 | 41.176 | 47.497 | 1.00 | 31.20 |
| 2964 | CA | GLU | 379 | 96.575 | 40.938 | 48.787 | 1.00 | 33.04 |
| 2965 | CB | GLU | 379 | 98.100 | 40.924 | 48.613 | 1.00 | 40.56 |
| 2966 | CG | GLU | 379 | 98.888 | 40.454 | 49.836 | 1.00 | 52.37 |
| 2967 | CD | GLU | 379 | 100.392 | 40.399 | 49.591 | 1.00 | 57.31 |
| 2968 | OE1 | GLU | 379 | 101.158 | 40.762 | 50.510 | 1.00 | 59.83 |
| 2969 | OE2 | GLU | 379 | 100.810 | 39.986 | 48.485 | 1.00 | 55.53 |
| 2970 | C | GLU | 379 | 96.166 | 41.984 | 49.825 | 1.00 | 31.53 |
| 2971 | O | GLU | 379 | 95.922 | 41.650 | 50.987 | 1.00 | 29.16 |
| 2972 | N | SER | 380 | 96.092 | 43.245 | 49.402 | 1.00 | 32.96 |
| 2973 | CA | SER | 380 | 95.706 | 44.331 | 50.300 | 1.00 | 37.42 |
| 2974 | CB | SER | 380 | 96.066 | 45.695 | 49.698 | 1.00 | 38.70 |
| 2975 | OG | SER | 380 | 95.348 | 45.945 | 48.504 | 1.00 | 49.17 |
| 2976 | C | SER | 380 | 94.212 | 44.264 | 50.604 | 1.00 | 38.16 |
| 2977 | O | SER | 380 | 93.789 | 44.512 | 51.737 | 1.00 | 31.46 |
| 2978 | N | THR | 381 | 93.424 | 43.915 | 49.587 | 1.00 | 36.08 |
| 2979 | CA | THR | 381 | 91.976 | 43.790 | 49.729 | 1.00 | 27.53 |
| 2980 | CB | THR | 381 | 91.320 | 43.333 | 48.413 | 1.00 | 22.85 |
| 2981 | OG1 | THR | 381 | 91.706 | 44.212 | 47.350 | 1.00 | 16.53 |
| 2982 | CG2 | THR | 381 | 89.812 | 43.351 | 48.543 | 1.00 | 23.91 |
| 2983 | C | THR | 381 | 91.662 | 42.762 | 50.814 | 1.00 | 27.68 |
| 2984 | O | THR | 381 | 90.813 | 42.996 | 51.670 | 1.00 | 29.54 |
| 2985 | N | TRP | 382 | 92.375 | 41.637 | 50.779 | 1.00 | 28.31 |
| 2986 | CA | TRP | 382 | 92.199 | 40.563 | 51.755 | 1.00 | 28.12 |
| 2987 | CB | TRP | 382 | 93.063 | 39.353 | 51.386 | 1.00 | 36.50 |
| 2988 | CG | TRP | 382 | 92.583 | 38.570 | 50.195 | 1.00 | 38.50 |
| 2989 | CD2 | TRP | 382 | 93.258 | 37.475 | 49.565 | 1.00 | 42.33 |
| 2990 | CE2 | TRP | 382 | 92.430 | 37.022 | 48.516 | 1.00 | 44.37 |
| 2991 | CE3 | TRP | 382 | 94.483 | 36.830 | 49.787 | 1.00 | 47.90 |
| 2992 | CD1 | TRP | 382 | 91.408 | 38.735 | 49.518 | 1.00 | 36.49 |
| 2993 | NE1 | TRP | 382 | 91.308 | 37.808 | 48.511 | 1.00 | 36.31 |
| 2994 | CZ2 | TRP | 382 | 92.787 | 35.951 | 47.688 | 1.00 | 51.17 |
| 2995 | CZ3 | TRP | 382 | 94.838 | 35.764 | 48.963 | 1.00 | 43.35 |
| 2996 | CH2 | TRP | 382 | 93.991 | 35.337 | 47.927 | 1.00 | 45.79 |
| 2997 | C | TRP | 382 | 92.567 | 41.030 | 53.157 | 1.00 | 30.09 |
| 2998 | O | TRP | 382 | 91.926 | 40.651 | 54.137 | 1.00 | 31.61 |
| 2999 | N | PHE | 383 | 93.617 | 41.841 | 53.240 | 1.00 | 36.62 |
| 3000 | CA | PHE | 383 | 94.092 | 42.378 | 54.510 | 1.00 | 38.24 |
| 3001 | CB | PHE | 383 | 95.411 | 43.138 | 54.298 | 1.00 | 36.46 |
| 3002 | CG | PHE | 383 | 95.885 | 43.880 | 55.516 | 1.00 | 32.91 |
| 3003 | CD1 | PHE | 383 | 96.157 | 43.202 | 56.701 | 1.00 | 32.24 |
| 3004 | CD2 | PHE | 383 | 96.020 | 45.264 | 55.490 | 1.00 | 33.47 |
| 3005 | CE1 | PHE | 383 | 96.553 | 43.892 | 57.843 | 1.00 | 34.44 |
| 3006 | CE2 | PHE | 383 | 96.415 | 45.963 | 56.628 | 1.00 | 34.81 |
| 3007 | CZ | PHE | 383 | 96.681 | 45.275 | 57.807 | 1.00 | 35.83 |
| 3008 | C | PHE | 383 | 93.045 | 43.296 | 55.144 | 1.00 | 38.45 |
| 3009 | O | PHE | 383 | 92.793 | 43.223 | 56.351 | 1.00 | 36.37 |
| 3010 | N | ILE | 384 | 92.436 | 44.144 | 54.315 | 1.00 | 36.46 |
| 3011 | CA | ILE | 384 | 91.410 | 45.091 | 54.756 | 1.00 | 34.56 |
| 3012 | CB | ILE | 384 | 91.025 | 46.062 | 53.615 | 1.00 | 27.26 |
| 3013 | CG2 | ILE | 384 | 89.917 | 46.996 | 54.066 | 1.00 | 33.92 |
| 3014 | CG1 | ILE | 384 | 92.249 | 46.870 | 53.171 | 1.00 | 30.39 |
| 3015 | CD1 | ILE | 384 | 92.881 | 47.691 | 54.278 | 1.00 | 31.10 |
| 3016 | C | ILE | 384 | 90.145 | 44.391 | 55.255 | 1.00 | 34.50 |
| 3017 | O | ILE | 384 | 89.634 | 44.702 | 56.333 | 1.00 | 36.61 |
| 3018 | N | GLU | 385 | 89.643 | 43.453 | 54.460 | 1.00 | 26.50 |
| 3019 | CA | GLU | 385 | 88.443 | 42.750 | 54.811 | 1.00 | 26.95 |
| 3020 | CB | GLU | 385 | 87.937 | 41.926 | 53.595 | 1.00 | 21.63 |
| 3021 | CG | GLU | 385 | 87.650 | 42.790 | 52.375 | 1.00 | 29.50 |
| 3022 | CD | GLU | 385 | 87.418 | 41.976 | 51.115 | 1.00 | 38.78 |
| 3023 | OE1 | GLU | 385 | 87.706 | 40.758 | 51.124 | 1.00 | 42.45 |
| 3024 | OE2 | GLU | 385 | 86.955 | 42.560 | 50.110 | 1.00 | 36.35 |
| 3025 | C | GLU | 385 | 88.711 | 41.732 | 55.954 | 1.00 | 32.21 |
| 3026 | O | GLU | 385 | 87.778 | 41.289 | 56.629 | 1.00 | 43.97 |
| 3027 | N | GLY | 386 | 89.985 | 41.419 | 56.184 | 1.00 | 30.98 |
| 3028 | CA | GLY | 386 | 90.341 | 40.486 | 57.238 | 1.00 | 29.71 |
| 3029 | C | GLY | 386 | 90.069 | 39.071 | 56.767 | 1.00 | 29.59 |
| 3030 | O | GLY | 386 | 89.738 | 38.178 | 57.557 | 1.00 | 27.61 |
| 3031 | N | TYR | 387 | 90.238 | 38.877 | 55.461 | 1.00 | 23.79 |
| 3032 | CA | TYR | 387 | 89.999 | 37.595 | 54.816 | 1.00 | 27.24 |
| 3033 | CB | TYR | 387 | 89.744 | 37.802 | 53.319 | 1.00 | 29.04 |
| 3034 | CG | TYR | 387 | 89.248 | 36.570 | 52.580 | 1.00 | 23.98 |
| 3035 | CD1 | TYR | 387 | 88.361 | 35.675 | 53.179 | 1.00 | 22.30 |
| 3036 | CE1 | TYR | 387 | 87.891 | 34.552 | 52.493 | 1.00 | 29.04 |
| 3037 | CD2 | TYR | 387 | 89.657 | 36.311 | 51.271 | 1.00 | 26.35 |
| 3038 | CE2 | TYR | 387 | 89.192 | 35.194 | 50.575 | 1.00 | 24.90 |
| 3039 | CZ | TYR | 387 | 88.311 | 34.320 | 51.191 | 1.00 | 29.66 |
| 3040 | OH | TYR | 387 | 87.848 | 33.218 | 50.510 | 1.00 | 26.42 |
| 3041 | C | TYR | 387 | 91.127 | 36.591 | 55.014 | 1.00 | 30.82 |
| 3042 | O | TYR | 387 | 92.311 | 36.917 | 54.874 | 1.00 | 39.13 |
| 3043 | N | THR | 388 | 90.721 | 35.375 | 55.364 | 1.00 | 37.65 |
| 3044 | CA | THR | 388 | 91.623 | 34.247 | 55.568 | 1.00 | 31.40 |
| 3045 | CB | THR | 388 | 91.576 | 33.728 | 57.025 | 1.00 | 33.01 |
| 3046 | OG1 | THR | 388 | 92.090 | 34.729 | 57.911 | 1.00 | 35.43 |
| 3047 | CG2 | THR | 388 | 92.416 | 32.462 | 57.179 | 1.00 | 38.16 |
| 3048 | C | THR | 388 | 91.140 | 33.148 | 54.609 | 1.00 | 31.72 |
| 3049 | O | THR | 388 | 90.343 | 32.282 | 54.981 | 1.00 | 39.68 |
| 3050 | N | PRO | 389 | 91.581 | 33.203 | 53.335 | 1.00 | 25.34 |
| 3051 | CD | PRO | 389 | 92.494 | 34.204 | 52.755 | 1.00 | 23.99 |
| 3052 | CA | PRO | 389 | 91.190 | 32.214 | 52.323 | 1.00 | 26.01 |
| 3053 | CB | PRO | 389 | 91.717 | 32.829 | 51.030 | 1.00 | 21.95 |
| 3054 | CG | PRO | 389 | 92.953 | 33.531 | 51.475 | 1.00 | 17.85 |
| 3055 | C | PRO | 389 | 91.779 | 30.825 | 52.537 | 1.00 | 30.44 |
| 3056 | O | PRO | 389 | 92.711 | 30.651 | 53.324 | 1.00 | 28.62 |
| 3057 | N | PRO | 390 | 91.177 | 29.805 | 51.909 | 1.00 | 32.36 |
| 3058 | CD | PRO | 390 | 89.921 | 29.814 | 51.135 | 1.00 | 26.81 |
| 3059 | CA | PRO | 390 | 91.691 | 28.442 | 52.047 | 1.00 | 33.56 |
| 3060 | CB | PRO | 390 | 90.600 | 27.601 | 51.379 | 1.00 | 32.56 |
| 3061 | CG | PRO | 390 | 90.024 | 28.532 | 50.356 | 1.00 | 23.42 |
| 3062 | C | PRO | 390 | 93.016 | 28.383 | 51.277 | 1.00 | 34.49 |
| 3063 | O | PRO | 390 | 93.222 | 29.160 | 50.335 | 1.00 | 30.76 |
| 3064 | N | VAL | 391 | 93.920 | 27.494 | 51.689 | 1.00 | 29.65 |
| 3065 | CA | VAL | 391 | 95.230 | 27.360 | 51.046 | 1.00 | 25.79 |
| 3066 | CB | VAL | 391 | 95.943 | 26.061 | 51.479 | 1.00 | 23.80 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 3067 | CG1 | VAL | 391 | 97.314 | 25.969 | 50.831 | 1.00 | 20.24 |
| 3068 | CG2 | VAL | 391 | 96.078 | 26.017 | 52.981 | 1.00 | 16.75 |
| 3069 | C | VAL | 391 | 95.155 | 27.393 | 49.523 | 1.00 | 25.32 |
| 3070 | O | VAL | 391 | 95.944 | 28.075 | 48.888 | 1.00 | 27.66 |
| 3071 | N | SER | 392 | 94.178 | 26.683 | 48.970 | 1.00 | 25.00 |
| 3072 | CA | SER | 392 | 93.993 | 26.621 | 47.527 | 1.00 | 25.90 |
| 3073 | CB | SER | 392 | 92.727 | 25.827 | 47.194 | 1.00 | 26.67 |
| 3074 | OG | SER | 392 | 92.570 | 25.684 | 45.794 | 1.00 | 47.32 |
| 3075 | C | SER | 392 | 93.911 | 28.015 | 46.918 | 1.00 | 18.85 |
| 3076 | O | SER | 392 | 94.671 | 28.350 | 46.011 | 1.00 | 19.28 |
| 3077 | N | GLU | 393 | 93.013 | 28.837 | 47.450 | 1.00 | 16.74 |
| 3078 | CA | GLU | 393 | 92.827 | 30.191 | 46.949 | 1.00 | 24.04 |
| 3079 | CB | GLU | 393 | 91.579 | 30.821 | 47.565 | 1.00 | 27.67 |
| 3080 | CG | GLU | 393 | 91.105 | 32.067 | 46.831 | 1.00 | 20.67 |
| 3081 | CD | GLU | 393 | 90.095 | 32.873 | 47.618 | 1.00 | 19.63 |
| 3082 | OE1 | GLU | 393 | 89.550 | 32.362 | 48.619 | 1.00 | 20.04 |
| 3083 | OE2 | GLU | 393 | 89.853 | 34.032 | 47.232 | 1.00 | 26.17 |
| 3084 | C | GLU | 393 | 94.044 | 31.071 | 47.226 | 1.00 | 27.53 |
| 3085 | O | GLU | 393 | 94.474 | 31.837 | 46.361 | 1.00 | 22.89 |
| 3086 | N | TYR | 394 | 94.590 | 30.960 | 48.435 | 1.00 | 26.05 |
| 3087 | CA | TYR | 394 | 95.762 | 31.736 | 48.829 | 1.00 | 26.22 |
| 3088 | CB | TYR | 394 | 96.252 | 31.293 | 50.211 | 1.00 | 32.15 |
| 3089 | CG | TYR | 394 | 97.597 | 31.868 | 50.595 | 1.00 | 37.24 |
| 3090 | CD1 | TYR | 394 | 97.739 | 33.224 | 50.890 | 1.00 | 37.33 |
| 3091 | CE1 | TYR | 394 | 98.980 | 33.762 | 51.214 | 1.00 | 33.89 |
| 3092 | CD2 | TYR | 394 | 98.733 | 31.061 | 50.639 | 1.00 | 35.64 |
| 3093 | CE2 | TYR | 394 | 99.979 | 31.590 | 50.961 | 1.00 | 31.95 |
| 3094 | CZ | TYR | 394 | 100.095 | 32.941 | 51.248 | 1.00 | 34.89 |
| 3095 | OH | TYR | 394 | 101.324 | 33.471 | 51.562 | 1.00 | 35.44 |
| 3096 | C | TYR | 394 | 96.900 | 31.615 | 47.813 | 1.00 | 27.71 |
| 3097 | O | TYR | 394 | 97.400 | 32.622 | 47.310 | 1.00 | 30.17 |
| 3098 | N | LEU | 395 | 97.278 | 30.379 | 47.496 | 1.00 | 19.47 |
| 3099 | CA | LEU | 395 | 98.356 | 30.112 | 46.551 | 1.00 | 18.70 |
| 3100 | CB | LEU | 395 | 98.664 | 28.615 | 46.506 | 1.00 | 23.07 |
| 3101 | CG | LEU | 395 | 99.219 | 28.005 | 47.796 | 1.00 | 25.20 |
| 3102 | CD1 | LEU | 395 | 99.416 | 26.512 | 47.609 | 1.00 | 19.35 |
| 3103 | CD2 | LEU | 395 | 100.532 | 28.681 | 48.180 | 1.00 | 17.74 |
| 3104 | C | LEU | 395 | 98.106 | 30.630 | 45.140 | 1.00 | 19.62 |
| 3105 | O | LEU | 395 | 99.030 | 31.112 | 44.485 | 1.00 | 19.16 |
| 3106 | N | SER | 396 | 96.862 | 30.549 | 44.676 | 1.00 | 25.13 |
| 3107 | CA | SER | 396 | 96.521 | 31.018 | 43.332 | 1.00 | 19.88 |
| 3108 | CB | SER | 396 | 95.047 | 30.749 | 43.022 | 1.00 | 25.09 |
| 3109 | OG | SER | 396 | 94.196 | 31.513 | 43.858 | 1.00 | 39.87 |
| 3110 | C | SER | 396 | 96.828 | 32.504 | 43.165 | 1.00 | 19.03 |
| 3111 | O | SER | 396 | 96.920 | 33.005 | 42.040 | 1.00 | 15.70 |
| 3112 | N | ASN | 397 | 96.999 | 33.198 | 44.290 | 1.00 | 14.51 |
| 3113 | CA | ASN | 397 | 97.308 | 34.624 | 44.281 | 1.00 | 20.25 |
| 3114 | CB | ASN | 397 | 96.252 | 35.401 | 45.072 | 1.00 | 21.33 |
| 3115 | CG | ASN | 397 | 96.348 | 36.901 | 44.858 | 1.00 | 25.70 |
| 3116 | OD1 | ASN | 397 | 95.985 | 37.411 | 43.795 | 1.00 | 26.44 |
| 3117 | ND2 | ASN | 397 | 96.840 | 37.617 | 45.868 | 1.00 | 14.18 |
| 3118 | C | ASN | 397 | 98.702 | 34.926 | 44.844 | 1.00 | 21.44 |
| 3119 | O | ASN | 397 | 99.446 | 35.727 | 44.277 | 1.00 | 16.68 |
| 3120 | N | ALA | 398 | 99.053 | 34.263 | 45.944 | 1.00 | 21.43 |
| 3121 | CA | ALA | 398 | 100.339 | 34.463 | 46.611 | 1.00 | 18.24 |
| 3122 | CB | ALA | 398 | 100.303 | 33.853 | 47.996 | 1.00 | 9.21 |
| 3123 | C | ALA | 398 | 101.576 | 33.973 | 45.861 | 1.00 | 22.03 |
| 3124 | O | ALA | 398 | 102.693 | 34.375 | 46.183 | 1.00 | 27.40 |
| 3125 | N | LEU | 399 | 101.392 | 33.099 | 44.878 | 1.00 | 24.29 |
| 3126 | CA | LEU | 399 | 102.530 | 32.590 | 44.123 | 1.00 | 21.14 |
| 3127 | CB | LEU | 399 | 102.133 | 31.379 | 43.276 | 1.00 | 16.51 |
| 3128 | CG | LEU | 399 | 101.814 | 30.092 | 44.047 | 1.00 | 22.47 |
| 3129 | CD1 | LEU | 399 | 101.475 | 28.979 | 43.068 | 1.00 | 23.59 |
| 3130 | CD2 | LEU | 399 | 102.986 | 29.686 | 44.929 | 1.00 | 24.50 |
| 3131 | C | LEU | 399 | 103.189 | 33.656 | 43.256 | 1.00 | 21.08 |
| 3132 | O | LEU | 399 | 104.414 | 33.724 | 43.181 | 1.00 | 27.40 |
| 3133 | N | ALA | 400 | 102.384 | 34.499 | 42.618 | 1.00 | 23.35 |
| 3134 | CA | ALA | 400 | 102.921 | 35.556 | 41.762 | 1.00 | 25.45 |
| 3135 | CB | ALA | 400 | 101.860 | 36.050 | 40.782 | 1.00 | 20.16 |
| 3136 | C | ALA | 400 | 103.500 | 36.724 | 42.562 | 1.00 | 21.72 |
| 3137 | O | ALA | 400 | 104.438 | 37.380 | 42.109 | 1.00 | 16.17 |
| 3138 | N | THR | 401 | 102.960 | 36.966 | 43.757 | 1.00 | 16.96 |
| 3139 | CA | THR | 401 | 103.445 | 38.054 | 44.605 | 1.00 | 19.18 |
| 3140 | CB | THR | 401 | 102.535 | 38.294 | 45.832 | 1.00 | 15.54 |
| 3141 | OG1 | THR | 401 | 102.407 | 37.090 | 46.592 | 1.00 | 24.65 |
| 3142 | CG2 | THR | 401 | 101.167 | 38.752 | 45.393 | 1.00 | 12.23 |
| 3143 | C | THR | 401 | 104.893 | 37.842 | 45.055 | 1.00 | 25.46 |
| 3144 | O | THR | 401 | 105.512 | 38.743 | 45.624 | 1.00 | 34.91 |
| 3145 | N | THR | 402 | 105.421 | 36.644 | 44.813 | 1.00 | 25.90 |
| 3146 | CA | THR | 402 | 106.807 | 36.336 | 45.151 | 1.00 | 21.29 |
| 3147 | CB | THR | 402 | 107.092 | 34.812 | 45.138 | 1.00 | 19.71 |
| 3148 | OG1 | THR | 402 | 106.944 | 34.300 | 43.806 | 1.00 | 12.44 |
| 3149 | CG2 | THR | 402 | 106.152 | 34.080 | 46.070 | 1.00 | 17.92 |
| 3150 | C | THR | 402 | 107.674 | 36.988 | 44.076 | 1.00 | 22.11 |
| 3151 | O | THR | 402 | 108.881 | 37.135 | 44.245 | 1.00 | 21.20 |
| 3152 | N | THR | 403 | 107.022 | 37.366 | 42.974 | 1.00 | 21.28 |
| 3153 | CA | THR | 403 | 107.629 | 38.010 | 41.804 | 1.00 | 18.85 |
| 3154 | CB | THR | 403 | 108.446 | 39.288 | 42.167 | 1.00 | 15.80 |
| 3155 | OG1 | THR | 403 | 109.662 | 38.922 | 42.827 | 1.00 | 16.98 |
| 3156 | CG2 | THR | 403 | 107.647 | 40.210 | 43.071 | 1.00 | 14.55 |
| 3157 | C | THR | 403 | 108.515 | 37.084 | 40.980 | 1.00 | 17.52 |
| 3158 | O | THR | 403 | 109.136 | 37.523 | 40.013 | 1.00 | 14.77 |
| 3159 | N | TYR | 404 | 108.533 | 35.799 | 41.326 | 1.00 | 19.57 |
| 3160 | CA | TYR | 404 | 109.375 | 34.842 | 40.617 | 1.00 | 16.03 |
| 3161 | CB | TYR | 404 | 109.560 | 33.560 | 41.431 | 1.00 | 23.52 |
| 3162 | CG | TYR | 404 | 110.799 | 33.611 | 42.295 | 1.00 | 19.00 |
| 3163 | CD1 | TYR | 404 | 111.271 | 34.828 | 42.785 | 1.00 | 20.18 |
| 3164 | CE1 | TYR | 404 | 112.430 | 34.903 | 43.536 | 1.00 | 26.20 |
| 3165 | CD2 | TYR | 404 | 111.527 | 32.459 | 42.586 | 1.00 | 21.26 |
| 3166 | CE2 | TYR | 404 | 112.695 | 32.523 | 43.345 | 1.00 | 26.60 |
| 3167 | CZ | TYR | 404 | 113.139 | 33.753 | 43.813 | 1.00 | 25.95 |
| 3168 | OH | TYR | 404 | 114.291 | 33.853 | 44.553 | 1.00 | 17.83 |
| 3169 | C | TYR | 404 | 109.040 | 34.545 | 39.164 | 1.00 | 16.09 |
| 3170 | O | TYR | 404 | 109.945 | 34.265 | 38.375 | 1.00 | 15.20 |
| 3171 | N | TYR | 405 | 107.760 | 34.593 | 38.803 | 1.00 | 14.07 |
| 3172 | CA | TYR | 405 | 107.375 | 34.360 | 37.411 | 1.00 | 18.64 |
| 3173 | CB | TYR | 405 | 105.852 | 34.353 | 37.250 | 1.00 | 21.43 |
| 3174 | CG | TYR | 405 | 105.096 | 33.276 | 37.991 | 1.00 | 14.20 |
| 3175 | CD1 | TYR | 405 | 104.458 | 33.557 | 39.196 | 1.00 | 25.61 |
| 3176 | CE1 | TYR | 405 | 103.687 | 32.599 | 39.844 | 1.00 | 26.54 |
| 3177 | CD2 | TYR | 405 | 104.949 | 31.998 | 37.452 | 1.00 | 18.03 |
| 3178 | CE2 | TYR | 405 | 104.178 | 31.031 | 38.094 | 1.00 | 15.71 |
| 3179 | CZ | TYR | 405 | 103.550 | 31.341 | 39.290 | 1.00 | 17.50 |
| 3180 | OH | TYR | 405 | 102.785 | 30.404 | 39.941 | 1.00 | 14.13 |
| 3181 | C | TYR | 405 | 107.922 | 35.558 | 36.638 | 1.00 | 16.83 |
| 3182 | O | TYR | 405 | 108.450 | 35.433 | 35.532 | 1.00 | 12.99 |
| 3183 | N | TYR | 406 | 107.784 | 36.718 | 37.271 | 1.00 | 19.05 |
| 3184 | CA | TYR | 406 | 108.213 | 38.005 | 36.749 | 1.00 | 20.07 |
| 3185 | CB | TYR | 406 | 107.708 | 39.095 | 37.709 | 1.00 | 20.76 |
| 3186 | CG | TYR | 406 | 108.060 | 40.523 | 37.365 | 1.00 | 13.44 |
| 3187 | CD1 | TYR | 406 | 108.092 | 40.965 | 36.044 | 1.00 | 16.24 |
| 3188 | CE1 | TYR | 406 | 108.412 | 42.284 | 35.739 | 1.00 | 19.34 |
| 3189 | CD2 | TYR | 406 | 108.355 | 41.436 | 38.373 | 1.00 | 2.00 |
| 3190 | CE2 | TYR | 406 | 108.673 | 42.751 | 38.081 | 1.00 | 7.86 |
| 3191 | CZ | TYR | 406 | 108.701 | 43.171 | 36.764 | 1.00 | 14.60 |
| 3192 | OH | TYR | 406 | 109.015 | 44.481 | 36.481 | 1.00 | 12.74 |
| 3193 | C | TYR | 406 | 109.735 | 38.068 | 36.570 | 1.00 | 18.51 |
| 3194 | O | TYR | 406 | 110.222 | 38.302 | 35.462 | 1.00 | 20.47 |
| 3195 | N | LEU | 407 | 110.478 | 37.822 | 37.647 | 1.00 | 18.49 |
| 3196 | CA | LEU | 407 | 111.944 | 37.854 | 37.602 | 1.00 | 17.48 |
| 3197 | CB | LEU | 407 | 112.536 | 37.617 | 38.994 | 1.00 | 9.18 |
| 3198 | CG | LEU | 407 | 112.066 | 38.535 | 40.125 | 1.00 | 11.41 |
| 3199 | CD1 | LEU | 407 | 112.894 | 38.261 | 41.366 | 1.00 | 4.35 |
| 3200 | CD2 | LEU | 407 | 112.179 | 40.001 | 39.714 | 1.00 | 14.20 |
| 3201 | C | LEU | 407 | 112.533 | 36.843 | 36.619 | 1.00 | 17.93 |
| 3202 | O | LEU | 407 | 113.506 | 37.142 | 35.925 | 1.00 | 23.70 |
| 3203 | N | ALA | 408 | 111.944 | 35.650 | 36.568 | 1.00 | 17.24 |
| 3204 | CA | ALA | 408 | 112.402 | 34.603 | 35.662 | 1.00 | 15.77 |
| 3205 | CB | ALA | 408 | 111.636 | 33.320 | 35.913 | 1.00 | 20.39 |
| 3206 | C | ALA | 408 | 112.233 | 35.046 | 34.214 | 1.00 | 15.32 |
| 3207 | O | ALA | 408 | 113.108 | 34.820 | 33.383 | 1.00 | 19.31 |
| 3208 | N | THR | 409 | 111.106 | 35.685 | 33.919 | 1.00 | 18.97 |
| 3209 | CA | THR | 409 | 110.830 | 36.174 | 32.570 | 1.00 | 20.42 |
| 3210 | CB | THR | 409 | 109.382 | 36.705 | 32.455 | 1.00 | 12.64 |
| 3211 | OG1 | THR | 409 | 108.465 | 35.679 | 32.853 | 1.00 | 23.03 |
| 3212 | CG2 | THR | 409 | 109.074 | 37.116 | 31.023 | 1.00 | 8.86 |

TABLE 10-continued

Structural Coordinates of Tobacco 5-Epi-Aristolochene Synthase
With Farnesyl Hydroxyphosphonate Bound

| Atom | Atom Type | Residue | Residue # | X | Y | Z | OCC | B-factor |
|---|---|---|---|---|---|---|---|---|
| 3213 | C | THR | 409 | 111.804 | 37.302 | 32.233 | 1.00 | 18.76 |
| 3214 | O | THR | 409 | 112.269 | 37.426 | 31.096 | 1.00 | 14.71 |
| 3215 | N | THR | 410 | 112.118 | 38.105 | 33.245 | 1.00 | 23.19 |
| 3216 | CA | THR | 410 | 113.031 | 39.232 | 33.105 | 1.00 | 22.03 |
| 3217 | CB | THR | 410 | 113.060 | 40.078 | 34.390 | 1.00 | 17.23 |
| 3218 | OG1 | THR | 410 | 111.751 | 40.600 | 34.652 | 1.00 | 20.47 |
| 3219 | CG2 | THR | 410 | 114.043 | 41.228 | 34.251 | 1.00 | 18.91 |
| 3220 | C | THR | 410 | 114.453 | 38.781 | 32.790 | 1.00 | 25.12 |
| 3221 | O | THR | 410 | 115.109 | 39.356 | 31.918 | 1.00 | 24.94 |
| 3222 | N | SER | 411 | 114.913 | 37.741 | 33.486 | 1.00 | 18.76 |
| 3223 | CA | SER | 411 | 116.264 | 37.221 | 33.298 | 1.00 | 11.15 |
| 3224 | CB | SER | 411 | 116.517 | 36.026 | 34.224 | 1.00 | 9.23 |
| 3225 | OG | SER | 411 | 115.722 | 34.911 | 33.871 | 1.00 | 10.06 |
| 3226 | C | SER | 411 | 116.586 | 36.859 | 31.848 | 1.00 | 15.22 |
| 3227 | O | SER | 411 | 117.744 | 36.915 | 31.431 | 1.00 | 22.78 |
| 3228 | N | TYR | 412 | 115.555 | 36.525 | 31.078 | 1.00 | 12.29 |
| 3229 | CA | TYR | 412 | 115.715 | 36.165 | 29.673 | 1.00 | 14.56 |
| 3230 | CB | TYR | 412 | 114.473 | 35.428 | 29.160 | 1.00 | 21.66 |
| 3231 | CG | TYR | 412 | 114.284 | 34.000 | 29.630 | 1.00 | 31.85 |
| 3232 | CD1 | TYR | 412 | 113.510 | 33.110 | 28.884 | 1.00 | 25.46 |
| 3233 | CE1 | TYR | 412 | 113.285 | 31.807 | 29.315 | 1.00 | 25.33 |
| 3234 | CD2 | TYR | 412 | 114.837 | 33.544 | 30.829 | 1.00 | 33.63 |
| 3235 | CE2 | TYR | 412 | 114.617 | 32.236 | 31.271 | 1.00 | 30.87 |
| 3236 | CZ | TYR | 412 | 113.837 | 31.377 | 30.508 | 1.00 | 30.43 |
| 3237 | OH | TYR | 412 | 113.589 | 30.095 | 30.941 | 1.00 | 25.14 |
| 3238 | C | TYR | 412 | 115.938 | 37.382 | 28.775 | 1.00 | 18.89 |
| 3239 | O | TYR | 412 | 116.473 | 37.252 | 27.672 | 1.00 | 21.47 |
| 3240 | N | LEU | 413 | 115.501 | 38.553 | 29.235 | 1.00 | 22.06 |
| 3241 | CA | LEU | 413 | 115.620 | 39.790 | 28.460 | 1.00 | 21.99 |
| 3242 | CB | LEU | 413 | 115.120 | 40.988 | 29.274 | 1.00 | 21.82 |
| 3243 | CG | LEU | 413 | 113.623 | 40.999 | 29.600 | 1.00 | 28.58 |
| 3244 | CD1 | LEU | 413 | 113.286 | 42.192 | 30.481 | 1.00 | 24.87 |
| 3245 | OD2 | LEU | 413 | 112.806 | 41.026 | 28.316 | 1.00 | 20.55 |
| 3246 | C | LEU | 413 | 117.008 | 40.081 | 27.901 | 1.00 | 23.58 |
| 3247 | O | LEU | 413 | 117.157 | 40.329 | 26.702 | 1.00 | 27.31 |
| 3248 | N | GLY | 414 | 118.018 | 40.041 | 28.764 | 1.00 | 17.88 |
| 3249 | CA | GLY | 414 | 119.376 | 40.309 | 28.324 | 1.00 | 19.54 |
| 3250 | C | GLY | 414 | 120.063 | 39.141 | 27.644 | 1.00 | 21.66 |
| 3251 | O | GLY | 414 | 121.088 | 39.319 | 26.981 | 1.00 | 32.10 |
| 3252 | N | MET | 415 | 119.500 | 37.947 | 27.804 | 1.00 | 20.71 |
| 3253 | CA | MET | 415 | 120.062 | 36.741 | 27.209 | 1.00 | 18.08 |
| 3254 | CB | MET | 415 | 119.440 | 35.504 | 27.850 | 1.00 | 15.67 |
| 3255 | CG | MET | 415 | 119.705 | 35.424 | 29.345 | 1.00 | 19.68 |
| 3256 | SD | MET | 415 | 118.883 | 34.052 | 30.144 | 1.00 | 21.56 |
| 3257 | CE | MET | 415 | 119.945 | 32.725 | 29.700 | 1.00 | 15.56 |
| 3258 | C | MET | 415 | 119.870 | 36.734 | 25.702 | 1.00 | 23.08 |
| 3259 | O | MET | 415 | 116.808 | 36.379 | 25.199 | 1.00 | 35.78 |
| 3260 | N | LYS | 416 | 120.930 | 37.112 | 24.996 | 1.00 | 32.44 |
| 3261 | CA | LYS | 416 | 120.953 | 37.207 | 23.538 | 1.00 | 38.05 |
| 3262 | CB | LYS | 416 | 122.360 | 37.608 | 23.090 | 1.00 | 47.08 |
| 3263 | CG | LYS | 416 | 122.865 | 38.875 | 23.776 | 1.00 | 61.44 |
| 3264 | CD | LYS | 416 | 124.358 | 39.084 | 23.581 | 1.00 | 67.69 |
| 3265 | CE | LYS | 416 | 124.846 | 40.273 | 24.399 | 1.00 | 67.49 |
| 3266 | NZ | LYS | 416 | 126.319 | 40.457 | 24.297 | 1.00 | 75.93 |
| 3267 | C | LYS | 416 | 120.486 | 35.970 | 22.767 | 1.00 | 39.94 |
| 3268 | O | LYS | 416 | 120.113 | 36.070 | 21.597 | 1.00 | 44.84 |
| 3269 | N | SER | 417 | 120.493 | 34.813 | 23.422 | 1.00 | 39.76 |
| 3270 | CA | SER | 417 | 120.071 | 33.571 | 22.780 | 1.00 | 39.16 |
| 3271 | CB | SER | 417 | 120.900 | 32.398 | 23.304 | 1.00 | 38.83 |
| 3272 | OG | SER | 417 | 122.282 | 32.610 | 23.076 | 1.00 | 46.53 |
| 3273 | C | SER | 417 | 118.581 | 33.270 | 22.956 | 1.00 | 40.99 |
| 3274 | O | SER | 417 | 118.040 | 32.385 | 22.289 | 1.00 | 41.33 |
| 3275 | N | ALA | 418 | 117.925 | 34.005 | 23.853 | 1.00 | 38.28 |
| 3276 | CA | ALA | 418 | 116.501 | 33.814 | 24.122 | 1.00 | 31.24 |
| 3277 | CB | ALA | 418 | 116.087 | 34.610 | 25.348 | 1.00 | 30.62 |
| 3278 | C | ALA | 418 | 115.628 | 34.186 | 22.930 | 1.00 | 31.48 |
| 3279 | O | ALA | 418 | 115.674 | 35.317 | 22.440 | 1.00 | 35.02 |
| 3280 | N | THR | 419 | 114.841 | 33.219 | 22.468 | 1.00 | 27.95 |
| 3281 | CA | THR | 419 | 113.942 | 33.409 | 21.332 | 1.00 | 26.20 |
| 3282 | CB | THR | 419 | 113.996 | 32.197 | 20.370 | 1.00 | 26.76 |
| 3283 | OG1 | THR | 419 | 113.511 | 31.027 | 21.039 | 1.00 | 27.32 |
| 3284 | CG2 | THR | 419 | 115.424 | 31.945 | 19.901 | 1.00 | 18.56 |
| 3285 | C | THR | 419 | 112.502 | 33.595 | 21.806 | 1.00 | 30.31 |
| 3286 | O | THR | 419 | 112.241 | 33.693 | 23.005 | 1.00 | 33.17 |
| 3287 | N | GLU | 420 | 111.573 | 33.662 | 20.857 | 1.00 | 35.12 |
| 3288 | CA | GLU | 420 | 110.158 | 33.818 | 21.183 | 1.00 | 39.51 |
| 3289 | CB | GLU | 420 | 109.349 | 34.179 | 19.935 | 1.00 | 46.05 |
| 3290 | CG | GLU | 420 | 108.972 | 35.653 | 19.828 | 1.00 | 51.65 |
| 3291 | CD | GLU | 420 | 108.013 | 36.104 | 20.919 | 1.00 | 54.36 |
| 3292 | OE1 | GLU | 420 | 107.027 | 35.384 | 21.192 | 1.00 | 55.36 |
| 3293 | OE2 | GLU | 420 | 108.245 | 37.186 | 21.500 | 1.00 | 58.01 |
| 3294 | C | GLU | 420 | 109.620 | 32.527 | 21.781 | 1.00 | 37.05 |
| 3295 | O | GLU | 420 | 108.852 | 32.550 | 22.742 | 1.00 | 36.79 |
| 3296 | N | GLN | 421 | 110.050 | 31.404 | 21.215 | 1.00 | 37.04 |
| 3297 | CA | GLN | 421 | 109.624 | 30.090 | 21.676 | 1.00 | 33.78 |
| 3298 | CB | GLN | 421 | 110.218 | 28.999 | 20.792 | 1.00 | 40.49 |
| 3299 | CG | GLN | 421 | 109.711 | 29.009 | 19.363 | 1.00 | 57.72 |
| 3300 | CD | GLN | 421 | 110.206 | 27.813 | 18.564 | 1.00 | 74.05 |
| 3301 | OE1 | GLN | 421 | 110.596 | 26.786 | 19.128 | 1.00 | 68.24 |
| 3302 | NE2 | GLN | 421 | 110.190 | 27.941 | 17.242 | 1.00 | 83.42 |
| 3303 | C | GLN | 421 | 109.999 | 29.826 | 23.128 | 1.00 | 31.12 |
| 3304 | O | GLN | 421 | 109.336 | 29.041 | 23.807 | 1.00 | 35.81 |
| 3305 | N | ASP | 422 | 111.071 | 30.466 | 23.592 | 1.00 | 27.52 |
| 3306 | CA | ASP | 422 | 111.527 | 30.304 | 24.971 | 1.00 | 25.90 |
| 3307 | CB | ASP | 422 | 112.963 | 30.821 | 25.137 | 1.00 | 25.75 |
| 3308 | CG | ASP | 422 | 113.985 | 29.971 | 24.396 | 1.00 | 29.11 |
| 3309 | OD1 | ASP | 422 | 114.983 | 30.537 | 23.902 | 1.00 | 33.41 |
| 3310 | OD2 | ASP | 422 | 113.800 | 28.736 | 24.311 | 1.00 | 32.66 |
| 3311 | C | ASP | 422 | 110.590 | 31.020 | 25.936 | 1.00 | 21.80 |
| 3312 | O | ASP | 422 | 110.282 | 30.502 | 27.011 | 1.00 | 19.43 |
| 3313 | N | PHE | 423 | 110.145 | 32.213 | 25.545 | 1.00 | 24.75 |
| 3314 | CA | PHE | 423 | 109.223 | 33.004 | 26.357 | 1.00 | 26.23 |
| 3315 | CB | PHE | 423 | 109.117 | 34.432 | 25.818 | 1.00 | 30.85 |
| 3316 | CG | PHE | 423 | 110.290 | 35.306 | 26.166 | 1.00 | 32.84 |
| 3317 | CD1 | PHE | 423 | 111.336 | 35.482 | 25.268 | 1.00 | 34.61 |
| 3318 | CD2 | PHE | 423 | 110.338 | 35.972 | 27.388 | 1.00 | 33.51 |
| 3319 | CE1 | PHE | 423 | 112.412 | 36.312 | 25.579 | 1.00 | 30.52 |
| 3320 | CE2 | PHE | 423 | 111.410 | 36.805 | 27.708 | 1.00 | 35.27 |
| 3321 | CZ | PHE | 423 | 112.448 | 36.974 | 26.801 | 1.00 | 23.59 |
| 3322 | C | PHE | 423 | 107.849 | 32.354 | 26.330 | 1.00 | 24.84 |
| 3323 | O | PHE | 423 | 107.106 | 32.392 | 27.311 | 1.00 | 31.10 |
| 3324 | N | GLU | 424 | 107.530 | 31.751 | 25.191 | 1.00 | 29.70 |
| 3325 | CA | GLU | 424 | 106.261 | 31.070 | 24.982 | 1.00 | 36.07 |
| 3326 | CB | GLU | 424 | 106.187 | 30.588 | 23.535 | 1.00 | 40.70 |
| 3327 | CG | GLU | 424 | 104.785 | 30.391 | 22.992 | 1.00 | 63.10 |
| 3328 | CD | GLU | 424 | 104.759 | 30.296 | 21.473 | 1.00 | 75.17 |
| 3329 | OE1 | GLU | 424 | 105.781 | 29.898 | 20.867 | 1.00 | 75.10 |
| 3330 | OE2 | GLU | 424 | 103.710 | 30.630 | 20.880 | 1.00 | 85.30 |
| 3331 | C | GLU | 424 | 106.164 | 29.892 | 25.949 | 1.00 | 31.83 |
| 3332 | O | GLU | 424 | 105.138 | 29.687 | 26.595 | 1.00 | 35.87 |
| 3333 | N | TRP | 425 | 107.258 | 29.148 | 26.066 | 1.00 | 29.46 |
| 3334 | CA | TRP | 425 | 107.339 | 27.999 | 26.958 | 1.00 | 23.86 |
| 3335 | CB | TRP | 425 | 108.680 | 27.285 | 26.753 | 1.00 | 25.55 |
| 3336 | CG | TRP | 425 | 108.991 | 26.265 | 27.803 | 1.00 | 29.41 |
| 3337 | CD2 | TRP | 425 | 109.808 | 26.455 | 28.965 | 1.00 | 27.61 |
| 3338 | CE2 | TRP | 425 | 109.779 | 25.249 | 29.697 | 1.00 | 24.31 |
| 3339 | CE3 | TRP | 425 | 110.557 | 27.529 | 29.460 | 1.00 | 30.25 |
| 3340 | CD1 | TRP | 425 | 108.521 | 24.984 | 27.871 | 1.00 | 28.89 |
| 3341 | NE1 | TRP | 425 | 108.987 | 24.369 | 29.007 | 1.00 | 29.83 |
| 3342 | CZ2 | TRP | 425 | 110.473 | 25.087 | 30.900 | 1.00 | 16.37 |
| 3343 | CZ3 | TRP | 425 | 111.245 | 27.367 | 30.658 | 1.00 | 25.72 |
| 3344 | CH2 | TRP | 425 | 111.196 | 26.154 | 31.363 | 1.00 | 19.53 |
| 3345 | C | TRP | 425 | 107.205 | 28.437 | 28.414 | 1.00 | 25.64 |
| 3346 | O | TRP | 425 | 106.523 | 27.792 | 29.213 | 1.00 | 26.99 |
| 3347 | N | LEU | 426 | 107.852 | 29.553 | 28.739 | 1.00 | 26.42 |
| 3348 | CA | LEU | 426 | 107.853 | 30.103 | 30.088 | 1.00 | 21.18 |
| 3349 | CB | LEU | 426 | 108.922 | 31.191 | 30.195 | 1.00 | 21.43 |
| 3350 | CG | LEU | 426 | 109.379 | 31.600 | 31.595 | 1.00 | 14.19 |
| 3351 | CD1 | LEU | 426 | 110.106 | 30.441 | 32.251 | 1.00 | 14.14 |
| 3352 | CD2 | LEU | 426 | 110.297 | 32.798 | 31.499 | 1.00 | 12.82 |
| 3353 | C | LEU | 426 | 106.504 | 30.664 | 30.523 | 1.00 | 23.80 |
| 3354 | O | LEU | 426 | 106.153 | 30.596 | 31.702 | 1.00 | 31.77 |
| 3355 | N | SER | 427 | 105.754 | 31.221 | 29.575 | 1.00 | 28.08 |
| 3356 | CA | SER | 427 | 104.444 | 31.802 | 29.871 | 1.00 | 30.28 |
| 3357 | CB | SER | 427 | 103.915 | 32.592 | 28.665 | 1.00 | 26.14 |
| 3358 | OG | SER | 427 | 103.742 | 31.763 | 27.528 | 1.00 | 29.08 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 3359 | C | SER | 427 | 103.406 | 30.773 | 30.325 | 1.00 | 29.36 |
| 3360 | O | SER | 427 | 102.497 | 31.099 | 31.088 | 1.00 | 31.12 |
| 3361 | N | LYS | 428 | 103.558 | 29.530 | 29.873 | 1.00 | 27.92 |
| 3362 | CA | LYS | 428 | 102.637 | 28.455 | 30.230 | 1.00 | 20.58 |
| 3363 | CB | LYS | 428 | 102.770 | 27.290 | 29.251 | 1.00 | 23.24 |
| 3364 | CG | LYS | 428 | 102.454 | 27.613 | 27.801 | 1.00 | 22.85 |
| 3365 | CD | LYS | 428 | 102.509 | 26.335 | 26.976 | 1.00 | 42.29 |
| 3366 | CE | LYS | 428 | 102.338 | 26.597 | 25.493 | 1.00 | 49.89 |
| 3367 | NZ | LYS | 428 | 102.345 | 25.316 | 24.727 | 1.00 | 62.04 |
| 3368 | C | LYS | 428 | 102.844 | 27.935 | 31.654 | 1.00 | 20.72 |
| 3369 | O | LYS | 428 | 102.183 | 26.980 | 32.067 | 1.00 | 29.09 |
| 3370 | N | ASN | 429 | 103.762 | 28.557 | 32.391 | 1.00 | 20.35 |
| 3371 | CA | ASN | 429 | 104.072 | 28.170 | 33.770 | 1.00 | 14.44 |
| 3372 | CB | ASN | 429 | 102.868 | 28.406 | 34.685 | 1.00 | 13.93 |
| 3373 | CG | ASN | 429 | 102.581 | 29.876 | 34.910 | 1.00 | 21.29 |
| 3374 | OD1 | ASN | 429 | 103.306 | 30.747 | 34.431 | 1.00 | 26.38 |
| 3375 | ND2 | ASN | 429 | 101.522 | 30.159 | 35.657 | 1.00 | 28.12 |
| 3376 | C | ASN | 429 | 104.545 | 26.724 | 33.900 | 1.00 | 19.87 |
| 3377 | O | ASN | 429 | 103.831 | 25.868 | 34.426 | 1.00 | 27.89 |
| 3378 | N | PRO | 430 | 105.764 | 26.433 | 33.418 | 1.00 | 18.35 |
| 3379 | CD | PRO | 430 | 106.650 | 27.362 | 32.701 | 1.00 | 19.00 |
| 3380 | CA | PRO | 430 | 106.358 | 25.096 | 33.468 | 1.00 | 11.22 |
| 3381 | CB | PRO | 430 | 107.711 | 25.309 | 32.808 | 1.00 | 15.49 |
| 3382 | CG | PRO | 430 | 107.444 | 26.425 | 31.859 | 1.00 | 26.05 |
| 3383 | C | PRO | 430 | 106.518 | 24.612 | 34.902 | 1.00 | 17.61 |
| 3384 | O | PRO | 430 | 106.617 | 25.416 | 35.828 | 1.00 | 19.92 |
| 3385 | N | LYS | 431 | 106.569 | 23.294 | 35.073 | 1.00 | 18.71 |
| 3386 | CA | LYS | 431 | 106.699 | 22.681 | 36.389 | 1.00 | 14.83 |
| 3387 | CB | LYS | 431 | 106.682 | 21.157 | 36.256 | 1.00 | 15.08 |
| 3388 | CG | LYS | 431 | 106.353 | 20.409 | 37.539 | 1.00 | 26.85 |
| 3389 | CD | LYS | 431 | 106.103 | 18.937 | 37.244 | 1.00 | 41.27 |
| 3390 | CE | LYS | 431 | 105.561 | 18.195 | 38.455 | 1.00 | 49.80 |
| 3391 | NZ | LYS | 431 | 105.297 | 16.760 | 38.140 | 1.00 | 45.04 |
| 3392 | C | LYS | 431 | 107.959 | 23.137 | 37.121 | 1.00 | 19.80 |
| 3393 | O | LYS | 431 | 107.937 | 23.333 | 38.338 | 1.00 | 20.81 |
| 3394 | N | ILE | 432 | 109.051 | 23.316 | 36.380 | 1.00 | 15.93 |
| 3395 | CA | ILE | 432 | 110.306 | 23.757 | 36.979 | 1.00 | 16.86 |
| 3396 | CB | ILE | 432 | 111.497 | 23.632 | 35.994 | 1.00 | 20.40 |
| 3397 | CG2 | ILE | 432 | 111.278 | 24.502 | 34.756 | 1.00 | 16.63 |
| 3398 | CG1 | ILE | 432 | 112.804 | 23.985 | 36.709 | 1.00 | 14.19 |
| 3399 | CD1 | ILE | 432 | 114.048 | 23.649 | 35.920 | 1.00 | 13.37 |
| 3400 | C | ILE | 432 | 110.182 | 25.187 | 37.499 | 1.00 | 17.42 |
| 3401 | O | ILE | 432 | 110.681 | 25.508 | 38.579 | 1.00 | 24.54 |
| 3402 | N | LEU | 433 | 109.488 | 26.035 | 36.742 | 1.00 | 15.09 |
| 3403 | CA | LEU | 433 | 109.277 | 27.420 | 37.146 | 1.00 | 14.83 |
| 3404 | CB | LEU | 433 | 108.728 | 28.245 | 35.978 | 1.00 | 13.49 |
| 3405 | CG | LEU | 433 | 108.378 | 29.708 | 36.272 | 1.00 | 10.45 |
| 3406 | CD1 | LEU | 433 | 109.564 | 30.430 | 36.896 | 1.00 | 15.23 |
| 3407 | CD2 | LEU | 433 | 107.939 | 30.400 | 34.993 | 1.00 | 9.30 |
| 3408 | C | LEU | 433 | 108.289 | 27.433 | 38.304 | 1.00 | 18.07 |
| 3409 | O | LEU | 433 | 108.481 | 28.140 | 39.295 | 1.00 | 21.14 |
| 3410 | N | GLU | 434 | 107.245 | 26.621 | 38.173 | 1.00 | 21.38 |
| 3411 | CA | GLU | 434 | 106.209 | 26.503 | 39.188 | 1.00 | 16.25 |
| 3412 | CB | GLU | 434 | 105.184 | 25.452 | 38.753 | 1.00 | 23.52 |
| 3413 | CG | GLU | 434 | 103.812 | 25.605 | 39.385 | 1.00 | 38.66 |
| 3414 | CD | GLU | 434 | 103.161 | 26.933 | 39.037 | 1.00 | 42.62 |
| 3415 | OE1 | GLU | 434 | 102.828 | 27.148 | 37.851 | 1.00 | 32.73 |
| 3416 | OE2 | GLU | 434 | 102.993 | 27.765 | 39.953 | 1.00 | 37.72 |
| 3417 | C | GLU | 434 | 106.850 | 26.095 | 40.511 | 1.00 | 14.12 |
| 3418 | O | GLU | 434 | 106.561 | 26.676 | 41.556 | 1.00 | 14.76 |
| 3419 | N | ALA | 435 | 107.753 | 25.120 | 40.440 | 1.00 | 17.75 |
| 3420 | CA | ALA | 435 | 108.465 | 24.610 | 41.610 | 1.00 | 16.67 |
| 3421 | CB | ALA | 435 | 109.303 | 23.410 | 41.214 | 1.00 | 8.83 |
| 3422 | C | ALA | 435 | 109.344 | 25.683 | 42.254 | 1.00 | 11.99 |
| 3423 | O | ALA | 435 | 109.372 | 25.827 | 43.477 | 1.00 | 7.99 |
| 3424 | N | SER | 436 | 110.057 | 26.435 | 41.422 | 1.00 | 15.97 |
| 3425 | CA | SER | 438 | 110.924 | 27.508 | 41.900 | 1.00 | 21.95 |
| 3426 | CB | SER | 436 | 111.636 | 28.163 | 40.713 | 1.00 | 14.20 |
| 3427 | OG | SER | 436 | 112.489 | 29.212 | 41.135 | 1.00 | 40.93 |
| 3428 | C | SER | 436 | 110.110 | 28.554 | 42.674 | 1.00 | 21.39 |
| 3429 | O | SER | 436 | 110.519 | 29.009 | 43.748 | 1.00 | 24.40 |
| 3430 | N | VAL | 437 | 108.951 | 28.912 | 42.125 | 1.00 | 18.68 |
| 3431 | CA | VAL | 437 | 108.054 | 29.889 | 42.739 | 1.00 | 8.95 |
| 3432 | CB | VAL | 437 | 106.855 | 30.188 | 41.818 | 1.00 | 11.54 |
| 3433 | CG1 | VAL | 437 | 105.917 | 31.169 | 42.478 | 1.00 | 11.34 |
| 3434 | CG2 | VAL | 437 | 107.339 | 30.734 | 40.486 | 1.00 | 5.44 |
| 3435 | C | VAL | 437 | 107.533 | 29.401 | 44.092 | 1.00 | 9.21 |
| 3436 | O | VAL | 437 | 107.452 | 30.176 | 45.048 | 1.00 | 12.18 |
| 3437 | N | ILE | 438 | 107.185 | 28.115 | 44.161 | 1.00 | 9.76 |
| 3438 | CA | ILE | 438 | 106.673 | 27.504 | 45.388 | 1.00 | 8.03 |
| 3439 | CB | ILE | 438 | 106.309 | 26.015 | 45.171 | 1.00 | 14.49 |
| 3440 | CG2 | ILE | 438 | 105.931 | 25.360 | 46.500 | 1.00 | 10.62 |
| 3441 | CG1 | ILE | 438 | 105.162 | 25.896 | 44.164 | 1.00 | 23.13 |
| 3442 | CD1 | ILE | 438 | 104.753 | 24.468 | 43.853 | 1.00 | 31.20 |
| 3443 | C | ILE | 438 | 107.692 | 27.603 | 46.520 | 1.00 | 12.21 |
| 3444 | O | ILE | 438 | 107.349 | 27.982 | 47.639 | 1.00 | 18.63 |
| 3445 | N | ILE | 439 | 108.941 | 27.258 | 46.216 | 1.00 | 14.08 |
| 3446 | CA | ILE | 439 | 110.033 | 27.307 | 47.188 | 1.00 | 9.89 |
| 3447 | CB | ILE | 439 | 111.369 | 26.901 | 46.525 | 1.00 | 12.54 |
| 3448 | CG2 | ILE | 439 | 112.540 | 27.161 | 47.459 | 1.00 | 11.31 |
| 3449 | CG1 | ILE | 439 | 111.321 | 25.424 | 46.136 | 1.00 | 2.00 |
| 3450 | CD1 | ILE | 439 | 112.441 | 24.990 | 45.233 | 1.00 | 14.05 |
| 3451 | C | ILE | 439 | 110.152 | 28.706 | 47.783 | 1.00 | 9.52 |
| 3452 | O | ILE | 439 | 110.213 | 28.871 | 49.003 | 1.00 | 10.13 |
| 3453 | N | CYS | 440 | 110.135 | 29.714 | 46.918 | 1.00 | 8.13 |
| 3454 | CA | CYS | 440 | 110.233 | 31.098 | 47.361 | 1.00 | 12.62 |
| 3455 | CB | CYS | 440 | 110.267 | 32.036 | 46.153 | 1.00 | 5.84 |
| 3456 | SG | CYS | 440 | 110.449 | 33.774 | 46.599 | 1.00 | 11.97 |
| 3457 | C | CYS | 440 | 109.073 | 31.482 | 48.283 | 1.00 | 17.47 |
| 3458 | O | CYS | 440 | 109.264 | 32.175 | 49.287 | 1.00 | 18.40 |
| 3459 | N | ARG | 441 | 107.875 | 31.012 | 47.940 | 1.00 | 18.94 |
| 3460 | CA | ARG | 441 | 106.669 | 31.296 | 48.714 | 1.00 | 11.76 |
| 3461 | CB | ARG | 441 | 105.433 | 30.810 | 47.949 | 1.00 | 10.60 |
| 3462 | CG | ARG | 441 | 104.093 | 31.083 | 48.629 | 1.00 | 6.45 |
| 3463 | CD | ARG | 441 | 103.718 | 32.559 | 48.590 | 1.00 | 19.08 |
| 3464 | NE | ARG | 441 | 104.454 | 33.353 | 49.571 | 1.00 | 23.16 |
| 3465 | CZ | ARG | 441 | 104.623 | 34.670 | 49.500 | 1.00 | 20.47 |
| 3466 | NH1 | ARG | 441 | 104.108 | 35.353 | 48.489 | 1.00 | 12.16 |
| 3467 | NH2 | ARG | 441 | 105.307 | 35.307 | 50.441 | 1.00 | 30.69 |
| 3468 | C | ARG | 441 | 106.716 | 30.637 | 50.089 | 1.00 | 17.00 |
| 3469 | O | ARG | 441 | 106.629 | 31.307 | 51.120 | 1.00 | 25.77 |
| 3470 | N | VAL | 442 | 106.858 | 29.317 | 50.086 | 1.00 | 22.16 |
| 3471 | CA | VAL | 442 | 106.920 | 28.518 | 51.306 | 1.00 | 22.25 |
| 3472 | CB | VAL | 442 | 107.112 | 27.032 | 50.959 | 1.00 | 23.82 |
| 3473 | CG1 | VAL | 442 | 107.624 | 26.261 | 52.164 | 1.00 | 26.50 |
| 3474 | CG2 | VAL | 442 | 105.796 | 26.450 | 50.471 | 1.00 | 31.37 |
| 3475 | C | VAL | 442 | 108.004 | 28.969 | 52.283 | 1.00 | 21.17 |
| 3476 | O | VAL | 442 | 107.765 | 29.058 | 53.488 | 1.00 | 25.05 |
| 3477 | N | ILE | 443 | 109.195 | 29.243 | 51.761 | 1.00 | 22.99 |
| 3478 | CA | ILE | 443 | 110.305 | 29.685 | 52.596 | 1.00 | 27.94 |
| 3479 | CB | ILE | 443 | 111.628 | 29.710 | 51.805 | 1.00 | 34.71 |
| 3480 | CG2 | ILE | 443 | 112.721 | 30.396 | 52.612 | 1.00 | 32.63 |
| 3481 | CG1 | ILE | 443 | 112.041 | 28.279 | 51.458 | 1.00 | 35.15 |
| 3482 | CD1 | ILE | 443 | 113.322 | 28.183 | 50.669 | 1.00 | 41.45 |
| 3483 | C | ILE | 443 | 110.024 | 31.054 | 53.208 | 1.00 | 24.50 |
| 3484 | O | ILE | 443 | 110.253 | 31.263 | 54.400 | 1.00 | 25.69 |
| 3485 | N | ASP | 444 | 109.500 | 31.972 | 52.398 | 1.00 | 24.21 |
| 3486 | CA | ASP | 444 | 109.178 | 33.314 | 52.875 | 1.00 | 26.25 |
| 3487 | CB | ASP | 444 | 108.695 | 34.203 | 51.721 | 1.00 | 29.76 |
| 3488 | CG | ASP | 444 | 108.365 | 35.624 | 52.169 | 1.00 | 39.45 |
| 3489 | CD1 | ASP | 444 | 109.179 | 36.535 | 51.910 | 1.00 | 45.87 |
| 3490 | OD2 | ASP | 444 | 107.288 | 35.841 | 52.768 | 1.00 | 45.57 |
| 3491 | C | ASP | 444 | 108.103 | 33.247 | 53.952 | 1.00 | 28.37 |
| 3492 | O | ASP | 444 | 108.228 | 33.883 | 54.995 | 1.00 | 29.64 |
| 3493 | N | ASP | 445 | 107.061 | 32.458 | 53.700 | 1.00 | 30.42 |
| 3494 | CA | ASP | 445 | 105.950 | 32.318 | 54.637 | 1.00 | 32.30 |
| 3495 | CB | ASP | 445 | 104.797 | 31.544 | 53.994 | 1.00 | 33.98 |
| 3496 | CG | ASP | 445 | 104.151 | 32.302 | 52.838 | 1.00 | 37.92 |
| 3497 | OD1 | ASP | 445 | 104.356 | 33.532 | 52.717 | 1.00 | 38.86 |
| 3498 | OD2 | ASP | 445 | 103.429 | 31.662 | 52.047 | 1.00 | 28.07 |
| 3499 | C | ASP | 445 | 106.335 | 31.690 | 55.970 | 1.00 | 33.30 |
| 3500 | O | ASP | 445 | 105.762 | 32.030 | 57.009 | 1.00 | 42.91 |
| 3501 | N | THR | 446 | 107.302 | 30.778 | 55.946 | 1.00 | 33.28 |
| 3502 | CA | THR | 446 | 107.758 | 30.124 | 57.168 | 1.00 | 30.88 |
| 3503 | CB | THR | 446 | 108.625 | 28.887 | 56.855 | 1.00 | 26.02 |
| 3504 | OG1 | THR | 446 | 107.873 | 27.969 | 56.050 | 1.00 | 21.99 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 3505 | CG2 | THR | 446 | 109.046 | 28.188 | 58.143 | 1.00 | 25.74 |
| 3506 | C | THR | 446 | 108.570 | 31.110 | 58.014 | 1.00 | 32.83 |
| 3507 | O | THR | 446 | 108.459 | 31.131 | 59.238 | 1.00 | 33.61 |
| 3508 | N | ALA | 447 | 109.357 | 31.944 | 57.339 | 1.00 | 40.56 |
| 3509 | CA | ALA | 447 | 110.202 | 32.937 | 57.996 | 1.00 | 45.46 |
| 3510 | CB | ALA | 447 | 111.313 | 33.374 | 57.056 | 1.00 | 42.21 |
| 3511 | C | ALA | 447 | 109.434 | 34.155 | 58.468 | 1.00 | 46.97 |
| 3512 | O | ALA | 447 | 109.596 | 34.617 | 59.599 | 1.00 | 54.11 |
| 3513 | N | THR | 448 | 108.599 | 34.690 | 57.581 | 1.00 | 47.28 |
| 3514 | CA | THR | 448 | 107.832 | 35.884 | 57.879 | 1.00 | 46.44 |
| 3515 | CB | THR | 448 | 107.689 | 36.787 | 56.618 | 1.00 | 41.12 |
| 3516 | OG1 | THR | 448 | 106.943 | 36.112 | 55.607 | 1.00 | 30.26 |
| 3517 | CG2 | THR | 448 | 109.064 | 37.170 | 56.071 | 1.00 | 32.60 |
| 3518 | C | THR | 448 | 106.446 | 35.694 | 58.497 | 1.00 | 51.30 |
| 3519 | O | THR | 448 | 105.708 | 36.657 | 58.620 | 1.00 | 53.69 |
| 3520 | N | TYR | 449 | 106.080 | 34.481 | 58.912 | 1.00 | 53.28 |
| 3521 | CA | TYR | 449 | 104.751 | 34.282 | 59.492 | 1.00 | 58.27 |
| 3522 | CB | TYR | 449 | 104.497 | 32.811 | 59.888 | 1.00 | 58.98 |
| 3523 | CG | TYR | 449 | 103.175 | 32.661 | 60.637 | 1.00 | 61.56 |
| 3524 | CD1 | TYR | 449 | 101.973 | 33.066 | 60.055 | 1.00 | 66.72 |
| 3525 | CE1 | TYR | 449 | 100.772 | 33.026 | 60.769 | 1.00 | 64.98 |
| 3526 | CD2 | TYR | 449 | 103.147 | 32.198 | 61.957 | 1.00 | 62.94 |
| 3527 | CE2 | TYR | 449 | 101.956 | 32.155 | 62.672 | 1.00 | 66.76 |
| 3528 | CZ | TYR | 449 | 100.773 | 32.575 | 62.080 | 1.00 | 67.45 |
| 3529 | OH | TYR | 449 | 99.601 | 32.590 | 62.810 | 1.00 | 73.04 |
| 3530 | C | TYR | 449 | 104.462 | 35.189 | 60.691 | 1.00 | 59.96 |
| 3531 | O | TYR | 449 | 103.576 | 36.051 | 60.638 | 1.00 | 60.11 |
| 3532 | N | GLU | 450 | 105.199 | 34.975 | 61.771 | 1.00 | 61.73 |
| 3533 | CA | GLU | 450 | 105.029 | 35.733 | 62.995 | 1.00 | 61.61 |
| 3534 | CB | GLU | 450 | 106.071 | 35.308 | 64.025 | 1.00 | 65.21 |
| 3535 | CG | GLU | 450 | 105.833 | 33.912 | 64.589 | 1.00 | 75.41 |
| 3536 | CD | GLU | 450 | 106.887 | 33.502 | 65.610 | 1.00 | 85.43 |
| 3537 | OE1 | GLU | 450 | 107.416 | 34.375 | 66.331 | 1.00 | 91.32 |
| 3538 | OE2 | GLU | 450 | 107.196 | 32.293 | 65.686 | 1.00 | 90.42 |
| 3539 | C | GLU | 450 | 105.026 | 37.251 | 62.841 | 1.00 | 59.86 |
| 3540 | O | GLU | 450 | 104.144 | 37.918 | 63.377 | 1.00 | 59.89 |
| 3541 | N | VAL | 451 | 105.995 | 37.787 | 62.098 | 1.00 | 61.44 |
| 3542 | CA | VAL | 451 | 106.092 | 39.234 | 61.873 | 1.00 | 63.11 |
| 3543 | CB | VAL | 451 | 107.408 | 39.596 | 61.116 | 1.00 | 64.01 |
| 3544 | CG1 | VAL | 451 | 107.256 | 40.886 | 60.304 | 1.00 | 63.92 |
| 3545 | CG2 | VAL | 451 | 108.541 | 39.761 | 62.123 | 1.00 | 71.39 |
| 3546 | C | VAL | 451 | 104.881 | 39.809 | 61.152 | 1.00 | 62.77 |
| 3547 | O | VAL | 451 | 104.336 | 40.841 | 61.555 | 1.00 | 65.95 |
| 3548 | N | GLU | 452 | 104.450 | 39.118 | 60.103 | 1.00 | 62.77 |
| 3549 | CA | GLU | 452 | 103.304 | 39.545 | 59.315 | 1.00 | 57.61 |
| 3550 | CB | GLU | 452 | 103.275 | 33.782 | 57.991 | 1.00 | 56.30 |
| 3551 | CG | GLU | 452 | 104.444 | 39.130 | 57.058 | 1.00 | 59.48 |
| 3552 | CD | GLU | 452 | 104.469 | 38.317 | 55.787 | 1.00 | 60.10 |
| 3553 | OE1 | GLU | 452 | 104.787 | 38.899 | 54.728 | 1.00 | 62.60 |
| 3554 | OE2 | GLU | 452 | 104.183 | 37.106 | 55.843 | 1.00 | 61.28 |
| 3555 | C | GLU | 452 | 101.984 | 39.392 | 60.081 | 1.00 | 56.17 |
| 3556 | O | GLU | 452 | 101.034 | 40.136 | 59.838 | 1.00 | 51.59 |
| 3557 | N | LYS | 453 | 101.946 | 38.466 | 61.040 | 1.00 | 58.80 |
| 3558 | CA | LYS | 453 | 100.753 | 38.241 | 61.858 | 1.00 | 58.04 |
| 3559 | CB | LYS | 453 | 100.863 | 36.913 | 62.611 | 1.00 | 59.76 |
| 3560 | CG | LYS | 453 | 99.644 | 36.565 | 63.453 | 1.00 | 60.02 |
| 3561 | CD | LYS | 453 | 99.925 | 35.384 | 64.366 | 1.00 | 58.67 |
| 3562 | CE | LYS | 453 | 98.732 | 35.093 | 65.262 | 1.00 | 61.72 |
| 3563 | NZ | LYS | 453 | 99.013 | 33.991 | 66.222 | 1.00 | 58.55 |
| 3564 | C | LYS | 453 | 100.584 | 39.385 | 62.863 | 1.00 | 57.99 |
| 3565 | O | LYS | 453 | 99.461 | 39.769 | 63.195 | 1.00 | 57.81 |
| 3566 | N | SER | 454 | 101.709 | 39.920 | 63.339 | 1.00 | 62.23 |
| 3567 | CA | SER | 454 | 101.712 | 41.026 | 64.295 | 1.00 | 61.09 |
| 3568 | CB | SER | 454 | 103.125 | 41.265 | 64.837 | 1.00 | 60.66 |
| 3569 | OG | SER | 454 | 103.548 | 40.191 | 65.654 | 1.00 | 66.36 |
| 3570 | C | SER | 454 | 101.185 | 42.311 | 63.665 | 1.00 | 58.28 |
| 3571 | O | SER | 454 | 100.632 | 43.163 | 64.360 | 1.00 | 56.27 |
| 3572 | N | ARG | 455 | 101.373 | 42.447 | 62.354 | 1.00 | 58.50 |
| 3573 | CA | ARG | 455 | 100.916 | 43.623 | 61.619 | 1.00 | 62.35 |
| 3574 | CB | ARG | 455 | 101.827 | 43.885 | 60.414 | 1.00 | 67.55 |
| 3575 | CG | ARG | 455 | 103.261 | 44.228 | 60.797 | 1.00 | 76.19 |
| 3576 | CD | ARG | 455 | 104.115 | 44.547 | 59.581 | 1.00 | 85.72 |
| 3577 | NE | ARG | 455 | 105.444 | 45.024 | 59.964 | 1.00 | 96.37 |
| 3578 | CZ | ARG | 455 | 106.292 | 45.634 | 59.140 | 1.00 | 100.00 |
| 3579 | NH1 | ARG | 455 | 105.960 | 45.845 | 57.872 | 1.00 | 100.00 |
| 3580 | NH2 | ARG | 455 | 107.470 | 46.051 | 59.587 | 1.00 | 99.29 |
| 3581 | C | ARG | 455 | 99.457 | 43.503 | 61.176 | 1.00 | 60.13 |
| 3582 | O | ARG | 455 | 98.922 | 44.399 | 60.519 | 1.00 | 58.35 |
| 3583 | N | GLY | 456 | 98.824 | 42.391 | 61.546 | 1.00 | 60.37 |
| 3584 | CA | GLY | 456 | 97.432 | 42.164 | 61.201 | 1.00 | 62.20 |
| 3585 | C | GLY | 456 | 97.183 | 41.378 | 59.925 | 1.00 | 67.18 |
| 3586 | O | GLY | 456 | 96.036 | 41.048 | 59.626 | 1.00 | 70.98 |
| 3587 | N | GLN | 457 | 98.238 | 41.091 | 59.166 | 1.00 | 69.31 |
| 3588 | CA | GLN | 457 | 98.108 | 40.340 | 57.917 | 1.00 | 68.54 |
| 3589 | CB | GLN | 457 | 99.397 | 40.438 | 57.089 | 1.00 | 69.51 |
| 3590 | CG | GLN | 457 | 99.764 | 41.859 | 56.671 | 1.00 | 74.48 |
| 3591 | CD | GLN | 457 | 101.105 | 41.941 | 55.965 | 1.00 | 78.04 |
| 3592 | OE1 | GLN | 457 | 102.099 | 41.389 | 56.428 | 1.00 | 87.45 |
| 3593 | NE2 | GLN | 457 | 101.140 | 42.651 | 54.840 | 1.00 | 80.41 |
| 3594 | C | GLN | 457 | 97.765 | 38.879 | 58.197 | 1.00 | 66.56 |
| 3595 | O | GLN | 457 | 98.645 | 38.020 | 58.262 | 1.00 | 70.53 |
| 3596 | N | ILE | 458 | 96.475 | 38.616 | 58.384 | 1.00 | 64.43 |
| 3597 | CA | ILE | 458 | 95.976 | 37.272 | 58.664 | 1.00 | 60.84 |
| 3598 | CB | ILE | 458 | 94.652 | 37.317 | 59.458 | 1.00 | 62.21 |
| 3599 | CG2 | ILE | 458 | 94.940 | 37.397 | 60.958 | 1.00 | 64.20 |
| 3600 | CG1 | ILE | 458 | 93.769 | 38.462 | 58.943 | 1.00 | 60.42 |
| 3601 | CD1 | ILE | 458 | 92.437 | 38.608 | 59.656 | 1.00 | 66.77 |
| 3602 | C | ILE | 458 | 95.768 | 36.440 | 57.403 | 1.00 | 55.84 |
| 3603 | O | ILE | 458 | 95.281 | 35.310 | 57.468 | 1.00 | 51.58 |
| 3604 | N | ALA | 459 | 96.145 | 37.005 | 56.259 | 1.00 | 58.27 |
| 3605 | CA | ALA | 459 | 96.011 | 36.318 | 54.979 | 1.00 | 56.90 |
| 3606 | CB | ALA | 459 | 95.609 | 37.305 | 53.888 | 1.00 | 56.20 |
| 3607 | C | ALA | 459 | 97.296 | 35.587 | 54.579 | 1.00 | 54.74 |
| 3608 | O | ALA | 459 | 97.434 | 35.158 | 53.433 | 1.00 | 54.48 |
| 3609 | N | THR | 460 | 98.236 | 35.455 | 55.513 | 1.00 | 49.39 |
| 3610 | CA | THR | 460 | 99.494 | 34.779 | 55.224 | 1.00 | 47.02 |
| 3611 | CB | THR | 460 | 100.603 | 35.180 | 56.200 | 1.00 | 50.43 |
| 3612 | OG1 | THR | 460 | 100.077 | 35.259 | 57.532 | 1.00 | 52.34 |
| 3613 | CG2 | THR | 460 | 101.194 | 36.507 | 55.781 | 1.00 | 56.05 |
| 3614 | C | THR | 460 | 99.399 | 33.264 | 55.164 | 1.00 | 45.28 |
| 3615 | O | THR | 460 | 98.566 | 32.651 | 55.832 | 1.00 | 47.09 |
| 3616 | N | GLY | 461 | 100.303 | 32.676 | 54.386 | 1.00 | 45.02 |
| 3617 | CA | GLY | 461 | 100.351 | 31.238 | 54.190 | 1.00 | 41.47 |
| 3618 | C | GLY | 461 | 100.107 | 30.318 | 55.367 | 1.00 | 38.12 |
| 3619 | O | GLY | 461 | 99.172 | 29.516 | 55.341 | 1.00 | 41.90 |
| 3620 | N | ILE | 462 | 100.962 | 30.399 | 56.380 | 1.00 | 36.28 |
| 3621 | CA | ILE | 462 | 100.825 | 29.545 | 57.552 | 1.00 | 41.08 |
| 3622 | CB | ILE | 462 | 101.954 | 29.813 | 58.580 | 1.00 | 34.80 |
| 3623 | CG2 | ILE | 462 | 101.814 | 28.893 | 59.792 | 1.00 | 33.01 |
| 3624 | CG1 | ILE | 462 | 103.319 | 29.613 | 57.917 | 1.00 | 21.22 |
| 3625 | CD1 | ILE | 462 | 103.525 | 28.231 | 57.322 | 1.00 | 17.74 |
| 3626 | C | ILE | 462 | 99.444 | 29.683 | 58.197 | 1.00 | 47.74 |
| 3627 | O | ILE | 462 | 98.823 | 28.682 | 58.556 | 1.00 | 53.27 |
| 3628 | N | GLU | 463 | 98.940 | 30.915 | 58.266 | 1.00 | 49.04 |
| 3629 | CA | GLU | 463 | 97.626 | 31.178 | 58.852 | 1.00 | 46.29 |
| 3630 | CB | GLU | 463 | 97.358 | 32.687 | 58.929 | 1.00 | 44.06 |
| 3631 | CG | GLU | 463 | 96.076 | 33.063 | 59.677 | 1.00 | 51.03 |
| 3632 | CD | GLU | 463 | 96.101 | 32.673 | 61.150 | 1.00 | 55.15 |
| 3633 | OE1 | GLU | 463 | 96.861 | 33.290 | 61.931 | 1.00 | 50.13 |
| 3634 | OE2 | GLU | 463 | 95.348 | 31.752 | 61.529 | 1.00 | 55.86 |
| 3635 | C | GLU | 463 | 96.530 | 30.483 | 58.041 | 1.00 | 44.39 |
| 3636 | O | GLU | 463 | 95.690 | 29.774 | 58.600 | 1.00 | 47.37 |
| 3637 | N | CYS | 464 | 96.559 | 30.680 | 56.723 | 1.00 | 39.81 |
| 3638 | CA | CYS | 464 | 95.589 | 30.068 | 55.816 | 1.00 | 37.44 |
| 3639 | CB | CYS | 464 | 95.916 | 30.426 | 54.362 | 1.00 | 29.94 |
| 3640 | SG | CYS | 464 | 95.879 | 32.186 | 53.990 | 1.00 | 33.66 |
| 3641 | C | CYS | 464 | 95.630 | 28.556 | 55.973 | 1.00 | 39.78 |
| 3642 | O | CYS | 464 | 94.594 | 27.903 | 56.091 | 1.00 | 43.58 |
| 3643 | N | CYS | 465 | 96.846 | 28.016 | 55.995 | 1.00 | 44.06 |
| 3644 | CA | CYS | 465 | 97.072 | 26.583 | 56.133 | 1.00 | 43.89 |
| 3645 | CB | CYS | 465 | 98.568 | 26.275 | 56.009 | 1.00 | 39.41 |
| 3646 | SG | CYS | 465 | 98.961 | 24.513 | 55.936 | 1.00 | 40.79 |
| 3647 | C | CYS | 465 | 96.532 | 26.052 | 57.454 | 1.00 | 44.77 |
| 3648 | O | CYS | 465 | 95.883 | 25.004 | 57.490 | 1.00 | 43.29 |
| 3649 | N | MET | 466 | 96.788 | 26.794 | 58.530 | 1.00 | 50.46 |
| 3650 | CA | MET | 466 | 96.342 | 26.418 | 59.870 | 1.00 | 59.83 |

TABLE 10-continued

Structural Coordinates of Tobacco 5-Epi-Aristolochene Synthase
With Farnesyl Hydroxyphosphonate Bound

| Atom | Atom Type | Residue | Residue # | X | Y | Z | OCC | B-factor |
|---|---|---|---|---|---|---|---|---|
| 3651 | CB | MET | 466 | 96.838 | 27.429 | 60.916 | 1.00 | 58.39 |
| 3652 | CG | MET | 466 | 98.343 | 27.424 | 61.149 | 1.00 | 55.57 |
| 3653 | SD | MET | 466 | 98.825 | 28.416 | 62.560 | 1.00 | 56.88 |
| 3654 | CE | MET | 466 | 98.266 | 29.965 | 62.036 | 1.00 | 50.47 |
| 3655 | C | MET | 466 | 94.825 | 26.271 | 59.979 | 1.00 | 64.16 |
| 3656 | O | MET | 466 | 94.334 | 25.227 | 60.409 | 1.00 | 65.97 |
| 3657 | N | ARG | 467 | 94.094 | 27.319 | 59.598 | 1.00 | 67.84 |
| 3658 | CA | ARG | 467 | 92.631 | 27.320 | 59.654 | 1.00 | 69.35 |
| 3659 | CB | ARG | 467 | 92.083 | 28.744 | 59.512 | 1.00 | 75.34 |
| 3660 | CG | ARG | 467 | 92.397 | 29.655 | 60.684 | 1.00 | 84.97 |
| 3661 | CD | ARG | 467 | 91.640 | 30.965 | 60.560 | 1.00 | 96.41 |
| 3662 | NE | ARG | 467 | 92.020 | 31.944 | 61.578 | 1.00 | 100.00 |
| 3663 | CZ | ARG | 467 | 91.475 | 33.152 | 61.696 | 1.00 | 100.00 |
| 3664 | NH1 | ARG | 467 | 90.515 | 33.541 | 60.862 | 1.00 | 100.00 |
| 3665 | NH2 | ARG | 467 | 91.901 | 33.982 | 62.639 | 1.00 | 100.00 |
| 3666 | C | ARG | 467 | 91.965 | 26.415 | 58.620 | 1.00 | 64.55 |
| 3667 | O | ARG | 467 | 90.863 | 25.907 | 58.853 | 1.00 | 66.78 |
| 3668 | N | ASP | 468 | 92.631 | 26.222 | 57.485 | 1.00 | 52.01 |
| 3669 | CA | ASP | 468 | 92.108 | 25.383 | 56.412 | 1.00 | 45.50 |
| 3670 | CB | ASP | 468 | 92.825 | 25.707 | 55.097 | 1.00 | 38.83 |
| 3671 | CG | ASP | 468 | 92.140 | 25.103 | 53.886 | 1.00 | 38.56 |
| 3672 | OD1 | ASP | 468 | 92.817 | 24.928 | 52.852 | 1.00 | 35.49 |
| 3673 | OD2 | ASP | 468 | 90.925 | 24.814 | 53.953 | 1.00 | 52.91 |
| 3674 | C | ASP | 468 | 92.201 | 23.882 | 56.718 | 1.00 | 49.65 |
| 3675 | O | ASP | 468 | 91.302 | 23.120 | 56.358 | 1.00 | 53.89 |
| 3676 | N | TYR | 469 | 93.271 | 23.469 | 57.397 | 1.00 | 48.30 |
| 3677 | CA | TYR | 469 | 93.475 | 22.059 | 57.740 | 1.00 | 47.34 |
| 3678 | CB | TYR | 469 | 94.887 | 21.611 | 57.345 | 1.00 | 49.69 |
| 3679 | CG | TYR | 469 | 95.110 | 21.555 | 55.851 | 1.00 | 50.72 |
| 3680 | CD1 | TYR | 469 | 95.085 | 20.339 | 55.169 | 1.00 | 53.63 |
| 3681 | CE1 | TYR | 469 | 95.255 | 20.284 | 53.787 | 1.00 | 51.76 |
| 3682 | CD2 | TYR | 469 | 95.318 | 22.719 | 55.113 | 1.00 | 50.18 |
| 3683 | CE2 | TYR | 469 | 95.489 | 22.675 | 53.732 | 1.00 | 50.61 |
| 3684 | CZ | TYR | 469 | 95.455 | 21.456 | 53.075 | 1.00 | 54.80 |
| 3685 | OH | TYR | 469 | 95.615 | 21.407 | 51.708 | 1.00 | 57.11 |
| 3686 | C | TYR | 469 | 93.230 | 21.743 | 59.215 | 1.00 | 46.62 |
| 3687 | O | TYR | 469 | 93.180 | 20.573 | 59.605 | 1.00 | 47.10 |
| 3688 | N | GLY | 470 | 93.069 | 22.788 | 60.026 | 1.00 | 43.51 |
| 3689 | CA | GLY | 470 | 92.837 | 22.610 | 61.449 | 1.00 | 43.21 |
| 3690 | C | GLY | 470 | 94.055 | 22.038 | 62.146 | 1.00 | 45.56 |
| 3691 | O | GLY | 470 | 93.952 | 21.077 | 62.912 | 1.00 | 44.25 |
| 3692 | N | ILE | 471 | 95.215 | 22.624 | 61.860 | 1.00 | 50.47 |
| 3693 | CA | ILE | 471 | 96.488 | 22.188 | 62.433 | 1.00 | 49.97 |
| 3694 | CB | ILE | 471 | 97.415 | 21.596 | 61.342 | 1.00 | 47.18 |
| 3695 | CG2 | ILE | 471 | 96.844 | 20.285 | 60.811 | 1.00 | 47.32 |
| 3696 | CG1 | ILE | 471 | 97.613 | 22.611 | 60.211 | 1.00 | 41.43 |
| 3697 | CD1 | ILE | 471 | 98.427 | 22.094 | 59.049 | 1.00 | 46.18 |
| 3698 | C | ILE | 471 | 97.217 | 23.339 | 63.124 | 1.00 | 49.28 |
| 3699 | O | ILE | 471 | 96.894 | 24.508 | 62.907 | 1.00 | 49.58 |
| 3700 | N | SER | 472 | 98.204 | 23.000 | 63.949 | 1.00 | 49.04 |
| 3701 | CA | SER | 472 | 98.986 | 23.998 | 64.674 | 1.00 | 52.64 |
| 3702 | CB | SER | 472 | 99.748 | 23.340 | 65.829 | 1.00 | 54.48 |
| 3703 | OG | SER | 472 | 100.699 | 22.404 | 65.351 | 1.00 | 56.26 |
| 3704 | C | SER | 472 | 99.969 | 24.716 | 63.753 | 1.00 | 53.26 |
| 3705 | O | SER | 472 | 100.101 | 24.369 | 62.578 | 1.00 | 53.95 |
| 3706 | N | THR | 473 | 100.650 | 25.725 | 64.292 | 1.00 | 53.55 |
| 3707 | CA | THR | 473 | 101.634 | 26.491 | 63.531 | 1.00 | 54.18 |
| 3708 | CB | THR | 473 | 102.233 | 27.639 | 64.384 | 1.00 | 60.37 |
| 3709 | OG1 | THR | 473 | 101.180 | 28.490 | 64.855 | 1.00 | 61.07 |
| 3710 | CG2 | THR | 473 | 103.210 | 28.469 | 63.562 | 1.00 | 58.84 |
| 3711 | C | THR | 473 | 102.760 | 25.550 | 63.105 | 1.00 | 51.25 |
| 3712 | O | THR | 473 | 103.203 | 25.573 | 61.956 | 1.00 | 44.22 |
| 3713 | N | LYS | 474 | 103.173 | 24.697 | 64.038 | 1.00 | 49.57 |
| 3714 | CA | LYS | 474 | 104.236 | 23.722 | 63.821 | 1.00 | 51.50 |
| 3715 | CB | LYS | 474 | 104.440 | 22.903 | 65.098 | 1.00 | 55.84 |
| 3716 | CG | LYS | 474 | 105.605 | 21.930 | 65.063 | 1.00 | 60.97 |
| 3717 | CD | LYS | 474 | 105.778 | 21.266 | 66.421 | 1.00 | 66.81 |
| 3718 | CE | LYS | 474 | 107.011 | 20.382 | 66.462 | 1.00 | 71.89 |
| 3719 | NZ | LYS | 474 | 107.261 | 19.853 | 67.832 | 1.00 | 72.76 |
| 3720 | C | LYS | 474 | 103.924 | 22.797 | 62.646 | 1.00 | 53.47 |
| 3721 | O | LYS | 474 | 104.759 | 22.603 | 61.759 | 1.00 | 56.55 |
| 3722 | N | GLU | 475 | 102.712 | 22.249 | 62.637 | 1.00 | 54.30 |
| 3723 | CA | GLU | 475 | 102.271 | 21.342 | 61.578 | 1.00 | 54.12 |
| 3724 | CB | GLU | 475 | 100.921 | 20.719 | 61.946 | 1.00 | 49.93 |
| 3725 | CG | GLU | 475 | 100.940 | 19.925 | 63.244 | 1.00 | 54.09 |
| 3726 | CD | GLU | 475 | 99.559 | 19.471 | 63.673 | 1.00 | 56.55 |
| 3727 | OE1 | GLU | 475 | 99.055 | 18.476 | 63.111 | 1.00 | 59.40 |
| 3728 | OE2 | GLU | 475 | 98.977 | 20.109 | 64.577 | 1.00 | 54.88 |
| 3729 | C | GLU | 475 | 102.170 | 22.043 | 60.224 | 1.00 | 48.29 |
| 3730 | O | GLU | 475 | 102.514 | 21.465 | 59.192 | 1.00 | 43.53 |
| 3731 | N | ALA | 476 | 101.706 | 23.291 | 60.240 | 1.00 | 47.85 |
| 3732 | CA | ALA | 476 | 101.556 | 24.085 | 59.023 | 1.00 | 48.40 |
| 3733 | CB | ALA | 476 | 100.857 | 25.400 | 59.335 | 1.00 | 44.20 |
| 3734 | C | ALA | 476 | 102.906 | 24.348 | 58.367 | 1.00 | 45.69 |
| 3735 | O | ALA | 476 | 103.043 | 24.246 | 57.148 | 1.00 | 40.88 |
| 3736 | N | MET | 477 | 103.897 | 24.690 | 59.185 | 1.00 | 46.31 |
| 3737 | CA | MET | 477 | 105.241 | 24.956 | 58.687 | 1.00 | 47.60 |
| 3738 | CB | MET | 477 | 106.097 | 25.600 | 59.777 | 1.00 | 41.69 |
| 3739 | CG | MET | 477 | 105.533 | 26.906 | 60.286 | 1.00 | 40.46 |
| 3740 | SD | MET | 477 | 106.643 | 27.743 | 61.402 | 1.00 | 51.90 |
| 3741 | CE | MET | 477 | 106.373 | 29.438 | 60.922 | 1.00 | 53.11 |
| 3742 | C | MET | 477 | 105.882 | 23.659 | 58.213 | 1.00 | 47.15 |
| 3743 | O | MET | 477 | 106.580 | 23.637 | 57.196 | 1.00 | 43.34 |
| 3744 | N | ALA | 478 | 105.617 | 22.580 | 58.948 | 1.00 | 44.29 |
| 3745 | CA | ALA | 478 | 106.146 | 21.262 | 58.617 | 1.00 | 43.92 |
| 3746 | CB | ALA | 478 | 105.808 | 20.264 | 59.716 | 1.00 | 37.80 |
| 3747 | C | ALA | 478 | 105.601 | 20.732 | 57.272 | 1.00 | 43.29 |
| 3748 | O | ALA | 478 | 106.312 | 20.127 | 56.509 | 1.00 | 44.64 |
| 3749 | N | LYS | 479 | 104.346 | 21.116 | 53.981 | 1.00 | 45.34 |
| 3750 | CA | LYS | 479 | 103.736 | 20.720 | 55.715 | 1.00 | 50.82 |
| 3751 | CB | LYS | 479 | 102.214 | 20.847 | 55.762 | 1.00 | 57.75 |
| 3752 | CG | LYS | 479 | 101.555 | 20.268 | 54.522 | 1.00 | 65.44 |
| 3753 | CD | LYS | 479 | 100.167 | 20.814 | 54.286 | 1.00 | 68.93 |
| 3754 | CE | LYS | 479 | 99.651 | 20.332 | 52.943 | 1.00 | 68.91 |
| 3755 | NZ | LYS | 479 | 98.384 | 20.999 | 52.566 | 1.00 | 74.62 |
| 3756 | C | LYS | 479 | 104.283 | 21.581 | 54.581 | 1.00 | 47.22 |
| 3757 | O | LYS | 479 | 104.451 | 21.109 | 53.455 | 1.00 | 50.00 |
| 3758 | N | PHE | 480 | 104.526 | 22.854 | 54.878 | 1.00 | 43.15 |
| 3759 | CA | PHE | 480 | 105.076 | 23.776 | 53.894 | 1.00 | 41.41 |
| 3760 | CB | PHE | 480 | 105.089 | 25.204 | 54.443 | 1.00 | 41.63 |
| 3761 | CG | PHE | 480 | 103.894 | 26.021 | 54.033 | 1.00 | 44.23 |
| 3762 | CD1 | PHE | 480 | 102.638 | 25.432 | 53.905 | 1.00 | 41.42 |
| 3763 | CD2 | PHE | 480 | 104.026 | 27.379 | 53.756 | 1.00 | 39.25 |
| 3764 | CE1 | PHE | 480 | 101.535 | 26.182 | 53.503 | 1.00 | 36.23 |
| 3765 | CE2 | PHE | 480 | 102.929 | 28.136 | 53.353 | 1.00 | 32.42 |
| 3766 | CZ | PHE | 480 | 101.682 | 27.536 | 53.227 | 1.00 | 29.83 |
| 3767 | C | PHE | 480 | 106.485 | 23.334 | 53.515 | 1.00 | 41.98 |
| 3768 | O | PHE | 480 | 106.881 | 23.434 | 52.353 | 1.00 | 37.95 |
| 3769 | N | GLN | 481 | 107.229 | 22.824 | 54.495 | 1.00 | 41.79 |
| 3770 | CA | GLN | 481 | 108.586 | 22.342 | 54.256 | 1.00 | 41.10 |
| 3771 | CB | GLN | 481 | 109.236 | 21.868 | 55.559 | 1.00 | 39.98 |
| 3772 | CG | GLN | 481 | 109.603 | 22.993 | 56.513 | 1.00 | 47.39 |
| 3773 | CD | GLN | 481 | 110.507 | 24.034 | 55.870 | 1.00 | 56.58 |
| 3774 | OE1 | GLN | 481 | 111.605 | 23.720 | 55.406 | 1.00 | 55.49 |
| 3775 | NE2 | GLN | 481 | 110.042 | 25.279 | 55.834 | 1.00 | 58.30 |
| 3776 | C | GLN | 481 | 108.553 | 21.204 | 53.245 | 1.00 | 38.69 |
| 3777 | O | GLN | 481 | 109.386 | 21.146 | 52.340 | 1.00 | 37.55 |
| 3778 | N | ASN | 482 | 107.564 | 20.324 | 53.391 | 1.00 | 35.14 |
| 3779 | CA | ASN | 482 | 107.394 | 19.189 | 52.491 | 1.00 | 35.59 |
| 3780 | CB | ASN | 482 | 106.302 | 18.250 | 53.009 | 1.00 | 41.18 |
| 3781 | CG | ASN | 482 | 106.647 | 17.642 | 54.355 | 1.00 | 52.28 |
| 3782 | OD1 | ASN | 482 | 107.756 | 17.148 | 54.560 | 1.00 | 53.57 |
| 3783 | ND2 | ASN | 482 | 105.697 | 17.678 | 55.282 | 1.00 | 61.08 |
| 3784 | C | ASN | 482 | 107.057 | 19.657 | 51.081 | 1.00 | 32.00 |
| 3785 | O | ASN | 482 | 107.358 | 18.971 | 50.105 | 1.00 | 35.80 |
| 3786 | N | MET | 483 | 106.421 | 20.822 | 50.981 | 1.00 | 30.00 |
| 3787 | CA | MET | 483 | 106.063 | 21.391 | 49.687 | 1.00 | 29.42 |
| 3788 | CB | MET | 483 | 105.092 | 22.562 | 49.855 | 1.00 | 33.61 |
| 3789 | CG | MET | 483 | 103.693 | 22.173 | 50.303 | 1.00 | 33.22 |
| 3790 | SD | MET | 483 | 102.589 | 23.605 | 50.374 | 1.00 | 34.18 |
| 3791 | CE | MET | 483 | 102.294 | 23.881 | 48.638 | 1.00 | 31.57 |
| 3792 | C | MET | 483 | 107.330 | 21.870 | 48.991 | 1.00 | 26.58 |
| 3793 | O | MET | 483 | 107.453 | 21.778 | 47.769 | 1.00 | 26.98 |
| 3794 | N | ALA | 484 | 108.267 | 22.386 | 49.782 | 1.00 | 24.14 |
| 3795 | CA | ALA | 484 | 109.539 | 22.874 | 49.261 | 1.00 | 20.18 |
| 3796 | CB | ALA | 484 | 110.260 | 23.687 | 50.323 | 1.00 | 15.48 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 3797 | C | ALA | 484 | 110.399 | 21.694 | 48.812 | 1.00 | 18.99 |
| 3798 | O | ALA | 484 | 111.070 | 21.762 | 47.777 | 1.00 | 18.13 |
| 3799 | N | GLU | 485 | 110.360 | 20.610 | 49.587 | 1.00 | 15.88 |
| 3800 | CA | GLU | 485 | 111.115 | 19.398 | 49.274 | 1.00 | 22.72 |
| 3301 | CB | GLU | 485 | 110.965 | 18.367 | 50.391 | 1.00 | 26.33 |
| 3802 | CG | GLU | 485 | 111.571 | 18.811 | 51.719 | 1.00 | 57.96 |
| 3803 | CD | GLU | 485 | 111.355 | 17.814 | 52.853 | 1.00 | 66.33 |
| 3804 | OE1 | GLU | 485 | 110.840 | 16.702 | 52.602 | 1.00 | 74.62 |
| 3805 | OE2 | GLU | 485 | 111.704 | 18.149 | 54.006 | 1.00 | 72.14 |
| 3806 | C | GLU | 485 | 110.625 | 18.806 | 47.962 | 1.00 | 19.07 |
| 3807 | O | GLU | 485 | 111.422 | 18.403 | 47.114 | 1.00 | 23.09 |
| 3808 | N | THR | 486 | 109.306 | 18.768 | 47.802 | 1.00 | 18.34 |
| 3809 | CA | THR | 486 | 108.680 | 18.247 | 46.594 | 1.00 | 13.68 |
| 3810 | CB | THR | 486 | 107.132 | 18.239 | 46.724 | 1.00 | 19.42 |
| 3811 | OG1 | THR | 486 | 106.740 | 17.320 | 47.753 | 1.00 | 18.34 |
| 3812 | CG2 | THR | 486 | 106.474 | 17.832 | 45.409 | 1.00 | 7.13 |
| 3813 | C | THR | 486 | 109.084 | 19.126 | 45.418 | 1.00 | 12.40 |
| 3814 | O | THR | 486 | 109.432 | 18.628 | 44.347 | 1.00 | 12.64 |
| 3815 | N | ALA | 487 | 109.054 | 20.437 | 45.641 | 1.00 | 18.37 |
| 3816 | CA | ALA | 487 | 109.420 | 21.406 | 44.618 | 1.00 | 14.12 |
| 3817 | CB | ALA | 487 | 109.224 | 22.812 | 45.137 | 1.00 | 12.83 |
| 3818 | C | ALA | 487 | 110.863 | 21.195 | 44.178 | 1.00 | 11.72 |
| 3819 | O | ALA | 487 | 111.182 | 21.312 | 42.993 | 1.00 | 14.71 |
| 3820 | N | TRP | 488 | 111.731 | 20.860 | 45.128 | 1.00 | 11.21 |
| 3821 | CA | TRP | 488 | 113.129 | 20.616 | 44.801 | 1.00 | 9.46 |
| 3822 | CB | TRP | 488 | 113.985 | 20.541 | 46.061 | 1.00 | 2.00 |
| 3823 | CG | TRP | 488 | 114.586 | 21.864 | 46.394 | 1.00 | 10.22 |
| 3824 | CD2 | TRP | 488 | 115.535 | 22.596 | 45.602 | 1.00 | 8.75 |
| 3825 | CE2 | TRP | 488 | 115.798 | 23.807 | 46.279 | 1.00 | 8.09 |
| 3826 | CE3 | TRP | 488 | 116.186 | 22.345 | 44.384 | 1.00 | 8.76 |
| 3827 | CD1 | TRP | 488 | 114.322 | 22.636 | 47.488 | 1.00 | 2.81 |
| 3828 | NE1 | TRP | 488 | 115.045 | 23.807 | 47.425 | 1.00 | 14.28 |
| 3829 | CZ2 | TRP | 488 | 116.686 | 24.768 | 45.780 | 1.00 | 4.43 |
| 3830 | CZ3 | TRP | 488 | 117.072 | 23.301 | 43.885 | 1.00 | 8.98 |
| 3831 | CH2 | TRP | 488 | 117.312 | 24.497 | 44.585 | 1.00 | 9.72 |
| 3832 | C | TRP | 488 | 113.306 | 19.378 | 43.936 | 1.00 | 9.87 |
| 3833 | O | TRP | 488 | 114.112 | 19.380 | 43.005 | 1.00 | 11.24 |
| 3834 | N | LYS | 489 | 112.526 | 18.335 | 44.214 | 1.00 | 7.93 |
| 3835 | CA | LYS | 489 | 112.601 | 17.110 | 43.427 | 1.00 | 2.00 |
| 3836 | CB | LYS | 489 | 111.815 | 15.987 | 44.096 | 1.00 | 7.82 |
| 3837 | CG | LYS | 489 | 112.350 | 15.603 | 45.470 | 1.00 | 9.24 |
| 3838 | CD | LYS | 489 | 111.550 | 14.471 | 46.069 | 1.00 | 2.14 |
| 3839 | CE | LYS | 489 | 111.921 | 14.248 | 47.517 | 1.00 | 16.24 |
| 3840 | NZ | LYS | 489 | 111.056 | 13.208 | 48.146 | 1.00 | 26.26 |
| 3841 | C | LYS | 489 | 112.051 | 17.390 | 42.037 | 1.00 | 7.99 |
| 3842 | O | LYS | 489 | 112.480 | 16.784 | 41.055 | 1.00 | 11.24 |
| 3843 | N | ASP | 490 | 111.115 | 18.333 | 41.960 | 1.00 | 9.24 |
| 3844 | CA | ASP | 490 | 110.518 | 18.716 | 40.687 | 1.00 | 12.50 |
| 3845 | CB | ASP | 490 | 109.234 | 19.514 | 40.901 | 1.00 | 15.83 |
| 3846 | CG | ASP | 490 | 108.083 | 18.648 | 41.360 | 1.00 | 23.66 |
| 3847 | OD1 | ASP | 490 | 107.949 | 17.509 | 40.856 | 1.00 | 20.17 |
| 3848 | OD2 | ASP | 490 | 107.308 | 19.111 | 42.221 | 1.00 | 28.73 |
| 3849 | C | ASP | 490 | 111.501 | 19.522 | 39.856 | 1.00 | 11.20 |
| 3850 | O | ASP | 490 | 111.519 | 19.409 | 38.629 | 1.00 | 17.78 |
| 3851 | N | ILE | 491 | 112.308 | 20.345 | 40.523 | 1.00 | 16.49 |
| 3852 | CA | ILE | 491 | 113.311 | 21.149 | 39.831 | 1.00 | 15.96 |
| 3853 | CB | ILE | 491 | 113.973 | 22.183 | 40.766 | 1.00 | 14.10 |
| 3854 | CG2 | ILE | 491 | 115.138 | 22.870 | 40.058 | 1.00 | 17.39 |
| 3855 | CG1 | ILE | 491 | 112.938 | 23.221 | 41.209 | 1.00 | 20.61 |
| 3856 | CD1 | ILE | 491 | 113.493 | 24.319 | 42.097 | 1.00 | 6.59 |
| 3857 | C | ILE | 491 | 114.372 | 20.207 | 39.279 | 1.00 | 11.72 |
| 3858 | O | ILE | 491 | 114.802 | 20.342 | 38.132 | 1.00 | 18.27 |
| 3859 | N | ASN | 492 | 114.744 | 19.217 | 40.084 | 1.00 | 9.30 |
| 3860 | CA | ASN | 492 | 115.739 | 18.232 | 39.684 | 1.00 | 8.49 |
| 3861 | CB | ASN | 492 | 116.078 | 17.320 | 40.866 | 1.00 | 8.53 |
| 3862 | CG | ASN | 492 | 116.793 | 18.062 | 41.986 | 1.00 | 2.00 |
| 3863 | OD1 | ASN | 492 | 117.444 | 19.081 | 41.756 | 1.00 | 2.00 |
| 3864 | ND2 | ASN | 492 | 116.674 | 17.554 | 43.204 | 1.00 | 9.30 |
| 3865 | C | ASN | 492 | 115.296 | 17.421 | 38.458 | 1.00 | 6.69 |
| 3866 | O | ASN | 492 | 116.120 | 17.067 | 37.618 | 1.00 | 15.10 |
| 3867 | N | GLU | 493 | 113.994 | 17.157 | 38.345 | 1.00 | 11.11 |
| 3868 | CA | GLU | 493 | 113.452 | 16.420 | 37.203 | 1.00 | 6.79 |
| 3869 | CB | GLU | 493 | 112.036 | 15.929 | 37.490 | 1.00 | 14.43 |
| 3870 | CG | GLU | 493 | 111.966 | 14.681 | 38.344 | 1.00 | 35.11 |
| 3871 | CD | GLU | 493 | 110.554 | 14.143 | 38.504 | 1.00 | 39.54 |
| 3872 | OE1 | GLU | 493 | 109.669 | 14.505 | 37.695 | 1.00 | 36.96 |
| 3873 | OE2 | GLU | 493 | 110.335 | 13.345 | 39.441 | 1.00 | 44.74 |
| 3874 | C | GLU | 493 | 113.420 | 17.284 | 35.947 | 1.00 | 15.20 |
| 3875 | O | GLU | 493 | 113.539 | 16.777 | 34.828 | 1.00 | 19.79 |
| 3876 | N | GLY | 494 | 113.234 | 18.588 | 36.140 | 1.00 | 15.92 |
| 3877 | CA | GLY | 494 | 113.176 | 19.512 | 35.021 | 1.00 | 13.61 |
| 3878 | C | GLY | 494 | 114.488 | 19.613 | 34.276 | 1.00 | 18.91 |
| 3879 | O | GLY | 494 | 114.507 | 19.822 | 33.061 | 1.00 | 23.19 |
| 3880 | N | LEU | 495 | 115.583 | 19.437 | 35.008 | 1.00 | 18.93 |
| 3881 | CA | LEU | 495 | 116.927 | 19.508 | 34.445 | 1.00 | 18.10 |
| 3882 | CB | LEU | 495 | 117.955 | 19.662 | 35.571 | 1.00 | 12.15 |
| 3883 | CG | LEU | 495 | 117.764 | 20.846 | 36.527 | 1.00 | 11.37 |
| 3884 | CD1 | LEU | 495 | 118.788 | 20.781 | 37.650 | 1.00 | 2.00 |
| 3885 | CD2 | LEU | 495 | 117.866 | 22.164 | 35.771 | 1.00 | 6.14 |
| 3886 | C | LEU | 495 | 117.279 | 18.289 | 33.593 | 1.00 | 21.97 |
| 3887 | O | LEU | 495 | 118.146 | 18.366 | 32.717 | 1.00 | 20.13 |
| 3888 | N | LEU | 496 | 116.602 | 17.171 | 33.849 | 1.00 | 21.91 |
| 3889 | CA | LEU | 496 | 116.851 | 15.931 | 33.118 | 1.00 | 15.41 |
| 3890 | CB | LEU | 496 | 116.126 | 14.760 | 33.784 | 1.00 | 8.37 |
| 3891 | CG | LEU | 496 | 116.604 | 14.435 | 35.204 | 1.00 | 10.05 |
| 3892 | CD1 | LEU | 496 | 115.819 | 13.269 | 35.769 | 1.00 | 2.00 |
| 3893 | CD2 | LEU | 496 | 118.094 | 14.121 | 35.206 | 1.00 | 5.54 |
| 3894 | C | LEU | 496 | 116.492 | 16.017 | 31.641 | 1.00 | 14.28 |
| 3895 | O | LEU | 496 | 115.471 | 16.593 | 31.269 | 1.00 | 19.94 |
| 3896 | N | ARG | 497 | 117.360 | 15.454 | 30.808 | 1.00 | 16.05 |
| 3897 | CA | ARG | 497 | 117.184 | 15.456 | 29.359 | 1.00 | 18.50 |
| 3898 | CB | ARG | 497 | 118.516 | 15.107 | 28.682 | 1.00 | 19.50 |
| 3899 | CG | ARG | 497 | 119.665 | 16.035 | 29.066 | 1.00 | 28.42 |
| 3900 | CD | ARG | 497 | 121.024 | 15.363 | 28.908 | 1.00 | 24.39 |
| 3901 | NE | ARG | 497 | 121.803 | 15.905 | 27.797 | 1.00 | 27.16 |
| 3902 | CZ | ARG | 497 | 122.978 | 16.517 | 27.927 | 1.00 | 26.59 |
| 3903 | NH1 | ARG | 497 | 123.525 | 16.677 | 29.125 | 1.00 | 14.53 |
| 3904 | NH2 | ARG | 497 | 123.618 | 16.955 | 26.850 | 1.00 | 32.59 |
| 3905 | C | ARG | 497 | 116.099 | 14.471 | 28.922 | 1.00 | 23.25 |
| 3906 | O | ARG | 497 | 115.890 | 13.441 | 29.566 | 1.00 | 25.86 |
| 3907 | N | PRO | 498 | 115.369 | 14.793 | 27.838 | 1.00 | 22.25 |
| 3908 | CD | PRO | 498 | 114.524 | 13.808 | 27.150 | 1.00 | 25.52 |
| 3909 | CA | PRO | 498 | 115.491 | 16.003 | 27.017 | 1.00 | 25.55 |
| 3910 | CB | PRO | 498 | 114.781 | 15.612 | 25.715 | 1.00 | 17.40 |
| 3911 | CG | PRO | 498 | 114.819 | 14.112 | 25.715 | 1.00 | 25.69 |
| 3912 | C | PRO | 498 | 114.785 | 17.192 | 27.662 | 1.00 | 28.98 |
| 3913 | O | PRO | 498 | 113.609 | 17.104 | 28.021 | 1.00 | 33.06 |
| 3914 | N | THR | 499 | 115.506 | 18.299 | 27.804 | 1.00 | 24.14 |
| 3915 | CA | THR | 499 | 114.949 | 19.511 | 28.391 | 1.00 | 15.92 |
| 3916 | CB | THR | 499 | 116.070 | 20.473 | 28.835 | 1.00 | 16.49 |
| 3917 | OG1 | THR | 499 | 116.946 | 20.735 | 27.730 | 1.00 | 6.47 |
| 3918 | CG2 | THR | 499 | 116.870 | 19.862 | 29.983 | 1.00 | 10.26 |
| 3919 | C | THR | 499 | 114.043 | 20.205 | 27.374 | 1.00 | 19.26 |
| 3920 | O | THR | 499 | 114.329 | 20.205 | 26.174 | 1.00 | 30.87 |
| 3921 | N | PRO | 500 | 112.919 | 20.776 | 27.836 | 1.00 | 16.60 |
| 3922 | CD | PRO | 500 | 112.472 | 20.794 | 29.239 | 1.00 | 9.65 |
| 3923 | CA | PRO | 500 | 111.959 | 21.473 | 26.971 | 1.00 | 19.15 |
| 3924 | CB | PRO | 500 | 110.870 | 21.907 | 27.954 | 1.00 | 16.41 |
| 3925 | CG | PRO | 500 | 111.599 | 22.004 | 29.267 | 1.00 | 14.64 |
| 3926 | C | PRO | 500 | 112.569 | 22.656 | 26.213 | 1.00 | 26.43 |
| 3927 | O | PRO | 500 | 112.131 | 23.001 | 25.111 | 1.00 | 28.97 |
| 3928 | N | VAL | 501 | 113.580 | 23.266 | 26.824 | 1.00 | 27.74 |
| 3929 | CA | VAL | 501 | 114.317 | 24.393 | 26.253 | 1.00 | 27.33 |
| 3930 | CB | VAL | 501 | 113.874 | 25.749 | 26.867 | 1.00 | 25.49 |
| 3931 | CG1 | VAL | 501 | 112.495 | 26.136 | 26.367 | 1.00 | 27.78 |
| 3932 | CG2 | VAL | 501 | 113.880 | 25.675 | 28.386 | 1.00 | 25.11 |
| 3933 | C | VAL | 501 | 115.792 | 24.149 | 26.572 | 1.00 | 27.50 |
| 3934 | O | VAL | 501 | 116.118 | 23.190 | 27.268 | 1.00 | 34.26 |
| 3935 | N | SER | 502 | 116.685 | 24.991 | 26.059 | 1.00 | 27.56 |
| 3936 | CA | SER | 502 | 118.111 | 24.821 | 26.336 | 1.00 | 26.62 |
| 3937 | CB | SER | 502 | 118.942 | 25.802 | 25.513 | 1.00 | 31.78 |
| 3938 | OG | SER | 502 | 118.853 | 25.497 | 24.133 | 1.00 | 55.84 |
| 3939 | C | SER | 502 | 118.407 | 25.000 | 27.823 | 1.00 | 30.86 |
| 3940 | O | SER | 502 | 117.759 | 25.801 | 28.505 | 1.00 | 31.25 |
| 3941 | N | THR | 503 | 119.387 | 24.247 | 28.318 | 1.00 | 31.45 |
| 3942 | CA | THR | 503 | 119.785 | 24.296 | 29.726 | 1.00 | 32.20 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 3943 | CB | THR | 503 | 121.008 | 23.389 | 29.989 | 1.00 | 33.25 |
| 3944 | OG1 | THR | 503 | 120.732 | 22.067 | 29.511 | 1.00 | 46.44 |
| 3945 | CG2 | THR | 503 | 121.316 | 23.320 | 31.478 | 1.00 | 33.35 |
| 3946 | C | THR | 503 | 120.119 | 25.722 | 30.162 | 1.00 | 25.43 |
| 3947 | O | THR | 503 | 119.955 | 26.087 | 31.331 | 1.00 | 17.17 |
| 3948 | N | GLU | 504 | 120.569 | 26.522 | 29.200 | 1.00 | 21.60 |
| 3949 | CA | GLU | 504 | 120.931 | 27.914 | 29.433 | 1.00 | 21.35 |
| 3950 | CB | GLU | 504 | 121.355 | 28.549 | 28.104 | 1.00 | 16.54 |
| 3951 | CG | GLU | 504 | 121.779 | 30.009 | 28.189 | 1.00 | 26.78 |
| 3952 | CD | GLU | 504 | 122.043 | 30.642 | 26.825 | 1.00 | 35.29 |
| 3953 | OE1 | GLU | 504 | 121.832 | 29.971 | 25.789 | 1.00 | 38.25 |
| 3954 | OE2 | GLU | 504 | 122.460 | 31.821 | 26.793 | 1.00 | 34.16 |
| 3955 | C | GLU | 504 | 119.747 | 28.680 | 30.028 | 1.00 | 20.56 |
| 3956 | O | GLU | 504 | 119.924 | 29.595 | 30.837 | 1.00 | 14.15 |
| 3957 | N | PHE | 505 | 118.541 | 28.251 | 29.665 | 1.00 | 18.81 |
| 3958 | CA | PHE | 505 | 117.320 | 28.896 | 30.126 | 1.00 | 15.87 |
| 3959 | CB | PHE | 505 | 116.330 | 28.995 | 28.966 | 1.00 | 13.36 |
| 3960 | CG | PHE | 505 | 116.892 | 29.710 | 27.769 | 1.00 | 20.57 |
| 3961 | CD1 | PHE | 505 | 117.193 | 29.013 | 26.602 | 1.00 | 24.10 |
| 3962 | CD2 | PHE | 505 | 117.183 | 31.070 | 27.831 | 1.00 | 20.76 |
| 3963 | CE1 | PHE | 505 | 117.782 | 29.658 | 25.517 | 1.00 | 19.64 |
| 3964 | CE2 | PHE | 505 | 117.772 | 31.724 | 26.754 | 1.00 | 25.52 |
| 3965 | CZ | PHE | 505 | 118.072 | 31.015 | 25.595 | 1.00 | 26.72 |
| 3966 | C | PHE | 505 | 116.675 | 28.274 | 31.358 | 1.00 | 15.98 |
| 3967 | O | PHE | 505 | 115.703 | 28.808 | 31.886 | 1.00 | 16.03 |
| 3968 | N | LEU | 506 | 117.232 | 27.162 | 31.829 | 1.00 | 16.47 |
| 3969 | CA | LEU | 506 | 116.712 | 26.492 | 33.018 | 1.00 | 10.03 |
| 3970 | CB | LEU | 506 | 116.774 | 24.972 | 32.856 | 1.00 | 19.45 |
| 3971 | CG | LEU | 506 | 115.962 | 24.330 | 31.729 | 1.00 | 25.84 |
| 3972 | CD1 | LEU | 506 | 116.268 | 22.852 | 31.690 | 1.00 | 29.46 |
| 3973 | CD2 | LEU | 506 | 114.473 | 24.557 | 31.928 | 1.00 | 24.50 |
| 3974 | C | LEU | 506 | 117.503 | 26.895 | 34.254 | 1.00 | 11.68 |
| 3975 | O | LEU | 506 | 116.967 | 26.926 | 35.365 | 1.00 | 15.18 |
| 3976 | N | THR | 507 | 118.781 | 27.210 | 34.054 | 1.00 | 10.27 |
| 3977 | CA | THR | 507 | 119.662 | 27.601 | 35.151 | 1.00 | 7.47 |
| 3978 | CB | THR | 507 | 121.108 | 27.838 | 34.671 | 1.00 | 10.86 |
| 3979 | OG1 | THR | 507 | 121.492 | 26.798 | 33.762 | 1.00 | 20.06 |
| 3980 | CG2 | THR | 507 | 122.058 | 27.824 | 35.852 | 1.00 | 2.66 |
| 3981 | C | THR | 507 | 119.181 | 28.824 | 35.936 | 1.00 | 10.65 |
| 3982 | O | THR | 507 | 119.229 | 28.821 | 37.167 | 1.00 | 14.58 |
| 3983 | N | PRO | 508 | 118.718 | 29.887 | 35.242 | 1.00 | 8.73 |
| 3984 | CD | PRO | 508 | 118.680 | 30.110 | 33.784 | 1.00 | 7.34 |
| 3985 | CA | PRO | 508 | 118.244 | 31.080 | 35.956 | 1.00 | 5.70 |
| 3986 | CB | PRO | 508 | 117.717 | 31.959 | 34.826 | 1.00 | 8.88 |
| 3987 | CG | PRO | 508 | 118.630 | 31.616 | 33.688 | 1.00 | 2.00 |
| 3988 | C | PRO | 508 | 117.141 | 30.742 | 36.955 | 1.00 | 16.13 |
| 3989 | O | PRO | 508 | 117.109 | 31.282 | 38.064 | 1.00 | 19.06 |
| 3990 | N | ILE | 509 | 116.254 | 29.831 | 36.555 | 1.00 | 12.82 |
| 3991 | CA | ILE | 509 | 115.149 | 29.390 | 37.401 | 1.00 | 7.60 |
| 3992 | CB | ILE | 509 | 114.201 | 28.444 | 36.635 | 1.00 | 13.85 |
| 3993 | CG2 | ILE | 509 | 113.160 | 27.865 | 37.577 | 1.00 | 3.89 |
| 3994 | CG1 | ILE | 509 | 113.533 | 29.189 | 35.477 | 1.00 | 8.63 |
| 3995 | CD1 | ILE | 509 | 112.681 | 28.301 | 34.597 | 1.00 | 16.09 |
| 3996 | C | ILE | 509 | 115.723 | 28.657 | 38.604 | 1.00 | 10.09 |
| 3997 | O | ILE | 509 | 115.320 | 28.906 | 39.744 | 1.00 | 13.81 |
| 3998 | N | LEU | 510 | 116.670 | 27.759 | 38.335 | 1.00 | 10.69 |
| 3999 | CA | LEU | 510 | 117.347 | 26.983 | 39.376 | 1.00 | 8.28 |
| 4000 | CB | LEU | 510 | 118.381 | 26.047 | 38.738 | 1.00 | 13.30 |
| 4001 | CG | LEU | 510 | 119.429 | 25.349 | 39.612 | 1.00 | 10.83 |
| 4002 | CD1 | LEU | 510 | 118.781 | 24.553 | 40.736 | 1.00 | 9.01 |
| 4003 | CD2 | LEU | 510 | 120.267 | 24.444 | 38.728 | 1.00 | 2.40 |
| 4004 | C | LEU | 510 | 118.033 | 27.927 | 40.358 | 1.00 | 4.13 |
| 4005 | O | LEU | 510 | 117.860 | 27.806 | 41.570 | 1.00 | 2.43 |
| 4006 | N | ASN | 511 | 118.778 | 28.890 | 39.819 | 1.00 | 12.14 |
| 4007 | CA | ASN | 511 | 119.487 | 29.875 | 40.627 | 1.00 | 11.57 |
| 4008 | CB | ASN | 511 | 120.347 | 30.773 | 39.743 | 1.00 | 12.88 |
| 4009 | CG | ASN | 511 | 121.567 | 30.054 | 39.208 | 1.00 | 18.35 |
| 4010 | OD1 | ASN | 511 | 122.137 | 29.196 | 39.881 | 1.00 | 15.86 |
| 4011 | ND2 | ASN | 511 | 121.972 | 30.396 | 37.991 | 1.00 | 27.20 |
| 4012 | C | ASN | 511 | 118.553 | 30.710 | 41.487 | 1.00 | 11.23 |
| 4013 | O | ASN | 511 | 118.883 | 31.018 | 42.634 | 1.00 | 9.07 |
| 4014 | N | LEU | 512 | 117.387 | 31.058 | 40.941 | 1.00 | 13.33 |
| 4015 | CA | LEU | 512 | 116.393 | 31.837 | 41.683 | 1.00 | 8.79 |
| 4016 | CB | LEU | 512 | 115.168 | 32.131 | 40.814 | 1.00 | 13.75 |
| 4017 | CG | LEU | 512 | 115.255 | 33.332 | 39.865 | 1.00 | 12.09 |
| 4018 | CD1 | LEU | 512 | 114.100 | 33.306 | 38.884 | 1.00 | 2.00 |
| 4019 | CD2 | LEU | 512 | 115.256 | 34.623 | 40.667 | 1.00 | 2.00 |
| 4020 | C | LEU | 512 | 115.975 | 31.083 | 42.940 | 1.00 | 10.14 |
| 4021 | O | LEU | 512 | 115.810 | 31.682 | 44.002 | 1.00 | 13.04 |
| 4022 | N | ALA | 513 | 115.836 | 29.764 | 42.819 | 1.00 | 10.74 |
| 4023 | CA | ALA | 513 | 115.464 | 28.916 | 43.951 | 1.00 | 12.16 |
| 4024 | CB | ALA | 513 | 115.097 | 27.523 | 43.464 | 1.00 | 14.93 |
| 4025 | C | ALA | 513 | 116.621 | 28.842 | 44.947 | 1.00 | 13.31 |
| 4026 | O | ALA | 513 | 116.408 | 28.757 | 46.157 | 1.00 | 9.13 |
| 4027 | N | ARG | 514 | 117.848 | 28.879 | 44.424 | 1.00 | 19.25 |
| 4028 | CA | ARG | 514 | 119.048 | 28.834 | 45.253 | 1.00 | 17.40 |
| 4029 | CB | ARG | 514 | 120.294 | 28.644 | 44.382 | 1.00 | 14.56 |
| 4030 | CG | ARG | 514 | 120.493 | 27.229 | 43.863 | 1.00 | 4.10 |
| 4031 | CD | ARG | 514 | 121.602 | 27.170 | 42.823 | 1.00 | 9.06 |
| 4032 | NE | ARG | 514 | 121.943 | 25.793 | 42.471 | 1.00 | 17.13 |
| 4033 | CZ | ARG | 514 | 122.653 | 25.434 | 41.403 | 1.00 | 16.59 |
| 4034 | NH1 | ARG | 514 | 123.107 | 26.346 | 40.554 | 1.00 | 8.47 |
| 4035 | NH2 | ARG | 514 | 122.929 | 24.154 | 41.197 | 1.00 | 15.58 |
| 4036 | C | ARG | 514 | 119.190 | 30.106 | 46.084 | 1.00 | 13.80 |
| 4037 | O | ARG | 514 | 119.522 | 30.051 | 47.270 | 1.00 | 10.51 |
| 4038 | N | ILE | 515 | 118.901 | 31.247 | 45.466 | 1.00 | 15.59 |
| 4039 | CA | ILE | 515 | 119.011 | 32.535 | 46.147 | 1.00 | 20.36 |
| 4040 | CB | ILE | 515 | 118.764 | 33.718 | 45.194 | 1.00 | 12.70 |
| 4041 | CG2 | ILE | 515 | 119.221 | 35.007 | 45.851 | 1.00 | 25.50 |
| 4042 | CG1 | ILE | 515 | 119.567 | 33.534 | 43.910 | 1.00 | 19.52 |
| 4043 | CD1 | ILE | 515 | 119.220 | 34.523 | 42.828 | 1.00 | 29.86 |
| 4044 | C | ILE | 515 | 118.085 | 32.672 | 47.353 | 1.00 | 17.44 |
| 4045 | O | ILE | 515 | 118.477 | 33.257 | 48.359 | 1.00 | 19.69 |
| 4046 | N | VAL | 516 | 116.868 | 32.136 | 47.258 | 1.00 | 21.26 |
| 4047 | CA | VAL | 516 | 115.915 | 32.218 | 48.369 | 1.00 | 23.09 |
| 4048 | CB | VAL | 516 | 114.504 | 31.679 | 48.008 | 1.00 | 32.21 |
| 4049 | CG1 | VAL | 516 | 113.444 | 32.441 | 48.787 | 1.00 | 27.43 |
| 4050 | CG2 | VAL | 516 | 114.244 | 31.755 | 46.526 | 1.00 | 29.34 |
| 4051 | C | VAL | 516 | 116.424 | 31.382 | 49.535 | 1.00 | 20.14 |
| 4052 | O | VAL | 516 | 116.429 | 31.835 | 50.681 | 1.00 | 22.46 |
| 4053 | N | GLU | 517 | 116.833 | 30.154 | 49.229 | 1.00 | 21.26 |
| 4054 | CA | GLU | 517 | 117.352 | 29.230 | 50.231 | 1.00 | 23.87 |
| 4055 | CB | GLU | 517 | 117.859 | 27.949 | 49.555 | 1.00 | 24.13 |
| 4056 | CG | GLU | 517 | 116.765 | 27.008 | 49.049 | 1.00 | 27.64 |
| 4057 | CD | GLU | 517 | 116.153 | 26.132 | 50.143 | 1.00 | 36.07 |
| 4058 | OE1 | GLU | 517 | 116.480 | 26.314 | 51.336 | 1.00 | 40.38 |
| 4059 | OE2 | GLU | 517 | 115.338 | 25.248 | 49.804 | 1.00 | 38.38 |
| 4060 | C | GLU | 517 | 118.484 | 29.872 | 51.024 | 1.00 | 25.33 |
| 4061 | O | GLU | 517 | 118.488 | 29.840 | 52.255 | 1.00 | 28.96 |
| 4062 | N | VAL | 518 | 119.411 | 30.492 | 50.297 | 1.00 | 22.43 |
| 4063 | CA | VAL | 518 | 120.577 | 31.156 | 50.874 | 1.00 | 22.95 |
| 4064 | CB | VAL | 518 | 121.605 | 31.482 | 49.762 | 1.00 | 24.42 |
| 4065 | CG1 | VAL | 518 | 122.767 | 32.289 | 50.313 | 1.00 | 23.12 |
| 4066 | CG2 | VAL | 518 | 122.105 | 30.194 | 49.125 | 1.00 | 20.43 |
| 4067 | C | VAL | 518 | 120.239 | 32.436 | 51.649 | 1.00 | 24.42 |
| 4068 | O | VAL | 518 | 120.850 | 32.725 | 52.683 | 1.00 | 23.34 |
| 4069 | N | THR | 519 | 119.267 | 33.192 | 51.145 | 1.00 | 22.60 |
| 4070 | CA | THR | 519 | 118.846 | 34.443 | 51.769 | 1.00 | 20.24 |
| 4071 | CB | THR | 519 | 118.044 | 35.305 | 50.773 | 1.00 | 23.46 |
| 4072 | OG1 | THR | 519 | 118.872 | 35.615 | 49.646 | 1.00 | 23.28 |
| 4073 | CG2 | THR | 519 | 117.597 | 36.601 | 51.410 | 1.00 | 22.46 |
| 4074 | C | THR | 519 | 118.051 | 34.232 | 53.058 | 1.00 | 25.34 |
| 4075 | O | THR | 519 | 118.164 | 35.020 | 54.000 | 1.00 | 24.48 |
| 4076 | N | TYR | 520 | 117.261 | 33.162 | 53.105 | 1.00 | 30.17 |
| 4077 | CA | TYR | 520 | 116.461 | 32.848 | 54.290 | 1.00 | 34.43 |
| 4078 | CB | TYR | 520 | 115.017 | 32.528 | 53.892 | 1.00 | 35.49 |
| 4079 | CG | TYR | 520 | 114.238 | 33.696 | 53.330 | 1.00 | 32.60 |
| 4080 | CD1 | TYR | 520 | 114.481 | 34.171 | 52.041 | 1.00 | 27.24 |
| 4081 | CE1 | TYR | 520 | 113.758 | 35.242 | 51.520 | 1.00 | 34.38 |
| 4082 | CD2 | TYR | 520 | 113.247 | 34.321 | 54.087 | 1.00 | 30.57 |
| 4083 | CE2 | TYR | 520 | 112.516 | 35.392 | 53.577 | 1.00 | 22.83 |
| 4084 | CZ | TYR | 520 | 112.777 | 35.848 | 52.294 | 1.00 | 34.91 |
| 4085 | OH | TYR | 520 | 112.070 | 36.916 | 51.787 | 1.00 | 38.85 |
| 4086 | C | TYR | 520 | 117.047 | 31.663 | 55.058 | 1.00 | 37.02 |
| 4087 | O | TYR | 520 | 116.321 | 30.937 | 55.740 | 1.00 | 41.01 |
| 4088 | N | ILE | 521 | 118.361 | 31.483 | 54.956 | 1.00 | 39.45 |

TABLE 10-continued

Structural Coordinates of Tobacco 5-Epi-Aristolochene Synthase
With Farnesyl Hydroxyphosphonate Bound

| Atom | Atom Type | Residue | Residue # | X | Y | Z | OCC | B-factor |
|---|---|---|---|---|---|---|---|---|
| 4089 | CA | ILE | 521 | 119.048 | 30.380 | 55.621 | 1.00 | 41.53 |
| 4090 | CB | ILE | 521 | 120.561 | 30.363 | 55.251 | 1.00 | 34.97 |
| 4091 | CG2 | ILE | 521 | 121.263 | 31.607 | 55.775 | 1.00 | 33.59 |
| 4092 | CG1 | ILE | 521 | 121.228 | 29.087 | 55.770 | 1.00 | 32.90 |
| 4093 | CD1 | ILE | 521 | 122.620 | 28.865 | 55.224 | 1.00 | 16.56 |
| 4094 | C | ILE | 521 | 118.841 | 30.384 | 57.140 | 1.00 | 51.61 |
| 4095 | O | ILE | 521 | 118.649 | 29.329 | 57.750 | 1.00 | 55.56 |
| 4096 | N | HIS | 522 | 118.840 | 31.573 | 57.737 | 1.00 | 57.98 |
| 4097 | CA | HIS | 522 | 118.634 | 31.715 | 59.176 | 1.00 | 63.62 |
| 4098 | CB | HIS | 522 | 119.500 | 32.851 | 59.730 | 1.00 | 73.38 |
| 4099 | CG | HIS | 522 | 120.971 | 32.581 | 59.659 | 1.00 | 84.65 |
| 4100 | CD2 | HIS | 522 | 122.020 | 33.405 | 59.421 | 1.00 | 85.52 |
| 4101 | ND1 | HIS | 522 | 121.508 | 31.324 | 59.848 | 1.00 | 87.86 |
| 4102 | CE1 | HIS | 522 | 122.822 | 31.386 | 59.729 | 1.00 | 88.53 |
| 4103 | NE2 | HIS | 522 | 123.158 | 32.637 | 59.470 | 1.00 | 88.81 |
| 4104 | C | HIS | 522 | 117.159 | 31.977 | 59.482 | 1.00 | 63.87 |
| 4105 | O | HIS | 522 | 116.816 | 32.500 | 60.546 | 1.00 | 62.90 |
| 4106 | N | ASN | 523 | 116.300 | 31.606 | 58.534 | 1.00 | 61.66 |
| 4107 | CA | ASN | 523 | 114.850 | 31.771 | 58.635 | 1.00 | 60.61 |
| 4108 | CB | ASN | 523 | 114.273 | 30.822 | 59.691 | 1.00 | 60.04 |
| 4109 | CG | ASN | 523 | 112.807 | 30.509 | 59.453 | 1.00 | 59.80 |
| 4110 | OD1 | ASN | 523 | 112.388 | 30.266 | 58.319 | 1.00 | 62.26 |
| 4111 | ND2 | ASN | 523 | 112.021 | 30.510 | 60.522 | 1.00 | 59.58 |
| 4112 | C | ASN | 523 | 114.434 | 33.220 | 58.910 | 1.00 | 60.32 |
| 4113 | O | ASN | 523 | 113.481 | 33.486 | 59.649 | 1.00 | 55.47 |
| 4114 | N | LEU | 524 | 115.162 | 34.149 | 58.295 | 1.00 | 61.14 |
| 4115 | CA | LEU | 524 | 114.905 | 35.577 | 58.436 | 1.00 | 59.79 |
| 4116 | CB | LEU | 524 | 115.935 | 36.223 | 59.371 | 1.00 | 62.62 |
| 4117 | CG | LEU | 524 | 115.945 | 35.764 | 60.835 | 1.00 | 65.24 |
| 4118 | CD1 | LEU | 524 | 117.147 | 36.347 | 61.567 | 1.00 | 65.21 |
| 4119 | CD2 | LEU | 524 | 114.642 | 36.163 | 61.521 | 1.00 | 62.62 |
| 4120 | C | LEU | 524 | 114.966 | 36.235 | 57.065 | 1.00 | 59.79 |
| 4121 | O | LEU | 524 | 115.721 | 35.800 | 56.189 | 1.00 | 56.91 |
| 4122 | N | ASP | 525 | 114.156 | 37.274 | 56.882 | 1.00 | 62.76 |
| 4123 | CA | ASP | 525 | 114.100 | 38.006 | 55.620 | 1.00 | 59.59 |
| 4124 | CB | ASP | 525 | 112.987 | 39.055 | 55.670 | 1.00 | 58.10 |
| 4125 | CG | ASP | 525 | 112.641 | 39.608 | 54.302 | 1.00 | 60.27 |
| 4126 | OD1 | ASP | 525 | 113.331 | 39.276 | 53.315 | 1.00 | 58.07 |
| 4127 | OD2 | ASP | 525 | 111.660 | 40.374 | 54.210 | 1.00 | 64.63 |
| 4128 | C | ASP | 525 | 115.448 | 38.668 | 55.332 | 1.00 | 59.32 |
| 4129 | O | ASP | 525 | 115.753 | 39.740 | 55.854 | 1.00 | 63.36 |
| 4130 | N | GLY | 526 | 116.239 | 38.028 | 54.478 | 1.00 | 58.65 |
| 4131 | CA | GLY | 526 | 117.557 | 38.536 | 54.149 | 1.00 | 55.69 |
| 4132 | C | GLY | 526 | 117.641 | 39.797 | 53.316 | 1.00 | 53.62 |
| 4133 | O | GLY | 526 | 118.648 | 40.502 | 53.372 | 1.00 | 60.05 |
| 4134 | N | TYR | 527 | 116.607 | 40.085 | 52.534 | 1.00 | 51.88 |
| 4135 | CA | TYR | 527 | 116.617 | 41.285 | 51.702 | 1.00 | 55.73 |
| 4136 | CB | TYR | 527 | 115.648 | 41.119 | 50.545 | 1.00 | 55.31 |
| 4137 | CG | TYR | 527 | 115.562 | 42.295 | 49.598 | 1.00 | 57.45 |
| 4138 | CD1 | TYR | 527 | 116.330 | 42.336 | 48.433 | 1.00 | 58.75 |
| 4139 | CE1 | TYR | 527 | 116.193 | 43.375 | 47.518 | 1.00 | 59.49 |
| 4140 | CD2 | TYR | 527 | 114.656 | 43.332 | 49.824 | 1.00 | 58.17 |
| 4141 | CE2 | TYR | 527 | 114.511 | 44.373 | 48.917 | 1.00 | 56.67 |
| 4142 | CZ | TYR | 527 | 115.282 | 44.388 | 47.767 | 1.00 | 57.63 |
| 4143 | OH | TYR | 527 | 115.159 | 45.420 | 46.868 | 1.00 | 55.43 |
| 4144 | C | TYR | 527 | 116.266 | 42.524 | 52.517 | 1.00 | 58.54 |
| 4145 | O | TYR | 527 | 116.862 | 43.593 | 52.342 | 1.00 | 58.64 |
| 4146 | N | THR | 528 | 115.271 | 42.383 | 53.386 | 1.00 | 59.24 |
| 4147 | CA | THR | 528 | 114.855 | 43.486 | 54.238 | 1.00 | 59.20 |
| 4148 | CB | THR | 528 | 113.447 | 43.253 | 54.836 | 1.00 | 54.20 |
| 4149 | OG1 | THR | 528 | 112.504 | 43.053 | 53.776 | 1.00 | 47.41 |
| 4150 | CG2 | THR | 528 | 113.010 | 44.458 | 55.655 | 1.00 | 54.59 |
| 4151 | C | THR | 528 | 115.887 | 43.653 | 55.356 | 1.00 | 60.28 |
| 4152 | O | THR | 528 | 116.168 | 44.773 | 55.787 | 1.00 | 63.64 |
| 4153 | N | HIS | 529 | 116.464 | 42.533 | 55.792 | 1.00 | 61.45 |
| 4154 | CA | HIS | 529 | 117.484 | 42.512 | 56.842 | 1.00 | 66.52 |
| 4155 | CB | HIS | 529 | 116.984 | 41.721 | 58.060 | 1.00 | 66.73 |
| 4156 | CG | HIS | 529 | 115.652 | 42.169 | 58.576 | 1.00 | 71.41 |
| 4157 | CD2 | HIS | 529 | 115.119 | 43.407 | 58.721 | 1.00 | 72.13 |
| 4158 | ND1 | HIS | 529 | 114.688 | 41.286 | 59.010 | 1.00 | 74.46 |
| 4159 | CE1 | HIS | 529 | 113.618 | 41.958 | 59.398 | 1.00 | 72.55 |
| 4160 | NE2 | HIS | 529 | 113.856 | 43.248 | 59.232 | 1.00 | 70.77 |
| 4161 | C | HIS | 529 | 118.743 | 41.844 | 56.273 | 1.00 | 66.01 |
| 4162 | O | HIS | 529 | 119.005 | 40.665 | 56.528 | 1.00 | 68.54 |
| 4163 | N | PRO | 530 | 119.540 | 42.598 | 55.492 | 1.00 | 63.94 |
| 4164 | CD | PRO | 530 | 119.254 | 43.981 | 55.082 | 1.00 | 59.34 |
| 4165 | CA | PRO | 530 | 120.778 | 42.128 | 54.856 | 1.00 | 66.66 |
| 4166 | CB | PRO | 530 | 121.137 | 43.284 | 53.914 | 1.00 | 62.98 |
| 4167 | CG | PRO | 530 | 119.837 | 44.009 | 53.711 | 1.00 | 59.02 |
| 4168 | C | PRO | 530 | 121.952 | 41.819 | 55.784 | 1.00 | 70.87 |
| 4169 | O | PRO | 530 | 122.567 | 40.757 | 55.682 | 1.00 | 73.58 |
| 4170 | N | GLU | 531 | 122.248 | 42.762 | 56.676 | 1.00 | 73.21 |
| 4171 | CA | GLU | 531 | 123.365 | 42.683 | 57.621 | 1.00 | 73.20 |
| 4172 | CB | GLU | 531 | 123.107 | 43.597 | 58.822 | 1.00 | 75.84 |
| 4173 | CG | GLU | 531 | 124.335 | 43.811 | 59.703 | 1.00 | 84.33 |
| 4174 | CD | GLU | 531 | 124.108 | 44.832 | 60.799 | 1.00 | 87.41 |
| 4175 | OE1 | GLU | 531 | 123.904 | 46.021 | 60.474 | 1.00 | 95.89 |
| 4176 | OE2 | GLU | 531 | 124.142 | 44.446 | 61.988 | 1.00 | 83.48 |
| 4177 | C | GLU | 531 | 123.843 | 41.312 | 58.106 | 1.00 | 71.16 |
| 4178 | O | GLU | 531 | 125.042 | 41.026 | 58.066 | 1.00 | 69.83 |
| 4179 | N | GLU | 532 | 122.923 | 40.470 | 58.563 | 1.00 | 69.84 |
| 4180 | CA | GLU | 532 | 123.299 | 39.151 | 59.064 | 1.00 | 69.95 |
| 4181 | CB | GLU | 532 | 122.239 | 38.621 | 60.028 | 1.00 | 76.12 |
| 4182 | CG | GLU | 532 | 122.200 | 39.350 | 61.360 | 1.00 | 90.10 |
| 4183 | CD | GLU | 532 | 121.231 | 38.719 | 62.343 | 1.00 | 99.66 |
| 4184 | OE1 | GLU | 532 | 121.294 | 37.485 | 62.540 | 1.00 | 100.00 |
| 4185 | OE2 | GLU | 532 | 120.407 | 39.460 | 62.922 | 1.00 | 100.00 |
| 4186 | C | GLU | 532 | 123.601 | 38.095 | 58.006 | 1.00 | 65.98 |
| 4187 | O | GLU | 532 | 124.484 | 37.257 | 58.202 | 1.00 | 65.68 |
| 4188 | N | VAL | 533 | 122.878 | 38.136 | 56.891 | 1.00 | 60.94 |
| 4189 | CA | VAL | 533 | 123.071 | 37.152 | 55.829 | 1.00 | 51.25 |
| 4190 | CB | VAL | 533 | 121.727 | 36.491 | 55.419 | 1.00 | 57.84 |
| 4191 | CG1 | VAL | 533 | 121.983 | 35.305 | 54.492 | 1.00 | 49.96 |
| 4192 | CG2 | VAL | 533 | 120.942 | 36.054 | 56.655 | 1.00 | 58.45 |
| 4193 | C | VAL | 533 | 123.741 | 37.704 | 54.574 | 1.00 | 44.33 |
| 4194 | O | VAL | 533 | 124.834 | 37.270 | 54.208 | 1.00 | 42.16 |
| 4195 | N | LEU | 534 | 123.085 | 38.662 | 53.925 | 1.00 | 37.63 |
| 4196 | CA | LEU | 534 | 123.590 | 39.249 | 52.687 | 1.00 | 27.92 |
| 4197 | CB | LEU | 534 | 122.499 | 40.068 | 52.002 | 1.00 | 24.48 |
| 4198 | CG | LEU | 534 | 121.258 | 39.299 | 51.554 | 1.00 | 25.70 |
| 4199 | CD1 | LEU | 534 | 120.395 | 40.207 | 50.696 | 1.00 | 29.78 |
| 4200 | CD2 | LEU | 534 | 121.657 | 38.064 | 50.769 | 1.00 | 19.34 |
| 4201 | C | LEU | 534 | 124.864 | 40.076 | 52.770 | 1.00 | 29.24 |
| 4202 | O | LEU | 534 | 125.661 | 40.069 | 51.834 | 1.00 | 31.85 |
| 4203 | N | LYS | 535 | 125.053 | 40.793 | 53.875 | 1.00 | 30.62 |
| 4204 | CA | LYS | 535 | 126.239 | 41.632 | 54.047 | 1.00 | 30.24 |
| 4205 | CB | LYS | 535 | 126.251 | 42.276 | 55.439 | 1.00 | 33.69 |
| 4206 | CG | LYS | 535 | 127.412 | 43.232 | 55.692 | 1.00 | 38.92 |
| 4207 | CD | LYS | 535 | 127.429 | 43.699 | 57.142 | 1.00 | 43.85 |
| 4208 | CE | LYS | 535 | 128.605 | 44.617 | 57.425 | 1.00 | 46.39 |
| 4209 | NZ | LYS | 535 | 128.657 | 45.016 | 58.861 | 1.00 | 46.21 |
| 4210 | C | LYS | 535 | 127.548 | 40.881 | 53.784 | 1.00 | 30.84 |
| 4211 | O | LYS | 535 | 128.328 | 41.286 | 52.918 | 1.00 | 28.96 |
| 4212 | N | PRO | 536 | 127.790 | 39.759 | 54.495 | 1.00 | 26.98 |
| 4213 | CD | PRO | 536 | 126.965 | 39.148 | 55.554 | 1.00 | 30.04 |
| 4214 | CA | PRO | 536 | 129.018 | 38.982 | 54.302 | 1.00 | 22.09 |
| 4215 | CB | PRO | 536 | 128.796 | 37.772 | 55.206 | 1.00 | 22.33 |
| 4216 | CG | PRO | 536 | 127.975 | 38.330 | 56.312 | 1.00 | 25.59 |
| 4217 | C | PRO | 536 | 129.213 | 38.551 | 52.853 | 1.00 | 23.63 |
| 4218 | O | PRO | 536 | 130.313 | 38.660 | 52.315 | 1.00 | 34.37 |
| 4219 | N | HIS | 537 | 128.137 | 38.082 | 52.226 | 1.00 | 21.41 |
| 4220 | CA | HIS | 537 | 128.180 | 37.635 | 50.836 | 1.00 | 16.74 |
| 4221 | CB | HIS | 537 | 126.812 | 37.108 | 50.393 | 1.00 | 17.36 |
| 4222 | CG | HIS | 537 | 126.392 | 35.849 | 51.086 | 1.00 | 26.82 |
| 4223 | CD2 | HIS | 537 | 125.171 | 35.406 | 51.467 | 1.00 | 19.54 |
| 4224 | ND1 | HIS | 537 | 127.289 | 34.872 | 51.465 | 1.00 | 20.86 |
| 4225 | CE1 | HIS | 537 | 126.638 | 33.883 | 52.050 | 1.00 | 21.91 |
| 4226 | NE2 | HIS | 537 | 125.351 | 34.182 | 52.064 | 1.00 | 18.99 |
| 4227 | C | HIS | 537 | 128.611 | 38.757 | 49.910 | 1.00 | 19.57 |
| 4228 | O | HIS | 537 | 129.477 | 38.569 | 49.060 | 1.00 | 24.18 |
| 4229 | N | ILE | 538 | 128.003 | 39.927 | 50.091 | 1.00 | 25.84 |
| 4230 | CA | ILE | 538 | 128.307 | 41.101 | 49.279 | 1.00 | 25.72 |
| 4231 | CB | ILE | 538 | 127.331 | 42.262 | 49.600 | 1.00 | 25.90 |
| 4232 | CG2 | ILE | 538 | 127.739 | 43.536 | 48.856 | 1.00 | 21.31 |
| 4233 | CG1 | ILE | 538 | 125.905 | 41.849 | 49.219 | 1.00 | 14.44 |
| 4234 | CD1 | ILE | 538 | 124.847 | 42.872 | 49.559 | 1.00 | 19.77 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 4235 | C | ILE | 538 | 129.760 | 41.545 | 49.467 | 1.00 | 24.83 |
| 4236 | O | ILE | 538 | 130.419 | 41.957 | 48.510 | 1.00 | 17.63 |
| 4237 | N | ILE | 539 | 130.255 | 41.440 | 50.698 | 1.00 | 19.39 |
| 4238 | CA | ILE | 539 | 131.632 | 41.809 | 51.002 | 1.00 | 25.84 |
| 4239 | CB | ILE | 539 | 131.882 | 41.864 | 52.532 | 1.00 | 31.48 |
| 4240 | CG2 | ILE | 539 | 133.375 | 41.923 | 52.835 | 1.00 | 28.38 |
| 4241 | CG1 | ILE | 539 | 131.172 | 43.078 | 53.137 | 1.00 | 26.00 |
| 4242 | CD1 | ILE | 539 | 131.381 | 43.224 | 54.633 | 1.00 | 28.00 |
| 4243 | C | ILE | 539 | 132.598 | 40.819 | 50.355 | 1.00 | 24.71 |
| 4244 | O | ILE | 539 | 133.587 | 41.218 | 49.742 | 1.00 | 30.21 |
| 4245 | N | ASN | 540 | 132.286 | 39.531 | 50.461 | 1.00 | 22.80 |
| 4246 | CA | ASN | 540 | 133.132 | 38.487 | 49.892 | 1.00 | 16.68 |
| 4247 | CB | ASN | 540 | 132.802 | 37.135 | 50.525 | 1.00 | 17.40 |
| 4248 | CG | ASN | 540 | 133.009 | 37.126 | 52.032 | 1.00 | 26.52 |
| 4249 | OD1 | ASN | 540 | 132.357 | 36.371 | 52.755 | 1.00 | 29.84 |
| 4250 | ND2 | ASN | 540 | 133.918 | 37.969 | 52.511 | 1.00 | 25.48 |
| 4251 | C | ASN | 540 | 133.039 | 38.386 | 48.371 | 1.00 | 16.85 |
| 4252 | O | ASN | 540 | 133.933 | 37.832 | 47.733 | 1.00 | 18.60 |
| 4253 | N | LEU | 541 | 131.979 | 38.944 | 47.789 | 1.00 | 16.65 |
| 4254 | CA | LEU | 541 | 131.791 | 36.889 | 46.340 | 1.00 | 19.54 |
| 4255 | CB | LEU | 541 | 130.393 | 38.360 | 46.001 | 1.00 | 16.13 |
| 4256 | CG | LEU | 541 | 130.003 | 36.954 | 46.463 | 1.00 | 16.63 |
| 4257 | CD1 | LEU | 541 | 128.588 | 36.662 | 46.017 | 1.00 | 9.71 |
| 4258 | CD2 | LEU | 541 | 130.960 | 35.919 | 45.901 | 1.00 | 11.40 |
| 4259 | C | LEU | 541 | 132.016 | 40.198 | 45.585 | 1.00 | 22.24 |
| 4260 | O | LEU | 541 | 132.528 | 40.186 | 44.464 | 1.00 | 22.51 |
| 4261 | N | LEU | 542 | 131.642 | 41.321 | 46.192 | 1.00 | 23.86 |
| 4262 | CA | LEU | 542 | 131.774 | 42.619 | 46.531 | 1.00 | 27.26 |
| 4263 | CB | LEU | 542 | 130.392 | 43.266 | 45.412 | 1.00 | 30.85 |
| 4264 | CG | LEU | 542 | 129.374 | 42.454 | 44.608 | 1.00 | 33.63 |
| 4265 | CD1 | LEU | 542 | 127.960 | 42.968 | 44.844 | 1.00 | 33.98 |
| 4266 | CD2 | LEU | 542 | 129.741 | 42.505 | 43.137 | 1.00 | 30.60 |
| 4267 | C | LEU | 542 | 132.770 | 43.621 | 46.124 | 1.00 | 30.35 |
| 4268 | O | LEU | 542 | 133.102 | 44.615 | 45.474 | 1.00 | 32.15 |
| 4269 | N | VAL | 543 | 133.234 | 43.373 | 47.348 | 1.00 | 20.35 |
| 4270 | CA | VAL | 543 | 134.192 | 44.263 | 48.008 | 1.00 | 17.15 |
| 4271 | CB | VAL | 543 | 133.758 | 44.564 | 49.406 | 1.00 | 22.13 |
| 4272 | CG1 | VAL | 543 | 134.761 | 45.485 | 50.147 | 1.00 | 18.99 |
| 4273 | CG2 | VAL | 543 | 132.369 | 45.184 | 49.485 | 1.00 | 25.56 |
| 4274 | C | VAL | 543 | 135.608 | 43.670 | 46.012 | 1.00 | 20.12 |
| 4275 | O | VAL | 543 | 136.484 | 44.106 | 47.259 | 1.00 | 14.30 |
| 4276 | N | ASP | 544 | 135.813 | 42.667 | 48.860 | 1.00 | 22.55 |
| 4277 | CA | ASP | 544 | 137.102 | 41.999 | 46.992 | 1.00 | 17.64 |
| 4278 | CB | ASP | 544 | 137.183 | 41.246 | 50.326 | 1.00 | 10.56 |
| 4279 | CG | ASP | 544 | 137.103 | 42.164 | 51.532 | 1.00 | 22.81 |
| 4280 | OD1 | ASP | 544 | 136.839 | 41.648 | 52.639 | 1.00 | 23.90 |
| 4281 | OD2 | ASP | 544 | 137.313 | 43.390 | 51.385 | 1.00 | 33.46 |
| 4282 | C | ASP | 544 | 137.389 | 41.018 | 47.868 | 1.00 | 18.71 |
| 4283 | O | ASP | 544 | 136.548 | 40.191 | 47.517 | 1.00 | 20.02 |
| 4284 | N | SER | 545 | 138.590 | 41.116 | 47.310 | 1.00 | 23.60 |
| 4285 | CA | SER | 545 | 139.022 | 40.215 | 46.253 | 1.00 | 27.74 |
| 4286 | CB | SER | 545 | 139.900 | 40.957 | 45.243 | 1.00 | 27.70 |
| 4287 | OG | SER | 545 | 141.043 | 41.512 | 45.871 | 1.00 | 32.50 |
| 4288 | C | SER | 545 | 139.823 | 39.098 | 46.920 | 1.00 | 31.23 |
| 4289 | O | SER | 545 | 140.409 | 39.303 | 47.987 | 1.00 | 32.16 |
| 4290 | N | ILE | 546 | 139.816 | 37.913 | 46.317 | 1.00 | 30.36 |
| 4291 | CA | ILE | 546 | 140.558 | 36.780 | 46.863 | 1.00 | 33.30 |
| 4292 | CB | ILE | 546 | 140.281 | 35.475 | 46.072 | 1.00 | 33.46 |
| 4293 | CG2 | ILE | 546 | 141.051 | 34.310 | 46.686 | 1.00 | 27.25 |
| 4294 | CG1 | ILE | 546 | 138.783 | 35.165 | 46.072 | 1.00 | 27.20 |
| 4295 | CD1 | ILE | 546 | 138.418 | 33.915 | 45.319 | 1.00 | 23.76 |
| 4296 | C | ILE | 546 | 142.041 | 37.113 | 46.765 | 1.00 | 35.94 |
| 4297 | O | ILE | 546 | 142.559 | 37.332 | 45.668 | 1.00 | 34.27 |
| 4298 | N | LYS | 547 | 142.708 | 37.200 | 47.913 | 1.00 | 37.96 |
| 4299 | CA | LYS | 547 | 144.131 | 37.518 | 47.929 | 1.00 | 45.36 |
| 4300 | CB | LYS | 547 | 144.581 | 37.989 | 49.318 | 1.00 | 53.18 |
| 4301 | CG | LYS | 547 | 144.193 | 37.086 | 50.476 | 1.00 | 62.91 |
| 4302 | CD | LYS | 547 | 144.627 | 37.709 | 51.796 | 1.00 | 73.57 |
| 4303 | CE | LYS | 547 | 144.241 | 36.839 | 52.982 | 1.00 | 81.58 |
| 4304 | NZ | LYS | 547 | 144.683 | 37.440 | 54.274 | 1.00 | 85.95 |
| 4305 | C | LYS | 547 | 144.986 | 36.359 | 47.425 | 1.00 | 43.05 |
| 4306 | O | LYS | 547 | 144.897 | 35.236 | 47.921 | 1.00 | 34.62 |
| 4307 | N | ILE | 548 | 145.778 | 36.648 | 46.396 | 1.00 | 45.90 |
| 4308 | CA | ILE | 548 | 146.656 | 35.666 | 45.771 | 1.00 | 45.52 |
| 4309 | CB | ILE | 548 | 147.148 | 36.170 | 44.394 | 1.00 | 41.81 |
| 4310 | CG2 | ILE | 548 | 147.927 | 35.073 | 43.679 | 1.00 | 45.55 |
| 4311 | CG1 | ILE | 548 | 145.951 | 36.603 | 43.540 | 1.00 | 39.14 |
| 4312 | CD1 | ILE | 548 | 146.327 | 37.269 | 42.238 | 1.00 | 45.90 |
| 4313 | C | ILE | 548 | 147.856 | 35.342 | 46.659 | 1.00 | 48.55 |
| 4314 | OT1 | ILE | 548 | 148.019 | 34.153 | 47.005 | 1.00 | 46.58 |
| 4315 | OT2 | ILE | 548 | 148.606 | 36.278 | 47.012 | 1.00 | 59.90 |
| 4316 | OH2 | WAT | 601 | 109.544 | 21.898 | 33.684 | 1.00 | 2.00 |
| 4317 | OH2 | WAT | 602 | 132.108 | 38.577 | 42.342 | 1.00 | 3.74 |
| 4318 | OH2 | WAT | 603 | 121.652 | 22.556 | 52.348 | 1.00 | 5.90 |
| 4319 | OH2 | WAT | 604 | 136.076 | 10.222 | 44.594 | 1.00 | 31.07 |
| 4320 | OH2 | WAT | 605 | 131.497 | 21.852 | 51.678 | 1.00 | 7.22 |
| 4321 | OH2 | WAT | 606 | 128.656 | 14.200 | 45.316 | 1.00 | 17.90 |
| 4322 | OH2 | WAT | 607 | 124.677 | 19.198 | 47.081 | 1.00 | 15.60 |
| 4323 | OH2 | WAT | 608 | 125.455 | 29.812 | 49.014 | 1.00 | 8.48 |
| 4324 | OH2 | WAT | 609 | 105.474 | 36.871 | 39.547 | 1.00 | 9.05 |
| 4325 | OH2 | WAT | 610 | 133.536 | 36.915 | 40.513 | 1.00 | 19.37 |
| 4326 | OH2 | WAT | 611 | 126.730 | 22.375 | 41.980 | 1.00 | 17.96 |
| 4327 | OH2 | WAT | 612 | 133.379 | 23.457 | 50.388 | 1.00 | 16.43 |
| 4328 | OH2 | WAT | 613 | 136.836 | 31.698 | 39.273 | 1.00 | 23.48 |
| 4329 | OH2 | WAT | 614 | 130.615 | 20.278 | 41.368 | 1.00 | 11.16 |
| 4330 | OH2 | WAT | 615 | 127.633 | 29.682 | 51.807 | 1.00 | 16.49 |
| 4331 | OH2 | WAT | 616 | 100.533 | 31.281 | 26.832 | 1.00 | 34.28 |
| 4332 | OH2 | WAT | 617 | 121.692 | 21.167 | 34.150 | 1.00 | 25.91 |
| 4333 | OH2 | WAT | 618 | 131.226 | 32.257 | 50.439 | 1.00 | 34.81 |
| 4334 | OH2 | WAT | 619 | 88.365 | 35.120 | 57.147 | 1.00 | 33.73 |
| 4335 | OH2 | WAT | 620 | 118.147 | 18.317 | 26.341 | 1.00 | 21.70 |
| 4336 | OH2 | WAT | 621 | 113.190 | 8.087 | 35.703 | 1.00 | 36.62 |
| 4337 | OH2 | WAT | 622 | 125.312 | 30.072 | 37.791 | 1.00 | 30.00 |
| 4338 | OH2 | WAT | 623 | 92.432 | 24.852 | 50.099 | 1.00 | 25.65 |
| 4339 | OH2 | WAT | 624 | 108.974 | 15.165 | 49.075 | 1.00 | 21.10 |
| 4340 | OH2 | WAT | 625 | 135.431 | 14.884 | 45.393 | 1.00 | 46.74 |
| 4341 | OH2 | WAT | 626 | 115.012 | 4.805 | 43.826 | 1.00 | 30.43 |
| 4342 | OH2 | WAT | 627 | 88.415 | 44.463 | 58.820 | 1.00 | 30.86 |
| 4343 | OH2 | WAT | 628 | 125.976 | 25.755 | 43.265 | 1.00 | 27.75 |
| 4344 | OH2 | WAT | 629 | 117.921 | 5.153 | 51.682 | 1.00 | 34.87 |
| 4345 | OH2 | WAT | 630 | 91.157 | 43.104 | 44.532 | 1.00 | 27.09 |
| 4346 | OH2 | WAT | 631 | 114.902 | 63.428 | 42.828 | 1.00 | 30.49 |
| 4347 | OH2 | WAT | 632 | 99.150 | 43.135 | 52.476 | 1.00 | 17.32 |
| 4348 | OH2 | WAT | 633 | 116.849 | 14.286 | 50.256 | 1.00 | 20.41 |
| 4349 | OH2 | WAT | 634 | 136.092 | 41.410 | 33.663 | 1.00 | 26.72 |
| 4350 | OH2 | WAT | 635 | 104.683 | 23.377 | 25.808 | 1.00 | 36.55 |
| 4351 | OH2 | WAT | 636 | 133.163 | 25.808 | 57.616 | 1.00 | 29.75 |
| 4352 | OH2 | WAT | 637 | 130.650 | 30.337 | 40.643 | 1.00 | 11.08 |
| 4353 | OH2 | WAT | 638 | 141.018 | 40.362 | 50.563 | 1.00 | 27.14 |
| 4354 | OH2 | WAT | 639 | 126.744 | 19.348 | 30.510 | 1.00 | 20.69 |
| 4355 | OH2 | WAT | 640 | 99.257 | 26.859 | 66.394 | 1.00 | 32.76 |
| 4356 | OH2 | WAT | 641 | 107.042 | 13.044 | 38.812 | 1.00 | 37.53 |
| 4357 | OH2 | WAT | 642 | 111.411 | 17.702 | 31.576 | 1.00 | 25.63 |
| 4358 | OH2 | WAT | 643 | 136.247 | 16.841 | 49.081 | 1.00 | 26.74 |
| 4359 | OH2 | WAT | 644 | 130.107 | 34.877 | 51.432 | 1.00 | 22.05 |
| 4360 | OH2 | WAT | 645 | 131.572 | 27.845 | 36.507 | 1.00 | 33.61 |
| 4361 | OH2 | WAT | 646 | 139.273 | 18.921 | 51.935 | 1.00 | 18.69 |
| 4362 | OH2 | WAT | 647 | 102.180 | 34.258 | 26.188 | 1.00 | 38.28 |
| 4363 | OH2 | WAT | 648 | 123.655 | 36.667 | 26.709 | 1.00 | 23.51 |
| 4364 | OH2 | WAT | 649 | 126.661 | 35.233 | 55.363 | 1.00 | 32.41 |
| 4365 | OH2 | WAT | 650 | 106.153 | 21.764 | 42.249 | 1.00 | 20.34 |
| 4366 | OH2 | WAT | 651 | 135.834 | 34.383 | 30.691 | 1.00 | 52.17 |
| 4367 | OH2 | WAT | 652 | 103.106 | 38.892 | 25.426 | 1.00 | 26.00 |
| 4368 | OH2 | WAT | 653 | 140.880 | 35.431 | 50.226 | 1.00 | 26.45 |
| 4369 | OH2 | WAT | 654 | 112.327 | 13.971 | 50.722 | 1.00 | 46.47 |
| 4370 | OH2 | WAT | 655 | 142.876 | 32.708 | 49.617 | 1.00 | 38.19 |
| 4371 | OH2 | WAT | 656 | 136.448 | 11.686 | 63.277 | 1.00 | 31.93 |
| 4372 | OH2 | WAT | 657 | 128.522 | 28.120 | 35.575 | 1.00 | 25.65 |
| 4373 | OH2 | WAT | 658 | 124.837 | 30.666 | 35.131 | 1.00 | 22.56 |
| 4374 | OH2 | WAT | 659 | 130.833 | 34.205 | 29.481 | 1.00 | 42.51 |
| 4375 | OH2 | WAT | 660 | 112.306 | 35.037 | 18.431 | 1.00 | 22.73 |
| 4376 | OH2 | WAT | 661 | 121.695 | 49.220 | 48.983 | 1.00 | 34.50 |
| 4377 | OH2 | WAT | 662 | 134.850 | 24.747 | 24.896 | 1.00 | 61.06 |
| 4378 | OH2 | WAT | 663 | 120.492 | 22.780 | 56.510 | 1.00 | 33.74 |
| 4379 | OH2 | WAT | 664 | 145.265 | 41.024 | 28.023 | 1.00 | 26.03 |
| 4380 | OH2 | WAT | 665 | 92.325 | 61.829 | 41.100 | 1.00 | 63.45 |

TABLE 10-continued

Structural Coordinates of Tobacco 5-Epi-Aristolochene Synthase With Farnesyl Hydroxyphosphonate Bound

| Atom | Atom Type | Residue | Residue # | X | Y | Z | OCC | B-factor |
|---|---|---|---|---|---|---|---|---|
| 4381 | OH2 | WAT | 666 | 122.583 | 51.518 | 33.284 | 1.00 | 48.58 |
| 4382 | OH2 | WAT | 667 | 134.126 | 51.766 | 45.296 | 1.00 | 19.94 |
| 4383 | OH2 | WAT | 668 | 99.217 | 28.001 | 33.331 | 1.00 | 36.10 |
| 4384 | OH2 | WAT | 669 | 116.117 | 48.969 | 45.889 | 1.00 | 27.24 |
| 4385 | OH2 | WAT | 670 | 90.118 | 37.836 | 45.821 | 1.00 | 21.42 |
| 4386 | OH2 | WAT | 671 | 140.530 | 43.280 | 48.000 | 1.00 | 25.45 |
| 4387 | OH2 | WAT | 672 | 91.812 | 21.421 | 53.465 | 1.00 | 25.28 |
| 4388 | OH2 | WAT | 673 | 133.156 | 2.402 | 49.442 | 1.00 | 44.64 |
| 4389 | OH2 | WAT | 674 | 124.710 | 30.183 | 52.286 | 1.00 | 27.01 |
| 4390 | OH2 | WAT | 675 | 108.048 | 22.156 | 30.804 | 1.00 | 29.23 |
| 4391 | OH2 | WAT | 676 | 141.812 | 18.051 | 53.703 | 1.00 | 33.60 |
| 4392 | OH2 | WAT | 677 | 122.438 | 4.780 | 34.061 | 1.00 | 22.75 |
| 4393 | OH2 | WAT | 678 | 106.890 | 50.310 | 27.843 | 1.00 | 27.59 |
| 4394 | OH2 | WAT | 679 | 99.813 | 44.123 | 49.703 | 1.00 | 35.15 |
| 4395 | OH2 | WAT | 680 | 114.424 | 25.540 | 53.859 | 1.00 | 59.82 |
| 4396 | OH2 | WAT | 681 | 120.122 | 17.036 | 61.627 | 1.00 | 33.13 |
| 4397 | OH2 | WAT | 682 | 123.491 | 39.726 | 28.595 | 1.00 | 39.84 |
| 4398 | OH2 | WAT | 683 | 120.197 | 47.611 | 55.219 | 1.00 | 29.64 |
| 4399 | OH2 | WAT | 684 | 103.132 | 41.401 | 52.472 | 1.00 | 31.67 |
| 4400 | OH2 | WAT | 685 | 95.409 | 27.232 | 43.768 | 1.00 | 40.36 |
| 4401 | OH2 | WAT | 686 | 93.494 | 47.869 | 47.074 | 1.00 | 41.27 |
| 4402 | OH2 | WAT | 687 | 101.201 | 66.857 | 39.062 | 1.00 | 78.46 |
| 4403 | OH2 | WAT | 688 | 117.640 | 29.026 | 61.987 | 1.00 | 47.48 |
| 4404 | OH2 | WAT | 689 | 125.779 | 23.773 | 30.324 | 1.00 | 37.41 |
| 4405 | OH2 | WAT | 690 | 118.394 | 14.351 | 39.712 | 1.00 | 8.48 |
| 4406 | OH2 | WAT | 691 | 115.774 | 17.384 | 46.942 | 1.00 | 55.16 |
| 4407 | OH2 | WAT | 692 | 125.846 | 32.742 | 40.650 | 1.00 | 30.56 |
| 4408 | OH2 | WAT | 693 | 134.539 | 32.766 | 51.897 | 1.00 | 52.33 |
| 4409 | OH2 | WAT | 694 | 132.231 | 24.088 | 46.766 | 1.00 | 63.16 |
| 4410 | OH2 | WAT | 695 | 120.423 | 11.828 | 28.871 | 1.00 | 44.89 |
| 4411 | OH2 | WAT | 696 | 109.529 | 18.849 | 35.510 | 1.00 | 41.86 |
| 4412 | OH2 | WAT | 697 | 126.344 | 22.049 | 35.670 | 1.00 | 37.93 |
| 4413 | OH2 | WAT | 698 | 140.761 | 46.564 | 40.929 | 1.00 | 36.10 |
| 4414 | OH2 | WAT | 699 | 149.712 | 28.211 | 43.996 | 1.00 | 63.77 |
| 4415 | OH2 | WAT | 700 | 122.788 | 19.483 | 59.019 | 1.00 | 46.07 |
| 4416 | OH2 | WAT | 701 | 133.230 | 48.486 | 44.266 | 1.00 | 36.68 |
| 4417 | OH2 | WAT | 702 | 121.294 | 17.890 | 56.388 | 1.00 | 45.00 |
| 4418 | OH2 | WAT | 703 | 129.924 | 31.321 | 53.670 | 1.00 | 28.12 |
| 4419 | OH2 | WAT | 704 | 130.041 | 22.759 | 34.128 | 1.00 | 58.80 |
| 4420 | OH2 | WAT | 705 | 120.990 | 14.019 | 62.153 | 1.00 | 90.42 |
| 4421 | OH2 | WAT | 706 | 144.565 | 20.274 | 60.540 | 1.00 | 57.31 |
| 4422 | OH2 | WAT | 707 | 122.007 | 30.989 | 34.128 | 1.00 | 74.81 |
| 4423 | OH2 | WAT | 708 | 136.782 | 18.854 | 45.912 | 1.00 | 38.89 |
| 4424 | OH2 | WAT | 709 | 148.608 | 25.064 | 51.823 | 1.00 | 69.75 |
| 4425 | OH2 | WAT | 710 | 129.546 | 23.547 | 49.088 | 1.00 | 59.55 |
| 4426 | OH2 | WAT | 711 | 98.361 | 36.814 | 48.633 | 1.00 | 48.61 |
| 4427 | OH2 | WAT | 712 | 135.173 | 8.831 | 61.117 | 1.00 | 57.62 |
| 4428 | OH2 | WAT | 713 | 125.025 | 32.134 | 55.885 | 1.00 | 46.77 |
| 4429 | OH2 | WAT | 714 | 109.222 | 19.287 | 57.955 | 1.00 | 58.38 |
| 4430 | OH2 | WAT | 715 | 137.206 | 8.347 | 56.384 | 1.00 | 48.16 |
| 4431 | OH2 | WAT | 716 | 105.407 | 21.522 | 45.303 | 1.00 | 55.42 |
| 4432 | OH2 | WAT | 717 | 108.948 | 9.853 | 39.154 | 1.00 | 73.91 |
| 4433 | OH2 | WAT | 718 | 96.255 | 23.880 | 48.000 | 1.00 | 73.23 |
| 4434 | OH2 | WAT | 719 | 101.728 | 36.619 | 50.363 | 1.00 | 57.83 |
| 4435 | OH2 | WAT | 720 | 116.536 | 13.569 | 56.095 | 1.00 | 62.99 |
| 4436 | OH2 | WAT | 721 | 128.739 | 23.611 | 38.616 | 1.00 | 70.69 |
| 4437 | OH2 | WAT | 722 | 126.664 | 3.370 | 36.233 | 1.00 | 79.09 |
| 4438 | OH2 | WAT | 723 | 120.338 | 3.428 | 58.493 | 1.00 | 86.19 |
| 4439 | OH2 | WAT | 724 | 132.490 | 26.185 | 26.764 | 1.00 | 67.03 |
| 4440 | OH2 | WAT | 725 | 119.137 | 22.564 | 24.070 | 1.00 | 75.84 |
| 4441 | OH2 | WAT | 726 | 98.004 | 28.038 | 42.458 | 1.00 | 72.19 |
| 4442 | OH2 | WAT | 727 | 99.674 | 33.037 | 41.131 | 1.00 | 69.00 |
| 4443 | OH2 | WAT | 728 | 113.394 | 11.413 | 52.820 | 1.00 | 69.11 |
| 4444 | OH2 | WAT | 729 | 129.629 | 27.848 | 38.891 | 1.00 | 31.80 |
| 4445 | OH2 | WAT | 730 | 138.391 | 3.193 | 36.697 | 1.00 | 88.33 |
| 4446 | OH2 | WAT | 731 | 101.751 | 58.675 | 54.521 | 1.00 | 69.41 |
| 4447 | OH2 | WAT | 732 | 146.260 | 39.908 | 45.702 | 1.00 | 71.98 |
| 4448 | OH2 | WAT | 733 | 99.632 | 27.238 | 39.217 | 1.00 | 65.15 |
| 4449 | OH2 | WAT | 734 | 139.029 | 16.241 | 44.768 | 1.00 | 76.36 |
| 4450 | OH2 | WAT | 735 | 93.410 | 43.367 | 39.907 | 1.00 | 51.51 |
| 4451 | OH2 | WAT | 736 | 99.833 | 50.411 | 52.960 | 1.00 | 40.10 |
| 4452 | OH2 | WAT | 737 | 121.822 | 63.145 | 36.945 | 1.00 | 88.71 |
| 4453 | OH2 | WAT | 738 | 123.231 | 52.111 | 47.051 | 1.00 | 59.41 |
| 4454 | OH2 | WAT | 739 | 112.095 | 2.568 | 44.854 | 1.00 | 87.55 |
| 4455 | OH2 | WAT | 740 | 105.823 | 21.588 | 32.912 | 1.00 | 65.78 |
| 4456 | OH2 | WAT | 741 | 112.121 | 15.677 | 29.574 | 1.00 | 63.57 |
| 4457 | OH2 | WAT | 742 | 116.006 | 23.098 | 23.234 | 1.00 | 66.58 |
| 4458 | OH2 | WAT | 743 | 101.396 | 34.063 | 30.976 | 1.00 | 67.78 |
| 4459 | OH2 | WAT | 744 | 105.307 | 25.170 | 29.199 | 1.00 | 41.04 |
| 4460 | OH2 | WAT | 745 | 138.659 | 10.582 | 45.837 | 1.00 | 59.51 |
| 4461 | OH2 | WAT | 746 | 114.904 | 60.800 | 37.648 | 1.00 | 51.77 |
| 4462 | OH2 | WAT | 747 | 124.430 | 21.295 | 33.036 | 1.00 | 63.60 |
| 4463 | OH2 | WAT | 748 | 107.809 | 9.528 | 45.664 | 1.00 | 96.91 |
| 4464 | OH2 | WAT | 749 | 129.675 | 48.310 | 54.546 | 1.00 | 50.35 |
| 4465 | OH2 | WAT | 750 | 104.938 | 42.943 | 50.401 | 1.00 | 73.99 |
| 4466 | OH2 | WAT | 751 | 127.598 | 19.431 | 38.063 | 1.00 | 50.28 |
| 4467 | OH2 | WAT | 752 | 107.804 | 42.960 | 53.690 | 1.00 | 100.00 |
| 4468 | OH2 | WAT | 753 | 106.996 | 46.067 | 52.208 | 1.00 | 80.89 |
| 4469 | OH2 | WAT | 754 | 115.697 | 53.285 | 33.391 | 1.00 | 88.83 |
| 4470 | OH2 | WAT | 755 | 107.557 | 43.929 | 23.164 | 1.00 | 97.00 |
| 4471 | OH2 | WAT | 756 | 104.503 | 37.526 | 36.972 | 1.00 | 58.13 |
| 4472 | MG | MG | 757 | 105.326 | 36.717 | 53.406 | 1.00 | 29.00 |
| 4473 | MG | MG | 758 | 103.375 | 43.256 | 48.861 | 1.00 | 41.96 |
| 4474 | MG | MG | 759 | 106.905 | 43.906 | 51.594 | 1.00 | 60.57 |
| 4475 | PA | HPH | 900 | 106.514 | 40.269 | 50.769 | 1.00 | 64.84 |
| 4476 | O1A | HPH | 900 | 106.467 | 39.079 | 51.657 | 1.00 | 56.34 |
| 4477 | O2A | HPH | 900 | 106.738 | 41.560 | 51.467 | 1.00 | 62.50 |
| 4478 | O3A | HPH | 900 | 105.506 | 40.292 | 49.674 | 1.00 | 62.63 |
| 4479 | O1 | HPH | 900 | 108.952 | 41.335 | 50.186 | 1.00 | 61.96 |
| 4480 | C1 | HPH | 900 | 108.025 | 40.315 | 49.769 | 1.00 | 64.00 |
| 4481 | C2 | HPH | 900 | 108.690 | 38.930 | 49.523 | 1.00 | 61.37 |
| 4482 | C3 | HPH | 900 | 109.069 | 38.562 | 48.285 | 1.00 | 51.27 |
| 4483 | C4 | HPH | 900 | 109.443 | 37.123 | 48.011 | 1.00 | 49.88 |
| 4484 | C5 | HPH | 900 | 110.870 | 36.593 | 48.349 | 1.00 | 48.79 |
| 4485 | C6 | HPH | 900 | 112.049 | 37.566 | 48.069 | 1.00 | 37.71 |
| 4486 | C7 | HPH | 900 | 112.320 | 38.019 | 46.829 | 1.00 | 34.33 |
| 4487 | C8 | HPH | 900 | 113.476 | 38.969 | 46.623 | 1.00 | 35.58 |
| 4488 | C9 | HPH | 900 | 113.227 | 40.333 | 47.247 | 1.00 | 56.66 |
| 4489 | C10 | HPH | 900 | 113.089 | 40.275 | 48.776 | 1.00 | 68.86 |
| 4490 | C11 | HPH | 900 | 112.157 | 41.010 | 49.392 | 1.00 | 73.13 |
| 4491 | C12 | HPH | 900 | 112.037 | 40.934 | 50.893 | 1.00 | 66.86 |
| 4492 | C15 | HPH | 900 | 108.853 | 39.500 | 47.137 | 1.00 | 54.81 |
| 4493 | C13 | HPH | 900 | 111.421 | 42.067 | 48.641 | 1.00 | 68.76 |
| 4494 | C14 | HPH | 900 | 111.753 | 37.299 | 45.656 | 1.00 | 41.06 |

TABLE 11

Structural Coordinates of Tobacco 5-Epi-Aristolochene Synthase In the Absence of Bound Substrate

| Atom | Atom Type | Residue | Residue # | X | Y | Z | OCC | B-factor |
|---|---|---|---|---|---|---|---|---|
| 1 | N | LEU | 24 | 121.956 | 50.261 | 52.247 | 1.00 | 124.05 |
| 2 | CA | LEU | 24 | 122.946 | 50.852 | 53.202 | 1.00 | 125.60 |
| 3 | C | LEU | 24 | 124.286 | 50.797 | 52.493 | 1.00 | 125.95 |
| 4 | O | LEU | 24 | 125.338 | 50.615 | 53.099 | 1.00 | 126.05 |
| 5 | CB | LEU | 24 | 123.008 | 50.020 | 54.477 | 1.00 | 127.81 |
| 6 | CG | LEU | 24 | 121.748 | 50.062 | 55.337 | 1.00 | 127.97 |
| 7 | CD1 | LEU | 24 | 121.898 | 49.121 | 56.526 | 1.00 | 126.52 |
| 8 | CD2 | LEU | 24 | 121.487 | 51.490 | 55.822 | 1.00 | 127.81 |
| 9 | 1H | LEU | 24 | 122.251 | 49.292 | 51.984 | 1.00 | 25.00 |
| 10 | 2H | LEU | 24 | 121.021 | 50.229 | 52.677 | 1.00 | 25.00 |
| 11 | 3H | LEU | 24 | 121.929 | 50.798 | 51.366 | 1.00 | 25.00 |
| 12 | N | TRP | 25 | 124.208 | 51.008 | 51.190 | 1.00 | 128.26 |
| 13 | CA | TRP | 25 | 125.348 | 50.953 | 50.308 | 1.00 | 126.64 |
| 14 | C | TRP | 25 | 125.910 | 52.322 | 49.937 | 1.00 | 128.50 |
| 15 | O | TRP | 25 | 127.131 | 52.480 | 49.824 | 1.00 | 130.12 |
| 16 | CB | TRP | 25 | 124.945 | 50.134 | 49.078 | 1.00 | 122.57 |
| 17 | CG | TRP | 25 | 124.537 | 48.725 | 49.460 | 1.00 | 116.55 |
| 18 | CD1 | TRP | 25 | 123.263 | 48.214 | 49.513 | 1.00 | 111.25 |
| 19 | CD2 | TRP | 25 | 125.407 | 47.685 | 49.877 | 1.00 | 114.36 |
| 20 | NE1 | TRP | 25 | 123.302 | 46.911 | 49.947 | 1.00 | 109.76 |

TABLE 11-continued

Structural Coordinates of Tobacco 5-Epi-Aristolochene Synthase
In the Absence of Bound Substrate

| Atom Type | Atom | Residue | Residue # | X | Y | Z | OCC | B-factor |
|---|---|---|---|---|---|---|---|---|
| 21 | CE2 | TRP | 25 | 124.612 | 46.556 | 50.178 | 1.00 | 113.64 |
| 22 | CE3 | TRP | 25 | 126.801 | 47.577 | 50.038 | 1.00 | 114.01 |
| 23 | CZ2 | TRP | 25 | 125.148 | 45.348 | 50.624 | 1.00 | 114.93 |
| 24 | CZ3 | TRP | 25 | 127.340 | 46.387 | 50.476 | 1.00 | 112.58 |
| 25 | CH2 | TRP | 25 | 126.515 | 45.282 | 50.767 | 1.00 | 114.08 |
| 26 | H | TRP | 25 | 123.358 | 51.275 | 50.804 | 1.00 | 25.00 |
| 27 | HE1 | TRP | 25 | 122.575 | 46.258 | 50.073 | 1.00 | 25.00 |
| 28 | N | GLY | 26 | 125.028 | 53.306 | 49.785 | 1.00 | 129.69 |
| 29 | CA | GLY | 26 | 125.460 | 54.647 | 49.432 | 1.00 | 129.22 |
| 30 | C | GLY | 26 | 126.079 | 54.744 | 48.049 | 1.00 | 128.72 |
| 31 | O | GLY | 26 | 125.794 | 53.929 | 47.177 | 1.00 | 128.98 |
| 32 | H | GLY | 26 | 124.083 | 53.132 | 49.888 | 1.00 | 25.00 |
| 33 | N | ASP | 27 | 126.962 | 55.721 | 47.868 | 1.00 | 128.05 |
| 34 | CA | ASP | 27 | 127.635 | 55.946 | 48.589 | 1.00 | 126.16 |
| 35 | C | ASP | 27 | 128.786 | 54.971 | 46.340 | 1.00 | 122.14 |
| 36 | O | ASP | 27 | 129.641 | 55.215 | 45.485 | 1.00 | 121.90 |
| 37 | CB | ASP | 27 | 128.154 | 57.390 | 46.495 | 1.00 | 128.56 |
| 38 | CG | ASP | 27 | 127.036 | 58.414 | 46.382 | 1.00 | 129.57 |
| 39 | OD1 | ASP | 27 | 126.092 | 58.200 | 45.590 | 1.00 | 129.32 |
| 40 | OD2 | ASP | 27 | 127.109 | 59.446 | 47.083 | 1.00 | 128.42 |
| 41 | H | ASP | 27 | 127.188 | 56.294 | 48.627 | 1.00 | 25.00 |
| 42 | N | GLN | 28 | 128.786 | 53.863 | 47.075 | 1.00 | 117.67 |
| 43 | CA | GLN | 28 | 129.811 | 52.833 | 46.950 | 1.00 | 112.25 |
| 44 | C | GLN | 28 | 129.807 | 52.195 | 45.554 | 1.00 | 112.76 |
| 45 | O | GLN | 28 | 130.803 | 51.612 | 45.131 | 1.00 | 110.25 |
| 46 | CB | GLN | 28 | 129.581 | 51.764 | 48.025 | 1.00 | 106.94 |
| 47 | CG | GLN | 28 | 130.657 | 50.691 | 48.117 | 1.00 | 101.12 |
| 48 | CD | GLN | 28 | 130.380 | 49.637 | 49.179 | 1.00 | 99.15 |
| 49 | OE1 | GLN | 28 | 131.021 | 48.585 | 49.199 | 1.00 | 98.20 |
| 50 | NE2 | GLN | 28 | 129.431 | 49.911 | 50.072 | 1.00 | 95.39 |
| 51 | H | GLN | 28 | 128.073 | 53.736 | 47.724 | 1.00 | 25.00 |
| 52 | 1HE2 | GLN | 28 | 129.287 | 49.206 | 50.749 | 1.00 | 25.00 |
| 53 | 2HE2 | GLN | 28 | 128.922 | 50.738 | 50.067 | 1.00 | 25.00 |
| 54 | N | PHE | 29 | 128.696 | 52.349 | 44.833 | 1.00 | 116.96 |
| 55 | CA | PHE | 29 | 128.536 | 51.766 | 43.496 | 1.00 | 118.70 |
| 56 | C | PHE | 29 | 128.026 | 52.717 | 42.398 | 1.00 | 122.05 |
| 57 | O | PHE | 29 | 127.643 | 52.249 | 41.318 | 1.00 | 123.10 |
| 58 | CB | PHE | 29 | 127.570 | 50.572 | 43.539 | 1.00 | 114.02 |
| 59 | CG | PHE | 29 | 127.906 | 49.532 | 44.568 | 1.00 | 111.57 |
| 60 | CD1 | PHE | 29 | 128.928 | 48.614 | 44.349 | 1.00 | 109.61 |
| 61 | CD2 | PHE | 29 | 127.148 | 49.429 | 45.731 | 1.00 | 108.83 |
| 62 | CE1 | PHE | 29 | 129.193 | 47.609 | 45.274 | 1.00 | 102.49 |
| 63 | CE2 | PHE | 29 | 127.401 | 48.432 | 46.663 | 1.00 | 101.60 |
| 64 | CZ | PHE | 29 | 128.425 | 47.514 | 46.434 | 1.00 | 101.60 |
| 65 | H | PHE | 29 | 127.985 | 52.899 | 45.209 | 1.00 | 25.00 |
| 66 | N | LEU | 30 | 127.984 | 54.022 | 42.669 | 1.00 | 124.46 |
| 67 | CA | LEU | 30 | 127.509 | 55.009 | 41.689 | 1.00 | 127.15 |
| 68 | C | LEU | 30 | 128.208 | 54.874 | 40.335 | 1.00 | 128.12 |
| 69 | O | LEU | 30 | 127.578 | 54.916 | 39.277 | 1.00 | 126.56 |
| 70 | CB | LEU | 30 | 127.732 | 56.433 | 42.230 | 1.00 | 128.23 |
| 71 | CG | LEU | 30 | 127.357 | 57.672 | 41.388 | 1.00 | 129.74 |
| 72 | CD1 | LEU | 30 | 126.987 | 58.843 | 42.316 | 1.00 | 126.98 |
| 73 | CD2 | LEU | 30 | 128.437 | 58.089 | 40.428 | 1.00 | 126.72 |
| 74 | H | LEU | 30 | 128.261 | 54.333 | 43.538 | 1.00 | 25.00 |
| 75 | N | SER | 331 | 129.527 | 54.725 | 40.400 | 1.00 | 129.78 |
| 76 | CA | SER | 31 | 130.384 | 54.608 | 39.222 | 1.00 | 130.48 |
| 77 | C | SER | 31 | 131.618 | 53.722 | 39.458 | 1.00 | 129.14 |
| 78 | O | SER | 31 | 132.211 | 53.745 | 40.535 | 1.00 | 127.41 |
| 79 | CB | SER | 31 | 130.831 | 56.004 | 38.781 | 1.00 | 133.08 |
| 80 | OG | SER | 31 | 131.481 | 56.700 | 39.845 | 1.00 | 136.17 |
| 81 | H | SER | 31 | 129.890 | 54.673 | 41.303 | 1.00 | 25.00 |
| 82 | HG | SER | 31 | 130.880 | 56.771 | 40.611 | 1.00 | 25.00 |
| 83 | N | PHE | 32 | 132.004 | 52.973 | 38.423 | 1.00 | 127.29 |
| 84 | CA | PHE | 32 | 133.156 | 52.065 | 38.458 | 1.00 | 126.38 |
| 85 | C | PHE | 32 | 134.056 | 52.249 | 37.231 | 1.00 | 129.92 |
| 86 | O | PHE | 32 | 133.693 | 51.847 | 36.122 | 1.00 | 131.71 |
| 87 | CB | PHE | 32 | 132.683 | 50.601 | 38.531 | 1.00 | 120.86 |
| 88 | CG | PHE | 32 | 133.805 | 49.581 | 38.475 | 1.00 | 117.02 |
| 89 | CD1 | PHE | 32 | 134.736 | 49.488 | 39.507 | 1.00 | 114.77 |
| 90 | CD2 | PHE | 32 | 133.912 | 48.701 | 37.396 | 1.00 | 113.67 |
| 91 | CE1 | PHE | 32 | 135.755 | 48.533 | 39.472 | 1.00 | 111.21 |
| 92 | CE2 | PHE | 32 | 134.927 | 47.742 | 37.349 | 1.00 | 111.87 |
| 93 | CZ | PHE | 32 | 135.851 | 47.658 | 38.389 | 1.00 | 111.43 |
| 94 | H | PHE | 32 | 131.485 | 53.046 | 37.602 | 1.00 | 25.00 |
| 95 | N | SER | 33 | 135.219 | 52.861 | 37.434 | 1.00 | 129.98 |
| 96 | CA | SER | 33 | 136.179 | 53.082 | 36.355 | 1.00 | 128.55 |
| 97 | C | SER | 33 | 137.014 | 51.819 | 36.136 | 1.00 | 128.72 |
| 98 | O | SER | 33 | 137.973 | 51.561 | 36.865 | 1.00 | 128.38 |
| 99 | CB | SER | 33 | 137.079 | 54.277 | 36.684 | 1.00 | 130.20 |
| 100 | OG | SER | 33 | 137.554 | 54.211 | 38.019 | 1.00 | 130.89 |
| 101 | H | SER | 33 | 135.440 | 53.163 | 38.329 | 1.00 | 25.00 |
| 102 | HG | SER | 33 | 136.817 | 54.182 | 38.626 | 1.00 | 25.00 |
| 103 | N | ILE | 34 | 136.616 | 51.017 | 35.153 | 1.00 | 128.06 |
| 104 | CA | ILE | 34 | 137.313 | 49.773 | 34.842 | 1.00 | 127.26 |
| 105 | C | ILE | 34 | 138.715 | 50.001 | 34.268 | 1.00 | 128.81 |
| 106 | O | ILE | 34 | 138.869 | 50.556 | 33.177 | 1.00 | 132.56 |
| 107 | CB | ILE | 34 | 136.483 | 48.884 | 33.865 | 1.00 | 125.22 |
| 108 | CG1 | ILE | 34 | 137.227 | 47.570 | 33.595 | 1.00 | 124.19 |
| 109 | CG2 | ILE | 34 | 136.174 | 49.640 | 32.570 | 1.00 | 123.27 |
| 110 | CD1 | ILE | 34 | 136.518 | 46.611 | 32.665 | 1.00 | 121.43 |
| 111 | H | ILE | 34 | 135.838 | 51.274 | 34.627 | 1.00 | 25.00 |
| 112 | N | ASP | 35 | 139.736 | 49.600 | 35.020 | 1.00 | 125.91 |
| 113 | CA | ASP | 35 | 141.105 | 49.749 | 34.548 | 1.00 | 120.92 |
| 114 | C | ASP | 35 | 141.437 | 48.728 | 33.464 | 1.00 | 116.38 |
| 115 | O | ASP | 35 | 141.993 | 47.661 | 33.726 | 1.00 | 115.56 |
| 116 | CB | ASP | 35 | 142.122 | 49.709 | 35.700 | 1.00 | 122.56 |
| 117 | CG | ASP | 35 | 141.780 | 48.684 | 36.761 | 1.00 | 123.82 |
| 118 | OD1 | ASP | 35 | 141.342 | 47.566 | 36.414 | 1.00 | 129.46 |
| 119 | OD2 | ASP | 35 | 141.952 | 49.002 | 37.955 | 1.00 | 123.01 |
| 120 | H | ASP | 35 | 139.577 | 49.234 | 35.909 | 1.00 | 25.00 |
| 121 | N | ASN | 36 | 141.017 | 49.067 | 32.254 | 1.00 | 111.08 |
| 122 | CA | ASN | 36 | 141.237 | 48.307 | 31.037 | 1.00 | 107.72 |
| 123 | C | ASN | 36 | 142.508 | 47.402 | 30.983 | 1.00 | 104.04 |
| 124 | O | ASN | 36 | 142.486 | 46.381 | 30.443 | 1.00 | 103.31 |
| 125 | CB | ASN | 38 | 141.160 | 49.215 | 29.783 | 1.00 | 108.78 |
| 126 | CG | ASN | 38 | 141.378 | 50.742 | 30.076 | 1.00 | 113.72 |
| 127 | OD1 | ASN | 38 | 141.308 | 51.535 | 29.156 | 1.00 | 115.16 |
| 128 | ND2 | ASN | 38 | 141.668 | 51.127 | 31.309 | 1.00 | 113.86 |
| 129 | H | ASN | 38 | 140.490 | 49.899 | 32.196 | 1.00 | 25.00 |
| 130 | 1HD2 | ASN | 36 | 141.642 | 52.070 | 31.558 | 1.00 | 25.00 |
| 131 | 2HD2 | ASN | 36 | 141.817 | 50.557 | 32.067 | 1.00 | 25.00 |
| 132 | N | GLN | 37 | 143.593 | 47.958 | 31.571 | 1.00 | 101.33 |
| 133 | CA | GLN | 37 | 144.857 | 47.226 | 31.576 | 1.00 | 97.84 |
| 134 | C | GLN | 37 | 144.752 | 45.887 | 32.306 | 1.00 | 91.48 |
| 135 | O | GLN | 37 | 145.120 | 44.848 | 31.756 | 1.00 | 87.36 |
| 138 | CB | GLN | 37 | 145.964 | 48.079 | 32.204 | 1.00 | 104.38 |
| 137 | CG | GLN | 37 | 147.329 | 47.907 | 31.541 | 1.00 | 109.27 |
| 138 | CD | GLN | 37 | 147.433 | 48.643 | 30.213 | 1.00 | 112.48 |
| 139 | OE1 | GLN | 37 | 148.192 | 49.604 | 30.088 | 1.00 | 116.42 |
| 140 | NE2 | GLN | 37 | 146.670 | 48.202 | 29.220 | 1.00 | 113.85 |
| 141 | H | GLN | 37 | 143.558 | 48.839 | 31.989 | 1.00 | 25.00 |
| 142 | IHE2 | GLN | 37 | 146.735 | 48.687 | 28.371 | 1.00 | 25.00 |
| 143 | 2HE2 | GLN | 37 | 146.083 | 47.438 | 29.358 | 1.00 | 25.00 |
| 144 | N | VAL | 38 | 144.242 | 45.916 | 33.536 | 1.00 | 85.52 |
| 145 | CA | VAL | 38 | 144.092 | 44.702 | 34.337 | 1.00 | 79.25 |
| 146 | C | VAL | 38 | 143.148 | 43.731 | 33.634 | 1.00 | 77.63 |
| 147 | O | VAL | 38 | 143.416 | 42.529 | 33.568 | 1.00 | 78.06 |
| 148 | CB | VAL | 38 | 143.542 | 45.018 | 35.752 | 1.00 | 78.16 |
| 149 | CG1 | VAL | 38 | 143.484 | 43.754 | 36.593 | 1.00 | 75.39 |
| 150 | CG2 | VAL | 38 | 144.409 | 46.061 | 36.437 | 1.00 | 78.10 |
| 151 | H | VAL | 38 | 143.943 | 46.770 | 33.907 | 1.00 | 25.00 |
| 152 | N | ALA | 39 | 142.060 | 44.268 | 33.086 | 1.00 | 71.24 |
| 153 | CA | ALA | 39 | 141.071 | 43.463 | 32.379 | 1.00 | 66.46 |
| 154 | C | ALA | 39 | 141.694 | 42.736 | 31.191 | 1.00 | 65.26 |
| 155 | O | ALA | 39 | 141.519 | 41.527 | 31.038 | 1.00 | 59.37 |
| 156 | CB | ALA | 39 | 139.910 | 44.338 | 31.916 | 1.00 | 64.84 |
| 157 | H | ALA | 39 | 141.924 | 45.233 | 33.161 | 1.00 | 25.00 |
| 158 | N | GLU | 40 | 142.436 | 43.472 | 30.366 | 1.00 | 66.68 |
| 159 | CA | GLU | 40 | 143.086 | 42.896 | 29.190 | 1.00 | 69.85 |
| 160 | C | GLU | 40 | 144.107 | 41.828 | 29.559 | 1.00 | 66.85 |
| 161 | O | GLU | 40 | 144.233 | 40.818 | 28.859 | 1.00 | 65.59 |
| 162 | CB | GLU | 40 | 143.744 | 43.985 | 28.342 | 1.00 | 75.56 |
| 163 | CG | GLU | 40 | 142.752 | 44.836 | 27.560 | 1.00 | 89.79 |
| 164 | CD | GLU | 40 | 143.409 | 45.993 | 26.828 | 1.00 | 98.34 |
| 165 | OE1 | GLU | 40 | 144.515 | 45.807 | 26.273 | 1.00 | 101.87 |
| 166 | OE2 | GLU | 40 | 142.814 | 47.092 | 26.808 | 1.00 | 102.72 |

TABLE 11-continued

Structural Coordinates of Tobacco 5-Epi-Aristolochene Synthase
In the Absence of Bound Substrate

| Atom Type | Atom | Residue | Residue # | X | Y | Z | OCC | B-factor |
|---|---|---|---|---|---|---|---|---|
| 167 | H | GLU | 40 | 142.551 | 44.427 | 30.550 | 1.00 | 25.00 |
| 168 | N | LYS | 41 | 144.830 | 42.048 | 30.656 | 1.00 | 62.69 |
| 169 | CA | LYS | 41 | 145.821 | 41.079 | 31.112 | 1.00 | 60.33 |
| 170 | C | LYS | 41 | 145.081 | 39.798 | 31.478 | 1.00 | 56.90 |
| 171 | O | LYS | 41 | 145.440 | 38.707 | 31.024 | 1.00 | 56.12 |
| 172 | CB | LYS | 41 | 146.588 | 41.603 | 32.331 | 1.00 | 64.30 |
| 173 | CG | LYS | 41 | 147.689 | 40.655 | 32.802 | 1.00 | 70.61 |
| 174 | CD | LYS | 41 | 148.373 | 41.137 | 34.070 | 1.00 | 74.86 |
| 175 | CE | LYS | 41 | 149.449 | 40.152 | 34.505 | 1.00 | 79.07 |
| 176 | NZ | LYS | 41 | 150.138 | 40.584 | 35.753 | 1.00 | 86.06 |
| 177 | H | LYS | 41 | 144.700 | 42.879 | 31.160 | 1.00 | 25.00 |
| 178 | 1HZ | LYS | 41 | 150.588 | 41.510 | 35.601 | 1.00 | 25.00 |
| 179 | 2HZ | LYS | 41 | 149.443 | 40.661 | 36.524 | 1.00 | 25.00 |
| 180 | 3HZ | LYS | 41 | 150.864 | 39.885 | 36.010 | 1.00 | 25.00 |
| 181 | N | TYR | 42 | 144.027 | 39.951 | 32.278 | 1.00 | 54.48 |
| 182 | CA | TYR | 42 | 143.200 | 38.831 | 32.712 | 1.00 | 49.46 |
| 183 | C | TYR | 42 | 142.687 | 38.048 | 31.508 | 1.00 | 49.51 |
| 184 | O | TYR | 42 | 142.886 | 36.837 | 31.418 | 1.00 | 46.83 |
| 185 | CB | TYR | 42 | 142.011 | 39.332 | 33.535 | 1.00 | 49.09 |
| 186 | CG | TYR | 42 | 142.316 | 39.665 | 34.981 | 1.00 | 51.81 |
| 187 | CD1 | TYR | 42 | 143.609 | 39.555 | 35.498 | 1.00 | 55.25 |
| 188 | CD2 | TYR | 42 | 141.297 | 40.067 | 35.844 | 1.00 | 51.34 |
| 189 | CE1 | TYR | 42 | 143.873 | 39.836 | 36.843 | 1.00 | 60.63 |
| 190 | CE2 | TYR | 42 | 141.548 | 40.347 | 37.180 | 1.00 | 51.18 |
| 191 | CZ | TYR | 42 | 142.832 | 40.231 | 37.677 | 1.00 | 57.44 |
| 192 | OH | TYR | 42 | 143.064 | 40.503 | 39.009 | 1.00 | 57.29 |
| 193 | H | TYR | 42 | 143.796 | 40.855 | 32.582 | 1.00 | 25.00 |
| 194 | HH | TYR | 42 | 142.245 | 40.765 | 39.435 | 1.00 | 25.00 |
| 195 | N | ALA | 43 | 142.067 | 38.756 | 30.568 | 1.00 | 48.90 |
| 196 | CA | ALA | 43 | 141.514 | 38.150 | 29.359 | 1.00 | 49.75 |
| 197 | C | ALA | 43 | 142.560 | 37.363 | 28.576 | 1.00 | 49.98 |
| 198 | O | ALA | 43 | 142.331 | 36.209 | 28.204 | 1.00 | 49.38 |
| 199 | CB | ALA | 43 | 140.897 | 39.223 | 28.477 | 1.00 | 46.66 |
| 200 | H | ALA | 43 | 141.980 | 39.722 | 30.693 | 1.00 | 25.00 |
| 201 | N | GLN | 44 | 143.711 | 37.987 | 22.344 | 1.00 | 52.04 |
| 202 | CA | GLN | 44 | 144.796 | 37.352 | 27.607 | 1.00 | 51.53 |
| 203 | C | GLN | 44 | 145.219 | 36.030 | 28.257 | 1.00 | 45.51 |
| 204 | O | GLN | 44 | 145.304 | 35.002 | 27.582 | 1.00 | 43.18 |
| 205 | CB | GLN | 44 | 145.994 | 38.299 | 27.506 | 1.00 | 58.59 |
| 206 | CG | GLN | 44 | 147.101 | 37.804 | 26.583 | 1.00 | 74.05 |
| 207 | CD | GLN | 44 | 148.364 | 38.649 | 26.658 | 1.00 | 84.03 |
| 208 | OE1 | GLN | 44 | 148.343 | 39.784 | 27.132 | 1.00 | 90.02 |
| 209 | NE2 | GLN | 44 | 149.475 | 38.092 | 26.187 | 1.00 | 34.98 |
| 210 | H | GLN | 44 | 143.837 | 38.900 | 28.677 | 1.00 | 25.00 |
| 211 | 1HE2 | GLN | 44 | 150.290 | 38.631 | 26.238 | 1.00 | 25.00 |
| 212 | 2HE2 | GLN | 44 | 149.438 | 37.187 | 25.820 | 1.00 | 25.00 |
| 213 | N | GLU | 45 | 145.468 | 36.047 | 29.565 | 1.00 | 40.03 |
| 214 | CA | GLU | 45 | 145.874 | 34.831 | 30.261 | 1.00 | 37.78 |
| 215 | C | GLU | 45 | 144.740 | 33.813 | 30.320 | 1.00 | 41.99 |
| 216 | O | GLU | 45 | 144.970 | 32.609 | 30.153 | 1.00 | 43.40 |
| 217 | CB | GLU | 45 | 146.374 | 35.134 | 31.673 | 1.00 | 38.09 |
| 218 | CG | GLU | 45 | 147.037 | 33.924 | 32.334 | 1.00 | 41.87 |
| 219 | CD | GLU | 45 | 147.595 | 34.209 | 33.718 | 1.00 | 52.34 |
| 220 | OE1 | GLU | 45 | 147.678 | 35.393 | 34.116 | 1.00 | 58.77 |
| 221 | OE2 | GLU | 45 | 147.962 | 33.235 | 34.409 | 1.00 | 53.14 |
| 222 | H | GLU | 45 | 145.372 | 36.890 | 30.064 | 1.00 | 25.00 |
| 223 | N | ILE | 46 | 143.521 | 34.296 | 30.553 | 1.00 | 38.09 |
| 224 | CA | ILE | 46 | 142.352 | 33.428 | 30.622 | 1.00 | 35.19 |
| 225 | C | ILE | 46 | 142.239 | 32.630 | 29.328 | 1.00 | 37.05 |
| 226 | O | ILE | 46 | 141.923 | 31.441 | 29.360 | 1.00 | 40.60 |
| 227 | CB | ILE | 46 | 141.054 | 34.236 | 30.886 | 1.00 | 33.29 |
| 228 | CG1 | ILE | 46 | 140.992 | 34.650 | 32.357 | 1.00 | 25.99 |
| 229 | CG2 | ILE | 46 | 139.817 | 33.420 | 30.528 | 1.00 | 33.03 |
| 230 | CD1 | ILE | 46 | 139.889 | 35.630 | 32.667 | 1.00 | 27.20 |
| 231 | H | ILE | 46 | 143.414 | 35.255 | 30.675 | 1.00 | 25.00 |
| 232 | N | GLU | 47 | 142.548 | 33.263 | 28.199 | 1.00 | 37.32 |
| 233 | CA | GLU | 47 | 142.485 | 32.581 | 26.910 | 1.00 | 43.67 |
| 234 | C | GLU | 47 | 143.420 | 31.379 | 26.870 | 1.00 | 44.27 |
| 235 | O | GLU | 47 | 143.061 | 30.324 | 26.341 | 1.00 | 48.49 |
| 236 | CB | GLU | 47 | 142.817 | 33.537 | 25.765 | 1.00 | 50.83 |
| 237 | CG | GLU | 47 | 141.700 | 34.516 | 25.422 | 1.00 | 72.13 |
| 238 | CD | GLU | 47 | 140.408 | 33.833 | 24.970 | 1.00 | 80.45 |
| 239 | OE1 | GLU | 47 | 140.440 | 32.643 | 24.577 | 1.00 | 82.39 |
| 240 | OE2 | GLU | 47 | 139.353 | 34.501 | 25.001 | 1.00 | 87.14 |
| 241 | H | GLU | 47 | 142.813 | 34.208 | 28.233 | 1.00 | 25.00 |
| 242 | N | ALA | 48 | 144.610 | 31.538 | 27.444 | 1.00 | 41.56 |
| 243 | CA | ALA | 48 | 145.597 | 30.464 | 27.489 | 1.00 | 36.13 |
| 244 | C | ALA | 48 | 145.078 | 29.340 | 28.375 | 1.00 | 38.33 |
| 245 | O | ALA | 48 | 145.027 | 28.176 | 27.964 | 1.00 | 40.71 |
| 246 | CB | ALA | 48 | 146.917 | 30.990 | 28.031 | 1.00 | 33.18 |
| 247 | H | ALA | 48 | 144.824 | 32.404 | 27.853 | 1.00 | 25.00 |
| 248 | N | LEU | 49 | 144.662 | 29.708 | 29.583 | 1.00 | 37.02 |
| 249 | CA | LEU | 49 | 144.136 | 28.757 | 30.554 | 1.00 | 34.21 |
| 250 | C | LEU | 49 | 142.894 | 28.044 | 30.029 | 1.00 | 33.34 |
| 251 | O | LEU | 49 | 142.694 | 26.860 | 30.296 | 1.00 | 34.71 |
| 252 | CB | LEU | 49 | 143.816 | 29.477 | 31.862 | 1.00 | 32.92 |
| 253 | CG | LEU | 49 | 145.013 | 30.132 | 32.551 | 1.00 | 29.78 |
| 254 | CD1 | LEU | 49 | 144.541 | 31.096 | 33.621 | 1.00 | 28.55 |
| 255 | CD2 | LEU | 49 | 145.915 | 29.062 | 33.139 | 1.00 | 31.11 |
| 256 | H | LEU | 49 | 144.717 | 30.657 | 29.827 | 1.00 | 25.00 |
| 257 | N | LYS | 50 | 142.083 | 28.759 | 29.254 | 1.00 | 35.43 |
| 258 | CA | LYS | 50 | 140.858 | 28.208 | 28.681 | 1.00 | 36.99 |
| 259 | C | LYS | 50 | 141.193 | 27.105 | 27.687 | 1.00 | 39.13 |
| 260 | O | LYS | 50 | 140.643 | 26.004 | 27.762 | 1.00 | 39.46 |
| 261 | CB | LYS | 50 | 140.056 | 29.307 | 27.981 | 1.00 | 38.20 |
| 262 | CG | LYS | 50 | 138.670 | 28.882 | 27.520 | 1.00 | 37.82 |
| 263 | CD | LYS | 50 | 138.021 | 29.947 | 26.638 | 1.00 | 41.56 |
| 264 | CE | LYS | 50 | 137.926 | 31.297 | 27.341 | 1.00 | 44.73 |
| 265 | NZ | LYS | 50 | 137.282 | 32.342 | 26.489 | 1.00 | 40.08 |
| 266 | H | LYS | 50 | 142.323 | 29.682 | 29.055 | 1.00 | 25.00 |
| 267 | 1HZ | LYS | 50 | 136.318 | 32.042 | 26.239 | 1.00 | 25.00 |
| 268 | 2HZ | LYS | 50 | 137.245 | 33.240 | 27.012 | 1.00 | 25.00 |
| 269 | 3HZ | LYS | 50 | 137.841 | 32.474 | 25.620 | 1.00 | 25.00 |
| 270 | N | GLU | 51 | 142.106 | 27.396 | 26.765 | 1.00 | 41.23 |
| 271 | CA | GLU | 51 | 142.516 | 26.419 | 25.762 | 1.00 | 44.62 |
| 272 | C | GLU | 51 | 143.174 | 25.226 | 26.446 | 1.00 | 42.95 |
| 273 | O | GLU | 51 | 142.931 | 24.073 | 26.091 | 1.00 | 43.13 |
| 274 | CB | GLU | 51 | 143.489 | 27.055 | 24.766 | 1.00 | 52.90 |
| 275 | CG | GLU | 51 | 143.846 | 26.162 | 23.581 | 1.00 | 70.21 |
| 276 | CD | GLU | 51 | 142.623 | 25.709 | 22.792 | 1.00 | 79.98 |
| 277 | OE1 | GLU | 51 | 141.917 | 26.575 | 22.226 | 1.00 | 86.16 |
| 278 | OE2 | GLU | 51 | 142.368 | 24.486 | 22.739 | 1.00 | 81.08 |
| 279 | H | GLU | 51 | 142.510 | 28.293 | 26.751 | 1.00 | 25.00 |
| 280 | N | GLN | 52 | 143.965 | 25.514 | 27.471 | 1.00 | 48.21 |
| 281 | CA | GLN | 52 | 144.662 | 24.480 | 28.223 | 1.00 | 49.28 |
| 282 | C | GLN | 52 | 143.657 | 23.563 | 28.933 | 1.00 | 44.99 |
| 283 | O | GLN | 52 | 143.817 | 22.337 | 28.936 | 1.00 | 42.93 |
| 284 | CB | GLN | 52 | 145.609 | 25.138 | 29.230 | 1.00 | 51.94 |
| 285 | CG | GLN | 52 | 146.728 | 24.247 | 29.736 | 1.00 | 57.86 |
| 286 | CD | GLN | 52 | 147.655 | 24.973 | 30.696 | 1.00 | 61.66 |
| 287 | OE1 | GLN | 52 | 147.719 | 26.205 | 30.711 | 1.00 | 53.55 |
| 288 | NE2 | GLN | 52 | 148.372 | 24.211 | 31.511 | 1.00 | 66.48 |
| 289 | H | GLN | 52 | 144.095 | 26.453 | 27.720 | 1.00 | 25.00 |
| 290 | 1HE2 | GLN | 52 | 148.989 | 24.676 | 32.114 | 1.00 | 25.00 |
| 291 | 2HE2 | GLN | 52 | 148.283 | 23.237 | 31.480 | 1.00 | 25.00 |
| 292 | N | THR | 53 | 142.615 | 24.160 | 29.512 | 1.00 | 42.37 |
| 293 | CA | THR | 53 | 141.578 | 23.404 | 30.214 | 1.00 | 41.44 |
| 294 | C | THR | 53 | 140.753 | 22.584 | 29.220 | 1.00 | 40.96 |
| 295 | O | THR | 53 | 140.334 | 21.462 | 29.519 | 1.00 | 38.12 |
| 296 | CB | THR | 53 | 140.648 | 24.338 | 31.027 | 1.00 | 42.33 |
| 297 | OG1 | THR | 53 | 141.420 | 25.054 | 32.001 | 1.00 | 42.93 |
| 298 | CG2 | THR | 53 | 139.569 | 23.534 | 31.746 | 1.00 | 41.61 |
| 299 | H | THR | 53 | 142.537 | 25.134 | 29.467 | 1.00 | 25.00 |
| 300 | HG1 | THR | 53 | 142.088 | 25.586 | 31.555 | 1.00 | 25.00 |
| 301 | N | ARG | 54 | 140.553 | 23.138 | 28.027 | 1.00 | 42.45 |
| 302 | CA | ARG | 54 | 139.802 | 22.461 | 26.9976 | 1.00 | 41.46 |
| 303 | C | ARG | 54 | 140.516 | 21.152 | 26.653 | 1.00 | 43.94 |
| 304 | O | ARG | 54 | 139.891 | 20.088 | 26.607 | 1.00 | 41.93 |
| 305 | CB | ARG | 54 | 139.731 | 23.344 | 25.727 | 1.00 | 43.17 |
| 306 | CG | ARG | 54 | 138.759 | 22.861 | 24.658 | 1.00 | 49.52 |
| 307 | CD | ARG | 54 | 138.792 | 23.783 | 23.428 | 1.00 | 55.06 |
| 308 | NE | ARG | 54 | 138.600 | 25.176 | 23.764 | 1.00 | 65.13 |
| 309 | CZ | ARG | 54 | 137.416 | 25.758 | 23.951 | 1.00 | 73.50 |
| 310 | NH1 | ARG | 54 | 136.293 | 25.058 | 23.836 | 1.00 | 78.69 |
| 311 | NH2 | ARG | 54 | 137.353 | 27.046 | 24.263 | 1.00 | 72.72 |
| 312 | H | ARG | 54 | 140.919 | 24.030 | 27.846 | 1.00 | 25.00 |

TABLE 11-continued

Structural Coordinates of Tobacco 5-Epi-Aristolochene Synthase In the Absence of Bound Substrate

| Atom Type | Atom | Residue | Residue # | X | Y | Z | OCC | B-factor |
|---|---|---|---|---|---|---|---|---|
| 313 | HE | ARG | 54 | 139.400 | 25.734 | 23.857 | 1.00 | 25.00 |
| 314 | IHH1 | ARG | 54 | 136.328 | 24.086 | 23.604 | 1.00 | 25.00 |
| 315 | 2HH1 | ARG | 54 | 135.410 | 25.505 | 23.976 | 1.00 | 25.00 |
| 316 | IHH2 | ARG | 54 | 138.196 | 27.578 | 24.357 | 1.00 | 25.00 |
| 317 | 2HH2 | ARG | 54 | 136.466 | 27.484 | 24.403 | 1.00 | 25.00 |
| 318 | N | SER | 55 | 141.834 | 21.233 | 26.480 | 1.00 | 41.53 |
| 319 | CA | SER | 55 | 142.645 | 20.062 | 26.176 | 1.00 | 41.04 |
| 320 | C | SER | 55 | 142.550 | 19.010 | 27.284 | 1.00 | 42.34 |
| 321 | O | SER | 55 | 142.587 | 17.810 | 27.005 | 1.00 | 42.66 |
| 322 | CB | SER | 55 | 144.100 | 20.469 | 25.916 | 1.00 | 46.50 |
| 323 | OG | SER | 55 | 144.208 | 21.230 | 24.719 | 1.00 | 41.12 |
| 324 | H | SER | 55 | 142.280 | 22.107 | 26.538 | 1.00 | 25.00 |
| 325 | HG | SER | 55 | 143.898 | 20.704 | 23.977 | 1.00 | 25.00 |
| 326 | N | MET | 56 | 142.399 | 19.458 | 28.531 | 1.00 | 41.33 |
| 327 | CA | MET | 56 | 142.265 | 18.544 | 29.668 | 1.00 | 40.87 |
| 328 | C | MET | 56 | 141.003 | 17.703 | 29.501 | 1.00 | 43.46 |
| 329 | O | MET | 56 | 141.017 | 16.489 | 29.711 | 1.00 | 41.72 |
| 330 | CB | MET | 56 | 142.164 | 19.312 | 30.989 | 1.00 | 44.45 |
| 331 | CG | MET | 56 | 143.461 | 19.894 | 31.500 | 1.00 | 46.36 |
| 332 | SD | MET | 56 | 143.231 | 20.659 | 33.118 | 1.00 | 45.60 |
| 333 | CE | MET | 56 | 143.715 | 22.320 | 32.763 | 1.00 | 44.30 |
| 334 | H | MET | 56 | 142.383 | 20.426 | 28.690 | 1.00 | 25.00 |
| 335 | N | LEU | 57 | 139.910 | 18.365 | 29.132 | 1.00 | 42.82 |
| 336 | CA | LEU | 57 | 138.632 | 17.696 | 28.929 | 1.00 | 41.38 |
| 337 | C | LEU | 57 | 138.684 | 16.700 | 27.779 | 1.00 | 43.36 |
| 338 | O | LEU | 57 | 138.042 | 15.653 | 27.831 | 1.00 | 45.75 |
| 339 | CB | LEU | 57 | 137.531 | 18.726 | 28.670 | 1.00 | 34.91 |
| 340 | CG | LEU | 57 | 137.047 | 19..512 | 29.887 | 1.00 | 31.36 |
| 341 | CD1 | LEU | 57 | 136.174 | 20.663 | 29.441 | 1.00 | 31.29 |
| 342 | CD2 | LEU | 57 | 136.287 | 18.592 | 30.833 | 1.00 | 25.33 |
| 343 | H | LEU | 57 | 139.968 | 19.335 | 28.990 | 1.00 | 25.00 |
| 344 | N | LEU | 58 | 139.466 | 17.016 | 26.754 | 1.00 | 43.66 |
| 345 | CA | LEU | 58 | 139.577 | 16.145 | 25.591 | 1.00 | 48.27 |
| 346 | C | LEU | 58 | 140.659 | 15.059 | 25.683 | 1.00 | 53.11 |
| 347 | O | LEU | 58 | 141.005 | 14.441 | 24.672 | 1.00 | 54.87 |
| 348 | CB | LEU | 58 | 139.762 | 16.987 | 24.325 | 1.00 | 45.38 |
| 349 | CG | LEU | 58 | 138.682 | 18.051 | 24.083 | 1.00 | 48.84 |
| 350 | CD1 | LEU | 58 | 138.936 | 18.772 | 22.772 | 1.00 | 46.56 |
| 351 | CD2 | LEU | 58 | 137.303 | 17.413 | 24.074 | 1.00 | 49.64 |
| 352 | H | LEU | 58 | 139.978 | 17.851 | 26.781 | 1.00 | 25.00 |
| 353 | N | ALA | 59 | 141.180 | 14.813 | 26.884 | 1.00 | 58.17 |
| 354 | CA | ALA | 59 | 142.208 | 13.788 | 27.078 | 1.00 | 61.28 |
| 355 | C | ALA | 59 | 141.605 | 12.397 | 26.874 | 1.00 | 66.17 |
| 356 | O | ALA | 59 | 140.672 | 11.998 | 27.572 | 1.00 | 65.17 |
| 357 | CB | ALA | 59 | 142.830 | 13.908 | 28.460 | 1.00 | 61.08 |
| 358 | H | ALA | 59 | 140.859 | 15.316 | 27.661 | 1.00 | 25.00 |
| 359 | N | THR | 60 | 142.188 | 11.651 | 25.943 | 1.00 | 71.93 |
| 360 | CA | THR | 60 | 141.717 | 10.317 | 25.572 | 1.00 | 78.50 |
| 361 | C | THR | 60 | 141.721 | 9.179 | 26.599 | 1.00 | 77.85 |
| 362 | O | THR | 60 | 140.694 | 8.536 | 26.812 | 1.00 | 82.48 |
| 363 | CB | THR | 60 | 142.443 | 9.828 | 24.304 | 1.00 | 80.20 |
| 364 | OG1 | THR | 60 | 143.852 | 10.053 | 24.449 | 1.00 | 82.38 |
| 365 | CG2 | THR | 60 | 141.933 | 10.573 | 23.076 | 1.00 | 82..60 |
| 366 | H | THR | 60 | 142.957 | 12.026 | 25.478 | 1.00 | 25.00 |
| 367 | HG1 | THR | 60 | 144.029 | 10.991 | 24.540 | 1.00 | 25.00 |
| 368 | N | GLY | 61 | 142.866 | 8.914 | 27.217 | 1.00 | 74.94 |
| 369 | CA | GLY | 61 | 142.942 | 7.813 | 28.165 | 1.00 | 75.87 |
| 370 | C | GLY | 61 | 142.662 | 8.104 | 29.626 | 1.00 | 73.64 |
| 371 | O | GLY | 61 | 143.494 | 7.804 | 30.484 | 1.00 | 73.89 |
| 372 | H | GLY | 61 | 143.654 | 9.465 | 27.047 | 1.00 | 25.00 |
| 373 | N | ARG | 62 | 141.491 | 8.651 | 29.925 | 1.00 | 70.85 |
| 374 | CA | ARG | 62 | 141.149 | 8.960 | 31.307 | 1.00 | 67.41 |
| 375 | C | ARG | 62 | 140.068 | 8.054 | 31.870 | 1.00 | 61.77 |
| 376 | O | ARG | 62 | 139.147 | 7.654 | 31.160 | 1.00 | 63.43 |
| 377 | CB | ARG | 62 | 140.755 | 10.429 | 31.444 | 1.00 | 69.30 |
| 378 | CG | ARG | 62 | 141.883 | 11.309 | 31.967 | 1.00 | 75.81 |
| 379 | CD | ARG | 62 | 141.666 | 12.780 | 31.647 | 1.00 | 78.22 |
| 380 | NE | ARG | 62 | 140.334 | 13.254 | 32.009 | 1.00 | 79.69 |
| 381 | CZ | ARG | 62 | 139.335 | 13.405 | 31.143 | 1.00 | 88.12 |
| 382 | NH1 | ARG | 62 | 139.508 | 13.118 | 29.859 | 1.00 | 90.62 |
| 383 | NH2 | ARG | 62 | 138.160 | 13.852 | 31.559 | 1.00 | 92.99 |
| 384 | H | ARG | 62 | 140.835 | 8.835 | 29.218 | 1.00 | 25.00 |
| 385 | HE | ARG | 62 | 140.163 | 13.477 | 32.948 | 1.00 | 25.00 |
| 386 | 1HH1 | ARG | 62 | 140.393 | 12.785 | 29.534 | 1.00 | 25.00 |
| 387 | 2HH1 | ARG | 62 | 138.752 | 13.233 | 29.216 | 1.00 | 25.00 |
| 388 | 1HH2 | ARG | 62 | 138.022 | 14.076 | 32.524 | 1.00 | 25.00 |
| 389 | 2HH2 | ARG | 62 | 137.408 | 13.963 | 30.909 | 1.00 | 25.00 |
| 390 | N | LYS | 63 | 140.214 | 7.702 | 33.143 | 1.00 | 56.71 |
| 391 | CA | LYS | 63 | 139.258 | 6.840 | 33.830 | 1.00 | 53.88 |
| 392 | C | LYS | 63 | 137.986 | 7.614 | 34.170 | 1.00 | 49.91 |
| 393 | O | LYS | 63 | 138.024 | 8.831 | 34.377 | 1.00 | 43.13 |
| 394 | CB | LYS | 63 | 139.876 | 6.284 | 35.114 | 1.00 | 60.17 |
| 395 | CG | LYS | 63 | 141.181 | 5.544 | 34.901 | 1.00 | 72.02 |
| 396 | CD | LYS | 63 | 141.807 | 5.141 | 36.225 | 1.00 | 82.26 |
| 397 | CE | LYS | 63 | 143.131 | 4.428 | 36.004 | 1.00 | 90.54 |
| 398 | NZ | LYS | 63 | 143.764 | 4.015 | 37.286 | 1.00 | 94.67 |
| 399 | H | LYS | 63 | 140.988 | 8.042 | 33.633 | 1.00 | 25.00 |
| 400 | 1HZ | LYS | 63 | 143.130 | 3.366 | 37.795 | 1.00 | 25.00 |
| 401 | 2HZ | LYS | 63 | 144.664 | 3.533 | 37.085 | 1.00 | 25.00 |
| 402 | 3HZ | LYS | 63 | 143.945 | 4.857 | 37.868 | 1.00 | 25.00 |
| 403 | N | LEU | 64 | 136.877 | 6.890 | 34.289 | 1.00 | 44.28 |
| 404 | CA | LEU | 64 | 135.583 | 7.487 | 34.603 | 1.00 | 40.75 |
| 405 | C | LEU | 64 | 135.650 | 8.425 | 35.805 | 1.00 | 38.00 |
| 406 | O | LEU | 64 | 135.273 | 9.592 | 35.708 | 1.00 | 38.34 |
| 407 | CB | LEU | 64 | 134.539 | 6.395 | 34.858 | 1.00 | 37.20 |
| 408 | CG | LEU | 64 | 133.128 | 6.897 | 35.170 | 1.00 | 35.50 |
| 409 | CD1 | LEU | 64 | 132.563 | 7.618 | 33.964 | 1.00 | 30.93 |
| 410 | CD2 | LEU | 64 | 132.232 | 5.741 | 35.572 | 1.00 | 32.83 |
| 411 | H | LEU | 64 | 136.930 | 5.926 | 34.145 | 1.00 | 25.00 |
| 412 | N | ALA | 65 | 136.149 | 7.915 | 36.927 | 1.00 | 34.87 |
| 413 | CA | ALA | 65 | 136.264 | 8.700 | 33.152 | 1.00 | 33.63 |
| 414 | C | ALA | 65 | 136.977 | 10.022 | 37.909 | 1.00 | 32.94 |
| 415 | O | ALA | 65 | 136.508 | 11.073 | 38.342 | 1.00 | 31.36 |
| 416 | CB | ALA | 65 | 136.991 | 7.900 | 39.222 | 1.00 | 26.54 |
| 417 | H | ALA | 65 | 136.437 | 6.983 | 36.932 | 1.00 | 25.00 |
| 418 | N | ASP | 66 | 138.094 | 9.965 | 37.188 | 1.00 | 35.39 |
| 419 | CA | ASP | 66 | 138.887 | 11.111 | 36.882 | 1.00 | 34.98 |
| 420 | C | ASP | 66 | 138.127 | 12.136 | 36.002 | 1.00 | 34.90 |
| 421 | O | ASP | 66 | 138.200 | 13.352 | 36.210 | 1.00 | 34.81 |
| 422 | CB | ASP | 66 | 140.202 | 10.755 | 36.202 | 1.00 | 42.66 |
| 423 | CG | ASP | 66 | 141.054 | 9.825 | 37.059 | 1.00 | 51.98 |
| 424 | OD1 | ASP | 66 | 141.008 | 9.934 | 38.306 | 1.00 | 48.05 |
| 425 | OD2 | ASP | 66 | 141.774 | 8.982 | 36.479 | 1.00 | 59.40 |
| 426 | H | ASP | 66 | 138.390 | 9.103 | 36.840 | 1.00 | 25.00 |
| 427 | N | THR | 67 | 137.400 | 11.607 | 35.023 | 1.00 | 32.76 |
| 428 | CA | THR | 67 | 136.617 | 12.433 | 34.110 | 1.00 | 29.98 |
| 429 | C | THR | 67 | 135.486 | 13.131 | 34.869 | 1.00 | 27.93 |
| 430 | O | THR | 67 | 135.262 | 14.337 | 34.708 | 1.00 | 26.55 |
| 431 | CB | THR | 67 | 136.033 | 11.582 | 32.963 | 1.00 | 33.36 |
| 432 | OG1 | THR | 67 | 137.102 | 10.914 | 32.278 | 1.00 | 32.56 |
| 433 | CG2 | THR | 67 | 135.272 | 12.460 | 31.972 | 1.00 | 24.21 |
| 434 | H | THR | 67 | 137.385 | 10.635 | 34.900 | 1.00 | 25.00 |
| 435 | HG1 | THR | 67 | 136.746 | 10.375 | 31.566 | 1.00 | 25.00 |
| 436 | N | LEU | 68 | 134.806 | 12.382 | 35.730 | 1.00 | 24.35 |
| 437 | CA | LEU | 68 | 133.717 | 12.938 | 36.513 | 1.00 | 23.41 |
| 438 | C | LEU | 68 | 134.223 | 14.025 | 37.449 | 1.00 | 28.28 |
| 439 | O | LEU | 68 | 133.644 | 15.112 | 37.507 | 1.00 | 26.82 |
| 440 | CB | LEU | 68 | 133.004 | 11.842 | 37.301 | 1.00 | 24.43 |
| 441 | CG | LEU | 68 | 132.221 | 10.841 | 136.447 | 1.00 | 32.03 |
| 442 | CD1 | LEU | 68 | 131.651 | 9.744 | 37.330 | 1.00 | 23.28 |
| 443 | CD2 | LEU | 68 | 131.112 | 11.556 | 35.680 | 1.00 | 27.61 |
| 444 | H | LEU | 68 | 135.049 | 11.442 | 35.844 | 1.00 | 25.00 |
| 445 | N | ASN | 69 | 135.323 | 13.750 | 38.147 | 1.00 | 26.79 |
| 446 | CA | ASN | 69 | 135.894 | 14.724 | 39.072 | 1.00 | 30.78 |
| 447 | C | ASN | 69 | 136.341 | 15.981 | 38.340 | 1.00 | 28.43 |
| 448 | O | ASN | 69 | 138.165 | 17.092 | 38.837 | 1.00 | 30.31 |
| 449 | CB | ASN | 69 | 137.061 | 14.125 | 39.867 | 1.00 | 40.14 |
| 450 | CG | ASN | 69 | 136.597 | 13.165 | 40.959 | 1.00 | 53.22 |
| 451 | OD1 | ASN | 69 | 135.478 | 13.271 | 41.467 | 1.00 | 52.67 |
| 452 | ND2 | ASN | 69 | 137.460 | 12.224 | 41.326 | 1.00 | 60.05 |
| 453 | H | ASN | 69 | 135.750 | 12.874 | 38.043 | 1.00 | 25.00 |
| 454 | 1HD2 | ASN | 69 | 137.165 | 11.608 | 42.027 | 1.00 | 25.00 |
| 455 | 2HD2 | ASN | 69 | 138.335 | 12.185 | 40.893 | 1.00 | 25.00 |
| 456 | N | LEU | 70 | 136.884 | 15.813 | 37.140 | 1.00 | 26.00 |
| 457 | CA | LEU | 70 | 137.327 | 16.958 | 36.358 | 1.00 | 27.21 |
| 458 | C | LEU | 70 | 136.135 | 17.867 | 36.053 | 1.00 | 29.79 |

TABLE 11-continued

Structural Coordinates of Tobacco 5-Epi-Aristolochene Synthase
In the Absence of Bound Substrate

| Atom Type | Atom | Residue | Residue # | X | Y | Z | OCC | B-factor |
|---|---|---|---|---|---|---|---|---|
| 459 | O | LEU | 70 | 136.192 | 19.076 | 36.287 | 1.00 | 27.18 |
| 460 | CB | LEU | 70 | 137.990 | 16.498 | 35.058 | 1.00 | 23.13 |
| 461 | CG | LEU | 70 | 138.417 | 17.624 | 34.109 | 1.00 | 30.77 |
| 462 | CD1 | LEU | 70 | 139.366 | 18.580 | 34.821 | 1.00 | 21.76 |
| 463 | CD2 | LEU | 70 | 139.062 | 17.045 | 32.860 | 1.00 | 27.07 |
| 464 | H | LEU | 70 | 136.995 | 14.908 | 36.777 | 1.00 | 25.00 |
| 465 | N | ILE | 71 | 135.053 | 17.272 | 35.553 | 1.00 | 30.05 |
| 466 | CA | ILE | 71 | 133.840 | 18.012 | 35.217 | 1.00 | 24.54 |
| 467 | C | ILE | 71 | 133.221 | 18.663 | 36.456 | 1.00 | 23.02 |
| 468 | O | ILE | 71 | 132.849 | 19.839 | 36.429 | 1.00 | 23.20 |
| 469 | CB | ILE | 71 | 132.809 | 17.095 | 34.516 | 1.00 | 26.68 |
| 470 | CG1 | ILE | 71 | 133.338 | 16.693 | 33.136 | 1.00 | 25.05 |
| 471 | CG2 | ILE | 71 | 131.459 | 11.795 | 34.383 | 1.00 | 23.87 |
| 472 | CD1 | ILE | 71 | 132.442 | 16.736 | 32.400 | 1.00 | 27.35 |
| 473 | H | ILE | 71 | 135.073 | 16.300 | 35.409 | 1.00 | 25.00 |
| 474 | N | ASP | 72 | 133.140 | 17.910 | 37.546 | 1.00 | 19.38 |
| 475 | CA | ASP | 72 | 132.585 | 18.429 | 38.789 | 1.00 | 22.68 |
| 476 | C | ASP | 72 | 133.376 | 19.657 | 39.266 | 1.00 | 25.06 |
| 477 | O | ASP | 72 | 132.784 | 20.680 | 39.626 | 1.00 | 24.92 |
| 478 | CB | ASP | 72 | 132.593 | 17.335 | 39.861 | 1.00 | 23.74 |
| 479 | CG | ASP | 72 | 131.900 | 17.760 | 41.147 | 1.00 | 27.65 |
| 480 | OD1 | ASP | 72 | 130.953 | 18.575 | 41.086 | 1.00 | 29.89 |
| 481 | OD2 | ASP | 72 | 132.303 | 17.268 | 42.223 | 1.00 | 30.37 |
| 482 | H | ASP | 72 | 133.459 | 16.986 | 37.512 | 1.00 | 25.00 |
| 483 | N | ILE | 73 | 134.705 | 19.565 | 39.228 | 1.00 | 26.02 |
| 484 | CA | ILE | 73 | 135.589 | 20.656 | 39.654 | 1.00 | 21.86 |
| 485 | C | ILE | 73 | 135.431 | 21.918 | 38.797 | 1.00 | 23.60 |
| 486 | O | ILE | 73 | 135.270 | 23.019 | 39.329 | 1.00 | 25.70 |
| 487 | CB | ILE | 73 | 137.075 | 20.198 | 39.671 | 1.00 | 20.21 |
| 488 | CG1 | ILE | 73 | 137.245 | 19.066 | 40.684 | 1.00 | 22.84 |
| 489 | CG2 | ILE | 73 | 137.992 | 21.351 | 40.058 | 1.00 | 17.62 |
| 490 | CD1 | ILE | 73 | 138.659 | 18.513 | 40.788 | 1.00 | 53.34 |
| 491 | H | ILE | 73 | 135.108 | 18.732 | 38.902 | 1.00 | 25.00 |
| 492 | N | ILE | 74 | 135.450 | 21.755 | 37.476 | 1.00 | 22.39 |
| 493 | CA | ILE | 74 | 135.297 | 22.884 | 36.556 | 1.00 | 22.15 |
| 494 | C | ILE | 74 | 133.955 | 23.581 | 36.784 | 1.00 | 24.59 |
| 495 | O | ILE | 74 | 133.858 | 24.807 | 36.702 | 1.00 | 29.58 |
| 496 | CB | ILE | 74 | 135.415 | 22.426 | 35.079 | 1.00 | 24.24 |
| 497 | CG1 | ILE | 74 | 136.835 | 21.909 | 34.811 | 1.00 | 25.85 |
| 498 | CG2 | ILE | 74 | 135.071 | 23.571 | 34.132 | 1.00 | 19.61 |
| 499 | CD1 | ILE | 74 | 137.054 | 21.340 | 33.420 | 1.00 | 23.74 |
| 500 | H | ILE | 74 | 135.571 | 20.851 | 37.109 | 1.00 | 25.00 |
| 501 | N | GLU | 75 | 132.925 | 22.797 | 37.083 | 1.00 | 23.15 |
| 502 | CA | GLU | 75 | 131.599 | 23.343 | 37.338 | 1.00 | 23.53 |
| 503 | C | GLU | 75 | 131.548 | 24.092 | 38.658 | 1.00 | 21.84 |
| 504 | O | GLU | 75 | 131.040 | 25.208 | 38.722 | 1.00 | 25.34 |
| 505 | CB | GLU | 75 | 130.550 | 22.237 | 37.342 | 1.00 | 26.71 |
| 506 | CG | GLU | 75 | 130.274 | 21.647 | 35.978 | 1.00 | 30.84 |
| 507 | CD | GLU | 75 | 129.073 | 20.720 | 35.969 | 1.00 | 36.10 |
| 508 | OE1 | GLU | 75 | 128.644 | 20.253 | 37.051 | 1.00 | 29.89 |
| 509 | OE2 | GLU | 75 | 128.559 | 20.460 | 34.865 | 1.00 | 31.50 |
| 510 | H | GLU | 75 | 133.056 | 21.822 | 37.122 | 1.00 | 25.00 |
| 511 | N | ARG | 76 | 132.060 | 23.474 | 39.717 | 1.00 | 19.68 |
| 512 | CA | ARG | 76 | 132.066 | 24.115 | 41.028 | 1.00 | 20.75 |
| 513 | C | ARG | 76 | 132.925 | 25.385 | 41.017 | 1.00 | 22.83 |
| 514 | O | ARG | 76 | 132.699 | 26.303 | 41.803 | 1.00 | 21.89 |
| 515 | CB | ARG | 76 | 132.581 | 23.148 | 42.091 | 1.00 | 16.07 |
| 516 | CG | ARG | 76 | 131.653 | 21.989 | 42.411 | 1.00 | 20.22 |
| 517 | CD | ARC | 76 | 132.331 | 21.061 | 43.395 | 1.00 | 21.08 |
| 518 | NE | ARG | 76 | 131.498 | 19.939 | 43.819 | 1.00 | 18.53 |
| 519 | CZ | ARG | 76 | 130.847 | 19.891 | 44.977 | 1.00 | 24.53 |
| 520 | NH1 | ARG | 76 | 130.917 | 20.907 | 45.829 | 1.00 | 17.48 |
| 521 | NH2 | ARG | 76 | 130.170 | 18.802 | 45.311 | 1.00 | 26.65 |
| 522 | H | ARG | 76 | 132.440 | 22.577 | 39.618 | 1.00 | 25.00 |
| 523 | HE | ARG | 76 | 131.417 | 19.172 | 43.218 | 1.00 | 25.00 |
| 524 | 1HH1 | ARG | 76 | 131.459 | 21.717 | 45.606 | 1.00 | 25.00 |
| 525 | 2HH1 | ARG | 76 | 130.423 | 20.565 | 46.697 | 1.00 | 25.00 |
| 526 | 1HH2 | ARG | 76 | 130.146 | 18.021 | 44.691 | 1.00 | 25.00 |
| 527 | 2HH2 | ARG | 76 | 129.678 | 18.766 | 46.181 | 1.00 | 25.00 |
| 528 | N | LEU | 77 | 133.913 | 25.425 | 40.126 | 1.00 | 22.29 |
| 529 | CA | LEU | 77 | 134.798 | 26.579 | 40.001 | 1.00 | 23.34 |
| 530 | C | LEU | 77 | 134.156 | 27.710 | 39.193 | 1.00 | 26.64 |
| 531 | O | LEU | 77 | 134.752 | 28.777 | 39.026 | 1.00 | 25.27 |
| 532 | CB | LEU | 77 | 136.131 | 26.167 | 39.372 | 1.00 | 18.34 |
| 533 | CG | LEU | 77 | 137.076 | 25.352 | 40.258 | 1.00 | 18.25 |
| 534 | CD1 | LEU | 77 | 138.266 | 24.893 | 39.443 | 1.00 | 15.60 |
| 535 | CD2 | LEU | 77 | 137.531 | 26.182 | 41.459 | 1.00 | 17.00 |
| 536 | H | LEU | 77 | 134.063 | 24.649 | 39.546 | 1.00 | 25.00 |
| 537 | N | GLY | 78 | 132.958 | 27.455 | 38.668 | 1.00 | 24.42 |
| 538 | CA | GLY | 78 | 132.228 | 28.464 | 37.914 | 1.00 | 20.32 |
| 539 | C | GLY | 78 | 132.741 | 28.807 | 36.531 | 1.00 | 20.16 |
| 540 | O | GLY | 78 | 132.375 | 29.841 | 35.970 | 1.00 | 22.90 |
| 541 | H | GLY | 78 | 132.553 | 26.576 | 38.793 | 1.00 | 25.00 |
| 542 | N | ILE | 79 | 133.550 | 27.927 | 335.952 | 1.00 | 22.82 |
| 543 | CA | ILE | 79 | 134.099 | 28.170 | 34.623 | 1.00 | 24.96 |
| 544 | C | ILE | 79 | 133.577 | 27.204 | 33.560 | 1.00 | 29.01 |
| 545 | O | ILE | 79 | 133.991 | 27.273 | 32.398 | 1.00 | 28.78 |
| 546 | CB | ILE | 79 | 135.646 | 28.133 | 34.635 | 1.00 | 24.44 |
| 547 | CG1 | ILE | 79 | 136.142 | 26.920 | 35.429 | 1.00 | 27.37 |
| 548 | CG2 | ILE | 79 | 136.195 | 29.426 | 35.210 | 1.00 | 25.45 |
| 549 | CD1 | ILE | 79 | 137.632 | 26.715 | 35.381 | 1.00 | 25.03 |
| 550 | H | ILE | 79 | 133.782 | 27.105 | 36.435 | 1.00 | 25.00 |
| 551 | N | SER | 80 | 132.629 | 26.347 | 33.935 | 1.00 | 27.52 |
| 552 | CA | SER | 80 | 132.079 | 25.381 | 32.986 | 1.00 | 29.32 |
| 553 | C | SER | 80 | 131.317 | 26.012 | 31.816 | 1.00 | 31.74 |
| 554 | O | SER | 80 | 131.187 | 25.391 | 30.761 | 1.00 | 34.93 |
| 555 | CB | SER | 80 | 131.205 | 24.338 | 33.694 | 1.00 | 26.24 |
| 556 | OG | SER | 80 | 130.096 | 24.932 | 34.338 | 1.00 | 29.78 |
| 557 | H | SER | 80 | 132.308 | 26.358 | 34.857 | 1.00 | 25.00 |
| 558 | HG | SER | 80 | 130.432 | 25.530 | 34.992 | 1.00 | 25.00 |
| 559 | N | TYR | 81 | 130.869 | 27.258 | 31.966 | 1.00 | 25.77 |
| 560 | CA | TYR | 81 | 130.134 | 27.914 | 30.887 | 1.00 | 23.28 |
| 561 | C | TYR | 81 | 130.965 | 28.063 | 29.605 | 1.00 | 30.16 |
| 562 | O | TYR | 81 | 130.418 | 28.302 | 28.527 | 1.00 | 32.12 |
| 563 | CB | TYR | 81 | 129.556 | 29.261 | 31.344 | 1.00 | 24.86 |
| 564 | CG | TYR | 81 | 130.557 | 30.381 | 31.543 | 1.00 | 29.19 |
| 565 | CD1 | TYR | 81 | 131.260 | 30.519 | 32.740 | 1.00 | 27.27 |
| 566 | CD2 | TYR | 81 | 130.768 | 31.329 | 30.545 | 1.00 | 28.18 |
| 567 | CE1 | TYR | 81 | 132.148 | 31.575 | 32.935 | 1.00 | 29.22 |
| 568 | CE2 | TYR | 81 | 131.649 | 32.384 | 30.729 | 1.00 | 29.85 |
| 569 | CZ | TYR | 81 | 132.336 | 32.504 | 31.923 | 1.00 | 29.78 |
| 570 | OH | TYR | 81 | 133.220 | 33.547 | 32.084 | 1.00 | 28.93 |
| 571 | H | TYR | 81 | 131.028 | 27.734 | 32.805 | 1.00 | 25.00 |
| 572 | HH | TYR | 81 | 133.196 | 34.121 | 31.313 | 1.00 | 25.00 |
| 573 | N | HIS | 82 | 132.284 | 27.904 | 29.727 | 1.00 | 32.51 |
| 574 | CA | HIS | 82 | 133.194 | 27.991 | 28.581 | 1.00 | 29.34 |
| 575 | C | HIS | 82 | 133.237 | 26.669 | 27.828 | 1.00 | 28.19 |
| 576 | O | HIS | 82 | 133.658 | 28.620 | 26.672 | 1.00 | 28.93 |
| 577 | CB | HIS | 82 | 134.631 | 28.280 | 29.038 | 1.00 | 27.19 |
| 578 | CG | HIS | 82 | 134.839 | 29.654 | 29.589 | 1.00 | 22.31 |
| 579 | ND1 | HIS | 82 | 134.702 | 30.793 | 28.825 | 1.00 | 24.56 |
| 580 | CD2 | HIS | 82 | 135.195 | 30.071 | 30.827 | 1.00 | 20.64 |
| 581 | CE1 | HIS | 82 | 134.964 | 31.853 | 29.568 | 1.00 | 22.72 |
| 582 | NE2 | HIS | 82 | 135.265 | 31.442 | 30.786 | 1.00 | 23.06 |
| 583 | H | HIS | 82 | 132.658 | 27.714 | 30.612 | 1.00 | 25.00 |
| 584 | HD1 | HIS | 82 | 134.458 | 30.815 | 27.872 | 1.00 | 25.00 |
| 585 | HE2 | HIS | 82 | 135.465 | 32.016 | 31.549 | 1.00 | 25.00 |
| 586 | N | PHE | 83 | 132.820 | 25.596 | 28.493 | 1.00 | 26.84 |
| 587 | CA | PHE | 83 | 132.878 | 24.266 | 27.903 | 1.00 | 33.10 |
| 588 | C | PHE | 83 | 131.549 | 23.521 | 27.811 | 1.00 | 36.98 |
| 589 | O | PHE | 83 | 131.511 | 22.296 | 27.973 | 1.00 | 34.23 |
| 590 | CB | PHE | 83 | 133.895 | 23.426 | 28.683 | 1.00 | 33.26 |
| 591 | CG | PHE | 83 | 135.171 | 24.159 | 28.985 | 1.00 | 36.23 |
| 592 | CD1 | PHE | 83 | 136.138 | 24.336 | 27.998 | 1.00 | 36.38 |
| 5993 | CD2 | PHE | 83 | 135.381 | 24.724 | 30.241 | 1.00 | 34.95 |
| 594 | CE1 | PHE | 83 | 137.295 | 25.067 | 28.254 | 1.00 | 36.74 |
| 595 | CE2 | PHE | 83 | 136.533 | 25.457 | 30.509 | 1.00 | 39.63 |
| 596 | CZ | PHE | 83 | 137.492 | 25.630 | 29.511 | 1.00 | 41.21 |
| 597 | H | PHE | 83 | 132.457 | 25.694 | 29.394 | 1.00 | 25.00 |
| 598 | N | GLU | 84 | 130.478 | 24.241 | 27.484 | 1.00 | 40.92 |
| 599 | CA | GLU | 84 | 129.146 | 23.641 | 27.365 | 1.00 | 46.14 |
| 600 | C | GLU | 84 | 129.159 | 22.422 | 26.431 | 1.00 | 42.13 |
| 601 | O | GLU | 84 | 128.753 | 21.325 | 26.819 | 1.00 | 38.24 |
| 602 | CB | GLU | 84 | 128.128 | 24.674 | 26.851 | 1.00 | 56.77 |
| 603 | CG | GLU | 84 | 128.042 | 25.978 | 27.660 | 1.00 | 74.38 |
| 604 | CD | GLU | 84 | 127.252 | 25.853 | 28.960 | 1.00 | 81.74 |

TABLE 11-continued

Structural Coordinates of Tobacco 5-Epi-Aristolochene Synthase
In the Absence of Bound Substrate

| Atom | Atom | Resi- | Resi- | X | Y | Z | OCC | B-factor |
|---|---|---|---|---|---|---|---|---|
| Type | | due | due # | | | | | |
| 605 | OE1 | GLU | 84 | 127.654 | 25.066 | 29.847 | 1.00 | 85.56 |
| 606 | OE2 | GLU | 84 | 126.233 | 26.564 | 29.101 | 1.00 | 84.80 |
| 607 | H | GLU | 84 | 130.590 | 25.203 | 27.330 | 1.00 | 25.00 |
| 608 | N | LYS | 85 | 129.674 | 22.614 | 25.218 | 1.00 | 40.25 |
| 609 | CA | LYS | 85 | 129.740 | 21.544 | 24.224 | 1.00 | 41.41 |
| 610 | C | LYS | 85 | 130.590 | 20.348 | 24.663 | 1.00 | 36.27 |
| 611 | O | LYS | 85 | 130.138 | 19.204 | 24.595 | 1.00 | 35.16 |
| 612 | CB | LYS | 85 | 130.268 | 22.085 | 22.890 | 1.00 | 46.40 |
| 613 | CG | LYS | 85 | 130.364 | 21.025 | 21.801 | 1.00 | 58.06 |
| 614 | CD | LYS | 85 | 131.176 | 21.498 | 20.605 | 1.00 | 70.05 |
| 615 | CE | LYS | 85 | 131.305 | 20.389 | 19.565 | 1.00 | 70.91 |
| 616 | NZ | LYS | 85 | 132.101 | 20.809 | 18.379 | 1.00 | 79.32 |
| 617 | H | LYS | 85 | 130.016 | 23.501 | 24.992 | 1.00 | 25.00 |
| 618 | 1HZ | LYS | 85 | 133.059 | 21.080 | 18.678 | 1.00 | 25.00 |
| 619 | 2HZ | LYS | 85 | 132.157 | 20.018 | 17.706 | 1.00 | 25.00 |
| 620 | 3HZ | LYS | 85 | 131.636 | 21.619 | 17.922 | 1.00 | 25.00 |
| 621 | N | GLU | 86 | 131.812 | 20.620 | 25.115 | 1.00 | 37.17 |
| 622 | CA | GLU | 86 | 132.736 | 19.573 | 25.545 | 1.00 | 35.98 |
| 623 | C | GLU | 86 | 132.162 | 18.714 | 26.663 | 1.00 | 36.73 |
| 624 | O | GLU | 86 | 132.156 | 17.483 | 26.571 | 1.00 | 38.05 |
| 625 | CB | GLU | 86 | 134.077 | 20.173 | 25.990 | 1.00 | 36.51 |
| 626 | CG | GLU | 86 | 134.938 | 20.773 | 24.866 | 1.00 | 40.91 |
| 627 | CD | GLU | 86 | 134.439 | 22.124 | 24.349 | 1.00 | 43.71 |
| 628 | OE1 | GLU | 86 | 133.728 | 22.840 | 25.085 | 1.00 | 42.43 |
| 629 | OE2 | GLU | 86 | 134.770 | 22.480 | 23.201 | 1.00 | 50.53 |
| 630 | H | GLU | 86 | 132.086 | 21.551 | 25.172 | 1.00 | 25.00 |
| 631 | N | ILE | 87 | 131.666 | 19.368 | 27.708 | 1.00 | 35.80 |
| 632 | CA | ILE | 87 | 131.092 | 18.662 | 28.845 | 1.00 | 30.66 |
| 633 | C | ILE | 87 | 129.871 | 17.844 | 28.428 | 1.00 | 32.98 |
| 634 | O | ILE | 87 | 129.692 | 16.711 | 28.887 | 1.00 | 32.50 |
| 635 | CB | ILE | 87 | 130.739 | 19.640 | 29.986 | 1.00 | 30.27 |
| 636 | CG1 | ILE | 87 | 132.027 | 20.253 | 30.546 | 1.00 | 29.89 |
| 637 | CG2 | ILE | 87 | 129.972 | 18.926 | 31.091 | 1.00 | 29.25 |
| 638 | CD1 | ILE | 87 | 131.814 | 21.264 | 31.654 | 1.00 | 25.52 |
| 639 | H | ILE | 87 | 131.681 | 20.348 | 27.719 | 1.00 | 25.00 |
| 640 | N | ASP | 88 | 129.054 | 18.393 | 27.534 | 1.00 | 32.95 |
| 641 | CA | ASP | 88 | 127.870 | 17.679 | 27.070 | 1.00 | 36.69 |
| 642 | C | ASP | 88 | 128.256 | 16.407 | 26.309 | 1.00 | 39.28 |
| 643 | O | ASP | 88 | 127.745 | 15.324 | 26.6601 | 1.00 | 40.13 |
| 644 | CB | ASP | 88 | 126.994 | 18.573 | 26.191 | 1.00 | 40.42 |
| 645 | CG | ASP | 88 | 125.682 | 17.901 | 25.800 | 1.00 | 49.09 |
| 646 | OD1 | ASP | 88 | 124.874 | 17.586 | 26.702 | 1.00 | 48.29 |
| 647 | OD2 | ASP | 88 | 125.464 | 17.677 | 24.590 | 1.00 | 57.24 |
| 648 | H | ASP | 88 | 129.245 | 19.291 | 27.185 | 1.00 | 25.00 |
| 649 | N | GLU | 89 | 129.178 | 16.532 | 25.359 | 1.00 | 38.92 |
| 650 | CA | GLU | 89 | 129.621 | 15.385 | 24.573 | 1.00 | 38.06 |
| 651 | C | GLU | 89 | 130.258 | 14.303 | 25.433 | 1.00 | 35.90 |
| 652 | O | GLU | 89 | 130.077 | 13.115 | 25.168 | 1.00 | 39.91 |
| 653 | CB | GLU | 89 | 130.572 | 15.829 | 23.466 | 1.00 | 44.42 |
| 654 | CG | GLU | 89 | 129.871 | 16.622 | 22.379 | 1.00 | 61.34 |
| 655 | CD | GLU | 89 | 130.822 | 17.159 | 21.333 | 1.00 | 75.40 |
| 656 | OE1 | GLU | 89 | 131.776 | 17.873 | 21.707 | 1.00 | 80.47 |
| 657 | OE2 | GLU | 89 | 130.609 | 16.878 | 20.134 | 1.00 | 86.74 |
| 658 | H | GLU | 89 | 129.569 | 17.416 | 25.185 | 1.00 | 25.00 |
| 659 | N | ILE | 90 | 130.985 | 14.708 | 26.470 | 1.00 | 32.75 |
| 660 | CA | ILE | 90 | 131.619 | 13.749 | 27.368 | 1.00 | 31.62 |
| 661 | C | ILE | 90 | 130.556 | 13.052 | 28.215 | 1.00 | 33.52 |
| 662 | O | ILE | 90 | 130.580 | 11.830 | 28.376 | 1.00 | 35.53 |
| 663 | CB | ILE | 90 | 132.646 | 14.427 | 28.302 | 1.00 | 31.23 |
| 664 | CG1 | ILE | 90 | 133.815 | 14.983 | 27.485 | 1.00 | 32.25 |
| 665 | CG2 | ILE | 90 | 133.153 | 13.431 | 29.340 | 1.00 | 23.52 |
| 666 | CD1 | ILE | 90 | 134.794 | 15.802 | 28.300 | 1.00 | 27.90 |
| 667 | H | ILE | 90 | 131.105 | 15.670 | 26.630 | 1.00 | 25.00 |
| 668 | N | LEU | 91 | 129.617 | 13.828 | 28.749 | 1.00 | 33.39 |
| 669 | CA | LEU | 91 | 128.551 | 13.266 | 29.569 | 1.00 | 33.57 |
| 670 | C | LEU | 91 | 127.642 | 12.351 | 28.756 | 1.00 | 35.23 |
| 671 | O | LEU | 91 | 127.145 | 11.346 | 29.269 | 1.00 | 32.55 |
| 672 | CB | LEU | 91 | 127.741 | 14.373 | 30.244 | 1.00 | 30.86 |
| 673 | CG | LEU | 91 | 128.430 | 15.017 | 31.447 | 1.00 | 28.62 |
| 674 | CD1 | LEU | 91 | 127.538 | 16.084 | 32.040 | 1.00 | 25.02 |
| 675 | CD2 | LEU | 91 | 128.752 | 13.952 | 32.490 | 1.00 | 25.28 |
| 676 | H | LEU | 91 | 129.643 | 14.796 | 28.591 | 1.00 | 25.00 |
| 677 | N | ASP | 92 | 127.445 | 12.692 | 27.486 | 1.00 | 34.80 |
| 678 | CA | ASP | 92 | 126.620 | 11.889 | 26.595 | 1.00 | 37.65 |
| 679 | C | ASP | 92 | 127.273 | 10.516 | 26.446 | 1.00 | 38.72 |
| 680 | O | ASP | 92 | 126.594 | 9.490 | 26.494 | 1.00 | 41.65 |
| 681 | CB | ASP | 92 | 126.491 | 12..569 | 25.231 | 1.00 | 44.12 |
| 682 | CG | ASP | 92 | 125.426 | 11.931 | 24.358 | 1.00 | 48.79 |
| 683 | OD1 | ASP | 92 | 124.235 | 12.268 | 24.531 | 1.00 | 49.33 |
| 684 | OD2 | ASP | 92 | 125.781 | 11.098 | 23.498 | 1.00 | 52.21 |
| 685 | H | ASP | 92 | 127.856 | 13.512 | 27.149 | 1.00 | 25.00 |
| 686 | N | GLN | 93 | 128.595 | 10.499 | 26.286 | 1.00 | 40.62 |
| 687 | CA | GLN | 93 | 129.337 | 9.247 | 26.155 | 1.00 | 41.87 |
| 688 | C | GLN | 93 | 129.209 | 8.415 | 27.424 | 1.00 | 41.38 |
| 689 | O | GLN | 93 | 129.038 | 7.198 | 27.356 | 1.00 | 44.29 |
| 690 | CB | GLN | 93 | 130.817 | 9.504 | 25.883 | 1.00 | 47.84 |
| 691 | CG | GLN | 93 | 131.124 | 10.061 | 24.511 | 1.00 | 65.26 |
| 692 | CD | GLN | 93 | 132.618 | 10.230 | 24.286 | 1.00 | 76.60 |
| 693 | OE1 | GLN | 93 | 133.402 | 9.308 | 24.532 | 1.00 | 78.42 |
| 694 | NE2 | GLN | 93 | 133.023 | 11.413 | 23.829 | 1.00 | 78.28 |
| 695 | H | GLN | 93 | 129.082 | 11.351 | 26.254 | 1.00 | 25.00 |
| 696 | 1HE2 | GLN | 93 | 133.983 | 11.522 | 23.685 | 1.00 | 25.00 |
| 697 | 2HE2 | GLN | 93 | 132.356 | 12.108 | 23.664 | 1.00 | 25.00 |
| 698 | N | ILE | 94 | 129.302 | 9.065 | 28.580 | 1.00 | 38.08 |
| 699 | CA | ILE | 94 | 129.186 | 8.360 | 29.851 | 1.00 | 38.56 |
| 700 | C | ILE | 94 | 127.783 | 7.763 | 30.011 | 1.00 | 37.25 |
| 701 | O | ILE | 94 | 127.631 | 6.623 | 30.464 | 1.00 | 40.45 |
| 702 | CB | ILE | 94 | 129.519 | 9.284 | 31.051 | 1.00 | 38.10 |
| 703 | CG1 | ILE | 94 | 130.982 | 9.729 | 30.973 | 1.00 | 33.78 |
| 704 | CG2 | ILE | 94 | 129.265 | 8.559 | 32.372 | 1.00 | 39.54 |
| 705 | CD1 | ILE | 94 | 131.426 | 10.590 | 32.131 | 1.00 | 28.73 |
| 706 | H | ILE | 94 | 129.455 | 10.035 | 28.576 | 1.00 | 25..00 |
| 707 | N | TYR | 95 | 126.769 | 8.527 | 29.616 | 1.00 | 35.79 |
| 708 | CA | TYR | 95 | 125.383 | 8.080 | 29.702 | 1.00 | 36.92 |
| 709 | C | TYR | 95 | 125.219 | 6.814 | 28.869 | 1.00 | 40.95 |
| 710 | O | TYR | 95 | 124.681 | 5.812 | 29.340 | 1.00 | 39.72 |
| 711 | CB | TYR | 95 | 124.438 | 9.170 | 29.176 | 1.00 | 31.04 |
| 712 | CG | TYR | 95 | 122.969 | 8.799 | 29.213 | 1.00 | 35.51 |
| 713 | CD1 | TYR | 95 | 122.356 | 8.420 | 30.407 | 1.00 | 37.94 |
| 714 | CD2 | TYR | 95 | 122.189 | 8.826 | 28.054 | 1.00 | 40.35 |
| 715 | CE1 | TYR | 95 | 121.002 | 8.073 | 30.452 | 1.00 | 42.00 |
| 716 | CE2 | TYR | 95 | 120.827 | 8.481 | 28.088 | 1.00 | 44.29 |
| 717 | CZ | TYR | 95 | 120.245 | 8.107 | 29.294 | 1.00 | 43.88 |
| 718 | OH | TYR | 95 | 118.912 | 7.763 | 29.351 | 1.00 | 49.08 |
| 719 | H | TYR | 95 | 126.959 | 9.421 | 29.265 | 1.00 | 25.00 |
| 720 | HH | TYR | 95 | 118.668 | 7.513 | 30.254 | 1.00 | 25.00 |
| 721 | N | AS5N | 96 | 125.744 | 6.861 | 27.649 | 1.00 | 42.27 |
| 722 | CA | ASN | 96 | 125.664 | 5.749 | 26.711 | 1.00 | 45.67 |
| 723 | C | ASN | 96 | 126.430 | 4.484 | 27.088 | 1.00 | 53.96 |
| 724 | O | ASN | 96 | 125.949 | 3.383 | 26.831 | 1.00 | 58.48 |
| 725 | CB | ASN | 96 | 126.068 | 6.215 | 25.310 | 1.00 | 41.30 |
| 726 | CG | ASN | 96 | 125.004 | 7.072 | 24.656 | 1.00 | 45.95 |
| 727 | OD1 | ASN | 96 | 123.922 | 6.590 | 24.339 | 1.00 | 50.40 |
| 728 | ND2 | ASN | 96 | 125.299 | 8.349 | 24.459 | 1.00 | 47.53 |
| 729 | H | ASN | 96 | 126.205 | 7.682 | 27.378 | 1.00 | 25.00 |
| 730 | 1HD2 | ASN | 96 | 124.616 | 8.910 | 24.040 | 1.00 | 25.00 |
| 731 | 2HD2 | ASN | 96 | 126.172 | 8.686 | 24.743 | 1.00 | 25.00 |
| 732 | N | GLN | 97 | 127.604 | 4.625 | 27.702 | 1.00 | 62.59 |
| 733 | CA | GLN | 97 | 128.397 | 3.453 | 28.081 | 1.00 | 69.96 |
| 734 | C | GLN | 97 | 127.898 | 2.701 | 29.320 | 1.00 | 74.06 |
| 735 | O | GLN | 97 | 128.255 | 1.540 | 29.521 | 1.00 | 71.27 |
| 736 | CB | GLN | 97 | 129.885 | 3.804 | 28.219 | 1.00 | 74.21 |
| 737 | CG | GLN | 97 | 130.227 | 4.801 | 29.315 | 1.00 | 82.49 |
| 738 | CD | GLN | 97 | 131.723 | 5.065 | 29.415 | 1.00 | 85.73 |
| 739 | OE1 | GLN | 97 | 132.336 | 4.837 | 30.456 | 1.00 | 88.41 |
| 740 | NE2 | GLN | 97 | 132.316 | 5.548 | 28.329 | 1.00 | 82.49 |
| 741 | H | GLN | 97 | 127.943 | 5.524 | 27.899 | 1.00 | 25.00 |
| 742 | 1HE2 | GLN | 97 | 133.277 | 5.711 | 28.402 | 1.00 | 25.00 |
| 743 | 2HE2 | GLN | 97 | 131.787 | 5.714 | 27.528 | 1.00 | 25.00 |
| 744 | N | ASN | 98 | 127.091 | 3.367 | 30.147 | 1.00 | 83.07 |
| 745 | CA | ASN | 98 | 126.517 | 2.769 | 31.360 | 1.00 | 95.02 |
| 746 | C | ASN | 98 | 127.459 | 1.854 | 32.148 | 1.00 | 101.68 |
| 747 | O | ASN | 98 | 127.088 | 0.737 | 32.517 | 1.00 | 106.47 |
| 748 | CB | ASN | 98 | 125.233 | 1.997 | 31.019 | 1.00 | 98.06 |
| 749 | CG | ASN | 98 | 124.034 | 2.902 | 30.830 | 1.00 | 100.62 |
| 750 | OD1 | ASN | 98 | 123.390 | 3.307 | 31.799 | 1.00 | 107.25 |

TABLE 11-continued

Structural Coordinates of Tobacco 5-Epi-Aristolochene Synthase
In the Absence of Bound Substrate

| Atom Type | Atom | Residue | Residue # | X | Y | Z | OCC | B-factor |
|---|---|---|---|---|---|---|---|---|
| 751 | ND2 | ASN | 98 | 123.711 | 3.207 | 29.580 | 1.00 | 100.51 |
| 752 | H | ASN | 98 | 126.876 | 4.301 | 29.938 | 1.00 | 25.00 |
| 753 | 1HD2 | ASN | 98 | 122.944 | 3.798 | 29.449 | 1.00 | 25.00 |
| 754 | 2HD2 | ASN | 98 | 124.241 | 2.849 | 28.838 | 1.00 | 25.00 |
| 755 | N | SER | 99 | 128.671 | 2.326 | 32.415 | 1.00 | 105.86 |
| 756 | CA | SER | 99 | 129.649 | 1.533 | 33.153 | 1.00 | 108.38 |
| 757 | C | SER | 999 | 129.389 | 1.528 | 34.659 | 1.00 | 109.53 |
| 758 | O | SER | 99 | 129.054 | 2.561 | 35.243 | 1.00 | 110.32 |
| 759 | CB | SER | 99 | 131.057 | 2.049 | 32.859 | 1.00 | 107.06 |
| 760 | OG | SER | 99 | 131.078 | 3.465 | 32.861 | 1.00 | 109.07 |
| 761 | H | SER | 99 | 128.927 | 3.224 | 32.122 | 1.00 | 25.00 |
| 762 | HG | SER | 99 | 130.810 | 3.805 | 33.720 | 1.00 | 25.00 |
| 763 | N | ASN | 100 | 129.534 | 0.361 | 35.280 | 1.00 | 111.83 |
| 764 | CA | ASN | 100 | 129.325 | 0.223 | 36.720 | 1.00 | 115.28 |
| 765 | C | ASN | 100 | 130.612 | 0.548 | 37.462 | 1.00 | 114.16 |
| 766 | O | ASN | 100 | 131.577 | -0.213 | 37.402 | 1.00 | 114.16 |
| 767 | CB | ASN | 100 | 128.873 | -1.195 | 37.072 | 1.00 | 117.88 |
| 768 | CG | ASN | 100 | 127.451 | -1.473 | 36.640 | 1.00 | 122.11 |
| 769 | OD1 | ASN | 100 | 126.518 | -0.785 | 37.056 | 1.00 | 119.89 |
| 770 | ND2 | ASN | 100 | 127.274 | -2.485 | 35.799 | 1.00 | 124.85 |
| 771 | H | ASN | 100 | 129.794 | -0.423 | 34.757 | 1.00 | 25.00 |
| 772 | 1HD2 | ASN | 100 | 126.354 | -2.663 | 35.510 | 1.00 | 25.00 |
| 773 | 2HD2 | ASN | 100 | 128.048 | -3.001 | 35.500 | 1.00 | 25.00 |
| 774 | N | CYS | 101 | 130.622 | 1.678 | 38.162 | 1.00 | 112.97 |
| 775 | CA | CYS | 101 | 131.804 | 2.103 | 38.902 | 1.00 | 109.49 |
| 776 | C | CYS | 101 | 132.046 | 1.309 | 40.184 | 1.00 | 104.47 |
| 777 | O | CYS | 101 | 133.178 | 1.226 | 40.662 | 1.00 | 107.64 |
| 778 | CB | CYS | 101 | 131.735 | 3.593 | 39.218 | 1.00 | 112.66 |
| 779 | SG | CYS | 101 | 133.273 | 4.224 | 39.908 | 1.00 | 125.35 |
| 780 | H | CYS | 101 | 129.822 | 2.244 | 38.153 | 1.00 | 25.00 |
| 781 | N | ASN | 102 | 130.976 | 0.765 | 40.756 | 1.00 | 95.01 |
| 782 | CA | ASN | 102 | 131.043 | -0.0488 | 41.975 | 1.00 | 88.33 |
| 783 | C | ASN | 102 | 131.235 | 0.673 | 43.315 | 1.00 | 78.73 |
| 784 | O | ASN | 102 | 131.005 | 0.074 | 44.367 | 1.00 | 78.57 |
| 785 | CB | ASN | 102 | 132.071 | -1.182 | 41.831 | 1.00 | 94.60 |
| 786 | CG | ASN | 102 | 131.727 | -2.147 | 40.704 | 1.00 | 99.33 |
| 787 | OD1 | ASN | 102 | 130.667 | -2.774 | 40.706 | 1.00 | 97.79 |
| 788 | ND2 | ASN | 102 | 132.618 | -2.256 | 39.727 | 1.00 | 103.54 |
| 789 | H | ASN | 102 | 130.102 | 0.912 | 40.350 | 1.00 | 25.00 |
| 790 | 1HD2 | ASN | 102 | 132.412 | -2.867 | 38.993 | 1.00 | 25.00 |
| 791 | 2HD2 | ASN | 102 | 133.439 | -1.721 | 39.766 | 1.00 | 25.00 |
| 792 | N | ASP | 103 | 131.684 | 1.926 | 43.301 | 1.00 | 65.57 |
| 793 | CA | ASP | 103 | 131.845 | 2.657 | 44.560 | 1.00 | 56.22 |
| 794 | C | ASP | 103 | 130.870 | 3.833 | 44.638 | 1.00 | 46.49 |
| 795 | O | ASP | 103 | 130.659 | 4.550 | 43.657 | 1.00 | 41.71 |
| 796 | CB | ASP | 103 | 133.296 | 3.102 | 44.796 | 1.00 | 56.91 |
| 797 | CG | ASP | 103 | 133.767 | 4.133 | 43.802 | 1.00 | 64.49 |
| 798 | OD1 | ASP | 103 | 134.215 | 3.735 | 42.707 | 1.00 | 74.22 |
| 799 | OD2 | ASP | 103 | 133.707 | 5.339 | 44.124 | 1.00 | 67.65 |
| 800 | H | ASP | 103 | 131.912 | 2.367 | 42.461 | 1.00 | 25.00 |
| 801 | N | LEU | 104 | 130.281 | 4.015 | 45.816 | 1.00 | 38.89 |
| 802 | CA | LEU | 104 | 129.291 | 5.060 | 46.071 | 1.00 | 36.92 |
| 803 | C | LEU | 104 | 129.672 | 6.457 | 45.591 | 1.00 | 36.45 |
| 804 | O | LEU | 104 | 128.898 | 7.109 | 44.895 | 1.00 | 35.19 |
| 805 | CB | LEU | 104 | 128.943 | 5.092 | 47.561 | 1.00 | 33.67 |
| 806 | CG | LEU | 104 | 127.824 | 6.031 | 48.011 | 1.00 | 36.34 |
| 807 | CD1 | LEU | 104 | 126.538 | 5.713 | 47.269 | 1.00 | 35.38 |
| 808 | CD2 | LEU | 104 | 127.622 | 5.893 | 49.510 | 1.00 | 35.29 |
| 809 | H | LEU | 104 | 130.509 | 3.401 | 46.542 | 1.00 | 25.00 |
| 810 | N | CYS | 105 | 130.872 | 6.895 | 45.951 | 1.00 | 36.36 |
| 811 | CA | CYS | 105 | 131.376 | 8.212 | 45.581 | 1.00 | 35.11 |
| 812 | C | CYS | 105 | 131.220 | 8.537 | 44.092 | 1.00 | 34.06 |
| 813 | O | CYS | 105 | 130.596 | 9.536 | 43.725 | 1.00 | 37.28 |
| 814 | CB | CYS | 105 | 132.847 | 8.325 | 45.993 | 1.00 | 35.03 |
| 815 | SG | CYS | 105 | 133.614 | 9.885 | 45.573 | 1.00 | 53.55 |
| 816 | H | CYS | 105 | 131.437 | 6.307 | 46.464 | 1.00 | 25.00 |
| 817 | N | THR | 106 | 131.761 | 7.679 | 43.236 | 1.00 | 30.74 |
| 818 | CA | THR | 106 | 131.697 | 7.890 | 41.797 | 1.00 | 28.00 |
| 819 | C | THR | 106 | 130.301 | 7.663 | 41.227 | 1.00 | 25.73 |
| 820 | O | THR | 106 | 129.870 | 8.396 | 40.339 | 1.00 | 28.92 |
| 821 | CB | THR | 106 | 132.714 | 7.000 | 41.074 | 1.00 | 33.61 |
| 822 | OG1 | THR | 106 | 134.000 | 7.172 | 41.684 | 1.00 | 38.24 |
| 823 | CG2 | THR | 106 | 132.807 | 7.369 | 39.598 | 1.00 | 30.78 |
| 824 | H | THR | 106 | 132.208 | 6.874 | 43.564 | 1.00 | 25.00 |
| 825 | HG1 | THR | 106 | 134.270 | 8.093 | 41.602 | 1.00 | 25.00 |
| 826 | N | SER | 107 | 129.592 | 6.670 | 41.751 | 1.00 | 23.29 |
| 827 | CA | SER | 107 | 128.237 | 6.371 | 41.294 | 1.00 | 27.37 |
| 828 | C | SER | 107 | 127.268 | 7.540 | 41.539 | 1.00 | 25.50 |
| 829 | O | SER | 107 | 126.518 | 7.932 | 40.643 | 1.00 | 25.99 |
| 830 | CB | SER | 107 | 127.721 | 5.101 | 41.978 | 1.00 | 26.16 |
| 831 | OG | SER | 107 | 128.552 | 3.993 | 41.676 | 1.00 | 34.57 |
| 832 | H | SER | 107 | 129.981 | 6.113 | 42.456 | 1.00 | 25.00 |
| 833 | HG | SER | 107 | 128.501 | 3.864 | 40.726 | 1.00 | 25.00 |
| 834 | N | ALA | 108 | 127.298 | 8.096 | 42.749 | 1.00 | 23.90 |
| 835 | CA | ALA | 108 | 126.441 | 9.219 | 43.121 | 1.00 | 23.63 |
| 836 | C | ALA | 108 | 126.779 | 10.466 | 42.307 | 1.00 | 25.62 |
| 837 | O | ALA | 108 | 125.887 | 11.189 | 41.861 | 1.00 | 27.88 |
| 838 | CB | ALA | 108 | 126.566 | 9.509 | 44.608 | 1.00 | 18.25 |
| 839 | H | ALA | 108 | 127.913 | 7.734 | 43.418 | 1.00 | 25.00 |
| 840 | N | LEU | 109 | 128.069 | 10.709 | 42.099 | 1.00 | 21.86 |
| 841 | CA | LEU | 109 | 128.493 | 11.861 | 41.322 | 1.00 | 21.96 |
| 842 | C | LEU | 109 | 128.009 | 11.704 | 39.881 | 1.00 | 25.59 |
| 843 | O | LEU | 109 | 127.458 | 12.640 | 39.297 | 1.00 | 26.33 |
| 844 | CB | LEU | 109 | 130.017 | 12.002 | 41.359 | 1.00 | 21.29 |
| 845 | CG | LEU | 109 | 130.611 | 13.161 | 40.550 | 1.00 | 23.03 |
| 846 | CD1 | LEU | 109 | 129.969 | 14.480 | 40.962 | 1.00 | 15.35 |
| 847 | CD2 | LEU | 109 | 132.111 | 13.210 | 40.751 | 1.00 | 17.60 |
| 848 | H | LEU | 109 | 128.742 | 10.101 | 42.475 | 1.00 | 25.00 |
| 849 | N | GLN | 110 | 128.205 | 10.509 | 39.325 | 1.00 | 27.12 |
| 850 | CA | GLN | 110 | 127.796 | 10.199 | 37.954 | 1.00 | 28.41 |
| 851 | C | GLN | 110 | 126.302 | 10.449 | 37.803 | 1.00 | 24.05 |
| 852 | O | GLN | 110 | 125.849 | 11.049 | 36.825 | 1.00 | 23.84 |
| 853 | CB | GLN | 110 | 128.098 | 8.732 | 37.632 | 1.00 | 26.80 |
| 854 | CG | GLN | 110 | 127.790 | 8.333 | 36.197 | 1.00 | 34.89 |
| 855 | CD | GLN | 110 | 127.942 | 6.843 | 35.947 | 1.00 | 37.60 |
| 856 | OE1 | GLN | 110 | 128.418 | 6.098 | 36.804 | 1.00 | 43.99 |
| 857 | NE2 | GLN | 110 | 127.538 | 6.401 | 34.765 | 1.00 | 38.91 |
| 858 | H | GLN | 110 | 128.641 | 9.810 | 39.852 | 1.00 | 25.00 |
| 859 | 1HE2 | GLN | 110 | 127.636 | 5.440 | 34.604 | 1.00 | 25.00 |
| 860 | 2HE2 | GLN | 110 | 127.167 | 7.030 | 34.117 | 1.00 | 25.00 |
| 861 | N | PHE | 111 | 125.543 | 9.970 | 38.779 | 1.00 | 20.86 |
| 862 | CA | PHE | 111 | 124.104 | 10.140 | 38.783 | 1.00 | 24.95 |
| 863 | C | PHE | 111 | 123.760 | 11.633 | 38.792 | 1.00 | 24.87 |
| 864 | O | PHE | 111 | 123.037 | 12.113 | 37.917 | 1.00 | 27.29 |
| 865 | CB | PHE | 111 | 123.511 | 9.442 | 40.008 | 1.00 | 21.47 |
| 866 | CG | PHE | 111 | 122.019 | 9.568 | 40.120 | 1.00 | 28.99 |
| 867 | CD1 | PHE | 111 | 121.183 | 8.649 | 39.494 | 1.00 | 24.39 |
| 868 | CD2 | PHE | 111 | 121.448 | 10.600 | 40.865 | 1.00 | 26.46 |
| 869 | CE1 | PHE | 111 | 119.799 | 8.753 | 39.610 | 1.00 | 26.64 |
| 870 | CE2 | PHE | 111 | 120.072 | 10.713 | 40.985 | 1.00 | 25.60 |
| 871 | CZ | PHE | 111 | 119.243 | 9.787 | 40.356 | 1.00 | 30.12 |
| 872 | H | PHE | 111 | 125.966 | 9.482 | 39.513 | 1.00 | 25.00 |
| 873 | N | ARG | 112 | 124.323 | 12.372 | 39.747 | 1.00 | 23.80 |
| 874 | CA | ARG | 112 | 124.055 | 13.802 | 39.858 | 1.00 | 18.05 |
| 875 | C | ARG | 112 | 124.384 | 14.598 | 38.601 | 1.00 | 22.05 |
| 876 | O | ARG | 112 | 123.539 | 15.341 | 38.103 | 1.00 | 28.69 |
| 877 | CB | ARG | 112 | 124.771 | 14.417 | 41.066 | 1.00 | 18.30 |
| 878 | CG | ARG | 112 | 124.503 | 15.911 | 41.209 | 1.00 | 16.54 |
| 879 | CD | ARG | 112 | 125.077 | 16.519 | 42.479 | 1.00 | 17.13 |
| 880 | NE | ARG | 112 | 126.540 | 16.520 | 42.517 | 1.00 | 19.87 |
| 881 | CZ | ARG | 112 | 127.323 | 17.379 | 41.866 | 1.00 | 22.23 |
| 882 | NH1 | ARG | 112 | 126.808 | 18.328 | 41.099 | 1.00 | 19.31 |
| 883 | NH2 | ARG | 112 | 128.636 | 17.311 | 42.012 | 1.00 | 25.31 |
| 884 | H | ARG | 112 | 124.929 | 11.945 | 40.387 | 1.00 | 25.00 |
| 885 | HE | ARG | 112 | 126.982 | 15.846 | 43.063 | 1.00 | 25.00 |
| 886 | 1HH1 | ARG | 112 | 125.815 | 18.407 | 40.998 | 1.00 | 25.00 |
| 887 | 2HH1 | ARG | 112 | 127.408 | 18.960 | 40.612 | 1.00 | 25.00 |
| 888 | 1HH2 | ARG | 112 | 129.037 | 16.615 | 42.608 | 1.00 | 25.00 |
| 889 | 2HH2 | ARG | 112 | 129.219 | 17.950 | 41.520 | 1.00 | 25.00 |
| 890 | N | LEU | 113 | 125.596 | 14.445 | 38.077 | 1.00 | 22.19 |
| 891 | CA | LEU | 113 | 125.994 | 15.192 | 36.883 | 1.00 | 23.19 |
| 892 | C | LEU | 113 | 125.112 | 14.907 | 35.665 | 1.00 | 27.49 |
| 893 | O | LEU | 113 | 124.752 | 15.828 | 34.921 | 1.00 | 24.19 |
| 894 | CB | LEU | 113 | 127.465 | 14.937 | 36.532 | 1.00 | 26.29 |
| 895 | CG | LEU | 113 | 128.547 | 15.323 | 37.546 | 1.00 | 28.48 |
| 896 | CD1 | LEEU | 113 | 129.911 | 15.110 | 36.905 | 1.00 | 21.83 |

TABLE 11-continued

Structural Coordinates of Tobacco 5-Epi-Aristolochene Synthase In the Absence of Bound Substrate

| Atom Type | Atom | Residue | Residue # | X | Y | Z | OCC | B-factor |
|---|---|---|---|---|---|---|---|---|
| 897 | CD2 | LEU | 113 | 128.391 | 16.772 | 37.993 | 1.00 | 17.87 |
| 898 | H | LEU | 113 | 126.225 | 13.821 | 38.492 | 1.00 | 25.00 |
| 899 | N | LEU | 114 | 124.776 | 13.638 | 35.451 | 1.00 | 24.90 |
| 900 | CA | LEU | 114 | 123.932 | 13.268 | 34.321 | 1.00 | 25.28 |
| 901 | C | LEU | 114 | 122.537 | 13.867 | 34.485 | 1.00 | 23.09 |
| 902 | O | LEU | 114 | 122.038 | 14.534 | 33.580 | 1.00 | 26.40 |
| 903 | CB | LEU | 114 | 123.866 | 11.746 | 34.168 | 1.00 | 23.58 |
| 904 | CG | LEU | 114 | 125.167 | 11.101 | 33.671 | 1.00 | 25.79 |
| 905 | CD1 | LEU | 114 | 125.043 | 9.591 | 33.660 | 1.00 | 24.20 |
| 906 | CD2 | LEU | 114 | 125.504 | 11.607 | 32.280 | 1.00 | 23.62 |
| 907 | H | LEU | 114 | 125.095 | 12.937 | 36.062 | 1.00 | 25.00 |
| 908 | N | ARG | 115 | 121.948 | 13.694 | 35.665 | 1.00 | 23.30 |
| 909 | CA | ARG | 115 | 120.620 | 14.228 | 35.955 | 1.00 | 21.07 |
| 910 | C | ARG | 115 | 120.551 | 15.748 | 35.787 | 1.00 | 26.37 |
| 911 | O | ARG | 115 | 119.628 | 16.267 | 35.148 | 1.00 | 26.34 |
| 912 | CB | ARG | 115 | 120.178 | 13.844 | 37.372 | 1.00 | 20.95 |
| 913 | CG | ARG | 115 | 119.749 | 12.394 | 37.528 | 1.00 | 21.24 |
| 914 | CD | ARG | 115 | 118.588 | 12.057 | 36.595 | 1.00 | 24.51 |
| 915 | NE | ARG | 115 | 118.086 | 10.702 | 36.813 | 1.00 | 20.45 |
| 916 | CZ | ARG | 115 | 117.090 | 10.394 | 37.639 | 1.00 | 25.55 |
| 917 | NH1 | ARG | 115 | 116.475 | 11.347 | 38.327 | 1.00 | 26.55 |
| 918 | NH2 | ARG | 115 | 116.729 | 9.128 | 37.807 | 1.00 | 21.55 |
| 919 | H | ARG | 115 | 122.416 | 13.187 | 36.361 | 1.00 | 25.00 |
| 920 | HE | ARG | 115 | 118.508 | 9.978 | 36.314 | 1.00 | 25.00 |
| 921 | 1HH1 | ARG | 115 | 116.757 | 12.300 | 38.232 | 1.00 | 25.00 |
| 922 | 2HH1 | ARG | 115 | 115.725 | 11.114 | 38.942 | 1.00 | 25.00 |
| 923 | 1HH2 | ARG | 115 | 117.205 | 8.402 | 37.314 | 1.00 | 25.00 |
| 924 | 2HH2 | ARG | 115 | 115.980 | 8.901 | 38.425 | 1.00 | 25.00 |
| 925 | N | GLN | 116 | 121.537 | 16.458 | 36.333 | 1.00 | 24.98 |
| 926 | CA | GLN | 116 | 121.573 | 17.917 | 36.235 | 1.00 | 21.36 |
| 927 | C | GLN | 116 | 121.696 | 18.366 | 34.792 | 1.00 | 23.11 |
| 928 | O | GLN | 116 | 121.331 | 19.491 | 34.450 | 1.00 | 20.94 |
| 929 | CB | GLN | 116 | 122.718 | 18.501 | 37.066 | 1.00 | 21.35 |
| 930 | CG | GLN | 116 | 122.536 | 18.322 | 38.561 | 1.00 | 24.02 |
| 931 | CD | GLN | 116 | 123.594 | 19.035 | 39.371 | 1.00 | 23.65 |
| 932 | OE1 | GLN | 116 | 123.278 | 19.835 | 40.252 | 1.00 | 30.06 |
| 933 | NE2 | GLN | 116 | 124.855 | 18.744 | 39.088 | 1.00 | 21.53 |
| 934 | H | GLN | 116 | 122.246 | 15.983 | 36.814 | 1.00 | 25.00 |
| 935 | 1HE2 | GLN | 116 | 125.538 | 19.210 | 39.609 | 1.00 | 25.00 |
| 936 | 2HE2 | GLN | 116 | 125.046 | 18.069 | 38.391 | 1.00 | 25.00 |
| 937 | N | HIS | 117 | 122.232 | 17.490 | 33.950 | 1.00 | 21.29 |
| 938 | CA | HIS | 117 | 122.381 | 17.804 | 32.537 | 1.00 | 21.02 |
| 939 | C | HIS | 117 | 121.264 | 17.235 | 31.666 | 1.00 | 23.62 |
| 940 | O | HIS | 117 | 121.389 | 17.192 | 30.445 | 1.00 | 22.85 |
| 941 | CB | HIS | 117 | 123.755 | 17.366 | 32.031 | 1.00 | 23.58 |
| 942 | CG | HIS | 117 | 124.863 | 18.267 | 32.475 | 1.00 | 27.17 |
| 943 | ND1 | HIS | 117 | 125.477 | 19.165 | 31.628 | 1.00 | 28.70 |
| 944 | CD2 | HIS | 117 | 125.421 | 18.456 | 33.693 | 1.00 | 26.70 |
| 945 | CE1 | HIS | 117 | 126.361 | 19.874 | 32.307 | 1.00 | 25.66 |
| 946 | NE2 | HIS | 117 | 126.346 | 19.464 | 33.562 | 1.00 | 29.17 |
| 947 | H | HIS | 117 | 122.526 | 16.612 | 34.277 | 1.00 | 25.00 |
| 948 | HD1 | HIS | 117 | 125.301 | 19.252 | 30.671 | 1.00 | 25.00 |
| 949 | HE2 | HIS | 117 | 126.861 | 19.825 | 34.298 | 1.00 | 25.00 |
| 950 | N | GLY | 118 | 120.183 | 16.784 | 32.301 | 1.00 | 24.12 |
| 951 | CA | GLY | 118 | 119.050 | 16.258 | 31.562 | 1.00 | 25.68 |
| 952 | C | GLY | 118 | 119.037 | 14.786 | 31.193 | 1.00 | 30.13 |
| 953 | O | GLY | 118 | 118.028 | 14.303 | 30.676 | 1.00 | 35.12 |
| 954 | H | GLY | 118 | 120.143 | 16.804 | 33.279 | 1.00 | 25.00 |
| 955 | N | PHE | 119 | 120.130 | 14.068 | 31.432 | 1.00 | 29.49 |
| 956 | CA | PHE | 119 | 120.184 | 12.644 | 31.102 | 1.00 | 26.30 |
| 957 | C | PHE | 119 | 119.435 | 11.887 | 32.172 | 1.00 | 28.96 |
| 958 | O | PHE | 119 | 119.836 | 11.861 | 33.337 | 1.00 | 25.84 |
| 959 | CB | PHE | 119 | 121.633 | 12.156 | 31.019 | 1.00 | 24.99 |
| 960 | CG | PHE | 119 | 122.447 | 12.845 | 29.964 | 1.00 | 23.43 |
| 961 | CD1 | PHE | 119 | 122.392 | 12.421 | 28.640 | 1.00 | 22.02 |
| 962 | CD2 | PHE | 119 | 123.267 | 13.922 | 30.291 | 1.00 | 23.36 |
| 963 | CE1 | PHE | 119 | 123.145 | 13.063 | 27.650 | 1.00 | 26.82 |
| 964 | CE2 | PHE | 119 | 124.023 | 14.572 | 29.312 | 1.00 | 20.73 |
| 965 | CZ | PHE | 119 | 123.962 | 14.141 | 27.988 | 1.00 | 22.11 |
| 966 | H | PHE | 119 | 120.902 | 14.496 | 31.856 | 1.00 | 25.00 |
| 967 | N | ASN | 120 | 118.351 | 11.207 | 31.779 | 1.00 | 31.42 |
| 968 | CA | ASN | 120 | 117.551 | 10.447 | 32.733 | 1.00 | 36.20 |
| 969 | C | ASN | 120 | 118.208 | 9.117 | 33.088 | 1.00 | 36.85 |
| 970 | O | ASN | 120 | 117.727 | 8.048 | 32.707 | 1.00 | 39.49 |
| 971 | CB | ASN | 120 | 116.126 | 10.232 | 32.200 | 1.00 | 33.41 |
| 972 | CG | ASN | 120 | 115.142 | 9.796 | 33.288 | 1.00 | 35.58 |
| 973 | OD1 | ASN | 120 | 115.481 | 9.721 | 34.465 | 1.00 | 38.24 |
| 974 | ND2 | ASN | 120 | 113.907 | 9.531 | 32.886 | 1.00 | 40.30 |
| 975 | H | ASN | 120 | 118.092 | 11.226 | 30.839 | 1.00 | 25.00 |
| 976 | 1HD2 | ASN | 120 | 113.277 | 9.246 | 33.576 | 1.00 | 25.00 |
| 977 | 2HD2 | ASN | 120 | 113.672 | 9.626 | 31.940 | 1.00 | 25.00 |
| 978 | N | ILE | 121 | 119.347 | 9.194 | 33.770 | 1.00 | 36.98 |
| 979 | CA | ILE | 121 | 120.054 | 7.997 | 34.192 | 1.00 | 29.59 |
| 980 | C | ILE | 121 | 119.207 | 7.323 | 35.264 | 1.00 | 29.55 |
| 981 | O | ILE | 121 | 118.647 | 7.984 | 36.134 | 1.00 | 30.63 |
| 982 | CB | ILE | 121 | 121.478 | 8.319 | 34.745 | 1.00 | 35.93 |
| 983 | CG1 | ILE | 121 | 122.130 | 7.046 | 35.300 | 1.00 | 34.57 |
| 984 | CG2 | ILE | 121 | 121.419 | 9.425 | 35.7798 | 1.00 | 27.62 |
| 985 | CD1 | ILE | 121 | 123.558 | 7.221 | 35.775 | 1.00 | 37.39 |
| 986 | H | ILE | 121 | 119.696 | 10.074 | 34.013 | 1.00 | 25.00 |
| 987 | N | SER | 122 | 119.086 | 6.007 | 35.172 | 1.00 | 32.39 |
| 988 | CA | SER | 122 | 118.299 | 5.245 | 36.129 | 1.00 | 27.80 |
| 989 | C | SER | 122 | 118.912 | 5.243 | 37.526 | 1.00 | 27.11 |
| 990 | O | SER | 122 | 120.130 | 5.143 | 37.685 | 1.00 | 30.59 |
| 991 | CB | SER | 122 | 118.145 | 3.801 | 35.642 | 1.00 | 28.47 |
| 992 | OG | SER | 122 | 117.529 | 2.993 | 36.633 | 1.00 | 27.99 |
| 993 | H | SER | 122 | 119.540 | 5.535 | 34.444 | 1.00 | 25.00 |
| 994 | HG | SER | 122 | 117.442 | 2.098 | 36.275 | 1.00 | 25.00 |
| 995 | N | PRO | 123 | 118.065 | 5.325 | 38.564 | 1.00 | 27.95 |
| 996 | CA | PRO | 123 | 118.542 | 5.323 | 39.949 | 1.00 | 27.26 |
| 997 | C | PRO | 123 | 118.941 | 3.904 | 40.372 | 1.00 | 33.55 |
| 998 | O | PRO | 123 | 119.325 | 3.664 | 41.521 | 1.00 | 34.51 |
| 999 | CB | PRO | 123 | 117.323 | 5.823 | 40.723 | 1.00 | 26.86 |
| 1000 | CG | PRO | 123 | 116.184 | 5.252 | 39.938 | 1.00 | 26.05 |
| 1001 | CD | PRO | 123 | 116.605 | 5.531 | 38.510 | 1.00 | 24.97 |
| 1002 | N | GLU | 124 | 118.849 | 2.967 | 39.431 | 1.00 | 34.65 |
| 1003 | CA | GLU | 124 | 119.199 | 1.569 | 39.673 | 1.00 | 42.28 |
| 1004 | C | GLU | 124 | 120.673 | 1.441 | 40.056 | 1.00 | 39.18 |
| 1005 | O | GLU | 124 | 121.072 | 0.492 | 40.735 | 1.00 | 41.59 |
| 1006 | CB | GLU | 124 | 118.902 | 0.732 | 38.424 | 1.00 | 48.21 |
| 1007 | CG | GLU | 124 | 119.074 | −0.773 | 38.601 | 1.00 | 61.85 |
| 1008 | CD | GLU | 124 | 118.112 | −1.379 | 39.615 | 1.00 | 71.29 |
| 1009 | OE1 | GLU | 124 | 117.022 | −0.803 | 39.851 | 1.00 | 70.67 |
| 1010 | OE2 | GLU | 124 | 118.450 | −2.447 | 40.170 | 1.00 | 76.93 |
| 1011 | H | GLU | 124 | 118.522 | 3.203 | 38.539 | 1.00 | 25.00 |
| 1012 | N | ILE | 125 | 121.466 | 2.430 | 39.657 | 1.00 | 36.76 |
| 1013 | CA | ILE | 125 | 122.892 | 2.458 | 39.955 | 1.00 | 35.15 |
| 1014 | C | ILE | 125 | 123.155 | 2.401 | 41.472 | 1.00 | 35.83 |
| 1015 | O | ILE | 125 | 124.237 | 2.016 | 41.900 | 1.00 | 36.05 |
| 1016 | CB | ILE | 125 | 123.557 | 3.718 | 39.319 | 1.00 | 33.60 |
| 1017 | CG1 | ILE | 125 | 125.082 | 3.610 | 39.368 | 1.00 | 32.56 |
| 1018 | CG2 | ILE | 125 | 123.087 | 4.988 | 40.017 | 1.00 | 28.43 |
| 1019 | CD1 | ILE | 125 | 125.789 | 4.705 | 38.586 | 1.00 | 28.58 |
| 1020 | H | ILE | 125 | 121.080 | 3.169 | 39.141 | 1.00 | 25.00 |
| 1021 | N | PHE | 126 | 122.145 | 2.733 | 42.276 | 1.00 | 33.20 |
| 1022 | CA | PHE | 126 | 122.276 | 2..717 | 43.731 | 1.00 | 33.30 |
| 1023 | C | PHE | 126 | 121.902 | 1.394 | 44.402 | 1.00 | 38.46 |
| 1024 | O | PHE | 126 | 122.171 | 1.211 | 45.591 | 1.00 | 38.34 |
| 1025 | CB | PHE | 126 | 121.444 | 3.843 | 44.362 | 1.00 | 29.75 |
| 1026 | CG | PHE | 126 | 121.937 | 5.218 | 44.030 | 1.00 | 32.61 |
| 1027 | CD1 | PHE | 126 | 123.084 | 5.724 | 44.631 | 1.00 | 29.30 |
| 1028 | CD2 | PHE | 126 | 121.263 | 6.007 | 43.103 | 1.00 | 33.58 |
| 1029 | CE1 | PHE | 126 | 123.558 | 6.997 | 44.310 | 1.00 | 31.83 |
| 1030 | CE2 | PHE | 126 | 121.726 | 7.279 | 42.775 | 1.00 | 36.03 |
| 1031 | CZ | PHE | 126 | 122.877 | 7.776 | 43.380 | 1.00 | 34.15 |
| 1032 | H | PHE | 126 | 121.286 | 3.004 | 41.891 | 1.00 | 25.00 |
| 1033 | N | SER | 127 | 121.285 | 0.477 | 43.662 | 1.00 | 37.94 |
| 1034 | CA | SER | 127 | 120.871 | −0.806 | 44.236 | 1.00 | 37.24 |
| 1035 | C | SER | 127 | 122.012 | −1.601 | 44.855 | 1.00 | 37.05 |
| 1036 | O | SER | 127 | 121.842 | −2.210 | 45.908 | 1.00 | 37.94 |
| 1037 | CB | SER | 127 | 120.141 | −1.658 | 43.201 | 1.00 | 34.22 |
| 1038 | OG | SER | 127 | 118.885 | −1.087 | 42.887 | 1.00 | 44.36 |
| 1039 | H | SER | 127 | 121.104 | 0.658 | 42.719 | 1.00 | 25.00 |
| 1040 | HG | SER | 127 | 119.018 | −0.202 | 42.539 | 1.00 | 25.00 |
| 1041 | N | LYS | 128 | 123.184 | −1.557 | 44.228 | 1.00 | 37.17 |
| 1042 | CA | LYS | 128 | 124.348 | −2.280 | 44.737 | 1.00 | 39.88 |

TABLE 11-continued

Structural Coordinates of Tobacco 5-Epi-Aristolochene Synthase In the Absence of Bound Substrate

| Atom Type | Atom | Residue | Residue # | X | Y | Z | OCC | B-factor |
|---|---|---|---|---|---|---|---|---|
| 1043 | C | LYS | 128 | 124.840 | −1.783 | 46.097 | 1.00 | 42.69 |
| 1044 | O | LYS | 128 | 125.690 | −2.417 | 46.720 | 1.00 | 48.65 |
| 1045 | CB | LYS | 128 | 125.492 | −2.257 | 43.715 | 1.00 | 39.92 |
| 1046 | CG | LYS | 128 | 125.877 | −0.882 | 43.210 | 1.00 | 41.79 |
| 1047 | CD | LYS | 128 | 126.864 | −0.983 | 42.061 | 1.00 | 45..38 |
| 1048 | CE | LYS | 128 | 127.112 | 0.380 | 41.430 | 1.00 | 57.33 |
| 1049 | NZ | LYS | 128 | 128.057 | 0.329 | 40.278 | 1.00 | 63.77 |
| 1050 | H | LYS | 128 | 123.266 | −1.028 | 43.408 | 1.00 | 25.00 |
| 1051 | 1HZ | LYS | 128 | 128.971 | −0.047 | 40.597 | 1.00 | 25.00 |
| 1052 | 2HZ | LYS | 128 | 127.667 | −0.293 | 39.541 | 1.00 | 25.00 |
| 1053 | 3HZ | LYS | 128 | 128.187 | 1.285 | 39.892 | 1.00 | 25.00 |
| 1054 | N | PHE | 129 | 124.305 | −0.656 | 46.556 | 1.00 | 41.03 |
| 1055 | CA | PHE | 129 | 124.697 | −0.090 | 47.844 | 1.00 | 38.56 |
| 1056 | C | PHE | 129 | 123.574 | −0.255 | 48.848 | 1.00 | 42.42 |
| 1057 | O | PHE | 129 | 123.617 | 0.319 | 49.940 | 1.00 | 44.74 |
| 1058 | CB | PHE | 129 | 125.013 | 1.396 | 47.695 | 1.00 | 32.52 |
| 1059 | CG | PHE | 129 | 125.984 | 1.691 | 46.604 | 1.00 | 28.29 |
| 1060 | CD1 | PHE | 129 | 127.291 | 1.225 | 46.677 | 1.00 | 27.71 |
| 1061 | CD2 | PHE | 129 | 125.585 | 2.402 | 45.481 | 1.00 | 27.23 |
| 1062 | CE1 | PHE | 129 | 128.186 | 1.461 | 45.645 | 1.00 | 27.92 |
| 1063 | CE2 | PHE | 129 | 126.473 | 2.644 | 44.442 | 1.00 | 29.82 |
| 1064 | CZ | PHE | 129 | 127.776 | 2.172 | 44.523 | 1.00 | 29.88 |
| 1065 | H | PHE | 129 | 123.617 | −0.193 | 46.037 | 1.00 | 25.00 |
| 1066 | N | GLN | 130 | 122.566 | −1.036 | 48.482 | 1.00 | 46.51 |
| 1067 | CA | GLN | 130 | 121.425 | −1.242 | 49.356 | 1.00 | 52.21 |
| 1068 | C | GLN | 130 | 121.181 | −2.700 | 49.659 | 1.00 | 60.08 |
| 1069 | O | GLN | 130 | 121.565 | −3.588 | 48.891 | 1.00 | 57.60 |
| 1070 | CB | GLN | 130 | 120.173 | −0.638 | 48.736 | 1.00 | 50.11 |
| 1071 | CG | GLN | 130 | 120.247 | 0.860 | 48.526 | 1.00 | 50.91 |
| 1072 | CD | GLN | 130 | 119.025 | 1.399 | 47.840 | 1.00 | 51.21 |
| 1073 | OE1 | GLN | 130 | 118.339 | 0.677 | 47.117 | 1.00 | 52.53 |
| 1074 | NE2 | GLN | 130 | 118.737 | 2.677 | 48.061 | 1.00 | 47.70 |
| 1075 | H | GLN | 130 | 122.585 | −1.533 | 47.632 | 1.00 | 25.00 |
| 1076 | 1HE2 | GLN | 130 | 117.922 | 2.996 | 47.623 | 1.00 | 25.00 |
| 1077 | 2HE2 | GLN | 130 | 119.296 | 3.221 | 48.627 | 1.00 | 25.00 |
| 1078 | N | ASP | 131 | 120.531 | −2.944 | 50.790 | 1.00 | 67.42 |
| 1079 | CA | ASP | 131 | 120.236 | −4.306 | 51.203 | 1.00 | 74.82 |
| 1080 | C | ASP | 131 | 118.975 | −4.746 | 50.421 | 1.00 | 79.83 |
| 1081 | O | ASP | 131 | 118.273 | −3.905 | 49.822 | 1.00 | 81.73 |
| 1082 | CB | ASP | 131 | 120.046 | −4.394 | 52.745 | 1.00 | 75.37 |
| 1083 | CG | ASP | 131 | 118.894 | −3.558 | 53.284 | 1.00 | 79.54 |
| 1084 | OD1 | ASP | 131 | 118.173 | −2.911 | 52.501 | 1.00 | 89.69 |
| 1085 | OD2 | ASP | 131 | 118.707 | −3.540 | 54.511 | 1.00 | 80.32 |
| 1086 | H | ASP | 131 | 120.203 | −2.147 | 51.259 | 1.00 | 25.00 |
| 1087 | N | GLU | 132 | 118.671 | −6.041 | 50.521 | 1.00 | 86.92 |
| 1088 | CA | GLU | 132 | 117.492 | −6.620 | 49.865 | 1.00 | 93.82 |
| 1089 | C | GLU | 132 | 116.183 | −5.970 | 50.310 | 1.00 | 94.42 |
| 1090 | O | GLU | 132 | 115.084 | −6.369 | 49.910 | 1.00 | 95.34 |
| 1091 | CB | GLU | 132 | 117.414 | −8.108 | 50.165 | 1.00 | 99.58 |
| 1092 | CG | GLU | 132 | 118.603 | −8.893 | 49.626 | 1.00 | 110.72 |
| 1093 | CD | GLU | 132 | 118.550 | −10.369 | 49.968 | 1.00 | 117.77 |
| 1094 | OE1 | GLU | 132 | 118.100 | −10.716 | 51.082 | 1.00 | 122.96 |
| 1095 | OE2 | GLU | 132 | 118.962 | −11.187 | 49.117 | 1.00 | 118.79 |
| 1096 | H | GLU | 132 | 119.347 | −6.569 | 50.930 | 1.00 | 25.00 |
| 1097 | N | ASN | 133 | 116.318 | −4.957 | 51.145 | 1.00 | 94.58 |
| 1098 | CA | ASN | 1333 | 115.214 | −4.208 | 51.715 | 1.00 | 92.72 |
| 1099 | C | ASN | 133 | 115.107 | −2.839 | 51.042 | 1.00 | 90.09 |
| 1100 | O | ASN | 133 | 114.134 | −2.112 | 51.210 | 1.00 | 90.03 |
| 1101 | CB | ASN | 133 | 115.492 | −4.043 | 53.214 | 1.00 | 99.96 |
| 1102 | CG | ASN | 133 | 114.389 | −3.337 | 53.923 | 1.00 | 106.41 |
| 1103 | OD1 | ASN | 133 | 113.275 | −3.847 | 54.016 | 1.00 | 108.32 |
| 1104 | ND2 | ASN | 133 | 114.683 | −2.159 | 54.447 | 1.00 | 111.37 |
| 1105 | H | ASN | 133 | 117.175 | −4.667 | 51.437 | 1.00 | 25.00 |
| 1106 | 1HD2 | ASN | 133 | 113.925 | −1.736 | 54.889 | 1.00 | 25.00 |
| 1107 | 2HD2 | ASN | 133 | 115.561 | −1.741 | 54.365 | 1.00 | 25.00 |
| 1108 | N | GLY | 134 | 116.139 | −2.501 | 50.284 | 1.00 | 84.16 |
| 1109 | CA | GLY | 134 | 116.195 | −1.224 | 49.597 | 1.00 | 77.66 |
| 1110 | C | GLY | 134 | 116.752 | −0.121 | 50.479 | 1.00 | 73.68 |
| 1111 | O | GLY | 134 | 116.780 | 1.040 | 50.072 | 1.00 | 72.39 |
| 1112 | H | GLY | 134 | 116.840 | −3.192 | 50.233 | 1.00 | 25.00 |
| 1113 | N | LYS | 135 | 117.141 | −0.462 | 51.704 | 1.00 | 70.01 |
| 1114 | CA | LYS | 135 | 117.724 | 0.524 | 52.606 | 1.00 | 61.88 |
| 1115 | C | LYS | 135 | 119.229 | 0.556 | 52.361 | 1.00 | 58.01 |
| 1116 | O | LYS | 135 | 119.831 | −0.473 | 52.038 | 1.00 | 52.64 |
| 1117 | CB | LYS | 135 | 117.429 | 0.190 | 54.069 | 1.00 | 62.54 |
| 1118 | CG | LYS | 135 | 116.279 | 0.994 | 54.661 | 1.00 | 69.58 |
| 1119 | CD | LYS | 135 | 114.935 | 0.594 | 54.062 | 1.00 | 74.13 |
| 1120 | CE | LYS | 135 | 113.799 | 1.517 | 54.474 | 1.00 | 77.90 |
| 1121 | NZ | LYS | 135 | 113.779 | 1.824 | 55.931 | 1.00 | 77.60 |
| 1122 | H | LYS | 135 | 117.045 | −1.379 | 52.010 | 1.00 | 25.00 |
| 1123 | 1HZ | LYS | 135 | 113.687 | 0.9599 | 56.499 | 1.00 | 25.00 |
| 1124 | 2HZ | LYS | 135 | 114.669 | 2.310 | 56.155 | 1.00 | 25.00 |
| 1125 | 3HZ | LYS | 135 | 112.977 | 2.461 | 56.110 | 1.00 | 25.00 |
| 1126 | N | PHE | 136 | 119.834 | 1.731 | 52.491 | 1.00 | 53.56 |
| 1127 | CA | PHE | 136 | 121.268 | 1.864 | 52.261 | 1.00 | 46.60 |
| 1128 | C | PHE | 136 | 122.075 | 1.074 | 53.275 | 1.00 | 46.58 |
| 1129 | O | PHE | 136 | 121.797 | 1.118 | 54.473 | 1.00 | 47.43 |
| 1130 | CB | PHE | 136 | 121.686 | 3.336 | 52.270 | 1.00 | 39.21 |
| 1131 | CG | PHE | 136 | 121.382 | 4.056 | 50.990 | 1.00 | 32.34 |
| 1132 | CD1 | PHE | 136 | 122.171 | 3.854 | 49.863 | 1.00 | 31.37 |
| 1133 | CD2 | PHE | 136 | 120.282 | 4.898 | 50.896 | 1.00 | 32.38 |
| 1134 | CE1 | PHE | 136 | 121.876 | 4.491 | 48.657 | 1.00 | 25.70 |
| 1135 | CE2 | PHE | 136 | 119.976 | 5.540 | 49.701 | 1.00 | 34.62 |
| 1136 | CZ | PHE | 136 | 120.771 | 5.330 | 48.573 | 1.00 | 28.91 |
| 1137 | H | PHE | 136 | 119.315 | 2.505 | 52.789 | 1.00 | 25.00 |
| 1138 | N | LYS | 137 | 123.046 | 0.315 | 52.776 | 1.00 | 48.31 |
| 1139 | CA | LYS | 137 | 123.910 | −0.487 | 53.629 | 1.00 | 53.52 |
| 1140 | C | LYS | 137 | 124.551 | 0.429 | 54.656 | 1.00 | 59.01 |
| 1141 | O | LYS | 137 | 125.408 | 1.247 | 54.316 | 1.00 | 64.30 |
| 1142 | CB | LYS | 137 | 125.007 | −1.160 | 52.801 | 1.00 | 48.57 |
| 1143 | CG | LYS | 137 | 124.526 | −2.258 | 51.872 | 1.00 | 52.37 |
| 1144 | CD | LYS | 137 | 125.683 | −2.796 | 51.049 | 1.00 | 56.61 |
| 1145 | CE | LYS | 137 | 125.266 | −3.980 | 50.199 | 1.00 | 55.76 |
| 1146 | NZ | LYS | 137 | 126.388 | −4.433 | 49.330 | 1.00 | 62.73 |
| 1147 | H | LYS | 137 | 123.197 | 0.306 | 51.808 | 1.00 | 25.00 |
| 1148 | 1HZ | LYS | 137 | 127.197 | −4.714 | 49.920 | 1.00 | 25.00 |
| 1149 | 2HZ | LYS | 137 | 126.077 | −5.245 | 48.758 | 1.00 | 25.00 |
| 1150 | 3HZ | LYS | 137 | 126.670 | −3.656 | 48.699 | 1.00 | 25.00 |
| 1151 | N | GLU | 138 | 124.151 | 0.281 | 55.914 | 1.00 | 61.30 |
| 1152 | CA | GLU | 138 | 124.688 | 1.107 | 56.991 | 1.00 | 62.65 |
| 1153 | C | GLU | 138 | 126.219 | 1.035 | 57.078 | 1.00 | 60.08 |
| 1154 | O | GLU | 138 | 126.855 | 1.862 | 57.732 | 1.00 | 61.14 |
| 1155 | CB | GLU | 138 | 124.049 | 0.720 | 58.324 | 1.00 | 63.46 |
| 1156 | CG | GLU | 138 | 122.561 | 1.033 | 58.457 | 1.00 | 67.41 |
| 1157 | CD | GLU | 138 | 122.276 | 2.499 | 58.743 | 1.00 | 68.98 |
| 1158 | OE1 | GLU | 138 | 122.994 | 3.105 | 59.568 | 1.00 | 67.92 |
| 1159 | OE2 | GLU | 138 | 121.317 | 3.043 | 58.154 | 1.00 | 72.44 |
| 1160 | H | GLU | 138 | 123.462 | −0.385 | 56.115 | 1.00 | 25.00 |
| 1161 | N | SER | 139 | 126.807 | 0.062 | 56.390 | 1.00 | 54.50 |
| 1162 | CA | SER | 139 | 128.255 | −0.105 | 56.357 | 1.00 | 54.27 |
| 1163 | C | SER | 139 | 128.960 | 1.037 | 55.609 | 1.00 | 51.34 |
| 1164 | O | SER | 139 | 130.144 | 1.292 | 55.828 | 1.00 | 53.27 |
| 1165 | CB | SER | 139 | 128.600 | −1.453 | 55.722 | 1.00 | 59.61 |
| 1166 | OG | SER | 139 | 127.596 | −1.846 | 54.800 | 1.00 | 67.84 |
| 1167 | H | SER | 139 | 126.266 | −0.582 | 55.893 | 1.00 | 25.00 |
| 1168 | HG | SER | 139 | 127.548 | −1.203 | 54.087 | 1.00 | 25.00 |
| 1169 | N | LEU | 140 | 128.225 | 1.714 | 54.728 | 1.00 | 46.50 |
| 1170 | CA | LEU | 140 | 128.751 | 2.839 | 53.953 | 1.00 | 37.91 |
| 1171 | C | LEU | 140 | 128.861 | 4.092 | 54.826 | 1.00 | 33.78 |
| 1172 | O | LEU | 140 | 129.454 | 5.090 | 54.422 | 1.00 | 30.69 |
| 1173 | CB | LEU | 140 | 127.821 | 3.151 | 52.777 | 1.00 | 39.38 |
| 1174 | CG | LEU | 140 | 127.643 | 2.142 | 51.639 | 1.00 | 42.09 |
| 1175 | CD1 | LEU | 140 | 126.330 | 2.417 | 50.919 | 1.00 | 38.48 |
| 1176 | CD2 | LEU | 140 | 128.819 | 2.212 | 50.672 | 1.00 | 38.39 |
| 1177 | H | LEU | 140 | 127.290 | 1.456 | 54.590 | 1.00 | 25.00 |
| 1178 | N | ALA | 141 | 128.295 | 4.024 | 56.026 | 1.00 | 28.75 |
| 1179 | CA | ALA | 141 | 128.288 | 5.141 | 56.964 | 1.00 | 29.20 |
| 1180 | C | ALA | 141 | 129.646 | 5.737 | 57.310 | 1.00 | 30.53 |
| 1181 | O | ALA | 141 | 129.713 | 6.825 | 57.882 | 1.00 | 30.24 |
| 1182 | CB | ALA | 141 | 127.565 | 4.742 | 58.235 | 1.00 | 28.51 |
| 1183 | H | ALA | 141 | 127.860 | 3.193 | 56.303 | 1.00 | 25.00 |
| 1184 | N | SER | 142 | 130.719 | 5.018 | 57.002 | 1.00 | 28.14 |
| 1185 | CA | SER | 142 | 132.062 | 5.500 | 57.297 | 1.00 | 30.43 |
| 1186 | C | SER | 142 | 132.788 | 6.004 | 56.051 | 1..00 | 30.66 |
| 1187 | O | SER | 142 | 133.961 | 6.371 | 56.107 | 1.00 | 39.46 |
| 1188 | CB | SER | 142 | 132.879 | 4.409 | 58.011 | 1.00 | 30.29 |

TABLE 11-continued

Structural Coordinates of Tobacco 5-Epi-Aristolochene Synthase
In the Absence of Bound Substrate

| Atom Type | Atom | Residue | Residue # | X | Y | Z | OCC | B-factor |
|---|---|---|---|---|---|---|---|---|
| 1189 | OG | SER | 142 | 132.790 | 3.146 | 57.358 | 1.00 | 26.69 |
| 1190 | H | SER | 142 | 130.627 | 4.146 | 56.569 | 1.00 | 25.00 |
| 1191 | HG | SER | 142 | 133.417 | 2.588 | 57.780 | 1.00 | 25.00 |
| 1192 | N | ASP | 143 | 132.069 | 6.053 | 54.937 | 1.00 | 27.41 |
| 1193 | CA | ASP | 143 | 132.614 | 6.512 | 53.663 | 1.00 | 28.00 |
| 1194 | C | ASP | 143 | 132.168 | 7.966 | 53.447 | 1.00 | 33.02 |
| 1195 | O | ASP | 143 | 131.211 | 8.232 | 52.714 | 1.00 | 34.43 |
| 1196 | CB | ASP | 143 | 132.085 | 5.603 | 52.540 | 1.00 | 26.21 |
| 1197 | CG | ASP | 143 | 132.609 | 5.978 | 51.160 | 1.00 | 32.37 |
| 1198 | OD1 | ASP | 143 | 133.578 | 6.762 | 51.045 | 1.00 | 34.10 |
| 1199 | OD2 | ASP | 143 | 132.041 | 5.465 | 50.174 | 1.00 | 37.80 |
| 1200 | H | ASP | 143 | 131.130 | 5.790 | 54.969 | 1.00 | 25.00 |
| 1201 | N | VAL | 144 | 132.884 | 8.906 | 54.060 | 1.00 | 31.09 |
| 1202 | CA | VAL | 144 | 132.548 | 10.328 | 53.958 | 1.00 | 27.23 |
| 1203 | C | VAL | 144 | 132.392 | 10.873 | 52.534 | 1.00 | 27.59 |
| 1204 | O | VAL | 144 | 131.404 | 11.545 | 52.243 | 1.00 | 25.91 |
| 1205 | CB | VAL | 144 | 133.541 | 11.204 | 54.758 | 1.00 | 27.72 |
| 1206 | CG1 | VAL | 144 | 133.183 | 12.684 | 54.621 | 1.00 | 21.28 |
| 1207 | CG2 | VAL | 144 | 133.509 | 10.804 | 56.227 | 1.00 | 34.69 |
| 1208 | H | VAL | 144 | 133.643 | 8.619 | 54.609 | 1.00 | 25.00 |
| 1209 | N | LEU | 145 | 133.344 | 10.580 | 51.649 | 1.00 | 25.30 |
| 1210 | CA | LEU | 145 | 133.266 | 11.063 | 50.268 | 1.00 | 27.68 |
| 1211 | C | LEU | 145 | 132.039 | 10.510 | 49.544 | 1.00 | 29.04 |
| 1212 | O | LEU | 145 | 131.392 | 11.218 | 48.773 | 1.00 | 26.76 |
| 1213 | CB | LEU | 145 | 134.541 | 10.722 | 49.487 | 1.00 | 27.26 |
| 1214 | CG | LEU | 145 | 135.839 | 11.375 | 49.970 | 1.00 | 29.50 |
| 1215 | CD1 | LEU | 145 | 136.956 | 11.087 | 48.983 | 1.00 | 25.10 |
| 1216 | CD2 | LEU | 145 | 135.648 | 12.875 | 50.113 | 1.00 | 31.66 |
| 1217 | H | LEU | 145 | 134.098 | 10.040 | 51.931 | 1.00 | 25.00 |
| 1218 | N | GLY | 146 | 131.717 | 9.247 | 49.806 | 1.00 | 27.11 |
| 1219 | CA | GLY | 146 | 130.552 | 8.643 | 49.185 | 1.00 | 25.43 |
| 1220 | C | GLY | 146 | 129.288 | 9.290 | 49.726 | 1.00 | 27.86 |
| 1221 | O | GLY | 146 | 128.373 | 9.621 | 48.968 | 1.00 | 24.45 |
| 1222 | H | GLY | 146 | 132.255 | 8.727 | 50.431 | 1.00 | 25.00 |
| 1223 | N | LEU | 147 | 129.251 | 9.485 | 51.043 | 1.00 | 21.13 |
| 1224 | CA | LEU | 147 | 128.114 | 10.102 | 551.712 | 1.00 | 23.48 |
| 1225 | C | LEU | 147 | 127.867 | 11.519 | 51.202 | 1.00 | 23.64 |
| 1226 | O | LEU | 147 | 126.722 | 11.922 | 51.002 | 1.00 | 25.30 |
| 1227 | CB | LEU | 147 | 128.338 | 10.140 | 53.226 | 1.00 | 23.15 |
| 1228 | CG | LEU | 147 | 128.286 | 8.821 | 54.003 | 1.00 | 30.78 |
| 1229 | CD1 | LEU | 147 | 128.667 | 9.059 | 55.455 | 1.00 | 24.16 |
| 1230 | CD2 | LEU | 147 | 126.892 | 8.210 | 53.911 | 1.00 | 22.86 |
| 1231 | H | LEU | 147 | 130.010 | 9.196 | 51.584 | 1.00 | 25.00 |
| 1232 | N | LEU | 148 | 128.943 | 12.265 | 50.978 | 1.00 | 20.29 |
| 1233 | CA | LEU | 148 | 128.831 | 13.633 | 50.498 | 1.00 | 24.04 |
| 1234 | C | LEU | 148 | 128.217 | 13.664 | 49.106 | 1.00 | 23.69 |
| 1235 | O | LEU | 148 | 127.267 | 14.408 | 48.855 | 1.00 | 26.51 |
| 1236 | CB | LEU | 148 | 130.198 | 14.328 | 50.506 | 1.00 | 22.43 |
| 1237 | CG | LEU | 148 | 130.240 | 15.787 | 50.033 | 1.00 | 24.68 |
| 1238 | CD1 | LEU | 148 | 129.285 | 16.649 | 50.853 | 1.00 | 16.95 |
| 1239 | CD2 | LEU | 148 | 131.662 | 16.314 | 50.136 | 1.00 | 19.49 |
| 1240 | H | LEU | 148 | 129.830 | 11.885 | 51.143 | 1.00 | 25.00 |
| 1241 | N | ASN | 149 | 128.742 | 12.845 | 48.203 | 1.00 | 23.38 |
| 1242 | CA | ASN | 149 | 128.210 | 12.801 | 46.850 | 1.00 | 20.71 |
| 1243 | C | ASN | 149 | 126.781 | 12.269 | 46.809 | 1.00 | 25.14 |
| 1244 | O | ASN | 149 | 125.990 | 12.678 | 45.956 | 1.00 | 25.34 |
| 1245 | CB | ASN | 149 | 129.125 | 12.008 | 45.932 | 1.00 | 15.21 |
| 1246 | CG | ASN | 149 | 130.320 | 12.817 | 45.489 | 1.00 | 19.96 |
| 1247 | OD1 | ASN | 149 | 131.340 | 12.856 | 46.167 | 1.00 | 34.43 |
| 1248 | ND2 | ASN | 149 | 130.185 | 13.505 | 44.369 | 1.00 | 25.72 |
| 1249 | H | ASN | 149 | 129.509 | 12.271 | 48.444 | 1.00 | 25.00 |
| 1250 | 1HD2 | ASN | 149 | 130.969 | 14.021 | 44.090 | 1.00 | 25.00 |
| 1251 | 2HD2 | ASN | 149 | 129.340 | 13.468 | 43.887 | 1.00 | 25.00 |
| 1252 | N | LEU | 150 | 126.445 | 11.379 | 47.743 | 1.00 | 21.91 |
| 1253 | CA | LEU | 150 | 125.096 | 10.829 | 47.827 | 1.00 | 24.64 |
| 1254 | C | LEU | 150 | 124.171 | 11.938 | 48.330 | 1.00 | 22.13 |
| 1255 | O | LEU | 150 | 123.058 | 12.104 | 47.831 | 1.00 | 27.92 |
| 1256 | CB | LEU | 150 | 125.051 | 9.630 | 48.780 | 1.00 | 17.59 |
| 1257 | CG | LEU | 150 | 123.659 | 9.057 | 49.062 | 1.00 | 21.25 |
| 1258 | CD1 | LEU | 150 | 123.054 | 8.510 | 47.780 | 1.00 | 18.26 |
| 1259 | CD2 | LEU | 150 | 123.739 | 7.976 | 50.118 | 1.00 | 19.18 |
| 1260 | H | LEU | 150 | 127.125 | 11.076 | 48.382 | 1.00 | 25.00 |
| 1261 | N | TYR | 151 | 124.652 | 12.706 | 49.301 | 1.00 | 20.18 |
| 1262 | CA | TYR | 151 | 123.892 | 13.818 | 49.858 | 1.00 | 20.96 |
| 1263 | C | TYR | 151 | 123.533 | 14.798 | 48.738 | 1.00 | 19.39 |
| 1264 | O | TYR | 151 | 122.380 | 15.204 | 48.592 | 1.00 | 21.76 |
| 1265 | CB | TYR | 151 | 124.723 | 14.535 | 50.929 | 1.00 | 20.29 |
| 1266 | CG | TYR | 151 | 124.115 | 15.828 | 51.418 | 1.00 | 22.32 |
| 1267 | CD1 | TYR | 151 | 123.202 | 15.834 | 52.470 | 1.00 | 20.29 |
| 1268 | CD2 | TYR | 151 | 124.432 | 17.047 | 50.811 | 1.00 | 21.17 |
| 1269 | CE1 | TYR | 151 | 122.614 | 17.021 | 52.907 | 1.00 | 20.42 |
| 1270 | CE2 | TYR | 151 | 123.850 | 18.236 | 51.237 | 1.00 | 21.39 |
| 1271 | CZ | TYR | 151 | 122.940 | 18.214 | 52.285 | 1.00 | 22.07 |
| 1272 | OH | TYR | 151 | 122.337 | 19.377 | 52.696 | 1.00 | 21.54 |
| 1273 | H | TYR | 151 | 125.542 | 12.522 | 49.655 | 1.00 | 25.00 |
| 1274 | HH | TYR | 151 | 121.769 | 19.210 | 53.457 | 1.00 | 25.00 |
| 12775 | N | GLU | 152 | 124.532 | 15.194 | 47.957 | 1.00 | 21.41 |
| 1276 | CA | GLU | 152 | 124.316 | 16.128 | 46.863 | 1.00 | 19.05 |
| 1277 | C | GLU | 152 | 123.388 | 15.546 | 45.800 | 1.00 | 23.34 |
| 1278 | O | GLU | 152 | 122.540 | 16.259 | 45.260 | 1.00 | 21.99 |
| 1279 | CB | GLU | 152 | 125.653 | 16.544 | 46.235 | 1.00 | 23.58 |
| 1280 | CG | GLU | 152 | 126.641 | 17.236 | 47.198 | 1.00 | 23.54 |
| 1281 | CD | GLU | 152 | 126.245 | 18.662 | 47.577 | 1.00 | 27.07 |
| 1282 | OE1 | GLU | 152 | 125.046 | 19.009 | 47.529 | 1.00 | 30.35 |
| 1283 | OE2 | GLU | 152 | 127.145 | 19.444 | 47.935 | 1.00 | 23.20 |
| 1284 | H | GLU | 152 | 125.434 | 14.851 | 48.136 | 1.00 | 25.00 |
| 1285 | N | ALA | 153 | 123.530 | 14.248 | 45.526 | 1.00 | 24.42 |
| 1286 | CA | ALA | 153 | 122.706 | 13.565 | 44.526 | 1.00 | 22.61 |
| 1287 | C | ALA | 153 | 121.251 | 13.409 | 44.964 | 1.00 | 19.49 |
| 1288 | O | ALA | 153 | 120.342 | 13.450 | 44.138 | 1.00 | 21.30 |
| 1289 | CB | ALA | 153 | 123.300 | 12.203 | 44.186 | 1.00 | 21.47 |
| 1290 | H | ALA | 153 | 124.211 | 13.731 | 46.006 | 1.00 | 25.00 |
| 1291 | N | SER | 154 | 121.026 | 13.262 | 46.264 | 1.00 | 16.33 |
| 1292 | CA | SER | 154 | 119.672 | 13.105 | 48.776 | 1.00 | 21.77 |
| 1293 | C | SER | 154 | 118.822 | 14.343 | 46.484 | 1.00 | 27.62 |
| 1294 | O | SER | 154 | 117.603 | 14.258 | 46.351 | 1.00 | 29.95 |
| 1295 | CB | SER | 154 | 119.688 | 12.820 | 48.288 | 1.00 | 15.72 |
| 1296 | OG | SER | 154 | 119.902 | 13.991 | 49.060 | 1.00 | 20.33 |
| 1297 | H | SER | 154 | 121.776 | 13.256 | 46.901 | 1.00 | 25.00 |
| 1298 | HG | SER | 154 | 119.193 | 14.609 | 48.898 | 1.00 | 25.00 |
| 1299 | N | HIS | 155 | 119.470 | 15.489 | 46.291 | 1.00 | 24.50 |
| 1300 | CA | HIS | 155 | 118.751 | 16.720 | 46.001 | 1.00 | 20.74 |
| 1301 | C | HIS | 155 | 118.320 | 16.907 | 44.552 | 1.00 | 22.52 |
| 1302 | O | HIS | 155 | 117.682 | 17.905 | 44.224 | 1.00 | 23.13 |
| 1303 | CB | HIS | 155 | 119.543 | 17.929 | 46.487 | 1.00 | 19.93 |
| 1304 | CG | HIS | 155 | 119.439 | 18.154 | 47.961 | 1.00 | 14.77 |
| 1305 | ND1 | HIS | 155 | 120.456 | 17.843 | 48.838 | 1.00 | 20.63 |
| 1306 | CD2 | HIS | 155 | 118.431 | 18.652 | 48.716 | 1.00 | 13.91 |
| 1307 | CE1 | HIS | 155 | 120.080 | 18.142 | 50.069 | 1.00 | 21.57 |
| 1308 | NE2 | HIS | 155 | 118.855 | 18.634 | 50.022 | 1.00 | 17.34 |
| 1309 | H | HIS | 155 | 120.451 | 15.494 | 46.346 | 1.00 | 25.00 |
| 1310 | HD1 | HIS | 155 | 121.317 | 17.420 | 48.603 | 1.00 | 25.00 |
| 1311 | HE2 | HIS | 155 | 118.336 | 18.952 | 50.793 | 1.00 | 25.00 |
| 1312 | N | VAL | 156 | 118.686 | 15.972 | 43.678 | 1.00 | 22.99 |
| 1313 | CA | VAL | 156 | 118.283 | 16.063 | 42.276 | 1.00 | 22.09 |
| 1314 | C | VAL | 156 | 117.265 | 14.970 | 41.940 | 1.00 | 22.99 |
| 1315 | O | VAL | 156 | 116.954 | 14.741 | 40.768 | 1.00 | 22.80 |
| 1316 | CB | VAL | 156 | 119.491 | 15.956 | 41.299 | 1.00 | 18.92 |
| 1317 | CG1 | VAL | 156 | 120.541 | 16.999 | 41.636 | 1.00 | 20.34 |
| 1318 | CG2 | VAL | 156 | 120.089 | 14.560 | 41.329 | 1.00 | 20.67 |
| 1319 | H | VAL | 156 | 119.229 | 15.207 | 43.966 | 1.00 | 25.00 |
| 1320 | N | ARG | 157 | 116.729 | 14.317 | 42.968 | 1.00 | 19.28 |
| 1321 | CA | ARG | 157 | 115.766 | 13.239 | 42.762 | 1.00 | 25.29 |
| 1322 | C | ARG | 157 | 114.394 | 13.708 | 42.272 | 1.00 | 26.91 |
| 1323 | O | ARG | 157 | 113.988 | 14.850 | 42.498 | 1.00 | 27.10 |
| 1324 | CB | ARG | 157 | 115.625 | 12.380 | 44.024 | 1.00 | 19.93 |
| 1325 | CG | ARG | 157 | 114.831 | 13.011 | 45.1144 | 1.00 | 19.14 |
| 1326 | CD | ARG | 157 | 114.914 | 12.156 | 46.397 | 1.00 | 20.33 |
| 1327 | NE | ARG | 157 | 114.069 | 12.674 | 47.473 | 1.00 | 30.46 |
| 1328 | CZ | ARG | 157 | 114.373 | 13.717 | 48.242 | 1.00 | 36.78 |
| 1329 | NH1 | ARG | 157 | 115.515 | 14.371 | 48.071 | 1.00 | 39.31 |
| 1330 | NH2 | ARG | 157 | 113.523 | 14.119 | 49.176 | 1.00 | 36.74 |
| 1331 | H | ARG | 157 | 116.972 | 14.566 | 43.881 | 1.00 | 25.00 |
| 1332 | HE | ARG | 157 | 113.214 | 12.230 | 47.643 | 1.00 | 25.00 |
| 1333 | 1HH1 | ARG | 157 | 116.149 | 14.079 | 47.364 | 1.00 | 25.00 |
| 1334 | 2HH1 | ARG | 157 | 115.736 | 15.154 | 48.652 | 1.00 | 25.00 |

TABLE 11-continued

Structural Coordinates of Tobacco 5-Epi-Aristolochene Synthase In the Absence of Bound Substrate

| Atom # | Atom Type | Residue | Residue # | X | Y | Z | OCC | B-factor |
|---|---|---|---|---|---|---|---|---|
| 1335 | 1HH2 | ARG | 157 | 112.655 | 13.643 | 49.305 | 1.00 | 25.00 |
| 1336 | 2HH2 | ARG | 157 | 113.751 | 14.905 | 49.753 | 1.00 | 25.00 |
| 1337 | N | THR | 158 | 113.709 | 12.813 | 41.569 | 1.00 | 30.13 |
| 1338 | CA | THR | 158 | 112.385 | 13.066 | 41.015 | 1.00 | 27.65 |
| 1339 | C | THR | 158 | 111.374 | 12.189 | 41.763 | 1.00 | 25.41 |
| 1340 | O | THR | 158 | 111.751 | 11.413 | 42.642 | 1.00 | 23.51 |
| 1341 | CB | THR | 158 | 112.350 | 12.703 | 39.513 | 1.00 | 24.84 |
| 1342 | OG1 | THR | 158 | 112.630 | 11.307 | 39.355 | 1.00 | 27.71 |
| 1343 | CG2 | THR | 158 | 113.391 | 13.496 | 38.738 | 1.00 | 19.09 |
| 1344 | H | THR | 158 | 114.102 | 11.937 | 41.427 | 1.00 | 25.00 |
| 1345 | HG1 | THR | 158 | 111.995 | 10.771 | 39.817 | 1.00 | 25.00 |
| 1346 | N | HIS | 159 | 110.103 | 12.268 | 41.377 | 1.00 | 26.77 |
| 1347 | CA | HIS | 159 | 109.051 | 11.473 | 42.016 | 1.00 | 27.30 |
| 1348 | C | HIS | 159 | 109.196 | 9.971 | 41.741 | 1.00 | 33.58 |
| 1349 | O | HIS | 159 | 108.630 | 9.150 | 42.462 | 1.00 | 33.82 |
| 1350 | CB | HIS | 159 | 107.663 | 11.939 | 41.557 | 1.00 | 26.01 |
| 1351 | CG | HIS | 159 | 107.337 | 13.350 | 41.941 | 1.00 | 23.00 |
| 1352 | ND1 | HIS | 159 | 106.999 | 13.711 | 43.226 | 1.00 | 24.86 |
| 1353 | CD2 | HIS | 159 | 107.311 | 14.490 | 41.210 | 1.00 | 18.70 |
| 1354 | CE1 | HIS | 159 | 106.782 | 15.012 | 43.275 | 1.00 | 24.72 |
| 1355 | NE2 | HIS | 159 | 106.966 | 15.509 | 42.064 | 1.00 | 23.55 |
| 1356 | H | HIS | 159 | 109.879 | 12.878 | 40.646 | 1.00 | 25.00 |
| 1357 | HD1 | HIS | 159 | 106.924 | 13.094 | 43.988 | 1.00 | 25.00 |
| 1358 | HE2 | HIS | 159 | 106.880 | 16.460 | 41.845 | 1.00 | 25.00 |
| 1359 | N | ALA | 160 | 109.948 | 9.624 | 40.697 | 1.00 | 32.77 |
| 1360 | CA | ALA | 160 | 110.167 | 8.229 | 40.315 | 1.00 | 31.64 |
| 1361 | C | ALA | 160 | 111.364 | 7.581 | 41.009 | 1.00 | 36.31 |
| 1362 | O | ALA | 160 | 111.509 | 6.361 | 41.002 | 1.00 | 37.53 |
| 1363 | CB | ALA | 160 | 110.326 | 8..130 | 38.803 | 1.00 | 25.40 |
| 1364 | H | ALA | 160 | 110.358 | 10.319 | 40.160 | 1.00 | 25.00 |
| 1365 | N | ASP | 161 | 112.217 | 8.401 | 41.612 | 1.00 | 40.41 |
| 1366 | CA | ASP | 161 | 113.415 | 7.904 | 42.281 | 1.00 | 40.26 |
| 1367 | C | ASP | 161 | 113.123 | 7.414 | 43.689 | 1.00 | 41.77 |
| 1368 | O | ASP | 161 | 113.634 | 7.937 | 44.678 | 1.00 | 41.48 |
| 1369 | CB | ASP | 161 | 114.508 | 8.976 | 42.291 | 1.00 | 34.22 |
| 1370 | CG | ASP | 161 | 114.959 | 9.354 | 40.898 | 1.00 | 34.94 |
| 1371 | OD1 | ASP | 161 | 114.954 | 8.486 | 40.002 | 1.00 | 33.51 |
| 1372 | OD2 | ASP | 161 | 115.319 | 10.532 | 40.697 | 1.00 | 32.35 |
| 1373 | H | ASP | 161 | 112.014 | 9.350 | 41.663 | 1.00 | 25.00 |
| 1374 | N | ASP | 162 | 112.353 | 6.342 | 43.742 | 1.00 | 46.26 |
| 1375 | CA | ASP | 162 | 111.932 | 5.726 | 44.985 | 1.00 | 46.59 |
| 1376 | C | ASP | 162 | 113.108 | 5.156 | 45.760 | 1.00 | 44.37 |
| 1377 | O | ASP | 162 | 113.127 | 5.172 | 46.990 | 1.00 | 37.28 |
| 1378 | CB | ASP | 162 | 110.916 | 4.630 | 44.670 | 1.00 | 56.78 |
| 1379 | CG | ASP | 162 | 109.654 | 5.185 | 44.046 | 1.00 | 69.65 |
| 1380 | OD1 | ASP | 162 | 108.899 | 5.870 | 44.766 | 1.00 | 67.08 |
| 1381 | OD2 | ASP | 162 | 109.435 | 4.978 | 42.830 | 1.00 | 79.19 |
| 1382 | H | ASP | 162 | 112.114 | 5.949 | 42.869 | 1.00 | 25.00 |
| 1383 | N | ILE | 163 | 114.106 | 4.699 | 45.015 | 1.00 | 41.87 |
| 1384 | CA | ILE | 163 | 115.314 | 4.112 | 45.575 | 1.00 | 43.77 |
| 1385 | C | ILE | 163 | 116.093 | 5.124 | 46.426 | 1.00 | 42.36 |
| 1386 | O | ILE | 163 | 116.764 | 4.757 | 47.385 | 1.00 | 45.56 |
| 1387 | CB | ILE | 163 | 116.200 | 3.561 | 44.433 | 1.00 | 47.25 |
| 1388 | CG1 | ILE | 163 | 115.385 | 2.571 | 43.595 | 1.00 | 56..48 |
| 1389 | CG2 | ILE | 163 | 117.433 | 2.870 | 44.986 | 1.00 | 49.93 |
| 1390 | CD1 | ILE | 163 | 116.134 | 1.994 | 42.404 | 1.00 | 60.37 |
| 1391 | H | ILE | 163 | 114.031 | 4.781 | 44.043 | 1.00 | 25.00 |
| 1392 | N | LEU | 164 | 115.955 | 6.404 | 46.097 | 1.00 | 37.87 |
| 1393 | CA | LEU | 164 | 116.650 | 7.473 | 46.805 | 1.00 | 33.53 |
| 1394 | C | LEU | 164 | 115.828 | 8.132 | 47.897 | 1.00 | 32.57 |
| 1395 | O | LEU | 164 | 116.206 | 9.192 | 48.400 | 1.00 | 36.58 |
| 1396 | CD | LEU | 164 | 117.102 | 8.542 | 45.815 | 1.00 | 30.53 |
| 1397 | CG | LEU | 164 | 118.184 | 8.139 | 44.815 | 1.00 | 36.53 |
| 1398 | CD1 | LEU | 164 | 118.416 | 9.266 | 43.820 | 1.00 | 26.74 |
| 1399 | CD2 | LEU | 164 | 119.468 | 7.794 | 45.562 | 1.00 | 30.59 |
| 1400 | H | LEU | 164 | 115.309 | 6.641 | 45.397 | 1.00 | 25.00 |
| 1401 | N | GLU | 165 | 114.737 | 7.489 | 48.290 | 1.00 | 32.57 |
| 1402 | CA | GLU | 165 | 113.854 | 8.022 | 49.320 | 1.00 | 32.62 |
| 1403 | C | GLU | 165 | 114.537 | 8.326 | 50.655 | 1.00 | 35.56 |
| 1404 | O | GLU | 165 | 114.298 | 9.368 | 51.267 | 1.00 | 35.70 |
| 1405 | CB | GLU | 165 | 112.683 | 7.058 | 49.551 | 1.00 | 39.90 |
| 1406 | CG | GLU | 165 | 111.645 | 7.571 | 50.549 | 1.00 | 50.03 |
| 1407 | CD | GLU | 165 | 111.021 | 8.886 | 50.115 | 1.00 | 59.83 |
| 1408 | OE1 | GLU | 165 | 110.492 | 8.952 | 48.983 | 1.00 | 63.90 |
| 1409 | OE2 | GLU | 165 | 111.069 | 9.862 | 50.899 | 1.00 | 58.42 |
| 1410 | H | GLU | 165 | 114.553 | 6.614 | 47.898 | 1.00 | 25.00 |
| 1411 | N | ASP | 166 | 115.411 | 7.431 | 51.091 | 1.00 | 37.81 |
| 1412 | CA | ASP | 166 | 116.079 | 7.609 | 52.369 | 1.00 | 43.12 |
| 1413 | C | ASP | 166 | 117.546 | 8.030 | 52.268 | 1.00 | 40.48 |
| 1414 | O | ASP | 166 | 118.274 | 8.039 | 53.262 | 1.00 | 40.91 |
| 1415 | CB | ASP | 166 | 115.899 | 6.352 | 53.234 | 1.00 | 51.99 |
| 1416 | CG | ASP | 166 | 114.532 | 6.303 | 53.902 | 1.00 | 67.29 |
| 1417 | OD1 | ASP | 166 | 114.268 | 7.173 | 54.761 | 1.00 | 74.04 |
| 1418 | OD2 | ASP | 166 | 113.712 | 5.423 | 53.552 | 1.00 | 74.06 |
| 1419 | H | ASP | 166 | 115.669 | 6.693 | 50.506 | 1.00 | 25.00 |
| 1420 | N | ALA | 167 | 117.939 | 8.459 | 51.075 | 1.00 | 34.07 |
| 1421 | CA | ALA | 167 | 119.298 | 8.902 | 50.806 | 1.00 | 30.06 |
| 1422 | C | ALA | 167 | 119.664 | 10.182 | 51.554 | 1.00 | 33.12 |
| 1423 | O | ALA | 167 | 120.759 | 10.292 | 52.103 | 1.00 | 34.41 |
| 1424 | CB | ALA | 167 | 119.488 | 9.090 | 49.308 | 1.00 | 25.56 |
| 1425 | H | ALA | 167 | 117.260 | 8.486 | 50.375 | 1.00 | 25.00 |
| 1426 | N | LEU | 168 | 118.737 | 11.134 | 51.593 | 1.00 | 34.35 |
| 1427 | CA | LEU | 168 | 118.975 | 12.403 | 52.268 | 1.00 | 29.26 |
| 1428 | C | LEU | 168 | 119.184 | 12.226 | 53.764 | 1.00 | 32.06 |
| 1429 | O | LEU | 168 | 120.199 | 12.656 | 54.311 | 1.00 | 34.07 |
| 1430 | CB | LEU | 168 | 117.820 | 13.381 | 52.024 | 1.00 | 25.73 |
| 1431 | CG | LEU | 168 | 117.980 | 14.767 | 52.671 | 1.00 | 29.40 |
| 1432 | CD1 | LEU | 168 | 119.241 | 15.454 | 52.153 | 1.00 | 22.56 |
| 1433 | CD2 | LEU | 168 | 116.765 | 15.635 | 52.397 | 1.00 | 28.30 |
| 1434 | H | LEU | 168 | 117.879 | 10.944 | 51.168 | 1.00 | 25.00 |
| 1435 | N | ALA | 169 | 118.224 | 11.593 | 54.425 | 1.00 | 32.55 |
| 1436 | CA | ALA | 169 | 118.317 | 11.372 | 55.865 | 1.00 | 37.53 |
| 1437 | C | ALA | 169 | 119.561 | 10.552 | 56.227 | 1.00 | 37.81 |
| 1438 | O | ALA | 169 | 120.273 | 10.873 | 57.185 | 1.00 | 38.90 |
| 1439 | CB | ALA | 1669 | 117.058 | 10.680 | 56.370 | 1.00 | 36.88 |
| 1440 | H | ALA | 169 | 117.444 | 11.265 | 53.938 | 1.00 | 25.00 |
| 1441 | N | PHE | 170 | 119.830 | 9.520 | 55.429 | 1.00 | 30.70 |
| 1442 | CA | PHE | 170 | 120.976 | 8.640 | 55.635 | 1.00 | 29.14 |
| 1443 | C | PHE | 170 | 122.296 | 9.413 | 55.592 | 1.00 | 31.93 |
| 1444 | O | PHE | 170 | 123.046 | 9.432 | 56.573 | 1.00 | 35.80 |
| 1445 | CB | PHE | 170 | 120.978 | 7.538 | 54.569 | 1.00 | 27.52 |
| 1446 | CG | PHE | 170 | 122.093 | 6.538 | 54.719 | 1.00 | 29.21 |
| 1447 | CD1 | PHE | 170 | 122.055 | 5.576 | 55.722 | 1.00 | 32.25 |
| 1448 | CD2 | PHE | 170 | 123.178 | 6.553 | 53.850 | 1.00 | 31.23 |
| 1449 | CE1 | PHE | 170 | 123.085 | 4.642 | 55.854 | 1.00 | 35.77 |
| 1450 | CE2 | PHE | 170 | 124.213 | 5.624 | 53.974 | 1.00 | 28.29 |
| 1451 | CZ | PHE | 170 | 124.166 | 4.668 | 54.977 | 1.00 | 33.63 |
| 1452 | H | PHE | 170 | 119.237 | 9.336 | 54.671 | 1.00 | 25.00 |
| 1453 | N | SER | 171 | 122.572 | 10.054 | 54.460 | 1.00 | 29.96 |
| 1454 | CA | SER | 171 | 123.803 | 10.817 | 54.297 | 1.00 | 23.74 |
| 1455 | C | SER | 171 | 123.888 | 11.970 | 55.293 | 1.00 | 25.49 |
| 1456 | O | SER | 171 | 124.951 | 12.232 | 55.845 | 1.00 | 30.00 |
| 1457 | CB | SER | 171 | 123.927 | 11.333 | 52.860 | 1.00 | 25.16 |
| 1458 | OG | SER | 171 | 122.818 | 12.137 | 52.501 | 1.00 | 31.46 |
| 1459 | H | SER | 171 | 121.937 | 10.029 | 53.708 | 1.00 | 25.00 |
| 1460 | HG | SER | 171 | 122.754 | 12.902 | 53.078 | 1.00 | 25.00 |
| 1461 | N | THR | 172 | 122.761 | 12.625 | 55.557 | 1.00 | 25.72 |
| 1462 | CA | THR | 172 | 122.728 | 13.746 | 56.490 | 1.00 | 25.18 |
| 1463 | C | THR | 172 | 123.183 | 13.367 | 57.902 | 1.00 | 30.69 |
| 1464 | O | THR | 172 | 124.122 | 13.961 | 58.438 | 1.00 | 29.76 |
| 1465 | CB | THR | 172 | 121.311 | 14.390 | 56.574 | 1.00 | 24.33 |
| 1466 | OG1 | THR | 172 | 120.958 | 14.958 | 55.307 | 1.00 | 19.73 |
| 1467 | CG2 | THR | 172 | 121.282 | 15.499 | 57.620 | 1.00 | 16.92 |
| 1468 | H | THR | 172 | 121.932 | 12.351 | 55.113 | 1.00 | 25.00 |
| 1469 | HG1 | THR | 172 | 120.938 | 14.264 | 54.646 | 1.00 | 25.00 |
| 1470 | N | ILE | 173 | 122.542 | 12.363 | 58.489 | 1.00 | 34.29 |
| 1471 | CA | ILE | 173 | 122.875 | 11.951 | 59.848 | 1.00 | 37.02 |
| 1472 | C | ILE | 173 | 124.319 | 11.488 | 60.017 | 1.00 | 31.30 |
| 1473 | O | ILE | 173 | 124.956 | 11.777 | 61.032 | 1.00 | 34.03 |
| 1474 | CB | ILE | 173 | 121.894 | 10.870 | 60.384 | 1.00 | 42.89 |
| 1475 | CG1 | ILE | 173 | 122.082 | 10.702 | 61.893 | 1.00 | 46.46 |
| 1476 | CG2 | ILE | 173 | 122.115 | 9.539 | 59.673 | 1.00 | 43.32 |
| 1477 | CD11 | ILE | 173 | 121.040 | 9.829 | 62.553 | 1.00 | 58.82 |
| 1478 | H | ILE | 173 | 121.833 | 11.884 | 58.002 | 1.00 | 25.00 |
| 1479 | N | HIS | 174 | 124.848 | 10.790 | 59.020 | 1.00 | 27.02 |
| 1480 | CA | HIS | 174 | 126.220 | 10.309 | 59.100 | 1.00 | 30.73 |

TABLE 11-continued

Structural Coordinates of Tobacco 5-Epi-Aristolochene Synthase In the Absence of Bound Substrate

| Atom Type | Atom | Residue | Residue # | X | Y | Z | OCC | B-factor |
|---|---|---|---|---|---|---|---|---|
| 1481 | C | HIS | 174 | 127.251 | 11.412 | 58.870 | 1.00 | 30.72 |
| 1482 | O | HIS | 174 | 128.261 | 11.477 | 59.574 | 1.00 | 32.05 |
| 1483 | CB | HIS | 174 | 126.431 | 9.118 | 58.166 | 1.00 | 32.72 |
| 1484 | CG | HIS | 174 | 125.701 | 7.884 | 58.603 | 1.00 | 42.58 |
| 1485 | ND1 | HIS | 174 | 125.738 | 7.418 | 59.902 | 1.00 | 43.81 |
| 1486 | CD2 | HIS | 174 | 124.891 | 7.036 | 57.925 | 1.00 | 39.61 |
| 1487 | CE1 | HIS | 174 | 124.981 | 6.339 | 60.005 | 1.00 | 38.39 |
| 1488 | NE2 | HIS | 174 | 124.457 | 6.086 | 58.820 | 1.00 | 38.65 |
| 1489 | H | HIS | 174 | 124.304 | 10.608 | 58.221 | 1.00 | 25.00 |
| 1490 | HD1 | HIS | 174 | 126.233 | 7.787 | 60.656 | 1.00 | 25.00 |
| 1491 | HE2 | HIS | 174 | 123.858 | 5.338 | 58.611 | 1.00 | 25.00 |
| 1492 | N | LEU | 175 | 126.970 | 12.310 | 57.931 | 1.00 | 30.47 |
| 1493 | CA | LEU | 175 | 127.874 | 13.420 | 57.655 | 1.00 | 24.51 |
| 1494 | C | LEU | 175 | 127.926 | 14.333 | 58.880 | 1.00 | 23.90 |
| 1495 | O | LEU | 175 | 128.999 | 14.803 | 59.267 | 1.00 | 27.49 |
| 1496 | CB | LEU | 175 | 127.429 | 14.193 | 56.408 | 1.00 | 18.74 |
| 1497 | CG | LEU | 175 | 127.687 | 13.517 | 55.054 | 1.00 | 19.75 |
| 1498 | CD1 | LEU | 175 | 127.007 | 14.295 | 53.935 | 1.00 | 19.14 |
| 1499 | CD2 | LEU | 175 | 129.187 | 13.404 | 54.789 | 1.00 | 13.66 |
| 1500 | H | LEU | 175 | 126.143 | 12.235 | 57.409 | 1.00 | 25.00 |
| 1501 | N | GLU | 176 | 126.781 | 14.535 | 59.524 | 1.00 | 23.45 |
| 1502 | CA | GLU | 176 | 126.7221 | 15.374 | 60.717 | 1.00 | 29.31 |
| 1503 | C | GLU | 176 | 127.596 | 14.788 | 61.814 | 1.00 | 29.58 |
| 1504 | O | GLU | 176 | 128.222 | 15.519 | 62.580 | 1.00 | 30.33 |
| 1505 | CB | GLU | 176 | 125.292 | 15.477 | 61.247 | 1.00 | 28.86 |
| 1506 | CG | GLU | 176 | 124.338 | 16.265 | 60.381 | 1.00 | 41.02 |
| 1507 | CD | GLU | 176 | 122.976 | 16.431 | 61.032 | 1.00 | 50.96 |
| 1508 | OE1 | GLU | 176 | 122.409 | 15.422 | 61.511 | 1.00 | 53.24 |
| 1509 | OE2 | GLU | 176 | 122.474 | 17.574 | 61.069 | 1.00 | 53.02 |
| 1510 | H | GLU | 176 | 125.956 | 14.127 | 59.182 | 1.00 | 25.00 |
| 1511 | N | SER | 177 | 127.615 | 13.461 | 61.890 | 1.00 | 31.99 |
| 1512 | CA | SER | 177 | 128.394 | 12.746 | 52.894 | 1.00 | 33.70 |
| 1513 | C | SER | 177 | 129.905 | 12.777 | 62.620 | 1.00 | 29.73 |
| 1514 | O | SER | 177 | 130.710 | 12.952 | 63.541 | 1.00 | 31.31 |
| 1515 | CB | SER | 177 | 127.896 | 11.299 | 62.986 | 1.00 | 33.08 |
| 1516 | OG | SER | 177 | 128.446 | 10.626 | 64.103 | 1.00 | 42.66 |
| 1517 | H | SER | 177 | 127.077 | 12.944 | 61.259 | 1.00 | 25.00 |
| 1518 | HG | SER | 177 | 128.220 | 11.094 | 64.907 | 1.00 | 25.00 |
| 1519 | N | ALA | 178 | 130.283 | 12.652 | 61.352 | 1.00 | 26.67 |
| 1520 | CA | ALA | 178 | 131.692 | 12.641 | 60.970 | 1.00 | 25.61 |
| 1521 | C | ALA | 178 | 132.351 | 14.013 | 60.858 | 1.00 | 28.58 |
| 1522 | O | ALA | 178 | 133.540 | 14.162 | 61.153 | 1.00 | 23.60 |
| 1523 | CB | ALA | 178 | 131.862 | 11.884 | 59.665 | 1.00 | 22.60 |
| 1524 | H | ALA | 178 | 129.599 | 12.566 | 60.656 | 1.00 | 25.00 |
| 1525 | N | ALA | 179 | 131.568 | 15.018 | 60.475 | 1.00 | 25.11 |
| 1526 | CA | ALA | 179 | 132.068 | 16.376 | 60.268 | 1.00 | 25.17 |
| 1527 | C | ALA | 179 | 133.071 | 16.983 | 61.254 | 1.00 | 25.37 |
| 1528 | O | ALA | 179 | 134.141 | 17.430 | 60.844 | 1.00 | 25.58 |
| 1529 | CB | ALA | 179 | 130.903 | 17.340 | 60.044 | 1.00 | 21.50 |
| 1530 | H | ALA | 179 | 130.617 | 14.840 | 60.325 | 1.00 | 25.00 |
| 1531 | N | PRO | 180 | 132.771 | 16.963 | 62.564 | 1.00 | 27.61 |
| 1532 | CA | PRO | 180 | 133.680 | 17.541 | 63.565 | 1.00 | 28.57 |
| 1533 | C | PRO | 180 | 135.132 | 17.058 | 63.584 | 1.00 | 30.64 |
| 1534 | O | PRO | 180 | 135.994 | 17.724 | 64.155 | 1.00 | 37.22 |
| 1535 | CB | PRO | 180 | 132.988 | 17.206 | 64.889 | 1.00 | 25.80 |
| 1536 | CG | PRO | 180 | 131.540 | 17.118 | 64.518 | 1.00 | 31.06 |
| 1537 | CD | PRO | 180 | 131.597 | 16.360 | 63.221 | 1.00 | 30.35 |
| 1538 | N | HIS | 181 | 135.414 | 15.910 | 62.980 | 1.00 | 28.35 |
| 1539 | CA | HIS | 181 | 136.772 | 15.377 | 63.013 | 1.00 | 27.57 |
| 1540 | C | HIS | 181 | 137.470 | 15.237 | 61.672 | 1.00 | 26.99 |
| 1541 | O | HIS | 181 | 138.529 | 14.611 | 61.584 | 1.00 | 29.22 |
| 1542 | CB | HIS | 181 | 136.764 | 14.035 | 63.740 | 1.00 | 30.76 |
| 1543 | CG | HIS | 181 | 136.153 | 14.103 | 65.104 | 1.00 | 32.51 |
| 1544 | ND1 | HIS | 181 | 134.893 | 13.619 | 65.379 | 1.00 | 34.64 |
| 1545 | CD2 | HIS | 181 | 136.607 | 14.652 | 66.257 | 1.00 | 34.04 |
| 1546 | CE1 | HIS | 181 | 134.593 | 13.870 | 66.641 | 1.00 | 35.16 |
| 1547 | NE2 | HIS | 181 | 135.615 | 14.495 | 67.196 | 1.00 | 38.60 |
| 1548 | H | HIS | 181 | 134.717 | 15.429 | 62.478 | 1.00 | 25.00 |
| 1549 | HD1 | HIS | 181 | 134.298 | 13.158 | 64.739 | 1.00 | 25.00 |
| 1550 | HE2 | HIS | 181 | 135.666 | 14.802 | 68.128 | 1.00 | 25.00 |
| 1551 | N | LEU | 182 | 136.890 | 15.827 | 60.635 | 1.00 | 22.56 |
| 1552 | CA | LEU | 182 | 137.468 | 15.750 | 59.303 | 1.00 | 22.65 |
| 1553 | C | LEU | 182 | 138.532 | 16.821 | 59.103 | 1.00 | 24.98 |
| 1554 | O | LEU | 182 | 138.494 | 17.878 | 59.741 | 1.00 | 22.99 |
| 1555 | CB | LEU | 182 | 136.372 | 15.900 | 58.243 | 1.00 | 25.05 |
| 1556 | CG | LEU | 182 | 135.271 | 14.835 | 58.205 | 1.00 | 23.65 |
| 1557 | CD1 | LEU | 182 | 134.178 | 15.274 | 57.249 | 1.00 | 17.28 |
| 1558 | CD2 | LEU | 182 | 135.849 | 13.483 | 57.786 | 1.00 | 20.03 |
| 1559 | H | LEU | 182 | 136.072 | 16.351 | 60.762 | 1.00 | 25.00 |
| 1560 | N | LYS | 183 | 139.494 | 16.528 | 58.236 | 1.00 | 22.16 |
| 1561 | CA | LYS | 183 | 140.556 | 17.469 | 57.926 | 1.00 | 25.90 |
| 1562 | C | LYS | 183 | 139.982 | 18.573 | 57.045 | 1.00 | 30.39 |
| 1563 | O | LYS | 183 | 138.898 | 18.429 | 56.468 | 1.00 | 31.71 |
| 1564 | CB | LYS | 183 | 141.696 | 16.767 | 57.183 | 1.00 | 27.62 |
| 1565 | CG | LYS | 183 | 141.274 | 16.122 | 555.871 | 1.00 | 37.10 |
| 1566 | CD | LYS | 183 | 142.437 | 15.441 | 55.169 | 1.00 | 45.13 |
| 1567 | CE | LYS | 183 | 141.974 | 14.764 | 53.885 | 1.00 | 50.33 |
| 1568 | NZ | LYS | 183 | 143.088 | 14.040 | 53.210 | 1.00 | 57.79 |
| 1569 | H | LYS | 183 | 139.473 | 15.658 | 57.786 | 1.00 | 25.00 |
| 1570 | 1HZ | LYS | 183 | 143.846 | 14.713 | 52.975 | 1.00 | 25.00 |
| 1571 | 2HZ | LYS | 183 | 143.463 | 13.311 | 53.852 | 1.00 | 25.00 |
| 1572 | 3HZ | LYS | 183 | 142.736 | 13.592 | 52.341 | 1.00 | 25.00 |
| 1573 | N | SER | 184 | 140.714 | 19.674 | 56.944 | 1.00 | 27.77 |
| 1574 | CA | SER | 184 | 140.304 | 20.802 | 56.122 | 1.00 | 28.80 |
| 1575 | C | SER | 184 | 140.970 | 20.675 | 54.752 | 1.00 | 27.61 |
| 1576 | O | SER | 184 | 142.084 | 20.158 | 54.645 | 1.00 | 26.37 |
| 1577 | CB | SER | 184 | 140.702 | 22.109 | 56.805 | 1.00 | 28.03 |
| 1578 | OG | SEER | 184 | 140.003 | 22.254 | 58.031 | 1.00 | 32.93 |
| 1579 | H | SER | 184 | 141.565 | 19.725 | 57.420 | 1.00 | 25.00 |
| 1580 | HG | SER | 184 | 140.193 | 21.517 | 58.620 | 1.00 | 25.00 |
| 1581 | N | PRO | 185 | 140.312 | 21.171 | 53.689 | 1.00 | 26.21 |
| 1582 | CA | PRO | 185 | 139.003 | 21.834 | 53.680 | 1.00 | 23.45 |
| 1583 | C | PRO | 185 | 137.767 | 20.926 | 53.597 | 1.00 | 24.54 |
| 1584 | O | PRO | 185 | 136.636 | 21.425 | 53.589 | 1.00 | 23.22 |
| 1585 | CB | PRO | 185 | 139.109 | 22.737 | 52.458 | 1.00 | 21.98 |
| 1586 | CG | PRO | 185 | 139.858 | 21.876 | 51.503 | 1.00 | 21.03 |
| 1587 | CD | PRO | 185 | 140.949 | 21.263 | 52.361 | 1.00 | 21.80 |
| 1588 | N | LEU | 186 | 137.969 | 19.608 | 53.570 | 1.00 | 21.43 |
| 1589 | CA | LEU | 186 | 136.852 | 18.666 | 53.483 | 1.00 | 21.42 |
| 1590 | C | LEU | 186 | 135.780 | 18.964 | 54.522 | 1.00 | 22.24 |
| 1591 | O | LEU | 186 | 134.586 | 18.987 | 54.210 | 1.00 | 20.84 |
| 1592 | CB | LEU | 186 | 137.331 | 17.220 | 53.654 | 1.00 | 23.63 |
| 1593 | CG | LEU | 186 | 136.217 | 16.160 | 53.646 | 1.00 | 21.09 |
| 1594 | CD1 | LEU | 186 | 135.491 | 16.145 | 52.292 | 1.00 | 20.03 |
| 1595 | CD2 | LEU | 186 | 136.800 | 14.800 | 53.943 | 1.00 | 21.57 |
| 1596 | H | LEU | 186 | 138.882 | 19.259 | 53.605 | 1.00 | 25.00 |
| 1597 | N | ARG | 187 | 136.221 | 19.208 | 55.751 | 1.00 | 16.73 |
| 1598 | CA | ARG | 187 | 135.326 | 19.515 | 56.859 | 1.00 | 22.57 |
| 1599 | C | ARG | 187 | 134.427 | 20.723 | 56.564 | 1.00 | 27.49 |
| 1600 | O | ARG | 187 | 133.225 | 20.693 | 56.848 | 1.00 | 26.35 |
| 1601 | CB | ARG | 187 | 136.146 | 19.777 | 58.117 | 1.00 | 17.71 |
| 1602 | CG | ARG | 187 | 135.325 | 20.087 | 59.343 | 1.00 | 21.93 |
| 1603 | CD | ARG | 187 | 136.235 | 20.478 | 60.483 | 1.00 | 31.75 |
| 1604 | NE | ARG | 187 | 135.507 | 20.685 | 61.727 | 1.00 | 46.15 |
| 1605 | CZ | ARG | 187 | 136.087 | 20.961 | 62.891 | 1.00 | 58.70 |
| 1606 | NH1 | ARG | 187 | 137.412 | 21.066 | 62.970 | 1.00 | 57.84 |
| 1607 | NH2 | ARG | 187 | 135.344 | 21.111 | 63.982 | 1.00 | 58.69 |
| 1608 | H | ARG | 187 | 137.182 | 19.161 | 55.923 | 1.00 | 25.00 |
| 1609 | HE | ARG | 187 | 134.530 | 20.613 | 61.708 | 1.00 | 25.00 |
| 1610 | 1HH1 | ARG | 187 | 137.977 | 20.941 | 62.156 | 1.00 | 25.00 |
| 1611 | 2HH1 | ARG | 187 | 137.843 | 21.275 | 63.848 | 1.00 | 25.00 |
| 1612 | 1HH2 | ARG | 187 | 134.351 | 21.012 | 63.926 | 1.00 | 25.00 |
| 1613 | 2HH2 | ARG | 187 | 135.779 | 21.316 | 64.858 | 1.00 | 25.00 |
| 1614 | N | GLU | 188 | 135.010 | 21.782 | 56.001 | 1.00 | 28.09 |
| 1615 | CA | GLU | 188 | 134.255 | 22.993 | 55.667 | 1.00 | 26.62 |
| 16116 | C | GLU | 188 | 133.293 | 22.726 | 54.516 | 1.00 | 22.97 |
| 1617 | O | GLU | 188 | 132.203 | 23.296 | 54.462 | 1.00 | 21.14 |
| 1618 | CB | GLU | 188 | 135.192 | 24.153 | 55.305 | 1.00 | 24.01 |
| 1619 | CG | GLU | 188 | 135.934 | 24.768 | 58.482 | 1.00 | 32.71 |
| 1620 | CD | GLU | 188 | 137.045 | 23.878 | 57.014 | 1.00 | 42.50 |
| 1621 | OE1 | GLU | 188 | 138.030 | 23.657 | 56.279 | 1.00 | 43.53 |
| 1622 | OE2 | GLU | 188 | 136.936 | 23.403 | 58.165 | 1.00 | 47.38 |
| 1623 | H | GLU | 188 | 135.965 | 21.747 | 55.798 | 1.00 | 25.00 |
| 1624 | N | GLN | 189 | 133.702 | 21.853 | 53.601 | 1.00 | 19.36 |
| 1625 | CA | GLN | 189 | 132.872 | 21.496 | 52.460 | 1.00 | 20.62 |
| 1626 | C | GLN | 189 | 131.636 | 20.728 | 52.927 | 1.00 | 22.47 |

TABLE 11-continued

Structural Coordinates of Tobacco 5-Epi-Aristolochene Synthase
In the Absence of Bound Substrate

| Atom | Atom | Resi- | Resi- | X | Y | Z | OCC | B-factor |
|---|---|---|---|---|---|---|---|---|
| Type | | due | due # | | | | | |
| 1627 | O | GLN | 189 | 130.522 | 21.010 | 52.483 | 1.00 | 25.58 |
| 1628 | CB | GLN | 189 | 133.672 | 20.662 | 51.461 | 1.00 | 17.31 |
| 1629 | CG | GLN | 189 | 132.915 | 20.359 | 50.187 | 1.00 | 24.12 |
| 1630 | CD | GLN | 189 | 133.796 | 19.780 | 49.104 | 1.00 | 25.67 |
| 1631 | OE1 | GLN | 189 | 133.691 | 20.162 | 47.939 | 1.00 | 28.92 |
| 1632 | NE2 | GLN | 189 | 134.666 | 18.850 | 49.477 | 1.00 | 28.68 |
| 1633 | H | GLN | 189 | 134.590 | 21.445 | 53.695 | 1.00 | 25.00 |
| 1634 | 1HE2 | GLN | 189 | 135.235 | 18.480 | 48.773 | 1.00 | 25.00 |
| 1635 | 2HE2 | GLN | 189 | 134.704 | 18.576 | 50.413 | 1.00 | 25.00 |
| 1636 | N | VAL | 190 | 131.833 | 19.783 | 53.846 | 1.00 | 22.03 |
| 1637 | CA | VAL | 190 | 130.734 | 18.983 | 54.388 | 1.00 | 22.50 |
| 1638 | C | VAL | 190 | 129.778 | 19.864 | 55.198 | 1.00 | 22.00 |
| 1639 | O | VAL | 190 | 128.565 | 19.846 | 54.977 | 1.00 | 26.49 |
| 1640 | CB | VAL | 190 | 131.255 | 17.808 | 55.274 | 1.00 | 18.21 |
| 1641 | CG1 | VAL | 190 | 130.093 | 17.093 | 55.947 | 1.00 | 19.13 |
| 1642 | CG2 | VAL | 190 | 132.037 | 16.815 | 54.422 | 1.00 | 13.74 |
| 1643 | H | VAL | 190 | 132.742 | 19.618 | 54.168 | 1.00 | 25.00 |
| 1644 | N | THR | 191 | 130.335 | 20.638 | 56.124 | 1.00 | 20.35 |
| 1645 | CA | THR | 191 | 129.555 | 21.541 | 56.967 | 1.00 | 23.43 |
| 1646 | C | THR | 191 | 128.733 | 22.504 | 56.116 | 1.00 | 23.79 |
| 1647 | O | THR | 191 | 127.564 | 22.772 | 56.410 | 1.00 | 27.12 |
| 1648 | CB | THR | 191 | 130.478 | 22.350 | 57.903 | 1.00 | 29.00 |
| 1649 | OG1 | THR | 191 | 131.124 | 21.454 | 58.814 | 1.00 | 35.12 |
| 1650 | CG2 | THR | 191 | 129.688 | 23.385 | 58.691 | 1.00 | 32.22 |
| 1651 | H | THR | 191 | 131.304 | 20.599 | 58.257 | 1.00 | 25.00 |
| 1652 | HG1 | THR | 191 | 131.661 | 20.824 | 58.321 | 1.00 | 25.00 |
| 1653 | N | HIS | 192 | 129.345 | 23.015 | 55.054 | 1.00 | 22.27 |
| 1654 | CA | HIS | 192 | 128.658 | 23.935 | 54.168 | 1.00 | 24.21 |
| 1655 | C | HIS | 192 | 127.530 | 23.226 | 53.417 | 1.00 | 24.78 |
| 1656 | O | HIS | 192 | 126.421 | 23.756 | 53.326 | 1.00 | 20.41 |
| 1657 | CB | HIS | 192 | 129.632 | 24.564 | 53.173 | 1.00 | 17.98 |
| 1658 | CG | HIS | 192 | 128.965 | 25.446 | 52.169 | 1.00 | 21.55 |
| 1659 | ND1 | HIS | 192 | 128.506 | 26.707 | 52.480 | 1.00 | 21.86 |
| 1660 | CD2 | HIS | 192 | 128.637 | 25.234 | 50.872 | 1.00 | 20.40 |
| 1661 | CE1 | HIS | 192 | 127.919 | 27.234 | 51.420 | 1.00 | 20.03 |
| 1662 | NE2 | HIS | 192 | 127.985 | 26.360 | 50.432 | 1.00 | 20.23 |
| 1663 | H | HIS | 192 | 130.278 | 22.766 | 54.870 | 1.00 | 25.00 |
| 1664 | HD1 | HIS | 192 | 128.594 | 27.143 | 53.355 | 1.00 | 25.00 |
| 1665 | HE2 | HIS | 192 | 127.614 | 26.486 | 49.551 | 1.00 | 25.00 |
| 1666 | N | ALA | 193 | 127.826 | 22.038 | 52.8888 | 1.00 | 22.45 |
| 1667 | CA | ALA | 193 | 126.854 | 21.242 | 52.139 | 1.00 | 20.56 |
| 1668 | C | ALA | 193 | 125.601 | 20.963 | 52.964 | 1.00 | 22.26 |
| 1669 | O | ALA | 193 | 124.485 | 21.072 | 52.459 | 1.00 | 21.49 |
| 1670 | CB | ALA | 193 | 127.483 | 19.938 | 51.679 | 1.00 | 18.73 |
| 1671 | H | ALA | 193 | 128.729 | 21.672 | 53.002 | 1.00 | 25.00 |
| 1672 | N | LEU | 194 | 125.791 | 20.623 | 54.236 | 1.00 | 23.86 |
| 1673 | CA | LEU | 194 | 124.678 | 20.344 | 55.136 | 1.00 | 25.16 |
| 1674 | C | LEU | 194 | 123.757 | 21.551 | 55.298 | 1.00 | 26.76 |
| 1675 | O | LEU | 194 | 122.573 | 21.391 | 55.579 | 1.00 | 28.61 |
| 1676 | CB | LEU | 194 | 125.194 | 19.902 | 56.509 | 1.00 | 23.10 |
| 1677 | CG | LEU | 194 | 125.924 | 18.556 | 56.579 | 1.00 | 26.60 |
| 1678 | CD1 | LEU | 194 | 126.426 | 18.319 | 57.992 | 1.00 | 20.06 |
| 1679 | CD2 | LEU | 194 | 124.998 | 17.433 | 56.149 | 1.00 | 18.24 |
| 1680 | H | LEU | 194 | 126.710 | 20.552 | 54.574 | 1.00 | 25.00 |
| 1681 | N | GLU | 195 | 124.309 | 22.754 | 55.149 | 1.00 | 33.01 |
| 1682 | CA | GLU | 195 | 123.529 | 23.987 | 55.277 | 1.00 | 34.61 |
| 1683 | C | GLU | 195 | 123.005 | 24.448 | 53.923 | 1.00 | 26.09 |
| 1684 | O | GLU | 195 | 121.952 | 25.074 | 53.834 | 1.00 | 29.66 |
| 1685 | CB | GLU | 195 | 124.385 | 25.102 | 55.884 | 1.00 | 38.35 |
| 1686 | CG | GLU | 195 | 124.885 | 24.816 | 57.288 | 1.00 | 59.66 |
| 1687 | CD | GLU | 195 | 125.945 | 25.803 | 57.751 | 1.00 | 72.22 |
| 1688 | OE1 | GLU | 195 | 126.800 | 26.203 | 56.927 | 1.00 | 75.42 |
| 1689 | OE2 | GLU | 195 | 125.931 | 26.169 | 58.947 | 1.00 | 82.70 |
| 1690 | H | GLU | 195 | 125.263 | 22.814 | 54.944 | 1.00 | 25.00 |
| 1691 | N | GLN | 196 | 123.747 | 24.130 | 52.871 | 1.00 | 22.78 |
| 1692 | CA | GLN | 196 | 123.376 | 24.529 | 51.527 | 1.00 | 20.33 |
| 1693 | C | GLN | 196 | 123.891 | 23.520 | 50.515 | 1.00 | 19.79 |
| 1694 | O | GLN | 196 | 125.094 | 23.463 | 50.258 | 1.00 | 24.78 |
| 1695 | CB | GLN | 196 | 123.980 | 25.903 | 51.219 | 1.00 | 20.38 |
| 1696 | CG | GLN | 196 | 123.727 | 26.397 | 49.807 | 1.00 | 24.47 |
| 1697 | CD | GLN | 196 | 122.253 | 26.591 | 49.524 | 1.00 | 28.74 |
| 1698 | OE1 | GLN | 196 | 121.622 | 27.490 | 50.074 | 1.00 | 32.30 |
| 1699 | NE2 | GLN | 196 | 121.694 | 25.744 | 48.667 | 1.00 | 21.06 |
| 1700 | H | GLN | 196 | 124.554 | 23.592 | 52.995 | 1.00 | 25.00 |
| 1701 | 1HE2 | GLN | 196 | 120.741 | 25.876 | 48.480 | 1.00 | 25.00 |
| 1702 | 2HE2 | GLN | 196 | 122.247 | 25.045 | 48.258 | 1.00 | 25.00 |
| 1703 | N | CYS | 197 | 122.992 | 22.727 | 49.942 | 1.00 | 19.52 |
| 1704 | CA | CYS | 197 | 123.399 | 21..749 | 48.944 | 1.00 | 17.94 |
| 1705 | C | CYS | 197 | 123.782 | 22.497 | 47.669 | 1.00 | 18.82 |
| 1706 | O | CYS | 197 | 123.316 | 23.614 | 47.428 | 1.00 | 19.62 |
| 1707 | CB | CYS | 197 | 122.278 | 20.743 | 48.669 | 1.00 | 21.42 |
| 1708 | SG | CYS | 197 | 120.832 | 21.394 | 47.800 | 1.00 | 42.82 |
| 1709 | H | CYS | 197 | 122.056 | 22.808 | 50.202 | 1.00 | 25.00 |
| 1710 | N | LEU | 198 | 124.626 | 21.878 | 46.856 | 1.00 | 19.01 |
| 1711 | CA | LEU | 198 | 125.094 | 22.489 | 45.620 | 1.00 | 20.23 |
| 1712 | C | LEU | 198 | 123.986 | 22.760 | 44.610 | 1.00 | 23.16 |
| 1713 | O | LEU | 198 | 123.868 | 23.867 | 44.096 | 1.00 | 26.68 |
| 1714 | CB | LEU | 198 | 126.174 | 21.608 | 44.981 | 1.00 | 13.53 |
| 1715 | CG | LEU | 198 | 126.762 | 22.058 | 43.640 | 1.00 | 20.37 |
| 1716 | CD1 | LEU | 198 | 127.388 | 23.440 | 43.773 | 1.00 | 19.35 |
| 1717 | CD2 | LEU | 198 | 127.789 | 21.044 | 43.158 | 1.00 | 18.28 |
| 1718 | H | LEU | 198 | 124.968 | 21.004 | 47.109 | 1.00 | 25.00 |
| 1719 | N | HIS | 199 | 123.160 | 21.752 | 44.354 | 1.00 | 24.27 |
| 1720 | CA | HIS | 199 | 122.079 | 21.859 | 43.379 | 1.00 | 22.48 |
| 1721 | C | HIS | 199 | 121.089 | 23.001 | 43.608 | 1.00 | 19.15 |
| 1722 | O | HIS | 199 | 120.586 | 23.582 | 42.653 | 1.00 | 19.66 |
| 1723 | CB | HIS | 199 | 121.327 | 20.523 | 43.277 | 1.00 | 22.51 |
| 1724 | CG | HIS | 199 | 120.225 | 20.519 | 42.261 | 1.00 | 16.72 |
| 1725 | ND1 | HIS | 199 | 120.452 | 20.697 | 40.911 | 1.00 | 19.56 |
| 1726 | CD2 | HIS | 199 | 118.885 | 20.360 | 42.396 | 1.00 | 15.14 |
| 1727 | CE1 | HIS | 199 | 119.303 | 20.648 | 40.261 | 1.00 | 15.68 |
| 1728 | NE2 | HIS | 199 | 118.338 | 20.444 | 41.138 | 1.00 | 19.96 |
| 1729 | H | HIS | 199 | 123.297 | 20.912 | 44.822 | 1.00 | 25..00 |
| 1730 | HD1 | HIS | 199 | 121.340 | 20.834 | 40.498 | 1.00 | 25.00 |
| 1731 | HE2 | HIS | 199 | 117.376 | 20.343 | 40.929 | 1.00 | 25.00 |
| 1732 | N | LYS | 200 | 120.811 | 23.323 | 44.864 | 1.00 | 18.06 |
| 1733 | CA | LYS | 200 | 119.853 | 24.377 | 45.170 | 1.00 | 19.34 |
| 1734 | C | LYS | 200 | 120.463 | 25.726 | 45.548 | 1.00 | 21.28 |
| 1735 | O | LYS | 200 | 119.755 | 26.617 | 46.012 | 1.00 | 20.62 |
| 1736 | CB | LYS | 200 | 118.898 | 23.893 | 46.264 | 1.00 | 17.06 |
| 1737 | CG | LYS | 200 | 118.144 | 22.630 | 45.875 | 1.00 | 17.06 |
| 1738 | CD | LYS | 200 | 117.287 | 22.086 | 47.005 | 1.00 | 18.82 |
| 1739 | CE | LYS | 200 | 116.597 | 20.804 | 46.559 | 1.00 | 16.83 |
| 1740 | NZ | LYS | 200 | 115.820 | 20.155 | 47.645 | 1.00 | 19.41 |
| 1741 | H | LYS | 200 | 121.264 | 22.869 | 45.599 | 1.00 | 25.00 |
| 1742 | 1HZ | LYS | 200 | 1166.454 | 19.923 | 48.436 | 1.00 | 25.00 |
| 1743 | 2HZ | LYS | 200 | 115.081 | 20.807 | 47.978 | 1.00 | 25.00 |
| 1744 | 3HZ | LYS | 200 | 115.377 | 19.285 | 47.288 | 1.00 | 25.00 |
| 1745 | N | GLY | 201 | 121.768 | 25.881 | 45.343 | 1.00 | 23.54 |
| 1746 | CA | GLY | 201 | 122.424 | 27.136 | 45.675 | 1.00 | 19.60 |
| 1747 | C | GLY | 201 | 122.583 | 28.062 | 44.482 | 1.00 | 19.35 |
| 1748 | O | GLY | 201 | 122.569 | 27.613 | 43.338 | 1.00 | 21.61 |
| 1749 | H | GLY | 201 | 122.299 | 25.166 | 44.933 | 1.00 | 25.00 |
| 1750 | N | VAL | 202 | 122.685 | 29.363 | 44.734 | 1.00 | 17.34 |
| 1751 | CA | VAL | 202 | 122.871 | 30.327 | 43.653 | 1.00 | 17.16 |
| 1752 | C | VAL | 202 | 124.281 | 30.084 | 43.108 | 1.00 | 20.63 |
| 1753 | O | VAL | 202 | 125.248 | 30.059 | 43.874 | 1.00 | 22.87 |
| 1754 | CB | VAL | 202 | 122.722 | 31.778 | 44.168 | 1.00 | 17.85 |
| 1755 | CG1 | VAL | 202 | 123.062 | 32.782 | 43.071 | 1.00 | 19.32 |
| 1756 | CG2 | VAL | 202 | 121.301 | 32.003 | 44.645 | 1.00 | 15.75 |
| 1757 | H | VAL | 202 | 122.625 | 29.676 | 45.655 | 1.00 | 25.00 |
| 1758 | N | PRO | 203 | 124.414 | 29.905 | 41.780 | 1.00 | 18.06 |
| 1759 | CA | PRO | 203 | 125.705 | 29.652 | 41.128 | 1.00 | 19.86 |
| 1760 | C | PRO | 203 | 126.889 | 30.506 | 41.588 | 1.00 | 23.15 |
| 1761 | O | PRO | 203 | 127.827 | 29.974 | 42.172 | 1.00 | 27.00 |
| 1762 | CB | PRO | 203 | 125.378 | 29.840 | 39.650 | 1.00 | 21.47 |
| 1763 | CG | PRO | 203 | 123.982 | 29.300 | 39.574 | 1.00 | 19.55 |
| 1764 | CD | PRO | 203 | 123.332 | 29.952 | 40.780 | 1.00 | 17.62 |
| 1765 | N | ARG | 204 | 126.844 | 31.817 | 41.365 | 1.00 | 21.91 |
| 1766 | CA | ARG | 204 | 127.949 | 32.683 | 41.781 | 1.00 | 20.91 |
| 1767 | C | ARG | 204 | 128.283 | 32.568 | 43.265 | 1.00 | 20.45 |
| 1768 | O | ARG | 204 | 129.455 | 32.598 | 43.638 | 1.00 | 25.04 |
| 1769 | CB | ARG | 204 | 127.681 | 34.149 | 41.426 | 1.00 | 22.61 |
| 1770 | CG | ARG | 204 | 127.940 | 34.519 | 39.972 | 1.00 | 18.14 |
| 1771 | CD | ARG | 204 | 129.420 | 34.487 | 39.618 | 1.00 | 21.89 |
| 1772 | NE | ARG | 204 | 129.852 | 33.202 | 39.074 | 1.00 | 23.42 |

TABLE 11-continued

Structural Coordinates of Tobacco 5-Epi-Aristolochene Synthase In the Absence of Bound Substrate

| Atom | Atom | Resi- | Resi- | X | Y | Z | OCC | B-factor |
|---|---|---|---|---|---|---|---|---|
| Type | | due | due # | | | | | |
| 1773 | CZ | ARG | 204 | 130.953 | 33.027 | 38.345 | 1.00 | 28.33 |
| 1774 | NH1 | ARG | 204 | 131.747 | 34.055 | 38.069 | 1.00 | 25.07 |
| 1775 | NH2 | ARG | 204 | 131.248 | 31.827 | 37.862 | 1.00 | 26.89 |
| 1776 | H | ARG | 204 | 126.071 | 32.201 | 40.913 | 1.00 | 25.00 |
| 1777 | HE | ARG | 204 | 129.297 | 32.416 | 39.258 | 1.00 | 25.00 |
| 1778 | 1HH1 | ARG | 204 | 131.521 | 34.967 | 38.404 | 1.00 | 25.00 |
| 1779 | 2HH1 | ARG | 204 | 132.570 | 33.921 | 37.522 | 1.00 | 25.00 |
| 1780 | 1HH2 | ARG | 2004 | 130.647 | 31.051 | 38.047 | 1.00 | 25.00 |
| 1781 | 2HH2 | ARG | 204 | 132.077 | 31.699 | 37.316 | 1.00 | 25.00 |
| 1782 | N | VAL | 205 | 127.264 | 32.431 | 44.108 | 1.00 | 17.32 |
| 1783 | CA | VAL | 205 | 127.496 | 32.312 | 45.545 | 1.00 | 18.99 |
| 1784 | C | VAL | 205 | 128.267 | 31.034 | 45.866 | 1.00 | 20.53 |
| 1785 | O | VAL | 205 | 129.220 | 31.048 | 46.647 | 1.00 | 24.18 |
| 1786 | CB | VAL | 205 | 126.175 | 32.309 | 46.339 | 1.00 | 19.83 |
| 1787 | CG1 | VAL | 205 | 126.442 | 32.022 | 47.811 | 1.00 | 14.97 |
| 1788 | CG2 | VAL | 205 | 125.473 | 33.642 | 46.190 | 1.00 | 21.52 |
| 1789 | H | VAL | 205 | 126.353 | 32.398 | 43.764 | 1.00 | 25.00 |
| 1790 | N | GLU | 206 | 127.862 | 29.933 | 45.249 | 1.00 | 22.23 |
| 1791 | CA | GLU | 206 | 128.519 | 28.649 | 45.478 | 1.00 | 22.70 |
| 1792 | C | GLU | 206 | 129.919 | 28.601 | 44.876 | 1.00 | 18.65 |
| 1793 | O | GLU | 206 | 130.836 | 28.029 | 45.469 | 1.00 | 20.84 |
| 1794 | CB | GLU | 206 | 127.648 | 27.506 | 44.957 | 1.00 | 17.73 |
| 1795 | CG | GLU | 206 | 126.317 | 27.413 | 45.683 | 1.00 | 20.17 |
| 1796 | CD | GLU | 206 | 126.478 | 27.407 | 47.201 | 1.00 | 26.03 |
| 1797 | OE1 | GLU | 206 | 127.190 | 26.523 | 47.721 | 1.00 | 21.64 |
| 1798 | OE2 | GLU | 206 | 125.895 | 28.283 | 47.876 | 1.00 | 20.28 |
| 1799 | H | GLU | 206 | 127.111 | 29.981 | 44.620 | 1.00 | 25.00 |
| 1800 | N | THR | 207 | 130.081 | 29.223 | 43.714 | 1.00 | 18.09 |
| 1801 | CA | THR | 207 | 131.369 | 29.291 | 43.038 | 1.00 | 21.23 |
| 1802 | C | THR | 207 | 132.373 | 30.057 | 43.909 | 1.00 | 25.71 |
| 1803 | O | THR | 207 | 133.474 | 29.568 | 44.179 | 1.00 | 28.93 |
| 1804 | CB | THR | 207 | 131.219 | 29.984 | 41.672 | 1.00 | 24.22 |
| 1805 | OG1 | THR | 207 | 130.529 | 29.1077 | 40.770 | 1.00 | 28.95 |
| 1806 | CG2 | THR | 207 | 132.573 | 30.379 | 41.088 | 1.00 | 23.10 |
| 1807 | H | THR | 207 | 129.311 | 29.644 | 43.289 | 1.00 | 25.00 |
| 1808 | HG1 | THR | 207 | 131.030 | 28.287 | 40.685 | 1.00 | 25.00 |
| 1809 | N | ARG | 208 | 131.973 | 31.238 | 44.374 | 1.00 | 24.65 |
| 1810 | CA | ARG | 208 | 132.825 | 32.070 | 45.221 | 1.00 | 25.56 |
| 1811 | C | ARG | 208 | 133.292 | 31.273 | 46.432 | 1.00 | 25.87 |
| 1812 | O | ARG | 208 | 134.472 | 31.289 | 46.780 | 1.00 | 27.73 |
| 1813 | CB | ARG | 208 | 132.059 | 33.314 | 45.682 | 1.00 | 25.72 |
| 1814 | CG | ARG | 208 | 132.836 | 34.258 | 46.588 | 1.00 | 31.65 |
| 1815 | CD | ARG | 208 | 134.062 | 34.826 | 45.892 | 1.00 | 39.53 |
| 1816 | NE | ARG | 208 | 134.374 | 36.184 | 46.344 | 1.00 | 46.43 |
| 1817 | CZ | ARG | 208 | 135.283 | 36.488 | 47.266 | 1.00 | 47.18 |
| 1818 | NH11 | ARG | 208 | 135.991 | 35.534 | 47.858 | 1.00 | 54.31 |
| 1819 | NH2 | ARG | 208 | 135.492 | 37.754 | 47.592 | 1.00 | 54.01 |
| 1820 | H | ARG | 208 | 131.077 | 31.566 | 44.139 | 1.00 | 25.00 |
| 1821 | HE | ARG | 208 | 133.881 | 36.924 | 45.937 | 1.00 | 25.00 |
| 1822 | 1HH1 | ARG | 208 | 135.847 | 34.577 | 47.610 | 1.00 | 25.00 |
| 1823 | 2HH1 | ARG | 208 | 136.673 | 35.775 | 48.548 | 1.00 | 25.00 |
| 1824 | 1HH2 | ARG | 208 | 134.962 | 38.478 | 47.150 | 1.00 | 25.00 |
| 1825 | 2HH2 | ARG | 208 | 136.172 | 37.986 | 48.287 | 1.00 | 25.00 |
| 1826 | N | PHE | 209 | 132.364 | 30.556 | 47.056 | 1.00 | 25.17 |
| 1827 | CA | PHE | 209 | 132.688 | 29.750 | 48.224 | 1.00 | 23.72 |
| 1828 | C | PHE | 209 | 133.677 | 28.632 | 47.908 | 1.00 | 24.69 |
| 1829 | O | PHE | 209 | 134.656 | 28.442 | 48.626 | 1.00 | 24.23 |
| 1830 | CB | PHE | 209 | 131.430 | 29.135 | 48.838 | 1.00 | 22.94 |
| 1831 | CG | PHE | 209 | 131.721 | 28.195 | 49.976 | 1.00 | 22.62 |
| 1832 | CD1 | PHE | 209 | 132.019 | 28.691 | 51.242 | 1.00 | 22.83 |
| 1833 | CD2 | PHE | 209 | 131.745 | 26.817 | 49.773 | 1.00 | 20.76 |
| 1834 | CE1 | PHE | 209 | 132.336 | 27.824 | 52.293 | 1.00 | 22.43 |
| 1835 | CE2 | PHE | 209 | 132.060 | 25.946 | 50.813 | 1.00 | 24.13 |
| 1836 | CZ | PHE | 209 | 132.358 | 26.450 | 52.075 | 1.00 | 22.16 |
| 1837 | H | PHE | 209 | 131.439 | 30.580 | 46.728 | 1.00 | 25.00 |
| 1838 | N | PHE | 210 | 133.399 | 27.872 | 46.856 | 1.00 | 24.89 |
| 1839 | CA | PHE | 210 | 134.263 | 26.765 | 46.486 | 1.00 | 21.48 |
| 1840 | C | PHE | 210 | 135.671 | 27.241 | 46.172 | 1.00 | 23.23 |
| 1841 | O | PHE | 210 | 136.645 | 26.676 | 48.671 | 1.00 | 24.15 |
| 1842 | CB | PHE | 210 | 133.688 | 25.989 | 45.296 | 1.00 | 18.25 |
| 1843 | CG | PHE | 210 | 134.477 | 624.754 | 44.944 | 1.00 | 20.04 |
| 1844 | CD1 | PHE | 210 | 134.506 | 23.661 | 45.811 | 1.00 | 17.95 |
| 1845 | CD2 | PHE | 210 | 135.212 | 24.694 | 43.763 | 1.00 | 19.06 |
| 1846 | CE1 | PHE | 210 | 135.260 | 22.525 | 45.510 | 1.00 | 17.28 |
| 1847 | CE2 | PHE | 210 | 135.972 | 23.563 | 43.450 | 1.00 | 21.18 |
| 1848 | CZ | PHE | 210 | 135.995 | 22.476 | 44.329 | 1.00 | 18.42 |
| 1849 | H | PHE | 210 | 132.602 | 28.062 | 46.315 | 1.00 | 25.00 |
| 1850 | N | ILE | 211 | 135.781 | 28.290 | 45.368 | 1.00 | 26.53 |
| 1851 | CA | ILE | 211 | 137.086 | 28.818 | 44.997 | 1.00 | 27.06 |
| 1852 | C | ILE | 211 | 137.917 | 29.248 | 48.205 | 1.00 | 27.01 |
| 1853 | O | ILE | 211 | 138.953 | 28.652 | 46.490 | 1.00 | 25.02 |
| 1854 | CB | ILE | 211 | 136.967 | 30.015 | 44.023 | 1.00 | 23.08 |
| 1855 | CG1 | ILE | 211 | 136.317 | 29.574 | 42.713 | 1.00 | 22.07 |
| 1856 | CG2 | ILE | 211 | 138.344 | 30.603 | 43.737 | 1.00 | 18.73 |
| 1857 | CD1 | ILE | 211 | 136.163 | 30.700 | 41.701 | 1.00 | 22.59 |
| 1858 | H | ILE | 211 | 134.968 | 28.712 | 45.022 | 1.00 | 25.00 |
| 1859 | N | SER | 212 | 137.430 | 30.233 | 46.949 | 1.00 | 26.45 |
| 1860 | CA | SER | 212 | 138.174 | 30.758 | 48.087 | 1.00 | 29.47 |
| 1861 | C | SER | 212 | 138.263 | 29.914 | 49.355 | 1.00 | 29.82 |
| 1862 | O | SER | 212 | 139.317 | 29.873 | 49.993 | 1.00 | 31.08 |
| 1863 | CB | SER | 212 | 137.691 | 32.173 | 48.425 | 1.00 | 28.90 |
| 1864 | OG | SER | 212 | 136.311 | 32.186 | 48.742 | 1.00 | 48.04 |
| 1865 | H | SER | 212 | 136.550 | 30.622 | 46.740 | 1.00 | 25.00 |
| 1866 | HG | SER | 212 | 136.156 | 31.647 | 49.517 | 1.00 | 25.00 |
| 1867 | N | SER | 213 | 137.175 | 29.249 | 49.728 | 1.00 | 25.54 |
| 1868 | CA | SER | 213 | 137.173 | 28.447 | 50.949 | 1..00 | 25.42 |
| 1869 | C | SER | 213 | 137.555 | 26.969 | 50.823 | 1.00 | 23.90 |
| 1870 | O | SER | 213 | 138.019 | 26.371 | 51.794 | 1.00 | 29.58 |
| 1871 | CB | SER | 213 | 135.820 | 28.556 | 51.662 | 1.00 | 19.77 |
| 1872 | OG | SER | 213 | 135.503 | 29.920 | 51.942 | 1.00 | 36.00 |
| 1873 | H | SER | 213 | 136.366 | 29.279 | 49.173 | 1.00 | 25.00 |
| 1874 | HG | SER | 213 | 135.449 | 30.406 | 51.120 | 1.00 | 25.00 |
| 1875 | N | ILE | 214 | 137.390 | 26.376 | 49.645 | 1.00 | 20.94 |
| 1876 | CA | ILE | 214 | 137.701 | 24.958 | 49.502 | 1.00 | 20.03 |
| 1877 | C | ILE | 214 | 138.869 | 24.617 | 48.591 | 1.00 | 20.98 |
| 1878 | O | ILE | 214 | 139.914 | 24.174 | 49.065 | 1.00 | 23.05 |
| 1879 | CB | ILE | 214 | 136.463 | 24.144 | 49.041 | 1.00 | 20.03 |
| 1880 | CG1 | ILE | 214 | 135.255 | 24.455 | 49.932 | 1.00 | 15.38 |
| 1881 | CG2 | ILE | 214 | 136.778 | 22.640 | 49.046 | 1.00 | 14.86 |
| 1882 | CD1 | ILE | 214 | 135.488 | 24.207 | 51.418 | 1.00 | 14.56 |
| 1883 | H | ILE | 214 | 137.066 | 26.887 | 48.873 | 1.00 | 25.00 |
| 1884 | N | TYR | 215 | 138.696 | 24.823 | 47.289 | 1.00 | 18.70 |
| 1885 | CA | TYR | 215 | 139.733 | 24.490 | 46.323 | 1.00 | 22.93 |
| 1886 | C | TYR | 215 | 141.076 | 25.168 | 46.582 | 1.00 | 25.73 |
| 1887 | O | TYR | 215 | 142.128 | 24.545 | 46.450 | 1.00 | 25.96 |
| 1888 | CB | TYR | 215 | 139.258 | 24.777 | 44.899 | 1.00 | 19.89 |
| 1889 | CG | TYR | 215 | 139.859 | 23.834 | 43.884 | 1.00 | 17.39 |
| 1890 | CD1 | TYR | 215 | 139.726 | 22.455 | 44.030 | 1.00 | 18.08 |
| 1891 | CD2 | TYR | 215 | 140.557 | 24.315 | 42.782 | 1.00 | 19.17 |
| 1892 | CE1 | TYR | 215 | 140.275 | 21.575 | 43.102 | 1.00 | 17.39 |
| 1893 | CE2 | TYR | 215 | 141.113 | 23.445 | 41.843 | 1.00 | 16.77 |
| 1894 | CZ | TYR | 215 | 140.967 | 22.076 | 42.010 | 1.00 | 21.36 |
| 1895 | OH | TYR | 215 | 141.517 | 21.212 | 41.088 | 1.00 | 25.91 |
| 1896 | H | TYR | 215 | 137.858 | 25.217 | 46.973 | 1.00 | 25.00 |
| 1897 | HH | TYR | 215 | 141.317 | 20.302 | 41.340 | 1.00 | 25.00 |
| 1898 | N | ASP | 216 | 141.037 | 26.434 | 46.969 | 1.00 | 26.71 |
| 1899 | CA | ASP | 216 | 142.254 | 27.184 | 47.250 | 1.00 | 32.33 |
| 1900 | C | ASP | 216 | 143.057 | 26.532 | 48.377 | 1.00 | 32.46 |
| 1901 | O | ASP | 216 | 144.288 | 26.589 | 48.387 | 1.00 | 33.87 |
| 1902 | CB | ASP | 216 | 141.895 | 28.621 | 47.636 | 1.00 | 35.77 |
| 1903 | CG | ASP | 216 | 143.111 | 29.514 | 47.769 | 1.00 | 36.73 |
| 1904 | OD1 | ASP | 218 | 143.842 | 29.670 | 46.769 | 1.00 | 37.16 |
| 1905 | OD2 | ASP | 216 | 143.327 | 30.062 | 48.871 | 1.00 | 41.08 |
| 1906 | H | ASP | 216 | 140.170 | 26.885 | 447.054 | 1.00 | 25.00 |
| 1907 | N | LYS | 217 | 142.350 | 25.910 | 49.316 | 1.00 | 31.70 |
| 1908 | CA | LYS | 217 | 142.978 | 25.255 | 50.459 | 1.00 | 29.37 |
| 1909 | C | LYS | 217 | 143.134 | 23.745 | 50.269 | 1.00 | 30.32 |
| 1910 | O | LYS | 217 | 143.506 | 23.029 | 51.200 | 1.00 | 31.00 |
| 1911 | CB | LYS | 217 | 142.170 | 25.553 | 51.724 | 1.00 | 26.09 |
| 1912 | CG | LYS | 217 | 142.062 | 27.033 | 52.017 | 1.00 | 27.73 |
| 1913 | CD | LYS | 217 | 141.185 | 27.312 | 53.213 | 1.00 | 35.35 |
| 1914 | CE | LYS | 217 | 141.091 | 28.807 | 53.463 | 1.00 | 40.60 |
| 1915 | NZ | LYS | 217 | 140.124 | 29.115 | 54.551 | 1.00 | 49.88 |
| 1916 | H | LYS | 217 | 141.376 | 25.876 | 49.235 | 1.00 | 25.00 |
| 1917 | 1HZ | LYS | 217 | 140.429 | 28.650 | 55.430 | 1.00 | 25.00 |
| 1918 | 2HZ | LYS | 217 | 140.083 | 30.143 | 54.698 | 1.00 | 25.00 |

TABLE 11-continued

Structural Coordinates of Tobacco 5-Epi-Aristolochene Synthase In the Absence of Bound Substrate

| Atom | Atom Type | Residue | Residue # | X | Y | Z | OCC | B-factor |
|---|---|---|---|---|---|---|---|---|
| 1919 | 3HZ | LYS | 217 | 139.181 | 28.767 | 54.284 | 1.00 | 25.00 |
| 1920 | N | GLU | 218 | 142.864 | 23.271 | 49.057 | 1.00 | 31.03 |
| 1921 | CA | GLU | 218 | 142.961 | 21.855 | 48.750 | 1.00 | 33.23 |
| 1922 | C | GLU | 218 | 144.391 | 21.489 | 48.357 | 1.00 | 42.71 |
| 1923 | O | GLU | 218 | 144.932 | 22.012 | 47.381 | 1.00 | 41.53 |
| 1924 | CB | GLU | 218 | 141.983 | 21.492 | 47.626 | 1.00 | 32.79 |
| 1925 | CG | GLU | 218 | 141.873 | 20.007 | 47.345 | 1.00 | 49.16 |
| 1926 | CD | GLU | 218 | 141.324 | 19.228 | 48.526 | 1.00 | 61.57 |
| 1927 | OE1 | GLU | 218 | 140.147 | 19.456 | 48.886 | 1.00 | 66.99 |
| 1928 | OE2 | GLU | 218 | 142.066 | 18.391 | 49.092 | 1.00 | 62.96 |
| 1929 | H | GLU | 218 | 142.616 | 23.896 | 48.343 | 1.00 | 25.00 |
| 1930 | N | GLN | 219 | 144.974 | 20.551 | 49.098 | 1.00 | 48.16 |
| 1931 | CA | GLN | 219 | 146.339 | 20.089 | 48.858 | 1.00 | 52.73 |
| 1932 | C | GLN | 219 | 146.533 | 19.487 | 47.467 | 1.00 | 49.21 |
| 1933 | O | GLN | 219 | 147.594 | 19.622 | 46.870 | 1.00 | 51.36 |
| 1934 | CB | GLN | 219 | 146.733 | 19.063 | 49.929 | 1.00 | 62.56 |
| 1935 | CG | GLN | 219 | 148.127 | 19.262 | 50.531 | 1.00 | 81.40 |
| 1936 | CD | GLN | 219 | 148.498 | 18.186 | 51.534 | 1.00 | 90.93 |
| 1937 | OE1 | GLN | 219 | 148.863 | 17.072 | 51.156 | 1.00 | 97.11 |
| 1938 | NE2 | GLN | 219 | 148.408 | 18.512 | 52.825 | 1.00 | 96.41 |
| 1939 | H | GLN | 219 | 144.450 | 20.162 | 49.821 | 1.00 | 25.00 |
| 1940 | 1HE2 | GLN | 219 | 148.113 | 19.389 | 53.115 | 1.00 | 25.00 |
| 1941 | 2HE2 | GLN | 219 | 148.656 | 17.793 | 53.455 | 1.00 | 25.00 |
| 1942 | N | SER | 220 | 145.496 | 18.842 | 46.950 | 1.00 | 47.51 |
| 1943 | CA | SER | 220 | 145.552 | 18.199 | 45.636 | 1.00 | 47.04 |
| 1944 | C | SER | 220 | 144.945 | 19.020 | 44.487 | 1.00 | 45.29 |
| 1945 | O | SER | 220 | 144.577 | 18.467 | 43.446 | 1.00 | 47.02 |
| 1946 | CB | SER | 220 | 144.862 | 16.833 | 45.713 | 1.00 | 51.73 |
| 1947 | OG | SER | 220 | 143.585 | 16.948 | 46.327 | 1.00 | 55.26 |
| 1948 | H | SER | 220 | 144.658 | 18.796 | 47.447 | 1.00 | 25.00 |
| 1949 | HG | SER | 220 | 143.671 | 17.280 | 47.217 | 1.00 | 25.00 |
| 1950 | N | LYS | 221 | 144.849 | 20.332 | 44.679 | 1.00 | 38.03 |
| 1951 | CA | LYS | 221 | 144.270 | 21.233 | 43.682 | 1.00 | 32.98 |
| 1952 | C | LYS | 221 | 145.037 | 21.284 | 42.363 | 1.00 | 30.63 |
| 1953 | O | LYS | 221 | 146.249 | 21.077 | 42.328 | 1.00 | 33.91 |
| 1954 | CB | LYS | 221 | 144.206 | 22.649 | 44.255 | 1.00 | 33.08 |
| 1955 | CG | LYS | 221 | 145.584 | 23.257 | 44.500 | 1.00 | 40.24 |
| 1956 | CD | LYS | 221 | 145.512 | 24.563 | 45.257 | 1.00 | 53.13 |
| 19557 | CE | LYS | 221 | 146.902 | 25.093 | 45.561 | 1.00 | 55.90 |
| 1958 | NZ | LYS | 221 | 146.843 | 26.358 | 46.344 | 1.00 | 67.32 |
| 1959 | H | LYS | 221 | 145.198 | 20.720 | 45.508 | 1.00 | 25.00 |
| 1960 | 1HZ | LYS | 221 | 146.350 | 26.191 | 47.244 | 1.00 | 25.00 |
| 1961 | 2HZ | LYS | 221 | 147.807 | 26.698 | 46.533 | 1.00 | 25.00 |
| 1962 | 3HZ | LYS | 221 | 146.326 | 27.080 | 45.800 | 1.00 | 25.00 |
| 1963 | N | ASN | 222 | 144.322 | 21.536 | 41.273 | 1.00 | 28.13 |
| 1964 | CA | ASN | 222 | 144.958 | 21.675 | 39.970 | 1.00 | 25.27 |
| 1965 | C | ASN | 222 | 145.154 | 23.174 | 39.816 | 1.00 | 30.00 |
| 1966 | O | ASN | 222 | 144.187 | 23.933 | 39.707 | 1.00 | 29.84 |
| 1967 | CB | ASN | 222 | 144.077 | 21.149 | 38.843 | 1.00 | 22.73 |
| 1968 | CG | ASN | 222 | 144.688 | 21.390 | 37.473 | 1.00 | 24.93 |
| 1969 | OD1 | ASN | 222 | 144.914 | 22.534 | 37.072 | 1.00 | 31.82 |
| 1970 | ND2 | ASN | 222 | 144.973 | 20.317 | 36.755 | 1.00 | 23.78 |
| 1971 | H | ASN | 222 | 143.353 | 21.640 | 41.343 | 1.00 | 25.00 |
| 1972 | 1HD2 | ASN | 222 | 145.364 | 20.460 | 35.868 | 1.00 | 25.00 |
| 1973 | 2HD2 | ASN | 222 | 144.784 | 19.432 | 37.125 | 1.00 | 25.00 |
| 1974 | N | ASN | 223 | 146.412 | 23.596 | 39.819 | 1.00 | 31.07 |
| 1975 | CA | ASN | 223 | 146.759 | 25.009 | 39.726 | 1.00 | 26.94 |
| 1976 | C | ASN | 223 | 146.273 | 25.730 | 38.477 | 1.00 | 25.82 |
| 1977 | O | ASN | 223 | 145.933 | 26.910 | 38.538 | 1.00 | 27.88 |
| 1978 | CB | ASN | 223 | 148.261 | 25.185 | 39.915 | 1.00 | 23.98 |
| 1979 | CG | ASN | 223 | 148.739 | 24.633 | 41.242 | 1.00 | 28.15 |
| 1980 | CD1 | ASN | 223 | 143.586 | 25.271 | 42.281 | 1.00 | 30.20 |
| 1981 | ND2 | ASN | 223 | 149.291 | 23.423 | 41.219 | 1.00 | 25.49 |
| 1982 | H | ASN | 223 | 147.118 | 22.925 | 39.901 | 1.00 | 25.00 |
| 1983 | 1HD2 | ASN | 223 | 149.595 | 23.063 | 42.082 | 1.00 | 25.00 |
| 1984 | 2HD2 | ASN | 223 | 149.377 | 22.938 | 40.382 | 1.00 | 25.00 |
| 1985 | N | VAL | 224 | 146.224 | 25.036 | 37.346 | 1.00 | 24.73 |
| 1986 | CA | VAL | 224 | 145.743 | 25.667 | 36.124 | 1.00 | 27.15 |
| 1987 | C | VAL | 224 | 144.263 | 26.026 | 36.304 | 1.00 | 28.87 |
| 1988 | O | VAL | 224 | 143.852 | 27.150 | 36.019 | 1.00 | 29.97 |
| 1989 | CB | VAL | 224 | 145.914 | 24.742 | 34.900 | 1.00 | 31.17 |
| 1990 | CG1 | VAL | 224 | 145.359 | 25.404 | 33.651 | 1.00 | 30.27 |
| 1991 | CG2 | VAL | 224 | 147.382 | 24.400 | 34.707 | 1.00 | 30.28 |
| 1992 | H | VAL | 224 | 148.488 | 24.096 | 37.329 | 1.00 | 25.00 |
| 1993 | N | LEU | 225 | 143.486 | 25.089 | 36.843 | 1.00 | 25.78 |
| 1994 | CA | LEU | 225 | 142.057 | 25.303 | 37.089 | 1.00 | 25.90 |
| 1995 | C | LEU | 225 | 141.792 | 26.380 | 38.125 | 1.00 | 26.51 |
| 1996 | O | LEU | 225 | 140.900 | 27.214 | 37.956 | 1.00 | 26.55 |
| 1997 | CB | LEU | 225 | 141.386 | 23.991 | 37.483 | 1.00 | 20.07 |
| 1998 | CG | LEU | 225 | 141.398 | 22.848 | 36.441 | 1.00 | 21.81 |
| 1999 | CD1 | LEU | 225 | 140.664 | 21.638 | 36.991 | 1.00 | 10.56 |
| 2000 | CD2 | LEU | 225 | 140.780 | 23.295 | 35.126 | 1.00 | 19.02 |
| 2001 | H | LEU | 225 | 143.883 | 24.229 | 37.092 | 1.00 | 25.00 |
| 2002 | N | LEU | 226 | 142.566 | 26.369 | 39.207 | 1.00 | 22.12 |
| 2003 | CA | LEU | 226 | 142.400 | 27.367 | 40.261 | 1.00 | 27.39 |
| 2004 | C | LEU | 226 | 142.724 | 28.775 | 39.743 | 1.00 | 28.78 |
| 2005 | O | LEU | 226 | 141.967 | 29.720 | 39.969 | 1.00 | 34.36 |
| 2006 | CB | LEU | 226 | 143.282 | 27.033 | 41.468 | 1.00 | 25.60 |
| 2007 | CG | LEU | 226 | 143.170 | 27.984 | 42.6665 | 1.00 | 26.39 |
| 2008 | CD1 | LEU | 226 | 141.731 | 28.037 | 43.183 | 1.00 | 20.17 |
| 2009 | CD2 | LEU | 226 | 144.110 | 27.532 | 43.763 | 1.00 | 26.04 |
| 2010 | H | LEU | 226 | 143.249 | 25.673 | 39.298 | 1.00 | 25.00 |
| 2011 | N | ARG | 227 | 143.842 | 28.904 | 39.036 | 1.00 | 28.64 |
| 2012 | CA | ARG | 227 | 144.270 | 30.183 | 38.473 | 1.00 | 30.51 |
| 2013 | C | ARG | 227 | 143.186 | 30.688 | 37.508 | 1.00 | 29.19 |
| 2014 | O | ARG | 227 | 142.770 | 31.849 | 37.567 | 1.00 | 25.86 |
| 2015 | CB | ARG | 227 | 145.607 | 29.989 | 37.742 | 1.00 | 30.51 |
| 2016 | CG | ARG | 227 | 146.171 | 31.215 | 37.037 | 1.00 | 32.00 |
| 2017 | CD | ARG | 227 | 146.883 | 32.162 | 37.981 | 1.00 | 35.49 |
| 2018 | NE | ARG | 227 | 147.414 | 33.314 | 37.256 | 1.00 | 34.46 |
| 2019 | CZ | ARG | 227 | 147.799 | 34.454 | 37.822 | 1.00 | 32.62 |
| 2020 | NH1 | ARG | 227 | 147.727 | 34.611 | 39.136 | 1.00 | 33.39 |
| 2021 | NH2 | ARG | 227 | 148.214 | 35.460 | 37.066 | 1.00 | 35.87 |
| 2022 | H | ARG | 227 | 144.402 | 28.114 | 38.884 | 1.00 | 25.00 |
| 2023 | HE | ARG | 227 | 147.480 | 33.245 | 36.292 | 1.00 | 25.00 |
| 2024 | 1HH1 | ARG | 227 | 147.381 | 33.871 | 39.712 | 1.00 | 25.00 |
| 2025 | 2HH1 | ARG | 227 | 148.020 | 35.470 | 39.554 | 1.00 | 25.00 |
| 2026 | 1HH2 | ARG | 227 | 148.236 | 35.359 | 36.073 | 1.00 | 25.00 |
| 2027 | 2HH2 | ARG | 227 | 148.505 | 36.315 | 37.491 | 1.00 | 25.00 |
| 2028 | N | PHE | 228 | 142.723 | 29.788 | 36.645 | 1.00 | 28.49 |
| 2029 | CA | PHE | 228 | 141.678 | 30.063 | 35.656 | 1.00 | 30.24 |
| 2030 | C | PHE | 228 | 140.411 | 30.575 | 36.369 | 1.00 | 29.56 |
| 2031 | O | PHE | 228 | 139.909 | 31.662 | 36.068 | 1.00 | 31.17 |
| 2032 | CB | PHE | 228 | 141.394 | 28.752 | 34.892 | 1.00 | 32.31 |
| 2033 | CG | PHE | 228 | 140.441 | 28.879 | 33.721 | 1.00 | 30.15 |
| 2034 | CD1 | PHE | 228 | 139.889 | 30.103 | 33.348 | 1.00 | 29.90 |
| 2035 | CD2 | PHE | 228 | 140.084 | 27.740 | 32.999 | 1.00 | 24.53 |
| 2036 | CE1 | PHE | 228 | 138.994 | 30.186 | 32.277 | 1.00 | 28.21 |
| 2037 | CE2 | PHE | 228 | 139.193 | 27.811 | 31.930 | 1.00 | 23.61 |
| 2038 | CZ | PHE | 228 | 138.646 | 29.036 | 31.568 | 1.00 | 29.31 |
| 2039 | H | PHE | 228 | 143.108 | 28.886 | 36.672 | 1.00 | 25.00 |
| 2040 | N | ALA | 229 | 139.935 | 29.809 | 37.344 | 1.00 | 25.42 |
| 2041 | CA | ALA | 229 | 138.737 | 30.156 | 38.099 | 1.00 | 25.11 |
| 2042 | C | ALA | 229 | 138.808 | 31.533 | 38.764 | 1.00 | 29.20 |
| 2043 | O | ALA | 229 | 137.847 | 32.310 | 38.703 | 1.00 | 26.99 |
| 2044 | CB | ALA | 229 | 138.456 | 29.085 | 39.135 | 1.00 | 20.89 |
| 2045 | H | ALA | 229 | 140.406 | 28..982 | 37.565 | 1.00 | 25.00 |
| 2046 | N | LYS | 230 | 139.944 | 31.838 | 39.389 | 1.00 | 29.21 |
| 2047 | CA | LYS | 230 | 140.127 | 33.121 | 40.068 | 1.00 | 29.75 |
| 2048 | C | LYS | 230 | 140.100 | 34.306 | 39.109 | 1.00 | 30.11 |
| 2049 | O | LYS | 230 | 139.405 | 35.298 | 39.350 | 1.00 | 30.69 |
| 2050 | CB | LYS | 230 | 141.434 | 33.136 | 40.866 | 1.00 | 30.27 |
| 2051 | CG | LYS | 230 | 141.422 | 32.247 | 42.100 | 1.00 | 29.79 |
| 2052 | CD | LYS | 230 | 142.686 | 32.430 | 42.923 | 1.00 | 24.40 |
| 2053 | CE | LYS | 230 | 142.595 | 31.664 | 44.227 | 1.00 | 29.55 |
| 2054 | NZ | LYS | 230 | 143.790 | 31.883 | 45.079 | 1.00 | 36.37 |
| 2055 | H | LYS | 230 | 140.676 | 31.183 | 39.394 | 1.00 | 25.00 |
| 2056 | 1HZ | LYS | 230 | 143.881 | 32.896 | 45.296 | 1.00 | 25.00 |
| 2057 | 2HZ | LYS | 230 | 143.689 | 31.356 | 45.965 | 1.00 | 25.00 |
| 2058 | 33HZ | LYS | 230 | 144.640 | 31.560 | 44.573 | 1.00 | 25.00 |
| 2059 | N | LEU | 231 | 140.852 | 34.201 | 38.016 | 1.00 | 31.56 |
| 2060 | CA | LEU | 231 | 140.911 | 35.275 | 37.032 | 1.00 | 30.17 |
| 2061 | C | LEU | 231 | 139.549 | 35.506 | 36.394 | 1.00 | 30.20 |
| 2062 | O | LEU | 231 | 139.085 | 36.645 | 36.299 | 1.00 | 26.72 |
| 2063 | CB | LEU | 231 | 141.941 | 34.959 | 35.941 | 1.00 | 29.21 |
| 2064 | CG | LEU | 231 | 143.408 | 34.790 | 36.340 | 1.00 | 26.11 |

TABLE 11-continued

Structural Coordinates of Tobacco 5-Epi-Aristolochene Synthase In the Absence of Bound Substrate

| Atom | Atom | Resi- | Resi- | X | Y | Z | OCC | B-factor |
|---|---|---|---|---|---|---|---|---|
| Type | | due | due # | | | | | |
| 2065 | CD1 | LEU | 231 | 144.232 | 34.631 | 35.077 | 1.00 | 22.49 |
| 2066 | CD2 | LEU | 231 | 143.890 | 35.990 | 37.139 | 1.00 | 22.48 |
| 2067 | H | LEU | 231 | 141.374 | 33.380 | 37.869 | 1.00 | 25.00 |
| 2068 | N | ASP | 232 | 138.898 | 34.417 | 35.995 | 1.00 | 29.28 |
| 2069 | CA | ASP | 232 | 137.593 | 34.490 | 35.351 | 1.00 | 28.41 |
| 2070 | C | ASP | 232 | 136.549 | 35.149 | 36.247 | 1.00 | 25..56 |
| 2071 | O | ASP | 232 | 135.820 | 36.044 | 35.813 | 1.00 | 25.21 |
| 2072 | CB | ASP | 232 | 137.131 | 33.097 | 34.932 | 1.00 | 26.05 |
| 2073 | CG | ASP | 232 | 136.143 | 33.143 | 33.793 | 1.00 | 33.93 |
| 2074 | OD1 | ASP | 232 | 136.587 | 33.188 | 32.627 | 1.00 | 32.45 |
| 2075 | OD2 | ASP | 232 | 134.927 | 33.157 | 34.060 | 1.00 | 29.97 |
| 2076 | H | ASP | 232 | 139.310 | 33.539 | 36.141 | 1.00 | 25.00 |
| 2077 | N | PHE | 233 | 136.510 | 34.730 | 37.507 | 1.00 | 24.45 |
| 2078 | CA | PHE | 233 | 135.569 | 35.286 | 38.466 | 1.00 | 22.77 |
| 2079 | C | PHE | 233 | 135.788 | 36.788 | 38.603 | 1.00 | 28.10 |
| 2080 | O | PHE | 233 | 134.835 | 37.568 | 38.516 | 1.00 | 31.99 |
| 2081 | CB | PHE | 233 | 135.732 | 34.605 | 39.831 | 1.00 | 19.36 |
| 2082 | CG | PHE | 233 | 134.714 | 35.035 | 40.854 | 1.00 | 22.51 |
| 2083 | CD1 | PHE | 233 | 1344.857 | 36.241 | 41.540 | 1.00 | 22.18 |
| 2084 | CD2 | PHE | 233 | 133.604 | 34.237 | 41.127 | 1.00 | 23.90 |
| 2085 | CE1 | PHE | 233 | 133.906 | 36.646 | 42.481 | 1.00 | 26.05 |
| 2086 | CE2 | PHE | 233 | 132.650 | 34.631 | 42.065 | 1.00 | 23.08 |
| 2087 | CZ | PHE | 233 | 132.801 | 35.839 | 42.743 | 1.00 | 24.51 |
| 2088 | H | PHE | 233 | 137.126 | 34.022 | 37.802 | 1.00 | 25.00 |
| 2089 | N | ASN | 234 | 137.044 | 37.189 | 38.801 | 1.00 | 28.39 |
| 2090 | CA | ASN | 234 | 137.393 | 38.602 | 38.965 | 1.00 | 28.37 |
| 2091 | C | ASN | 234 | 137.079 | 39.446 | 37.743 | 1.00 | 27.25 |
| 2092 | O | ASN | 234 | 136.606 | 40.575 | 37.868 | 1.00 | 32.70 |
| 2093 | CB | ASN | 234 | 138.867 | 38.762 | 39.342 | 1.00 | 27.32 |
| 2094 | CG | ASN | 234 | 139.152 | 38.353 | 40.776 | 1.00 | 30.63 |
| 2095 | OD1 | ASN | 234 | 138.242 | 38.219 | 41.595 | 1.00 | 29.34 |
| 2096 | ND2 | ASN | 234 | 140.426 | 38.166 | 41.092 | 1.00 | 37.28 |
| 2097 | H | ASN | 234 | 137.753 | 36.513 | 38.851 | 1.00 | 25.00 |
| 2098 | 1HD2 | ASN | 234 | 140.628 | 37.901 | 42.015 | 1.00 | 25.00 |
| 2099 | 2HD2 | ASN | 234 | 141.114 | 38.292 | 40.408 | 1.00 | 25.00 |
| 2100 | N | LEU | 235 | 137.339 | 38.902 | 36.561 | 1.00 | 28.66 |
| 2101 | CA | LEU | 235 | 137.059 | 39.616 | 35.321 | 1.00 | 29.93 |
| 2102 | C | LEU | 235 | 135.551 | 39.830 | 35.167 | 1.00 | 30.84 |
| 2103 | O | LEU | 235 | 135.106 | 40.949 | 34.908 | 1.00 | 31.89 |
| 2104 | CB | LEU | 235 | 137.625 | 38.852 | 34.119 | 1.00 | 29.05 |
| 2105 | CG | LEU | 235 | 137.476 | 39.509 | 32.742 | 1.00 | 30.21 |
| 2106 | CD1 | LEU | 235 | 138.045 | 40.922 | 32.769 | 1.00 | 29.02 |
| 2107 | CD2 | LEU | 235 | 138.173 | 38.667 | 31.684 | 1.00 | 31.45 |
| 2108 | H | LEU | 235 | 137.721 | 38.001 | 36.525 | 1.00 | 25.00 |
| 2109 | N | LEU | 236 | 134.766 | 38.769 | 35.352 | 1.00 | 29.90 |
| 2110 | CA | LEU | 236 | 133.311 | 38.875 | 35.245 | 1.00 | 28.94 |
| 2111 | C | LEU | 236 | 132.774 | 39.874 | 36.263 | 1.00 | 28.31 |
| 2112 | O | LEU | 236 | 131.833 | 40.623 | 35.979 | 1.00 | 29.04 |
| 2113 | CB | LEU | 236 | 132.632 | 37.518 | 35.463 | 1.00 | 26.96 |
| 2114 | CG | LEU | 236 | 132.722 | 36.463 | 34.359 | 1.00 | 32.49 |
| 2115 | CD1 | LEU | 236 | 131.797 | 35.299 | 34.694 | 1.00 | 28.63 |
| 2116 | CD2 | LEU | 236 | 132.326 | 37.068 | 33.026 | 1.00 | 30.07 |
| 2117 | H | LEU | 236 | 135.173 | 37.900 | 35.561 | 1.00 | 25.00 |
| 2118 | N | GLN | 237 | 133.362 | 39.870 | 37.454 | 1.00 | 25.46 |
| 2119 | CA | GLN | 237 | 132.953 | 40.777 | 38.521 | 1.00 | 25.58 |
| 2120 | C | GLN | 237 | 133.059 | 42.231 | 38.062 | 1.00 | 27.92 |
| 2121 | O | GLN | 2337 | 132.201 | 43.054 | 38.387 | 1.00 | 29.65 |
| 2122 | CB | GLN | 237 | 133.807 | 40.549 | 39.769 | 1.00 | 20.55 |
| 2123 | CG | GLN | 237 | 133.342 | 41.314 | 40.993 | 1.00 | 23.60 |
| 2124 | CD | GLN | 237 | 134.216 | 41.046 | 42.197 | 1.00 | 31.25 |
| 2125 | OE1 | GLN | 237 | 135.435 | 41.196 | 42.134 | 1.00 | 31.93 |
| 2126 | NE2 | GLN | 237 | 133.602 | 40.634 | 43.298 | 1.00 | 28.03 |
| 2127 | H | GLN | 237 | 134.094 | 39.237 | 37.625 | 1.00 | 25.00 |
| 2128 | 1HE2 | GLN | 237 | 134.156 | 40.446 | 44.081 | 1.00 | 25.00 |
| 2129 | 2HE2 | GLN | 237 | 132.635 | 40.519 | 43.287 | 1.00 | 25.00 |
| 2130 | N | MET | 238 | 134.096 | 42.537 | 37.286 | 1.00 | 28.91 |
| 2131 | CA | MET | 238 | 134.288 | 43.888 | 36.776 | 1.00 | 33.08 |
| 2132 | C | MET | 238 | 133.084 | 44.282 | 35.924 | 1.00 | 33.53 |
| 2133 | O | MET | 238 | 132.562 | 45.391 | 36.049 | 1.00 | 37.31 |
| 2134 | CB | MET | 238 | 135.573 | 43.976 | 35.954 | 1.00 | 32.86 |
| 2135 | CG | MET | 238 | 136.836 | 43.837 | 36.782 | 1.00 | 39.06 |
| 2136 | SD | MET | 238 | 138.318 | 43.815 | 35.763 | 1.00 | 43.74 |
| 2137 | CE | MET | 238 | 139.508 | 43.186 | 36.929 | 1.00 | 46.28 |
| 2138 | H | MET | 238 | 134.751 | 41.842 | 37.055 | 1.00 | 25.00 |
| 2139 | N | LEU | 239 | 132.624 | 43.356 | 35.087 | 1.00 | 31.84 |
| 2140 | CA | LEU | 239 | 131.465 | 43.599 | 34.233 | 1.00 | 30.89 |
| 2141 | C | LEU | 239 | 130.219 | 43.801 | 35.097 | 1.00 | 28.36 |
| 2142 | O | LEU | 239 | 129.450 | 44.742 | 34.885 | 1.00 | 32.90 |
| 2143 | CB | LEU | 239 | 131.255 | 42.427 | 33.271 | 1.00 | 29.61 |
| 2144 | CG | LEU | 239 | 129.969 | 42.432 | 32.436 | 1.00 | 29.85 |
| 2145 | CD1 | LEU | 239 | 129.929 | 43.636 | 31.499 | 1.00 | 25.22 |
| 2146 | CD2 | LEU | 239 | 129.870 | 41.138 | 31.649 | 1.00 | 26.65 |
| 2147 | H | LEU | 239 | 133.084 | 42.491 | 35.043 | 1.00 | 25.00 |
| 2148 | N | HIS | 240 | 130.042 | 42.942 | 36.095 | 1.00 | 25.85 |
| 2149 | CA | HIS | 240 | 128.891 | 43.042 | 36.990 | 1.00 | 28.32 |
| 2150 | C | HIS | 240 | 128.885 | 44.406 | 37.671 | 1.00 | 30.20 |
| 2151 | O | HIS | 240 | 127.824 | 44.974 | 37.940 | 1.00 | 30.10 |
| 2152 | CB | HIS | 240 | 128.925 | 41.926 | 38.036 | 1.00 | 25.55 |
| 2153 | CG | HIS | 240 | 128.881 | 40.545 | 37.448 | 1.00 | 24.20 |
| 2154 | ND1 | HIS | 240 | 129.449 | 39.455 | 38.058 | 1.00 | 25.29 |
| 2155 | CD2 | HIS | 240 | 128.358 | 40.103 | 36.283 | 1.00 | 21.44 |
| 2156 | CE1 | HIS | 240 | 129.289 | 38.394 | 37.302 | 1.00 | 27.58 |
| 2157 | NE2 | HIS | 240 | 128.627 | 38.750 | 36.209 | 1.00 | 21.74 |
| 2158 | H | HIS | 240 | 130.713 | 42.244 | 36.233 | 1.00 | 25.00 |
| 2159 | HD11 | HIS | 240 | 129.918 | 39.455 | 38.924 | 1.00 | 25.00 |
| 2160 | HE2 | HIS | 240 | 128.362 | 38.151 | 35.470 | 1.00 | 25.00 |
| 2161 | N | LYS | 241 | 130.079 | 44.926 | 37.935 | 1.00 | 34.60 |
| 2162 | CA | LYS | 241 | 130.239 | 46.230 | 38.563 | 1.00 | 32.03 |
| 2163 | C | LYS | 241 | 129.855 | 47.374 | 37.613 | 1.00 | 31.99 |
| 2164 | O | LYS | 241 | 129.280 | 48.374 | 38.045 | 1.00 | 29.66 |
| 2165 | CB | LYS | 241 | 131.675 | 46.391 | 39.072 | 1.00 | 32.10 |
| 2166 | CG | LYS | 241 | 131.984 | 45.614 | 40.356 | 1.00 | 34.40 |
| 2167 | CD | LYS | 241 | 133.447 | 45.807 | 40.758 | 1.00 | 41.19 |
| 2168 | CE | LYS | 241 | 133.701 | 45.417 | 42.208 | 1.00 | 49.51 |
| 2169 | NZ | LYS | 241 | 135.044 | 45.881 | 42.698 | 1.00 | 56.06 |
| 2170 | H | LYS | 241 | 130.875 | 44.403 | 37.703 | 1.00 | 25.00 |
| 2171 | 1HZ | LYS | 241 | 135.111 | 46.916 | 42.625 | 1.00 | 25.00 |
| 2172 | 2HZ | LYS | 241 | 135.179 | 45.610 | 43.698 | 1.00 | 25.00 |
| 2173 | 3HZ | LYS | 241 | 135.803 | 45.446 | 42.135 | 1.00 | 25.00 |
| 2174 | N | GLN | 242 | 130.121 | 47.201 | 36.316 | 1.00 | 34.13 |
| 2175 | CA | GLN | 242 | 129.799 | 48.211 | 35.303 | 1.00 | 38.39 |
| 2176 | C | GLN | 242 | 128.288 | 48.278 | 35.161 | 1.00 | 39.98 |
| 2177 | O | GLN | 242 | 127.702 | 49.353 | 34.990 | 1.00 | 45.19 |
| 2178 | CB | GLN | 242 | 130.376 | 47.827 | 33.942 | 1.00 | 42.52 |
| 2179 | CG | GLN | 242 | 131.883 | 47.683 | 33.920 | 1.00 | 60.88 |
| 2180 | CD | GLN | 242 | 132.417 | 47.252 | 32.574 | 1.00 | 69.61 |
| 2181 | OE1 | GLN | 242 | 131.663 | 47.052 | 31.620 | 1.00 | 75.13 |
| 2182 | NE2 | GLN | 242 | 133.730 | 47.102 | 32.488 | 1.00 | 78.40 |
| 2183 | H | GLN | 242 | 130.490 | 46.358 | 35.996 | 1.00 | 25.00 |
| 2184 | 1HE2 | GLN | 242 | 134.0772 | 46.820 | 31.621 | 1.00 | 25.00 |
| 2185 | 2HE2 | GLN | 242 | 134.282 | 47.272 | 33.272 | 1.00 | 25.00 |
| 2186 | N | GLU | 243 | 127.674 | 47.105 | 35.219 | 1.00 | 33.89 |
| 2187 | CA | GLU | 243 | 126.233 | 46.975 | 35.107 | 1.00 | 28.66 |
| 2188 | C | GLU | 243 | 125.568 | 47.591 | 36.325 | 1.00 | 28.27 |
| 2189 | O | GLU | 243 | 124.635 | 48.381 | 36.193 | 1.00 | 32.26 |
| 2190 | CB | GLU | 243 | 125.857 | 45.505 | 34.982 | 1.00 | 25.09 |
| 2191 | CG | GLU | 243 | 126.416 | 44.820 | 33.741 | 1.00 | 24.03 |
| 2192 | CD | GLU | 243 | 126.182 | 43.329 | 33.738 | 1.00 | 26.58 |
| 2193 | OE1 | GLU | 243 | 125.633 | 42.810 | 34.726 | 1.00 | 24.63 |
| 2194 | OE2 | GLU | 243 | 126.556 | 42.665 | 32.750 | 1.00 | 29.69 |
| 2195 | H | GLU | 243 | 128.248 | 46.333 | 35.341 | 1.00 | 25.00 |
| 2196 | N | LEU | 244 | 126.078 | 47.267 | 37.508 | 1.00 | 24.94 |
| 2197 | CA | LEU | 244 | 125.522 | 47.798 | 38.745 | 1.00 | 30.48 |
| 2198 | C | LEU | 244 | 125.635 | 49.324 | 38.766 | 1.00 | 36.45 |
| 2199 | O | LEU | 244 | 124.700 | 50.021 | 39.163 | 1.00 | 35.07 |
| 2200 | CB | LEU | 244 | 126.233 | 47.185 | 39.957 | 1.00 | 28.96 |
| 2201 | CG | LEU | 244 | 125.765 | 47.658 | 41.339 | 1.00 | 29.10 |
| 2202 | CD1 | LEU | 244 | 124.249 | 47.527 | 41.484 | 1.00 | 25.23 |
| 2203 | CD2 | LEU | 244 | 126.484 | 46.859 | 42.423 | 1.00 | 27.57 |
| 2204 | H | LEU | 244 | 126.855 | 48.662 | 37.535 | 1.00 | 25.00 |
| 2205 | N | ALA | 245 | 126.778 | 49.832 | 38.318 | 1.00 | 37.15 |
| 2206 | CA | ALA | 245 | 127.023 | 51.268 | 38.270 | 1.00 | 38.62 |
| 2207 | C | ALA | 245 | 126.030 | 51.937 | 37.325 | 1.00 | 39.57 |
| 2208 | O | ALA | 245 | 125.352 | 52.902 | 37.692 | 1.00 | 43.21 |
| 2209 | CB | ALA | 245 | 128.452 | 51.539 | 37.802 | 1.00 | 35.23 |
| 2210 | H | ALA | 245 | 127.477 | 49.215 | 38.032 | 1.00 | 25.00 |

TABLE 11-continued

Structural Coordinates of Tobacco 5-Epi-Aristolochene Synthase
In the Absence of Bound Substrate

| Atom Type | Atom | Resi-due | Resi-due # | X | Y | Z | OCC | B-factor |
|---|---|---|---|---|---|---|---|---|
| 2211 | N | GLN | 240 | 125.920 | 51.380 | 36.123 | 1.00 | 35.82 |
| 2212 | CA | GLN | 246 | 125.025 | 51.888 | 35.086 | 1.00 | 40.78 |
| 2213 | C | GLN | 248 | 123.577 | 51.989 | 35.566 | 1.00 | 43.61 |
| 2214 | O | GLN | 248 | 122.907 | 53.016 | 35.404 | 1.00 | 43.37 |
| 2215 | CB | GLN | 246 | 125.088 | 50.963 | 33.872 | 1.00 | 42.45 |
| 2216 | CG | GLN | 246 | 124.151 | 51.350 | 32.733 | 1.00 | 59.73 |
| 2217 | CD | GLN | 246 | 124.146 | 50.338 | 31.610 | 1.00 | 65.77 |
| 2218 | OE1 | GLN | 246 | 125.149 | 49.663 | 31.357 | 1.00 | 67.95 |
| 2219 | NE2 | GLN | 246 | 123.009 | 50.223 | 30.920 | 1.00 | 66.48 |
| 2220 | H | GLN | 246 | 126.450 | 50.576 | 35.964 | 1.00 | 25.00 |
| 2221 | 1HE2 | GLN | 246 | 123.038 | 49.559 | 30.198 | 1.00 | 25.00 |
| 2222 | 2HE2 | GLN | 246 | 122.232 | 50.763 | 31.132 | 1.00 | 25.00 |
| 2223 | N | VAL | 247 | 123.115 | 50.916 | 36.185 | 1.00 | 39.07 |
| 2224 | CA | VAL | 247 | 121.762 | 50.830 | 36.692 | 1.00 | 37.02 |
| 2225 | C | VAL | 247 | 121.538 | 51.732 | 37.908 | 1.00 | 40.33 |
| 2226 | O | VAL | 247 | 120.435 | 52.240 | 38.106 | 1.00 | 39.92 |
| 2227 | CB | VAL | 247 | 121.387 | 49.341 | 36.946 | 1.00 | 35.95 |
| 2228 | CG1 | VAL | 247 | 120.417 | 49.201 | 38.091 | 1.00 | 37.82 |
| 2229 | CG2 | VAL | 247 | 120.794 | 48.754 | 35.686 | 1.00 | 32.90 |
| 2230 | H | VAL | 247 | 123.730 | 50.170 | 36.340 | 1.00 | 25.00 |
| 2231 | N | SER | 248 | 122.579 | 51.926 | 38.715 | 1.00 | 44.51 |
| 2232 | CA | SER | 248 | 122.483 | 52.798 | 39.887 | 1.00 | 46.80 |
| 2233 | C | SER | 248 | 122.250 | 54.234 | 39.410 | 1.00 | 47.29 |
| 2234 | O | SER | 248 | 121.454 | 54.976 | 39.997 | 1.00 | 46.67 |
| 2235 | CB | SER | 248 | 123.759 | 52.727 | 40.726 | 1.00 | 44.77 |
| 2236 | OG | SER | 248 | 123.859 | 51.479 | 41.381 | 1.00 | 45.74 |
| 2237 | H | SER | 248 | 123.423 | 51.465 | 38.531 | 1.00 | 25.00 |
| 2238 | HG | SER | 248 | 123.876 | 50.777 | 40.722 | 1.00 | 25.00 |
| 2239 | N | ARG | 249 | 122.938 | 54.615 | 38.334 | 1.00 | 44.35 |
| 2240 | CA | ARG | 249 | 122.789 | 55.943 | 37.750 | 1.00 | 48.22 |
| 2241 | C | ARG | 249 | 121.354 | 56.097 | 37.256 | 1.00 | 47.00 |
| 2242 | O | ARG | 249 | 120.710 | 57.119 | 37.504 | 1.00 | 47.12 |
| 2243 | CB | ARG | 249 | 123.785 | 56.147 | 36.604 | 1.00 | 52.69 |
| 2244 | CG | ARG | 249 | 125.165 | 56.590 | 37.075 | 1.00 | 66.38 |
| 2245 | CD | ARG | 249 | 126.154 | 56.712 | 35.924 | 1.00 | 73.20 |
| 2246 | NE | ARG | 249 | 126.919 | 55.484 | 35.712 | 1.00 | 75.40 |
| 2247 | CZ | ARG | 249 | 126.922 | 54.778 | 334.584 | 1.00 | 77.33 |
| 2248 | NH1 | ARG | 249 | 126.194 | 55.165 | 33.542 | 1.00 | 74.66 |
| 2249 | NH2 | ARG | 249 | 127.669 | 53.686 | 34.493 | 1.00 | 83.65 |
| 2250 | H | ARG | 249 | 123.579 | 53.986 | 37.936 | 1.00 | 25.00 |
| 2251 | HE | ARG | 249 | 127.471 | 55.153 | 36.453 | 1.00 | 25.00 |
| 2252 | 1HH1 | ARG | 249 | 125.633 | 55.990 | 33.598 | 1.00 | 25.00 |
| 2253 | 2HH1 | ARG | 249 | 126.203 | 54.625 | 32.700 | 1.00 | 25.00 |
| 2254 | 1HH2 | ARG | 249 | 128.229 | 53.396 | 35.269 | 1.00 | 25.00 |
| 2255 | 2HH2 | ARG | 249 | 127.675 | 53.153 | 33.646 | 1.00 | 25.00 |
| 2256 | N | TRP | 250 | 120.848 | 55.053 | 36.603 | 1.00 | 46.33 |
| 2257 | CA | TRP | 250 | 119.480 | 55.024 | 36.092 | 1.00 | 43.84 |
| 2258 | C | TRP | 250 | 118.488 | 55.311 | 37.230 | 1.00 | 46.38 |
| 2259 | O | TRP | 250 | 117.566 | 56.118 | 37.075 | 1.00 | 44.72 |
| 2260 | CB | TRRP | 250 | 119.201 | 53.652 | 35.456 | 1.00 | 38.48 |
| 2261 | CG | TRP | 250 | 117.747 | 53.324 | 35.232 | 1.00 | 37.37 |
| 2262 | CD1 | TRP | 250 | 116.986 | 53.661 | 34.150 | 1.00 | 33.31 |
| 2263 | CD2 | TRP | 250 | 116.891 | 52.569 | 36.105 | 1.00 | 36.85 |
| 2264 | NE1 | TRP | 250 | 115.713 | 53.164 | 34.293 | 1.00 | 34.01 |
| 2265 | CE2 | TRP | 250 | 115.626 | 52.490 | 35.483 | 1.00 | 36.82 |
| 2266 | CE3 | TRP | 250 | 117.070 | 51.952 | 37.352 | 1.00 | 34.91 |
| 2267 | CZ2 | TRP | 250 | 114.543 | 51.816 | 36.065 | 1.00 | 39.04 |
| 2268 | CZ3 | TRP | 250 | 115.992 | 51.281 | 37.932 | 1.00 | 39.64 |
| 2269 | CH2 | TRP | 250 | 114.746 | 51.220 | 37.286 | 1.00 | 39.49 |
| 2270 | H | TRP | 250 | 121.423 | 54.272 | 36.448 | 1.00 | 25.00 |
| 2271 | HE1 | TRP | 250 | 114.984 | 53.281 | 33.650 | 1.00 | 25.00 |
| 2272 | N | TRP | 251 | 118.718 | 54.683 | 38.382 | 1.00 | 46.65 |
| 2273 | CA | TRP | 251 | 117.859 | 54.851 | 39.551 | 1.00 | 54.20 |
| 2274 | C | TRP | 251 | 117.864 | 56.279 | 40.089 | 1.00 | 59.43 |
| 2275 | O | TRP | 251 | 116.814 | 56.823 | 40.445 | 1.00 | 62.13 |
| 2276 | CB | TRP | 251 | 118.284 | 53.889 | 40.657 | 1.00 | 51.89 |
| 2277 | CG | TRP | 251 | 117.358 | 53.872 | 41.836 | 1.00 | 58.17 |
| 2278 | CD1 | TRP | 251 | 117.596 | 54.402 | 43.071 | 1.00 | 60.91 |
| 2279 | CD2 | TRP | 251 | 116.069 | 53.246 | 41.908 | 1.00 | 60.72 |
| 2280 | NE1 | TRP | 251 | 116.541 | 54.136 | 43.912 | 1.00 | 64.22 |
| 2281 | CE2 | TRP | 251 | 115.589 | 53.429 | 43.225 | 1.00 | 60.87 |
| 2282 | CE3 | TRP | 251 | 115.274 | 52.546 | 40.989 | 1.00 | 56.90 |
| 2283 | CZ2 | TRP | 251 | 114.351 | 52.934 | 43.648 | 1.00 | 58.08 |
| 2284 | CZ3 | TRP | 251 | 114.042 | 52.054 | 41.410 | 1.00 | 53.15 |
| 2285 | CH2 | TRP | 251 | 113.594 | 52.252 | 42.729 | 1.00 | 53.35 |
| 2286 | H | TRP | 251 | 119.485 | 54.076 | 38.442 | 1.00 | 25.00 |
| 2287 | HE1 | TRP | 251 | 116.481 | 54.409 | 44.851 | 1.00 | 25.00 |
| 2288 | N | LYS | 252 | 119.049 | 56.875 | 40.167 | 1.00 | 64.71 |
| 2289 | CA | LYS | 252 | 119.191 | 58.241 | 40.661 | 1.00 | 68.07 |
| 2290 | C | LYS | 252 | 118.440 | 59.227 | 39.779 | 1.00 | 65.20 |
| 2291 | O | LYS | 252 | 117.831 | 60.169 | 40.283 | 1.00 | 65.28 |
| 2292 | CB | LYS | 252 | 120.668 | 58.621 | 40.755 | 1.00 | 75.64 |
| 2293 | CG | LYS | 252 | 121.400 | 57.815 | 41.803 | 1.00 | 85.57 |
| 2294 | CD | LYS | 252 | 122.890 | 57.818 | 41.588 | 1.00 | 92.92 |
| 2295 | CE | LYS | 252 | 123.526 | 56.776 | 42.486 | 1.00 | 95.43 |
| 2296 | NZ | LYS | 252 | 124.902 | 56.526 | 42.101 | 1.00 | 94.64 |
| 2297 | H | LYS | 252 | 119.849 | 56.379 | 39.887 | 1.00 | 25.00 |
| 22998 | 1HZ | LYS | 252 | 125.056 | 56.256 | 41.101 | 1.00 | 25.00 |
| 2299 | 2HZ | LYS | 252 | 125.376 | 57.437 | 42.219 | 1.00 | 25.00 |
| 2300 | 3HZ | LYS | 252 | 125.417 | 55.867 | 42.716 | 1.00 | 25.00 |
| 2301 | N | ASP | 253 | 118.453 | 58.983 | 38.469 | 1.00 | 63.40 |
| 2302 | CA | ASP | 253 | 117.762 | 59.846 | 37.515 | 1.00 | 63.30 |
| 2303 | C | ASP | 253 | 116.265 | 59.872 | 37.796 | 1.00 | 63.95 |
| 2304 | O | ASP | 253 | 115.635 | 60.925 | 37.729 | 1.00 | 68.15 |
| 2305 | CB | ASP | 253 | 118.003 | 59.376 | 36.077 | 1.00 | 68.18 |
| 2306 | CG | ASP | 253 | 119.467 | 59.453 | 35.664 | 1.00 | 76.46 |
| 2307 | OD1 | ASP | 253 | 120.293 | 60.015 | 36.419 | 1.00 | 78.84 |
| 2308 | OD2 | ASP | 253 | 119.793 | 58.943 | 34.570 | 1.00 | 79.35 |
| 2309 | H | ASP | 253 | 118.948 | 58.203 | 38.137 | 1.00 | 25.00 |
| 2310 | N | LEU | 254 | 115.697 | 58.710 | 38.105 | 1.00 | 66.44 |
| 2311 | CA | LEU | 254 | 114.271 | 58.611 | 38.409 | 1.00 | 65.57 |
| 2312 | C | LEU | 254 | 113.947 | 59.482 | 39.618 | 1.00 | 67.65 |
| 2313 | O | LEU | 254 | 112.815 | 59.931 | 39.784 | 1.00 | 68.72 |
| 2314 | CB | LEU | 254 | 113.885 | 57.162 | 38.698 | 1.00 | 61.14 |
| 2315 | CG | LEU | 254 | 114.124 | 56.166 | 37.564 | 1.00 | 57.75 |
| 2316 | CD1 | LEU | 254 | 113.718 | 54.785 | 38.021 | 1.00 | 58.43 |
| 2317 | CD2 | LEU | 254 | 113.343 | 56.571 | 36.328 | 1.00 | 55.32 |
| 2318 | H | LEU | 254 | 116.252 | 57.902 | 38.125 | 1.00 | 25.00 |
| 2319 | N | ASP | 255 | 114.947 | 59.661 | 40.475 | 1.00 | 73.64 |
| 2320 | CA | ASP | 255 | 114.842 | 60.490 | 41.670 | 1.00 | 78.31 |
| 2321 | C | ASP | 255 | 113.664 | 60.123 | 42.574 | 1.00 | 79.28 |
| 2322 | O | ASP | 255 | 113.079 | 60.985 | 43.230 | 1.00 | 81.76 |
| 2323 | CB | ASP | 255 | 114.777 | 61.971 | 41.261 | 1.00 | 83.27 |
| 2324 | CG | ASP | 255 | 115.238 | 62.915 | 42.364 | 1.00 | 87.17 |
| 2325 | OD1 | ASP | 255 | 115.719 | 62.443 | 43.420 | 1.00 | 86.98 |
| 2326 | OD2 | ASP | 255 | 115.121 | 64.144 | 42.165 | 1.00 | 87.49 |
| 2327 | H | ASP | 255 | 115.805 | 59.226 | 40.294 | 1.00 | 25.00 |
| 2328 | N | PHE | 256 | 113.357 | 58.834 | 42.659 | 1.00 | 80.00 |
| 2329 | CA | PHE | 256 | 112.254 | 58.378 | 43.500 | 1.00 | 84.32 |
| 2330 | C | PHE | 256 | 112.504 | 58.649 | 44.976 | 1.00 | 89.15 |
| 2331 | O | PHE | 256 | 111.562 | 58.742 | 45.759 | 1.00 | 87.59 |
| 2332 | CB | PHE | 256 | 111.987 | 56.887 | 43.290 | 1.00 | 81.00 |
| 2333 | CG | PHE | 256 | 111.352 | 56.566 | 41.972 | 1.00 | 76.86 |
| 2334 | CD1 | PHE | 256 | 110.671 | 57.544 | 41.251 | 1.00 | 76.59 |
| 2335 | CD2 | PHE | 256 | 111.431 | 55.283 | 41.449 | 1.00 | 73.54 |
| 2336 | CE1 | PHE | 256 | 110.080 | 57.247 | 40.030 | 1.00 | 76.03 |
| 2337 | CE2 | PHE | 256 | 110.844 | 54.976 | 40.229 | 1.00 | 71.61 |
| 2338 | CZ | PHE | 256 | 110.167 | 55.958 | 39.518 | 1.00 | 74.95 |
| 2339 | H | PHE | 256 | 113.874 | 58.189 | 42.139 | 1.00 | 25.00 |
| 2340 | N | VAL | 257 | 113.774 | 53.796 | 45.344 | 1.00 | 97.79 |
| 2341 | CA | VAL | 257 | 114.160 | 59.053 | 46.730 | 1.00 | 104.36 |
| 2342 | C | VAL | 257 | 113.428 | 60.269 | 47.303 | 1.00 | 105.53 |
| 2343 | O | VAL | 257 | 112.952 | 60.239 | 48.439 | 1.00 | 106.91 |
| 2344 | CB | VAL | 257 | 115.692 | 59.270 | 46.854 | 1.00 | 107.20 |
| 2345 | CG1 | VAL | 257 | 116.092 | 59.432 | 48.310 | 1.00 | 107.16 |
| 2346 | CG2 | VAL | 257 | 116.445 | 58.101 | 46.220 | 1.00 | 106.33 |
| 2347 | H | VAL | 257 | 114.464 | 58.732 | 44.658 | 1.00 | 25.00 |
| 2348 | N | THR | 258 | 113.332 | 61.329 | 46.5506 | 1.00 | 105.84 |
| 2349 | CA | THR | 258 | 112.660 | 62.550 | 46.935 | 1.00 | 104.41 |
| 2350 | C | THR | 258 | 111.183 | 62.608 | 46.531 | 1.00 | 104.31 |
| 2351 | O | THR | 258 | 110.339 | 63.047 | 47.314 | 1.00 | 104.07 |
| 2352 | CB | THR | 258 | 113.392 | 63.805 | 46.408 | 1.00 | 104.30 |
| 2353 | CG1 | THR | 258 | 113.620 | 63.674 | 45.000 | 1.00 | 104.41 |
| 2354 | CG2 | THR | 258 | 114.729 | 63.982 | 47.117 | 1.00 | 105.42 |
| 2355 | H | THR | 258 | 113.711 | 61.308 | 45.603 | 1.00 | 25.00 |
| 2356 | HG1 | THR | 258 | 114.068 | 64.458 | 44.669 | 1.00 | 25.00 |

TABLE 11-continued

Structural Coordinates of Tobacco 5-Epi-Aristolochene Synthase
In the Absence of Bound Substrate

| Atom Type | Atom | Residue | Residue # | X | Y | Z | OCC | B-factor |
|---|---|---|---|---|---|---|---|---|
| 2357 | N | THR | 259 | 110.872 | 62.161 | 45.317 | 1.00 | 103.41 |
| 2358 | CA | THR | 259 | 109.497 | 62.182 | 44.825 | 1.00 | 100.89 |
| 2359 | C | THR | 259 | 108.599 | 61.133 | 45.482 | 1.00 | 101.97 |
| 2360 | O | THR | 259 | 107.414 | 61.375 | 45.707 | 1.00 | 103.53 |
| 2361 | CB | THR | 259 | 109.445 | 62.022 | 43.289 | 1.00 | 97.37 |
| 2362 | CG1 | THR | 259 | 110.219 | 60.883 | 42.894 | 1.00 | 95.69 |
| 2363 | CG2 | THR | 259 | 109.988 | 63.267 | 42.602 | 1.00 | 95.50 |
| 2364 | H | THR | 259 | 111.579 | 61.811 | 44.728 | 1.00 | 25.00 |
| 2365 | HG1 | THR | 259 | 109.870 | 60.086 | 43.290 | 1.00 | 25.00 |
| 2366 | N | LEU | 260 | 109.164 | 59.969 | 45.783 | 1.00 | 102.18 |
| 2367 | CA | LEU | 260 | 108.415 | 58.884 | 46.412 | 1.00 | 103.22 |
| 2368 | C | LEU | 260 | 109.112 | 58.431 | 47.696 | 1.00 | 106.86 |
| 2369 | O | LEU | 260 | 109.742 | 57.372 | 47.732 | 1.00 | 107.73 |
| 2370 | CB | LEU | 260 | 108.282 | 57.700 | 45.445 | 1.00 | 98.81 |
| 2371 | CG | LEU | 260 | 107.552 | 57.928 | 44.119 | 1.00 | 94.81 |
| 2372 | CD1 | LEU | 260 | 107.620 | 56.670 | 43.269 | 1.00 | 89.99 |
| 2373 | CD2 | LEU | 260 | 106.108 | 58.320 | 44.380 | 1.00 | 92.83 |
| 2374 | H | LEU | 260 | 110.112 | 59.844 | 45.595 | 1.00 | 25.00 |
| 2375 | N | PRO | 261 | 108.963 | 59.204 | 48.784 | 1.00 | 110.17 |
| 2376 | CA | PRO | 261 | 109.580 | 58.889 | 50.077 | 1.00 | 112.52 |
| 2377 | C | PRO | 261 | 108.951 | 57.726 | 50.855 | 1.00 | 114.04 |
| 2378 | O | PRO | 261 | 108.783 | 57.813 | 52.073 | 1.00 | 117.31 |
| 2379 | CB | PRO | 261 | 109.441 | 60.207 | 50.836 | 1.00 | 113.40 |
| 2380 | CG | PRO | 261 | 108.124 | 60.715 | 50.347 | 1.00 | 112.70 |
| 2381 | CD | PRO | 261 | 108.223 | 60.477 | 48.856 | 1.00 | 111.17 |
| 2382 | N | TYR | 262 | 108.599 | 56.646 | 50.163 | 1.00 | 113.40 |
| 2383 | CA | TYR | 262 | 108.012 | 55.479 | 50.822 | 1.00 | 112.08 |
| 2384 | C | TYR | 262 | 108.608 | 54.178 | 50.284 | 1.00 | 112.01 |
| 2385 | O | TYR | 262 | 108.125 | 53.086 | 50.582 | 1.00 | 110.30 |
| 2386 | CB | TYR | 262 | 106.477 | 55..478 | 50.702 | 1.00 | 109.31 |
| 2387 | CG | TYR | 262 | 105.931 | 55.286 | 49.303 | 1.00 | 104.93 |
| 2388 | CD1 | TYR | 262 | 105.777 | 56.369 | 46.440 | 1.00 | 103.18 |
| 2389 | CD2 | TYR | 262 | 105.555 | 54.021 | 48.846 | 1.00 | 102.84 |
| 2390 | CE1 | TYR | 262 | 105.262 | 56.201 | 47.159 | 1.00 | 101.09 |
| 2391 | CE2 | TYR | 262 | 105.040 | 53.842 | 47.565 | 1.00 | 100.35 |
| 2392 | CZ | TYR | 262 | 104.897 | 54.938 | 46.727 | 1.00 | 100.07 |
| 2393 | OH | TYR | 262 | 104.386 | 54.781 | 45.459 | 1.00 | 97.25 |
| 2394 | H | TYR | 262 | 108.755 | 56.615 | 49.199 | 1.00 | 25.00 |
| 2395 | HH | TYR | 262 | 104.276 | 53.862 | 45.236 | 1.00 | 25.00 |
| 2396 | N | ALA | 263 | 109.671 | 54.310 | 49.497 | 1.00 | 113.11 |
| 2397 | CA | ALA | 263 | 110.360 | 53.168 | 48.913 | 1.00 | 114.09 |
| 2398 | C | ALA | 263 | 111.856 | 53.343 | 49.146 | 1.00 | 114.75 |
| 2399 | O | ALA | 263 | 112.375 | 54.457 | 49.055 | 1.00 | 115.90 |
| 2400 | CB | ALA | 263 | 110.064 | 53.077 | 47.428 | 1.00 | 112.96 |
| 2401 | H | ALA | 263 | 110.034 | 55.202 | 49.305 | 1.00 | 25.00 |
| 2402 | N | ARG | 264 | 112.543 | 52.252 | 49.467 | 1.00 | 113.69 |
| 2403 | CA | ARG | 264 | 113.979 | 52.309 | 49.726 | 1.00 | 114.09 |
| 2404 | C | ARG | 264 | 114.847 | 51.948 | 48.526 | 1.00 | 109.03 |
| 2405 | O | ARG | 264 | 114.394 | 51.280 | 47.594 | 1.00 | 109.80 |
| 2406 | CB | ARG | 264 | 114.355 | 51.448 | 50.945 | 1.00 | 116.51 |
| 2407 | CG | ARG | 264 | 113.434 | 50.258 | 51.235 | 1.00 | 118.71 |
| 2408 | CD | ARG | 264 | 113.486 | 49.190 | 50.151 | 1.00 | 120.73 |
| 2409 | NE | ARG | 264 | 112.543 | 48.105 | 50.418 | 1.00 | 118.02 |
| 2410 | CZ | ARG | 264 | 111.607 | 47.696 | 49.565 | 1.00 | 115.79 |
| 2411 | NH1 | ARG | 264 | 111.479 | 48.277 | 48.380 | 1.00 | 114..07 |
| 2412 | NH2 | ARG | 264 | 110.788 | 46.709 | 49.904 | 1.00 | 113.33 |
| 2413 | H | ARG | 264 | 112.079 | 51.393 | 49.495 | 1.00 | 25.00 |
| 2414 | HE | ARG | 264 | 112.602 | 47.651 | 51.284 | 1.00 | 25.00 |
| 2415 | 1HH1 | ARG | 264 | 112.083 | 49.029 | 48.120 | 1.00 | 25.00 |
| 2416 | 2HH1 | ARG | 264 | 110.766 | 47.967 | 47.751 | 1.00 | 25.00 |
| 2417 | 1HH2 | ARG | 264 | 110.868 | 46.283 | 50.807 | 1.00 | 25.00 |
| 2418 | 2HH2 | ARG | 264 | 110.074 | 46.408 | 49.273 | 1.00 | 25.00 |
| 2419 | N | ASP | 265 | 116.089 | 52.421 | 48.550 | 1.00 | 103.18 |
| 2420 | CA | ASP | 265 | 117.045 | 52.152 | 47.485 | 1.00 | 97.60 |
| 2421 | C | ASP | 265 | 117.480 | 50.688 | 47.579 | 1.00 | 92.70 |
| 2422 | O | ASP | 265 | 118.533 | 50.371 | 48.138 | 1.00 | 96.57 |
| 2423 | CB | ASP | 265 | 118.255 | 53.086 | 47.619 | 1.00 | 100.16 |
| 2424 | CG | ASP | 265 | 1199.317 | 52.826 | 46.565 | 1.00 | 106.00 |
| 2425 | OD1 | ASP | 265 | 118.992 | 52.887 | 45.363 | 1.00 | 107.25 |
| 2426 | OD2 | ASP | 265 | 120.479 | 52.556 | 46.940 | 1.00 | 109.23 |
| 2427 | H | ASP | 265 | 116.373 | 52.965 | 49.310 | 1.00 | 25.00 |
| 2428 | N | ARG | 266 | 116.654 | 49.799 | 47.041 | 1.00 | 82.19 |
| 2429 | CA | ARG | 266 | 116.942 | 48.372 | 47.073 | 1.00 | 73.27 |
| 2430 | C | ARG | 266 | 117.613 | 47.910 | 45.775 | 1.00 | 63.23 |
| 2431 | O | ARG | 266 | 117.711 | 46.712 | 45.511 | 1.00 | 66.31 |
| 2432 | CB | ARG | 266 | 115.646 | 47.585 | 47.320 | 1.00 | 77.54 |
| 2433 | CG | ARG | 266 | 115.801 | 46.402 | 48.274 | 1.00 | 83.80 |
| 2434 | CD | ARG | 266 | 114.480 | 45.672 | 48.520 | 1.00 | 86.40 |
| 2435 | NE | ARG | 266 | 114.015 | 44.911 | 47.358 | 1.00 | 87.97 |
| 2436 | CZ | ARG | 266 | 114.383 | 43.661 | 47.077 | 1.00 | 87.83 |
| 2437 | NH1 | ARG | 266 | 115.229 | 43.014 | 47.869 | 1.00 | 86.43 |
| 2438 | NH2 | ARG | 266 | 113.895 | 43.049 | 46.005 | 1.00 | 80.67 |
| 2439 | H | ARG | 266 | 115.816 | 50.112 | 46.631 | 1.00 | 25.00 |
| 2440 | HE | ARG | 266 | 113.386 | 45.348 | 46.747 | 1.00 | 25.00 |
| 2441 | 1HH1 | ARG | 266 | 115.600 | 43.463 | 48.681 | 1.00 | 25.00 |
| 2442 | 2HH1 | ARG | 266 | 115.502 | 42.079 | 47.647 | 1.00 | 25.00 |
| 2443 | 1NH2 | ARG | 266 | 113.246 | 43.525 | 45.410 | 1.00 | 25.00 |
| 2444 | 2HH2 | ARG | 266 | 114.170 | 42.111 | 45.794 | 1.00 | 25.00 |
| 2445 | N | VAL | 267 | 118.130 | 48.859 | 45.000 | 1.00 | 54.00 |
| 2446 | CA | VAL | 267 | 118.778 | 48.560 | 43.722 | 1.00 | 46.85 |
| 2447 | C | VAL | 267 | 119.855 | 47.496 | 43.784 | 1.00 | 44.14 |
| 2448 | O | VAL | 267 | 119.911 | 46.609 | 42.935 | 1.00 | 45.14 |
| 2449 | CB | VAL | 267 | 119.361 | 49.827 | 43.076 | 1.00 | 45.45 |
| 2450 | CG1 | VAL | 267 | 119.991 | 49.499 | 41.733 | 1.00 | 42.99 |
| 2451 | CG2 | VAL | 267 | 118.273 | 50.848 | 42.892 | 1.00 | 51.05 |
| 2452 | H | VAL | 267 | 118.072 | 49.785 | 45.299 | 1.00 | 25.00 |
| 2453 | N | VAL | 268 | 120.738 | 47.576 | 44.781 | 1.00 | 40.56 |
| 2454 | CA | VAL | 268 | 121.813 | 46.597 | 44.910 | 1.00 | 38.21 |
| 2455 | C | VAL | 268 | 121.242 | 45.185 | 45.125 | 1.00 | 35.40 |
| 2456 | O | VAL | 268 | 121.708 | 44.220 | 44.513 | 1.00 | 29.56 |
| 2457 | CB | VAL | 268 | 122.785 | 46.976 | 46.046 | 1.00 | 40.34 |
| 2458 | CG1 | VAL | 268 | 123.983 | 46.055 | 46.040 | 1.00 | 41.41 |
| 2459 | CG2 | VAL | 268 | 123.239 | 48.414 | 45.880 | 1.00 | 43.02 |
| 2460 | H | VAL | 268 | 120.663 | 48.303 | 45.428 | 1.00 | 25.00 |
| 2461 | N | GLU | 269 | 120.202 | 45.081 | 45.952 | 1.00 | 33.49 |
| 2462 | CA | GLU | 2669 | 119.553 | 43.796 | 46.220 | 1.00 | 31.75 |
| 2463 | C | GLU | 269 | 118.910 | 43.278 | 44.936 | 1.00 | 31.29 |
| 2464 | O | GLU | 269 | 119.023 | 42.095 | 44.607 | 1.00 | 34.74 |
| 2465 | CB | GLU | 269 | 118.477 | 43.940 | 47.300 | 1.00 | 30.42 |
| 2466 | CG | GLU | 269 | 118.998 | 44.124 | 48.719 | 1.00 | 41.96 |
| 2467 | CD | GLU | 269 | 119.777 | 45.418 | 48.921 | 1.00 | 53.70 |
| 2468 | OE1 | GLU | 269 | 119.387 | 46.465 | 48.356 | 1.00 | 52.14 |
| 2469 | OE2 | GLU | 269 | 120.785 | 45.385 | 49.658 | 1.00 | 60.44 |
| 2470 | H | GLU | 269 | 119.849 | 45.888 | 46.369 | 1.00 | 25.00 |
| 2471 | N | CYS | 270 | 118.258 | 44.179 | 44.204 | 1.00 | 25.87 |
| 2472 | CA | CYS | 270 | 117.603 | 43.829 | 42.948 | 1.00 | 31.04 |
| 2473 | C | CYS | 270 | 118.628 | 43.330 | 41.944 | 1.00 | 31.66 |
| 2474 | O | CYS | 270 | 118.352 | 42.406 | 41.170 | 1.00 | 34.14 |
| 2475 | CB | CYS | 270 | 116.841 | 45.029 | 42.380 | 1.00 | 31.00 |
| 2478 | SG | CYS | 270 | 115.468 | 45.566 | 43.429 | 1.00 | 41.23 |
| 2477 | H | CYS | 270 | 118.204 | 45.102 | 44.523 | 1.00 | 25.00 |
| 2478 | N | TYR | 271 | 119.817 | 43.927 | 41.968 | 1.00 | 30.55 |
| 2479 | CA | TYR | 271 | 120.875 | 43.506 | 41.065 | 1.00 | 29.41 |
| 2480 | C | TYR | 271 | 121.365 | 42.109 | 41.459 | 1.00 | 29.51 |
| 2481 | O | TYR | 271 | 121.662 | 41.284 | 40.592 | 1.00 | 30.16 |
| 2482 | CB | TYR | 271 | 122.048 | 44.496 | 41.048 | 1.00 | 27.85 |
| 2483 | CG | TYR | 271 | 123.125 | 44.061 | 40.077 | 1.00 | 27.35 |
| 2484 | CD1 | TYR | 271 | 123.006 | 44.327 | 38.714 | 1.00 | 25.72 |
| 2485 | CD2 | TYR | 271 | 124.198 | 43.279 | 40.502 | 1.00 | 20.62 |
| 2486 | CE1 | TYR | 271 | 123.923 | 43.813 | 37.798 | 1.00 | 22.98 |
| 2487 | CE2 | TYR | 271 | 125.116 | 42.762 | 39.593 | 1.00 | 27.42 |
| 2488 | CZ | TYR | 271 | 124.970 | 43.030 | 38.245 | 1.00 | 21.79 |
| 2489 | OH | TYR | 271 | 125.859 | 42.497 | 37.343 | 1.00 | 23.43 |
| 2490 | H | TYR | 271 | 119.985 | 44.662 | 42.594 | 1.00 | 25.00 |
| 2491 | HH | TYR | 271 | 126.485 | 41.987 | 37.843 | 1.00 | 25.00 |
| 2492 | N | PHE | 272 | 121.453 | 41.845 | 42.760 | 1.00 | 26.47 |
| 2493 | CA | PHE | 272 | 121.892 | 40.535 | 43.220 | 1.00 | 28.71 |
| 2494 | C | PHE | 272 | 120.957 | 39.486 | 42.633 | 1.00 | 31.32 |
| 2495 | O | PHE | 272 | 121.408 | 38.470 | 42.102 | 1.00 | 31.50 |
| 2496 | CB | PHE | 272 | 121.881 | 40.442 | 44.747 | 1.00 | 32.64 |
| 2497 | CG | PHE | 272 | 122.165 | 39.058 | 45.264 | 1.00 | 34.15 |
| 2498 | CD1 | PHE | 272 | 123.471 | 38.577 | 45.323 | 1.00 | 32.37 |
| 2499 | CD2 | PHE | 272 | 121.120 | 38.211 | 45.838 | 1.00 | 34.09 |
| 2500 | CE11 | PHE | 272 | 123.732 | 37.271 | 45.739 | 1.00 | 35.66 |
| 2501 | CE2 | PHE | 272 | 121.369 | 36.902 | 46.055 | 1.00 | 34.18 |
| 2502 | CZ | PHE | 272 | 122.679 | 36.431 | 46.105 | 1.00 | 36.58 |

TABLE 11-continued

Structural Coordinates of Tobacco 5-Epi-Aristolochene Synthase In the Absence of Bound Substrate

| Atom Type | Atom | Residue | Residue # | X | Y | Z | OCC | B-factor |
|---|---|---|---|---|---|---|---|---|
| 2503 | H | PHE | 272 | 121.228 | 42.541 | 43.413 | 1.00 | 25.00 |
| 2504 | N | TRP | 273 | 119.656 | 39.744 | 42.712 | 1.00 | 29.73 |
| 2505 | CA | TRP | 273 | 118.670 | 38.817 | 42.167 | 1.00 | 30.60 |
| 2506 | C | TRP | 273 | 118.924 | 38.551 | 40.685 | 1.00 | 30.33 |
| 2507 | O | TRP | 273 | 118.971 | 37.396 | 40.250 | 1.00 | 32.10 |
| 2508 | CB | TRP | 273 | 117.255 | 39.357 | 42.365 | 1.00 | 28.17 |
| 2509 | CG | TRP | 273 | 116.707 | 39.092 | 43.721 | 1.00 | 33.41 |
| 2510 | CD1 | TRP | 273 | 117.241 | 39.478 | 44.915 | 1.00 | 37.71 |
| 2511 | CD2 | TRP | 273 | 115.506 | 38.381 | 44.029 | 1.00 | 41.82 |
| 2512 | NE1 | TRP | 273 | 116.445 | 39.053 | 45.950 | 1.00 | 39.11 |
| 2513 | CE2 | TRP | 273 | 115.372 | 38.378 | 45.435 | 1.00 | 43.90 |
| 2514 | CE3 | TRP | 273 | 114.528 | 37.747 | 43.253 | 1.00 | 47.13 |
| 2515 | CZ2 | TRP | 273 | 114.296 | 37.764 | 46.083 | 1.00 | 49.35 |
| 2516 | CZ3 | TRP | 273 | 113.458 | 37.138 | 43.898 | 1.00 | 53.38 |
| 2517 | CH2 | TRP | 273 | 113.352 | 37.150 | 45.300 | 1.00 | 53.17 |
| 2518 | H | TRP | 273 | 119.359 | 40.569 | 43.153 | 1.00 | 25.00 |
| 2519 | HE1 | TRP | 273 | 116.622 | 39.201 | 46.903 | 1.00 | 25.00 |
| 2520 | N | ALA | 274 | 119.117 | 39.617 | 39.915 | 1.00 | 26.20 |
| 2521 | CA | ALA | 274 | 119.371 | 39.472 | 38.489 | 1.00 | 25.12 |
| 2522 | C | ALA | 274 | 120.638 | 38.657 | 38.263 | 1.00 | 27.03 |
| 2523 | O | ALA | 274 | 120.686 | 37.816 | 37.386 | 1.00 | 29.08 |
| 2524 | CB | ALA | 274 | 119.491 | 40.832 | 37.831 | 1.00 | 22.68 |
| 2525 | H | ALA | 274 | 119.0884 | 40.514 | 40.313 | 1.00 | 25.00 |
| 2526 | N | LEU | 275 | 121.646 | 38.886 | 39.104 | 1.00 | 26.74 |
| 2527 | CA | LEU | 275 | 122.922 | 38.175 | 39.011 | 1.00 | 23.65 |
| 2528 | C | LEU | 275 | 122.727 | 36.689 | 39.329 | 1.00 | 20.19 |
| 2529 | O | LEU | 275 | 123.432 | 35.825 | 38.798 | 1.00 | 18.69 |
| 2530 | CB | LEU | 275 | 123.945 | 38.802 | 39.963 | 1.00 | 22.77 |
| 2531 | CG | LEU | 275 | 125.377 | 38.280 | 39.867 | 1.00 | 22.23 |
| 2532 | CD1 | LEU | 275 | 125.859 | 38.352 | 38.427 | 1.00 | 20.45 |
| 2533 | CD2 | LEU | 275 | 126.274 | 39.097 | 40.779 | 1.00 | 24.10 |
| 2534 | H | LEU | 275 | 121.532 | 39.552 | 39.808 | 1.00 | 25.00 |
| 2535 | N | GLY | 276 | 121.765 | 36.406 | 40.204 | 1.00 | 19.17 |
| 2536 | CA | GLY | 276 | 121.453 | 35.035 | 40.561 | 1.00 | 19.61 |
| 2537 | C | GLY | 276 | 120.811 | 34.299 | 39.392 | 1.00 | 25.48 |
| 2538 | O | GLY | 276 | 121.060 | 33.108 | 39.199 | 1.00 | 28.59 |
| 2539 | H | GLY | 276 | 121.266 | 37.137 | 40.623 | 1.00 | 25.00 |
| 2540 | N | VAL | 277 | 120.000 | 35.006 | 38.603 | 1.00 | 20.84 |
| 2541 | CA | VAL | 277 | 119.323 | 34.415 | 37.440 | 1.00 | 19.19 |
| 2542 | C | VAL | 277 | 120.304 | 34.028 | 36.319 | 1.00 | 19.17 |
| 2543 | O | VAL | 277 | 120.086 | 33.048 | 35.606 | 1.00 | 21.35 |
| 2544 | CB | VAL | 277 | 118.201 | 35.355 | 36.904 | 1.00 | 21.19 |
| 2545 | CG1 | VAL | 277 | 117.560 | 34.777 | 35.650 | 1.00 | 15.33 |
| 2546 | CG2 | VAL | 277 | 117.138 | 35.550 | 37.976 | 1.00 | 11.13 |
| 2547 | H | VAL | 277 | 119.858 | 35.954 | 38.810 | 1.00 | 25.00 |
| 2548 | N | TYR | 278 | 121.345 | 34.834 | 36.137 | 1.00 | 21.16 |
| 2549 | CA | TYR | 278 | 122.401 | 34.587 | 35.150 | 1.00 | 24.77 |
| 2550 | C | TYR | 278 | 123.583 | 35.532 | 35.351 | 1.00 | 29.35 |
| 2551 | O | TYR | 278 | 123.405 | 36.738 | 35.531 | 1.00 | 27.69 |
| 2552 | CB | TYR | 278 | 121.910 | 34.611 | 33.687 | 1.00 | 25.96 |
| 2553 | CG | TYR | 278 | 120.741 | 35.517 | 33.341 | 1.00 | 26.89 |
| 2554 | CD1 | TYR | 278 | 120.580 | 36.768 | 33.937 | 1.00 | 25.88 |
| 2555 | CD2 | TYR | 278 | 119.800 | 35.116 | 32.388 | 1.00 | 27.14 |
| 2556 | CE1 | TYR | 278 | 119.508 | 37.595 | 33.594 | 1.00 | 29.19 |
| 2557 | CE2 | TYR | 278 | 118.729 | 35.934 | 32.037 | 1.00 | 31.49 |
| 2558 | CZ | TYR | 278 | 118.587 | 37.171 | 32.643 | 1.00 | 31.78 |
| 2559 | OH | TYR | 278 | 117.522 | 37.976 | 32.301 | 1.00 | 31.66 |
| 2560 | H | TYR | 278 | 121.419 | 35.652 | 36.684 | 1.00 | 25.00 |
| 2561 | HH | TYR | 278 | 117.022 | 37.548 | 31.600 | 1.00 | 25.00 |
| 2562 | N | PHE | 279 | 124.789 | 34.968 | 35.332 | 1.00 | 31.85 |
| 2563 | CA | PHE | 279 | 126.017 | 35.732 | 35.549 | 1.00 | 28.28 |
| 2564 | C | PHE | 279 | 126.910 | 35.844 | 34.318 | 1.00 | 28.86 |
| 2565 | O | PHE | 279 | 127.855 | 36.636 | 34.310 | 1.00 | 28.24 |
| 2566 | CB | PHE | 279 | 126.829 | 35.087 | 36.678 | 1.00 | 24.38 |
| 2567 | CG | PHE | 279 | 127.334 | 33.707 | 36.344 | 1.00 | 23.04 |
| 2568 | CD1 | PHE | 279 | 128.563 | 33.535 | 35.706 | 1.00 | 16.44 |
| 2569 | CD2 | PHE | 279 | 126.557 | 32.582 | 36.616 | 1.00 | 22.61 |
| 2570 | CE1 | PHE | 279 | 129.005 | 32.265 | 35.339 | 1.00 | 22.82 |
| 2571 | CE2 | PHE | 279 | 126.989 | 31.309 | 36.254 | 1.00 | 22.81 |
| 2572 | CZ | PHE | 279 | 128.214 | 31.149 | 35.613 | 1.00 | 20.63 |
| 2573 | H | PHE | 279 | 124.845 | 34.006 | 35.181 | 1.00 | 25.00 |
| 2574 | N | GLU | 280 | 126.653 | 35.010 | 33.315 | 1.00 | 25.83 |
| 2575 | CA | GLU | 280 | 127.450 | 34.995 | 32.093 | 1.00 | 25.96 |
| 2576 | C | GLU | 280 | 127.464 | 36.347 | 31.384 | 1.00 | 32.09 |
| 2577 | O | GLU | 280 | 126.461 | 37.067 | 31.378 | 1.00 | 33.29 |
| 2578 | CB | GLU | 280 | 126.947 | 33.909 | 31.140 | 1.00 | 29.64 |
| 2579 | CG | GLU | 280 | 127.116 | 32.479 | 31.652 | 1.00 | 31.98 |
| 2580 | CD | GLU | 280 | 125.873 | 31.921 | 32.338 | 1.00 | 41.40 |
| 2581 | OE1 | GLU | 280 | 125.089 | 32.696 | 32.938 | 1.00 | 33.42 |
| 2582 | OE2 | GLU | 280 | 125.681 | 30.688 | 32.273 | 1.00 | 43.76 |
| 2583 | H | GLU | 280 | 125.894 | 34.421 | 33.402 | 1.00 | 25.00 |
| 2584 | N | PRO | 281 | 128.593 | 36.687 | 30.735 | 1.00 | 34.75 |
| 2585 | CA | PRO | 281 | 128.736 | 37.961 | 30.018 | 1.00 | 32.48 |
| 2586 | C | PRO | 281 | 127.718 | 38.182 | 28.899 | 1.00 | 30.11 |
| 2587 | O | PRO | 281 | 127.273 | 39.309 | 28.675 | 1.00 | 33.55 |
| 2588 | CB | PRO | 281 | 130.177 | 37.901 | 229.492 | 1.00 | 33.45 |
| 2589 | CG | PRO | 281 | 130.447 | 36.426 | 29.366 | 1.00 | 34.83 |
| 2590 | CD | PRO | 281 | 129.824 | 35.882 | 30.625 | 1.00 | 32.94 |
| 2591 | N | GLN | 282 | 127.319 | 37.106 | 28.226 | 1.00 | 30.38 |
| 2592 | CA | GLN | 282 | 126.350 | 37.195 | 27.134 | 1.00 | 31.74 |
| 2593 | C | GLN | 282 | 124.980 | 37.704 | 27.600 | 1.00 | 33.53 |
| 2594 | O | GLN | 282 | 124.194 | 38.202 | 26.792 | 1.00 | 34.52 |
| 2595 | CB | GLN | 282 | 126.183 | 35.829 | 26.462 | 1.00 | 35.52 |
| 2596 | CG | GLN | 282 | 125.442 | 34.819 | 27.323 | 1.00 | 47.53 |
| 2597 | CD | GLN | 282 | 125.543 | 33.400 | 26.807 | 1.00 | 54.68 |
| 2598 | OE1 | GLN | 282 | 126.378 | 32.624 | 27.273 | 1.00 | 58.66 |
| 2599 | NE2 | GLN | 282 | 124.675 | 33.040 | 25.866 | 1.00 | 55.48 |
| 2600 | H | GLN | 282 | 127.685 | 36.233 | 28.468 | 1.00 | 25.00 |
| 2601 | 1HE2 | GLN | 282 | 124.740 | 32.122 | 25.538 | 1.00 | 25.00 |
| 2602 | 2HE2 | GLN | 282 | 124.018 | 33.690 | 25.551 | 1.00 | 25.00 |
| 2603 | N | TYR | 283 | 124.698 | 37.577 | 28.896 | 1.00 | 27.81 |
| 2604 | CA | TYR | 283 | 123.417 | 38.015 | 29.447 | 1.00 | 26.64 |
| 2605 | C | TYR | 283 | 123.470 | 39.392 | 30.099 | 1.00 | 29.80 |
| 2606 | O | TYR | 283 | 122.615 | 39.732 | 30.922 | 1.00 | 29.85 |
| 2607 | CB | TYR | 283 | 122.885 | 36.982 | 30.444 | 1.00 | 24.82 |
| 2608 | CG | TYR | 283 | 122.670 | 35.614 | 29.840 | 1.00 | 26.77 |
| 2609 | CD1 | TYR | 283 | 121.786 | 35.432 | 28.775 | 1.00 | 28.94 |
| 2610 | CD2 | TYR | 283 | 123.373 | 34.506 | 30.313 | 1.00 | 26.51 |
| 2611 | CE1 | TYR | 283 | 121.610 | 34.174 | 28.192 | 1.00 | 32.76 |
| 2612 | CE2 | TYR | 283 | 123.205 | 33.247 | 29.740 | 1.00 | 28.52 |
| 2613 | CZ | TYR | 283 | 122.324 | 33.086 | 28.680 | 1.00 | 30.97 |
| 2614 | OH | TYR | 283 | 122.164 | 31.845 | 28.104 | 1.00 | 25.13 |
| 2615 | H | TYR | 283 | 125.361 | 37.198 | 29.509 | 1.00 | 25.00 |
| 2616 | HH | TYR | 283 | 122.723 | 31.208 | 28.556 | 1.00 | 25.00 |
| 2617 | N | SER | 284 | 124.449 | 40.196 | 29.697 | 1.00 | 30.66 |
| 2618 | CA | SER | 284 | 124.620 | 41.539 | 30.239 | 1.00 | 33.15 |
| 2619 | C | SER | 284 | 123.375 | 42.412 | 30.040 | 1.00 | 32.37 |
| 2620 | O | SER | 284 | 122.858 | 42.999 | 30.999 | 1.00 | 32.25 |
| 2621 | CB | SER | 284 | 125.848 | 42.201 | 29.609 | 1.00 | 32.60 |
| 2622 | OG | SER | 284 | 126.037 | 43.511 | 30.110 | 1.00 | 38.65 |
| 2623 | H | SER | 284 | 125.090 | 39.876 | 29.027 | 1.00 | 25.00 |
| 2624 | HG | SER | 284 | 126.140 | 43.520 | 31.058 | 1.00 | 25.00 |
| 2625 | N | GLN | 285 | 122.882 | 42.477 | 28.805 | 1.00 | 35.28 |
| 2626 | CA | GLN | 285 | 121.693 | 43.273 | 28.505 | 1.00 | 36.59 |
| 2627 | C | GLN | 285 | 120.489 | 42.735 | 29.284 | 1.00 | 33.06 |
| 2628 | O | GLN | 285 | 119.713 | 43.504 | 29.856 | 1.00 | 33.43 |
| 2629 | CB | GLN | 285 | 121.399 | 43.255 | 27.002 | 1.00 | 36.57 |
| 2630 | CG | GLN | 285 | 120.138 | 44.020 | 26.611 | 1.00 | 48.54 |
| 2631 | CD | GLN | 285 | 119.829 | 43.943 | 25.123 | 1.00 | 54.77 |
| 2632 | OE1 | GLN | 285 | 120.079 | 42.927 | 24.470 | 1.00 | 55.77 |
| 2633 | NE2 | GLN | 285 | 119.280 | 45.024 | 24.581 | 1.00 | 56.33 |
| 2634 | H | GLN | 285 | 123.323 | 41.984 | 28.088 | 1.00 | 25.00 |
| 2635 | 1HE2 | GLN | 285 | 119.084 | 44.982 | 23.621 | 1.00 | 25.00 |
| 2636 | 2HE2 | GLN | 285 | 119.099 | 45.802 | 25.141 | 1.00 | 25.00 |
| 2637 | N | ALA | 286 | 120.364 | 41.410 | 29.324 | 1.00 | 32.38 |
| 2638 | CA | ALA | 286 | 119.272 | 40.750 | 30.032 | 1.00 | 28.79 |
| 2639 | C | ALA | 286 | 119.254 | 41.117 | 31.512 | 1.00 | 26.70 |
| 2640 | O | ALA | 286 | 118.200 | 41.438 | 32.060 | 1.00 | 31.71 |
| 2641 | CB | ALA | 286 | 119.370 | 39.244 | 29.859 | 1.00 | 30.35 |
| 2642 | H | ALA | 286 | 121.023 | 40.859 | 28.861 | 1.00 | 25.00 |
| 2643 | N | ARG | 287 | 120.422 | 41.097 | 32.152 | 1.00 | 26.48 |
| 2644 | CA | ARG | 287 | 120.517 | 41.442 | 33.568 | 1.00 | 27.31 |
| 2645 | C | ARG | 287 | 120.056 | 42.870 | 33.826 | 1.00 | 27.08 |
| 2646 | O | ARG | 287 | 119.290 | 43.118 | 34.760 | 1.00 | 28.78 |
| 2647 | CB | ARG | 287 | 121.946 | 41.266 | 34.096 | 1.00 | 28.17 |
| 2648 | CG | ARG | 287 | 122.240 | 39.891 | 34.652 | 1.00 | 25.50 |

TABLE 11-continued

Structural Coordinates of Tobacco 5-Epi-Aristolochene Synthase In the Absence of Bound Substrate

| Atom Type | Atom | Residue | Residue # | X | Y | Z | OCC | B-factor |
|---|---|---|---|---|---|---|---|---|
| 2649 | CD | ARG | 287 | 123.566 | 39.859 | 35.396 | 1.00 | 24.46 |
| 2650 | NE | ARG | 287 | 124.703 | 40.191 | 34.535 | 1.00 | 20.40 |
| 2651 | CZ | ARG | 287 | 125.252 | 39.373 | 33.641 | 1.00 | 23.12 |
| 2652 | NH1 | ARG | 287 | 124.781 | 38.146 | 33.473 | 1.00 | 23.32 |
| 2653 | NH2 | ARG | 287 | 126.268 | 39.703 | 32.897 | 1.00 | 22.53 |
| 2654 | H | ARG | 287 | 121.232 | 40.840 | 31.670 | 1.00 | 25.00 |
| 2655 | HE | ARG | 287 | 125.093 | 41.050 | 34.627 | 1.00 | 25.00 |
| 2656 | 1HH1 | ARG | 287 | 124.002 | 37.833 | 34.014 | 1.00 | 25.00 |
| 2657 | 2HH1 | ARG | 287 | 125.192 | 37.542 | 32.796 | 1.00 | 25.00 |
| 2658 | 1HH2 | ARG | 287 | 126.623 | 40.719 | 33.014 | 1.00 | 25.00 |
| 2659 | 2HH2 | ARG | 287 | 126.677 | 39.179 | 32.225 | 1.00 | 25.00 |
| 2660 | N | VAL | 288 | 120.512 | 43.802 | 32.992 | 1.00 | 30.28 |
| 2661 | CA | VAL | 288 | 120.144 | 45.208 | 33.148 | 1.00 | 29.94 |
| 2662 | C | VAL | 288 | 118.628 | 45.388 | 33.043 | 1.00 | 28.55 |
| 2663 | O | VAL | 288 | 118.018 | 46.044 | 33.890 | 1.00 | 35.55 |
| 2664 | CB | VAL | 288 | 120.874 | 46.106 | 32.120 | 1.00 | 35.29 |
| 2665 | CG1 | VAL | 288 | 120.536 | 47.572 | 32.363 | 1.00 | 30.30 |
| 2666 | CG2 | VAL | 288 | 122.378 | 45.896 | 32.221 | 1.00 | 31.86 |
| 2667 | H | VAL | 288 | 121.107 | 43.535 | 32.256 | 1.00 | 25.00 |
| 2668 | N | MET | 289 | 118.018 | 44.775 | 32.031 | 1.00 | 27.91 |
| 2669 | CA | MET | 289 | 116.567 | 44.856 | 31.854 | 1.00 | 27.36 |
| 2670 | C | MET | 289 | 115.857 | 44.248 | 33.068 | 1.00 | 27.49 |
| 2671 | O | MET | 289 | 114.938 | 44.845 | 33.627 | 1.00 | 29.43 |
| 2672 | CB | MET | 289 | 116.138 | 44.129 | 30.572 | 1.00 | 28.18 |
| 2673 | CG | MET | 289 | 116.578 | 44.819 | 29.282 | 1.00 | 28.82 |
| 2674 | SD | MET | 289 | 116.207 | 43.882 | 27.770 | 1.00 | 38.33 |
| 2675 | CE | MET | 289 | 114.526 | 44.384 | 27.438 | 1.00 | 39.91 |
| 2676 | H | MET | 289 | 118.554 | 44.257 | 31.391 | 1.00 | 25.00 |
| 2677 | N | LEU | 290 | 116.335 | 43.089 | 33.511 | 1.00 | 25.99 |
| 2678 | CA | LEU | 290 | 115.743 | 42.408 | 34.654 | 1.00 | 25.33 |
| 2679 | C | LEU | 290 | 115.805 | 43.222 | 35.949 | 1.00 | 26.44 |
| 2680 | O | LEU | 290 | 114.815 | 43.289 | 36.687 | 1.00 | 30.04 |
| 2681 | CB | LEU | 290 | 116.393 | 41.035 | 34.843 | 1.00 | 25.28 |
| 2682 | CG | LEU | 290 | 115.880 | 40.125 | 35.964 | 1.00 | 25.88 |
| 2683 | CD1 | LEU | 290 | 114.357 | 40.043 | 35.951 | 1.00 | 19.53 |
| 2684 | CD2 | LEU | 290 | 118.499 | 38.741 | 35.796 | 1.00 | 18.49 |
| 2685 | H | LEU | 290 | 117.098 | 42.681 | 33.057 | 1.00 | 25.00 |
| 2686 | N | VAL | 291 | 116.947 | 43.857 | 36.210 | 1.00 | 27.54 |
| 2687 | CA | VAL | 291 | 117.124 | 44.667 | 37.421 | 1.00 | 28.37 |
| 2688 | C | VAL | 291 | 116.101 | 45.799 | 37.502 | 1.00 | 27.52 |
| 2689 | O | VAL | 291 | 115.487 | 46.023 | 38.5550 | 1.00 | 27.61 |
| 2690 | CB | VAL | 291 | 118.544 | 45.289 | 37.507 | 1.00 | 28.94 |
| 2691 | CG1 | VAL | 291 | 118.706 | 46.054 | 38.803 | 1.00 | 25.65 |
| 2692 | CG2 | VAL | 291 | 119.592 | 44.214 | 37.431 | 1.00 | 36.38 |
| 2693 | H | VAL | 291 | 117.687 | 43.782 | 35.573 | 1.00 | 25.00 |
| 2694 | N | LYS | 292 | 115.911 | 46.502 | 36.392 | 1.00 | 27.46 |
| 2695 | CA | LYS | 292 | 114.968 | 47.611 | 36.345 | 1.00 | 28.57 |
| 2696 | C | LYS | 292 | 113.548 | 47.158 | 36.677 | 1.00 | 30.77 |
| 2697 | O | LYS | 292 | 112.834 | 47.824 | 37.433 | 1.00 | 31.18 |
| 2698 | CB | LYS | 292 | 115.029 | 48.285 | 34.976 | 1.00 | 29.35 |
| 2699 | CG | LYS | 292 | 116.391 | 48.890 | 34.676 | 1.00 | 29.57 |
| 2700 | CD | LYS | 292 | 116.463 | 49.431 | 33.261 | 1.00 | 34.35 |
| 2701 | CE | LYS | 292 | 117.810 | 50.079 | 32.999 | 1.00 | 37.92 |
| 2702 | NZ | LYS | 292 | 117.909 | 50.619 | 31.619 | 1.00 | 40.64 |
| 2703 | H | LYS | 292 | 116.413 | 46.260 | 35.581 | 1.00 | 25.00 |
| 2704 | 1HZ | LYS | 292 | 117.780 | 49.846 | 30.936 | 1.00 | 25.00 |
| 2705 | 2HZ | LYS | 292 | 117.169 | 51.334 | 31.476 | 1.00 | 25.00 |
| 2706 | 3HZ | LYS | 292 | 118.844 | 51.052 | 31.483 | 1.00 | 25.00 |
| 2707 | N | THR | 293 | 113.146 | 46.010 | 36.137 | 1.00 | 34.24 |
| 2708 | CA | THR | 293 | 111.817 | 45.463 | 36.395 | 1.00 | 27.43 |
| 2709 | C | THR | 293 | 111.657 | 45.123 | 37.872 | 1.00 | 31.58 |
| 2710 | O | THR | 293 | 110.655 | 45.493 | 38.491 | 1.00 | 28.71 |
| 2711 | CB | THR | 293 | 111.561 | 44.214 | 35.534 | 1.00 | 25.43 |
| 2712 | OG1 | THR | 293 | 111.354 | 44.616 | 34.175 | 1.00 | 30.49 |
| 2713 | CG2 | THR | 293 | 110.348 | 43.433 | 36.029 | 1.00 | 22.44 |
| 2714 | H | THR | 293 | 113.756 | 45.525 | 35.533 | 1.00 | 25.00 |
| 2715 | HG1 | THR | 293 | 110.577 | 45.180 | 34.129 | 1.00 | 25.00 |
| 2716 | N | ILE | 294 | 112.647 | 44.439 | 38.440 | 1.00 | 30.35 |
| 2717 | CA | ILE | 294 | 112.596 | 44.064 | 39.853 | 1.00 | 30.45 |
| 2718 | C | ILE | 294 | 112.481 | 45.317 | 40.725 | 1.00 | 28.69 |
| 2719 | O | ILE | 294 | 111.709 | 45.348 | 41.685 | 1.00 | 30.57 |
| 2720 | CB | ILE | 294 | 113.837 | 43.230 | 40.272 | 1.00 | 29.95 |
| 2721 | CG1 | ILE | 294 | 113.948 | 41.977 | 39.399 | 1.00 | 24.34 |
| 2722 | CG2 | ILE | 294 | 113.733 | 42.818 | 41.734 | 1.00 | 18.35 |
| 2723 | CD1 | ILE | 294 | 115.165 | 41.133 | 39.687 | 1.00 | 30.84 |
| 2724 | H | ILE | 294 | 113.432 | 44.182 | 37.906 | 1.00 | 25.00 |
| 2725 | N | SER | 295 | 113.219 | 46.381 | 40.359 | 1.00 | 32.61 |
| 2726 | CA | SER | 295 | 113.196 | 47.623 | 41.097 | 1.00 | 37.07 |
| 2727 | C | SER | 295 | 111.820 | 48..276 | 41.002 | 1.00 | 35.65 |
| 2728 | O | SER | 295 | 111.227 | 48.673 | 42.011 | 1.00 | 33.09 |
| 2729 | CB | SER | 295 | 114.246 | 48.584 | 40.533 | 1.00 | 35.83 |
| 2730 | OG | SER | 295 | 115.543 | 48.024 | 40.608 | 1.00 | 42.38 |
| 2731 | H | SER | 295 | 113.804 | 46.290 | 39.575 | 1.00 | 25.00 |
| 2732 | HG | SER | 295 | 115.756 | 47.823 | 41.523 | 1.00 | 25.00 |
| 2733 | N | MET | 296 | 111.306 | 48.342 | 39.779 | 1.00 | 34.54 |
| 2734 | CA | MET | 296 | 110.017 | 48.951 | 39.506 | 1.00 | 35.02 |
| 2735 | C | MET | 296 | 108.864 | 48.263 | 40.230 | 1.00 | 36.33 |
| 2736 | O | MET | 296 | 108.080 | 48.919 | 40.923 | 1.00 | 35.61 |
| 2737 | CB | MET | 296 | 109.768 | 48.966 | 37.999 | 1.00 | 39.18 |
| 2738 | CG | MET | 296 | 109.109 | 50.234 | 37.507 | 1.00 | 49.37 |
| 2739 | SD | MET | 296 | 109.993 | 51.708 | 38.067 | 1.00 | 51.57 |
| 2740 | CE | MET | 296 | 108.888 | 52.271 | 39.359 | 1.00 | 53.40 |
| 2741 | H | MET | 296 | 111.819 | 47.966 | 39.036 | 1.00 | 25.00 |
| 2742 | N | ILE | 297 | 108.780 | 46.941 | 40.103 | 1.00 | 37.42 |
| 2743 | CA | ILE | 297 | 107.709 | 46.185 | 40.745 | 1.00 | 34.54 |
| 2744 | C | ILE | 297 | 107.813 | 46.267 | 42.267 | 1.00 | 36.45 |
| 2745 | O | ILE | 297 | 106.817 | 46.101 | 42.976 | 1.00 | 35.56 |
| 2746 | CB | ILE | 297 | 107.675 | 44.709 | 40.265 | 1.00 | 36.67 |
| 2747 | CG1 | ILE | 297 | 106.342 | 44.059 | 40.648 | 1.00 | 30.90 |
| 2748 | CG2 | ILE | 297 | 108.858 | 43.925 | 40.821 | 1.00 | 34.15 |
| 2749 | CD1 | ILE | 297 | 105.135 | 44.654 | 39.935 | 1.00 | 28.47 |
| 2750 | H | ILE | 297 | 109.454 | 46.468 | 39.576 | 1.00 | 25.00 |
| 2751 | N | SER | 298 | 109.015 | 46.559 | 42.761 | 1.00 | 37.95 |
| 2752 | CA | SER | 298 | 109.250 | 46.696 | 44.195 | 1.00 | 40..22 |
| 2753 | C | SER | 298 | 108.531 | 47.961 | 44.673 | 1.00 | 38.96 |
| 2754 | O | SER | 298 | 107.934 | 47.979 | 45.753 | 1.00 | 36.43 |
| 2755 | CB | SER | 298 | 110.751 | 46.791 | 44.481 | 1.00 | 43.72 |
| 2756 | OG | SER | 298 | 111.00 | 9 | 46.764 | 45.873 | 1.00 |
|  |  |  |  |  |  |  |  | 62.08 |
| 2757 | H | SER | 298 | 109.775 | 46.674 | 42.153 | 1.00 | 25.00 |
| 2758 | HG | SER | 298 | 110.573 | 47.504 | 46.304 | 1.00 | 25.00 |
| 2759 | N | ILE | 299 | 108.582 | 49.011 | 43.857 | 1.00 | 39.57 |
| 2760 | CA | ILE | 299 | 107.912 | 50.271 | 44.175 | 1.00 | 40.91 |
| 2761 | C | ILE | 299 | 106.412 | 49.996 | 44.293 | 1.00 | 40.75 |
| 2762 | O | ILE | 299 | 105.771 | 50.378 | 45.276 | 1.00 | 40.26 |
| 2763 | CB | ILE | 299 | 108.128 | 51.329 | 43.060 | 1.00 | 37.27 |
| 2764 | CG1 | ILE | 299 | 109.614 | 51.653 | 42.908 | 1.00 | 37.90 |
| 2765 | CG2 | ILE | 299 | 1077.345 | 52.592 | 43.370 | 1.00 | 42.54 |
| 2766 | CD1 | ILE | 299 | 110.260 | 52.146 | 44.173 | 1.00 | 39.79 |
| 2767 | H | ILE | 299 | 109.091 | 48.942 | 43.021 | 1.00 | 25.00 |
| 2768 | N | VAL | 300 | 105.876 | 49.290 | 43.301 | 1.00 | 34.47 |
| 2769 | CA | VAL | 300 | 104.462 | 48.949 | 43.267 | 1.00 | 33.70 |
| 2770 | C | VAL | 300 | 104.050 | 48.145 | 44.497 | 1.00 | 38.81 |
| 2771 | O | VAL | 300 | 103.020 | 48.431 | 45.116 | 1.00 | 39.02 |
| 2772 | CB | VAL | 300 | 104.116 | 48.166 | 41.990 | 1.00 | 35.45 |
| 2773 | CG1 | VAL | 300 | 102.629 | 47.848 | 41.951 | 1.00 | 37.16 |
| 2774 | CG2 | VAL | 300 | 104.522 | 48.970 | 40.762 | 1.00 | 29.01 |
| 2775 | H | VAL | 300 | 106.459 | 48.994 | 42.572 | 1.00 | 25.00 |
| 2776 | N | ASP | 301 | 104.866 | 47.162 | 44.865 | 1.00 | 39.28 |
| 2777 | CA | ASP | 301 | 104.585 | 46.327 | 46.030 | 1.00 | 39.76 |
| 2778 | C | ASP | 301 | 104.477 | 47.200 | 47.281 | 1.00 | 43.93 |
| 2779 | O | ASP | 301 | 103.588 | 47.002 | 48.113 | 1.00 | 43.98 |
| 2780 | CB | ASP | 301 | 105.684 | 45.270 | 46.205 | 1.00 | 41.93 |
| 2781 | CG | ASP | 301 | 105.401 | 44.299 | 47.348 | 1.00 | 47.18 |
| 2782 | OD1 | ASP | 301 | 104.219 | 44.006 | 47.633 | 1.00 | 52.50 |
| 2783 | OD2 | ASP | 301 | 106.375 | 43.817 | 47.959 | 1.00 | 53.58 |
| 2784 | H | ASP | 301 | 105.672 | 46.984 | 44.338 | 1.00 | 25.00 |
| 2785 | N | ASP | 302 | 105.373 | 48.175 | 47.401 | 1.00 | 48.10 |
| 2786 | CA | ASP | 302 | 105.371 | 49.088 | 48.541 | 1.00 | 51.62 |
| 2787 | C | ASP | 302 | 104.090 | 49.918 | 48.560 | 1.00 | 50.46 |
| 2788 | O | ASP | 302 | 103.480 | 50.114 | 49.615 | 1.00 | 51.17 |
| 2789 | CB | ASP | 302 | 106.587 | 50.017 | 48.487 | 1.00 | 55.75 |
| 2790 | CG | ASP | 302 | 107.904 | 49.271 | 48.619 | 1.00 | 62.15 |
| 2791 | OD1 | ASP | 302 | 107.922 | 48.165 | 49.207 | 1.00 | 63.08 |
| 2792 | OD2 | ASP | 302 | 108.928 | 49.798 | 48.133 | 1.00 | 68.25 |
| 2793 | H | ASP | 302 | 106.056 | 48.281 | 46.704 | 1.00 | 25.00 |

TABLE 11-continued

Structural Coordinates of Tobacco 5-Epi-Aristolochene Synthase
In the Absence of Bound Substrate

| Atom | Atom | Resi- | Resi- | X | Y | Z | OCC | B-factor |
|---|---|---|---|---|---|---|---|---|
| 2794 | N | THR | 303 | 103.684 | 50.388 | 47.383 | 1.00 | 50.52 |
| 2795 | CA | THR | 303 | 102.479 | 51.192 | 47.230 | 1.00 | 50.05 |
| 2796 | C | THR | 303 | 101.260 | 50.472 | 47.808 | 1.00 | 51.84 |
| 2797 | O | THR | 303 | 100.563 | 51.013 | 48.668 | 1.00 | 56.07 |
| 2798 | CB | THR | 303 | 102.222 | 51.512 | 45.745 | 1.00 | 50.09 |
| 2799 | OG1 | THR | 303 | 103.377 | 52.153 | 45.190 | 1.00 | 45.79 |
| 2800 | CG2 | THR | 303 | 101.015 | 52.425 | 45.593 | 1.00 | 50.31 |
| 2801 | H | THR | 303 | 104.219 | 50.190 | 46.581 | 1.00 | 25.00 |
| 2802 | HG1 | THR | 303 | 103.480 | 52.938 | 45.719 | 1.00 | 25.00 |
| 2803 | N | PHE | 304 | 101.025 | 49.246 | 47.352 | 1.00 | 50.29 |
| 2804 | CA | PHE | 304 | 99.893 | 48.450 | 47.817 | 1.00 | 53.29 |
| 2805 | C | PHE | 304 | 99.997 | 48.024 | 49.275 | 1.00 | 59.68 |
| 2806 | O | PHE | 304 | 98.981 | 47.832 | 49.940 | 1.00 | 62.17 |
| 2807 | CB | PHE | 304 | 99.744 | 47.182 | 46.971 | 1.00 | 43.62 |
| 2808 | CG | PHE | 304 | 99.065 | 47.398 | 45.654 | 1.00 | 37.53 |
| 2809 | CD1 | PHE | 304 | 99.780 | 47.857 | 44.555 | 1.00 | 32.17 |
| 2810 | CD2 | PHE | 304 | 97.711 | 47.113 | 45.506 | 1.00 | 35.92 |
| 2811 | CE1 | PHE | 304 | 99.156 | 48.029 | 43.326 | 1.00 | 36.26 |
| 2812 | CE2 | PHE | 304 | 97.079 | 47.280 | 44.283 | 1.00 | 29.26 |
| 2813 | CZ | PHE | 304 | 97.802 | 47.739 | 43.189 | 1.00 | 34.73 |
| 2814 | H | PHE | 304 | 101.636 | 48.860 | 46.683 | 1.00 | 25.00 |
| 2815 | N | ASP | 305 | 101.223 | 47.873 | 49.765 | 1.00 | 69.36 |
| 2816 | CA | ASP | 305 | 101.450 | 47.405 | 51.129 | 1.00 | 78.46 |
| 2817 | C | ASP | 305 | 101.326 | 48.406 | 52.279 | 1.00 | 80.92 |
| 2818 | O | ASP | 305 | 100.774 | 48.064 | 53.329 | 1.00 | 79.13 |
| 2819 | CB | ASP | 305 | 102.798 | 46.675 | 51.210 | 1.00 | 84.84 |
| 2820 | CG | ASP | 305 | 102.851 | 45.663 | 52.345 | 1.00 | 90.63 |
| 2821 | OD1 | ASP | 305 | 102.142 | 44.635 | 52.265 | 1.00 | 90.70 |
| 2822 | OD2 | ASP | 305 | 103.610 | 45.891 | 53.312 | 1.00 | 92.23 |
| 2823 | H | ASP | 305 | 101.996 | 48.072 | 49.197 | 1.00 | 25.00 |
| 2824 | N | ALA | 306 | 101.818 | 49.631 | 52.104 | 1.00 | 84.70 |
| 2825 | CA | ALA | 306 | 101.752 | 50.595 | 53.201 | 1.00 | 89.65 |
| 2826 | C | ALA | 306 | 101.457 | 52.057 | 52.874 | 1.00 | 91.11 |
| 2827 | O | ALA | 306 | 101.606 | 52.916 | 53.745 | 1.00 | 93.41 |
| 2828 | CB | ALA | 306 | 103.027 | 50.500 | 54.040 | 1.00 | 89.50 |
| 2829 | H | ALA | 306 | 102.229 | 49.879 | 51.249 | 1.00 | 25.00 |
| 2830 | N | TYR | 307 | 101.022 | 52.359 | 51.655 | 1.00 | 90.94 |
| 2831 | CA | TYR | 307 | 100.743 | 53.752 | 51.329 | 1.00 | 92.48 |
| 2832 | C | TYR | 307 | 99.374 | 54.011 | 50.701 | 1.00 | 90.37 |
| 2833 | O | TYR | 307 | 98.599 | 54.824 | 51.207 | 1.00 | 91.55 |
| 2834 | CB | TYR | 307 | 101.858 | 54.336 | 50.453 | 1.00 | 98.27 |
| 2835 | CG | TYR | 307 | 102.031 | 55.837 | 50.609 | 1.00 | 106.75 |
| 2836 | CD1 | TYR | 307 | 101.301 | 56.732 | 49.825 | 1.00 | 109.71 |
| 2837 | CD2 | TYR | 307 | 102.918 | 56.364 | 51.552 | 1.00 | 107.24 |
| 2838 | CE1 | TYR | 307 | 101.447 | 58.113 | 49.973 | 1.00 | 107.24 |
| 2839 | CE2 | TYR | 307 | 103.072 | 57.744 | 51.708 | 1.00 | 106.57 |
| 2840 | CZ | TYR | 307 | 102.332 | 58.611 | 50.915 | 1.00 | 106.75 |
| 2841 | OH | TYR | 307 | 102.477 | 59.971 | 51.060 | 1.00 | 103.97 |
| 2842 | H | TYR | 307 | 100.876 | 51.657 | 50.988 | 1.00 | 25.00 |
| 2843 | HH | TYR | 307 | 101.900 | 60.427 | 50.443 | 1.00 | 25.00 |
| 2844 | N | GLY | 308 | 99.079 | 53.325 | 49.603 | 1.00 | 85.79 |
| 2845 | CA | GLY | 308 | 97.808 | 53.522 | 48.930 | 1.00 | 82.54 |
| 2846 | C | GLY | 308 | 96.583 | 53.120 | 49.730 | 1.00 | 81.67 |
| 2847 | O | GLY | 308 | 96.589 | 52.105 | 50.428 | 1.00 | 80.43 |
| 2848 | H | GLY | 308 | 99.710 | 52.666 | 49.258 | 1.00 | 25.00 |
| 2849 | N | THR | 309 | 95.531 | 53.928 | 49.637 | 1.00 | 82.42 |
| 2850 | CA | THR | 309 | 94.282 | 53.649 | 50.338 | 1.00 | 82.64 |
| 2851 | C | THR | 309 | 93.397 | 52.796 | 49.433 | 1.00 | 83.27 |
| 2852 | O | THR | 309 | 93.592 | 52.771 | 48.215 | 1.00 | 87.28 |
| 2853 | CB | THR | 309 | 93.519 | 54.946 | 50.696 | 1.00 | 80.48 |
| 2854 | OG1 | THR | 309 | 93.166 | 55.648 | 49.495 | 1.00 | 74.90 |
| 2855 | CG2 | THR | 309 | 94.371 | 55.844 | 51.583 | 1.00 | 75.37 |
| 2856 | H | THR | 309 | 95.600 | 54.729 | 49.085 | 1.00 | 25.00 |
| 2857 | HG1 | THR | 309 | 92.598 | 55.106 | 48.954 | 1.00 | 25.00 |
| 2858 | N | VAL | 310 | 92.383 | 52.172 | 50.025 | 1.00 | 80.18 |
| 2859 | CA | VAL | 310 | 91.447 | 51.304 | 49.309 | 1.00 | 75.06 |
| 2860 | C | VAL | 310 | 91.067 | 51.822 | 47.919 | 1.00 | 74.05 |
| 2861 | O | VAL | 310 | 91.209 | 51.115 | 46.921 | 1.00 | 73.13 |
| 2862 | CB | VAL | 310 | 90.149 | 51.103 | 50.127 | 1.00 | 79.21 |
| 2863 | CG1 | VAL | 310 | 89.284 | 50.020 | 49.494 | 1.00 | 80.28 |
| 2864 | CG2 | VAL | 310 | 90.478 | 50.760 | 51.575 | 1.00 | 78.07 |
| 2865 | H | VAL | 310 | 92.275 | 52.293 | 50.987 | 1.00 | 25.00 |
| 2866 | N | LYS | 311 | 90.622 | 53.072 | 47.859 | 1.00 | 73.34 |
| 2867 | CA | LYS | 311 | 90.210 | 53.682 | 46.600 | 1.00 | 71.58 |
| 2868 | C | LYS | 311 | 91.366 | 53.946 | 45.639 | 1.00 | 67.72 |
| 2869 | O | LYS | 311 | 91.269 | 53.642 | 44.448 | 1.00 | 65.13 |
| 2870 | CB | LYS | 311 | 89.433 | 54.977 | 46.866 | 1.00 | 79.85 |
| 2871 | CG | LYS | 311 | 87.977 | 54.774 | 47.306 | 1.00 | 89.57 |
| 2872 | CD | LYS | 311 | 87.842 | 53.976 | 48.607 | 1.00 | 98.38 |
| 2873 | CE | LYS | 311 | 88.473 | 54.694 | 49.795 | 1.00 | 102.39 |
| 2874 | NZ | LYS | 311 | 87.808 | 55.997 | 50.082 | 1.00 | 107.12 |
| 2875 | H | LYS | 311 | 90.572 | 53.594 | 48.679 | 1.00 | 25.00 |
| 2876 | 1HZ | LYS | 311 | 87.884 | 56.617 | 49.250 | 1.00 | 25.00 |
| 2877 | 2HZ | LYS | 311 | 86.804 | 55.833 | 50.299 | 1.00 | 25.00 |
| 2878 | 3HZ | LYS | 311 | 88.268 | 56.452 | 50.896 | 1.00 | 25.00 |
| 2879 | N | GLU | 312 | 92.461 | 54.495 | 46.162 | 1.00 | 64.41 |
| 2880 | CA | GLU | 312 | 93.634 | 54.805 | 45.346 | 1.00 | 61.39 |
| 2881 | C | GLU | 312 | 94.189 | 53.556 | 44.667 | 1.00 | 61.26 |
| 2882 | O | GLU | 312 | 94.533 | 53.585 | 43.483 | 1.00 | 59.48 |
| 2883 | CB | GLU | 312 | 94.724 | 55.465 | 46.194 | 1.00 | 63.39 |
| 2884 | CG | GLU | 312 | 94.348 | 56.830 | 46.748 | 1.00 | 70.79 |
| 2885 | CD | GLU | 312 | 95.456 | 57.456 | 47.578 | 1.00 | 75.21 |
| 2886 | OE1 | GLU | 312 | 95.879 | 56.840 | 48.579 | 1.00 | 77.19 |
| 2887 | OE2 | GLU | 312 | 95.903 | 58.570 | 47.233 | 1.00 | 79.86 |
| 2888 | H | GLU | 312 | 92.482 | 54.687 | 47.128 | 1.00 | 25.00 |
| 2889 | N | LEU | 313 | 94.257 | 52.459 | 45.418 | 1.00 | 57.55 |
| 2890 | CA | LEU | 313 | 94.765 | 51.198 | 44.891 | 1.00 | 52.69 |
| 2891 | C | LEU | 313 | 93.885 | 50.678 | 43.762 | 1.00 | 52.82 |
| 2892 | O | LEU | 313 | 94.391 | 50.281 | 42.713 | 1.00 | 51.15 |
| 2893 | CB | LEU | 313 | 94.883 | 50.158 | 46.005 | 1.00 | 48.63 |
| 2894 | CG | LEU | 313 | 95.886 | 50.519 | 47.102 | 1.00 | 46.47 |
| 2895 | CD1 | LEU | 313 | 95.941 | 49.416 | 48.140 | 1.00 | 48.38 |
| 2896 | CD2 | LEU | 313 | 97.259 | 50.748 | 46.495 | 1.00 | 48.00 |
| 2897 | H | LEU | 313 | 93.952 | 52.495 | 46.346 | 1.00 | 25.00 |
| 2898 | N | GLU | 314 | 92.569 | 50.724 | 43.957 | 1.00 | 52.92 |
| 2899 | CA | GLU | 314 | 91.634 | 50.269 | 42.933 | 1.00 | 54.92 |
| 2900 | C | GLU | 314 | 91.840 | 51.087 | 41.651 | 1.00 | 52.05 |
| 2901 | O | GLU | 314 | 91.801 | 50.548 | 40.541 | 1.00 | 49.73 |
| 2902 | CB | GLU | 314 | 90.189 | 50.400 | 43.431 | 1.00 | 58.82 |
| 2903 | CG | GLU | 314 | 89.137 | 49.809 | 42.488 | 1.00 | 68.28 |
| 2904 | CD | GLU | 314 | 89.281 | 48.303 | 42.292 | 1.00 | 74.40 |
| 2905 | OE1 | GLU | 314 | 89.097 | 47.550 | 43.275 | 1.00 | 76.74 |
| 2906 | OE2 | GLU | 314 | 89.568 | 47.871 | 41.152 | 1.00 | 74.09 |
| 2907 | H | GLU | 314 | 92.221 | 51.057 | 44.810 | 1.00 | 25.00 |
| 2908 | N | ALA | 315 | 92.088 | 52.383 | 41.813 | 1.00 | 51.92 |
| 2909 | CA | ALA | 315 | 92.323 | 53.270 | 40.678 | 1.00 | 54.57 |
| 2910 | C | ALA | 315 | 93.649 | 52.920 | 39.993 | 1.00 | 51.51 |
| 2911 | O | ALA | 315 | 93.762 | 52.977 | 38.753 | 1.00 | 49.98 |
| 2912 | CB | ALA | 315 | 92.335 | 54.722 | 41.142 | 1.00 | 52.19 |
| 2913 | H | ALA | 315 | 92.103 | 52.753 | 42.723 | 1.00 | 25.00 |
| 2914 | N | TYR | 316 | 94.640 | 52.542 | 40.796 | 1.00 | 49.90 |
| 2915 | CA | TYR | 316 | 95.960 | 52.177 | 40.289 | 1.00 | 46.00 |
| 2916 | C | TYR | 316 | 95.911 | 50.864 | 39.506 | 1.00 | 42.05 |
| 2917 | O | TYR | 316 | 96.503 | 50.756 | 38.424 | 1.00 | 36.96 |
| 2918 | CB | TYR | 316 | 96.954 | 52.070 | 41.445 | 1.00 | 48.32 |
| 2919 | CG | TYR | 316 | 98.405 | 52.154 | 41.029 | 1.00 | 52.17 |
| 2920 | CD1 | TYR | 316 | 98.975 | 53.371 | 40.657 | 1.00 | 53.66 |
| 2921 | CD2 | TYR | 316 | 99.218 | 51.023 | 41.033 | 1.00 | 58.41 |
| 2922 | CE1 | TYR | 316 | 100.320 | 53.461 | 40.303 | 1.00 | 56.28 |
| 2923 | CE2 | TYR | 316 | 100.566 | 51.101 | 40.681 | 1.00 | 63.22 |
| 2924 | CZ | TYR | 316 | 101.110 | 52.323 | 40.319 | 1.00 | 58.59 |
| 2925 | OH | TYR | 316 | 102.442 | 52.405 | 39.986 | 1.00 | 51.77 |
| 2926 | H | TYR | 316 | 94.483 | 52.514 | 41.763 | 1.00 | 25.00 |
| 2927 | HH | TYR | 316 | 102.631 | 53.311 | 39.758 | 1.00 | 25.00 |
| 2928 | N | THR | 317 | 95.186 | 49.881 | 40.040 | 1.00 | 38.98 |
| 2929 | CA | THR | 317 | 95.044 | 48.574 | 39.396 | 1.00 | 40.08 |
| 2930 | C | THR | 317 | 94.391 | 48.732 | 38.025 | 1.00 | 41.19 |
| 2931 | O | THR | 317 | 94.755 | 48.046 | 37.065 | 1.00 | 40.64 |
| 2932 | CB | THR | 317 | 94.189 | 47.619 | 40.245 | 1.00 | 39.21 |
| 2933 | OG1 | THR | 317 | 94.658 | 47.632 | 41.598 | 1.00 | 40.99 |
| 2934 | CG2 | THR | 317 | 94.277 | 46.198 | 39.698 | 1.00 | 41.75 |
| 2935 | H | THR | 317 | 94.740 | 50.022 | 40.900 | 1.00 | 25.00 |
| 2936 | HG1 | THR | 317 | 94.120 | 47.056 | 42.134 | 1.00 | 25.00 |
| 2937 | N | ASP | 318 | 93.423 | 49.641 | 37.945 | 1.00 | 46.22 |
| 2938 | CA | ASP | 318 | 92.719 | 49.920 | 36.700 | 1.00 | 44.99 |
| 2939 | C | ASP | 318 | 93.631 | 50.595 | 35.693 | 1.00 | 38.74 |

TABLE 11-continued

Structural Coordinates of Tobacco 5-Epi-Aristolochene Synthase In the Absence of Bound Substrate

| Atom Type | Atom | Resi-due | Resi-due # | X | Y | Z | OCC | B-factor |
|---|---|---|---|---|---|---|---|---|
| 2940 | O | ASP | 318 | 93.695 | 50.183 | 34.536 | 1.00 | 39.12 |
| 2941 | CB | ASP | 318 | 91.497 | 50.799 | 36.959 | 1.00 | 55.80 |
| 2942 | CG | ASP | 318 | 90.215 | 50.006 | 36.977 | 1.00 | 64.67 |
| 2943 | OD1 | ASP | 318 | 89.924 | 49.364 | 38.010 | 1.00 | 73.33 |
| 2944 | OD2 | ASP | 318 | 89.507 | 50.014 | 35.948 | 1.00 | 72.06 |
| 2945 | H | ASP | 318 | 93.171 | 50.138 | 38.755 | 1.00 | 25.00 |
| 2946 | N | ALA | 319 | 94.340 | 51.628 | 36.135 | 1.00 | 37.74 |
| 2947 | CA | ALA | 319 | 95.258 | 52.347 | 35.260 | 1.00 | 40.21 |
| 2948 | C | ALA | 319 | 96.245 | 51.360 | 34.644 | 1.00 | 42.98 |
| 2949 | O | ALA | 319 | 96.528 | 51.422 | 33.446 | 1.00 | 41.24 |
| 2950 | CB | ALA | 319 | 95.995 | 53.426 | 36.039 | 1.00 | 42.19 |
| 2951 | H | ALA | 319 | 94.240 | 51.923 | 37.067 | 1.00 | 25.00 |
| 2952 | N | ILE | 320 | 96.727 | 50.423 | 35.462 | 1.00 | 41.94 |
| 2953 | CA | ILE | 320 | 97.670 | 49.403 | 35.005 | 1.00 | 40.80 |
| 2954 | C | ILE | 320 | 97.064 | 48.488 | 33.934 | 1.00 | 37.20 |
| 2955 | O | ILE | 320 | 97.711 | 48.200 | 32.923 | 1.00 | 31.26 |
| 2956 | CB | ILE | 320 | 98.198 | 48.549 | 36.191 | 1.00 | 40.22 |
| 2957 | CG1 | ILE | 320 | 99.093 | 49.404 | 37.091 | 1.00 | 38.13 |
| 2958 | CG2 | ILE | 320 | 98.973 | 47.332 | 35.680 | 1.00 | 36.19 |
| 2959 | CD1 | ILE | 320 | 100.340 | 49.924 | 36.392 | 1.00 | 35.64 |
| 2960 | H | ILE | 320 | 96.447 | 50.429 | 36.402 | 1.00 | 25.00 |
| 2961 | N | GLN | 321 | 95.830 | 48.037 | 34.149 | 1.00 | 37.70 |
| 2962 | CA | GLN | 321 | 95.167 | 47.161 | 33.180 | 1.00 | 13.79 |
| 2963 | C | GLN | 321 | 94.959 | 47.367 | 31.839 | 1.00 | 44.60 |
| 2964 | O | GLN | 321 | 95.104 | 47.254 | 30.777 | 1.00 | 43.29 |
| 2965 | CB | GLN | 321 | 93.818 | 46.662 | 33.713 | 1.00 | 45.39 |
| 2966 | CG | GLN | 321 | 93.879 | 45.997 | 35.079 | 1.00 | 50.49 |
| 2967 | CD | GLN | 321 | 94.981 | 44.963 | 35.182 | 1.00 | 52.12 |
| 2968 | OE1 | GLN | 321 | 95.097 | 44.073 | 34.341 | 1.00 | 53.96 |
| 2969 | NE2 | GLN | 321 | 95.801 | 45.078 | 36.220 | 1.00 | 49.92 |
| 2970 | H | GLN | 321 | 95.360 | 48.301 | 34.967 | 1.00 | 25.00 |
| 2971 | 1HE2 | GLN | 321 | 96.511 | 44.405 | 36.295 | 1.00 | 25.00 |
| 2972 | 2HE2 | GLN | 321 | 95.664 | 45.810 | 36.855 | 1.00 | 25.00 |
| 2973 | N | ARG | 322 | 94.595 | 49.148 | 31.894 | 1.00 | 48.28 |
| 2974 | CA | ARG | 322 | 94.376 | 49.935 | 30.683 | 1.00 | 48.66 |
| 2975 | C | ARG | 322 | 95.697 | 50.181 | 29.976 | 1.00 | 48.74 |
| 2976 | O | ARG | 322 | 95.756 | 50.167 | 28.745 | 1.00 | 52.54 |
| 2977 | CB | ARG | 322 | 93.701 | 51.272 | 31.003 | 1.00 | 53.96 |
| 2978 | CG | ARG | 322 | 92.175 | 51.230 | 31.029 | 1.00 | 62.97 |
| 2979 | CD | ARG | 322 | 91.642 | 50.367 | 32.164 | 1.00 | 68.65 |
| 2980 | O | ARG | 322 | 90.183 | 50.288 | 32.167 | 1.00 | 71.23 |
| 2981 | CZ | ARG | 322 | 89.377 | 51.274 | 32.546 | 1.00 | 73.12 |
| 2982 | NH1 | ARG | 322 | 89.878 | 52.432 | 32.959 | 1.00 | 75.57 |
| 2983 | NH2 | ARG | 322 | 88.064 | 51.101 | 32.512 | 1.00 | 75.20 |
| 2984 | H | ARG | 322 | 94.477 | 49.570 | 32.771 | 1.00 | 25.00 |
| 2985 | HE | ARG | 322 | 89.771 | 49.449 | 31.873 | 1.00 | 25.00 |
| 2986 | 1HH1 | ARG | 322 | 90.868 | 52.574 | 32.983 | 1.00 | 25.00 |
| 2987 | 2HH1 | ARG | 322 | 89.263 | 53.172 | 33.235 | 1.00 | 25.00 |
| 2988 | 1HH2 | ARG | 322 | 87.684 | 50.229 | 32.203 | 1.00 | 25.00 |
| 2989 | 2HH2 | ARG | 322 | 87.455 | 51.842 | 32.793 | 1.00 | 25.00 |
| 2990 | N | TRP | 323 | 96.740 | 50.434 | 30.765 | 1.00 | 48.78 |
| 2991 | CA | TRP | 323 | 98.086 | 50.674 | 30.248 | 1.00 | 50.53 |
| 2992 | C | TRP | 323 | 98.036 | 51.721 | 29.139 | 1.00 | 51.62 |
| 2993 | O | TRP | 323 | 98.368 | 51.442 | 27.984 | 1.00 | 46.60 |
| 2994 | CB | TRP | 323 | 98.676 | 49.361 | 29.719 | 1.00 | 45.66 |
| 2995 | CG | TRP | 323 | 100.171 | 49.334 | 29.673 | 1.00 | 43.84 |
| 2996 | CD1 | TRP | 323 | 100.972 | 49.778 | 28.660 | 1.00 | 41.07 |
| 2997 | CD2 | TRP | 323 | 101.045 | 48.811 | 30.677 | 1.00 | 42.00 |
| 2998 | NE1 | TRP | 323 | 102.292 | 49.559 | 28.969 | 1.00 | 41.37 |
| 2999 | CE2 | TRP | 323 | 102.367 | 48.967 | 30.202 | 1.00 | 42.95 |
| 3000 | CE3 | TRP | 323 | 100.841 | 48.222 | 31.932 | 1.00 | 43.56 |
| 3001 | CZ2 | TRP | 323 | 103.483 | 48.555 | 30.939 | 1.00 | 41.64 |
| 3002 | CZ3 | TRP | 323 | 101.952 | 47.812 | 32.666 | 1.00 | 46.00 |
| 3003 | CH2 | TRP | 323 | 103.256 | 47.982 | 32.164 | 1.00 | 42.99 |
| 3004 | H | TRP | 323 | 96.604 | 50.455 | 31.735 | 1.00 | 25.90 |
| 3005 | HE1 | TRP | 323 | 103.052 | 49.790 | 28.396 | 1.00 | 25.00 |
| 3006 | N | ASP | 324 | 97.624 | 52.931 | 29.503 | 1.00 | 59.55 |
| 3007 | CA | ASP | 324 | 97.500 | 54.015 | 28.539 | 1.00 | 65.59 |
| 3008 | C | ASP | 324 | 98.480 | 55.143 | 28.844 | 1.00 | 64.51 |
| 3009 | O | ASP | 324 | 99.591 | 55.176 | 28.316 | 1.00 | 68.35 |
| 3010 | CB | ASP | 324 | 96.056 | 54.541 | 28.552 | 1.00 | 70.35 |
| 3011 | CG | ASP | 324 | 95.713 | 55.365 | 27.320 | 1.00 | 74.75 |
| 3012 | OD1 | ASP | 324 | 96.439 | 56.333 | 27.008 | 1.00 | 77.92 |
| 3013 | OD2 | ASP | 324 | 94.698 | 55.043 | 26.668 | 1.00 | 77.68 |
| 3014 | H | ASP | 324 | 97.422 | 53.067 | 30.447 | 1.00 | 25.00 |
| 3015 | N | ILE | 325 | 98.025 | 56.067 | 29.685 | 1.00 | 59.63 |
| 3016 | CA | ILE | 325 | 98.765 | 57.248 | 30.131 | 1.00 | 62.22 |
| 3017 | C | ILE | 325 | 97.699 | 58.281 | 30.472 | 1.00 | 62.36 |
| 3018 | O | ILE | 325 | 97.807 | 58.988 | 31.467 | 1.00 | 57.92 |
| 3019 | CB | ILE | 325 | 99.752 | 57.824 | 29.066 | 1.00 | 58.28 |
| 3020 | CG1 | ILE | 325 | 100.656 | 58.874 | 29.713 | 1.00 | 56.91 |
| 3021 | CG2 | ILE | 325 | 99.004 | 58.424 | 27.882 | 1.00 | 53.60 |
| 3022 | CD1 | ILE | 325 | 101.760 | 59.364 | 28.812 | 1.00 | 65.51 |
| 3023 | H | ILE | 325 | 97.138 | 55.950 | 30.059 | 1.00 | 25.00 |
| 3024 | N | ASN | 326 | 96.622 | 58.287 | 29.687 | 1.00 | 64.69 |
| 3025 | CA | ASN | 326 | 95.504 | 59.203 | 29.902 | 1.00 | 68.20 |
| 3026 | C | ASN | 326 | 94.857 | 58.860 | 31.238 | 1.00 | 71.30 |
| 3027 | O | ASN | 326 | 94.171 | 59.684 | 31.846 | 1.00 | 76.27 |
| 3028 | CB | ASN | 326 | 94.462 | 59.058 | 28.787 | 1.00 | 67.58 |
| 3029 | CG | ASN | 326 | 95.041 | 59.297 | 27.406 | 1.00 | 69.04 |
| 3030 | OD1 | ASN | 326 | 96.055 | 59.975 | 27.225 | 1.00 | 68.18 |
| 3031 | ND2 | ASN | 326 | 94.410 | 58.716 | 26.395 | 1.00 | 67.11 |
| 3032 | H | ASN | 326 | 96.599 | 57.685 | 28.918 | 1.00 | 25.00 |
| 3033 | 1HD2 | ASN | 326 | 94.783 | 58.869 | 25.501 | 1.00 | 25.00 |
| 3034 | 2HD2 | ASN | 326 | 93.618 | 58.173 | 26.568 | 1.00 | 25.00 |
| 3035 | N | GLU | 327 | 95.095 | 57.631 | 31.691 | 1.00 | 70.98 |
| 3036 | CA | GLU | 327 | 94.553 | 57.144 | 32.952 | 1.00 | 69.92 |
| 3037 | C | GLU | 327 | 95.259 | 57.798 | 34.138 | 1.00 | 67.58 |
| 3038 | O | GLU | 327 | 94.751 | 57.777 | 35.260 | 1.00 | 68.23 |
| 3039 | CB | GLU | 327 | 94.709 | 55.622 | 33.034 | 1.00 | 69.72 |
| 3040 | CG | GLU | 327 | 94.147 | 54.858 | 31.838 | 1.00 | 66.84 |
| 3041 | CD | GLU | 327 | 92.650 | 55.040 | 31.659 | 1.00 | 69.61 |
| 3042 | OE1 | GLU | 327 | 91.899 | 54.845 | 32.639 | 1.00 | 69.86 |
| 3043 | OE2 | GLU | 327 | 92.225 | 55.369 | 30.530 | 1.00 | 66.87 |
| 3044 | H | GLU | 327 | 95.646 | 57.037 | 31.159 | 1.00 | 25.00 |
| 3045 | N | ILE | 328 | 96.411 | 58.407 | 33.872 | 1.00 | 64.07 |
| 3046 | CA | ILE | 328 | 97.212 | 59.065 | 34.901 | 1.00 | 63.90 |
| 3047 | C | ILE | 328 | 96.425 | 60.142 | 35.657 | 1.00 | 70.44 |
| 3048 | O | ILE | 328 | 96.624 | 60.338 | 36.857 | 1.00 | 69.65 |
| 3049 | CB | ILE | 328 | 98.508 | 59.669 | 34.286 | 1.00 | 56.23 |
| 3050 | CG1 | ILE | 328 | 99.578 | 59.844 | 35.359 | 1.00 | 56.00 |
| 3051 | CG2 | ILE | 328 | 98.223 | 61.007 | 33.618 | 1.00 | 53.09 |
| 3052 | CD1 | ILE | 328 | 100.948 | 60.162 | 34.799 | 1.00 | 58.67 |
| 3053 | H | ILE | 328 | 96.744 | 58.430 | 32.958 | 1.00 | 25.00 |
| 3054 | N | ASP | 329 | 95.487 | 60.780 | 34.961 | 1.00 | 75.68 |
| 3055 | CA | ASP | 329 | 94.659 | 61.844 | 35.531 | 1.00 | 79.88 |
| 3056 | C | ASP | 329 | 93.764 | 61.377 | 36.677 | 1.00 | 79.44 |
| 3057 | O | ASP | 329 | 93.303 | 62.188 | 37.483 | 1.00 | 79.71 |
| 3058 | CB | ASP | 329 | 93.796 | 62.476 | 34.435 | 1.00 | 85.36 |
| 3059 | CG | ASP | 329 | 94.608 | 62.912 | 33.226 | 1.00 | 90.96 |
| 3060 | OD1 | ASP | 329 | 95.719 | 63.461 | 33.409 | 1.00 | 93.02 |
| 3061 | OD2 | ASP | 329 | 94.133 | 62.699 | 32.090 | 1.00 | 93.14 |
| 3062 | H | ASP | 329 | 95.344 | 60.527 | 34.026 | 1.00 | 25.00 |
| 3063 | N | ARG | 330 | 93.501 | 60.074 | 36.730 | 1.00 | 76.85 |
| 3064 | CA | ARG | 330 | 92.658 | 59.501 | 37.775 | 1.00 | 75.38 |
| 3065 | C | ARG | 330 | 93.488 | 59.059 | 38.981 | 1.00 | 71.57 |
| 3066 | O | ARG | 330 | 92.935 | 58.631 | 39.998 | 1.00 | 69.70 |
| 3067 | CB | ARG | 330 | 91.881 | 58.300 | 37.227 | 1.00 | 75.33 |
| 3068 | CG | ARG | 330 | 91.177 | 58.562 | 35.905 | 1.00 | 78.99 |
| 3069 | CD | ARG | 330 | 90.383 | 57.350 | 35.454 | 1.00 | 80.32 |
| 3070 | NE | ARG | 330 | 89.861 | 57.517 | 34.100 | 1.00 | 86.31 |
| 3071 | CZ | ARG | 330 | 88.851 | 56.816 | 33.592 | 1.00 | 88.51 |
| 3072 | NH1 | ARG | 330 | 88.239 | 55.894 | 34.325 | 1.00 | 91.01 |
| 3073 | NH2 | ARG | 330 | 88.458 | 57.030 | 32.344 | 1.00 | 89.50 |
| 3074 | H | ARG | 330 | 93.891 | 59.477 | 36.060 | 1.00 | 25.00 |
| 3075 | HE | ARG | 330 | 90.281 | 58.188 | 33.523 | 1.00 | 25.00 |
| 3076 | 1HH1 | ARG | 330 | 88.533 | 55.723 | 35.265 | 1.00 | 25.00 |
| 3077 | 2HH1 | ARG | 330 | 87.475 | 55.375 | 33.942 | 1.00 | 25.00 |
| 3078 | 1HH2 | ARG | 330 | 88.917 | 57.720 | 31.786 | 1.00 | 25.00 |
| 3079 | 2HH2 | ARG | 330 | 87.692 | 56.508 | 31.966 | 1.00 | 25.00 |
| 3080 | N | LEU | 331 | 94.809 | 59.174 | 38.867 | 1.00 | 67.63 |
| 3081 | CA | LEU | 331 | 95.723 | 58.761 | 39.930 | 1.00 | 62.95 |
| 3082 | C | LEU | 331 | 96.290 | 59.919 | 40.735 | 1.00 | 60.42 |
| 3083 | O | LEU | 331 | 96.590 | 60.974 | 40.186 | 1.00 | 58.28 |
| 3084 | CB | LEU | 331 | 96.906 | 57.985 | 39.338 | 1.00 | 58.68 |
| 3085 | CG | LEU | 331 | 96.664 | 56.739 | 38.486 | 1.00 | 54.70 |

TABLE 11-continued

Structural Coordinates of Tobacco 5-Epi-Aristolochene Synthase In the Absence of Bound Substrate

| Atom Type | Atom | Residue | Residue # | X | Y | Z | OCC | B-factor |
|---|---|---|---|---|---|---|---|---|
| 3086 | CD1 | LEU | 331 | 97.992 | 56.255 | 37.941 | 1.00 | 46.64 |
| 3087 | CD2 | LEU | 331 | 95.988 | 55.654 | 39.304 | 1.00 | 48.82 |
| 3088 | H | LEU | 331 | 95.195 | 59.574 | 38.061 | 1.00 | 25.00 |
| 3089 | N | PRO | 332 | 96.426 | 59.743 | 42.058 | 1.00 | 57.70 |
| 3090 | CA | PRO | 332 | 96.981 | 60.814 | 42.886 | 1.00 | 58.87 |
| 3091 | C | PRO | 332 | 98.455 | 60.977 | 42.521 | 1.00 | 61.32 |
| 3092 | O | PRO | 332 | 99.132 | 59.997 | 42.207 | 1.00 | 63.75 |
| 3093 | CB | PRO | 332 | 96.800 | 60.278 | 44.307 | 1.00 | 58..32 |
| 3094 | CG | PRO | 332 | 96.819 | 58.793 | 44.122 | 1.00 | 60.80 |
| 3095 | CD | PRO | 332 | 95.978 | 58.616 | 42.892 | 1.00 | 59.09 |
| 3096 | N | ASP | 333 | 98.944 | 62.210 | 42.585 | 1.00 | 68.56 |
| 3097 | CA | ASP | 333 | 100.324 | 62.554 | 42.237 | 1.00 | 71.37 |
| 3098 | C | ASP | 333 | 101.432 | 61.520 | 42.437 | 1.00 | 68.42 |
| 3099 | O | ASP | 333 | 102.188 | 61.247 | 41.504 | 1.00 | 65.66 |
| 3100 | CB | ASP | 333 | 100.715 | 63.879 | 42.891 | 1.00 | 79.84 |
| 3101 | CG | ASP | 333 | 99.967 | 65.057 | 42.298 | 1.00 | 86.67 |
| 3102 | OD1 | ASP | 333 | 100.442 | 65.608 | 41.283 | 1.00 | 91.38 |
| 3103 | OD2 | ASP | 333 | 98.897 | 65.418 | 42.834 | 1.00 | 90.77 |
| 3104 | H | ASP | 333 | 98.343 | 62.928 | 42.866 | 1.00 | 25.00 |
| 3105 | N | TYR | 334 | 101.538 | 60.936 | 43.627 | 1.00 | 65.59 |
| 3106 | CA | TYR | 334 | 1022.588 | 59.953 | 43.861 | 1.00 | 63.25 |
| 3107 | C | TYR | 334 | 102.455 | 58.740 | 42.938 | 1.00 | 60.61 |
| 3108 | O | TYR | 334 | 103.452 | 58.243 | 42.411 | 1.00 | 63.00 |
| 3109 | CB | TYR | 334 | 102.664 | 59.545 | 45.341 | 1.00 | 65.74 |
| 3110 | CC | TYR | 334 | 101.539 | 58.674 | 45.852 | 1.00 | 68.46 |
| 3111 | CD1 | TYR | 334 | 100.343 | 59.232 | 46.303 | 1.00 | 69.57 |
| 3112 | CD2 | TYR | 334 | 101.690 | 57.289 | 45.929 | 1.00 | 68.64 |
| 3113 | CE1 | TYR | 334 | 99.326 | 58.432 | 46.824 | 1.00 | 69.54 |
| 3114 | CE2 | TYR | 334 | 100.682 | 56.482 | 46.446 | 1.00 | 69.64 |
| 3115 | CZ | TYR | 334 | 99.504 | 57.058 | 46.892 | 1.00 | 70.47 |
| 3116 | OH | TYR | 334 | 98.515 | 56.257 | 47.413 | 1.00 | 68.60 |
| 3117 | H | TYR | 334 | 100.910 | 61.170 | 44.337 | 1.00 | 25.00 |
| 3118 | HH | TYR | 334 | 97.786 | 56.812 | 47.691 | 1.00 | 25.00 |
| 3119 | N | MET | 335 | 101.220 | 58.311 | 42.691 | 1.00 | 51.84 |
| 3120 | CA | MET | 335 | 100.977 | 57.174 | 41.809 | 1.00 | 46.91 |
| 3121 | C | MET | 335 | 101.236 | 57.558 | 40.356 | 1.00 | 46.00 |
| 3122 | O | MET | 335 | 101.540 | 56.701 | 39.525 | 1.00 | 49.65 |
| 3123 | CB | MET | 335 | 99.552 | 56.646 | 41.969 | 1.00 | 41.83 |
| 3124 | CG | MET | 335 | 99.268 | 56.054 | 43.333 | 1.00 | 37.39 |
| 3125 | SD | MET | 335 | 97.625 | 55.322 | 43.450 | 1.00 | 44.89 |
| 3126 | CE | MET | 335 | 97.914 | 54.042 | 44.666 | 1.00 | 45.77 |
| 3127 | H | MET | 335 | 100.460 | 58.772 | 43.094 | 1.00 | 25.00 |
| 3128 | N | LYS | 336 | 101.122 | 58.848 | 40.052 | 1.00 | 47.61 |
| 3129 | CA | LYS | 336 | 101.366 | 59.340 | 38.699 | 1.00 | 48.27 |
| 3130 | C | LYS | 336 | 102.836 | 59.143 | 38.325 | 1.00 | 46.89 |
| 3131 | O | LYS | 336 | 103.161 | 58.829 | 37.177 | 1.00 | 49.33 |
| 3132 | CB | LYS | 336 | 101.000 | 60.824 | 38.588 | 1.00 | 51.58 |
| 3133 | CG | LYS | 336 | 99.517 | 61.132 | 38.743 | 1.00 | 54.94 |
| 3134 | CD | LYS | 336 | 99.233 | 62.600 | 38.446 | 1.00 | 60.67 |
| 3135 | CE | LYS | 336 | 97.739 | 62.882 | 38.431 | 1.00 | 63.81 |
| 3136 | NZ | LYS | 336 | 97.404 | 64.287 | 38.083 | 1.00 | 68.16 |
| 3137 | H | LYS | 336 | 100.869 | 59.485 | 40.750 | 1.00 | 25.00 |
| 3138 | 1HZ | LYS | 336 | 97.836 | 64.931 | 38.776 | 1.00 | 25.00 |
| 3139 | 2HZ | LYS | 336 | 97.770 | 64.503 | 37.134 | 1.00 | 25.00 |
| 3140 | 3HZ | LYS | 336 | 96.371 | 64.409 | 38.092 | 1.00 | 25.00 |
| 3141 | N | ILE | 337 | 103.719 | 59.321 | 39.303 | 1.00 | 44.56 |
| 3142 | CA | ILE | 337 | 105.154 | 59.162 | 39.089 | 1.00 | 47.99 |
| 3143 | C | ILE | 337 | 105.469 | 57.701 | 38.782 | 1.00 | 50.21 |
| 3144 | O | ILE | 3337 | 106.153 | 57.400 | 37.800 | 1.00 | 52.97 |
| 3145 | CB | ILE | 337 | 105.957 | 59.595 | 40.336 | 1.00 | 51.57 |
| 3146 | CG1 | ILE | 337 | 105.533 | 61.001 | 40.770 | 1.00 | 54.20 |
| 3147 | CG2 | ILE | 337 | 107.455 | 59.569 | 40.034 | 1.00 | 49.66 |
| 3148 | CD1 | ILE | 337 | 106.048 | 61.406 | 42.131 | 1.00 | 53.35 |
| 3149 | H | ILE | 337 | 103.390 | 59.566 | 40.195 | 1.00 | 25.00 |
| 3150 | N | SER | 338 | 104.951 | 56.802 | 39.618 | 1.00 | 46.40 |
| 3151 | CA | SER | 338 | 105.161 | 55.364 | 39.458 | 1.00 | 41.92 |
| 3152 | C | SER | 338 | 104.640 | 54.905 | 38.098 | 1.00 | 39.82 |
| 3153 | O | SER | 338 | 105.385 | 54.347 | 37.286 | 1.00 | 36.78 |
| 3154 | CB | SER | 338 | 104.423 | 54.598 | 40.560 | 1.00 | 37.35 |
| 3155 | OG | SER | 338 | 104.502 | 55.268 | 41.805 | 1.00 | 52.45 |
| 3156 | H | SER | 338 | 104.411 | 57.109 | 40.381 | 1.00 | 25.00 |
| 3157 | HG | SER | 338 | 105.419 | 55.324 | 42.084 | 1.00 | 25.00 |
| 3158 | N | TYR | 339 | 103.363 | 55.183 | 37.848 | 1.00 | 39.53 |
| 3159 | CA | TYR | 339 | 102.697 | 54.804 | 36.606 | 1.00 | 40.68 |
| 3160 | C | TYR | 339 | 103.468 | 55.247 | 35.362 | 1.00 | 39.79 |
| 3161 | O | TYR | 339 | 103.719 | 54.444 | 34.458 | 1.00 | 39.78 |
| 3162 | CB | TYR | 339 | 101.272 | 55.374 | 36.586 | 1.00 | 39.96 |
| 3163 | CG | TYR | 339 | 100.388 | 54.833 | 35.480 | 1.00 | 44.71 |
| 3164 | CD1 | TYR | 339 | 99.948 | 53.507 | 35.494 | 1.00 | 40.18 |
| 3165 | CD2 | TYR | 339 | 99.992 | 55.646 | 34.416 | 1.00 | 42.64 |
| 3166 | CE1 | TYR | 339 | 99.136 | 53.004 | 34.475 | 1.00 | 40.02 |
| 3167 | CE2 | TYR | 339 | 99.180 | 55.151 | 33.393 | 1.00 | 46.52 |
| 3168 | CZ | TYR | 339 | 98.758 | 53.830 | 33.431 | 1.00 | 40.74 |
| 3169 | OH | TYR | 339 | 97.968 | 53.3422 | 32.417 | 1.00 | 44.28 |
| 3170 | H | TYR | 339 | 102.843 | 55.668 | 38.522 | 1.00 | 25.00 |
| 3171 | HH | TYR | 339 | 97.819 | 54.042 | 31.792 | 1.00 | 25.00 |
| 3172 | N | LYS | 340 | 103.864 | 56.515 | 35.324 | 1.00 | 42.19 |
| 3173 | CA | LYS | 340 | 104.599 | 57.032 | 34.179 | 1.00 | 42.37 |
| 3174 | C | LYS | 340 | 105.930 | 56.306 | 33.992 | 1.00 | 40.71 |
| 3175 | O | LYS | 340 | 106.264 | 55.885 | 32.882 | 1.00 | 41.93 |
| 3176 | CB | LYS | 340 | 104.826 | 58.541 | 34.306 | 1.00 | 48.48 |
| 3177 | CG | LYS | 340 | 105.461 | 59.136 | 33.063 | 1.00 | 61.36 |
| 3178 | CD | LYS | 340 | 105.412 | 60.647 | 33.041 | 1.00 | 76.14 |
| 3179 | CE | LYS | 340 | 105.947 | 61.164 | 31.713 | 1.00 | 85.02 |
| 3180 | NZ | LYS | 340 | 105.783 | 62.636 | 31.566 | 1.00 | 94.84 |
| 3181 | H | LYS | 340 | 103.661 | 57.115 | 36.074 | 1.00 | 25.00 |
| 3182 | 1HZ | LYS | 340 | 104.774 | 62.881 | 31.624 | 1.00 | 25.00 |
| 3183 | 2HZ | LYS | 340 | 106.302 | 63.119 | 32.327 | 1.00 | 25.00 |
| 3184 | 3HZ | LYS | 340 | 106.160 | 62.937 | 30.645 | 1.00 | 25.00 |
| 3185 | N | ALA | 341 | 106.668 | 56.134 | 35.084 | 1.00 | 40.84 |
| 3186 | CA | ALA | 341 | 107.963 | 55.455 | 35.052 | 1.00 | 36.82 |
| 3187 | C | ALA | 341 | 107.837 | 54.053 | 34.469 | 1.00 | 35.10 |
| 3188 | O | ALA | 341 | 108.657 | 53.635 | 33.650 | 1.00 | 34.92 |
| 3189 | CB | ALA | 341 | 108.548 | 55.388 | 36.451 | 1.00 | 37.09 |
| 3190 | H | ALA | 341 | 106.336 | 56.478 | 35.942 | 1.00 | 25.00 |
| 3191 | N | ILE | 342 | 106.796 | 53.338 | 34.884 | 1.00 | 32.81 |
| 3192 | CA | ILE | 342 | 106.547 | 51.983 | 34.409 | 1.00 | 31.78 |
| 3193 | C | ILE | 342 | 106.357 | 51.982 | 32.891 | 1.00 | 38.13 |
| 3194 | O | ILE | 342 | 107.061 | 51.269 | 32.163 | 1.00 | 37.84 |
| 3195 | CB | ILE | 342 | 105.306 | 51.377 | 35.109 | 1.00 | 27.44 |
| 3196 | CG1 | ILE | 342 | 105.585 | 51.219 | 36.606 | 1.00 | 30.45 |
| 3197 | CG2 | ILE | 342 | 104.943 | 50.031 | 34.499 | 1.00 | 29.34 |
| 3198 | CD1 | ILE | 342 | 104.399 | 50.759 | 37.420 | 1.00 | 30.40 |
| 3199 | H | ILE | 342 | 106.179 | 53.740 | 35.532 | 1.00 | 25.00 |
| 3200 | N | LEU | 343 | 105.447 | 52.827 | 32.414 | 1.00 | 44.76 |
| 3201 | CA | LEU | 343 | 105.168 | 52.920 | 30.984 | 1.00 | 42.79 |
| 3202 | C | LEU | 343 | 106.428 | 53.290 | 30.214 | 1.00 | 40.23 |
| 3203 | O | LEU | 343 | 106.706 | 52.724 | 29.153 | 1.00 | 39.11 |
| 3204 | CB | LEU | 343 | 104.061 | 53.943 | 30.715 | 1.00 | 42.96 |
| 3205 | CG | LEU | 343 | 102.731 | 53.704 | 31.436 | 1.00 | 46.89 |
| 3206 | CD1 | LEU | 343 | 101.704 | 54.723 | 30.978 | 1.00 | 51.34 |
| 3207 | CD2 | LEU | 343 | 102.233 | 52.302 | 31.166 | 1.00 | 44.17 |
| 3208 | H | LEU | 343 | 104.954 | 53.403 | 33.039 | 1.00 | 25.00 |
| 3209 | N | ASP | 344 | 107.202 | 54.218 | 30.770 | 1.00 | 40.93 |
| 3210 | CA | ASP | 344 | 108.442 | 54.660 | 30.144 | 1.00 | 43.89 |
| 3211 | C | ASP | 344 | 109.443 | 53.515 | 30.053 | 1.00 | 43.08 |
| 3212 | O | ASP | 344 | 110.049 | 53.299 | 29.001 | 1.00 | 38.31 |
| 3213 | CB | ASP | 344 | 109.056 | 55.831 | 30.921 | 1.00 | 50.27 |
| 3214 | CG | ASP | 344 | 108.259 | 57.124 | 30.775 | 1.00 | 58.66 |
| 3215 | OD1 | ASP | 344 | 107.376 | 57.206 | 29.891 | 1.00 | 59.02 |
| 3216 | OD2 | ASP | 344 | 108.525 | 58.070 | 31.549 | 1.00 | 62.70 |
| 3217 | H | ASP | 344 | 106.928 | 54.612 | 31.623 | 1.00 | 25.00 |
| 3218 | N | LEU | 345 | 109.585 | 52.764 | 31.144 | 1.00 | 40.54 |
| 3219 | CA | LEU | 345 | 110.511 | 51.633 | 31.196 | 1.00 | 36.66 |
| 3220 | C | LEU | 345 | 110.256 | 50.661 | 30.048 | 1.00 | 36.17 |
| 3221 | O | LEU | 345 | 111.188 | 50.256 | 29.343 | 1.00 | 35.58 |
| 3222 | CB | LEU | 345 | 110.393 | 50.903 | 32.540 | 1.00 | 38.27 |
| 3223 | CG | LEU | 345 | 111.284 | 49.672 | 32.755 | 1.00 | 35.02 |
| 3224 | CD1 | LEU | 345 | 112.750 | 50.043 | 32.587 | 1.00 | 28.76 |
| 3225 | CD2 | LEU | 345 | 111.030 | 49.087 | 34.132 | 1.00 | 30.95 |
| 3226 | H | LEU | 345 | 109.050 | 52.975 | 31.934 | 1.00 | 25.00 |
| 3227 | N | TYR | 346 | 108.992 | 50.304 | 29.844 | 1.00 | 35.43 |
| 3228 | CA | TYR | 346 | 108.650 | 49.389 | 28.768 | 1.00 | 32.38 |
| 3229 | C | TYR | 346 | 108.906 | 49.969 | 27.388 | 1.00 | 34.86 |
| 3230 | O | TYR | 346 | 109.183 | 49.228 | 26.446 | 1.00 | 36.74 |
| 3231 | CB | TYR | 346 | 107.227 | 48.870 | 28.927 | 1.00 | 33.82 |

TABLE 11-continued

Structural Coordinates of Tobacco 5-Epi-Aristolochene Synthase
In the Absence of Bound Substrate

| Atom | Atom | Resi- | Resi- | | | | | |
|------|------|-------|-------|---|---|---|---|---|
| Type | Atom | due | due # | X | Y | Z | OCC | B-factor |
| 3232 | CG | TYR | 346 | 107.173 | 47.798 | 29.980 | 1.00 | 31.79 |
| 3233 | CD1 | TYR | 346 | 107.531 | 46.487 | 29.675 | 1.00 | 34.43 |
| 3234 | CD2 | TYR | 346 | 106.856 | 48.107 | 31.302 | 1.00 | 34.30 |
| 3235 | CE1 | TYR | 346 | 107.585 | 45.507 | 30.659 | 1.00 | 32.57 |
| 3236 | CE2 | TYR | 346 | 106.906 | 47.137 | 32.296 | 1.00 | 34.14 |
| 3237 | CZ | TYR | 346 | 107.275 | 45.839 | 31.965 | 1.00 | 34.31 |
| 3238 | OH | TYR | 346 | 107.351 | 44.878 | 32.938 | 1.00 | 32.03 |
| 3239 | H | TYR | 346 | 108.288 | 50.665 | 30.428 | 1.00 | 25.00 |
| 3240 | HH | TYR | 346 | 107.610 | 44.038 | 32.562 | 1.00 | 25.00 |
| 3241 | N | LYS | 347 | 108.861 | 51.295 | 27.276 | 1.00 | 44.24 |
| 3242 | CA | LYS | 347 | 109.143 | 51.955 | 26.004 | 1.00 | 44.41 |
| 3243 | C | LYS | 347 | 110.630 | 51.792 | 25.716 | 1.00 | 43.81 |
| 3244 | O | LYS | 347 | 111.030 | 51.558 | 24.572 | 1.00 | 42.39 |
| 3245 | CB | LYS | 347 | 108.762 | 53.437 | 26.060 | 1.00 | 51.50 |
| 3246 | CG | LYS | 347 | 107.268 | 53.672 | 25.945 | 1.00 | 55.25 |
| 3247 | CD | LYS | 347 | 106.759 | 53.062 | 24.650 | 1.00 | 59.99 |
| 3248 | CE | LYS | 347 | 105.251 | 52.978 | 24.608 | 1.00 | 60.17 |
| 3249 | NZ | LYS | 347 | 104.841 | 52.152 | 23.446 | 1.00 | 53.42 |
| 3250 | H | LYS | 347 | 108.627 | 51.840 | 28.057 | 1.00 | 25.00 |
| 3251 | 1HZ | LYS | 347 | 105.241 | 51.196 | 23.537 | 1.00 | 25.00 |
| 3252 | 2HZ | LYS | 347 | 103.803 | 52.090 | 23.409 | 1.00 | 25.00 |
| 3253 | 3HZ | LYS | 347 | 105.190 | 52.590 | 22.569 | 1.00 | 25.00 |
| 3254 | N | ASP | 348 | 111.439 | 51.874 | 26.771 | 1.00 | 45.04 |
| 3255 | CA | ASP | 348 | 112.884 | 51.712 | 26.654 | 1.00 | 47.19 |
| 3256 | C | ASP | 348 | 113.178 | 50.289 | 26.211 | 1.00 | 44.53 |
| 3257 | O | ASP | 348 | 113.992 | 50.074 | 25.316 | 1.00 | 46.94 |
| 3258 | CB | ASP | 348 | 113.582 | 51.981 | 27.991 | 1.00 | 55.77 |
| 3259 | CG | ASP | 348 | 113.469 | 53.430 | 28.441 | 1.00 | 63.79 |
| 3260 | OD1 | ASP | 348 | 113.017 | 54.288 | 27.648 | 1.00 | 66.77 |
| 3261 | OD2 | ASP | 348 | 113.846 | 53.710 | 29.600 | 1.00 | 65.20 |
| 3262 | H | ASP | 348 | 111.048 | 52.057 | 27.652 | 1.00 | 25.00 |
| 3263 | N | TYR | 349 | 112.507 | 49.321 | 26.835 | 1.00 | 39.87 |
| 3264 | CA | TYR | 349 | 112.692 | 47.913 | 26.491 | 1.00 | 40.93 |
| 3265 | C | TYR | 349 | 112.412 | 47.704 | 25.008 | 1.00 | 41.26 |
| 3266 | O | TYR | 349 | 113.189 | 47.051 | 24.302 | 1.00 | 40.44 |
| 3267 | CB | TYR | 349 | 111.752 | 47.015 | 27.310 | 1.00 | 35.88 |
| 3268 | CG | TYR | 349 | 112.115 | 46.841 | 28.773 | 1.00 | 33.98 |
| 3269 | CD1 | TYR | 349 | 113.396 | 47.144 | 29.250 | 1.00 | 29.99 |
| 3270 | CD2 | TYR | 349 | 111.172 | 46.360 | 29.680 | 1.00 | 27.01 |
| 3271 | CE1 | TYR | 349 | 113.723 | 45.971 | 30.596 | 1.00 | 27.43 |
| 3272 | CE2 | TYR | 349 | 111.485 | 46.162 | 31.021 | 1.00 | 32.24 |
| 3273 | CZ | TYR | 349 | 112.759 | 46.491 | 31.476 | 1.00 | 34.71 |
| 3274 | OH | TYR | 349 | 113.045 | 46.346 | 32.813 | 1.00 | 31.76 |
| 3275 | H | TYR | 349 | 111.880 | 49.567 | 27.549 | 1.00 | 25.00 |
| 3276 | HH | TYR | 349 | 112.295 | 45.961 | 33.270 | 1.00 | 25.00 |
| 3277 | N | GLU | 350 | 111.302 | 48.269 | 24.541 | 1.00 | 44.18 |
| 3278 | CA | GLU | 350 | 110.911 | 48.156 | 23.140 | 1.00 | 47.18 |
| 3279 | C | GLU | 350 | 111.972 | 43.767 | 22.235 | 1.00 | 45.46 |
| 3280 | O | GLU | 350 | 112.337 | 48.175 | 21.221 | 1.00 | 45.14 |
| 3281 | CB | GLU | 350 | 109.557 | 48.828 | 22.903 | 1.00 | 48.54 |
| 3282 | CG | GLU | 350 | 108.396 | 48.141 | 23.609 | 1.00 | 52.79 |
| 3283 | CD | GLLU | 350 | 107.076 | 48.883 | 23.473 | 1.00 | 59.87 |
| 3284 | OE1 | GLU | 350 | 107.070 | 50.040 | 23.000 | 1.00 | 66.09 |
| 3285 | OE2 | GLU | 350 | 106.037 | 48.304 | 23.852 | 1.00 | 65.68 |
| 3286 | H | GLU | 350 | 110.728 | 48.772 | 25.158 | 1.00 | 25.00 |
| 3287 | N | LYS | 351 | 112.497 | 49.923 | 22.636 | 1.00 | 48.01 |
| 3288 | CA | LYS | 351 | 113.530 | 50.618 | 21.871 | 1.00 | 51.81 |
| 3289 | C | LYS | 351 | 114.794 | 49.756 | 21.788 | 1.00 | 52.11 |
| 3290 | O | LYS | 351 | 115.311 | 49.505 | 20.696 | 1.00 | 48.04 |
| 3291 | CB | LYS | 351 | 113.861 | 51.973 | 22.518 | 1.00 | 53.86 |
| 3292 | CG | LYS | 351 | 114.151 | 53.095 | 21.520 | 1.00 | 60.98 |
| 3293 | CD | LYS | 351 | 115.235 | 52.708 | 20.517 | 1.00 | 68.26 |
| 3294 | CE | LYS | 351 | 115.153 | 53.551 | 19.253 | 1.00 | 75.67 |
| 3295 | NZ | LYS | 351 | 115.951 | 52.975 | 18.132 | 1.00 | 74.32 |
| 3296 | H | LYS | 351 | 112.180 | 50.322 | 23.471 | 1.00 | 25.00 |
| 3297 | 1HZ | LYS | 351 | 116.950 | 52.914 | 18.410 | 1.00 | 25.00 |
| 3298 | 2HZ | LYS | 351 | 115.590 | 52.025 | 17.907 | 1.00 | 25.00 |
| 3299 | 3HZ | LYS | 351 | 115.855 | 53.584 | 17.293 | 1.00 | 25.00 |
| 3300 | N | GLU | 352 | 115.275 | 49.297 | 22.944 | 1.00 | 56.12 |
| 3301 | CA | GLU | 352 | 116.474 | 48.461 | 23.031 | 1.00 | 54.04 |
| 3302 | C | GLU | 352 | 116.409 | 47.241 | 22.120 | 1.00 | 52.28 |
| 3303 | O | GLU | 352 | 117.410 | 46.851 | 21.514 | 1.00 | 52.78 |
| 3304 | CB | GLU | 352 | 116.688 | 47.971 | 24.406 | 1.00 | 58.92 |
| 3305 | CG | GLU | 352 | 117.135 | 49.023 | 25.460 | 1.00 | 67.31 |
| 3306 | CD | GLU | 352 | 117.386 | 48.438 | 26.842 | 1.00 | 71.98 |
| 3307 | OE1 | GLU | 352 | 118.383 | 47.694 | 27.004 | 1.00 | 69.15 |
| 3308 | OE2 | GLU | 352 | 116.582 | 48.718 | 27.760 | 1.00 | 65.74 |
| 3309 | H | GLU | 352 | 114.800 | 49.527 | 23.762 | 1.00 | 25.00 |
| 3310 | N | LEU | 353 | 115.235 | 46.624 | 22.052 | 1.00 | 49.88 |
| 3311 | CA | LEU | 353 | 115.053 | 45.435 | 21.233 | 1.00 | 51.47 |
| 3312 | C | LEU | 353 | 114.701 | 45.732 | 19.772 | 1.00 | 55.82 |
| 3313 | O | LEU | 353 | 114.606 | 44.809 | 18.955 | 1.00 | 56.53 |
| 3314 | CB | LEU | 353 | 114.009 | 44.511 | 21.876 | 1.00 | 44.77 |
| 3315 | CG | LEU | 353 | 114.320 | 44.017 | 23.297 | 1.00 | 40.31 |
| 3316 | CD1 | LEU | 353 | 113.151 | 43.224 | 23.855 | 1.00 | 35.62 |
| 3317 | CD2 | LEU | 353 | 115.586 | 43.172 | 23.302 | 1.00 | 33.71 |
| 3318 | H | LEU | 353 | 114.478 | 46.975 | 22.571 | 1.00 | 25.00 |
| 3319 | N | SER | 354 | 114.538 | 47.012 | 19.437 | 1.00 | 62.13 |
| 3320 | CA | SER | 354 | 114.202 | 47.423 | 18.071 | 1.00 | 66.31 |
| 33221 | N | SER | 354 | 115.245 | 46.970 | 17.058 | 1.00 | 64.64 |
| 3322 | O | SER | 354 | 114.904 | 46.378 | 16.035 | 1.00 | 66.26 |
| 3323 | CB | SER | 354 | 114.043 | 48.945 | 17.978 | 1.00 | 69.09 |
| 3324 | OG | SER | 354 | 112.959 | 49.406 | 18.763 | 1.00 | 80.83 |
| 3325 | H | SER | 354 | 114.623 | 47.710 | 20.121 | 1.00 | 25.00 |
| 3326 | HG | SER | 354 | 112.888 | 50.360 | 18.684 | 1.00 | 25.00 |
| 3327 | N | SER | 355 | 116.516 | 47.223 | 17.359 | 1.00 | 65.77 |
| 3328 | CA | SER | 355 | 117.616 | 46.850 | 16.472 | 1.00 | 67.77 |
| 3329 | C | SER | 355 | 117.631 | 45.364 | 16.110 | 1.00 | 68.81 |
| 3330 | O | SER | 355 | 118.082 | 44.990 | 15.028 | 1.00 | 69.36 |
| 3331 | CB | SER | 355 | 118.956 | 47.245 | 17.099 | 1.00 | 66.08 |
| 3332 | OG | SER | 355 | 119.067 | 46.741 | 18.419 | 1.00 | 68.44 |
| 3333 | H | SER | 355 | 116.729 | 47.670 | 18.209 | 1.00 | 25.00 |
| 3334 | HG | SER | 355 | 119.043 | 45.780 | 18.416 | 1.00 | 25.00 |
| 3335 | N | ALA | 356 | 117.150 | 44.525 | 17.024 | 1.00 | 69.39 |
| 3336 | CA | ALA | 356 | 117.115 | 43.082 | 16.802 | 1.00 | 68.66 |
| 3337 | C | ALA | 356 | 115.741 | 42.585 | 16.347 | 1.00 | 69.25 |
| 3338 | O | ALA | 356 | 115.561 | 41.395 | 16.084 | 1.00 | 71.52 |
| 3339 | CB | ALA | 356 | 117.549 | 42.347 | 18.067 | 1.00 | 64.46 |
| 3340 | H | ALA | 356 | 116.806 | 44.884 | 17.867 | 1.00 | 25.00 |
| 3341 | N | GLY | 357 | 114.773 | 43.493 | 16.270 | 1.00 | 67.77 |
| 3342 | CA | GLY | 357 | 113.432 | 43.118 | 15.854 | 1.00 | 62.16 |
| 3343 | C | GLY | 357 | 112.754 | 42.202 | 16.856 | 1.00 | 58.02 |
| 3344 | O | GLY | 357 | 111.969 | 41.327 | 16.481 | 1.00 | 58.07 |
| 3345 | H | GLY | 357 | 114.965 | 44.428 | 16.477 | 1.00 | 25.00 |
| 3346 | N | ARG | 358 | 113.039 | 42.416 | 18.138 | 1.00 | 53.28 |
| 3347 | CA | ARG | 358 | 112.461 | 41.601 | 19.204 | 1.00 | 50.96 |
| 3348 | C | ARG | 358 | 111.488 | 42.359 | 20.106 | 1.00 | 50.55 |
| 3349 | O | ARG | 358 | 110.885 | 41.774 | 20.999 | 1.00 | 51.85 |
| 3350 | CB | ARG | 358 | 113.568 | 40.953 | 20.047 | 1.00 | 44.69 |
| 3351 | CG | ARG | 358 | 114.360 | 39.872 | 19.314 | 1.00 | 43.66 |
| 3352 | CD | ARG | 358 | 115.389 | 39.206 | 20.217 | 1.00 | 43.11 |
| 3353 | NE | ARG | 358 | 114.768 | 38.503 | 21.338 | 1.00 | 42.40 |
| 3354 | CZ | ARG | 358 | 114.997 | 38.783 | 22.618 | 1.00 | 43.84 |
| 3355 | NH1 | ARG | 358 | 115.836 | 39.754 | 22.951 | 1.00 | 49.95 |
| 3356 | NH2 | ARG | 358 | 114.389 | 38.089 | 23.571 | 1.00 | 45.03 |
| 3357 | H | ARG | 358 | 113.684 | 43.136 | 18.368 | 1.00 | 25.00 |
| 3358 | HE | ARG | 358 | 114.142 | 37.776 | 21.138 | 1.00 | 25.00 |
| 3359 | 1HH1 | ARG | 358 | 116.301 | 40.282 | 22.241 | 1.00 | 25.00 |
| 3360 | 2HH1 | ARG | 358 | 116.006 | 39.958 | 23.915 | 1.00 | 25.00 |
| 3361 | 1HH2 | ARG | 358 | 113.755 | 37.355 | 23.327 | 1.00 | 25.00 |
| 3362 | 2HH2 | ARG | 358 | 114.562 | 38.301 | 24.533 | 1.00 | 25.00 |
| 3363 | N | SER | 359 | 111.270 | 43.619 | 19.826 | 1.00 | 50.59 |
| 3364 | CA | SER | 359 | 110.363 | 44.464 | 20.625 | 1.00 | 47.98 |
| 3365 | C | SER | 359 | 108.948 | 43.888 | 20.767 | 1.00 | 48.46 |
| 3366 | O | SER | 359 | 108.247 | 44.177 | 21.737 | 1.00 | 46.16 |
| 3367 | CB | SER | 359 | 110.315 | 45.879 | 20.050 | 1.00 | 51.38 |
| 3368 | OG | SER | 359 | 110.450 | 45.839 | 18.639 | 1.00 | 63.31 |
| 3369 | H | SER | 359 | 111.730 | 44.045 | 19.067 | 1.00 | 25.00 |
| 3370 | HG | SER | 359 | 111.323 | 45.514 | 18.419 | 1.00 | 25.00 |
| 3371 | N | HIS | 360 | 108.559 | 43.029 | 19.8829 | 1.00 | 46.52 |
| 3372 | CA | HIS | 360 | 107.234 | 42.401 | 19.837 | 1.00 | 47.05 |
| 3373 | C | HIS | 360 | 106.998 | 41.398 | 20.974 | 1.00 | 48.80 |
| 3374 | O | HIS | 360 | 105.893 | 40.871 | 21.124 | 1.00 | 46.79 |
| 3375 | CB | HIS | 360 | 106.971 | 41.713 | 18.492 | 1.00 | 47.13 |
| 3376 | CG | HIS | 360 | 108.026 | 40.724 | 18.100 | 1.00 | 47.23 |
| 3377 | ND1 | HIS | 360 | 107.885 | 39.365 | 18.289 | 1.00 | 50.30 |

TABLE 11-continued

Structural Coordinates of Tobacco 5-Epi-Aristolochene Synthase
In the Absence of Bound Substrate

| Atom Type | Atom | Residue | Residue # | X | Y | Z | OCC | B-factor |
|---|---|---|---|---|---|---|---|---|
| 3378 | CD2 | HIS | 360 | 109.242 | 40.899 | 17.532 | 1.00 | 49.82 |
| 3379 | CE1 | HIS | 360 | 108.969 | 38.746 | 17.855 | 1.00 | 47.18 |
| 3380 | NE2 | HIS | 360 | 109.808 | 39.655 | 17.391 | 1.00 | 46.40 |
| 3381 | H | HIS | 360 | 109.183 | 42.837 | 19.111 | 1.00 | 25.00 |
| 3382 | HD1 | HIS | 360 | 107.098 | 38.919 | 18.675 | 1.00 | 25.00 |
| 3383 | HE2 | HIS | 360 | 110.702 | 39.494 | 16.992 | 1.00 | 25.00 |
| 3384 | N | ILE | 361 | 108.042 | 41.098 | 21.741 | 1.00 | 47.17 |
| 3385 | CA | ILE | 361 | 107.922 | 40.152 | 22.845 | 1.00 | 40.37 |
| 3386 | C | ILE | 361 | 107.657 | 40.850 | 24.175 | 1.00 | 35.93 |
| 3387 | O | ILE | 361 | 107.118 | 40.240 | 25.103 | 1.00 | 41.86 |
| 3388 | CB | ILE | 361 | 109.187 | 39.277 | 22.987 | 1.00 | 44.49 |
| 3389 | CG1 | ILE | 361 | 110.392 | 40.152 | 23.346 | 1.00 | 39.20 |
| 3390 | CG2 | ILE | 361 | 109.421 | 38.477 | 21.707 | 1.00 | 38.28 |
| 3391 | CD1 | ILE | 361 | 111.680 | 39.405 | 23.464 | 1.00 | 49.02 |
| 3392 | H | ILE | 361 | 108.913 | 41.517 | 21.574 | 1.00 | 25.00 |
| 3393 | N | VAL | 362 | 108.007 | 42.131 | 24.256 | 1.00 | 29.83 |
| 3394 | CA | VAL | 362 | 107.818 | 42.911 | 25.478 | 1.00 | 28.00 |
| 3395 | C | VAL | 362 | 106.396 | 42.815 | 26.041 | 1.00 | 32.52 |
| 3396 | O | VAL | 362 | 106.209 | 42.788 | 27.262 | 1.00 | 34.43 |
| 3397 | CB | VAL | 362 | 108.203 | 44.401 | 25.259 | 1.00 | 30.93 |
| 3398 | CG1 | VAL | 362 | 107.851 | 45.233 | 26.484 | 1.00 | 28.70 |
| 3399 | CG2 | VAL | 362 | 109.699 | 44.524 | 24.952 | 1.00 | 22.99 |
| 3400 | H | VAL | 362 | 108.395 | 42.568 | 23.472 | 1.00 | 25.00 |
| 3401 | N | CYS | 363 | 105.405 | 42.701 | 25.160 | 1.00 | 29.77 |
| 3402 | CA | CYS | 363 | 104.011 | 42.610 | 25.592 | 1.00 | 31.29 |
| 3403 | C | CYS | 363 | 103.757 | 41.470 | 26.581 | 1.00 | 29.63 |
| 3404 | O | CYS | 363 | 102.942 | 41.610 | 27.499 | 1.00 | 25.93 |
| 3405 | CB | CYS | 363 | 103.066 | 42.504 | 24.387 | 1.00 | 33.73 |
| 3406 | SG | CYS | 363 | 103.387 | 41.126 | 23.270 | 1.00 | 40.61 |
| 3407 | H | CYS | 363 | 105.612 | 42.677 | 24.204 | 1.00 | 25.00 |
| 3408 | N | HIS | 364 | 104.480 | 40.362 | 26.421 | 1.00 | 26.78 |
| 3409 | CA | HIS | 384 | 104.332 | 39.216 | 27.315 | 1.00 | 24.36 |
| 3410 | C | HIS | 364 | 104.685 | 39.599 | 28.754 | 1.00 | 31.26 |
| 3411 | O | HIS | 364 | 104.029 | 39.163 | 29.703 | 1.00 | 32.48 |
| 3412 | CB | HIS | 364 | 105.220 | 38.064 | 26.855 | 1.00 | 26.25 |
| 3413 | CG | HIS | 364 | 104.826 | 37.486 | 25.531 | 1.00 | 29.86 |
| 3414 | ND1 | HIS | 364 | 103.731 | 36.663 | 25.372 | 1.00 | 39.99 |
| 3415 | CD2 | HIS | 364 | 105.398 | 37.588 | 24.308 | 1.00 | 32.37 |
| 3416 | CE1 | HIS | 364 | 103.646 | 36.282 | 24.110 | 1.00 | 36.28 |
| 3417 | NE2 | HIS | 364 | 104.646 | 36.829 | 23.444 | 1.00 | 32.87 |
| 3418 | H | HIS | 364 | 105.139 | 40.332 | 25.695 | 1.00 | 25.00 |
| 3419 | HD1 | HIS | 364 | 103.113 | 36.392 | 26.086 | 1.00 | 25.00 |
| 3420 | HE2 | HIS | 364 | 104.819 | 36.718 | 22.488 | 1.00 | 25.00 |
| 3421 | N | ALA | 365 | 105.711 | 40.431 | 28.911 | 1.00 | 28.85 |
| 3422 | CA | ALA | 365 | 106.134 | 40.880 | 30.232 | 1.00 | 30.11 |
| 3423 | C | ALA | 365 | 105.075 | 41.813 | 30.826 | 1.00 | 31.00 |
| 3424 | O | ALA | 365 | 104.727 | 41.708 | 32.005 | 1.00 | 31.25 |
| 3425 | CB | ALA | 365 | 107.482 | 41.585 | 30.140 | 1.00 | 31.82 |
| 3426 | H | ALA | 365 | 106.191 | 40.762 | 28.123 | 1.00 | 25.00 |
| 3427 | N | ILE | 366 | 104.548 | 42.708 | 29.992 | 1.00 | 33.54 |
| 3428 | CA | ILE | 366 | 103.512 | 43.653 | 30.417 | 1.00 | 33.21 |
| 3429 | C | ILE | 366 | 102.287 | 42.889 | 30.922 | 1.00 | 29.56 |
| 3430 | O | ILE | 366 | 101.743 | 43.199 | 31.987 | 1.00 | 31.04 |
| 3431 | CB | ILE | 366 | 103.066 | 44.582 | 29.255 | 1.00 | 33.17 |
| 3432 | CG1 | ILE | 366 | 104.264 | 45.455 | 28.823 | 1.00 | 30.87 |
| 3433 | CG2 | ILE | 366 | 101.908 | 45.453 | 29.674 | 1.00 | 28.96 |
| 3434 | CD1 | ILE | 366 | 103.987 | 46.289 | 27.599 | 1.00 | 35..02 |
| 3435 | H | ILE | 366 | 104.869 | 42.731 | 29.067 | 1.00 | 25.00 |
| 3436 | N | GLU | 367 | 101.874 | 41.875 | 30.167 | 1.00 | 28.47 |
| 3437 | CA | GLU | 367 | 100.726 | 41.061 | 30.548 | 1.00 | 30.13 |
| 3438 | C | GLU | 367 | 100.945 | 40.439 | 31.929 | 1.00 | 30.58 |
| 3439 | O | GLU | 367 | 100.029 | 40.407 | 32.754 | 1.00 | 31.55 |
| 3440 | CB | GLU | 367 | 100.461 | 39.966 | 29.507 | 1.00 | 38.78 |
| 3441 | CG | GLU | 367 | 100.228 | 40.472 | 28.074 | 1.00 | 52.31 |
| 3442 | CD | GLU | 367 | 99.180 | 41.585 | 27.970 | 1.00 | 62.83 |
| 3443 | OE1 | GLU | 367 | 98.144 | 41.525 | 28.675 | 1.00 | 55.58 |
| 3444 | OE2 | GLU | 367 | 99.395 | 42.523 | 27.168 | 1.00 | 63.90 |
| 3445 | H | GLU | 367 | 102.351 | 41.673 | 29.337 | 1.00 | 25.00 |
| 3446 | N | ARG | 368 | 102.167 | 39.985 | 32.196 | 1.00 | 28.25 |
| 3447 | CA | ARG | 368 | 102.479 | 39.385 | 33.487 | 1.00 | 21.98 |
| 3448 | C | ARG | 368 | 102.462 | 40.420 | 34.607 | 1.00 | 22.36 |
| 3449 | O | ARG | 368 | 102.080 | 40.108 | 35.738 | 1.00 | 22.36 |
| 3450 | CB | ARG | 368 | 103.821 | 38.661 | 33.440 | 1.00 | 23.96 |
| 3451 | CG | ARG | 368 | 103.796 | 37.364 | 32.642 | 1.00 | 17.80 |
| 3452 | CD | ARG | 368 | 102.812 | 36.352 | 33.224 | 1.00 | 19.62 |
| 3453 | NE | ARG | 368 | 103.008 | 35.034 | 32.626 | 1.00 | 19.60 |
| 3454 | CZ | ARG | 368 | 102.516 | 33.897 | 33.113 | 1.00 | 20.41 |
| 3455 | NH1 | ARG | 368 | 101.773 | 33.898 | 34.211 | 1.00 | 26.21 |
| 3456 | NH2 | ARG | 368 | 102.843 | 32.743 | 32.548 | 1.00 | 22.02 |
| 3457 | H | ARG | 368 | 102.868 | 40.046 | 31.510 | 1.00 | 25.00 |
| 3458 | HE | ARG | 388 | 103.526 | 34.993 | 31.804 | 1.00 | 25.00 |
| 3459 | 1HH1 | ARG | 368 | 101.580 | 34.754 | 34.688 | 1.00 | 25.00 |
| 3460 | 2HH1 | ARG | 368 | 101.410 | 33.036 | 34.566 | 1.00 | 25.00 |
| 3461 | 1HH2 | ARG | 368 | 103.454 | 32.730 | 31.755 | 1.00 | 25.00 |
| 3462 | 2HH2 | ARG | 368 | 102.476 | 31.888 | 32.904 | 1.00 | 25.00 |
| 3463 | N | MET | 369 | 102.849 | 41.654 | 34.293 | 1.00 | 23.19 |
| 3464 | CA | MET | 369 | 102.845 | 42.716 | 35.295 | 1.00 | 20.55 |
| 3465 | C | MET | 369 | 101.410 | 43.060 | 35.657 | 1.00 | 20.66 |
| 3466 | O | MET | 369 | 101.085 | 43.248 | 36.833 | 1.00 | 24.28 |
| 3467 | CB | MET | 369 | 103.565 | 43.966 | 34.789 | 1.00 | 24.43 |
| 3468 | CG | MET | 369 | 103.575 | 45.097 | 35.806 | 1.00 | 27.10 |
| 3469 | SD | MET | 369 | 104.503 | 46.538 | 35.283 | 1.00 | 33.91 |
| 3470 | CE | MET | 369 | 105.378 | 46.942 | 36.804 | 1.00 | 36.11 |
| 3471 | H | MET | 369 | 103.151 | 41.852 | 33.380 | 1.00 | 25.00 |
| 3472 | N | LYS | 370 | 100.550 | 43.142 | 34.645 | 1.00 | 27.52 |
| 3473 | CA | LYS | 370 | 99.135 | 43.441 | 34.865 | 1.00 | 27.03 |
| 3474 | C | LYS | 370 | 98.572 | 42.392 | 35.817 | 1.00 | 26.80 |
| 3475 | O | LYS | 370 | 97.854 | 42.720 | 36.766 | 1.00 | 31.01 |
| 3476 | CB | LYS | 370 | 98.361 | 43.415 | 33.545 | 1.00 | 28.62 |
| 3477 | CG | LYS | 370 | 98.699 | 44.546 | 32.591 | 1.00 | 26.77 |
| 3478 | CD | LYS | 370 | 97.881 | 44.437 | 31.318 | 1.00 | 32.86 |
| 3479 | CE | LYS | 370 | 98.174 | 46.591 | 30.371 | 1.00 | 40.98 |
| 3480 | NZ | LYS | 370 | 97.397 | 45.502 | 29.099 | 1.00 | 45.53 |
| 3481 | H | LYS | 370 | 100.870 | 43.001 | 33.729 | 1.00 | 25.00 |
| 3482 | 1HZ | LYS | 370 | 96.379 | 45.511 | 29.313 | 1.00 | 25.00 |
| 3483 | 2HZ | LYS | 370 | 97.630 | 46.314 | 28.492 | 1.00 | 25.00 |
| 3484 | 3HZ | LYS | 370 | 97.640 | 44.619 | 28.607 | 1.00 | 25.00 |
| 3485 | N | GLU | 3771 | 98.959 | 41.139 | 35.581 | 1.00 | 26.63 |
| 3486 | CA | GLU | 371 | 98.541 | 40.006 | 36.398 | 1.00 | 23.16 |
| 3487 | C | GLU | 371 | 98.981 | 40.191 | 37.854 | 1.00 | 31.56 |
| 3488 | O | GLU | 371 | 98.180 | 40.023 | 38.782 | 1.00 | 33.30 |
| 3489 | CB | GLU | 371 | 99.125 | 38.719 | 35.815 | 1.00 | 24.88 |
| 3490 | CG | GLU | 371 | 98.779 | 37.449 | 36.569 | 1.00 | 25.01 |
| 3491 | CD | GLU | 371 | 99.346 | 36.212 | 35.892 | 1.00 | 38.13 |
| 3492 | OE1 | GLU | 371 | 100.588 | 36.080 | 35.815 | 1.00 | 34.30 |
| 3493 | OE2 | GLU | 371 | 98.549 | 35.373 | 35.425 | 1.00 | 44.97 |
| 3494 | H | GLU | 371 | 99.542 | 40.972 | 34.811 | 1.00 | 25.00 |
| 3495 | N | VAL | 372 | 100.243 | 40.567 | 38.056 | 1.00 | 29.02 |
| 3496 | CA | VAL | 372 | 100.765 | 40.789 | 39.406 | 1.00 | 26.07 |
| 3497 | C | VAL | 372 | 99.952 | 41.869 | 40.126 | 1.00 | 28.22 |
| 3498 | O | VAL | 372 | 99.582 | 41.705 | 41.293 | 1.00 | 27.36 |
| 3499 | CB | VAL | 372 | 102.261 | 41.216 | 39.388 | 1.00 | 27.23 |
| 3500 | CG1 | VAL | 372 | 102.738 | 41.520 | 40.801 | 1.00 | 19.82 |
| 3501 | CG2 | VAL | 372 | 103.124 | 40.119 | 38.770 | 1.00 | 23.40 |
| 3502 | H | VAL | 372 | 100.836 | 40.688 | 37.283 | 1.00 | 25.00 |
| 3503 | N | VAL | 373 | 99.657 | 42.964 | 39.426 | 1.00 | 31.06 |
| 3504 | CA | VAL | 373 | 98.893 | 44.063 | 40.018 | 1.00 | 32.80 |
| 3505 | C | VAL | 373 | 97.453 | 43.670 | 40.378 | 1.00 | 33.82 |
| 3506 | O | VAL | 373 | 96.952 | 44.054 | 41.441 | 1.00 | 30.74 |
| 3507 | CB | VAL | 373 | 98.908 | 45.314 | 39.118 | 1.00 | 34.89 |
| 3508 | CG1 | VAL | 373 | 98.134 | 46.454 | 39.775 | 1.00 | 32.71 |
| 3509 | CG2 | VAL | 373 | 100.345 | 45.741 | 38.855 | 1.00 | 34.17 |
| 3510 | H | VAL | 373 | 99.960 | 43.0288 | 38.495 | 1.00 | 25.00 |
| 3511 | N | ARG | 374 | 96.794 | 42.900 | 39.512 | 1.00 | 31.81 |
| 3512 | CA | ARG | 374 | 95.428 | 42.447 | 39.789 | 1.00 | 29.59 |
| 3513 | C | ARG | 374 | 95.422 | 41.667 | 41.093 | 1.00 | 31.35 |
| 3514 | O | ARG | 374 | 94.613 | 41.933 | 41.989 | 1.00 | 36.45 |
| 3515 | CB | ARG | 374 | 94.910 | 41.519 | 38.689 | 1.00 | 29.25 |
| 3516 | CG | ARG | 374 | 94.668 | 42.166 | 37.349 | 1.00 | 32.69 |
| 3517 | CD | ARG | 374 | 94.034 | 41.169 | 36.396 | 1.00 | 33.05 |
| 3518 | NE | ARG | 374 | 94.840 | 40.973 | 35.194 | 1.00 | 37.26 |
| 3519 | CZ | ARG | 374 | 95.399 | 39.817 | 34.846 | 1.00 | 38.15 |
| 3520 | NH1 | ARG | 374 | 95.247 | 38.741 | 35.608 | 1.00 | 41.80 |
| 3521 | NH2 | ARG | 374 | 96.114 | 39.738 | 33.733 | 1.00 | 40.61 |
| 3522 | H | ARG | 374 | 97.230 | 42.625 | 38.677 | 1.00 | 25.00 |
| 3523 | HE | ARG | 374 | 94.974 | 41.744 | 34.603 | 1.00 | 25.00 |

TABLE 11-continued

Structural Coordinates of Tobacco 5-Epi-Aristolochene Synthase In the Absence of Bound Substrate

| Atom Type | Atom | Residue | Residue # | X | Y | Z | OCC | B-factor |
|---|---|---|---|---|---|---|---|---|
| 3524 | 1HH1 | ARG | 374 | 94.711 | 38.795 | 36.448 | 1.00 | 25.00 |
| 3525 | 2HH1 | ARG | 374 | 95.672 | 37.878 | 35.336 | 1.00 | 25.00 |
| 3526 | 1HH2 | ARG | 374 | 96.232 | 40.550 | 33.158 | 1.00 | 25.00 |
| 3527 | 2HH2 | ARG | 374 | 96.537 | 38.873 | 33.467 | 1.00 | 25.00 |
| 3528 | N | ASN | 375 | 96.351 | 40.721 | 41.202 | 1.00 | 31.47 |
| 3529 | CA | ASN | 375 | 96.458 | 39.883 | 42.388 | 1.00 | 28.79 |
| 3530 | C | ASN | 375 | 96.897 | 40.652 | 43.625 | 1.00 | 26.40 |
| 3531 | O | ASN | 375 | 96.561 | 40.266 | 44.746 | 1.00 | 27.83 |
| 3532 | CB | ASN | 375 | 97.358 | 38.683 | 42.112 | 1.00 | 35.48 |
| 3533 | CG | ASN | 375 | 96.744 | 37.720 | 41.111 | 1.00 | 32.04 |
| 3534 | OD1 | ASN | 375 | 95.982 | 38.125 | 40.237 | 1.00 | 33.82 |
| 3535 | ND2 | ASN | 375 | 97.075 | 36.442 | 41.231 | 1.00 | 34.73 |
| 3536 | H | ASN | 375 | 96.970 | 40.566 | 40.454 | 1.00 | 25.00 |
| 3537 | 1HD2 | ASN | 375 | 96.671 | 35.322 | 40.590 | 1.00 | 25.00 |
| 3538 | 2HD2 | ASN | 375 | 97.686 | 36.184 | 41.941 | 1.00 | 25.00 |
| 3539 | N | TYR | 376 | 97.643 | 41.736 | 43.422 | 1.00 | 32.41 |
| 3540 | CA | TYR | 376 | 98.075 | 42.599 | 44.526 | 1.00 | 36.00 |
| 3541 | C | TYR | 376 | 96.803 | 43.220 | 45.101 | 1.00 | 36.51 |
| 3542 | O | TYR | 376 | 96.585 | 43.247 | 46.316 | 1.00 | 32.23 |
| 3543 | CB | TYR | 376 | 98.960 | 43.739 | 44.010 | 1.00 | 34.19 |
| 3544 | CG | TYR | 376 | 100.447 | 43.464 | 43.979 | 1.00 | 41.46 |
| 3545 | CD1 | TYR | 376 | 100.993 | 42.339 | 44.601 | 1.00 | 40.12 |
| 3546 | CD2 | TYR | 376 | 101.315 | 44.350 | 43.336 | 1.00 | 41.43 |
| 3547 | CE1 | TYR | 376 | 102.365 | 42.104 | 44.580 | 1.00 | 38.75 |
| 3548 | CE2 | TYR | 376 | 102.688 | 44.127 | 43.310 | 1.00 | 37.68 |
| 3549 | CZ | TYR | 376 | 103.203 | 43.005 | 43.932 | 1.00 | 41.58 |
| 3550 | OH | TYR | 376 | 104.560 | 42.785 | 43.895 | 1.00 | 43.07 |
| 3551 | H | TYR | 376 | 97.915 | 41.956 | 42.506 | 1.00 | 25.00 |
| 3552 | HH | TYR | 376 | 104.761 | 41.958 | 44.341 | 1.00 | 25.00 |
| 3553 | N | ASN | 377 | 95.965 | 43.713 | 44.194 | 1.00 | 37.58 |
| 3554 | CA | ASN | 377 | 94.704 | 44.343 | 44.550 | 1.00 | 36.82 |
| 3555 | C | ASN | 377 | 93.807 | 43.352 | 45.285 | 1.00 | 35.16 |
| 3556 | O | ASN | 377 | 93.276 | 43.658 | 46.353 | 1.00 | 35.66 |
| 3557 | CB | ASN | 377 | 94.011 | 44.846 | 43.287 | 1.00 | 38.60 |
| 3558 | CG | ASN | 377 | 92.858 | 45.770 | 43.587 | 1.00 | 43.38 |
| 3559 | OD1 | ASN | 377 | 92.949 | 46.628 | 44.462 | 1.00 | 38.97 |
| 3560 | ND2 | ASN | 377 | 91.774 | 45.622 | 42.838 | 1.00 | 46.57 |
| 3561 | H | ASN | 377 | 96.210 | 43.651 | 43.245 | 1.00 | 25.00 |
| 3562 | 1HD2 | ASN | 377 | 91.023 | 46.218 | 43.029 | 1.00 | 25.00 |
| 3563 | 2HD2 | ASN | 377 | 91.765 | 44.936 | 42.143 | 1.00 | 25.00 |
| 3564 | N | VAL | 378 | 93.683 | 42.147 | 44.735 | 1.00 | 32.14 |
| 3565 | CA | VAL | 378 | 92.857 | 41.106 | 45.344 | 1.00 | 28.96 |
| 3566 | C | VAL | 378 | 93.339 | 40.801 | 46.766 | 1.00 | 33.76 |
| 3567 | O | VAL | 378 | 92.532 | 40.647 | 47.690 | 1.00 | 32.35 |
| 3568 | CB | VAL | 378 | 92.858 | 39.818 | 44.490 | 1.00 | 30.20 |
| 3569 | CG1 | VAL | 378 | 92.051 | 38.732 | 45.169 | 1.00 | 28.32 |
| 3570 | CG2 | VAL | 378 | 92.285 | 40.104 | 43.105 | 1.00 | 26.65 |
| 3571 | H | VAL | 378 | 94.153 | 41.951 | 43.897 | 1.00 | 25.00 |
| 3572 | N | GLU | 379 | 94.657 | 40.741 | 46.940 | 1.00 | 36.35 |
| 3573 | CA | GLU | 379 | 95.258 | 40.478 | 48.246 | 1.00 | 38.43 |
| 3574 | C | GLU | 379 | 94.875 | 41.598 | 49.209 | 1.00 | 36.80 |
| 3575 | O | GLU | 379 | 94.579 | 41.352 | 50.383 | 1.00 | 37.49 |
| 3576 | CB | GLU | 379 | 96.780 | 40.395 | 48.114 | 1.00 | 43.01 |
| 3577 | CG | GLU | 379 | 97.544 | 40.416 | 49.436 | 1.00 | 52.96 |
| 3578 | CD | GLU | 379 | 99.055 | 40.403 | 49.250 | 1.00 | 61.44 |
| 3579 | OE1 | GLU | 379 | 99.526 | 40.225 | 48.107 | 1.00 | 70.64 |
| 3580 | OE2 | GLU | 379 | 99.776 | 40.568 | 50.255 | 1.00 | 66.21 |
| 3581 | H | GLU | 379 | 95.247 | 40.882 | 46.167 | 1.00 | 25.00 |
| 3582 | N | SER | 380 | 94.894 | 42.827 | 48.700 | 1.00 | 37.49 |
| 3583 | CA | SER | 380 | 94.531 | 44.003 | 49.480 | 1.00 | 38.42 |
| 3584 | C | SER | 380 | 93.070 | 43.865 | 49.906 | 1.00 | 37.35 |
| 3585 | O | SER | 380 | 92.740 | 44.018 | 51.085 | 1.00 | 38.35 |
| 3586 | CB | SER | 380 | 94.721 | 45.264 | 48.634 | 1.00 | 37.87 |
| 3587 | OG | SER | 380 | 94.344 | 46.428 | 49.349 | 1.00 | 51.23 |
| 3588 | H | SER | 380 | 95.167 | 42.951 | 47.767 | 1.00 | 25.00 |
| 3589 | HG | SER | 380 | 94.903 | 46.518 | 50.127 | 1.00 | 25.00 |
| 3590 | N | THR | 381 | 92.209 | 43.535 | 48.945 | 1.00 | 36.73 |
| 3591 | CA | THR | 381 | 90.785 | 43.349 | 49.198 | 1.00 | 31.81 |
| 3592 | C | THR | 381 | 90.574 | 42.286 | 50.278 | 1.00 | 33.52 |
| 3593 | O | THR | 381 | 89.846 | 42.514 | 51.245 | 1.00 | 35.95 |
| 3594 | CB | THR | 381 | 90.043 | 42.922 | 47.912 | 1.00 | 27.90 |
| 3595 | OG1 | THR | 381 | 90.230 | 43.914 | 46.894 | 1.00 | 30.65 |
| 3596 | CG2 | THR | 381 | 88.564 | 42.762 | 48.174 | 1.00 | 30.75 |
| 3597 | H | THR | 381 | 92.531 | 43.424 | 48.030 | 1.00 | 25.00 |
| 3598 | HG1 | THR | 381 | 89.901 | 44.765 | 47.202 | 1.00 | 25.00 |
| 3599 | N | TRP | 382 | 91.246 | 41.146 | 50.137 | 1.00 | 31.98 |
| 3600 | CA | TRP | 382 | 91.124 | 40.059 | 51.106 | 1.00 | 34.10 |
| 3601 | C | TRP | 382 | 91.498 | 40.511 | 52.513 | 1.00 | 37.61 |
| 3602 | O | TRP | 382 | 90.840 | 40.145 | 53.490 | 1.00 | 37.71 |
| 3603 | CB | TRP | 382 | 92.001 | 38.870 | 50.701 | 1.00 | 29.03 |
| 3604 | CG | TRP | 382 | 91.465 | 38.064 | 49.553 | 1.00 | 34.52 |
| 3605 | CD1 | TRP | 382 | 90.298 | 38.272 | 48.872 | 1.00 | 32.13 |
| 3606 | CD2 | TRP | 382 | 92.073 | 36.907 | 48.962 | 1.00 | 41.36 |
| 3607 | NE1 | TRP | 382 | 90.141 | 37.315 | 47.897 | 1.00 | 33.27 |
| 3608 | CE2 | TRP | 382 | 91.215 | 36.485 | 47.929 | 1.00 | 39.81 |
| 3609 | CE3 | TRP | 382 | 93.262 | 36.198 | 49.205 | 1.00 | 42.10 |
| 3610 | CZ2 | TRP | 382 | 91.507 | 35.344 | 47.138 | 1.00 | 41.24 |
| 3611 | CZ3 | TRP | 382 | 93.552 | 35.082 | 48.417 | 1.00 | 37.35 |
| 3612 | CH2 | TRP | 382 | 92.676 | 34.669 | 47.396 | 1.00 | 37.45 |
| 3613 | H | TRP | 382 | 91.841 | 41.035 | 49.370 | 1.00 | 25.00 |
| 3614 | HE1 | TRP | 382 | 89.384 | 37.250 | 47.275 | 1.00 | 25.00 |
| 3615 | N | PHE | 383 | 92.551 | 41.317 | 52.601 | 1.00 | 42.79 |
| 3616 | CA | PHE | 383 | 93.040 | 41.836 | 53.875 | 1.00 | 44.89 |
| 3617 | C | PHE | 383 | 92.005 | 42.728 | 54.561 | 1.00 | 45.32 |
| 3618 | O | PHE | 383 | 91.714 | 42.557 | 55.748 | 1.00 | 44.05 |
| 3619 | CB | PHE | 383 | 94.346 | 42.611 | 53.657 | 1.00 | 45.88 |
| 3620 | CG | PHE | 383 | 94.818 | 43.358 | 54.869 | 1.00 | 46.79 |
| 3621 | CD1 | PHE | 383 | 95.254 | 42.674 | 55.997 | 1.00 | 47.27 |
| 3622 | CD2 | PHE | 383 | 94.800 | 44.751 | 54.893 | 1.00 | 50.35 |
| 3623 | CE1 | PHE | 383 | 95.665 | 43.368 | 57.137 | 1.00 | 53.01 |
| 3624 | CE2 | PHHE | 383 | 95.208 | 45.453 | 56.026 | 1.00 | 50.27 |
| 3625 | CZ | PHE | 383 | 95.641 | 44.759 | 57.151 | 1.00 | 48.55 |
| 3626 | H | PHE | 383 | 93.023 | 41.569 | 51.778 | 1.00 | 25.00 |
| 3627 | N | ILE | 384 | 91.462 | 43.677 | 53.803 | 1.00 | 46.83 |
| 3628 | CA | ILE | 384 | 90.458 | 44.610 | 54.306 | 1.00 | 46.17 |
| 3629 | C | ILE | 384 | 89.185 | 43.894 | 54.774 | 1.00 | 47.27 |
| 3630 | O | ILE | 384 | 88.608 | 44.253 | 55.799 | 1.00 | 47.11 |
| 3631 | CB | ILE | 384 | 90.091 | 45.648 | 53.227 | 1.00 | 41.64 |
| 3632 | CG1 | ILE | 384 | 91.337 | 46.434 | 52.817 | 1.00 | 42.54 |
| 3633 | CG2 | ILE | 384 | 89.031 | 46.597 | 53.750 | 1.00 | 46.00 |
| 3634 | CD1 | ILE | 384 | 91.148 | 47.270 | 51.568 | 1.00 | 40.69 |
| 3635 | H | ILE | 384 | 91.753 | 43.749 | 52.867 | 1.00 | 25.00 |
| 3636 | N | GLU | 385 | 88.756 | 42.884 | 54.022 | 1.00 | 45.25 |
| 3637 | CA | GLU | 385 | 87.554 | 42.123 | 54.360 | 1.00 | 43.73 |
| 3638 | C | GLU | 385 | 87.791 | 41.137 | 55.495 | 1.00 | 46.22 |
| 3639 | O | GLU | 385 | 86.842 | 40.636 | 56.097 | 1.00 | 51.43 |
| 3640 | CB | GLU | 385 | 87.051 | 41.346 | 53.142 | 1.00 | 42.68 |
| 3641 | CG | GLU | 385 | 86.657 | 42.211 | 51.956 | 1.00 | 46.85 |
| 3642 | CD | GLU | 385 | 86.265 | 41.397 | 50.730 | 1.00 | 50.00 |
| 3643 | OE1 | GLU | 385 | 86.535 | 40.175 | 50.696 | 1.00 | 44.05 |
| 3644 | OE2 | GLU | 385 | 85.689 | 41.988 | 49.791 | 1.00 | 52.88 |
| 3645 | H | GLU | 385 | 89.262 | 42.652 | 53.215 | 1.00 | 25.00 |
| 3646 | N | GLY | 386 | 89.055 | 40.846 | 55.777 | 1.00 | 45.48 |
| 3647 | CA | GLY | 386 | 89.371 | 39.893 | 56.824 | 1.00 | 41.52 |
| 3648 | C | GLY | 386 | 89.038 | 38.499 | 56.328 | 1.00 | 42.60 |
| 3649 | O | GLY | 386 | 88.656 | 37.625 | 57.104 | 1.00 | 44.94 |
| 3650 | H | GLY | 386 | 89.784 | 41.273 | 55.279 | 1.00 | 25.00 |
| 3651 | N | TYR | 387 | 89.190 | 38.277 | 55.023 | 1.00 | 42.34 |
| 3652 | CA | TYR | 387 | 88.897 | 37.020 | 54.382 | 1.00 | 43.55 |
| 3653 | C | TYR | 387 | 90.042 | 36.010 | 54.474 | 1.00 | 45.46 |
| 3654 | O | TYR | 387 | 91.191 | 36.329 | 54.162 | 1.00 | 49.16 |
| 3655 | CB | TYR | 387 | 88.545 | 37.254 | 52.908 | 1.00 | 38.26 |
| 3656 | CG | TYR | 387 | 88.082 | 36.017 | 52.108 | 1.00 | 36.21 |
| 3657 | CD1 | TYR | 387 | 87.152 | 35.142 | 52.727 | 1.00 | 36.57 |
| 3658 | CD2 | TYR | 387 | 88.555 | 35.736 | 50.880 | 1.00 | 31.64 |
| 3659 | CE1 | TYR | 387 | 86.704 | 34.015 | 52.035 | 1.00 | 32.07 |
| 3660 | CE2 | TYR | 387 | 88.112 | 34.616 | 50.178 | 1.00 | 32.41 |
| 3661 | CZ | TYR | 387 | 87.187 | 33.759 | 50.763 | 1.00 | 34.67 |
| 36662 | OH | TYR | 387 | 86.749 | 32.646 | 50.082 | 1.00 | 38.16 |
| 3663 | H | TYR | 387 | 89.541 | 39.025 | 54.474 | 1.00 | 25.00 |
| 3664 | HH | TYR | 387 | 87.147 | 32.629 | 49.211 | 1.00 | 25.00 |
| 3665 | N | THR | 388 | 89.706 | 34.787 | 54.872 | 1.00 | 45.36 |
| 3666 | CA | THR | 388 | 90.671 | 33.692 | 54.986 | 1.00 | 43.34 |
| 3667 | C | THR | 388 | 90.199 | 32.571 | 54.048 | 1.00 | 41.02 |
| 3668 | O | THR | 388 | 89.474 | 31.660 | 54.459 | 1.00 | 45.75 |
| 3669 | CB | THR | 388 | 90.748 | 33.161 | 56.444 | 1.00 | 42.74 |

TABLE 11-continued

Structural Coordinates of Tobacco 5-Epi-Aristolochene Synthase In the Absence of Bound Substrate

| Atom Type | Atom | Residue | Residue # | X | Y | Z | OCC | B-factor |
|---|---|---|---|---|---|---|---|---|
| 3670 | OG1 | THR | 388 | 91.169 | 34.220 | 57.314 | 1.00 | 43.28 |
| 3671 | CG2 | THR | 388 | 91.741 | 32.008 | 56.561 | 1.00 | 39.83 |
| 3672 | H | THR | 388 | 88.782 | 34.613 | 55.129 | 1.00 | 25.00 |
| 3673 | HG1 | THR | 388 | 91.243 | 33.885 | 58.206 | 1.00 | 25.00 |
| 3674 | N | PRO | 389 | 90.575 | 32.649 | 52.761 | 1.00 | 34.93 |
| 3675 | CA | PRO | 389 | 90.184 | 31.645 | 51.769 | 1.00 | 34.82 |
| 3676 | C | PRO | 389 | 90.846 | 30.293 | 51.974 | 1.00 | 39.00 |
| 3677 | O | PRO | 389 | 91.864 | 30.185 | 52.658 | 1.00 | 44.20 |
| 3678 | CB | PRO | 389 | 90.654 | 32.273 | 50.460 | 1.00 | 29.22 |
| 3679 | CG | PRO | 389 | 91.878 | 33.003 | 50.869 | 1.00 | 31.21 |
| 3680 | CD | PRO | 389 | 91.444 | 33.671 | 52.151 | 1.00 | 33.29 |
| 3681 | N | PRO | 390 | 90.243 | 29.231 | 51.425 | 1.00 | 39.35 |
| 3682 | CA | PRO | 390 | 90.830 | 27.896 | 51.566 | 1.00 | 38.80 |
| 3683 | C | PRO | 390 | 92.130 | 27.894 | 50.744 | 1.00 | 42.47 |
| 3684 | O | PRO | 390 | 92.264 | 28.683 | 49.801 | 1.00 | 41.59 |
| 3685 | CB | PRO | 390 | 89.756 | 26.991 | 50.960 | 1.00 | 35.31 |
| 3686 | CG | PRO | 390 | 89.094 | 27.876 | 49.944 | 1.00 | 39.05 |
| 3687 | CD | PRO | 390 | 88.968 | 29.177 | 50.690 | 1.00 | 35.38 |
| 3688 | N | VAL | 391 | 93.070 | 27.015 | 51.085 | 1.00 | 42.92 |
| 3689 | CA | VAL | 391 | 94.367 | 26.947 | 50.396 | 1.00 | 40.91 |
| 3690 | C | VAL | 391 | 94.310 | 27.035 | 48.869 | 1.00 | 40.48 |
| 3691 | O | VAL | 391 | 95.026 | 27.832 | 48.266 | 1.00 | 37.26 |
| 3692 | CB | VAL | 391 | 95.163 | 25.685 | 50.800 | 1.00 | 42.01 |
| 3693 | CG1 | VAL | 391 | 96.542 | 25.698 | 50.149 | 1.00 | 37.12 |
| 3694 | CG2 | VAL | 391 | 95.298 | 25.616 | 52.307 | 1.00 | 37.77 |
| 3695 | H | VAL | 391 | 92.886 | 26.404 | 51.823 | 1.00 | 25.00 |
| 3696 | N | SER | 392 | 93.455 | 26.228 | 48.251 | 1.00 | 37.92 |
| 3697 | CA | SER | 392 | 93.316 | 26.223 | 46.799 | 1.00 | 36.67 |
| 3698 | C | SER | 392 | 93.065 | 27.627 | 46.253 | 1.00 | 37.70 |
| 3699 | O | SER | 392 | 93.699 | 28.056 | 45.289 | 1.00 | 39.57 |
| 3700 | CB | SER | 392 | 92.167 | 25.301 | 46.399 | 1.00 | 41.29 |
| 3701 | OG | SER | 392 | 91.008 | 25.599 | 47.163 | 1.00 | 53.55 |
| 3702 | H | SER | 392 | 92.894 | 25.625 | 48.776 | 1.00 | 25.00 |
| 3703 | HG | SER | 392 | 90.720 | 26.495 | 46.965 | 1.00 | 25.00 |
| 3704 | N | GLU | 393 | 92.140 | 28.342 | 46.883 | 1.00 | 35.95 |
| 3705 | CA | GLU | 393 | 91.806 | 29.692 | 46.455 | 1.00 | 34.88 |
| 3706 | C | GLU | 393 | 92.951 | 30.643 | 46.783 | 1.00 | 31.14 |
| 3707 | O | GLU | 393 | 93.293 | 31.516 | 45.984 | 1.00 | 29.96 |
| 3708 | CB | GLU | 393 | 90.518 | 30.159 | 47.130 | 1.00 | 35.59 |
| 3709 | CG | GLU | 393 | 89.956 | 31.447 | 46.559 | 1.00 | 35.57 |
| 3710 | CD | GLU | 393 | 88.745 | 31.951 | 47.318 | 1.00 | 39.64 |
| 3711 | OE1 | GLU | 393 | 88.064 | 31.141 | 47.985 | 1.00 | 40.88 |
| 3712 | OE2 | GLU | 393 | 88.475 | 33.167 | 47.2242 | 1.00 | 40.96 |
| 3713 | H | GLU | 393 | 91.694 | 27.967 | 47.669 | 1.00 | 25.00 |
| 3714 | N | TYR | 394 | 93.539 | 30.476 | 47.962 | 1.00 | 32.04 |
| 3715 | CA | TYR | 394 | 94.655 | 31.318 | 48.371 | 1.00 | 29.74 |
| 3716 | C | TYR | 394 | 95.743 | 31.287 | 47.302 | 1.00 | 31.70 |
| 3717 | O | TYR | 394 | 96.180 | 32.335 | 46.822 | 1.00 | 33.06 |
| 3718 | CB | TYR | 394 | 95.238 | 30.844 | 49.706 | 1.00 | 33.01 |
| 3719 | CG | TYR | 394 | 96.546 | 31.520 | 50.059 | 1.00 | 42.08 |
| 3720 | CD1 | TYR | 394 | 96.585 | 32.876 | 50.392 | 1.00 | 45.51 |
| 3721 | CD2 | TYR | 394 | 97.752 | 30.815 | 50.021 | 1.00 | 35.80 |
| 3722 | CE1 | TYR | 394 | 97.791 | 33.517 | 50.675 | 1.00 | 45.10 |
| 3723 | CE2 | TYR | 394 | 98.963 | 31.448 | 50.299 | 1.00 | 36.76 |
| 3724 | CZ | TYR | 394 | 98.975 | 32.798 | 50.627 | 1.00 | 42.58 |
| 3725 | OH | TYR | 394 | 100.164 | 33.430 | 50.915 | 1.00 | 41.43 |
| 3726 | H | TYR | 394 | 93.225 | 29.778 | 48.567 | 1.00 | 25.00 |
| 3727 | HH | TYR | 394 | 99.991 | 34.360 | 51.082 | 1.00 | 25.00 |
| 3728 | N | LEU | 395 | 96.145 | 30.082 | 46.909 | 1.00 | 28.83 |
| 3729 | CA | LEU | 395 | 97.189 | 29.897 | 45.910 | 1.00 | 26.16 |
| 3730 | C | LEU | 395 | 96.865 | 30.472 | 44.541 | 1.00 | 29.12 |
| 3731 | O | LEU | 395 | 97.737 | 31.063 | 43.901 | 1.00 | 28.83 |
| 3732 | CB | LEU | 395 | 97.550 | 28.415 | 45.770 | 1.00 | 28.06 |
| 3733 | CG | LEU | 395 | 98.263 | 27.754 | 46.951 | 1.00 | 27.93 |
| 3734 | CD1 | LEU | 395 | 98.511 | 26.290 | 46.636 | 1.00 | 28.97 |
| 3735 | CD2 | LEU | 395 | 99.575 | 28.475 | 47.245 | 1.00 | 24.02 |
| 3736 | H | LEU | 395 | 95.720 | 29.293 | 47.301 | 1.00 | 25.00 |
| 3737 | N | SER | 396 | 95.620 | 30.324 | 44.093 | 1.00 | 29.97 |
| 3738 | CA | SER | 396 | 95.239 | 30.836 | 42.780 | 1.00 | 32.88 |
| 3739 | C | SER | 396 | 95.535 | 32.329 | 42.624 | 1.00 | 28.77 |
| 3740 | O | SER | 396 | 95.715 | 32.318 | 41.508 | 1.00 | 27.80 |
| 3741 | CB | SER | 396 | 93.770 | 30.518 | 42.465 | 1.00 | 39.24 |
| 3742 | OG | SER | 396 | 92.896 | 30.992 | 43.472 | 1.00 | 46.99 |
| 3743 | H | SER | 396 | 94.943 | 29.666 | 44.642 | 1.00 | 25.00 |
| 3744 | HG | SER | 396 | 92.971 | 31.948 | 43.546 | 1.00 | 25.00 |
| 3745 | N | ASN | 397 | 95.597 | 33.046 | 43.745 | 1.00 | 25.18 |
| 3746 | CA | ASN | 397 | 95.907 | 34.472 | 43.723 | 1.00 | 29.15 |
| 3747 | C | ASN | 397 | 97.333 | 34.739 | 44.226 | 1.00 | 27.87 |
| 3748 | O | ASN | 397 | 98.106 | 35.459 | 43.588 | 1.00 | 28.50 |
| 3749 | CB | ASN | 397 | 94.909 | 35.264 | 44.577 | 1.00 | 29.41 |
| 3750 | CG | ASN | 397 | 95.146 | 36.770 | 44.505 | 1.00 | 35.89 |
| 3751 | OD1 | ASN | 397 | 94.831 | 37.404 | 43.502 | 1.00 | 37.46 |
| 3752 | ND2 | ASN | 397 | 95.715 | 37.343 | 45.564 | 1.00 | 30.17 |
| 3753 | H | ASN | 397 | 95.421 | 32.602 | 44.603 | 1.00 | 25.00 |
| 3754 | 1HD2 | ASN | 397 | 95.872 | 38.310 | 45.510 | 1.00 | 25.00 |
| 3755 | 2HD2 | ASN | 397 | 95.953 | 36.794 | 46.336 | 1.00 | 25.00 |
| 3756 | N | ALA | 398 | 97.682 | 34.123 | 45.351 | 1.00 | 26.89 |
| 3757 | CA | ALA | 398 | 98.986 | 34.300 | 45.980 | 1.00 | 24.87 |
| 3758 | C | ALA | 398 | 100.205 | 33.854 | 45.178 | 1.00 | 28.89 |
| 3759 | O | ALA | 398 | 101.303 | 34.358 | 45.395 | 1.00 | 31.67 |
| 3760 | CB | ALA | 398 | 98.992 | 33.646 | 47.337 | 1.00 | 24.15 |
| 3761 | H | ALA | 398 | 97.035 | 33.533 | 45.770 | 1.00 | 25.00 |
| 3762 | N | LEU | 399 | 100.039 | 32.910 | 44.262 | 1.00 | 27.33 |
| 3763 | CA | LEU | 399 | 101.181 | 32.464 | 43.474 | 1.00 | 29.45 |
| 3764 | C | LEU | 399 | 101.755 | 33.589 | 42.617 | 1.00 | 32.27 |
| 3765 | O | LEU | 399 | 102.967 | 33.807 | 42.603 | 1.00 | 34.30 |
| 3766 | CB | LEU | 399 | 100.823 | 31.254 | 42.611 | 1.00 | 25.44 |
| 3767 | CG | LEU | 399 | 100.621 | 29.949 | 43.390 | 1.00 | 24.86 |
| 3768 | CD1 | LEU | 399 | 100.172 | 28.853 | 42.451 | 1.00 | 20.68 |
| 3769 | CD2 | LEU | 399 | 101.900 | 29.549 | 44.104 | 1.00 | 22.68 |
| 3770 | H | LEU | 399 | 99.159 | 32.500 | 44.121 | 1.00 | 25.00 |
| 3771 | N | ALA | 400 | 100.887 | 34.336 | 41.943 | 1.00 | 29.07 |
| 3772 | CA | ALA | 400 | 101.343 | 35.434 | 41.094 | 1.00 | 31.03 |
| 3773 | C | ALA | 400 | 101.939 | 36.601 | 41.882 | 1.00 | 29.34 |
| 3774 | O | ALA | 400 | 102.813 | 37.303 | 41.373 | 1.00 | 26.86 |
| 3775 | CB | ALA | 400 | 100.215 | 35.925 | 40.192 | 1.00 | 32..40 |
| 3776 | H | ALA | 400 | 99.932 | 34.143 | 42.022 | 1.00 | 25.00 |
| 3777 | N | THR | 401 | 101.500 | 36.796 | 43.125 | 1.00 | 27.66 |
| 3778 | CA | THR | 401 | 102.024 | 37.896 | 43.929 | 1.00 | 30.92 |
| 3779 | C | THR | 401 | 103.505 | 37.728 | 44.303 | 1.00 | 35.35 |
| 3780 | O | THR | 401 | 104.118 | 38.649 | 44.847 | 1.00 | 36.05 |
| 3781 | CB | THR | 401 | 101.170 | 38.174 | 45.194 | 1.00 | 27.88 |
| 3782 | OG1 | THR | 401 | 101.106 | 37.007 | 46.021 | 1.00 | 27.11 |
| 3783 | CG2 | THR | 401 | 99.768 | 38.593 | 44.803 | 1.00 | 25.60 |
| 3784 | H | THR | 401 | 100.837 | 36.193 | 43.521 | 1.00 | 25.00 |
| 3785 | HG1 | THR | 401 | 101.990 | 36.769 | 46.324 | 1.00 | 25.00 |
| 3786 | N | THR | 402 | 104.076 | 36.558 | 44.016 | 1.00 | 30.98 |
| 3787 | CA | THR | 402 | 105.492 | 36.310 | 44.295 | 1.00 | 28.76 |
| 3788 | C | THR | 402 | 106.317 | 37.040 | 43.240 | 1.00 | 28.41 |
| 3789 | O | THR | 402 | 107.509 | 37.248 | 43.422 | 1.00 | 30.86 |
| 3790 | OB | THR | 402 | 105.861 | 34.807 | 44.173 | 1.00 | 24.70 |
| 3791 | OG1 | THR | 402 | 105.656 | 34.372 | 42.820 | 1.00 | 22.39 |
| 3792 | CG2 | THR | 402 | 105.039 | 33.954 | 45.117 | 1.00 | 21.26 |
| 3793 | H | THR | 402 | 103.554 | 35.829 | 43.612 | 1.00 | 25.00 |
| 3794 | HG1 | THR | 402 | 105.851 | 33.431 | 42.770 | 1.00 | 25.00 |
| 3795 | N | THR | 403 | 105.656 | 37.373 | 42.130 | 1.00 | 28.49 |
| 3796 | CA | THR | 403 | 106.207 | 38.045 | 40.946 | 1.00 | 25.51 |
| 3797 | C | THR | 403 | 107.032 | 37.110 | 40.077 | 1.00 | 27.25 |
| 3798 | O | THR | 403 | 107.499 | 37.495 | 39.009 | 1.00 | 29.50 |
| 3799 | CB | THR | 403 | 107.060 | 39.323 | 41.246 | 1.00 | 29.54 |
| 3800 | OG1 | THR | 403 | 108.335 | 38.954 | 41.781 | 1.00 | 24.64 |
| 3801 | CG2 | THR | 403 | 106.339 | 40.267 | 42.203 | 1.00 | 26.87 |
| 3802 | H | THR | 403 | 104.707 | 37.143 | 42.086 | 1.00 | 25.00 |
| 3803 | HG1 | THR | 403 | 108.246 | 38.543 | 42.630 | 1.00 | 25.00 |
| 3804 | N | TYR | 404 | 107.120 | 35.833 | 40.474 | 1.00 | 25.89 |
| 3805 | CA | TYR | 404 | 107.914 | 34.860 | 39.728 | 1.00 | 22.27 |
| 3806 | C | TYR | 404 | 107.544 | 34.611 | 38.272 | 1.00 | 24.30 |
| 3807 | O | TYR | 404 | 108.439 | 34.511 | 37.434 | 1.00 | 26.21 |
| 3808 | CB | TYR | 404 | 108.062 | 33.551 | 40.509 | 1.00 | 30.29 |
| 3809 | CG | TYR | 404 | 109.278 | 33.544 | 41.419 | 1.00 | 30.18 |
| 3810 | CD1 | TYR | 404 | 109.800 | 34.736 | 41.922 | 1.00 | 31.88 |
| 3811 | CD2 | TYR | 404 | 109.925 | 32.352 | 41.755 | 1.00 | 28.35 |
| 3812 | CE1 | TYR | 404 | 110.937 | 34.747 | 42.732 | 1.00 | 30.99 |
| 3813 | CE2 | TYR | 404 | 111.065 | 32.353 | 42.569 | 1.00 | 29.01 |
| 3814 | CZ | TYR | 404 | 111.563 | 33.558 | 43.051 | 1.00 | 29.70 |
| 3815 | OH | TYR | 404 | 112.683 | 33.593 | 43.847 | 1.00 | 27.42 |

TABLE 11-continued

Structural Coordinates of Tobacco 5-Epi-Aristolochene Synthase
In the Absence of Bound Substrate

| Atom Type | Atom | Residue | Residue # | X | Y | Z | OCC | B-factor |
|---|---|---|---|---|---|---|---|---|
| 3816 | H | TYR | 404 | 106.644 | 35.551 | 41.285 | 1.00 | 25.00 |
| 3817 | HH | TYR | 404 | 113.022 | 32.697 | 43.955 | 1.00 | 25.00 |
| 3818 | N | TYR | 405 | 106.253 | 34.508 | 37.952 | 1.00 | 24.23 |
| 3819 | CA | TYR | 405 | 105.844 | 34.306 | 36.553 | 1.00 | 24.60 |
| 3820 | C | TYR | 405 | 106.361 | 35.507 | 35.766 | 1.00 | 23.35 |
| 3821 | O | TYR | 405 | 106.912 | 35.378 | 34.672 | 1.00 | 23.93 |
| 3822 | CB | TYR | 405 | 104.317 | 34.292 | 36.406 | 1.00 | 25.23 |
| 3823 | CG | TYR | 405 | 103.593 | 33.163 | 37.099 | 1.00 | 24.35 |
| 3824 | CD1 | TYR | 405 | 103.561 | 31.879 | 36.548 | 1.00 | 23.45 |
| 3825 | CD2 | TYR | 405 | 102.894 | 33.390 | 38.282 | 1.00 | 23.55 |
| 3826 | CE1 | TYR | 4005 | 102.846 | 30.852 | 37.161 | 1.00 | 23.28 |
| 3827 | CE2 | TYR | 405 | 102.179 | 32.374 | 38.901 | 1.00 | 27.86 |
| 3828 | CZ | TYR | 405 | 102.155 | 31.111 | 38.337 | 1.00 | 26.80 |
| 3829 | OH | TYR | 405 | 101.428 | 30.121 | 38.956 | 1.00 | 26.06 |
| 3830 | H | TYR | 405 | 105.577 | 34.557 | 38.658 | 1.00 | 25.00 |
| 3831 | HH | TYR | 405 | 101.510 | 29.308 | 38.452 | 1.00 | 25.00 |
| 3832 | N | TYR | 406 | 106.160 | 36.676 | 36.363 | 1.00 | 23.37 |
| 3833 | CA | TYR | 406 | 106.553 | 37.964 | 35.813 | 1.00 | 21.93 |
| 3834 | C | TYR | 406 | 108.072 | 38.084 | 35.621 | 1.00 | 25.55 |
| 3835 | O | TYR | 406 | 108.535 | 38.439 | 34.538 | 1.00 | 24.19 |
| 3836 | CB | TYR | 406 | 106.021 | 39.047 | 36.751 | 1.00 | 22.96 |
| 3837 | CG | TYR | 406 | 106.379 | 40.468 | 36.408 | 1.00 | 21.90 |
| 3838 | CD1 | TYR | 406 | 106.352 | 40.926 | 35.093 | 1.00 | 20.58 |
| 3839 | CD2 | TYR | 406 | 106.703 | 41.375 | 37.416 | 1.00 | 27.70 |
| 3840 | CE1 | TYR | 406 | 106.634 | 42.252 | 34.796 | 1.00 | 21.17 |
| 3841 | CE2 | TYR | 406 | 106.985 | 42.700 | 37.128 | 1.00 | 24.51 |
| 3842 | CZ | TYR | 406 | 106.947 | 43.131 | 35.820 | 1.00 | 23.02 |
| 3843 | OH | TYR | 406 | 107.207 | 44.449 | 35.541 | 1.00 | 28.99 |
| 3844 | H | TYR | 406 | 105.729 | 36.670 | 37.238 | 1.00 | 25.00 |
| 3845 | HH | TYR | 406 | 107.398 | 44.923 | 36.351 | 1.00 | 25.00 |
| 3846 | N | LEU | 407 | 108.844 | 37.750 | 36.652 | 1.00 | 25.38 |
| 3847 | CA | LEU | 407 | 110.303 | 37.826 | 36.574 | 1.00 | 23.31 |
| 3848 | C | LEU | 407 | 110.873 | 36.825 | 35.575 | 1.00 | 20.18 |
| 3849 | O | LEU | 407 | 111.803 | 37.147 | 34.836 | 1.00 | 22.15 |
| 3850 | CB | LEU | 407 | 110.940 | 37.620 | 37.952 | 1.00 | 20.82 |
| 3851 | CG | LEU | 407 | 110.514 | 38.602 | 39.048 | 1.00 | 25.79 |
| 3852 | CD1 | LEU | 407 | 111.362 | 38.376 | 40.287 | 1.00 | 24.12 |
| 3853 | CD2 | LEU | 407 | 110.635 | 40.045 | 38.562 | 1.00 | 15.72 |
| 3854 | H | LEU | 407 | 108.434 | 37.445 | 37.475 | 1.00 | 25.00 |
| 3855 | N | ALA | 408 | 110.299 | 35.625 | 35.539 | 1.00 | 14.35 |
| 3856 | CA | ALA | 408 | 110.747 | 34.591 | 34.609 | 1.00 | 17.38 |
| 3857 | C | ALA | 408 | 110.520 | 35.083 | 33.183 | 1.00 | 22.75 |
| 3858 | O | ALA | 408 | 111.382 | 34.931 | 32.318 | 1.00 | 25.21 |
| 3859 | CB | ALA | 408 | 109.991 | 33.293 | 34.852 | 1.00 | 17.26 |
| 3860 | H | ALA | 408 | 109.560 | 35.429 | 36.149 | 1.00 | 25.00 |
| 3861 | N | THR | 409 | 109.362 | 35.695 | 32.949 | 1.00 | 23.86 |
| 3862 | CA | THR | 409 | 109.037 | 36.228 | 31.632 | 1.00 | 22.93 |
| 3863 | C | THR | 409 | 110.012 | 37.353 | 31.294 | 1.00 | 25.61 |
| 3864 | O | THR | 409 | 110.507 | 37.443 | 30.165 | 1.00 | 26.75 |
| 3865 | CB | THR | 409 | 107.598 | 36.776 | 31.589 | 1.00 | 26.26 |
| 3866 | OG1 | THR | 409 | 106.689 | 35.765 | 32.042 | 1.00 | 26.48 |
| 3867 | CG2 | THR | 409 | 107.222 | 37.170 | 30.173 | 1.00 | 18.58 |
| 3868 | H | THR | 409 | 108.709 | 35.780 | 33.672 | 1.00 | 25.00 |
| 3869 | HG1 | THR | 409 | 106.917 | 35.516 | 32.932 | 1.00 | 25.00 |
| 3870 | N | THR | 410 | 110.316 | 38.185 | 32.287 | 1.00 | 26.70 |
| 3871 | CA | THR | 410 | 111.233 | 39.299 | 32.095 | 1.00 | 26.67 |
| 3872 | C | THR | 410 | 112.650 | 38.835 | 31.757 | 1.00 | 29.09 |
| 3873 | O | THR | 410 | 113.298 | 39.411 | 30.877 | 1.00 | 29.16 |
| 3874 | CB | THR | 410 | 111.281 | 40.208 | 33.333 | 1.00 | 28.30 |
| 3875 | OG1 | THR | 410 | 109.962 | 40.684 | 33.626 | 1.00 | 30.05 |
| 3876 | CG2 | THR | 410 | 112.189 | 41.404 | 33.082 | 1.00 | 28.81 |
| 3877 | H | THR | 410 | 109.905 | 38.064 | 33.169 | 1.00 | 25.00 |
| 3878 | HG1 | THR | 410 | 109.991 | 41.259 | 34.393 | 1.00 | 25.00 |
| 3879 | N | SER | 411 | 113.105 | 37.760 | 32.399 | 1.00 | 24.71 |
| 3880 | CA | SER | 411 | 114.452 | 37.254 | 32.155 | 1.00 | 24.18 |
| 3881 | C | SER | 411 | 114.688 | 36.909 | 30.687 | 1.00 | 25.08 |
| 3882 | O | SER | 411 | 115.822 | 36.964 | 30.204 | 1.00 | 27.75 |
| 3883 | CB | SER | 411 | 114.753 | 36.046 | 33.043 | 1.00 | 20.40 |
| 3884 | OG | SER | 411 | 114.010 | 34.914 | 32.644 | 1.00 | 21.48 |
| 3885 | H | SER | 411 | 112.534 | 37.287 | 33.041 | 1.00 | 25.00 |
| 3886 | HG | SER | 411 | 114.205 | 34.667 | 31.738 | 1.00 | 25.00 |
| 3887 | N | TYR | 412 | 113.613 | 36.573 | 29.979 | 1.00 | 23.79 |
| 3888 | CA | TYR | 412 | 113.692 | 36.227 | 28.562 | 1.00 | 24.39 |
| 3889 | C | TYR | 412 | 113.8774 | 37.44 | 27.655 | 1.00 | 25.24 |
| 3890 | O | TYR | 412 | 114.437 | 37.326 | 26.570 | 1.00 | 27.76 |
| 3891 | CB | TYR | 412 | 112.419 | 35.511 | 28.116 | 1.00 | 25.37 |
| 3892 | CG | TYR | 412 | 112.273 | 34.072 | 28.539 | 1.00 | 29.38 |
| 3893 | CD1 | TYR | 412 | 113.043 | 33.531 | 29.569 | 1.00 | 29.32 |
| 3894 | CD2 | TYR | 412 | 111.338 | 33.248 | 27.910 | 1.00 | 24.28 |
| 3895 | CE1 | TYR | 412 | 112.878 | 32.199 | 29.964 | 1.00 | 26.36 |
| 3896 | CE2 | TYR | 412 | 111.169 | 31.927 | 28.291 | 1.00 | 25.08 |
| 3897 | CZ | TYR | 412 | 111.937 | 31.408 | 29.318 | 1.00 | 29.45 |
| 3898 | OH | TYR | 412 | 111.750 | 30.099 | 29.693 | 1.00 | 27.61 |
| 3899 | H | TYR | 412 | 112.738 | 36.552 | 30.423 | 1.00 | 25.00 |
| 3900 | HH | TYR | 412 | 112.347 | 29.879 | 30.418 | 1.00 | 25.00 |
| 3901 | N | LEU | 413 | 113.396 | 38.604 | 28.100 | 1.00 | 25.11 |
| 3902 | CA | LEU | 413 | 113.467 | 39.832 | 27.304 | 1.00 | 27.32 |
| 3903 | C | LEU | 413 | 114.835 | 40.149 | 26.726 | 1.00 | 30.49 |
| 3904 | O | LEU | 413 | 114.957 | 40.434 | 25.533 | 1.00 | 30.50 |
| 3905 | CB | LEU | 413 | 112.959 | 41.039 | 28.103 | 1.00 | 23.58 |
| 3906 | CG | LEU | 413 | 111.476 | 41.081 | 28.478 | 1.00 | 31.45 |
| 3907 | CD1 | LEU | 413 | 111.179 | 42.362 | 29.242 | 1.00 | 31.49 |
| 3908 | CD2 | LEU | 413 | 110.613 | 40.996 | 27.231 | 1.00 | 30.34 |
| 3909 | H | LEU | 413 | 112.980 | 38.636 | 28.989 | 1.00 | 25.00 |
| 3910 | N | GLY | 414 | 115.859 | 40.098 | 27.573 | 1.00 | 28.96 |
| 3911 | CA | GLY | 414 | 117.203 | 40.404 | 27.129 | 1.00 | 27.47 |
| 3912 | C | GLY | 414 | 117.990 | 39.233 | 26.586 | 1.00 | 28.88 |
| 3913 | O | GLY | 414 | 119.186 | 39.362 | 26.340 | 1.00 | 34.59 |
| 3914 | H | GLY | 414 | 115.698 | 39.833 | 28.496 | 1.00 | 25.00 |
| 3915 | N | MET | 415 | 117.353 | 38.079 | 26.436 | 1.00 | 29.79 |
| 3916 | CA | MET | 415 | 118.043 | 36.909 | 25.906 | 1.00 | 29.75 |
| 3917 | C | MET | 415 | 117.861 | 36.868 | 24.393 | 1.00 | 35.70 |
| 3918 | O | MET | 415 | 116.795 | 36.522 | 23.893 | 1.00 | 39.21 |
| 3919 | CB | MET | 415 | 117.515 | 35.630 | 26.554 | 1.00 | 22.67 |
| 3920 | CG | MET | 415 | 117.728 | 35.581 | 28.050 | 1.00 | 23.60 |
| 3921 | SD | MET | 415 | 117.062 | 34.095 | 28.794 | 1.00 | 32.91 |
| 3922 | CE | MET | 415 | 118.255 | 32.896 | 28.242 | 1.00 | 24.83 |
| 3923 | H | MET | 415 | 116.398 | 38.012 | 26.652 | 1.00 | 25.00 |
| 3924 | N | LYS | 416 | 118.933 | 37.181 | 23.677 | 1.00 | 40.25 |
| 3925 | CA | LYS | 416 | 118.942 | 37.233 | 22.218 | 1.00 | 43.20 |
| 3926 | C | LYS | 416 | 118.370 | 36.031 | 21.468 | 1.00 | 42.08 |
| 3927 | O | LYS | 416 | 118.037 | 36.143 | 20.289 | 1.00 | 44.24 |
| 3928 | CB | LYS | 416 | 120.362 | 37.539 | 21.735 | 1.00 | 48.69 |
| 3929 | CG | LYS | 416 | 120.916 | 38.828 | 22.333 | 1.00 | 60.37 |
| 3930 | CD | LYS | 416 | 122.427 | 38.949 | 22.191 | 1.00 | 70.42 |
| 3931 | CE | LYS | 416 | 122.936 | 40.173 | 22.949 | 1.00 | 72.06 |
| 3932 | NZ | LYS | 416 | 124.412 | 40.319 | 22.863 | 1.00 | 78.00 |
| 3933 | H | LYS | 416 | 119.749 | 37.416 | 24.164 | 1.00 | 25.00 |
| 3934 | 1HZ | LYS | 416 | 124.870 | 39.475 | 23.262 | 1.00 | 25.00 |
| 3935 | 2HZ | LYS | 416 | 124.687 | 40.423 | 21.865 | 1.00 | 25.00 |
| 3936 | 3HZ | LYS | 416 | 124.709 | 41.163 | 23.393 | 1.00 | 25.00 |
| 3937 | N | SER | 417 | 118.239 | 34.893 | 22.138 | 1.00 | 39.46 |
| 3938 | CA | SER | 417 | 117.706 | 33.698 | 21.491 | 1.00 | 36.96 |
| 3939 | C | SER | 417 | 116.247 | 33.395 | 21.833 | 1.00 | 34.08 |
| 3940 | O | SER | 417 | 115.637 | 32.518 | 21.226 | 1.00 | 35.80 |
| 3941 | CB | SER | 417 | 118.580 | 32.488 | 21.823 | 1.00 | 39.51 |
| 3942 | OG | SER | 417 | 119.907 | 32.675 | 21.358 | 1.00 | 45.86 |
| 3943 | H | SER | 417 | 118.485 | 34.856 | 23.077 | 1.00 | 25.00 |
| 3944 | HG | SER | 417 | 120.288 | 33.461 | 21.743 | 1.00 | 25.00 |
| 3945 | N | ALA | 418 | 115.688 | 34.106 | 22.806 | 1.00 | 30.28 |
| 3946 | CA | ALA | 418 | 114.303 | 33.879 | 23.208 | 1.00 | 38.39 |
| 3947 | C | ALA | 418 | 113.331 | 34.250 | 22.087 | 1.00 | 40.58 |
| 3948 | O | ALA | 418 | 113.145 | 35.427 | 21.779 | 1.00 | 42.57 |
| 3949 | CB | ALA | 418 | 113.981 | 34.659 | 24.484 | 1.00 | 32.32 |
| 3950 | H | ALA | 418 | 116.190 | 34.823 | 23.238 | 1.00 | 25.00 |
| 3951 | N | THR | 419 | 112.750 | 33.232 | 21.457 | 1.00 | 41.43 |
| 3952 | CA | THR | 419 | 111.799 | 33.420 | 220.362 | 1.00 | 41.21 |
| 3953 | C | THR | 419 | 110.357 | 33.504 | 20.865 | 1.00 | 40.11 |
| 3954 | O | THR | 419 | 110.077 | 33.235 | 22.036 | 1.00 | 39.88 |
| 3955 | CB | THR | 419 | 111.892 | 32.264 | 19.338 | 1.00 | 39.89 |
| 3956 | OG1 | THR | 419 | 111.666 | 31.016 | 20.005 | 1.00 | 50.18 |
| 3957 | CG2 | THR | 419 | 113.261 | 32.238 | 18.672 | 1.00 | 37.82 |
| 3958 | H | THR | 419 | 112.987 | 32.335 | 21.728 | 1.00 | 25.00 |
| 3959 | HG1 | THR | 419 | 112.370 | 30.881 | 20.644 | 1.00 | 25.00 |
| 3960 | N | GLU | 420 | 109.443 | 33.848 | 19.963 | 1.00 | 39.64 |
| 3961 | CA | GLU | 420 | 108.027 | 33.958 | 20.292 | 1.00 | 39.75 |

TABLE 11-continued

Structural Coordinates of Tobacco 5-Epi-Aristolochene Synthase
In the Absence of Bound Substrate

| Atom Type | Atom | Residue | Residue # | X | Y | Z | OCC | B-factor |
|---|---|---|---|---|---|---|---|---|
| 3962 | C | GLU | 420 | 107.496 | 32.650 | 20.871 | 1.00 | 35.49 |
| 3963 | O | GLU | 420 | 106.718 | 32.652 | 21.828 | 1.00 | 35.76 |
| 3964 | CB | GLU | 420 | 107.222 | 34.321 | 19.041 | 1.00 | 46.65 |
| 3965 | CG | GLU | 420 | 106.741 | 35.765 | 18.980 | 1.00 | 56.30 |
| 3966 | CD | GLU | 420 | 105.668 | 36.081 | 20.015 | 1.00 | 65.12 |
| 3967 | OE1 | GLU | 420 | 104.685 | 35.311 | 20.130 | 1.00 | 62.03 |
| 3968 | OE2 | GLU | 420 | 105.804 | 37.112 | 20.707 | 1.00 | 72.02 |
| 3969 | H | GLU | 420 | 109.732 | 34.021 | 19.047 | 1.00 | 25.00 |
| 3970 | N | GLN | 421 | 107.938 | 31.537 | 20.291 | 1.00 | 32.71 |
| 3971 | CA | GLN | 421 | 107.520 | 30.206 | 20.722 | 1.00 | 36.14 |
| 3972 | C | GLN | 421 | 107.883 | 29.959 | 22.184 | 1.00 | 36.63 |
| 3973 | O | GLN | 421 | 107.105 | 29.365 | 22.936 | 1.00 | 37.57 |
| 3974 | CB | GLN | 421 | 108.155 | 29.133 | 19.830 | 1.00 | 40.03 |
| 3975 | CG | GLN | 421 | 107.622 | 29.088 | 18.398 | 1.00 | 53.07 |
| 3976 | CD | GLN | 421 | 107.819 | 30.390 | 17.636 | 1.00 | 62.17 |
| 3977 | OE1 | GLN | 421 | 108.877 | 31.017 | 17.711 | 1.00 | 65.66 |
| 3978 | NE2 | GLN | 421 | 106.788 | 30.815 | 16.917 | 1.00 | 68.97 |
| 3979 | H | GLN | 421 | 108.580 | 31.620 | 19.555 | 1.00 | 25.00 |
| 3980 | 1HE2 | GLN | 421 | 106.906 | 31.650 | 16.419 | 1.00 | 25.00 |
| 3981 | 2HE2 | GLN | 421 | 105.963 | 30.289 | 16.903 | 1.00 | 25.00 |
| 3982 | N | ASP | 422 | 109.052 | 30.448 | 22.589 | 1.00 | 34.98 |
| 3983 | CA | ASP | 422 | 109.521 | 30.292 | 23.960 | 1.00 | 32.53 |
| 3984 | C | ASP | 422 | 108.607 | 31.039 | 24.924 | 1.00 | 30.54 |
| 3985 | O | ASP | 422 | 108.272 | 30.525 | 25.992 | 1.00 | 33.81 |
| 3986 | CB | ASP | 422 | 110.972 | 30.767 | 24.085 | 1.00 | 28.20 |
| 3987 | CG | ASP | 422 | 111.929 | 29.945 | 23.233 | 1.00 | 28.18 |
| 3988 | OD1 | ASP | 422 | 111.755 | 28.710 | 23.148 | 1.00 | 33.24 |
| 3989 | OD2 | ASP | 422 | 112.855 | 30.529 | 22.638 | 1.00 | 33.81 |
| 3990 | H | ASP | 422 | 109.610 | 30.933 | 21.946 | 1.00 | 25.00 |
| 3991 | N | PHE | 423 | 108.166 | 32.229 | 24.523 | 1.00 | 29.33 |
| 3992 | CA | PHE | 423 | 107.261 | 33.022 | 25.348 | 1.00 | 28.15 |
| 3993 | C | PHE | 423 | 105.877 | 32.373 | 25.407 | 1.00 | 29.51 |
| 3994 | O | PHE | 423 | 105.205 | 32.424 | 26.441 | 1.00 | 30.32 |
| 3995 | CB | PHE | 423 | 107.143 | 34.448 | 24.808 | 1.00 | 31.32 |
| 3996 | CG | PHE | 423 | 108.275 | 35.353 | 25.214 | 1.00 | 27.99 |
| 3997 | CD1 | PHE | 423 | 108.227 | 36.045 | 26.421 | 1.00 | 26.74 |
| 3998 | CD2 | PHE | 423 | 109.375 | 35.529 | 24.387 | 1.00 | 26.53 |
| 3999 | CE1 | PHE | 423 | 109.255 | 36.900 | 26.794 | 1.00 | 21.72 |
| 4000 | CE2 | PHE | 423 | 110.412 | 36.385 | 24.753 | 1.00 | 23.04 |
| 4001 | CZ | PHE | 423 | 110.350 | 37.070 | 25.958 | 1.00 | 23.46 |
| 4002 | H | PHE | 423 | 108.456 | 32.575 | 23.652 | 1.00 | 25.00 |
| 40003 | N | GLU | 424 | 105.450 | 31.771 | 24.297 | 1.00 | 30.80 |
| 4004 | CA | GLU | 424 | 104.146 | 31.107 | 24.233 | 1.00 | 36.62 |
| 4005 | C | GLU | 424 | 104.128 | 29.911 | 25.172 | 1.00 | 34.48 |
| 4006 | O | GLU | 424 | 103.131 | 29.651 | 25.843 | 1.00 | 34.44 |
| 4007 | CB | GLU | 424 | 103.823 | 30.661 | 22.805 | 1.00 | 42.57 |
| 4008 | CG | GLU | 424 | 103.590 | 31.813 | 21.839 | 1.00 | 63.38 |
| 4009 | CD | GLU | 424 | 103.322 | 31.357 | 20.414 | 1.00 | 70.12 |
| 4010 | OE1 | GLU | 424 | 103.895 | 30.329 | 19.988 | 1.00 | 72.19 |
| 4011 | OE2 | GLU | 424 | 102.543 | 32.039 | 19.715 | 1.00 | 79.30 |
| 4012 | H | GLU | 424 | 106.023 | 31.773 | 23.503 | 1.00 | 25.00 |
| 4013 | N | TRP | 425 | 105.242 | 29.187 | 25.221 | 1.00 | 32.02 |
| 4014 | CA | TRP | 425 | 105.367 | 28.038 | 26.107 | 1.00 | 28.78 |
| 4015 | C | TRP | 425 | 105.262 | 28.531 | 27.553 | 1.00 | 33.19 |
| 4016 | O | TRP | 425 | 104.518 | 27.974 | 28.365 | 1.00 | 30.47 |
| 4017 | CB | TRP | 425 | 106.719 | 27.352 | 25.881 | 1.00 | 29.01 |
| 4018 | CG | TRP | 425 | 107.077 | 26.340 | 26.927 | 1.00 | 29.69 |
| 4019 | CD1 | TRP | 425 | 106.621 | 25.058 | 27.019 | 1.00 | 28.88 |
| 4020 | CD2 | TRP | 425 | 107.970 | 26.530 | 28.034 | 1.00 | 29.87 |
| 4021 | NE1 | TRP | 425 | 107.171 | 24.437 | 28.116 | 1.00 | 29.58 |
| 4022 | CE2 | TRP | 425 | 108.003 | 25.316 | 28.757 | 1.00 | 32.75 |
| 4023 | CE3 | TRP | 425 | 108.742 | 27.609 | 28.488 | 1.00 | 30.70 |
| 4024 | CZ2 | TRP | 425 | 108.781 | 25.149 | 29.912 | 1.00 | 27.26 |
| 4025 | CZ3 | TRP | 425 | 109.514 | 27.444 | 29.638 | 1.00 | 26.04 |
| 4026 | CH2 | TRP | 425 | 109.525 | 26.222 | 30.335 | 1.00 | 27.12 |
| 4027 | H | TRP | 425 | 105.993 | 29.429 | 24.639 | 1.00 | 25.00 |
| 4028 | HE1 | TRP | 425 | 106.983 | 23.517 | 28.395 | 1.00 | 25.00 |
| 4029 | N | LEU | 426 | 105.974 | 29.615 | 27.848 | 1.00 | 31.46 |
| 4030 | CA | LEU | 426 | 105.994 | 30.186 | 29.188 | 1.00 | 28.35 |
| 4031 | C | LEU | 426 | 104.627 | 30.692 | 29.650 | 1.00 | 31.98 |
| 4032 | O | LEU | 426 | 104.293 | 30.585 | 30.832 | 1.00 | 29.19 |
| 4033 | CB | LEU | 426 | 107.039 | 31.302 | 29.268 | 1.00 | 21.80 |
| 4034 | CG | LEU | 426 | 107.525 | 31.703 | 30.664 | 1.00 | 25.44 |
| 4035 | CD1 | LEU | 426 | 108.240 | 30.535 | 31.331 | 1.00 | 20.60 |
| 4036 | CD2 | LEU | 426 | 108.454 | 32.900 | 30.560 | 1.00 | 23.92 |
| 4037 | H | LEU | 426 | 106.512 | 30.035 | 27.141 | 1.00 | 25.00 |
| 4038 | N | SER | 427 | 103.824 | 31.208 | 28.720 | 1.00 | 33.95 |
| 4039 | CA | SER | 427 | 102.497 | 31.722 | 29.066 | 1.00 | 33.39 |
| 4040 | C | SER | 427 | 101.502 | 30.647 | 29.502 | 1.00 | 30.91 |
| 4041 | O | SER | 427 | 100.515 | 30.951 | 30.170 | 1.00 | 31.38 |
| 4042 | CB | SER | 427 | 101.917 | 32.568 | 27.925 | 1.00 | 37.83 |
| 4043 | OG | SER | 427 | 101.970 | 31.892 | 26.683 | 1.00 | 46.06 |
| 4044 | H | SER | 427 | 104.124 | 31.247 | 27.790 | 1.00 | 25.00 |
| 4045 | HG | SER | 427 | 102.886 | 31.692 | 26.470 | 1.00 | 25.00 |
| 4046 | N | LYS | 428 | 101.780 | 29.392 | 29.151 | 1.00 | 30.99 |
| 4047 | CA | LYS | 428 | 100.914 | 28.271 | 29.518 | 1.00 | 30.38 |
| 4048 | C | LYS | 428 | 101.124 | 27.817 | 30.964 | 1.00 | 33.22 |
| 4049 | O | LYS | 428 | 100.505 | 26.845 | 31.410 | 1.00 | 34.36 |
| 4050 | CB | LYS | 428 | 101.166 | 27.070 | 28.601 | 1.00 | 33.08 |
| 4051 | CG | LYS | 428 | 100.690 | 27.213 | 27.166 | 1.00 | 40.80 |
| 4052 | CD | LYS | 428 | 100.885 | 25.888 | 26.433 | 1.00 | 48.04 |
| 4053 | CE | LYS | 428 | 100.314 | 25.910 | 25.002 | 1.00 | 54.20 |
| 4054 | NZ | LYS | 428 | 100.438 | 24.571 | 24.377 | 1.00 | 59.29 |
| 4055 | H | LYS | 428 | 102.587 | 29.209 | 28.628 | 1.00 | 25.00 |
| 4056 | 1HZ | LYS | 428 | 99.919 | 23.866 | 24.937 | 1.00 | 25.00 |
| 4057 | 2HZ | LYS | 428 | 100.037 | 24.613 | 23.418 | 1.00 | 25.00 |
| 4058 | 3HZ | LYS | 428 | 101.440 | 24.300 | 24.323 | 1.00 | 25.00 |
| 4059 | N | ASN | 429 | 101.992 | 28.518 | 31.693 | 1.00 | 36.19 |
| 4060 | CA | ASN | 429 | 102.313 | 28.172 | 33.081 | 1.00 | 31.97 |
| 4061 | C | ASN | 429 | 102.855 | 26.740 | 33.172 | 1.00 | 29.89 |
| 4062 | O | ASN | 429 | 102.272 | 25.882 | 33.839 | 1.00 | 25.78 |
| 4063 | CB | ASN | 429 | 101.092 | 28.334 | 33.995 | 1.00 | 32.22 |
| 4064 | CG | ASN | 429 | 100.814 | 29.782 | 34.358 | 1.00 | 36.78 |
| 4065 | OD1 | ASN | 429 | 101.488 | 30.699 | 33.894 | 1.00 | 40.44 |
| 4066 | ND2 | ASN | 429 | 99.826 | 29.991 | 35.215 | 1.00 | 41.36 |
| 4067 | H | ASN | 429 | 102.436 | 29.294 | 31.299 | 1.00 | 25.00 |
| 4068 | 1HD2 | ASN | 429 | 99.643 | 30.918 | 35.449 | 1.00 | 25.00 |
| 4069 | 2HD2 | ASN | 429 | 99.331 | 29.226 | 35.566 | 1.00 | 25.00 |
| 4070 | N | PRO | 430 | 103.997 | 26.472 | 32.508 | 1.00 | 29.30 |
| 4071 | CA | PRO | 430 | 104.649 | 25.157 | 32.492 | 1.00 | 25.30 |
| 4072 | C | PRO | 430 | 104.897 | 24.669 | 33.913 | 1.00 | 27.01 |
| 4073 | O | PRO | 430 | 105.218 | 25.463 | 34.801 | 1.00 | 27.38 |
| 4074 | CB | PRO | 430 | 105.975 | 25.447 | 31.799 | 1.00 | 24.23 |
| 4075 | CG | PRO | 430 | 105.664 | 26.610 | 30.932 | 1.00 | 30.06 |
| 4076 | CD | PRO | 430 | 104.835 | 27.648 | 31.820 | 1.00 | 30.25 |
| 4077 | N | LYS | 431 | 104.824 | 23.358 | 34.108 | 1.00 | 25.65 |
| 4078 | CA | LYS | 431 | 105.020 | 22.774 | 35.426 | 1.00 | 25.93 |
| 4079 | C | LYS | 431 | 106.308 | 23.248 | 36.107 | 1.00 | 24.81 |
| 4080 | O | LYS | 431 | 106.297 | 23.570 | 37.292 | 1.00 | 24.36 |
| 4081 | CB | LYS | 431 | 105.000 | 21.252 | 35.325 | 1.00 | 26.70 |
| 4082 | CG | LYS | 431 | 104.584 | 20.547 | 36.604 | 1.00 | 40.34 |
| 4083 | CD | LYS | 431 | 104.361 | 19.068 | 36.330 | 1.00 | 52.65 |
| 4084 | CE | LYS | 431 | 103.775 | 18.345 | 37.531 | 1.00 | 60.92 |
| 4085 | NZ | LYS | 431 | 103.587 | 16.892 | 37.247 | 1.00 | 58.59 |
| 4086 | H | LYS | 431 | 104.610 | 22.777 | 33.352 | 1.00 | 25.00 |
| 4087 | 1HZ | LYS | 431 | 102.939 | 16.775 | 36.442 | 1.00 | 25.00 |
| 4088 | 2HZ | LYS | 431 | 104.506 | 16.462 | 37.018 | 1.00 | 25.00 |
| 4089 | 3HZ | LYS | 431 | 103.189 | 16.424 | 38.086 | 1.00 | 25.00 |
| 4090 | N | ILE | 432 | 107.401 | 23.338 | 35.353 | 1.00 | 25.03 |
| 4091 | CA | ILE | 432 | 108.667 | 23.774 | 35.934 | 1.00 | 21.64 |
| 4092 | C | ILE | 432 | 108.561 | 25.188 | 36.505 | 1.00 | 24.42 |
| 4093 | O | ILE | 432 | 109.058 | 25.459 | 37.602 | 1.00 | 25.07 |
| 4094 | CB | ILE | 432 | 109.847 | 23.646 | 34.928 | 1.00 | 22.09 |
| 4095 | CG1 | ILE | 432 | 111.179 | 23.898 | 35.647 | 1.00 | 20.75 |
| 4096 | CG2 | ILE | 432 | 109.662 | 24.587 | 33.739 | 1.00 | 20.53 |
| 4097 | CD1 | ILE | 432 | 112.403 | 23.511 | 34.838 | 1.00 | 17.10 |
| 4098 | H | ILE | 432 | 107.354 | 23.103 | 34.410 | 1.00 | 25.00 |
| 4099 | N | LEU | 433 | 107.868 | 26.070 | 35.788 | 1.00 | 25.32 |
| 4100 | CA | LEU | 433 | 107.674 | 27.448 | 36.240 | 1.00 | 23.97 |
| 4101 | C | LEU | 433 | 106.758 | 27.446 | 37.464 | 1.00 | 27.11 |
| 4102 | O | LEU | 433 | 107.051 | 28.078 | 38.483 | 1.00 | 28.11 |
| 4103 | CB | LEU | 433 | 107.057 | 28.298 | 35.126 | 1.00 | 24.53 |
| 4104 | CG | LEU | 433 | 106.721 | 29.754 | 35.473 | 1.00 | 28.30 |
| 4105 | CD1 | LEU | 433 | 107.968 | 30.488 | 35.945 | 1.00 | 23.75 |
| 4106 | CD2 | LEU | 433 | 106.108 | 30.456 | 34.265 | 1.00 | 27.09 |
| 4107 | H | LEU | 433 | 107.456 | 25.788 | 34.948 | 1.00 | 25.00 |

TABLE 11-continued

Structural Coordinates of Tobacco 5-Epi-Aristolochene Synthase
In the Absence of Bound Substrate

| Atom | Atom | Resi-due | Resi-due # | X | Y | Z | OCC | B-factor |
|---|---|---|---|---|---|---|---|---|
| 4108 | N | GLU | 434 | 105.667 | 26.698 | 37.360 | 1.00 | 26.39 |
| 4109 | CA | GLU | 434 | 104.690 | 26.566 | 38.429 | 1.00 | 28.21 |
| 4110 | C | GLU | 434 | 105.393 | 26.139 | 39.723 | 1.00 | 25.73 |
| 4111 | O | GLU | 434 | 105.159 | 26.711 | 40.790 | 1.00 | 25.92 |
| 4112 | CB | GLU | 434 | 103.656 | 25.510 | 38.027 | 1.00 | 40.62 |
| 4113 | CG | GLU | 434 | 102.371 | 25.510 | 38.835 | 1.00 | 59.16 |
| 4114 | CD | GLU | 434 | 101.447 | 26.650 | 38.457 | 1.00 | 69.11 |
| 4115 | OE1 | GLU | 434 | 101.135 | 26.803 | 37.255 | 1.00 | 76.28 |
| 4116 | OE2 | GLU | 434 | 101.026 | 27.391 | 39.366 | 1.00 | 78..90 |
| 4117 | H | GLU | 434 | 105.516 | 26.206 | 36.531 | 1.00 | 25.00 |
| 4118 | N | ALA | 435 | 106.272 | 25.147 | 39.614 | 1.00 | 23.71 |
| 4119 | CA | ALA | 435 | 107.015 | 24.632 | 40.764 | 1.00 | 21.25 |
| 4120 | C | ALA | 435 | 107.915 | 25.704 | 41.377 | 1.00 | 21.57 |
| 4121 | O | ALA | 435 | 107.973 | 25.864 | 42.599 | 1.00 | 21.94 |
| 4122 | CB | ALA | 435 | 107.838 | 23.424 | 40.353 | 1.00 | 17.11 |
| 4123 | H | ALA | 435 | 106.427 | 24.748 | 38.737 | 1.00 | 25.00 |
| 4124 | N | SER | 436 | 108.603 | 26.448 | 40.519 | 1.00 | 20.07 |
| 4125 | CA | SER | 436 | 109.486 | 27.510 | 40.969 | 1.00 | 21.72 |
| 4126 | C | SER | 436 | 108.676 | 28.531 | 41.759 | 1.00 | 23.51 |
| 4127 | O | SER | 436 | 109.095 | 28.979 | 42.832 | 1.00 | 25.11 |
| 4128 | CB | SER | 436 | 110.147 | 28.179 | 39.765 | 1.00 | 21.38 |
| 4129 | OG | SER | 436 | 111.040 | 29.196 | 40.173 | 1.00 | 36.67 |
| 4130 | H | SER | 436 | 108.521 | 26.272 | 39.556 | 1.00 | 25.00 |
| 4131 | HG | SER | 436 | 110.568 | 29.867 | 40.669 | 1.00 | 25.00 |
| 4132 | N | VAL | 437 | 107.501 | 28.876 | 41.235 | 1.00 | 23.94 |
| 4133 | CA | VAL | 437 | 106.622 | 29.846 | 41.880 | 1.00 | 18.07 |
| 4134 | C | VAL | 437 | 106.134 | 29.330 | 43.226 | 1.00 | 19.00 |
| 4135 | O | VAL | 437 | 106.179 | 30.048 | 44.227 | 1.00 | 24.40 |
| 4136 | CB | VAL | 437 | 105.410 | 30.192 | 40.990 | 1.00 | 22.63 |
| 4137 | CG1 | VAL | 437 | 104.498 | 31.163 | 41.709 | 1.00 | 24.13 |
| 4138 | CG2 | VAL | 437 | 105.879 | 30.794 | 39.677 | 1.00 | 13.85 |
| 4139 | H | VAL | 437 | 107.218 | 28.463 | 40.391 | 1.00 | 25.00 |
| 4140 | N | ILE | 438 | 105.693 | 28.076 | 43.249 | 1.00 | 22.97 |
| 4141 | CA | ILE | 438 | 105.204 | 27.443 | 44.472 | 1.00 | 25.17 |
| 4142 | C | ILE | 438 | 106.279 | 27.478 | 45.566 | 1.00 | 27.56 |
| 4143 | O | ILE | 438 | 105.996 | 27.831 | 46.718 | 1.00 | 25.37 |
| 4144 | CB | ILE | 438 | 104.776 | 25.975 | 44.200 | 1.00 | 28.36 |
| 4145 | CG1 | ILE | 438 | 103.565 | 25.952 | 43.262 | 1.00 | 33.63 |
| 4146 | CG2 | ILE | 438 | 104.457 | 25.255 | 45.505 | 1.00 | 31.72 |
| 4147 | CD1 | ILE | 438 | 103.130 | 24.569 | 42.836 | 1.00 | 33.54 |
| 4148 | H | ILE | 438 | 105.697 | 27.559 | 42.417 | 1.00 | 25.00 |
| 4149 | N | ILE | 439 | 107.512 | 27.134 | 45.196 | 1.00 | 27.24 |
| 4150 | CA | ILE | 439 | 108.635 | 27.130 | 46.135 | 1.00 | 24.88 |
| 4151 | C | ILE | 439 | 108.769 | 28.502 | 46.787 | 1.00 | 20.20 |
| 4152 | O | ILE | 439 | 108.842 | 28.610 | 48.007 | 1.00 | 20.39 |
| 4153 | CB | ILE | 439 | 109.961 | 26.739 | 45.429 | 1.00 | 23.09 |
| 4154 | CG1 | ILE | 439 | 109.915 | 25.264 | 45.023 | 1.00 | 21.73 |
| 4155 | CG2 | ILE | 439 | 111.154 | 26.989 | 46.345 | 1.00 | 17.14 |
| 4156 | CD1 | ILE | 439 | 110.984 | 24.859 | 44.043 | 1.00 | 22.40 |
| 4157 | H | ILE | 439 | 107.670 | 26.870 | 44.265 | 1.00 | 25.00 |
| 4158 | N | CYS | 440 | 108.763 | 29.552 | 45.974 | 1.00 | 21.23 |
| 4159 | CA | CYS | 440 | 103.873 | 30.901 | 46.508 | 1.00 | 23.58 |
| 4160 | C | CYS | 440 | 107.718 | 31.209 | 47.458 | 1.00 | 27.42 |
| 4161 | O | CYS | 440 | 107.933 | 31.707 | 48.563 | 1.00 | 29.41 |
| 4162 | CB | CYS | 440 | 108.897 | 31.928 | 45.376 | 1.00 | 26.26 |
| 4163 | SG | CYS | 440 | 109.015 | 33.625 | 45.934 | 1.00 | 17.39 |
| 4164 | H | CYS | 440 | 108.685 | 29.406 | 45.006 | 1.00 | 25.00 |
| 4165 | N | ARG | 441 | 106.502 | 30.889 | 47.038 | 1.00 | 30.12 |
| 4166 | CA | ARG | 441 | 105.295 | 31.118 | 47.825 | 1.00 | 28.33 |
| 4167 | C | ARG | 4441 | 105.280 | 30.448 | 49.197 | 1.00 | 28.78 |
| 4168 | O | ARG | 441 | 105.225 | 31.125 | 50.223 | 1.00 | 28.38 |
| 4169 | CB | ARG | 441 | 104.056 | 30.693 | 47.031 | 1.00 | 26.28 |
| 4170 | CG | ARG | 441 | 102.722 | 30.927 | 47.734 | 1.00 | 26.09 |
| 4171 | CD | ARG | 441 | 102.312 | 32.391 | 47.725 | 1.00 | 32.68 |
| 4172 | NE | ARG | 441 | 103.001 | 33.195 | 48.731 | 1.00 | 35.67 |
| 4173 | CZ | ARG | 441 | 103.243 | 34.499 | 48.611 | 1.00 | 31.42 |
| 4174 | NH1 | ARG | 441 | 102.861 | 35.159 | 47.526 | 1.00 | 25.83 |
| 4175 | NH2 | ARG | 441 | 103.851 | 35.153 | 49.591 | 1.00 | 32.87 |
| 4176 | H | ARG | 441 | 106.413 | 30.429 | 46.165 | 1.00 | 25.00 |
| 4177 | HE | ARG | 441 | 103.307 | 32.748 | 49.547 | 1.00 | 25.00 |
| 4178 | 1HH1 | ARG | 441 | 102.391 | 34.678 | 46.792 | 1.00 | 25.00 |
| 4179 | 2HH1 | ARG | 441 | 103.043 | 36.138 | 47.443 | 1.00 | 25.00 |
| 4180 | 1HH2 | ARG | 441 | 104.133 | 34.668 | 50.417 | 1.00 | 25.00 |
| 4181 | 2HH2 | ARG | 441 | 104.032 | 36.133 | 49.498 | 1.00 | 25.00 |
| 4182 | N | VAL | 442 | 105.329 | 29.120 | 49.220 | 1.00 | 28.03 |
| 4183 | CA | VAL | 442 | 105.289 | 28.392 | 50.484 | 1.00 | 29.35 |
| 4184 | C | VAL | 442 | 106.443 | 28.708 | 51.430 | 1.00 | 29.48 |
| 4185 | O | VAL | 442 | 106.248 | 28.754 | 52.644 | 1.00 | 30.67 |
| 4186 | CB | VAL | 442 | 105.171 | 26.864 | 50.272 | 1.00 | 28.34 |
| 4187 | CG1 | VAL | 442 | 103.906 | 26.546 | 49.489 | 1.00 | 20.42 |
| 4188 | CG2 | VAL | 442 | 106.394 | 26.322 | 49.562 | 1.00 | 28.17 |
| 4189 | H | VAL | 442 | 105.405 | 28.625 | 48.376 | 1.00 | 25.00 |
| 4190 | N | ILE | 443 | 107.635 | 28.941 | 50.885 | 1.00 | 32.67 |
| 4191 | CA | ILE | 443 | 108.788 | 29.266 | 51.722 | 1.00 | 32.60 |
| 4192 | C | ILE | 443 | 108.619 | 30.6722 | 52.283 | 1.00 | 34.90 |
| 4193 | O | ILE | 443 | 108.866 | 30.908 | 53.469 | 1.00 | 33.18 |
| 4194 | CB | ILE | 443 | 110.134 | 29.150 | 50.955 | 1.00 | 34.36 |
| 4195 | CG1 | ILE | 443 | 110.394 | 27.689 | 50.574 | 1.00 | 27.67 |
| 4196 | CG2 | ILE | 443 | 111.290 | 29.649 | 51.822 | 1.00 | 28.68 |
| 4197 | CD1 | ILE | 443 | 110.456 | 26.745 | 51.765 | 1.00 | 31.24 |
| 4198 | H | ILE | 443 | 107.746 | 28.891 | 49.910 | 1.00 | 25.00 |
| 4199 | N | ASP | 444 | 108.170 | 31.599 | 51.441 | 1.00 | 33.84 |
| 4200 | CA | ASP | 444 | 107.954 | 32.968 | 51.889 | 1.00 | 35.72 |
| 4201 | C | ASP | 444 | 106.935 | 32.959 | 53.023 | 1.00 | 38.14 |
| 4202 | O | ASP | 444 | 107.184 | 33.520 | 54.091 | 1.00 | 37.60 |
| 4203 | CB | ASP | 444 | 107.450 | 33.848 | 50.744 | 1.00 | 39.61 |
| 4204 | CG | ASP | 444 | 107.110 | 35.260 | 51.199 | 1.00 | 48.15 |
| 4205 | OD11 | ASP | 444 | 105.972 | 35.485 | 51.667 | 1.00 | 51.59 |
| 4206 | OD2 | ASP | 444 | 107.980 | 36.147 | 51.091 | 1.00 | 51.59 |
| 4207 | H | ASP | 444 | 107.985 | 31.384 | 50.507 | 1.00 | 25.00 |
| 4208 | N | ASP | 445 | 105.812 | 32.279 | 52.803 | 1.00 | 40.33 |
| 4209 | CA | ASP | 445 | 104.749 | 32.199 | 53.803 | 1.00 | 39.63 |
| 4210 | C | ASP | 445 | 105.221 | 31.599 | 55.124 | 1.00 | 36.43 |
| 4211 | O | ASP | 445 | 104.826 | 32.060 | 56.195 | 1.00 | 38.68 |
| 4212 | CB | ASP | 445 | 103.549 | 31.415 | 53.259 | 1.00 | 34.74 |
| 4213 | CG | ASP | 445 | 102.867 | 32.115 | 52.087 | 1.00 | 37.47 |
| 4214 | OD1 | ASP | 445 | 103.173 | 33.301 | 51.818 | 1.00 | 32.84 |
| 4215 | OD2 | ASP | 445 | 102.022 | 31.474 | 51.429 | 1.00 | 34.75 |
| 4216 | H | ASP | 445 | 105.694 | 31.823 | 51.945 | 1.00 | 25.00 |
| 4217 | N | THR | 446 | 106.061 | 30.574 | 55.047 | 1.00 | 36.21 |
| 4218 | CA | THR | 446 | 106.586 | 29.933 | 56.247 | 1.00 | 34.20 |
| 4219 | C | THR | 446 | 107.469 | 30.902 | 57.034 | 1.00 | 34.56 |
| 4220 | O | THR | 446 | 107.396 | 30.968 | 58.259 | 1.00 | 36.69 |
| 4221 | CB | THR | 446 | 107.398 | 28.674 | 55.890 | 1.00 | 29.80 |
| 4222 | OG1 | THR | 446 | 106.545 | 27.735 | 55.227 | 1.00 | 31.60 |
| 4223 | CG2 | THR | 446 | 107.970 | 28.029 | 57.136 | 1.00 | 31.33 |
| 4224 | H | THR | 446 | 106.322 | 30.221 | 54.170 | 1.00 | 25.00 |
| 4225 | HG1 | THR | 446 | 107.041 | 26.946 | 54.992 | 1.00 | 25.00 |
| 4226 | N | ALA | 447 | 108.266 | 31.687 | 56.318 | 1.00 | 39.84 |
| 4227 | CA | ALA | 447 | 109.172 | 32.644 | 56.941 | 1.00 | 42.07 |
| 4228 | C | ALA | 447 | 108.495 | 33.902 | 57.483 | 1.00 | 45.04 |
| 4229 | O | ALA | 447 | 108.675 | 34.259 | 58.647 | 1.00 | 48.71 |
| 4230 | CB | ALA | 447 | 110.2776 | 33.025 | 55.959 | 1.00 | 36.91 |
| 4231 | H | ALA | 447 | 108.237 | 31.624 | 55.337 | 1.00 | 25.00 |
| 4232 | N | THR | 448 | 107.708 | 34.565 | 56.644 | 1.00 | 50.59 |
| 4233 | CA | THR | 448 | 107.036 | 35.799 | 57.039 | 1.00 | 49.97 |
| 4234 | C | THR | 448 | 105.729 | 35.644 | 57.818 | 1.00 | 51.43 |
| 4235 | O | THR | 448 | 105.100 | 36.646 | 58.159 | 1.00 | 56.61 |
| 4236 | CB | THR | 448 | 106.790 | 36.715 | 55.811 | 1.00 | 47.11 |
| 4237 | OG1 | THR | 448 | 106.095 | 35.986 | 54.793 | 1.00 | 50.09 |
| 4238 | CG2 | THR | 448 | 108.106 | 37.214 | 55.245 | 1.00 | 47.36 |
| 4239 | H | THR | 448 | 107.555 | 34.230 | 55.741 | 1.00 | 25.00 |
| 4240 | HG1 | THR | 448 | 105.951 | 36.556 | 54.034 | 1.00 | 25.00 |
| 4241 | N | TYR | 449 | 105.352 | 34.415 | 58.157 | 1.00 | 51.91 |
| 4242 | CA | TYR | 449 | 104.103 | 34.182 | 58.881 | 1.00 | 53.63 |
| 4243 | C | TYR | 449 | 103.927 | 35.020 | 60.148 | 1.00 | 58.13 |
| 4244 | O | TYR | 449 | 102.939 | 35.745 | 60.282 | 1.00 | 57.88 |
| 4245 | CB | TYR | 449 | 103.926 | 32.696 | 59.218 | 1.00 | 50.75 |
| 4246 | CG | TYR | 449 | 102.674 | 32.406 | 60.025 | 1.00 | 55.96 |
| 4247 | CD1 | TYR | 449 | 101.419 | 32.856 | 59.596 | 1.00 | 60.14 |
| 4248 | CD2 | TYR | 449 | 102.746 | 31.716 | 61.235 | 1.00 | 56.00 |
| 4249 | CE1 | TYR | 449 | 100.273 | 32.629 | 60.353 | 1.00 | 55.79 |
| 4250 | CE2 | TYR | 449 | 101.605 | 31.483 | 62.000 | 1.00 | 57.85 |
| 4251 | CZ | TYR | 449 | 100.375 | 31.943 | 61.554 | 1.00 | 60.06 |
| 4252 | OH | TYR | 449 | 99.250 | 31.724 | 62.316 | 1.00 | 61.67 |
| 4253 | H | TYR | 449 | 105.912 | 33.653 | 57.905 | 1.00 | 25.00 |

TABLE 11-continued

Structural Coordinates of Tobacco 5-Epi-Aristolochene Synthase In the Absence of Bound Substrate

| Atom Type | Atom | Residue | Residue # | X | Y | Z | OCC | B-factor |
|---|---|---|---|---|---|---|---|---|
| 4254 | HH | TYR | 449 | 98.487 | 32.104 | 61.878 | 1.00 | 25.00 |
| 4255 | N | GLU | 450 | 104.883 | 34.927 | 61.067 | 1.00 | 64.21 |
| 4256 | CA | GLU | 450 | 104.810 | 35.662 | 62.329 | 1.00 | 67.19 |
| 4257 | C | GLU | 450 | 104.604 | 37.167 | 62.173 | 1.00 | 68.02 |
| 4258 | O | GLU | 450 | 103.698 | 37.742 | 62.781 | 1.00 | 68.60 |
| 4259 | CB | GLU | 450 | 106.053 | 35.386 | 63.178 | 1.00 | 73.69 |
| 4260 | CG | GLU | 450 | 106.228 | 33.917 | 63.557 | 1.00 | 87.48 |
| 4261 | CD | GLU | 450 | 104.988 | 33.311 | 64.211 | 1.00 | 95.20 |
| 4262 | OE1 | GLU | 450 | 104.311 | 34.009 | 65.000 | 1.00 | 100.27 |
| 4263 | OE2 | GLU | 430 | 104.690 | 32.129 | 63.934 | 1.00 | 96.38 |
| 4264 | H | GLU | 450 | 105.651 | 34.348 | 60.883 | 1.00 | 25.00 |
| 4265 | N | VAL | 451 | 105.427 | 37.790 | 61.336 | 1.00 | 69.29 |
| 4266 | CA | VAL | 451 | 105.351 | 39.228 | 61.091 | 1.00 | 69.79 |
| 4267 | C | VAL | 451 | 104.011 | 39.634 | 60.479 | 1.00 | 71.86 |
| 4268 | O | VAL | 451 | 103.383 | 40.594 | 60.925 | 1.00 | 73.87 |
| 4269 | CB | VAL | 451 | 106.482 | 39.692 | 60.149 | 1.00 | 68.77 |
| 4270 | CG1 | VAL | 451 | 106.490 | 41.211 | 60.036 | 1.00 | 67.70 |
| 4271 | CG2 | VAL | 451 | 107.825 | 39.180 | 60.647 | 1.00 | 74.55 |
| 4272 | H | VAL | 451 | 106.100 | 37.263 | 60.866 | 1.00 | 25.00 |
| 4273 | N | GLU | 452 | 103.572 | 38.893 | 59.467 | 1.00 | 73.34 |
| 4274 | CA | GLU | 452 | 102.311 | 39.191 | 58.798 | 1.00 | 74.52 |
| 4275 | C | GLU | 452 | 101.096 | 38.987 | 59.700 | 1.00 | 75.62 |
| 4276 | O | GLU | 452 | 100.107 | 39.715 | 59.575 | 1.00 | 75.03 |
| 4277 | CB | GLU | 452 | 102.176 | 38.385 | 57.502 | 1.00 | 73.01 |
| 4278 | CG | GLU | 452 | 103.194 | 38.774 | 56.427 | 1.00 | 77.67 |
| 4279 | CD | GLU | 452 | 103.032 | 38.007 | 55.118 | 1.00 | 81.85 |
| 4280 | OE1 | GLU | 452 | 102.537 | 36.858 | 55.137 | 1.00 | 80.20 |
| 4281 | OE2 | GLU | 452 | 103.417 | 38.558 | 54.061 | 1.00 | 82.09 |
| 4282 | H | GLU | 452 | 104.100 | 38.124 | 59.165 | 1.00 | 25.00 |
| 4283 | N | LYS | 453 | 101.173 | 38.038 | 60.631 | 1.00 | 78.11 |
| 4284 | CA | LYS | 453 | 100.050 | 37.799 | 61.538 | 1.00 | 81.43 |
| 4285 | C | LYS | 453 | 99.887 | 38.943 | 62.532 | 1.00 | 84.49 |
| 4286 | O | LYS | 453 | 98.768 | 39.393 | 62.783 | 1.00 | 88.82 |
| 4287 | CB | LYS | 453 | 100.176 | 36.468 | 62.280 | 1.00 | 79.17 |
| 4288 | CG | LYS | 453 | 98.907 | 36.134 | 63.054 | 1.00 | 78.09 |
| 4289 | CD | LYS | 453 | 98.928 | 34.759 | 63.674 | 1.00 | 79.02 |
| 4290 | CE | LYS | 453 | 97.583 | 34.462 | 64.319 | 1.00 | 81.56 |
| 4291 | NZ | LYS | 453 | 97.525 | 33.093 | 64.899 | 1.00 | 87.65 |
| 4292 | H | LYS | 453 | 101.981 | 37.486 | 60.701 | 1.00 | 25.00 |
| 4293 | 1HZ | LYS | 453 | 98.261 | 32.991 | 665.627 | 1.00 | 25.00 |
| 4294 | 2HZ | LYS | 453 | 96.590 | 32.937 | 65.327 | 1.00 | 25.00 |
| 4295 | 3HZ | LYS | 453 | 97.682 | 32.390 | 64.148 | 1.00 | 25.00 |
| 4296 | N | SER | 454 | 100.996 | 39.424 | 63.088 | 1.00 | 84.86 |
| 4297 | CA | SER | 454 | 100.943 | 40.535 | 64.037 | 1.00 | 83.61 |
| 4298 | C | SER | 454 | 100.521 | 41.835 | 63.336 | 1.00 | 83.52 |
| 4299 | O | SER | 454 | 100.210 | 42.830 | 63.991 | 1.00 | 82.37 |
| 4300 | CB | SER | 454 | 102.286 | 40.703 | 64.755 | 1.00 | 81.64 |
| 4301 | OG | SER | 454 | 103.363 | 40.771 | 63.838 | 1.00 | 82.19 |
| 4302 | H | SER | 454 | 101.863 | 39.025 | 62.862 | 1.00 | 25.00 |
| 4303 | HG | SER | 454 | 103.411 | 39.963 | 63.320 | 1.00 | 25.00 |
| 4304 | N | ARG | 455 | 100.515 | 41.813 | 62.003 | 1.00 | 83.63 |
| 4305 | CA | ARG | 455 | 100.102 | 42.961 | 61.197 | 1.00 | 86.97 |
| 4306 | C | ARRG | 455 | 98.616 | 42.870 | 60.854 | 1.00 | 89.33 |
| 4307 | O | ARG | 455 | 98.073 | 43.748 | 60.183 | 1.00 | 89.55 |
| 4308 | CB | ARG | 455 | 100.892 | 43.025 | 59.891 | 1.00 | 86.51 |
| 4309 | CG | ARG | 455 | 102.319 | 43.493 | 60.014 | 1.00 | 89.64 |
| 4310 | CD | ARG | 455 | 102.926 | 43.581 | 58.632 | 1.00 | 98.07 |
| 4311 | NE | ARG | 455 | 104.296 | 44.078 | 58.647 | 1.00 | 109.66 |
| 4312 | CZ | ARG | 455 | 104.976 | 44.415 | 57.555 | 1.00 | 114.68 |
| 4313 | NH1 | ARG | 455 | 104.411 | 44.309 | 56.357 | 1.00 | 117.44 |
| 4314 | NH2 | ARG | 455 | 106.220 | 44.863 | 57.659 | 1.00 | 113.39 |
| 4315 | H | ARG | 455 | 100.816 | 41.007 | 61.542 | 1.00 | 25.00 |
| 4316 | HE | ARG | 455 | 104.745 | 44.172 | 59.512 | 1.00 | 25.00 |
| 4317 | 1HH1 | ARG | 455 | 103.471 | 43.978 | 56.270 | 1.00 | 25.00 |
| 4318 | 2HH1 | ARG | 455 | 104.920 | 44.568 | 55.536 | 1.00 | 25.00 |
| 4319 | 1HH2 | ARG | 455 | 106.646 | 44.949 | 58.558 | 1.00 | 25.00 |
| 4320 | 2HH2 | ARG | 455 | 106.724 | 45.120 | 56.834 | 1.00 | 25.00 |
| 4321 | N | GLY | 456 | 97.980 | 41.773 | 61.259 | 1.00 | 90.67 |
| 4322 | CA | GLY | 456 | 96.566 | 41.584 | 60.989 | 1.00 | 90.27 |
| 4323 | C | GLY | 456 | 96.256 | 40.876 | 59.681 | 1.00 | 91.84 |
| 4324 | O | GLY | 456 | 95.087 | 40.636 | 59.371 | 1.00 | 90.99 |
| 4325 | H | GLY | 456 | 98.464 | 41.081 | 61.752 | 1.00 | 25.00 |
| 4326 | N | GLN | 457 | 97.290 | 40.528 | 58.917 | 1.00 | 92.16 |
| 4327 | CA | GLN | 457 | 97.107 | 39.842 | 57.638 | 1.00 | 90.85 |
| 4328 | C | GLN | 457 | 96.662 | 38.395 | 57.846 | 1.00 | 89.74 |
| 4329 | O | GLN | 457 | 97.442 | 37.462 | 57.659 | 1.00 | 92.66 |
| 4330 | CB | GLN | 457 | 98.402 | 39.868 | 56.817 | 1.00 | 89.90 |
| 4331 | CG | GLN | 457 | 98.905 | 41.257 | 56.457 | 1.00 | 95.19 |
| 4332 | CD | GLN | 457 | 100.145 | 41.221 | 55.576 | 1.00 | 99.21 |
| 4333 | OE1 | GLN | 457 | 100.325 | 40.303 | 54.775 | 1.00 | 102.27 |
| 4334 | NE2 | GLN | 457 | 101.002 | 42.225 | 55.718 | 1.00 | 97.71 |
| 4335 | H | GLN | 457 | 98.199 | 40.716 | 59.228 | 1.00 | 25.00 |
| 4336 | 1HE2 | GLN | 457 | 101.798 | 42.200 | 55.151 | 1.00 | 25.00 |
| 4337 | 2HE2 | GLN | 457 | 100.809 | 42.931 | 56.364 | 1.00 | 25.00 |
| 4338 | N | ILE | 458 | 95.397 | 38.207 | 58.209 | 1.00 | 88.19 |
| 4339 | CA | ILE | 458 | 94.859 | 36.867 | 58.439 | 1.00 | 82.29 |
| 4340 | C | ILE | 458 | 94.715 | 36.043 | 57.159 | 1.00 | 75.34 |
| 4341 | O | ILE | 458 | 94.305 | 34.887 | 57.205 | 1.00 | 73.69 |
| 4342 | CB | ILE | 458 | 93.510 | 36.907 | 59.199 | 1.00 | 85.78 |
| 4343 | CC1 | ILE | 458 | 92.566 | 37.933 | 58.562 | 1.00 | 86.17 |
| 43444 | CG2 | ILE | 458 | 93.751 | 37.191 | 60.681 | 1.00 | 85.33 |
| 4345 | CD1 | ILE | 458 | 91.240 | 38.069 | 59.277 | 1.00 | 89.41 |
| 4346 | H | ILE | 458 | 94.823 | 38.995 | 58.338 | 1.00 | 25.00 |
| 4347 | N | ALA | 459 | 95.077 | 36.632 | 56.025 | 1.00 | 68.80 |
| 4348 | CA | ALA | 459 | 95.007 | 35.938 | 54.747 | 1.00 | 62.63 |
| 4349 | C | ALA | 459 | 96.368 | 35.324 | 54.389 | 1.00 | 62.33 |
| 4350 | O | ALA | 459 | 96.664 | 35.093 | 53.216 | 1.00 | 62.33 |
| 4351 | CB | ALA | 459 | 94.549 | 36.893 | 53.653 | 1.00 | 62.28 |
| 4352 | H | ALA | 459 | 95.387 | 37.554 | 56.036 | 1.00 | 25.00 |
| 4353 | N | THR | 460 | 97.210 | 35.097 | 55.396 | 1.00 | 59.27 |
| 4354 | CA | THR | 460 | 98.531 | 34.513 | 55.170 | 1.00 | 57.11 |
| 4355 | C | THR | 460 | 98.424 | 33.034 | 54.826 | 1.00 | 53.62 |
| 4356 | O | THR | 460 | 97.587 | 32.319 | 55.383 | 1.00 | 53.81 |
| 4357 | CB | THR | 460 | 99.453 | 34.671 | 56.400 | 1.00 | 58.87 |
| 4358 | OG1 | THR | 460 | 98.763 | 34.257 | 57.588 | 1.00 | 56.81 |
| 4359 | CG2 | THR | 460 | 99.901 | 36.100 | 56.541 | 1.00 | 60.73 |
| 4360 | H | THR | 460 | 96.933 | 35.314 | 56.305 | 1.00 | 25.00 |
| 4361 | HG1 | THR | 460 | 98.004 | 34.838 | 57.727 | 1.00 | 25.00 |
| 4362 | N | GLY | 461 | 99.298 | 32.574 | 53.937 | 1.00 | 44.28 |
| 4363 | CA | GLY | 461 | 99.289 | 31.184 | 53.526 | 1.00 | 37.76 |
| 4364 | C | GLY | 461 | 99.138 | 30.186 | 54.652 | 1.00 | 39.21 |
| 4365 | O | GLY | 461 | 98.265 | 29.318 | 54.599 | 1.00 | 37.71 |
| 4366 | H | GLY | 461 | 99.947 | 33.183 | 53.532 | 1.00 | 25.00 |
| 4367 | N | ILE | 462 | 99.965 | 30.320 | 55.684 | 1.00 | 41.07 |
| 4368 | CA | ILE | 462 | 99.915 | 29.405 | 56.821 | 1.00 | 43.03 |
| 4369 | C | ILE | 462 | 98.567 | 29.461 | 57.539 | 1.00 | 43.30 |
| 4370 | O | ILE | 462 | 98.063 | 28.430 | 57.991 | 1.00 | 44.23 |
| 4371 | CB | ILE | 462 | 101.079 | 29.658 | 57.814 | 1.00 | 35.94 |
| 4372 | CG1 | ILE | 462 | 102.418 | 29.419 | 57.116 | 1.00 | 34.23 |
| 4373 | CG2 | ILE | 462 | 100.979 | 28.720 | 59.011 | 1.00 | 26.77 |
| 4374 | CD1 | ILE | 462 | 102.625 | 27.987 | 56.675 | 1.00 | 31.75 |
| 4375 | H | ILE | 462 | 100.618 | 31.046 | 55.680 | 1.00 | 25.00 |
| 4376 | N | GLU | 463 | 97.972 | 30.652 | 57.602 | 1.00 | 47.45 |
| 4377 | CA | GLU | 463 | 96.673 | 30.842 | 58.253 | 1.00 | 48.26 |
| 4378 | C | GLU | 463 | 95.600 | 30.064 | 57.495 | 1.00 | 43.95 |
| 4379 | O | GLU | 463 | 94.876 | 29.250 | 58.077 | 1.00 | 45.29 |
| 4380 | CB | GLU | 463 | 96.307 | 32.329 | 58.291 | 1.00 | 55.50 |
| 4381 | CG | GLU | 463 | 95.120 | 32.664 | 59.182 | 1.00 | 60.77 |
| 4382 | CD | GLU | 463 | 95.448 | 32.555 | 60.656 | 1.00 | 66.36 |
| 4383 | OE1 | GLU | 463 | 96.195 | 33.419 | 61.166 | 1.00 | 70.77 |
| 4384 | OE2 | GLU | 463 | 94.957 | 31.605 | 61.303 | 1.00 | 66.97 |
| 4385 | H | GLU | 463 | 98.403 | 31.430 | 57.193 | 1.00 | 25.00 |
| 4386 | N | CYS | 464 | 95.534 | 30.295 | 56.186 | 1.00 | 38.49 |
| 4387 | CA | CYS | 464 | 94.575 | 29.616 | 55.322 | 1.00 | 40.30 |
| 4388 | C | CYS | 464 | 94.751 | 28.113 | 55.451 | 1.00 | 40.72 |
| 4389 | O | CYS | 464 | 93.778 | 27.364 | 55.550 | 1.00 | 43.89 |
| 4390 | CB | CYS | 464 | 94.798 | 30.010 | 53.860 | 1.00 | 33.19 |
| 4391 | SG | CYS | 464 | 94.721 | 31.780 | 53.533 | 1.00 | 41.13 |
| 4392 | H | CYS | 464 | 96.143 | 30.954 | 55.789 | 1.00 | 25.00 |
| 4393 | N | CYS | 465 | 96.007 | 27.682 | 55.464 | 1.00 | 42.83 |
| 4394 | CA | CYS | 465 | 96.337 | 26.271 | 55.557 | 1.00 | 45.44 |
| 4395 | C | CYS | 465 | 95.791 | 25.654 | 56.852 | 1.00 | 48.27 |
| 4396 | O | CYS | 465 | 95.165 | 24.591 | 56.818 | 1.00 | 47.36 |
| 4397 | CB | CYS | 465 | 97.850 | 26.074 | 55.487 | 1.00 | 39.55 |
| 4398 | SG | CYS | 465 | 98.332 | 24.350 | 55.349 | 1.00 | 40.18 |
| 4399 | H | CYS | 465 | 96.735 | 28.334 | 55.396 | 1.00 | 25.00 |

TABLE 11-continued

Structural Coordinates of Tobacco 5-Epi-Aristolochene Synthase
In the Absence of Bound Substrate

| Atom Type | Atom | Residue | Residue # | X | Y | Z | OCC | B-factor |
|---|---|---|---|---|---|---|---|---|
| 4400 | N | MET | 466 | 96.000 | 26.340 | 57.972 | 1.00 | 51.35 |
| 4401 | CA | MET | 466 | 95.531 | 25.854 | 59.267 | 1.00 | 55.36 |
| 4402 | C | MET | 466 | 94.019 | 25.699 | 59.312 | 1.00 | 56.30 |
| 4403 | O | MET | 466 | 93.512 | 24.647 | 59.698 | 1.00 | 55.90 |
| 4404 | CB | MET | 466 | 95.977 | 26.786 | 60.391 | 1.00 | 52.93 |
| 4405 | CG | MET | 466 | 97.464 | 26.797 | 60.618 | 1.00 | 49.91 |
| 4406 | SD | MET | 466 | 97.890 | 27.866 | 61.980 | 1.00 | 56.57 |
| 4407 | CE | MET | 466 | 97.679 | 29.434 | 61.228 | 1.00 | 45.63 |
| 4408 | H | MET | 466 | 96.483 | 27.193 | 57.936 | 1.00 | 25.00 |
| 4409 | N | ARG | 467 | 93.303 | 26.744 | 58.916 | 1.00 | 57.72 |
| 4410 | CA | ARG | 467 | 91.849 | 26.704 | 58.921 | 1.00 | 60.99 |
| 4411 | C | ARG | 467 | 91.271 | 25.700 | 57.935 | 1.00 | 57.48 |
| 4412 | O | ARG | 467 | 90.406 | 24.901 | 58.295 | 1.00 | 61.64 |
| 4413 | CB | ARG | 467 | 91.270 | 28.089 | 58.642 | 1.00 | 69.59 |
| 4414 | CG | ARG | 467 | 91.304 | 29.011 | 59.839 | 1.00 | 84.26 |
| 4415 | CD | ARG | 467 | 90.397 | 30.202 | 59.616 | 1.00 | 96.57 |
| 4416 | NE | ARG | 467 | 90.163 | 30.938 | 60.853 | 1.00 | 103.82 |
| 4417 | CZ | ARG | 467 | 89.074 | 31.660 | 61.099 | 1.00 | 107.61 |
| 4418 | NH1 | ARG | 467 | 88.109 | 31.749 | 60.192 | 1.00 | 108.04 |
| 4419 | NH2 | ARG | 467 | 88.946 | 32.284 | 62.261 | 1.00 | 109.38 |
| 4420 | H | ARG | 467 | 93.769 | 27.556 | 58.623 | 1.00 | 25.00 |
| 4421 | HE | ARG | 467 | 90.848 | 30.890 | 61.554 | 1.00 | 25.00 |
| 4422 | 1HH1 | ARG | 467 | 88.194 | 31.273 | 59.318 | 1.00 | 25.00 |
| 4423 | 2HH1 | ARG | 467 | 87.293 | 32.293 | 60.390 | 1.00 | 25.00 |
| 4424 | 1HH2 | ARG | 467 | 89.669 | 32.209 | 62.950 | 1.00 | 25.00 |
| 4425 | 2HH2 | ARG | 467 | 88.130 | 32.827 | 62.457 | 1.00 | 25.00 |
| 4426 | N | ASP | 468 | 91.769 | 25.726 | 56.704 | 1.00 | 52.60 |
| 4427 | CA | ASP | 468 | 91.287 | 24.832 | 55.660 | 1.00 | 51.80 |
| 4428 | C | ASP | 468 | 91.404 | 23.354 | 56.032 | 1.00 | 52.54 |
| 4429 | O | ASP | 468 | 90.488 | 22.574 | 55.767 | 1.00 | 57.49 |
| 4430 | CB | ASP | 468 | 92.026 | 25.111 | 54.346 | 1.00 | 49.09 |
| 4431 | CG | ASP | 468 | 91.328 | 24.513 | 53.133 | 1.00 | 52.94 |
| 4432 | OD1 | ASP | 468 | 90.127 | 24.170 | 53.218 | 1.00 | 55.18 |
| 4433 | OD2 | ASP | 468 | 91.983 | 24.402 | 52.076 | 1.00 | 54.77 |
| 4434 | H | ASP | 468 | 92.480 | 26.362 | 56.496 | 1.00 | 25.00 |
| 4435 | N | TYR | 469 | 92.524 | 22.973 | 56.646 | 1.00 | 52.44 |
| 4436 | CA | TYR | 469 | 92.755 | 21.581 | 57.040 | 1.00 | 49.37 |
| 4437 | C | TYR | 469 | 92.458 | 21.283 | 58.511 | 1.00 | 48.25 |
| 4438 | O | TYR | 469 | 92.316 | 20.121 | 58.894 | 1.00 | 46.98 |
| 4439 | CB | TYR | 469 | 94.200 | 21.165 | 56.730 | 1.00 | 46.99 |
| 4440 | CG | TYR | 469 | 94.546 | 21.129 | 55.260 | 1.00 | 47.76 |
| 4441 | CD1 | TYR | 469 | 94.994 | 22.273 | 54.602 | 1.00 | 51.80 |
| 4442 | CD2 | TYR | 469 | 94.431 | 19.947 | 54.524 | 1.00 | 50.13 |
| 4443 | CE1 | TYR | 469 | 95.317 | 22.246 | 53.248 | 1.00 | 56.40 |
| 4444 | CE2 | TYR | 469 | 94.753 | 19.908 | 53.167 | 1.00 | 54.09 |
| 4445 | CZ | TYR | 469 | 95.195 | 21.063 | 52.537 | 1.00 | 57.04 |
| 4446 | OH | TYR | 469 | 95.514 | 21.044 | 51.198 | 1.00 | 62.08 |
| 4447 | H | TYR | 469 | 93.216 | 23.642 | 56.837 | 1.00 | 25.00 |
| 4448 | HH | TYR | 469 | 95.802 | 21.916 | 50.922 | 1.00 | 25.00 |
| 4449 | N | GLY | 470 | 92.371 | 22.328 | 59.328 | 1.00 | 49.37 |
| 4450 | CA | GLY | 470 | 92.113 | 22.147 | 60.746 | 1.00 | 51.47 |
| 4451 | C | GLY | 470 | 93.332 | 21.551 | 61.425 | 1.00 | 52.90 |
| 4452 | O | GLY | 470 | 93.247 | 20.499 | 62.064 | 1.00 | 54.39 |
| 4453 | H | GLY | 470 | 92.471 | 23.228 | 58.968 | 1.00 | 25.00 |
| 4454 | N | ILE | 471 | 94.467 | 22.238 | 61.300 | 1.00 | 53.10 |
| 4455 | CA | ILE | 471 | 95.728 | 21.771 | 61.874 | 1.00 | 48.51 |
| 4456 | C | ILE | 471 | 96.521 | 22.877 | 62.571 | 1.00 | 49.16 |
| 4457 | O | ILE | 471 | 96.230 | 24.063 | 62.408 | 1.00 | 48..02 |
| 4458 | CB | ILE | 471 | 96.617 | 21.131 | 60.781 | 1.00 | 44.19 |
| 4459 | CG1 | ILE | 471 | 96.816 | 22.116 | 59.621 | 1.00 | 43.37 |
| 4460 | CG2 | ILE | 471 | 95.991 | 19.829 | 60.288 | 1.00 | 41.20 |
| 4461 | CD1 | ILE | 471 | 97.608 | 21.558 | 58.449 | 1.00 | 38.24 |
| 4462 | H | ILE | 471 | 94.452 | 23.094 | 60.822 | 1.00 | 25.00 |
| 4463 | N | SER | 472 | 97.517 | 22.475 | 63.357 | 1.00 | 53.02 |
| 4464 | CA | SER | 472 | 98.371 | 23.414 | 64.085 | 1.00 | 57.32 |
| 4465 | C | SER | 472 | 99.352 | 24.117 | 63.146 | 1.00 | 60.76 |
| 4466 | O | SER | 472 | 99.689 | 23.587 | 62.084 | 1.00 | 61.94 |
| 4467 | CB | SER | 472 | 99.148 | 22.672 | 65.180 | 1.00 | 59.87 |
| 4468 | OG | SER | 472 | 99.873 | 21.568 | 64.653 | 1.00 | 59.66 |
| 4469 | H | SER | 472 | 97.697 | 21.518 | 63.453 | 1.00 | 25.00 |
| 4470 | HG | SER | 472 | 100.314 | 21.103 | 65.376 | 1.00 | 25.00 |
| 4471 | N | THR | 473 | 99.838 | 25.287 | 63.557 | 1.00 | 61.86 |
| 4472 | CA | THR | 473 | 100.794 | 26.053 | 62.755 | 1.00 | 63.28 |
| 4473 | C | THR | 473 | 101.959 | 25.160 | 62.340 | 1.00 | 66.44 |
| 4474 | O | THR | 473 | 102.374 | 25.158 | 61.179 | 1.00 | 66.96 |
| 4475 | CB | THR | 473 | 101.366 | 27.248 | 63.547 | 1.00 | 62.70 |
| 4476 | OG1 | THR | 473 | 100.295 | 28.083 | 63.997 | 1.00 | 63.68 |
| 4477 | CG2 | THR | 473 | 102.306 | 28.068 | 62.677 | 1.00 | 63.27 |
| 4478 | H | THR | 473 | 99.529 | 25.654 | 64.404 | 1.00 | 25.00 |
| 4479 | HG1 | THR | 473 | 99.682 | 27.608 | 64.552 | 1.00 | 25.00 |
| 4480 | N | LYS | 474 | 102.454 | 24.380 | 63.296 | 1.00 | 65.27 |
| 4481 | CA | LYS | 474 | 103.568 | 23.470 | 63.065 | 1.00 | 67.87 |
| 4482 | C | LYS | 474 | 103.248 | 22.508 | 61.922 | 1.00 | 65.57 |
| 4483 | O | LYS | 474 | 104.051 | 22.325 | 61.001 | 1.00 | 66.11 |
| 4484 | CB | LYS | 474 | 103.863 | 22.686 | 64.349 | 1.00 | 71.33 |
| 4485 | CG | LYS | 474 | 105.150 | 21.875 | 64.320 | 1.00 | 77.07 |
| 4486 | CD | LYS | 474 | 105.422 | 21.234 | 65.673 | 1.00 | 77.42 |
| 4487 | CE | LYS | 474 | 106.776 | 20.544 | 65.698 | 1.00 | 78.55 |
| 4488 | NZ | LYS | 474 | 107.067 | 19.962 | 67.037 | 1.00 | 75.57 |
| 4489 | H | LYS | 474 | 102.058 | 24.422 | 64.186 | 1.00 | 25.00 |
| 4490 | 1HZ | LYS | 474 | 106.336 | 19.263 | 67.278 | 1.00 | 25.00 |
| 4491 | 2HZ | LYS | 474 | 107.998 | 19.500 | 67.020 | 1.00 | 25.00 |
| 4492 | 3HZ | LYS | 474 | 107.070 | 20.720 | 67.750 | 1.00 | 25.00 |
| 4493 | N | GLU | 475 | 102.047 | 21.944 | 61.960 | 1.00 | 61.44 |
| 4494 | CA | GLU | 475 | 101.612 | 20.998 | 60.945 | 1.00 | 57.77 |
| 4495 | C | GLU | 475 | 101.378 | 21.683 | 59.599 | 1.00 | 53.01 |
| 4496 | O | GLU | 475 | 101.623 | 21.091 | 58.545 | 1.00 | 55.03 |
| 4497 | CB | GLU | 475 | 100.352 | 20.282 | 61.418 | 1.00 | 59.71 |
| 4498 | CG | GLU | 475 | 100.104 | 18.950 | 60.737 | 1.00 | 73.81 |
| 4499 | CD | GLU | 475 | 98.994 | 18.148 | 61.399 | 1.00 | 84.47 |
| 4500 | OE1 | GLU | 475 | 98.562 | 18.513 | 62.518 | 1.00 | 88.32 |
| 4501 | OE2 | GLU | 475 | 98.555 | 17.144 | 60.797 | 1.00 | 88.90 |
| 4502 | H | GLU | 475 | 101.423 | 22.181 | 62.675 | 1.00 | 25.00 |
| 4503 | N | ALA | 476 | 100.931 | 22.936 | 59.637 | 1.00 | 46.25 |
| 4504 | CA | ALA | 476 | 100.681 | 23.703 | 58.420 | 1.00 | 43.91 |
| 4505 | C | ALA | 476 | 102.003 | 23.972 | 57.712 | 1.00 | 44.05 |
| 4506 | O | ALA | 476 | 102.124 | 23.774 | 56.501 | 1.00 | 42.50 |
| 4507 | CB | ALA | 476 | 99.984 | 25.018 | 58.749 | 1.00 | 34.16 |
| 4508 | H | ALA | 4776 | 100.761 | 23.358 | 60.501 | 1.00 | 25.00 |
| 4509 | N | MET | 477 | 103.000 | 24.402 | 58.480 | 1.00 | 45.42 |
| 4510 | CA | MET | 477 | 104.321 | 24.689 | 57.932 | 1.00 | 46.57 |
| 4511 | C | MET | 477 | 104.954 | 23.414 | 57.395 | 1.00 | 46.73 |
| 4512 | O | MET | 477 | 105.640 | 23.434 | 56.369 | 1.00 | 48.81 |
| 4513 | CB | MET | 477 | 105.217 | 25.331 | 58.990 | 1.00 | 41.20 |
| 4514 | CG | MET | 477 | 104.699 | 26.674 | 59.459 | 1.00 | 45.53 |
| 4515 | SD | MET | 477 | 105.842 | 27.539 | 60.529 | 1.00 | 50.24 |
| 4516 | CE | MET | 477 | 105.403 | 29.229 | 60.204 | 1.00 | 44.87 |
| 4517 | H | MET | 477 | 102.838 | 24.531 | 59.436 | 1.00 | 25.00 |
| 4518 | N | ALA | 478 | 104.689 | 22.301 | 58.071 | 1.00 | 43.88 |
| 4519 | CA | ALA | 478 | 105.214 | 21.012 | 57.646 | 1.00 | 40.24 |
| 4520 | C | ALA | 478 | 104.608 | 20.664 | 56.288 | 1.00 | 39.48 |
| 4521 | O | ALA | 478 | 105.301 | 20.158 | 55.404 | 1.00 | 42.61 |
| 4522 | CB | ALA | 478 | 104.887 | 19.941 | 58.673 | 1.00 | 38.44 |
| 4523 | H | ALA | 478 | 134.140 | 22.350 | 58.883 | 1.00 | 25.00 |
| 4524 | N | LYS | 479 | 103.324 | 20.969 | 56.113 | 1.00 | 37.41 |
| 4525 | CA | LYS | 479 | 102.642 | 20.700 | 54.850 | 1.00 | 36.91 |
| 4526 | C | LYS | 479 | 103.214 | 21.598 | 53.754 | 1.00 | 33.62 |
| 4527 | O | LYS | 479 | 103.408 | 21.164 | 52.616 | 1.00 | 32.37 |
| 4528 | CB | LYS | 479 | 101.136 | 20.931 | 54.986 | 1.00 | 39.38 |
| 4529 | CG | LYS | 479 | 100.338 | 20.573 | 53.736 | 1.00 | 46.00 |
| 4530 | CD | LYS | 479 | 98.850 | 20.797 | 53.947 | 1.00 | 51.63 |
| 4531 | CE | LYS | 479 | 98.273 | 19.858 | 55.003 | 1.00 | 53.61 |
| 4532 | NZ | LYS | 479 | 98.180 | 18.451 | 54.525 | 1.00 | 57.01 |
| 4533 | H | LYS | 479 | 102.820 | 21.3777 | 56.852 | 1.00 | 25.00 |
| 4534 | 1HZ | LYS | 479 | 99.126 | 18.106 | 54.269 | 1.00 | 25.00 |
| 4535 | 2HZ | LYS | 479 | 97.776 | 17.853 | 55.274 | 1.00 | 25.00 |
| 4536 | 3HZ | LYS | 479 | 97.561 | 18.416 | 53.688 | 1.00 | 25.00 |
| 4537 | N | PHE | 480 | 103.502 | 22.845 | 54.107 | 1.00 | 30.92 |
| 4538 | CA | PHE | 480 | 104.067 | 23.790 | 53.157 | 1.00 | 31.88 |
| 4539 | C | PHE | 480 | 105.457 | 23.356 | 52.714 | 1.00 | 34.12 |
| 4540 | O | PHE | 480 | 105.812 | 23.493 | 51.540 | 1.00 | 37.15 |
| 4541 | CB | PHE | 480 | 104.107 | 25.198 | 53.749 | 1.00 | 29.35 |
| 4542 | CG | PHE | 480 | 102.902 | 26.028 | 53.408 | 1.00 | 37.28 |
| 4543 | CD1 | PHE | 480 | 101.662 | 25.427 | 53.190 | 1.00 | 37.60 |
| 4544 | CD2 | PHE | 480 | 103.008 | 27.411 | 53.283 | 1.00 | 36.73 |
| 4545 | CE1 | PHE | 480 | 100.548 | 26.192 | 52.850 | 1.00 | 36.20 |

TABLE 11-continued

Structural Coordinates of Tobacco 5-Epi-Aristolochene Synthase
In the Absence of Bound Substrate

| Atom Type | Atom | Residue | Residue # | X | Y | Z | OCC | B-factor |
|---|---|---|---|---|---|---|---|---|
| 4546 | CE22 | PHE | 480 | 101.898 | 28.185 | 52.942 | 1.00 | 38.45 |
| 4547 | CZ | PHE | 480 | 100.665 | 27.574 | 52.726 | 1.00 | 36.96 |
| 4548 | H | PHE | 480 | 103.315 | 23.138 | 55.024 | 1.00 | 25.00 |
| 4549 | N | GLN | 481 | 106.238 | 22.810 | 53.641 | 1.00 | 33.79 |
| 4550 | CA | GLN | 481 | 107.573 | 22.352 | 53.292 | 1.00 | 35.43 |
| 4551 | C | GLN | 481 | 107.453 | 21.180 | 52.323 | 1.00 | 35.55 |
| 4552 | O | GLN | 481 | 108.200 | 21.103 | 51.347 | 1.00 | 35.63 |
| 4553 | CB | GLN | 481 | 108.368 | 21.930 | 54.524 | 1.00 | 46.60 |
| 4554 | CG | GLN | 481 | 109.844 | 21.688 | 54.210 | 1.00 | 70.92 |
| 4555 | CD | GLN | 481 | 110.583 | 20.933 | 55.302 | 1.00 | 83.38 |
| 4556 | OE1 | GLN | 481 | 110.036 | 20.658 | 56.371 | 1.00 | 93.92 |
| 4557 | NE2 | GLN | 481 | 111.836 | 20.588 | 55.032 | 1.00 | 88.62 |
| 4558 | H | GLN | 481 | 105.919 | 22.723 | 54.562 | 1.00 | 25.00 |
| 4559 | 1HE2 | GLN | 481 | 112.316 | 20.105 | 55.735 | 1.00 | 25.00 |
| 4560 | 2HE2 | GLN | 481 | 112.220 | 20.824 | 54.166 | 1.00 | 25.00 |
| 4561 | N | ASN | 482 | 106.486 | 20.297 | 52.561 | 1.00 | 33.51 |
| 4562 | CA | ASN | 482 | 106.272 | 19.146 | 51.682 | 1.00 | 36.28 |
| 4563 | C | ASN | 482 | 105.950 | 19.606 | 50.267 | 1.00 | 36.07 |
| 4564 | O | ASN | 482 | 106.380 | 18.989 | 49.288 | 1.00 | 35.83 |
| 4565 | CB | ASN | 482 | 105.140 | 18.252 | 52.200 | 1.00 | 40.65 |
| 4566 | CG | ASN | 482 | 105.535 | 17.465 | 53.436 | 1.00 | 54.20 |
| 4567 | OD1 | ASN | 482 | 106.698 | 17.095 | 53.607 | 1.00 | 57.37 |
| 4568 | ND2 | ASN | 482 | 104.565 | 17.204 | 54.307 | 1.00 | 59.54 |
| 4569 | H | ASN | 482 | 105.916 | 20.415 | 53.350 | 1.00 | 25.00 |
| 4570 | 1HD2 | ASN | 482 | 104.821 | 16.698 | 55.105 | 1.00 | 25.00 |
| 4571 | 2HD2 | ASN | 482 | 103.6661 | 17.519 | 54.121 | 1.00 | 25.00 |
| 4572 | N | MET | 483 | 105.199 | 20.698 | 50.163 | 1.00 | 33.64 |
| 4573 | CA | MET | 483 | 104.831 | 21.250 | 48.866 | 1.00 | 29.91 |
| 4574 | C | MET | 483 | 106.080 | 21.757 | 48.152 | 1.00 | 27.30 |
| 4575 | O | MET | 483 | 106.240 | 21.556 | 46.947 | 1.00 | 32.31 |
| 4576 | CB | MET | 483 | 103.814 | 22.373 | 49.036 | 1.00 | 29.58 |
| 4577 | CG | MET | 483 | 102.488 | 21.916 | 49.626 | 1.00 | 32.65 |
| 4578 | SD | MET | 483 | 101.388 | 23.311 | 49.943 | 1.00 | 37.42 |
| 4579 | CE | MET | 483 | 100.988 | 23.770 | 48.275 | 1.00 | 33.87 |
| 4580 | H | MET | 483 | 104.879 | 21.134 | 50.982 | 1.00 | 25.00 |
| 4581 | N | ALA | 484 | 106.979 | 22.385 | 48.903 | 1.00 | 24.24 |
| 4582 | CA | ALA | 484 | 108.226 | 22.895 | 48.339 | 1.00 | 25.37 |
| 4583 | C | ALA | 484 | 109.086 | 21.724 | 47.845 | 1.00 | 27.23 |
| 4584 | O | ALA | 484 | 109.696 | 21.792 | 46.772 | 1.00 | 26.13 |
| 4585 | CB | ALA | 484 | 108.979 | 23.703 | 49.385 | 1.00 | 20.73 |
| 4586 | H | ALA | 484 | 106.799 | 22.516 | 49.859 | 1.00 | 25.00 |
| 4587 | N | GLU | 485 | 109.103 | 20.642 | 48.622 | 1.00 | 27.25 |
| 4588 | CA | GLU | 485 | 109.864 | 19.437 | 48.289 | 1.00 | 29.59 |
| 4589 | C | GLU | 485 | 109.317 | 18.807 | 47.015 | 1.00 | 26.53 |
| 4590 | O | GLU | 485 | 110.070 | 18.386 | 46.139 | 1.00 | 32.01 |
| 4591 | CB | GLU | 485 | 109.792 | 18.425 | 49.437 | 1.00 | 39.77 |
| 4592 | CG | GLU | 485 | 110.327 | 18.942 | 50.779 | 1.00 | 61.11 |
| 4593 | CD | GLU | 485 | 110.170 | 17.953 | 51.934 | 1.00 | 69.27 |
| 4594 | OE1 | GLU | 485 | 109.663 | 16.830 | 51.716 | 1.00 | 73.83 |
| 4595 | OE2 | GLU | 485 | 110.561 | 18.302 | 53.073 | 1.00 | 69.26 |
| 4596 | H | GLU | 485 | 108.574 | 20.683 | 49.449 | 1.00 | 25.00 |
| 4597 | N | THR | 486 | 107.997 | 18.755 | 46.917 | 1.00 | 26.56 |
| 4598 | CA | THR | 486 | 107.323 | 18.207 | 45.749 | 1.00 | 26.51 |
| 4599 | C | THR | 486 | 107.673 | 19.050 | 44.520 | 1.00 | 24.78 |
| 4600 | O | THR | 486 | 107.961 | 18.514 | 43.437 | 1.00 | 24.00 |
| 4601 | CB | THR | 486 | 105.790 | 18.211 | 45.973 | 1.00 | 30.57 |
| 4602 | OG1 | THR | 486 | 105.463 | 17.277 | 47.010 | 1.00 | 30.11 |
| 4603 | CG2 | THR | 486 | 105.034 | 17.855 | 44.694 | 1.00 | 27.79 |
| 4604 | H | THR | 486 | 107.446 | 19.085 | 47.660 | 1.00 | 25.00 |
| 4605 | HG1 | THR | 486 | 105.755 | 16.396 | 46.782 | 1.00 | 25.00 |
| 4606 | N | ALA | 487 | 107.672 | 20.367 | 44.712 | 1.00 | 20.69 |
| 4607 | CA | ALA | 487 | 107.980 | 21.319 | 43.651 | 1.00 | 19.32 |
| 4608 | C | ALA | 487 | 109.401 | 21.127 | 43.141 | 1.00 | 18.49 |
| 4609 | O | ALA | 487 | 109.654 | 21.149 | 41.929 | 1.00 | 15.86 |
| 4610 | CB | ALA | 487 | 107.768 | 22.750 | 44.152 | 1.00 | 15.08 |
| 4611 | H | ALA | 487 | 107.454 | 20.716 | 45.604 | 1.00 | 25.00 |
| 4612 | N | TRP | 488 | 110.349 | 20.909 | 44.058 | 1.00 | 20.11 |
| 4613 | CA | TRP | 488 | 111.736 | 20.695 | 43.661 | 1.00 | 19.04 |
| 4614 | C | TRP | 488 | 111.856 | 19.461 | 42.781 | 1.00 | 20.42 |
| 4615 | O | TRP | 488 | 112.555 | 19.486 | 41.768 | 1.00 | 23.27 |
| 4616 | CB | TRP | 488 | 112.656 | 20.590 | 44.879 | 1.00 | 19.13 |
| 4617 | CG | TRP | 488 | 113.256 | 21.905 | 45.262 | 1.00 | 20.79 |
| 4618 | CD1 | TRP | 488 | 113.017 | 22.619 | 46.402 | 1.00 | 19.35 |
| 4619 | CD2 | TRP | 488 | 114.173 | 22.689 | 44.481 | 1.00 | 18.53 |
| 4620 | NE1 | TRP | 488 | 113.723 | 23.801 | 46.376 | 1.00 | 21.34 |
| 4621 | CE2 | TRP | 488 | 114.441 | 23.869 | 45.210 | 1.00 | 17.70 |
| 4622 | CE3 | TRP | 488 | 114.793 | 22.507 | 43.237 | 1.00 | 18.03 |
| 4623 | CZ2 | TRP | 488 | 115.305 | 24.863 | 44.736 | 1.00 | 16.71 |
| 4624 | CZ3 | TRP | 488 | 115.654 | 23.499 | 42.765 | 1.00 | 15.24 |
| 4625 | CH2 | TRP | 488 | 115.899 | 24.659 | 43.515 | 1.00 | 14.14 |
| 4626 | H | TRP | 488 | 110.109 | 20.905 | 45.009 | 1.00 | 25.00 |
| 4627 | HE1 | TRP | 488 | 113.699 | 24.482 | 47.075 | 1.00 | 25.00 |
| 4628 | N | LYS | 489 | 111.136 | 18.399 | 43.138 | 1.00 | 21.51 |
| 4629 | CA | LYS | 489 | 111.162 | 17.175 | 42.345 | 1.00 | 17.89 |
| 4630 | C | LYS | 489 | 110.604 | 17.476 | 40.961 | 1.00 | 19.66 |
| 4631 | O | LYS | 489 | 111.091 | 16.947 | 39.960 | 1.00 | 22.89 |
| 4632 | CB | LYS | 489 | 110.351 | 16.069 | 43.019 | 1.00 | 17.77 |
| 4633 | CG | LYS | 489 | 110.922 | 15.624 | 44.344 | 1.00 | 15.98 |
| 4634 | CD | LYS | 489 | 110.074 | 14.540 | 44.972 | 1.00 | 22.31 |
| 4635 | CE | LYS | 489 | 110.525 | 14.254 | 46.392 | 1.00 | 24.45 |
| 4636 | NZ | LYS | 489 | 109.694 | 13.199 | 47.029 | 1.00 | 26.46 |
| 4637 | H | LYS | 489 | 110.589 | 18.443 | 43.952 | 1.00 | 25.00 |
| 4638 | 1HZ | LYS | 489 | 108.703 | 13.510 | 47.052 | 1.00 | 25.00 |
| 4639 | 2HZ | LYS | 489 | 109.772 | 12.320 | 46.482 | 1.00 | 25.00 |
| 4640 | 3HZ | LYS | 489 | 110.028 | 13.037 | 47.997 | 1.00 | 25.00 |
| 4641 | N | ASP | 490 | 109.590 | 18.338 | 40.906 | 1.00 | 20.77 |
| 4642 | CA | ASP | 490 | 108.991 | 18.721 | 39.630 | 1.00 | 21.97 |
| 4643 | C | ASP | 490 | 110.008 | 19.479 | 38.786 | 1.00 | 24.19 |
| 4644 | O | ASP | 490 | 110.098 | 19.264 | 37.575 | 1.00 | 21.17 |
| 4645 | CB | ASP | 490 | 107.739 | 19.585 | 39.837 | 1.00 | 26.18 |
| 4646 | CG | ASP | 490 | 106.561 | 18.799 | 40.395 | 1.00 | 29.44 |
| 4647 | OD1 | ASSP | 490 | 106.524 | 17.562 | 40.236 | 1.00 | 35.64 |
| 4648 | OD2 | ASP | 490 | 105.657 | 19.425 | 40.982 | 1.00 | 29.87 |
| 4649 | H | ASP | 490 | 109.245 | 18.731 | 41.736 | 1.00 | 25.00 |
| 4650 | N | ILE | 491 | 110.776 | 20.362 | 39.419 | 1.00 | 20.68 |
| 4651 | CA | ILE | 491 | 111.789 | 21.120 | 38.692 | 1.00 | 20.37 |
| 4652 | C | ILE | 491 | 112.810 | 20.146 | 38.115 | 1.00 | 19.25 |
| 4653 | O | ILE | 491 | 113.158 | 20.221 | 36.934 | 1.00 | 20.39 |
| 4654 | CB | ILE | 491 | 112.508 | 22.153 | 39.595 | 1.00 | 22.00 |
| 4655 | CG1 | ILE | 491 | 111.540 | 23.278 | 39.975 | 1.00 | 21.39 |
| 4656 | CG2 | ILE | 491 | 113.737 | 22.716 | 38.877 | 1.00 | 21.00 |
| 4657 | CD1 | ILE | 491 | 112.159 | 24.376 | 40.803 | 1.00 | 22.99 |
| 4658 | H | ILE | 491 | 110.657 | 20.508 | 40.379 | 1.00 | 25.00 |
| 4659 | N | ASN | 492 | 113.239 | 19.198 | 38.943 | 1.00 | 19.07 |
| 4660 | CA | ASN | 492 | 114.216 | 18.196 | 38.529 | 1.00 | 18.67 |
| 4661 | C | ASN | 492 | 113.700 | 17.404 | 37.337 | 1.00 | 20.34 |
| 4662 | O | ASN | 492 | 114.446 | 17.133 | 36.393 | 1.00 | 20.40 |
| 4663 | CB | ASN | 492 | 114.567 | 17.271 | 39.699 | 1.00 | 16.62 |
| 4664 | CG | ASN | 492 | 115.269 | 18.007 | 40.839 | 1.00 | 18.56 |
| 4665 | OD1 | ASN | 492 | 115.924 | 19.035 | 40.625 | 1.00 | 15.51 |
| 4666 | ND2 | ASN | 492 | 115.140 | 17.484 | 42.050 | 1.00 | 15.73 |
| 4667 | H | ASN | 492 | 112.899 | 19.181 | 39.862 | 1.00 | 25.00 |
| 4668 | 1HD2 | ASN | 492 | 115.583 | 17.939 | 42.793 | 1.00 | 25.00 |
| 4669 | 2HD2 | ASN | 492 | 114.613 | 16.661 | 42.164 | 1.00 | 25.00 |
| 4670 | N | GLU | 493 | 112.412 | 17.073 | 37.341 | 1.00 | 21.12 |
| 4671 | CA | GLU | 493 | 111.816 | 16.341 | 36.225 | 1.00 | 22.19 |
| 4672 | C | GLU | 493 | 111.736 | 17.225 | 34.985 | 1.00 | 24.12 |
| 4673 | O | GLU | 493 | 111.958 | 16.755 | 33.869 | 1.00 | 26.10 |
| 4674 | CB | GLU | 493 | 110.416 | 15.850 | 36.578 | 1.00 | 19.71 |
| 4675 | CG | GLU | 493 | 110.394 | 14.831 | 37.690 | 1.00 | 30.24 |
| 4676 | CD | GLU | 493 | 109.056 | 14.143 | 37.849 | 1.00 | 25.61 |
| 4677 | OE1 | GLU | 493 | 108.111 | 14.460 | 37.100 | 1.00 | 36.10 |
| 4678 | OE2 | GLU | 493 | 108.953 | 13.268 | 38.728 | 1.00 | 35.77 |
| 4679 | H | GLU | 493 | 111.859 | 17.328 | 38.111 | 1.00 | 25.00 |
| 4680 | N | GLY | 494 | 111.423 | 18.504 | 35.194 | 1.00 | 24.81 |
| 4681 | CA | GLY | 494 | 111.311 | 19.451 | 34.096 | 1.00 | 18.06 |
| 4682 | C | GLY | 494 | 112.614 | 19.686 | 33.352 | 1.00 | 25.75 |
| 4683 | O | GLY | 494 | 112.605 | 20.176 | 32.217 | 1.00 | 25.47 |
| 4684 | H | GLY | 494 | 111.263 | 18.819 | 36.107 | 1.00 | 25.00 |
| 46885 | N | LEU | 495 | 113.735 | 19.350 | 33.986 | 1.00 | 24.09 |
| 4686 | CA | LEU | 495 | 115.047 | 19.523 | 33.367 | 1.00 | 23.57 |
| 4687 | C | LEU | 495 | 115.465 | 18.331 | 32.503 | 1.00 | 23.66 |
| 4688 | O | LEU | 495 | 116.385 | 18.445 | 31.700 | 1.00 | 25.21 |
| 4689 | CB | LEU | 495 | 116.111 | 19.781 | 34.439 | 1.00 | 21.29 |
| 4690 | CG | LEU | 495 | 115.968 | 21.063 | 35.270 | 1.00 | 24.69 |
| 4691 | CD1 | LEU | 495 | 116.913 | 21.024 | 36.459 | 1.00 | 15.49 |

TABLE 11-continued

Structural Coordinates of Tobacco 5-Epi-Aristolochene Synthase
In the Absence of Bound Substrate

| Atom Type | Atom | Residue | Residue # | X | Y | Z | OCC | B-factor |
|---|---|---|---|---|---|---|---|---|
| 4692 | CD2 | LEU | 495 | 116.230 | 22.287 | 34.409 | 1.00 | 21.41 |
| 4693 | H | LEU | 495 | 113.681 | 18.985 | 34.893 | 1.00 | 25.00 |
| 4694 | N | LEU | 496 | 114.781 | 17.200 | 32.651 | 1.00 | 22.59 |
| 4695 | CA | LEU | 496 | 115.118 | 15.996 | 31.889 | 1.00 | 20.47 |
| 4696 | C | LEU | 496 | 114.749 | 16.049 | 30.409 | 1.00 | 24.46 |
| 4697 | O | LEU | 496 | 113.692 | 16.556 | 30.033 | 1.00 | 22.73 |
| 4698 | CB | LEU | 496 | 114.504 | 14.758 | 32.548 | 1.00 | 20.18 |
| 4699 | CG | LEU | 496 | 115.016 | 14.454 | 33.959 | 1.00 | 23.38 |
| 4700 | CD1 | LEU | 496 | 114.276 | 13.265 | 34.524 | 1.00 | 21.31 |
| 4701 | CD2 | LEU | 496 | 116.523 | 14.187 | 33.938 | 1.00 | 20.33 |
| 4702 | H | LEU | 496 | 114.020 | 17.172 | 33.267 | 1.00 | 25.00 |
| 4703 | N | ARG | 497 | 115.642 | 15.530 | 29.573 | 1.00 | 26.43 |
| 4704 | CA | ARG | 497 | 115.443 | 15.501 | 28.128 | 1.00 | 31.12 |
| 4705 | C | ARG | 497 | 114.347 | 14.498 | 27.766 | 1.00 | 32.68 |
| 4706 | O | ARG | 497 | 114.217 | 13.457 | 28.411 | 1.00 | 27.55 |
| 4707 | CB | ARG | 497 | 116.757 | 15.124 | 27.431 | 1.00 | 30.06 |
| 4708 | CG | ARG | 497 | 117.863 | 16.155 | 27.626 | 1.00 | 38.94 |
| 4709 | CD | ARG | 497 | 119.217 | 15.505 | 27.851 | 1.00 | 37.77 |
| 4710 | NE | ARG | 497 | 120.087 | 15.584 | 26.683 | 1.00 | 50.61 |
| 4711 | CZ | ARG | 497 | 121.282 | 16.173 | 26.676 | 1.00 | 51.72 |
| 4712 | NH1 | ARG | 497 | 121.754 | 18.744 | 27.777 | 1.00 | 46.52 |
| 4713 | NH2 | ARG | 497 | 122.023 | 16.166 | 25.575 | 1.00 | 51.65 |
| 4714 | H | ARG | 497 | 116.457 | 15.140 | 29.946 | 1.00 | 25.00 |
| 4715 | HE | ARG | 497 | 119.773 | 15.180 | 25.847 | 1.00 | 25.00 |
| 4716 | 1HH1 | ARG | 497 | 121.213 | 16.733 | 28.615 | 1.00 | 25.00 |
| 4717 | 2HH1 | ARG | 497 | 122.653 | 17.183 | 27.766 | 1.00 | 25.00 |
| 4718 | 1HH2 | ARG | 497 | 121.685 | 15.718 | 24.748 | 1.00 | 25.00 |
| 4719 | 2HH2 | ARG | 497 | 122.920 | 16.608 | 25.576 | 1.00 | 25.00 |
| 4720 | N | PRO | 498 | 113.542 | 14.798 | 26.731 | 1.00 | 34.46 |
| 4721 | CA | PRO | 498 | 113.595 | 16.005 | 25.897 | 1.00 | 31.05 |
| 4722 | C | PRO | 498 | 112.886 | 17.179 | 26.568 | 1.00 | 32.44 |
| 4723 | O | PRO | 498 | 111.757 | 17.040 | 27.043 | 1.00 | 32.35 |
| 4724 | CB | PRO | 498 | 112.831 | 15.587 | 24.635 | 1.00 | 30.63 |
| 4725 | CG | PRO | 498 | 112.768 | 14.079 | 24.707 | 1.00 | 38.95 |
| 4726 | CD | PRO | 498 | 112.593 | 13.830 | 26.162 | 1.00 | 34.35 |
| 4727 | N | THR | 499 | 113.544 | 18.332 | 26.612 | 1.00 | 33.10 |
| 4728 | CA | THR | 499 | 112.940 | 19.513 | 27.218 | 1.00 | 30.18 |
| 4729 | C | THR | 499 | 112.075 | 20.223 | 26.170 | 1.00 | 31.00 |
| 4730 | O | THR | 499 | 112.389 | 20.172 | 24.974 | 1.00 | 33.56 |
| 4731 | CB | THR | 499 | 114.016 | 20.474 | 27.795 | 1.00 | 25.39 |
| 4732 | OG1 | THR | 499 | 115.004 | 20.752 | 26.798 | 1.00 | 24.84 |
| 4733 | CG2 | THR | 499 | 114.703 | 19.843 | 28.996 | 1.00 | 22.98 |
| 4734 | H | THR | 499 | 114.435 | 18.421 | 26.223 | 1.00 | 25.00 |
| 4735 | HG1 | THR | 499 | 115.646 | 21.357 | 27.117 | 1.00 | 25.00 |
| 4736 | N | PRO | 500 | 110.963 | 20.844 | 26.600 | 1.00 | 31.06 |
| 4737 | CA | PRO | 500 | 110.053 | 21.558 | 25.692 | 1.00 | 32.31 |
| 4738 | C | PRO | 500 | 110.705 | 22.740 | 24.967 | 1.00 | 34.94 |
| 4739 | O | PRO | 500 | 110.328 | 23.075 | 23.843 | 1.00 | 39.31 |
| 4740 | CB | PRO | 500 | 108.916 | 21.994 | 26.620 | 1.00 | 29.71 |
| 4741 | CG | PRO | 500 | 109.576 | 22.086 | 27.968 | 1.00 | 28.06 |
| 4742 | CD | PRO | 500 | 110.460 | 20.876 | 27.984 | 1.00 | 23.70 |
| 4743 | N | VAL | 501 | 111.642 | 23.398 | 25.641 | 1.00 | 32.94 |
| 4744 | CA | VAL | 501 | 112.390 | 24.523 | 25.078 | 1.00 | 33.22 |
| 4745 | C | VAL | 501 | 113.858 | 24.257 | 25.421 | 1.00 | 33.52 |
| 4746 | O | VAL | 501 | 114.154 | 23.347 | 26.204 | 1.00 | 33.00 |
| 4747 | CB | VAL | 501 | 111.959 | 25.887 | 25.686 | 1.00 | 29.14 |
| 4748 | CG1 | VAL | 501 | 110.515 | 26.198 | 25.330 | 1.00 | 26.33 |
| 4749 | CG2 | VAL | 501 | 112.153 | 25.887 | 27.195 | 1.00 | 24.60 |
| 4750 | H | VAL | 501 | 111.875 | 23.112 | 26.546 | 1.00 | 25.00 |
| 4751 | N | SER | 502 | 114.775 | 25.026 | 24.844 | 1.00 | 30.56 |
| 4752 | CA | SER | 502 | 116.194 | 24.832 | 25.128 | 1.00 | 33.20 |
| 4753 | C | SER | 502 | 116.485 | 25.025 | 26.611 | 1.00 | 32.05 |
| 4754 | O | SER | 502 | 115.869 | 25.869 | 27.265 | 1.00 | 34.57 |
| 4755 | CB | SER | 502 | 117.039 | 25.807 | 24.316 | 1.00 | 35.54 |
| 4756 | OG | SER | 502 | 116.837 | 25.601 | 22.934 | 1.00 | 56.52 |
| 4757 | H | SER | 502 | 114.502 | 25.729 | 24.224 | 1.00 | 25.00 |
| 4758 | HG | SER | 502 | 117.098 | 24.709 | 22.686 | 1.00 | 25.00 |
| 4759 | N | THR | 503 | 117.443 | 24.260 | 27.126 | 1.00 | 29.15 |
| 4760 | CA | THR | 503 | 117.836 | 24.333 | 28.530 | 1.00 | 33.23 |
| 4761 | C | THR | 503 | 118.166 | 25.771 | 28.927 | 1.00 | 31.90 |
| 4762 | O | THR | 503 | 117.977 | 26.177 | 30.078 | 1.00 | 32.13 |
| 4763 | CB | THR | 503 | 119.058 | 23.443 | 28.797 | 1.00 | 38.70 |
| 4764 | OG1 | THR | 503 | 118.767 | 22.110 | 28.366 | 1.00 | 51.69 |
| 4765 | CG2 | THR | 503 | 119.395 | 23.420 | 30.278 | 1.00 | 40.66 |
| 4766 | H | THR | 503 | 117.884 | 23.611 | 26.547 | 1.00 | 25.00 |
| 4767 | HG1 | THR | 503 | 118.560 | 22.075 | 27.436 | 1.00 | 25.00 |
| 4768 | N | GLU | 504 | 118.637 | 26.542 | 27.956 | 1.00 | 27.88 |
| 4769 | CA | GLU | 504 | 118.982 | 27.935 | 28.184 | 1.00 | 31.30 |
| 4770 | C | GLU | 504 | 117.801 | 28.706 | 28.789 | 1.00 | 31.46 |
| 4771 | O | GLU | 504 | 117.987 | 29.643 | 29.568 | 1.00 | 29.72 |
| 4772 | CB | GLU | 504 | 119.396 | 28.578 | 26.863 | 1.00 | 32.18 |
| 4773 | CG | GLU | 504 | 119.754 | 30.042 | 26.997 | 1.00 | 44.47 |
| 4774 | CD | GLU | 504 | 120.045 | 30.714 | 25.672 | 1.00 | 47.35 |
| 4775 | OE1 | GLU | 504 | 119.634 | 30.183 | 24.618 | 1.00 | 49.18 |
| 4776 | OE2 | GLU | 504 | 120.683 | 31.788 | 25.691 | 1.00 | 48.31 |
| 4777 | H | GLU | 504 | 118.771 | 26.169 | 27.067 | 1.00 | 25.00 |
| 4778 | N | PHE | 505 | 116.588 | 28.274 | 28.464 | 1.00 | 27.10 |
| 4779 | CA | PHE | 505 | 115.390 | 28.936 | 28.957 | 1.00 | 23.02 |
| 4780 | C | PHE | 505 | 114.809 | 28.314 | 30.218 | 1.00 | 24.14 |
| 4781 | O | PHE | 505 | 113.888 | 28.869 | 30.818 | 1.00 | 22.77 |
| 4782 | CB | PHE | 505 | 114.356 | 29.036 | 27.835 | 1.00 | 28.22 |
| 4783 | CG | PHE | 505 | 114.888 | 29.711 | 26.602 | 1.00 | 28.58 |
| 4784 | CD1 | PHE | 505 | 115.307 | 31.039 | 26.651 | 1.00 | 28.23 |
| 4785 | CD2 | PHE | 505 | 115.048 | 29.001 | 25.417 | 1.00 | 28.81 |
| 4786 | CE1 | PHE | 505 | 115.884 | 31.646 | 25.539 | 1.00 | 25.11 |
| 4787 | CE2 | PHE | 505 | 115.623 | 29.597 | 24.300 | 1.00 | 28.43 |
| 4788 | CZ | PHE | 505 | 116.043 | 30.922 | 24.362 | 1.00 | 29.72 |
| 4789 | H | PHE | 505 | 116.489 | 27.504 | 27.881 | 1.00 | 25.00 |
| 4790 | N | LEU | 506 | 115.367 | 27.182 | 30.641 | 1.00 | 21.53 |
| 4791 | CA | LEU | 506 | 114.915 | 26.516 | 31.862 | 1.00 | 20.00 |
| 4792 | C | LEU | 506 | 115.763 | 26.980 | 33.054 | 1.00 | 20.28 |
| 4793 | O | LEU | 506 | 115.270 | 27.120 | 34.176 | 1.00 | 21.38 |
| 4794 | CB | LEU | 506 | 115.033 | 24.995 | 31.732 | 1.00 | 17.84 |
| 4795 | CG | LEU | 506 | 114.265 | 24.277 | 30.621 | 1.00 | 23.70 |
| 4796 | CD1 | LEU | 506 | 114.409 | 22.781 | 30.832 | 1.00 | 19.27 |
| 4797 | CD2 | LEU | 506 | 112.797 | 24.671 | 30.645 | 1.00 | 20.22 |
| 4798 | H | LEU | 506 | 116.092 | 26.791 | 30.120 | 1.00 | 25..00 |
| 4799 | N | THR | 507 | 117.040 | 27.237 | 32.796 | 1.00 | 24.00 |
| 4800 | CA | THR | 507 | 117.968 | 27.666 | 33.837 | 1.00 | 21.87 |
| 4801 | C | THR | 507 | 117.508 | 28.894 | 34.634 | 1.00 | 21.92 |
| 4802 | O | THR | 507 | 117.636 | 28.913 | 35.858 | 1.00 | 25.77 |
| 4803 | CB | THR | 507 | 119.382 | 27.870 | 33.260 | 1.00 | 22.57 |
| 4804 | OG1 | THR | 507 | 119.728 | 26.728 | 32.465 | 1.00 | 23.76 |
| 4805 | CG2 | THR | 507 | 120.400 | 28.014 | 34.381 | 1.00 | 20.42 |
| 4806 | H | THR | 507 | 117.372 | 27.127 | 31.883 | 1.00 | 25.00 |
| 4807 | HG1 | THR | 507 | 119.106 | 26.624 | 31.739 | 1.00 | 25.00 |
| 4808 | N | PRO | 508 | 116.960 | 29.928 | 33.963 | 1.00 | 17.26 |
| 4809 | CA | PRO | 508 | 116.503 | 31.114 | 34.698 | 1.00 | 18.03 |
| 4810 | C | PRO | 508 | 115.423 | 30.774 | 35.735 | 1.00 | 19.69 |
| 4811 | O | PRO | 508 | 1155.417 | 31.309 | 36.847 | 1.00 | 22.29 |
| 4812 | CB | PRO | 508 | 115.943 | 31.999 | 33.583 | 1.00 | 18.28 |
| 4813 | CG | PRO | 508 | 116.841 | 31.690 | 32.444 | 1.00 | 16.25 |
| 4814 | CD | PRO | 508 | 116.909 | 30.177 | 32.510 | 1.00 | 14.75 |
| 4815 | N | ILE | 509 | 114.528 | 29.864 | 35.362 | 1.00 | 21.35 |
| 4816 | CA | ILE | 509 | 113.435 | 29.420 | 36.230 | 1.00 | 22.73 |
| 4817 | C | ILE | 509 | 114.024 | 28.653 | 37.412 | 1.00 | 19.96 |
| 4818 | O | ILE | 509 | 113.627 | 28.854 | 38.561 | 1.00 | 22.40 |
| 4819 | CB | ILE | 509 | 112.450 | 28.523 | 35.441 | 1.00 | 18.26 |
| 4820 | CG1 | ILE | 509 | 111.867 | 29.317 | 34.267 | 1.00 | 20.40 |
| 4821 | CG2 | ILE | 509 | 111.360 | 27.998 | 36.351 | 1.00 | 12.67 |
| 4822 | CD1 | ILE | 509 | 111.082 | 28.486 | 33.280 | 1.00 | 22.89 |
| 4823 | H | ILE | 509 | 114.759 | 29.468 | 34.470 | 1.00 | 25.00 |
| 4824 | N | LEU | 510 | 114.989 | 27.788 | 37.114 | 1.00 | 21.34 |
| 4825 | CA | LEU | 510 | 115.684 | 27.003 | 38.130 | 1.00 | 19.45 |
| 4826 | C | LEU | 510 | 116.420 | 27.956 | 39.075 | 1.00 | 18.03 |
| 4827 | O | LEU | 510 | 116.372 | 27.799 | 40.300 | 1.00 | 23.54 |
| 4828 | CB | LEU | 510 | 116.693 | 26.064 | 37.454 | 1.00 | 18.99 |
| 4829 | CG | LEU | 510 | 117.747 | 25.351 | 38.309 | 1.00 | 17.88 |
| 4830 | CD1 | LEU | 510 | 117.092 | 24.447 | 39.347 | 1.00 | 13.70 |
| 4831 | CD2 | LEU | 510 | 118.660 | 24.548 | 37.401 | 1.00 | 12.82 |
| 4832 | H | LEU | 510 | 115.234 | 27.670 | 36.174 | 1.00 | 25.00 |
| 4833 | N | ASN | 511 | 117.070 | 28.966 | 38.502 | 1.00 | 16.84 |
| 4834 | CA | ASN | 511 | 117.816 | 29.940 | 39.293 | 1.00 | 18.52 |
| 4835 | C | ASN | 511 | 116.918 | 30.774 | 40.185 | 1.00 | 19.49 |
| 4836 | O | ASN | 511 | 117.299 | 31.111 | 41.307 | 1.00 | 21.10 |
| 4837 | CB | ASN | 511 | 118.704 | 30.806 | 38.400 | 1.00 | 14.99 |

TABLE 11-continued

Structural Coordinates of Tobacco 5-Epi-Aristolochene Synthase In the Absence of Bound Substrate

| Atom | Atom | Resi-due | Resi-due # | X | Y | Z | OCC | B-factor |
|---|---|---|---|---|---|---|---|---|
| 4838 | CG | ASN | 511 | 119.926 | 30.046 | 37.903 | 1.00 | 19.61 |
| 4839 | OD1 | ASN | 511 | 120.276 | 29.004 | 38.456 | 1.00 | 22.94 |
| 4840 | ND2 | ASN | 511 | 120.562 | 30.543 | 36.849 | 1.00 | 17.54 |
| 4841 | H | ASN | 511 | 117.040 | 29.059 | 37.540 | 1.00 | 25.00 |
| 4842 | 1HD2 | ASN | 511 | 121.341 | 30.052 | 36.532 | 1.00 | 25.00 |
| 4843 | 2HD2 | ASN | 511 | 120.230 | 31.364 | 36.438 | 1.00 | 25.00 |
| 4844 | N | LEU | 512 | 115.705 | 31.061 | 39.719 | 1.00 | 18.46 |
| 4845 | CA | LEU | 512 | 114.751 | 31.814 | 40.527 | 1.00 | 15.00 |
| 4846 | C | LEU | 512 | 114.415 | 31.007 | 41.778 | 1.00 | 16.15 |
| 4847 | O | LEU | 512 | 114.304 | 31.561 | 42.872 | 1.00 | 24.00 |
| 4848 | CB | LEU | 512 | 113.484 | 32.114 | 39.727 | 1.00 | 17.19 |
| 4849 | CG | LEU | 5122 | 113.569 | 33.341 | 38.818 | 1.00 | 16.79 |
| 4850 | CD1 | LEU | 512 | 112.331 | 33.430 | 37.943 | 1.00 | 22.39 |
| 4851 | CD2 | LEU | 512 | 113.702 | 34.591 | 39.672 | 1.00 | 14.37 |
| 4852 | H | LEU | 512 | 115.450 | 30.773 | 38.817 | 1.00 | 25.00 |
| 4853 | N | ALA | 513 | 114.279 | 29.692 | 41.624 | 1.00 | 19.31 |
| 4854 | CA | ALA | 513 | 113.979 | 28.814 | 42.760 | 1.00 | 18.01 |
| 4855 | C | ALA | 513 | 115.178 | 28.789 | 43.710 | 1.00 | 18.19 |
| 4856 | O | ALA | 513 | 115.017 | 28.802 | 44.933 | 1.00 | 16.94 |
| 4857 | CB | ALA | 513 | 113.654 | 27.403 | 42.274 | 1.00 | 12.64 |
| 4858 | H | ALA | 513 | 114.362 | 29.302 | 40.726 | 1.00 | 25.00 |
| 4859 | N | ARG | 514 | 116.381 | 28.767 | 43.140 | 1.00 | 19.70 |
| 4860 | CA | ARG | 514 | 117.609 | 28.763 | 43.934 | 1.00 | 18.80 |
| 4861 | C | ARG | 514 | 117.696 | 30.031 | 44.784 | 1.00 | 17.46 |
| 4862 | O | ARG | 514 | 118.041 | 29.978 | 45.967 | 1.00 | 21.48 |
| 4863 | CB | ARG | 514 | 118.832 | 28.638 | 43.024 | 1.00 | 13.68 |
| 4864 | CG | ARG | 514 | 118.981 | 27.255 | 42.404 | 1.00 | 14.32 |
| 4865 | CD | ARG | 514 | 120.084 | 27.218 | 41.354 | 1.00 | 17.33 |
| 4866 | NE | ARG | 514 | 120.490 | 25.848 | 41.066 | 1.00 | 16.97 |
| 4867 | CZ | ARG | 514 | 121.107 | 25.453 | 39.958 | 1.00 | 19.03 |
| 4868 | NH1 | ARG | 514 | 121.398 | 26.320 | 38.998 | 1.00 | 15.08 |
| 4869 | NH2 | ARG | 514 | 121.450 | 24.180 | 39.821 | 1.00 | 15.36 |
| 4870 | H | ARG | 514 | 116.440 | 28.744 | 42.160 | 1.00 | 25.00 |
| 4871 | HE | ARG | 514 | 120.282 | 25.180 | 41.738 | 1.00 | 25.00 |
| 4872 | 1HH1 | ARG | 514 | 121.159 | 27.283 | 39.100 | 1.00 | 25.00 |
| 4873 | 2HH1 | ARG | 514 | 121.862 | 26.006 | 38.170 | 1.00 | 25.00 |
| 4874 | 1HH2 | ARG | 514 | 121.245 | 23.5244 | 40.547 | 1.00 | 25.00 |
| 4875 | 2HH2 | ARG | 514 | 121.913 | 23.875 | 38.988 | 1.00 | 25.00 |
| 4876 | N | ILE | 515 | 117.330 | 31.164 | 44.196 | 1.00 | 20.52 |
| 4877 | CA | ILE | 515 | 117.352 | 32.438 | 44.911 | 1.00 | 22.89 |
| 4878 | C | ILE | 515 | 116.489 | 32.357 | 46.169 | 1.00 | 25.55 |
| 4879 | O | ILE | 515 | 116.851 | 32.914 | 47.206 | 1.00 | 28.26 |
| 4880 | CB | ILE | 515 | 116.863 | 33.591 | 44.018 | 1.00 | 18.86 |
| 4881 | CG1 | ILE | 515 | 117.857 | 33.824 | 42.883 | 1.00 | 18.35 |
| 4882 | CG2 | ILE | 515 | 116.695 | 34.855 | 44.832 | 1.00 | 23.30 |
| 4883 | CD1 | ILE | 515 | 117.408 | 34.863 | 41.885 | 1.00 | 19.17 |
| 4884 | H | ILE | 515 | 117.045 | 31.141 | 43.257 | 1.00 | 25.00 |
| 4885 | N | VAL | 516 | 115.372 | 31.637 | 46.082 | 1.00 | 27.24 |
| 4886 | CA | VAL | 516 | 114.467 | 31.463 | 47.220 | 1.00 | 26.85 |
| 4887 | C | VAL | 516 | 115.229 | 30.838 | 48.378 | 1.00 | 30.63 |
| 4888 | O | VAL | 516 | 115.219 | 31.354 | 49.496 | 1.00 | 28.87 |
| 4889 | CB | VAL | 518 | 113.280 | 30.512 | 46.881 | 1.00 | 28.84 |
| 4890 | CG1 | VAL | 516 | 112.433 | 30.248 | 48.122 | 1.00 | 23.42 |
| 4891 | CG2 | VAL | 516 | 112.423 | 31.096 | 45.776 | 1.00 | 22.08 |
| 4892 | H | VAL | 516 | 115.144 | 31.219 | 45.225 | 1.00 | 25.00 |
| 4893 | N | GLU | 517 | 115.910 | 29.736 | 48.085 | 1.00 | 35.61 |
| 4894 | CA | GLU | 517 | 116.680 | 28.997 | 49.081 | 1.00 | 41.24 |
| 4895 | C | GLU | 517 | 117.696 | 29.890 | 49.796 | 1.00 | 42.08 |
| 4896 | O | GLU | 517 | 117.872 | 29.789 | 51.009 | 1.00 | 46.37 |
| 4897 | CB | GLU | 517 | 117.385 | 27.802 | 48.424 | 1.00 | 41.58 |
| 4898 | CG | GLU | 517 | 116.496 | 26.950 | 47.503 | 1.00 | 52.96 |
| 4899 | CD | GLU | 517 | 115.344 | 26.242 | 48.223 | 1.00 | 59.58 |
| 4900 | OE1 | GLU | 517 | 115.593 | 25.557 | 49.236 | 1.00 | 60.41 |
| 4901 | OE2 | GLU | 517 | 114.187 | 26.352 | 47.762 | 1.00 | 63.04 |
| 4902 | H | GLU | 517 | 115.899 | 29.407 | 47.161 | 1.00 | 25.00 |
| 4903 | N | VAL | 518 | 118.314 | 30.799 | 49.050 | 1.00 | 40.18 |
| 4904 | CA | VAL | 518 | 119.310 | 31.714 | 49.600 | 1.00 | 42.32 |
| 4905 | C | VAL | 518 | 118.704 | 32.885 | 50.386 | 1.00 | 47.45 |
| 4906 | O | VAL | 518 | 119.269 | 33.326 | 51.389 | 1.00 | 48.49 |
| 4907 | CB | VAL | 518 | 120.219 | 32.251 | 48.474 | 1.00 | 41.14 |
| 4908 | CG1 | VAL | 518 | 121.133 | 33.350 | 48.986 | 1.00 | 39.83 |
| 4909 | CG2 | VAL | 518 | 121.034 | 31.108 | 47.896 | 1.00 | 45.30 |
| 4910 | H | VAL | 518 | 118.097 | 30.844 | 48.095 | 1.00 | 25.00 |
| 4911 | N | THR | 519 | 117.563 | 33.387 | 49.923 | 1.00 | 45.49 |
| 4912 | CA | THR | 519 | 116.899 | 34.505 | 50.577 | 1.00 | 44.49 |
| 4913 | C | THR | 519 | 116.183 | 34.117 | 51.884 | 1.00 | 44.03 |
| 4914 | O | THR | 519 | 115.983 | 34.964 | 52.754 | 1.00 | 41.48 |
| 4915 | CB | THR | 519 | 115.868 | 35.165 | 49.622 | 1.00 | 45.40 |
| 4916 | OG1 | THR | 519 | 116.518 | 35.516 | 48.394 | 1.00 | 47.45 |
| 4917 | CG2 | THR | 519 | 115.283 | 36.424 | 50.240 | 1.00 | 50.81 |
| 4918 | H | THR | 519 | 117.161 | 32.996 | 49.123 | 1.00 | 25.00 |
| 4919 | HG1 | THR | 519 | 116.872 | 34.719 | 47.980 | 1.00 | 25.00 |
| 4920 | N | TYR | 520 | 115.827 | 32.843 | 52.034 | 1.00 | 49.74 |
| 4921 | CA | TYR | 520 | 115.130 | 32.385 | 53.240 | 1.00 | 54.71 |
| 4922 | C | TYR | 520 | 115.783 | 31.213 | 53.984 | 1.00 | 60.58 |
| 4923 | O | TYR | 520 | 115.129 | 30.191 | 54.209 | 1.00 | 65.16 |
| 4924 | CB | TYR | 520 | 113.686 | 31.988 | 52.905 | 1.00 | 52.58 |
| 4925 | CG | TYR | 520 | 112.886 | 33.018 | 52.142 | 1.00 | 53.27 |
| 4926 | CD1 | TYR | 520 | 112.885 | 33.027 | 50.748 | 1.00 | 54.77 |
| 4927 | CD2 | TYR | 520 | 112.105 | 33.962 | 52.809 | 1.00 | 50.10 |
| 4928 | CE1 | TYR | 520 | 112.127 | 33.946 | 50.032 | 1.00 | 57.50 |
| 4929 | CE2 | TYR | 520 | 111.340 | 34.889 | 52.102 | 1.00 | 54.19 |
| 4930 | CZ | TYR | 520 | 111.357 | 34.873 | 50.713 | 1.00 | 56.86 |
| 4931 | OH | TYR | 520 | 110.604 | 35.777 | 49.999 | 1.00 | 58.70 |
| 4932 | H | TYR | 520 | 116.029 | 32.189 | 51.330 | 1.00 | 25.00 |
| 4933 | HH | TYR | 520 | 110.726 | 35.626 | 49.057 | 1.00 | 25.00 |
| 4934 | N | ILE | 521 | 117.056 | 31.340 | 54.350 | 1.00 | 67.35 |
| 4935 | CA | ILE | 521 | 117.729 | 30.269 | 55.091 | 1.00 | 74.89 |
| 4936 | C | ILE | 521 | 117.425 | 30.428 | 56.583 | 1.00 | 75.44 |
| 4937 | O | ILE | 521 | 117.194 | 29.397 | 57.255 | 1.00 | 76.20 |
| 4938 | CB | ILE | 521 | 119.276 | 30.258 | 54.856 | 1.00 | 75.70 |
| 4939 | CG1 | ILE | 521 | 119.586 | 29.919 | 53.394 | 1.00 | 76.18 |
| 4940 | CG2 | ILE | 521 | 119.953 | 29.222 | 55.766 | 1.00 | 77.50 |
| 4941 | CD1 | ILE | 521 | 121.064 | 29.755 | 53.080 | 1.00 | 71.61 |
| 4942 | H | ILE | 521 | 117.546 | 32.156 | 54.145 | 1.00 | 25.00 |
| 4943 | N | VAL | 533 | 120.428 | 39.967 | 55.248 | 1.00 | 55.02 |
| 4944 | CA | VAL | 533 | 120.478 | 38.584 | 54.683 | 1.00 | 57.02 |
| 4945 | C | VAL | 533 | 121.277 | 38.505 | 53.373 | 1.00 | 55.80 |
| 4946 | O | VAL | 533 | 122.075 | 37.588 | 53.181 | 1.00 | 56.73 |
| 4947 | CB | VAL | 533 | 119.048 | 37.995 | 54.485 | 1.00 | 56.30 |
| 4948 | CG1 | VAL | 533 | 118.225 | 38.868 | 53.539 | 1.00 | 56.90 |
| 4949 | CG2 | VAL | 533 | 119.125 | 36.552 | 53.986 | 1.00 | 50.74 |
| 4950 | 1H | VAL | 533 | 119.970 | 40.608 | 54.578 | 1.00 | 25.00 |
| 4951 | 2H | VAL | 533 | 119.880 | 39.938 | 56.132 | 1.00 | 25.00 |
| 4952 | 3H | VAL | 533 | 121.396 | 40.274 | 55.462 | 1.00 | 25.00 |
| 4953 | N | LEU | 534 | 121.095 | 39.483 | 52.491 | 1.00 | 49.61 |
| 4954 | CA | LEU | 534 | 121.812 | 39.490 | 51.218 | 1.00 | 48.50 |
| 4955 | C | LEU | 534 | 123.194 | 40.138 | 51.300 | 1.00 | 47.52 |
| 4956 | O | LEU | 534 | 124.075 | 39.830 | 50.496 | 1.00 | 44.98 |
| 4957 | CB | LEU | 534 | 120.983 | 40.190 | 50.137 | 1.00 | 48.86 |
| 4958 | CG | LEU | 534 | 119.659 | 39.533 | 49.744 | 1.00 | 50.00 |
| 4959 | CD1 | LEU | 534 | 119.054 | 40.290 | 48.567 | 1.00 | 46.00 |
| 4960 | CD2 | LEU | 534 | 119.886 | 38.066 | 49.384 | 1.00 | 42.36 |
| 4961 | H | LEU | 534 | 120.456 | 40.200 | 52.652 | 1.00 | 25.00 |
| 4962 | N | LYS | 535 | 123.382 | 40.993 | 52.303 | 1.00 | 45.93 |
| 4963 | CA | LYS | 535 | 124.633 | 41.722 | 52.510 | 1.00 | 45.11 |
| 4964 | C | LYS | 535 | 125.921 | 40.923 | 52.284 | 1.00 | 43.08 |
| 4965 | O | LYS | 535 | 126.729 | 41.288 | 51.428 | 1.00 | 42.36 |
| 4966 | CB | LYS | 535 | 124.651 | 42.385 | 53.895 | 1.00 | 46.19 |
| 4967 | CG | LYS | 535 | 125.855 | 43.288 | 54.130 | 1.00 | 54.44 |
| 4968 | CD | LYS | 535 | 125.868 | 43.868 | 55.536 | 1.00 | 57.76 |
| 4969 | CE | LYS | 535 | 127.075 | 44.774 | 55.767 | 1.00 | 61.61 |
| 4970 | NZ | LYS | 535 | 127.099 | 45.378 | 57.111 | 1.00 | 62.66 |
| 4971 | H | LYS | 535 | 122.651 | 41.156 | 52.915 | 1.00 | 25.00 |
| 4972 | 1HZ | LYS | 535 | 127.134 | 44.621 | 57.824 | 1.00 | 25.00 |
| 4973 | 2HZ | LYS | 535 | 127.936 | 45.986 | 57.207 | 1.00 | 25.00 |
| 4974 | 3HZ | LYS | 535 | 126.239 | 45.946 | 57.252 | 1.00 | 25.00 |
| 4975 | N | PRO | 536 | 126.115 | 39.809 | 53.019 | 1.00 | 39.15 |
| 4976 | CA | PRO | 536 | 127.337 | 39.020 | 52.829 | 1.00 | 37.51 |
| 4977 | C | PRO | 536 | 127.564 | 38.579 | 51.386 | 1.00 | 33.92 |
| 4978 | O | PRO | 536 | 128.684 | 38.644 | 50.877 | 1.00 | 33.28 |
| 4979 | CB | PRO | 536 | 127.128 | 37.827 | 53.770 | 1.00 | 38.16 |
| 4980 | CG | PRO | 536 | 125.638 | 37.724 | 53.893 | 1.00 | 42.17 |
| 4981 | CD | PRO | 536 | 125.233 | 39.164 | 54.008 | 1.00 | 38.53 |
| 4982 | N | HIS | 537 | 126.488 | 38.181 | 50.714 | 1.00 | 33.98 |
| 4983 | CA | HIS | 537 | 126.575 | 37.730 | 49.327 | 1.00 | 34.56 |

TABLE 11-continued

Structural Coordinates of Tobacco 5-Epi-Aristolochene Synthase In the Absence of Bound Substrate

| Atom | Atom | Resi- | Resi- | | | | | |
|---|---|---|---|---|---|---|---|---|
| Type | | due | due # | X | Y | Z | OCC | B-factor |
| 4984 | C | HIS | 537 | 126.929 | 38.877 | 48.390 | 1.00 | 34.75 |
| 4985 | O | HIS | 537 | 127.742 | 38.714 | 47.479 | 1.00 | 29.05 |
| 4986 | CB | HIS | 537 | 125.264 | 37.071 | 48.900 | 1.00 | 34.41 |
| 4987 | CG | HIS | 537 | 124.917 | 35.855 | 49.703 | 1.00 | 41.27 |
| 4988 | ND1 | HIS | 537 | 123.749 | 35.746 | 50.426 | 1.00 | 43.98 |
| 4989 | CD2 | HIS | 537 | 125.601 | 34.705 | 49.917 | 1.00 | 37.03 |
| 4990 | CE1 | HIS | 537 | 123.726 | 34.584 | 51.053 | 1.00 | 40.28 |
| 4991 | NE2 | HIS | 537 | 124.838 | 33.933 | 50.760 | 1.00 | 39.05 |
| 4992 | H | HIS | 537 | 125.616 | 38.225 | 51.154 | 1.00 | 25.00 |
| 4993 | HD1 | HIS | 537 | 123.030 | 36.418 | 50.483 | 1.00 | 25.00 |
| 4994 | HE2 | HIS | 537 | 125.072 | 33.038 | 51.088 | 1.00 | 25.00 |
| 4995 | N | ILE | 538 | 126.333 | 40.040 | 48.634 | 1.00 | 34.95 |
| 4996 | CA | ILE | 538 | 126.596 | 41.225 | 47.829 | 1.00 | 35.08 |
| 4997 | C | ILE | 538 | 128.063 | 41.612 | 47.969 | 1.00 | 36.46 |
| 4998 | O | ILE | 538 | 128.703 | 41.999 | 46.990 | 1.00 | 38.58 |
| 4999 | CB | ILE | 538 | 125.701 | 42.406 | 48.263 | 1.00 | 35.99 |
| 5000 | CG1 | ILE | 538 | 124.230 | 42.072 | 47.983 | 1.00 | 37.36 |
| 5001 | CG2 | ILE | 538 | 126.124 | 43.681 | 47.542 | 1.00 | 34.76 |
| 5002 | CD1 | ILE | 538 | 123.248 | 43.112 | 48.460 | 1.00 | 36.39 |
| 5003 | H | ILE | 538 | 125.708 | 40.113 | 49.385 | 1.00 | 25.00 |
| 5004 | N | ILE | 539 | 128.588 | 41.491 | 49.185 | 1.00 | 34.70 |
| 5005 | CA | ILE | 539 | 129.979 | 41.807 | 49.473 | 1.00 | 33.68 |
| 5006 | C | ILE | 539 | 130.912 | 40.828 | 48.769 | 1.00 | 34.74 |
| 5007 | O | ILE | 539 | 131.868 | 41.239 | 48.093 | 1.00 | 30.49 |
| 5008 | CB | ILE | 539 | 130.253 | 41.761 | 51.004 | 1.00 | 35.37 |
| 5009 | CG1 | ILE | 539 | 129.559 | 42.939 | 51.686 | 1.00 | 33.35 |
| 5010 | CG2 | ILE | 539 | 131.749 | 41.790 | 51.285 | 1.00 | 32.80 |
| 5011 | CD1 | ILE | 539 | 129.684 | 42.933 | 53.189 | 1.00 | 34.58 |
| 5012 | H | ILE | 539 | 127.999 | 41.207 | 49.913 | 1.00 | 25.00 |
| 5013 | N | ASN | 540 | 130.603 | 39.538 | 48.864 | 1.00 | 33.09 |
| 5014 | CA | ASN | 540 | 131.440 | 38.505 | 48.263 | 1.00 | 33.80 |
| 5015 | C | ASN | 540 | 131.355 | 38.498 | 46.749 | 1.00 | 34.25 |
| 5016 | O | ASN | 540 | 132.298 | 38.166 | 46.065 | 1.00 | 33.46 |
| 5017 | CB | ASN | 540 | 131.047 | 37.127 | 48.775 | 1.00 | 33.03 |
| 5018 | CG | ASN | 540 | 131.463 | 38.902 | 50.198 | 1.00 | 39.77 |
| 5019 | OD1 | ASN | 540 | 130.776 | 36.219 | 50.965 | 1.00 | 45.10 |
| 5020 | ND2 | ASN | 540 | 132.581 | 37.502 | 50.579 | 1.00 | 36.91 |
| 5021 | H | ASN | 540 | 129.781 | 39.280 | 49.311 | 1.00 | 25.00 |
| 5022 | 1HD2 | ASN | 540 | 132.850 | 37.386 | 51.503 | 1.00 | 25.00 |
| 5023 | 2HD2 | ASN | 540 | 133.079 | 38.025 | 49.919 | 1.00 | 25.00 |
| 5024 | N | LEU | 541 | 130.185 | 38.821 | 46.253 | 1.00 | 30.66 |
| 5025 | CA | LEU | 541 | 129.997 | 38.848 | 44.821 | 1.00 | 31.93 |
| 5026 | C | LEU | 541 | 130.262 | 40.166 | 44.110 | 1.00 | 33.86 |
| 5027 | O | LEU | 541 | 130.805 | 40.129 | 42.977 | 1.00 | 30.07 |
| 5028 | CB | LEU | 541 | 128.600 | 38.308 | 44.486 | 1.00 | 34.62 |
| 5029 | CG | LEU | 541 | 128.194 | 36.907 | 44.990 | 1.00 | 35.64 |
| 5030 | CD1 | LEU | 541 | 126.882 | 36.542 | 44.345 | 1.00 | 31.26 |
| 5031 | CD2 | LEU | 541 | 129.256 | 35.866 | 44.669 | 1.00 | 29.53 |
| 5032 | H | LEU | 541 | 129.518 | 38.998 | 46.982 | 1.00 | 25.00 |
| 5033 | N | LEU | 542 | 129.910 | 41.305 | 44.706 | 1.00 | 35.33 |
| 5034 | CA | LEU | 542 | 130.075 | 42.581 | 44.033 | 1.00 | 39.16 |
| 5035 | C | LEU | 542 | 131.084 | 43.566 | 44.635 | 1.00 | 42.69 |
| 5036 | O | LEU | 542 | 131.361 | 44.614 | 44.055 | 1.00 | 45.28 |
| 5037 | CB | LEU | 542 | 128.721 | 43.258 | 43.921 | 1.00 | 37.88 |
| 5038 | CG | LEU | 542 | 127.685 | 42.494 | 43.105 | 1.00 | 37.82 |
| 5039 | CD1 | LEU | 542 | 126.275 | 42.902 | 43.505 | 1.00 | 37.78 |
| 5040 | CD2 | LEU | 542 | 127.947 | 42.728 | 41.619 | 1.00 | 33.54 |
| 5041 | H | LEU | 542 | 129.525 | 41.317 | 45.569 | 1.00 | 25.00 |
| 5042 | N | VAL | 543 | 131.590 | 43.264 | 45.822 | 1.00 | 40.06 |
| 5043 | CA | VAL | 543 | 132.536 | 44.157 | 46.483 | 1.00 | 39.52 |
| 5044 | C | VAL | 543 | 133.960 | 43.601 | 46.457 | 1.00 | 40.35 |
| 5045 | O | VAL | 543 | 134.834 | 44.117 | 45.766 | 1.00 | 36.40 |
| 5046 | CB | VAL | 543 | 132.112 | 44.458 | 47.351 | 1.00 | 38.67 |
| 5047 | CG1 | VAL | 543 | 133.154 | 45.323 | 48.643 | 1.00 | 41.60 |
| 5048 | CG2 | VAL | 543 | 130.762 | 45.137 | 47.966 | 1.00 | 33.55 |
| 5049 | H | VAL | 543 | 131.348 | 42.421 | 46.245 | 1.00 | 25.00 |
| 5050 | N | ASP | 544 | 134.175 | 42.518 | 47.191 | 1.00 | 39.19 |
| 5051 | CA | ASP | 544 | 135.485 | 41.887 | 47.274 | 1.00 | 37.12 |
| 5052 | C | ASP | 544 | 135.802 | 40.970 | 46.112 | 1.00 | 38.65 |
| 5053 | O | ASP | 544 | 134.991 | 40.124 | 45.739 | 1.00 | 42.40 |
| 5054 | CB | ASP | 544 | 135.609 | 41.070 | 48.566 | 1.00 | 37.00 |
| 5055 | CG | ASP | 544 | 135.384 | 41.894 | 49.812 | 1.00 | 42.35 |
| 5056 | OD1 | ASP | 544 | 135.659 | 43.114 | 49.803 | 1.00 | 49.35 |
| 5057 | OD2 | ASP | 544 | 134.933 | 41.304 | 50.813 | 1.00 | 50.35 |
| 5058 | H | ASP | 544 | 133.427 | 42.119 | 47.665 | 1.00 | 25.00 |
| 5059 | N | SER | 545 | 136.984 | 41.153 | 45.543 | 1.00 | 36.71 |
| 5060 | CA | SER | 545 | 137.444 | 40.303 | 44.464 | 1.00 | 39.73 |
| 5061 | C | SER | 545 | 138.200 | 39.158 | 45.142 | 1.00 | 38.96 |
| 5062 | O | SER | 545 | 138.585 | 39.269 | 46.310 | 1.00 | 40.93 |
| 5063 | CB | SER | 545 | 138.379 | 41.084 | 43.540 | 1.00 | 43.38 |
| 5064 | OG | SER | 545 | 139.362 | 41.790 | 44.280 | 1.00 | 51.44 |
| 5065 | H | SER | 545 | 137.544 | 41.896 | 45.832 | 1.00 | 25.00 |
| 5066 | HG | SER | 545 | 139.870 | 41.166 | 44.808 | 1.00 | 25.00 |
| 5067 | N | ILE | 546 | 138.377 | 38.040 | 44.442 | 1.00 | 36.92 |
| 5068 | CA | ILE | 546 | 139.109 | 36.920 | 45.011 | 1.00 | 40.59 |
| 5069 | C | ILE | 546 | 140.602 | 37.261 | 44.954 | 1.00 | 45.93 |
| 5070 | O | ILE | 546 | 141.117 | 37.620 | 43.889 | 1.00 | 46.41 |
| 5071 | CB | ILE | 546 | 138.839 | 35.612 | 44.226 | 1.00 | 36.34 |
| 5072 | CG1 | ILE | 546 | 137.346 | 35.288 | 44.264 | 1.00 | 34.10 |
| 5073 | CG2 | ILE | 546 | 139.629 | 34.456 | 44.829 | 1.00 | 31.04 |
| 5074 | CO1 | ILE | 546 | 136.979 | 34.011 | 43.525 | 1.00 | 36.46 |
| 5075 | H | ILE | 546 | 138.009 | 37.990 | 43.533 | 1.00 | 25.00 |
| 5076 | N | LYS | 547 | 141.282 | 37.201 | 46.009 | 1.00 | 52.49 |
| 5077 | CA | LYS | 547 | 142.706 | 37.502 | 46.134 | 1.00 | 58.52 |
| 5078 | C | LYS | 547 | 143.483 | 36.450 | 45.353 | 1.00 | 60.95 |
| 5079 | O | LYS | 547 | 143.488 | 35.273 | 45.713 | 1.00 | 60.42 |
| 5080 | CB | LYS | 547 | 143.217 | 37.599 | 47.572 | 1.00 | 59.36 |
| 5081 | CG | LYS | 547 | 144.684 | 38.023 | 47.659 | 1.00 | 68.28 |
| 5082 | CD | LYS | 547 | 145.065 | 38.553 | 49.037 | 1.00 | 72.08 |
| 5083 | CE | LYS | 547 | 146.486 | 39.105 | 49.029 | 1.00 | 74.86 |
| 5084 | NZ | LYS | 547 | 146.796 | 39.880 | 50.265 | 1.00 | 78.47 |
| 5085 | H | LYS | 547 | 140.806 | 36.948 | 46.910 | 1.00 | 25.00 |
| 5086 | 1HZ | LYS | 547 | 146.680 | 39.273 | 51.099 | 1.00 | 25.00 |
| 5087 | 2HZ | LYS | 547 | 147.770 | 40.240 | 50.222 | 1.00 | 25.00 |
| 5088 | 3HZ | LYS | 547 | 146.139 | 40.685 | 50.334 | 1.00 | 25.00 |
| 5089 | N | ILE | 548 | 144.086 | 36.890 | 44.254 | 1.00 | 67.72 |
| 5090 | CA | ILE | 548 | 144.868 | 36.018 | 43.381 | 1.00 | 76.79 |
| 5091 | C | ILE | 548 | 146.198 | 35.622 | 44.025 | 1.00 | 83.68 |
| 5092 | O | ILE | 548 | 146.583 | 34.440 | 43.897 | 1.00 | 86.24 |
| 5093 | CB | ILE | 548 | 145.120 | 36.678 | 41.986 | 1.00 | 75.68 |
| 5094 | CG1 | ILE | 548 | 145.604 | 38.125 | 42.152 | 1.00 | 78.47 |
| 5095 | CG2 | ILE | 548 | 143.855 | 36.623 | 41.137 | 1.00 | 68.49 |
| 5096 | CD1 | ILE | 548 | 145.930 | 38.827 | 40.831 | 1.00 | 78.93 |
| 5097 | OXT | ILE | 548 | 146.823 | 36.492 | 44.672 | 1.00 | 92.78 |
| 5098 | H | ILE | 548 | 144.032 | 37.836 | 44.045 | 1.00 | 25.00 |
| 5099 | ILE | | 548 | | | | | |
| 5100 | MG | MG | 851 | 104.185 | 36.235 | 53.030 | 1.00 | 61.83 |
| 5101 | MG | MG | 852 | 102.138 | 43.657 | 49.009 | 1.00 | 62.23 |
| 5102 | O | HOH | 601 | 107.742 | 22.057 | 32.406 | 1.00 | 15.11 |
| 5103 | O | HOH | 602 | 122.540 | 22.695 | 37.531 | 1.00 | 32.44 |
| 5104 | O | HOH | 603 | 127.188 | 14.109 | 43.835 | 1.00 | 23.85 |
| 5105 | O | HOH | 604 | 123.257 | 32.177 | 37.651 | 1.00 | 25.21 |
| 5106 | O | HOH | 605 | 131.975 | 36.814 | 38.945 | 1.00 | 20.08 |
| 5107 | O | HOH | 606 | 130.320 | 38.579 | 40.729 | 1.00 | 28.69 |
| 5108 | O | HOH | 607 | 124.735 | 33.181 | 39.810 | 1.00 | 19.46 |
| 5109 | O | HOH | 608 | 119.958 | 22.714 | 50.725 | 1.00 | 24.82 |
| 5110 | O | HOH | 609 | 125.172 | 22.654 | 40.253 | 1.00 | 21.47 |
| 5111 | O | HOH | 610 | 106.047 | 21.994 | 29.826 | 1.00 | 26.03 |
| 5112 | O | HOH | 611 | 123.659 | 29.782 | 47.444 | 1.00 | 22.10 |
| 5113 | O | HOH | 612 | 129.924 | 22.165 | 49.955 | 1.00 | 20.33 |
| 5114 | O | HOH | 613 | 117.254 | 16..672 | 36.732 | 1.00 | 18.88 |
| 5115 | O | HOH | 614 | 131.911 | 22.935 | 48.204 | 1.00 | 23.59 |
| 5116 | O | HOH | 615 | 123.421 | 30.030 | 35.911 | 1.00 | 23.89 |
| 5117 | O | HOH | 616 | 128.952 | 30.316 | 38.829 | 1.00 | 22.41 |
| 5118 | O | HOH | 617 | 98.347 | 33.326 | 40.948 | 1.00 | 28.07 |
| 5119 | O | HOH | 618 | 126.062 | 19.250 | 36.922 | 1.00 | 29.11 |
| 5120 | O | HOH | 619 | 133.788 | 33.099 | 36.415 | 1.00 | 20.10 |
| 5121 | O | HOH | 620 | 127.252 | 22.013 | 48.848 | 1.00 | 24.10 |
| 5122 | O | HOH | 621 | 123.122 | 19.043 | 45.472 | 1.00 | 19.68 |
| 5123 | O | HOH | 622 | 124.636 | 25.767 | 41.845 | 1.00 | 42.37 |
| 5124 | 0 | HOH | 623 | 138.021 | 26.937 | 54.497 | 1.00 | 33.32 |
| 5125 | O | HOH | 624 | 130.604 | 16.213 | 44.273 | 1.00 | 25.46 |
| 5126 | O | HOH | 625 | 119.735 | 17.425 | 55.175 | 1.00 | 23.51 |
| 5127 | O | HOH | 626 | 109.560 | 43.332 | 32.386 | 1.00 | 27.79 |
| 5128 | O | HOH | 627 | 104.016 | 36.817 | 39.018 | 1.00 | 24.34 |
| 5129 | O | HOH | 628 | 134.051 | 35.256 | 29.604 | 1.00 | 37.22 |

TABLE 11-continued

Structural Coordinates of Tobacco 5-Epi-Aristolochene Synthase
In the Absence of Bound Substrate

| Atom Type | Atom | Resi-due | Resi-due # | X | Y | Z | OCC | B-factor |
|---|---|---|---|---|---|---|---|---|
| 5130 | O | HOH | 629 | 107.947 | 18.792 | 36.023 | 1.00 | 35.84 |
| 5131 | O | HOH | 630 | 129.821 | 19.576 | 48.096 | 1.00 | 29.63 |
| 5132 | O | HOH | 631 | 104.550 | 21.758 | 41.675 | 1.00 | 38.10 |
| 5133 | O | HOH | 632 | 111.970 | 10.709 | 47.161 | 1.00 | 23.86 |
| 5134 | O | HOH | 633 | 125.976 | 29.448 | 50.341 | 1.00 | 26.42 |
| 5135 | O | HOH | 634 | 97.143 | 36.787 | 48.102 | 1.00 | 35.12 |
| 5136 | O | HOH | 635 | 121.582 | 36.805 | 25.111 | 1.00 | 35.51 |
| 5137 | O | HOH | 636 | 113.756 | 26.801 | 22.571 | 1.00 | 30.58 |
| 5138 | O | HOH | 637 | 124.698 | 19.485 | 28.803 | 1.00 | 29.60 |
| 5139 | O | HOH | 638 | 130.563 | 25.567 | 43.476 | 1.00 | 29..93 |
| 5140 | O | HOH | 639 | 121.706 | 39.646 | 27.124 | 1.00 | 32.61 |
| 5141 | O | HOH | 640 | 104.749 | 34.099 | 30.683 | 1.00 | 28.14 |
| 5142 | O | HOH | 641 | 111.751 | 8.174 | 35.080 | 1.00 | 34.23 |
| 5143 | O | HOH | 642 | 120.339 | 31.400 | 41.487 | 1.00 | 52.69 |
| 5144 | O | HOH | 643 | 95.163 | 26.623 | 43.384 | 1.00 | 36.83 |
| 5145 | O | HOH | 644 | 137.113 | 41.980 | 40.124 | 1.00 | 30.35 |
| 5146 | O | HOH | 645 | 116.126 | 11.318 | 49.986 | 1.00 | 25.34 |
| 5147 | O | HOH | 646 | 110.165 | 35.328 | 17.495 | 1.00 | 37.81 |
| 5148 | O | HOH | 647 | 118.054 | 20.287 | 30.749 | 1.00 | 33.12 |
| 5149 | O | HOH | 648 | 115.899 | 40.354 | 30.351 | 1.00 | 29.82 |
| 5150 | O | HOH | 649 | 113.524 | 54.000 | 32.295 | 1.00 | 30.14 |
| 5151 | O | HOH | 650 | 127.950 | 27.982 | 37.184 | 1.00 | 28.39 |
| 5152 | O | HOH | 651 | 108.770 | 18.109 | 30.127 | 1.00 | 36.94 |
| 5153 | O | HOH | 652 | 112.843 | 23.036 | 50.160 | 1.00 | 41.87 |
| 5154 | O | HOH | 653 | 132.804 | 32.747 | 50.167 | 1.00 | 34.56 |
| 5155 | O | HOH | 654 | 99.278 | 32.670 | 36.214 | 1.00 | 31.88 |
| 5156 | O | HOH | 655 | 93.100 | 36.093 | 41.777 | 1.00 | 39.13 |
| 5157 | O | HOH | 656 | 114.575 | 17.087 | 50.058 | 1.00 | 29.96 |
| 5158 | O | HOH | 657 | 134.890 | 18.651 | 45.599 | 1.00 | 29.79 |
| 5159 | O | HOH | 658 | 134.764 | 16.354 | 47.235 | 1.00 | 41.87 |
| 5160 | O | HOH | 659 | 138.146 | 19.452 | 46.210 | 1.00 | 40.62 |
| 5161 | O | HOH | 660 | 113.498 | 7.243 | 37.601 | 1.00 | 44.14 |
| 5162 | O | HOH | 661 | 118.735 | 25.324 | 49.539 | 1.00 | 32.46 |
| 5163 | O | HOH | 662 | 121.072 | 19.323 | 57.037 | 1.00 | 28.13 |
| 5164 | O | HOH | 663 | 120.647 | 52.139 | 31.726 | 1.00 | 31.21 |
| 5165 | O | HOH | 664 | 125.201 | 27.805 | 35.886 | 1.00 | 35.41 |
| 5166 | O | HOH | 665 | 103.040 | 17.910 | 41.249 | 1.00 | 34.74 |
| 5167 | O | HOH | 666 | 92.281 | 23.719 | 49.317 | 1.00 | 36.36 |
| 5168 | O | HOH | 667 | 120.731 | 30.312 | 30.736 | 1.00 | 40.91 |
| 5169 | O | HOH | 668 | 111.010 | 16.805 | 31.260 | 1.00 | 37.18 |
| 5170 | O | HOH | 669 | 98.374 | 30.892 | 39.496 | 1.00 | 39.09 |
| 5171 | O | HOH | 670 | 142.913 | 20.086 | 59.043 | 1.00 | 40.89 |
| 5172 | O | HOH | 671 | 120.070 | 4.238 | 32.203 | 1.00 | 32.10 |
| 5173 | O | HOH | 672 | 116.885 | 14.360 | 38.230 | 1.00 | 19.20 |
| 5174 | O | HOH | 673 | 135.198 | 31.364 | 38.159 | 1.00 | 21.99 |
| 5175 | O | HOH | 674 | 130.652 | 23.815 | 45.653 | 1.00 | 22.37 |
| 5176 | O | HOH | 675 | 116.184 | 18.170 | 25.042 | 1.00 | 33.65 |
| 5177 | O | HOH | 676 | 102.763 | 37.505 | 36.535 | 1.00 | 29.50 |
| 5178 | O | HOH | 677 | 113.482 | 17.709 | 47.318 | 1.00 | 24.10 |
| 5179 | O | HOH | 678 | 128.292 | 24.082 | 47.295 | 1.00 | 27.62 |
| 5180 | O | HOH | 679 | 128.934 | 20.011 | 39.747 | 1.00 | 26.34 |
| 5181 | O | HOH | 680 | 129.840 | 32.556 | 48.799 | 1.00 | 34.07 |
| 5182 | O | HOH | 681 | 115.123 | 17.894 | 45.342 | 1.00 | 23.02 |
| 5183 | O | HOH | 682 | 134.875 | 11.928 | 61.810 | 1.00 | 24.68 |
| 5184 | O | HOH | 683 | 140.837 | 17.873 | 38.782 | 1.00 | 33.65 |
| 5185 | O | HOH | 684 | 135.724 | 8.315 | 55.152 | 1.00 | 37.93 |
| 5186 | O | HOH | 685 | 131.660 | 25.765 | 56.520 | 1.00 | 36.71 |
| 5187 | O | HOH | 686 | 148.447 | 27.966 | 42.675 | 1.00 | 38.11 |
| 5188 | O | HOH | 687 | 110.190 | 10.176 | 45.195 | 1.00 | 35.74 |
| 5189 | O | HOH | 688 | 109.091 | 17.883 | 25.410 | 1.00 | 38.94 |
| 5190 | O | HOH | 6889 | 104.860 | 34.526 | 28.030 | 1.00 | 38.81 |
| 5191 | O | HOH | 690 | 102.070 | 36.177 | 27.889 | 1.00 | 35.60 |
| 5192 | O | HOH | 691 | 118.113 | 11.174 | 28.782 | 1.00 | 38.94 |
| 5193 | O | HOH | 692 | 131.635 | 20.640 | 62.725 | 1.00 | 33.60 |
| 5194 | O | HOH | 693 | 136.344 | 35.530 | 31.124 | 1.00 | 36.08 |
| 5195 | O | HOH | 694 | 120.257 | 31.406 | 33.335 | 1.00 | 31.14 |
| 5196 | O | HOH | 695 | 102.005 | 32.616 | 56.124 | 1.00 | 33.30 |
| 5197 | O | HOH | 696 | 124.575 | 21.994 | 35.468 | 1.00 | 36.59 |
| 5198 | O | HOH | 697 | 101.923 | 20.169 | 46.398 | 1.00 | 40.37 |
| 5199 | O | HOH | 698 | 129.243 | 49.171 | 40.765 | 1.00 | 49.17 |
| 5200 | O | HOH | 699 | 139.196 | 35.578 | 48.616 | 1.00 | 31.26 |
| 5201 | O | HOH | 700 | 134.064 | 15.022 | 43.146 | 1.00 | 40.48 |
| 5202 | O | HOH | 701 | 128.514 | 31.051 | 51.675 | 1.00 | 39.32 |
| 5203 | O | HOH | 702 | 112.958 | 10.222 | 36.694 | 1.00 | 47.07 |
| 5204 | O | HOH | 703 | 109.649 | 15.841 | 28.459 | 1.00 | 35.43 |
| 5205 | O | HOH | 704 | 140.094 | 42.685 | 39.958 | 1.00 | 41.31 |
| 5206 | O | HOH | 705 | 86.608 | 31.749 | 55.350 | 1.00 | 36.82 |
| 5207 | O | HOH | 706 | 128.605 | 34.147 | 28.351 | 1.00 | 35.79 |
| 5208 | O | HOH | 707 | 87.075 | 34.369 | 56.433 | 1.00 | 42.04 |
| 5209 | O | HOH | 708 | 89.030 | 34.345 | 44.620 | 1.00 | 40.07 |
| 5210 | O | HOH | 709 | 104.535 | 51.407 | 27.998 | 1.00 | 39.44 |
| 5211 | O | HOH | 710 | 120.125 | 34.187 | 24.397 | 1.00 | 63.74 |
| 5212 | O | HOH | 711 | 100.184 | 37.778 | 52.580 | 1.00 | 43.18 |
| 5213 | O | HOH | 712 | 109.218 | 37.444 | 46.111 | 1.00 | 37.68 |
| 5214 | O | HOH | 713 | 139.550 | 20.401 | 60.539 | 1.00 | 40.82 |
| 5215 | O | HOH | 714 | 140.612 | 17.7933 | 52.684 | 1.00 | 42.33 |
| 5216 | O | HOH | 715 | 120.330 | 21.170 | 32.392 | 1.00 | 31.20 |
| 5217 | O | HOH | 716 | 100.372 | 35.917 | 30.033 | 1.00 | 43.22 |
| 5218 | O | HOH | 717 | 120.163 | 23.899 | 33.930 | 1.00 | 33.67 |
| 5219 | O | HOH | 718 | 146.383 | 28.556 | 40.921 | 1.00 | 38.01 |
| 5220 | O | HOH | 719 | 109.966 | 20.788 | 31.041 | 1.00 | 38.62 |
| 5221 | O | HOH | 720 | 105.493 | 40.925 | 45.887 | 1.00 | 35.53 |
| 5222 | O | HOH | 721 | 119.171 | 27.937 | 23.152 | 1.00 | 55.39 |
| 5223 | O | HOH | 722 | 124.424 | 41.390 | 25.938 | 1.00 | 43.52 |
| 5224 | O | HOH | 723 | 102.779 | 17.993 | 48.134 | 1.00 | 38.38 |
| 5225 | O | HOH | 724 | 112.387 | 5.685 | 33.453 | 1.00 | 48.35 |
| 5226 | O | HOH | 725 | 151.082 | 25.140 | 44.349 | 1.00 | 35.50 |
| 5227 | O | HOH | 726 | 127.089 | 21.203 | 29.049 | 1.00 | 45.21 |
| 5228 | O | HOH | 727 | 133.178 | 5.551 | 47.734 | 1.00 | 39.38 |
| 5229 | O | HOH | 728 | 151.127 | 34.628 | 33.927 | 1.00 | 42.02 |
| 5230 | O | HOH | 729 | 150.405 | 22.240 | 44.559 | 1.00 | 38.43 |
| 5231 | O | HOH | 730 | 131.660 | 2.107 | 47.933 | 1.00 | 37.78 |
| 5232 | O | HOH | 731 | 135.465 | 8.584 | 52.047 | 1.00 | 40.15 |
| 5233 | O | HOH | 732 | 147.814 | 29.664 | 45.229 | 1.00 | 44.50 |
| 5234 | O | HOH | 733 | 140.989 | 33.094 | 47.707 | 1.00 | 43.19 |
| 5235 | O | HOH | 734 | 103.951 | 49.441 | 25.596 | 1.00 | 38.72 |
| 5236 | O | HOH | 735 | 86.471 | 53.747 | 29.731 | 1.00 | 43.56 |
| 5237 | O | HOH | 736 | 134.470 | 31.168 | 25.546 | 1.00 | 52.39 |
| 5238 | O | HOH | 737 | 122.918 | 25.484 | 36.469 | 1.00 | 42.39 |
| 5239 | O | HOH | 738 | 99.309 | 33.456 | 31.178 | 1.00 | 48.32 |
| 5240 | O | HOH | 739 | 91.548 | 47.290 | 47.278 | 1.00 | 45.43 |
| 5241 | O | HOH | 740 | 92.024 | 43.380 | 40.690 | 1.00 | 42.02 |
| 5242 | O | HOH | 741 | 149.190 | 38.195 | 52.530 | 1.00 | 47.74 |
| 5243 | O | HOH | 742 | 153.088 | 41.575 | 36.804 | 1.00 | 46.51 |
| 5244 | O | HOH | 743 | 138.714 | 31.651 | 53.657 | 1.00 | 43.64 |
| 5245 | O | HOH | 744 | 143.900 | 19.054 | 51.722 | 1.00 | 40.32 |
| 5246 | O | HOH | 745 | 138.795 | 15.536 | 49.608 | 1.00 | 43.79 |
| 5247 | O | HOH | 746 | 124.711 | −3.430 | 56.077 | 1.00 | 44.40 |
| 5248 | O | HOH | 747 | 145.969 | 30.921 | 42.825 | 1.00 | 39.08 |
| 5249 | O | HOH | 748 | 134.979 | 10.249 | 59.470 | 1.00 | 35.78 |
| 5250 | O | HOH | 749 | 133.932 | 40.151 | 29.911 | 1.00 | 41.40 |
| 5251 | O | HOH | 750 | 114.521 | 21.309 | 22.697 | 1.00 | 38.72 |
| 5252 | O | HOH | 751 | 129.614 | 38.180 | 25.426 | 1.00 | 39.89 |
| 5253 | O | HOH | 752 | 111.6443 | 13.087 | 29.735 | 1.00 | 45.90 |
| 5254 | O | HOH | 753 | 104.216 | 21.388 | 44.848 | 1.00 | 33.35 |
| 5255 | O | HOH | 754 | 110.986 | 12.520 | 49.459 | 1.00 | 49.32 |
| 5256 | O | HOH | 755 | 139.600 | 40.725 | 48.728 | 1.00 | 46.07 |
| 5257 | O | HOH | 756 | 113.295 | 9.448 | 29.832 | 1.00 | 35.78 |
| 5258 | O | HOH | 757 | 127.101 | 23.382 | 34.156 | 1.00 | 48.02 |
| 5259 | O | HOH | 758 | 127.933 | 18.490 | 63.251 | 1.00 | 46.33 |
| 5260 | O | HOH | 759 | 130.420 | 26.867 | 25.702 | 1.00 | 40.40 |
| 5261 | O | HOH | 760 | 122.231 | 3.237 | 35.918 | 1.00 | 44.61 |
| 5262 | O | HOH | 761 | 128.310 | 26.484 | 40.968 | 1.00 | 32.14 |
| 5263 | O | HOH | 762 | 88.443 | 24.530 | 48.586 | 1.00 | 57.07 |
| 5264 | O | HOH | 763 | 103.542 | 23.739 | 25.080 | 1.00 | 45.05 |
| 5265 | O | HOH | 764 | 116.278 | 57.331 | 34.559 | 1.00 | 42.40 |
| 5266 | O | HOH | 765 | 120.787 | 5.886 | 61.156 | 1.00 | 43.73 |
| 5267 | O | HOH | 766 | 142.631 | 40.352 | 42.775 | 1.00 | 65.94 |
| 5268 | O | HOH | 767 | 124.244 | 13.057 | 63.666 | 1.00 | 43.68 |
| 5269 | O | HOH | 768 | 101.830 | 22.900 | 29.735 | 1.00 | 36.47 |
| 5270 | O | HOH | 769 | 137.190 | 5.022 | 37.071 | 1.00 | 50.65 |
| 5271 | O | HOH | 770 | 135.078 | 34.403 | 50.639 | 1.00 | 51.53 |
| 5272 | O | HOH | 771 | 103.266 | 58.719 | 26.225 | 1.00 | 46.58 |
| 5273 | O | HOH | 772 | 144.319 | 16.861 | 24.565 | 1.00 | 53.32 |
| 5274 | O | HOH | 773 | 127.856 | 47.718 | 31.019 | 1.00 | 45.45 |
| 5275 | O | HOH | 774 | 95.530 | 18.110 | 49.546 | 1.00 | 52.47 |

TABLE 11-continued

Structural Coordinates of Tobacco 5-Epi-Aristolochene Synthase
In the Absence of Bound Substrate

| Atom Type | Atom | Residue | Residue # | X | Y | Z | OCC | B-factor |
|---|---|---|---|---|---|---|---|---|
| 5276 | O | HOH | 775 | 148.435 | 20.165 | 43.831 | 1.00 | 49.25 |
| 5277 | O | HOH | 776 | 118.026 | 13.535 | 59.021 | 1.00 | 48.41 |
| 5278 | O | HOH | 777 | 110.119 | 43.903 | 16.201 | 1.00 | 37.10 |
| 5279 | O | HOH | 778 | 110.457 | 61.356 | 39.879 | 1.00 | 44.66 |
| 5280 | O | HOH | 779 | 105.313 | 56.879 | 27.692 | 1.00 | 51.08 |
| 5281 | O | HOH | 780 | 106.267 | 19.656 | 28.049 | 1.00 | 45.55 |
| 5282 | O | HOH | 781 | 122.226 | 20.789 | 29.638 | 1.00 | 45.73 |
| 5283 | O | HOH | 782 | 107.680 | 19.165 | 33.248 | 1.00 | 35.37 |
| 5284 | O | HOH | 783 | 141.434 | 30.527 | 58.190 | 1.00 | 56.49 |
| 5285 | O | HOH | 784 | 121.953 | 27.180 | 30.544 | 1.00 | 43.22 |
| 5286 | O | HOH | 785 | 116.050 | 27.492 | 52.913 | 1.00 | 59.86 |
| 5287 | O | HOH | 786 | 115.271 | 11.494 | 53.629 | 1.00 | 47.46 |
| 5288 | O | HOH | 787 | 136.166 | 43.700 | 43.430 | 1.00 | 44.89 |
| 5289 | O | HOH | 788 | 123.135 | 5.923 | 32.296 | 1.00 | 61.24 |
| 5290 | O | HOH | 789 | 148.342 | 38.089 | 38.232 | 1.00 | 41.22 |
| 5291 | O | HOH | 790 | 112.195 | 39.980 | 44.065 | 1.00 | 44.26 |
| 5292 | O | HOH | 791 | 108.340 | 50.773 | 20.100 | 1.00 | 62.55 |
| 5293 | O | HOH | 792 | 126.140 | 29.670 | 29.775 | 1.00 | 38.87 |
| 5294 | O | HOH | 793 | 122.347 | 26.176 | 27.904 | 1.00 | 47.43 |
| 5295 | O | HOH | 794 | 105.375 | 13.283 | 37.860 | 1.00 | 40.63 |
| 5296 | O | HOH | 795 | 146.608 | 19.061 | 33.529 | 1.00 | 50.53 |
| 5297 | O | HOH | 796 | 112.240 | 28.192 | 56.028 | 1.00 | 54.08 |
| 5298 | O | HOH | 797 | 106.519 | 16.717 | 37.160 | 1.00 | 39.17 |
| 5299 | O | HOH | 798 | 122.257 | -2.147 | 57.632 | 1.00 | 59.87 |
| 5300 | O | HOH | 799 | 105.969 | 47.469 | 20.174 | 1.00 | 42.44 |
| 5301 | O | HOH | 800 | 124.201 | 23.387 | 29.951 | 1.00 | 51.85 |
| 5302 | O | HOH | 801 | 104.010 | 26.139 | 23.199 | 1.00 | 57.02 |
| 5303 | O | HOH | 802 | 106.547 | 37.540 | 47.839 | 1.00 | 46.00 |
| 5304 | O | HOH | 803 | 126.083 | 27.795 | 33.246 | 1.00 | 45.66 |
| 5305 | O | HOH | 804 | 93.229 | 25.530 | 63.301 | 1.00 | 50.45 |
| 5306 | O | HOH | 805 | 126.637 | 14.627 | 66.291 | 1.00 | 54.63 |
| 5307 | O | HOH | 806 | 117.649 | 48.031 | 30.248 | 1.00 | 44.41 |
| 5308 | O | HOH | 807 | 112.889 | 34.483 | 46.820 | 1.00 | 41.77 |
| 5309 | O | HOH | 808 | 143.749 | 8.474 | 39.051 | 1.00 | 58.35 |
| 5310 | O | HOH | 809 | 117.223 | 16.467 | 56.527 | 1.00 | 54.55 |
| 5311 | O | HOH | 810 | 136.640 | 48.794 | 42.640 | 1.00 | 59.70 |
| 5312 | O | HOH | 811 | 130.573 | 47.631 | 52.219 | 1.00 | 43.65 |
| 5313 | O | HOH | 812 | 119.790 | 22.620 | 53.732 | 1.00 | 49.88 |
| 5314 | O | HOH | 813 | 105.220 | 9.911 | 43.334 | 1.00 | 53.82 |
| 5315 | O | HOH | 814 | 94.459 | 22.230 | 65.891 | 1.00 | 53.43 |
| 5316 | O | HOH | 815 | 145.893 | 33.119 | 447.904 | 1.00 | 50.15 |
| 5317 | O | HOH | 816 | 137.540 | 19.003 | 49.581 | 1.00 | 32.04 |
| 5318 | O | HOH | 817 | 127.395 | 18.676 | 22.177 | 1.00 | 58.02 |
| 5319 | O | HOH | 818 | 135.930 | 19.361 | 20.695 | 1.00 | 61.65 |
| 5320 | O | HOH | 819 | 122.368 | -4.865 | 43.028 | 1.00 | 43.72 |
| 5321 | O | HOH | 820 | 117.352 | 52.131 | 24.538 | 1.00 | 49.67 |
| 5322 | O | HOH | 821 | 129.874 | 51.577 | 33.814 | 1.00 | 58.12 |
| 5323 | O | HOH | 822 | 129.360 | 28.179 | 34.594 | 1.00 | 43.67 |
| 5324 | O | HOH | 823 | 97.243 | 40.051 | 31.308 | 1.00 | 40.94 |
| 5325 | O | HOH | 824 | 119.361 | 23.189 | 24.691 | 1.00 | 55.59 |
| 5326 | O | HOH | 825 | 105.947 | 8.433 | 39.961 | 1.00 | 47.78 |
| 5327 | O | HOH | 826 | 124.177 | -6.929 | 48.285 | 1.00 | 50.47 |
| 5328 | O | HOH | 827 | 143.743 | 41.219 | 49.977 | 1.00 | 54.42 |
| 5329 | O | HOH | 828 | 117.815 | 15.765 | 23.926 | 1.00 | 47.10 |
| 5330 | O | HOH | 829 | 106.852 | 11.509 | 45.366 | 1.00 | 59.91 |
| 5331 | O | HOH | 830 | 114.340 | 49.442 | 45.031 | 1.00 | 54.21 |
| 5332 | O | HOH | 831 | 107.212 | 10.319 | 38.018 | 1.00 | 47.91 |
| 5333 | O | HOH | 832 | 89.843 | 54.539 | 37.711 | 1.00 | 55.79 |
| 5334 | O | HOH | 833 | 115.120 | 21.415 | 49.941 | 1.00 | 40.64 |
| 5335 | O | HOH | 834 | 119.324 | 14.942 | 62.472 | 1.00 | 63.27 |
| 5336 | O | HOH | 835 | 149.479 | 14.241 | 50.723 | 1.00 | 65.18 |
| 5337 | O | HOH | 836 | 99.208 | 46.311 | 26.331 | 1.00 | 59.48 |
| 5338 | O | HOH | 837 | 146.479 | 34.108 | 25.046 | 1.00 | 49.79 |
| 5339 | O | HOH | 838 | 117.731 | 49.616 | 19.065 | 1.00 | 60.65 |
| 5340 | O | HOH | 839 | 115.539 | 6.301 | 34.276 | 1.00 | 51.97 |
| 5341 | O | HOH | 840 | 97.213 | 27.831 | 34.233 | 1.00 | 45.30 |
| 5342 | O | HOH | 841 | 89.788 | 22.728 | 43.919 | 1.00 | 61.79 |
| 5343 | O | HOH | 842 | 147.830 | 32.323 | 40.885 | 1.00 | 46.95 |
| 5344 | O | HOH | 843 | 132.462 | 17.381 | 68.762 | 1.00 | 50.53 |
| 5345 | O | HOH | 844 | 140.816 | 13.261 | 39.613 | 1.00 | 50.48 |
| 5346 | O | HOH | 845 | 131.788 | 48.689 | 43.107 | 1.00 | 55.44 |
| 5347 | O | HOH | 846 | 106.451 | 38.430 | 52.704 | 1.00 | 44.59 |
| 5348 | O | HOH | 847 | 112.522 | 3.225 | 51.067 | 1.00 | 62.24 |
| 5349 | O | HOH | 848 | 116.588 | 33.059 | 17.286 | 1.00 | 51.54 |
| 5350 | O | HOH | 849 | 121.984 | 13.530 | 21.831 | 1.00 | 59.69 |
| 5351 | O | HOH | 850 | 121.351 | 34.646 | 19.580 | 1.00 | 63.69 |
| 5352 | O | HOH | 853 | 119.444 | 26.300 | 52.657 | 1.00 | 48.12 |
| 5353 | O | HOH | 854 | 119.223 | 18.972 | 28.280 | 1.00 | 43.53 |
| 5354 | O | HOH | 855 | 109.476 | 29.077 | 61.498 | 1.00 | 46.95 |
| 5355 | O | HOH | 856 | 96.378 | 36.846 | 50.773 | 1.00 | 37.88 |
| 5356 | O | HOH | 857 | 96.918 | 46.467 | 51.605 | 1.00 | 69.73 |
| 5357 | O | HOH | 858 | 97.861 | 35.983 | 32.096 | 1.00 | 48.71 |
| 5358 | O | HOH | 859 | 105.582 | 44.217 | 22.626 | 1.00 | 52.96 |
| 5359 | O | HOH | 860 | 111.207 | 54.577 | 33.852 | 1.00 | 44.86 |
| 5360 | O | HOH | 861 | 106.475 | 45.773 | 50.620 | 1.00 | 52.70 |
| 5361 | O | HOH | 862 | 136.750 | 45.222 | 40.123 | 1.00 | 53.92 |
| 5362 | O | HOH | 863 | 134.438 | 43.600 | 31.414 | 1.00 | 51.51 |
| 5363 | O | HOH | 864 | 147.130 | 24.676 | 49.884 | 1.00 | 42.49 |
| 5364 | O | HOH | 865 | 126.425 | 22.757 | 59.405 | 1.00 | 54.25 |
| 5365 | O | HOH | 866 | 135.514 | 7.098 | 48.245 | 1.00 | 59.13 |
| 5366 | O | HOH | 867 | 114.942 | 1.622 | 48.125 | 1.00 | 56.08 |
| 5367 | O | HOH | 868 | 119.740 | -4.108 | 46.312 | 1.00 | 51.35 |
| 5368 | O | HOH | 869 | 134.478 | 8.308 | 29.219 | 1.00 | 53.23 |
| 5369 | O | HOH | 870 | 127.297 | 14.232 | 21.009 | 1.00 | 54.19 |
| 5370 | O | HOH | 871 | 134.315 | 17.294 | 22.547 | 1.00 | 59.58 |
| 5371 | O | HOH | 872 | 130.159 | 26.543 | 36.441 | 1.00 | 34.46 |
| 5372 | O | H0H | 873 | 136.207 | 18.694 | 43.344 | 1.00 | 35.20 |
| 5373 | O | HOH | 874 | 134.779 | 10.368 | 41.428 | 1.00 | 45.81 |
| 5374 | O | HOH | 875 | 137.054 | 3.899 | 33.453 | 1.00 | 51.47 |
| 5375 | O | HOH | 876 | 145.762 | 17.318 | 28.638 | 1.00 | 52.42 |
| 5376 | O | HOH | 877 | 146.344 | 20.944 | 29.342 | 1.00 | 47.62 |

TABLE 12

```
Score = 167 bits (419), Expect = 5e-41
Identities = 88/270 (32%), Positives = 152/270 (55%), Gaps = 5/270 (1%)
Query:     1 DRVVECYFWALGVYFEPQYSQARVMLVKTISMISIVDDTFDAYGTVKELEAYTDAIQRWD 60
             DR+VECYFW  G+    Q++ AR+M+ K  ++I+++DD +D YGT++ELE +TD I+RWD
Sbjct:   316 DRLVECYFWNTGIIEPRQHASARIMMGKVNALITVIDDIYDVYGTLEELEQFTDLIRRWD 375
```

TABLE 12-continued

```
Query:    61 INEIDRLPDYMKISYKAILDLYKDYEKELSSAGRSHIVCHAIERMKEVVRNYNVESTWFI 120
             IN ID+LPDYN++ + A+ +   D    +++ + +   ++  Y VE+ WF
Sbjct:   376 INSIDQLPDYMQLCFLALNNFVDDTSYDVMKEKGVNVIPYLRQSWVDLADKYMVEARWFY 435

Query:   121 EGYMPPVSEYLSNALATTTYYYLATTSYLGM-KSATEQDFEWLSKNPKILEASVIICRVI 179
             G+ P + EYL N+ + +    + T  + + S T++  + L K  ++ S  + R+
Sbjct:   436 GGHKPSLEEYLENSWQSISGPCMLTHIFFRVTDSFTKETVDSLYKYHDLVRWSSFVLRLA 495

Query:   180 DDTATYEVEKSRGQIATGIECCMRDYGISTKEAMAKFQNMAETAWKDIN-EGLLRPTPVS 238
             DD T   E SRG +    ++C M DY  S  EA    + +    WK +N E + + +P
Sbjct:   496 DDLGTSVEEVSRGDVPKSLQCYMSDYNASEAEARKHVKWLIAEVWKKMNAERVSKDSPFG 555

Query:   239 TEFLTPILNLARIVEVTYIHNLDGY--THP 266
             +F+   ++L R+ ++ Y HN DG+   HP
Sbjct:   556 KDFIGCAVDLGRMAQLMY-HNGDGHGTQHP 584
```

TABLE 13

```
Score =  116 bits (289), Expect = 1e-25
Identities = 77/270 (28%), Positives = 126/270 (46%), Gaps = 6/270 (2%)
Query:     3 VAEVYFSSATFEP-EYSATRIAFTKIGCLQVLFDDMADIFATLDELKSFTEGVKRWDTSL 61
             V    +++  FEP ++     R   I  L + DD+ D++ FT+   KRWDT
Sbjct:   318 VESFFWAVGMFEPHQHGYQRKMAATIIVLATVIDDIYDVYGTLDELELFTDTFKRWDTES 377

Query:    62 LNEIPECMQTCFKVWFKLMEEVNNDVVKVQGRDMLAHIRKPWELYFNCYVQEREWLEAGY 121
             + +P MQ C+   + + D++K  G  L ++RK      Y  E +W  +GY
Sbjct:   378 ITRLPYYMQLCYWGVHNYISDAAYDILKEHGFFCLQYLRKSVVDLVEAYFHEAKWYHSGY 437

Query:   122 IPTFEEYLKTYAISVGLGPCTLQPILLMGELVKDD--VVEKVHYPSNMFELVSLSWRLTN 179
             P+ +EYL   ISV  P  + P          D V++ ++  ++ L  + RL +
Sbjct:   438 TPSLDEYLNIAKISVA-SPAIISPTYFTFANASHDTAVIDSLYQYHDILCLAGIILRLPD 496

Query:   180 DTKTYQAEKARGQQASGIACYMKDNPGATEEDAIKHICRVVDRALKEASFEYFKPSNDIP 239
             D   T   E ARG    I  CYMK+  A+EE+A++H+  ++    A K+ +          P
Sbjct:   497 DLGTSYFELARGDVPKTIQCYMKET-NASEEEAVEHVKFLIREAWKDMN-TAIAAGYPFP 554

Query:   240 MGCKSFIFNLRLCVQIFYKFIDGYGIANEE 269
             G + N+    Q Y   DG+G+ + +
Sbjct:   555 DGMVAGAANIGRVAQFIYLHGDGFGVQHSK 584
```

TABLE 14

```
Score = 120 bits (299), Expect = 6e-27
Identities = 70/272 (25%), Positives = 137/272 (49%), Gaps = 3/272 (1%)
Query:     2 RVVECYFWALGVYFEPQYSQARVMLVKTISMISIVDDTFDAYGTVKELEAYTDAIQRWDI 61
             R VE Y W +    FEP++S++R+    KT  + +++DD +D + T+ E++    T+ ++RWD+
Sbjct:   296 RHVEYYSWVVMCIFEPEFSESRIAFAKTAILCTVLDDLYDTHATLHEIKIMTEGVRRWDL 355

Query:    62 NEIDRLPDYMKISYKAILDLYKDYEKELSSAGRSHIVCHAIERMKEVVRNYNVESTWFIE 121
             + D LPDY+KI+++ +     +    E+         +     + K  ++Y  E+ W
Sbjct:   356 SLTDDLPDYIKIAFQFFFNTVNELIVEIVKRQGRDMTTIVKDCWKRYTESYLQEAEWIAT 415

Query:   122 GYMPPVSEYLSNALATTTYYYLATTSYLGM-KSATEQDFEWLSKNPKILEASVIICRVID 180
             G++P +EY+ N +A++      L    L+K  + E+    KIL+  + R+ D
Sbjct:   416 GHIPTFNEYIKNGMASSGMCILNLNPLLLLDKLLPDNILEQIHSPSKILDLLELTGRIAD 475

Query:   181 DTATYEVEKSRGQIATGIECCMRDYGISTKE-AMAKFQNMAETAWKDINEGLLRPTPVST 239
             D   +E EK RG++A+ ++C M++  ST E A+   +  +  + + +  N   ++    V
Sbjct:   476 DLKDFEDEKERGEMASSLQCYMKENPESTVENALNHIKGILNRSLEEFNWEFMKQDSVPM 535

Query:   240 EFLTPILNLARIVEVTYIHNLDGYTHPEKVLK 271
                    N+ R  ++ Y +  DG    +K +K
Sbjct:   536 CCKKFTFNIGRGLQFIYKYR-DGLYISDKEVK 566
```

TABLE 15

```
Score = 221 bits (557), Expect = 4e-57
Identities = 120/263 (42%), Positives = 178/233 (62%), Gaps = 6/283 (2%)
Query:     5 EFYFWMAAAISEPEFSGSRVAFTKIAILMTMLDDLYDTHGTLQQLKIFTEGVRRWDVSLV 64
             E YF A+ I EPEFS  R  +TK +    +LDDLYD HG+LD LK FTE V+RWD+SLV
Sbjct:   589 EIYFSPASFIFEPEFSKCREVYTKTSNFTVILDDLYDAHGSLDDLKLFTESVKRWDLSLV 648

Query:    65 EGLPDFMKIAFEFWLKTSNELIAEAVKAQGQDMAAYIRKNAWERYLEAYLQDAEWIATGH 124
             + +P  MKI F +  T N++ E  + QG+D+  YI +N W+    LEAY ++AEW +
Sbjct:   649 DQMPQQMKICFVGFYNTFNDIAKEGRERQGRDVLGYI-QNVWKVQLEAYTKEAEWSEAKY 707

Query:   125 VPTFDEYLNNGTPNTGMCVLNLIPLLLMGEHLPIDILEQIFLPSRFHHLIELASRLVDDA 184
             VP+F+EY+ N + +  +  + + LI   L GE L  ++L +I   SRF  L+ L RLV+D
Sbjct:   708 VPSFNEYIENASVSIALGTVVLISALFTGEVLTDEVLSKIDRESRFQLMGLTGRLVNDT 767

Query:   185 RDFQAEKDHGDL-SCIECYLKDHPESTVEDALNHVNGLLGNCLLEMNWKFLKKQDSVPLS 243
             + +QAE+ G++ S I+CY+KDHP  +   E+AL HV  ++ N L E+N +F+   + +P
```

TABLE 15-continued

```
Sbjct:  768  KTYQAERGQGEVASAIQCYMKDHPKISEEEALQHVYSVMENALEELNREFV--NNKIPDI  825
Query:  244  CKKYSFHVLARSIQFMYNQGDGFSISNKV-IKDQVQKVLIVPV  285
             K+   F    AR +Q  Y QGDG ++S +  + IK+ V+   L  PV
Sbjct:  826  YKRLVFET-ARIMQLFYMQGDGLTLSHDMEIKEHVKNCLFQPV  867
```

---

We claim the following:

1. An isolated terpene synthase having a region with 20% or greater sequence identity to residues 265 to 535 of SEQ ID NO: 2, said synthase comprising nine α-carbons having interatomic distances in Angstroms between said α-carbons that are ±2.3 Angstroms of the following interatomic distances:

| α-Carbon | 1 | 2 | 3 | 4 | 5 | 6 | 7 | 8 | 9 |
|---|---|---|---|---|---|---|---|---|---|
| 1 | 0.0 | 8.4 | 13.7 | 12.7 | 11.9 | 10.2 | 13.1 | 9.4 | 12.8 |
| 2 | 8.4 | 0.0 | 11.3 | 8.7 | 10.2 | 7.2 | 14.8 | 15.1 | 17.4 |
| 3 | 13.7 | 11.3 | 0.0 | 3.8 | 5.4 | 9.3 | 6.6 | 13.9 | 13.7 |
| 4 | 12.7 | 8.7 | 3.8 | 0.0 | 3.8 | 6.0 | 9.2 | 15.4 | 16.1 |
| 5 | 11.9 | 10.2 | 5.4 | 3.8 | 0.0 | 5.0 | 7.8 | 14.6 | 15.5 |
| 6 | 10.2 | 7.2 | 9.3 | 6.0 | 5.0 | 0.0 | 12.0 | 16.1 | 18.0 |
| 7 | 13.1 | 14.8 | 6.6 | 9.2 | 7.8 | 12.0 | 0.0 | 10.2 | 9.5 |
| 8 | 9.4 | 15.1 | 13.9 | 15.4 | 14.6 | 16.1 | 10.2 | 0.0 | 3.8 |
| 9 | 12.8 | 17.4 | 13.7 | 16.1 | 15.5 | 18.0 | 9.5 | 3.8 | 0.0 | the center point of each said α-carbon positioned within a sphere having a radius of 2.3 Angstroms, the center points of each said sphere having the following structural coordinates:

| α-Carbon Number | X Position | Y Position | Z Position |
|---|---|---|---|
| 1 | 120.203 | 38.695 | 43.506 |
| 2 | 114.058 | 43.884 | 41.015 |
| 3 | 106.807 | 36.336 | 45.151 |
| 4 | 107.629 | 38.010 | 41.804 |
| 5 | 109.375 | 34.842 | 40.617 |
| 6 | 111.944 | 37.854 | 37.602 |
| 7 | 110.233 | 31.098 | 47.361 |

-continued

| α-Carbon Number | X Position | Y Position | Z Position |
|---|---|---|---|
| 8 | 118.846 | 34.443 | 51.796 |
| 9 | 116.461 | 32.848 | 54.290 | each said α-carbon having an associated R-group, said synthase having an ordered arrangement of said R-groups other than the following ordered arrangements of R-groups:

TABLE 9

| | Ordered Arrangements of α-Carbons 1–9 | | | | | | | | |
|---|---|---|---|---|---|---|---|---|---|
| | 1 | 2 | 3 | 4 | 5 | 6 | 7 | 8 | 9 |
| A | W | I | T | T | Y | L | C | T | Y |
| B | W | I | S | T | Y | L | C | T | Y |
| C | W | I | C | G | Y | L | C | L | Y |
| D | W | I | S | G | Y | L | C | L | Y |
| E | W | L | A | G | Y | I | A | L | Y |
| F | W | L | T | V | H | L | G | V | Y |
| G | W | L | A | G | Y | I | A | L | Y |
| H | W | I | V | G | N | L | F | L | Y |
| I | W | I | T | A | G | L | S | C | Y |
| J | W | V | S | C | I | M | G | S | Y |
| K | F | F | I | T | A | T | G | T | Y |
| L | W | N | I | S | G | M | L | M | Y |
| M | W | V | S | S | Y | L | G | L | Y |
| N | F | F | T | L | A | L | G | S | Y |
| O | W | N | S | G | P | L | L | M | Y |
| P | W | N | G | G | I | L | L | I | Y |
| Q | Y | L | V | T | M | T | G | T | Y |
| R | W | I | I | S | A | I | L | I | Y |
| S | W | F | S | S | V | I | L | I | Y |
| T | W | I | V | A | S | I | L | I | Y |
| U | W | N | I | S | S | I | F | M | Y |
| V | L | A | I | G | Q | L | S | I | F |
| W | S | S | I | A | L | V | G | F | Y |
| X | L | C | C | G | H | S | L | G | Y |

TABLE 9-continued

Ordered Arrangements of α-Carbons 1–9

|    | 1 | 2 | 3 | 4 | 5 | 6 | 7 | 8 | 9 |
|----|---|---|---|---|---|---|---|---|---|
| Y  | S | F | S | S | V | I | L | V | Y |
| Z  | W | A | S | G | M | L | G | I | Y |
| AA | A | N | L | T | S | T | C | L | Y |
| BB | L | C | S | A | Y | V | L | L | Y |
| CC | W | A | T | G | M | L | S | M | Y |
| DD | M | C | S | S | G | I | L | V | Y |
| EE | S | G | V | G | L | C | W | F | Y |
| FF | S | G | A | L | G | V | G | F | Y |
| GG | S | G | F | A | L | I | G | F | Y |
| HH | A | G | F | A | L | I | G | F | Y |
| II | W | V | T | G | L | V | I | S | Y |
| JJ | W | A | S | G | M | L | G | I | Y |
| KK | W | I | S | T | Y | L | C | T | Y |
| LL | W | I | T | T | Y | L | C | T | Y |
| MM | W | N | I | S | G | M | L | M | Y |
| NN | A | A | I | G | Q | L | S | I | F |
| OO | A | I | V | A | S | I | L | I | Y |

2. The synthase of claim 1, wherein said synthase has 25% or greater sequence identity to residues 265 to 535 of SEC ID 2.

3. The synthase cf claim 2, wherein said synthase has 35% or greater sequence identity to residues 265 to 535 of SEQ ID 2.

4. The synthase of claim 1, wherein said synthase catalyses the formation of a terpenoid product from a monoterpene substrate.

5. The synthase of claim 1, wherein said synthase catalyses the formation of a terpenoid product from a sesquiterpene substrate.

6. The synthase of claim 1, wherein said synthase catalyses the formation of a terpenoid product from a diterpene substrate.

7. The synthase of claim 4, wherein said product is a cyclic terpenoid hydrocarbon.

8. The synthase of claim 4, wherein said product is an acyclic terpenoid hydrocarbon.

9. The synthase of claim 4, wherein said product is a cyclic hydroxylated terpenoid hydrocarbon.

10. The synthase of claim 4, wherein said product is an acyclic hydroxylated terpenoid hydrocarbon.

11. The synthase of claim 1, wherein said R-group associated with said α-carbon 1 is selected from the group consisting of Cys, Ser, and Thr.

12. The synthase of claim 1, wherein said R-group associated with said α-carbon 1 is selected from the group consisting of Phe, Tyr and Trp.

13. The synthase of claim 1, wherein said R-group associated with said α-carbon 1 is selected from the group consisting of Pro, Gly, and Ala.

14. The synthase of claim 1, Wherein said R-group associated with said α-carbon 1 is selected from the group consisting of Glu and Asp.

15. The synthase of claim 1, wherein said R-group associated with said α-carbon 1 is selected from the group consisting of Met, Ile, Val and Leu.

16. The synthase of claim 1, wherein said R-group associated with said α-carbon 1 is selected from the group consisting of Arg and Lys.

17. The synthase of claim 1, wherein said R-group associated with said α-carbon 1 is selected from the group consisting of Gln, Asn and His.

18. The synthase of claim 1, wherein said R-group associated with said α-carbon 2 is selected from the group consisting of Cys, Ser and Thr.

19. The synthase of claim 1, wherein said R-group associated with said α-carbon 2 is selected from the group consisting of Phe, Tyr and Trp.

20. The synthase of claim 1, wherein said R-group associated with said α-carbon 2 is selected from the group consisting of Pro, Gly, and Ala.

21. The synthase of claim 1, wherein said R-group associated with said α-carbon 2 is selected from the group consisting of Glu and Asp.

22. The synthase of claim 1, wherein said R-group associated with said α-carbon 2 is selected from the group consisting of Met, Ile, Val and Leu.

23. The synthase of claim 1, wherein said R-group associated with said α-carbon 2 is selected from the group consisting of Arg and Lys.

24. The synthase of claim 1, wherein said R-group associated with said α-carbon 2 is selected from the group consisting of Gln, Asn and His.

25. The synthase of claim 1, wherein said R-group associated with said α-carbon 3 is selected from the group consisting of Cys, Ser and Thr.

26. The synthase of claim 1, wherein said R-group associated with said α-carbon 3 is selected from the group consisting of Phe, Tyr and Trp.

27. The synthase of claim 1, wherein said R-group associated with said α-carbon 3 is selected from the group consisting of Pro, Gly, and Ala.

28. The synthase of claim 1, wherein said R-group associated with said α-carbon 3 is selected from the group consisting of Glu and Asp.

29. The synthase of claim 1, wherein said R-group associated with said α-carbon 3 is selected from the group consisting of Met, Ile, Val and Leu.

30. The synthase of claim 1, wherein said R-group associated with said α-carbon 3 is selected from the group consisting of Arg and Lys.

31. The synthase of claim 1, wherein said R-group associated with said α-carbon 3 is selected from the group consisting of Gln, Asn and His.

32. The synthase of claim 1, wherein said R-group associated with said α-carbon 4 is selected from the group consisting of Cys, Ser and Thr.

33. The synthase of claim 1, wherein said R-group associated with said α-carbon 4 is selected from the group consisting of Phe, Tyr and Trp.

34. The synthase of claim 1, wherein said R-group associated with said α-carbon 4 is selected from the group consisting of Pro, Gly, and Ala.

35. The synthase of claim 1, wherein said R-group associated with said α-carbon 4 is selected from the group consisting of Glu and Asp.

36. The synthase of claim 1, wherein said R-group associated with said α-carbon 4 is selected from the group consisting of Met, Ile, Val and Leu.

37. The synthase of claim 1, wherein said R-group associated with said α-carbon 4 is selected from the group consisting of Arg and Lys.

38. The synthase of claim 1, wherein said R-group associated with said α-carbon 4 is selected from the group consisting of Gln, Asn and His.

39. The synthase of claim 1, wherein said R-group associated with said α-carbon 5 is selected from the group consisting of Cys, Ser and Thr.

40. The synthase of claim 1, wherein said R-group associated with said α-carbon 5 is selected from the group consisting of Phe, Tyr and Trp.

41. The synthase of claim 1, wherein said R-group associated with said α-carbon 5 is selected from the group consisting of Pro, Gly, and Ala.

42. The synthase of claim 1, wherein said R-group associated with said α-carbon 5 is selected from the group consisting of Glu and Asp.

43. The synthase of claim 1, wherein said R-group associated with said α-carbon 5 is selected from the group consisting of Met, Ile, Val and Leu.

44. The synthase of claim 1, wherein said R-group associated with said α-carbon 5 is selected from the group consisting of Arg and Lys.

45. The synthase of claim 1, wherein said R-group associated with said α-carbon 5 is selected from the group consisting of Gln, Asn and His.

46. The synthase of claim 1, wherein said R-group associated with said α-carbon 6 is selected from the group consisting of Cys, Ser and Thr.

47. The synthase of claim 1, wherein said R-group associated with said α-carbon 6 is selected from the group consisting of Phe, Tyr and Trp.

48. The synthase of claim 1, wherein said R-group associated with said α-carbon 6 is selected from the group consisting of Pro, Gly, and Ala.

49. The synthase of claim 1, wherein said R-group associated with said α-carbon 6 is selected from the group consisting of Glu and Asp.

50. The synthase of claim 1, wherein said R-group associated with said α-carbon 6 is selected from the group consisting of Met, Ile, Val and Leu.

51. The synthase of claim 1, wherein said R-group associated with said α-carbon 6 is selected from the group consisting of Arg and Lys.

52. The synthase of claim 1, wherein said R-group associated with said α-carbon 6 is selected from the group consisting of Gln, Asn and His.

53. The synthase of claim 1, wherein said R-group associated with said α-carbon 7 is selected from the group consisting of Cys, Ser and Thr.

54. The synthase of claim 1, wherein said R-group associated with said α-carbon 7 is selected from the group consisting of Phe, Tyr and Trp.

55. The synthase of claim 1, wherein said R-group associated with said α-carbon 7 is selected from the group consisting of Pro, Gly, and Ala.

56. The synthase of claim 1, wherein said R-group associated with said α-carbon 7 is selected from the group consisting of Glu and Asp.

57. The synthase of claim 1, wherein said R-group associated with said α-carbon 7 is selected from the group consisting of Met, Ile, Val and Leu.

58. The synthase of claim 1, wherein said R-group associated with said α-carbon 7 is selected from the group consisting of Arg and Lys.

59. The synthase of claim 1, wherein said R-group associated with said α-carbon 7 is selected from the group consisting of Gln, Asn and His.

60. The synthase of claim 1, wherein said R-group associated with said α-carbon 8 is selected from the group consisting of Cys, Ser and Thr.

61. The synthase ot claim 1, wherein said R-group associated with said α-carbon 8 is selected from the group consisting of Phe, Tyr and Trp.

62. The synthase of claim 1, wherein said R-group associated with said α-carbon 8 is selected from the group consisting of Pro, Gly, and Ala.

63. The synthase of claim 1, wherein said R-group associated with said α-carbon 8 is selected from the group consisting of Glu and Asp.

64. The synthase of claim 1, wherein said R-group associated with said α-carbon 8 is selected from the group consisting of Met, Ile, Val and Leu.

65. The synthase of claim 1, wherein said R-group associated with said α-carbon 8 is selected from the group consisting of Arg and Lys.

66. The synthase of claim 1, wherein said R-group associated with said α-carbon 8 is selected from the group consisting of Gln, Asn and His.

67. The synthase of claim 1, wherein said R-group associated with said α-carbon 9 is selected from the group consisting of Cys, Ser and Thr.

68. The synthase of claim 1, wherein said R-group associated with said α-carbon 9 is selected from the group consisting of Phe, Tyr and Trp.

69. The synthase of claim 1, wherein said R-group associated with said α-carbon 9 is selected from the group consisting of Pro, Gly, and Ala.

70. The synthase of claim 1, wherein said R-group associated with said α-carbon 9 is selected from the group consisting of Glu and Asp.

71. The synthase of claim 1, wherein said R-group associated with said α-carbon 9 is selected from the group consisting of Met, Ile, Val and Leu.

72. The synthase of claim 1, wherein said R-group associated with said α-carbon 9 is selected from the group consisting of Arg and Lys.

73. The synthase of claim 1, wherein said R-group associated with said α-carbon 9 is selected from the group consisting of Gln, Asn and His.

74. The synthase of claim 1, wherein said ordered arrangement of R-groups in said synthase associated with said α-carbons 1 to 9 is Trp, Ile, Thr, Thr, Tyr, Leu, Cys, Thr and Phe, respectively.

75. The synthase of claim 1, wherein said ordered arrangement of R-groups in said synthase associated with said carbons 1 to 9 is Ser, Ile, Thr, Thr, Tyr, Leu, Cys, Thr and Tyr, respectively.

76. The synthase of claim 1, wherein said ordered arrangement of R-groups in said synthase associated with said α-carbons 1 to 9 is Trp, Ile, Thr, Thr, Tyr, Leu, Trp, Thr and Tyr, respectively.

77. The synthase of claim 1, wherein said ordered arrangement of R-groups in said synthase associated with said α-carbons 1 to 9 is Ser, Ile, Thr, Thr, Tyr, Leu, Trp, Thr and Tyr, respectively.

78. The synthase of claim 1, wherein said ordered arrangement of R-groups in said synthase associated with said α-carbons 1 to 9 is Glu, Ile, Thr, Thr, Tyr, Leu, Cys, Thr and Tyr, respectively.

79. The synthase of claim 5, wherein said product is a cyclic terpenoid hydrocarbon.

80. The synthase of claim 5, wherein said product is an acyclic terpenoid hydrocarbon.

81. The synthase of claim 5, wherein said product is a cyclic hydroxylated terpenoid hydrocarbon.

82. The synthase of claim 5, wherein said product is an acyclic hydroxylated terpenoid hydrocarbon.

83. The synthase of claim 5, wherein said product is a cyclic terpenoid hydrocarbon.

84. The synthase of claim 5, wherein said product is an acyclic terpenoid hydrocarbon.

85. The synthase of claim 5, wherein said product is a cyclic hydroxylated terpenoid hydrocarbon.

86. The synthase of claim 5, wherein said product is an acyclic hydroxylated terpenoid hydrocarbon.

* * * * *

UNITED STATES PATENT AND TRADEMARK OFFICE
CERTIFICATE OF CORRECTION

PATENT NO. : 6,495,354 B2
APPLICATION NO. : 09/887586
DATED : December 17, 2002
INVENTOR(S) : Chappell et al.

Page 1 of 2

It is certified that error appears in the above-identified patent and that said Letters Patent is hereby corrected as shown below:

IN THE CLAIMS: should read

Column 363, line 22 to line 24
2. The synthase of claim 1, wherein said synthase has 25% or greater sequence identity to residues 265 to 535 of SEQ ID 2.

Column 363, line 25 to line 27
3. The synthase of claim 2, wherein said synthase has 35% or greater sequence identity to residues 265 to 535 of SEQ ID 2.

Column 363, line 53 to line 55
14. The synthase of claim 1, wherein said R-group associated with said α-carbon 1 is selected from the group consisting of Glu and Asp.

Column 366, line 33 to line 36
75. The synthase of claim 1, wherein said ordered arrangement of R-groups in said synthase associated with said α-carbons 1 to 9 is Ser, Ile, Thr, Thr, Tyr, Leu, Cys, Thr and Tyr, respectively.

Column 366, line 58 to line 59
83. The synthase of claim 6, wherein said product is a cyclic terpenoid hydrocarbon.

Column 366, line 60 to line 61
84. The synthase of claim 6, wherein said product is an acyclic terpenoid hydrocarbon.

Column 366, line 62 to line 63
85. The synthase of claim 6, wherein said product is a cyclic hydroxylated terpenoid hydrocarbon.

Signed and Sealed this
Fifth Day of April, 2011

David J. Kappos
*Director of the United States Patent and Trademark Office*

Column 366, line 64 to line 65

86. The synthase of claim 6, wherein said product is an acyclic hydroxylated terpenoid hydrocarbon.

SEQUENCE LISTING

<160> NUMBER OF SEQ ID NOS: 58

<210> SEQ ID NO 1
<211> LENGTH: 1671
<212> TYPE: DNA
<213> ORGANISM: Nicotiana tabacum
<220> FEATURE:
<221> NAME/KEY: CDS
<222> LOCATION: (25)...(1668)

<400> SEQUENCE: 1

| | | |
|---|---|---|
| atggtccatc atcatcatca tcat atg gcc tca gca gca gtt gca aac tat<br>                                      Met Ala Ser Ala Ala Val Ala Asn Tyr<br>                                         1                5 | | 51 |

```
gaa gaa gag att gtt cgc ccc gtc gcc gac ttc tcc cct agt ttg tgg      99
Glu Glu Glu Ile Val Arg Pro Val Ala Asp Phe Ser Pro Ser Leu Trp
 10              15                  20                  25 ggt gat cag ttc ctt tca ttc tcc att aaa aat cag gtt gca gaa aag     147
Gly Asp Gln Phe Leu Ser Phe Ser Ile Lys Asn Gln Val Ala Glu Lys
                 30                  35                  40 tat gct caa gag att gaa gca ttg aag gaa caa acg agg aat atg ctg     195
Tyr Ala Gln Glu Ile Glu Ala Leu Lys Glu Gln Thr Arg Asn Met Leu
             45                  50                  55 tta gca act gga atg aaa ttg gct gat aca ctg aat ttg ata gac act     243
Leu Ala Thr Gly Met Lys Leu Ala Asp Thr Leu Asn Leu Ile Asp Thr
         60                  65                  70 att gaa cgc ctt ggc ata tcc tac cac ttt gag aaa gaa att gat gat     291
Ile Glu Arg Leu Gly Ile Ser Tyr His Phe Glu Lys Glu Ile Asp Asp
     75                  80                  85 att ttg gat cag att tac aac caa aac tca aac tgc aac gat ttg tgc     339
Ile Leu Asp Gln Ile Tyr Asn Gln Asn Ser Asn Cys Asn Asp Leu Cys
 90                  95                 100                 105 act tct gca ctt caa ttt cga ttg ctc agg caa cat ggt ttc aac atc     387
Thr Ser Ala Leu Gln Phe Arg Leu Leu Arg Gln His Gly Phe Asn Ile
                110                 115                 120 tct cct gaa att ttc agc aaa ttc caa gac gaa aat ggc aaa ttc aag     435
Ser Pro Glu Ile Phe Ser Lys Phe Gln Asp Glu Asn Gly Lys Phe Lys
            125                 130                 135 gaa tct ctt gct agt gat gtc tta gga tta ttg aac ttg tat gaa gct     483
Glu Ser Leu Ala Ser Asp Val Leu Gly Leu Leu Asn Leu Tyr Glu Ala
        140                 145                 150 tca cat gta agg act cat gct gac gat atc tta gaa gac gca ctt gct     531
Ser His Val Arg Thr His Ala Asp Asp Ile Leu Glu Asp Ala Leu Ala
    155                 160                 165 ttc tcc act atc cat ctt gaa tct gca gct cca cat ttg aaa tct cca     579
Phe Ser Thr Ile His Leu Glu Ser Ala Ala Pro His Leu Lys Ser Pro
170                 175                 180                 185 ctt agg gag caa gtg aca cat gcc ctt gag caa tgt ttg cac aag ggt     627
Leu Arg Glu Gln Val Thr His Ala Leu Glu Gln Cys Leu His Lys Gly
                190                 195                 200 gtt cct aga gtc gag acc cga ttc ttc atc tca tca atc tat gac aag     675
Val Pro Arg Val Glu Thr Arg Phe Phe Ile Ser Ser Ile Tyr Asp Lys
```

-continued

```
                  205                 210                 215
gaa caa tcg aag aat aat gtg tta ctt cga ttt gcc aaa ttg gat ttc      723
Glu Gln Ser Lys Asn Asn Val Leu Leu Arg Phe Ala Lys Leu Asp Phe
            220                 225                 230 aac ttg ctc cag atg ttg cac aaa caa gaa ctt gct caa gta tca agg      771
Asn Leu Leu Gln Met Leu His Lys Gln Glu Leu Ala Gln Val Ser Arg
        235                 240                 245 tgg tgg aaa gat ttg gat ttt gta aca aca ctt cca tat gct aga gat      819
Trp Trp Lys Asp Leu Asp Phe Val Thr Thr Leu Pro Tyr Ala Arg Asp
250                 255                 260                 265 cga gta gtt gaa tgc tac ttt tgg gca tta gga gtt tat ttt gag cct      867
Arg Val Val Glu Cys Tyr Phe Trp Ala Leu Gly Val Tyr Phe Glu Pro
                270                 275                 280 caa tac tct caa gct cgc gtc atg ctc gtt aag acc ata tca atg att      915
Gln Tyr Ser Gln Ala Arg Val Met Leu Val Lys Thr Ile Ser Met Ile
            285                 290                 295 tcg att gtc gat gac acc ttt gat gct tac ggt aca gtt aaa gaa ctt      963
Ser Ile Val Asp Asp Thr Phe Asp Ala Tyr Gly Thr Val Lys Glu Leu
        300                 305                 310 gag gca tac aca gat gcc ata caa aga tgg gat atc aac gaa att gat     1011
Glu Ala Tyr Thr Asp Ala Ile Gln Arg Trp Asp Ile Asn Glu Ile Asp
315                 320                 325 cgg ctt cct gat tac atg aaa atc agt tac aaa gct att cta gat ctc     1059
Arg Leu Pro Asp Tyr Met Lys Ile Ser Tyr Lys Ala Ile Leu Asp Leu
330                 335                 340                 345 tac aag gat tat gaa aag gaa ttg tct agt gcc gga aga tct cat att     1107
Tyr Lys Asp Tyr Glu Lys Glu Leu Ser Ser Ala Gly Arg Ser His Ile
                350                 355                 360 gtc tgc cat gca ata gaa aga atg aaa gaa gta gta aga aat tat aat     1155
Val Cys His Ala Ile Glu Arg Met Lys Glu Val Val Arg Asn Tyr Asn
            365                 370                 375 gtc gag tca aca tgg ttt att gaa gga tat acg cca cct gtt tct gaa     1203
Val Glu Ser Thr Trp Phe Ile Glu Gly Tyr Thr Pro Pro Val Ser Glu
        380                 385                 390 tac cta agc aat gca cta gca act acc aca tat tac tac ctc gcg aca     1251
Tyr Leu Ser Asn Ala Leu Ala Thr Thr Thr Tyr Tyr Tyr Leu Ala Thr
    395                 400                 405 aca tcg tat ttg ggc atg aag tct gcc acg gag caa gat ttt gag tgg     1299
Thr Ser Tyr Leu Gly Met Lys Ser Ala Thr Glu Gln Asp Phe Glu Trp
410                 415                 420                 425 ttg tca aag aat cca aaa att ctt gaa gct agt gta att ata tgt cga     1347
Leu Ser Lys Asn Pro Lys Ile Leu Glu Ala Ser Val Ile Ile Cys Arg
                430                 435                 440 gtt atc gat gac aca gcc acg tac gag gtt gag aaa agc agg gga caa     1395
Val Ile Asp Asp Thr Ala Thr Tyr Glu Val Glu Lys Ser Arg Gly Gln
            445                 450                 455 att gca act gga att gag tgc tgc atg aga gat tat ggt ata tca aca     1443
Ile Ala Thr Gly Ile Glu Cys Cys Met Arg Asp Tyr Gly Ile Ser Thr
        460                 465                 470 aaa gag gca atg gct aaa ttt caa aat atg gct gag aca gca tgg aaa     1491
Lys Glu Ala Met Ala Lys Phe Gln Asn Met Ala Glu Thr Ala Trp Lys
    475                 480                 485 gat att aat gaa gga ctt ctt agg ccc act ccc gtc tct aca gaa ttt     1539
Asp Ile Asn Glu Gly Leu Leu Arg Pro Thr Pro Val Ser Thr Glu Phe
490                 495                 500                 505 tta act cct att ctc aat ctt gct cgt att gtt gag gtt aca tat ata     1587
Leu Thr Pro Ile Leu Asn Leu Ala Arg Ile Val Glu Val Thr Tyr Ile
                510                 515                 520 cac aat cta gat gga tac act cat ccg gag aaa gtc tta aaa cct cac     1635
His Asn Leu Asp Gly Tyr Thr His Pro Glu Lys Val Leu Lys Pro His
```

```
                525              530              535
att att aac cta ctt gtg gac tcc atc aaa att tga                    1671
Ile Ile Asn Leu Leu Val Asp Ser Ile Lys Ile
        540              545
```

<210> SEQ ID NO 2
<211> LENGTH: 548
<212> TYPE: PRT
<213> ORGANISM: Nicotiana tabacum

<400> SEQUENCE: 2

```
Met Ala Ser Ala Ala Val Ala Asn Tyr Glu Glu Ile Val Arg Pro
 1               5                  10                  15

Val Ala Asp Phe Ser Pro Ser Leu Trp Gly Asp Gln Phe Leu Ser Phe
                20                  25                  30

Ser Ile Lys Asn Gln Val Ala Glu Lys Tyr Ala Gln Glu Ile Glu Ala
            35                  40                  45

Leu Lys Glu Gln Thr Arg Asn Met Leu Leu Ala Thr Gly Met Lys Leu
    50                  55                  60

Ala Asp Thr Leu Asn Leu Ile Asp Thr Ile Glu Arg Leu Gly Ile Ser
65                  70                  75                  80

Tyr His Phe Glu Lys Glu Ile Asp Asp Ile Leu Asp Gln Ile Tyr Asn
                85                  90                  95

Gln Asn Ser Asn Cys Asn Asp Leu Cys Thr Ser Ala Leu Gln Phe Arg
            100                 105                 110

Leu Leu Arg Gln His Gly Phe Asn Ile Ser Pro Glu Ile Phe Ser Lys
        115                 120                 125

Phe Gln Asp Glu Asn Gly Lys Phe Lys Glu Ser Leu Ala Ser Asp Val
    130                 135                 140

Leu Gly Leu Leu Asn Leu Tyr Glu Ala Ser His Val Arg Thr His Ala
145                 150                 155                 160

Asp Asp Ile Leu Glu Asp Ala Leu Ala Phe Ser Thr Ile His Leu Glu
                165                 170                 175

Ser Ala Ala Pro His Leu Lys Ser Pro Leu Arg Glu Gln Val Thr His
            180                 185                 190

Ala Leu Glu Gln Cys Leu His Lys Gly Val Pro Arg Val Glu Thr Arg
        195                 200                 205

Phe Phe Ile Ser Ser Ile Tyr Asp Lys Glu Gln Ser Lys Asn Asn Val
    210                 215                 220

Leu Leu Arg Phe Ala Lys Leu Asp Phe Asn Leu Leu Gln Met Leu His
225                 230                 235                 240

Lys Gln Glu Leu Ala Gln Val Ser Arg Trp Trp Lys Asp Leu Asp Phe
                245                 250                 255

Val Thr Thr Leu Pro Tyr Ala Arg Asp Arg Val Val Glu Cys Tyr Phe
            260                 265                 270

Trp Ala Leu Gly Val Tyr Phe Glu Pro Gln Tyr Ser Gln Ala Arg Val
        275                 280                 285

Met Leu Val Lys Thr Ile Ser Met Ile Ser Ile Val Asp Asp Thr Phe
    290                 295                 300

Asp Ala Tyr Gly Thr Val Lys Glu Leu Glu Ala Tyr Thr Asp Ala Ile
305                 310                 315                 320

Gln Arg Trp Asp Ile Asn Glu Ile Asp Arg Leu Pro Asp Tyr Met Lys
                325                 330                 335

Ile Ser Tyr Lys Ala Ile Leu Asp Leu Tyr Lys Asp Tyr Glu Lys Glu
            340                 345                 350
```

```
Leu Ser Ser Ala Gly Arg Ser His Ile Val Cys His Ala Ile Glu Arg
            355                 360                 365
Met Lys Glu Val Val Arg Asn Tyr Asn Val Glu Ser Thr Trp Phe Ile
    370                 375                 380
Glu Gly Tyr Thr Pro Pro Val Ser Glu Tyr Leu Ser Asn Ala Leu Ala
385                 390                 395                 400
Thr Thr Thr Tyr Tyr Tyr Leu Ala Thr Thr Ser Tyr Leu Gly Met Lys
                405                 410                 415
Ser Ala Thr Glu Gln Asp Phe Glu Trp Leu Ser Lys Asn Pro Lys Ile
            420                 425                 430
Leu Glu Ala Ser Val Ile Ile Cys Arg Val Ile Asp Asp Thr Ala Thr
            435                 440                 445
Tyr Glu Val Glu Lys Ser Arg Gly Gln Ile Ala Thr Gly Ile Glu Cys
    450                 455                 460
Cys Met Arg Asp Tyr Gly Ile Ser Thr Lys Glu Ala Met Ala Lys Phe
465                 470                 475                 480
Gln Asn Met Ala Glu Thr Ala Trp Lys Asp Ile Asn Glu Gly Leu Leu
                485                 490                 495
Arg Pro Thr Pro Val Ser Thr Glu Phe Leu Thr Pro Ile Leu Asn Leu
            500                 505                 510
Ala Arg Ile Val Glu Val Thr Tyr Ile His Asn Leu Asp Gly Tyr Thr
            515                 520                 525
His Pro Glu Lys Val Leu Lys Pro His Ile Ile Asn Leu Leu Val Asp
    530                 535                 540
Ser Ile Lys Ile
545

<210> SEQ ID NO 3
<211> LENGTH: 1644
<212> TYPE: DNA
<213> ORGANISM: Nicotiana tabacum
<220> FEATURE:
<221> NAME/KEY: CDS
<222> LOCATION: (1)...(1644)

<400> SEQUENCE: 3 atg gcc tca gca gca gtt gca aac tat gaa gaa gag att gtt cgc ccc      48
Met Ala Ser Ala Ala Val Ala Asn Tyr Glu Glu Glu Ile Val Arg Pro
1               5                   10                  15 gtc gcc gac ttc tcc cct agt ctc tgg ggt gat cag ttc ctt tca ttc      96
Val Ala Asp Phe Ser Pro Ser Leu Trp Gly Asp Gln Phe Leu Ser Phe
            20                  25                  30 tcc att gat aat cag gtt gcg gaa aag tat gct caa gag att gaa gca     144
Ser Ile Asp Asn Gln Val Ala Glu Lys Tyr Ala Gln Glu Ile Glu Ala
        35                  40                  45 ttg aag gaa caa acg agg agt atg ctg tta gca acc gga agg aaa ttg     192
Leu Lys Glu Gln Thr Arg Ser Met Leu Leu Ala Thr Gly Arg Lys Leu
    50                  55                  60 gcc gat aca ttg aat ttg att gac att att gaa cgc ctt ggt ata tcc     240
Ala Asp Thr Leu Asn Leu Ile Asp Ile Ile Glu Arg Leu Gly Ile Ser
65                  70                  75                  80 tac cac ttt gag aaa gaa att gat gag att ttg gat cag att tac aac     288
Tyr His Phe Glu Lys Glu Ile Asp Glu Ile Leu Asp Gln Ile Tyr Asn
                85                  90                  95 caa aac tca aac tgc aat gat ttg tgc acc tct gca ctt caa ttt cga     336
Gln Asn Ser Asn Cys Asn Asp Leu Cys Thr Ser Ala Leu Gln Phe Arg
            100                 105                 110
```

```
ttg ctc agg caa cac ggt ttc aac atc tct cct gaa att ttc agc aaa      384
Leu Leu Arg Gln His Gly Phe Asn Ile Ser Pro Glu Ile Phe Ser Lys
        115                 120                 125 ttc caa gat gaa aat ggc aaa ttc aag gag tct ctt gct agt gat gtc      432
Phe Gln Asp Glu Asn Gly Lys Phe Lys Glu Ser Leu Ala Ser Asp Val
    130                 135                 140 tta gga tta tta aac ttg tat gaa gct tca cat gta agg act cat gct      480
Leu Gly Leu Leu Asn Leu Tyr Glu Ala Ser His Val Arg Thr His Ala
145                 150                 155                 160 gac gat atc tta gaa gac gca ctt gct ttc tcc act atc cat ctt gaa      528
Asp Asp Ile Leu Glu Asp Ala Leu Ala Phe Ser Thr Ile His Leu Glu
                165                 170                 175 tct gca gct cca cat ttg aaa tct cca ctt agg gag caa gtg aca cat      576
Ser Ala Ala Pro His Leu Lys Ser Pro Leu Arg Glu Gln Val Thr His
            180                 185                 190 gcc ctt gag caa tgt ttg cac aag ggt gtt cct aga gtc gag acc cga      624
Ala Leu Glu Gln Cys Leu His Lys Gly Val Pro Arg Val Glu Thr Arg
        195                 200                 205 ttc ttc atc tca tca atc tat gac aag gaa caa tcg aag aat aat gtg      672
Phe Phe Ile Ser Ser Ile Tyr Asp Lys Glu Gln Ser Lys Asn Asn Val
    210                 215                 220 tta ctt cga ttt gcc aaa ttg gat ttc aac ttg ctc cag atg ttg cac      720
Leu Leu Arg Phe Ala Lys Leu Asp Phe Asn Leu Leu Gln Met Leu His
225                 230                 235                 240 aaa caa gaa ctt gct caa gta tca agg tgg tgg aaa gat ttg gat ttt      768
Lys Gln Glu Leu Ala Gln Val Ser Arg Trp Trp Lys Asp Leu Asp Phe
                245                 250                 255 gta aca aca ctt cca tat gct aga gat cga gta gtt gaa tgc tac ttt      816
Val Thr Thr Leu Pro Tyr Ala Arg Asp Arg Val Val Glu Cys Tyr Phe
            260                 265                 270 gag gca tta gga gtt tat ttt gag cct caa tac tct caa gct cgc gtc      864
Glu Ala Leu Gly Val Tyr Phe Glu Pro Gln Tyr Ser Gln Ala Arg Val
        275                 280                 285 atg ctc gtt aag acc ata tca atg att tcg att gtc gat gac acc ttt      912
Met Leu Val Lys Thr Ile Ser Met Ile Ser Ile Val Asp Asp Thr Phe
    290                 295                 300 gat gct tac ggt aca gtt aaa gaa ctt gag gca tac aca gat gcc ata      960
Asp Ala Tyr Gly Thr Val Lys Glu Leu Glu Ala Tyr Thr Asp Ala Ile
305                 310                 315                 320 caa aga tgg gat atc aac gaa att gat cgg ctt cct gat tac atg aaa     1008
Gln Arg Trp Asp Ile Asn Glu Ile Asp Arg Leu Pro Asp Tyr Met Lys
                325                 330                 335 atc agt tat aaa gct att cta gat ctc tac aag gat tat gaa aag gaa     1056
Ile Ser Tyr Lys Ala Ile Leu Asp Leu Tyr Lys Asp Tyr Glu Lys Glu
            340                 345                 350 ttg tct agt gcc gga aga tct cat att gtc tgc cat gca ata gaa aga     1104
Leu Ser Ser Ala Gly Arg Ser His Ile Val Cys His Ala Ile Glu Arg
        355                 360                 365 atg aaa gaa gta gta aga aat tat aat gtc gag tca aca tgg ttt att     1152
Met Lys Glu Val Val Arg Asn Tyr Asn Val Glu Ser Thr Trp Phe Ile
    370                 375                 380 gaa gga tat atg cca cct gtt tct gaa tac cta agc aat gca cta gca     1200
Glu Gly Tyr Met Pro Pro Val Ser Glu Tyr Leu Ser Asn Ala Leu Ala
385                 390                 395                 400 act acc aca tat tac tac ctc gcg aca aca tcg tat ttg ggc atg aag     1248
Thr Thr Thr Tyr Tyr Tyr Leu Ala Thr Thr Ser Tyr Leu Gly Met Lys
                405                 410                 415 tct gcc acg gag caa gat ttt gag tgg ttg tca aag aat cca aaa att     1296
Ser Ala Thr Glu Gln Asp Phe Glu Trp Leu Ser Lys Asn Pro Lys Ile
            420                 425                 430
```

```
ctt gaa gct agt gta att ata tgt cga gtt atc gat gac aca gcc acg    1344
Leu Glu Ala Ser Val Ile Ile Cys Arg Val Ile Asp Asp Thr Ala Thr
            435                 440                 445 tac gag gtt gag aaa agc agg gga caa att gca act gga att gag tgc    1392
Tyr Glu Val Glu Lys Ser Arg Gly Gln Ile Ala Thr Gly Ile Glu Cys
        450                 455                 460 tgc atg aga gat tat ggt ata tca aca aaa gag gca atg gct aaa ttt    1440
Cys Met Arg Asp Tyr Gly Ile Ser Thr Lys Glu Ala Met Ala Lys Phe
465                 470                 475                 480 caa aat atg gct gag aca gca tgg aaa gat att aat gaa gga ctt ctt    1488
Gln Asn Met Ala Glu Thr Ala Trp Lys Asp Ile Asn Glu Gly Leu Leu
                485                 490                 495 agg ccc act ccc gtc tct aca gaa ttt tta act cct att ctc aat ctt    1536
Arg Pro Thr Pro Val Ser Thr Glu Phe Leu Thr Pro Ile Leu Asn Leu
            500                 505                 510 gct cgt att gtt gag gtt aca tat ata cac aat cta gat gga tac act    1584
Ala Arg Ile Val Glu Val Thr Tyr Ile His Asn Leu Asp Gly Tyr Thr
        515                 520                 525 cat ccg gag aaa gtc tta aaa cct cac att att aac cta ctt gtg gac    1632
His Pro Glu Lys Val Leu Lys Pro His Ile Ile Asn Leu Leu Val Asp
530                 535                 540 tcc atc aaa att                                                     1644
Ser Ile Lys Ile
545

<210> SEQ ID NO 4
<211> LENGTH: 548
<212> TYPE: PRT
<213> ORGANISM: Nicotiana tabacum

<400> SEQUENCE: 4

Met Ala Ser Ala Ala Val Ala Asn Tyr Glu Glu Glu Ile Val Arg Pro
1               5                   10                  15

Val Ala Asp Phe Ser Pro Ser Leu Trp Gly Asp Gln Phe Leu Ser Phe
            20                  25                  30

Ser Ile Asp Asn Gln Val Ala Glu Lys Tyr Ala Gln Glu Ile Glu Ala
        35                  40                  45

Leu Lys Glu Gln Thr Arg Ser Met Leu Leu Ala Thr Gly Arg Lys Leu
    50                  55                  60

Ala Asp Thr Leu Asn Leu Ile Asp Ile Ile Glu Arg Leu Gly Ile Ser
65                  70                  75                  80

Tyr His Phe Glu Lys Glu Ile Asp Glu Ile Leu Asp Gln Ile Tyr Asn
                85                  90                  95

Gln Asn Ser Asn Cys Asn Asp Leu Cys Thr Ser Ala Leu Gln Phe Arg
            100                 105                 110

Leu Leu Arg Gln His Gly Phe Asn Ile Ser Pro Glu Ile Phe Ser Lys
        115                 120                 125

Phe Gln Asp Glu Asn Gly Lys Phe Lys Glu Ser Leu Ala Ser Asp Val
    130                 135                 140

Leu Gly Leu Leu Asn Leu Tyr Glu Ala Ser His Val Arg Thr His Ala
145                 150                 155                 160

Asp Asp Ile Leu Glu Asp Ala Leu Ala Phe Ser Thr Ile His Leu Glu
                165                 170                 175

Ser Ala Ala Pro His Leu Lys Ser Pro Leu Arg Glu Gln Val Thr His
            180                 185                 190

Ala Leu Glu Gln Cys Leu His Lys Gly Val Pro Arg Val Glu Thr Arg
        195                 200                 205
```

Phe Phe Ile Ser Ser Ile Tyr Asp Lys Glu Gln Ser Lys Asn Asn Val
210                 215                 220

Leu Leu Arg Phe Ala Lys Leu Asp Phe Asn Leu Leu Gln Met Leu His
225                 230                 235                 240

Lys Gln Glu Leu Ala Gln Val Ser Arg Trp Trp Lys Asp Leu Asp Phe
                245                 250                 255

Val Thr Thr Leu Pro Tyr Ala Arg Asp Arg Val Val Glu Cys Tyr Phe
                260                 265                 270

Glu Ala Leu Gly Val Tyr Phe Glu Pro Gln Tyr Ser Gln Ala Arg Val
                275                 280                 285

Met Leu Val Lys Thr Ile Ser Met Ile Ser Ile Val Asp Asp Thr Phe
290                 295                 300

Asp Ala Tyr Gly Thr Val Lys Glu Leu Glu Ala Tyr Thr Asp Ala Ile
305                 310                 315                 320

Gln Arg Trp Asp Ile Asn Glu Ile Asp Arg Leu Pro Asp Tyr Met Lys
                325                 330                 335

Ile Ser Tyr Lys Ala Ile Leu Asp Leu Tyr Lys Asp Tyr Glu Lys Glu
                340                 345                 350

Leu Ser Ser Ala Gly Arg Ser His Ile Val Cys His Ala Ile Glu Arg
                355                 360                 365

Met Lys Glu Val Val Arg Asn Tyr Asn Val Glu Ser Thr Trp Phe Ile
370                 375                 380

Glu Gly Tyr Met Pro Pro Val Ser Glu Tyr Leu Ser Asn Ala Leu Ala
385                 390                 395                 400

Thr Thr Thr Tyr Tyr Tyr Leu Ala Thr Thr Ser Tyr Leu Gly Met Lys
                405                 410                 415

Ser Ala Thr Glu Gln Asp Phe Glu Trp Leu Ser Lys Asn Pro Lys Ile
                420                 425                 430

Leu Glu Ala Ser Val Ile Ile Cys Arg Val Ile Asp Asp Thr Ala Thr
                435                 440                 445

Tyr Glu Val Glu Lys Ser Arg Gly Gln Ile Ala Thr Gly Ile Glu Cys
450                 455                 460

Cys Met Arg Asp Tyr Gly Ile Ser Thr Lys Glu Ala Met Ala Lys Phe
465                 470                 475                 480

Gln Asn Met Ala Glu Thr Ala Trp Lys Asp Ile Asn Glu Gly Leu Leu
                485                 490                 495

Arg Pro Thr Pro Val Ser Thr Glu Phe Leu Thr Pro Ile Leu Asn Leu
                500                 505                 510

Ala Arg Ile Val Glu Val Thr Tyr Ile His Asn Leu Asp Gly Tyr Thr
                515                 520                 525

His Pro Glu Lys Val Leu Lys Pro His Ile Ile Asn Leu Leu Val Asp
530                 535                 540

Ser Ile Lys Ile
545

<210> SEQ ID NO 5
<211> LENGTH: 1644
<212> TYPE: DNA
<213> ORGANISM: Nicotiana tabacum
<220> FEATURE:
<221> NAME/KEY: CDS
<222> LOCATION: (1)...(1644)

<400> SEQUENCE: 5 atg gcc tca gca gca gtt gca aac tat gaa gaa gag att gtt cgc ccc                48

```
Met Ala Ser Ala Ala Val Ala Asn Tyr Glu Glu Ile Val Arg Pro
 1               5                  10                  15 gtc gcc gac ttc tcc cct agt ctc tgg ggt gat cag ttc ctt tca ttc      96
Val Ala Asp Phe Ser Pro Ser Leu Trp Gly Asp Gln Phe Leu Ser Phe
             20                  25                  30 tcc att gat aat cag gtt gcg gaa aag tat gct caa gag att gaa gca     144
Ser Ile Asp Asn Gln Val Ala Glu Lys Tyr Ala Gln Glu Ile Glu Ala
         35                  40                  45 ttg aag gaa caa acg agg agt atg ctg tta gca acc gga agg aaa ttg     192
Leu Lys Glu Gln Thr Arg Ser Met Leu Leu Ala Thr Gly Arg Lys Leu
     50                  55                  60 gcc gat aca ttg aat ttg att gac att att gaa cgc ctt ggt ata tcc     240
Ala Asp Thr Leu Asn Leu Ile Asp Ile Ile Glu Arg Leu Gly Ile Ser
 65                  70                  75                  80 tac cac ttt gag aaa gaa att gat gag att ttg gat cag att tac aac     288
Tyr His Phe Glu Lys Glu Ile Asp Glu Ile Leu Asp Gln Ile Tyr Asn
                 85                  90                  95 caa aac tca aac tgc aat gat ttg tgc acc tct gca ctt caa ttt cga     336
Gln Asn Ser Asn Cys Asn Asp Leu Cys Thr Ser Ala Leu Gln Phe Arg
             100                 105                 110 ttg ctc agg caa cac ggt ttc aac atc tct cct gaa att ttc agc aaa     384
Leu Leu Arg Gln His Gly Phe Asn Ile Ser Pro Glu Ile Phe Ser Lys
         115                 120                 125 ttc caa gat gaa aat ggc aaa ttc aag gag tct ctt gct agt gat gtc     432
Phe Gln Asp Glu Asn Gly Lys Phe Lys Glu Ser Leu Ala Ser Asp Val
     130                 135                 140 tta gga tta tta aac ttg tat gaa gct tca cat gta agg act cat gct     480
Leu Gly Leu Leu Asn Leu Tyr Glu Ala Ser His Val Arg Thr His Ala
145                 150                 155                 160 gac gat atc tta gaa gac gca ctt gct ttc tcc act atc cat ctt gaa     528
Asp Asp Ile Leu Glu Asp Ala Leu Ala Phe Ser Thr Ile His Leu Glu
                 165                 170                 175 tct gca gct cca cat ttg aaa tct cca ctt agg gag caa gtg aca cat     576
Ser Ala Ala Pro His Leu Lys Ser Pro Leu Arg Glu Gln Val Thr His
             180                 185                 190 gcc ctt gag caa tgt ttg cac aag ggt gtt cct aga gtc gag acc cga     624
Ala Leu Glu Gln Cys Leu His Lys Gly Val Pro Arg Val Glu Thr Arg
         195                 200                 205 ttc ttc atc tca tca atc tat gac aag gaa caa tcg aag aat aat gtg     672
Phe Phe Ile Ser Ser Ile Tyr Asp Lys Glu Gln Ser Lys Asn Asn Val
     210                 215                 220 tta ctt cga ttt gcc aaa ttg gat ttc aac ttg ctc cag atg ttg cac     720
Leu Leu Arg Phe Ala Lys Leu Asp Phe Asn Leu Leu Gln Met Leu His
225                 230                 235                 240 aaa caa gaa ctt gct caa gta tca agg tgg tgg aaa gat ttg gat ttt     768
Lys Gln Glu Leu Ala Gln Val Ser Arg Trp Trp Lys Asp Leu Asp Phe
                 245                 250                 255 gta aca aca ctt cca tat gct aga gat cga gta gtt gaa tgc tac ttt     816
Val Thr Thr Leu Pro Tyr Ala Arg Asp Arg Val Val Glu Cys Tyr Phe
             260                 265                 270 tgg gca tta gga gtt tat ttt gag cct caa tac tct caa gct cgc gtc     864
Trp Ala Leu Gly Val Tyr Phe Glu Pro Gln Tyr Ser Gln Ala Arg Val
         275                 280                 285 atg ctc gtt aag acc ata tca atg att tcg att gtc gat gac acc ttt     912
Met Leu Val Lys Thr Ile Ser Met Ile Ser Ile Val Asp Asp Thr Phe
     290                 295                 300 gat gct tac ggt aca gtt aaa gaa ctt gag gca tac aca gat gcc ata     960
Asp Ala Tyr Gly Thr Val Lys Glu Leu Glu Ala Tyr Thr Asp Ala Ile
305                 310                 315                 320
```

| | | |
|---|---|---|
| caa aga tgg gat atc aac gaa att gat cgg ctt cct gat tac atg aaa<br>Gln Arg Trp Asp Ile Asn Glu Ile Asp Arg Leu Pro Asp Tyr Met Lys<br>              325                          330                    335 | 1008 |
| atc agt tat aaa gct att cta gat ctc tac aag gat tat gaa aag gaa<br>Ile Ser Tyr Lys Ala Ile Leu Asp Leu Tyr Lys Asp Tyr Glu Lys Glu<br>              340                          345                    350 | 1056 |
| ttg tct agt gcc gga aga tct cat att gtc tgc cat gca ata gaa aga<br>Leu Ser Ser Ala Gly Arg Ser His Ile Val Cys His Ala Ile Glu Arg<br>              355                          360                    365 | 1104 |
| atg aaa gaa gta gta aga aat tat aat gtc gag tca aca tgg ttt att<br>Met Lys Glu Val Val Arg Asn Tyr Asn Val Glu Ser Thr Trp Phe Ile<br>370                          375                          380 | 1152 |
| gaa gga tat atg cca cct gtt tct gaa tac cta agc aat gca cta gca<br>Glu Gly Tyr Met Pro Pro Val Ser Glu Tyr Leu Ser Asn Ala Leu Ala<br>385                          390                          395                    400 | 1200 |
| act acc aca tat tac tac ctc gcg aca aca tcg tat ttg ggc atg aag<br>Thr Thr Thr Tyr Tyr Tyr Leu Ala Thr Thr Ser Tyr Leu Gly Met Lys<br>              405                          410                    415 | 1248 |
| tct gcc acg gag caa gat ttt gag tgg ttg tca aag aat cca aaa att<br>Ser Ala Thr Glu Gln Asp Phe Glu Trp Leu Ser Lys Asn Pro Lys Ile<br>              420                          425                    430 | 1296 |
| ctt gaa gct agt gta att ata tgt cga gtt atc gat gac aca gcc acg<br>Leu Glu Ala Ser Val Ile Ile Cys Arg Val Ile Asp Asp Thr Ala Thr<br>              435                          440                    445 | 1344 |
| tac gag gtt gag aaa agc agg gga caa att gca act gga att gag tgc<br>Tyr Glu Val Glu Lys Ser Arg Gly Gln Ile Ala Thr Gly Ile Glu Cys<br>450                          455                          460 | 1392 |
| tgc atg aga gat tat ggt ata tca aca aaa gag gca atg gct aaa ttt<br>Cys Met Arg Asp Tyr Gly Ile Ser Thr Lys Glu Ala Met Ala Lys Phe<br>465                          470                          475                    480 | 1440 |
| caa aat atg gct gag aca gca tgg aaa gat att aat gaa gga ctt ctt<br>Gln Asn Met Ala Glu Thr Ala Trp Lys Asp Ile Asn Glu Gly Leu Leu<br>              485                          490                    495 | 1488 |
| agg ccc act ccc gtc tct aca gaa ttt tta act cct att ctc aat ctt<br>Arg Pro Thr Pro Val Ser Thr Glu Phe Leu Thr Pro Ile Leu Asn Leu<br>                  500                          505                    510 | 1536 |
| gct cgt att gtt gag gtt aca ttc ata cac aat cta gat gga tac act<br>Ala Arg Ile Val Glu Val Thr Phe Ile His Asn Leu Asp Gly Tyr Thr<br>              515                          520                    525 | 1584 |
| cat ccg gag aaa gtc tta aaa cct cac att att aac cta ctt gtg gac<br>His Pro Glu Lys Val Leu Lys Pro His Ile Ile Asn Leu Leu Val Asp<br>530                          535                          540 | 1632 |
| tcc atc aaa att<br>Ser Ile Lys Ile<br>545 | 1644 |

<210> SEQ ID NO 6
<211> LENGTH: 548
<212> TYPE: PRT
<213> ORGANISM: Nicotiana tabacum

<400> SEQUENCE: 6

Met Ala Ser Ala Ala Val Ala Asn Tyr Glu Glu Ile Val Arg Pro
1               5                   10                  15

Val Ala Asp Phe Ser Pro Ser Leu Trp Gly Asp Gln Phe Leu Ser Phe
                20                  25                  30

Ser Ile Asp Asn Gln Val Ala Glu Lys Tyr Ala Gln Glu Ile Glu Ala
            35                  40                  45

Leu Lys Glu Gln Thr Arg Ser Met Leu Leu Ala Thr Gly Arg Lys Leu
    50                  55                  60

-continued

```
Ala Asp Thr Leu Asn Leu Ile Asp Ile Ile Glu Arg Leu Gly Ile Ser
 65                  70                  75                  80

Tyr His Phe Glu Lys Glu Ile Asp Glu Ile Leu Asp Gln Ile Tyr Asn
                 85                  90                  95

Gln Asn Ser Asn Cys Asn Asp Leu Cys Thr Ser Ala Leu Gln Phe Arg
            100                 105                 110

Leu Leu Arg Gln His Gly Phe Asn Ile Ser Pro Glu Ile Phe Ser Lys
        115                 120                 125

Phe Gln Asp Glu Asn Gly Lys Phe Lys Glu Ser Leu Ala Ser Asp Val
    130                 135                 140

Leu Gly Leu Leu Asn Leu Tyr Glu Ala Ser His Val Arg Thr His Ala
145                 150                 155                 160

Asp Asp Ile Leu Glu Asp Ala Leu Ala Phe Ser Thr Ile His Leu Glu
                165                 170                 175

Ser Ala Ala Pro His Leu Lys Ser Pro Leu Arg Glu Gln Val Thr His
            180                 185                 190

Ala Leu Glu Gln Cys Leu His Lys Gly Val Pro Arg Val Glu Thr Arg
        195                 200                 205

Phe Phe Ile Ser Ser Ile Tyr Asp Lys Glu Gln Ser Lys Asn Asn Val
    210                 215                 220

Leu Leu Arg Phe Ala Lys Leu Asp Phe Asn Leu Leu Gln Met Leu His
225                 230                 235                 240

Lys Gln Glu Leu Ala Gln Val Ser Arg Trp Trp Lys Asp Leu Asp Phe
                245                 250                 255

Val Thr Thr Leu Pro Tyr Ala Arg Asp Arg Val Val Glu Cys Tyr Phe
            260                 265                 270

Trp Ala Leu Gly Val Tyr Phe Glu Pro Gln Tyr Ser Gln Ala Arg Val
        275                 280                 285

Met Leu Val Lys Thr Ile Ser Met Ile Ser Ile Val Asp Asp Thr Phe
    290                 295                 300

Asp Ala Tyr Gly Thr Val Lys Glu Leu Glu Ala Tyr Thr Asp Ala Ile
305                 310                 315                 320

Gln Arg Trp Asp Ile Asn Glu Ile Asp Arg Leu Pro Asp Tyr Met Lys
                325                 330                 335

Ile Ser Tyr Lys Ala Ile Leu Asp Leu Tyr Lys Asp Tyr Glu Lys Glu
            340                 345                 350

Leu Ser Ser Ala Gly Arg Ser His Ile Val Cys His Ala Ile Glu Arg
        355                 360                 365

Met Lys Glu Val Val Arg Asn Tyr Asn Val Glu Ser Thr Trp Phe Ile
    370                 375                 380

Glu Gly Tyr Met Pro Pro Val Ser Glu Tyr Leu Ser Asn Ala Leu Ala
385                 390                 395                 400

Thr Thr Thr Tyr Tyr Tyr Leu Ala Thr Thr Ser Tyr Leu Gly Met Lys
                405                 410                 415

Ser Ala Thr Glu Gln Asp Phe Glu Trp Leu Ser Lys Asn Pro Lys Ile
            420                 425                 430

Leu Glu Ala Ser Val Ile Ile Cys Arg Val Ile Asp Asp Thr Ala Thr
        435                 440                 445

Tyr Glu Val Glu Lys Ser Arg Gly Gln Ile Ala Thr Gly Ile Glu Cys
    450                 455                 460

Cys Met Arg Asp Tyr Gly Ile Ser Thr Lys Glu Ala Met Ala Lys Phe
465                 470                 475                 480
```

```
Gln Asn Met Ala Glu Thr Ala Trp Lys Asp Ile Asn Glu Gly Leu Leu
                485                 490                 495

Arg Pro Thr Pro Val Ser Thr Glu Phe Leu Thr Pro Ile Leu Asn Leu
            500                 505                 510

Ala Arg Ile Val Glu Val Thr Phe Ile His Asn Leu Asp Gly Tyr Thr
        515                 520                 525

His Pro Glu Lys Val Leu Lys Pro His Ile Ile Asn Leu Leu Val Asp
    530                 535                 540

Ser Ile Lys Ile
545

<210> SEQ ID NO 7
<211> LENGTH: 1644
<212> TYPE: DNA
<213> ORGANISM: Nicotiana tabacum
<220> FEATURE:
<221> NAME/KEY: CDS
<222> LOCATION: (1)...(1644)

<400> SEQUENCE: 7 atg gcc tca gca gca gtt gca aac tat gaa gaa gag att gtt cgc ccc      48
Met Ala Ser Ala Ala Val Ala Asn Tyr Glu Glu Glu Ile Val Arg Pro
  1               5                  10                  15 gtc gcc gac ttc tcc cct agt ctc tgg ggt gat cag ttc ctt tca ttc      96
Val Ala Asp Phe Ser Pro Ser Leu Trp Gly Asp Gln Phe Leu Ser Phe
             20                  25                  30 tcc att gat aat cag gtt gcg gaa aag tat gct caa gag att gaa gca     144
Ser Ile Asp Asn Gln Val Ala Glu Lys Tyr Ala Gln Glu Ile Glu Ala
         35                  40                  45 ttg aag gaa caa acg agg agt atg ctg tta gca acc gga agg aaa ttg     192
Leu Lys Glu Gln Thr Arg Ser Met Leu Leu Ala Thr Gly Arg Lys Leu
     50                  55                  60 gcc gat aca ttg aat ttg att gac att att gaa cgc ctt ggt ata tcc     240
Ala Asp Thr Leu Asn Leu Ile Asp Ile Ile Glu Arg Leu Gly Ile Ser
 65                  70                  75                  80 tac cac ttt gag aaa gaa att gat gag att ttg gat cag att tac aac     288
Tyr His Phe Glu Lys Glu Ile Asp Glu Ile Leu Asp Gln Ile Tyr Asn
                 85                  90                  95 caa aac tca aac tgc aat gat ttg tgc acc tct gca ctt caa ttt cga     336
Gln Asn Ser Asn Cys Asn Asp Leu Cys Thr Ser Ala Leu Gln Phe Arg
            100                 105                 110 ttg ctc agg caa cac ggt ttc aac atc tct cct gaa att ttc agc aaa     384
Leu Leu Arg Gln His Gly Phe Asn Ile Ser Pro Glu Ile Phe Ser Lys
        115                 120                 125 ttc caa gat gaa aat ggc aaa ttc aag gag tct ctt gct agt gat gtc     432
Phe Gln Asp Glu Asn Gly Lys Phe Lys Glu Ser Leu Ala Ser Asp Val
    130                 135                 140 tta gga tta tta aac ttg tat gaa gct tca cat gta agg act cat gct     480
Leu Gly Leu Leu Asn Leu Tyr Glu Ala Ser His Val Arg Thr His Ala
145                 150                 155                 160 gac gat atc tta gaa gac gca ctt gct ttc tcc act atc cat ctt gaa     528
Asp Asp Ile Leu Glu Asp Ala Leu Ala Phe Ser Thr Ile His Leu Glu
                165                 170                 175 tct gca gct cca cat ttg aaa tct cca ctt agg gag caa gtg aca cat     576
Ser Ala Ala Pro His Leu Lys Ser Pro Leu Arg Glu Gln Val Thr His
            180                 185                 190 gcc ctt gag caa tgt ttg cac aag ggt gtt cct aga gtc gag acc cga     624
Ala Leu Glu Gln Cys Leu His Lys Gly Val Pro Arg Val Glu Thr Arg
        195                 200                 205 ttc ttc atc tca tca atc tat gac aag gaa caa tcg aag aat aat gtg     672
```

```
Phe Phe Ile Ser Ser Ile Tyr Asp Lys Glu Gln Ser Lys Asn Asn Val
    210                 215                 220 tta ctt cga ttt gcc aaa ttg gat ttc aac ttg ctc cag atg ttg cac        720
Leu Leu Arg Phe Ala Lys Leu Asp Phe Asn Leu Leu Gln Met Leu His
225                 230                 235                 240 aaa caa gaa ctt gct caa gta tca agg tgg tgg aaa gat ttg gat ttt        768
Lys Gln Glu Leu Ala Gln Val Ser Arg Trp Trp Lys Asp Leu Asp Phe
                245                 250                 255 gta aca aca ctt cca tat gct aga gat cga gta gtt gaa tgc tac ttt        816
Val Thr Thr Leu Pro Tyr Ala Arg Asp Arg Val Val Glu Cys Tyr Phe
                    260                 265                 270 tgg gca tta gga gtt tat ttt gag cct caa tac tct caa gct cgc gtc        864
Trp Ala Leu Gly Val Tyr Phe Glu Pro Gln Tyr Ser Gln Ala Arg Val
                275                 280                 285 atg ctc gtt aag acc ata tca atg att tcg att gtc gat gac acc ttt        912
Met Leu Val Lys Thr Ile Ser Met Ile Ser Ile Val Asp Asp Thr Phe
290                 295                 300 gat gct tac ggt aca gtt aaa gaa ctt gag gca tac aca gat gcc ata        960
Asp Ala Tyr Gly Thr Val Lys Glu Leu Glu Ala Tyr Thr Asp Ala Ile
305                 310                 315                 320 caa aga tgg gat atc aac gaa att gat cgg ctt cct gat tac atg aaa       1008
Gln Arg Trp Asp Ile Asn Glu Ile Asp Arg Leu Pro Asp Tyr Met Lys
                325                 330                 335 atc agt tat aaa gct att cta gat ctc tac aag gat tat gaa aag gaa       1056
Ile Ser Tyr Lys Ala Ile Leu Asp Leu Tyr Lys Asp Tyr Glu Lys Glu
                340                 345                 350 ttg tct agt gcc gga aga tct cat att gtc tgc cat gca ata gaa aga       1104
Leu Ser Ser Ala Gly Arg Ser His Ile Val Cys His Ala Ile Glu Arg
                355                 360                 365 atg aaa gaa gta gta aga aat tat aat gtc gag tca aca tgg ttt att       1152
Met Lys Glu Val Val Arg Asn Tyr Asn Val Glu Ser Thr Trp Phe Ile
370                 375                 380 gaa gga tat atg cca cct gtt tct gaa tac cta agc aat gca cta gca       1200
Glu Gly Tyr Met Pro Pro Val Ser Glu Tyr Leu Ser Asn Ala Leu Ala
385                 390                 395                 400 act acc aca tat tac tac ctc gcg aca aca tcg tat ttg ggc atg aag       1248
Thr Thr Thr Tyr Tyr Tyr Leu Ala Thr Thr Ser Tyr Leu Gly Met Lys
                405                 410                 415 tct gcc acg gag caa gat ttt gag tgg ttg tca aag aat cca aaa att       1296
Ser Ala Thr Glu Gln Asp Phe Glu Trp Leu Ser Lys Asn Pro Lys Ile
                420                 425                 430 ctt gaa gct agt gta att ata tgt cga gtt atc gat gac aca gcc acg       1344
Leu Glu Ala Ser Val Ile Ile Cys Arg Val Ile Asp Asp Thr Ala Thr
                435                 440                 445 tac gag gtt gag aaa agc agg gga caa att gca act gga att gag tgc       1392
Tyr Glu Val Glu Lys Ser Arg Gly Gln Ile Ala Thr Gly Ile Glu Cys
450                 455                 460 tgc atg aga gat tat ggt ata tca aca aaa gag gca atg gct aaa ttt       1440
Cys Met Arg Asp Tyr Gly Ile Ser Thr Lys Glu Ala Met Ala Lys Phe
465                 470                 475                 480 caa aat atg gct gag aca gca tgg aaa gat att aat gaa gga ctt ctt       1488
Gln Asn Met Ala Glu Thr Ala Trp Lys Asp Ile Asn Glu Gly Leu Leu
                485                 490                 495 agg ccc act ccc gtc tct aca gaa ttt tta act cct att ctc aat ctt       1536
Arg Pro Thr Pro Val Ser Thr Glu Phe Leu Thr Pro Ile Leu Asn Leu
                500                 505                 510 gct cgt att gtt gag gtt aca tat ata cac aat cta gat gga ttc act       1584
Ala Arg Ile Val Glu Val Thr Tyr Ile His Asn Leu Asp Gly Phe Thr
                515                 520                 525
```

```
cat ccg gag aaa gtc tta aaa cct cac att att aac cta ctt gtg gac     1632
His Pro Glu Lys Val Leu Lys Pro His Ile Ile Asn Leu Leu Val Asp
        530                 535                 540 tcc atc aaa att                                                     1644
Ser Ile Lys Ile
545
```

<210> SEQ ID NO 8
<211> LENGTH: 548
<212> TYPE: PRT
<213> ORGANISM: Nicotiana tabacum

<400> SEQUENCE: 8

```
Met Ala Ser Ala Ala Val Ala Asn Tyr Glu Glu Ile Val Arg Pro
  1               5                  10                  15

Val Ala Asp Phe Ser Pro Ser Leu Trp Gly Asp Gln Phe Leu Ser Phe
                 20                  25                  30

Ser Ile Asp Asn Gln Val Ala Glu Lys Tyr Ala Gln Ile Glu Ala
             35                  40                  45

Leu Lys Glu Gln Thr Arg Ser Met Leu Leu Ala Thr Gly Arg Lys Leu
 50                  55                  60

Ala Asp Thr Leu Asn Leu Ile Asp Ile Ile Glu Arg Leu Gly Ile Ser
 65                  70                  75                  80

Tyr His Phe Glu Lys Glu Ile Asp Glu Ile Leu Asp Gln Ile Tyr Asn
                 85                  90                  95

Gln Asn Ser Asn Cys Asn Asp Leu Cys Thr Ser Ala Leu Gln Phe Arg
            100                 105                 110

Leu Leu Arg Gln His Gly Phe Asn Ile Ser Pro Glu Ile Phe Ser Lys
            115                 120                 125

Phe Gln Asp Glu Asn Gly Lys Phe Lys Glu Ser Leu Ala Ser Asp Val
130                 135                 140

Leu Gly Leu Leu Asn Leu Tyr Glu Ala Ser His Val Arg Thr His Ala
145                 150                 155                 160

Asp Asp Ile Leu Glu Asp Ala Leu Ala Phe Ser Thr Ile His Leu Glu
                165                 170                 175

Ser Ala Ala Pro His Leu Lys Ser Pro Leu Arg Glu Gln Val Thr His
            180                 185                 190

Ala Leu Glu Gln Cys Leu His Lys Gly Val Pro Arg Val Glu Thr Arg
            195                 200                 205

Phe Phe Ile Ser Ser Ile Tyr Asp Lys Glu Gln Ser Lys Asn Asn Val
210                 215                 220

Leu Leu Arg Phe Ala Lys Leu Asp Phe Asn Leu Leu Gln Met Leu His
225                 230                 235                 240

Lys Gln Glu Leu Ala Gln Val Ser Arg Trp Trp Lys Asp Leu Asp Phe
                245                 250                 255

Val Thr Thr Leu Pro Tyr Ala Arg Asp Arg Val Val Glu Cys Tyr Phe
            260                 265                 270

Trp Ala Leu Gly Val Tyr Phe Glu Pro Gln Tyr Ser Gln Ala Arg Val
            275                 280                 285

Met Leu Val Lys Thr Ile Ser Met Ile Ser Ile Val Asp Asp Thr Phe
290                 295                 300

Asp Ala Tyr Gly Thr Val Lys Glu Leu Glu Ala Tyr Thr Asp Ala Ile
305                 310                 315                 320

Gln Arg Trp Asp Ile Asn Glu Ile Asp Arg Leu Pro Asp Tyr Met Lys
                325                 330                 335
```

```
Ile Ser Tyr Lys Ala Ile Leu Asp Leu Tyr Lys Asp Tyr Glu Lys Glu
            340                 345                 350

Leu Ser Ser Ala Gly Arg Ser His Ile Val Cys His Ala Ile Glu Arg
            355                 360                 365

Met Lys Glu Val Val Arg Asn Tyr Asn Val Glu Ser Thr Trp Phe Ile
            370                 375                 380

Glu Gly Tyr Met Pro Pro Val Ser Glu Tyr Leu Ser Asn Ala Leu Ala
385                 390                 395                 400

Thr Thr Thr Tyr Tyr Tyr Leu Ala Thr Thr Ser Tyr Leu Gly Met Lys
            405                 410                 415

Ser Ala Thr Glu Gln Asp Phe Glu Trp Leu Ser Lys Asn Pro Lys Ile
            420                 425                 430

Leu Glu Ala Ser Val Ile Ile Cys Arg Val Ile Asp Asp Thr Ala Thr
            435                 440                 445

Tyr Glu Val Glu Lys Ser Arg Gly Gln Ile Ala Thr Gly Ile Glu Cys
            450                 455                 460

Cys Met Arg Asp Tyr Gly Ile Ser Thr Lys Glu Ala Met Ala Lys Phe
465                 470                 475                 480

Gln Asn Met Ala Glu Thr Ala Trp Lys Asp Ile Asn Glu Gly Leu Leu
            485                 490                 495

Arg Pro Thr Pro Val Ser Thr Glu Phe Leu Thr Pro Ile Leu Asn Leu
            500                 505                 510

Ala Arg Ile Val Glu Val Thr Tyr Ile His Asn Leu Asp Gly Phe Thr
            515                 520                 525

His Pro Glu Lys Val Leu Lys Pro His Ile Ile Asn Leu Leu Val Asp
            530                 535                 540

Ser Ile Lys Ile
545

<210> SEQ ID NO 9
<211> LENGTH: 1644
<212> TYPE: DNA
<213> ORGANISM: Nicotiana tabacum
<220> FEATURE:
<221> NAME/KEY: CDS
<222> LOCATION: (1)...(1644)

<400> SEQUENCE: 9 atg gcc tca gca gca gtt gca aac tat gaa gaa gag att gtt cgc ccc      48
Met Ala Ser Ala Ala Val Ala Asn Tyr Glu Glu Glu Ile Val Arg Pro
 1               5                  10                  15 gtc gcc gac ttc tcc cct agt ctc tgg ggt gat cag ttc ctt tca ttc      96
Val Ala Asp Phe Ser Pro Ser Leu Trp Gly Asp Gln Phe Leu Ser Phe
                20                  25                  30 tcc att gat aat cag gtt gcg gaa aag tat gct caa gag att gaa gca     144
Ser Ile Asp Asn Gln Val Ala Glu Lys Tyr Ala Gln Glu Ile Glu Ala
            35                  40                  45 ttg aag gaa caa acg agg agt atg ctg tta gca acc gga agg aaa ttg     192
Leu Lys Glu Gln Thr Arg Ser Met Leu Leu Ala Thr Gly Arg Lys Leu
        50                  55                  60 gcc gat aca ttg aat ttg att gac att att gaa cgc ctt ggt ata tcc     240
Ala Asp Thr Leu Asn Leu Ile Asp Ile Ile Glu Arg Leu Gly Ile Ser
 65                  70                  75                  80 tac cac ttt gag aaa gaa att gat gag att ttg gat cag att tac aac     288
Tyr His Phe Glu Lys Glu Ile Asp Glu Ile Leu Asp Gln Ile Tyr Asn
                85                  90                  95 caa aac tca aac tgc aat gat ttg tgc acc tct gca ctt caa ttt cga     336
Gln Asn Ser Asn Cys Asn Asp Leu Cys Thr Ser Ala Leu Gln Phe Arg
```

-continued

```
                 100                 105                 110
ttg ctc agg caa cac ggt ttc aac atc tct cct gaa att ttc agc aaa        384
Leu Leu Arg Gln His Gly Phe Asn Ile Ser Pro Glu Ile Phe Ser Lys
             115                 120                 125 ttc caa gat gaa aat ggc aaa ttc aag gag tct ctt gct agt gat gtc        432
Phe Gln Asp Glu Asn Gly Lys Phe Lys Glu Ser Leu Ala Ser Asp Val
         130                 135                 140 tta gga tta tta aac ttg tat gaa gct tca cat gta agg act cat gct        480
Leu Gly Leu Leu Asn Leu Tyr Glu Ala Ser His Val Arg Thr His Ala
145                 150                 155                 160 gac gat atc tta gaa gac gca ctt gct ttc tcc act atc cat ctt gaa        528
Asp Asp Ile Leu Glu Asp Ala Leu Ala Phe Ser Thr Ile His Leu Glu
                 165                 170                 175 tct gca gct cca cat ttg aaa tct cca ctt agg gag caa gtg aca cat        576
Ser Ala Ala Pro His Leu Lys Ser Pro Leu Arg Glu Gln Val Thr His
             180                 185                 190 gcc ctt gag caa tgt ttg cac aag ggt gtt cct aga gtc gag acc cga        624
Ala Leu Glu Gln Cys Leu His Lys Gly Val Pro Arg Val Glu Thr Arg
         195                 200                 205 ttc ttc atc tca tca atc tat gac aag gaa caa tcg aag aat aat gtg        672
Phe Phe Ile Ser Ser Ile Tyr Asp Lys Glu Gln Ser Lys Asn Asn Val
     210                 215                 220 tta ctt cga ttt gcc aaa ttg gat ttc aac ttg ctc cag atg ttg cac        720
Leu Leu Arg Phe Ala Lys Leu Asp Phe Asn Leu Leu Gln Met Leu His
225                 230                 235                 240 aaa caa gaa ctt gct caa gta tca agg tgg tgg aaa gat ttg gat ttt        768
Lys Gln Glu Leu Ala Gln Val Ser Arg Trp Trp Lys Asp Leu Asp Phe
                 245                 250                 255 gta aca aca ctt cca tat gct aga gat cga gta gtt gaa tgc tac ttt        816
Val Thr Thr Leu Pro Tyr Ala Arg Asp Arg Val Val Glu Cys Tyr Phe
             260                 265                 270 tcg gca tta gga gtt tat ttt gag cct caa tac tct caa gct cgc gtc        864
Ser Ala Leu Gly Val Tyr Phe Glu Pro Gln Tyr Ser Gln Ala Arg Val
         275                 280                 285 atg ctc gtt aag acc ata tca atg att tcg att gtc gat gac acc ttt        912
Met Leu Val Lys Thr Ile Ser Met Ile Ser Ile Val Asp Asp Thr Phe
     290                 295                 300 gat gct tac ggt aca gtt aaa gaa ctt gag gca tac aca gat gcc ata        960
Asp Ala Tyr Gly Thr Val Lys Glu Leu Glu Ala Tyr Thr Asp Ala Ile
305                 310                 315                 320 caa aga tgg gat atc aac gaa att gat cgg ctt cct gat tac atg aaa       1008
Gln Arg Trp Asp Ile Asn Glu Ile Asp Arg Leu Pro Asp Tyr Met Lys
                 325                 330                 335 atc agt tat aaa gct att cta gat ctc tac aag gat tat gaa aag gaa       1056
Ile Ser Tyr Lys Ala Ile Leu Asp Leu Tyr Lys Asp Tyr Glu Lys Glu
             340                 345                 350 ttg tct agt gcc gga aga tct cat att gtc tgc cat gca ata gaa aga       1104
Leu Ser Ser Ala Gly Arg Ser His Ile Val Cys His Ala Ile Glu Arg
         355                 360                 365 atg aaa gaa gta gta aga aat tat aat gtc gag tca aca tgg ttt att       1152
Met Lys Glu Val Val Arg Asn Tyr Asn Val Glu Ser Thr Trp Phe Ile
     370                 375                 380 gaa gga tat atg cca cct gtt tct gaa tac cta agc aat gca cta gca       1200
Glu Gly Tyr Met Pro Pro Val Ser Glu Tyr Leu Ser Asn Ala Leu Ala
385                 390                 395                 400 act acc aca tat tac tac ctc gcg aca aca tcg tat ttg ggc atg aag       1248
Thr Thr Thr Tyr Tyr Tyr Leu Ala Thr Thr Ser Tyr Leu Gly Met Lys
                 405                 410                 415 tct gcc acg gag caa gat ttt gag tgg ttg tca aag aat cca aaa att       1296
```

```
Ser Ala Thr Glu Gln Asp Phe Glu Trp Leu Ser Lys Asn Pro Lys Ile
            420                 425                 430 ctt gaa gct agt gta att ata tgg cga gtt atc gat gac aca gcc acg      1344
Leu Glu Ala Ser Val Ile Ile Trp Arg Val Ile Asp Asp Thr Ala Thr
            435                 440                 445 tac gag gtt gag aaa agc agg gga caa att gca act gga att gag tgc      1392
Tyr Glu Val Glu Lys Ser Arg Gly Gln Ile Ala Thr Gly Ile Glu Cys
450                 455                 460 tgc atg aga gat tat ggt ata tca aca aaa gag gca atg gct aaa ttt      1440
Cys Met Arg Asp Tyr Gly Ile Ser Thr Lys Glu Ala Met Ala Lys Phe
465                 470                 475                 480 caa aat atg gct gag aca gca tgg aaa gat att aat gaa gga ctt ctt      1488
Gln Asn Met Ala Glu Thr Ala Trp Lys Asp Ile Asn Glu Gly Leu Leu
            485                 490                 495 agg ccc act ccc gtc tct aca gaa ttt tta act cct att ctc aat ctt      1536
Arg Pro Thr Pro Val Ser Thr Glu Phe Leu Thr Pro Ile Leu Asn Leu
            500                 505                 510 gct cgt att gtt gag gtt aca tat ata cac aat cta gat gga tac act      1584
Ala Arg Ile Val Glu Val Thr Tyr Ile His Asn Leu Asp Gly Tyr Thr
            515                 520                 525 cat ccg gag aaa gtc tta aaa cct cac att att aac cta ctt gtg gac      1632
His Pro Glu Lys Val Leu Lys Pro His Ile Ile Asn Leu Leu Val Asp
530                 535                 540 tcc atc aaa att                                                      1644
Ser Ile Lys Ile
545

<210> SEQ ID NO 10
<211> LENGTH: 548
<212> TYPE: PRT
<213> ORGANISM: Nicotiana tabacum

<400> SEQUENCE: 10

Met Ala Ser Ala Ala Val Ala Asn Tyr Glu Glu Glu Ile Val Arg Pro
1               5                   10                  15

Val Ala Asp Phe Ser Pro Ser Leu Trp Gly Asp Gln Phe Leu Ser Phe
            20                  25                  30

Ser Ile Asp Asn Gln Val Ala Glu Lys Tyr Ala Gln Glu Ile Glu Ala
        35                  40                  45

Leu Lys Glu Gln Thr Arg Ser Met Leu Leu Ala Thr Gly Arg Lys Leu
    50                  55                  60

Ala Asp Thr Leu Asn Leu Ile Asp Ile Ile Glu Arg Leu Gly Ile Ser
65                  70                  75                  80

Tyr His Phe Glu Lys Glu Ile Asp Glu Ile Leu Asp Gln Ile Tyr Asn
                85                  90                  95

Gln Asn Ser Asn Cys Asn Asp Leu Cys Thr Ser Ala Leu Gln Phe Arg
            100                 105                 110

Leu Leu Arg Gln His Gly Phe Asn Ile Ser Pro Glu Ile Phe Ser Lys
        115                 120                 125

Phe Gln Asp Glu Asn Gly Lys Phe Lys Glu Ser Leu Ala Ser Asp Val
    130                 135                 140

Leu Gly Leu Leu Asn Leu Tyr Glu Ala Ser His Val Arg Thr His Ala
145                 150                 155                 160

Asp Asp Ile Leu Glu Asp Ala Leu Ala Phe Ser Thr Ile His Leu Glu
                165                 170                 175

Ser Ala Ala Pro His Leu Lys Ser Pro Leu Arg Glu Gln Val Thr His
            180                 185                 190
```

```
Ala Leu Glu Gln Cys Leu His Lys Gly Val Pro Arg Val Glu Thr Arg
            195                 200                 205

Phe Phe Ile Ser Ser Ile Tyr Asp Lys Glu Gln Ser Lys Asn Asn Val
        210                 215                 220

Leu Leu Arg Phe Ala Lys Leu Asp Phe Asn Leu Leu Gln Met Leu His
225                 230                 235                 240

Lys Gln Glu Leu Ala Gln Val Ser Arg Trp Trp Lys Asp Leu Asp Phe
                245                 250                 255

Val Thr Thr Leu Pro Tyr Ala Arg Asp Arg Val Val Glu Cys Tyr Phe
            260                 265                 270

Ser Ala Leu Gly Val Tyr Phe Glu Pro Gln Tyr Ser Gln Ala Arg Val
        275                 280                 285

Met Leu Val Lys Thr Ile Ser Met Ile Ser Ile Val Asp Asp Thr Phe
290                 295                 300

Asp Ala Tyr Gly Thr Val Lys Glu Leu Glu Ala Tyr Thr Asp Ala Ile
305                 310                 315                 320

Gln Arg Trp Asp Ile Asn Glu Ile Asp Arg Leu Pro Asp Tyr Met Lys
                325                 330                 335

Ile Ser Tyr Lys Ala Ile Leu Asp Leu Tyr Lys Asp Tyr Glu Lys Glu
            340                 345                 350

Leu Ser Ser Ala Gly Arg Ser His Ile Val Cys His Ala Ile Glu Arg
        355                 360                 365

Met Lys Glu Val Val Arg Asn Tyr Asn Val Glu Ser Thr Trp Phe Ile
370                 375                 380

Glu Gly Tyr Met Pro Pro Val Ser Glu Tyr Leu Ser Asn Ala Leu Ala
385                 390                 395                 400

Thr Thr Thr Tyr Tyr Tyr Leu Ala Thr Thr Ser Tyr Leu Gly Met Lys
                405                 410                 415

Ser Ala Thr Glu Gln Asp Phe Glu Trp Leu Ser Lys Asn Pro Lys Ile
            420                 425                 430

Leu Glu Ala Ser Val Ile Ile Trp Arg Val Ile Asp Asp Thr Ala Thr
        435                 440                 445

Tyr Glu Val Glu Lys Ser Arg Gly Gln Ile Ala Thr Gly Ile Glu Cys
    450                 455                 460

Cys Met Arg Asp Tyr Gly Ile Ser Thr Lys Glu Ala Met Ala Lys Phe
465                 470                 475                 480

Gln Asn Met Ala Glu Thr Ala Trp Lys Asp Ile Asn Glu Gly Leu Leu
                485                 490                 495

Arg Pro Thr Pro Val Ser Thr Glu Phe Leu Thr Pro Ile Leu Asn Leu
            500                 505                 510

Ala Arg Ile Val Glu Val Thr Tyr Ile His Asn Leu Asp Gly Tyr Thr
        515                 520                 525

His Pro Glu Lys Val Leu Lys Pro His Ile Ile Asn Leu Leu Val Asp
    530                 535                 540

Ser Ile Lys Ile
545

<210> SEQ ID NO 11
<211> LENGTH: 1644
<212> TYPE: DNA
<213> ORGANISM: Nicotiana tabacum
<220> FEATURE:
<221> NAME/KEY: CDS
<222> LOCATION: (1)...(1644)
<221> NAME/KEY: misc_feature
<222> LOCATION: (1)...(1644)
```

-continued

<223> OTHER INFORMATION: n = A,T,C or G

<400> SEQUENCE: 11

```
atg gcc tca gca gca gtt gca aac tat gaa gaa gag att gtt cgc ccc      48
Met Ala Ser Ala Ala Val Ala Asn Tyr Glu Glu Glu Ile Val Arg Pro
 1               5                  10                  15 gtc gcc gac ttc tcc cct agt ctc tgg ggt gat cag ttc ctt tca ttc      96
Val Ala Asp Phe Ser Pro Ser Leu Trp Gly Asp Gln Phe Leu Ser Phe
                20                  25                  30 tcc att gat aat cag gtt gcg gaa aag tat gct caa gag att gaa gca     144
Ser Ile Asp Asn Gln Val Ala Glu Lys Tyr Ala Gln Glu Ile Glu Ala
            35                  40                  45 ttg aag gaa caa acg agg agt atg ctg tta gca acc gga agg aaa ttg     192
Leu Lys Glu Gln Thr Arg Ser Met Leu Leu Ala Thr Gly Arg Lys Leu
        50                  55                  60 gcc gat aca ttg aat ttg att gac att att gaa cgc ctt ggt ata tcc     240
Ala Asp Thr Leu Asn Leu Ile Asp Ile Ile Glu Arg Leu Gly Ile Ser
 65                  70                  75                  80 tac cac ttt gag aaa gaa att gat gag att ttg gat cag att tac aac     288
Tyr His Phe Glu Lys Glu Ile Asp Glu Ile Leu Asp Gln Ile Tyr Asn
                85                  90                  95 caa aac tca aac tgc aat gat ttg tgc acc tct gca ctt caa ttt cga     336
Gln Asn Ser Asn Cys Asn Asp Leu Cys Thr Ser Ala Leu Gln Phe Arg
            100                 105                 110 ttg ctc agg caa cac ggt ttc aac atc tct cct gaa att ttc agc aaa     384
Leu Leu Arg Gln His Gly Phe Asn Ile Ser Pro Glu Ile Phe Ser Lys
        115                 120                 125 ttc caa gat gaa aat ggc aaa ttc aag gag tct ctt gct agt gat gtc     432
Phe Gln Asp Glu Asn Gly Lys Phe Lys Glu Ser Leu Ala Ser Asp Val
    130                 135                 140 tta gga tta tta aac ttg tat gaa gct tca cat gta agg act cat gct     480
Leu Gly Leu Leu Asn Leu Tyr Glu Ala Ser His Val Arg Thr His Ala
145                 150                 155                 160 gac gat atc tta gaa gac gca ctt gct ttc tcc act atc cat ctt gaa     528
Asp Asp Ile Leu Glu Asp Ala Leu Ala Phe Ser Thr Ile His Leu Glu
                165                 170                 175 tct gca gct cca cat ttg aaa tct cca ctt agg gag caa gtg aca cat     576
Ser Ala Ala Pro His Leu Lys Ser Pro Leu Arg Glu Gln Val Thr His
            180                 185                 190 gcc ctt gag caa tgt ttg cac aag ggt gtt cct aga gtc gag acc cga     624
Ala Leu Glu Gln Cys Leu His Lys Gly Val Pro Arg Val Glu Thr Arg
        195                 200                 205 ttc ttc atc tca tca atc tat gac aag gaa caa tcg aag aat aat gtg     672
Phe Phe Ile Ser Ser Ile Tyr Asp Lys Glu Gln Ser Lys Asn Asn Val
    210                 215                 220 tta ctt cga ttt gcc aaa ttg gat ttc aac ttg ctc cag atg ttg cac     720
Leu Leu Arg Phe Ala Lys Leu Asp Phe Asn Leu Leu Gln Met Leu His
225                 230                 235                 240 aaa caa gaa ctt gct caa gta tca agg tgg tgg aaa gat ttg gat ttt     768
Lys Gln Glu Leu Ala Gln Val Ser Arg Trp Trp Lys Asp Leu Asp Phe
                245                 250                 255 gta aca aca ctt cca tat gct aga gat cga gta gtt gaa tgc tac ttt     816
Val Thr Thr Leu Pro Tyr Ala Arg Asp Arg Val Val Glu Cys Tyr Phe
            260                 265                 270 tgg gca tta gga gtt tat ttt gag cct caa tac tct caa gct cgc gtc     864
Trp Ala Leu Gly Val Tyr Phe Glu Pro Gln Tyr Ser Gln Ala Arg Val
        275                 280                 285 atg ctc gtt aag acc ata tca atg att tcg att gtc gat gac acc ttt     912
Met Leu Val Lys Thr Ile Ser Met Ile Ser Ile Val Asp Asp Thr Phe
    290                 295                 300
```

```
gat gct tac ggt aca gtt aaa gaa ctt gag gca tac aca gat gcc ata       960
Asp Ala Tyr Gly Thr Val Lys Glu Leu Glu Ala Tyr Thr Asp Ala Ile
305                 310                 315                 320 caa aga tgg gat atc aac gaa att gat cgg ctt cct gat tac atg aaa      1008
Gln Arg Trp Asp Ile Asn Glu Ile Asp Arg Leu Pro Asp Tyr Met Lys
                325                 330                 335 atc agt tat aaa gct att cta gat ctc tac aag gat tat gaa aag gaa      1056
Ile Ser Tyr Lys Ala Ile Leu Asp Leu Tyr Lys Asp Tyr Glu Lys Glu
            340                 345                 350 ttg tct agt gcc gga aga tct cat att gtc tgc cat gca ata gaa aga      1104
Leu Ser Ser Ala Gly Arg Ser His Ile Val Cys His Ala Ile Glu Arg
        355                 360                 365 atg aaa gaa gta gta aga aat tat aat gtc gag tca aca tgg ttt att      1152
Met Lys Glu Val Val Arg Asn Tyr Asn Val Glu Ser Thr Trp Phe Ile
    370                 375                 380 gaa gga tat atg cca cct gtt tct gaa tac cta agc aat gca cta gca      1200
Glu Gly Tyr Met Pro Pro Val Ser Glu Tyr Leu Ser Asn Ala Leu Ala
385                 390                 395                 400 act acc aca tat tac nns nns gcg aca aca tcg tat ttg ggc atg aag      1248
Thr Thr Thr Tyr Tyr Xaa Xaa Ala Thr Thr Ser Tyr Leu Gly Met Lys
                405                 410                 415 tct gcc acg gag caa gat ttt gag tgg ttg tca aag aat cca aaa att      1296
Ser Ala Thr Glu Gln Asp Phe Glu Trp Leu Ser Lys Asn Pro Lys Ile
            420                 425                 430 ctt gaa gct agt gta att ata tgt cga gtt atc gat gac aca gcc acg      1344
Leu Glu Ala Ser Val Ile Ile Cys Arg Val Ile Asp Asp Thr Ala Thr
        435                 440                 445 tac gag gtt gag aaa agc agg gga caa att gca act gga att gag tgc      1392
Tyr Glu Val Glu Lys Ser Arg Gly Gln Ile Ala Thr Gly Ile Glu Cys
    450                 455                 460 tgc atg aga gat tat ggt ata tca aca aaa gag gca atg gct aaa ttt      1440
Cys Met Arg Asp Tyr Gly Ile Ser Thr Lys Glu Ala Met Ala Lys Phe
465                 470                 475                 480 caa aat atg gct gag aca gca tgg aaa gat att aat gaa gga ctt ctt      1488
Gln Asn Met Ala Glu Thr Ala Trp Lys Asp Ile Asn Glu Gly Leu Leu
                485                 490                 495 agg ccc act ccc gtc tct aca gaa ttt tta act cct att ctc aat ctt      1536
Arg Pro Thr Pro Val Ser Thr Glu Phe Leu Thr Pro Ile Leu Asn Leu
            500                 505                 510 gct cgt att gtt gag gtt aca tat ata cac aat cta gat gga tac act      1584
Ala Arg Ile Val Glu Val Thr Tyr Ile His Asn Leu Asp Gly Tyr Thr
        515                 520                 525 cat ccg gag aaa gtc tta aaa cct cac att att aac cta ctt gtg gac      1632
His Pro Glu Lys Val Leu Lys Pro His Ile Ile Asn Leu Leu Val Asp
    530                 535                 540 tcc atc aaa att                                                       1644
Ser Ile Lys Ile
545

<210> SEQ ID NO 12
<211> LENGTH: 548
<212> TYPE: PRT
<213> ORGANISM: Nicotiana tabacum
<220> FEATURE:
<221> NAME/KEY: VARIANT
<222> LOCATION: (1)...(548)
<223> OTHER INFORMATION: Xaa = Any Amino Acid

<400> SEQUENCE: 12

Met Ala Ser Ala Ala Val Ala Asn Tyr Glu Glu Glu Ile Val Arg Pro
1               5                   10                  15
```

```
Val Ala Asp Phe Ser Pro Ser Leu Trp Gly Asp Gln Phe Leu Ser Phe
             20                  25                  30

Ser Ile Asp Asn Gln Val Ala Glu Lys Tyr Ala Gln Glu Ile Glu Ala
         35                  40                  45

Leu Lys Glu Gln Thr Arg Ser Met Leu Leu Ala Thr Gly Arg Lys Leu
     50                  55                  60

Ala Asp Thr Leu Asn Leu Ile Asp Ile Ile Glu Arg Leu Gly Ile Ser
 65                  70                  75                  80

Tyr His Phe Glu Lys Glu Ile Asp Glu Ile Leu Asp Gln Ile Tyr Asn
                 85                  90                  95

Gln Asn Ser Asn Cys Asn Asp Leu Cys Thr Ser Ala Leu Gln Phe Arg
                100                 105                 110

Leu Leu Arg Gln His Gly Phe Asn Ile Ser Pro Glu Ile Phe Ser Lys
         115                 120                 125

Phe Gln Asp Glu Asn Gly Lys Phe Lys Glu Ser Leu Ala Ser Asp Val
     130                 135                 140

Leu Gly Leu Leu Asn Leu Tyr Glu Ala Ser His Val Arg Thr His Ala
145                 150                 155                 160

Asp Asp Ile Leu Glu Asp Ala Leu Ala Phe Ser Thr Ile His Leu Glu
                165                 170                 175

Ser Ala Ala Pro His Leu Lys Ser Pro Leu Arg Glu Gln Val Thr His
                180                 185                 190

Ala Leu Glu Gln Cys Leu His Lys Gly Val Pro Arg Val Glu Thr Arg
         195                 200                 205

Phe Phe Ile Ser Ser Ile Tyr Asp Lys Glu Gln Ser Lys Asn Asn Val
     210                 215                 220

Leu Leu Arg Phe Ala Lys Leu Asp Phe Asn Leu Leu Gln Met Leu His
225                 230                 235                 240

Lys Gln Glu Leu Ala Gln Val Ser Arg Trp Trp Lys Asp Leu Asp Phe
                245                 250                 255

Val Thr Thr Leu Pro Tyr Ala Arg Asp Arg Val Val Glu Cys Tyr Phe
                260                 265                 270

Trp Ala Leu Gly Val Tyr Phe Glu Pro Gln Tyr Ser Gln Ala Arg Val
         275                 280                 285

Met Leu Val Lys Thr Ile Ser Met Ile Ser Ile Val Asp Asp Thr Phe
     290                 295                 300

Asp Ala Tyr Gly Thr Val Lys Glu Leu Glu Ala Tyr Thr Asp Ala Ile
305                 310                 315                 320

Gln Arg Trp Asp Ile Asn Glu Ile Asp Arg Leu Pro Asp Tyr Met Lys
                325                 330                 335

Ile Ser Tyr Lys Ala Ile Leu Asp Leu Tyr Lys Asp Tyr Glu Lys Glu
                340                 345                 350

Leu Ser Ser Ala Gly Arg Ser His Ile Val Cys His Ala Ile Glu Arg
         355                 360                 365

Met Lys Glu Val Val Arg Asn Tyr Asn Val Glu Ser Thr Trp Phe Ile
     370                 375                 380

Glu Gly Tyr Met Pro Pro Val Ser Glu Tyr Leu Ser Asn Ala Leu Ala
385                 390                 395                 400

Thr Thr Thr Tyr Tyr Xaa Xaa Ala Thr Thr Ser Tyr Leu Gly Met Lys
                405                 410                 415

Ser Ala Thr Glu Gln Asp Phe Glu Trp Leu Ser Lys Asn Pro Lys Ile
         420                 425                 430
```

```
Leu Glu Ala Ser Val Ile Ile Cys Arg Val Ile Asp Asp Thr Ala Thr
            435                 440                 445

Tyr Glu Val Glu Lys Ser Arg Gly Gln Ile Ala Thr Gly Ile Glu Cys
        450                 455                 460

Cys Met Arg Asp Tyr Gly Ile Ser Thr Lys Glu Ala Met Ala Lys Phe
465                 470                 475                 480

Gln Asn Met Ala Glu Thr Ala Trp Lys Asp Ile Asn Glu Gly Leu Leu
                485                 490                 495

Arg Pro Thr Pro Val Ser Thr Glu Phe Leu Thr Pro Ile Leu Asn Leu
            500                 505                 510

Ala Arg Ile Val Glu Val Thr Tyr Ile His Asn Leu Asp Gly Tyr Thr
        515                 520                 525

His Pro Glu Lys Val Leu Lys Pro His Ile Ile Asn Leu Leu Val Asp
            530                 535                 540

Ser Ile Lys Ile
545

<210> SEQ ID NO 13
<211> LENGTH: 33
<212> TYPE: DNA
<213> ORGANISM: Artificial Sequence
<220> FEATURE:
<223> OTHER INFORMATION: primer for mutagenesis

<400> SEQUENCE: 13
gttgaatgct acttttcggc attaggagtt tat                           33

<210> SEQ ID NO 14
<211> LENGTH: 33
<212> TYPE: DNA
<213> ORGANISM: Artificial Sequence
<220> FEATURE:
<223> OTHER INFORMATION: primer for mutagenesis

<400> SEQUENCE: 14
ataaactcct aatgccgaaa agtagcattc aac                           33

<210> SEQ ID NO 15
<211> LENGTH: 33
<212> TYPE: DNA
<213> ORGANISM: Artificial Sequence
<220> FEATURE:
<223> OTHER INFORMATION: primer for mutagenesis

<400> SEQUENCE: 15
gctagtgtaa ttatatggcg agttatcgat gac                           33

<210> SEQ ID NO 16
<211> LENGTH: 33
<212> TYPE: DNA
<213> ORGANISM: Artificial Sequence
<220> FEATURE:
<223> OTHER INFORMATION: primer for mutagenesis

<400> SEQUENCE: 16
gtcatcgata actcgccata taattacact agc                           33

<210> SEQ ID NO 17
<211> LENGTH: 54
<212> TYPE: DNA
<213> ORGANISM: Artificial Sequence
<220> FEATURE:
<223> OTHER INFORMATION: primer for mutagenesis
```

-continued

```
<221> NAME/KEY: misc_feature
<222> LOCATION: (1)...(54)
<223> OTHER INFORMATION: n = A,T,C or G
<400> SEQUENCE: 17
gcactagcaa ctaccacata ttacnnsnns gcgacaacat cgtatttggg catg          54

<210> SEQ ID NO 18
<211> LENGTH: 54
<212> TYPE: DNA
<213> ORGANISM: Artificial Sequence
<220> FEATURE:
<223> OTHER INFORMATION: primer for mutagenesis
<221> NAME/KEY: misc_feature
<222> LOCATION: (1)...(54)
<223> OTHER INFORMATION: n = A,T,C or G

<400> SEQUENCE: 18
catgcccaaa tacgatgttg tcgcsnnsnn gtaatatgtg gtagttgcta gtgc          54

<210> SEQ ID NO 19
<211> LENGTH: 2018
<212> TYPE: DNA
<213> ORGANISM: Abies grandis
<220> FEATURE:
<221> NAME/KEY: CDS
<222> LOCATION: (6)...(1889)
<223> OTHER INFORMATION: pinene synthase

<400> SEQUENCE: 19
```

| | | | | | | | | | | | | | | | | |
|---|---|---|---|---|---|---|---|---|---|---|---|---|---|---|---|---|
| cagca | atg | gct | cta | gtt | tct | acc | gca | ccg | ttg | gct | tcc | aaa | tca | tgc | ctg | 50 |
| | Met | Ala | Leu | Val | Ser | Thr | Ala | Pro | Leu | Ala | Ser | Lys | Ser | Cys | Leu | |
| | 1 | | | 5 | | | | | 10 | | | | | 15 | | |

| cac | aaa | tcg | ttg | atc | agt | tct | acc | cat | gag | ctt | aag | gct | ctc | tct | aga | 98 |
|---|---|---|---|---|---|---|---|---|---|---|---|---|---|---|---|---|
| His | Lys | Ser | Leu | Ile | Ser | Ser | Thr | His | Glu | Leu | Lys | Ala | Leu | Ser | Arg | |
| | | | 20 | | | | | 25 | | | | | 30 | | | |

| aca | att | cca | gct | cta | gga | atg | agt | agg | cga | ggg | aaa | tct | atc | act | cct | 146 |
|---|---|---|---|---|---|---|---|---|---|---|---|---|---|---|---|---|
| Thr | Ile | Pro | Ala | Leu | Gly | Met | Ser | Arg | Arg | Gly | Lys | Ser | Ile | Thr | Pro | |
| | | | 35 | | | | | 40 | | | | | 45 | | | |

| tcc | atc | agc | atg | agc | tct | acc | acc | gtt | gta | acc | gat | gat | ggt | gta | cga | 194 |
|---|---|---|---|---|---|---|---|---|---|---|---|---|---|---|---|---|
| Ser | Ile | Ser | Met | Ser | Ser | Thr | Thr | Val | Val | Thr | Asp | Asp | Gly | Val | Arg | |
| | 50 | | | | | 55 | | | | | 60 | | | | | |

| aga | cgc | atg | ggc | gat | ttc | cat | tcc | aac | ctc | tgg | gac | gat | gat | gtc | ata | 242 |
|---|---|---|---|---|---|---|---|---|---|---|---|---|---|---|---|---|
| Arg | Arg | Met | Gly | Asp | Phe | His | Ser | Asn | Leu | Trp | Asp | Asp | Asp | Val | Ile | |
| 65 | | | | | 70 | | | | | 75 | | | | | | |

| cag | tct | tta | cca | acg | gct | tat | gag | gaa | aaa | tcg | tac | ctg | gag | cgt | gct | 290 |
|---|---|---|---|---|---|---|---|---|---|---|---|---|---|---|---|---|
| Gln | Ser | Leu | Pro | Thr | Ala | Tyr | Glu | Glu | Lys | Ser | Tyr | Leu | Glu | Arg | Ala | |
| 80 | | | | | 85 | | | | | 90 | | | | | 95 | |

| gag | aaa | ctg | atc | ggg | gaa | gta | aag | aac | atg | ttc | aat | tcg | atg | tca | tta | 338 |
|---|---|---|---|---|---|---|---|---|---|---|---|---|---|---|---|---|
| Glu | Lys | Leu | Ile | Gly | Glu | Val | Lys | Asn | Met | Phe | Asn | Ser | Met | Ser | Leu | |
| | | | | 100 | | | | | 105 | | | | | 110 | | |

| gaa | gat | gga | gag | tta | atg | agt | ccg | ctc | aat | gat | ctc | att | caa | cgc | ctt | 386 |
|---|---|---|---|---|---|---|---|---|---|---|---|---|---|---|---|---|
| Glu | Asp | Gly | Glu | Leu | Met | Ser | Pro | Leu | Asn | Asp | Leu | Ile | Gln | Arg | Leu | |
| | | | 115 | | | | | 120 | | | | | 125 | | | |

| tgg | att | gtc | gac | agc | ctt | gaa | cgt | ttg | ggg | atc | cat | aga | cat | ttc | aaa | 434 |
|---|---|---|---|---|---|---|---|---|---|---|---|---|---|---|---|---|
| Trp | Ile | Val | Asp | Ser | Leu | Glu | Arg | Leu | Gly | Ile | His | Arg | His | Phe | Lys | |
| | | 130 | | | | | 135 | | | | | 140 | | | | |

| gat | gag | ata | aaa | tcg | gcg | ctt | gat | tat | gtt | tac | agt | tat | tgg | ggc | gaa | 482 |
|---|---|---|---|---|---|---|---|---|---|---|---|---|---|---|---|---|
| Asp | Glu | Ile | Lys | Ser | Ala | Leu | Asp | Tyr | Val | Tyr | Ser | Tyr | Trp | Gly | Glu | |
| | 145 | | | | | 150 | | | | | 155 | | | | | |

| aat | ggc | atc | gga | tgc | ggg | agg | gag | agt | gtt | gtt | act | gat | ctg | aac | tca | 530 |
|---|---|---|---|---|---|---|---|---|---|---|---|---|---|---|---|---|
| Asn | Gly | Ile | Gly | Cys | Gly | Arg | Glu | Ser | Val | Val | Thr | Asp | Leu | Asn | Ser | |
| 160 | | | | | 165 | | | | | 170 | | | | | 175 | |

| act | gcg | ttg | ggg | ctt | cga | acc | cta | cga | cta | cac | gga | tac | ccg | gtg | tct | 578 |
|---|---|---|---|---|---|---|---|---|---|---|---|---|---|---|---|---|

```
Thr Ala Leu Gly Leu Arg Thr Leu Arg Leu His Gly Tyr Pro Val Ser
            180                 185                 190 tca gat gtt ttc aaa gct ttc aaa ggc caa aat ggg cag ttt tcc tgc         626
Ser Asp Val Phe Lys Ala Phe Lys Gly Gln Asn Gly Gln Phe Ser Cys
            195                 200                 205 tct gaa aat att cag aca gat gaa gag atc aga ggc gtt ctg aat tta         674
Ser Glu Asn Ile Gln Thr Asp Glu Glu Ile Arg Gly Val Leu Asn Leu
            210                 215                 220 ttc cgg gcc tcc ctc att gcc ttt cca ggg gag aaa att atg gat gag         722
Phe Arg Ala Ser Leu Ile Ala Phe Pro Gly Glu Lys Ile Met Asp Glu
225                 230                 235 gct gaa atc ttc tct acc aaa tat tta aaa gaa gcc ctg caa aag att         770
Ala Glu Ile Phe Ser Thr Lys Tyr Leu Lys Glu Ala Leu Gln Lys Ile
240                 245                 250                 255 ccg gtc tcc agt ctt tcg cga gag atc ggg gac gtt ttg gaa tat ggt         818
Pro Val Ser Ser Leu Ser Arg Glu Ile Gly Asp Val Leu Glu Tyr Gly
                260                 265                 270 tgg cac aca tat ttg ccg cga ttg gaa gca agg aat tac atc caa gtc         866
Trp His Thr Tyr Leu Pro Arg Leu Glu Ala Arg Asn Tyr Ile Gln Val
                275                 280                 285 ttt gga cag gac act gag aac acg aag tca tat gtg aag agc aaa aaa         914
Phe Gly Gln Asp Thr Glu Asn Thr Lys Ser Tyr Val Lys Ser Lys Lys
            290                 295                 300 ctt tta gaa ctc gca aaa ttg gag ttc aac atc ttt caa tcc tta caa         962
Leu Leu Glu Leu Ala Lys Leu Glu Phe Asn Ile Phe Gln Ser Leu Gln
305                 310                 315 aag agg gag tta gaa agt ctg gtc aga tgg tgg aaa gaa tcg ggt ttt        1010
Lys Arg Glu Leu Glu Ser Leu Val Arg Trp Trp Lys Glu Ser Gly Phe
320                 325                 330                 335 cct gag atg acc ttc tgc cga cat cgt cac gtg gaa tac tac act ttg        1058
Pro Glu Met Thr Phe Cys Arg His Arg His Val Glu Tyr Tyr Thr Leu
                340                 345                 350 gct tcc tgc att gcg ttc gag cct caa cat tct gga ttc aga ctc ggc        1106
Ala Ser Cys Ile Ala Phe Glu Pro Gln His Ser Gly Phe Arg Leu Gly
                355                 360                 365 ttt gcc aag acg tgt cat ctt atc acg gtt ctt gac gat atg tac gac        1154
Phe Ala Lys Thr Cys His Leu Ile Thr Val Leu Asp Asp Met Tyr Asp
            370                 375                 380 acc ttc ggc aca gta gac gag ctg gaa ctc ttc aca gcg aca atg aag        1202
Thr Phe Gly Thr Val Asp Glu Leu Glu Leu Phe Thr Ala Thr Met Lys
            385                 390                 395 aga tgg gat ccg tcc tcg ata gat tgc ctt cca gaa tat atg aaa gga        1250
Arg Trp Asp Pro Ser Ser Ile Asp Cys Leu Pro Glu Tyr Met Lys Gly
400                 405                 410                 415 gtg tac ata gcg gtt tac gac acc gta aat gaa atg gct cga gag gca        1298
Val Tyr Ile Ala Val Tyr Asp Thr Val Asn Glu Met Ala Arg Glu Ala
                420                 425                 430 gag gag gct caa ggc cga gat acg ctc aca tat gct cgg gaa gct tgg        1346
Glu Glu Ala Gln Gly Arg Asp Thr Leu Thr Tyr Ala Arg Glu Ala Trp
                435                 440                 445 gag gct tat att gat tcg tat atg caa gaa gca agg tgg atc gcc act        1394
Glu Ala Tyr Ile Asp Ser Tyr Met Gln Glu Ala Arg Trp Ile Ala Thr
            450                 455                 460 ggt tac ctg ccc tcc ttt gat gag tac tac gag aat ggg aaa gtt agc        1442
Gly Tyr Leu Pro Ser Phe Asp Glu Tyr Tyr Glu Asn Gly Lys Val Ser
            465                 470                 475 tgt ggt cat cgc ata tcc gca ttg caa ccc att ctg aca atg gac atc        1490
Cys Gly His Arg Ile Ser Ala Leu Gln Pro Ile Leu Thr Met Asp Ile
480                 485                 490                 495
```

```
ccc ttt cct gat cat atc ctc aag gaa gtt gac ttc cca tca aag ctt    1538
Pro Phe Pro Asp His Ile Leu Lys Glu Val Asp Phe Pro Ser Lys Leu
            500                 505                 510 aac gac ttg gca tgt gcc atc ctt cga tta cga ggt gat acg cgg tgc    1586
Asn Asp Leu Ala Cys Ala Ile Leu Arg Leu Arg Gly Asp Thr Arg Cys
            515                 520                 525 tac aag gcg gac agg gct cgt gga gaa gaa gct tcc tct ata tca tgt    1634
Tyr Lys Ala Asp Arg Ala Arg Gly Glu Glu Ala Ser Ser Ile Ser Cys
            530                 535                 540 tat atg aaa gac aat cct gga gta tca gag gaa gat gct ctc gat cat    1682
Tyr Met Lys Asp Asn Pro Gly Val Ser Glu Glu Asp Ala Leu Asp His
        545                 550                 555 atc aac gcc atg atc agt gac gta atc aaa gga tta aat tgg gaa ctt    1730
Ile Asn Ala Met Ile Ser Asp Val Ile Lys Gly Leu Asn Trp Glu Leu
560                 565                 570                 575 ctc aaa cca gac atc aat gtt ccc atc tcg gcg aag aaa cat gct ttt    1778
Leu Lys Pro Asp Ile Asn Val Pro Ile Ser Ala Lys Lys His Ala Phe
                580                 585                 590 gac atc gcc aga gct ttc cat tac ggc tac aaa tac cga gac ggc tac    1826
Asp Ile Ala Arg Ala Phe His Tyr Gly Tyr Lys Tyr Arg Asp Gly Tyr
            595                 600                 605 agc gtt gcc aac gtt gaa acg aag agt ttg gtc acg aga acc ctc ctt    1874
Ser Val Ala Asn Val Glu Thr Lys Ser Leu Val Thr Arg Thr Leu Leu
            610                 615                 620 gaa tct gtg cct ttg tag caacagctca aatctatgcc ctatgctatg           1922
Glu Ser Val Pro Leu
        625 tcgggttaaa atatatgtgg aaggtagccg ttggatgtag aggataagtt tgttataatt  1982 taataaagtt gtaatttaaa aaaaaaaaaa aaaaaa                            2018

<210> SEQ ID NO 20
<211> LENGTH: 628
<212> TYPE: PRT
<213> ORGANISM: Abies grandis

<400> SEQUENCE: 20

Met Ala Leu Val Ser Thr Ala Pro Leu Ala Ser Lys Ser Cys Leu His
1               5                   10                  15

Lys Ser Leu Ile Ser Ser Thr His Glu Leu Lys Ala Leu Ser Arg Thr
            20                  25                  30

Ile Pro Ala Leu Gly Met Ser Arg Arg Gly Lys Ser Ile Thr Pro Ser
        35                  40                  45

Ile Ser Met Ser Ser Thr Thr Val Val Thr Asp Asp Gly Val Arg Arg
    50                  55                  60

Arg Met Gly Asp Phe His Ser Asn Leu Trp Asp Asp Val Ile Gln
65                  70                  75                  80

Ser Leu Pro Thr Ala Tyr Glu Glu Lys Ser Tyr Leu Glu Arg Ala Glu
            85                  90                  95

Lys Leu Ile Gly Glu Val Lys Asn Met Phe Asn Ser Met Ser Leu Glu
        100                 105                 110

Asp Gly Glu Leu Met Ser Pro Leu Asn Asp Leu Ile Gln Arg Leu Trp
    115                 120                 125

Ile Val Asp Ser Leu Glu Arg Leu Gly Ile His Arg His Phe Lys Asp
130                 135                 140

Glu Ile Lys Ser Ala Leu Asp Tyr Val Tyr Ser Tyr Trp Gly Glu Asn
145                 150                 155                 160
```

-continued

```
Gly Ile Gly Cys Gly Arg Glu Ser Val Val Thr Asp Leu Asn Ser Thr
                165                 170                 175
Ala Leu Gly Leu Arg Thr Leu Arg Leu His Gly Tyr Pro Val Ser Ser
            180                 185                 190
Asp Val Phe Lys Ala Phe Lys Gly Gln Asn Gly Gln Phe Ser Cys Ser
        195                 200                 205
Glu Asn Ile Gln Thr Asp Glu Glu Ile Arg Gly Val Leu Asn Leu Phe
    210                 215                 220
Arg Ala Ser Leu Ile Ala Phe Pro Gly Glu Lys Ile Met Asp Glu Ala
225                 230                 235                 240
Glu Ile Phe Ser Thr Lys Tyr Leu Lys Glu Ala Leu Gln Lys Ile Pro
                245                 250                 255
Val Ser Ser Leu Ser Arg Glu Ile Gly Asp Val Leu Glu Tyr Gly Trp
            260                 265                 270
His Thr Tyr Leu Pro Arg Leu Glu Ala Arg Asn Tyr Ile Gln Val Phe
        275                 280                 285
Gly Gln Asp Thr Glu Asn Thr Lys Ser Tyr Val Lys Ser Lys Lys Leu
    290                 295                 300
Leu Glu Leu Ala Lys Leu Glu Phe Asn Ile Phe Gln Ser Leu Gln Lys
305                 310                 315                 320
Arg Glu Leu Glu Ser Leu Val Arg Trp Trp Lys Glu Ser Gly Phe Pro
                325                 330                 335
Glu Met Thr Phe Cys Arg His Arg His Val Glu Tyr Tyr Thr Leu Ala
            340                 345                 350
Ser Cys Ile Ala Phe Glu Pro Gln His Ser Gly Phe Arg Leu Gly Phe
        355                 360                 365
Ala Lys Thr Cys His Leu Ile Thr Val Leu Asp Asp Met Tyr Asp Thr
    370                 375                 380
Phe Gly Thr Val Asp Glu Leu Glu Leu Phe Thr Ala Thr Met Lys Arg
385                 390                 395                 400
Trp Asp Pro Ser Ser Ile Asp Cys Leu Pro Glu Tyr Met Lys Gly Val
                405                 410                 415
Tyr Ile Ala Val Tyr Asp Thr Val Asn Glu Met Ala Arg Glu Ala Glu
            420                 425                 430
Glu Ala Gln Gly Arg Asp Thr Leu Thr Tyr Ala Arg Glu Ala Trp Glu
        435                 440                 445
Ala Tyr Ile Asp Ser Tyr Met Gln Glu Ala Arg Trp Ile Ala Thr Gly
    450                 455                 460
Tyr Leu Pro Ser Phe Asp Glu Tyr Tyr Glu Asn Gly Lys Val Ser Cys
465                 470                 475                 480
Gly His Arg Ile Ser Ala Leu Gln Pro Ile Leu Thr Met Asp Ile Pro
                485                 490                 495
Phe Pro Asp His Ile Leu Lys Glu Val Asp Phe Pro Ser Lys Leu Asn
            500                 505                 510
Asp Leu Ala Cys Ala Ile Leu Arg Leu Arg Gly Asp Thr Arg Cys Tyr
        515                 520                 525
Lys Ala Asp Arg Ala Arg Gly Glu Ala Ser Ser Ile Ser Cys Tyr
    530                 535                 540
Met Lys Asp Asn Pro Gly Val Ser Glu Glu Asp Ala Leu Asp His Ile
545                 550                 555                 560
Asn Ala Met Ile Ser Asp Val Ile Lys Gly Leu Asn Trp Glu Leu Leu
                565                 570                 575
Lys Pro Asp Ile Asn Val Pro Ile Ser Ala Lys Lys His Ala Phe Asp
```

-continued

```
                    580                 585                 590
Ile Ala Arg Ala Phe His Tyr Gly Tyr Lys Tyr Arg Asp Gly Tyr Ser
            595                 600                 605
Val Ala Asn Val Glu Thr Lys Ser Leu Val Thr Arg Thr Leu Leu Glu
        610                 615                 620
Ser Val Pro Leu
625

<210> SEQ ID NO 21
<211> LENGTH: 2170
<212> TYPE: DNA
<213> ORGANISM: Mentha spicata
<220> FEATURE:
<221> NAME/KEY: CDS
<222> LOCATION: (29)...(1825)
<223> OTHER INFORMATION: 4S-limonene synthase

<400> SEQUENCE: 21
agagagagag aggaaggaaa gattaatc atg gct ctc aaa gtg tta agt gtt        52
                             Met Ala Leu Lys Val Leu Ser Val
                              1               5 gca act caa atg gcg att cct agc aac cta acg aca tgt ctt caa ccc      100
Ala Thr Gln Met Ala Ile Pro Ser Asn Leu Thr Thr Cys Leu Gln Pro
 10                  15                  20 tca cac ttc aaa tct tct cca aaa ctg tta tct agc act aac agt agt     148
Ser His Phe Lys Ser Ser Pro Lys Leu Leu Ser Ser Thr Asn Ser Ser
 25                  30                  35                  40 agt cgg tct cgc ctc cgt gtg tat tgc tcc tcc tcg caa ctc act act     196
Ser Arg Ser Arg Leu Arg Val Tyr Cys Ser Ser Ser Gln Leu Thr Thr
                 45                  50                  55 gaa aga cga tcc gga aac tac aac cct tct cgt tgg gat gtc aac ttc     244
Glu Arg Arg Ser Gly Asn Tyr Asn Pro Ser Arg Trp Asp Val Asn Phe
             60                  65                  70 atc caa tcg ctt ctc agt gac tat aag gag gac aaa cac gtg att agg     292
Ile Gln Ser Leu Leu Ser Asp Tyr Lys Glu Asp Lys His Val Ile Arg
     75                  80                  85 gct tct gag ctg gtc act ttg gtg aag atg gaa ctg gag aaa gaa acg     340
Ala Ser Glu Leu Val Thr Leu Val Lys Met Glu Leu Glu Lys Glu Thr
 90                  95                 100 gat caa att cga caa ctt gag ttg atc gat gac ttg cag agg atg ggg     388
Asp Gln Ile Arg Gln Leu Glu Leu Ile Asp Asp Leu Gln Arg Met Gly
105                 110                 115                 120 ctg tcc gat cat ttc caa aat gag ttc aaa gaa atc ttg tcc tct ata     436
Leu Ser Asp His Phe Gln Asn Glu Phe Lys Glu Ile Leu Ser Ser Ile
                125                 130                 135 tat ctc gac cat cac tat tac aag aac cct ttt cca aaa gaa gaa agg     484
Tyr Leu Asp His His Tyr Tyr Lys Asn Pro Phe Pro Lys Glu Glu Arg
            140                 145                 150 gat ctc tac tcc aca tct ctt gca ttt agg ctc ctc aga gaa cat ggt     532
Asp Leu Tyr Ser Thr Ser Leu Ala Phe Arg Leu Leu Arg Glu His Gly
        155                 160                 165 ttt caa gtc gca caa gag gta ttc gat agt ttc aag aac gag gag ggt     580
Phe Gln Val Ala Gln Glu Val Phe Asp Ser Phe Lys Asn Glu Glu Gly
    170                 175                 180 gag ttc aaa gaa agc ctt agc gac gac acc aga gga ttg ttg caa ctg     628
Glu Phe Lys Glu Ser Leu Ser Asp Asp Thr Arg Gly Leu Leu Gln Leu
185                 190                 195                 200 tat gaa gct tcc ttt ctg ttg acg gaa ggc gaa acc acg ctc gag tca     676
Tyr Glu Ala Ser Phe Leu Leu Thr Glu Gly Glu Thr Thr Leu Glu Ser
                205                 210                 215
```

```
gcg agg gaa ttc gcc acc aaa ttt ttg gag gaa aaa gtg aac gag ggt      724
Ala Arg Glu Phe Ala Thr Lys Phe Leu Glu Glu Lys Val Asn Glu Gly
        220                 225                 230 ggt gtt gat ggc gac ctt tta aca aga atc gca tat tct ttg gac atc      772
Gly Val Asp Gly Asp Leu Leu Thr Arg Ile Ala Tyr Ser Leu Asp Ile
235                 240                 245 cct ctt cat tgg agg att aaa agg cca aat gca cct gtg tgg atc gaa      820
Pro Leu His Trp Arg Ile Lys Arg Pro Asn Ala Pro Val Trp Ile Glu
    250                 255                 260 tgg tat agg aag agg ccc gac atg aat cca gta gtg ttg gag ctt gcc      868
Trp Tyr Arg Lys Arg Pro Asp Met Asn Pro Val Val Leu Glu Leu Ala
265                 270                 275                 280 ata ctc gac tta aat att gtt caa gca caa ttt caa gaa gag ctc aaa      916
Ile Leu Asp Leu Asn Ile Val Gln Ala Gln Phe Gln Glu Glu Leu Lys
                285                 290                 295 gaa tcc ttc agg tgg tgg aga aat act ggg ttt gtt gag aag ctg ccc      964
Glu Ser Phe Arg Trp Trp Arg Asn Thr Gly Phe Val Glu Lys Leu Pro
            300                 305                 310 ttc gca agg gat aga ctg gtg gaa tgc tac ttt tgg aat act ggg atc     1012
Phe Ala Arg Asp Arg Leu Val Glu Cys Tyr Phe Trp Asn Thr Gly Ile
        315                 320                 325 atc gag cca cgt cag cat gca agt gca agg ata atg atg ggc aaa gtc     1060
Ile Glu Pro Arg Gln His Ala Ser Ala Arg Ile Met Met Gly Lys Val
330                 335                 340 aac gct ctg att acg gtg atc gat gat att tat gat gtc tat ggc acc     1108
Asn Ala Leu Ile Thr Val Ile Asp Asp Ile Tyr Asp Val Tyr Gly Thr
345                 350                 355                 360 tta gaa gaa ctc gaa caa ttc act gac ctc att cga aga tgg gat ata     1156
Leu Glu Glu Leu Glu Gln Phe Thr Asp Leu Ile Arg Arg Trp Asp Ile
                365                 370                 375 aac tca atc gac caa ctt ccc gat tac atg caa ctg tgc ttt ctt gca     1204
Asn Ser Ile Asp Gln Leu Pro Asp Tyr Met Gln Leu Cys Phe Leu Ala
            380                 385                 390 ctc aac aac ttc gtc gat gat aca tcg tac gat gtt atg aag gag aaa     1252
Leu Asn Asn Phe Val Asp Asp Thr Ser Tyr Asp Val Met Lys Glu Lys
        395                 400                 405 ggc gtc aac gtt ata ccc tac ctg cgg caa tcg tgg gtt gat ttg gcg     1300
Gly Val Asn Val Ile Pro Tyr Leu Arg Gln Ser Trp Val Asp Leu Ala
410                 415                 420 gat aag tat atg gta gag gca cgg tgg ttc tac ggc ggg cac aaa cca     1348
Asp Lys Tyr Met Val Glu Ala Arg Trp Phe Tyr Gly Gly His Lys Pro
425                 430                 435                 440 agt ttg gaa gag tat ttg gag aac tca tgg cag tcg ata agt ggg ccc     1396
Ser Leu Glu Glu Tyr Leu Glu Asn Ser Trp Gln Ser Ile Ser Gly Pro
                445                 450                 455 tgt atg tta acg cac ata ttc ttc cga gta aca gat tcg ttc aca aag     1444
Cys Met Leu Thr His Ile Phe Phe Arg Val Thr Asp Ser Phe Thr Lys
            460                 465                 470 gag acc gtc gac agt ttg tac aaa tac cac gat tta gtt cgt tgg tca     1492
Glu Thr Val Asp Ser Leu Tyr Lys Tyr His Asp Leu Val Arg Trp Ser
        475                 480                 485 tcc ttc gtt ctg cgg ctt gct gat gat ttg gga acc tcg gtg gaa gag     1540
Ser Phe Val Leu Arg Leu Ala Asp Asp Leu Gly Thr Ser Val Glu Glu
    490                 495                 500 gtg agc aga ggg gat gtg ccg aaa tca ctt cag tgc tac atg agt gac     1588
Val Ser Arg Gly Asp Val Pro Lys Ser Leu Gln Cys Tyr Met Ser Asp
505                 510                 515                 520 tac aat gca tcg gag gcg gag gcg cgg aag cac gtg aaa tgg ctg ata     1636
Tyr Asn Ala Ser Glu Ala Glu Ala Arg Lys His Val Lys Trp Leu Ile
                525                 530                 535
```

```
gcg gag gtg tgg aag aag atg aat gcg gag agg gtg tcg aag gat tct      1684
Ala Glu Val Trp Lys Lys Met Asn Ala Glu Arg Val Ser Lys Asp Ser
            540                 545                 550 cca ttc ggc aaa gat ttt ata gga tgt gca gtt gat tta gga agg atg      1732
Pro Phe Gly Lys Asp Phe Ile Gly Cys Ala Val Asp Leu Gly Arg Met
            555                 560                 565 gcg cag ttg atg tac cat aat gga gat ggg cac ggc aca caa cac cct      1780
Ala Gln Leu Met Tyr His Asn Gly Asp Gly His Gly Thr Gln His Pro
            570                 575                 580 att ata cat caa caa atg acc aga acc tta ttc gag ccc ttt gca tga      1828
Ile Ile His Gln Gln Met Thr Arg Thr Leu Phe Glu Pro Phe Ala
585                 590                 595 gagatgatga cgagccatcg tttacttact taaattctac caaagttttt cgaaggcata   1888
gttcgtaatt tttcaagcac caataaataa ggagaatcgg ctcaaacaaa cgtggcattt   1948
gccaccacgt gagcacaagg gagagtctgt cgtcgtttat ggatgaacta ttcaattttt   2008
atgcatgtaa taattaagtt caagttcaag agccttctgc atatttaact atgtatttga   2068
atttatcgag tgtgattttc tgtctttggc aacatatatt tttgtcatat gtggcatctt   2128
attatgatat catacagtgt ttatggatga tatgatacta tc                      2170
```

<210> SEQ ID NO 22
<211> LENGTH: 599
<212> TYPE: PRT
<213> ORGANISM: Mentha spicata

<400> SEQUENCE: 22

```
Met Ala Leu Lys Val Leu Ser Val Ala Thr Gln Met Ala Ile Pro Ser
1               5                   10                  15

Asn Leu Thr Thr Cys Leu Gln Pro Ser His Phe Lys Ser Ser Pro Lys
            20                  25                  30

Leu Leu Ser Ser Thr Asn Ser Ser Arg Ser Arg Leu Arg Val Tyr
        35                  40                  45

Cys Ser Ser Ser Gln Leu Thr Thr Glu Arg Arg Ser Gly Asn Tyr Asn
    50                  55                  60

Pro Ser Arg Trp Asp Val Asn Phe Ile Gln Ser Leu Leu Ser Asp Tyr
65                  70                  75                  80

Lys Glu Asp Lys His Val Ile Arg Ala Ser Glu Leu Val Thr Leu Val
                85                  90                  95

Lys Met Glu Leu Glu Lys Glu Thr Asp Gln Ile Arg Gln Leu Glu Leu
            100                 105                 110

Ile Asp Asp Leu Gln Arg Met Gly Leu Ser Asp His Phe Gln Asn Glu
        115                 120                 125

Phe Lys Glu Ile Leu Ser Ser Ile Tyr Leu Asp His His Tyr Tyr Lys
    130                 135                 140

Asn Pro Phe Pro Lys Glu Glu Arg Asp Leu Tyr Ser Thr Ser Leu Ala
145                 150                 155                 160

Phe Arg Leu Leu Arg Glu His Gly Phe Gln Val Ala Gln Glu Val Phe
                165                 170                 175

Asp Ser Phe Lys Asn Glu Glu Gly Glu Phe Lys Glu Ser Leu Ser Asp
            180                 185                 190

Asp Thr Arg Gly Leu Leu Gln Leu Tyr Glu Ala Ser Phe Leu Leu Thr
        195                 200                 205

Glu Gly Glu Thr Thr Leu Glu Ser Ala Arg Glu Phe Ala Thr Lys Phe
    210                 215                 220
```

```
Leu Glu Glu Lys Val Asn Glu Gly Val Asp Gly Asp Leu Leu Thr
225                 230                 235                 240

Arg Ile Ala Tyr Ser Leu Asp Ile Pro Leu His Trp Arg Ile Lys Arg
            245                 250                 255

Pro Asn Ala Pro Val Trp Ile Glu Trp Tyr Arg Lys Arg Pro Asp Met
                260                 265                 270

Asn Pro Val Val Leu Glu Leu Ala Ile Leu Asp Leu Asn Ile Val Gln
            275                 280                 285

Ala Gln Phe Gln Glu Glu Leu Lys Glu Ser Phe Arg Trp Trp Arg Asn
        290                 295                 300

Thr Gly Phe Val Glu Lys Leu Pro Phe Ala Arg Asp Arg Leu Val Glu
305                 310                 315                 320

Cys Tyr Phe Trp Asn Thr Gly Ile Ile Glu Pro Arg Gln His Ala Ser
                325                 330                 335

Ala Arg Ile Met Met Gly Lys Val Asn Ala Leu Ile Thr Val Ile Asp
            340                 345                 350

Asp Ile Tyr Asp Val Tyr Gly Thr Leu Glu Glu Leu Glu Gln Phe Thr
        355                 360                 365

Asp Leu Ile Arg Arg Trp Asp Ile Asn Ser Ile Asp Gln Leu Pro Asp
370                 375                 380

Tyr Met Gln Leu Cys Phe Leu Ala Leu Asn Asn Phe Val Asp Asp Thr
385                 390                 395                 400

Ser Tyr Asp Val Met Lys Glu Lys Gly Val Asn Val Ile Pro Tyr Leu
                405                 410                 415

Arg Gln Ser Trp Val Asp Leu Ala Asp Lys Tyr Met Val Glu Ala Arg
            420                 425                 430

Trp Phe Tyr Gly Gly His Lys Pro Ser Leu Glu Glu Tyr Leu Glu Asn
        435                 440                 445

Ser Trp Gln Ser Ile Ser Gly Pro Cys Met Leu Thr His Ile Phe Phe
450                 455                 460

Arg Val Thr Asp Ser Phe Thr Lys Glu Thr Val Asp Ser Leu Tyr Lys
465                 470                 475                 480

Tyr His Asp Leu Val Arg Trp Ser Ser Phe Val Leu Arg Leu Ala Asp
                485                 490                 495

Asp Leu Gly Thr Ser Val Glu Glu Val Ser Arg Gly Asp Val Pro Lys
            500                 505                 510

Ser Leu Gln Cys Tyr Met Ser Asp Tyr Asn Ala Ser Glu Ala Glu Ala
        515                 520                 525

Arg Lys His Val Lys Trp Leu Ile Ala Glu Val Trp Lys Lys Met Asn
530                 535                 540

Ala Glu Arg Val Ser Lys Asp Ser Pro Phe Gly Lys Asp Phe Ile Gly
545                 550                 555                 560

Cys Ala Val Asp Leu Gly Arg Met Ala Gln Leu Met Tyr His Asn Gly
                565                 570                 575

Asp Gly His Gly Thr Gln His Pro Ile Ile His Gln Gln Met Thr Arg
            580                 585                 590

Thr Leu Phe Glu Pro Phe Ala
            595

<210> SEQ ID NO 23
<211> LENGTH: 1967
<212> TYPE: DNA
<213> ORGANISM: Salvia officinalis
<220> FEATURE:
<221> NAME/KEY: CDS
```

<222> LOCATION: (13)...(1785)
<223> OTHER INFORMATION: 1,8-cineole synthase

<400> SEQUENCE: 23

| | | | | | | | | | | | | | |
|---|---|---|---|---|---|---|---|---|---|---|---|---|---|
| gatcaccaca ag | atg | tcg | agt | ctt | ata | atg | caa | gtt | gtt | att | cct | aag cca | 51 |
| | Met | Ser | Ser | Leu | Ile | Met | Gln | Val | Val | Ile | Pro | Lys Pro | |
| | 1 | | | | 5 | | | | | 10 | | | |
| gcc | aaa | att | ttt | cac | aat | aac | tta | ttc | agc | gtg | att | tca | aaa cga cat | 99 |
| Ala | Lys | Ile | Phe | His | Asn | Asn | Leu | Phe | Ser | Val | Ile | Ser | Lys Arg His | |
| 15 | | | | | 20 | | | | | 25 | | | | |
| cgt | ttc | agt | act | aca | atc | acc | act | cgt | ggt | ggc | agg | tgg | gca cat tgc | 147 |
| Arg | Phe | Ser | Thr | Thr | Ile | Thr | Thr | Arg | Gly | Gly | Arg | Trp | Ala His Cys | |
| 30 | | | | 35 | | | | | 40 | | | | 45 | |
| tca | cta | caa | atg | ggt | aat | gag | atc | caa | act | gga | cga | cga | act gga ggc | 195 |
| Ser | Leu | Gln | Met | Gly | Asn | Glu | Ile | Gln | Thr | Gly | Arg | Arg | Thr Gly Gly | |
| | | | | 50 | | | | | 55 | | | | 60 | |
| tac | cag | cct | acc | ctt | tgg | gat | ttc | agc | acc | att | caa | ttg | ttc gac tct | 243 |
| Tyr | Gln | Pro | Thr | Leu | Trp | Asp | Phe | Ser | Thr | Ile | Gln | Leu | Phe Asp Ser | |
| | | | 65 | | | | | 70 | | | | | 75 | |
| gag | tat | aag | gaa | gag | aag | cac | ttg | atg | agg | gcc | gca | ggt | atg ata gcc | 291 |
| Glu | Tyr | Lys | Glu | Glu | Lys | His | Leu | Met | Arg | Ala | Ala | Gly | Met Ile Ala | |
| | | 80 | | | | | 85 | | | | | 90 | | |
| caa | gtg | aat | atg | ttg | ttg | cag | gaa | gaa | gta | gat | tcg | att | caa cgg ttg | 339 |
| Gln | Val | Asn | Met | Leu | Leu | Gln | Glu | Glu | Val | Asp | Ser | Ile | Gln Arg Leu | |
| 95 | | | | | 100 | | | | | 105 | | | | |
| gag | ttg | att | gat | gac | cta | cga | agg | ctg | ggt | ata | tct | tgc | cat ttt gac | 387 |
| Glu | Leu | Ile | Asp | Asp | Leu | Arg | Arg | Leu | Gly | Ile | Ser | Cys | His Phe Asp | |
| 110 | | | | 115 | | | | | 120 | | | | 125 | |
| cgc | gag | atc | gtt | gaa | ata | tta | aac | tca | aaa | tat | tat | acc | aac aat gag | 435 |
| Arg | Glu | Ile | Val | Glu | Ile | Leu | Asn | Ser | Lys | Tyr | Tyr | Thr | Asn Asn Glu | |
| | | | 130 | | | | | 135 | | | | | 140 | |
| ata | gat | gaa | agt | gat | cta | tac | tca | aca | gcc | ctt | aga | ttc | aag ctc cta | 483 |
| Ile | Asp | Glu | Ser | Asp | Leu | Tyr | Ser | Thr | Ala | Leu | Arg | Phe | Lys Leu Leu | |
| | | | | 145 | | | | | 150 | | | | | 155 |
| aga | caa | tac | gat | ttt | agc | gtc | tct | caa | gag | gta | ttt | gat | tgt ttc aag | 531 |
| Arg | Gln | Tyr | Asp | Phe | Ser | Val | Ser | Gln | Glu | Val | Phe | Asp | Cys Phe Lys | |
| | | 160 | | | | | 165 | | | | | 170 | | |
| aat | gac | aag | ggt | act | gat | ttc | aag | cca | agc | cta | gtc | gat | gat act aga | 579 |
| Asn | Asp | Lys | Gly | Thr | Asp | Phe | Lys | Pro | Ser | Leu | Val | Asp | Asp Thr Arg | |
| 175 | | | | | 180 | | | | | 185 | | | | |
| gga | ttg | tta | caa | ttg | tac | gaa | gct | tcg | ttt | tta | tca | gca | caa ggc gaa | 627 |
| Gly | Leu | Leu | Gln | Leu | Tyr | Glu | Ala | Ser | Phe | Leu | Ser | Ala | Gln Gly Glu | |
| 190 | | | | 195 | | | | | 200 | | | | 205 | |
| gaa | acc | cta | cat | ctt | gcc | aga | gat | ttt | gct | act | aaa | ttt | ctg cat aaa | 675 |
| Glu | Thr | Leu | His | Leu | Ala | Arg | Asp | Phe | Ala | Thr | Lys | Phe | Leu His Lys | |
| | | | 210 | | | | | 215 | | | | | 220 | |
| aga | gta | cta | gtt | gat | aaa | gac | att | aat | ctc | tta | tca | tca | att gaa cgt | 723 |
| Arg | Val | Leu | Val | Asp | Lys | Asp | Ile | Asn | Leu | Leu | Ser | Ser | Ile Glu Arg | |
| | | 225 | | | | | 230 | | | | | 235 | | |
| gcg | ttg | gag | ttg | cct | act | cat | tgg | agg | gtt | caa | atg | ccc | aac gca aga | 771 |
| Ala | Leu | Glu | Leu | Pro | Thr | His | Trp | Arg | Val | Gln | Met | Pro | Asn Ala Arg | |
| | | 240 | | | | | 245 | | | | | 250 | | |
| tcc | ttc | att | gat | gct | tat | aag | agg | aga | ccc | gac | atg | aat | ccg act gtg | 819 |
| Ser | Phe | Ile | Asp | Ala | Tyr | Lys | Arg | Arg | Pro | Asp | Met | Asn | Pro Thr Val | |
| | 255 | | | | | 260 | | | | | 265 | | | |
| cta | gaa | cta | gct | aaa | ttg | gac | ttc | aat | atg | gtt | caa | gca | caa ttt caa | 867 |
| Leu | Glu | Leu | Ala | Lys | Leu | Asp | Phe | Asn | Met | Val | Gln | Ala | Gln Phe Gln | |
| 270 | | | | 275 | | | | | 280 | | | | 285 | |
| caa | gag | ctc | aaa | gag | gcc | tct | agg | tgg | tgg | aat | agt | acg | ggt ctt gtc | 915 |
| Gln | Glu | Leu | Lys | Glu | Ala | Ser | Arg | Trp | Trp | Asn | Ser | Thr | Gly Leu Val | |

-continued

|  |  |  |  |  |  |  |  |  |  |  |  |  |  |  |  |
|---|---|---|---|---|---|---|---|---|---|---|---|---|---|---|---|
|  |  |  | 290 |  |  |  | 295 |  |  |  | 300 |  |  |  |  |
| cac | gag | ctt | ccc | ttt | gtg | aga | gat | agg | att | gtg | gaa | tgc | tac | tac tgg | 963 |
| His | Glu | Leu | Pro | Phe | Val | Arg | Asp | Arg | Ile | Val | Glu | Cys | Tyr | Tyr Trp |  |
|  |  |  | 305 |  |  |  | 310 |  |  |  | 315 |  |  |  |  |
| acg | aca | gga | gtg | gtt | gag | cgt | cgt | gaa | cat | gga | tac | gag | agg | ata atg | 1011 |
| Thr | Thr | Gly | Val | Val | Glu | Arg | Arg | Glu | His | Gly | Tyr | Glu | Arg | Ile Met |  |
|  |  | 320 |  |  |  |  | 325 |  |  |  |  | 330 |  |  |  |
| ctc | acc | aaa | ata | aat | gct | ctt | gtt | aca | aca | ata | gac | gat | gtc | ttt gat | 1059 |
| Leu | Thr | Lys | Ile | Asn | Ala | Leu | Val | Thr | Thr | Ile | Asp | Asp | Val | Phe Asp |  |
|  | 335 |  |  |  |  | 340 |  |  |  |  | 345 |  |  |  |  |
| att | tat | ggt | acg | ctt | gaa | gag | cta | caa | cta | ttc | aca | act | gct | att caa | 1107 |
| Ile | Tyr | Gly | Thr | Leu | Glu | Glu | Leu | Gln | Leu | Phe | Thr | Thr | Ala | Ile Gln |  |
| 350 |  |  |  |  | 355 |  |  |  |  | 360 |  |  |  | 365 |  |
| aga | tgg | gat | att | gaa | tca | atg | aag | caa | ctc | cct | cct | tac | atg | caa ata | 1155 |
| Arg | Trp | Asp | Ile | Glu | Ser | Met | Lys | Gln | Leu | Pro | Pro | Tyr | Met | Gln Ile |  |
|  |  |  |  | 370 |  |  |  |  | 375 |  |  |  |  | 380 |  |
| tgt | tat | ctt | gct | ctc | ttc | aac | ttt | gtg | aat | gag | atg | gct | tat | gat act | 1203 |
| Cys | Tyr | Leu | Ala | Leu | Phe | Asn | Phe | Val | Asn | Glu | Met | Ala | Tyr | Asp Thr |  |
|  |  |  | 385 |  |  |  |  | 390 |  |  |  |  | 395 |  |  |
| ctt | agg | gat | aaa | ggt | ttc | aac | tcc | acc | cca | tat | cta | cga | aaa | gcg tgg | 1251 |
| Leu | Arg | Asp | Lys | Gly | Phe | Asn | Ser | Thr | Pro | Tyr | Leu | Arg | Lys | Ala Trp |  |
|  |  | 400 |  |  |  |  | 405 |  |  |  |  | 410 |  |  |  |
| gtt | gat | ttg | gtt | gag | tca | tat | cta | ata | gag | gca | aag | tgg | tac | tac atg | 1299 |
| Val | Asp | Leu | Val | Glu | Ser | Tyr | Leu | Ile | Glu | Ala | Lys | Trp | Tyr | Tyr Met |  |
|  | 415 |  |  |  |  | 420 |  |  |  |  | 425 |  |  |  |  |
| gga | cat | aaa | cct | agt | ttg | gaa | gaa | tat | atg | aag | aat | agt | tgg | ata tca | 1347 |
| Gly | His | Lys | Pro | Ser | Leu | Glu | Glu | Tyr | Met | Lys | Asn | Ser | Trp | Ile Ser |  |
| 430 |  |  |  |  | 435 |  |  |  |  | 440 |  |  |  | 445 |  |
| atc | gga | ggc | atc | ccc | att | cta | tct | cat | cta | ttt | ttc | cgg | cta | aca gat | 1395 |
| Ile | Gly | Gly | Ile | Pro | Ile | Leu | Ser | His | Leu | Phe | Phe | Arg | Leu | Thr Asp |  |
|  |  |  |  | 450 |  |  |  |  | 455 |  |  |  |  | 460 |  |
| tcg | att | gag | gaa | gag | gat | gct | gag | agt | atg | cat | aaa | tac | cat | gat att | 1443 |
| Ser | Ile | Glu | Glu | Glu | Asp | Ala | Glu | Ser | Met | His | Lys | Tyr | His | Asp Ile |  |
|  |  |  | 465 |  |  |  |  | 470 |  |  |  |  | 475 |  |  |
| gtt | cgt | gca | tcg | tgt | act | att | cta | agg | ctt | gct | gat | gat | atg | gga aca | 1491 |
| Val | Arg | Ala | Ser | Cys | Thr | Ile | Leu | Arg | Leu | Ala | Asp | Asp | Met | Gly Thr |  |
|  |  | 480 |  |  |  |  | 485 |  |  |  |  | 490 |  |  |  |
| tcg | ctg | gat | gag | gtg | gag | aga | ggc | gac | gtg | ccc | aaa | tca | gtt | cag tgc | 1539 |
| Ser | Leu | Asp | Glu | Val | Glu | Arg | Gly | Asp | Val | Pro | Lys | Ser | Val | Gln Cys |  |
|  | 495 |  |  |  |  | 500 |  |  |  |  | 505 |  |  |  |  |
| tac | atg | aat | gag | aag | aat | gct | tcg | gaa | gaa | gaa | gcg | cga | gag | cat gtg | 1587 |
| Tyr | Met | Asn | Glu | Lys | Asn | Ala | Ser | Glu | Glu | Glu | Ala | Arg | Glu | His Val |  |
| 510 |  |  |  |  | 515 |  |  |  |  | 520 |  |  |  | 525 |  |
| cga | tca | ctc | ata | gac | caa | aca | tgg | aag | atg | atg | aac | aag | gaa | atg atg | 1635 |
| Arg | Ser | Leu | Ile | Asp | Gln | Thr | Trp | Lys | Met | Met | Asn | Lys | Glu | Met Met |  |
|  |  |  |  | 530 |  |  |  |  | 535 |  |  |  |  | 540 |  |
| acg | tca | tca | ttt | tcc | aaa | tat | ttt | gta | caa | gtt | tct | gct | aat | ctt gca | 1683 |
| Thr | Ser | Ser | Phe | Ser | Lys | Tyr | Phe | Val | Gln | Val | Ser | Ala | Asn | Leu Ala |  |
|  |  |  | 545 |  |  |  |  | 550 |  |  |  |  | 555 |  |  |
| aga | atg | gcg | caa | tgg | ata | tac | cag | cat | gaa | tct | gat | gga | ttt | ggc atg | 1731 |
| Arg | Met | Ala | Gln | Trp | Ile | Tyr | Gln | His | Glu | Ser | Asp | Gly | Phe | Gly Met |  |
|  |  | 560 |  |  |  |  | 565 |  |  |  |  | 570 |  |  |  |
| caa | cat | tca | ttg | gtg | aac | aaa | atg | ctc | aga | ggg | ttg | ttg | ttc | gac cgc | 1779 |
| Gln | His | Ser | Leu | Val | Asn | Lys | Met | Leu | Arg | Gly | Leu | Leu | Phe | Asp Arg |  |
|  | 575 |  |  |  |  | 580 |  |  |  |  | 585 |  |  |  |  |
| tat | gag | taa | ctaatcttcg | cccgggttcc | aaatgaatca | atctgttgtg |  |  |  |  |  |  |  |  | 1828 |
| Tyr | Glu |  |  |  |  |  |  |  |  |  |  |  |  |  |  |
| 590 |  |  |  |  |  |  |  |  |  |  |  |  |  |  |  |
| ttgctgttcc | acctgatatc | aataataatt | agacaaatgt | ttctgtacgg | gtggcccaac |  |  |  |  |  |  |  |  |  | 1888 | cgtcaggccc atttcgctca tgttcataat aaataataaa actgttaatc aataacaaaa     1948 aaaaaaaaaa aaaaaaaaa                                                   1967

<210> SEQ ID NO 24
<211> LENGTH: 591
<212> TYPE: PRT
<213> ORGANISM: Salvia officinalis

<400> SEQUENCE: 24

Met Ser Ser Leu Ile Met Gln Val Val Ile Pro Lys Pro Ala Lys Ile
1               5                   10                  15

Phe His Asn Asn Leu Phe Ser Val Ile Ser Lys Arg His Arg Phe Ser
            20                  25                  30

Thr Thr Ile Thr Thr Arg Gly Gly Arg Trp Ala His Cys Ser Leu Gln
        35                  40                  45

Met Gly Asn Glu Ile Gln Thr Gly Arg Arg Thr Gly Gly Tyr Gln Pro
    50                  55                  60

Thr Leu Trp Asp Phe Ser Thr Ile Gln Leu Phe Asp Ser Glu Tyr Lys
65                  70                  75                  80

Glu Glu Lys His Leu Met Arg Ala Ala Gly Met Ile Ala Gln Val Asn
                85                  90                  95

Met Leu Leu Gln Glu Glu Val Asp Ser Ile Gln Arg Leu Glu Leu Ile
            100                 105                 110

Asp Asp Leu Arg Arg Leu Gly Ile Ser Cys His Phe Asp Arg Glu Ile
        115                 120                 125

Val Glu Ile Leu Asn Ser Lys Tyr Tyr Thr Asn Asn Glu Ile Asp Glu
    130                 135                 140

Ser Asp Leu Tyr Ser Thr Ala Leu Arg Phe Lys Leu Leu Arg Gln Tyr
145                 150                 155                 160

Asp Phe Ser Val Ser Gln Glu Val Phe Asp Cys Phe Lys Asn Asp Lys
                165                 170                 175

Gly Thr Asp Phe Lys Pro Ser Leu Val Asp Asp Thr Arg Gly Leu Leu
            180                 185                 190

Gln Leu Tyr Glu Ala Ser Phe Leu Ser Ala Gln Gly Glu Glu Thr Leu
        195                 200                 205

His Leu Ala Arg Asp Phe Ala Thr Lys Phe Leu His Lys Arg Val Leu
    210                 215                 220

Val Asp Lys Asp Ile Asn Leu Leu Ser Ser Ile Glu Arg Ala Leu Glu
225                 230                 235                 240

Leu Pro Thr His Trp Arg Val Gln Met Pro Asn Ala Arg Ser Phe Ile
                245                 250                 255

Asp Ala Tyr Lys Arg Arg Pro Asp Met Asn Pro Thr Val Leu Glu Leu
            260                 265                 270

Ala Lys Leu Asp Phe Asn Met Val Gln Ala Gln Phe Gln Gln Glu Leu
        275                 280                 285

Lys Glu Ala Ser Arg Trp Trp Asn Ser Thr Gly Leu Val His Glu Leu
    290                 295                 300

Pro Phe Val Arg Asp Arg Ile Val Glu Cys Tyr Tyr Trp Thr Thr Gly
305                 310                 315                 320

Val Val Glu Arg Arg Glu His Gly Tyr Glu Arg Ile Met Leu Thr Lys
                325                 330                 335

Ile Asn Ala Leu Val Thr Thr Ile Asp Asp Val Phe Asp Ile Tyr Gly
            340                 345                 350

```
Thr Leu Glu Glu Leu Gln Leu Phe Thr Thr Ala Ile Gln Arg Trp Asp
        355                 360                 365
Ile Glu Ser Met Lys Gln Leu Pro Pro Tyr Met Gln Ile Cys Tyr Leu
    370                 375                 380
Ala Leu Phe Asn Phe Val Asn Glu Met Ala Tyr Asp Thr Leu Arg Asp
385                 390                 395                 400
Lys Gly Phe Asn Ser Thr Pro Tyr Leu Arg Lys Ala Trp Val Asp Leu
                405                 410                 415
Val Glu Ser Tyr Leu Ile Glu Ala Lys Trp Tyr Tyr Met Gly His Lys
            420                 425                 430
Pro Ser Leu Glu Glu Tyr Met Lys Asn Ser Trp Ile Ser Ile Gly Gly
        435                 440                 445
Ile Pro Ile Leu Ser His Leu Phe Phe Arg Leu Thr Asp Ser Ile Glu
    450                 455                 460
Glu Glu Asp Ala Glu Ser Met His Lys Tyr His Asp Ile Val Arg Ala
465                 470                 475                 480
Ser Cys Thr Ile Leu Arg Leu Ala Asp Asp Met Gly Thr Ser Leu Asp
                485                 490                 495
Glu Val Glu Arg Gly Asp Val Pro Lys Ser Val Gln Cys Tyr Met Asn
            500                 505                 510
Glu Lys Asn Ala Ser Glu Glu Ala Arg Glu His Val Arg Ser Leu
        515                 520                 525
Ile Asp Gln Thr Trp Lys Met Met Asn Lys Glu Met Met Thr Ser Ser
    530                 535                 540
Phe Ser Lys Tyr Phe Val Gln Val Ser Ala Asn Leu Ala Arg Met Ala
545                 550                 555                 560
Gln Trp Ile Tyr Gln His Glu Ser Asp Gly Phe Gly Met Gln His Ser
                565                 570                 575
Leu Val Asn Lys Met Leu Arg Gly Leu Leu Phe Asp Arg Tyr Glu
            580                 585                 590

<210> SEQ ID NO 25
<211> LENGTH: 2024
<212> TYPE: DNA
<213> ORGANISM: Salvia officinalis
<220> FEATURE:
<221> NAME/KEY: CDS
<222> LOCATION: (11)...(1804)
<223> OTHER INFORMATION: (+)-bornyl diphosphate synthase

<400> SEQUENCE: 25
gatcacaaaa atg tct atc att agc atg aac gta tcg atc ctt agc aag        49
           Met Ser Ile Ile Ser Met Asn Val Ser Ile Leu Ser Lys
             1               5                  10 cca cta aat tgc ctc cac aac ttg gag agg aga cct tca aaa gcc ttg       97
Pro Leu Asn Cys Leu His Asn Leu Glu Arg Arg Pro Ser Lys Ala Leu
     15                  20                  25 ctt gtc cct tgc act gca ccc acc gct cgc ctc cgg gca tct tgc tcc      145
Leu Val Pro Cys Thr Ala Pro Thr Ala Arg Leu Arg Ala Ser Cys Ser
 30                  35                  40                  45 tca aaa cta caa gaa gct cat caa atc cga cga tct gga aac tac caa      193
Ser Lys Leu Gln Glu Ala His Gln Ile Arg Arg Ser Gly Asn Tyr Gln
             50                  55                  60 cct gcc ctt tgg gat tcc aat tac att cag tct ctc aat act cca tat      241
Pro Ala Leu Trp Asp Ser Asn Tyr Ile Gln Ser Leu Asn Thr Pro Tyr
         65                  70                  75 acg gag gag agg cac ttg gat aga aaa gca gag ctg att gtg caa gtg      289
```

```
                                                                     -continued Thr Glu Glu Arg His Leu Asp Arg Lys Ala Glu Leu Ile Val Gln Val
        80                  85                  90 agg ata ctg cta aag gaa aaa atg gag cct gtt caa caa ttg gag ttg       337
Arg Ile Leu Leu Lys Glu Lys Met Glu Pro Val Gln Gln Leu Glu Leu
    95                 100                 105 att cat gac ttg aaa tat ttg ggg ctc tcg gat ttt ttt caa gat gag       385
Ile His Asp Leu Lys Tyr Leu Gly Leu Ser Asp Phe Phe Gln Asp Glu
110                 115                 120                 125 att aag gag atc tta ggt gtt ata tac aat gag cac aaa tgc ttt cac       433
Ile Lys Glu Ile Leu Gly Val Ile Tyr Asn Glu His Lys Cys Phe His
                130                 135                 140 aat aat gaa gta gag aaa atg gat ttg tat ttc aca gct ctt gga ttc       481
Asn Asn Glu Val Glu Lys Met Asp Leu Tyr Phe Thr Ala Leu Gly Phe
            145                 150                 155 aga ctc ctc aga caa cat ggt ttt aat att tcc caa gat gta ttt aat       529
Arg Leu Leu Arg Gln His Gly Phe Asn Ile Ser Gln Asp Val Phe Asn
        160                 165                 170 tgt ttc aag aac gag aag ggt att gat ttc aag gca agc ctt gct caa       577
Cys Phe Lys Asn Glu Lys Gly Ile Asp Phe Lys Ala Ser Leu Ala Gln
    175                 180                 185 gat acg aag gga atg tta caa ctg tat gaa gcg tct ttc ctt ttg aga       625
Asp Thr Lys Gly Met Leu Gln Leu Tyr Glu Ala Ser Phe Leu Leu Arg
190                 195                 200                 205 aaa ggt gaa gat aca ttg gag ctt gca aga gaa ttt gcc aca aaa tgt       673
Lys Gly Glu Asp Thr Leu Glu Leu Ala Arg Glu Phe Ala Thr Lys Cys
                210                 215                 220 ctg cag aaa aaa ctt gat gaa ggt ggt aat gaa att gat gag aat cta       721
Leu Gln Lys Lys Leu Asp Glu Gly Gly Asn Glu Ile Asp Glu Asn Leu
            225                 230                 235 tta ttg tgg att cgc cac tct ttg gat ctt cct ctc cac tgg agg att       769
Leu Leu Trp Ile Arg His Ser Leu Asp Leu Pro Leu His Trp Arg Ile
        240                 245                 250 caa agt gta gag gca aga tgg ttc ata gat gct tat gcg aga agg cca       817
Gln Ser Val Glu Ala Arg Trp Phe Ile Asp Ala Tyr Ala Arg Arg Pro
    255                 260                 265 gac atg aat cca ctt att ttc gag ctt gcc aaa ctc aac ttc aat att       865
Asp Met Asn Pro Leu Ile Phe Glu Leu Ala Lys Leu Asn Phe Asn Ile
270                 275                 280                 285 att caa gca aca cat caa caa gaa ctg aaa gat ctc tcg agg tgg tgg       913
Ile Gln Ala Thr His Gln Gln Glu Leu Lys Asp Leu Ser Arg Trp Trp
                290                 295                 300 agt aga tta tgc ttc cct gaa aag ctc cca ttt gtg agg gat agg ctc       961
Ser Arg Leu Cys Phe Pro Glu Lys Leu Pro Phe Val Arg Asp Arg Leu
            305                 310                 315 gtt gaa tcc ttc ttt tgg gcg gtt ggg atg ttt gag cca cat caa cat      1009
Val Glu Ser Phe Phe Trp Ala Val Gly Met Phe Glu Pro His Gln His
        320                 325                 330 gga tat cag aga aaa atg gcc gcc aca att att gtt tta gca aca gtt      1057
Gly Tyr Gln Arg Lys Met Ala Ala Thr Ile Ile Val Leu Ala Thr Val
    335                 340                 345 ata gat gat att tac gat gtg tat ggt aca cta gat gaa cta gaa cta      1105
Ile Asp Asp Ile Tyr Asp Val Tyr Gly Thr Leu Asp Glu Leu Glu Leu
350                 355                 360                 365 ttt aca gac acg ttt aag aga tgg gat act gaa tca ata acc cga ctt      1153
Phe Thr Asp Thr Phe Lys Arg Trp Asp Thr Glu Ser Ile Thr Arg Leu
                370                 375                 380 cct tat tac atg caa tta tgt tat tgg ggt gtc cac aac tat att tcc      1201
Pro Tyr Tyr Met Gln Leu Cys Tyr Trp Gly Val His Asn Tyr Ile Ser
            385                 390                 395
```

-continued

```
gat gca gca tat gat att ctc aaa gaa cat ggt ttc ttt tgt ctc caa    1249
Asp Ala Ala Tyr Asp Ile Leu Lys Glu His Gly Phe Phe Cys Leu Gln
            400                 405                 410 tat ctc cgg aaa tcg gtg gta gat ttg gtt gaa gca tat ttt cac gag    1297
Tyr Leu Arg Lys Ser Val Val Asp Leu Val Glu Ala Tyr Phe His Glu
        415                 420                 425 gca aag tgg tac cac agc ggt tat aca cca agc ctg gat gaa tat ctc    1345
Ala Lys Trp Tyr His Ser Gly Tyr Thr Pro Ser Leu Asp Glu Tyr Leu
430                 435                 440                 445 aac atc gcc aag att tca gtg gcg tct cct gca ata ata tcc cca acc    1393
Asn Ile Ala Lys Ile Ser Val Ala Ser Pro Ala Ile Ile Ser Pro Thr
                450                 455                 460 tat ttc aca ttc gca aac gcg tct cat gac aca gca gtc atc gac agc    1441
Tyr Phe Thr Phe Ala Asn Ala Ser His Asp Thr Ala Val Ile Asp Ser
            465                 470                 475 ttg tac caa tat cat gac ata ctt tgc cta gca gga att att ttg agg    1489
Leu Tyr Gln Tyr His Asp Ile Leu Cys Leu Ala Gly Ile Ile Leu Arg
        480                 485                 490 ctt ccc gac gat ctt ggg aca tca tat ttt gag ctg gcg aga ggc gac    1537
Leu Pro Asp Asp Leu Gly Thr Ser Tyr Phe Glu Leu Ala Arg Gly Asp
495                 500                 505 gtg ccg aaa aca atc cag tgc tac atg aag gaa aca aat gct agt gag    1585
Val Pro Lys Thr Ile Gln Cys Tyr Met Lys Glu Thr Asn Ala Ser Glu
510                 515                 520                 525 gag gag gcg gtg gag cac gtg aag ttt ctg ata agg gag gcg tgg aag    1633
Glu Glu Ala Val Glu His Val Lys Phe Leu Ile Arg Glu Ala Trp Lys
                530                 535                 540 gat atg aac acg gcc ata gca gcc ggt tat ccg ttt ccg gat ggt atg    1681
Asp Met Asn Thr Ala Ile Ala Ala Gly Tyr Pro Phe Pro Asp Gly Met
            545                 550                 555 gtg gcg ggc gca gct aat att ggg cgc gtg gcg cag ttt att tat ctc    1729
Val Ala Gly Ala Ala Asn Ile Gly Arg Val Ala Gln Phe Ile Tyr Leu
        560                 565                 570 cac gga gat ggg ttt ggc gtg caa cac tcg aaa acg tac gag cat atc    1777
His Gly Asp Gly Phe Gly Val Gln His Ser Lys Thr Tyr Glu His Ile
575                 580                 585 gcc ggc cta ctg ttc gag cct tat gca tga acaaatggga gactgcttga     1827
Ala Gly Leu Leu Phe Glu Pro Tyr Ala
590                 595 tatatattaa tttggcacac caataattgc atgttatata tgttggaaaa taagtgtctg    1887
gttgagatgt catgtggtgt attatctaaa taattcaagg ttgccttgtt tatgtagccg    1947
gtggtgcaac tacctcccat tcaaatcaat taaatctaaa cagtcgagtc aagctcgagc    2007
tcgaggaaaa aaaaaaa                                                   2024
```

<210> SEQ ID NO 26
<211> LENGTH: 598
<212> TYPE: PRT
<213> ORGANISM: Salvia officinalis

<400> SEQUENCE: 26

Met Ser Ile Ile Ser Met Asn Val Ser Ile Leu Ser Lys Pro Leu Asn
1               5                   10                  15

Cys Leu His Asn Leu Glu Arg Arg Pro Ser Lys Ala Leu Leu Val Pro
            20                  25                  30

Cys Thr Ala Pro Thr Ala Arg Leu Arg Ala Ser Cys Ser Ser Lys Leu
        35                  40                  45

Gln Glu Ala His Gln Ile Arg Arg Ser Gly Asn Tyr Gln Pro Ala Leu
    50                  55                  60

```
Trp Asp Ser Asn Tyr Ile Gln Ser Leu Asn Thr Pro Tyr Thr Glu Glu
 65                  70                  75                  80

Arg His Leu Asp Arg Lys Ala Glu Leu Ile Val Gln Val Arg Ile Leu
                 85                  90                  95

Leu Lys Glu Lys Met Glu Pro Val Gln Gln Leu Glu Leu Ile His Asp
            100                 105                 110

Leu Lys Tyr Leu Gly Leu Ser Asp Phe Phe Gln Asp Glu Ile Lys Glu
            115                 120                 125

Ile Leu Gly Val Ile Tyr Asn Glu His Lys Cys Phe His Asn Asn Glu
        130                 135                 140

Val Glu Lys Met Asp Leu Tyr Phe Thr Ala Leu Gly Phe Arg Leu Leu
145                 150                 155                 160

Arg Gln His Gly Phe Asn Ile Ser Gln Asp Val Phe Asn Cys Phe Lys
                165                 170                 175

Asn Glu Lys Gly Ile Asp Phe Lys Ala Ser Leu Ala Gln Asp Thr Lys
            180                 185                 190

Gly Met Leu Gln Leu Tyr Glu Ala Ser Phe Leu Leu Arg Lys Gly Glu
            195                 200                 205

Asp Thr Leu Glu Leu Ala Arg Glu Phe Ala Thr Lys Cys Leu Gln Lys
        210                 215                 220

Lys Leu Asp Glu Gly Gly Asn Glu Ile Asp Glu Asn Leu Leu Leu Trp
225                 230                 235                 240

Ile Arg His Ser Leu Asp Leu Pro Leu His Trp Arg Ile Gln Ser Val
                245                 250                 255

Glu Ala Arg Trp Phe Ile Asp Ala Tyr Ala Arg Arg Pro Asp Met Asn
            260                 265                 270

Pro Leu Ile Phe Glu Leu Ala Lys Leu Asn Phe Asn Ile Ile Gln Ala
            275                 280                 285

Thr His Gln Gln Glu Leu Lys Asp Leu Ser Arg Trp Trp Ser Arg Leu
        290                 295                 300

Cys Phe Pro Glu Lys Leu Pro Phe Val Arg Asp Arg Leu Val Glu Ser
305                 310                 315                 320

Phe Phe Trp Ala Val Gly Met Phe Glu Pro His Gln His Gly Tyr Gln
                325                 330                 335

Arg Lys Met Ala Ala Thr Ile Ile Val Leu Ala Thr Val Ile Asp Asp
            340                 345                 350

Ile Tyr Asp Val Tyr Gly Thr Leu Asp Glu Leu Glu Leu Phe Thr Asp
        355                 360                 365

Thr Phe Lys Arg Trp Asp Thr Glu Ser Ile Thr Arg Leu Pro Tyr Tyr
370                 375                 380

Met Gln Leu Cys Tyr Trp Gly Val His Asn Tyr Ile Ser Asp Ala Ala
385                 390                 395                 400

Tyr Asp Ile Leu Lys Glu His Gly Phe Phe Cys Leu Gln Tyr Leu Arg
                405                 410                 415

Lys Ser Val Val Asp Leu Val Glu Ala Tyr Phe His Glu Ala Lys Trp
            420                 425                 430

Tyr His Ser Gly Tyr Thr Pro Ser Leu Asp Glu Tyr Leu Asn Ile Ala
        435                 440                 445

Lys Ile Ser Val Ala Ser Pro Ala Ile Ile Ser Pro Thr Tyr Phe Thr
        450                 455                 460

Phe Ala Asn Ala Ser His Asp Thr Ala Val Ile Asp Ser Leu Tyr Gln
465                 470                 475                 480
```

```
Tyr His Asp Ile Leu Cys Leu Ala Gly Ile Ile Leu Arg Leu Pro Asp
                485                 490                 495

Asp Leu Gly Thr Ser Tyr Phe Glu Leu Ala Arg Gly Asp Val Pro Lys
            500                 505                 510

Thr Ile Gln Cys Tyr Met Lys Glu Thr Asn Ala Ser Glu Glu Glu Ala
        515                 520                 525

Val Glu His Val Lys Phe Leu Ile Arg Glu Ala Trp Lys Asp Met Asn
    530                 535                 540

Thr Ala Ile Ala Ala Gly Tyr Pro Phe Pro Asp Gly Met Val Ala Gly
545                 550                 555                 560

Ala Ala Asn Ile Gly Arg Val Ala Gln Phe Ile Tyr Leu His Gly Asp
                565                 570                 575

Gly Phe Gly Val Gln His Ser Lys Thr Tyr Glu His Ile Ala Gly Leu
            580                 585                 590

Leu Phe Glu Pro Tyr Ala
        595

<210> SEQ ID NO 27
<211> LENGTH: 1959
<212> TYPE: DNA
<213> ORGANISM: Mentha x piperita
<220> FEATURE:
<221> NAME/KEY: CDS
<222> LOCATION: (71)...(1720)
<223> OTHER INFORMATION: (E)-B-farnesene synthase

<400> SEQUENCE: 27
aaactctgca atttcatata taacatcata aaatcagaga gagagacaga gagtttgttg      60
tagtgaaaaa atg gct aca aac ggc gtc gta att agt tgc tta agg gaa       109
            Met Ala Thr Asn Gly Val Val Ile Ser Cys Leu Arg Glu
              1               5                  10 gta agg cca cct atg acg aag cat gcg cca agc atg tgg act gat acc     157
Val Arg Pro Pro Met Thr Lys His Ala Pro Ser Met Trp Thr Asp Thr
         15                  20                  25 ttt tct aac ttt tct ctt gac gat aag gaa caa caa aag tgc tca gaa     205
Phe Ser Asn Phe Ser Leu Asp Asp Lys Glu Gln Gln Lys Cys Ser Glu
 30                  35                  40                  45 acc atc gaa gca ctt aag caa gaa gca aga ggc atg ctt atg gct gca     253
Thr Ile Glu Ala Leu Lys Gln Glu Ala Arg Gly Met Leu Met Ala Ala
                 50                  55                  60 acc act cct ctc caa caa atg aca cta atc gac act ctc gag cgt ttg     301
Thr Thr Pro Leu Gln Gln Met Thr Leu Ile Asp Thr Leu Glu Arg Leu
             65                  70                  75 gga ttg tct ttc cat ttt gag acg gag atc gaa tac aaa atc gaa cta     349
Gly Leu Ser Phe His Phe Glu Thr Glu Ile Glu Tyr Lys Ile Glu Leu
         80                  85                  90 atc aac gct gca gaa gac gac ggc ttt gat ttg ttc gct act gct ctt     397
Ile Asn Ala Ala Glu Asp Asp Gly Phe Asp Leu Phe Ala Thr Ala Leu
     95                 100                 105 cgt ttc cgt ttg ctc aga caa cat caa cgc cac gtt tct tgt gat gtt     445
Arg Phe Arg Leu Leu Arg Gln His Gln Arg His Val Ser Cys Asp Val
110                 115                 120                 125 ttc gac aag ttc atc gac aaa gat ggc aag ttc gaa gaa tcc ctt agc     493
Phe Asp Lys Phe Ile Asp Lys Asp Gly Lys Phe Glu Glu Ser Leu Ser
                130                 135                 140 aat aat gtt gaa ggc cta tta agc ttg tat gaa gca gct cat gtt ggg     541
Asn Asn Val Glu Gly Leu Leu Ser Leu Tyr Glu Ala Ala His Val Gly
            145                 150                 155 ttt cgc gaa gaa aga ata tta caa gag gct gta aat ttt acg agg cat     589
```

```
Phe Arg Glu Glu Arg Ile Leu Gln Glu Ala Val Asn Phe Thr Arg His
        160                 165                 170 cac ttg gaa gga gca gag tta gat cag tct cca tta ttg att aga gag        637
His Leu Glu Gly Ala Glu Leu Asp Gln Ser Pro Leu Leu Ile Arg Glu
    175                 180                 185 aaa gtg aag cga gct ttg gag cac cct ctt cat agg gat ttc ccc att        685
Lys Val Lys Arg Ala Leu Glu His Pro Leu His Arg Asp Phe Pro Ile
190                 195                 200                 205 gtc tat gca cgc ctt ttc atc tcc att tac gaa aag gat gac tct aga        733
Val Tyr Ala Arg Leu Phe Ile Ser Ile Tyr Glu Lys Asp Asp Ser Arg
                210                 215                 220 gat gaa tta ctt ctc aag cta tcc aaa gtc aac ttc aaa ttc atg cag        781
Asp Glu Leu Leu Leu Lys Leu Ser Lys Val Asn Phe Lys Phe Met Gln
                225                 230                 235 aat ttg tat aag gaa gag ctc tcc caa ctc tcc agg tgg tgg aac aca        829
Asn Leu Tyr Lys Glu Glu Leu Ser Gln Leu Ser Arg Trp Trp Asn Thr
            240                 245                 250 tgg aat ctg aaa tca aaa tta cca tat gca aga gat cga gtc gtg gag        877
Trp Asn Leu Lys Ser Lys Leu Pro Tyr Ala Arg Asp Arg Val Val Glu
        255                 260                 265 gct tat gtt tgg gga gta ggt tac cat tac gaa ccc caa tac tca tat        925
Ala Tyr Val Trp Gly Val Gly Tyr His Tyr Glu Pro Gln Tyr Ser Tyr
270                 275                 280                 285 gtt cga atg gga ctt gcc aaa ggc gta cta att tgt gga atc atg gac        973
Val Arg Met Gly Leu Ala Lys Gly Val Leu Ile Cys Gly Ile Met Asp
                290                 295                 300 gat aca tat gat aat tat gct aca ctc aat gaa gct caa ctt ttt act        1021
Asp Thr Tyr Asp Asn Tyr Ala Thr Leu Asn Glu Ala Gln Leu Phe Thr
                305                 310                 315 caa gtc tta gac aag tgg gat aga gat gaa gct gaa cga ctc cca gaa        1069
Gln Val Leu Asp Lys Trp Asp Arg Asp Glu Ala Glu Arg Leu Pro Glu
            320                 325                 330 tac atg aaa atc gtt tat cga ttt att ttg agt ata tat gaa aat tat        1117
Tyr Met Lys Ile Val Tyr Arg Phe Ile Leu Ser Ile Tyr Glu Asn Tyr
        335                 340                 345 gaa cgt gat gca gcg aaa ctt gga aaa agc ttt gca gct cct tat ttt        1165
Glu Arg Asp Ala Ala Lys Leu Gly Lys Ser Phe Ala Ala Pro Tyr Phe
350                 355                 360                 365 aag gaa acc gtg aaa caa ctg gca agg gca ttt aat gag gag cag aag        1213
Lys Glu Thr Val Lys Gln Leu Ala Arg Ala Phe Asn Glu Glu Gln Lys
                370                 375                 380 tgg gtt atg gaa agg cag cta ccg tca ttc caa gac tac gta aag aat        1261
Trp Val Met Glu Arg Gln Leu Pro Ser Phe Gln Asp Tyr Val Lys Asn
                385                 390                 395 tca gag aaa acc agc tgc att tat acc atg ttt gct tct atc atc cca        1309
Ser Glu Lys Thr Ser Cys Ile Tyr Thr Met Phe Ala Ser Ile Ile Pro
            400                 405                 410 ggc ttg aaa tct gtt acc caa gaa acc att gat tgg atc aag agt gaa        1357
Gly Leu Lys Ser Val Thr Gln Glu Thr Ile Asp Trp Ile Lys Ser Glu
        415                 420                 425 ccc acg ctc gca aca tcg acc gct atg atc ggt cgg tat tgg aat gac        1405
Pro Thr Leu Ala Thr Ser Thr Ala Met Ile Gly Arg Tyr Trp Asn Asp
430                 435                 440                 445 acc agc tct cag ctc cgt gaa agc aaa gga ggg gaa atg ctg act gcg        1453
Thr Ser Ser Gln Leu Arg Glu Ser Lys Gly Gly Glu Met Leu Thr Ala
                450                 455                 460 ttg gat ttc cac atg aaa gaa tat ggt ctg acg aag gaa gag gcg gca        1501
Leu Asp Phe His Met Lys Glu Tyr Gly Leu Thr Lys Glu Glu Ala Ala
            465                 470                 475
```

```
tct aag ttt gaa gga ttg gtt gag gaa aca tgg aag gat ata aac aag    1549
Ser Lys Phe Glu Gly Leu Val Glu Glu Thr Trp Lys Asp Ile Asn Lys
        480                 485                 490 gaa ttc ata gcc aca act aat tat aat gtg ggt aga gaa att gcc atc    1597
Glu Phe Ile Ala Thr Thr Asn Tyr Asn Val Gly Arg Glu Ile Ala Ile
495                 500                 505 aca ttc ctc aac tac gct cgg ata tgt gaa gcc agt tac agc aaa act    1645
Thr Phe Leu Asn Tyr Ala Arg Ile Cys Glu Ala Ser Tyr Ser Lys Thr
510                 515                 520                 525 gac gga gac gct tat tca gat cct aat gtt gcc aag gca aat gtc gtt    1693
Asp Gly Asp Ala Tyr Ser Asp Pro Asn Val Ala Lys Ala Asn Val Val
                530                 535                 540 gct ctc ttt gtt gat gcc ata gtc ttt tga tttgcataat caaagaccct      1743
Ala Leu Phe Val Asp Ala Ile Val Phe
                545                 550 ataattataa ttatatgtgt ttaagaaact aataagcttg ctttatgtat agttgtcaat  1803
tgaataataa tgtattaatt agtagagtta agaagttata aagaataaag aggagctggt  1863
agacgtaaac aagaaataat gtgtcaaaat aacttcaact ttttcaagaa taaagaattg  1923
gaagagacca atatatacaa aaaaaaaaaa aaaaaa                            1959

<210> SEQ ID NO 28
<211> LENGTH: 550
<212> TYPE: PRT
<213> ORGANISM: Mentha x piperita

<400> SEQUENCE: 28

Met Ala Thr Asn Gly Val Val Ile Ser Cys Leu Arg Glu Val Arg Pro
1               5                   10                  15

Pro Met Thr Lys His Ala Pro Ser Met Trp Thr Asp Thr Phe Ser Asn
                20                  25                  30

Phe Ser Leu Asp Asp Lys Glu Gln Gln Lys Cys Ser Glu Thr Ile Glu
            35                  40                  45

Ala Leu Lys Gln Glu Ala Arg Gly Met Leu Met Ala Ala Thr Thr Pro
        50                  55                  60

Leu Gln Gln Met Thr Leu Ile Asp Thr Leu Glu Arg Leu Gly Leu Ser
65                  70                  75                  80

Phe His Phe Glu Thr Glu Ile Glu Tyr Lys Ile Glu Leu Ile Asn Ala
                85                  90                  95

Ala Glu Asp Asp Gly Phe Asp Leu Phe Ala Thr Ala Leu Arg Phe Arg
            100                 105                 110

Leu Leu Arg Gln His Gln Arg His Val Ser Cys Asp Val Phe Asp Lys
        115                 120                 125

Phe Ile Asp Lys Asp Gly Lys Phe Glu Glu Ser Leu Ser Asn Asn Val
130                 135                 140

Glu Gly Leu Leu Ser Leu Tyr Glu Ala Ala His Val Gly Phe Arg Glu
145                 150                 155                 160

Glu Arg Ile Leu Gln Glu Ala Val Asn Phe Thr Arg His His Leu Glu
                165                 170                 175

Gly Ala Glu Leu Asp Gln Ser Pro Leu Leu Ile Arg Glu Lys Val Lys
            180                 185                 190

Arg Ala Leu Glu His Pro Leu His Arg Asp Phe Pro Ile Val Tyr Ala
        195                 200                 205

Arg Leu Phe Ile Ser Ile Tyr Glu Lys Asp Asp Ser Arg Asp Glu Leu
210                 215                 220

Leu Leu Lys Leu Ser Lys Val Asn Phe Lys Phe Met Gln Asn Leu Tyr
```

```
                225                 230                 235                 240
Lys Glu Glu Leu Ser Gln Leu Ser Arg Trp Trp Asn Thr Trp Asn Leu
                245                 250                 255
Lys Ser Lys Leu Pro Tyr Ala Arg Asp Arg Val Val Glu Ala Tyr Val
                260                 265                 270
Trp Gly Val Gly Tyr His Tyr Glu Pro Gln Tyr Ser Tyr Val Arg Met
                275                 280                 285
Gly Leu Ala Lys Gly Val Leu Ile Cys Gly Ile Met Asp Asp Thr Tyr
                290                 295                 300
Asp Asn Tyr Ala Thr Leu Asn Glu Ala Gln Leu Phe Thr Gln Val Leu
305                 310                 315                 320
Asp Lys Trp Asp Arg Asp Glu Ala Glu Arg Leu Pro Glu Tyr Met Lys
                325                 330                 335
Ile Val Tyr Arg Phe Ile Leu Ser Ile Tyr Glu Asn Tyr Glu Arg Asp
                340                 345                 350
Ala Ala Lys Leu Gly Lys Ser Phe Ala Ala Pro Tyr Phe Lys Glu Thr
                355                 360                 365
Val Lys Gln Leu Ala Arg Ala Phe Asn Glu Glu Gln Lys Trp Val Met
                370                 375                 380
Glu Arg Gln Leu Pro Ser Phe Gln Asp Tyr Val Lys Asn Ser Glu Lys
385                 390                 395                 400
Thr Ser Cys Ile Tyr Thr Met Phe Ala Ser Ile Ile Pro Gly Leu Lys
                405                 410                 415
Ser Val Thr Gln Glu Thr Ile Asp Trp Ile Lys Ser Glu Pro Thr Leu
                420                 425                 430
Ala Thr Ser Thr Ala Met Ile Gly Arg Tyr Trp Asn Asp Thr Ser Ser
                435                 440                 445
Gln Leu Arg Glu Ser Lys Gly Gly Glu Met Leu Thr Ala Leu Asp Phe
                450                 455                 460
His Met Lys Glu Tyr Gly Leu Thr Lys Glu Glu Ala Ala Ser Lys Phe
465                 470                 475                 480
Glu Gly Leu Val Glu Glu Thr Trp Lys Asp Ile Asn Lys Glu Phe Ile
                485                 490                 495
Ala Thr Thr Asn Tyr Asn Val Gly Arg Glu Ile Ala Ile Thr Phe Leu
                500                 505                 510
Asn Tyr Ala Arg Ile Cys Glu Ala Ser Tyr Ser Lys Thr Asp Gly Asp
                515                 520                 525
Ala Tyr Ser Asp Pro Asn Val Ala Lys Ala Asn Val Val Ala Leu Phe
                530                 535                 540
Val Asp Ala Ile Val Phe
545                 550

<210> SEQ ID NO 29
<211> LENGTH: 2196
<212> TYPE: DNA
<213> ORGANISM: Abies grandis
<220> FEATURE:
<221> NAME/KEY: CDS
<222> LOCATION: (69)...(1949)
<223> OTHER INFORMATION: myrcene synthase

<400> SEQUENCE: 29
tgccggcacg aggttatctt gagcttcctc catataggcc aacacatatc atatcaaagg    60 gagcaaga atg gct ctg gtt tct atc tca ccg ttg gct tcg aaa tct tgc    110
         Met Ala Leu Val Ser Ile Ser Pro Leu Ala Ser Lys Ser Cys
           1               5                  10
```

```
ctg cgc aag tcg ttg atc agt tca att cat gaa cat aag cct ccc tat      158
Leu Arg Lys Ser Leu Ile Ser Ser Ile His Glu His Lys Pro Pro Tyr
 15                  20                  25                  30 aga aca atc cca aat ctt gga atg cgt agg cga ggg aaa tct gtc acg      206
Arg Thr Ile Pro Asn Leu Gly Met Arg Arg Arg Gly Lys Ser Val Thr
                 35                  40                  45 cct tcc atg agc atc agt ttg gcc acc gct gca cct gat gat ggt gta      254
Pro Ser Met Ser Ile Ser Leu Ala Thr Ala Ala Pro Asp Asp Gly Val
             50                  55                  60 caa aga cgc ata ggt gac tac cat tcc aat atc tgg gac gat gat ttc      302
Gln Arg Arg Ile Gly Asp Tyr His Ser Asn Ile Trp Asp Asp Asp Phe
                 65                  70                  75 ata cag tct cta tca acg cct tat ggg gaa ccc tct tac cag gaa cgt      350
Ile Gln Ser Leu Ser Thr Pro Tyr Gly Glu Pro Ser Tyr Gln Glu Arg
 80                  85                  90 gct gag aga tta att gtg gag gta aag aag ata ttc aat tca atg tac      398
Ala Glu Arg Leu Ile Val Glu Val Lys Lys Ile Phe Asn Ser Met Tyr
 95                 100                 105                 110 ctg gat gat gga aga tta atg agt tcc ttt aat gat ctc atg caa cgc      446
Leu Asp Asp Gly Arg Leu Met Ser Ser Phe Asn Asp Leu Met Gln Arg
                115                 120                 125 ctt tgg ata gtc gat agc gtt gaa cgt ttg ggg ata gct aga cat ttc      494
Leu Trp Ile Val Asp Ser Val Glu Arg Leu Gly Ile Ala Arg His Phe
            130                 135                 140 aag aac gag ata aca tca gct ctg gat tat gtt ttc cgt tac tgg gag      542
Lys Asn Glu Ile Thr Ser Ala Leu Asp Tyr Val Phe Arg Tyr Trp Glu
                145                 150                 155 gaa aac ggc att gga tgt ggg aga gac agt att gtt act gat ctc aac      590
Glu Asn Gly Ile Gly Cys Gly Arg Asp Ser Ile Val Thr Asp Leu Asn
160                 165                 170 tca act gcg ttg ggg ttt cga act ctt cga tta cac ggg tac act gta      638
Ser Thr Ala Leu Gly Phe Arg Thr Leu Arg Leu His Gly Tyr Thr Val
175                 180                 185                 190 tct cca gag gtt tta aaa gct ttt caa gat caa aat gga cag ttt gta      686
Ser Pro Glu Val Leu Lys Ala Phe Gln Asp Gln Asn Gly Gln Phe Val
                195                 200                 205 tgc tcc ccc ggt cag aca gag ggt gag atc aga agc gtt ctt aac tta      734
Cys Ser Pro Gly Gln Thr Glu Gly Glu Ile Arg Ser Val Leu Asn Leu
            210                 215                 220 tat cgg gct tcc ctc att gcc ttc cct ggt gag aaa gtt atg gaa gaa      782
Tyr Arg Ala Ser Leu Ile Ala Phe Pro Gly Glu Lys Val Met Glu Glu
            225                 230                 235 gct gaa atc ttc tcc aca aga tat ttg aaa gaa gct cta caa aag att      830
Ala Glu Ile Phe Ser Thr Arg Tyr Leu Lys Glu Ala Leu Gln Lys Ile
240                 245                 250 cca gtc tcc gct ctt tca caa gag ata aag ttt gtt atg gaa tat ggc      878
Pro Val Ser Ala Leu Ser Gln Glu Ile Lys Phe Val Met Glu Tyr Gly
255                 260                 265                 270 tgg cac aca aat ttg cca aga ttg gaa gca aga aat tac ata gac aca      926
Trp His Thr Asn Leu Pro Arg Leu Glu Ala Arg Asn Tyr Ile Asp Thr
                275                 280                 285 ctt gag aaa gac acc agt gca tgg ctc aat aaa aat gct ggg aag aag      974
Leu Glu Lys Asp Thr Ser Ala Trp Leu Asn Lys Asn Ala Gly Lys Lys
            290                 295                 300 ctt tta gaa ctt gca aaa ttg gag ttc aat ata ttt aac tcc tta caa     1022
Leu Leu Glu Leu Ala Lys Leu Glu Phe Asn Ile Phe Asn Ser Leu Gln
            305                 310                 315 caa aag gaa tta caa tat ctt ttg aga tgg tgg aaa gag tcg gat ttg     1070
Gln Lys Glu Leu Gln Tyr Leu Leu Arg Trp Trp Lys Glu Ser Asp Leu
```

```
                320                 325                 330
cct aaa ttg aca ttt gct cgg cat cgt cat gtg gaa ttc tac act ttg    1118
Pro Lys Leu Thr Phe Ala Arg His Arg His Val Glu Phe Tyr Thr Leu
335                 340                 345                 350 gcc tct tgt att gcc att gac cca aaa cat tct gca ttc aga cta ggc    1166
Ala Ser Cys Ile Ala Ile Asp Pro Lys His Ser Ala Phe Arg Leu Gly
                355                 360                 365 ttc gcc aaa atg tgt cat ctt gtc aca gtt ttg gac gat att tac gac    1214
Phe Ala Lys Met Cys His Leu Val Thr Val Leu Asp Asp Ile Tyr Asp
            370                 375                 380 act ttt gga acg att gac gag ctt gaa ctc ttc aca tct gca att aag    1262
Thr Phe Gly Thr Ile Asp Glu Leu Glu Leu Phe Thr Ser Ala Ile Lys
        385                 390                 395 aga tgg aat tca tca gag ata gaa cac ctt cca gaa tat atg aaa tgt    1310
Arg Trp Asn Ser Ser Glu Ile Glu His Leu Pro Glu Tyr Met Lys Cys
    400                 405                 410 gtg tac atg gtc gtg ttt gaa act gta aat gaa ctg aca cga gag gcg    1358
Val Tyr Met Val Val Phe Glu Thr Val Asn Glu Leu Thr Arg Glu Ala
415                 420                 425                 430 gag aag act caa ggg aga aac act ctc aac tat gtt cga aag gct tgg    1406
Glu Lys Thr Gln Gly Arg Asn Thr Leu Asn Tyr Val Arg Lys Ala Trp
                435                 440                 445 gag gct tat ttt gat tca tat atg gaa gaa gca aaa tgg atc tct aat    1454
Glu Ala Tyr Phe Asp Ser Tyr Met Glu Glu Ala Lys Trp Ile Ser Asn
            450                 455                 460 ggt tat ctg cca atg ttt gaa gag tac cat gag aat ggg aaa gtg agc    1502
Gly Tyr Leu Pro Met Phe Glu Glu Tyr His Glu Asn Gly Lys Val Ser
        465                 470                 475 tct gca tat cgc gta gca aca ttg caa ccc atc ctc act ttg aat gca    1550
Ser Ala Tyr Arg Val Ala Thr Leu Gln Pro Ile Leu Thr Leu Asn Ala
    480                 485                 490 tgg ctt cct gat tac atc ttg aag gga att gat ttt cca tcc agg ttc    1598
Trp Leu Pro Asp Tyr Ile Leu Lys Gly Ile Asp Phe Pro Ser Arg Phe
495                 500                 505                 510 aat gat ttg gca tcg tcc ttc ctt cgg cta cga ggt gac aca cgc tgc    1646
Asn Asp Leu Ala Ser Ser Phe Leu Arg Leu Arg Gly Asp Thr Arg Cys
                515                 520                 525 tac aag gcc gat agg gat cgt ggt gaa gaa gct tcg tgt ata tca tgt    1694
Tyr Lys Ala Asp Arg Asp Arg Gly Glu Glu Ala Ser Cys Ile Ser Cys
            530                 535                 540 tat atg aaa gac aat cct gga tca acc gaa gaa gat gcc ctc aat cat    1742
Tyr Met Lys Asp Asn Pro Gly Ser Thr Glu Glu Asp Ala Leu Asn His
        545                 550                 555 atc aat gcc atg gtc aat gac ata atc aaa gaa tta aat tgg gaa ctt    1790
Ile Asn Ala Met Val Asn Asp Ile Ile Lys Glu Leu Asn Trp Glu Leu
    560                 565                 570 cta aga tcc aac gac aat att cca atg ctg gcc aag aaa cat gct ttt    1838
Leu Arg Ser Asn Asp Asn Ile Pro Met Leu Ala Lys Lys His Ala Phe
575                 580                 585                 590 gac ata aca aga gct ctc cac cat ctc tac ata tat cga gat ggc ttt    1886
Asp Ile Thr Arg Ala Leu His His Leu Tyr Ile Tyr Arg Asp Gly Phe
                595                 600                 605 agt gtt gcc aac aag gaa aca aaa aaa ttg gtt atg gaa aca ctc ctt    1934
Ser Val Ala Asn Lys Glu Thr Lys Lys Leu Val Met Glu Thr Leu Leu
            610                 615                 620 gaa tct atg ctt ttt taa ctataaccat atccataata ataagctcat           1982
Glu Ser Met Leu Phe
            625 aatgctaaat tattggcctt atgacatagt ttatgtatgt acttgtgtga attcaatcat  2042
```

```
atcgtgtggg tatgattaaa aagctagagc ttactaggtt agtaacatgg tgataaaagt    2102
tataaaatgt gagttataga gatacccatg ttgaataatg aattacaaaa agagaaattt    2162
atgtagaata agattggaag cttttcaatt gttt                                2196
```

<210> SEQ ID NO 30
<211> LENGTH: 627
<212> TYPE: PRT
<213> ORGANISM: Abies grandis

<400> SEQUENCE: 30

```
Met Ala Leu Val Ser Ile Ser Pro Leu Ala Ser Lys Ser Cys Leu Arg
  1               5                  10                  15

Lys Ser Leu Ile Ser Ser Ile His Glu His Lys Pro Pro Tyr Arg Thr
             20                  25                  30

Ile Pro Asn Leu Gly Met Arg Arg Gly Lys Ser Val Thr Pro Ser
         35                  40                  45

Met Ser Ile Ser Leu Ala Thr Ala Ala Pro Asp Asp Gly Val Gln Arg
     50                  55                  60

Arg Ile Gly Asp Tyr His Ser Asn Ile Trp Asp Asp Phe Ile Gln
 65                  70                  75                  80

Ser Leu Ser Thr Pro Tyr Gly Glu Pro Ser Tyr Gln Glu Arg Ala Glu
                 85                  90                  95

Arg Leu Ile Val Glu Val Lys Lys Ile Phe Asn Ser Met Tyr Leu Asp
                100                 105                 110

Asp Gly Arg Leu Met Ser Ser Phe Asn Asp Leu Met Gln Arg Leu Trp
            115                 120                 125

Ile Val Asp Ser Val Glu Arg Leu Gly Ile Ala Arg His Phe Lys Asn
        130                 135                 140

Glu Ile Thr Ser Ala Leu Asp Tyr Val Phe Arg Tyr Trp Glu Asn
145                 150                 155                 160

Gly Ile Gly Cys Gly Arg Asp Ser Ile Val Thr Asp Leu Asn Ser Thr
                165                 170                 175

Ala Leu Gly Phe Arg Thr Leu Arg Leu His Gly Tyr Thr Val Ser Pro
            180                 185                 190

Glu Val Leu Lys Ala Phe Gln Asp Gln Asn Gly Gln Phe Val Cys Ser
        195                 200                 205

Pro Gly Gln Thr Glu Gly Glu Ile Arg Ser Val Leu Asn Leu Tyr Arg
    210                 215                 220

Ala Ser Leu Ile Ala Phe Pro Gly Glu Lys Val Met Glu Glu Ala Glu
225                 230                 235                 240

Ile Phe Ser Thr Arg Tyr Leu Lys Glu Ala Leu Gln Lys Ile Pro Val
                245                 250                 255

Ser Ala Leu Ser Gln Glu Ile Lys Phe Val Met Glu Tyr Gly Trp His
            260                 265                 270

Thr Asn Leu Pro Arg Leu Glu Ala Arg Asn Tyr Ile Asp Thr Leu Glu
        275                 280                 285

Lys Asp Thr Ser Ala Trp Leu Asn Lys Asn Ala Gly Lys Lys Leu Leu
    290                 295                 300

Glu Leu Ala Lys Leu Glu Phe Asn Ile Phe Asn Ser Leu Gln Gln Lys
305                 310                 315                 320

Glu Leu Gln Tyr Leu Leu Arg Trp Trp Lys Glu Ser Asp Leu Pro Lys
                325                 330                 335

Leu Thr Phe Ala Arg His Arg His Val Glu Phe Tyr Thr Leu Ala Ser
```

```
                      340                 345                 350
Cys Ile Ala Ile Asp Pro Lys His Ser Ala Phe Arg Leu Gly Phe Ala
            355                 360                 365
Lys Met Cys His Leu Val Thr Val Leu Asp Asp Ile Tyr Asp Thr Phe
370                 375                 380
Gly Thr Ile Asp Glu Leu Glu Leu Phe Thr Ser Ala Ile Lys Arg Trp
385                 390                 395                 400
Asn Ser Ser Glu Ile Glu His Leu Pro Glu Tyr Met Lys Cys Val Tyr
                405                 410                 415
Met Val Val Phe Glu Thr Val Asn Glu Leu Thr Arg Glu Ala Glu Lys
                420                 425                 430
Thr Gln Gly Arg Asn Thr Leu Asn Tyr Val Arg Lys Ala Trp Glu Ala
            435                 440                 445
Tyr Phe Asp Ser Tyr Met Glu Glu Ala Lys Trp Ile Ser Asn Gly Tyr
450                 455                 460
Leu Pro Met Phe Glu Glu Tyr His Glu Asn Gly Lys Val Ser Ser Ala
465                 470                 475                 480
Tyr Arg Val Ala Thr Leu Gln Pro Ile Leu Thr Leu Asn Ala Trp Leu
                485                 490                 495
Pro Asp Tyr Ile Leu Lys Gly Ile Asp Phe Pro Ser Arg Phe Asn Asp
                500                 505                 510
Leu Ala Ser Ser Phe Leu Arg Leu Arg Gly Asp Thr Arg Cys Tyr Lys
            515                 520                 525
Ala Asp Arg Asp Arg Gly Glu Glu Ala Ser Cys Ile Ser Cys Tyr Met
        530                 535                 540
Lys Asp Asn Pro Gly Ser Thr Glu Glu Asp Ala Leu Asn His Ile Asn
545                 550                 555                 560
Ala Met Val Asn Asp Ile Ile Lys Glu Leu Asn Trp Glu Leu Leu Arg
                565                 570                 575
Ser Asn Asp Asn Ile Pro Met Leu Ala Lys Lys His Ala Phe Asp Ile
                580                 585                 590
Thr Arg Ala Leu His His Leu Tyr Ile Tyr Arg Asp Gly Phe Ser Val
            595                 600                 605
Ala Asn Lys Glu Thr Lys Lys Leu Val Met Glu Thr Leu Leu Glu Ser
        610                 615                 620
Met Leu Phe
625

<210> SEQ ID NO 31
<211> LENGTH: 1944
<212> TYPE: DNA
<213> ORGANISM: Solanum tuberosum
<220> FEATURE:
<221> NAME/KEY: CDS
<222> LOCATION: (57)...(1724)
<223> OTHER INFORMATION: vetispiradiene synthase

<400> SEQUENCE: 31
gaaagaaaga aaattctctc tgttttttcc acaagcaaag agtacacaca ctagaa atg       59
                                                                 Met
                                                                  1 acc cca gct gct gta gta atg agt aac tac gga gag gag gag att gtt      107
Thr Pro Ala Ala Val Val Met Ser Asn Tyr Gly Glu Glu Glu Ile Val
            5                  10                  15 cgc ccc ata gct gac ttc tct cca agt ctt tgg ggt gat cgt ttt cat      155
Arg Pro Ile Ala Asp Phe Ser Pro Ser Leu Trp Gly Asp Arg Phe His
       20                  25                  30
```

-continued

| | | |
|---|---|---|
| tca ttc tcc ctc gac aat cag att gct gga aaa tat gct caa gag atc<br>Ser Phe Ser Leu Asp Asn Gln Ile Ala Gly Lys Tyr Ala Gln Glu Ile<br>35      40      45 | | 203 |
| gaa act ttg aag gaa caa tca aga att ata tta tct gca tct tct cga<br>Glu Thr Leu Lys Glu Gln Ser Arg Ile Ile Leu Ser Ala Ser Ser Arg<br>50      55      60      65 | | 251 |
| aga aca ttg gct gag aaa ttg gat ctg ata gac att gtt gag cgc ctt<br>Arg Thr Leu Ala Glu Lys Leu Asp Leu Ile Asp Ile Val Glu Arg Leu<br>      70      75      80 | | 299 |
| ggc att gct tat cat ttt gaa aaa caa ata gat gat atg ttg gat caa<br>Gly Ile Ala Tyr His Phe Glu Lys Gln Ile Asp Asp Met Leu Asp Gln<br>        85      90      95 | | 347 |
| ttt tac aaa gca gat cct aac ttt gag gct cac gag tac aat gat tta<br>Phe Tyr Lys Ala Asp Pro Asn Phe Glu Ala His Glu Tyr Asn Asp Leu<br>        100      105      110 | | 395 |
| caa act tta tcc gtt caa ttt cga cta ttg aga caa cat ggt tac aat<br>Gln Thr Leu Ser Val Gln Phe Arg Leu Leu Arg Gln His Gly Tyr Asn<br>115      120      125 | | 443 |
| atc tcc cca aaa ctt ttt att aga ttc caa gat gca aaa ggc aaa ttt<br>Ile Ser Pro Lys Leu Phe Ile Arg Phe Gln Asp Ala Lys Gly Lys Phe<br>130      135      140      145 | | 491 |
| aaa gaa tct ctt tgt aac gac atc aag ggt ctt ttg aac tta tac gaa<br>Lys Glu Ser Leu Cys Asn Asp Ile Lys Gly Leu Leu Asn Leu Tyr Glu<br>      150      155      160 | | 539 |
| gcc tcg cat gta agg act cat gga gaa gat att ttg gaa gag gca ctt<br>Ala Ser His Val Arg Thr His Gly Glu Asp Ile Leu Glu Glu Ala Leu<br>        165      170      175 | | 587 |
| gct ttc tct act gct cat ctt gaa tct gca gct cca cat ttg aag tca<br>Ala Phe Ser Thr Ala His Leu Glu Ser Ala Ala Pro His Leu Lys Ser<br>        180      185      190 | | 635 |
| cct ctg agt aag caa gtg aca cat gcc ctt gag caa tct ctc cat aag<br>Pro Leu Ser Lys Gln Val Thr His Ala Leu Glu Gln Ser Leu His Lys<br>195      200      205 | | 683 |
| agc att cca aga gtt gag aca cgc tac ttc atc tct atc tac gaa gag<br>Ser Ile Pro Arg Val Glu Thr Arg Tyr Phe Ile Ser Ile Tyr Glu Glu<br>210      215      220      225 | | 731 |
| gag gaa cag aag aat gat gtg ttg ctt caa ttt gca aaa ctg gac ttc<br>Glu Glu Gln Lys Asn Asp Val Leu Leu Gln Phe Ala Lys Leu Asp Phe<br>      230      235      240 | | 779 |
| aac tta ctt cag atg ttg cac aaa caa gaa ctt agt gaa gta tca agg<br>Asn Leu Leu Gln Met Leu His Lys Gln Glu Leu Ser Glu Val Ser Arg<br>        245      250      255 | | 827 |
| tgg tgg aaa gat ttg gat ttt gtg aca aca ctt cca tat gct agg gat<br>Trp Trp Lys Asp Leu Asp Phe Val Thr Thr Leu Pro Tyr Ala Arg Asp<br>      260      265      270 | | 875 |
| aga gca gtg gaa tgc tac ttt tgg acg atg ggg gta tat gct gaa cct<br>Arg Ala Val Glu Cys Tyr Phe Trp Thr Met Gly Val Tyr Ala Glu Pro<br>275      280      285 | | 923 |
| caa tac tct cag gct cgt gtc atg ctt gct aag act ata gca atg att<br>Gln Tyr Ser Gln Ala Arg Val Met Leu Ala Lys Thr Ile Ala Met Ile<br>290      295      300      305 | | 971 |
| tct ata gta gat gac aca ttc gat gct tat ggc att gtc aaa gaa ctt<br>Ser Ile Val Asp Asp Thr Phe Asp Ala Tyr Gly Ile Val Lys Glu Leu<br>      310      315      320 | | 1019 |
| gag atc tac acc gat gcc ata cag agg tgg gat att agc caa att gat<br>Glu Ile Tyr Thr Asp Ala Ile Gln Arg Trp Asp Ile Ser Gln Ile Asp<br>        325      330      335 | | 1067 |
| cgg ctc cct gat tac atg aaa atc agt tac aaa gca ctt tta gat ctc<br>Arg Leu Pro Asp Tyr Met Lys Ile Ser Tyr Lys Ala Leu Leu Asp Leu | | 1115 |

-continued

```
                340                 345                 350
tac aat gat tat gaa atg gag ttg tcc aag gat ggt aga tct gat gtt      1163
Tyr Asn Asp Tyr Glu Met Glu Leu Ser Lys Asp Gly Arg Ser Asp Val
    355                 360                 365 gtt cac tac gcg aaa gaa aga atg aaa gaa atc gtg aga aac tat ttt      1211
Val His Tyr Ala Lys Glu Arg Met Lys Glu Ile Val Arg Asn Tyr Phe
370                 375                 380                 385 gtg gaa gca aaa tgg ttc att gaa gga tat atg ccg cca gtc tct gag      1259
Val Glu Ala Lys Trp Phe Ile Glu Gly Tyr Met Pro Pro Val Ser Glu
                390                 395                 400 tat ctt agc aat gca tta gct acc agc act tat tac ttg ctt acg act      1307
Tyr Leu Ser Asn Ala Leu Ala Thr Ser Thr Tyr Tyr Leu Leu Thr Thr
            405                 410                 415 aca tct tat ttg ggc atg aag tct gct aac aag caa gat ttt gaa tgg      1355
Thr Ser Tyr Leu Gly Met Lys Ser Ala Asn Lys Gln Asp Phe Glu Trp
        420                 425                 430 ttg gcc aag aac cct aaa att ctt gag gct aat gtg acg tta tgc cga      1403
Leu Ala Lys Asn Pro Lys Ile Leu Glu Ala Asn Val Thr Leu Cys Arg
    435                 440                 445 gtc ata gat gac ata gcc acc tat gag gtt gag aag ggt aga ggt cag      1451
Val Ile Asp Asp Ile Ala Thr Tyr Glu Val Glu Lys Gly Arg Gly Gln
450                 455                 460                 465 att gcc act gga att gaa tgt tac atg aga gat tat ggt gta tcc aca      1499
Ile Ala Thr Gly Ile Glu Cys Tyr Met Arg Asp Tyr Gly Val Ser Thr
                470                 475                 480 gaa aag gcc atg gaa aaa ttc caa gaa atg gct gag aca gca tgg aag      1547
Glu Lys Ala Met Glu Lys Phe Gln Glu Met Ala Glu Thr Ala Trp Lys
            485                 490                 495 gat gta aat gaa gga atc ctt cga cca act ccc gtc tct aca gag att      1595
Asp Val Asn Glu Gly Ile Leu Arg Pro Thr Pro Val Ser Thr Glu Ile
        500                 505                 510 ctc act cgc att ctc aat ctt gct cgc att atc gat gtt act tat aag      1643
Leu Thr Arg Ile Leu Asn Leu Ala Arg Ile Ile Asp Val Thr Tyr Lys
    515                 520                 525 cac aat caa gat gga tac act cat ccg gaa aaa gta cta aaa cct cat      1691
His Asn Gln Asp Gly Tyr Thr His Pro Glu Lys Val Leu Lys Pro His
530                 535                 540                 545 att att gcg ttg ttg gtg gac tct att gaa att taa atcatcgatt           1737
Ile Ile Ala Leu Leu Val Asp Ser Ile Glu Ile
                550                 555 gttttgtaca tctgggagca cttgcttccc atccctaaa attataagta tttgattgat    1797
gccttgttgg tatctatgct gctaggcgct agctaagata ggagttgctg agatacatg    1857 ttatagtgca gtgcagttaa ttccttaatt ttttttgta tcattattga cattttaaat    1917
atatatatat atatcactgc tttttat                                        1944

<210> SEQ ID NO 32
<211> LENGTH: 556
<212> TYPE: PRT
<213> ORGANISM: Solanum tuberosum

<400> SEQUENCE: 32

Met Thr Pro Ala Ala Val Val Met Ser Asn Tyr Gly Glu Glu Glu Ile
1               5                   10                  15

Val Arg Pro Ile Ala Asp Phe Ser Pro Ser Leu Trp Gly Asp Arg Phe
            20                  25                  30

His Ser Phe Ser Leu Asp Asn Gln Ile Ala Gly Lys Tyr Ala Gln Glu
        35                  40                  45
```

-continued

```
Ile Glu Thr Leu Lys Glu Gln Ser Arg Ile Ile Leu Ser Ala Ser Ser
 50                  55                  60

Arg Arg Thr Leu Ala Glu Lys Leu Asp Leu Ile Asp Ile Val Glu Arg
 65                  70                  75                  80

Leu Gly Ile Ala Tyr His Phe Glu Lys Gln Ile Asp Asp Met Leu Asp
                     85                  90                  95

Gln Phe Tyr Lys Ala Asp Pro Asn Phe Glu Ala His Glu Tyr Asn Asp
                100                 105                 110

Leu Gln Thr Leu Ser Val Gln Phe Arg Leu Leu Arg Gln His Gly Tyr
            115                 120                 125

Asn Ile Ser Pro Lys Leu Phe Ile Arg Phe Gln Asp Ala Lys Gly Lys
130                 135                 140

Phe Lys Glu Ser Leu Cys Asn Asp Ile Lys Gly Leu Leu Asn Leu Tyr
145                 150                 155                 160

Glu Ala Ser His Val Arg Thr His Gly Glu Asp Ile Leu Glu Glu Ala
                165                 170                 175

Leu Ala Phe Ser Thr Ala His Leu Glu Ser Ala Ala Pro His Leu Lys
            180                 185                 190

Ser Pro Leu Ser Lys Gln Val Thr His Ala Leu Glu Gln Ser Leu His
        195                 200                 205

Lys Ser Ile Pro Arg Val Glu Thr Arg Tyr Phe Ile Ser Ile Tyr Glu
210                 215                 220

Glu Glu Glu Gln Lys Asn Asp Val Leu Leu Gln Phe Ala Lys Leu Asp
225                 230                 235                 240

Phe Asn Leu Leu Gln Met Leu His Lys Gln Glu Leu Ser Glu Val Ser
                245                 250                 255

Arg Trp Trp Lys Asp Leu Asp Phe Val Thr Thr Leu Pro Tyr Ala Arg
            260                 265                 270

Asp Arg Ala Val Glu Cys Tyr Phe Trp Thr Met Gly Val Tyr Ala Glu
        275                 280                 285

Pro Gln Tyr Ser Gln Ala Arg Val Met Leu Ala Lys Thr Ile Ala Met
290                 295                 300

Ile Ser Ile Val Asp Asp Thr Phe Asp Ala Tyr Gly Ile Val Lys Glu
305                 310                 315                 320

Leu Glu Ile Tyr Thr Asp Ala Ile Gln Arg Trp Asp Ile Ser Gln Ile
                325                 330                 335

Asp Arg Leu Pro Asp Tyr Met Lys Ile Ser Tyr Lys Ala Leu Leu Asp
            340                 345                 350

Leu Tyr Asn Asp Tyr Glu Met Glu Leu Ser Lys Asp Gly Arg Ser Asp
        355                 360                 365

Val Val His Tyr Ala Lys Glu Arg Met Lys Glu Ile Val Arg Asn Tyr
370                 375                 380

Phe Val Glu Ala Lys Trp Phe Ile Glu Gly Tyr Met Pro Pro Val Ser
385                 390                 395                 400

Glu Tyr Leu Ser Asn Ala Leu Ala Thr Ser Thr Tyr Tyr Leu Leu Thr
                405                 410                 415

Thr Thr Ser Tyr Leu Gly Met Lys Ser Ala Asn Lys Gln Asp Phe Glu
            420                 425                 430

Trp Leu Ala Lys Asn Pro Lys Ile Leu Glu Ala Asn Val Thr Leu Cys
        435                 440                 445

Arg Val Ile Asp Asp Ile Ala Thr Tyr Glu Val Glu Lys Gly Arg Gly
450                 455                 460

Gln Ile Ala Thr Gly Ile Glu Cys Tyr Met Arg Asp Tyr Gly Val Ser
```

```
                465                 470                 475                 480
Thr Glu Lys Ala Met Glu Lys Phe Gln Glu Met Ala Glu Thr Ala Trp
                            485                 490                 495
Lys Asp Val Asn Glu Gly Ile Leu Arg Pro Thr Pro Val Ser Thr Glu
                500                 505                 510
Ile Leu Thr Arg Ile Leu Asn Leu Ala Arg Ile Ile Asp Val Thr Tyr
                515                 520                 525
Lys His Asn Gln Asp Gly Tyr Thr His Pro Glu Lys Val Leu Lys Pro
        530                 535                 540
His Ile Ile Ala Leu Leu Val Asp Ser Ile Glu Ile
545                 550                 555

<210> SEQ ID NO 33
<211> LENGTH: 3950
<212> TYPE: DNA
<213> ORGANISM: Gossypium arboreum
<220> FEATURE:
<221> NAME/KEY: CDS
<222> LOCATION: (1457)...(1579)
<223> OTHER INFORMATION: cadinene synthase
<221> NAME/KEY: CDS
<222> LOCATION: (1670)...(1939)
<221> NAME/KEY: CDS
<222> LOCATION: (2092)...(2466)
<221> NAME/KEY: CDS
<222> LOCATION: (2559)...(2774)
<221> NAME/KEY: CDS
<222> LOCATION: (2963)...(3103)
<221> NAME/KEY: CDS
<222> LOCATION: (3206)...(3454)
<221> NAME/KEY: CDS
<222> LOCATION: (3596)...(3886)

<400> SEQUENCE: 33
```

| | | | | | |
|---|---|---|---|---|---|
| aatttaactt | ttattaattt | aaaatttaaa | gatttcaaag | gggttctaaa | atggaaattt | 60 |
| ttcgatttta | agggaattgt | gccagcccct | agtttcgccc | ttgtttgtag | tgctttattt | 120 |
| taaaaaagta | aatataatag | aatatgtata | tatatata | tataaaccaa | agtgaaagat | 180 |
| gaaaatttat | ataaatgatc | gctgcaagct | tcaagctcac | aataatatga | ttctttacca | 240 |
| tcaagaaaca | ttggtgcttt | atacagagaa | aagaaaaact | ttggtcctcc | tcgtagctaa | 300 |
| tattttaaca | atttaatttt | tatataataa | atttttaaca | attatttcat | atttttttaaa | 360 |
| tatattcatg | ttgaatgtag | cagtatatag | ttatattagt | tatgctcata | aattttggat | 420 |
| gcattagatt | ttcctatgt | aatttgataa | caatgattat | tattttact | tctaacaaat | 480 |
| aattaaaatat | ttttttgttg | attcgataaa | tatcattatt | ttttaaatga | tttaaaaatat | 540 |
| aaaaataata | atagattcga | ccgaacgctc | accctattga | gtgagtatat | caattattag | 600 |
| aatttaatta | aaaaggaaa | ccaaatatag | ccggcttaat | tttgtttaat | attaatttat | 660 |
| gtgtggaaat | tcacttaaaa | acagagtcca | tggctgctaa | catattatat | attaaaccat | 720 |
| ttcctattaa | taaatttatg | aacgagagtt | acatccttct | aaattcattt | tacttagagg | 780 |
| cggagtataa | tattttatgt | agtagttatt | cttttactat | ataaataaat | aaataaaatt | 840 |
| ttaatcgcct | gtgtattatg | attgattcag | ctgaatcaaa | gttggaataa | tattttaatt | 900 |
| tgggatccca | attaattgag | attggttga | ttttggttg | taaatatttt | ttattaattt | 960 |
| tagataaaatt | attggaagtt | ggagtcaaaa | ttgaccgtct | cagctaatta | tacaaaataat | 1020 |
| aataatatag | agaaatgggt | atattgctca | acactcacat | ttactacgtc | agcaatagtc | 1080 |
| agacagactg | ctaagtaaac | aatgtacact | caattcgagt | caaacaaatc | ctttatccca | 1140 |

```
agattctaaa ataatgtgtt tgaggcacca attttgaagg atagaaagtg gaaacaaaca    1200
aaaggatatt aaaaaacaag gaaatttctc actgtatttg catattttc tccttccagt    1260 ataattaaaa tacgtgcaat ttacgttgta ctttgttgac tcctatctta tacctataaa    1320
tacatgcaac aattgcacac atcgtctcat ccaaaacctg tgttttaaac actaaacagt    1380
aagcaaaggc agcaaattaa tctttgaatt atttgcttcc aaaaccctac acttttcctt    1440
caacacatcc tagaaa atg gct tca caa gct tct caa gtt ctt gct tca ccc    1492
              Met Ala Ser Gln Ala Ser Gln Val Leu Ala Ser Pro
                1           5                  10 cat ccc gcc att tca tcc gaa aat cga ccc aag gct gat ttt cat ccc    1540
His Pro Ala Ile Ser Ser Glu Asn Arg Pro Lys Ala Asp Phe His Pro
             15                  20                  25 ggt att tgg ggt gat atg ttc atc atc tgt cct gat acg gtaatctata    1589
Gly Ile Trp Gly Asp Met Phe Ile Ile Cys Pro Asp Thr
 30                  35                  40 atttttttct tactttctct tttatcgatt tttaagtttt ttggagattt catggaaaag    1649
cattatacgt acttgagcag gat atc gat gct gca act gaa tta caa tat gaa    1702
                      Asp Ile Asp Ala Ala Thr Glu Leu Gln Tyr Glu
                                       45                  50 gaa tta aaa gca caa gtg agg aag atg att atg gaa cct gtt gat gat    1750
Glu Leu Lys Ala Gln Val Arg Lys Met Ile Met Glu Pro Val Asp Asp
         55                  60                  65 tca aac caa aag ttg ccc ttc att gat gct gtt caa aga tta ggt gtg    1798
Ser Asn Gln Lys Leu Pro Phe Ile Asp Ala Val Gln Arg Leu Gly Val
 70                  75                  80 agt tat cat ttt gag aaa gag att gaa gat gaa cta gag aat att tac    1846
Ser Tyr His Phe Glu Lys Glu Ile Glu Asp Glu Leu Glu Asn Ile Tyr
 85                  90                  95                 100 cgt gac acc aac aac aat gat gcg gac acc gat ctc tac act aca gct    1894
Arg Asp Thr Asn Asn Asn Asp Ala Asp Thr Asp Leu Tyr Thr Thr Ala
                105                 110                 115 ctt cga ttc cgg tta ctt aga gag cat ggc ttc gat att tct tgt    1939
Leu Arg Phe Arg Leu Leu Arg Glu His Gly Phe Asp Ile Ser Cys
             120                 125                 130 ggtaattaag tcttaaactt tcataactct tcttatccat ttatcaatta atattatcaa    1999
actttacatt aataatcatc tgtacaatac ttcaatatat atatatttat tgatgaaact    2059
aatgtttgat gatgattttg ggtgcttgac ca gat gca ttc aac aag ttc aaa    2112
                                  Asp Ala Phe Asn Lys Phe Lys
                                                 135 gat gag gca ggg aac ttc aag gca tca ttg aca agt gat gtg caa ggg    2160
Asp Glu Ala Gly Asn Phe Lys Ala Ser Leu Thr Ser Asp Val Gln Gly
140                 145                 150 ttg ttg gaa ctt tat gaa gct tcc tat atg agg gtc cat ggg gaa gat    2208
Leu Leu Glu Leu Tyr Glu Ala Ser Tyr Met Arg Val His Gly Glu Asp
155                 160                 165                 170 ata ctt gat gaa gcc att tct ttc acc act gct caa ctt aca ctt gct    2256
Ile Leu Asp Glu Ala Ile Ser Phe Thr Thr Ala Gln Leu Thr Leu Ala
            175                 180                 185 cta cca act tta cac cat cct tta tcg gaa cag gtc ggc cat gcc tta    2304
Leu Pro Thr Leu His His Pro Leu Ser Glu Gln Val Gly His Ala Leu
            190                 195                 200 aag cag tct atc cga agg ggc ttg cca agg gtt gag gcc cgg aat ttc    2352
Lys Gln Ser Ile Arg Arg Gly Leu Pro Arg Val Glu Ala Arg Asn Phe
            205                 210                 215 att tcg ata tac caa gat tta gaa tcc cat aac aaa tcg ttg ctt caa    2400
Ile Ser Ile Tyr Gln Asp Leu Glu Ser His Asn Lys Ser Leu Leu Gln
220                 225                 230
```

```
ttt gca aag att gat ttc aac ttg ttg cag ctt ttg cat agg aaa gag       2448
Phe Ala Lys Ile Asp Phe Asn Leu Leu Gln Leu Leu His Arg Lys Glu
235                 240                 245                 250 cta agt gag atc tgc agg taagtgtttg gagatcttta aagctatgaa              2496
Leu Ser Glu Ile Cys Arg
                255 gtctaatact atttcaattg atcacacgac tgttgctgac attttatgat gcttttttta     2556 gg tgg tgg aaa gat tta gac ttt aca aga aaa cta cca ttt gca aga        2603
   Trp Trp Lys Asp Leu Asp Phe Thr Arg Lys Leu Pro Phe Ala Arg
               260                 265                 270 gat aga gtg gtt gaa ggc tat ttt tgg ata atg gga gtt tac ttt gaa       2651
Asp Arg Val Val Glu Gly Tyr Phe Trp Ile Met Gly Val Tyr Phe Glu
            275                 280                 285 ccc caa tac tct ctt ggt aga aag atg ttg aca aaa gtc ata gca atg       2699
Pro Gln Tyr Ser Leu Gly Arg Lys Met Leu Thr Lys Val Ile Ala Met
            290                 295                 300 gct tcc att gtt gat gat act tat gat tca tat gca acc tat gat gaa       2747
Ala Ser Ile Val Asp Asp Thr Tyr Asp Ser Tyr Ala Thr Tyr Asp Glu
            305                 310                 315 ctc att ccc tat aca aat gca att gaa ggtgagattt tttttccttt             2794
Leu Ile Pro Tyr Thr Asn Ala Ile Glu
320                 325 cctccaaaaa aaaaaaaagt ttttgagatc ccccaagaat aggggaaaat atatgttttt     2854
aaacgttagg atattcactc caacttgcag ttgctcatat tttaatggtg atagtatgaa     2914
ctaaccaggc taagttttag attcaaatta accctgaaat tgtgttttt agg tgg gat     2971
                                                        Arg Trp Asp
                                                                330 att aaa tgc atg aac caa ctc ccg aat tac atg aaa ata agc tac aag       3019
Ile Lys Cys Met Asn Gln Leu Pro Asn Tyr Met Lys Ile Ser Tyr Lys
                335                 340                 345 gca cta tta gat gtt tat gaa gaa atg gaa cag ctg ttg gca aat caa       3067
Ala Leu Leu Asp Val Tyr Glu Glu Met Glu Gln Leu Leu Ala Asn Gln
            350                 355                 360 ggg aga cag tac cga gtt gag tat gcg aaa aag gcg gtatgtaatg            3113
Gly Arg Gln Tyr Arg Val Glu Tyr Ala Lys Lys Ala
365                 370                 375 atacaatagt atgatatgct ttaatcataa acgtataaaa tttgaaaatt acattagcaa     3173
tttgcttact tttttatgcc tttaatcctc ag atg ata cgt ctt gtt caa gct       3226
                                   Met Ile Arg Leu Val Gln Ala
                                                           380 tac ctt ttg gag gcc aaa tgg act cat caa aat tat aaa cca acc ttt       3274
Tyr Leu Leu Glu Ala Lys Trp Thr His Gln Asn Tyr Lys Pro Thr Phe
                385                 390                 395 gag gaa ttt aga gat aat gca ttg cca acc tct ggc tat gcc atg ctt       3322
Glu Glu Phe Arg Asp Asn Ala Leu Pro Thr Ser Gly Tyr Ala Met Leu
400                 405                 410 gct ata acg gcg ttt gtc ggc atg ggc gaa gtt ata acc cct gag acc       3370
Ala Ile Thr Ala Phe Val Gly Met Gly Glu Val Ile Thr Pro Glu Thr
            415                 420                 425                 430 ttc aaa tgg gcc gcc agt gac ccc aag atc att aag gct tcc acc att       3418
Phe Lys Trp Ala Ala Ser Asp Pro Lys Ile Ile Lys Ala Ser Thr Ile
                435                 440                 445 att tgc agg ttc atg gac gat att gct gaa cat aag gtatactata            3464
Ile Cys Arg Phe Met Asp Asp Ile Ala Glu His Lys
            450                 455 tattcatatt caagaattct aaaaatcgat tatggtatat atatgcactt aaatctatat     3524
```

```
catagaattg taaggcttct agggtttgca tttgctaagt taattaatat acatggttca   3584
tatgggtgca g ttc aac cat agg aga gaa gac gat tgc tca gcg atc gaa   3634
            Phe Asn His Arg Arg Glu Asp Asp Cys Ser Ala Ile Glu
                460                 465                 470 tgt tac atg aaa caa tat ggg gtg aca gcg cag gaa gca tac aat gaa   3682
Cys Tyr Met Lys Gln Tyr Gly Val Thr Ala Gln Glu Ala Tyr Asn Glu
            475                 480                 485 ttc aac aaa cac att gag agt tca tgg aaa gat gta aat gaa gag ttc   3730
Phe Asn Lys His Ile Glu Ser Ser Trp Lys Asp Val Asn Glu Glu Phe
            490                 495                 500 ttg aaa ccg aca gaa atg ccg aca ccc gtt ctt tgt cgt agc ctc aac   3778
Leu Lys Pro Thr Glu Met Pro Thr Pro Val Leu Cys Arg Ser Leu Asn
    505                 510                 515 ctt gct agg gtt atg gat gta ctt tac aga gaa ggt gac ggt tat aca   3826
Leu Ala Arg Val Met Asp Val Leu Tyr Arg Glu Gly Asp Gly Tyr Thr
520                 525                 530                 535 cat gtt ggg aaa gct gct aaa ggt ggg atc act tca tta ttg att gat   3874
His Val Gly Lys Ala Ala Lys Gly Gly Ile Thr Ser Leu Leu Ile Asp
                540                 545                 550 cca ata caa att tga aattcaacat tggcttaaga tttactatga gataaaatta   3929
Pro Ile Gln Ile
            555 ataaggtttg tacaatgaag g                                            3950

<210> SEQ ID NO 34
<211> LENGTH: 41
<212> TYPE: PRT
<213> ORGANISM: Gossypium arboreum

<400> SEQUENCE: 34

Met Ala Ser Gln Ala Ser Gln Val Leu Ala Ser Pro His Pro Ala Ile
 1               5                  10                  15

Ser Ser Glu Asn Arg Pro Lys Ala Asp Phe His Pro Gly Ile Trp Gly
            20                  25                  30

Asp Met Phe Ile Ile Cys Pro Asp Thr
        35                  40

<210> SEQ ID NO 35
<211> LENGTH: 90
<212> TYPE: PRT
<213> ORGANISM: Gossypium arboreum

<400> SEQUENCE: 35

Asp Ile Asp Ala Ala Thr Glu Leu Gln Tyr Glu Glu Leu Lys Ala Gln
 1               5                  10                  15

Val Arg Lys Met Ile Met Glu Pro Val Asp Asp Ser Asn Gln Lys Leu
            20                  25                  30

Pro Phe Ile Asp Ala Val Gln Arg Leu Gly Val Ser Tyr His Phe Glu
        35                  40                  45

Lys Glu Ile Glu Asp Glu Leu Glu Asn Ile Tyr Arg Asp Thr Asn Asn
    50                  55                  60

Asn Asp Ala Asp Thr Asp Leu Tyr Thr Thr Ala Leu Arg Phe Arg Leu
65                  70                  75                  80

Leu Arg Glu His Gly Phe Asp Ile Ser Cys
                85                  90

<210> SEQ ID NO 36
<211> LENGTH: 125
<212> TYPE: PRT
```

<213> ORGANISM: Gossypium arboreum

<400> SEQUENCE: 36

```
Asp Ala Phe Asn Lys Phe Lys Asp Glu Ala Gly Asn Phe Lys Ala Ser
1               5                   10                  15

Leu Thr Ser Asp Val Gln Gly Leu Leu Glu Leu Tyr Glu Ala Ser Tyr
            20                  25                  30

Met Arg Val His Gly Glu Asp Ile Leu Asp Glu Ala Ile Ser Phe Thr
        35                  40                  45

Thr Ala Gln Leu Thr Leu Ala Leu Pro Thr Leu His His Pro Leu Ser
    50                  55                  60

Glu Gln Val Gly His Ala Leu Lys Gln Ser Ile Arg Arg Gly Leu Pro
65                  70                  75                  80

Arg Val Glu Ala Arg Asn Phe Ile Ser Ile Tyr Gln Asp Leu Glu Ser
                85                  90                  95

His Asn Lys Ser Leu Leu Gln Phe Ala Lys Ile Asp Phe Asn Leu Leu
            100                 105                 110

Gln Leu Leu His Arg Lys Glu Leu Ser Glu Ile Cys Arg
        115                 120                 125
```

<210> SEQ ID NO 37
<211> LENGTH: 72
<212> TYPE: PRT
<213> ORGANISM: Gossypium arboreum

<400> SEQUENCE: 37

```
Trp Trp Lys Asp Leu Asp Phe Thr Arg Lys Leu Pro Phe Ala Arg Asp
1               5                   10                  15

Arg Val Val Glu Gly Tyr Phe Trp Ile Met Gly Val Tyr Phe Glu Pro
            20                  25                  30

Gln Tyr Ser Leu Gly Arg Lys Met Leu Thr Lys Val Ile Ala Met Ala
        35                  40                  45

Ser Ile Val Asp Asp Thr Tyr Asp Ser Tyr Ala Thr Tyr Asp Glu Leu
    50                  55                  60

Ile Pro Tyr Thr Asn Ala Ile Glu
65                  70
```

<210> SEQ ID NO 38
<211> LENGTH: 47
<212> TYPE: PRT
<213> ORGANISM: Gossypium arboreum

<400> SEQUENCE: 38

```
Arg Trp Asp Ile Lys Cys Met Asn Gln Leu Pro Asn Tyr Met Lys Ile
1               5                   10                  15

Ser Tyr Lys Ala Leu Leu Asp Val Tyr Glu Glu Met Glu Gln Leu Leu
            20                  25                  30

Ala Asn Gln Gly Arg Gln Tyr Arg Val Glu Tyr Ala Lys Lys Ala
        35                  40                  45
```

<210> SEQ ID NO 39
<211> LENGTH: 83
<212> TYPE: PRT
<213> ORGANISM: Gossypium arboreum

<400> SEQUENCE: 39

```
Met Ile Arg Leu Val Gln Ala Tyr Leu Leu Glu Ala Lys Trp Thr His
1               5                   10                  15
```

```
Gln Asn Tyr Lys Pro Thr Phe Glu Glu Phe Arg Asp Asn Ala Leu Pro
            20                  25                  30

Thr Ser Gly Tyr Ala Met Leu Ala Ile Thr Ala Phe Val Gly Met Gly
        35                  40                  45

Glu Val Ile Thr Pro Glu Thr Phe Lys Trp Ala Ala Ser Asp Pro Lys
 50                  55                  60

Ile Ile Lys Ala Ser Thr Ile Ile Cys Arg Phe Met Asp Asp Ile Ala
65                  70                  75                  80

Glu His Lys

<210> SEQ ID NO 40
<211> LENGTH: 97
<212> TYPE: PRT
<213> ORGANISM: Gossypium arboreum

<400> SEQUENCE: 40

Phe Asn His Arg Arg Glu Asp Asp Cys Ser Ala Ile Glu Cys Tyr Met
 1               5                  10                  15

Lys Gln Tyr Gly Val Thr Ala Gln Glu Ala Tyr Asn Glu Phe Asn Lys
            20                  25                  30

His Ile Glu Ser Ser Trp Lys Asp Val Asn Glu Glu Phe Leu Lys Pro
        35                  40                  45

Thr Glu Met Pro Thr Pro Val Leu Cys Arg Ser Leu Asn Leu Ala Arg
 50                  55                  60

Val Met Asp Val Leu Tyr Arg Glu Gly Asp Gly Tyr Thr His Val Gly
65                  70                  75                  80

Lys Ala Ala Lys Gly Gly Ile Thr Ser Leu Leu Ile Asp Pro Ile Gln
            85                  90                  95

Ile

<210> SEQ ID NO 41
<211> LENGTH: 1994
<212> TYPE: DNA
<213> ORGANISM: Ricinus communis
<220> FEATURE:
<221> NAME/KEY: CDS
<222> LOCATION: (67)...(1869)
<223> OTHER INFORMATION: casbene synthase

<400> SEQUENCE: 41
actcagcagc cgcctctcct accccaatta gcacagaaga tttggtggtt cctctccttg     60 tgaaac atg gca ttg cca tca gct gct atg caa tcc aac cct gaa aag       108
       Met Ala Leu Pro Ser Ala Ala Met Gln Ser Asn Pro Glu Lys
        1               5                  10 ctt aac tta ttt cac aga ttg tca agc tta ccc acc act agc ttg gaa     156
Leu Asn Leu Phe His Arg Leu Ser Ser Leu Pro Thr Thr Ser Leu Glu
 15                  20                  25                  30 tat ggc aat aat cgc ttc cct ttc ttt tcc tca tct gcc aag tca cac     204
Tyr Gly Asn Asn Arg Phe Pro Phe Phe Ser Ser Ser Ala Lys Ser His
                 35                  40                  45 ttt aaa aaa cca act caa gca tgt tta tcc tca aca acc cac caa gaa     252
Phe Lys Lys Pro Thr Gln Ala Cys Leu Ser Ser Thr Thr His Gln Glu
             50                  55                  60 gtt cgt cca tta gca tac ttt cct cct act gtc tgg ggc aat cgc ttt     300
Val Arg Pro Leu Ala Tyr Phe Pro Pro Thr Val Trp Gly Asn Arg Phe
         65                  70                  75 gct tcc ttg acc ttc aat cca tcg gaa ttt gaa tcg tat gat gaa cgg     348
Ala Ser Leu Thr Phe Asn Pro Ser Glu Phe Glu Ser Tyr Asp Glu Arg
 80                  85                  90
```

```
gta att gtg ctg aag aaa aaa gtt aag gac ata tta att tca tct aca    396
Val Ile Val Leu Lys Lys Lys Val Lys Asp Ile Leu Ile Ser Ser Thr
 95             100                 105                 110 agt gat tca gtg gag acc gtt att tta atc gac tta tta tgt cgg ctt    444
Ser Asp Ser Val Glu Thr Val Ile Leu Ile Asp Leu Leu Cys Arg Leu
            115                 120                 125 ggc gta tca tat cac ttt gaa aat gat att gaa gag cta cta agt aaa    492
Gly Val Ser Tyr His Phe Glu Asn Asp Ile Glu Glu Leu Leu Ser Lys
        130                 135                 140 atc ttc aac tcc cag cct gac ctt gtc gat gaa aaa gaa tgt gat ctc    540
Ile Phe Asn Ser Gln Pro Asp Leu Val Asp Glu Lys Glu Cys Asp Leu
    145                 150                 155 tac act gcg gca att gta ttc cga gtt ttc aga cag cat ggt ttt aaa    588
Tyr Thr Ala Ala Ile Val Phe Arg Val Phe Arg Gln His Gly Phe Lys
160                 165                 170 atg tct tcg gat gtg ttt agc aaa ttc aag gac agt gat ggt aag ttc    636
Met Ser Ser Asp Val Phe Ser Lys Phe Lys Asp Ser Asp Gly Lys Phe
175                 180                 185                 190 aag gaa tcc cta cgg ggt gat gct aag ggt atg ctc agc ctt ttt gaa    684
Lys Glu Ser Leu Arg Gly Asp Ala Lys Gly Met Leu Ser Leu Phe Glu
                195                 200                 205 gct tcc cat cta agt gtg cat gga gaa gac att ctt gaa gaa gcc ttt    732
Ala Ser His Leu Ser Val His Gly Glu Asp Ile Leu Glu Glu Ala Phe
            210                 215                 220 gct ttc acc aag gat tac tta cag tcc tct gca gtt gag tta ttc cct    780
Ala Phe Thr Lys Asp Tyr Leu Gln Ser Ser Ala Val Glu Leu Phe Pro
        225                 230                 235 aat ctc aaa agg cat ata acg aac gcc cta gag cag cct ttc cac agt    828
Asn Leu Lys Arg His Ile Thr Asn Ala Leu Glu Gln Pro Phe His Ser
240                 245                 250 ggc gtg ccg agg cta gag gcc agg aaa ttc atc gat cta tac gaa gct    876
Gly Val Pro Arg Leu Glu Ala Arg Lys Phe Ile Asp Leu Tyr Glu Ala
255                 260                 265                 270 gat att gaa tgc cgg aat gaa act ctg ctc gag ttt gca aag ttg gat    924
Asp Ile Glu Cys Arg Asn Glu Thr Leu Leu Glu Phe Ala Lys Leu Asp
                275                 280                 285 tat aat aga gtt cag tta ttg cac caa caa gag ctg tgc cag ttc tca    972
Tyr Asn Arg Val Gln Leu Leu His Gln Gln Glu Leu Cys Gln Phe Ser
            290                 295                 300 aag tgg tgg aaa gac ctg aat ctt gct tcg gat att cct tat gca aga   1020
Lys Trp Trp Lys Asp Leu Asn Leu Ala Ser Asp Ile Pro Tyr Ala Arg
        305                 310                 315 gac aga atg gca gag att ttc ttt tgg gca gtc gcg atg tac ttt gag   1068
Asp Arg Met Ala Glu Ile Phe Phe Trp Ala Val Ala Met Tyr Phe Glu
320                 325                 330 cct gac tat gca cac acc cga atg att att gcg aag gtt gta ttg ctt   1116
Pro Asp Tyr Ala His Thr Arg Met Ile Ile Ala Lys Val Val Leu Leu
335                 340                 345                 350 ata tca cta ata gat gat aca att gat gcg tat gca aca atg gag gaa   1164
Ile Ser Leu Ile Asp Asp Thr Ile Asp Ala Tyr Ala Thr Met Glu Glu
                355                 360                 365 act cat att ctt gct gaa gca gtc gca agg tgg gac atg agc tgc ctc   1212
Thr His Ile Leu Ala Glu Ala Val Ala Arg Trp Asp Met Ser Cys Leu
            370                 375                 380 gag aag ctg cca gat tac atg aaa gtt att tat aaa cta ttg cta aac   1260
Glu Lys Leu Pro Asp Tyr Met Lys Val Ile Tyr Lys Leu Leu Leu Asn
        385                 390                 395 acc ttc tct gaa ttc gag aaa gaa ttg acg gcg gaa ggc aag tcc tac   1308
Thr Phe Ser Glu Phe Glu Lys Glu Leu Thr Ala Glu Gly Lys Ser Tyr
```

-continued

```
    400                 405                 410 agc gtc aaa tac gga agg gaa gcg ttt caa gaa cta gtg aga ggt tac     1356
Ser Val Lys Tyr Gly Arg Glu Ala Phe Gln Glu Leu Val Arg Gly Tyr
415                 420                 425                 430 tac ctg gag gct gta tgg cgc gac gag ggt aaa ata cca tcg ttc gat     1404
Tyr Leu Glu Ala Val Trp Arg Asp Glu Gly Lys Ile Pro Ser Phe Asp
                435                 440                 445 gac tac ttg tat aat gga tcc atg acc acc gga ttg cct ctc gtc tca     1452
Asp Tyr Leu Tyr Asn Gly Ser Met Thr Thr Gly Leu Pro Leu Val Ser
            450                 455                 460 aca gct tct ttc atg gga gtt caa gaa att aca ggt ctc aac gaa ttc     1500
Thr Ala Ser Phe Met Gly Val Gln Glu Ile Thr Gly Leu Asn Glu Phe
        465                 470                 475 caa tgg ctg gaa act aat ccc aaa tta agt tat gct tcc ggt gca ttc     1548
Gln Trp Leu Glu Thr Asn Pro Lys Leu Ser Tyr Ala Ser Gly Ala Phe
    480                 485                 490 atc cga ctt gtc aac gac tta act tct cat gtg act gaa caa caa aga     1596
Ile Arg Leu Val Asn Asp Leu Thr Ser His Val Thr Glu Gln Gln Arg
495                 500                 505                 510 gga cac gtt gca tct tgc atc gac tgc tat atg aac caa cat gga gtt     1644
Gly His Val Ala Ser Cys Ile Asp Cys Tyr Met Asn Gln His Gly Val
                515                 520                 525 tcc aaa gac gaa gca gtc aaa ata ctt caa aaa atg gct aca gat tgt     1692
Ser Lys Asp Glu Ala Val Lys Ile Leu Gln Lys Met Ala Thr Asp Cys
            530                 535                 540 tgg aaa gaa att aat gaa gaa tgt atg agg cag agt caa gtg tca gtg     1740
Trp Lys Glu Ile Asn Glu Glu Cys Met Arg Gln Ser Gln Val Ser Val
        545                 550                 555 ggt cac cta atg aga ata gtt aat ctg gca cgt ctt acg gat gtg agt     1788
Gly His Leu Met Arg Ile Val Asn Leu Ala Arg Leu Thr Asp Val Ser
    560                 565                 570 tac aag tat gga gac ggt tac act gat tcc cag caa ttg aaa caa ttt     1836
Tyr Lys Tyr Gly Asp Gly Tyr Thr Asp Ser Gln Gln Leu Lys Gln Phe
575                 580                 585                 590 gtt aag gga ttg ttc gtt gat cca att tct att tgaactcaat aattcctttt   1889
Val Lys Gly Leu Phe Val Asp Pro Ile Ser Ile
                595                 600 ttcattttgt acttcaataa gttataaatg acccgtgcac tagcggtggt gattattgta   1949
tttaaattgc cttttaaatt aatatatgaa tcaagaattt tatag                   1994

<210> SEQ ID NO 42
<211> LENGTH: 601
<212> TYPE: PRT
<213> ORGANISM: Ricinus communis

<400> SEQUENCE: 42

Met Ala Leu Pro Ser Ala Ala Met Gln Ser Asn Pro Glu Lys Leu Asn
 1               5                  10                  15

Leu Phe His Arg Leu Ser Ser Leu Pro Thr Thr Ser Leu Glu Tyr Gly
            20                  25                  30

Asn Asn Arg Phe Pro Phe Phe Ser Ser Ser Ala Lys Ser His Phe Lys
        35                  40                  45

Lys Pro Thr Gln Ala Cys Leu Ser Ser Thr Thr His Gln Glu Val Arg
    50                  55                  60

Pro Leu Ala Tyr Phe Pro Pro Thr Val Trp Gly Asn Arg Phe Ala Ser
65                  70                  75                  80

Leu Thr Phe Asn Pro Ser Glu Phe Glu Ser Tyr Asp Glu Arg Val Ile
                85                  90                  95
```

-continued

```
Val Leu Lys Lys Val Lys Asp Ile Leu Ile Ser Thr Ser Asp
            100                 105                 110

Ser Val Glu Thr Val Ile Leu Ile Asp Leu Leu Cys Arg Leu Gly Val
        115                 120                 125

Ser Tyr His Phe Glu Asn Asp Ile Glu Glu Leu Leu Ser Lys Ile Phe
        130                 135                 140

Asn Ser Gln Pro Asp Leu Val Asp Glu Lys Glu Cys Asp Leu Tyr Thr
145                 150                 155                 160

Ala Ala Ile Val Phe Arg Val Phe Arg Gln His Gly Phe Lys Met Ser
                165                 170                 175

Ser Asp Val Phe Ser Lys Phe Lys Asp Ser Asp Gly Lys Phe Lys Glu
            180                 185                 190

Ser Leu Arg Gly Asp Ala Lys Gly Met Leu Ser Leu Phe Glu Ala Ser
        195                 200                 205

His Leu Ser Val His Gly Glu Asp Ile Leu Glu Glu Ala Phe Ala Phe
        210                 215                 220

Thr Lys Asp Tyr Leu Gln Ser Ser Ala Val Glu Leu Phe Pro Asn Leu
225                 230                 235                 240

Lys Arg His Ile Thr Asn Ala Leu Glu Gln Pro Phe His Ser Gly Val
                245                 250                 255

Pro Arg Leu Glu Ala Arg Lys Phe Ile Asp Leu Tyr Glu Ala Asp Ile
            260                 265                 270

Glu Cys Arg Asn Glu Thr Leu Leu Glu Phe Ala Lys Leu Asp Tyr Asn
        275                 280                 285

Arg Val Gln Leu Leu His Gln Gln Glu Leu Cys Gln Phe Ser Lys Trp
        290                 295                 300

Trp Lys Asp Leu Asn Leu Ala Ser Asp Ile Pro Tyr Ala Arg Asp Arg
305                 310                 315                 320

Met Ala Glu Ile Phe Phe Trp Ala Val Ala Met Tyr Phe Glu Pro Asp
                325                 330                 335

Tyr Ala His Thr Arg Met Ile Ile Ala Lys Val Val Leu Leu Ile Ser
            340                 345                 350

Leu Ile Asp Asp Thr Ile Asp Ala Tyr Ala Thr Met Glu Glu Thr His
        355                 360                 365

Ile Leu Ala Glu Ala Val Ala Arg Trp Asp Met Ser Cys Leu Glu Lys
        370                 375                 380

Leu Pro Asp Tyr Met Lys Val Ile Tyr Lys Leu Leu Leu Asn Thr Phe
385                 390                 395                 400

Ser Glu Phe Glu Lys Glu Leu Thr Ala Glu Gly Lys Ser Tyr Ser Val
                405                 410                 415

Lys Tyr Gly Arg Glu Ala Phe Gln Glu Leu Val Arg Gly Tyr Tyr Leu
            420                 425                 430

Glu Ala Val Trp Arg Asp Glu Gly Lys Ile Pro Ser Phe Asp Asp Tyr
        435                 440                 445

Leu Tyr Asn Gly Ser Met Thr Thr Gly Leu Pro Leu Val Ser Thr Ala
        450                 455                 460

Ser Phe Met Gly Val Gln Glu Ile Thr Gly Leu Asn Glu Phe Gln Trp
465                 470                 475                 480

Leu Glu Thr Asn Pro Lys Leu Ser Tyr Ala Ser Gly Ala Phe Ile Arg
                485                 490                 495

Leu Val Asn Asp Leu Thr Ser His Val Thr Glu Gln Gln Arg Gly His
            500                 505                 510
```

```
Val Ala Ser Cys Ile Asp Cys Tyr Met Asn Gln His Gly Val Ser Lys
        515                 520                 525

Asp Glu Ala Val Lys Ile Leu Gln Lys Met Ala Thr Asp Cys Trp Lys
    530                 535                 540

Glu Ile Asn Glu Glu Cys Met Arg Gln Ser Gln Val Ser Val Gly His
545                 550                 555                 560

Leu Met Arg Ile Val Asn Leu Ala Arg Leu Thr Asp Val Ser Tyr Lys
                565                 570                 575

Tyr Gly Asp Gly Tyr Thr Asp Ser Gln Gln Leu Lys Gln Phe Val Lys
            580                 585                 590

Gly Leu Phe Val Asp Pro Ile Ser Ile
        595                 600

<210> SEQ ID NO 43
<211> LENGTH: 2700
<212> TYPE: DNA
<213> ORGANISM: Taxus brevifolia
<220> FEATURE:
<221> NAME/KEY: CDS
<222> LOCATION: (22)...(2607)
<223> OTHER INFORMATION: taxadiene synthase

<400> SEQUENCE: 43
ttcccctgcc tctctggaga a atg gct cag ctc tca ttt aat gca gcg ctg      51
                       Met Ala Gln Leu Ser Phe Asn Ala Ala Leu
                         1               5                  10 aag atg aac gca ttg ggg aac aag gca atc cac gat cca acg aat tgc     99
Lys Met Asn Ala Leu Gly Asn Lys Ala Ile His Asp Pro Thr Asn Cys
             15                  20                  25 aga gcc aaa tct gag cgc caa atg atg tgg gtt tgc tcc aga tca ggg    147
Arg Ala Lys Ser Glu Arg Gln Met Met Trp Val Cys Ser Arg Ser Gly
         30                  35                  40 cga acc aga gta aaa atg tcg aga gga agt ggt ggt cct ggt cct gtc    195
Arg Thr Arg Val Lys Met Ser Arg Gly Ser Gly Gly Pro Gly Pro Val
     45                  50                  55 gta atg atg agc agc agc act ggc act agc aag gtg gtt tcc gag act    243
Val Met Met Ser Ser Ser Thr Gly Thr Ser Lys Val Val Ser Glu Thr
 60                  65                  70 tcc agt acc att gtg gat gat atc cct cga ctc tcc gcc aat tat cat    291
Ser Ser Thr Ile Val Asp Asp Ile Pro Arg Leu Ser Ala Asn Tyr His
 75                  80                  85                  90 ggc gat ctg tgg cac cac aat gtt ata caa act ctg gag aca ccg ttt    339
Gly Asp Leu Trp His His Asn Val Ile Gln Thr Leu Glu Thr Pro Phe
                 95                 100                 105 cgt gag agt tct act tac caa gaa cgg gca gat gag ctg gtt gtg aaa    387
Arg Glu Ser Ser Thr Tyr Gln Glu Arg Ala Asp Glu Leu Val Val Lys
             110                 115                 120 att aaa gat atg ttc aat gcg ctc gga gac gga gat atc agt ccg tct    435
Ile Lys Asp Met Phe Asn Ala Leu Gly Asp Gly Asp Ile Ser Pro Ser
         125                 130                 135 gca tac gac act gcg tgg gtg gcg agg ctg gcg acc att tcc tct gat    483
Ala Tyr Asp Thr Ala Trp Val Ala Arg Leu Ala Thr Ile Ser Ser Asp
     140                 145                 150 gga tct gag aag cca cgg ttt cct cag gcc ctc aac tgg gtt ttc aac    531
Gly Ser Glu Lys Pro Arg Phe Pro Gln Ala Leu Asn Trp Val Phe Asn
155                 160                 165                 170 aac cag ctc cag gat gga tcg tgg ggt atc gaa tcg cac ttt agt tta    579
Asn Gln Leu Gln Asp Gly Ser Trp Gly Ile Glu Ser His Phe Ser Leu
                175                 180                 185 tgc gat cga ttg ctt aac acg acc aat tct gtt atc gcc ctc tcg gtt    627
```

```
                                                       -continued

Cys Asp Arg Leu Leu Asn Thr Thr Asn Ser Val Ile Ala Leu Ser Val
            190                 195                 200 tgg aaa aca ggg cac agc caa gta caa caa ggt gct gag ttt att gca        675
Trp Lys Thr Gly His Ser Gln Val Gln Gln Gly Ala Glu Phe Ile Ala
            205                 210                 215 gag aat cta aga tta ctc aat gag gaa gat gag ttg tcc ccg gat ttc        723
Glu Asn Leu Arg Leu Leu Asn Glu Glu Asp Glu Leu Ser Pro Asp Phe
220                 225                 230 caa ata atc ttt cct gct ctg ctg caa aag gca aaa gcg ttg ggg atc        771
Gln Ile Ile Phe Pro Ala Leu Leu Gln Lys Ala Lys Ala Leu Gly Ile
235                 240                 245                 250 aat ctt cct tac gat ctt cca ttt atc aaa tat ttg tcg aca aca cgg        819
Asn Leu Pro Tyr Asp Leu Pro Phe Ile Lys Tyr Leu Ser Thr Thr Arg
                255                 260                 265 gaa gcc agg ctt aca gat gtt tct gcg gca gca gac aat att cca gcc        867
Glu Ala Arg Leu Thr Asp Val Ser Ala Ala Ala Asp Asn Ile Pro Ala
            270                 275                 280 aac atg ttg aat gcg ttg gaa ggt ctc gag gaa gtt att gac tgg aac        915
Asn Met Leu Asn Ala Leu Glu Gly Leu Glu Glu Val Ile Asp Trp Asn
        285                 290                 295 aag att atg agg ttt caa agt aaa gat gga tct ttc ctg agc tcc cct        963
Lys Ile Met Arg Phe Gln Ser Lys Asp Gly Ser Phe Leu Ser Ser Pro
300                 305                 310 gcc tcc act gcc tgt gta ctg atg aat aca ggg gac gaa aaa tgt ttc       1011
Ala Ser Thr Ala Cys Val Leu Met Asn Thr Gly Asp Glu Lys Cys Phe
315                 320                 325                 330 act ttt ctc aac aat ctg ctc gac aaa ttc ggc ggc tgc gtg ccc tgt       1059
Thr Phe Leu Asn Asn Leu Leu Asp Lys Phe Gly Gly Cys Val Pro Cys
                335                 340                 345 atg tat tcc atc gat ctg ctg gaa cgc ctt tcg ctg gtt gat aac att       1107
Met Tyr Ser Ile Asp Leu Leu Glu Arg Leu Ser Leu Val Asp Asn Ile
            350                 355                 360 gag cat ctc gga atc ggt cgc cat ttc aaa caa gaa atc aaa gga gct       1155
Glu His Leu Gly Ile Gly Arg His Phe Lys Gln Glu Ile Lys Gly Ala
        365                 370                 375 ctt gat tat gtc tac aga cat tgg agt gaa agg ggc atc ggt tgg ggc       1203
Leu Asp Tyr Val Tyr Arg His Trp Ser Glu Arg Gly Ile Gly Trp Gly
380                 385                 390 aga gac agc ctt gtt cca gat ctc aac acc aca gcc ctc ggc ctg cga       1251
Arg Asp Ser Leu Val Pro Asp Leu Asn Thr Thr Ala Leu Gly Leu Arg
395                 400                 405                 410 act ctt cgc atg cac gga tac aat gtt tct tca gac gtt ttg aat aat       1299
Thr Leu Arg Met His Gly Tyr Asn Val Ser Ser Asp Val Leu Asn Asn
                415                 420                 425 ttc aaa gat gaa aac ggg cgg ttc ttc tcc tct gcg ggc caa acc cat       1347
Phe Lys Asp Glu Asn Gly Arg Phe Phe Ser Ser Ala Gly Gln Thr His
            430                 435                 440 gtc gaa ttg aga agc gtg gtg aat ctt ttc aga gct tcc gac ctt gca       1395
Val Glu Leu Arg Ser Val Val Asn Leu Phe Arg Ala Ser Asp Leu Ala
        445                 450                 455 ttt cct gac gaa aga gct atg gac gat gct aga aaa ttt gca gaa cca       1443
Phe Pro Asp Glu Arg Ala Met Asp Asp Ala Arg Lys Phe Ala Glu Pro
460                 465                 470 tat ctt aga gag gca ctt gca acg aaa atc tca acc aat aca aaa cta       1491
Tyr Leu Arg Glu Ala Leu Ala Thr Lys Ile Ser Thr Asn Thr Lys Leu
475                 480                 485                 490 ttc aaa gag att gag tac gtg gtg gag tac cct tgg cac atg agt atc       1539
Phe Lys Glu Ile Glu Tyr Val Val Glu Tyr Pro Trp His Met Ser Ile
                495                 500                 505
```

```
                                                         -continued cca cgc tta gaa gcc aga agt tat att gat tca tat gac gac aat tat    1587
Pro Arg Leu Glu Ala Arg Ser Tyr Ile Asp Ser Tyr Asp Asp Asn Tyr
        510                 515                 520 gta tgg cag agg aag act cta tat aga atg cca tct ttg agt aat tca    1635
Val Trp Gln Arg Lys Thr Leu Tyr Arg Met Pro Ser Leu Ser Asn Ser
525                 530                 535 aaa tgt tta gaa ttg gca aaa ttg gac ttc aat atc gta caa tct ttg    1683
Lys Cys Leu Glu Leu Ala Lys Leu Asp Phe Asn Ile Val Gln Ser Leu
540                 545                 550 cat caa gag gag ttg aag ctt cta aca aga tgg tgg aag gaa tcc ggc    1731
His Gln Glu Glu Leu Lys Leu Leu Thr Arg Trp Trp Lys Glu Ser Gly
555                 560                 565                 570 atg gca gat ata aat ttc act cga cac cga gtg gcg gag gtt tat ttt    1779
Met Ala Asp Ile Asn Phe Thr Arg His Arg Val Ala Glu Val Tyr Phe
            575                 580                 585 tca tca gct aca ttt gaa ccc gaa tat tct gcc act aga att gcc ttc    1827
Ser Ser Ala Thr Phe Glu Pro Glu Tyr Ser Ala Thr Arg Ile Ala Phe
                590                 595                 600 aca aaa att ggt tgt tta caa gtc ctt ttt gat gat atg gct gac atc    1875
Thr Lys Ile Gly Cys Leu Gln Val Leu Phe Asp Asp Met Ala Asp Ile
            605                 610                 615 ttt gca aca cta gat gaa ttg aaa agt ttc act gag gga gta aag aga    1923
Phe Ala Thr Leu Asp Glu Leu Lys Ser Phe Thr Glu Gly Val Lys Arg
620                 625                 630 tgg gat aca tct ttg cta cat gag att cca gag tgt atg caa act tgc    1971
Trp Asp Thr Ser Leu Leu His Glu Ile Pro Glu Cys Met Gln Thr Cys
635                 640                 645                 650 ttt aaa gtt tgg ttc aaa tta atg gaa gaa gta aat aat gat gtg gtt    2019
Phe Lys Val Trp Phe Lys Leu Met Glu Glu Val Asn Asn Asp Val Val
            655                 660                 665 aag gta caa gga cgt gac atg ctc gct cac ata aga aaa ccc tgg gag    2067
Lys Val Gln Gly Arg Asp Met Leu Ala His Ile Arg Lys Pro Trp Glu
                670                 675                 680 ttg tac ttc aat tgt tat gta caa gaa agg gag tgg ctt gaa gcc ggg    2115
Leu Tyr Phe Asn Cys Tyr Val Gln Glu Arg Glu Trp Leu Glu Ala Gly
            685                 690                 695 tat ata cca act ttt gaa gag tac tta aag act tat gct ata tca gta    2163
Tyr Ile Pro Thr Phe Glu Glu Tyr Leu Lys Thr Tyr Ala Ile Ser Val
700                 705                 710 ggc ctt gga ccg tgt acc cta caa cca ata cta cta atg ggt gag ctt    2211
Gly Leu Gly Pro Cys Thr Leu Gln Pro Ile Leu Leu Met Gly Glu Leu
715                 720                 725                 730 gtg aaa gat gat gtt gtt gag aaa gtg cac tat ccc tca aat atg ttt    2259
Val Lys Asp Asp Val Val Glu Lys Val His Tyr Pro Ser Asn Met Phe
                735                 740                 745 gag ctt gta tcc ttg agc tgg cga cta aca aac gac acc aaa aca tat    2307
Glu Leu Val Ser Leu Ser Trp Arg Leu Thr Asn Asp Thr Lys Thr Tyr
            750                 755                 760 cag gct gaa aag gct cga gga caa caa gcc tca ggc ata gca tgc tat    2355
Gln Ala Glu Lys Ala Arg Gly Gln Gln Ala Ser Gly Ile Ala Cys Tyr
                765                 770                 775 atg aag gat aat cca gga gca act gag gaa gat gcc att aag cac ata    2403
Met Lys Asp Asn Pro Gly Ala Thr Glu Glu Asp Ala Ile Lys His Ile
780                 785                 790 tgt cgt gtt gtt gat cgg gcc ttg aaa gaa gca agc ttt gaa tat ttc    2451
Cys Arg Val Val Asp Arg Ala Leu Lys Glu Ala Ser Phe Glu Tyr Phe
795                 800                 805                 810 aaa cca tcc aat gat atc cca atg ggt tgc aag tcc ttt att ttt aac    2499
Lys Pro Ser Asn Asp Ile Pro Met Gly Cys Lys Ser Phe Ile Phe Asn
            815                 820                 825
```

```
ctt aga ttg tgt gtc caa atc ttt tac aag ttt ata gat ggg tac gga    2547
Leu Arg Leu Cys Val Gln Ile Phe Tyr Lys Phe Ile Asp Gly Tyr Gly
            830                 835                 840 atc gcc aat gag gag att aag gac tat ata aga aaa gtt tat att gat    2595
Ile Ala Asn Glu Glu Ile Lys Asp Tyr Ile Arg Lys Val Tyr Ile Asp
            845                 850                 855 cca att caa gta tga tatatcatgt aaaacctctt tttcatgata aattgactta    2650
Pro Ile Gln Val
        860 ttattgtatt ggcaaaaaaa aaaaaaaaaa aaaaaaaaa aaaaaaaaaa             2700

<210> SEQ ID NO 44
<211> LENGTH: 862
<212> TYPE: PRT
<213> ORGANISM: Taxus brevifolia

<400> SEQUENCE: 44
```

Met Ala Gln Leu Ser Phe Asn Ala Ala Leu Lys Met Asn Ala Leu Gly
1               5                   10                  15

Asn Lys Ala Ile His Asp Pro Thr Asn Cys Arg Ala Lys Ser Glu Arg
            20                  25                  30

Gln Met Met Trp Val Cys Ser Arg Ser Gly Arg Thr Arg Val Lys Met
        35                  40                  45

Ser Arg Gly Ser Gly Gly Pro Gly Pro Val Val Met Met Ser Ser Ser
    50                  55                  60

Thr Gly Thr Ser Lys Val Val Ser Glu Thr Ser Ser Thr Ile Val Asp
65                  70                  75                  80

Asp Ile Pro Arg Leu Ser Ala Asn Tyr His Gly Asp Leu Trp His His
                85                  90                  95

Asn Val Ile Gln Thr Leu Glu Thr Pro Phe Arg Glu Ser Ser Thr Tyr
            100                 105                 110

Gln Glu Arg Ala Asp Glu Leu Val Val Lys Ile Lys Asp Met Phe Asn
        115                 120                 125

Ala Leu Gly Asp Gly Asp Ile Ser Pro Ser Ala Tyr Asp Thr Ala Trp
    130                 135                 140

Val Ala Arg Leu Ala Thr Ile Ser Ser Asp Gly Ser Glu Lys Pro Arg
145                 150                 155                 160

Phe Pro Gln Ala Leu Asn Trp Val Phe Asn Asn Gln Leu Gln Asp Gly
                165                 170                 175

Ser Trp Gly Ile Glu Ser His Phe Ser Leu Cys Asp Arg Leu Leu Asn
            180                 185                 190

Thr Thr Asn Ser Val Ile Ala Leu Ser Val Trp Lys Thr Gly His Ser
        195                 200                 205

Gln Val Gln Gln Gly Ala Glu Phe Ile Ala Glu Asn Leu Arg Leu Leu
    210                 215                 220

Asn Glu Glu Asp Glu Leu Ser Pro Asp Phe Gln Ile Ile Phe Pro Ala
225                 230                 235                 240

Leu Leu Gln Lys Ala Lys Ala Leu Gly Ile Asn Leu Pro Tyr Asp Leu
                245                 250                 255

Pro Phe Ile Lys Tyr Leu Ser Thr Thr Arg Glu Ala Arg Leu Thr Asp
            260                 265                 270

Val Ser Ala Ala Ala Asp Asn Ile Pro Ala Asn Met Leu Asn Ala Leu
        275                 280                 285

Glu Gly Leu Glu Glu Val Ile Asp Trp Asn Lys Ile Met Arg Phe Gln
    290                 295                 300

```
Ser Lys Asp Gly Ser Phe Leu Ser Ser Pro Ala Ser Thr Ala Cys Val
305                 310                 315                 320

Leu Met Asn Thr Gly Asp Glu Lys Cys Phe Thr Phe Leu Asn Asn Leu
            325                 330                 335

Leu Asp Lys Phe Gly Gly Cys Val Pro Cys Met Tyr Ser Ile Asp Leu
            340                 345                 350

Leu Glu Arg Leu Ser Leu Val Asp Asn Ile Glu His Leu Gly Ile Gly
            355                 360                 365

Arg His Phe Lys Gln Glu Ile Lys Gly Ala Leu Asp Tyr Val Tyr Arg
    370                 375                 380

His Trp Ser Glu Arg Gly Ile Gly Trp Gly Arg Asp Ser Leu Val Pro
385                 390                 395                 400

Asp Leu Asn Thr Thr Ala Leu Gly Leu Arg Thr Leu Arg Met His Gly
                405                 410                 415

Tyr Asn Val Ser Ser Asp Val Leu Asn Asn Phe Lys Asp Glu Asn Gly
            420                 425                 430

Arg Phe Phe Ser Ser Ala Gly Gln Thr His Val Glu Leu Arg Ser Val
        435                 440                 445

Val Asn Leu Phe Arg Ala Ser Asp Leu Ala Phe Pro Asp Glu Arg Ala
    450                 455                 460

Met Asp Asp Ala Arg Lys Phe Ala Glu Pro Tyr Leu Arg Glu Ala Leu
465                 470                 475                 480

Ala Thr Lys Ile Ser Thr Asn Thr Lys Leu Phe Lys Glu Ile Glu Tyr
                485                 490                 495

Val Val Glu Tyr Pro Trp His Met Ser Ile Pro Arg Leu Glu Ala Arg
            500                 505                 510

Ser Tyr Ile Asp Ser Tyr Asp Asp Asn Tyr Val Trp Gln Arg Lys Thr
        515                 520                 525

Leu Tyr Arg Met Pro Ser Leu Ser Asn Ser Lys Cys Leu Glu Leu Ala
    530                 535                 540

Lys Leu Asp Phe Asn Ile Val Gln Ser Leu His Gln Glu Glu Leu Lys
545                 550                 555                 560

Leu Leu Thr Arg Trp Trp Lys Glu Ser Gly Met Ala Asp Ile Asn Phe
                565                 570                 575

Thr Arg His Arg Val Ala Glu Val Tyr Phe Ser Ser Ala Thr Phe Glu
            580                 585                 590

Pro Glu Tyr Ser Ala Thr Arg Ile Ala Phe Thr Lys Ile Gly Cys Leu
        595                 600                 605

Gln Val Leu Phe Asp Asp Met Ala Asp Ile Phe Ala Thr Leu Asp Glu
    610                 615                 620

Leu Lys Ser Phe Thr Glu Gly Val Lys Arg Trp Asp Thr Ser Leu Leu
625                 630                 635                 640

His Glu Ile Pro Glu Cys Met Gln Thr Cys Phe Lys Val Trp Phe Lys
                645                 650                 655

Leu Met Glu Glu Val Asn Asn Asp Val Val Lys Val Gln Gly Arg Asp
            660                 665                 670

Met Leu Ala His Ile Arg Lys Pro Trp Glu Leu Tyr Phe Asn Cys Tyr
        675                 680                 685

Val Gln Glu Arg Glu Trp Leu Glu Ala Gly Tyr Ile Pro Thr Phe Glu
    690                 695                 700

Glu Tyr Leu Lys Thr Tyr Ala Ile Ser Val Gly Leu Gly Pro Cys Thr
705                 710                 715                 720
```

```
Leu Gln Pro Ile Leu Leu Met Gly Glu Leu Val Lys Asp Asp Val Val
                725                 730                 735

Glu Lys Val His Tyr Pro Ser Asn Met Phe Glu Leu Val Ser Leu Ser
            740                 745                 750

Trp Arg Leu Thr Asn Asp Thr Lys Thr Tyr Gln Ala Glu Lys Ala Arg
        755                 760                 765

Gly Gln Gln Ala Ser Gly Ile Ala Cys Tyr Met Lys Asp Asn Pro Gly
    770                 775                 780

Ala Thr Glu Glu Asp Ala Ile Lys His Ile Cys Arg Val Val Asp Arg
785                 790                 795                 800

Ala Leu Lys Glu Ala Ser Phe Glu Tyr Phe Lys Pro Ser Asn Asp Ile
            805                 810                 815

Pro Met Gly Cys Lys Ser Phe Ile Phe Asn Leu Arg Leu Cys Val Gln
                820                 825                 830

Ile Phe Tyr Lys Phe Ile Asp Gly Tyr Gly Ile Ala Asn Glu Glu Ile
            835                 840                 845

Lys Asp Tyr Ile Arg Lys Val Tyr Ile Asp Pro Ile Gln Val
        850                 855                 860

<210> SEQ ID NO 45
<211> LENGTH: 2424
<212> TYPE: DNA
<213> ORGANISM: Abies grandis
<220> FEATURE:
<221> NAME/KEY: CDS
<222> LOCATION: (2)...(2347)
<223> OTHER INFORMATION: E-alpha-bisabolene synthase

<400> SEQUENCE: 45 g ggt tat gat ctt gtg cat tct ctt aaa tca cct tat att gat tct agt       49
  Gly Tyr Asp Leu Val His Ser Leu Lys Ser Pro Tyr Ile Asp Ser Ser
  1               5                   10                  15 tac aga gaa cgc gcg gag gtc ctt gtt agc gag att aaa gtg atg ctt        97
Tyr Arg Glu Arg Ala Glu Val Leu Val Ser Glu Ile Lys Val Met Leu
                20                  25                  30 aat cca gct att aca gga gat gga gaa tca atg att act cca tct gct       145
Asn Pro Ala Ile Thr Gly Asp Gly Glu Ser Met Ile Thr Pro Ser Ala
            35                  40                  45 tat gac aca gca tgg gta gcg agg gtg ccc gcc att gat ggc tct gct       193
Tyr Asp Thr Ala Trp Val Ala Arg Val Pro Ala Ile Asp Gly Ser Ala
        50                  55                  60 cgc ccg caa ttt ccc caa aca gtt gac tgg att ttg aaa aac cag tta       241
Arg Pro Gln Phe Pro Gln Thr Val Asp Trp Ile Leu Lys Asn Gln Leu
65                  70                  75                  80 aaa gat ggt tca tgg gga att cag tcc cac ttt ctg ctg tcc gac cgt       289
Lys Asp Gly Ser Trp Gly Ile Gln Ser His Phe Leu Leu Ser Asp Arg
                85                  90                  95 ctt ctt gcc act ctt tct tgt gtt ctt gtg ctc ctt aaa tgg aac gtt       337
Leu Leu Ala Thr Leu Ser Cys Val Leu Val Leu Leu Lys Trp Asn Val
            100                 105                 110 ggg gat ctg caa gta gag cag gga att gaa ttc ata aag agc aat ctg       385
Gly Asp Leu Gln Val Glu Gln Gly Ile Glu Phe Ile Lys Ser Asn Leu
        115                 120                 125 gaa cta gta aag gat gaa acc gat caa gat agc ttg gta aca gac ttt       433
Glu Leu Val Lys Asp Glu Thr Asp Gln Asp Ser Leu Val Thr Asp Phe
    130                 135                 140 gag atc ata ttt cct tct ctg tta aga gaa gct caa tct ctg cgc ctc       481
Glu Ile Ile Phe Pro Ser Leu Leu Arg Glu Ala Gln Ser Leu Arg Leu
145                 150                 155                 160
```

-continued

```
gga ctt ccc tac gac ctg cct tat ata cat ctg ttg cag act aaa cgg      529
Gly Leu Pro Tyr Asp Leu Pro Tyr Ile His Leu Leu Gln Thr Lys Arg
            165                 170                 175 cag gaa aga tta gca aaa ctt tca agg gag gaa att tat gcg gtt ccg      577
Gln Glu Arg Leu Ala Lys Leu Ser Arg Glu Glu Ile Tyr Ala Val Pro
        180                 185                 190 tcg cca ttg ttg tat tct tta gag gga ata caa gat ata gtt gaa tgg      625
Ser Pro Leu Leu Tyr Ser Leu Glu Gly Ile Gln Asp Ile Val Glu Trp
    195                 200                 205 gaa cga ata atg gaa gtt caa agt cag gat ggg tct ttc tta agc tca      673
Glu Arg Ile Met Glu Val Gln Ser Gln Asp Gly Ser Phe Leu Ser Ser
210                 215                 220 cct gct tct act gcc tgc gtt ttc atg cac aca gga gac gcg aaa tgc      721
Pro Ala Ser Thr Ala Cys Val Phe Met His Thr Gly Asp Ala Lys Cys
225                 230                 235                 240 ctt gaa ttc ttg aac agt gtg atg atc aag ttt gga aat ttt gtt ccc      769
Leu Glu Phe Leu Asn Ser Val Met Ile Lys Phe Gly Asn Phe Val Pro
                245                 250                 255 tgc ctg tat cct gtg gat ctg ctg gaa cgc ctg ttg atc gta gat aat      817
Cys Leu Tyr Pro Val Asp Leu Leu Glu Arg Leu Leu Ile Val Asp Asn
                260                 265                 270 att gta cgc ctt gga atc tat aga cac ttt gaa aag gaa atc aag gaa      865
Ile Val Arg Leu Gly Ile Tyr Arg His Phe Glu Lys Glu Ile Lys Glu
            275                 280                 285 gct ctt gat tat gtt tac agg cat tgg aac gaa aga gga att ggg tgg      913
Ala Leu Asp Tyr Val Tyr Arg His Trp Asn Glu Arg Gly Ile Gly Trp
        290                 295                 300 ggc aga cta aat ccc ata gca gat ctt gag acc act gct ttg gga ttt      961
Gly Arg Leu Asn Pro Ile Ala Asp Leu Glu Thr Thr Ala Leu Gly Phe
305                 310                 315                 320 cga ttg ctt cgg ctg cat agg tac aat gta tct cca gcc att ttt gac     1009
Arg Leu Leu Arg Leu His Arg Tyr Asn Val Ser Pro Ala Ile Phe Asp
                325                 330                 335 aac ttc aaa gat gcc aat ggg aaa ttc att tgc tcg acc ggt caa ttc     1057
Asn Phe Lys Asp Ala Asn Gly Lys Phe Ile Cys Ser Thr Gly Gln Phe
                340                 345                 350 aac aaa gat gta gca agc atg ctg aat ctt tat aga gct tcc cag ctc     1105
Asn Lys Asp Val Ala Ser Met Leu Asn Leu Tyr Arg Ala Ser Gln Leu
            355                 360                 365 gca ttt ccc gga gaa aac att ctt gat gaa gct aaa agc ttc gct act     1153
Ala Phe Pro Gly Glu Asn Ile Leu Asp Glu Ala Lys Ser Phe Ala Thr
        370                 375                 380 aaa tat ttg aga gaa gct ctt gag aaa agt gag act tcc agt gca tgg     1201
Lys Tyr Leu Arg Glu Ala Leu Glu Lys Ser Glu Thr Ser Ser Ala Trp
385                 390                 395                 400 aac aac aaa caa aac ctg agc caa gag atc aaa tac gcg ctg aag act     1249
Asn Asn Lys Gln Asn Leu Ser Gln Glu Ile Lys Tyr Ala Leu Lys Thr
                405                 410                 415 tct tgg cat gcc agt gtt ccg aga gtg gaa gca aag aga tac tgt caa     1297
Ser Trp His Ala Ser Val Pro Arg Val Glu Ala Lys Arg Tyr Cys Gln
                420                 425                 430 gtg tat cgc cca gat tat gca cgc ata gca aaa tgc gtt tac aag cta     1345
Val Tyr Arg Pro Asp Tyr Ala Arg Ile Ala Lys Cys Val Tyr Lys Leu
            435                 440                 445 ccc tac gtg aac aat gaa aag ttt tta gag ctg gga aaa tta gat ttc     1393
Pro Tyr Val Asn Asn Glu Lys Phe Leu Glu Leu Gly Lys Leu Asp Phe
        450                 455                 460 aac att atc cag tcc atc cac caa gaa gaa atg aag aat gtt acc agc     1441
Asn Ile Ile Gln Ser Ile His Gln Glu Glu Met Lys Asn Val Thr Ser
465                 470                 475                 480
```

```
tgg ttt aga gat tcg ggg ttg cca cta ttc acc ttc gct cgg gag agg    1489
Trp Phe Arg Asp Ser Gly Leu Pro Leu Phe Thr Phe Ala Arg Glu Arg
                485                 490                 495 ccg ctg gaa ttc tac ttc tta gta gcg gcg ggg acc tat gaa ccc cag    1537
Pro Leu Glu Phe Tyr Phe Leu Val Ala Ala Gly Thr Tyr Glu Pro Gln
            500                 505                 510 tat gcc aaa tgc agg ttc ctc ttt aca aaa gtg gca tgc ttg cag act    1585
Tyr Ala Lys Cys Arg Phe Leu Phe Thr Lys Val Ala Cys Leu Gln Thr
        515                 520                 525 gtt ctg gac gat atg tat gac act tat gga acc cta gat gaa ttg aag    1633
Val Leu Asp Asp Met Tyr Asp Thr Tyr Gly Thr Leu Asp Glu Leu Lys
    530                 535                 540 cta ttc act gag gct gtg aga aga tgg gac ctc tcc ttt aca gaa aac    1681
Leu Phe Thr Glu Ala Val Arg Arg Trp Asp Leu Ser Phe Thr Glu Asn
545                 550                 555                 560 ctt cca gac tat atg aaa cta tgt tac caa atc tat tat gac ata gtt    1729
Leu Pro Asp Tyr Met Lys Leu Cys Tyr Gln Ile Tyr Tyr Asp Ile Val
                565                 570                 575 cac gag gtg gct tgg gag gca gag aag gaa cag ggg cgt gaa ttg gtc    1777
His Glu Val Ala Trp Glu Ala Glu Lys Glu Gln Gly Arg Glu Leu Val
            580                 585                 590 agc ttt ttc aga aag gga tgg gag gat tat ctt ctg ggt tat tat gaa    1825
Ser Phe Phe Arg Lys Gly Trp Glu Asp Tyr Leu Leu Gly Tyr Tyr Glu
        595                 600                 605 gaa gct gaa tgg tta gct gct gag tat gtg cct acc ttg gac gag tac    1873
Glu Ala Glu Trp Leu Ala Ala Glu Tyr Val Pro Thr Leu Asp Glu Tyr
    610                 615                 620 ata aag aat gga atc aca tct atc ggc caa cgt ata ctt ctg ttg agt    1921
Ile Lys Asn Gly Ile Thr Ser Ile Gly Gln Arg Ile Leu Leu Leu Ser
625                 630                 635                 640 gga gtg ttg ata atg gat ggg caa ctc ctt tcg caa gag gca tta gag    1969
Gly Val Leu Ile Met Asp Gly Gln Leu Leu Ser Gln Glu Ala Leu Glu
                645                 650                 655 aaa gta gat tat cca gga aga cgt gtt ctc aca gag ctg aat agc ctc    2017
Lys Val Asp Tyr Pro Gly Arg Arg Val Leu Thr Glu Leu Asn Ser Leu
            660                 665                 670 att tcc cgc ctg gcg gat gac acg aag aca tat aaa gct gag aag gct    2065
Ile Ser Arg Leu Ala Asp Asp Thr Lys Thr Tyr Lys Ala Glu Lys Ala
        675                 680                 685 cgt gga gaa ttg gcg tcc agc att gaa tgt tac atg aaa gac cat cct    2113
Arg Gly Glu Leu Ala Ser Ser Ile Glu Cys Tyr Met Lys Asp His Pro
    690                 695                 700 gaa tgt aca gag gaa gag gct ctc gat cac atc tat agc att ctg gag    2161
Glu Cys Thr Glu Glu Glu Ala Leu Asp His Ile Tyr Ser Ile Leu Glu
705                 710                 715                 720 ccg gcg gtg aag gaa ctg aca aga gag ttt ctg aag ccc gac gac gtc    2209
Pro Ala Val Lys Glu Leu Thr Arg Glu Phe Leu Lys Pro Asp Asp Val
                725                 730                 735 cca ttc gcc tgc aag aag atg ctt ttc gag gag aca aga gtg acg atg    2257
Pro Phe Ala Cys Lys Lys Met Leu Phe Glu Glu Thr Arg Val Thr Met
            740                 745                 750 gtg ata ttc aag gat gga gat gga ttc ggt gtt tcc aaa tta gaa gtc    2305
Val Ile Phe Lys Asp Gly Asp Gly Phe Gly Val Ser Lys Leu Glu Val
        755                 760                 765 aaa gat cat atc aaa gag tgt ctc att gaa ccg ctg cca ctg taa       2350
Lys Asp His Ile Lys Glu Cys Leu Ile Glu Pro Leu Pro Leu
    770                 775                 780 tcaaaatagt tgcaataata attgaaataa tgtcaactat gtttcacaaa aaaaaaaaa   2410
```
aaaaaaaaaa aaaa                                                      2424

<210> SEQ ID NO 46
<211> LENGTH: 782
<212> TYPE: PRT
<213> ORGANISM: Abies grandis

<400> SEQUENCE: 46

Gly Tyr Asp Leu Val His Ser Leu Lys Ser Pro Tyr Ile Asp Ser Ser
 1               5                  10                  15

Tyr Arg Glu Arg Ala Glu Val Leu Ser Glu Ile Lys Val Met Leu
            20                  25                  30

Asn Pro Ala Ile Thr Gly Asp Gly Glu Ser Met Ile Thr Pro Ser Ala
        35                  40                  45

Tyr Asp Thr Ala Trp Val Ala Arg Val Pro Ala Ile Asp Gly Ser Ala
    50                  55                  60

Arg Pro Gln Phe Pro Gln Thr Val Asp Trp Ile Leu Lys Asn Gln Leu
65                  70                  75                  80

Lys Asp Gly Ser Trp Gly Ile Gln Ser His Phe Leu Leu Ser Asp Arg
                85                  90                  95

Leu Leu Ala Thr Leu Ser Cys Val Leu Val Leu Leu Lys Trp Asn Val
            100                 105                 110

Gly Asp Leu Gln Val Glu Gln Gly Ile Glu Phe Ile Lys Ser Asn Leu
        115                 120                 125

Glu Leu Val Lys Asp Glu Thr Asp Gln Asp Ser Leu Val Thr Asp Phe
    130                 135                 140

Glu Ile Ile Phe Pro Ser Leu Leu Arg Glu Ala Gln Ser Leu Arg Leu
145                 150                 155                 160

Gly Leu Pro Tyr Asp Leu Pro Tyr Ile His Leu Leu Gln Thr Lys Arg
                165                 170                 175

Gln Glu Arg Leu Ala Lys Leu Ser Arg Glu Glu Ile Tyr Ala Val Pro
            180                 185                 190

Ser Pro Leu Leu Tyr Ser Leu Glu Gly Ile Gln Asp Ile Val Glu Trp
        195                 200                 205

Glu Arg Ile Met Glu Val Gln Ser Gln Asp Gly Ser Phe Leu Ser Ser
    210                 215                 220

Pro Ala Ser Thr Ala Cys Val Phe Met His Thr Gly Asp Ala Lys Cys
225                 230                 235                 240

Leu Glu Phe Leu Asn Ser Val Met Ile Lys Phe Gly Asn Phe Val Pro
                245                 250                 255

Cys Leu Tyr Pro Val Asp Leu Leu Glu Arg Leu Leu Ile Val Asp Asn
            260                 265                 270

Ile Val Arg Leu Gly Ile Tyr Arg His Phe Glu Lys Glu Ile Lys Glu
        275                 280                 285

Ala Leu Asp Tyr Val Tyr Arg His Trp Asn Glu Arg Gly Ile Gly Trp
    290                 295                 300

Gly Arg Leu Asn Pro Ile Ala Asp Leu Glu Thr Thr Ala Leu Gly Phe
305                 310                 315                 320

Arg Leu Leu Arg Leu His Arg Tyr Asn Val Ser Pro Ala Ile Phe Asp
                325                 330                 335

Asn Phe Lys Asp Ala Asn Gly Lys Phe Ile Cys Ser Thr Gly Gln Phe
            340                 345                 350

Asn Lys Asp Val Ala Ser Met Leu Asn Leu Tyr Arg Ala Ser Gln Leu
        355                 360                 365

```
Ala Phe Pro Gly Glu Asn Ile Leu Asp Glu Ala Lys Ser Phe Ala Thr
            370                 375                 380

Lys Tyr Leu Arg Glu Ala Leu Glu Lys Ser Glu Thr Ser Ser Ala Trp
385                 390                 395                 400

Asn Asn Lys Gln Asn Leu Ser Gln Glu Ile Lys Tyr Ala Leu Lys Thr
                405                 410                 415

Ser Trp His Ala Ser Val Pro Arg Val Glu Ala Lys Arg Tyr Cys Gln
            420                 425                 430

Val Tyr Arg Pro Asp Tyr Ala Arg Ile Ala Lys Cys Val Tyr Lys Leu
            435                 440                 445

Pro Tyr Val Asn Asn Glu Lys Phe Leu Glu Leu Gly Lys Leu Asp Phe
            450                 455                 460

Asn Ile Ile Gln Ser Ile His Gln Glu Glu Met Lys Asn Val Thr Ser
465                 470                 475                 480

Trp Phe Arg Asp Ser Gly Leu Pro Leu Phe Thr Phe Ala Arg Glu Arg
                485                 490                 495

Pro Leu Glu Phe Tyr Phe Leu Val Ala Ala Gly Thr Tyr Glu Pro Gln
            500                 505                 510

Tyr Ala Lys Cys Arg Phe Leu Phe Thr Lys Val Ala Cys Leu Gln Thr
            515                 520                 525

Val Leu Asp Asp Met Tyr Asp Thr Tyr Gly Thr Leu Asp Glu Leu Lys
            530                 535                 540

Leu Phe Thr Glu Ala Val Arg Arg Trp Asp Leu Ser Phe Thr Glu Asn
545                 550                 555                 560

Leu Pro Asp Tyr Met Lys Leu Cys Tyr Gln Ile Tyr Tyr Asp Ile Val
                565                 570                 575

His Glu Val Ala Trp Glu Ala Glu Lys Glu Gln Gly Arg Glu Leu Val
            580                 585                 590

Ser Phe Phe Arg Lys Gly Trp Glu Asp Tyr Leu Leu Gly Tyr Tyr Glu
            595                 600                 605

Glu Ala Glu Trp Leu Ala Ala Gly Tyr Val Pro Thr Leu Asp Glu Tyr
610                 615                 620

Ile Lys Asn Gly Ile Thr Ser Ile Gly Gln Arg Ile Leu Leu Leu Ser
625                 630                 635                 640

Gly Val Leu Ile Met Asp Gly Gln Leu Leu Ser Gln Glu Ala Leu Glu
                645                 650                 655

Lys Val Asp Tyr Pro Gly Arg Arg Val Leu Thr Glu Leu Asn Ser Leu
            660                 665                 670

Ile Ser Arg Leu Ala Asp Asp Thr Lys Thr Tyr Lys Ala Glu Lys Ala
            675                 680                 685

Arg Gly Glu Leu Ala Ser Ser Ile Glu Cys Tyr Met Lys Asp His Pro
            690                 695                 700

Glu Cys Thr Glu Glu Glu Ala Leu Asp His Ile Tyr Ser Ile Leu Glu
705                 710                 715                 720

Pro Ala Val Lys Glu Leu Thr Arg Glu Phe Leu Lys Pro Asp Asp Val
                725                 730                 735

Pro Phe Ala Cys Lys Lys Met Leu Phe Glu Glu Thr Arg Val Thr Met
            740                 745                 750

Val Ile Phe Lys Asp Gly Asp Gly Phe Gly Val Ser Lys Leu Glu Val
            755                 760                 765

Lys Asp His Ile Lys Glu Cys Leu Ile Glu Pro Leu Pro Leu
770                 775                 780
```

<210> SEQ ID NO 47
<211> LENGTH: 1865
<212> TYPE: DNA
<213> ORGANISM: Abies grandis
<220> FEATURE:
<221> NAME/KEY: CDS
<222> LOCATION: (1)...(1743)
<223> OTHER INFORMATION: d-selinene synthase

<400> SEQUENCE: 47

| | | | | | | | | | | | | | | | | |
|---|---|---|---|---|---|---|---|---|---|---|---|---|---|---|---|---|
| atg | gct | gag | att | tct | gaa | tct | tcc | atc | cct | cga | cgc | aca | ggg | aat | cat | 48 |
| Met | Ala | Glu | Ile | Ser | Glu | Ser | Ser | Ile | Pro | Arg | Arg | Thr | Gly | Asn | His | |
| 1 | | | | 5 | | | | | 10 | | | | | 15 | | |
| cac | gga | aat | gtg | tgg | gac | gat | gac | ctc | ata | cac | tct | ctc | aac | tcg | ccc | 96 |
| His | Gly | Asn | Val | Trp | Asp | Asp | Asp | Leu | Ile | His | Ser | Leu | Asn | Ser | Pro | |
| | | | 20 | | | | | 25 | | | | | 30 | | | |
| tat | ggg | gca | cct | gca | tat | tat | gag | ctc | ctt | caa | aag | ctt | att | cag | gag | 144 |
| Tyr | Gly | Ala | Pro | Ala | Tyr | Tyr | Glu | Leu | Leu | Gln | Lys | Leu | Ile | Gln | Glu | |
| | | 35 | | | | | 40 | | | | | 45 | | | | |
| atc | aag | cat | tta | ctt | ttg | act | gaa | atg | gaa | atg | gat | gat | ggc | gat | cat | 192 |
| Ile | Lys | His | Leu | Leu | Leu | Thr | Glu | Met | Glu | Met | Asp | Asp | Gly | Asp | His | |
| | 50 | | | | | 55 | | | | | 60 | | | | | |
| gat | tta | atc | aaa | cgt | ctt | cag | atc | gtt | gac | act | ttg | gaa | tgc | ctg | gga | 240 |
| Asp | Leu | Ile | Lys | Arg | Leu | Gln | Ile | Val | Asp | Thr | Leu | Glu | Cys | Leu | Gly | |
| 65 | | | | | 70 | | | | | 75 | | | | | 80 | |
| atc | gat | aga | cat | ttt | gaa | cac | gaa | ata | caa | aca | gct | gct | tta | gat | tac | 288 |
| Ile | Asp | Arg | His | Phe | Glu | His | Glu | Ile | Gln | Thr | Ala | Ala | Leu | Asp | Tyr | |
| | | | | 85 | | | | | 90 | | | | | 95 | | |
| gtt | tac | aga | tgg | tgg | aac | gaa | aaa | ggt | atc | ggg | gag | gga | tca | aga | gat | 336 |
| Val | Tyr | Arg | Trp | Trp | Asn | Glu | Lys | Gly | Ile | Gly | Glu | Gly | Ser | Arg | Asp | |
| | | | 100 | | | | | 105 | | | | | 110 | | | |
| tcc | ttc | agc | aaa | gat | ctg | aac | gct | acg | gct | tta | gga | ttt | cgc | gct | ctc | 384 |
| Ser | Phe | Ser | Lys | Asp | Leu | Asn | Ala | Thr | Ala | Leu | Gly | Phe | Arg | Ala | Leu | |
| | | 115 | | | | | 120 | | | | | 125 | | | | |
| cga | ctg | cat | cga | tat | aac | gta | tcg | tca | ggt | gtg | ttg | aag | aat | ttc | aag | 432 |
| Arg | Leu | His | Arg | Tyr | Asn | Val | Ser | Ser | Gly | Val | Leu | Lys | Asn | Phe | Lys | |
| | 130 | | | | | 135 | | | | | 140 | | | | | |
| gat | gaa | aac | ggg | aag | ttc | ttc | tgc | aac | ttt | act | ggt | gaa | gaa | gga | aga | 480 |
| Asp | Glu | Asn | Gly | Lys | Phe | Phe | Cys | Asn | Phe | Thr | Gly | Glu | Glu | Gly | Arg | |
| 145 | | | | | 150 | | | | | 155 | | | | | 160 | |
| gga | gat | aaa | caa | gtg | aga | agc | atg | ttg | tcg | tta | ctt | cga | gct | tca | gag | 528 |
| Gly | Asp | Lys | Gln | Val | Arg | Ser | Met | Leu | Ser | Leu | Leu | Arg | Ala | Ser | Glu | |
| | | | | 165 | | | | | 170 | | | | | 175 | | |
| att | tcg | ttt | ccc | gga | gaa | aaa | gtg | atg | gaa | gag | gcc | aag | gca | ttc | aca | 576 |
| Ile | Ser | Phe | Pro | Gly | Glu | Lys | Val | Met | Glu | Glu | Ala | Lys | Ala | Phe | Thr | |
| | | | 180 | | | | | 185 | | | | | 190 | | | |
| aga | gaa | tat | cta | aac | caa | gtt | tta | gct | gga | cac | ggg | gat | gtg | act | gac | 624 |
| Arg | Glu | Tyr | Leu | Asn | Gln | Val | Leu | Ala | Gly | His | Gly | Asp | Val | Thr | Asp | |
| | | 195 | | | | | 200 | | | | | 205 | | | | |
| gtg | gat | caa | agc | ctt | ttg | aga | gag | gtg | aag | tac | gca | ttg | gag | ttt | cca | 672 |
| Val | Asp | Gln | Ser | Leu | Leu | Arg | Glu | Val | Lys | Tyr | Ala | Leu | Glu | Phe | Pro | |
| | 210 | | | | | 215 | | | | | 220 | | | | | |
| tgg | cat | tgc | agt | gtg | ccg | aga | tgg | gag | gca | agg | agc | ttt | ctc | gaa | ata | 720 |
| Trp | His | Cys | Ser | Val | Pro | Arg | Trp | Glu | Ala | Arg | Ser | Phe | Leu | Glu | Ile | |
| 225 | | | | | 230 | | | | | 235 | | | | | 240 | |
| tat | gga | cac | aac | cat | tcg | tgg | ctc | aag | tcg | aat | atc | aac | caa | aaa | atg | 768 |
| Tyr | Gly | His | Asn | His | Ser | Trp | Leu | Lys | Ser | Asn | Ile | Asn | Gln | Lys | Met | |
| | | | | 245 | | | | | 250 | | | | | 255 | | |
| ttg | aag | tta | gcc | aaa | ttg | gac | ttc | aat | att | ctg | caa | tgc | aaa | cat | cac | 816 |
| Leu | Lys | Leu | Ala | Lys | Leu | Asp | Phe | Asn | Ile | Leu | Gln | Cys | Lys | His | His | |
| | | | 260 | | | | | 265 | | | | | 270 | | | |

-continued

| | |
|---|---|
| aag gag ata cag ttt att aca agg tgg tgg aga gac tcg ggt ata tcg<br>Lys Glu Ile Gln Phe Ile Thr Arg Trp Trp Arg Asp Ser Gly Ile Ser<br>           275                    280                   285 | 864 |
| cag ctg aat ttc tat cga aag cga cac gtg gaa tat tat tct tgg gtt<br>Gln Leu Asn Phe Tyr Arg Lys Arg His Val Glu Tyr Tyr Ser Trp Val<br>        290                    295                    300 | 912 |
| gtt atg tgc att ttt gag cca gag ttc tct gaa agt aga att gcc ttc<br>Val Met Cys Ile Phe Glu Pro Glu Phe Ser Glu Ser Arg Ile Ala Phe<br>305                    310                    315                  320 | 960 |
| gcc aaa act gct atc ctg tgt act gtt cta gat gac ctc tat gat acg<br>Ala Lys Thr Ala Ile Leu Cys Thr Val Leu Asp Asp Leu Tyr Asp Thr<br>                    325                    330                  335 | 1008 |
| cac gca aca ttg cat gaa atc aaa atc atg aca gag gga gtg aga cga<br>His Ala Thr Leu His Glu Ile Lys Ile Met Thr Glu Gly Val Arg Arg<br>                  340                    345                  350 | 1056 |
| tgg gat ctt tcg ttg aca gat gac ctc cca gac tac att aaa att gca<br>Trp Asp Leu Ser Leu Thr Asp Asp Leu Pro Asp Tyr Ile Lys Ile Ala<br>                    355                    360                  365 | 1104 |
| ttc cag ttc ttc ttc aat aca gtg aat gaa ttg ata gtt gaa atc gtg<br>Phe Gln Phe Phe Phe Asn Thr Val Asn Glu Leu Ile Val Glu Ile Val<br>        370                    375                    380 | 1152 |
| aaa cgg caa ggg cgg gat atg aca acc ata gtt aaa gat tgc tgg aag<br>Lys Arg Gln Gly Arg Asp Met Thr Thr Ile Val Lys Asp Cys Trp Lys<br>385                    390                    395                  400 | 1200 |
| cga tac att gag tct tat ctg caa gaa gcg gaa tgg ata gca act gga<br>Arg Tyr Ile Glu Ser Tyr Leu Gln Glu Ala Glu Trp Ile Ala Thr Gly<br>                    405                    410                  415 | 1248 |
| cat att ccc act ttt aac gaa tac ata aag aac ggc atg gct agc tca<br>His Ile Pro Thr Phe Asn Glu Tyr Ile Lys Asn Gly Met Ala Ser Ser<br>                420                    425                  430 | 1296 |
| ggg atg tgt att cta aat ttg aat cca ctt ctc ttg ttg gat aaa ctt<br>Gly Met Cys Ile Leu Asn Leu Asn Pro Leu Leu Leu Leu Asp Lys Leu<br>                  435                    440                  445 | 1344 |
| ctc ccc gac aac att ctg gag caa ata cat tct cca tcc aag atc ctg<br>Leu Pro Asp Asn Ile Leu Glu Gln Ile His Ser Pro Ser Lys Ile Leu<br>        450                    455                    460 | 1392 |
| gac ctc tta gaa ttg acg ggc aga atc gcc gat gac tta aaa gat ttc<br>Asp Leu Leu Glu Leu Thr Gly Arg Ile Ala Asp Asp Leu Lys Asp Phe<br>465                    470                    475                  480 | 1440 |
| gag gac gag aag gaa cgc ggg gag atg gct tca tct tta cag tgt tat<br>Glu Asp Glu Lys Glu Arg Gly Glu Met Ala Ser Ser Leu Gln Cys Tyr<br>                    485                    490                  495 | 1488 |
| atg aaa gaa aat cct gaa tct aca gtg gaa aat gct tta aat cac ata<br>Met Lys Glu Asn Pro Glu Ser Thr Val Glu Asn Ala Leu Asn His Ile<br>        500                    505                    510 | 1536 |
| aaa ggc atc ctt aat cgt tcc ctt gag gaa ttt aat tgg gag ttt atg<br>Lys Gly Ile Leu Asn Arg Ser Leu Glu Glu Phe Asn Trp Glu Phe Met<br>515                    520                    525 | 1584 |
| aag cag gat agt gtc cca atg tgt tgc aag aaa ttc act ttc aat ata<br>Lys Gln Asp Ser Val Pro Met Cys Cys Lys Lys Phe Thr Phe Asn Ile<br>                530                    535                  540 | 1632 |
| ggt cga gga ctt caa ttc atc tac aaa tac aga gac ggc tta tac att<br>Gly Arg Gly Leu Gln Phe Ile Tyr Lys Tyr Arg Asp Gly Leu Tyr Ile<br>545                    550                    555                  560 | 1680 |
| tct gac aag gaa gta aag gac cag ata ttc aaa att cta gtc cac caa<br>Ser Asp Lys Glu Val Lys Asp Gln Ile Phe Lys Ile Leu Val His Gln<br>                    565                    570                  575 | 1728 |
| gtt cca atg gag gaa tag tgatggtctt ggttgtagtt gtctattatg<br>Val Pro Met Glu Glu | 1776 |

```
                    580
gtatattgca ttgacattta tgcttaaagg tgtttcttaa acgtttaggg cggaccgtta      1836
aataagttgg caataattaa tatctcgag                                        1865
```

<210> SEQ ID NO 48
<211> LENGTH: 581
<212> TYPE: PRT
<213> ORGANISM: Abies grandis

<400> SEQUENCE: 48

```
Met Ala Glu Ile Ser Glu Ser Ser Ile Pro Arg Arg Thr Gly Asn His
 1               5                  10                  15

His Gly Asn Val Trp Asp Asp Leu Ile His Ser Leu Asn Ser Pro
             20                  25                  30

Tyr Gly Ala Pro Ala Tyr Tyr Glu Leu Leu Gln Lys Leu Ile Gln Glu
             35                  40                  45

Ile Lys His Leu Leu Leu Thr Glu Met Glu Met Asp Asp Gly Asp His
 50                  55                  60

Asp Leu Ile Lys Arg Leu Gln Ile Val Asp Thr Leu Glu Cys Leu Gly
 65                  70                  75                  80

Ile Asp Arg His Phe Glu His Glu Ile Gln Thr Ala Ala Leu Asp Tyr
                 85                  90                  95

Val Tyr Arg Trp Trp Asn Glu Lys Gly Ile Gly Glu Gly Ser Arg Asp
            100                 105                 110

Ser Phe Ser Lys Asp Leu Asn Ala Thr Ala Leu Gly Phe Arg Ala Leu
            115                 120                 125

Arg Leu His Arg Tyr Asn Val Ser Ser Gly Val Leu Lys Asn Phe Lys
130                 135                 140

Asp Glu Asn Gly Lys Phe Phe Cys Asn Phe Thr Gly Glu Glu Gly Arg
145                 150                 155                 160

Gly Asp Lys Gln Val Arg Ser Met Leu Ser Leu Leu Arg Ala Ser Glu
                165                 170                 175

Ile Ser Phe Pro Gly Glu Lys Val Met Glu Ala Lys Ala Phe Thr
            180                 185                 190

Arg Glu Tyr Leu Asn Gln Val Leu Ala Gly His Gly Asp Val Thr Asp
            195                 200                 205

Val Asp Gln Ser Leu Leu Arg Glu Val Lys Tyr Ala Leu Glu Phe Pro
210                 215                 220

Trp His Cys Ser Val Pro Arg Trp Glu Ala Arg Ser Phe Leu Glu Ile
225                 230                 235                 240

Tyr Gly His Asn His Ser Trp Leu Lys Ser Asn Ile Asn Gln Lys Met
                245                 250                 255

Leu Lys Leu Ala Lys Leu Asp Phe Asn Ile Leu Gln Cys Lys His His
            260                 265                 270

Lys Glu Ile Gln Phe Ile Thr Arg Trp Trp Arg Asp Ser Gly Ile Ser
            275                 280                 285

Gln Leu Asn Phe Tyr Arg Lys Arg His Val Glu Tyr Tyr Ser Trp Val
            290                 295                 300

Val Met Cys Ile Phe Glu Pro Glu Phe Ser Glu Ser Arg Ile Ala Phe
305                 310                 315                 320

Ala Lys Thr Ala Ile Leu Cys Thr Val Leu Asp Asp Leu Tyr Asp Thr
                325                 330                 335

His Ala Thr Leu His Glu Ile Lys Ile Met Thr Glu Gly Val Arg Arg
            340                 345                 350
```

```
Trp Asp Leu Ser Leu Thr Asp Asp Leu Pro Asp Tyr Ile Lys Ile Ala
        355                 360                 365
Phe Gln Phe Phe Phe Asn Thr Val Asn Glu Leu Ile Val Glu Ile Val
        370                 375                 380
Lys Arg Gln Gly Arg Asp Met Thr Thr Ile Val Lys Asp Cys Trp Lys
385                 390                 395                 400
Arg Tyr Ile Glu Ser Tyr Leu Gln Glu Ala Glu Trp Ile Ala Thr Gly
                405                 410                 415
His Ile Pro Thr Phe Asn Glu Tyr Ile Lys Asn Gly Met Ala Ser Ser
            420                 425                 430
Gly Met Cys Ile Leu Asn Leu Asn Pro Leu Leu Leu Asp Lys Leu
        435                 440                 445
Leu Pro Asp Asn Ile Leu Glu Gln Ile His Ser Pro Ser Lys Ile Leu
    450                 455                 460
Asp Leu Leu Glu Leu Thr Gly Arg Ile Ala Asp Asp Leu Lys Asp Phe
465                 470                 475                 480
Glu Asp Glu Lys Glu Arg Gly Glu Met Ala Ser Ser Leu Gln Cys Tyr
                485                 490                 495
Met Lys Glu Asn Pro Glu Ser Thr Val Glu Asn Ala Leu Asn His Ile
            500                 505                 510
Lys Gly Ile Leu Asn Arg Ser Leu Glu Glu Phe Asn Trp Glu Phe Met
        515                 520                 525
Lys Gln Asp Ser Val Pro Met Cys Cys Lys Phe Thr Phe Asn Ile
    530                 535                 540
Gly Arg Gly Leu Gln Phe Ile Tyr Lys Tyr Arg Asp Gly Leu Tyr Ile
545                 550                 555                 560
Ser Asp Lys Glu Val Lys Asp Gln Ile Phe Lys Ile Leu Val His Gln
                565                 570                 575
Val Pro Met Glu Glu
            580

<210> SEQ ID NO 49
<211> LENGTH: 1785
<212> TYPE: DNA
<213> ORGANISM: Abies grandis
<220> FEATURE:
<221> NAME/KEY: CDS
<222> LOCATION: (4)...(1782)
<223> OTHER INFORMATION: gamma-humulene synthase

<400> SEQUENCE: 49 tcc atg gct cag att tct gaa tct gta tca ccc tct acc gat ttg aag      48
    Met Ala Gln Ile Ser Glu Ser Val Ser Pro Ser Thr Asp Leu Lys
      1               5                  10                  15 agc acc gaa tct tcc att acc tct aat cga cat gga aat atg tgg gag      96
Ser Thr Glu Ser Ser Ile Thr Ser Asn Arg His Gly Asn Met Trp Glu
                 20                  25                  30 gac gat cgc ata cag tct ctc aac tca cct tat ggg gca cct gca tat     144
Asp Asp Arg Ile Gln Ser Leu Asn Ser Pro Tyr Gly Ala Pro Ala Tyr
            35                  40                  45 caa gaa cgc agc gaa aag ctt att gaa gag atc aaa ctt tta ttt ttg     192
Gln Glu Arg Ser Glu Lys Leu Ile Glu Glu Ile Lys Leu Leu Phe Leu
        50                  55                  60 agt gac atg gac gat agc tgc aat gat agc gat cgt gat tta atc aaa     240
Ser Asp Met Asp Asp Ser Cys Asn Asp Ser Asp Arg Asp Leu Ile Lys
    65                  70                  75 cgt ctt gag atc gtt gat act gtc gag tgt ctg gga att gat cga cat     288
```

-continued

```
Arg Leu Glu Ile Val Asp Thr Val Glu Cys Leu Gly Ile Asp Arg His
 80                  85                  90                  95 ttt caa cct gag ata aaa tta gct ctg gat tac gtt tac aga tgt tgg     336
Phe Gln Pro Glu Ile Lys Leu Ala Leu Asp Tyr Val Tyr Arg Cys Trp
                100                 105                 110 aac gaa aga ggc atc gga gag gga tca aga gat tcc ctc aag aaa gat     384
Asn Glu Arg Gly Ile Gly Glu Gly Ser Arg Asp Ser Leu Lys Lys Asp
            115                 120                 125 ctg aac gct aca gct ttg gga ttc cgg gct ctc cga ctc cat cga tat     432
Leu Asn Ala Thr Ala Leu Gly Phe Arg Ala Leu Arg Leu His Arg Tyr
        130                 135                 140 aac gta tcc tca ggt gtc ttg gag aat ttc aga gat gat aac ggg cag     480
Asn Val Ser Ser Gly Val Leu Glu Asn Phe Arg Asp Asp Asn Gly Gln
145                 150                 155 ttc ttc tgc ggt tct aca gtt gaa gaa gaa gga gca gaa gca tat aat     528
Phe Phe Cys Gly Ser Thr Val Glu Glu Glu Gly Ala Glu Ala Tyr Asn
160                 165                 170                 175 aaa cac gta aga tgc atg ctg tca tta tcg cga gct tca aac att tta     576
Lys His Val Arg Cys Met Leu Ser Leu Ser Arg Ala Ser Asn Ile Leu
                180                 185                 190 ttt ccg ggc gaa aaa gtg atg gaa gag gcg aag gca ttc aca aca aat     624
Phe Pro Gly Glu Lys Val Met Glu Glu Ala Lys Ala Phe Thr Thr Asn
            195                 200                 205 tat cta aag aaa gtt tta gca gga cgg gag gct acc cac gtc gat gaa     672
Tyr Leu Lys Lys Val Leu Ala Gly Arg Glu Ala Thr His Val Asp Glu
        210                 215                 220 agc ctt ttg gga gag gtg aag tac gca ttg gag ttt cca tgg cat tgc     720
Ser Leu Leu Gly Glu Val Lys Tyr Ala Leu Glu Phe Pro Trp His Cys
225                 230                 235 agt gtg cag aga tgg gag gca agg agc ttt atc gaa ata ttt gga caa     768
Ser Val Gln Arg Trp Glu Ala Arg Ser Phe Ile Glu Ile Phe Gly Gln
240                 245                 250                 255 att gat tca gag ctt aag tcg aat ttg agc aaa aaa atg tta gag ttg     816
Ile Asp Ser Glu Leu Lys Ser Asn Leu Ser Lys Lys Met Leu Glu Leu
                260                 265                 270 gcg aaa ttg gac ttc aat att ctg caa tgc aca cat cag aaa gaa ctg     864
Ala Lys Leu Asp Phe Asn Ile Leu Gln Cys Thr His Gln Lys Glu Leu
            275                 280                 285 cag att atc tca agg tgg ttc gca gac tca agt ata gca tcc ctg aat     912
Gln Ile Ile Ser Arg Trp Phe Ala Asp Ser Ser Ile Ala Ser Leu Asn
        290                 295                 300 ttc tat cgg aaa tgt tac gtc gaa ttt tac ttt tgg atg gct gca gcc     960
Phe Tyr Arg Lys Cys Tyr Val Glu Phe Tyr Phe Trp Met Ala Ala Ala
305                 310                 315 atc tcc gag ccg gag ttt tct gga agc aga gtt gcc ttc aca aaa att    1008
Ile Ser Glu Pro Glu Phe Ser Gly Ser Arg Val Ala Phe Thr Lys Ile
320                 325                 330                 335 gct ata ctg atg aca atg cta gat gac ctg tac gat act cac gga acc    1056
Ala Ile Leu Met Thr Met Leu Asp Asp Leu Tyr Asp Thr His Gly Thr
                340                 345                 350 ttg gac caa ctc aaa atc ttt aca gag gga gtg aga cga tgg gat gtt    1104
Leu Asp Gln Leu Lys Ile Phe Thr Glu Gly Val Arg Arg Trp Asp Val
            355                 360                 365 tcg ttg gta gag ggc ctc cca gac ttc atg aaa att gca ttc gag ttc    1152
Ser Leu Val Glu Gly Leu Pro Asp Phe Met Lys Ile Ala Phe Glu Phe
        370                 375                 380 tgg tta aag aca tct aat gaa ttg att gct gaa gct gtt aaa gcg caa    1200
Trp Leu Lys Thr Ser Asn Glu Leu Ile Ala Glu Ala Val Lys Ala Gln
385                 390                 395
```

```
ggg caa gat atg gcg gcc tac ata aga aaa aat gca tgg gag cga tac    1248
Gly Gln Asp Met Ala Ala Tyr Ile Arg Lys Asn Ala Trp Glu Arg Tyr
400                 405                 410                 415 ctt gaa gct tat ctg caa gat gcg gaa tgg ata gcc act gga cat gtc    1296
Leu Glu Ala Tyr Leu Gln Asp Ala Glu Trp Ile Ala Thr Gly His Val
            420                 425                 430 ccc acc ttt gat gag tac ttg aat aat ggc aca cca aac act ggg atg    1344
Pro Thr Phe Asp Glu Tyr Leu Asn Asn Gly Thr Pro Asn Thr Gly Met
        435                 440                 445 tgt gta ttg aat ttg att ccg ctt ctg tta atg ggt gaa cat tta cca    1392
Cys Val Leu Asn Leu Ile Pro Leu Leu Leu Met Gly Glu His Leu Pro
    450                 455                 460 atc gac att ctg gag caa ata ttc ttg ccc tcc agg ttc cac cat ctc    1440
Ile Asp Ile Leu Glu Gln Ile Phe Leu Pro Ser Arg Phe His His Leu
465                 470                 475 att gaa ttg gct tcc agg ctc gtc gat gac gcg aga gat ttc cag gcg    1488
Ile Glu Leu Ala Ser Arg Leu Val Asp Asp Ala Arg Asp Phe Gln Ala
480                 485                 490                 495 gag aag gat cat ggg gat tta tcg tgt att gag tgt tat tta aaa gat    1536
Glu Lys Asp His Gly Asp Leu Ser Cys Ile Glu Cys Tyr Leu Lys Asp
            500                 505                 510 cat cct gag tct aca gta gaa gat gct tta aat cat gtt aat ggc ctc    1584
His Pro Glu Ser Thr Val Glu Asp Ala Leu Asn His Val Asn Gly Leu
        515                 520                 525 ctt ggc aat tgc ctt ctg gaa atg aat tgg aag ttc tta aag aag cag    1632
Leu Gly Asn Cys Leu Leu Glu Met Asn Trp Lys Phe Leu Lys Lys Gln
    530                 535                 540 gac agt gtg cca ctc tcg tgt aag aag tac agc ttc cat gta ttg gca    1680
Asp Ser Val Pro Leu Ser Cys Lys Lys Tyr Ser Phe His Val Leu Ala
545                 550                 555 cga agc atc caa ttc atg tac aat caa ggc gat ggc ttc tcc att tcg    1728
Arg Ser Ile Gln Phe Met Tyr Asn Gln Gly Asp Gly Phe Ser Ile Ser
560                 565                 570                 575 aac aaa gtg atc aag gat caa gtg cag aaa gtt ctt att gtc ccc gtg    1776
Asn Lys Val Ile Lys Asp Gln Val Gln Lys Val Leu Ile Val Pro Val
            580                 585                 590 cct att tga                                                        1785
Pro Ile

<210> SEQ ID NO 50
<211> LENGTH: 593
<212> TYPE: PRT
<213> ORGANISM: Abies grandis

<400> SEQUENCE: 50

Met Ala Gln Ile Ser Glu Ser Val Ser Pro Ser Thr Asp Leu Lys Ser
1               5                   10                  15

Thr Glu Ser Ser Ile Thr Ser Asn Arg His Gly Asn Met Trp Glu Asp
            20                  25                  30

Asp Arg Ile Gln Ser Leu Asn Ser Pro Tyr Gly Ala Pro Ala Tyr Gln
        35                  40                  45

Glu Arg Ser Glu Lys Leu Ile Glu Glu Ile Lys Leu Leu Phe Leu Ser
    50                  55                  60

Asp Met Asp Asp Ser Cys Asn Asp Ser Asp Arg Asp Leu Ile Lys Arg
65                  70                  75                  80

Leu Glu Ile Val Asp Thr Val Glu Cys Leu Gly Ile Asp Arg His Phe
                85                  90                  95

Gln Pro Glu Ile Lys Leu Ala Leu Asp Tyr Val Tyr Arg Cys Trp Asn
            100                 105                 110
```

-continued

```
Glu Arg Gly Ile Gly Glu Gly Ser Arg Asp Ser Leu Lys Lys Asp Leu
            115                 120                 125
Asn Ala Thr Ala Leu Gly Phe Arg Ala Leu Arg Leu His Arg Tyr Asn
            130                 135                 140
Val Ser Ser Gly Val Leu Glu Asn Phe Arg Asp Asp Asn Gly Gln Phe
145                 150                 155                 160
Phe Cys Gly Ser Thr Val Glu Glu Gly Ala Glu Ala Tyr Asn Lys
                    165                 170                 175
His Val Arg Cys Met Leu Ser Leu Ser Arg Ala Ser Asn Ile Leu Phe
            180                 185                 190
Pro Gly Glu Lys Val Met Glu Glu Ala Lys Ala Phe Thr Thr Asn Tyr
            195                 200                 205
Leu Lys Lys Val Leu Ala Gly Arg Glu Ala Thr His Val Asp Glu Ser
210                 215                 220
Leu Leu Gly Glu Val Lys Tyr Ala Leu Glu Phe Pro Trp His Cys Ser
225                 230                 235                 240
Val Gln Arg Trp Glu Ala Arg Ser Phe Ile Glu Ile Phe Gly Gln Ile
                    245                 250                 255
Asp Ser Glu Leu Lys Ser Asn Leu Ser Lys Lys Met Leu Glu Leu Ala
            260                 265                 270
Lys Leu Asp Phe Asn Ile Leu Gln Cys Thr His Gln Lys Glu Leu Gln
            275                 280                 285
Ile Ile Ser Arg Trp Phe Ala Asp Ser Ser Ile Ala Ser Leu Asn Phe
            290                 295                 300
Tyr Arg Lys Cys Tyr Val Glu Phe Tyr Phe Trp Met Ala Ala Ala Ile
305                 310                 315                 320
Ser Glu Pro Glu Phe Ser Gly Ser Arg Val Ala Phe Thr Lys Ile Ala
                    325                 330                 335
Ile Leu Met Thr Met Leu Asp Asp Leu Tyr Asp Thr His Gly Thr Leu
            340                 345                 350
Asp Gln Leu Lys Ile Phe Thr Glu Gly Val Arg Arg Trp Asp Val Ser
            355                 360                 365
Leu Val Glu Gly Leu Pro Asp Phe Met Lys Ile Ala Phe Glu Phe Trp
370                 375                 380
Leu Lys Thr Ser Asn Glu Leu Ile Ala Glu Ala Val Lys Ala Gln Gly
385                 390                 395                 400
Gln Asp Met Ala Ala Tyr Ile Arg Lys Asn Ala Trp Glu Arg Tyr Leu
                    405                 410                 415
Glu Ala Tyr Leu Gln Asp Ala Glu Trp Ile Ala Thr Gly His Val Pro
            420                 425                 430
Thr Phe Asp Glu Tyr Leu Asn Asn Gly Thr Pro Asn Thr Gly Met Cys
            435                 440                 445
Val Leu Asn Leu Ile Pro Leu Leu Met Gly Glu His Leu Pro Ile
450                 455                 460
Asp Ile Leu Glu Gln Ile Phe Leu Pro Ser Arg Phe His His Leu Ile
465                 470                 475                 480
Glu Leu Ala Ser Arg Leu Val Asp Asp Ala Arg Asp Phe Gln Ala Glu
                    485                 490                 495
Lys Asp His Gly Asp Leu Ser Cys Ile Glu Cys Tyr Leu Lys Asp His
            500                 505                 510
Pro Glu Ser Thr Val Glu Asp Ala Leu Asn His Val Asn Gly Leu Leu
            515                 520                 525
```

```
Gly Asn Cys Leu Leu Glu Met Asn Trp Lys Phe Leu Lys Lys Gln Asp
    530                 535                 540

Ser Val Pro Leu Ser Cys Lys Lys Tyr Ser Phe His Val Leu Ala Arg
545                 550                 555                 560

Ser Ile Gln Phe Met Tyr Asn Gln Gly Asp Gly Phe Ser Ile Ser Asn
                565                 570                 575

Lys Val Ile Lys Asp Gln Val Gln Lys Val Leu Ile Val Pro Val Pro
                580                 585                 590

Ile

<210> SEQ ID NO 51
<211> LENGTH: 2024
<212> TYPE: DNA
<213> ORGANISM: Lycopersicon esculentum
<220> FEATURE:
<221> NAME/KEY: CDS
<222> LOCATION: (32)...(1675)
<223> OTHER INFORMATION: VFNT germacrene C synthase

<400> SEQUENCE: 51
```

| | |
|---|---|
| aaaaaaagcc aaaccttaga acaaacaagc a atg gct gct tct tct gct gat<br>                                                              Met Ala Ala Ser Ser Ala Asp<br>                                                              1             5 | 52 |
| aag tgt cgc ccc ttg gct aat ttt cac cca tct gtt tgg gga tat cat<br>Lys Cys Arg Pro Leu Ala Asn Phe His Pro Ser Val Trp Gly Tyr His<br>         10                 15                 20 | 100 |
| ttc ctt tct tat act cat gaa att act aat caa gaa aaa gtt gaa gtt<br>Phe Leu Ser Tyr Thr His Glu Ile Thr Asn Gln Glu Lys Val Glu Val<br> 25                 30                 35 | 148 |
| gat gag tac aaa gag aca att aga aaa atg ctg gtg gaa act tgc gac<br>Asp Glu Tyr Lys Glu Thr Ile Arg Lys Met Leu Val Glu Thr Cys Asp<br> 40                 45                 50                 55 | 196 |
| aat agc act caa aag ctt gtg ttg ata gac gcg atg caa cga ttg gga<br>Asn Ser Thr Gln Lys Leu Val Leu Ile Asp Ala Met Gln Arg Leu Gly<br>               60                 65                 70 | 244 |
| gtg gct tat cat ttc gat aat gaa att gaa aca tcc att caa aac att<br>Val Ala Tyr His Phe Asp Asn Glu Ile Glu Thr Ser Ile Gln Asn Ile<br>               75                 80                 85 | 292 |
| ttt gat gca tcg tcc aaa cag aat gat aat gac aac aac ctt tac gtt<br>Phe Asp Ala Ser Ser Lys Gln Asn Asp Asn Asp Asn Asn Leu Tyr Val<br>         90                 95               100 | 340 |
| gtg tct ctt cgt ttt cga ctt gtg agg caa caa ggc cat tac atg tct<br>Val Ser Leu Arg Phe Arg Leu Val Arg Gln Gln Gly His Tyr Met Ser<br>        105               110               115 | 388 |
| tca gat gtg ttc aag caa ttc acc aac caa gat ggg aaa ttc aag gaa<br>Ser Asp Val Phe Lys Gln Phe Thr Asn Gln Asp Gly Lys Phe Lys Glu<br>120                 125               130               135 | 436 |
| aca ctt act aat gat gtc caa gga tta ttg agt ttg tat gaa gca tca<br>Thr Leu Thr Asn Asp Val Gln Gly Leu Leu Ser Leu Tyr Glu Ala Ser<br>               140                 145                 150 | 484 |
| cat ctg aga gtg cgt aat gag gag att ctt gaa gaa gct ctt aca ttt<br>His Leu Arg Val Arg Asn Glu Glu Ile Leu Glu Glu Ala Leu Thr Phe<br>        155               160               165 | 532 |
| acc acc act cat ctc gag tct att gtc tcc aac ttg agc aat aat aat<br>Thr Thr Thr His Leu Glu Ser Ile Val Ser Asn Leu Ser Asn Asn Asn<br>               170                 175                 180 | 580 |
| aac tct ctt aag gtt gaa gtt ggt gaa gcc tta act cag cct att cgc<br>Asn Ser Leu Lys Val Glu Val Gly Glu Ala Leu Thr Gln Pro Ile Arg<br>        185               190               195 | 628 |
| atg act tta cca agg atg gga gct aga aaa tac ata tcc att tac gaa | 676 |

```
Met Thr Leu Pro Arg Met Gly Ala Arg Lys Tyr Ile Ser Ile Tyr Glu
200                 205                 210                 215 aac aat gat gca cac cac cat ttg ctt ttg aaa ttt gct aaa ttg gat      724
Asn Asn Asp Ala His His His Leu Leu Leu Lys Phe Ala Lys Leu Asp
                220                 225                 230 ttt aac atg ctg caa aag ttt cac caa aga gag ctt agt gat ctt aca      772
Phe Asn Met Leu Gln Lys Phe His Gln Arg Glu Leu Ser Asp Leu Thr
            235                 240                 245 agg tgg tgg aaa gat ttg gat ttt gca aat aaa tat cca tat gca aga      820
Arg Trp Trp Lys Asp Leu Asp Phe Ala Asn Lys Tyr Pro Tyr Ala Arg
        250                 255                 260 gac agg ttg gtt gag tgt tac ttc tgg ata tta gga gtg tat ttt gag      868
Asp Arg Leu Val Glu Cys Tyr Phe Trp Ile Leu Gly Val Tyr Phe Glu
    265                 270                 275 cca aaa tat agt cgt gcg aga aaa atg atg aca aaa gta ctc aac ctg      916
Pro Lys Tyr Ser Arg Ala Arg Lys Met Met Thr Lys Val Leu Asn Leu
280                 285                 290                 295 acc tcc att att gac gac act ttt gat gct tat gca acc ttt gac gaa      964
Thr Ser Ile Ile Asp Asp Thr Phe Asp Ala Tyr Ala Thr Phe Asp Glu
                300                 305                 310 ctt gtg act ttc aat gat gca atc cag aga tgg gat gct aat gca att     1012
Leu Val Thr Phe Asn Asp Ala Ile Gln Arg Trp Asp Ala Asn Ala Ile
            315                 320                 325 gat tca ata caa cca tat atg aga cct gct tat caa gct ctt cta gac     1060
Asp Ser Ile Gln Pro Tyr Met Arg Pro Ala Tyr Gln Ala Leu Leu Asp
        330                 335                 340 att tac agt gaa atg gaa caa gtg ttg tcc aaa gaa ggt aaa ctg gac     1108
Ile Tyr Ser Glu Met Glu Gln Val Leu Ser Lys Glu Gly Lys Leu Asp
    345                 350                 355 cgt gta tac tat gca aaa aat gag atg aaa aag ttg gtg aga gcc tat     1156
Arg Val Tyr Tyr Ala Lys Asn Glu Met Lys Lys Leu Val Arg Ala Tyr
360                 365                 370                 375 ttt aag gaa acc caa tgg ttg aat gat tgt gac cat att cca aaa tat     1204
Phe Lys Glu Thr Gln Trp Leu Asn Asp Cys Asp His Ile Pro Lys Tyr
                380                 385                 390 gag gaa caa gtg gag aat gca atc gta agt gct ggc tat atg atg ata     1252
Glu Glu Gln Val Glu Asn Ala Ile Val Ser Ala Gly Tyr Met Met Ile
            395                 400                 405 tca aca act tgc ttg gtc ggt ata gaa gaa ttt ata tcc cac gag act     1300
Ser Thr Thr Cys Leu Val Gly Ile Glu Glu Phe Ile Ser His Glu Thr
        410                 415                 420 ttt gaa tgg ttg atg aat gag tct gtg att gtt cga gct tcc gca ttg     1348
Phe Glu Trp Leu Met Asn Glu Ser Val Ile Val Arg Ala Ser Ala Leu
    425                 430                 435 att gcc aga gca atg aac gat att gtt gga cat gaa gat gaa caa gaa     1396
Ile Ala Arg Ala Met Asn Asp Ile Val Gly His Glu Asp Glu Gln Glu
440                 445                 450                 455 aga gga cat gta gct tca ctt att gaa tgt tac atg aaa gat tat gga     1444
Arg Gly His Val Ala Ser Leu Ile Glu Cys Tyr Met Lys Asp Tyr Gly
                460                 465                 470 gct tca aag caa gag act tac att aag ttc ctg aaa gag gtc acc aat     1492
Ala Ser Lys Gln Glu Thr Tyr Ile Lys Phe Leu Lys Glu Val Thr Asn
            475                 480                 485 gca tgg aag gac ata aac aaa caa ttc tcc cgt cca act gaa gta cca     1540
Ala Trp Lys Asp Ile Asn Lys Gln Phe Ser Arg Pro Thr Glu Val Pro
        490                 495                 500 atg ttt gtc ctt gaa cga gtt cta aat ttg aca cgt gtg gct gac acg     1588
Met Phe Val Leu Glu Arg Val Leu Asn Leu Thr Arg Val Ala Asp Thr
    505                 510                 515
```

```
tta tat aag gag aaa gat aca tat tca acc gcc aaa gga aaa ctt aaa      1636
Leu Tyr Lys Glu Lys Asp Thr Tyr Ser Thr Ala Lys Gly Lys Leu Lys
520                 525                 530                 535 aac atg att aat cca ata cta att gaa tct gtc aaa ata taa              1678
Asn Met Ile Asn Pro Ile Leu Ile Glu Ser Val Lys Ile
                540                 545 atataatgct gaaattgcac cttcatcatc caactattca cagcaaaata aggcatataa    1738
taaattgaag actcacaaca tatgagttgt taattcctgg gatgtttgaa ataaacaata    1798
attgttttta tttaatttgc taagccaaag tgaaatatac aacacttgag ttgtattaaa    1858
tcatgtttta tctcatttcc agcttgtgag tttggattat tatattgtta attatcatca    1918
ctttataatg tactgtaatc gtattgtatt tgtattgtag tgttgtcata ataaaatttg    1978
aataaaatat atttttgttt caattccaaa aaaaaaaaaa aaaaaa                   2024
```

<210> SEQ ID NO 52
<211> LENGTH: 548
<212> TYPE: PRT
<213> ORGANISM: Lycopersicon esculentum

<400> SEQUENCE: 52

```
Met Ala Ala Ser Ser Ala Asp Lys Cys Arg Pro Leu Ala Asn Phe His
1               5                   10                  15

Pro Ser Val Trp Gly Tyr His Phe Leu Ser Tyr Thr His Glu Ile Thr
            20                  25                  30

Asn Gln Glu Lys Val Glu Val Asp Glu Tyr Lys Glu Thr Ile Arg Lys
        35                  40                  45

Met Leu Val Glu Thr Cys Asp Asn Ser Thr Gln Lys Leu Val Leu Ile
    50                  55                  60

Asp Ala Met Gln Arg Leu Gly Val Ala Tyr His Phe Asp Asn Glu Ile
65                  70                  75                  80

Glu Thr Ser Ile Gln Asn Ile Phe Asp Ala Ser Ser Lys Gln Asn Asp
                85                  90                  95

Asn Asp Asn Asn Leu Tyr Val Val Ser Leu Arg Phe Arg Leu Val Arg
            100                 105                 110

Gln Gln Gly His Tyr Met Ser Ser Asp Val Phe Lys Gln Phe Thr Asn
        115                 120                 125

Gln Asp Gly Lys Phe Lys Glu Thr Leu Thr Asn Asp Val Gln Gly Leu
    130                 135                 140

Leu Ser Leu Tyr Glu Ala Ser His Leu Arg Val Arg Asn Glu Glu Ile
145                 150                 155                 160

Leu Glu Glu Ala Leu Thr Phe Thr Thr Thr His Leu Glu Ser Ile Val
                165                 170                 175

Ser Asn Leu Ser Asn Asn Asn Ser Leu Lys Val Glu Val Gly Glu
            180                 185                 190

Ala Leu Thr Gln Pro Ile Arg Met Thr Leu Pro Arg Met Gly Ala Arg
        195                 200                 205

Lys Tyr Ile Ser Ile Tyr Glu Asn Asn Asp Ala His His Leu Leu
    210                 215                 220

Leu Lys Phe Ala Lys Leu Asp Phe Asn Met Leu Gln Lys Phe His Gln
225                 230                 235                 240

Arg Glu Leu Ser Asp Leu Thr Arg Trp Trp Lys Asp Leu Asp Phe Ala
                245                 250                 255

Asn Lys Tyr Pro Tyr Ala Arg Asp Arg Leu Val Glu Cys Tyr Phe Trp
            260                 265                 270
```

```
Ile Leu Gly Val Tyr Phe Glu Pro Lys Tyr Ser Arg Ala Arg Lys Met
        275                 280                 285

Met Thr Lys Val Leu Asn Leu Thr Ser Ile Ile Asp Asp Thr Phe Asp
        290                 295                 300

Ala Tyr Ala Thr Phe Asp Glu Leu Val Thr Phe Asn Asp Ala Ile Gln
305                 310                 315                 320

Arg Trp Asp Ala Asn Ala Ile Asp Ser Ile Gln Pro Tyr Met Arg Pro
                325                 330                 335

Ala Tyr Gln Ala Leu Leu Asp Ile Tyr Ser Glu Met Glu Gln Val Leu
                340                 345                 350

Ser Lys Glu Gly Lys Leu Asp Arg Val Tyr Tyr Ala Lys Asn Glu Met
        355                 360                 365

Lys Lys Leu Val Arg Ala Tyr Phe Lys Glu Thr Gln Trp Leu Asn Asp
        370                 375                 380

Cys Asp His Ile Pro Lys Tyr Glu Glu Gln Val Glu Asn Ala Ile Val
385                 390                 395                 400

Ser Ala Gly Tyr Met Met Ile Ser Thr Thr Cys Leu Val Gly Ile Glu
                405                 410                 415

Glu Phe Ile Ser His Glu Thr Phe Glu Trp Leu Met Asn Glu Ser Val
                420                 425                 430

Ile Val Arg Ala Ser Ala Leu Ile Ala Arg Ala Met Asn Asp Ile Val
        435                 440                 445

Gly His Glu Asp Glu Gln Glu Arg Gly His Val Ala Ser Leu Ile Glu
        450                 455                 460

Cys Tyr Met Lys Asp Tyr Gly Ala Ser Lys Gln Glu Thr Tyr Ile Lys
465                 470                 475                 480

Phe Leu Lys Glu Val Thr Asn Ala Trp Lys Asp Ile Asn Lys Gln Phe
                485                 490                 495

Ser Arg Pro Thr Glu Val Pro Met Phe Val Leu Glu Arg Val Leu Asn
                500                 505                 510

Leu Thr Arg Val Ala Asp Thr Leu Tyr Lys Glu Lys Asp Thr Tyr Ser
        515                 520                 525

Thr Ala Lys Gly Lys Leu Lys Asn Met Ile Asn Pro Ile Leu Ile Glu
        530                 535                 540

Ser Val Lys Ile
545

<210> SEQ ID NO 53
<211> LENGTH: 1912
<212> TYPE: DNA
<213> ORGANISM: Salvia officinalis
<220> FEATURE:
<221> NAME/KEY: CDS
<222> LOCATION: (26)...(1795)
<223> OTHER INFORMATION: (+)-sabinene syntase

<400> SEQUENCE: 53
agcaatatta caactaacaa taaaa atg tct tcc att agc ata aac ata gct        52
                            Met Ser Ser Ile Ser Ile Asn Ile Ala
                              1               5 atg cca ctg aat tcc ctc cac aac ttt gag agg aaa cct tca aaa gca       100
Met Pro Leu Asn Ser Leu His Asn Phe Glu Arg Lys Pro Ser Lys Ala
 10              15                  20                  25 tgg tct acc tct tgc act gca ccc gca gct cgc ctc cgg gca tct tcc       148
Trp Ser Thr Ser Cys Thr Ala Pro Ala Ala Arg Leu Arg Ala Ser Ser
             30                  35                  40 tcc tta caa caa gaa aaa cct cac caa atc cga cgc tct ggg gat tac       196
```

```
                                                                -continued

Ser Leu Gln Gln Glu Lys Pro His Gln Ile Arg Arg Ser Gly Asp Tyr
            45                  50                  55 caa ccc tct ctt tgg gat ttc aat tac ata cag tct ctc aac act ccg   244
Gln Pro Ser Leu Trp Asp Phe Asn Tyr Ile Gln Ser Leu Asn Thr Pro
         60                  65                  70 tat aag gag cag aga cac ttt aat agg caa gca gag ttg att atg caa   292
Tyr Lys Glu Gln Arg His Phe Asn Arg Gln Ala Glu Leu Ile Met Gln
 75                  80                  85 gtg agg atg ttg ctc aag gta aag atg gag gca att caa cag ttg gag   340
Val Arg Met Leu Leu Lys Val Lys Met Glu Ala Ile Gln Gln Leu Glu
 90                  95                 100                 105 ttg att gat gac ttg caa tac ctg gga ctg tct tat ttc ttt caa gat   388
Leu Ile Asp Asp Leu Gln Tyr Leu Gly Leu Ser Tyr Phe Phe Gln Asp
                    110                 115                 120 gag att aaa caa atc tta agt tct ata cac aat gag ccc aga tat ttc   436
Glu Ile Lys Gln Ile Leu Ser Ser Ile His Asn Glu Pro Arg Tyr Phe
            125                 130                 135 cac aat aat gat ttg tat ttc aca gct ctt gga ttc aga atc ctc aga   484
His Asn Asn Asp Leu Tyr Phe Thr Ala Leu Gly Phe Arg Ile Leu Arg
        140                 145                 150 caa cat ggt ttt aat gtt tcc gaa gat gta ttt gat tgt ttc aaa att   532
Gln His Gly Phe Asn Val Ser Glu Asp Val Phe Asp Cys Phe Lys Ile
155                 160                 165 gag aag tgc agt gat ttc aat gca aac ctt gct caa gat acg aag gga   580
Glu Lys Cys Ser Asp Phe Asn Ala Asn Leu Ala Gln Asp Thr Lys Gly
170                 175                 180                 185 atg tta caa ctt tat gaa gca tct ttc ctt ttg aga gaa ggt gaa gat   628
Met Leu Gln Leu Tyr Glu Ala Ser Phe Leu Leu Arg Glu Gly Glu Asp
                190                 195                 200 aca ttg gag cta gca aga cga ttt tcc acc aga tct cta cga gaa aaa   676
Thr Leu Glu Leu Ala Arg Arg Phe Ser Thr Arg Ser Leu Arg Glu Lys
            205                 210                 215 ttt gat gaa ggt ggt gat gaa att gat gaa gat cta tca tcg tgg att   724
Phe Asp Glu Gly Gly Asp Glu Ile Asp Glu Asp Leu Ser Ser Trp Ile
        220                 225                 230 cgc cat tcc ttg gat ctt cct ctt cat tgg agg gtc caa gga tta gag   772
Arg His Ser Leu Asp Leu Pro Leu His Trp Arg Val Gln Gly Leu Glu
    235                 240                 245 gca aga tgg ttc tta gat gct tat gcg agg agg ccg gac atg aat cca   820
Ala Arg Trp Phe Leu Asp Ala Tyr Ala Arg Arg Pro Asp Met Asn Pro
250                 255                 260                 265 ctt att ttc aaa ctc gcc aaa ctc aac ttc aat att gtt cag gca aca   868
Leu Ile Phe Lys Leu Ala Lys Leu Asn Phe Asn Ile Val Gln Ala Thr
                270                 275                 280 tat caa gaa gaa ctg aaa gat atc tca agg tgg tgg aat agt tcg tgc   916
Tyr Gln Glu Glu Leu Lys Asp Ile Ser Arg Trp Trp Asn Ser Ser Cys
            285                 290                 295 ctt gct gag aaa ctc cca ttt gtg aga gat agg att gtg gaa tgc ttc   964
Leu Ala Glu Lys Leu Pro Phe Val Arg Asp Arg Ile Val Glu Cys Phe
        300                 305                 310 ttt tgg gcc atc gcg gct ttt gag cct cac caa tat agt tat cag aga   1012
Phe Trp Ala Ile Ala Ala Phe Glu Pro His Gln Tyr Ser Tyr Gln Arg
    315                 320                 325 aaa atg gcc gcc gtt att att act ttc ata aca att atc gat gat gtt   1060
Lys Met Ala Ala Val Ile Ile Thr Phe Ile Thr Ile Ile Asp Asp Val
330                 335                 340                 345 tat gat gtg tat gga aca ata gaa gaa cta gaa cta tta aca gat atg   1108
Tyr Asp Val Tyr Gly Thr Ile Glu Glu Leu Glu Leu Leu Thr Asp Met
                350                 355                 360
```

```
att cgc aga tgg gat aat aaa tca ata agc caa ctt cca tat tat atg    1156
Ile Arg Arg Trp Asp Asn Lys Ser Ile Ser Gln Leu Pro Tyr Tyr Met
        365                 370                 375 caa gtg tgc tat ttg gca cta tac aac ttc gtt tct gag cgg gct tac    1204
Gln Val Cys Tyr Leu Ala Leu Tyr Asn Phe Val Ser Glu Arg Ala Tyr
    380                 385                 390 gat att cta aaa gat caa cat ttc aac agc atc cca tat tta cag aga    1252
Asp Ile Leu Lys Asp Gln His Phe Asn Ser Ile Pro Tyr Leu Gln Arg
395                 400                 405 tcg tgg gta agt ttg gtt gaa gga tat ctt aag gag gca tac tgg tac    1300
Ser Trp Val Ser Leu Val Glu Gly Tyr Leu Lys Glu Ala Tyr Trp Tyr
410                 415                 420                 425 tac aat ggc tat aaa cca agc ttg gaa gaa tat ctc aac aac gcc aag    1348
Tyr Asn Gly Tyr Lys Pro Ser Leu Glu Glu Tyr Leu Asn Asn Ala Lys
                430                 435                 440 att tca ata tcg gct cct aca atc ata tcc cag ctt tat ttt aca tta    1396
Ile Ser Ile Ser Ala Pro Thr Ile Ile Ser Gln Leu Tyr Phe Thr Leu
                445                 450                 455 gca aac tcg att gat gaa aca gct atc gag agc ttg tac caa tat cat    1444
Ala Asn Ser Ile Asp Glu Thr Ala Ile Glu Ser Leu Tyr Gln Tyr His
            460                 465                 470 aac ata ctt tac cta tca gga acc ata tta agg ctt gct gac gat ctt    1492
Asn Ile Leu Tyr Leu Ser Gly Thr Ile Leu Arg Leu Ala Asp Asp Leu
475                 480                 485 ggg aca tca caa cat gag ctg gag aga gga gac gta ccg aaa gca atc    1540
Gly Thr Ser Gln His Glu Leu Glu Arg Gly Asp Val Pro Lys Ala Ile
490                 495                 500                 505 cag tgc tac atg aat gac aca aat gct tcg gag aga gag gcg gtg gaa    1588
Gln Cys Tyr Met Asn Asp Thr Asn Ala Ser Glu Arg Glu Ala Val Glu
                510                 515                 520 cac gtg aag ttt ctg ata agg gag gcg tgg aag gag atg aac acg gtc    1636
His Val Lys Phe Leu Ile Arg Glu Ala Trp Lys Glu Met Asn Thr Val
                525                 530                 535 aca aca gcc agc gat tgt ccg ttt acg gat gat ttg gtt gcg gcc gca    1684
Thr Thr Ala Ser Asp Cys Pro Phe Thr Asp Asp Leu Val Ala Ala Ala
            540                 545                 550 gct aat ctt gca agg gcg gct cag ttt ata tat ctc gac ggg gat ggg    1732
Ala Asn Leu Ala Arg Ala Ala Gln Phe Ile Tyr Leu Asp Gly Asp Gly
555                 560                 565 cat ggc gtg caa cac tca gaa ata cat caa cag atg gga ggc ctg cta    1780
His Gly Val Gln His Ser Glu Ile His Gln Gln Met Gly Gly Leu Leu
570                 575                 580                 585 ttc cag cct tat gtc tga ataaatcgaa aatccaacct actatgtatc          1828
Phe Gln Pro Tyr Val
                590 cctcgataat atattcttgg ggttaacatg tttaattaaa gttctaattd aaagagctga    1888 atcgatcctc aaaaaaaaaa aaaa                                          1912

<210> SEQ ID NO 54
<211> LENGTH: 590
<212> TYPE: PRT
<213> ORGANISM: Salvia officinalis

<400> SEQUENCE: 54

Met Ser Ser Ile Ser Ile Asn Ile Ala Met Pro Leu Asn Ser Leu His
 1               5                  10                  15

Asn Phe Glu Arg Lys Pro Ser Lys Ala Trp Ser Thr Ser Cys Thr Ala
            20                  25                  30

Pro Ala Ala Arg Leu Arg Ala Ser Ser Ser Leu Gln Gln Glu Lys Pro
```

-continued

```
              35                  40                  45
His Gln Ile Arg Arg Ser Gly Asp Tyr Gln Pro Ser Leu Trp Asp Phe
         50                  55                  60
Asn Tyr Ile Gln Ser Leu Asn Thr Pro Tyr Lys Glu Gln Arg His Phe
 65                  70                  75                  80
Asn Arg Gln Ala Glu Leu Ile Met Gln Val Arg Met Leu Leu Lys Val
                 85                  90                  95
Lys Met Glu Ala Ile Gln Gln Leu Glu Leu Ile Asp Asp Leu Gln Tyr
                100                 105                 110
Leu Gly Leu Ser Tyr Phe Phe Gln Asp Glu Ile Lys Gln Ile Leu Ser
            115                 120                 125
Ser Ile His Asn Glu Pro Arg Tyr Phe His Asn Asn Asp Leu Tyr Phe
        130                 135                 140
Thr Ala Leu Gly Phe Arg Ile Leu Arg Gln His Gly Phe Asn Val Ser
145                 150                 155                 160
Glu Asp Val Phe Asp Cys Phe Lys Ile Glu Lys Cys Ser Asp Phe Asn
                165                 170                 175
Ala Asn Leu Ala Gln Asp Thr Lys Gly Met Leu Gln Leu Tyr Glu Ala
            180                 185                 190
Ser Phe Leu Leu Arg Glu Gly Glu Asp Thr Leu Glu Leu Ala Arg Arg
        195                 200                 205
Phe Ser Thr Arg Ser Leu Arg Glu Lys Phe Asp Glu Gly Gly Asp Glu
210                 215                 220
Ile Asp Glu Asp Leu Ser Ser Trp Ile Arg His Ser Leu Asp Leu Pro
225                 230                 235                 240
Leu His Trp Arg Val Gln Gly Leu Glu Ala Arg Trp Phe Leu Asp Ala
                245                 250                 255
Tyr Ala Arg Arg Pro Asp Met Asn Pro Leu Ile Phe Lys Leu Ala Lys
            260                 265                 270
Leu Asn Phe Asn Ile Val Gln Ala Thr Tyr Gln Glu Glu Leu Lys Asp
        275                 280                 285
Ile Ser Arg Trp Trp Asn Ser Cys Leu Ala Glu Lys Leu Pro Phe
290                 295                 300
Val Arg Asp Arg Ile Val Glu Cys Phe Phe Trp Ala Ile Ala Ala Phe
305                 310                 315                 320
Glu Pro His Gln Tyr Ser Tyr Gln Arg Lys Met Ala Ala Val Ile Ile
                325                 330                 335
Thr Phe Ile Thr Ile Asp Asp Val Tyr Asp Val Tyr Gly Thr Ile
            340                 345                 350
Glu Glu Leu Glu Leu Leu Thr Asp Met Ile Arg Arg Trp Asp Asn Lys
        355                 360                 365
Ser Ile Ser Gln Leu Pro Tyr Tyr Met Gln Val Cys Tyr Leu Ala Leu
370                 375                 380
Tyr Asn Phe Val Ser Glu Arg Ala Tyr Asp Ile Leu Lys Asp Gln His
385                 390                 395                 400
Phe Asn Ser Ile Pro Tyr Leu Gln Arg Ser Trp Val Ser Leu Val Glu
                405                 410                 415
Gly Tyr Leu Lys Glu Ala Tyr Trp Tyr Tyr Asn Gly Tyr Lys Pro Ser
            420                 425                 430
Leu Glu Glu Tyr Leu Asn Asn Ala Lys Ile Ser Ile Ser Ala Pro Thr
        435                 440                 445
Ile Ile Ser Gln Leu Tyr Phe Thr Leu Ala Asn Ser Ile Asp Glu Thr
450                 455                 460
```

-continued

```
Ala Ile Glu Ser Leu Tyr Gln Tyr His Asn Ile Leu Tyr Leu Ser Gly
465                 470                 475                 480

Thr Ile Leu Arg Leu Ala Asp Asp Leu Gly Thr Ser Gln His Glu Leu
            485                 490                 495

Glu Arg Gly Asp Val Pro Lys Ala Ile Gln Cys Tyr Met Asn Asp Thr
        500                 505                 510

Asn Ala Ser Glu Arg Glu Ala Val Glu His Val Lys Phe Leu Ile Arg
    515                 520                 525

Glu Ala Trp Lys Glu Met Asn Thr Val Thr Thr Ala Ser Asp Cys Pro
530                 535                 540

Phe Thr Asp Asp Leu Val Ala Ala Ala Asn Leu Ala Arg Ala Ala
545                 550                 555                 560

Gln Phe Ile Tyr Leu Asp Gly Asp Gly His Gly Val Gln His Ser Glu
                565                 570                 575

Ile His Gln Gln Met Gly Gly Leu Leu Phe Gln Pro Tyr Val
                580                 585                 590

<210> SEQ ID NO 55
<211> LENGTH: 2861
<212> TYPE: DNA
<213> ORGANISM: Abies grandis
<220> FEATURE:
<221> NAME/KEY: CDS
<222> LOCATION: (3)...(2606)
<223> OTHER INFORMATION: abietadiene synthase

<400> SEQUENCE: 55 ag atg gcc atg cct tcc tct tca ttg tca tca cag att ccc act gct        47
   Met Ala Met Pro Ser Ser Ser Leu Ser Ser Gln Ile Pro Thr Ala
   1               5                   10                  15 gct cat cat cta act gct aac gca caa tcc att ccg cat ttc tcc acg       95
Ala His His Leu Thr Ala Asn Ala Gln Ser Ile Pro His Phe Ser Thr
                20                  25                  30 acg ctg aat gct gga agc agt gct agc aaa cgg aga agc ttg tac cta      143
Thr Leu Asn Ala Gly Ser Ser Ala Ser Lys Arg Arg Ser Leu Tyr Leu
            35                  40                  45 cga tgg ggt aaa ggt tca aac aag atc att gcc tgt gtt gga gaa ggt      191
Arg Trp Gly Lys Gly Ser Asn Lys Ile Ile Ala Cys Val Gly Glu Gly
        50                  55                  60 ggt gca acc tct gtt cct tat cag tct gct gaa aag aat gat tcg ctt      239
Gly Ala Thr Ser Val Pro Tyr Gln Ser Ala Glu Lys Asn Asp Ser Leu
    65                  70                  75 tct tct tct aca ttg gtg aaa cga gaa ttt cct cca gga ttt tgg aag      287
Ser Ser Ser Thr Leu Val Lys Arg Glu Phe Pro Pro Gly Phe Trp Lys
80                  85                  90                  95 gat gat ctt atc gat tct cta acg tca tct cac aag gtt gca gca tca      335
Asp Asp Leu Ile Asp Ser Leu Thr Ser Ser His Lys Val Ala Ala Ser
                100                 105                 110 gac gag aag cgt atc gag aca tta ata tcc gag att aag aat atg ttt      383
Asp Glu Lys Arg Ile Glu Thr Leu Ile Ser Glu Ile Lys Asn Met Phe
            115                 120                 125 aga tgt atg ggc tat ggc gaa acg aat ccc tct gca tat gac act gct      431
Arg Cys Met Gly Tyr Gly Glu Thr Asn Pro Ser Ala Tyr Asp Thr Ala
        130                 135                 140 tgg gta gca agg att cca gca gtt gat ggc tct gac aac cct cac ttt      479
Trp Val Ala Arg Ile Pro Ala Val Asp Gly Ser Asp Asn Pro His Phe
    145                 150                 155 cct gag acg gtt gaa tgg att ctt caa aat cag ttg aaa gat ggg tct      527
Pro Glu Thr Val Glu Trp Ile Leu Gln Asn Gln Leu Lys Asp Gly Ser
```

-continued

```
             160                 165                 170                 175
tgg ggt gaa gga ttc tac ttc ttg gca tat gac aga ata ctg gct aca         575
Trp Gly Glu Gly Phe Tyr Phe Leu Ala Tyr Asp Arg Ile Leu Ala Thr
                        180                 185                 190 ctt gca tgt att att acc ctt acc ctc tgg cgt act ggg gag aca caa         623
Leu Ala Cys Ile Ile Thr Leu Thr Leu Trp Arg Thr Gly Glu Thr Gln
                195                 200                 205 gta cag aaa ggt att gaa ttc ttc agg aca caa gct gga aag atg gaa         671
Val Gln Lys Gly Ile Glu Phe Phe Arg Thr Gln Ala Gly Lys Met Glu
            210                 215                 220 gat gaa gct gat agt cat agg cca agt gga ttt gaa ata gta ttt cct         719
Asp Glu Ala Asp Ser His Arg Pro Ser Gly Phe Glu Ile Val Phe Pro
        225                 230                 235 gca atg cta aag gaa gct aaa atc tta ggc ttg gat ctg cct tac gat         767
Ala Met Leu Lys Glu Ala Lys Ile Leu Gly Leu Asp Leu Pro Tyr Asp
240                 245                 250                 255 ttg cca ttc ctg aaa caa atc atc gaa aag cgg gag gct aag ctt aaa         815
Leu Pro Phe Leu Lys Gln Ile Ile Glu Lys Arg Glu Ala Lys Leu Lys
                260                 265                 270 agg att ccc act gat gtt ctc tat gcc ctt cca aca acg tta ttg tat         863
Arg Ile Pro Thr Asp Val Leu Tyr Ala Leu Pro Thr Thr Leu Leu Tyr
            275                 280                 285 tct ttg gaa ggt tta caa gaa ata gta gac tgg cag aaa ata atg aaa         911
Ser Leu Glu Gly Leu Gln Glu Ile Val Asp Trp Gln Lys Ile Met Lys
        290                 295                 300 ctt caa tcc aag gat gga tca ttt ctc agc tct ccg gca tct aca gcg         959
Leu Gln Ser Lys Asp Gly Ser Phe Leu Ser Ser Pro Ala Ser Thr Ala
    305                 310                 315 gct gta ttc atg cgt aca ggg aac aaa aag tgc ttg gat ttc ttg aac        1007
Ala Val Phe Met Arg Thr Gly Asn Lys Lys Cys Leu Asp Phe Leu Asn
320                 325                 330                 335 ttt gtc ttg aag aaa ttc gga aac cat gtg cct tgt cac tat ccg ctt        1055
Phe Val Leu Lys Lys Phe Gly Asn His Val Pro Cys His Tyr Pro Leu
                340                 345                 350 gat cta ttt gaa cgt ttg tgg gcg gtt gat aca gtt gag cgg cta ggt        1103
Asp Leu Phe Glu Arg Leu Trp Ala Val Asp Thr Val Glu Arg Leu Gly
            355                 360                 365 atc gat cgt cat ttc aaa gag gag atc aag gaa gca ttg gat tat gtt        1151
Ile Asp Arg His Phe Lys Glu Glu Ile Lys Glu Ala Leu Asp Tyr Val
        370                 375                 380 tac agc cat tgg gac gaa aga ggc att gga tgg gcg aga gag aat cct        1199
Tyr Ser His Trp Asp Glu Arg Gly Ile Gly Trp Ala Arg Glu Asn Pro
    385                 390                 395 gtt cct gat att gat gat aca gcc atg ggc ctt cga atc ttg aga tta        1247
Val Pro Asp Ile Asp Asp Thr Ala Met Gly Leu Arg Ile Leu Arg Leu
400                 405                 410                 415 cat gga tac aat gta tcc tca gat gtt tta aaa aca ttt aga gat gag        1295
His Gly Tyr Asn Val Ser Ser Asp Val Leu Lys Thr Phe Arg Asp Glu
                420                 425                 430 aat ggg gag ttc ttt tgc ttc ttg ggt caa aca cag aga gga gtt aca        1343
Asn Gly Glu Phe Phe Cys Phe Leu Gly Gln Thr Gln Arg Gly Val Thr
            435                 440                 445 gac atg tta aac gtc aat cgt tgt tca cat gtt tca ttt ccg gga gaa        1391
Asp Met Leu Asn Val Asn Arg Cys Ser His Val Ser Phe Pro Gly Glu
        450                 455                 460 acg atc atg gaa gaa gca aaa ctc tgt acc gaa agg tat ctg agg aat        1439
Thr Ile Met Glu Glu Ala Lys Leu Cys Thr Glu Arg Tyr Leu Arg Asn
    465                 470                 475 gct ctg gaa aat gtg gat gcc ttt gac aaa tgg gct ttt aaa aag aat        1487
Ala Leu Glu Asn Val Asp Ala Phe Asp Lys Trp Ala Phe Lys Lys Asn
```

```
                                                       -continued

Ala Leu Glu Asn Val Asp Ala Phe Asp Lys Trp Ala Phe Lys Lys Asn
480             485                 490                 495 att cgg gga gag gta gag tat gca ctc aaa tat ccc tgg cat aag agt    1535
Ile Arg Gly Glu Val Glu Tyr Ala Leu Lys Tyr Pro Trp His Lys Ser
                    500                 505                 510 atg cca agg ttg gag gct aga agc tat att gaa aac tat ggg cca gat    1583
Met Pro Arg Leu Glu Ala Arg Ser Tyr Ile Glu Asn Tyr Gly Pro Asp
                515                 520                 525 gat gtg tgg ctt gga aaa act gta tat atg atg cca tac att tcg aat    1631
Asp Val Trp Leu Gly Lys Thr Val Tyr Met Met Pro Tyr Ile Ser Asn
            530                 535                 540 gaa aag tat tta gaa cta gcg aaa ctg gac ttc aat aag gtg cag tct    1679
Glu Lys Tyr Leu Glu Leu Ala Lys Leu Asp Phe Asn Lys Val Gln Ser
        545                 550                 555 ata cac caa aca gag ctt caa gat ctt cga agg tgg tgg aaa tca tcc    1727
Ile His Gln Thr Glu Leu Gln Asp Leu Arg Arg Trp Trp Lys Ser Ser
560                 565                 570                 575 ggt ttc acg gat ctg aat ttc act cgt gag cgt gtg acg gaa ata tat    1775
Gly Phe Thr Asp Leu Asn Phe Thr Arg Glu Arg Val Thr Glu Ile Tyr
                580                 585                 590 ttc tca ccg gca tcc ttt atc ttt gag ccc gag ttt tct aag tgc aga    1823
Phe Ser Pro Ala Ser Phe Ile Phe Glu Pro Glu Phe Ser Lys Cys Arg
                595                 600                 605 gag gtt tat aca aaa act tcc aat ttc act gtt att tta gat gat ctt    1871
Glu Val Tyr Thr Lys Thr Ser Asn Phe Thr Val Ile Leu Asp Asp Leu
            610                 615                 620 tat gac gcc cat gga tct tta gac gat ctt aag ttg ttc aca gaa tca    1919
Tyr Asp Ala His Gly Ser Leu Asp Asp Leu Lys Leu Phe Thr Glu Ser
625                 630                 635 gtc aaa aga tgg gat cta tca cta gtg gac caa atg cca caa caa atg    1967
Val Lys Arg Trp Asp Leu Ser Leu Val Asp Gln Met Pro Gln Gln Met
640                 645                 650                 655 aaa ata tgt ttt gtg ggt ttc tac aat act ttt aat gat ata gca aaa    2015
Lys Ile Cys Phe Val Gly Phe Tyr Asn Thr Phe Asn Asp Ile Ala Lys
                660                 665                 670 gaa gga cgt gag agg caa ggg cgc gat gtg cta ggc tac att caa aat    2063
Glu Gly Arg Glu Arg Gln Gly Arg Asp Val Leu Gly Tyr Ile Gln Asn
                675                 680                 685 gtt tgg aaa gtc caa ctt gaa gct tac acg aaa gaa gca gaa tgg tct    2111
Val Trp Lys Val Gln Leu Glu Ala Tyr Thr Lys Glu Ala Glu Trp Ser
            690                 695                 700 gaa gct aaa tat gtg cca tcc ttc aat gaa tac ata gag aat gcg agt    2159
Glu Ala Lys Tyr Val Pro Ser Phe Asn Glu Tyr Ile Glu Asn Ala Ser
        705                 710                 715 gtg tca ata gca ttg gga aca gtc gtt ctc att agt gct ctt ttc act    2207
Val Ser Ile Ala Leu Gly Thr Val Val Leu Ile Ser Ala Leu Phe Thr
720                 725                 730                 735 ggg gag gtt ctt aca gat gaa gta ctc tcc aaa att gat cgc gaa tct    2255
Gly Glu Val Leu Thr Asp Glu Val Leu Ser Lys Ile Asp Arg Glu Ser
                740                 745                 750 aga ttt ctt caa ctc atg ggc tta aca ggg cgt ttg gtg aat gac acc    2303
Arg Phe Leu Gln Leu Met Gly Leu Thr Gly Arg Leu Val Asn Asp Thr
                755                 760                 765 aaa act tat cag gca gag aga ggt caa ggt gag gtg gct tct gcc ata    2351
Lys Thr Tyr Gln Ala Glu Arg Gly Gln Gly Glu Val Ala Ser Ala Ile
            770                 775                 780 caa tgt tat atg aag gac cat cct aaa atc tct gaa gaa gaa gct cta    2399
Gln Cys Tyr Met Lys Asp His Pro Lys Ile Ser Glu Glu Glu Ala Leu
785                 790                 795
```

-continued

```
caa cat gtc tat agt gtc atg gaa aat gcc ctc gaa gag ttg aat agg     2447
Gln His Val Tyr Ser Val Met Glu Asn Ala Leu Glu Glu Leu Asn Arg
800                 805                 810                 815 gag ttt gtg aat aac aaa ata ccg gat att tac aaa aga ctg gtt ttt     2495
Glu Phe Val Asn Asn Lys Ile Pro Asp Ile Tyr Lys Arg Leu Val Phe
                820                 825                 830 gaa act gca aga ata atg caa ctc ttt tat atg caa ggg gat ggt ttg     2543
Glu Thr Ala Arg Ile Met Gln Leu Phe Tyr Met Gln Gly Asp Gly Leu
            835                 840                 845 aca cta tca cat gat atg gaa att aaa gag cat gtc aaa aat tgc ctc     2591
Thr Leu Ser His Asp Met Glu Ile Lys Glu His Val Lys Asn Cys Leu
        850                 855                 860 ttc caa cca gtt gcc tag attaaattat tcagttaaag gccctcatgg            2639
Phe Gln Pro Val Ala
    865 tattgtgtta acattataat aacagatgct caaaagcttt gagcggtatt tgttaaggct   2699 atctttgttt gtttgtttgt ttactgccaa ccaaaaagcg ttcctaaacc tttgaagaca   2759 tttccatcca agagatggag tctacatttt atttatgaga ttgaattatt tcaagagaat   2819 atactacata tatttaaaag taaaaaaaaa aaaaaaaaaa aa                      2861
```

<210> SEQ ID NO 56
<211> LENGTH: 868
<212> TYPE: PRT
<213> ORGANISM: Abies grandis

<400> SEQUENCE: 56

```
Met Ala Met Pro Ser Ser Leu Ser Ser Gln Ile Pro Thr Ala Ala
1               5                   10                  15

His His Leu Thr Ala Asn Ala Gln Ser Ile Pro His Phe Ser Thr Thr
                20                  25                  30

Leu Asn Ala Gly Ser Ser Ala Ser Lys Arg Arg Ser Leu Tyr Leu Arg
            35                  40                  45

Trp Gly Lys Gly Ser Asn Lys Ile Ile Ala Cys Val Gly Glu Gly Gly
        50                  55                  60

Ala Thr Ser Val Pro Tyr Gln Ser Ala Glu Lys Asn Asp Ser Leu Ser
65                  70                  75                  80

Ser Ser Thr Leu Val Lys Arg Glu Phe Pro Pro Gly Phe Trp Lys Asp
                85                  90                  95

Asp Leu Ile Asp Ser Leu Thr Ser Ser His Lys Val Ala Ala Ser Asp
                100                 105                 110

Glu Lys Arg Ile Glu Thr Leu Ile Ser Glu Ile Lys Asn Met Phe Arg
            115                 120                 125

Cys Met Gly Tyr Gly Glu Thr Asn Pro Ser Ala Tyr Asp Thr Ala Trp
        130                 135                 140

Val Ala Arg Ile Pro Ala Val Asp Gly Ser Asp Asn Pro His Phe Pro
145                 150                 155                 160

Glu Thr Val Glu Trp Ile Leu Gln Asn Gln Leu Lys Asp Gly Ser Trp
                165                 170                 175

Gly Glu Gly Phe Tyr Phe Leu Ala Tyr Asp Arg Ile Leu Ala Thr Leu
                180                 185                 190

Ala Cys Ile Ile Thr Leu Thr Leu Trp Arg Thr Gly Thr Gln Val
            195                 200                 205

Gln Lys Gly Ile Glu Phe Phe Arg Thr Gln Ala Gly Lys Met Glu Asp
        210                 215                 220

Glu Ala Asp Ser His Arg Pro Ser Gly Phe Glu Ile Val Phe Pro Ala
```

-continued

```
             225                 230                 235                 240
Met Leu Lys Glu Ala Lys Ile Leu Gly Leu Asp Leu Pro Tyr Asp Leu
                 245                 250                 255
Pro Phe Leu Lys Gln Ile Ile Glu Lys Arg Glu Ala Lys Leu Lys Arg
                 260                 265                 270
Ile Pro Thr Asp Val Leu Tyr Ala Leu Pro Thr Thr Leu Leu Tyr Ser
             275                 280                 285
Leu Glu Gly Leu Gln Glu Ile Val Asp Trp Gln Lys Ile Met Lys Leu
         290                 295                 300
Gln Ser Lys Asp Gly Ser Phe Leu Ser Ser Pro Ala Ser Thr Ala Ala
305                 310                 315                 320
Val Phe Met Arg Thr Gly Asn Lys Lys Cys Leu Asp Phe Leu Asn Phe
                 325                 330                 335
Val Leu Lys Lys Phe Gly Asn His Val Pro Cys His Tyr Pro Leu Asp
                 340                 345                 350
Leu Phe Glu Arg Leu Trp Ala Val Asp Thr Val Glu Arg Leu Gly Ile
             355                 360                 365
Asp Arg His Phe Lys Glu Ile Lys Glu Ala Leu Asp Tyr Val Tyr
         370                 375                 380
Ser His Trp Asp Glu Arg Gly Ile Gly Trp Ala Arg Glu Asn Pro Val
385                 390                 395                 400
Pro Asp Ile Asp Asp Thr Ala Met Gly Leu Arg Ile Leu Arg Leu His
                 405                 410                 415
Gly Tyr Asn Val Ser Ser Asp Val Leu Lys Thr Phe Arg Asp Glu Asn
             420                 425                 430
Gly Glu Phe Phe Cys Phe Leu Gly Gln Thr Gln Arg Gly Val Thr Asp
         435                 440                 445
Met Leu Asn Val Asn Arg Cys Ser His Val Ser Phe Pro Gly Glu Thr
450                 455                 460
Ile Met Glu Glu Ala Lys Leu Cys Thr Glu Arg Tyr Leu Arg Asn Ala
465                 470                 475                 480
Leu Glu Asn Val Asp Ala Phe Asp Lys Trp Ala Phe Lys Lys Asn Ile
                 485                 490                 495
Arg Gly Glu Val Glu Tyr Ala Leu Lys Tyr Pro Trp His Lys Ser Met
             500                 505                 510
Pro Arg Leu Glu Ala Arg Ser Tyr Ile Glu Asn Tyr Gly Pro Asp Asp
         515                 520                 525
Val Trp Leu Gly Lys Thr Val Tyr Met Met Pro Tyr Ile Ser Asn Glu
     530                 535                 540
Lys Tyr Leu Glu Leu Ala Lys Leu Asp Phe Asn Lys Val Gln Ser Ile
545                 550                 555                 560
His Gln Thr Glu Leu Gln Asp Leu Arg Arg Trp Trp Lys Ser Ser Gly
                 565                 570                 575
Phe Thr Asp Leu Asn Phe Thr Arg Glu Arg Val Thr Glu Ile Tyr Phe
             580                 585                 590
Ser Pro Ala Ser Phe Ile Phe Glu Pro Glu Phe Ser Lys Cys Arg Glu
         595                 600                 605
Val Tyr Thr Lys Thr Ser Asn Phe Thr Val Ile Leu Asp Asp Leu Tyr
     610                 615                 620
Asp Ala His Gly Ser Leu Asp Asp Leu Lys Leu Phe Thr Glu Ser Val
625                 630                 635                 640
Lys Arg Trp Asp Leu Ser Leu Val Asp Gln Met Pro Gln Gln Met Lys
                 645                 650                 655
```

-continued

```
Ile Cys Phe Val Gly Phe Tyr Asn Thr Phe Asn Asp Ile Ala Lys Glu
            660                 665                 670

Gly Arg Glu Arg Gln Gly Arg Asp Val Leu Gly Tyr Ile Gln Asn Val
        675                 680                 685

Trp Lys Val Gln Leu Glu Ala Tyr Thr Lys Glu Ala Glu Trp Ser Glu
    690                 695                 700

Ala Lys Tyr Val Pro Ser Phe Asn Glu Tyr Ile Glu Asn Ala Ser Val
705                 710                 715                 720

Ser Ile Ala Leu Gly Thr Val Leu Ile Ser Ala Leu Phe Thr Gly
                725                 730                 735

Glu Val Leu Thr Asp Glu Val Leu Ser Lys Ile Asp Arg Glu Ser Arg
            740                 745                 750

Phe Leu Gln Leu Met Gly Leu Thr Gly Arg Leu Val Asn Asp Thr Lys
        755                 760                 765

Thr Tyr Gln Ala Glu Arg Gly Gln Gly Glu Val Ala Ser Ala Ile Gln
    770                 775                 780

Cys Tyr Met Lys Asp His Pro Lys Ile Ser Glu Glu Ala Leu Gln
785                 790                 795                 800

His Val Tyr Ser Val Met Glu Asn Ala Leu Glu Glu Leu Asn Arg Glu
                805                 810                 815

Phe Val Asn Asn Lys Ile Pro Asp Ile Tyr Lys Arg Leu Val Phe Glu
            820                 825                 830

Thr Ala Arg Ile Met Gln Leu Phe Tyr Met Gln Gly Asp Gly Leu Thr
        835                 840                 845

Leu Ser His Asp Met Glu Ile Lys Glu His Val Lys Asn Cys Leu Phe
    850                 855                 860

Gln Pro Val Ala
865
```

<210> SEQ ID NO 57
<211> LENGTH: 2089
<212> TYPE: DNA
<213> ORGANISM: Abies grandis
<220> FEATURE:
<221> NAME/KEY: CDS
<222> LOCATION: (73)...(1983)
<223> OTHER INFORMATION: (−)-4S-limonene synthase

<400> SEQUENCE: 57

```
tgccgtttaa tcggtttaaa gaagctacca tagttcggtt taaagaagct accatagttt        60
aggcaggaat cc atg gct ctc ctt tct atc gta tct ttg cag gtt ccc aaa       111
              Met Ala Leu Leu Ser Ile Val Ser Leu Gln Val Pro Lys
                1               5                  10 tcc tgc ggg ctg aaa tcg ttg atc agt tcc agc aat gtg cag aag gct         159
Ser Cys Gly Leu Lys Ser Leu Ile Ser Ser Ser Asn Val Gln Lys Ala
    15                  20                  25 ctc tgt atc tct aca gca gtc cca aca ctc aga atg cgt agg cga cag         207
Leu Cys Ile Ser Thr Ala Val Pro Thr Leu Arg Met Arg Arg Arg Gln
30                  35                  40                  45 aaa gct ctg gtc atc aac atg aaa ttg acc act gta tcc cat cgt gat         255
Lys Ala Leu Val Ile Asn Met Lys Leu Thr Thr Val Ser His Arg Asp
                50                  55                  60 gat aat ggt ggt ggt gta ctg caa aga cgc ata gcc gat cat cat ccc         303
Asp Asn Gly Gly Gly Val Leu Gln Arg Arg Ile Ala Asp His His Pro
            65                  70                  75 aac ctg tgg gaa gat gat ttc ata caa tca ttg tcc tca cct tat ggg         351
Asn Leu Trp Glu Asp Asp Phe Ile Gln Ser Leu Ser Ser Pro Tyr Gly
```

```
                  80                  85                  90
gga tct tcg tac agt gaa cgt gct gag aca gtc gtt gag gaa gta aaa     399
Gly Ser Ser Tyr Ser Glu Arg Ala Glu Thr Val Val Glu Glu Val Lys
         95                 100                 105 gag atg ttc aat tca ata cca aat aat aga gaa tta ttt ggt tcc caa     447
Glu Met Phe Asn Ser Ile Pro Asn Asn Arg Glu Leu Phe Gly Ser Gln
110                 115                 120                 125 aat gat ctc ctt aca cgc ctt tgg atg gtg gat agc att gaa cgt ctg     495
Asn Asp Leu Leu Thr Arg Leu Trp Met Val Asp Ser Ile Glu Arg Leu
             130                 135                 140 ggg ata gat aga cat ttc caa aat gag ata aga gta gcc ctc gat tat     543
Gly Ile Asp Arg His Phe Gln Asn Glu Ile Arg Val Ala Leu Asp Tyr
         145                 150                 155 gtt tac agt tat tgg aag gaa aag gaa ggc att ggg tgt ggc aga gat     591
Val Tyr Ser Tyr Trp Lys Glu Lys Glu Gly Ile Gly Cys Gly Arg Asp
             160                 165                 170 tct act ttt cct gat ctc aac tcg act gcc ttg gcg ctt cga act ctt     639
Ser Thr Phe Pro Asp Leu Asn Ser Thr Ala Leu Ala Leu Arg Thr Leu
         175                 180                 185 cga ctg cac gga tac aat gtg tct tca gat gtg ctg gaa tac ttc aaa     687
Arg Leu His Gly Tyr Asn Val Ser Ser Asp Val Leu Glu Tyr Phe Lys
190                 195                 200                 205 gat gaa aag ggg cat ttt gcc tgc cct gca atc cta acc gag gga cag     735
Asp Glu Lys Gly His Phe Ala Cys Pro Ala Ile Leu Thr Glu Gly Gln
             210                 215                 220 atc act aga agt gtt cta aat tta tat cgg gct tcc ctg gtc gcc ttt     783
Ile Thr Arg Ser Val Leu Asn Leu Tyr Arg Ala Ser Leu Val Ala Phe
         225                 230                 235 ccc ggg gag aaa gtt atg gaa gag gct gaa atc ttc tcg gca tct tat     831
Pro Gly Glu Lys Val Met Glu Glu Ala Glu Ile Phe Ser Ala Ser Tyr
240                 245                 250 ttg aaa aaa gtc tta caa aag att ccg gtc tcc aat ctt tca gga gag     879
Leu Lys Lys Val Leu Gln Lys Ile Pro Val Ser Asn Leu Ser Gly Glu
         255                 260                 265 ata gaa tat gtt ttg gaa tat ggt tgg cac acg aat ttg ccg aga ttg     927
Ile Glu Tyr Val Leu Glu Tyr Gly Trp His Thr Asn Leu Pro Arg Leu
270                 275                 280                 285 gaa gca aga aat tat atc gag gtc tac gag cag agc ggc tat gaa agc     975
Glu Ala Arg Asn Tyr Ile Glu Val Tyr Glu Gln Ser Gly Tyr Glu Ser
             290                 295                 300 tta aac gag atg cca tat atg aac atg aag aag ctt tta caa ctt gca    1023
Leu Asn Glu Met Pro Tyr Met Asn Met Lys Lys Leu Leu Gln Leu Ala
         305                 310                 315 aaa ttg gag ttc aat atc ttt cac tct ttg caa cta aga gag tta caa    1071
Lys Leu Glu Phe Asn Ile Phe His Ser Leu Gln Leu Arg Glu Leu Gln
320                 325                 330 tct atc tcc aga tgg tgg aaa gaa tca ggt tcg tct caa ctg act ttt    1119
Ser Ile Ser Arg Trp Trp Lys Glu Ser Gly Ser Ser Gln Leu Thr Phe
             335                 340                 345 aca cgg cat cgt cac gtg gaa tac tac act atg gca tct tgc att tct    1167
Thr Arg His Arg His Val Glu Tyr Tyr Thr Met Ala Ser Cys Ile Ser
350                 355                 360                 365 atg ttg cca aaa cat tca gct ttc aga atg gag ttt gtc aaa gtg tgt    1215
Met Leu Pro Lys His Ser Ala Phe Arg Met Glu Phe Val Lys Val Cys
             370                 375                 380 cat ctt gta aca gtt ctc gat gat ata tat gac act ttt gga aca atg    1263
His Leu Val Thr Val Leu Asp Asp Ile Tyr Asp Thr Phe Gly Thr Met
         385                 390                 395 aac gaa ctc caa ctt ttt acg gat gca att aag aga tgg gat ttg tca    1311
```

```
Asn Glu Leu Gln Leu Phe Thr Asp Ala Ile Lys Arg Trp Asp Leu Ser
            400                 405                 410 acg aca agg tgg ctt cca gaa tat atg aaa gga gtg tac atg gac ttg      1359
Thr Thr Arg Trp Leu Pro Glu Tyr Met Lys Gly Val Tyr Met Asp Leu
        415                 420                 425 tat caa tgc att aat gaa atg gtg gaa gag gct gag aag act caa ggc      1407
Tyr Gln Cys Ile Asn Glu Met Val Glu Glu Ala Glu Lys Thr Gln Gly
430                 435                 440                 445 cga gat atg ctc aac tat att caa aat gct tgg gaa gcc cta ttt gat      1455
Arg Asp Met Leu Asn Tyr Ile Gln Asn Ala Trp Glu Ala Leu Phe Asp
                450                 455                 460 acc ttt atg caa gaa gca aag tgg atc tcc agc agt tat ctc cca acg      1503
Thr Phe Met Gln Glu Ala Lys Trp Ile Ser Ser Ser Tyr Leu Pro Thr
            465                 470                 475 ttt gag gag tac ttg aag aat gca aaa gtt agt tct ggt tct cgc ata      1551
Phe Glu Glu Tyr Leu Lys Asn Ala Lys Val Ser Ser Gly Ser Arg Ile
        480                 485                 490 gcc aca tta caa ccc att ctc act ttg gat gta cca ctt cct gat tac      1599
Ala Thr Leu Gln Pro Ile Leu Thr Leu Asp Val Pro Leu Pro Asp Tyr
495                 500                 505 ata ctg caa gaa att gat tat cca tcc aga ttc aat gag tta gct tcg      1647
Ile Leu Gln Glu Ile Asp Tyr Pro Ser Arg Phe Asn Glu Leu Ala Ser
510                 515                 520                 525 tcc atc ctt cga cta cga ggt gac acg cgc tgc tac aag gcg gat agg      1695
Ser Ile Leu Arg Leu Arg Gly Asp Thr Arg Cys Tyr Lys Ala Asp Arg
                530                 535                 540 gcc cgt gga gaa gaa gct tca gct ata tcg tgt tat atg aaa gac cat      1743
Ala Arg Gly Glu Glu Ala Ser Ala Ile Ser Cys Tyr Met Lys Asp His
            545                 550                 555 cct gga tca ata gag gaa gat gct ctc aat cat atc aac gcc atg atc      1791
Pro Gly Ser Ile Glu Glu Asp Ala Leu Asn His Ile Asn Ala Met Ile
        560                 565                 570 agt gat gca atc aga gaa tta aat tgg gag ctt ctc aga ccg gat agc      1839
Ser Asp Ala Ile Arg Glu Leu Asn Trp Glu Leu Leu Arg Pro Asp Ser
575                 580                 585 aaa agt ccc atc tct tcc aag aaa cat gct ttt gac atc acc aga gct      1887
Lys Ser Pro Ile Ser Ser Lys Lys His Ala Phe Asp Ile Thr Arg Ala
590                 595                 600                 605 ttc cat cat gtc tac aaa tat cga gat ggt tac act gtt tcc aac aac      1935
Phe His His Val Tyr Lys Tyr Arg Asp Gly Tyr Thr Val Ser Asn Asn
                610                 615                 620 gaa aca aag aat ttg gtg atg aaa acc gtt ctt gaa cct ctc gct ttg      1983
Glu Thr Lys Asn Leu Val Met Lys Thr Val Leu Glu Pro Leu Ala Leu
            625                 630                 635 taa aaacatatag aatgcattaa aatgtgggaa gtctataatc tagactattc           2036
tctatctttc ataatgtaga tctggatgtg tattgaactc taaaaaaaaa aaa            2089

<210> SEQ ID NO 58
<211> LENGTH: 637
<212> TYPE: PRT
<213> ORGANISM: Abies grandis

<400> SEQUENCE: 58

Met Ala Leu Leu Ser Ile Val Ser Leu Gln Val Pro Lys Ser Cys Gly
 1               5                  10                  15

Leu Lys Ser Leu Ile Ser Ser Asn Val Gln Lys Ala Leu Cys Ile
            20                  25                  30

Ser Thr Ala Val Pro Thr Leu Arg Met Arg Arg Gln Lys Ala Leu
        35                  40                  45
```

-continued

```
Val Ile Asn Met Lys Leu Thr Thr Val Ser His Arg Asp Asp Asn Gly
    50                  55                  60
Gly Gly Val Leu Gln Arg Arg Ile Ala Asp His His Pro Asn Leu Trp
65                  70                  75                  80
Glu Asp Asp Phe Ile Gln Ser Leu Ser Ser Pro Tyr Gly Gly Ser Ser
                85                  90                  95
Tyr Ser Glu Arg Ala Glu Thr Val Val Glu Glu Val Lys Glu Met Phe
                100                 105                 110
Asn Ser Ile Pro Asn Asn Arg Glu Leu Phe Gly Ser Gln Asn Asp Leu
                115                 120                 125
Leu Thr Arg Leu Trp Met Val Asp Ser Ile Glu Arg Leu Gly Ile Asp
    130                 135                 140
Arg His Phe Gln Asn Glu Ile Arg Val Ala Leu Asp Tyr Val Tyr Ser
145                 150                 155                 160
Tyr Trp Lys Glu Lys Glu Gly Ile Gly Cys Gly Arg Asp Ser Thr Phe
                165                 170                 175
Pro Asp Leu Asn Ser Thr Ala Leu Ala Leu Arg Thr Leu Arg Leu His
                180                 185                 190
Gly Tyr Asn Val Ser Ser Asp Val Leu Glu Tyr Phe Lys Asp Glu Lys
    195                 200                 205
Gly His Phe Ala Cys Pro Ala Ile Leu Thr Glu Gly Gln Ile Thr Arg
    210                 215                 220
Ser Val Leu Asn Leu Tyr Arg Ala Ser Leu Val Ala Phe Pro Gly Glu
225                 230                 235                 240
Lys Val Met Glu Glu Ala Glu Ile Phe Ser Ala Ser Tyr Leu Lys Lys
                245                 250                 255
Val Leu Gln Lys Ile Pro Val Ser Asn Leu Ser Gly Glu Ile Glu Tyr
                260                 265                 270
Val Leu Glu Tyr Gly Trp His Thr Asn Leu Pro Arg Leu Glu Ala Arg
    275                 280                 285
Asn Tyr Ile Glu Val Tyr Glu Gln Ser Gly Tyr Glu Ser Leu Asn Glu
    290                 295                 300
Met Pro Tyr Met Asn Met Lys Lys Leu Leu Gln Leu Ala Lys Leu Glu
305                 310                 315                 320
Phe Asn Ile Phe His Ser Leu Gln Leu Arg Glu Leu Gln Ser Ile Ser
                325                 330                 335
Arg Trp Trp Lys Glu Ser Gly Ser Ser Gln Leu Thr Phe Thr Arg His
                340                 345                 350
Arg His Val Glu Tyr Tyr Thr Met Ala Ser Cys Ile Ser Met Leu Pro
    355                 360                 365
Lys His Ser Ala Phe Arg Met Glu Phe Val Lys Val Cys His Leu Val
    370                 375                 380
Thr Val Leu Asp Asp Ile Tyr Asp Thr Phe Gly Thr Met Asn Glu Leu
385                 390                 395                 400
Gln Leu Phe Thr Asp Ala Ile Lys Arg Trp Asp Leu Ser Thr Thr Arg
                405                 410                 415
Trp Leu Pro Glu Tyr Met Lys Gly Val Tyr Met Asp Leu Tyr Gln Cys
                420                 425                 430
Ile Asn Glu Met Val Glu Glu Ala Glu Lys Thr Gln Gly Arg Asp Met
                435                 440                 445
Leu Asn Tyr Ile Gln Asn Ala Trp Glu Ala Leu Phe Asp Thr Phe Met
    450                 455                 460
```

-continued

```
Gln Glu Ala Lys Trp Ile Ser Ser Tyr Leu Pro Thr Phe Glu Glu
465             470             475             480

Tyr Leu Lys Asn Ala Lys Val Ser Ser Gly Ser Arg Ile Ala Thr Leu
            485             490                 495

Gln Pro Ile Leu Thr Leu Asp Val Pro Leu Pro Asp Tyr Ile Leu Gln
            500             505             510

Glu Ile Asp Tyr Pro Ser Arg Phe Asn Glu Leu Ala Ser Ser Ile Leu
        515             520             525

Arg Leu Arg Gly Asp Thr Arg Cys Tyr Lys Ala Asp Arg Ala Arg Gly
        530             535             540

Glu Glu Ala Ser Ala Ile Ser Cys Tyr Met Lys Asp His Pro Gly Ser
545             550             555             560

Ile Glu Glu Asp Ala Leu Asn His Ile Asn Ala Met Ile Ser Asp Ala
            565             570             575

Ile Arg Glu Leu Asn Trp Glu Leu Leu Arg Pro Asp Ser Lys Ser Pro
            580             585             590

Ile Ser Ser Lys Lys His Ala Phe Asp Ile Thr Arg Ala Phe His His
        595             600             605

Val Tyr Lys Tyr Arg Asp Gly Tyr Thr Val Ser Asn Asn Glu Thr Lys
        610             615             620

Asn Leu Val Met Lys Thr Val Leu Glu Pro Leu Ala Leu
625             630             635
```